United States Patent
Malhotra et al.

(10) Patent No.: US 12,208,088 B2
(45) Date of Patent: Jan. 28, 2025

(54) SPIROCYCLIC 2,3-DIHYDRO-7-AZAINDOLE COMPOUNDS AND USES THEREOF

(71) Applicant: Genentech, Inc., South San Francisco, CA (US)

(72) Inventors: Sushant Malhotra, Burlingame, CA (US); Craig Stivala, San Mateo, CA (US); BinQing Wei, Belmont, CA (US); Bryan K. Chan, Foster City, CA (US); Timothy Heffron, Burlingame, CA (US); Michael Lainchbury, Harlow (GB); Andrew Madin, Harlow (GB); Terry Aaron Panchal, Harlow (GB); Eileen Mary Seward, Harlow (GB); Toby Blench, Harlow (GB); Matthew W. Cartwright, Harlow (GB); Elsa Amandine Dechaux, Harlow (GB); Richard Elliott, Harlow (GB); Emanuela Gancia, Harlow (GB)

(73) Assignee: Genentech, Inc., South San Francisco, CA (US)

( * ) Notice: Subject to any disclaimer, the term of this patent is extended or adjusted under 35 U.S.C. 154(b) by 700 days.

(21) Appl. No.: 17/204,089

(22) Filed: Mar. 17, 2021

(65) Prior Publication Data

US 2022/0370420 A1  Nov. 24, 2022

Related U.S. Application Data

(63) Continuation of application No. PCT/US2019/052023, filed on Sep. 19, 2019.

(30) Foreign Application Priority Data

Sep. 19, 2018  (WO) ................ PCT/CN2018/106536

(51) Int. Cl.
| | |
|---|---|
| A61K 31/437 | (2006.01) |
| A61K 31/444 | (2006.01) |
| A61K 31/496 | (2006.01) |
| A61K 31/4985 | (2006.01) |
| A61K 31/513 | (2006.01) |
| A61K 31/5377 | (2006.01) |
| A61K 45/06 | (2006.01) |
| A61P 35/00 | (2006.01) |
| C07D 471/04 | (2006.01) |
| C07D 471/10 | (2006.01) |
| C07D 471/20 | (2006.01) |
| C07D 487/04 | (2006.01) |
| C07D 487/20 | (2006.01) |
| C07D 491/20 | (2006.01) |
| C07D 519/00 | (2006.01) |

(52) U.S. Cl.
CPC .......... *A61K 31/437* (2013.01); *A61K 31/444* (2013.01); *A61K 31/496* (2013.01); *A61K 31/4985* (2013.01); *A61K 31/513* (2013.01); *A61K 31/5377* (2013.01); *A61K 45/06* (2013.01); *A61P 35/00* (2018.01); *C07D 471/04* (2013.01); *C07D 471/10* (2013.01); *C07D 471/20* (2013.01); *C07D 487/04* (2013.01); *C07D 487/20* (2013.01); *C07D 491/20* (2013.01); *C07D 519/00* (2013.01)

(58) Field of Classification Search
CPC .................................................... A61K 31/437
See application file for complete search history.

(56) References Cited

FOREIGN PATENT DOCUMENTS

| WO | 2006/049890 A1 | 5/2006 | |
|---|---|---|---|
| WO | WO-2010068483 A2 * | 6/2010 | .......... A61K 31/437 |
| WO | 2011/149950 A2 | 12/2011 | |
| WO | 2014/085795 A1 | 6/2014 | |
| WO | 2017/161045 A1 | 9/2017 | |

OTHER PUBLICATIONS

International Preliminary Report on Patentability (IPRP) for PCT/US2019/052023 dated Mar. 23, 2021.
International Search Report for PCT/US2019/052023 dated Dec. 16, 2019.
Fradera, X., et al., "Design of selective PI3Kδ inhibitors using an iterative scaffold-hopping workflow" Bioorg Med Chem Lett (EPUB: Aug. 5, 2019), 29(18):2575-2580 (Sep. 15, 2019).

* cited by examiner

*Primary Examiner* — Craig D Ricci

(57) ABSTRACT

Spirocyclic 2,3-dihydro-7-azaindole compounds of formula (I):

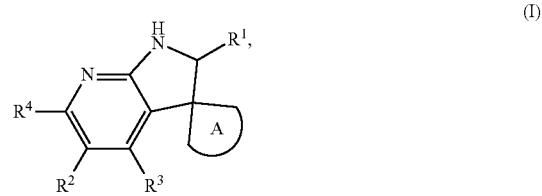

variations thereof, and their use as inhibitors of HPK1 (hematopoietic kinase 1) are described. The compounds are useful in treating HPK1-dependent disorders and enhancing an immune response. Also described are methods of inhibiting HPK1, methods of treating HPK1-dependent disorders, methods for enhancing an immune response, and methods for preparing the spirocyclic 2,3-dihydro-7-azaindole compounds.

29 Claims, No Drawings

SPIROCYCLIC 2,3-DIHYDRO-7-AZAINDOLE COMPOUNDS AND USES THEREOF

CROSS-REFERENCE TO RELATED APPLICATIONS

This application is a continuation of International Patent Application No. PCT/US2019/052023 filed on 19 Sep. 2019, which claims the benefit of priority to International Patent Application No. PCT/CN2018/106536 filed on 19 Sep. 2018, the contents of which are hereby incorporated by reference in their entirety.

BACKGROUND OF THE INVENTION

The major treatment modalities used by oncologists to treat cancer are surgical resection, radiation therapy, and classical chemotherapeutic drugs. Unfortunately, surgical resection is not a viable option for many tumors or forms of cancers. Further, radiation therapy and chemotherapeutic drugs do not target only diseased cells and therefore, end up damaging healthy cells. Therapeutics that more specifically target tumor cells are being developed by taking advantage of tumor-specific expression of antigens or inappropriate overexpression or activation of specific proteins within tumor cells, but tumor cells are prone to mutation and can become resistant to drugs that specifically target tumor cells.

A new cancer treatment paradigm has emerged that harnesses the patient's own immune system to overcome immunoevasive strategies utilized by many cancers and to enhance anti-tumor immunity. One such strategy is to inhibit negative regulators of immune responses that normally function to maintain peripheral tolerance, allowing tumor antigens to be recognized as non-self entities.

The hematopoietic progenitor kinase 1 (HPK1) is an example of a negative regulator of dendritic cell activation, and T and B cell responses that can be targeted to enhance anti-tumor immunity. HPK1 is expressed predominantly by hematopoietic cells, including early progenitors. In T cells, it is believed that HPK1 negatively regulates T cell activation by reducing the persistence of signaling microclusters by phosphorylating SLP76 at Ser376 (Di Bartolo et al. (2007) *JEM* 204:681-691) and Gads at Thr254, which leads to the recruitment of 14-3-3 proteins that bind to the phosphorylated SLP76 and Gads, releasing the SLP76-Gads-14-3-3 complex from LAT-containing microclusters (Lasserre et al. (2011) *J Cell Biol* 195(5):839-853). HPK1 can also become activated in response to prostaglandin E2, which is often secreted by tumors, contributing to the escape of tumor cells from the immune system.

BRIEF SUMMARY OF THE INVENTION

Disclosed are spirocyclic 2,3-dihydro-7-azaindole compounds that are inhibitors of HPK1, compositions containing these compounds, and methods for enhancing an immune response and treating HPK1-dependent disorders such as cancer.

In one aspect, provided is a compound of Formula (I), or any variation thereof, or a salt thereof (e.g., a pharmaceutically acceptable salt thereof), as detailed herein. Also provided is a pharmaceutical composition comprising a compound of Formula (I), or any variation thereof detailed herein, or a pharmaceutically acceptable salt thereof, and a pharmaceutically acceptable carrier or excipient.

In another aspect, provided is a method for inhibiting HPK1, comprising contacting HPK1 in a subject with an effective amount of the compound of Formula (I), or any variation thereof detailed herein, or a pharmaceutically acceptable salt thereof. Also provided is a method for enhancing an immune response in a subject in need thereof, comprising administering to the subject an effective amount of the compound of Formula (I), or any variation thereof detailed herein, or a pharmaceutically acceptable salt thereof.

Further provided is a method for treating a HPK1-dependent disorder, comprising administering to a subject in need thereof an effective amount of the compound of Formula (I), or any variation thereof detailed herein, or a pharmaceutically acceptable salt thereof. In some embodiments, the subject is a human. In some embodiments, the HPK1-dependent disorder is a cancer, for example, colorectal cancer, melanoma, non-small cell lung cancer, ovarian cancer, breast cancer, pancreatic cancer, a hematological malignancy, and a renal cell carcinoma. In some embodiments, the method further comprises administering a chemotherapeutic agent to the subject.

Also provided is a compound of Formula (I), or any variation thereof detailed herein, or a pharmaceutically acceptable salt thereof, for use in a method of inhibiting HPK1, enhancing an immune response, or treating a HPK1-dependent disorder such as cancer.

Also provided is use of a compound of Formula (I), or any variation thereof detailed herein, or a pharmaceutically acceptable salt thereof, in a method detailed herein (e.g., treatment of a HPK1-dependent disorder such as cancer.

Also provided is use of a compound of Formula (I), or any variation thereof detailed herein, or a pharmaceutically acceptable salt thereof, for the manufacture of a medicament for use in a method detailed herein (e.g., treatment of a HPK1-dependent disorder such as cancer.

Also provided is a kit for treating a HPK1-dependent disorder, the kit comprising a pharmaceutical composition comprising a the compound of Formula (I), or any variation thereof detailed herein, or a pharmaceutically acceptable salt thereof; and instructions for use.

In another aspect, provided is a method of making a compound of Formula (I) or any variation thereof. Also provided are compound intermediates useful in synthesis of a compound of Formula (I), or any variation thereof.

DETAILED DESCRIPTION OF THE INVENTION

Disclosed herein, are compounds of Formula (I), or variations thereof such as Formula (IA), (IB) and (IC), and pharmaceutical compositions thereof that are inhibitors or modulators of HPK1 (hematopoietic progenitor kinase 1). As such, the compounds and compositions are useful in treating diseases and disorders mediated by HPK1. An example of a method of treating is in the case of a subject who is suffering from cancer. The compounds can be used not only to combat cancer, but can also advantageously be used to enhance an immune response in a subject in need thereof.

The presently disclosed subject matter will now be described more fully hereinafter. However, many modifications and other embodiments of the presently disclosed subject matter set forth herein will come to mind to one skilled in the art to which the presently disclosed subject matter pertains having the benefit of the teachings presented in the foregoing descriptions. Therefore, it is to be understood that the presently disclosed subject matter is not to be limited to the specific embodiments disclosed and that modifications and other embodiments are intended to be included within the scope of the appended claims. In other words, the subject matter described herein covers all alternatives, modifications, and equivalents. In the event that one or more of the incorporated literature, patents, and similar materials differs from or contradicts this application, including but not limited to defined terms, term usage, described techniques, or the like, this application controls. Unless otherwise defined, all technical and scientific terms used herein have the same meaning as commonly understood by one of ordinary skill in this field. All publications, patent applications, patents, and other references mentioned herein are incorporated by reference in their entirety.

Definitions

"Alkyl" as used herein refers to a saturated linear (i.e. unbranched) or branched univalent hydrocarbon chain or combination thereof, having the number of carbon atoms designated (i.e., $C_{1-10}$ means one to ten carbon atoms). Particular alkyl groups are those having 1 to 20 carbon atoms (a "$C_{1-20}$ alkyl"), having a 1 to 8 carbon atoms (a "$C_{1-8}$ alkyl"), having 1 to 6 carbon atoms (a "$C_{1-6}$ alkyl"), having 2 to 6 carbon atoms (a "$C_{2-6}$ alkyl"), or having 1 to 4 carbon atoms (a "$C_{1-4}$ alkyl"). Examples of alkyl group include, but are not limited to, groups such as methyl, ethyl, n-propyl, isopropyl, n-butyl, t-butyl, isobutyl, sec-butyl, homologs and isomers of, for example, n-pentyl, n-hexyl, n-heptyl, n-octyl, and the like.

"Alkenyl" as used herein refers to an unsaturated linear (i.e., unbranched) or branched univalent hydrocarbon chain or combination thereof, having at least one site of olefinic unsaturation (i.e., having at least one moiety of the formula C=C) and having the number of carbon atoms designated (i.e., $C_{2-10}$ means two to ten carbon atoms). The alkenyl group may be in "cis" or "trans" configurations, or alternatively in "E" or "Z" configurations. Particular alkenyl groups are those having 2 to 20 carbon atoms (a "$C_{2-20}$ alkenyl"), having a 2 to 8 carbon atoms (a "$C_{2-8}$ alkenyl"), having 2 to 6 carbon atoms (a "$C_{2-6}$ alkenyl"), or having 2 to 4 carbon atoms (a "$C_{2-4}$ alkenyl"). Example of alkenyl group include, but are not limited to, groups such as ethenyl (or vinyl), prop-1-enyl, prop-2-enyl (or allyl), 2-methylprop-1-enyl, but-1-enyl, but-2-enyl, but-3-enyl, buta-1,3-dienyl, 2-methylbuta-1,3-dienyl, homologs and isomers thereof, and the like.

"Alkynyl" as used herein refers to an unsaturated linear (i.e. unbranched) or branched univalent hydrocarbon chain or combination thereof, having at least one site of acetylenic unsaturation (i.e., having at least one moiety of the formula C≡C) having the number of carbon atoms designated (i.e., $C_{2-10}$ means two to ten carbon atoms). Particular alkynyl groups are those having 2 to 20 carbon atoms (a "$C_{2-20}$ alkynyl"), having a 2 to 8 carbon atoms (a "$C_{2-8}$ alkynyl"), having 2 to 6 carbon atoms (a "$C_{2-6}$ alkynyl"), having 2 to 4 carbon atoms (a "$C_{2-4}$ alkynyl"). Examples of alkynyl group include, but are not limited to, groups such as ethynyl (or acetylenyl), prop-1-ynyl, prop-2-ynyl (or propargyl), but-1-ynyl, but-2-ynyl, but-3-ynyl, homologs and isomers thereof, and the like.

"Alkylene" as used herein refers to the same residues as alkyl, but having bivalency. Particular alkylene groups are those having 1 to 6 carbon atoms (a "$C_{1-6}$ alkylene"), 1 to 5 carbon atoms (a "$C_{1-5}$ alkylene"), having 1 to 4 carbon atoms (a "$C_{1-4}$ alkylene"), or 1 to 3 carbon atoms (a "$C_{1-3}$ alkylene"). Examples of alkylene include, but are not limited to, groups such as methylene (—$CH_2$—), ethylene (—$CH_2$—$CH_2$—), 1,3-propylene (—$CH_2$—$CH_2$—$CH_2$—), 1,2-propylene (—$CH(CH_3)$—$CH_2$—), 1,4-butylene (—$CH_2$—$CH_2$—$CH_2$—$CH_2$—), and the like.

"Alkylidene" as used herein refers to the same residues as alkyl, but having bivalency at the attachment point and is attached to the parent structure via a double bond. Particular alkylidene groups are those having 1 to 6 carbon atoms (a "$C_{1-6}$ alkylidene"), 1 to 5 carbon atoms (a "$C_{1-5}$ alkylidene"), having 1 to 4 carbon atoms (a "$C_{1-4}$ alkylidene"), or 1 to 3 carbon atoms (a "$C_{1-3}$ alkylidene"). Examples of alkylene include, but are not limited to, groups such as methylidene (=$CH_2$), ethylidene (=CH—$CH_3$), 1-propylidene (=CH—$CH_2$—$CH_3$), 2-propylidene (=C($CH_3$)$_2$), 1-butylidene (=$CH_2$—$CH_2$—$CH_2$—$CH_3$), and the like.

"Cycloalkyl" as used herein refers to non-aromatic, saturated or unsaturated cyclic univalent hydrocarbon structures having the number of carbon atoms designated (i.e., ($C_{3-10}$ means three to ten carbon atoms). Cycloalkyl can consist of one ring, such as cyclohexyl, or multiple rings, such as adamantly, but excludes aryl groups. A cycloalkyl comprising more than one ring may be fused, spiro, or bridged, or combinations thereof. Particular cycloalkyl groups are those having from 3 to 12 annular carbon atoms. A preferred cycloalkyl is a cyclic hydrocarbon having from 3 to 8 annular carbon atoms (a "$C_{3-8}$ cycloalkyl"), or having 3 to 6-carbon atoms (a "$C_{3-6}$ alkynyl"). Examples of cycloalkyl include, but are not limited to, cyclopropyl, cyclobutyl, cyclopentyl, cyclohyxyl, 1-cyclohexenyl, 3-cyclohexenyl, cycloheptyl, norbornyl, and the like.

"Aryl" as used herein refers to an unsaturated aromatic carbocyclic group having a single ring (e.g., phenyl) or multiple condensed rings (e.g., naphthyl or anthryl) which condensed rings may or may not be aromatic. Particular aryl groups are those having from 6 to 14 annular (i.e., ring) carbon atoms (a "$C_{6-14}$ aryl"). An aryl group having more than one ring where at least one ring is non-aromatic may be connected to the parent structure at either an aromatic ring position or at a non-aromatic ring position. In one variation, an aryl group having more than one ring where at least one ring is non-aromatic is connected to the parent structure at an aromatic ring position.

"Heteroaryl" as used herein refers to an unsaturated aromatic cyclic group having from 1 to 14 annular (i.e., ring) carbon atoms and at least one annular heteroatom, including but not limited to heteroatoms such as nitrogen, phosphorus, oxygen and sulfur. A heteroaryl group may have a single ring (e.g., pyridyl, furyl) or multiple condensed rings (e.g., indolizinyl, benzothienyl) which condensed rings may or may not be aromatic. Particular heteroaryl groups are 5- to 14-membered rings having 1 to 12 annular (i.e., ring) carbon atoms and 1 to 6 annular (i.e., ring) heteroatoms independently selected from nitrogen, phosphorus, oxygen and sulfur; 5- to 10-membered rings having 1 to 8 annular carbon atoms and 1 to 4 annular heteroatoms independently selected from nitrogen, phosphorus, oxygen and sulfur; and 5-, 6- or 7-membered rings having 1 to 5 annular carbon atoms and 1 to 4 annular heteroatoms independently selected from nitrogen, oxygen and sulfur In one variation, heteroaryl include monocyclic aromatic 5-, 6- or 7-membered rings having from 1 to 6 annular carbon atoms and 1 to 4 annular heteroatoms independently selected from nitrogen, oxygen and sulfur. In another variation, heteroaryl includes polycyclic aromatic rings having from 1 to 12 annular carbon atoms and 1 to 6 annular heteroatoms independently selected from nitrogen, phosphorus, oxygen and sulfur. A heteroaryl group having more than one ring where at least one ring is non-aromatic may be connected to the parent structure at either an aromatic ring position or at a non-aromatic ring position. In one variation, a heteroaryl group having more than one ring where at least one ring is non-aromatic is connected to the parent structure at an aromatic ring position.

"Heterocycle", "heterocyclic", or "heterocyclyl" as used herein refers to a saturated or an unsaturated non-aromatic cyclic group having a single ring or multiple condensed rings, and having from 1 to 14 annular (i.e., ring) carbon atoms and from 1 to 6 annular (i.e., ring) heteroatoms, such as nitrogen, phosphorus, sulfur or oxygen, and the like. A heterocycle comprising more than one ring may be fused, spiro or bridged, or any combination thereof. In fused ring systems, one or more may be fused rings can be cycloalkyl. Particular heterocyclyl groups are 3- to 14-membered rings having 1 to 13 annular carbon atoms and 1 to 6 annular heteroatoms independently selected from nitrogen, phosphorus, oxygen and sulfur; 3- to 12-membered rings having 1 to 11 annular carbon atoms and 1 to 6 annular heteroatoms independently selected from nitrogen, phosphorus, oxygen and sulfur; 3- to 10-membered rings having 1 to 9 annular carbon atoms and 1 to 4 annular heteroatoms independently selected from nitrogen, phosphorus, oxygen and sulfur; 3- to 8-membered rings having 1 to 7 annular carbon atoms and 1 to 4 annular heteroatoms independently selected from nitrogen, phosphorus, oxygen and sulfur; and 3- to 6-membered rings having 1 to 5 annular carbon atoms and 1 to 4 annular heteroatoms independently selected from nitrogen, phosphorus, oxygen and sulfur. In one variation, heterocyclyl include monocyclic 3-, 4-, 5-, 6- or 7-membered rings having from 1 to 2, 1 to 3, 1 to 4, 1 to 5 or 1 to 6 annular carbon atoms and 1 to 2, 1 to 3 or 1 to 4 annular heteroatoms independently selected from nitrogen, phosphorus, oxygen and sulfur. In another variation, heterocyclyl includes polycyclic non-aromatic rings having from 1 to 12 annular carbon atoms and 1 to 6 annular heteroatoms independently selected from nitrogen, phosphorus, oxygen and sulfur.

"Halo" or "Halogen" refers to fluoro, chloro, bromo and/or iodo. "Haloalkyl" refers to an alkyl group substituted with one or more halogen that may be the same or different. Where a residue is substituted with more than one halogen, it may be referred to by using a prefix corresponding to the number of halogen moieties attached, e.g., dihaloaryl, dihaloalkyl, trihaloaryl etc. refer to aryl and alkyl substituted with two ("di") or three ("tri") halo groups, which may be but are not necessarily the same halo; thus 4-chloro-3-fluorophenyl is within the scope of dihaloaryl. An alkyl group in which each hydrogen is replaced with a halo group is referred to as a "perhaloalkyl." A preferred perhaloalkyl group is trifluoroalkyl ($-CF_3$). Similarly, "perhaloalkoxy" refers to an alkoxy group in which a halogen takes the place of each H in the hydrocarbon making up the alkyl moiety of the alkoxy group. An example of a perhaloalkoxy group is trifluoromethoxy ($-OCF_3$).

"Carbonyl" refers to the group C=O.

"Oxo" refers to the moiety =O.

"Geminal" refers to the relationship between two moieties that are attached to the same atom. For example, in the residue $-CH_2-CR^xR^y-$, $R^x$ and $R^y$ are geminal and $R^x$ may be referred to as a geminal R group to $R^y$.

"Vicinal" refers to the relationship between two moieties that are attached to adjacent atoms. For example, in the residue $-CHR^x-CHR^y-$, $R^x$ and $R^y$ are vicinal and $R^x$ may be referred to as a vicinal R group to $R^y$.

"Optionally substituted" unless otherwise specified means that a group may be unsubstituted or substituted by one or more (e.g., 1, 2, 3, 4 or 5) of the substituents listed for that group in which the substituents may be the same or different. In one embodiment, an optionally substituted group has one substituent. In another embodiment, an optionally substituted group has two substituents. In another embodiment, an optionally substituted group has three substituents. In another embodiment, an optionally substituted group has four substituents. In some embodiments, an optionally substituted group has 1 to 2, 1 to 3, 1 to 4 or 1 to 5 substituents.

Use of the word "inhibitor" herein is meant to mean a molecule that inhibits activity of HPK1. By "inhibit" herein is meant to decrease the activity of the target enzyme, as compared to the activity of that enzyme in the absence of the inhibitor. In some embodiments, the term "inhibit" means a decrease in HPK1 activity of at least about 5%, at least about 10%, at least about 20%, at least about 25%, at least about 50%, at least about 60%, at least about 70%, at least about 80%, at least about 90%, or at least about 95%. In other embodiments, inhibit means a decrease in HPK1 activity of about 5% to about 25%, about 25% to about 50%, about 50% to about 75%, or about 75% to 100%. In some embodiments, inhibit means a decrease in HPK1 activity of about 95% to 100%, e.g., a decrease in activity of 95%, 96%, 97%, 98%, 99%, or 100%. Such decreases can be measured using a variety of techniques that would be recognizable by one of skill in the art, including in vitro kinase assays.

As used herein, a "HPK1 antagonist" or a "HPK1 inhibitor" is a molecule that reduces, inhibits, or otherwise diminishes one or more of the biological activities of HPK1 (e.g., serine/threonine kinase activity, recruitment to the TCR complex upon TCR activation, interaction with a protein binding partner, such as SLP76). Antagonism using the HPK1 antagonist does not necessarily indicate a total elimination of the HPK1 activity. Instead, the activity could decrease by a statistically significant amount including, for example, a decrease of at least about 5%, 10%, 15%, 20%, 25%, 30%, 35%, 40%, 45%, 50%, 55%, 60%, 65%, 70%, 75%, 80%, 85%, 95% or 100% of the activity of HPK1 compared to an appropriate control. In some embodiments, the HPK1 antagonist reduces, inhibits, or otherwise diminishes the serine/threonine kinase activity of HPK1. In some of these embodiments, the HPK1 antagonist reduces, inhibits, or otherwise diminishes the HPK1-mediated phosphorylation of SLP76 and/or Gads. The presently disclosed compounds bind directly to HPK1 and inhibit its kinase activity.

By "specific antagonist" is intended an agent that reduces, inhibits, or otherwise diminishes the activity of a defined target greater than that of an unrelated target. For example, a HPK1 specific antagonist reduces at least one biological activity of HPK1 by an amount that is statistically greater than the inhibitory effect of the antagonist on any other protein (e.g., other serine/threonine kinases). In some embodiments, the $IC_{50}$ of the antagonist for the target is about 90%, 80%, 70%, 60%, 50%, 40%, 30%, 20%, 10%, 5%, 1%, 0.1%, 0.01%, 0.001% or less of the $IC_{50}$ of the antagonist for a non-target. The presently disclosed compounds may or may not be a specific HPK1 antagonist. A specific HPK1 antagonist reduces the biological activity of HPK1 by an amount that is statistically greater than the inhibitory effect of the antagonist on any other protein (e.g., other serine/threonine kinases). In certain embodiments, the HPK1 antagonist specifically inhibits the serine/threonine kinase activity of HPK1. In some of these embodiments, the $IC_{50}$ of the HPK1 antagonist for HPK1 is about 90%, 80%, 70%, 60%, 50%, 40%, 30%, 20%, 10%, 0.1%, 0.01%, 0.001%, or less of the IC$_{50}$ of the HPK1 antagonist for another serine/threonine kinase or other type of kinase (e.g., tyrosine kinase).

As used herein, "treatment" or "treating" is an approach for obtaining beneficial or desired results including clinical results. For purposes of this invention, beneficial or desired clinical results include, but are not limited to, one or more of the following: decreasing one or more symptoms resulting from the disease, diminishing the extent of the disease, stabilizing the disease (e.g., preventing or delaying the worsening of the disease), preventing or delaying the spread (e.g., metastasis) or the disease, delay or slowing the progression of the disease, ameliorating the disease state, providing a remission (whether partial or total) of the disease, decreasing the dose of one or more medications required to treat the disease, enhancing effect of another medication, delaying the progression of the disease, increasing the quality of life, and/or prolonging survival. Also encompassed by "treatment" is a reduction of pathological consequence of cancer. The methods of the invention contemplate any one or more of these aspects of treatment.

As used here, "delaying" the development of cancer means to defer, hinder, slow, retard, stabilize, and/or postpone development of the disease. This delay can be of varying lengths of time, depending on the history of the disease and/or subject being treated. As is evident to one skilled in the art, a sufficient or significant delay can, in effect, encompass prevention, in that the subject does not develop the disease. A method that "delays" development of cancer is a method that reduces probability of disease development in a given time frame and/or reduces the extent of the disease in a given time frame, when compared to not using the method. Such comparisons are typically based on clinical studies, using a statistically significant number of subjects. Cancer development can be detectable using standard methods, such as routine physical exams, mammography, imaging, or biopsy. Development may also refer to disease progression that may be initially undetectable and includes occurrence, recurrence, and onset.

As used herein, an "at risk" subject is a subject who is at risk of developing cancer. A subject "at risk" may or may not have detectable disease, and may or may not have displayed detectable disease prior to the treatment methods described herein. "At risk" denotes that a subject has one or more so-called risk factors, which are measurable parameters that correlate with development or cancer, which are described herein. A subject having one or more of these risk factors has a higher probability of developing cancer than a subject without these risk factor(s).

As used herein, by "combination therapy" is meant a therapy that includes two or more different compounds. Thus, in one aspect, a combination therapy comprising a compound detailed herein and another compound is provided. In some variations, the combination therapy optionally includes one or more pharmaceutically acceptable carriers or excipients, non-pharmaceutically active compounds, and/or inert substances.

As used herein, the term "effective amount" intends such amount of a compound of the invention which in combination with its parameters of efficacy and toxicity, should be effective in a given therapeutic form. As is understood in the art, an effective amount may be in one or more doses, i.e., a single dose or multiple doses may be required to achieve the desired treatment endpoint. An effective amount may be considered in the context of administering one or more therapeutic agents, and a single agent may be considered to be given in an effective amount if, in conjunction with one or more other agents, a desirable or beneficial results may be or is achieved. Suitable doses of any of the co-administered compounds may optionally be lowered due to the combined action (e.g., additive or synergistic effects) of the compounds. In various embodiments, an effective amount of the composition or therapy may (i) reduce the number of cancer cells;)(ii) reduce tumor size; (iii) inhibit, retard, slow to some extent, and preferably stop cancer cell infiltration into peripheral organs; (iv) inhibit (e.g., slow to some extent and preferably stop) tumor metastasis; (v) inhibit tumor growth; (vi) prevent or delay occurrence and/or recurrence of a tumor; and/or (vii) relieve to some extent one or more of the symptoms associated with the cancer. In various embodiments, the amount is sufficient to ameliorate, palliate, lessen, and/or delay one or more of symptoms of cancer.

As is understood in the art, an "effective amount" may be in one or more doses, i.e., a single dose or multiple doses may be required to achieve the desired treatment endpoint. An effective amount may be considered in the context of administering one or more therapeutic agents, and a compound, or pharmaceutically acceptable salt thereof, may be considered to be given in an effective amount if, in conjunction with one or more other agents a desirable or beneficial result may be or is achieved.

A "therapeutically effective amount" refers to an amount of a compound or salt thereof sufficient to produce a desired therapeutic outcome (e.g., reducing the severity or duration of, stabilizing the severity of, or eliminating one or more symptoms of cancer). For therapeutic use, beneficial or desired results include, e.g., decreasing one or more symptoms resulting from the disease (biochemical, histologic and/or behavioral), including its complications and intermediate pathological phenotypes presenting during development of the disease, increasing the quality of life of those suffering from the disease, decreasing the dose of other medications required to treat the disease, enhancing effect of another medication, delaying the progression of the disease, and/or prolonging survival of patients.

A "prophylactically effective amount" refers to an amount of a compound, or pharmaceutically acceptable salt thereof, sufficient to prevent or reduce the severity of one or more future symptoms of cancer when administered to a subject who is susceptible and/or who may develop cancer. For prophylactic use, beneficial or desired results include, e.g., results such as eliminating or reducing the risk, lessening the severity of future disease, or delaying the onset of the disease (e.g., delaying biochemical, histologic and/or behavioral symptoms of the disease, its complications, and intermediate pathological phenotype presenting during future development of the disease).

It is understood that an effective amount of a compound or pharmaceutically acceptable salt thereof, including a prophylactically effective amount, may be given to a subject in the adjuvant setting, which refers to a clinical setting in which a subject has had a history of cancer, and generally (but not necessarily) has been responsive to therapy, which includes, but is not limited to, surgery (e.g., surgical resection), radiotherapy, and chemotherapy. However, because of their history of the cancer, these subjects are considered at risk of developing cancer. Treatment or administration in the "adjuvant setting" refers to a subsequent mode of treatment.

As used herein, "unit dosage form" refers to physically discrete units, suitable as unit dosages, each unit containing predetermined quantity of active ingredient calculated to produce the desired therapeutic effect in association with the required pharmaceutical carrier or excipient. Unit dosage forms may contain a single or a combination therapy.

As used herein, the term "controlled release" refers to a drug-containing formulation or fraction thereof in which release of the drug is not immediate, i.e., with a "controlled release" formulation, administration does not result in immediate release of the drug into an absorption pool. The term encompasses depot formulations designed to gradually release the drug compound over an extended period of time. Controlled release formulation can include a wide variety of drug delivery systems, generally involving mixing the drug compound with carriers, polymers or other compounds having the desired release characteristics (e.g., pH-dependent or non-pH-dependent solubility, different degrees of water solubility, and the like) and formulating the mixture according to the desired route of delivery (e.g., coated capsules, implantable reservoirs, injectable solutions containing biodegradable capsules, and the like).

As used herein, by "pharmaceutically acceptable" or "pharmacologically acceptable" is meant a material that is not biologically or otherwise undesirable, e.g., the material may be incorporated into a pharmaceutical composition administered to a patient without causing any significant undesirable biological effects or interacting in a deleterious manner with any of the other components of the composition in which it is contained. Pharmaceutically acceptable carriers or excipients have preferably met the required standards of toxicological and manufacturing testing and/or are included on the Inactive Ingredient Guide prepared by the U.S. Food and Drug Administration.

In some embodiments, the salts of the compounds of the invention are pharmaceutically acceptable salts. "Pharmaceutically acceptable salts" are those salts which retain at least some of the biological activity of the free (non-salt) compound and which can be administered as drugs or pharmaceuticals to a subject. Such salts, for example, include: (1) acid addition salts, formed with inorganic acids such as hydrochloric acid, hydrobromic acid, sulfuric acid, nitric acid, phosphoric acid, and the like; or formed with organic acids such as acetic acid, oxalic acid, propionic acid, succinic acid, maleic acid, tartaric acid and the like; (2) salts formed when an acidic proton present in the parent compound either is replaced by a metal ion, e.g., an alkali metal ion, an alkaline earth ion, or an aluminum ion; or coordinates with an organic base. Acceptable organic bases include ethanolamine, diethanolamine, triethanolamine and the like. Acceptable inorganic bases include aluminum hydroxide, calcium hydroxide, potassium hydroxide, sodium carbonate, sodium hydroxide, and the like. Pharmaceutically acceptable salts can be prepared in situ in the manufacturing process, or by separately reacting a purified compound of the invention in its free acid or base form with a suitable organic or inorganic base or acid respectively, and isolating the salt thus formed during subsequent purification.

The term "excipient" as used herein means an inert or inactive substance that may be used in the production of a drug or pharmaceutical, such as a tablet containing a compound of the invention as an active ingredient. Various substances may be embraced by the term excipient, including without limitation any substance used as a binder, disintegrant, coating, compression/encapsulation aid, cream or lotion, lubricant, solutions for parenteral administration, materials for chewable tablets, sweetener or flavoring, suspending/gelling agent, or wet granulation agent. Binders include, e.g., carbomers, povidone, xanthan gum, etc.; coatings include, e.g., cellulose acetate phthalate, ethylcellulose, gellan gum, maltodextrin, enteric coatings, etc.; compression/encapsulation aids include e.g. calcium carbonate, dextrose, fructose dc (dc—"directly compressible"), honey dc, lactose (anhydrate or monohydrate; optionally in combination with aspartame, cellulose, or microcrystalline cellulose), starch dc, sucrose, etc.; disintegrants include, e.g., croscarmellose sodium, gellan gum, sodium starch glycolate, etc.; creams or lotions include, e.g., maltodextrin, carrageenans, etc.; lubricants include, e.g., magnesium stearate, stearic acid, sodium stearyl fumarate, etc.; materials for chewable tablets include, e.g. dextrose, fructose dc, lactose (monohydrate, optionally in combination with aspartame or cellulose), etc.; suspending/gelling agents include, e.g., carrageenan, sodium starch glycolate, xanthan gum, etc.; sweeteners include, e.g., aspartame, dextrose, fructose dc, sorbitol, sucrose dc, etc.; and wet granulation agents include, e.g., calcium carbonate, maltodextrin, microcrystalline cellulose, etc. In some cases, the terms "excipient" and "carrier" are used interchangeably.

The term "subject" or "patient" refers to animals such as mammals, including, but not limited to, primates (e.g., humans), cows, sheep, goats, horses, dogs, cats, rabbits, rats, mice and the like. In certain embodiments, the subject is a human or a human patient.

The terms "abnormal cell growth," "unregulated cell growth," and "hyperproliferative disorder" are used interchangeably in this application. "Abnormal cell growth", as used herein, unless otherwise indicated, refers to cell growth that is independent of normal regulatory mechanisms (e.g., loss of contact inhibition).

The term "cancer" refers to the condition in a subject that is characterized by unregulated cell growth, wherein the cancerous cells are capable of local invasion and/or metastasis to noncontiguous sites. As used herein, "cancer cells," "cancerous cells," or "tumor cells" refer to the cells that are characterized by this unregulated cell growth and invasive property. The term "cancer" encompasses all types of cancers, including, but not limited to, all forms of carcinomas, melanomas, blastomas, sarcomas, lymphomas and leukemias, including without limitation, bladder cancer, bladder carcinoma, brain tumors, breast cancer, cervical cancer, colorectal cancer, esophageal cancer, endometrial cancer, hepatocellular carcinoma, laryngeal cancer, lung cancer, osteosarcoma, ovarian cancer, pancreatic cancer, prostate cancer, renal carcinoma and thyroid cancer, acute lymphocytic leukemia, acute myeloid leukemia, ependymoma, Ewing's sarcoma, glioblastoma, medulloblastoma, neuroblastoma, osteosarcoma, rhabdomyosarcoma, rhabdoid cancer, and nephroblastoma (Wilm's tumor).

A "chemotherapeutic agent" is a chemical compound or biologic useful in the treatment of cancer. Examples of chemotherapeutic agents include alkylating agents such as thiotepa and cyclophosphamide (CYTOXAN®); alkyl sulfonates such as busulfan, improsulfan, and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-aminocamptothecin); bryostatin; pemetrexed; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; TLK-286; CDP323, an oral alpha-4 integrin inhibitor; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e. g., calicheamicin, especially calicheamicin gammaII and calicheamicin omegaII (see, e.g., Nicolaou et al., Angew. Chem Intl. Ed. Engl., 33: 183-186 (1994)); dynemicin, including dynemicin A; an esperamicin; as well as neocarzinostatin chromophore and related chromoprotein enediyne antibiotic chromophores), aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (including ADRIAMYCIN®, morpholino-doxorubicin, cyanomorpholino-doxorubicin, 2-pyrrolino-doxorubicin, doxorubicin HCl liposome injection (DOXIL®) and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate, gemcitabine (GEMZAR®), tegafur (UFTORAL®), capecitabine (XELODA®), an epothilone, and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, and floxuridine; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, OR); razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine (ELDISINE®, FILDESIN®); dacarbazine; mannomustine; mitobronitol; mitolactol; pipobroman; gacytosine; arabinoside ("Ara-C"); thiotepa; taxoids, e.g., paclitaxel (TAXOL®), albumin-engineered nanoparticle formulation of paclitaxel (ABRAXANE™), and doxetaxel (TAXOTERE®); chloranbucil; 6-thioguanine; mercaptopurine; methotrexate; platinum analogs such as cisplatin and carboplatin; vinblastine (VELBAN®); platinum; etoposide (VP-16); ifosfamide; mitoxantrone; vincristine (ONCOVIN®); oxaliplatin; leucovorin; vinorelbine (NAVELBINE®); novantrone; edatrexate; daunomycin; aminopterin; ibandronate; topoisomerase inhibitor RFS 2000; difluorometlylornithine (DMFO); retinoids such as retinoic acid; pharmaceutically acceptable salts, acids or derivatives of any of the above; as well as combinations of two or more of the above such as CHOP, an abbreviation for a combined therapy of cyclophosphamide, doxorubicin, vincristine, and prednisolone, and FOLFOX, an abbreviation for a treatment regimen with oxaliplatin (ELOXATIN™) combined with 5-FU and leucovovin.

Additional examples of chemotherapeutic agents include anti-hormonal agents that act to regulate, reduce, block, or inhibit the effects of hormones that can promote the growth of cancer, and are often in the form of systemic, or whole-body treatment. They may be hormones themselves. Examples include anti-estrogens and selective estrogen receptor modulators (SERMs), including, for example, tamoxifen (including NOLVADEX® tamoxifen), raloxifene (EVISTA®), droloxifene, 4-hydroxytamoxifen, trioxifene, keoxifene, LY117018, onapristone, and toremifene (FARESTON®); anti-progesterones; estrogen receptor down-regulators (ERDs); estrogen receptor antagonists such as fulvestrant (FASLODEX®); agents that function to suppress or shut down the ovaries, for example, leutinizing hormone-releasing hormone (LHRH) agonists such as leuprolide acetate (LUPRON® and ELIGARD®), goserelin acetate, buserelin acetate and tripterelin; anti-androgens such as flutamide, nilutamide and bicalutamide; and aromatase inhibitors that inhibit the enzyme aromatase, which regulates estrogen production in the adrenal glands, such as, for example, 4(5)-imidazoles, aminoglutethimide, megestrol acetate (MEGASE®), exemestane (AROMASIN®), formestanie, fadrozole, vorozole (RIVISOR®), letrozole (FEMARA®), and anastrozole (ARIMIDEX®). In addition, such definition of chemotherapeutic agents includes bisphosphonates such as clodronate (for example, BONEFOS® or OSTAC®), etidronate (DIDROCAL®), NE-58095, zoledronic acid/zoledronate (ZOMETA®), alendronate (FOSAMAX®), pamidronate (AREDIA®), tiludronate (SKELID®), or risedronate (ACTONEL®); as well as troxacitabine (a 1,3-dioxolane nucleoside cytosine analog); antisense oligonucleotides, particularly those that inhibit expression of genes in signaling pathways implicated in abherant cell proliferation, such as, for example, PKC-alpha, Raf, H-Ras, and epidermal growth factor receptor (EGF-R); vaccines such as THERATOPE® vaccine and gene therapy vaccines, for example, ALLOVECTIN® vaccine, LEUVECTIN® vaccine, and VAXID® vaccine; topoisomerase 1 inhibitor (e.g., LURTOTECAN®); an anti-estrogen such as fulvestrant; EGFR inhibitor such as erlotinib or cetuximab; an anti-VEGF inhibitor such as bevacizumab; arinotecan; rmRH (e.g., ABARELIX®); 17AAG (geldanamycin derivative that is a heat shock protein (Hsp) 90 poison), and pharmaceutically acceptable salts, acids or derivatives of any of the above.

Also included in the definition of "chemotherapeutic agent" are: (i) anti-hormonal agents that act to regulate or inhibit hormone action on tumors such as anti-estrogens and selective estrogen receptor modulators (SERMs), including, for example, tamoxifen (including NOLVADEX®; tamoxifen citrate), raloxifene, droloxifene, 4-hydroxytamoxifen, trioxifene, keoxifene, LY117018, onapristone, and FARESTON® (toremifine citrate); (ii) aromatase inhibitors that inhibit the enzyme aromatase, which regulates estrogen production in the adrenal glands, such as, for example, 4(5)-imidazoles, aminoglutethimide, MEGASE® (megestrol acetate), AROMASIN® (exemestane; Pfizer), formestanie, fadrozole, RIVISOR® (vorozole), FEMARA® (letrozole; Novartis), and ARIMIDEX® (anastrozole; AstraZeneca); (iii) anti-androgens such as flutamide, nilutamide, bicalutamide, leuprolide, and goserelin; as well as troxacitabine (a 1,3-dioxolane nucleoside cytosine analog); (iv) protein kinase inhibitors; (v) lipid kinase inhibitors; (vi) antisense oligonucleotides, particularly those which inhibit expression of genes in signaling pathways implicated in aberrant cell proliferation, such as, for example, PKC-alpha, Ralf and H-Ras; (vii) ribozymes such as VEGF expression inhibitors (e.g., ANGIOZYME®) and HER2 expression inhibitors; (viii) vaccines such as gene therapy vaccines, for example, ALLOVECTIN®, LEUVECTIN®, and VAXID®; PROLEUKIN® rIL-2; a topoisomerase 1 inhibitor such as LURTOTECAN®; ABARELIX® rmRH; (ix) anti-angiogenic agents such as bevacizumab (AVASTIN®, Genentech); and (x) pharmaceutically acceptable salts, acids and derivatives of any of the above.

In some embodiments, the chemotherapeutic agent is an immunotherapeutic agent. As used herein, an "immunotherapeutic agent" is a compound that enhances the immune system to help fight cancer, specifically or non-specifically. Immunotherapeutics include monoclonal antibodies and non-specific immunotherapies that boost the immune system, such as cytokines, interleukins (e.g., IL-2, IL-7, IL-12, IL-15, IL-21), interferons (e.g., IFN-α, IFN-β, IFN-γ), GM-CSF, thalidomide, (THALOMID®, Celgene), lenalidomide (REVLIMID®, Celgene), pomalidomide (POMALYST®, Celgene), imiquimod (ZYCLARA®, Valeant). Non-limiting examples of monoclonal antibodies that are useful as a chemotherapeutic agent include trastuzumab (HERCEPTIN®, Genentech), bevacizumab (AVASTIN®, Genentech), cetuximab (ERBITUX®, Bristol-Myers Squibb), panitumumab (VECTIBIX®, Amgen), ipilimumab (YERVOY®, Bristol-Myers Squibb), rituximab (RITUXAN®, Genentech), alemtuzumab (CAMPATH®, Genzyme), ofatumumab (ARZERRA®, Genmab), gemtuzumab ozogamicin (MYLOTARG®, Wyeth), brentuximab vedotin (ADCETRIS®, Seattle Genetics), $^{90}$Y-labelled ibritumomab tiuxetan (ZEVALIN®, Biogen Idec), $^{131}$I-labelled tositumomab (BEXXAR®, GlaxoSmithKline), ado-trastuzumab emtansine (KADCYLA®, Genentech) blinatumomab (BLINCYTO®, Amgen), pertuzumab (PERJETA®, Genentech), obinutuzumab (GAZYVA®, Genentech), nivolumab (OPDIVO®) Bristol-Myers Squibb), pembrolizumab (KEYTRUDA®, Merck), pidilizumab (CureTech), MPDL3280A (described in WO2010/077634, herein incorporated by reference in its entirety), MDX-1105 (described in WO2007/005874, herein incorporated by reference in its entirety), and MEDI4736 (described in WO2011/066389 and US2013/034559, each of which is herein incorporated by reference in its entirety). Another useful immunotherapeutic agent is AMP-224 (described in WO2010/027827 and WO2011/066342, each of which is incorporated herein in its entirety).

Compounds

The compounds disclosed herein are compounds of Formula (I), or salts (e.g., pharmaceutically acceptable salts), solvates (e.g., hydrates), prodrugs, metabolites, or derivatives thereof. These compounds are useful inhibitors of HPK1.

In one aspect, provided is a compound of Formula (I):

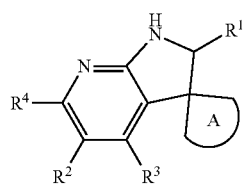

(I)

or a salt (e.g., a pharmaceutically acceptable salt), solvate (e.g., hydrate), prodrug, metabolites or derivative thereof; wherein:

$R^1$ is hydrogen, $C_{1-6}$ alkyl or oxo;

A is $C_{3-12}$ cycloalkyl, 3- to 14-membered heterocyclyl, $C_{6-14}$ aryl or 5- to 14-membered heteroaryl, wherein the $C_{3-12}$ cycloalkyl, 3- to 14-membered heterocyclyl, $C_{6-14}$ aryl and 5- to 14-membered heteroaryl of A are each optionally substituted with 1, 2, 3, 4 or 5 substituents independently selected from $R^9$;

$R^2$ is $C_{6-14}$ aryl optionally substituted with 1, 2, 3, 4 or 5 substituents independently selected from $R^{10}$, or 5- to 14-membered heteroaryl optionally substituted with 1, 2, 3, 4 or 5 substituents independently selected from $R^{10}$;

$R^3$ is hydrogen, halogen, cyano, $C_{1-6}$ alkyl, $C_{1-6}$ haloalkyl, $C_{3-6}$ cycloalkyl, —$OR^7$, or —$NR^{8a}R^{8b}$;

$R^4$ is hydrogen, halogen, cyano, $C_{1-6}$ alkyl, or $C_{3-6}$ cycloalkyl;

$R^7$ is hydrogen or $C_{1-6}$ alkyl optionally substituted with 1, 2, 3, 4 or 5 substituents independently selected from $R^{10}$;

each $R^{8a}$ and $R^{8b}$ is independently hydrogen or $C_{1-6}$ alkyl optionally substituted with 1, 2, 3, 4 or 5 substituents independently selected from $R^{10}$;

each $R^9$ is independently $R^{10}$, or $C_{1-6}$ alkylidene optionally substituted with 1, 2, 3 or 4 substituents independently selected from $R^{11}$;

each $R^{10}$ is independently oxo, $C_{1-6}$ alkyl, $C_{2-6}$ alkenyl, $C_{2-6}$ alkynyl, $C_{3-8}$ cycloalkyl, $C_{6-10}$ aryl, 5- to 10-membered heteroaryl, 3- to 12-membered heterocyclyl, halogen, cyano, —$C(O)R^a$, —$C(O)OR^b$, —$C(O)NR^cR^d$, —$OR^b$, —$OC(O)R^a$, —$OC(O)NR^cR^d$, —$SR^b$, —$S(O)R^e$, —$S(O)_2R^e$, —$S(O)(=NH)R^e$, —$S(O)_2NR^eR^d$, —$NR^cR^d$, —$N(R^f)C(O)R^a$, —$N(R^f)C(O)OR^b$, —$N(R^f)C(O)NR^cR^d$, —$N(R^f)S(O)_2R^e$, —$N(R^f)S(O)_2NR^cR^d$, or —$P(O)R^gR^h$; wherein the $C_{1-6}$ alkyl, $C_{2-6}$ alkenyl, $C_{2-6}$ alkynyl, $C_{3-8}$ cycloalkyl, $C_{6-14}$ aryl, 5- to 14-membered heteroaryl and 3- to 14-membered heterocyclyl of $R^{10}$ are each optionally substituted with 1, 2, 3 or 4 substituents independently selected from $R^{11}$;

each $R^a$ is independently hydrogen, $C_{1-6}$ alkyl, $C_{2-6}$ alkenyl, $C_{2-6}$ alkynyl, $C_{3-8}$ cycloalkyl, $C_{6-10}$ aryl, 5- to 10-membered heteroaryl or 3- to 12-membered heterocyclyl; wherein the $C_{1-6}$ alkyl, $C_{2-6}$ alkenyl, $C_{2-6}$ alkynyl, $C_{3-8}$ cycloalkyl, $C_{6-10}$ aryl, 5- to 10-membered heteroaryl and 3- to 12-membered heterocyclyl of $R^a$ are each optionally substituted with 1, 2, 3 or 4 substituents independently selected from $R^{11}$;

each $R^b$ is independently hydrogen, $C_{1-6}$ alkyl, $C_{3-8}$ cycloalkyl, $C_{6-10}$ aryl, 5- to 10-membered heteroaryl or 3- to 12-membered heterocyclyl; wherein the $C_{1-6}$ alkyl, $C_{3-8}$ cycloalkyl, $C_{6-10}$ aryl, 5- to 10-membered heteroaryl and 3- to 12-membered heterocyclyl of $R^b$ are each optionally substituted with 1, 2, 3 or 4 substituents independently selected from $R^{11}$;

each $R^c$ and $R^d$ is independently hydrogen, $C_{1-6}$ alkyl, $C_{3-8}$ cycloalkyl, $C_{6-10}$ aryl, 5- to 10-membered heteroaryl or 3- to 12-membered heterocyclyl; wherein the $C_{1-6}$ alkyl, $C_{3-8}$ cycloalkyl, $C_{6-10}$ aryl, 5- to 10-membered heteroaryl and 3- to 12-membered heterocyclyl of $R^c$ and $R^d$ are each optionally substituted with 1, 2, 3 or 4 substituents independently selected from $R^{11}$;

or $R^c$ and $R^d$ are taken together with the nitrogen atom to which they are attached to form a 4- to 12-membered heterocyclyl optionally substituted with 1, 2, 3 or 4 substituents independently selected from $R^{11}$;

each $R^e$ is independently $C_{1-6}$ alkyl, $C_{3-8}$ cycloalkyl, $C_{6-10}$ aryl, 5- to 10-membered heteroaryl or 3- to 12-membered heterocyclyl; wherein the $C_{1-6}$ alkyl, $C_{3-8}$ cycloalkyl, $C_{6-10}$ aryl, 5- to 10-membered heteroaryl and 3- to 12-membered heterocyclyl of $R^e$ are each optionally substituted with 1, 2, 3 or 4 substituents independently selected from $R^{11}$;

each $R^f$ is independently hydrogen or $C_{1-6}$ alkyl;

each $R^g$ and $R^h$ is independently $C_{1-6}$ alkyl, $C_{3-8}$ cycloalkyl, $C_{6-10}$ aryl, 5- to 10-membered heteroaryl, 3- to 12-membered heterocyclyl, or —O—$C_{1-6}$ alkyl; wherein the $C_{1-6}$ alkyl, $C_{3-8}$ cycloalkyl, $C_{6-10}$ aryl, 5- to 10-membered heteroaryl and 3- to 12-membered heterocyclyl of $R^g$ and $R^h$ are each optionally substituted with 1, 2, 3 or 4 substituents independently selected from $R^{11}$;

or $R^g$ and $R^h$ are taken together with the phosphorus atom to which they are attached to form a 4- to 12-membered heterocyclyl optionally substituted with 1, 2, 3 or 4 substituents independently selected from $R^{11}$;

each $R^{11}$ is independently oxo, $C_{1-6}$ alkyl, $C_{2-6}$ alkenyl, $C_{2-6}$ alkynyl, $C_{3-6}$ cycloalkyl, $C_{6-10}$ aryl, 5- to 10-membered heteroaryl, 3- to 8-membered heterocyclyl, halogen, cyano, —C(O)$R^{a1}$, —C(O)O$R^{b1}$, —C(O)N$R^{c1}R^{d1}$, —O$R^{b1}$, —OC(O)$R^{a1}$, —OC(O)N$R^{c1}R^{d1}$, —S$R^{b1}$, —S(O)$R^{e1}$, —S(O)$_2R^{e1}$, —S(O)$_2$N$R^{c1}R^{d1}$, —N$R^{c1}R^{d1}$, —N($R^{f1}$)C(O)$R^{a1}$, —N($R^{f1}$)C(O)O$R^{b1}$, —N($R^{f1}$)C(O)N$R^{c1}R^{d1}$, —N($R^{f1}$)S(O)$_2R^{e1}$, —N($R^{f1}$)S(O)$_2$N$R^{c1}R^{d1}$, or —P(O)$R^{g1}R^{h1}$; wherein the $C_{1-6}$ alkyl, $C_{2-6}$ alkenyl, $C_{2-6}$ alkynyl, $C_{3-6}$ cycloalkyl, $C_{6-14}$ aryl, 5- to 14-membered heteroaryl and 3- to 14-membered heterocyclyl of $R^{11}$ are each optionally substituted with 1, 2, 3 or 4 substituents independently selected from $R^{12}$;

each $R^{a1}$ is independently hydrogen, $C_{1-6}$ alkyl, $C_{2-6}$ alkenyl, $C_{2-6}$ alkynyl, $C_{3-6}$ cycloalkyl, $C_{6-10}$ aryl, 5- to 10-membered heteroaryl or 3- to 8-membered heterocyclyl; wherein the $C_{1-6}$ alkyl, $C_{2-6}$ alkenyl, $C_{2-6}$ alkynyl, $C_{3-6}$ cycloalkyl, $C_{6-10}$ aryl, 5- to 10-membered heteroaryl and 3- to 8-membered heterocyclyl of $R^{a1}$ are each optionally substituted with 1, 2, 3 or 4 substituents independently selected from $R^{12}$;

each $R^{b1}$ is independently hydrogen, $C_{1-6}$ alkyl, $C_{3-6}$ cycloalkyl, $C_{6-10}$ aryl, 5- to 10-membered heteroaryl or 3- to 8-membered heterocyclyl; wherein the $C_{1-6}$ alkyl, $C_{3-6}$ cycloalkyl, $C_{6-10}$ aryl, 5- to 10-membered heteroaryl and 3- to 8-membered heterocyclyl of $R^{h1}$ are each optionally substituted with 1, 2, 3 or 4 substituents independently selected from $R^{12}$;

each $R^{c1}$ and $R^{d1}$ is independently hydrogen, $C_{1-6}$ alkyl, $C_{3-6}$ cycloalkyl, $C_{6-10}$ aryl, 5- to 10-membered heteroaryl or 3- to 8-membered heterocyclyl; wherein the $C_{1-6}$ alkyl, $C_{3-6}$ cycloalkyl, $C_{6-10}$ aryl, 5- to 10-membered heteroaryl and 3- to 8-membered heterocyclyl of $R^{c1}$ and $R^{d1}$ are each optionally substituted with 1, 2, 3 or 4 substituents independently selected from $R^{12}$;

or $R^{c1}$ and $R^{d1}$ are taken together with the nitrogen atom to which they are attached to form a 4- to 8-membered heterocyclyl optionally substituted with 1, 2, 3 or 4 substituents independently selected from $R^{12}$;

each $R^{e1}$ is independently $C_{1-6}$ alkyl, $C_{3-6}$ cycloalkyl, $C_{6-10}$ aryl, 5- to 10-membered heteroaryl or 3- to 8-membered heterocyclyl; wherein the $C_{1-6}$ alkyl, $C_{3-6}$ cycloalkyl, $C_{6-10}$ aryl, 5- to 10-membered heteroaryl and 3- to 8-membered heterocyclyl of $R^{e1}$ are each optionally substituted with 1, 2, 3 or 4 substituents independently selected from $R^{12}$;

each $R^{f1}$ is independently hydrogen or $C_{1-6}$ alkyl;

each $R^{g1}$ and $R^{h1}$ is independently $C_{1-6}$ alkyl, $C_{3-6}$ cycloalkyl, $C_{6-10}$ aryl, 5- to 10-membered heteroaryl, 3- to 8-membered heterocyclyl, or —O—$C_{1-6}$ alkyl; wherein the $C_{1-6}$ alkyl, $C_{3-6}$ cycloalkyl, $C_{6-10}$ aryl, 5- to 10-membered heteroaryl and 3- to 8-membered heterocyclyl of $R^{g1}$ and $R^{h1}$ are each optionally substituted with 1, 2, 3 or 4 substituents independently selected from $R^{12}$;

or $R^{g1}$ and $R^{h1}$ are taken together with the phosphorus atom to which they are attached to form a 4- to 8-membered heterocyclyl optionally substituted with 1, 2, 3 or 4 substituents independently selected from $R^{12}$;

each $R^{12}$ is independently oxo, $C_{1-6}$ alkyl, $C_{3-6}$ cycloalkyl, $C_6$ aryl, 5- to 6-membered heteroaryl, 3- to 6-membered heterocyclyl, halogen, cyano, —C(O)$R^{a2}$, —C(O)O$R^{b2}$, —C(O)N$R^{c2}R^{d2}$, —O$R^{b2}$, —OC(O)$R^{a1}$, —OC(O)N$R^{c2}R^{d2}$, —S(O)$_2R^{e2}$, —S(O)$_2$N$R^{c2}R^{d2}$, —N$R^{c2}R^{d2}$, —N($R^{f2}$)C(O)$R^{a2}$, —N($R^{f2}$)C(O)O$R^{b2}$, —N($R^{f2}$)C(O)N$R^{c2}R^{d2}$, —N($R^{f2}$)S(O)$_2R^{e2}$, —N($R^{f2}$)S(O)$_2$N$R^{c2}R^{d2}$, or —P(O)$R^{g2}R^{h2}$; wherein the $C_{1-6}$ alkyl, $C_{3-6}$ cycloalkyl, $C_6$ aryl, 5- to 6-membered heteroaryl and 3- to 6-membered heterocyclyl of $R^{12}$ are each optionally substituted with 1, 2, 3 or 4 substituents independently selected from $R^{13}$;

each $R^{a2}$ is independently hydrogen, $C_{1-6}$ alkyl, $C_{3-6}$ cycloalkyl, $C_6$ aryl, 5- to 6-membered heteroaryl or 3- to 6-membered heterocyclyl; wherein the $C_{1-6}$ alkyl, $C_{3-6}$ cycloalkyl, $C_6$ aryl, 5- to 6-membered heteroaryl and 3- to 6-membered heterocyclyl of $R^{a2}$ are each optionally substituted with 1, 2, 3 or 4 substituents independently selected from $R^{13}$;

each $R^{b2}$ is independently hydrogen, $C_{1-6}$ alkyl, $C_{3-6}$ cycloalkyl or 3- to 6-membered heterocyclyl; wherein the $C_{1-6}$ alkyl, $C_{3-6}$ cycloalkyl and 3- to 6-membered heterocyclyl of $R^{b2}$ are each optionally substituted with 1, 2, 3 or 4 substituents independently selected from $R^{13}$;

each $R^{c2}$ and $R^{d2}$ is independently hydrogen, $C_{1-6}$ alkyl, $C_{3-6}$ cycloalkyl or 3- to 8-membered heterocyclyl; wherein the $C_{1-6}$ alkyl, $C_{3-6}$ cycloalkyl and 3- to 8-membered heterocyclyl of $R^{c2}$ and $R^{d2}$ are each optionally substituted with 1, 2, 3 or 4 substituents independently selected from $R^{13}$;

or $R^{c2}$ and $R^{d2}$ are taken together with the nitrogen atom to which they are attached to form a 4- to 6-membered heterocyclyl optionally substituted with 1, 2, 3 or 4 substituents independently selected from $R^{13}$;

each $R^{e2}$ is independently $C_{1-6}$ alkyl, $C_{3-6}$ cycloalkyl, $C_6$ aryl, 5- to 6-membered heteroaryl or 3- to 6-membered heterocyclyl; wherein the $C_{1-6}$ alkyl, $C_{3-6}$ cycloalkyl, $C_6$ aryl, 5- to 6-membered heteroaryl and 3- to 6-membered heterocyclyl of $R^{e2}$ are each optionally substituted with 1, 2, 3 or 4 substituents independently selected from $R^{13}$;

each $R^{f2}$ is independently hydrogen or $C_{1-6}$ alkyl;

each $R^{g2}$ and $R^{h2}$ is independently $C_{1-6}$ alkyl, $C_{3-6}$ cycloalkyl, 3- to 8-membered heterocyclyl, or —O—$C_{1-6}$ alkyl; wherein the $C_{1-6}$ alkyl, $C_{3-6}$ cycloalkyl, and 3- to 8-membered heterocyclyl of $R^{g2}$ and $R^{h2}$ are each optionally substituted with 1, 2, 3 or 4 substituents independently selected from $R^{13}$;

or $R^{g2}$ and $R^{h2}$ are taken together with the phosphorus atom to which they are attached to form a 4- to 6-membered heterocyclyl optionally substituted with 1, 2, 3 or 4 substituents independently selected from $R^{13}$; and each $R^{13}$ is independently oxo, halogen, hydroxyl, —O($C_{1-6}$ alkyl), cyano, $C_{1-6}$ alkyl or $C_{1-6}$ haloalkyl.

In some embodiments, the compound is other than a compound in Table 1X and salts thereof. In some embodiments, the compound herein, such as a compound of Formula (I), is other than a compound selected from one or more of Compound Nos. 1x-4x in Table 1X. In some embodiments, the compounds of the disclosure, and methods of using the compounds detailed herein, encompass any of the compounds of Formula (I), including those listed Table 1X and salts thereof.

TABLE 1X

| No. | Name |
|---|---|
| 1x | spiro[cyclopropane-1,3'-[3H]pyrrolo[2,3-b]pyridin]-2'(1'H)-one, 5'-[4-(2-(5-trifluoromethylpyridin-3-yl)amino-2-oxoethyl)-3-fluorophenyl]- |
| 2x | spiro[cyclopropane-1,3'-[3H]pyrrolo[2,3-b]pyridin]-2'(1'H)-one, 5'-[4-(2-(5-trifluoromethyl-6-methylpyridin-3-yl)amino-2-oxoethyl)-3-fluorophenyl]- |
| 3x | spiro[cyclopentane-1,3'-[3H]pyrrolo[2,3-b]pyridin]-2'(1'H)-one, 5'-(3,4,5-trimethoxyphenyl)- |
| 4x | spiro[cyclohexane-1,3'-[3H]pyrrolo[2,3-b]pyridin]-2'(1'H)-one, 5'-(3-fluorophenyl)- |

In one aspect, provided is a compound of Formula (I), or a salt (e.g., a pharmaceutically acceptable salt), solvate (e.g., hydrate), prodrug, metabolites or derivative thereof, wherein $R^1$ is hydrogen or $C_{1-6}$ alkyl (e.g., methyl); A, $R^2$, $R^3$ and $R^4$ are as defined above.

In one aspect, provided is a compound of Formula (IA):

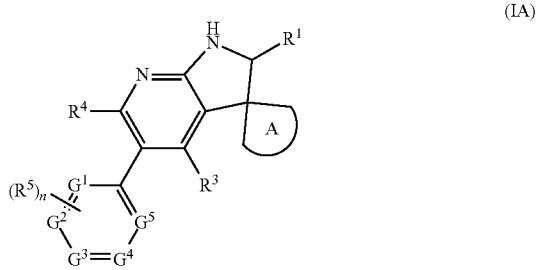

(IA)

or a salt (e.g., a pharmaceutically acceptable salt) thereof, wherein:

$G^1$, $G^2$, $G^3$, $G^4$ and $G^5$ are independently N, CH or $CR^5$, provided that no more than two of $G^1$, $G^2$, $G^3$, $G^4$ and $G^5$ are N;

n is 0, 1, 2, 3, 4 or 5;

each $R^5$ is independently selected from $R^{10}$, optionally two vicinal $R^5$ groups are taken together with the carbon atoms to which they are attached to form a ring which is optionally substituted with 1, 2, 3 or 4 substituents independently selected from $R^{10}$; and A, $R^1$, $R^3$, $R^4$ and $R^{10}$ are as defined for Formula (I).

In one variation, the compound is other than a compound selected from one or more of Compound Nos. 1x-4x in Table 1X and salts thereof. In another variation, $R^1$ is hydrogen or $C_{1-6}$ alkyl.

In one aspect, provided is a compound of Formula (IB):

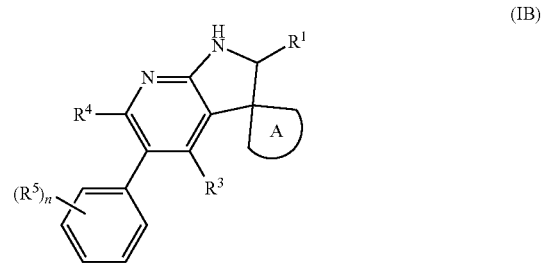

(IB)

or a salt (e.g., a pharmaceutically acceptable salt) thereof, wherein n is 0, 1, 2, 3, 4 or 5; each $R^5$ is independently selected from $R^{10}$; and A, $R^1$, $R^3$, $R^4$ and $R^{10}$ are as defined for Formula (I). In another variation, $R^1$ is hydrogen or $C_{1-6}$ alkyl. In one variation, the compound is other than a compound selected from one or more of Compound Nos. 1x-4x in Table 1X and salts thereof.

In one aspect, provided is a compound of Formula (IC):

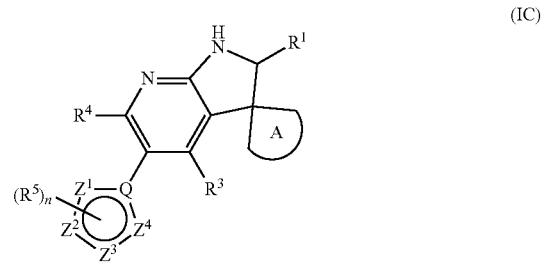

(IC)

or a salt (e.g., a pharmaceutically acceptable salt) thereof, wherein:

Q is C or N, $Z^1$, $Z^2$, $Z^3$ and $Z^4$ are independently N, NH, $NR^5$, CH or $CR^5$, provided that at least one of Q, $Z^1$, $Z^2$, $Z^3$ and $Z^4$ is N, NH or $NR^5$;

n is 0, 1, 2, 3 or 4;

each $R^5$ is independently selected from $R^{10}$, optionally two vicinal $R^5$ groups are taken together with the atoms to which they are attached to form a ring which is optionally substituted with 1, 2, 3 or 4 substituents independently selected from $R^{10}$; and A, $R^1$, $R^3$, $R^4$ and $R^{10}$ are as defined for Formula (I).

In some embodiments, the compound is of the Formula (I), or variations thereof such as Formula (IA), (IB) and (IC), or a salt (e.g., a pharmaceutically acceptable salt) thereof, wherein $R^1$ is hydrogen, $C_{1-6}$ alkyl or oxo. In some embodiments, $R^1$ is hydrogen or $C_{1-6}$ alkyl (e.g., methyl). In some embodiments, $R^1$ is hydrogen or methyl. In another variation, $R^1$ is methyl. In another variation, $R^1$ is hydrogen.

In some embodiments, the compound is of the Formula (I), or variations thereof such as Formula (IA), (IB) and (IC), or a salt (e.g., a pharmaceutically acceptable salt) thereof, wherein $R^3$ is hydrogen, halogen, cyano, $C_{1-6}$ alkyl, $C_{1-6}$ haloalkyl, $C_{3-6}$ cycloalkyl, —$OR^7$, or —$NR^{8a}R^{8b}$. In some embodiments, $R^3$ is hydrogen, halogen (e.g., chloro or fluoro), $C_{1-6}$ alkyl (e.g., methyl), or —$OR^7$. In one variation, $R^3$ is hydrogen, chloro, methyl or methoxy. In another variation, $R^3$ is hydrogen or chloro. In another variation, $R^3$ is hydrogen.

In some embodiments, $R^3$ is hydrogen, $C_{1-6}$ alkyl (e.g., methyl), $C_{1-6}$ haloalkyl (e.g., trifluoromethyl), or $C_{3-6}$ cycloalkyl (e.g., cyclopropyl). In some embodiments, $R^3$ is —$OR^7$ wherein $R^7$ is hydrogen or $C_{1-6}$ alkyl optionally substituted with 1, 2, 3, 4 or 5 substituents independently selected from $R^{10}$. In one variation, $R^7$ is hydrogen or $C_{1-6}$ alkyl (e.g., methyl). In some embodiments, $R^3$ is —$NR^{8a}R^{8b}$ wherein each $R^{8a}$ and $R^{8b}$ is independently hydrogen or $C_{1-6}$ alkyl optionally substituted with 1, 2, 3, 4 or 5 substituents independently selected from $R^{10}$. In one variation, each $R^{8a}$ and $R^{8b}$ is independently hydrogen or $C_{1-6}$ alkyl (e.g., methyl).

In some embodiments, the compound is of the Formula (I), or variations thereof such as Formula (IA), (IB) and (IC), or a salt (e.g., a pharmaceutically acceptable salt) thereof, wherein $R^4$ is hydrogen, halogen, cyano, $C_{1-6}$ alkyl, or $C_{3-6}$ cycloalkyl. In some embodiments, $R^4$ is hydrogen, halogen (e.g., fluoro or chloro), or cyano. In some embodiments, $R^4$ is $C_{1-6}$ alkyl (e.g., methyl) or $C_{3-6}$ cycloalkyl (e.g., cyclopropyl). In some embodiments, $R^5$ is hydrogen.

It is intended and understood that each and every variation of $R^1$, $R^3$ and $R^4$ described for the Formula (I), (IA), (IB) or (IC) may be combined, the same as if each and every combination is specifically and individually described. For example, in some embodiments, $R^1$ is hydrogen or $C_{1-6}$ alkyl (e.g., methyl); $R^3$ is hydrogen, halogen (e.g., chloro), $C_{1-6}$ alkyl (e.g., methyl), or —O($C_{1-6}$ alkyl) (e.g., methoxy); and $R^4$ is hydrogen.

In some embodiments, the compound is of the Formula (I), or variations thereof such as Formula (IA), (IB) and (IC), or a salt (e.g., a pharmaceutically acceptable salt) thereof, wherein A is $C_{3-12}$ cycloalkyl, 3- to 14-membered heterocyclyl, $C_{6-14}$ aryl or 5- to 14-membered heteroaryl, wherein the $C_{3-12}$ cycloalkyl, 3- to 14-membered heterocyclyl, $C_{6-14}$ aryl and 5- to 14-membered heteroaryl of A are each optionally substituted with 1, 2, 3, 4 or 5 substituents independently selected from $R^9$.

In some embodiments, A is

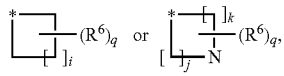

wherein the * indicates the point of attachment;
i is 0, 1, 2 or 3;
j is 1, 2 or 3;
k is 1 or 2;
each q is independently 0, 1, 2, 3, 4 or 5; and
each $R^6$, where present, is independently selected from $R^9$; wherein optionally two $R^6$ groups are taken together to form a spiro, fused or bridged ring which is optionally substituted with 1, 2, 3 or 4 substituents independently selected from $R^{10}$, or two vicinal $R^6$ groups are taken together to form a bond.

In some embodiments, A is:

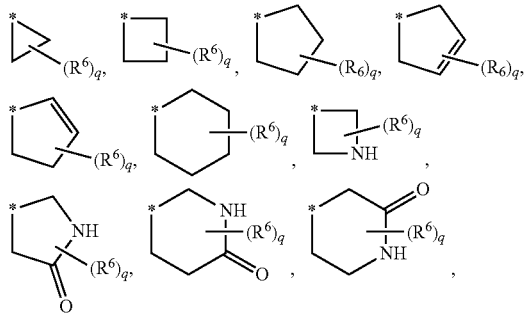

-continued

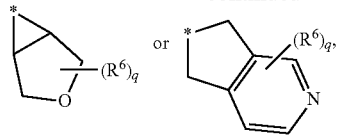

wherein the * indicates the point of attachment, each q is independently 0, 1, 2, 3, or 4; and each $R^6$, where present, is independently selected from $R^9$.

In some of these embodiments, q is 0. The A ring structures described above are unsubstituted.

In some of these embodiments, each $R^6$, where present, is independently oxo, $C_{1-6}$ alkyl, $C_{1-6}$ alkylidene, $C_{3-8}$ cycloalkyl, $C_{6-10}$ aryl, 5- to 10-membered heteroaryl, 3- to 12-membered heterocyclyl, halogen, cyano, —C(O)$R^a$, —C(O)O$R^b$, —C(O)N$R^cR^d$, —O$R^b$, —S(O)$_2R^e$, —S(O)(=NH)$R^e$, —S(O)$_2$N$R^cR^d$, —N$R^cR^d$, —N($R^f$)C(O)$R^a$, —N($R^f$)S(O)$_2R^e$, or —N($R^f$)S(O)$_2$N$R^cR^d$; wherein the $C_{1-6}$ alkyl, $C_{1-6}$ alkylidene, $C_{3-8}$ cycloalkyl, $C_{6-10}$ aryl, 5- to 10-membered heteroaryl and 3- to 12-membered heterocyclyl of $R^6$ are optionally substituted with 1, 2, 3 or 4 substituents independently selected from $R^{11}$.

In some of these embodiments, each q is independently 1, 2, 3, or 4; and at least one $R^6$ is oxo, or $C_{1-6}$ alkylidene optionally substituted with 1, 2, 3 or 4 substituents independently selected from $R^{11}$.

In some of these embodiments, each q is independently 1, 2, 3, or 4; and at least one $R^6$ is 3- to 12-membered heterocyclyl optionally substituted with 1, 2, 3 or 4 substituents independently selected from $R^{11}$, 5- to 10-membered heteroaryl optionally substituted with 1, 2, 3 or 4 substituents independently selected from $R^{11}$, or $C_{6-10}$ aryl optionally substituted with 1, 2, 3 or 4 substituents independently selected from $R^{11}$.

In some of these embodiments, each q is independently 1, 2 or 3; and each $R^6$ is independently selected from the group consisting of halogen, cyano, —C(O)$R^a$, —C(O)O$R^b$, —C(O)N$R^cR^d$, —O$R^b$, —S(O)$_2R^e$, —N$R^cR^d$, —N($R^f$)C(O)$R^a$, and $C_{1-6}$ alkyl optionally substituted with 1, 2 or 4 substituents independently selected from $R^{11}$.

In some embodiments, A is selected from the group consisting of:

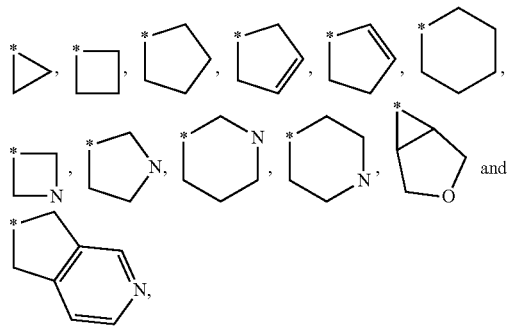

each of which is optionally substituted with 1, 2, 3, 4 or 5 substituents independently selected from $R^9$; wherein the * indicates the point of attachment.

It is intended and understood that each and every variation of $R^1$, $R^3$ and $R^4$, or a combination thereof, described for the Formula (I), (IA), (IB) or (IC) may be combined with each and every variation of A described for the Formula (I), (IA), (IB) or (IC), the same as if each and every combination is specifically and individually described. For example, in some embodiments, $R^1$ is hydrogen or $C_{1-6}$ alkyl (e.g., methyl); $R^3$ is hydrogen, halogen (e.g., chloro), $C_{1-6}$ alkyl (e.g., methyl), or —O($C_{1-6}$ alkyl) (e.g., methoxy); $R^4$ is hydrogen; and A is selected from the group consisting of:

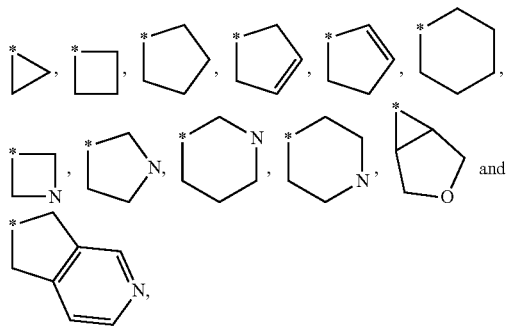

each of which is optionally substituted with 1, 2, 3, 4 or 5 substituents independently selected from $R^9$; wherein the * indicates the point of attachment.

In some embodiments, the compound is of the Formula (I), or a salt (e.g., a pharmaceutically acceptable salt) thereof, wherein $R^2$ is $C_{6-14}$ aryl optionally substituted with 1, 2, 3, 4 or 5 substituents independently selected from $R^{10}$, or 5- to 14-membered heteroaryl optionally substituted with 1, 2, 3, 4 or 5 substituents independently selected from $R^{10}$. In some embodiments, $R^2$ is $C_{6-14}$ aryl optionally substituted with 1, 2, 3, 4 or 5 substituents independently selected from $R^{10}$. In one variation, $R^2$ is phenyl optionally substituted with 1, 2, 3, 4 or 5 substituents independently selected from $R^{10}$. In some embodiments, $R^2$ is 5- to 14-membered heteroaryl optionally substituted with 1, 2, 3, 4 or 5 substituents independently selected from $R^{10}$. In some of these embodiments, $R^2$ is 5- to 10-membered heteroaryl optionally substituted with 1, 2, 3, 4 or 5 substituents independently selected from $R^{10}$, and wherein the 5- to 10-membered heteroaryl contains 1, 2 or 3 heteroatoms independently selected from the group consisting of N and O. In some of these embodiments, $R^2$ is pyrazolyl, pyridinyl, pyrimidinyl, indolyl, indolinyl, indazolyl, benzo[d]imidazolyl, benzo[d][1,2,3]triazolyl, or pyrrolo[2,3-b]pyridinyl; each is optionally substituted with 1, 2, 3, 4 or 5 substituents independently selected from $R^{10}$.

In some embodiments, the compound is of the Formula (IA), (IB) and (IC), or a salt (e.g., a pharmaceutically acceptable salt) thereof, each $R^5$, where present, is independently oxo, $C_{1-6}$ alkyl, $C_{3-8}$ cycloalkyl, $C_{6-10}$ aryl, 5- to 10-membered heteroaryl, 3- to 12-membered heterocyclyl, halogen, cyano, —C(O)$R^a$, —C(O)O$R^b$, —C(O)NR$^c$R$^d$, —OR$^b$, —S(O)$_2$R$^e$, —S(O)(=NH)R$^e$, —S(O)$_2$NR$^c$R$^d$, —NR$^c$R$^d$, —N(R$^f$)C(O)R$^a$, —N(R$^f$)S(O)$_2$R$^e$, or —N(R$^f$)S(O)$_2$NR$^c$R$^d$; wherein the $C_{1-6}$ alkyl, $C_{3-8}$ cycloalkyl, $C_{6-10}$ aryl, 5- to 10-membered heteroaryl and 3- to 12-membered heterocyclyl of $R^5$ are optionally substituted with 1, 2, 3 or 4 substituents independently selected from $R^{11}$.

In some of these embodiments, n is 1, 2, 3 or 4; at least one $R^5$ is —C(O)NR$^c$R$^d$ or —NR$^c$R$^d$. In one variation, n is 2, 3 or 4; and one $R^5$ is halogen, cyano, or $C_{1-6}$ alkyl optionally substituted with 1, 2, 3 or 4 substituents independently selected from $R^{11}$.

In some of these embodiments, n is 1, 2, 3 or 4; and at least one $R^5$ is 3- to 12-membered heterocyclyl optionally substituted with 1, 2, 3 or 4 substituents independently selected from $R^{11}$; 5- to 10-membered heteroaryl optionally substituted with 1, 2, 3 or 4 substituents independently selected from $R^{11}$; or $C_{3-8}$cycloalkyl optionally substituted with 1, 2, 3 or 4 substituents independently selected from $R^{11}$. In one variation, n is 2, 3 or 4; and one $R^5$ is halogen, cyano, or $C_{1-6}$ alkyl optionally substituted with 1, 2, 3 or 4 substituents independently selected from $R^{11}$.

In some of these embodiments, n is 1, 2, 3 or 4; and at least one $R^5$ is halogen, cyano, —C(O)R$^a$, —C(O)OR$^b$, —C(O)NR$^c$R$^d$, —OR$^b$, —S(O)$_2$R$^e$, —S(O)(=NH)R$^e$, —S(O)$_2$NR$^c$R$^d$, —NR$^c$R$^d$, —N(R$^f$)C(O)R$^a$, —N(R$^f$)S(O)$_2$R$^e$, or —N(R$^f$)S(O)$_2$NR$^c$R$^d$.

In some of these embodiments, n is 1, 2, 3 or 4; and at least one $R^5$ is $C_{1-6}$ alkyl optionally substituted with 1, 2, 3 or 4 substituents independently selected from $R^{11}$.

It is intended and understood that each and every variation of $R^1$, $R^3$, $R^4$ and A, or a combination thereof, described for the Formula (I), (IA), (IB) or (IC) may be combined with each and every variation of $R^2$ described for the Formula (I), or the Formula (IA), (IB) or (IC) where applicable, the same as if each and every combination is specifically and individually described. For example, in some embodiments, $R^1$ is hydrogen or $C_{1-6}$ alkyl (e.g., methyl); $R^3$ is hydrogen, halogen (e.g., chloro), $C_{1-6}$ alkyl (e.g., methyl), or —O($C_{1-6}$ alkyl) (e.g., methoxy); $R^4$ is hydrogen; A is selected from the group consisting of:

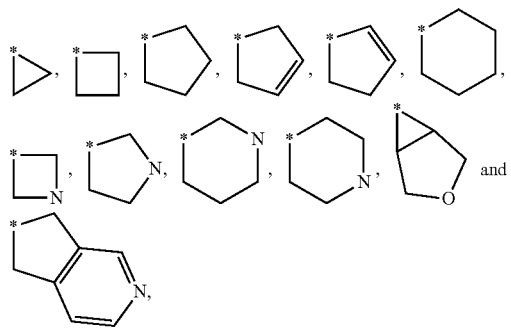

each of which is optionally substituted with 1, 2, 3, 4 or 5 substituents independently selected from $R^9$; wherein the * indicates the point of attachment; and $R^2$ is phenyl optionally substituted with 1, 2, 3, 4 or 5 substituents independently selected from $R^{10}$, or 5- to 10-membered heteroaryl containing 1, 2 or 3 heteroatoms independently selected from the group consisting of N and O, and optionally substituted with 1, 2, 3, 4 or 5 substituents independently selected from $R^{10}$.

In some embodiments of the compound of the Formula (I), or variations thereof such as Formula (IA), (IB) and (IC) where applicable, or a salt (e.g., a pharmaceutically acceptable salt) thereof, each $R^9$ is independently $R^{10}$, or $C_{1-6}$ alkylidene optionally substituted with 1, 2, 3 or 4 substituents independently selected from $R^{10}$. In some embodiments, $R^9$ is $C_{1-6}$ alkylidene optionally substituted with 1, 2, 3 or 4 substituents independently selected from $R^{10}$. In some embodiments, $R^9$ is selected from $R^{10}$.

In some embodiments of the compound of the Formula (I), or variations thereof such as Formula (IA), (IB) and (IC) where applicable, or a salt (e.g., a pharmaceutically acceptable salt) thereof, each $R^{10}$ is independently oxo, $C_{1-6}$ alkyl, $C_{2-6}$ alkenyl, $C_{2-6}$ alkynyl, $C_{3-8}$ cycloalkyl, $C_{6-10}$ aryl, 5- to 10-membered heteroaryl, 3- to 12-membered heterocyclyl, halogen, cyano, —C(O)R$^a$, —C(O)OR$^b$, —C(O)NR$^c$R$^d$, —OR$^b$, —OC(O)R$^a$, —OC(O)NR$^c$R$^d$, —SR$^b$, —S(O)R$^e$, —S(O)$_2$R$^e$, —S(O)(=NH)R$^e$, —S(O)$_2$NR$^c$R$^d$, —NR$^c$R$^d$, —N(R$^f$)C(O)R$^a$, —N(R$^f$)C(O)OR$^b$, —N(R$^f$)C(O)NR$^c$R$^d$, —N(R$^f$)S(O)$_2$R$^e$, or —N(R$^f$)S(O)$_2$NR$^c$R$^d$; wherein the C$_{1-6}$ alkyl, C$_{2-6}$ alkenyl, C$_{2-6}$ alkynyl, C$_{3-8}$cycloalkyl, C$_{6-14}$ aryl, 5- to 14-membered heteroaryl and 3- to 14-membered heterocyclyl of R$^{10}$ are each optionally substituted with 1, 2, 3 or 4 substituents independently selected from R$^{11}$.

In one variation, R$^{th}$ is independently oxo, C$_{1-6}$ alkyl, C$_{1-6}$ alkylidene, C$_{3-8}$ cycloalkyl, C$_{6-10}$ aryl, 5- to 10-membered heteroaryl, 3- to 12-membered heterocyclyl, halogen, cyano, —C(O)R$^a$, —C(O)OR$^b$, —C(O)NR$^c$R$^d$, —OR$^b$, —S(O)$_2$R$^e$, —S(O)(=NH)R$^e$, —S(O)$_2$NR$^c$R$^d$, —NR$^c$R$^d$, —N(R$^f$)C(O)R$^a$, —N(R$^f$)S(O)$_2$R$^e$, or —N(R$^f$)S(O)$_2$NR$^c$R$^d$; wherein the C$_{1-6}$ alkyl, C$_{1-6}$ alkylidene, C$_{3-8}$cycloalkyl, C$_{6-10}$ aryl, 5- to 10-membered heteroaryl and 3- to 12-membered heterocyclyl of R$^6$ are optionally substituted with 1, 2, 3 or 4 substituents independently selected from R$^{11}$.

In one variation, R$^{10}$ is 3- to 12-membered heterocyclyl optionally substituted with 1, 2, 3 or 4 substituents independently selected from R$^{11}$, 5- to 10-membered heteroaryl optionally substituted with 1, 2, 3 or 4 substituents independently selected from R$^{11}$, or C$_{6-10}$ aryl optionally substituted with 1, 2, 3 or 4 substituents independently selected from R$^{11}$.

In one variation, R$^{10}$ is independently selected from the group consisting of halogen, cyano, —C(O)R$^a$, —C(O)OR$^b$, —C(O)NR$^c$R$^d$, —OR$^b$, —S(O)$_2$R$^e$, —NR$^c$R$^d$, —N(R$^f$)C(O)R$^a$, and C$_{1-6}$alkyl optionally substituted with 1, 2, 3 or 4 substituents independently selected from R$^{11}$.

In one variation, R$^{10}$ is —C(O)NR$^c$R$^d$ or —NR$^c$R$^d$.

In one variation, R$^{10}$ is halogen, cyano, or C$_{1-6}$ alkyl optionally substituted with 1, 2, 3 or 4 substituents independently selected from R$^{11}$.

In one variation, R$^{10}$ is 3- to 12-membered heterocyclyl optionally substituted with 1, 2, 3 or 4 substituents independently selected from R$^{11}$; 5- to 10-membered heteroaryl optionally substituted with 1, 2, 3 or 4 substituents independently selected from R$^{11}$; or C$_{3-8}$ cycloalkyl optionally substituted with 1, 2, 3 or 4 substituents independently selected from R$^{11}$.

In one variation, R$^{10}$ is halogen, cyano, or C$_{1-6}$ alkyl optionally substituted with 1, 2, 3 or 4 substituents independently selected from R$^{11}$.

In one variation, R$^{10}$ is halogen, cyano, —C(O)R$^a$, —C(O)OR$^b$, —C(O)NR$^c$R$^d$, —OR$^b$, —S(O)$_2$R$^e$, —S(O)(=NH)R$^e$, —S(O)$_2$NR$^c$R$^d$, —NR$^c$R$^d$, —N(R$^f$)C(O)R$^a$, —N(R$^f$)S(O)$_2$R$^e$, or —N(R$^f$)S(O)$_2$NR$^c$R$^d$.

In one variation, R$^{10}$ is C$_{1-6}$ alkyl optionally substituted with 1, 2, 3 or 4 substituents independently selected from R$^{11}$.

In one variation, R$^{10}$ is independently oxo; C$_{1-6}$ alkyl optionally substituted with 1, 2, 3 or 4 substituents independently selected from R$^{11}$; 5- to 10-membered heteroaryl optionally substituted with 1, 2, 3 or 4 substituents independently selected from R$^{11}$; halogen, —OR$^b$, —S(O)(=NH)R$^e$, —NR$^c$R$^d$, —N(R$^f$)C(O)R$^a$, or —N(R$^f$)S(O)$_2$NR$^c$R$^d$.

In one variation, R$^{10}$ is independently oxo, halogen, cyano, C$_{1-6}$ alkyl optionally substituted with 1, 2, 3 or 4 substituents independently selected from R$^{11}$, or —OR$^b$.

In one variation, R$^{10}$ is independently —NR$^c$R$^d$, —N(R$^f$)C(O)R$^a$, —N(R$^f$)C(O)OR$^b$, —N(R$^f$)C(O)NR$^c$R$^d$, —N(R$^f$)S(O)$_2$R$^e$, or —N(R$^f$)S(O)$_2$NR$^c$R$^d$.

In one variation, R$^{10}$ is independently oxo, —OR$^b$, —OC(O)R$^a$, —OC(O)NR$^c$R$^d$, —SR$^b$, —S(O)R$^e$, —S(O)$_2$R$^e$, —S(O)(=NH)R$^e$, or —S(O)$_2$NR$^c$R$^d$.

In one variation, each R$^{10}$ is independently C$_{1-6}$ alkyl, C$_{2-6}$ alkenyl, C$_{2-6}$ alkynyl, C$_{3-8}$ cycloalkyl, C$_{6-10}$ aryl, 5- to 10-membered heteroaryl, 3- to 12-membered heterocyclyl, halogen, cyano, —C(O)R$^a$, —C(O)OR$^b$, —C(O)NR$^c$R$^d$; wherein the C$_{1-6}$ alkyl, C$_{2-6}$ alkenyl, C$_{2-6}$ alkynyl, C$_{3-8}$ cycloalkyl, C$_{6-14}$ aryl, 5- to 14-membered heteroaryl and 3- to 14-membered heterocyclyl of R$^{10}$ are each optionally substituted with 1, 2, 3 or 4 substituents independently selected from R$^{11}$.

In one variation, each R$^{10}$ is independently C$_{1-6}$ alkyl, C$_{2-6}$ alkenyl, C$_{2-6}$ alkynyl, each optionally substituted with 1, 2, 3 or 4 substituents independently selected from R$^{11}$.

In one variation, R$^{10}$ is C$_{1-6}$ alkyl optionally substituted with 1, 2, 3 or 4 substituents independently selected from R$^{10}$. In one variation, R$^{10}$ is 3- to 12-membered heterocyclyl optionally substituted with 1, 2, 3 or 4 substituents independently selected from R$^{11}$.

In one variation, R$^{10}$ is halogen, cyano, —NR$^c$R$^d$, —C(O)NR$^c$R$^d$, —OR$^b$, —S(O)$_2$R$^e$, C$_{1-6}$ haloalkyl, —(C$_{1-6}$ alkylene)-OH, or —(C$_{1-6}$ alkylene)-OH.

In one variation, R$^{10}$ is hydroxyl, cyano, halogen, —CHF$_2$, —CF$_3$, —NH$_2$, —NH(C$_{1-6}$ alkyl), alkyl)$_2$, —O(C$_{1-6}$ alkyl), —SO$_2$(C$_{1-6}$ alkyl), —S(O)$_2$NR$^c$R$^d$, —C(O)NR$^c$R$^d$, or —N(R$^f$)C(O)R$^a$.

In some embodiments, each R$^a$ is independently hydrogen, C$_{1-6}$ alkyl, C$_{2-6}$ alkenyl, C$_{2-6}$ alkynyl, C$_{3-8}$ cycloalkyl, C$_{6-10}$ aryl, 5- to 10-membered heteroaryl or 3- to 12-membered heterocyclyl; wherein the C$_{1-6}$ alkyl, C$_{2-6}$ alkenyl, C$_{2-6}$ alkynyl, C$_{3-8}$ cycloalkyl, C$_{6-10}$ aryl, 5- to 10-membered heteroaryl and 3- to 12-membered heterocyclyl of R$^a$ are each optionally substituted with 1, 2, 3 or 4 substituents independently selected from R$^{10}$. In one variation, R$^a$ is independently hydrogen or C$_{1-6}$ alkyl.

In some embodiments, each R$^b$ is independently hydrogen, C$_{1-6}$ alkyl, C$_{3-8}$cycloalkyl, C$_{6-10}$ aryl, 5- to 10-membered heteroaryl or 3- to 12-membered heterocyclyl; wherein the C$_{1-6}$ alkyl, C$_{3-8}$ cycloalkyl, C$_{6-10}$ aryl, 5- to 10-membered heteroaryl and 3- to 12-membered heterocyclyl of R$^b$ are each optionally substituted with 1, 2, 3 or 4 substituents independently selected from R$^{11}$. In one variation, R$^b$ is independently hydrogen or C$_{1-6}$ alkyl.

In some embodiments, each R$^e$ and R$^d$ is independently hydrogen, C$_{1-6}$ alkyl, C$_{3-8}$cycloalkyl, C$_{6-10}$ aryl, 5- to 10-membered heteroaryl or 3- to 12-membered heterocyclyl; wherein the C$_{1-6}$ alkyl, C$_{3-8}$ cycloalkyl, C$_{6-10}$ aryl, 5- to 10-membered heteroaryl and 3- to 12-membered heterocyclyl of R$^e$ and R$^d$ are each optionally substituted with 1, 2, 3 or 4 substituents independently selected from R$^{11}$; or R$^e$ and R$^d$ are taken together with the nitrogen atom to which they are attached to form a 4- to 12-membered heterocyclyl optionally substituted with 1, 2, 3 or 4 substituents independently selected from R$^{11}$. In one variation, each R$^e$ and R$^d$ is independently hydrogen or C$_{1-6}$ alkyl.

In some embodiments, each R$^e$ is independently C$_{1-6}$ alkyl, C$_{3-8}$ cycloalkyl, C$_{6-10}$ aryl, 5- to 10-membered heteroaryl or 3- to 12-membered heterocyclyl; wherein the C$_{1-6}$ alkyl, C$_{3-8}$ cycloalkyl, C$_{6-10}$ aryl, 5- to 10-membered heteroaryl and 3- to 12-membered heterocyclyl of R$^e$ are each optionally substituted with 1, 2, 3 or 4 substituents independently selected from R$^{11}$. In one variation, R$^e$ is independently C$_{1-6}$ alkyl.

In some embodiments, each R$^f$ independently hydrogen or C$_{1-6}$ alkyl. In one variation, R$^f$ is hydrogen.

In some embodiments, each R$^{11}$ is independently oxo, C$_{1-6}$ alkyl, C$_{2-6}$ alkenyl, C$_{2-6}$ alkynyl, C$_{3-6}$ cycloalkyl, C$_{6-10}$ aryl, 5- to 10-membered heteroaryl, 3- to 8-membered heterocyclyl, halogen, cyano, —C(O)R$^{a1}$, —C(O)OR$^{b1}$, —C(O)NR$^{c1}$R$^{d1}$, —OR$^{b1}$, —OC(O)R$^{a1}$, —OC(O)NR$^{c1}$R$^{d1}$, —SR$^{b1}$, —S(O)R$^{e1}$, —S(O)$_2$R$^{e1}$, —S(O)$_2$NR$^{c1}$R$^{d1}$, —NR$^{c1}$R$^{d1}$, —N(R$^{f1}$)C(O)R$^{a1}$, —N(R$^{f1}$)C(O)OR$^{b1}$, —N(R$^{f1}$)C(O)NR$^{c1}$R$^{d1}$, —N(R$^{11}$)S(O)$_2$R$^{e1}$, or —N(R$^{f1}$)S(O)$_2$NR$^{c1}$R$^{d1}$; wherein the $C_{1-6}$ alkyl, $C_{2-6}$ alkenyl, $C_{2-6}$ alkynyl, $C_{3-6}$ cycloalkyl, $C_{6-14}$ aryl, 5- to 14-membered heteroaryl and 3- to 14-membered heterocyclyl of R$^{11}$ are each optionally substituted with 1, 2, 3 or 4 substituents independently selected from R$^{10}$.

In one variation, each R$^{11}$ is independently oxo, $C_{1-6}$ alkyl, $C_{3-6}$ cycloalkyl, 3- to 8-membered heterocyclyl, halogen, cyano, or —OR$^{b1}$; wherein the $C_{1-6}$ alkyl, $C_{3-6}$cycloalkyl, and 3- to 14-membered heterocyclyl of R$^{11}$ are each optionally substituted with 1, 2, 3 or 4 substituents independently selected from R$^{10}$.

In one variation, R$^{11}$ is $C_{1-6}$ alkyl optionally substituted with 1, 2, 3 or 4 substituents independently selected from R$^{11}$. In one variation, R$^{11}$ is 3- to 8-membered heterocyclyl optionally substituted with 1, 2, 3 or 4 substituents independently selected from R$^{10}$.

In one variation, R$^{11}$ is halogen, cyano, —NR$^{c1}$R$^{d1}$, —C(O)NR$^{c1}$R$^{d1}$, —OR$^{b1}$, —S(O)$_2$R$^{e1}$, $C_{1-6}$haloalkyl, —($C_{1-6}$ alkylene)-OH, or —($C_{1-6}$ alkylene)-OH.

In one variation, R$^{11}$ is hydroxl, cyano, halogen, —CHF$_2$, —CF$_3$, —NH$_2$, —NH($C_{1-6}$ alkyl), —N($C_{1-6}$ alkyl)$_2$, —O($C_{1-6}$ alkyl), —SO$_2$($C_{1-6}$ alkyl), —S(O)$_2$NR$^{c1}$R$^{d1}$, —C(O)NR$^{c1}$R$^{d1}$, or —N(R$^{f1}$)C(O)R$^{a1}$.

In one variation, R$^{11}$ is halogen, cyano, —O($C_{1-6}$ alkyl), —O($C_{1-6}$ alkylene)-NH$_2$, or —($C_{1-6}$ alkylene)-OH.

In some embodiments, each R$^{a1}$ is independently hydrogen, $C_{1-6}$ alkyl, $C_{2-6}$ alkenyl, $C_{2-6}$alkynyl, $C_{3-6}$ cycloalkyl, $C_{6-10}$ aryl, 5- to 10-membered heteroaryl or 3- to 8-membered heterocyclyl; wherein the $C_{1-6}$ alkyl, $C_{2-6}$ alkenyl, $C_{2-6}$ alkynyl, $C_{3-6}$ cycloalkyl, $C_{6-10}$ aryl, 5- to 10-membered heteroaryl and 3- to 8-membered heterocyclyl of R$^{a1}$ are each optionally substituted with 1, 2, 3 or 4 substituents independently selected from R$^{11}$.

In some embodiments, each R$^{b1}$ is independently hydrogen, $C_{1-6}$ alkyl, $C_{3-6}$ cycloalkyl, $C_{6-10}$ aryl, 5- to 10-membered heteroaryl or 3- to 8-membered heterocyclyl; wherein the $C_{1-6}$ alkyl, $C_{3-6}$ cycloalkyl, $C_{6-10}$ aryl, 5- to 10-membered heteroaryl and 3- to 8-membered heterocyclyl of R$^{b1}$ are each optionally substituted with 1, 2, 3 or 4 substituents independently selected from R$^{12}$. In one variation, R$^{b1}$ is independently hydrogen or $C_{1-6}$ alkyl.

In some embodiments, each R$^{c1}$ and R$^{d1}$ is independently hydrogen, $C_{1-6}$ alkyl, $C_{3-6}$ cycloalkyl, $C_{6-10}$ aryl, 5- to 10-membered heteroaryl or 3- to 8-membered heterocyclyl; wherein the $C_{1-6}$ alkyl, $C_{3-6}$ cycloalkyl, $C_{6-10}$ aryl, 5- to 10-membered heteroaryl and 3- to 8-membered heterocyclyl of R$^{c1}$ and R$^{d1}$ are each optionally substituted with 1, 2, 3 or 4 substituents independently selected from R$^{12}$; or R$^{c1}$ and R$^{d1}$ are taken together with the nitrogen atom to which they are attached to form a 4- to 8-membered heterocyclyl optionally substituted with 1, 2, 3 or 4 substituents independently selected from R$^{12}$. In one variation, each R$^{c1}$ and R$^{d1}$ is independently hydrogen or $C_{1-6}$ alkyl.

In some embodiments, each R$^{e1}$ is independently $C_{1-6}$ alkyl, $C_{3-6}$ cycloalkyl, $C_{6-10}$ aryl, 5- to 10-membered heteroaryl or 3- to 8-membered heterocyclyl; wherein the $C_{1-6}$ alkyl, $C_{3-6}$ cycloalkyl, $C_{6-10}$ aryl, 5- to 10-membered heteroaryl and 3- to 8-membered heterocyclyl of R$^{e1}$ are each optionally substituted with 1, 2, 3 or 4 substituents independently selected from R$^{12}$. In one variation, R$^{e1}$ is independently $C_{1-6}$ alkyl.

In some embodiments, each IV is independently hydrogen or $C_{1-6}$ alkyl. In one variation, R$^{f1}$ is hydrogen.

In some embodiments, each R$^{12}$ is independently oxo, $C_{1-6}$ alkyl, $C_{3-6}$ cycloalkyl, $C_6$ aryl, 5- to 6-membered heteroaryl, 3- to 6-membered heterocyclyl, halogen, cyano, —C(O)R$^{a2}$, —C(O)OR$^{b2}$, —C(O)NR$^{c2}$R$^{d2}$, —OR$^{b2}$, —OC(O)R$^{a2}$, —OC(O)NR$^{c2}$R$^{d2}$, —S(O)$_2$R$^{e2}$, —S(O)$_2$NR$^{c2}$R$^{d2}$, —NR$^{c2}$R$^{d2}$, —N(R$^{f2}$)C(O)R$^{a2}$, —N(R$^{f2}$)C(O)OR$^{b2}$, —N(R$^{f2}$)C(O)NR$^{c2}$R$^{d2}$, —N(R$^{f2}$)S(O)$_2$R$^{e2}$, or —N(R$^{f2}$)S(O)$_2$NR$^{c2}$R$^{d2}$; wherein the $C_{1-6}$ alkyl, $C_{3-6}$cycloalkyl, $C_6$ aryl, 5- to 6-membered heteroaryl and 3- to 6-membered heterocyclyl of R$^{12}$ are each optionally substituted with 1, 2, 3 or 4 substituents independently selected from R$^{13}$.

In one variation, each R$^{12}$ is independently oxo, halogen, cyano, —OR$^{b2}$, or $C_{1-6}$ alkyl optionally substituted with 1, 2, 3 or 4 substituents independently selected from R$^{13}$. In one variation, each R$^{12}$ is independently oxo, halogen, cyano, or hydroxyl.

In one variation, R$^{12}$ is $C_{1-6}$ alkyl optionally substituted with 1, 2, 3 or 4 substituents independently selected from R$^{13}$.

In one variation, R$^{12}$ is oxo, hydroxyl, $C_{1-6}$ alkyl, or —O($C_{1-6}$ alkyl).

In some embodiments, each R$^{a2}$ is independently hydrogen, $C_{1-6}$ alkyl, $C_{3-6}$ cycloalkyl, $C_6$ aryl, 5- to 6-membered heteroaryl or 3- to 6-membered heterocyclyl; wherein the $C_{1-6}$ alkyl, $C_{3-6}$ cycloalkyl, $C_6$ aryl, 5- to 6-membered heteroaryl and 3- to 6-membered heterocyclyl of R$^{a2}$ are each optionally substituted with 1, 2, 3 or 4 substituents independently selected from R$^{13}$. In one variation, R$^{a2}$ is independently hydrogen or $C_{1-6}$ alkyl.

In some embodiments, each R$^{b2}$ is independently hydrogen, $C_{1-6}$ alkyl, $C_{3-6}$cycloalkyl or 3- to 6-membered heterocyclyl; wherein the $C_{1-6}$ alkyl, $C_{3-6}$ cycloalkyl and 3- to 6-membered heterocyclyl of R$^{b2}$ are each optionally substituted with 1, 2, 3 or 4 substituents independently selected from R$^{13}$. In one variation, R$^{b2}$ is hydrogen.

In some embodiments, each R$^{c2}$ and R$^{d2}$ is independently hydrogen, $C_{1-6}$ alkyl, $C_{3-6}$cycloalkyl or 3- to 8-membered heterocyclyl; wherein the $C_{1-6}$ alkyl, $C_{3-6}$ cycloalkyl and 3- to 8-membered heterocyclyl of R$^{c2}$ and R$^{d2}$ are each optionally substituted with 1, 2, 3 or 4 substituents independently selected from R$^{13}$; or R$^{c2}$ and R$^{d2}$ are taken together with the nitrogen atom to which they are attached to form a 4- to 6-membered heterocyclyl optionally substituted with 1, 2, 3 or 4 substituents independently selected from R$^{13}$. In one variation, each R$^{c2}$ and R$^{d2}$ is independently hydrogen or $C_{1-6}$ alkyl.

In some embodiments, each R$^{e2}$ is independently $C_{1-6}$ alkyl, $C_{3-6}$ cycloalkyl, $C_6$ aryl, 5- to 6-membered heteroaryl or 3- to 6-membered heterocyclyl; wherein the $C_{1-6}$ alkyl, $C_{3-6}$ cycloalkyl, $C_6$ aryl, 5- to 6-membered heteroaryl and 3- to 6-membered heterocyclyl of R$^{e2}$ are each optionally substituted with 1, 2, 3 or 4 substituents independently selected from R$^{13}$. In one variation, R$^{e2}$ is independently $C_{1-6}$ alkyl.

In some embodiments, each R$^{f2}$ is independently hydrogen or $C_{1-6}$ alkyl. In one variation, R$^{f2}$ is hydrogen.

In some embodiments, each R$^{13}$ is independently oxo, halogen, hydroxyl, —O($C_{1-6}$ alkyl), cyano, $C_{1-6}$ alkyl or $C_1$-t haloalkyl.

In one variation, each R$^{13}$ is independently halogen, hydroxyl, —O($C_{1-6}$ alkyl), cyano, or $C_{1-6}$ alkyl.

In one variation, R$^{13}$ is oxo, hydroxyl, $C_{1-6}$ alkyl, or —O($C_{1-6}$ alkyl).

Representative compounds are listed in Table 1. It is understood that individual enatiomers and diastereomers are included in the table below by Compound No. and Compound Name, and their corresponding structures can bereadily determined therefrom. In some instances, the enan tiomers or diastereomers are identified by their respective properties, for example, retention times on a chiral HPLC or its biological activities, and the absolute stereo configurations of the chiral centers are arbitrarily assigned.

TABLE 1

| No. | Structure | Name |
| --- | --- | --- |
| 1 | 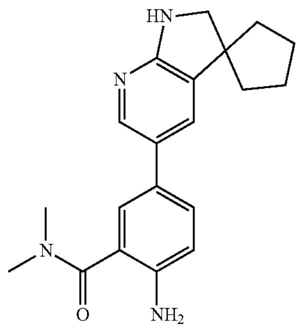 [SMILES: CN(C)C(=O)c1cc(-c2cnc3c(c2)C2(CCCC2)CN3)ccc1N] | 2-Amino-5-(1',2'-dihydrospiro[cyclopentane-1,3'-pyrrolo[2,3-b]pyridin]-5'-yl)-N,N-dimethylbenzamide |
| 2 | 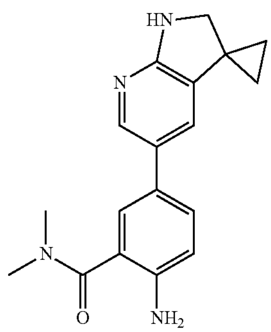 [SMILES: CN(C)C(=O)c1cc(-c2cnc3c(c2)C2(CC2)CN3)ccc1N] | 2-Amino-5-(1',2'-dihydrospiro[cyclopropane-1,3'-pyrrolo[2,3-b]pyridin]-5'-yl)-N,N-dimethylbenzamide |
| 3 | 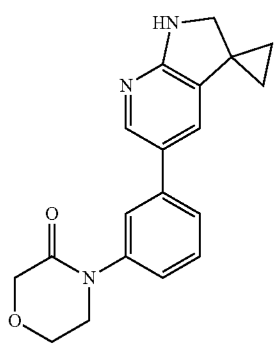 [SMILES: O=C1COCCN1c1cccc(-c2cnc3c(c2)C2(CC2)CN3)c1] | 4-(3-(1',2'-Dihydrospiro[cyclopropane-1,3'-pyrrolo[2,3-b]pyridin]-5'-yl)phenyl)morpholin-3-one |
| 4 | 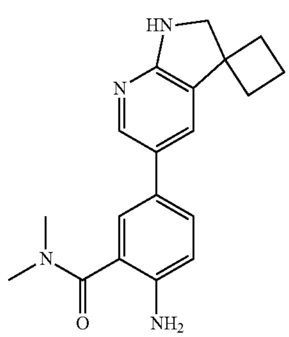 [SMILES: CN(C)C(=O)c1cc(-c2cnc3c(c2)C2(CCC2)CN3)ccc1N] | 2-Amino-5-(1',2'-dihydrospiro[cyclobutane-1,3'-pyrrolo[2,3-b]pyridin]-5'-yl)-N,N-dimethylbenzamide |

TABLE 1-continued

| No. | Structure | Name |
|---|---|---|
| 5 | 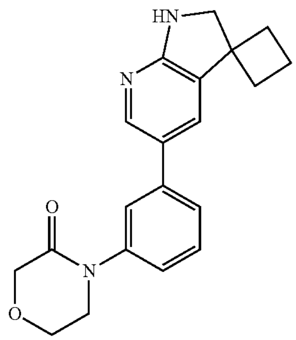 [SMILES: O=C1COCCN1c1cccc(-c2cnc3c(c2)C2(CCC2)CN3)c1] | 4-(3-(1',2'-Dihydrospiro[cyclobutane-1,3'-pyrrolo[2,3-b]pyridin]-5'-yl)phenyl)morpholin-3-one |
| 6 | 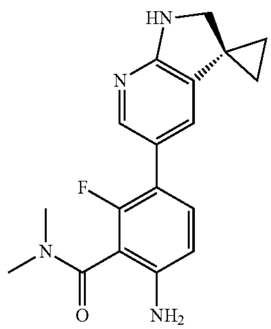 | 6-Amino-3-(1',2'-dihydrospiro[cyclopropane-1,3'-pyrrolo[2,3-b]pyridin]-5'-yl)-2-fluoro-N,N-dimethylbenzamide |
| 7 | 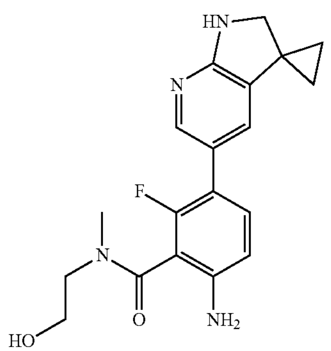 [SMILES: CN(CCO)C(=O)c1c(N)ccc(-c2cnc3c(c2)C2(CC2)CN3)c1F] | 6-amino-3-(1',2'-dihydrospiro[cyclopropane-1,3'-pyrrolo[2,3-b]pyridin]-5'-yl)-2-fluoro-N-(2-hydroxyethyl)-N-methylbenzamide |
| 8 | 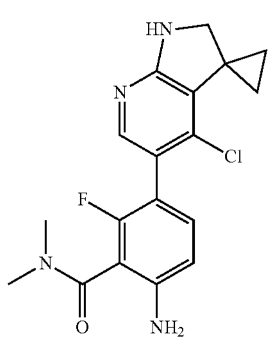 [SMILES: CN(C)C(=O)c1c(N)ccc(-c2cnc3c(c2Cl)C2(CC2)CN3)c1F] | 6-Amino-3-(4'-chloro-1',2'-dihydrospiro[cyclopropane-1,3'-pyrrolo[2,3-b]pyridin]-5'-yl)-2-fluoro-N,N-dimethylbenzamide |

TABLE 1-continued

| No. | Structure | Name |
|---|---|---|
| 9 | 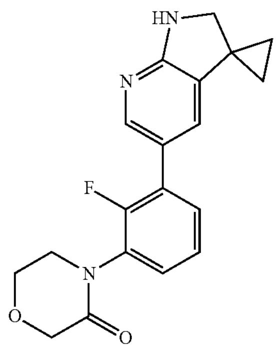 [SMILES: O=C1COCCN1c1cccc(-c2cnc3c(c2)C2(CC2)CN3)c1F] | 4-(3-(1',2'-Dihydrospiro[cyclopropane-1,3'-pyrrolo[2,3-b]pyridin]-5'-yl)-2-fluorophenyl)morpholin-3-one |
| 10 | 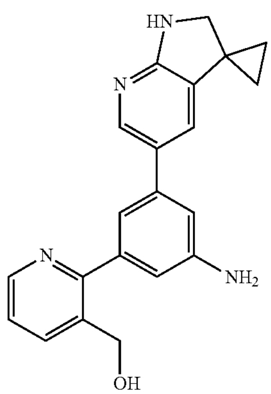 [SMILES: Nc1cc(-c2cnc3c(c2)C2(CC2)CN3)cc(-c2ncccc2CO)c1] | (2-(3-Amino-5-(1',2'-dihydrospiro[cyclopropane-1,3'-pyrrolo[2,3-b]pyridin]-5'-yl)phenyl)pyridin-3-yl)methanol |
| 11 | 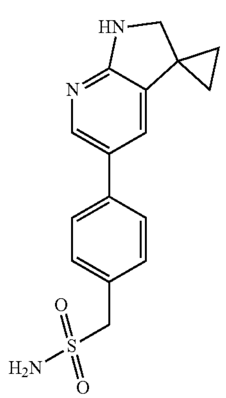 [SMILES: NS(=O)(=O)Cc1ccc(-c2cnc3c(c2)C2(CC2)CN3)cc1] | (4-(1',2'-Dihydrospiro[cyclopropane-1,3'-pyrrolo[2,3-b]pyridin]-5'-yl)phenyl)methanesulfonamide |
| 12 | 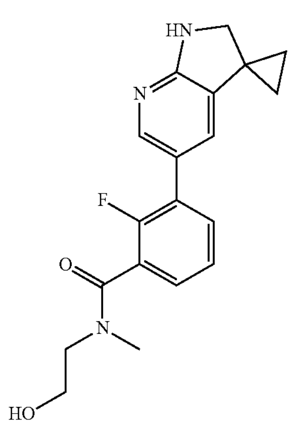 [SMILES: CN(CCO)C(=O)c1cccc(-c2cnc3c(c2)C2(CC2)CN3)c1F] | 3-(1',2'-Dihydrospiro[cyclopropane-1,3'-pyrrolo[2,3-b]pyridin]-5'-yl)-2-fluoro-N-(2-hydroxyethyl)-N-methylbenzamide |

TABLE 1-continued

| No. | Structure | Name |
| --- | --- | --- |
| 13 | 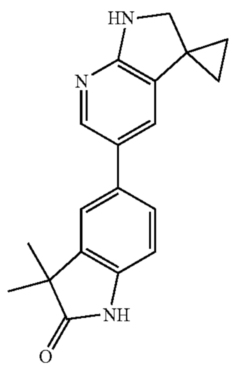 [SMILES: CC1(C)C(=O)Nc2ccc(-c3cnc4c(c3)C3(CC3)CN4)cc21] | 5-(1',2'-dihydrospiro[cyclopropane-1,3'-pyrrolo[2,3-b]pyridin]-5'-yl)-3,3-dimethylindolin-2-one |
| 14 | 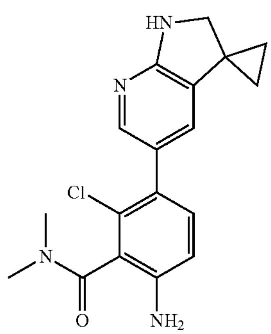 [SMILES: CN(C)C(=O)c1c(N)ccc(-c2cnc3c(c2)C2(CC2)CN3)c1Cl] | 6-amino-2-chloro-3-(1',2'-dihydrospiro[cyclopropane-1,3'-pyrrolo[2,3-b]pyridin]-5'-yl)-N,N-dimethylbenzamide |
| 15 | 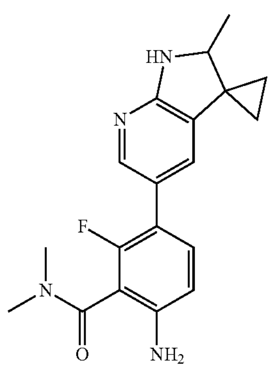 [SMILES: CC1Nc2ncc(-c3ccc(N)c(C(=O)N(C)C)c3F)cc2C12CC2] | 6-Amino-2-fluoro-N,N-dimethyl-3-(2'-methyl-1',2'-dihydrospiro[cyclopropane-1,3'-pyrrolo[2,3-b]pyridin]-5'-yl)benzamide |
| 16 | 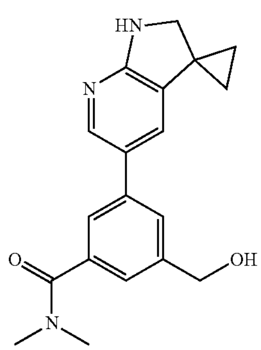 [SMILES: CN(C)C(=O)c1cc(CO)cc(-c2cnc3c(c2)C2(CC2)CN3)c1] | 3-(1',2'-dihydrospiro[cyclopropane-1,3'-pyrrolo[2,3-b]pyridin]-5'-yl)-5-(hydroxymethyl)-N,N-dimethylbenzamide |

TABLE 1-continued

| No. | Structure | Name |
| --- | --- | --- |
| 17 | 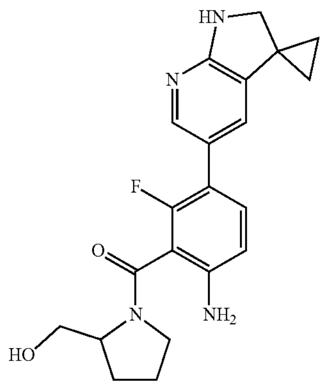 [SMILES: Nc1ccc(-c2cnc3c(c2)C2(CC2)CN3)c(F)c1C(=O)N1CCCC1CO] | (6-amino-3-(1',2'-dihydrospiro[cyclopropane-1,3'-pyrrolo[2,3-b]pyridin]-5'-yl)-2-fluorophenyl)(2-(hydroxymethyl)pyrrolidin-1-yl)methanone |
| 17a 17b | | (R)-(6-amino-3-(1',2'-dihydrospiro[cyclopropane-1,3'-pyrrolo[2,3-b]pyridin]-5'-yl)-2-fluorophenyl)(2-(hydroxymethyl)pyrrolidin-1-yl)methanone<br>(S)-(6-amino-3-(1',2'-dihydrospiro[cyclopropane-1,3'-pyrrolo[2,3-b]pyridin]-5'-yl)-2-fluorophenyl)(2-(hydroxymethyl)pyrrolidin-1-yl)methanone |
| 18 | 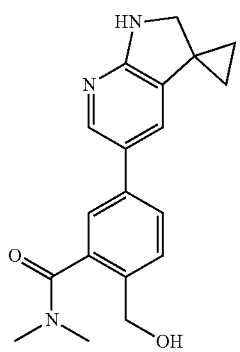 [SMILES: CN(C)C(=O)c1cc(-c2cnc3c(c2)C2(CC2)CN3)ccc1CO] | 5-(1',2'-dihydrospiro[cyclopropane-1,3'-pyrrolo[2,3-b]pyridin]-5'-yl)-2-(hydroxymethyl)-N,N-dimethylbenzamide |
| 19 | 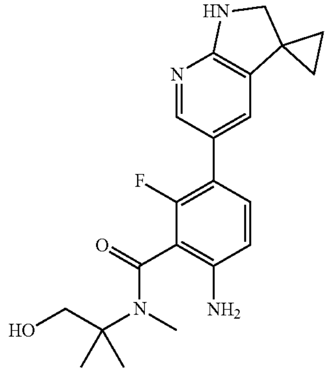 [SMILES: CN(C(=O)c1c(N)ccc(-c2cnc3c(c2)C2(CC2)CN3)c1F)C(C)(C)CO] | 6-amino-3-(1',2'-dihydrospiro[cyclopropane-1,3'-pyrrolo[2,3-b]pyridin]-5'-yl)-2-fluoro-N-(1-hydroxy-2-methylpropan-2-yl)-N-methylbenzamide |

TABLE 1-continued

| No. | Structure | Name |
|---|---|---|
| 20 | 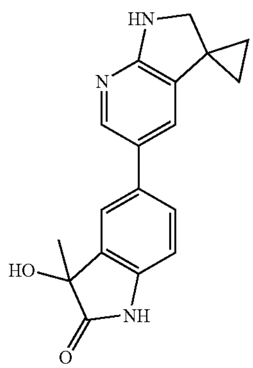 [SMILES: CC1(O)C(=O)Nc2ccc(-c3cnc4c(c3)C3(CC3)CN4)cc21] | 5-(1',2'-dihydrospiro[cyclopropane-1,3'-pyrrolo[2,3-b]pyridin]-5'-yl)-3-hydroxy-3-methylindolin-2-one |
| 21 | 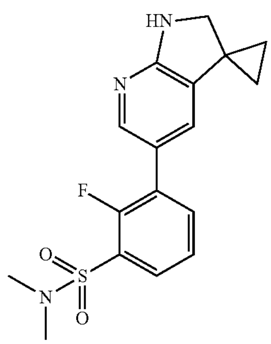 [SMILES: CN(C)S(=O)(=O)c1cccc(-c2cnc3c(c2)C2(CC2)CN3)c1F] | 3-(1',2'-dihydrospiro[cyclopropane-1,3'-pyrrolo[2,3-b]pyridin]-5'-yl)-2-fluoro-N,N-dimethylbenzenesulfonamide |
| 22 | 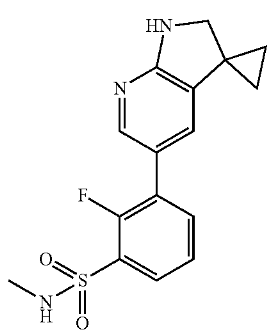 [SMILES: CNS(=O)(=O)c1cccc(-c2cnc3c(c2)C2(CC2)CN3)c1F] | 3-(1',2'-dihydrospiro[cyclopropane-1,3'-pyrrolo[2,3-b]pyridin]-5'-yl)-2-fluoro-N-methylbenzenesulfonamide |
| 23 | 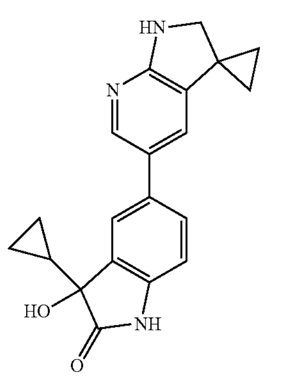 [SMILES: O=C1Nc2ccc(-c3cnc4c(c3)C3(CC3)CN4)cc2C1(O)C1CC1] | 3-cyclopropyl-5-(1',2'-dihydrospiro[cyclopropane-1,3'-pyrrolo[2,3-b]pyridin]-5'-yl)-3-hydroxyindolin-2-one |
| 23a 23b | | (R)-3-cyclopropyl-5-(1',2'-dihydrospiro[cyclopropane-1,3'-pyrrolo[2,3-b]pyridin]-5'-yl)-3-hydroxyindolin-2-one (S)-3-cyclopropyl-5-(1',2'-dihydrospiro[cyclopropane-1,3'-pyrrolo[2,3-b]pyridin]-5'-yl)-3-hydroxyindolin-2-one |

TABLE 1-continued

| No. | Structure | Name |
|---|---|---|
| 24 | 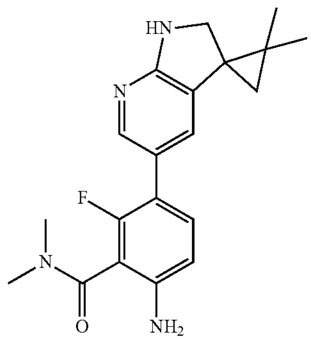 | 6-Amino-3-(2,2-dimethyl-1',2'-dihydrospiro[cyclopropane-1,3'-pyrrolo[2,3-b]pyridin]-5'-yl)-2-fluoro-N,N-dimethylbenzamide |
| 24a<br>24b | | (R)-6-Amino-3-(2,2-dimethyl-1',2'-dihydrospiro[cyclopropane-1,3'-pyrrolo[2,3-b]pyridin]-5'-yl)-2-fluoro-N,N-dimethylbenzamide<br>(S)-6-Amino-3-(2,2-dimethyl-1',2'-dihydrospiro[cyclopropane-1,3'-pyrrolo[2,3-b]pyridin]-5'-yl)-2-fluoro-N,N-dimethylbenzamide |
| 25 | 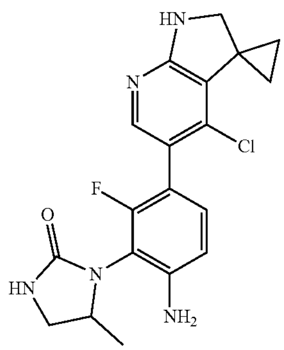 [SMILES: CC1CNC(=O)N1c1c(N)ccc(-c2cnc3c(c2Cl)C2(CC2)CN3)c1F] | 1-(6-amino-3-(4'-chloro-1',2'-dihydrospiro[cyclopropane-1,3'-pyrrolo[2,3-b]pyridin]-5'-yl)-2-fluorophenyl)-5-methylimidazolidin-2-one |
| 25a<br>25b | | (R)-1-(6-amino-3-(4'-chloro-1',2'-dihydrospiro[cyclopropane-1,3'-pyrrolo[2,3-b]pyridin]-5'-yl)-2-fluorophenyl)-5-methylimidazolidin-2-one<br>(S)-1-(6-amino-3-(4'-chloro-1',2'-dihydrospiro[cyclopropane-1,3'-pyrrolo[2,3-b]pyridin]-5'-yl)-2-fluorophenyl)-5-methylimidazolidin-2-one |
| 26 | 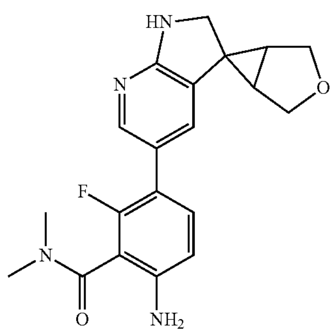 [SMILES: CN(C)C(=O)c1c(N)ccc(-c2cnc3c(c2)C2(CN3)C3COCC32)c1F] | 6-amino-3-(1',2'-dihydro-3-oxaspiro[bicyclo[3.1.0]hexane-6,3'-pyrrolo[2,3-b]pyridin]-5'-yl)-2-fluoro-N,N-dimethylbenzamide |

TABLE 1-continued

| No. | Structure | Name |
|---|---|---|
| 27 | 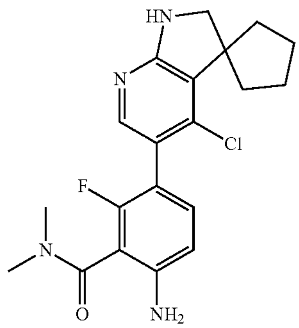 [SMILES: CN(C)C(=O)c1c(N)ccc(-c2cnc3c(c2Cl)C2(CCCC2)CN3)c1F] | 6-Amino-3-(4'-chloro-1',2'-dihydrospiro[cyclopentane-1,3'-pyrrolo[2,3-b]pyridin]-5'-yl)-2-fluoro-N,N-dimethylbenzamide |
| 28 | 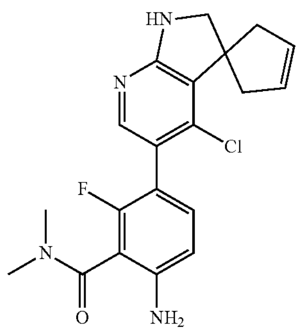 [SMILES: CN(C)C(=O)c1c(N)ccc(-c2cnc3c(c2Cl)C2(CC=CC2)CN3)c1F] | 6-Amino-3-(4'-chloro-1',2'-dihydrospiro[cyclopentane-1,3'-pyrrolo[2,3-b]pyridin]-3-en-5'-yl)-2-fluoro-N,N-dimethylbenzamide |
| 29 | 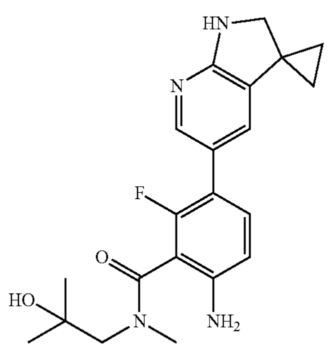 [SMILES: CN(CC(C)(C)O)C(=O)c1c(N)ccc(-c2cnc3c(c2)C2(CC2)CN3)c1F] | 6-amino-3-(1',2'-dihydrospiro[cyclopropane-1,3'-pyrrolo[2,3-b]pyridin]-5'-yl)-2-fluoro-N-(2-hydroxy-2-methylpropyl)-N-methylbenzamide |
| 30 | 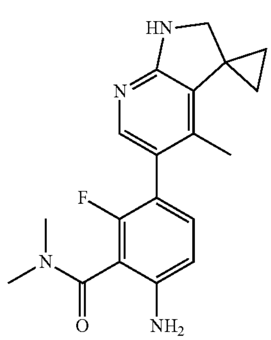 [SMILES: Cc1c(-c2ccc(N)c(C(=O)N(C)C)c2F)cnc2c1C1(CC1)CN2] | 6-Amino-2-fluoro-N,N-dimethyl-3-(4'-methyl-1',2'-dihydrospiro[cyclopropane-1,3'-pyrrolo[2,3-b]pyridin]-5'-yl)benzamide |

TABLE 1-continued

| No. | Structure | Name |
|---|---|---|
| 31 | 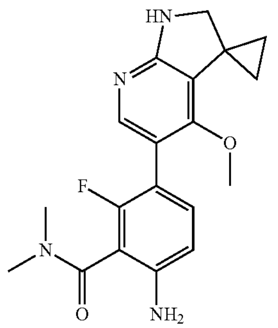 [SMILES: COc1c(-c2ccc(N)c(C(=O)N(C)C)c2F)cnc2c1C1(CC1)CN2] | 6-Amino-2-fluoro-3-(4'-methoxy-1',2'-dihydrospiro[cyclopropane-1,3'-pyrrolo[2,3-b]pyridin]-5'-yl)-N,N-dimethylbenzamide |
| 32 | 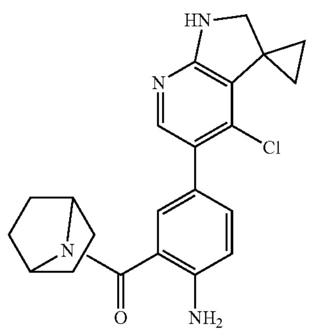 | (2-Amino-5-(4'-chloro-1',2'-dihydrospiro[cyclopropane-1,3'-pyrrolo[2,3-b]pyridin]-5'-yl)phenyl)(7-azabicyclo[2.2.1]heptan-7-yl)methanone |
| 33 | 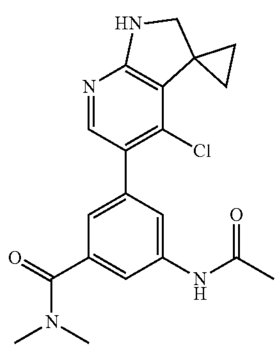 [SMILES: CC(=O)Nc1cc(C(=O)N(C)C)cc(-c2cnc3c(c2Cl)C2(CC2)CN3)c1] | 3-acetamido-5-(4'-chloro-1',2'-dihydrospiro[cyclopropane-1,3'-pyrrolo[2,3-b]pyridin]-5'-yl)-N,N-dimethylbenzamide |
| 34 | 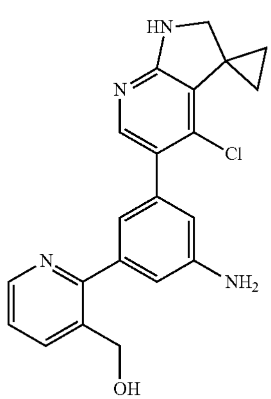 [SMILES: Nc1cc(-c2cnc3c(c2Cl)C2(CC2)CN3)cc(-c2ncccc2CO)c1] | (2-(3-Amino-5-(4'-chloro-1',2'-dihydrospiro[cyclopropane-1,3'-pyrrolo[2,3-b]pyridin]-5'-yl)phenyl)pyridin-3-yl)methanol |

TABLE 1-continued

| No. | Structure | Name |
|---|---|---|
| 35 | 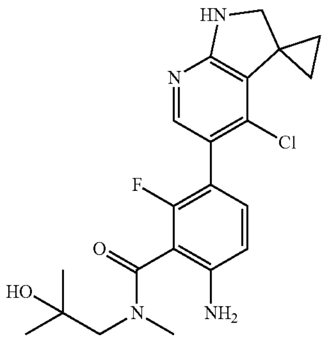 [SMILES: CN(CC(C)(C)O)C(=O)c1c(N)ccc(-c2cnc3c(c2Cl)C2(CC2)CN3)c1F] | 6-amino-3-(4'-chloro-1',2'-dihydrospiro[cyclopropane-1,3'-pyrrolo[2,3-b]pyridin]-5'-yl)-2-fluoro-N-(2-hydroxy-2-methylpropyl)-N-methylbenzamide |
| 36 | 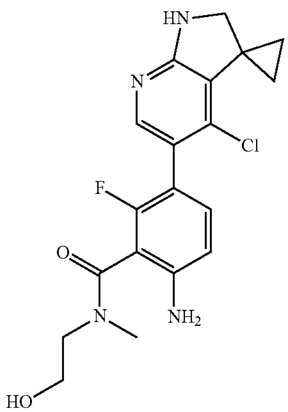 [SMILES: CN(CCO)C(=O)c1c(N)ccc(-c2cnc3c(c2Cl)C2(CC2)CN3)c1F] | 6-Amino-3-(4'-chloro-1',2'-dihydrospiro[cyclopropane-1,3'-pyrrolo[2,3-b]pyridin]-5'-yl)-2-fluoro-N-(2-hydroxyethyl)-N-methylbenzamide |
| 37 | 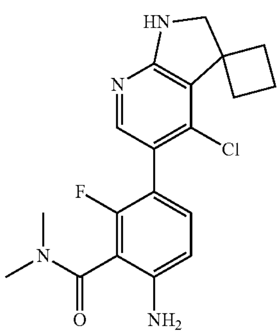 [SMILES: CN(C)C(=O)c1c(N)ccc(-c2cnc3c(c2Cl)C2(CCC2)CN3)c1F] | 6-Amino-3-(4'-chloro-1',2'-dihydrospiro[cyclobutane-1,3'-pyrrolo[2,3-b]pyridin]-5'-yl)-2-fluoro-N,N-dimethylbenzamide |
| 38 | 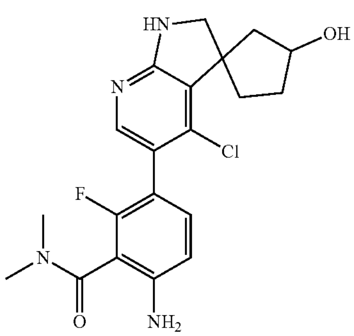 [SMILES: CN(C)C(=O)c1c(N)ccc(-c2cnc3c(c2Cl)C2(CCC(O)C2)CN3)c1F] | 6-Amino-3-(4'-chloro-3-hydroxy-1',2'-dihydrospiro[cyclopentane-1,3'-pyrrolo[2,3-b]pyridin]-5'-yl)-2-fluoro-N,N-dimethylbenzamide |
| 38a 38b | | 6-Amino-3-((1R,3R)-4'-chloro-3-hydroxy-1',2'-dihydrospiro[cyclopentane-1,3'-pyrrolo[2,3-b]pyridin]-5'-yl)-2-fluoro-N,N-dimethylbenzamide 6-Amino-3-((1S,3S)-4'-chloro-3-hydroxy-1',2'-dihydrospiro[cyclopentane-1,3'-pyrrolo[2,3-b]pyridin]-5'-yl)-2-fluoro-N,N-dimethylbenzamide |

TABLE 1-continued

| No. | Structure | Name |
|---|---|---|
| 38c<br>38d | | 6-Amino-3-((1R,3S)-4'-chloro-3-hydoxy-1',2'-dihydrospiro[cyclopentane-1,3'-pyrrolo[2,3-b]pyridin]5'-yl)-2-fluoro-N,N-dimethylbenzamide<br>6-Amino-3-((1S,3R)-4'-chloro-3-hydroxy-1',2'-dihydrospiro[cyclopentane-1,3'-pyrrolo[2,3-b]pyridin]-5'-yl)-2-fluoro-N,N-dimethylbenzamide |
| 39 | 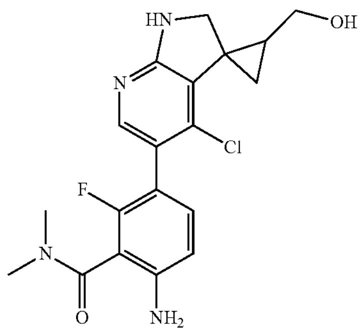 [SMILES: CN(C)C(=O)c1c(N)ccc(-c2cnc3c(c2Cl)C2(CN3)CC2CO)c1F] | 6-Amino-3-(4'-chloro-2-(hydroxymethyl)-1',2'-dihydrospiro[cyclopropane-1,3'-pyrrolo[2,3-b]pyridin]-5'-yl)-2-fluoro-N,N-dimethylbenzamide |
| 39a<br>39b | | 6-Amino-3-((1R,2R)-4'-chloro-2-(hydroxymethyl)-1',2'-dihydrospiro[cyclopropane-1,3'-pyrrolo[2,3-b]pyridin]-5'-yl)-2-fluoro-N,N-dimethylbenzamide<br>6-Amino-3-((1S,2S)-4'-chloro-2-(hydroxymethyl)-1',2'-dihydrospiro[cyclopropane-1,3'-pyrrolo[2,3-b]pyridin]-5'-yl)-2-fluoro-N,N-dimethylbenzamide |
| 39c<br>39d | | 6-Amino-3-((1R,2S)-4'-chloro-2-(hydroxymethyl)-1',2'-dihydrospiro[cyclopropane-1,3'-pyrrolo[2,3-b]pyridin]-5'-yl)-2-fluoro-N,N-dimethylbenzamide<br>6-Amino-3-((1S,2R)-4'-chloro-2-(hydroxymethyl)-1',2'-dihydrospiro[cyclopropane-1,3'-pyrrolo[2,3-b]pyridin]-5'-yl)-2-fluoro-N,N-dimethylbenzamide |
| 40 | 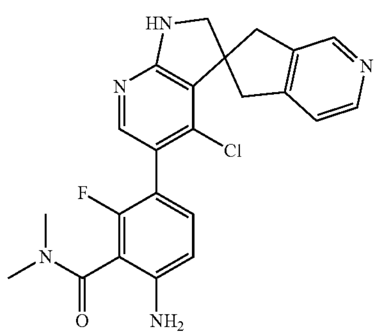 [SMILES: CN(C)C(=O)c1c(N)ccc(-c2cnc3c(c2Cl)C2(CN3)Cc3ccncc3C2)c1F] | 6-Amino-3-(4'-chloro-1',2',5,7-tetrahydrospiro[cyclopenta[c]pyridine-6,3'-pyrrolo[2,3-b]pyridin]-5'-yl)-2-fluoro-N,N-dimethylbenzamide |
| 40a<br>40b | | (R)-6-Amino-3-(4'-chloro-1',2',5,7-tetrahydrospiro[cyclopenta[c]pyridine-6,3'-pyrrolo[2,3-b]pyridin]-5'-yl)-2-fluoro-N,N-dimethylbenzamide<br>(S)-6-Amino-3-(4'-chloro-1',2',5,7-tetrahydrospiro[cyclopenta[c]pyridine-6,3'-pyrrolo[2,3-b]pyridin]-5'-yl)-2-fluoro-N,N-dimethylbenzamide |
| 41 | 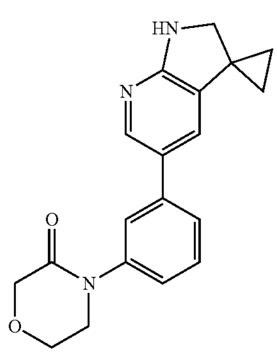 [SMILES: O=C1COCCN1c1cccc(-c2cnc3c(c2)C2(CC2)CN3)c1] | 4-(3-(1',2'-Dihydrospiro[cyclopropane-1,3'-pyrrolo[2,3-b]pyridin]-5'-yl)phenyl)morpholin-3-one |

TABLE 1-continued

| No. | Structure | Name |
|---|---|---|
| 42 | 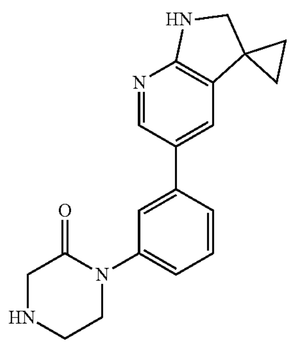 [SMILES: O=C1CNCCN1c1cccc(-c2cnc3c(c2)C2(CC2)CN3)c1] | 1-(3-(1',2'-Dihydrospiro[cyclopropane-1,3'-pyrrolo[2,3-b]pyridin]-5'-yl)phenyl)piperazin-2-one |
| 43 | 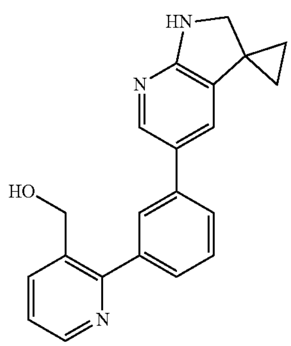 [SMILES: OCc1cccnc1-c1cccc(-c2cnc3c(c2)C2(CC2)CN3)c1] | (2-(3-(1',2'-Dihydrospiro[cyclopropane-1,3'-pyrrolo[2,3-b]pyridin]-5'-yl)phenyl)pyridin-3-yl)methanol |
| 44 | 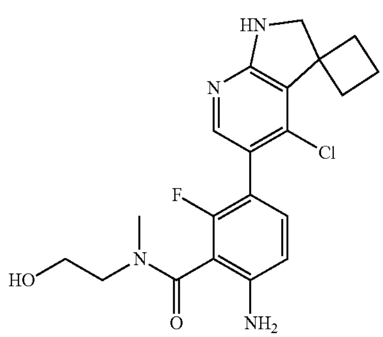 [SMILES: CN(CCO)C(=O)c1c(N)ccc(-c2cnc3c(c2Cl)C2(CCC2)CN3)c1F] | 6-Amino-3-(4'-chloro-1',2'-dihydrospiro[cyclobutane-1,3'-pyrrolo[2,3-b]pyridin]-5'-yl)-2-fluoro-N-(2-hydroxyethyl)-N-methylbenzamide |
| 45 | 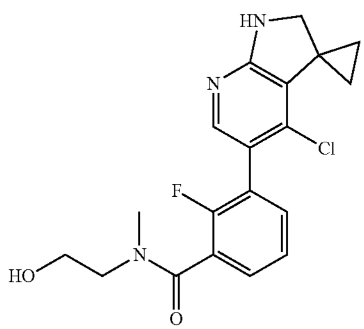 [SMILES: CN(CCO)C(=O)c1cccc(-c2cnc3c(c2Cl)C2(CC2)CN3)c1F] | 3-(4'-Chloro-1',2'-dihydrospiro[cyclopropane-1,3'-pyrrolo[2,3-b]pyridin]-5'-yl)-2-fluoro-N-(2-hydroxyethyl)-N-methylbenzamide |

TABLE 1-continued

| No. | Structure | Name |
|---|---|---|
| 46 | 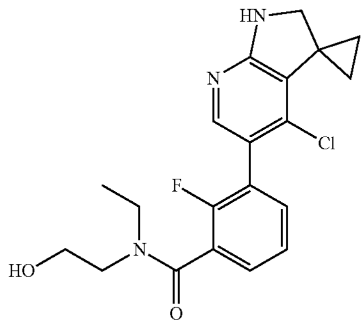 [SMILES: CCN(CCO)C(=O)c1cccc(-c2cnc3c(c2Cl)C2(CC2)CN3)c1F] | 3-(4'-Chloro-1',2'-dihydrospiro[cyclopropane-1,3'-pyrrolo[2,3-b]pyridin]-5'-yl)-N-ethyl-2-fluoro-N-(2-hydroxyethyl)benzamide |
| 47 | 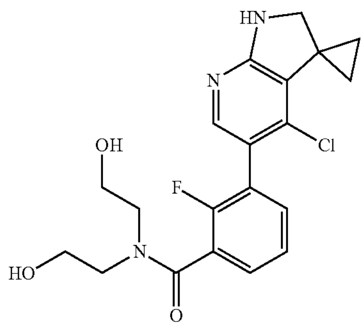 [SMILES: O=C(c1cccc(-c2cnc3c(c2Cl)C2(CC2)CN3)c1F)N(CCO)CCO] | 3-(4'-Chloro-1',2'-dihydrospiro[cyclopropane-1,3'-pyrrolo[2,3-b]pyridin]-5'-yl)-2-fluoro-N,N-bis(2-hydroxyethyl)benzamide |
| 48 | 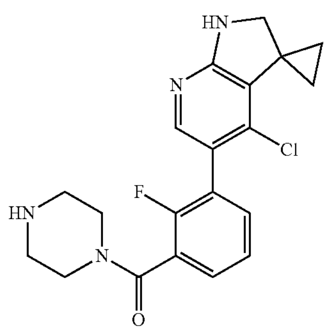 [SMILES: O=C(c1cccc(-c2cnc3c(c2Cl)C2(CC2)CN3)c1F)N1CCNCC1] | (3-(4'-Chloro-1',2'-dihydrospiro[cyclopropane-1,3'-pyrrolo[2,3-b]pyridin]-5'-yl)-2-fluorophenyl)(piperazin-1-yl)methanone |
| 49 | 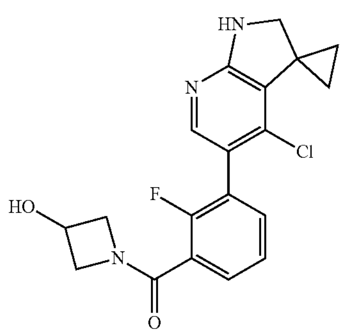 [SMILES: O=C(c1cccc(-c2cnc3c(c2Cl)C2(CC2)CN3)c1F)N1CC(O)C1] | ((3-(4'-Chloro-1',2'-dihydrospiro[cyclopropane-1,3'-pyrrolo[2,3-b]pyridin]-5'-yl)-2-fluorophenyl)(3-hydroxyazetidin-1-yl)methanone |

TABLE 1-continued

| No. | Structure | Name |
|---|---|---|
| 50 | 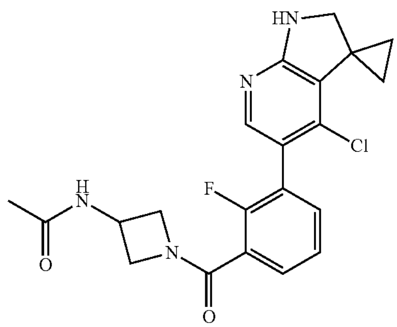 [SMILES: CC(=O)NC1CN(C(=O)c2cccc(-c3cnc4c(c3Cl)C3(CC3)CN4)c2F)C1] | N-(1-(3-(4'-Chloro-1',2'-dihydrospiro[cyclopropane-1,3'-pyrrolo[2,3-b]pyridin]-5'-yl)-2-fluorobenzoyl)azetidin-3-yl)acetamide |
| 51 | 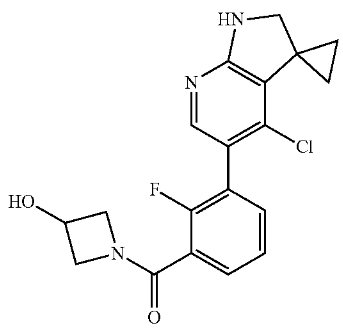 [SMILES: O=C(c1cccc(-c2cnc3c(c2Cl)C2(CC2)CN3)c1F)N1CC(O)C1] | (3-Aminoazetidin-1-yl)(3-(4'-chloro-1',2'-dihydrospiro[cyclopropane-1,3'-pyrrolo[2,3-b]pyridin]-5'-yl)-2-fluorophenyl)methanone |
| 52 | 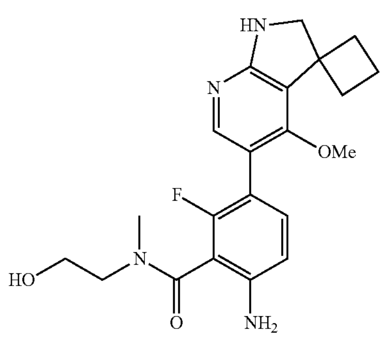 [SMILES: COc1c(-c2ccc(N)c(C(=O)N(C)CCO)c2F)cnc2c1C1(CCC1)CN2] | 6-Amino-2-fluoro-N-(2-hydroxyethyl)-3-(4'-methoxy-1',2'-dihydrospiro[cyclobutane-1,3'-pyrrolo[2,3-b]pyridin]-5'-yl)-N-methylbenzamide |
| 53 | 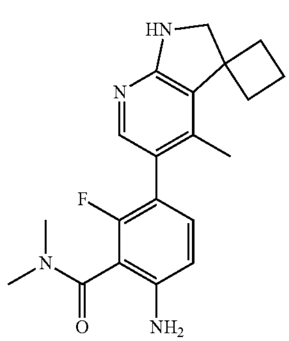 [SMILES: Cc1c(-c2ccc(N)c(C(=O)N(C)C)c2F)cnc2c1C1(CCC1)CN2] | 6-Amino-2-fluoro-N,N-dimethyl-3-(4'-methyl-1',2'-dihydrospiro[cyclobutane-1,3'-pyrrolo[2,3-b]pyridin]-5'-yl)benzamide |

TABLE 1-continued

| No. | Structure | Name |
|---|---|---|
| 54 | 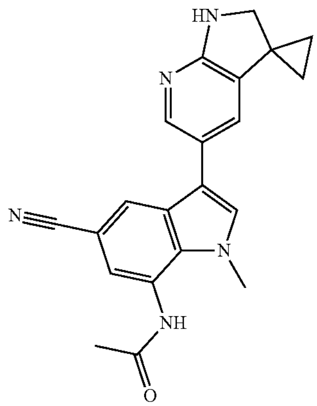 [SMILES: CC(=O)Nc1cc(C#N)cc2c(-c3cnc4c(c3)C3(CC3)CN4)cn(C)c12] | N-(5-Cyano-3-(1',2'-dihydrospiro[cyclopropane-1,3'-pyrrolo[2,3-b]pyridin]-5'-yl)-1-methyl-1H-indol-7-yl)acetamide |
| 55 | 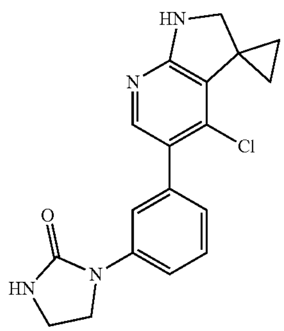 [SMILES: O=C1NCCN1c1cccc(-c2cnc3c(c2Cl)C2(CC2)CN3)c1] | 1-(3-(4'-Chloro-1',2'-dihydrospiro[cyclopropane-1,3'-pyrrolo[2,3-b]pyridin]-5'-yl)phenyl)imidazolidin-2-one |
| 56 | 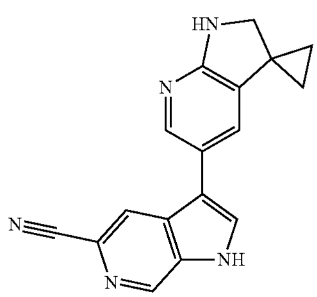 [SMILES: N#Cc1cc2c(-c3cnc4c(c3)C3(CC3)CN4)c[nH]c2cn1] | 3-(1',2'-Dihydrospiro[cyclopropane-1,3'-pyrrolo[2,3-b]pyridin]-5'-yl)-1H-pyrrolo[2,3-c]pyridine-5-carbonitrile |
| 57 | 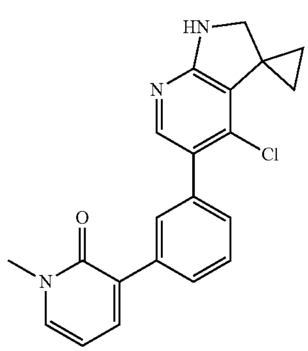 [SMILES: Cn1cccc(-c2cccc(-c3cnc4c(c3Cl)C3(CC3)CN4)c2)c1=O] | 3-(3-(4'-Chloro-1',2'-dihydrospiro[cyclopropane-1,3'-pyrrolo[2,3-b]pyridin]-5'-yl)phenyl)-1-methylpyridin-2(1H)-one |

TABLE 1-continued

| No. | Structure | Name |
|---|---|---|
| 58 | 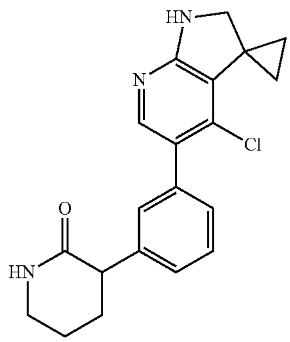 | 3-(3-(4'-Chloro-1',2'-dihydrospiro[cyclopropane-1,3'-pyrrolo[2,3-b]pyridin]-5'-yl)phenyl)piperidin-2-one |
| 59 | 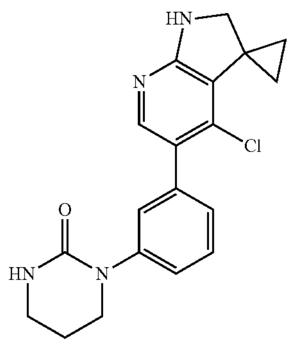 | 1-(3-(4'-Chloro-1',2'-dihydrospiro[cyclopropane-1,3'-pyrrolo[2,3-b]pyridin]-5'-yl)phenyl)tetrahydropyrimidin-2(1H)-one |
| 60 | 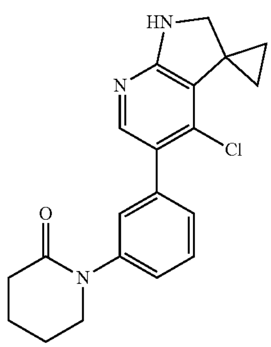 [SMILES: O=C1CCCCN1c1cccc(-c2cnc3c(c2Cl)C2(CC2)CN3)c1] | 1-(3-(4'-Chloro-1',2'-dihydrospiro[cyclopropane-1,3'-pyrrolo[2,3-b]pyridin]-5'-yl)phenyl)piperidin-2-one |
| 61 | 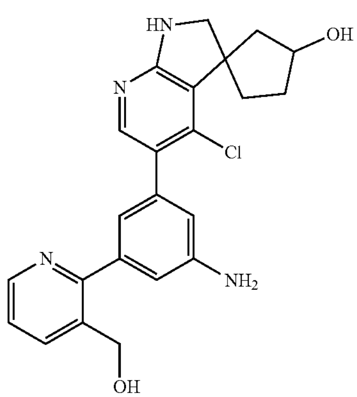 [SMILES: Nc1cc(-c2cnc3c(c2Cl)C2(CCC(O)C2)CN3)cc(-c2ncccc2CO)c1] | 5'-(3-Amino-5-(3-(hydroxymethyl)pyridin-2-yl)phenyl)-4'-chloro-1',2'-dihydrospiro[cyclopentane-1,3'-pyrrolo[2,3-b]pyridin]-3-ol |
| 61a 61b | | (1R,3S)-5'-(3-Amino-5-(3-(hydroxymethyl)pyridin-2-yl)phenyl)-4'-chloro-1',2'-dihydrospiro[cyclopentane-1,3'-pyrrolo[2,3-b]pyridin]-3-ol (1S,3R)-5'-(3-Amino-5-(3-(hydroxymethyl)pyridin-2-yl)phenyl)-4'-chloro-1',2'-dihydrospiro[cyclopentane-1,3'-pyrrolo[2,3-b]pyridin]-3-ol |

TABLE 1-continued

| No. | Structure | Name |
|---|---|---|
| 61c | | (1R,3R)-5'-(3-Amino-5-(3-(hydroxymethyl)pyridin-2-yl)phenyl)-4'-chloro-1',2'-dihydrospiro[cyclopentane-1,3'-pyrrolo[2,3-b]pyridin]-3-ol |
| 61d | | (1S,3S)-5'-(3-Amino-5-(3-(hydroxymethyl)pyridin-2-yl)phenyl)-4'-chloro-1',2'-dihydrospiro[cyclopentane-1,3'-pyrrolo[2,3-b]pyridin]-3-ol |
| 62 | 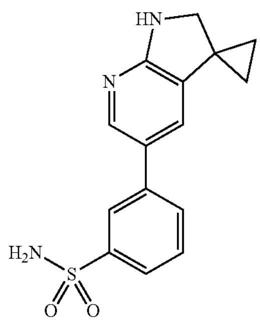 [SMILES: NS(=O)(=O)c1cccc(-c2cnc3c(c2)C2(CC2)CN3)c1] | 3-(1',2'-Dihydrospiro[cyclopropane-1,3'-pyrrolo[2,3-b]pyridin]-5'-yl)benzenesulfonamide |
| 63 | 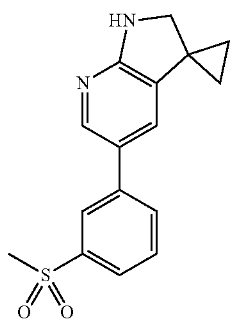 [SMILES: CS(=O)(=O)c1cccc(-c2cnc3c(c2)C2(CC2)CN3)c1] | 5'-(3-(Methylsulfonyl)phenyl)-1',2'-dihydrospiro[cyclopropane-1,3'-pyrrolo[2,3-b]pyridine] |
| 64 | 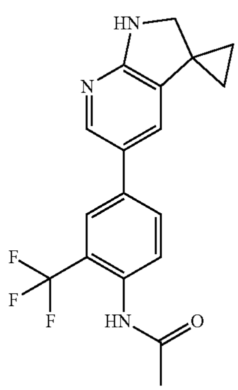 [SMILES: CC(=O)Nc1ccc(-c2cnc3c(c2)C2(CC2)CN3)cc1C(F)(F)F] | N-(4-(1',2'-Dihydrospiro[cyclopropane-1,3'-pyrrolo[2,3-b]pyridin]-5'-yl)-2-(trifluoromethyl)phenyl)acetamide |
| 65 | 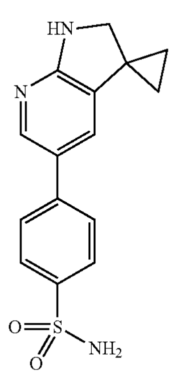 [SMILES: NS(=O)(=O)c1ccc(-c2cnc3c(c2)C2(CC2)CN3)cc1] | 4-(1',2'-Dihydrospiro[cyclopropane-1,3'-pyrrolo[2,3-b]pyridin]-5'-yl)benzenesulfonamide |

TABLE 1-continued

| No. | Structure | Name |
|---|---|---|
| 66 | 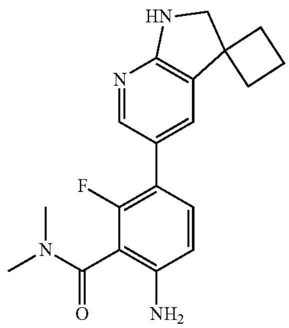 [SMILES: CN(C)C(=O)c1c(N)ccc(-c2cnc3c(c2)C2(CCC2)CN3)c1F] | 6-Amino-3-(1',2'-dihydrospiro[cyclobutane-1,3'-pyrrolo[2,3-b]pyridin]-5'-yl)-2-fluoro-N,N-dimethylbenzamide |
| 67 | 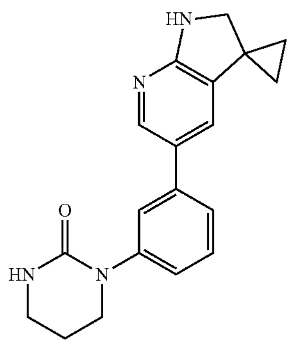 | 1-(3-(1',2'-Dihydrospiro[cyclopropane-1,3'-pyrrolo[2,3-b]pyridin]-5'-yl)phenyl)tetrahydropyrimidin-2(1H)-one |
| 68 | 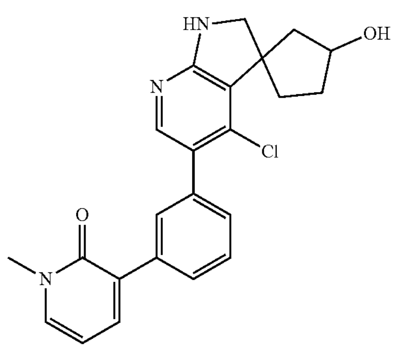 [SMILES: Cn1cccc(-c2cccc(-c3cnc4c(c3Cl)C3(CCC(O)C3)CN4)c2)c1=O] | 3-(3-(4'-chloro-3-hydroxy-1',2'-dihydrospiro[cyclopentane-1,3'-pyrrolo[2,3-b]pyridin]-5'-yl)phenyl)-1-methylpyridin-2(1H)-one |
| 68a | | 3-(3-((1R,3R)-4'-chloro-3-hydroxy-1',2'-dihydrospiro[cyclopentane-1,3'-pyrrolo[2,3-b]pyridin]-5'-yl)phenyl)-1-methylpyridin-2(1H)-one |
| 68b | | 3-(3-((1S,3S)-4'-chloro-3-hydroxy-1',2'-dihydrospiro[cyclopentane-1,3'-pyrrolo[2,3-b]pyridin]-5'-yl)phenyl)-1-methylpyridin-2(1H)-one |
| 68c | | 3-(3-((1R,3S)-4'-chloro-3-hydroxy-1',2'-dihydrospiro[cyclopentane-1,3'-pyrrolo[2,3-b]pyridin]-5'-yl)phenyl)-1-methylpyridin-2(1H)-one |
| 68d | | 3-(3-((1S,3R)-4'-chloro-3-hydroxy-1',2'-dihydrospiro[cyclopentane-1,3'-pyrrolo[2,3-b]pyridin]-5'-yl)phenyl)-1-methylpyridin-2(1H)-one |

TABLE 1-continued

| No. | Structure | Name |
|---|---|---|
| 69 | 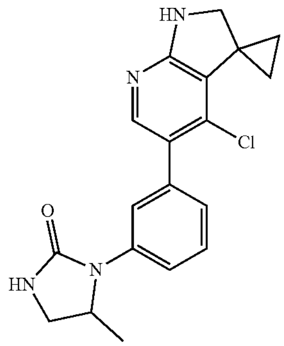 [SMILES: CC1CNC(=O)N1c1cccc(-c2cnc3c(c2Cl)C2(CC2)CN3)c1] | 1-(3-(4'-Chloro-1',2'-dihydrospiro[cyclopropane-1,3'-pyrrolo[2,3-b]pyridin]-5'-yl)phenyl)-5-methylimidazolidin-2-one |
| 69a | | (R)-1-(3-(4'-Chloro-1',2'-dihydrospiro[cyclopropane-1,3'-pyrrolo[2,3-b]pyridin]-5'-yl)phenyl)-5-methylimidazolidin-2-one |
| 69b | | (S)-1-(3-(4'-Chloro-1',2'-dihydrospiro[cyclopropane-1,3'-pyrrolo[2,3-b]pyridin]-5'-yl)phenyl)-5-methylimidazolidin-2-one |
| 70 | 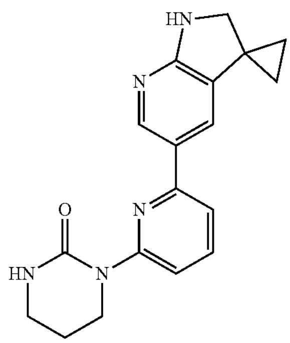 | 1-(6-(1',2'-Dihydrospiro[cyclopropane-1,3'-pyrrolo[2,3-b]pyridin]-5'-yl)pyridin-2-yl)tetrahydropyrimidin-2(1H)-one |
| 71 | 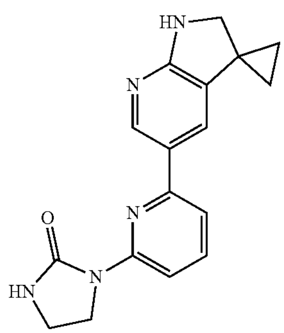 [SMILES: O=C1NCCN1c1cccc(-c2cnc3c(c2)C2(CC2)CN3)n1] | 1-(6-(1',2'-Dihydrospiro[cyclopropane-1,3'-pyrrolo[2,3-b]pyridin]-5'-yl)pyridin-2-yl)imidazolidin-2-one |
| 72 | 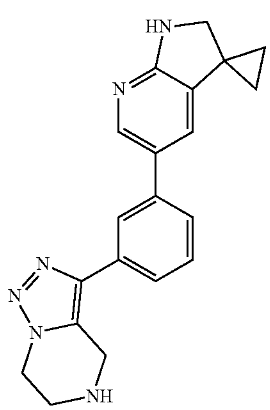 [SMILES: c1cc(-c2cnc3c(c2)C2(CC2)CN3)cc(-c2nnn3c2CNCC3)c1] | 5'-(3-(4,5,6,7-Tetrahydro-[1,2,3]triazolo[1,5-a]pyrazin-3-yl)phenyl)-1',2'-dihydrospiro[cyclopropane-1,3'-pyrrolo[2,3-b]pyridine] |

TABLE 1-continued

| No. | Structure | Name |
|---|---|---|
| 73 | 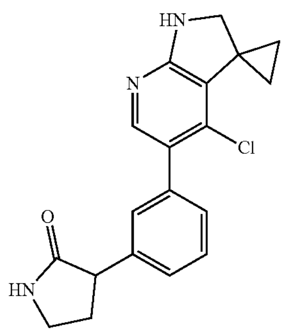 [SMILES: O=C1NCCC1c1cccc(-c2cnc3c(c2Cl)C2(CC2)CN3)c1] | 3-(3-(4'-Chloro-1',2'-dihydrospiro[cyclopropane-1,3'-pyrrolo[2,3-b]pyridin]-5'-yl)phenyl)piperidin-2-one |
| 73a<br>73b | | (R)-3-(3-(4'-Chloro-1',2'-dihydrospiro[cyclopropane-1,3'-pyrrolo[2,3-b]pyridin]-5'-yl)phenyl)piperidin-2-one<br>(S)-3-(3-(4'-Chloro-1',2'-dihydrospiro[cyclopropane-1,3'-pyrrolo[2,3-b]pyridin]-5'-yl)phenyl)piperidin-2-one |
| 74 | 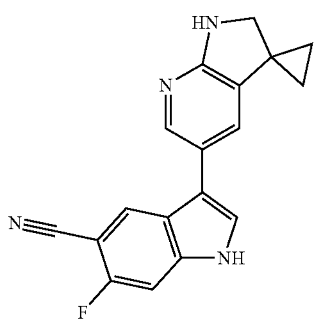 [SMILES: N#Cc1cc2c(-c3cnc4c(c3)C3(CC3)CN4)c[nH]c2cc1F] | 3-(1',2'-Dihydrospiro[cyclopropane-1,3'-pyrrolo[2,3-b]pyridin]-5'-yl)-6-fluoro-1H-indole-5-carbonitrile] |
| 75 | 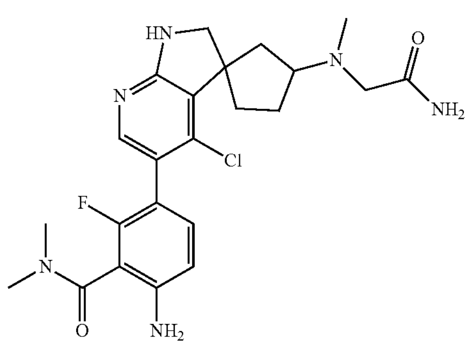 [SMILES: CN(C)C(=O)c1c(N)ccc(-c2cnc3c(c2Cl)C2(CCC(N(C)CC(N)=O)C2)CN3)c1F] | 6-Amino-3-(3-((2-amino-2-oxoethyl)(methyl)amino)-4'-chloro-1',2'-dihydrospiro[cyclopentane-1,3'-pyrrolo[2,3-b]pyridin]-5'-yl)-2-fluoro-N,N-dimethylbenzamide |
| 76 | 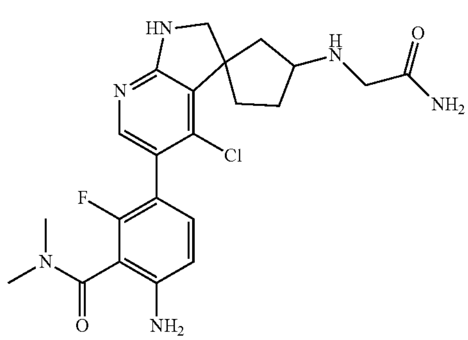 [SMILES: CN(C)C(=O)c1c(N)ccc(-c2cnc3c(c2Cl)C2(CCC(NCC(N)=O)C2)CN3)c1F] | 6-Amino-3-(3-((2-amino-2-oxoethyl)amino)-4'-chloro-1',2'-dihydrospiro[cyclopentane-1,3'-pyrrolo[2,3-b]pyridin]-5'-yl)-2-fluoro-N,N-dimethylbenzamide |

TABLE 1-continued

| No. | Structure | Name |
|---|---|---|
| 77 | 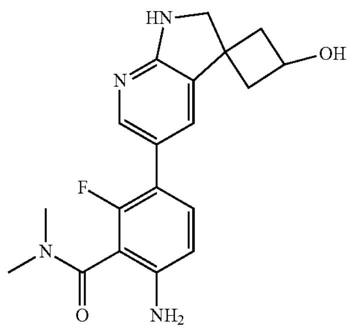 [SMILES: CN(C)C(=O)c1c(N)ccc(-c2cnc3c(c2)C2(CN3)CC(O)C2)c1F] | 6-Amino-2-fluoro-3-(3-hydroxy-1',2'-dihydrospiro[cyclobutane-1,3'-pyrrolo[2,3-b]pyridin]-5'-yl)-N,N-dimethylbenzamide |
| 77a | | 6-Amino-2-fluoro-3-((1r,3r)-3-hydroxy-1',2'-dihydrospiro[cyclobutane-1,3'-pyrrolo[2,3-b]pyridin]-5'-yl)-N,N-dimethylbenzamide |
| 77b | | 6-Amino-2-fluoro-3-((1s,3s)-3-hydroxy-1',2'-dihydrospiro[cyclobutane-1,3'-pyrrolo[2,3-b]pyridin]-5'-yl)-N,N-dimethylbenzamide |
| 78 | 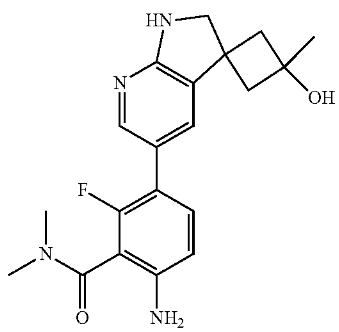 [SMILES: CN(C)C(=O)c1c(N)ccc(-c2cnc3c(c2)C2(CN3)CC(C)(O)C2)c1F] | 6-Amino-2-fluoro-3-(3-hydroxy-3-methyl-1',2'-dihydrospiro[cyclobutane-1,3'-pyrrolo[2,3-b]pyridin]-5'-yl)-N,N-dimethylbenzamide |
| 78a | | 6-Amino-2-fluoro-3-((1r,3r)-3-hydroxy-3-methyl-1',2'-dihydrospiro[cyclobutane-1,3'-pyrrolo[2,3-b]pyridin]-5'-yl)-N,N-dimethylbenzamide |
| 78b | | 6-Amino-2-fluoro-3-((1s,3s)-3-hydroxy-3-methyl-1',2'-dihydrospiro[cyclobutane-1,3'-pyrrolo[2,3-b]pyridin]-5'-yl)-N,N-dimethylbenzamide |
| 79 | 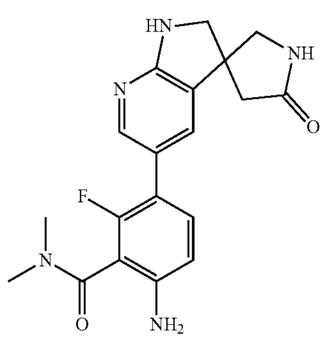 [SMILES: CN(C)C(=O)c1c(N)ccc(-c2cnc3c(c2)C2(CNC(=O)C2)CN3)c1F] | 6-Amino-2-fluoro-N,N-dimethyl-3-(5-oxo-1',2'-dihydrospiro[pyrrolidine-3,3'-pyrrolo[2,3-b]pyridin]-5'-yl)benzamide |
| 79a | | (R)-6-Amino-2-fluoro-N,N-dimethyl-3-(5-oxo-1',2'-dihydrospiro[pyrrolidine-3,3'-pyrrolo[2,3-b]pyridin]-5'-yl)benzamide |
| 79b | | (S)-6-Amino-2-fluoro-N,N-dimethyl-3-(5-oxo-1',2'-dihydrospiro[pyrrolidine-3,3'-pyrrolo[2,3-b]pyridin]-5'-yl)benzamide |

TABLE 1-continued

| No. | Structure | Name |
|---|---|---|
| 80 | | 6-Amino-3-(4'-chloro-3-methoxy-1',2'-dihydrospiro[cyclobutane-1,3'-pyrrolo[2,3-b]pyridin]-5'-yl)-2-fluoro-N,N-dimethylbenzamide |
| 80a | | 6-Amino-3-((1r,3r)-4'-chloro-3-methoxy-1',2'-dihydrospiro[cyclobutane-1,3'-pyrrolo[2,3-b]pyridin]-5'-yl)-2-fluoro-N,N-dimethylbenzamide |
| 80b | | 6-Amino-3-((1s,3s)-4'-chloro-3-methoxy-1',2'-dihydrospiro[cyclobutane-1,3'-pyrrolo[2,3-b]pyridin]-5'-yl)-2-fluoro-N,N-dimethylbenzamide |
| 81 | | 6-Amino-3-(4'-chloro-3-methoxy-1',2'-dihydrospiro[cyclopentane-1,3'-pyrrolo[2,3-b]pyridin]-5'-yl)-2-fluoro-N,N-dimethylbenzamide |
| 81a | | 6-Amino-3-((1R,3R)-4'-chloro-3-methoxy-1',2'-dihydrospiro[cyclopentane-1,3'-pyrrolo[2,3-b]pyridin]-5'-yl)-2-fluoro-N,N-dimethylbenzamide |
| 81b | | 6-Amino-3-((1S,3S)-4'-chloro-3-methoxy-1',2'-dihydrospiro[cyclopentane-1,3'-pyrrolo[2,3-b]pyridin]-5'-yl)-2-fluoro-N,N-dimethylbenzamide |
| 81c | | 6-Amino-3-((1R,3S)-4'-chloro-3-methoxy-1',2'-dihydrospiro[cyclopentane-1,3'-pyrrolo[2,3-b]pyridin]-5'-yl)-2-fluoro-N,N-dimethylbenzamide |
| 81d | | 6-Amino-3-((1S,3R)-4'-chloro-3-methoxy-1',2'-dihydrospiro[cyclopentane-1,3'-pyrrolo[2,3-b]pyridin]-5'-yl)-2-fluoro-N,N-dimethylbenzamide |
| 82 | | 6-Amino-3-(4'-chloro-3-hydroxy-3-methyl-1',2'-dihydrospiro[cyclopentane-1,3'-pyrrolo[2,3-b]pyridin]-5'-yl)-2-fluoro-N,N-dimethylbenzamide |
| 82a | | 6-Amino-3-((1R,3S)-4'-chloro-3-hydroxy-3-methyl-1',2'-dihydrospiro[cyclopentane-1,3'-pyrrolo[2,3-b]pyridin]-5'-yl)-2-fluoro-N,N-dimethylbenzamide |
| 82b | | 6-Amino-3-((1S,3R)-4'-chloro-3-hydroxy-3-methyl-1',2'-dihydrospiro[cyclopentane-1,3'-pyrrolo[2,3-b]pyridin]-5'-yl)-2-fluoro-N,N-dimethylbenzamide |

TABLE 1-continued

| No. | Structure | Name |
|---|---|---|
| 82c<br>82d | | 6-Amino-3-((1R,3R)-4'-chloro-3-hydroxy-3-methyl-1',2'-dihydrospiro[cyclopentane-1,3'-pyrrolo[2,3-b]pyridin]-5'-yl)-2-fluoro-N,N-dimethylbenzamide<br>6-Amino-3-((1S,3S)-4'-chloro-3-hydroxy-3-methyl-1',2'-dihydrospiro[cyclopentane-1,3'-pyrrolo[2,3-b]pyridin]-5'-yl)-2-fluoro-N,N-dimethylbenzamide |
| 83 | 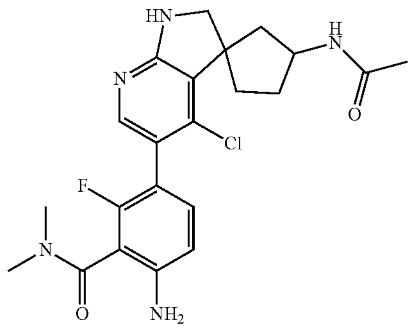 [SMILES: CC(=O)NC1CCC2(CNc3ncc(-c4ccc(N)c(C(=O)N(C)C)c4F)c(Cl)c32)C1] | 3-(3-Acetamido-4'-chloro-1',2'-dihydrospiro[cyclopentane-1,3'-pyrrolo[2,3-b]pyridin]-5'-yl)-6-amino-2-fluoro-N,N-dimethylbenzamide |
| 83a<br>83b | | 3-((1R,3S)-3-Acetamido-4'-chloro-1',2'-dihydrospiro[cyclopentane-1,3'-pyrrolo[2,3-b]pyridin]-5'-yl)-6-amino-2-fluoro-N,N-dimethylbenzamide<br>3-((1S,3R)-3-Acetamido-4'-chloro-1',2'-dihydrospiro[cyclopentane-1,3'-pyrrolo[2,3-b]pyridin]-5'-yl)-6-amino-2-fluoro-N,N-dimethylbenzamide |
| 83c<br>83d | | 3-((1R,3R)-3-Acetamido-4'-chloro-1',2'-dihydrospiro[cyclopentane-1,3'-pyrrolo[2,3-b]pyridin]-5'-yl)-6-amino-2-fluoro-N,N-dimethylbenzamide<br>3-((1S,3S)-3-Acetamido-4'-chloro-1',2'-dihydrospiro[cyclopentane-1,3'-pyrrolo[2,3-b]pyridin]-5'-yl)-6-amino-2-fluoro-N,N-dimethylbenzamide |
| 84 | 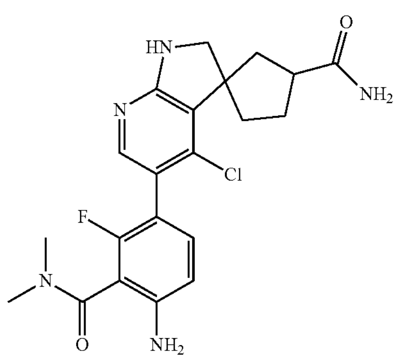 [SMILES: CN(C)C(=O)c1c(N)ccc(-c2cnc3c(c2Cl)C2(CCC(C(N)=O)C2)CN3)c1F] | 5'-(4-amino-3-(dimethylcarbamoyl)-2-fluorophenyl)-4'-chloro-1',2'-dihydrospiro[cyclopentane-1,3'-pyrrolo[2,3-b]pyridine]-3-carboxamide |
| 84a<br>84b | | (1R,3R)-5'-(4-amino-3-(dimethylcarbamoyl)-2-fluorophenyl)-4'-chloro-1',2'-dihydrospiro[cyclopentane-1,3'-pyrrolo[2,3-b]pyridine]-3-carboxamide<br>(1S,3S)-5'-(4-amino-3-(dimethylcarbamoyl)-2-fluorophenyl)-4'-chloro-1',2'-dihydrospiro[cyclopentane-1,3'-pyrrolo[2,3-b]pyridine]-3-carboxamide |
| 84c<br>84d | | (1R,3S)-5'-(4-amino-3-(dimethylcarbamoyl)-2-fluorophenyl)-4'-chloro-1',2'-dihydrospiro[cyclopentane-1,3'-pyrrolo[2,3-b]pyridine]-3-carboxamide<br>(1S,3R)-5'-(4-amino-3-(dimethylcarbamoyl)-2-fluorophenyl)-4'-chloro-1',2'-dihydrospiro[cyclopentane-1,3'-pyrrolo[2,3-b]pyridine]-3-carboxamide |

TABLE 1-continued

| No. | Structure | Name |
|---|---|---|
| 85 | 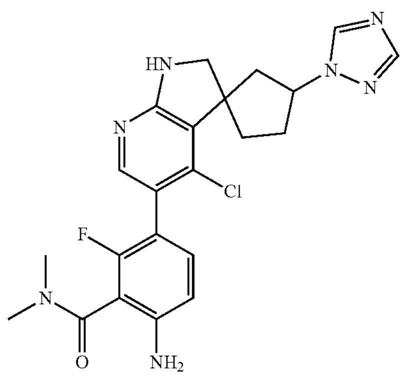 [SMILES: CN(C)C(=O)c1c(N)ccc(-c2cnc3c(c2Cl)C2(CCC(n4cncn4)C2)CN3)c1F] | 6-Amino-3-(4'-chloro-3-(1H-1,2,4-triazol-1-yl)-1',2'-dihydrospiro[cyclopentane-1,3'-pyrrolo[2,3-b]pyridin]-5'-yl)-2-fluoro-N,N-dimethylbenzamide |
| 85a<br>85b | | 6-Amino-3-((1R,3S)-4'-chloro-3-(1H-1,2,4-triazol-1-yl)-1',2'-dihydrospiro[cyclopentane-1,3'-pyrrolo[2,3-b]pyridin]-5'-yl)-2-fluoro-N,N-dimethylbenzamide<br>6-Amino-3-((1S,3R)-4'-chloro-3-(1H-1,2,4-triazol-1-yl)-1',2'-dihydrospiro[cyclopentane-1,3'-pyrrolo[2,3-b]pyridin]-5'-yl)-2-fluoro-N,N-dimethylbenzamide |
| 85c<br>85d | | 6-Amino-3-((1R,3R)-4'-chloro-3-(1H-1,2,4-triazol-1-yl)-1',2'-dihydrospiro[cyclopentane-1,3'-pyrrolo[2,3-b]pyridin]-5'-yl)-2-fluoro-N,N-dimethylbenzamide<br>6-Amino-3-((1S,3S)-4'-chloro-3-(1H-1,2,4-triazol-1-yl)-1',2'-dihydrospiro[cyclopentane-1,3'-pyrrolo[2,3-b]pyridin]-5'-yl)-2-fluoro-N,N-dimethylbenzamide |
| 86 | 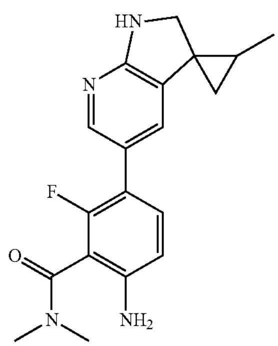 [SMILES: CC1CC12CNc1ncc(-c3ccc(N)c(C(=O)N(C)C)c3F)cc12] | 6-Amino-2-fluoro-N,N-dimethyl-3-(2-methyl-1',2'-dihydrospiro[cyclopropane-1,3'-pyrrolo[2,3-b]pyridin]-5'-yl)benzamide |
| 86a<br>86b | | 6-Amino-2-fluoro-N,N-dimethyl-3-((1R,2S)-2-methyl-1',2'-dihydrospiro[cyclopropane-1,3'-pyrrolo[2,3-b]pyridin]-5'-yl)benzamide<br>6-Amino-2-fluoro-N,N-dimethyl-3-((1S,2R)-2-methyl-1',2'-dihydrospiro[cyclopropane-1,3'-pyrrolo[2,3-b]pyridin]-5'-yl)benzamide |
| 86c<br>86d | | 6-Amino-2-fluoro-N,N-dimethyl-3-((1R,2R)-2-methyl-1',2'-dihydrospiro[cyclopropane-1,3'-pyrrolo[2,3-b]pyridin]-5'-yl)benzamide<br>6-Amino-2-fluoro-N,N-dimethyl-3-((1S,2S)-2-methyl-1',2'-dihydrospiro[cyclopropane-1,3'-pyrrolo[2,3-b]pyridin]-5'-yl)benzamide |

TABLE 1-continued

| No. | Structure | Name |
|---|---|---|
| 87 | 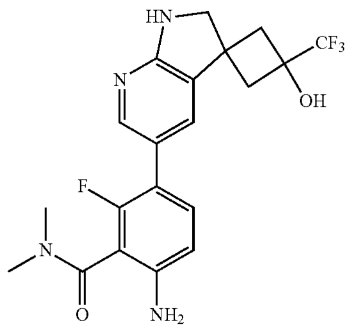 [SMILES: CN(C)C(=O)c1c(N)ccc(-c2cnc3c(c2)C2(CN3)CC(O)(C(F)(F)F)C2)c1F] | 6-Amino-3-(4'-chloro-3-hydroxy-3-(trifluoromethyl)-1',2'-dihydrospiro[cyclobutane-1,3'-pyrrolo[2,3-b]pyridin]-5'-yl)-2-fluoro-N,N-dimethylbenzamide |
| 87a | | 6-Amino-3-((1r,3r)-4'-chloro-3-hydroxy-3-(trifluoromethyl)-1',2'-dihydrospiro[cyclobutane-1,3'-pyrrolo[2,3-b]pyridin]-5'-yl)-2-fluoro-N,N-dimethylbenzamide |
| 87b | | 6-Amino-3-((1s,3s)-4'-chloro-3-hydroxy-3-(trifluoromethyl)-1',2'-dihydrospiro[cyclobutane-1,3'-pyrrolo[2,3-b]pyridin]-5'-yl)-2-fluoro-N,N-dimethylbenzamide |
| 88 | 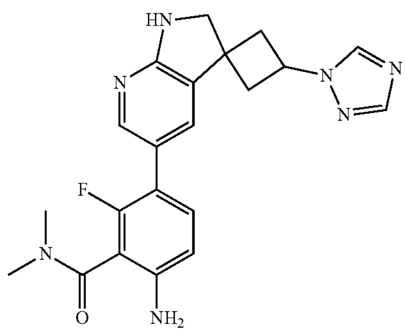 [SMILES: CN(C)C(=O)c1c(N)ccc(-c2cnc3c(c2)C2(CN3)CC(n3cncn3)C2)c1F] | 6-Amino-3-(4'-chloro-3-(1H-1,2,4-triazol-1-yl)-1',2'-dihydrospiro[cyclobutane-1,3'-pyrrolo[2,3-b]pyridin]-5'-yl)-2-fluoro-N,N-dimethylbenzamide |
| 88a | | 6-Amino-3-((1s,3s)-4'-chloro-3-(1H-1,2,4-triazol-1-yl)-1',2'-dihydrospiro[cyclobutane-1,3'-pyrrolo[2,3-b]pyridin]-5'-yl)-2-fluoro-N,N-dimethylbenzamide |
| 88b | | 6-Amino-3-((1r,3r)-4'-chloro-3-(1H-1,2,4-triazol-1-yl)-1',2'-dihydrospiro[cyclobutane-1,3'-pyrrolo[2,3-b]pyridin]-5'-yl)-2-fluoro-N,N-dimethylbenzamide |
| 89 | 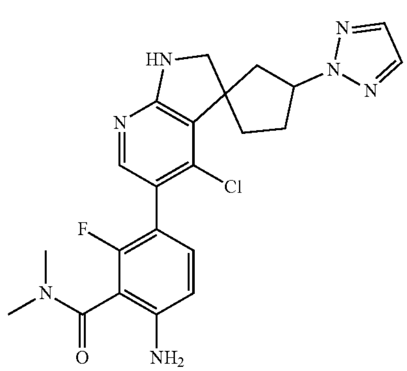 | 6-Amino-3-(4'-chloro-3-(2H-1,2,3-triazol-2-yl)-1',2'-dihydrospiro[cyclopentane-1,3'-pyrrolo[2,3-b]pyridin]-5'-yl)-2-fluoro-N,N-dimethylbenzamide |
| 89a | | 6-Amino-3-((1R,3S)-4'-chloro-3-(2H-1,2,3-triazol-2-yl)-1',2'-dihydrospiro[cyclopentane-1,3'-pyrrolo[2,3-b]pyridin]-5'-yl)-2-fluoro-N,N-dimethylbenzamide |
| 89b | | 6-Amino-3-((1S,3R)-4'-chloro-3-(2H-1,2,3-triazol-2-yl)-1',2'-dihydrospiro[cyclopentane-1,3'-pyrrolo[2,3-b]pyridin]-5'-yl)-2-fluoro-N,N-dimethylbenzamide |

TABLE 1-continued

| No. | Structure | Name |
|---|---|---|
| 89c 89d | | 6-Amino-3-((1R,3R)-4'-chloro-3-(2H-1,2,3-triazol-2-yl)-1',2'-dihydrospiro[cyclopentane-1,3'-pyrrolo[2,3-b]pyridin]-5'-yl)-2-fluoro-N,N-dimethylbenzamide<br>6-Amino-3-((1S,3S)-4'-chloro-3-(2H-1,2,3-triazol-2-yl)-1',2'-dihydrospiro[cyclopentane-1,3'-pyrrolo[2,3-b]pyridin]-5'-yl)-2-fluoro-N,N-dimethylbenzamide |
| 90 | (structure) | 6-Amino-3-(4'-chloro-3-(1H-1,2,3-triazol-1-yl)-1',2'-dihydrospiro[cyclopentane-1,3'-pyrrolo[2,3-b]pyridin]-5'-yl)-2-fluoro-N,N-dimethylbenzamide |
| 90a 90b | | 6-amino-3-((1R,3S)-4'-chloro-3-(1H-1,2,3-triazol-1-yl)-1',2'-dihydrospiro[cyclopentane-1,3'-pyrrolo[2,3-b]pyridin]-5'-yl)-2-fluoro-N,N-dimethylbenzamide<br>6-amino-3-((1S,3R)-4'-chloro-3-(1H-1,2,3-triazol-1-yl)-1',2'-dihydrospiro[cyclopentane-1,3'-pyrrolo[2,3-b]pyridin]-5'-yl)-2-fluoro-N,N-dimethylbenzamide |
| 90c 90d | | 6-Amino-3-((1R,3R)-4'-chloro-3-(1H-1,2,3-triazol-1-yl)-1',2'-dihydrospiro[cyclopentane-1,3'-pyrrolo[2,3-b]pyridin]-5'-yl)-2-fluoro-N,N-dimethylbenzamide<br>6-Amino-3-((1S,3S)-4'-chloro-3-(1H-1,2,3-triazol-1-yl)-1',2'-dihydrospiro[cyclopentane-1,3'-pyrrolo[2,3-b]pyridin]-5'-yl)-2-fluoro-N,N-dimethylbenzamide |
| 91 | (structure) | 6-Amino-3-(4'-chloro-3-cyano-1',2'-dihydrospiro[cyclopentane-1,3'-pyrrolo[2,3-b]pyridin]-5'-yl)-2-fluoro-N,N-dimethylbenzamide |
| 91a 91b | | 6-Amino-3-((1R,3S)-4'-chloro-3-cyano-1',2'-dihydrospiro[cyclopentane-1,3'-pyrrolo[2,3-b]pyridin]-5'-yl)-2-fluoro-N,N-dimethylbenzamide<br>6-Amino-3-((1S,3R)-4'-chloro-3-cyano-1',2'-dihydrospiro[cyclopentane-1,3'-pyrrolo[2,3-b]pyridin]-5'-yl)-2-fluoro-N,N-dimethylbenzamide |
| 91c 91d | | 6-Amino-3-((1R,3R)-4'-chloro-3-cyano-1',2'-dihydrospiro[cyclopentane-1,3'-pyrrolo[2,3-b]pyridin]-5'-yl)-2-fluoro-N,N-dimethylbenzamide<br>6-Amino-3-((1S,3S)-4'-chloro-3-cyano-1',2'-dihydrospiro[cyclopentane-1,3'-pyrrolo[2,3-b]pyridin]-5'-yl)-2-fluoro-N,N-dimethylbenzamide |

TABLE 1-continued

| No. | Structure | Name |
|---|---|---|
| 92 | 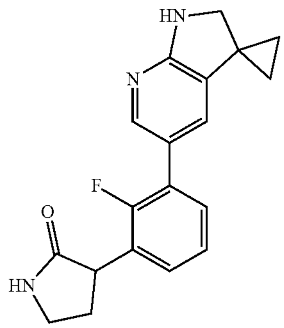 [SMILES: O=C1NCCC1c1cccc(-c2cnc3c(c2)C2(CC2)CN3)c1F] | 3-(3-(1',2'-dihydrospiro[cyclopropane-1,3'-pyrrolo[2,3-b]pyridin]-5'-yl)-2-fluorophenyl)pyrrolidin-2-one |
| 92a<br>92b | | (R)-3-(3-(1',2'-dihydrospiro[cyclopropane-1,3'-pyrrolo[2,3-b]pyridin]-5'-yl)-2-fluorophenyl)pyrrolidin-2-one<br>(S)-3-(3-(1',2'-dihydrospiro[cyclopropane-1,3'-pyrrolo[2,3-b]pyridin]-5'-yl)-2-fluorophenyl)pyrrolidin-2-one |
| 93 | 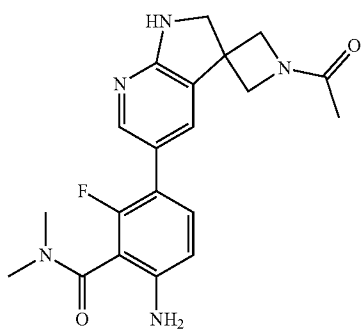 [SMILES: CC(=O)N1CC2(CNc3ncc(-c4ccc(N)c(C(=O)N(C)C)c4F)cc32)C1] | 3-(1-Acetyl-1',2'-dihydrospiro[azetidine-3,3'-pyrrolo[2,3-b]pyridin]-5'-yl)-6-amino-2-fluoro-N,N-dimethylbenzamide |
| 94 | 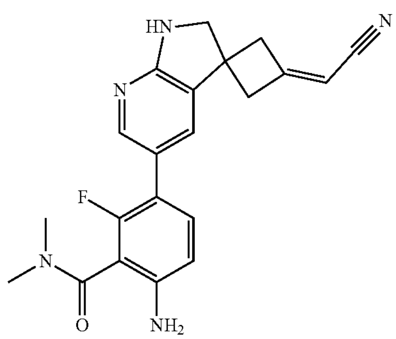 [SMILES: CN(C)C(=O)c1c(N)ccc(-c2cnc3c(c2)C2(CN3)CC(=CC#N)C2)c1F] | 6-Amino-3-(3-(cyanomethylene)-1',2'-dihydrospiro[cyclobutane-1,3'-pyrrolo[2,3-b]pyridin]-5'-yl)-2-fluoro-N,N-dimethylbenzamide |
| 94a<br>94b | | (s,E)-6-Amino-3-(3-(cyanomethylene)-1',2'-dihydrospiro[cyclobutane-1,3'-pyrrolo[2,3-b]pyridin]-5'-yl)-2-fluoro-N,N-dimethylbenzamide<br>(r,Z)-6-amino-3-(3-(cyanomethylene)-1',2'-dihydrospiro[cyclobutane-1,3'-pyrrolo[2,3-b]pyridin]-5'-yl)-2-fluoro-N,N-dimethylbenzamide |
| 95 | 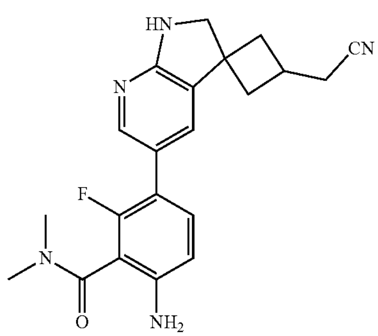 [SMILES: CN(C)C(=O)c1c(N)ccc(-c2cnc3c(c2)C2(CN3)CC(CC#N)C2)c1F] | 6-Amino-3-(3-(cyanomethyl)-1',2'-dihydrospiro[cyclobutane-1,3'-pyrrolo[2,3-b]pyridin]-5'-yl)-2-fluoro-N,N-dimethylbenzamide |

TABLE 1-continued

| No. | Structure | Name |
|---|---|---|
| 95a | | 6-Amino-3-((1r,3r)-3-(cyanomethyl)-1',2'-dihydrospiro[cyclobutane-1,3'-pyrrolo[2,3-b]pyridin]-5'-yl)-2-fluoro-N,N-dimethylbenzamide |
| 95b | | 6-Amino-3-((1s,3s)-3-(cyanomethyl)-1',2'-dihydrospiro[cyclobutane-1,3'-pyrrolo[2,3-b]pyridin]-5'-yl)-2-fluoro-N,N-dimethylbenzamide |
| 96 | (structure) | 6-Amino-3-(4'-chloro-3-cyano-1',2'-dihydrospiro[cyclobutane-1,3'-pyrrolo[2,3-b]pyridin]-5'-yl)-2-fluoro-N,N-dimethylbenzamide |
| 96a | | 6-Amino-3-((1s, 3s)-4'-chloro-3-cyano-1',2'-dihydrospiro[cyclobutane-1,3'-pyrrolo[2,3-b]pyridin]-5'-yl)-2-fluoro-N,N-dimethylbenzamide |
| 96b | | 6-Amino-3-((1r,3r)-4'-chloro-3-cyano-1',2'-dihydrospiro[cyclobutane-1,3'-pyrrolo[2,3-b]pyridin]-5'-yl)-2-fluoro-N,N-dimethylbenzamide |
| 97 | (structure) | 5'-(4-Amino-3-(dimethylcarbamoyl)-2-fluorophenyl)-4'-chloro-1',2'-dihydrospiro[cyclobutane-1,3'-pyrrolo[2,3-b]pyridine]-3-carboxamide |
| 97a | | (1s,3s)-5'-(4-Amino-3-(dimethylcarbamoyl)-2-fluorophenyl)-4'-chloro-1',2'-dihydrospiro[cyclobutane-1,3'-pyrrolo[2,3-b]pyridine]-3-carboxamide |
| 97b | | (1r,3r)-5'-(4-Amino-3-(dimethylcarbamoyl)-2-fluorophenyl)-4'-chloro-1',2'-dihydrospiro[cyclobutane-1,3'-pyrrolo[2,3-b]pyridine]-3-carboxamide |
| 98 | (structure) | 5'-(4-Amino-3-(dimethylcarbamoyl)-2-fluorophenyl)-4'-chloro-N-methyl-1',2'-dihydrospiro[cyclopentane-1,3'-pyrrolo[2,3-b]pyridine]-3-carboxamide |
| 98a 98b | | (1R,3S)-5'-(4-Amino-3-(dimethylcarbamoyl)-2-fluorophenyl)-4'-chloro-N-methyl-1',2'-dihydrospiro[cyclopentane-1,3'-pyrrolo[2,3-b]pyridine]-3-carboxamide |

TABLE 1-continued

| No. | Structure | Name |
|---|---|---|
| 98c | | (1S,3R)-5'-(4-Amino-3-(dimethylcarbamoyl)-2-fluorophenyl)-4'-chloro-N-methyl-1',2'-dihydrospiro[cyclopentane-1,3'-pyrrolo[2,3-b]pyridine]-3-carboxamide |
| 98d | | (1S,3S)-5'-(4-Amino-3-(dimethylcarbamoyl)-2-fluorophenyl)-4'-chloro-N-methyl-1',2'-dihydrospiro[cyclopentane-1,3'-pyrrolo[2,3-b]pyridine]-3-carboxamide (1R,3R)-5'-(4-Amino-3-(dimethylcarbamoyl)-2-fluorophenyl)-4'-chloro-N-methyl-1',2'-dihydrospiro[cyclopentane-1,3'-pyrrolo[2,3-b]pyridine]-3-carboxamide |
| 99 | 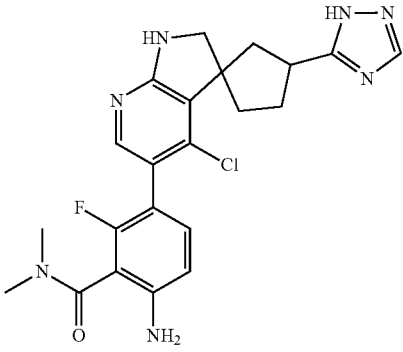 [SMILES: CN(C)C(=O)c1c(N)ccc(-c2cnc3c(c2Cl)C2(CCC(c4ncn[nH]4)C2)CN3)c1F] | 6-Amino-3-(4'-chloro-3-(1H-1,2,4-triazol-5-yl)-1',2'-dihydrospiro[cyclopentane-1,3'-pyrrolo[2,3-b]pyridin]-5'-yl)-2-fluoro-N,N-dimethylbenzamide |
| 99a 99b | | 6-Amino-3-((1R,3S)-4'-chloro-3-(1H-1,2,4-triazol-5-yl)-1',2'-dihydrospiro[cyclopentane-1,3'-pyrrolo[2,3-b]pyridin]-5'-yl)-2-fluoro-N,N-dimethylbenzamide 6-Amino-3-((1S,3S)-4'-chloro-3-(1H-1,2,4-triazol-5-yl)-1',2'-dihydrospiro[cyclopentane-1,3'-pyrrolo[2,3-b]pyridin]-5'-yl)-2-fluoro-N,N-dimethylbenzamide |
| 99c 99d | | 6-Amino-3-((1S,3S)-4'-chloro-3-(1H-1,2,4-triazol-5-yl)-1',2'-dihydrospiro[cyclopentane-1,3'-pyrrolo[2,3-b]pyridin]-5'-yl)-2-fluoro-N,N-dimethylbenzamide 6-Amino-3-((1R,3R)-4'-chloro-3-(1H-1,2,4-triazol-5-yl)-1',2'-dihydrospiro[cyclopentane-1,3'-pyrrolo[2,3-b]pyridin]-5'-yl)-2-fluoro-N,N-dimethylbenzamide |
| 100 | 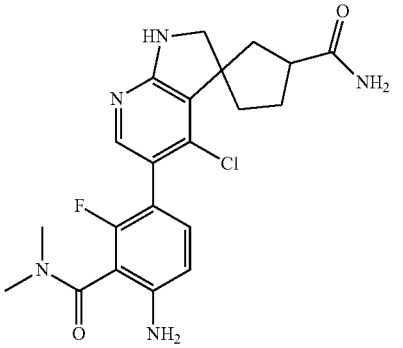 [SMILES: CN(C)C(=O)c1c(N)ccc(-c2cnc3c(c2Cl)C2(CCC(C(N)=O)C2)CN3)c1F] | 5'-(4-Amino-3-(dimethylcarbamoyl)-2-fluorophenyl)-4'-chloro-1',2'-dihydrospiro[cyclopentane-1,3'-pyrrolo[2,3-b]pyridine]-3-carboxamide |
| 100a 100b | | (1R,3S)-5'-(4-Amino-3-(dimethylcarbamoyl)-2-fluorophenyl)-4'-chloro-1',2'-dihydrospiro[cyclopentane-1,3'-pyrrolo[2,3-b]pyridine]-3-carboxamide (1S,3R)-5'-(4-Amino-3-(dimethylcarbamoyl)-2-fluorophenyl)-4'-chloro-1',2'-dihydrospiro[cyclopentane-1,3'-pyrrolo[2,3-b]pyridine]-3-carboxamide |
| 100c 100d | | (1R,3R)-5'-(4-Amino-3-(dimethylcarbamoyl)-2-fluorophenyl)-4'-chloro-1',2'-dihydrospiro[cyclopentane-1,3'-pyrrolo[2,3-b]pyridine]-3-carboxamide |

TABLE 1-continued

| No. | Structure | Name |
|---|---|---|
| | | (1S,3S)-5'-(4-Amino-3-(dimethylcarbamoyl)-2-fluorophenyl)-4'-chloro-1',2'-dihydrospiro[cyclopentane-1,3'-pyrrolo[2,3-b]pyridine]-3-carboxamide |
| 101 | 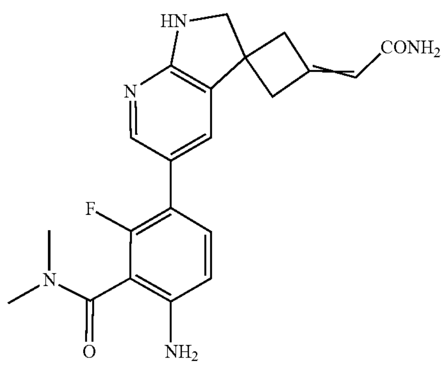 [SMILES: CN(C)C(=O)c1c(N)ccc(-c2cnc3c(c2)C2(CN3)CC(=CC(N)=O)C2)c1F] | 6-Amino-3-(3-(2-amino-2-oxoethylidene)-1',2'-dihydrospiro[cyclobutane-1,3'-pyrrolo[2,3-b]pyridin]-5'-yl)-2-fluoro-N,N-dimethylbenzamide |
| 101a 101b | | (R)-6-Amino-3-(3-(2-amino-2-oxoethylidene)-1',2'-dihydrospiro[cyclobutane-1,3'-pyrrolo[2,3-b]pyridin]-5'-yl)-2-fluoro-N,N-dimethylbenzamide (S)-6-Amino-3-(3-(2-amino-2-oxoethylidene)-1',2'-dihydrospiro[cyclobutane-1,3'-pyrrolo[2,3-b]pyridin]-5'-yl)-2-fluoro-N,N-dimethylbenzamide |
| 102 | 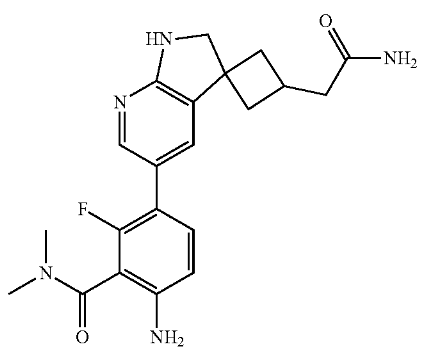 [SMILES: CN(C)C(=O)c1c(N)ccc(-c2cnc3c(c2)C2(CN3)CC(CC(N)=O)C2)c1F] | 6-Amino-3-(3-(2-amino-2-oxoethyl)-1',2'-dihydrospiro[cyclobutane-1,3'-pyrrolo[2,3-b]pyridin]-5'-yl)-2-fluoro-N,N-dimethylbenzamide |
| 102a 102b | | 6-Amino-3-((1r,3r)-3-(2-amino-2-oxoethyl)-1',2'-dihydrospiro[cyclobutane-1,3'-pyrrolo[2,3-b]pyridin]-5'-yl)-2-fluoro-N,N-dimethylbenzamide 6-Amino-3-((1s,3s)-3-(2-amino-2-oxoethyl)-1',2'-dihydrospiro[cyclobutane-1,3'-pyrrolo[2,3-b]pyridin]-5'-yl)-2-fluoro-N,N-dimethylbenzamide |
| 103 | 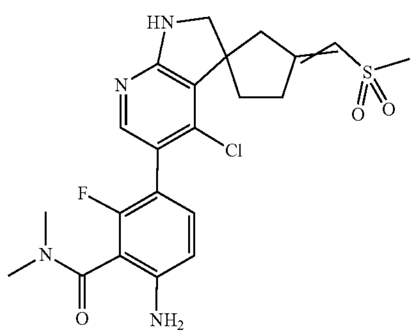 | 6-Amino-3-(4'-chloro-3-((methylsulfonyl)methylene)-1',2'-dihydrospiro[cyclopentane-1,3'-pyrrolo[2,3-b]pyridin]-5'-yl)-2-fluoro-N,N-dimethylbenzamide |

TABLE 1-continued

| No. | Structure | Name |
| --- | --- | --- |
| 104 | | 6-Amino-3-(4'-chloro-3-(cyanomethylene)-1',2'-dihydrospiro[cyclopentane-1,3'-pyrrolo[2,3-b]pyridin]-5'-yl)-2-fluoro-N,N-dimethylbenzamide |
| 104a | | (R,E)-6-Amino-3-(4'-chloro-3-(cyanomethylene)-1',2'-dihydrospiro[cyclopentane-1,3'-pyrrolo[2,3-b]pyridin]-5'-yl)-2-fluoro-N,N-dimethylbenzamide |
| 104b | | |
| 104c | | (S,E)-6-Amino-3-(4'-chloro-3-(cyanomethylene)-1',2'-dihydrospiro[cyclopentane-1,3'-pyrrolo[2,3-b]pyridin]-5'-yl)-2-fluoro-N,N-dimethylbenzamide |
| 104d | | (R,Z)-6-Amino-3-(4'-chloro-3-(cyanomethylene)-1',2'-dihydrospiro[cyclopentane-1,3'-pyrrolo[2,3-b]pyridin]-5'-yl)-2-fluoro-N,N-dimethylbenzamide |
| | | (S,Z)-6-Amino-3-(4'-chloro-3-(cyanomethylene)-1',2'-dihydrospiro[cyclopentane-1,3'-pyrrolo[2,3-b]pyridin]-5'-yl)-2-fluoro-N,N-dimethylbenzamide |
| 105 | | 5'-(4-Amino-3-(dimethylcarbamoyl)-2-fluorophenyl)-4'-chloro-1',2'-dihydrospiro[cyclopentane-1,3'-pyrrolo[2,3-b]pyridine]-3-carboxylic acid |
| 105a | | (1R,3S)-5'-(4-Amino-3-(dimethylcarbamoyl)-2-fluorophenyl)-4'-chloro-1',2'-dihydrospiro[cyclopentane-1,3'-pyrrolo[2,3-b]pyridine]-3-carboxylic acid |
| 105b | | (1S,3R)-5'-(4-Amino-3-(dimethylcarbamoyl)-2-fluorophenyl)-4'-chloro-1',2'-dihydrospiro[cyclopentane-1,3'-pyrrolo[2,3-b]pyridine]-3-carboxylic acid |
| 105c | | (1S,3S)-5'-(4-Amino-3-(dimethylcarbamoyl)-2-fluorophenyl)-4'-chloro-1',2'-dihydrospiro[cyclopentane-1,3'-pyrrolo[2,3-b]pyridine]-3-carboxylic acid |
| 105d | | (1R,3R)-5'-(4-Amino-3-(dimethylcarbamoyl)-2-fluorophenyl)-4'-chloro-1',2'-dihydrospiro[cyclopentane-1,3'-pyrrolo[2,3-b]pyridine]-3-carboxylic acid |

TABLE 1-continued

| No. | Structure | Name |
|---|---|---|
| 106 | | 5'-(4-Amino-3-(dimethylcarbamoyl)-2-fluorophenyl)-4'-chloro-N-(2-hydroxyethyl)-1',2'-dihydrospiro[cyclopentane-1,3'-pyrrolo[2,3-b]pyridine]-3-carboxamide |
| 106a 106b | | (1R,3S)-5'-(4-Amino-3-(dimethylcarbamoyl)-2-fluorophenyl)-4'-chloro-N-(2-hydroxyethyl)-1',2'-dihydrospiro[cyclopentane-1,3'-pyrrolo[2,3-b]pyridine]-3-carboxamide (1S,3R)-5'-(4-Amino-3-(dimethylcarbamoyl)-2-fluorophenyl)-4'-chloro-N-(2-hydroxyethyl)-1',2'-dihydrospiro[cyclopentane-1,3'-pyrrolo[2,3-b]pyridine]-3-carboxamide |
| 106c 106d | | (1R,3R)-5'-(4-Amino-3-(dimethylcarbamoyl)-2-fluorophenyl)-4'-chloro-N-(2-hydroxyethyl)-1',2'-dihydrospiro[cyclopentane-1,3'-pyrrolo[2,3-b]pyridine]-3-carboxamide (1S,3S)-5'-(4-Amino-3-(dimethylcarbamoyl)-2-fluorophenyl)-4'-chloro-N-(2-hydroxyethyl)-1',2'-dihydrospiro[cyclopentane-1,3'-pyrrolo[2,3-b]pyridine]-3-carboxamide |
| 107 | | 5'-(4-Amino-3-(dimethylcarbamoyl)-2-fluorophenyl)-4'-chloro-N,N-dimethyl-1',2'-dihydrospiro[cyclopentane-1,3'-pyrrolo[2,3-b]pyridine]-3-carboxamide |
| 107a 107b | | (1R,3S)-5'-(4-Amino-3-(dimethylcarbamoyl)-2-fluorophenyl)-4'-chloro-N,N-dimethyl-1',2'-dihydrospiro[cyclopentane-1,3'-pyrrolo[2,3-b]pyridine]-3-carboxamide (1S,3R)-5'-(4-Amino-3-(dimethylcarbamoyl)-2-fluorophenyl)-4'-chloro-N,N-dimethyl-1',2'-dihydrospiro[cyclopentane-1,3'-pyrrolo[2,3-b]pyridine]-3-carboxamide |
| 107c 107d | | (1R,3R)-5'-(4-Amino-3-(dimethylcarbamoyl)-2-fluorophenyl)-4'-chloro-N,N-dimethyl-1',2'-dihydrospiro[cyclopentane-1,3'-pyrrolo[2,3-b]pyridine]-3-carboxamide (1S,3S)-5'-(4-Amino-3-(dimethylcarbamoyl)-2-fluorophenyl)-4'-chloro-N,N-dimethyl-1',2'-dihydrospiro[cyclopentane-1,3'-pyrrolo[2,3-b]pyridine]-3-carboxamide |

TABLE 1-continued

| No. | Structure | Name |
|---|---|---|
| 108 | | 6-Amino-3-(4'-chloro-3-(3-methyl-1,2,4-oxadiazol-5-yl)-1',2'-dihydrospiro[cyclopentane-1,3'-pyrrolo[2,3-b]pyridin]-5'-yl)-2-fluoro-N,N-dimethylbenzamide |
| 108a 108b | | 6-Amino-3-((1R,3S)-4'-chloro-3-(3-methyl-1,2,4-oxadiazol-5-yl)-1',2'-dihydrospiro[cyclopentane-1,3'-pyrrolo[2,3-b]pyridin]-5'-yl)-2-fluoro-N,N-dimethylbenzamide<br>6-Amino-3-((1S,3R)-4'-chloro-3-(3-methyl-1,2,4-oxadiazol-5-yl)-1',2'-dihydrospiro[cyclopentane-1,3'-pyrrolo[2,3-b]pyridin]-5'-yl)-2-fluoro-N,N-dimethylbenzamide |
| 108c 108d | | 6-Amino-3-((1R,3R)-4'-chloro-3-(3-methyl-1,2,4-oxadiazol-5-yl)-1',2'-dihydrospiro[cyclopentane-1,3'-pyrrolo[2,3-b]pyridin]-5'-yl)-2-fluoro-N,N-dimethylbenzamide<br>6-Amino-3-((1S,3S)-4'-chloro-3-(3-methyl-1,2,4-oxadiazol-5-yl)-1',2'-dihydrospiro[cyclopentane-1,3'-pyrrolo[2,3-b]pyridin]-5'-yl)-2-fluoro-N,N-dimethylbenzamide |
| 109 | | 6-Amino-3-(4'-chloro-3-(cyanomethyl)-3-hydroxy-1',2'-dihydrospiro[cyclopentane-1,3'-pyrrolo[2,3-b]pyridin]-5'-yl)-2-fluoro-N,N-dimethylbenzamide |
| 109a 109b | | 6-Amino-3-((1R,3R)-4'-chloro-3-(cyanomethyl)-3-hydroxy-1',2'-dihydrospiro[cyclopentane-1,3'-pyrrolo[2,3-b]pyridin]-5'-yl)-2-fluoro-N,N-dimethylbenzamide<br>6-Amino-3-((1S,3S)-4'-chloro-3-(cyanomethyl)-3-hydroxy-1',2'-dihydrospiro[cyclopentane-1,3'-pyrrolo[2,3-b]pyridin]-5'-yl)-2-fluoro-N,N-dimethylbenzamide |
| 109c 109d | | 6-Amino-3-((1R,3S)-4'-chloro-3-(cyanomethyl)-3-hydroxy-1',2'-dihydrospiro[cyclopentane-1,3'-pyrrolo[2,3-b]pyridin]-5'-yl)-2-fluoro-N,N-dimethylbenzamide<br>6-Amino-3-((1S,3R)-4'-chloro-3-(cyanomethyl)-3-hydroxy-1',2'-dihydrospiro[cyclopentane-1,3'-pyrrolo[2,3-b]pyridin]-5'-yl)-2-fluoro-N,N-dimethylbenzamide |

TABLE 1-continued

| No. | Structure | Name |
|---|---|---|
| 110 | 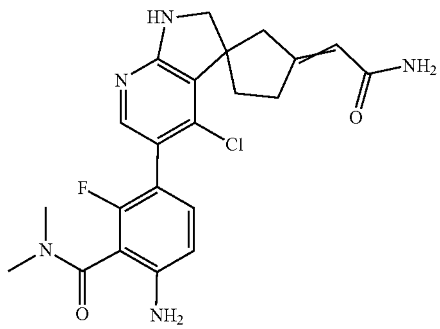 [SMILES: CN(C)C(=O)c1c(N)ccc(-c2cnc3c(c2Cl)C2(CCC(=CC(N)=O)C2)CN3)c1F] | 6-Amino-3-(3-(2-amino-2-oxoethylidene)-4'-chloro-1',2'-dihydrospiro[cyclopentane-1,3'-pyrrolo[2,3-b]pyridin]-5'-yl)-2-fluoro-N,N-dimethylbenzamide |
| 110a 110b 110c 110d | | (R,E)-6-Amino-3-(3-(2-amino-2-oxoethylidene)-4'-chloro-1',2'-dihydrospiro[cyclopentane-1,3'-pyrrolo[2,3-b]pyridin]-5'-yl)-2-fluoro-N,N-dimethylbenzamide (S,E)-6-Amino-3-(3-(2-amino-2-oxoethyhdene)-4'-chloro-1',2'-dihydrospiro[cyclopentane-1,3'-pyrrolo[2,3-b]pyridin]-5'-yl)-2-fluoro-N,N-dimethylbenzamide (R,Z)-6-Amino-3-(3-(2-amino-2-oxoethylidene)-4'-chloro-1',2'-dihydrospiro[cyclopentane-1,3'-pyrrolo[2,3-b]pyridin]-5'-yl)-2-fluoro-N,N-dimethylbenzamide (S,Z)-6-Amino-3-(3-(2-amino-2-oxoethylidene)-4'-chloro-1',2'-dihydrospiro[cyclopentane-1,3'-pyrrolo[2,3-b]pyridin]-5'-yl)-2-fluoro-N,N-dimethylbenzamide |
| 111 | 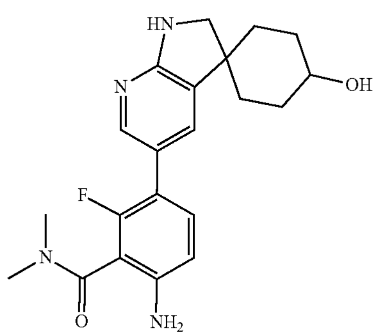 [SMILES: CN(C)C(=O)c1c(N)ccc(-c2cnc3c(c2)C2(CCC(O)CC2)CN3)c1F] | 6-Amino-2-fluoro-3-(4-hydroxy-1',2'-dihydrospiro[cyclohexane-1,3'-pyrrolo[2,3-b]pyridin]-5'-yl)-N,N-dimethylbenzamide |
| 111a | | 6-Amino-2-fluoro-3-((1s,4s)-4-hydroxy-1',2'-dihydrospiro[cyclohexane-1,3'-pyrrolo[2,3-b]pyridin]-5'-yl)-N,N-dimethylbenzamide |
| 111b | | 6-Amino-2-fluoro-3-((1r,4r)-4-hydroxy-1',2'-dihydrospiro[cyclohexane-1,3'-pyrrolo[2,3-b]pyridin]-5'-yl)-N,N-dimethylbenzamide |
| 112 | 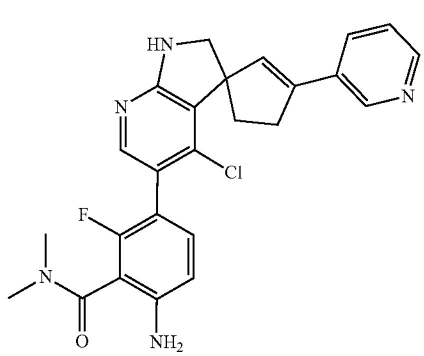 [SMILES: CN(C)C(=O)c1c(N)ccc(-c2cnc3c(c2Cl)C2(C=C(c4cccnc4)CC2)CN3)c1F] | 6-Amino-3-(4'-chloro-3-(pyridin-3-yl)-1',2'-dihydrospiro[cyclopentane-1,3'-pyrrolo[2,3-b]pyridin]-2-en-5'-yl)-2-fluoro-N,N-dimethylbenzamide |

TABLE 1-continued

| No. | Structure | Name |
|---|---|---|
| 112a<br>112b | | (R)-6-Amino-3-(4'-chloro-3-(pyridin-3-yl)-1',2'-dihydrospiro[cyclopentane-1,3'-pyrrolo[2,3-b]pyridin]-2-en-5'-yl)-2-fluoro-N,N-dimethylbenzamide<br>(S)-6-Amino-3-(4'-chloro-3-(pyridin-3-yl)-1',2'-dihydrospiro[cyclopentane-1,3'-pyrrolo[2,3-b]pyridin]-2-en-5'-yl)-2-fluoro-N,N-dimethylbenzamide |
| 113 | 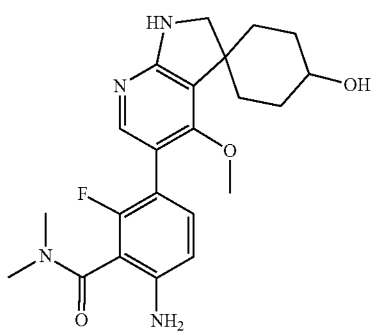 [SMILES: COc1c(-c2ccc(N)c(C(=O)N(C)C)c2F)cnc2c1C1(CCC(O)CC1)CN2] | 6-Amino-2-fluoro-3-(4-hydroxy-4'-methoxy-1',2'-dihydrospiro[cyclohexane-1,3'-pyrrolo[2,3-b]pyridin]-5'-yl)-N,N-dimethylbenzamide |
| 113a | | 6-Amino-2-fluoro-3-((1r,4r)-4-hydroxy-4'-methoxy-1',2'-dihydrospiro[cyclohexane-1,3'-pyrrolo[2,3-b]pyridin]-5'-yl)-N,N-dimethylbenzamide |
| 113b | | 6-Amino-2-fluoro-3-((1s,4s)-4-hydroxy-4'-methoxy-1',2'-dihydrospiro[cyclohexane-1,3'-pyrrolo[2,3-b]pyridin]-5'-yl)-N,N-dimethylbenzamide |
| 114 | 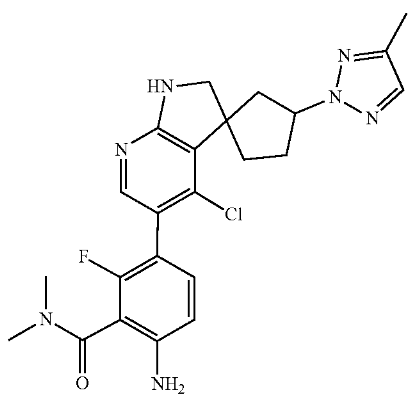 | 6-Amino-3-(4'-chloro-3-(4-methyl-2H-1,2,3-triazol-2-yl)-1',2'-dihydrospiro[cyclopentane-1,3'-pyrrolo[2,3-b]pyridin]-5'-yl)-2-fluoro-N,N-dimethylbenzamide |
| 114a<br>114b | | 6-Amino-3-((1R,3S)-4'-chloro-3-(4-methyl-2H-1,2,3-triazol-2-yl)-1',2'-dihydrospiro[cyclopentane-1,3'-pyrrolo[2,3-b]pyridin]-5'-yl)-2-fluoro-N,N-dimethylbenzamide<br>6-Amino-3-((1S,3R)-4'-chloro-3-(4-methyl-2H-1,2,3-triazol-2-yl)-1',2'-dihydrospiro[cyclopentane-1,3'-pyrrolo[2,3-b]pyridin]-5'-yl)-2-fluoro-N,N-dimethylbenzamide |
| 114c<br>114d | | 6-Amino-3-((1R,3R)-4'-chloro-3-(4-methyl-2H-1,2,3-triazol-2-yl)-1',2'-dihydrospiro[cyclopentane-1,3'-pyrrolo[2,3-b]pyridin]-5'-yl)-2-fluoro-N,N-dimethylbenzamide<br>6-Amino-3-((1S,3S)-4'-chloro-3-(4-methyl-2H-1,2,3-triazol-2-yl)-1',2'-dihydrospiro[cyclopentane-1,3'-pyrrolo[2,3-b]pyridin]-5'-yl)-2-fluoro-N,N-dimethylbenzamide |

TABLE 1-continued

| No. | Structure | Name |
|---|---|---|
| 115 | | 6-Amino-3-(4'-chloro-3-(2-oxoimidazolidin-1-yl)-1',2'-dihydrospiro[cyclopentane-1,3'-pyrrolo[2,3-b]pyridin]-5'-yl)-2-fluoro-N,N-dimethylbenzamide |
| 115a 115b | | 6-Amino-3-((1R,3S)-4'-chloro-3-(2-oxoimidazolidin-1-yl)-1',2'-dihydrospiro[cyclopentane-1,3'-pyrrolo[2,3-b]pyridin]-5'-yl)-2-fluoro-N,N-dimethylbenzamide<br>6-Amino-3-((1S,3R)-4'-chloro-3-(2-oxoimidazolidin-1-yl)-1',2'-dihydrospiro[cyclopentane-1,3'-pyrrolo[2,3-b]pyridin]-5'-yl)-2-fluoro-N,N-dimethylbenzamide |
| 115c 115d | | 6-Amino-3-((1R,3R)-4'-chloro-3-(2-oxoimidazolidin-1-yl)-1',2'-dihydrospiro[cyclopentane-1,3'-pyrrolo[2,3-b]pyridin]-5'-yl)-2-fluoro-N,N-dimethylbenzamide<br>6-Amino-3-((1S,3S)-4'-chloro-3-(2-oxoimidazolidin-1-yl)-1',2'-dihydrospiro[cyclopentane-1,3'-pyrrolo[2,3-b]pyridin]-5'-yl)-2-fluoro-N,N-dimethylbenzamide |
| 116 | | 3-(3-((1H-1,2,4-Triazol-1-yl)methyl)-4'-chloro-3-hydroxy-1',2'-dihydrospiro[cyclopentane-1,3'-pyrrolo[2,3-b]pyridin]-5'-yl)-6-amino-2-fluoro-N,N-dimethylbenzamide |
| 116a 116b | | 3-((1R,3S)-3-((1H-1,2,4-Triazol-1-yl)methyl)-4-chloro-3-hydroxy-1',2'-dihydrospiro[cyclopentane-1,3'-pyrrolo[2,3-b]pyridin]-5'-yl)-6-amino-2-fluoro-N, N-dimethylbenzamide<br>3-((1S,3R)-3-((1H-1,2,4-Triazol-1-yl)methyl)-4-chloro-3-hydroxy-1',2'-dihydrospiro[cyclopentane-1,3'-pyrrolo[2,3-b]pyridin]-5'-yl)-6-amino-2-fluoro-N, N-dimethylbenzamide |
| 116c 116d | | 3-((1R,3R)-3-((1H-1,2,4-Triazol-1-yl)methyl)-4-chloro-3-hydroxy-1',2'-dihydrospiro[cyclopentane-1,3'-pyrrolo[2,3-b]pyridin]-5'-yl)-6-amino-2-fluoro-N, N-dimethylbenzamide<br>3-((1S,3S)-3-((1H-1,2,4-Triazol-1-yl)methyl)-4'-chloro-3-hydroxy-1',2'-dihydrospiro[cyclopentane-1,3'-pyrrolo[2,3-b]pyridin]-5'-yl)-6-amino-2-fluoro-N, N-dimethylbenzamide |

TABLE 1-continued

| No. | Structure | Name |
|---|---|---|
| 117 | | 3-(3-((1H-Imidazol-1-yl)methyl)-4'-chloro-3-hydroxy-1',2'-dihydrospiro[cyclopentane-1,3'-pyrrolo[2,3-b]pyridin]-5'-yl)-6-amino-2-fluoro-N,N-dimethylbenzamide |
| 117a 117b | | 3-((1R,3S)-3-((1H-Imidazol-1-yl)methyl)-4'-chloro-3-hydroxy-1',2'-dihydrospiro[cyclopentane-1,3'-pyrrolo[2,3-b]pyridin]-5'-yl)-6-amino-2-fluoro-N, N-dimethylbenzamide<br>3-((1S,3R)-3-((1H-Imidazol-1-yl)methyl)-4'-chloro-3-hydroxy-1',2'-dihydrospiro[cyclopentane-1,3'-pyrrolo[2,3-b]pyridin]-5'-yl)-6-amino-2-fluoro-N, N-dimethylbenzamide |
| 117c 117d | | 3-((1R,3R)-3-((1H-Imidazol-1-yl)methyl)-4'-chloro-3-hydroxy-1',2'-dihydrospiro[cyclopentane-1,3'-pyrrolo[2,3-b]pyridin]-5'-yl)-6-amino-2-fluoro-N, N-dimethylbenzamide<br>3-((1S,3S)-3-((1H-Imidazol-1-yl)methyl)-4'-chloro-3-hydroxy-1',2'-dihydrospiro[cyclopentane-1,3'-pyrrolo[2,3-b]pyridin]-5'-yl)-6-amino-2-fluoro-N, N-dimethylbenzamide |
| 118 | | 6-Amino-3-((1RS,3SR)-3-(5-amino-1H-1,2,4-triazol-1-yl)-4'-chloro-1',2'-dihydrospiro[cyclopentane-1,3'-pyrrolo[2,3-b]pyridin]-5'-yl)-2-fluoro-N,N-dimethylbenzamide |
| 118a 118b | | 6-Amino-3-((1R,3S)-3-(5-amino-1H-1,2,4-triazol-1-yl)-4'-chloro-1',2'-dihydrospiro[cyclopentane-1,3'-pyrrolo[2,3-b]pyridin]-5'-yl)-2-fluoro-N,N-dimethylbenzamide<br>6-Amino-3-((1S,3R)-3-(5-amino-1H-1,2,4-triazol-1-yl)-4'-chloro-1',2'-dihydrospiro[cyclopentane-1,3'-pyrrolo[2,3-b]pyridin]-5'-yl)-2-fluoro-N,N-dimethylbenzamide |
| 118c 118d | | 6-Amino-3-((1R,3R)-3-(5-amino-1H-1,2,4-triazol-1-yl)-4'-chloro-1',2'-dihydrospiro[cyclopentane-1,3'-pyrrolo[2,3-b]pyridin]-5'-yl)-2-fluoro-N,N-dimethylbenzamide<br>6-Amino-3-((1S,3S)-3-(5-amino-1H-1,2,4-triazol-1-yl)-4'-chloro-1',2'-dihydrospiro[cyclopentane-1,3'-pyrrolo[2,3-b]pyridin]-5'-yl)-2-fluoro-N,N-dimethylbenzamide |

TABLE 1-continued

| No. | Structure | Name |
|---|---|---|
| 119 | | 6-Amino-3-(3-(3-amino-1H-1,2,4-triazol-1-yl)-4-chloro-1',2'-dihydrospiro[cyclopentane-1,3'-pyrrolo[2,3-b]pyridin]-5'-yl)-2-fluoro-N,N-dimethylbenzamide |
| 119a 119b | | 6-Amino-3-((1R,3S)-3-(3-amino-1H-1,2,4-triazol-1-yl)-4'-chloro-1',2'-dihydrospiro[cyclopentane-1,3'-pyrrolo[2,3-b]pyridin]-5'-yl)-2-fluoro-N,N-dimethylbenzamide<br>6-Amino-3-((1S,3R)-3-(3-amino-1H-1,2,4-triazol-1-yl)-4'-chloro-1',2'-dihydrospiro[cyclopentane-1,3'-pyrrolo[2,3-b]pyridin]-5'-yl)-2-fluoro-N,N-dimethylbenzamide |
| 119c 119d | | 6-Amino-3-((1R,3R)-3-(3-amino-1H-1,2,4-triazol-1-yl)-4'-chloro-1',2'-dihydrospiro[cyclopentane-1,3'-pyrrolo[2,3-b]pyridin]-5'-yl)-2-fluoro-N,N-dimethylbenzamide<br>6-Amino-3-((1S,3S)-3-(3-amino-1H-1,2,4-triazol-1-yl)-4'-chloro-1',2'-dihydrospiro[cyclopentane-1,3'-pyrrolo[2,3-b]pyridin]-5'-yl)-2-fluoro-N,N-dimethylbenzamide |
| 120 | | 6-Amino-3-(4'-chloro-3-morpholino-1',2'-dihydrospiro[cyclopentane-1,3'-pyrrolo[2,3-b]pyridin]-5'-yl)-2-fluoro-N,N-dimethylbenzamide |
| 120a 120b | | 6-Amino-3-((1R,3S)-4'-chloro-3-morpholino-1',2'-dihydrospiro[cyclopentane-1,3'-pyrrolo[2,3-b]pyridin]-5'-yl)-2-fluoro-N,N-dimethylbenzamide<br>6-Amino-3-((1S,3R)-4'-chloro-3-morpholino-1',2'-dihydrospiro[cyclopentane-1,3'-pyrrolo[2,3-b]pyridin]-5'-yl)-2-fluoro-N,N-dimethylbenzamide |
| 120c 120d | | 6-Amino-3-((1R,3R)-4'-chloro-3-morpholino-1',2'-dihydrospiro[cyclopentane-1,3'-pyrrolo[2,3-b]pyridin]-5'-yl)-2-fluoro-N,N-dimethylbenzamide<br>6-Amino-3-((1S,3S)-4'-chloro-3-morpholino-1',2'-dihydrospiro[cyclopentane-1,3'-pyrrolo[2,3-b]pyridin]-5'-yl)-2-fluoro-N,N-dimethylbenzamide |

TABLE 1-continued

| No. | Structure | Name |
|---|---|---|
| 121 | | 6-Amino-3-(4'-chloro-3-(pyrrolidin-1-yl)-1',2'-dihydrospiro[cyclopentane-1,3'-pyrrolo[2,3-b]pyridin]-5'-yl)-2-fluoro-N,N-dimethylbenzamide |
| 121a<br>121b | | 6-Amino-3-((1R,3S)-4'-chloro-3-(pyrrolidin-1-yl)-1',2'-dihydrospiro[cyclopentane-1,3'-pyrrolo[2,3-b]pyridin]-5'-yl)-2-fluoro-N,N-dimethylbenzamide<br>6-Amino-3-((1S,3R)-4'-chloro-3-(pyrrolidin-1-yl)-1',2'-dihydrospiro[cyclopentane-1,3'-pyrrolo[2,3-b]pyridin]-5'-yl)-2-fluoro-N,N-dimethylbenzamide |
| 121c<br>121d | | 6-Amino-3-((1R,3R)-4'-chloro-3-(pyrrolidin-1-yl)-1',2'-dihydrospiro[cyclopentane-1,3'-pyrrolo[2,3-b]pyridin]-5'-yl)-2-fluoro-N,N-dimethylbenzamide<br>6-Amino-3-((1S,3S)-4'-chloro-3-(pyrrolidin-1-yl)-1',2'-dihydrospiro[cyclopentane-1,3'-pyrrolo[2,3-b]pyridin]-5'-yl)-2-fluoro-N,N-dimethylbenzamide |
| 122 | | 6-Amino-3-(4'-chloro-2-oxo-1',2'-dihydrospiro[piperidine-4,3'-pyrrolo[2,3-b]pyridin]-5'-yl)-2-fluoro-N,N-dimethylbenzamide |
| 122a<br>122b | | (R)-6-Amino-3-(4'-chloro-2-oxo-1',2'-dihydrospiro[piperidine-4,3'-pyrrolo[2,3-b]pyridin]-5'-yl)-2-fluoro-N,N-dimethylbenzamide<br>(S)-6-Amino-3-(4'-chloro-2-oxo-1',2'-dihydrospiro[piperidine-4,3'-pyrrolo[2,3-b]pyridin]-5'-yl)-2-fluoro-N,N-dimethylbenzamide |
| 123 | | 6-Amino-3-(4'-chloro-6-oxo-1',2'-dihydrospiro[piperidine-3,3'-pyrrolo[2,3-b]pyridin]-5'-yl)-2-fluoro-N,N-dimethylbenzamide |
| 123a<br>123b | | (R)-6-Amino-3-(4'-chloro-6-oxo-1',2'-dihydrospiro[piperidine-3,3'-pyrrolo[2,3-b]pyridin]-5'-yl)-2-fluoro-N,N-dimethylbenzamide<br>(S)-6-Amino-3-(4'-chloro-6-oxo-1',2'-dihydrospiro[piperidine-3,3'-pyrrolo[2,3-b]pyridin]-5'-yl)-2-fluoro-N,N-dimethylbenzamide |

TABLE 1-continued

| No. | Structure | Name |
|---|---|---|
| 124 | | 6-Amino-3-(4'-chloro-3-(2-oxooxazolidin-3-yl)-1',2'-dihydrospiro[cyclopentane-1,3'-pyrrolo[2,3-b]pyridin]-5'-yl)-2-fluoro-N,N-dimethylbenzamide |
| 124a 124b | | 6-Amino-3-((1R,3S)-4'-chloro-3-(2-oxooxazolidin-3-yl)-1',2'-dihydrospiro[cyclopentane-1,3'-pyrrolo[2,3-b]pyridin]-5'-yl)-2-fluoro-N,N-dimethylbenzamide<br>6-Amino-3-((1S,3R)-4'-chloro-3-(2-oxooxazolidin-3-yl)-1',2'-dihydrospiro[cyclopentane-1,3'-pyrrolo[2,3-b]pyridin]-5'-yl)-2-fluoro-N,N-dimethylbenzamide |
| 124c 124d | | 6-Amino-3-((1R,3R)-4'-chloro-3-(2-oxooxazolidin-3-yl)-1',2'-dihydrospiro[cyclopentane-1,3'-pyrrolo[2,3-b]pyridin]-5'-yl)-2-fluoro-N,N-dimethylbenzamide<br>6-Amino-3-((1S,3S)-4'-chloro-3-(2-oxooxazolidin-3-yl)-1',2'-dihydrospiro[cyclopentane-1,3'-pyrrolo[2,3-b]pyridin]-5'-yl)-2-fluoro-N,N-dimethylbenzamide |
| 125 | | 6-Amino-3-(4'-chloro-3-(4-methyl-1H-pyrazol-1-yl)-1',2'-dihydrospiro[cyclopentane-1,3'-pyrrolo[2,3-b]pyridin]-5'-yl)-2-fluoro-N,N-dimethylbenzamide |
| 125a 125b | | 6-Amino-3-((1R,3S)-4'-chloro-3-(4-methyl-1H-pyrazol-1-yl)-1',2'-dihydrospiro[cyclopentane-1,3'-pyrrolo[2,3-b]pyridin]-5'-yl)-2-fluoro-N,N-dimethylbenzamide<br>6-Amino-3-((1S,3R)-4'-chloro-3-(4-methyl-1H-pyrazol-1-yl)-1',2'-dihydrospiro[cyclopentane-1,3'-pyrrolo[2,3-b]pyridin]-5'-yl)-2-fluoro-N,N-dimethylbenzamide |
| 125c 125d | | 6-Amino-3-((1R,3R)-4'-chloro-3-(4-methyl-1H-pyrazol-1-yl)-1',2'-dihydrospiro[cyclopentane-1,3'-pyrrolo[2,3-b]pyridin]-5'-yl)-2-fluoro-N,N-dimethylbenzamide<br>6-Amino-3-((1S,3S)-4'-chloro-3-(4-methyl-1H-pyrazol-1-yl)-1',2'-dihydrospiro[cyclopentane-1,3'-pyrrolo[2,3-b]pyridin]-5'-yl)-2-fluoro-N,N-dimethylbenzamide |

TABLE 1-continued

| No. | Structure | Name |
|---|---|---|
| 126 | | 6-Amino-3-(4'-chloro-3-(1H-pyrazol-1-yl)-1',2'-dihydrospiro[cyclopentane-1,3'-pyrrolo[2,3-b]pyridin]-5'-yl)-2-fluoro-N,N-dimethylbenzamide |
| 126a 126b | | 6-Amino-3-((1R,3S)-4'-chloro-3-(1H-pyrazol-1-yl)-1',2'-dihydrospiro[cyclopentane-1,3'-pyrrolo[2,3-b]pyridin]-5'-yl)-2-fluoro-N,N-dimethylbenzamide<br>6-Amino-3-((1S,3R)-4'-chloro-3-(1H-pyrazol-1-yl)-1',2'-dihydrospiro[cyclopentane-1,3'-pyrrolo[2,3-b]pyridin]-5'-yl)-2-fluoro-N,N-dimethylbenzamide |
| 126c 126d | | 6-Amino-3-((1R,3R)-4'-chloro-3-(1H-pyrazol-1-yl)-1',2'-dihydrospiro[cyclopentane-1,3'-pyrrolo[2,3-b]pyridin]-5'-yl)-2-fluoro-N,N-dimethylbenzamide<br>6-Amino-3-((1S,3S)-4'-chloro-3-(1H-pyrazol-1-yl)-1',2'-dihydrospiro[cyclopentane-1,3'-pyrrolo[2,3-b]pyridin]-5'-yl)-2-fluoro-N,N-dimethylbenzamide |
| 127 | | 6-Amino-3-(3-(aminomethyl)-4'-chloro-1',2'-dihydrospiro[cyclopentane-1,3'-pyrrolo[2,3-b]pyridin]-5'-yl)-2-fluoro-N,N-dimethylbenzamide |
| 127a 127b | | 6-Amino-3-((1R,3S)-3-(aminomethyl)-4'-chloro-1',2'-dihydrospiro[cyclopentane-1,3'-pyrrolo[2,3-b]pyridin]-5'-yl)-2-fluoro-N,N-dimethylbenzamide<br>6-Amino-3-((1S,3R)-3-(aminomethyl)-4'-chloro-1',2'-dihydrospiro[cyclopentane-1,3'-pyrrolo[2,3-b]pyridin]-5'-yl)-2-fluoro-N,N-dimethylbenzamide |
| 127c 127d | | 6-Amino-3-((1R,3R)-3-(aminomethyl)-4'-chloro-1',2'-dihydrospiro[cyclopentane-1,3'-pyrrolo[2,3-b]pyridin]-5'-yl)-2-fluoro-N,N-dimethylbenzamide<br>6-Amino-3-((7S,3S)-3-(aminomethyl)-4'-chloro-1',2'-dihydrospiro[cyclopentane-1,3'-pyrrolo[2,3-b]pyridin]-5'-yl)-2-fluoro-N,N-dimethylbenzamide |

TABLE 1-continued

| No. | Structure | Name |
|---|---|---|
| 128 | 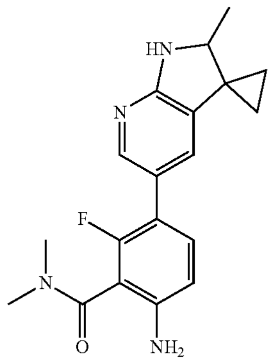 [SMILES: CC1Nc2ncc(-c3ccc(N)c(C(=O)N(C)C)c3F)cc2C12CC2] | 6-Amino-2-fluoro-N,N-dimethyl-3-(2'-methyl-1',2'-dihydrospiro[cyclopropane-1,3'-pyrrolo[2,3-b]pyridin]-5'-yl)benzamide |
| 128a<br>128b | | (R)-6-Amino-2-fluoro-N,N-dimethyl-3-(2'-methyl-1',2'-dihydrospiro[cyclopropane-1,3'-pyrrolo[2,3-b]pyridin]-5'-yl)benzamide<br>(S)-6-Amino-2-fluoro-N,N-dimethyl-3-(2'-methyl-1',2'-dihydrospiro[cyclopropane-1,3'-pyrrolo[2,3-b]pyridin]-5'-yl)benzamide |
| 129 | 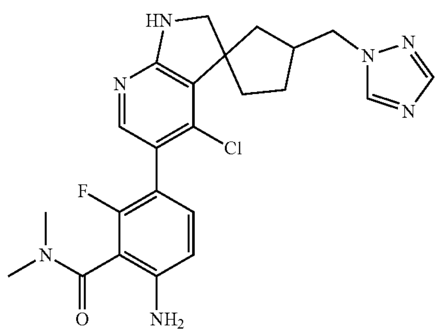 [SMILES: CN(C)C(=O)c1c(N)ccc(-c2cnc3c(c2Cl)C2(CCC(Cn4cncn4)C2)CN3)c1F] | 3-(3-((1H-1,2,4-Triazol-1-yl)methyl)-4-chloro-1',2'-dihydrospiro[cyclopentane-1,3'-pyrrolo[2,3-b]pyridin]-5'-yl)-6-amino-2-fluoro-N,N-dimethylbenzamide |
| 129a<br>129b | | 3-((1R,3S)-3-((1H-1,2,4-Triazol-1-yl)methyl)-4-chloro-1',2'-dihydrospiro[cyclopentane-1,3'-pyrrolo[2,3-b]pyridin]-5'-yl)-6-amino-2-fluoro-N,N-dimethylbenzamide<br>3-((1S,3R)-3-((1H-1,2,4-Triazol-1-yl)methyl)-4-chloro-1',2'-dihydrospiro[cyclopentane-1,3'-pyrrolo[2,3-b]pyridin]-5'-yl)-6-amino-2-fluoro-N,N-dimethyl benzamide |
| 129c<br>129c | | 3-((1R,3R)-3-((1H-1,2,4-Triazol-1-yl)methyl)-4'-chloro-1',2'-dihydrospiropcyclopentane-1,3-pyrrolo[2,3-b]pyridin]-5'-yl)-6-amino-2-fluoro-N,N-dimethylbenzamide<br>3-((1S,3S)-3-((1H-1,2,4-Triazol-1-yl)methyl)-4'-chloro-1',2'-dihydrospiro[cyclopentane-1,3'-pyrrolo[2,3-b]pyridin]-5'-yl)-6-amino-2-fluoro-N,N-dimethylbenzamide |
| 130 | 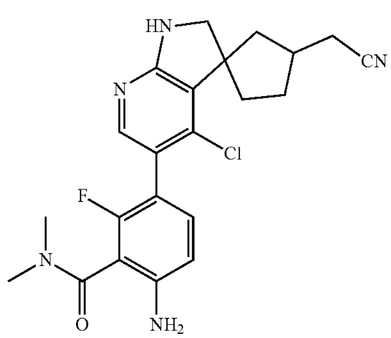 | 6-Amino-3-(4'-chloro-3-(cyanomethyl)-1',2'-dihydrospiro[cyclopentane-1,3'-pyrrolo[2,3-b]pyridin]-5'-yl)-2-fluoro-N,N-dimethylbenzamide |
| 130a<br>130b | | 6-Amino-3-((1R,3S)-4'-chloro-3-(cyanomethyl)-1',2'-dihydrospiro[cyclopentane-1,3'-pyrrolo[2,3-b]pyridin]-5'-yl)-2-fluoro-N,N-dimethylbenzamide<br>6-Amino-3-((1S,3R)-4'-chloro-3-(cyanomethyl)- |

TABLE 1-continued

| No. | Structure | Name |
|---|---|---|
| 130c | | 1',2'-dihydrospiro[cyclopentane-1,3'-pyrrolo[2,3-b]pyridin]-5'-yl)-2-fluoro-N,N-dimethylbenzamide<br>6-Amino-3-((1R,3R)-4'-chloro-3-(cyanomethyl)-1',2'-dihydrospiro[cyclopentane-1,3'-pyrrolo[2,3-b]pyridin]-5'-yl)-2-fluoro-N,N-dimethylbenzamide |
| 130d | | 6-Amino-3-((1S,3S)-4'-chloro-3-(cyanomethyl)-1',2'-dihydrospiro[cyclopentane-1,3'-pyrrolo[2,3-b]pyridin]-5'-yl)-2-fluoro-N,N-dimethylbenzamide |
| 131 | (structure) | 6-Amino-3-(4'-chloro-3-cyano-3-methyl-1',2'-dihydrospiro[cyclopentane-1,3'-pyrrolo[2,3-b]pyridin]-5'-yl)-2-fluoro-N,N-dimethylbenzamide |
| 131a | | 6-Amino-3-((1R,3S)-4'-chloro-3-cyano-3-methyl-1',2'-dihydrospiro[cyclopentane-1,3'-pyrrolo[2,3-b]pyridin]-5'-yl)-2-fluoro-N,N-dimethylbenzamide |
| 131b | | 6-Amino-3-((1S,3R)-4'-chloro-3-cyano-3-methyl-1',2'-dihydrospiro[cyclopentane-1,3'-pyrrolo[2,3-b]pyridin]-5'-yl)-2-fluoro-N,N-dimethylbenzamide |
| 131c | | 6-Amino-3-((1R,3R)-4'-chloro-3-cyano-3-methyl-1',2'-dihydrospiro[cyclopentane-1,3'-pyrrolo[2,3-b]pyridin]-5'-yl)-2-fluoro-N,N-dimethylbenzamide |
| 131d | | 6-Amino-3-((1S,3S)-4'-chloro-3-cyano-3-methyl-1',2'-dihydrospiro[cyclopentane-1,3'-pyrrolo[2,3-b]pyridin]-5'-yl)-2-fluoro-N,N-dimethylbenzamide |
| 132 | (structure) | 5'-(4-Amino-3-(dimethylcarbamoyl)-2-fluorophenyl)-4'-chloro-3-methyl-1',2'-dihydrospiro[cyclopentane-1,3'-pyrrolo[2,3-b]pyridine]-3-carboxamide |
| 132a | | (1R,3S)-5'-(4-Amino-3-(dimethylcarbamoyl)-2-fluorophenyl)-4'-chloro-3-methyl-1',2'-dihydrospiro[cyclopentane-1,3'-pyrrolo[2,3-b]pyridine]-3-carboxamide |
| 132b | | (1S,3R)-5'-(4-Amino-3-(dimethylcarbamoyl)-2-fluorophenyl)-4'-chloro-3-methyl-1',2'-dihydrospiro[cyclopentane-1,3'-pyrrolo[2,3-b]pyridine]-3-carboxamide |
| 132c | | (1R,3R)-5'-(4-Amino-3-(dimethylcarbamoyl)-2-fluorophenyl)-4'-chloro-3-methyl-1',2'-dihydrospiro[cyclopentane-1,3'-pyrrolo[2,3-b]pyridine]-3-carboxamide |
| 132d | | (1S,3S)-5'-(4-Amino-3-(dimethylcarbamoyl)-2-fluorophenyl)-4'-chloro-3-methyl-1',2'-dihydrospiro[cyclopentane-1,3'-pyrrolo[2,3-b]pyridine]-3-carboxamide |

TABLE 1-continued

| No. | Structure | Name |
|---|---|---|
| 133 | 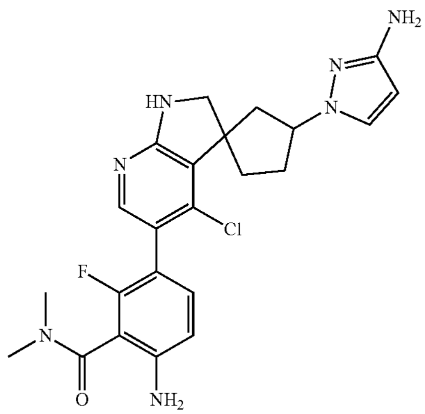 [SMILES: CN(C)C(=O)c1c(N)ccc(-c2cnc3c(c2Cl)C2(CCC(n4ccc(N)n4)C2)CN3)c1F] | 6-Amino-3-(3-(3-amino-1H-pyrazol-1-yl)-4'-chloro-1',2'-dihydrospiro[cyclopentane-1,3'-pyrrolo[2,3-b]pyridin]-5'-yl)-2-fluoro-N,N-dimethylbenzamide |
| 133a<br>133b | | 6-Amino-3-((1R,3S)-3-(3-amino-1H-pyrazol-1-yl)-4'-chloro-1',2'-dihydrospiro[cyclopentane-1,3'-pyrrolo[2,3-b]pyridin]-5'-yl)-2-fluoro-N,N-dimethylbenzamide<br>6-Amino-3-((1S,3R)-3-(3-amino-1H-pyrazol-1-yl)-4'-chloro-1',2'-dihydrospiro[cyclopentane-1,3'-pyrrolo[2,3-b]pyridin]-5'-yl)-2-fluoro-N,N-dimethylbenzamide |
| 133c<br>133d | | 6-Amino-3-((1R,3R)-3-(3-amino-1H-pyrazol-1-yl)-4'-chloro-1',2'-dihydrospiro[cyclopentane-1,3'-pyrrolo[2,3-b]pyridin]-5'-yl)-2-fluoro-N,N-dimethylbenzamide<br>6-Amino-3-((1S,3S)-3-(3-amino-1H-pyrazol-1-yl)-4'-chloro-1',2'-dihydrospiro[cyclopentane-1,3'-pyrrolo[2,3-b]pyridin]-5'-yl)-2-fluoro-N,N-dimethylbenzamide |
| 134 | 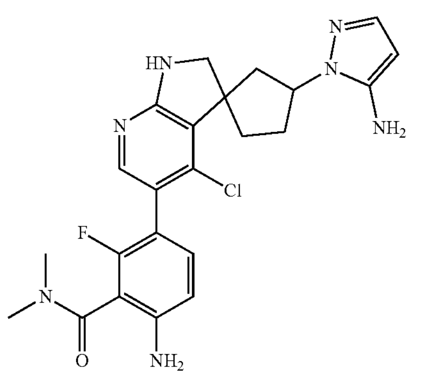 [SMILES: CN(C)C(=O)c1c(N)ccc(-c2cnc3c(c2Cl)C2(CCC(n4nccc4N)C2)CN3)c1F] | 6-Amino-3-(3-(5-amino-1H-pyrazol-1-yl)-4'-chloro-1',2'-dihydrospiro[cyclopentane-1,3'-pyrrolo[2,3-b]pyridin]-5'-yl)-2-fluoro-N,N-dimethylbenzamide |
| 134a<br>134b | | 6-Amino-3-((1R,3S)-3-(5-amino-1H-pyrazol-1-yl)-4'-chloro-1',2'-dihydrospiro[cyclopentane-1,3'-pyrrolo[2,3-b]pyridin]-5'-yl)-2-fluoro-N,N-dimethylbenzamide<br>6-Amino-3-((1S,3R)-3-(5-amino-1H-pyrazol-1-yl)-4'-chloro-1',2'-dihydrospiro[cyclopentane-1,3'-pyrrolo[2,3-b]pyridin]-5'-yl)-2-fluoro-N,N-dimethylbenzamide |
| 134c<br>134d | | 6-Amino-3-((1R,3R)-3-(5-amino-1H-pyrazol-1-yl)-4'-chloro-1',2'-dihydrospiro[cyclopentane-1,3'-pyrrolo[2,3-b]pyridin]-5'-yl)-2-fluoro-N,N-dimethylbenzamide<br>6-Amino-3-((1S,3S)-3-(5-amino-1H-pyrazol-1-yl)-4'-chloro-1',2'-dihydrospiro[cyclopentane-1,3'-pyrrolo[2,3-b]pyridin]-5'-yl)-2-fluoro-N,N-dimethylbenzamide |

TABLE 1-continued

| No. | Structure | Name |
|---|---|---|
| 135 | 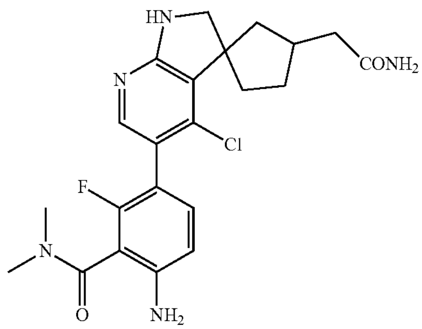 [SMILES: CN(C)C(=O)c1c(N)ccc(-c2cnc3c(c2Cl)C2(CCC(CC(N)=O)C2)CN3)c1F] | 6-Amino-3-(3-(2-amino-2-oxoethyl)-4'-chloro-1',2'-dihydrospiro[cyclopentane-1,3'-pyrrolo[2,3-b]pyridin]-5'-yl)-2-fluoro-N,N-dimethylbenzamide |
| 135a 135b | | 6-Amino-3-((1R,3S)-3-(2-amino-2-oxoethyl)-4'-chloro-1',2'-dihydrospiro[cyclopentane-1,3'-pyrrolo[2,3-b]pyridin]-5'-yl)-2-fluoro-N,N-dimethylbenzamide<br>6-Amino-3-((1S,3R)-3-(2-amino-2-oxoethyl)-4'-chloro-1',2'-dihydrospiro[cyclopentane-1,3'-pyrrolo[2,3-b]pyridin]-5'-yl)-2-fluoro-N,N-dimethylbenzamide |
| 135c 135d | | 6-Amino-3-((1R,3R)-3-(2-amino-2-oxoethyl)-4'-chloro-1',2'-dihydrospiro[cyclopentane-1,3'-pyrrolo[2,3-b]pyridin]-5'-yl)-2-fluoro-N,N-dimethylbenzamide<br>6-Amino-3-((1S,3S)-3-(2-amino-2-oxoethyl)-4'-chloro-1',2'-dihydrospiro[cyclopentane-1,3'-pyrrolo[2,3-b]pyridin]-5'-yl)-2-fluoro-N,N-dimethylbenzamide |
| 136 | 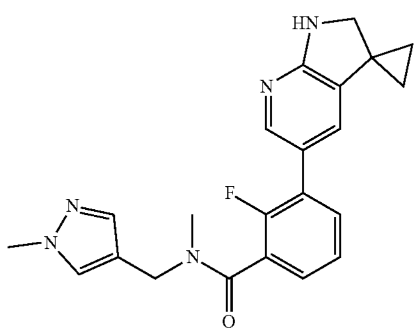 [SMILES: CN(Cc1cnn(C)c1)C(=O)c1cccc(-c2cnc3c(c2)C2(CC2)CN3)c1F] | 3-(1',2'-dihydrospiro[cyclopropane-1,3'-pyrrolo[2,3-b]pyridin]-5'-yl)-2-fluoro-N-methyl-N-((1-methyl-1H-pyrazol-4-yl)methyl)benzamide |
| 137 | 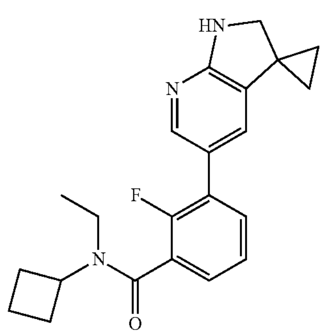 [SMILES: CCN(C(=O)c1cccc(-c2cnc3c(c2)C2(CC2)CN3)c1F)C1CCC1] | N-cyclobutyl-3-(1',2'-dihydrospiro[cyclopropane-1,3'-pyrrolo[2,3-b]pyridin]-5'-yl)-N-ethyl-2-fluorobenzamide |

TABLE 1-continued

| No. | Structure | Name |
|---|---|---|
| 138 | 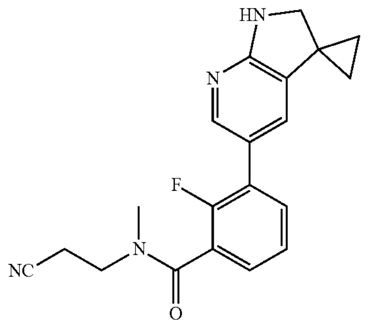 [SMILES: CN(CCC#N)C(=O)c1cccc(-c2cnc3c(c2)C2(CC2)CN3)c1F] | N-(2-cyanoethyl)-3-(1',2'-dihydrospiro[cyclopropane-1,3'-pyrrolo[2,3-b]pyridin]-5'-yl)-2-fluoro-N-methylbenzamide |
| 139 | 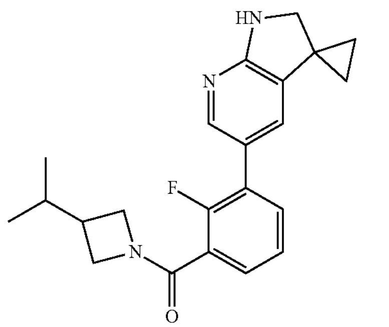 [SMILES: CC(C)C1CN(C(=O)c2cccc(-c3cnc4c(c3)C3(CC3)CN4)c2F)C1] | (3-(1',2'-dihydrospiro[cyclopropane-1,3'-pyrrolo[2,3-b]pyridin]-5'-yl)-2-fluorophenyl)(3-isopropylazetidin-1-yl)methanone |
| 140 | 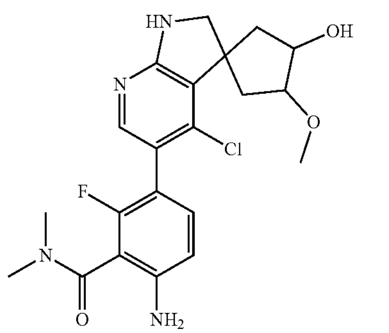 [SMILES: COC1CC2(CNc3ncc(-c4ccc(N)c(C(=O)N(C)C)c4F)c(Cl)c32)CC1O] | 6-Amino-3-(4'-chloro-3-hydroxy-4-methoxy-1',2'-dihydrospiro[cyclopentane-1,3'-pyrrolo[2,3-b]pyridin]-5'-yl)-2-fluoro-N,N-dimethylbenzamide |
| 140a 140b | | 6-Amino-3-((1R,3S,4S)-4'-chloro-3-hydroxy-4-methoxy-1',2'-dihydrospiro[cyclopentane-1,3'-pyrrolo[2,3-b]pyridin]-5'-yl)-2-fluoro-N,N-dimethylbenzamide<br>6-Amino-3-((1S,3R,4R)-4'-chloro-3-hydroxy-4-methoxy-1',2'-dihydrospiro[cyclopentane-1,3'-pyrrolo[2,3-b]pyridin]-5'-yl)-2-fluoro-N,N-dimethylbenzamide |
| 140c 140d | | 6-Amino-3-((1R,3S,4R)-4'-chloro-3-hydroxy-4-methoxy-1',2'-dihydrospiro[cyclopentane-1,3'-pyrrolo[2,3-b]pyridin]-5'-yl)-2-fluoro-N,N-dimethylbenzamide<br>6-Amino-3-((1S,3R,4S)-4'-chloro-3-hydroxy-4-methoxy-1',2'-dihydrospiro[cyclopentane-1,3'-pyrrolo[2,3-b]pyridin]-5'-yl)-2-fluoro-N,N-dimethylbenzamide |
| 140e 140f | | 6-Amino-3-((1R,3R,4S)-4'-chloro-3-hydroxy-4-methoxy-1',2'-dihydrospiro[cyclopentane-1,3'-pyrrolo[2,3-b]pyridin]-5'-yl)-2-fluoro-N,N-dimethylbenzamide<br>6-Amino-3-((1S,3S,4R)-4'-chloro-3-hydroxy-4-methoxy-1',2'-dihydrospiro[cyclopentane-1,3'-pyrrolo[2,3-b]pyridin]-5'-yl)-2-fluoro-N,N-dimethylbenzamide |

TABLE 1-continued

| No. | Structure | Name |
|---|---|---|
| 140g 140h | | 6-Amino-3-((1R,3R,4R)-4'-chloro-3-hydroxy-4-methoxy-1',2'-dihydrospiro[cyclopentane-1,3'-pyrrolo[2,3-b]pyridin]-5'-yl)-2-fluoro-N,N-dimethylbenzamide 6-Amino-3-((1S,3S,4S)-4'-chloro-3-hydroxy-4-methoxy-1',2'-dihydrospiro[cyclopentane-1,3'-pyrrolo[2,3-b]pyridin]-5'-yl)-2-fluoro-N,N-dimethylbenzamide |
| 141 | 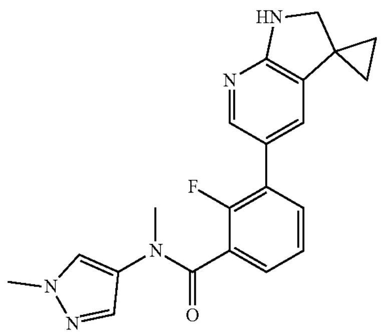 [SMILES: CN(C(=O)c1cccc(-c2cnc3c(c2)C2(CC2)CN3)c1F)c1cnn(C)c1] | 3-(1',2'-dihydrospiro[cyclopropane-1,3'-pyrrolo[2,3-b]pyridin]-5'-yl)-2-fluoro-N-methyl-N-(1-methyl-1H-pyrazol-4-yl)benzamide |
| 142 | 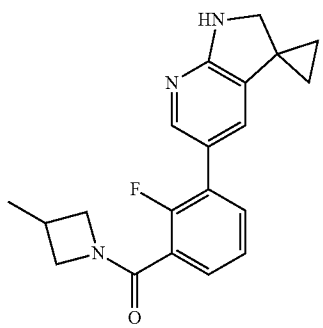 [SMILES: CC1CN(C(=O)c2cccc(-c3cnc4c(c3)C3(CC3)CN4)c2F)C1] | (3-(1',2'-dihydrospiro[cyclopropane-1,3'-pyrrolo[2,3-b]pyridin]-5'-yl)-2-fluorophenyl)(3-methylazetidin-1-yl)methanone |
| 143 | 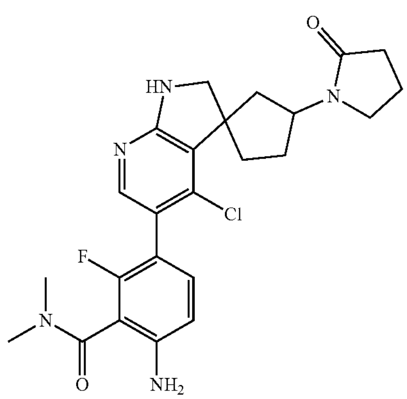 [SMILES: CN(C)C(=O)c1c(N)ccc(-c2cnc3c(c2Cl)C2(CCC(N4CCCC4=O)C2)CN3)c1F] | 6-Amino-3-(4'-chloro-3-(2-oxopyrrolidin-1-yl)-1',2'-dihydrospiro[cyclopentane-1,3'-pyrrolo[2,3-b]pyridin]-5'-yl)-2-fluoro-N,N-dimethylbenzamide |
| 143a 143b | | 6-Amino-3-((1R,3S)-4'-chloro-3-(2-oxopyrrolidin-1-yl)-1',2'-dihydrospiro[cyclopentane-1,3'-pyrrolo[2,3-b]pyridin]-5'-yl)-2-fluoro-N,N-dimethylbenzamide 6-Amino-3-((1S,3R)-4'-chloro-3-(2-oxopyrrolidin-1-yl)-1',2'-dihydrospiro[cyclopentane-1,3'-pyrrolo[2,3-b]pyridin]-5'-yl)-2-fluoro-N,N-dimethylbenzamide |
| 143c 143d | | 6-Amino-3-((1R,3R)-4'-chloro-3-(2-oxopyrrolidin-1-yl)-1',2'-dihydrospiro[cyclopentane-1,3'-pyrrolo[2,3-b]pyridin]-5'-yl)-2-fluoro-N,N-dimethylbenzamide 6-Amino-3-((1S,3S)-4'-chloro-3-(2-oxopyrrolidin-1-yl)-1',2'-dihydrospiro[cyclopentane-1,3'-pyrrolo[2,3-b]pyridin]-5'-yl)-2-fluoro-N,N-dimethylbenzamide |

TABLE 1-continued

| No. | Structure | Name |
|---|---|---|
| 144 | 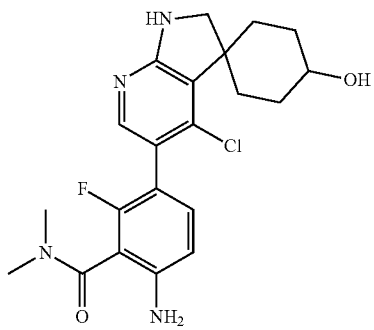 [SMILES: CN(C)C(=O)c1c(N)ccc(-c2cnc3c(c2Cl)C2(CCC(O)CC2)CN3)c1F] | 6-Amino-3-(4'-chloro-4-hydroxy-1',2'-dihydrospiro[cyclohexane-1,3'-pyrrolo[2,3-b]pyridin]-5'-yl)-2-fluoro-N,N-dimethylbenzamide |
| 144a | | 6-Amino-3-((1r,4r)-4'-chloro-4-hydroxy-1',2'-dihydrospiro[cyclohexane-1,3'-pyrrolo[2,3-b]pyridin]-5'-yl)-2-fluoro-N,N-dimethylbenzamide |
| 144b | | 6-Amino-3-((1s,4s)-4'-chloro-4-hydroxy-1',2'-dihydrospiro[cyclohexane-1,3'-pyrrolo[2,3-b]pyridin]-5'-yl)-2-fluoro-N,N-dimethylbenzamide |
| 145 | 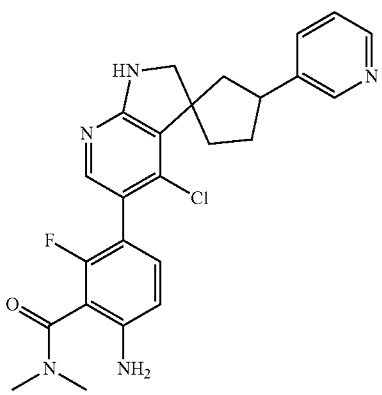 [SMILES: CN(C)C(=O)c1c(N)ccc(-c2cnc3c(c2Cl)C2(CCC(c4cccnc4)C2)CN3)c1F] | 6-Amino-3-(4'-chloro-3-(pyridin-3-yl)-1',2'-dihydrospiro[cyclopentane-1,3'-pyrrolo[2,3-b]pyridin]-5'-yl)-2-fluoro-N,N-dimethylbenzamide |
| 145a | | 6-Amino-3-((1R,3R)-4'-chloro-3-(pyridin-3-yl)-1',2'-dihydrospiro[cyclopentane-1,3'-pyrrolo[2,3-b]pyridin]-5'-yl)-2-fluoro-N,N-dimethylbenzamide |
| 145b | | 6-Amino-3-((1S,3S)-4'-chloro-3-(pyridin-3-yl)-1',2'-dihydrospiro[cyclopentane-1,3'-pyrrolo[2,3-b]pyridin]-5'-yl)-2-fluoro-N,N-dimethylbenzamide |
| 145c | | 6-Amino-3-((1R,3S)-4'-chloro-3-(pyridin-3-yl)-1',2'-dihydrospiro[cyclopentane-1,3'-pyrrolo[2,3-b]pyridin]-5'-yl)-2-fluoro-N,N-dimethylbenzamide |
| 145d | | 6-Amino-3-((1S,3R)-4'-chloro-3-(pyridin-3-yl)-1',2'-dihydrospiro[cyclopentane-1,3'-pyrrolo[2,3-b]pyridin]-5'-yl)-2-fluoro-N,N-dimethylbenzamide |
| 146 | 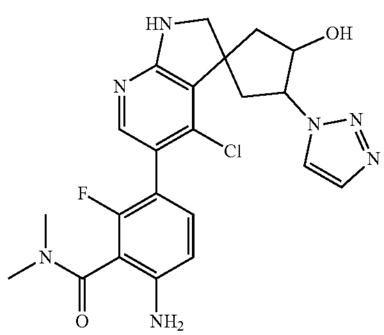 [SMILES: CN(C)C(=O)c1c(N)ccc(-c2cnc3c(c2Cl)C2(CN3)CC(O)C(n3ccnn3)C2)c1F] | 6-Amino-3-(4'-chloro-3-hydroxy-4-(1H-1,2,3-triazol-1-yl)-1',2'-dihydrospiro[cyclopentane-1,3'-pyrrolo[2,3-b]pyridin]-5'-yl)-2-fluoro-N,N-dimethylbenzamide |

TABLE 1-continued

| No. | Structure | Name |
|---|---|---|
| 146a | | 6-Amino-3-((1R,3S,4S)-4'-chloro-3-hydroxy-4-(1H-1,2,3-triazol-1-yl)-1',2'-dihydrospiro[cyclopentane-1,3'-pyrrolo[2,3-b]pyridin]-5'-yl)-2-fluoro-N,N-dimethylbenzamide |
| 146b | | 6-Amino-3-((1S,3R,4R)-4'-chloro-3-hydroxy-4-(1H-1,2,3-triazol-1-yl)-1',2'-dihydrospiro[cyclopentane-1,3'-pyrrolo[2,3-b]pyridin]-5'-yl)-2-fluoro-N,N-dimethylbenzamide |
| 146c | | 6-Amino-3-((1R,3R,4R)-4'-chloro-3-hydroxy-4-(1H-1,2,3-triazol-1-yl)-1',2'-dihydrospiro[cyclopentane-1,3'-pyrrolo[2,3-b]pyridin]-5'-yl)-2-fluoro-N,N-dimethylbenzamide |
| 146d | | 6-Amino-3-((1S,3S,4S)-4'-chloro-3-hydroxy-4-(1H-1,2,3-triazol-1-yl)-1',2'-dihydrospiro[cyclopentane-1,3'-pyrrolo[2,3-b]pyridin]-5'-yl)-2-fluoro-N,N-dimethylbenzamide |
| 146e | | 6-Amino-3-((1R,3S,4R)-4'-chloro-3-hydroxy-4-(1H-1,2,3-triazol-1-yl)-1',2'-dihydrospiro[cyclopentane-1,3'-pyrrolo[2,3-b]pyridin]-5'-yl)-2-fluoro-N,N-dimethylbenzamide |
| 146f | | 6-Amino-3-((1S,3R,4S)-4'-chloro-3-hydroxy-4-(1H-1,2,3-triazol-1-yl)-1',2'-dihydrospiro[cyclopentane-1,3'-pyrrolo[2,3-b]pyridin]-5'-yl)-2-fluoro-N,N-dimethylbenzamide |
| 146g | | 6-Amino-3-((1R,3R,4S)-4'-chloro-3-hydroxy-4-(1H-1,2,3-triazol-1-yl)-1',2'-dihydrospiro[cyclopentane-1,3'-pyrrolo[2,3-b]pyridin]-5'-yl)-2-fluoro-N,N-dimethylbenzamide |
| 146h | | 6-Amino-3-((1S,3S,4R)-4'-chloro-3-hydroxy-4-(1H-1,2,3-triazol-1-yl)-1',2'-dihydrospiro[cyclopentane-1,3'-pyrrolo[2,3-b]pyridin]-5'-yl)-2-fluoro-N,N-dimethylbenzamide |
| 147 | | (3-(1',2'-dihydrospiro[cyclopropane-1,3'-pyrrolo[2,3-b]pyridin]-5'-yl)-2-fluorophenyl)(6-oxa-1-azaspiro[3.3]heptan-1-yl)methanone |
| 148 | | 6-Amino-3-(4'-chloro-4-(4-methyl-1H-pyrazol-1-yl)-1',2'-dihydrospiro[cyclohexane-1,3'-pyrrolo[2,3-b]pyridin]-5'-yl)-2-fluoro-N,N-dimethylbenzamide |
| 148a | | 6-Amino-3-((1s,4s)-4'-chloro-4-(4-methyl-1H-pyrazol-1-yl)-1',2'-dihydrospiro[cyclohexane-1,3'-pyrrolo[2,3-b]pyridin]-5'-yl)-2-fluoro-N,N-dimethylbenzamide |
| 148b | | 6-Amino-3-((1r,4r)-4'-chloro-4-(4-methyl-1H-pyrazol-1-yl)-1',2'-dihydrospiro[cyclohexane-1,3'-pyrrolo[2,3-b]pyridin]-5'-yl)-2-fluoro-N,N-dimethylbenzamide |

TABLE 1-continued

| No. | Structure | Name |
|---|---|---|
| 149 | 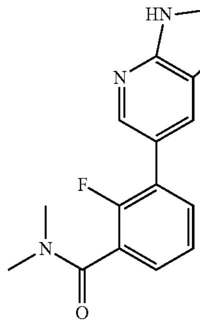 | 3-(1',2'-dihydrospiro[cyclopropane-1,3'-pyrrolo[2,3-b]pyridin]-5'-yl)-2-fluoro-N,N-dimethylbenzamide |
| 150 | 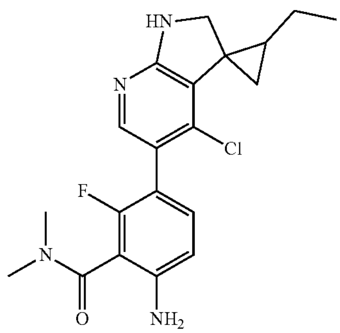 [SMILES: CCC1CC12CNc1ncc(-c3ccc(N)c(C(=O)N(C)C)c3F)c(Cl)c12] | 6-Amino-3-(4'-chloro-2-ethyl-1',2'-dihydrospiro[cyclopropane-1,3'-pyrrolo[2,3-b]pyridin]-5'-yl)-2-fluoro-N,N-dimethylbenzamide |
| 150a<br>150b | | 6-Amino-3-((1R,2S)-4'-chloro-2-ethyl-1',2'-dihydrospiro[cyclopropane-1,3'-pyrrolo[2,3-b]pyridin]-5'-yl)-2-fluoro-N,N-dimethylbenzamide<br>6-Amino-3-((1S,2R)-4'-chloro-2-ethyl-1',2'-dihydrospiro[cyclopropane-1,3'-pyrrolo[2,3-b]pyridin]-5'-yl)-2-fluoro-N,N-dimethylbenzamide |
| 150c<br>150d | | 6-Amino-3-((1R,2R)-4'-chloro-2-ethyl-1',2'-dihydrospiro[cyclopropane-1,3'-pyrrolo[2,3-b]pyridin]-5'-yl)-2-fluoro-N,N-dimethylbenzamide<br>6-Amino-3-((1S,2S)-4'-chloro-2-ethyl-1',2'-dihydrospiro[cyclopropane-1,3'-pyrrolo[2,3-b]pyridin]-5'-yl)-2-fluoro-N,N-dimethylbenzamide |
| 151 | 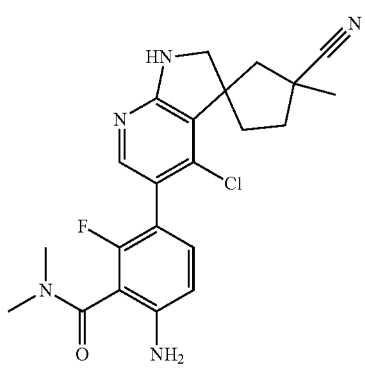 [SMILES: CN(C)C(=O)c1c(N)ccc(-c2cnc3c(c2Cl)C2(CCC(C)(C#N)C2)CN3)c1F] | 6-Amino-3-(4'-chloro-3-cyano-3-methyl-1',2'-dihydrospiro[cyclopentane-1,3'-pyrrolo[2,3-b]pyridin]-5'-yl)-2-fluoro-N,N-dimethylbenzamide |
| 151a<br>151b | | 6-Amino-3-((1R,3R)-4'-chloro-3-cyano-3-methyl-1',2'-dihydrospiro[cyclopentane-1,3'-pyrrolo[2,3-b]pyridin]-5'-yl)-2-fluoro-N,N-dimethylbenzamide<br>6-Amino-3-((1S,3S)-4'-chloro-3-cyano-3-methyl-1',2'-dihydrospiro[cyclopentane-1,3'-pyrrolo[2,3-b]pyridin]-5'-yl)-2-fluoro-N,N-dimethylbenzamide |
| 151c<br>151d | | 6-Amino-3-((1R,3S)-4'-chloro-3-cyano-3-methyl-1',2'-dihydrospiro[cyclopentane-1,3'-pyrrolo[2,3-b]pyridin]-5'-yl)-2-fluoro-N,N-dimethylbenzamide<br>6-Amino-3-((1S,3R)-4'-chloro-3-cyano-3-methyl-1',2'-dihydrospiro[cyclopentane-1,3'-pyrrolo[2,3-b]pyridin]-5'-yl)-2-fluoro-N,N-dimethylbenzamide |

TABLE 1-continued

| No. | Structure | Name |
|---|---|---|
| 152 | | 6-Amino-3-(4'-chloro-3-cyano-3-ethyl-1',2'-dihydrospiro[cyclopentane-1,3'-pyrrolo[2,3-b]pyridin]-5'-yl)-2-fluoro-N,N-dimethylbenzamide |
| 152a 152b | | 6-Amino-3-((1R,3S)-4'-chloro-3-cyano-3-ethyl-1',2'-dihydrospiro[cyclopentane-1,3'-pyrrolo[2,3-b]pyridin]-5'-yl)-2-fluoro-N,N-dimethylbenzamide<br>6-Amino-3-((1S,3R)-4'-chloro-3-cyano-3-ethyl-1',2'-dihydrospiro[cyclopentane-1,3'-pyrrolo[2,3-b]pyridin]-5'-yl)-2-fluoro-N,N-dimethylbenzamide |
| 152c 152d | | 6-Amino-3-((1R,3R)-4'-chloro-3-cyano-3-ethyl-1',2'-dihydrospiro[cyclopentane-1,3'-pyrrolo[2,3-b]pyridin]-5'-yl)-2-fluoro-N,N-dimethylbenzamide<br>6-Amino-3-((1S,3S)-4'-chloro-3-cyano-3-ethyl-1',2'-dihydrospiro[cyclopentane-1,3'-pyrrolo[2,3-b]pyridin]-5'-yl)-2-fluoro-N,N-dimethylbenzamide |
| 153 | | 5'-(4-Amino-3-(dimethylcarbamoyl)-2-fluorophenyl)-4'-chloro-3-ethyl-1',2'-dihydrospiro[cyclopentane-1,3'-pyrrolo[2,3-b]pyridine]-3-carboxamide |
| 153a 153b | | (1R,3S)-5'-(4-Amino-3-(dimethylcarbamoyl)-2-fluorophenyl)-4'-chloro-3-ethyl-1',2'-dihydrospiro[cyclopentane-1,3'-pyrrolo[2,3-b]pyridine]-3-carboxamide<br>(1S,3R)-5'-(4-Amino-3-(dimethylcarbamoyl)-2-fluorophenyl)-4'-chloro-3-ethyl-1',2'-dihydrospiro[cyclopentane-1,3'-pyrrolo[2,3-b]pyridine]-3-carboxamide |
| 153c 153d | | (1R,3R)-5'-(4-Amino-3-(dimethylcarbamoyl)-2-fluorophenyl)-4'-chloro-3-ethyl-1',2'-dihydrospiro[cyclopentane-1,3'-pyrrolo[2,3-b]pyridine]-3-carboxamide<br>(1S,3S)-5'-(4-Amino-3-(dimethylcarbamoyl)-2-fluorophenyl)-4'-chloro-3-ethyl-1',2'-dihydrospiro[cyclopentane-1,3'-pyrrolo[2,3-b]pyridine]-3-carboxamide |

TABLE 1-continued

| No. | Structure | Name |
|---|---|---|
| 154 | 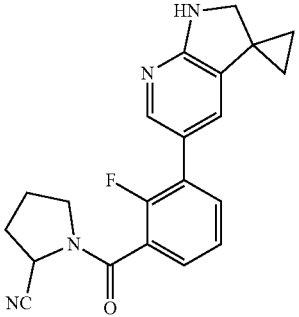 [SMILES: N#CC1CCCN1C(=O)c1cccc(-c2cnc3c(c2)C2(CC2)CN3)c1F] | 1-(3-(1',2'-dihydrospiro[cyclopropane-1,3'-pyrrolo[2,3-b]pyridin]-5'-yl)-2-fluorobenzoyl)pyrrolidine-2-carbonitrile |
| 154a | | (R)-1-(3-(1',2'-dihydrospiro[cyclopropane-1,3'-pyrrolo[2,3-b]pyridin]-5'-yl)-2-fluorobenzoyl)pyrrolidine-2-carbonitrile |
| 154b | | (S)-1-(3-(1',2'-dihydrospiro[cyclopropane-1,3'-pyrrolo[2,3-b]pyridin]-5'-yl)-2-fluorobenzoyl)pyrrolidine-2-carbonitrile |
| 155 | 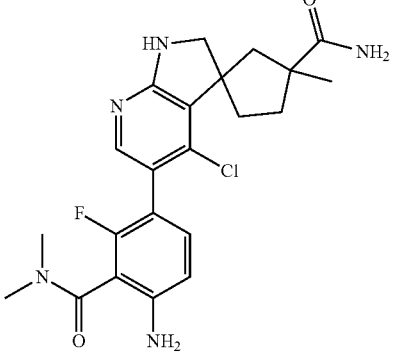 | 5'-(4-Amino-3-(dimethylcarbamoyl)-2-fluorophenyl)-4'-chloro-3-methyl-1',2'-dihydrospiro[cyclopentane-1,3'-pyrrolo[2,3-b]pyridine]-3-carboxamide |
| 155a 155b | | (1R,3S)-5'-(4-Amino-3-(dimethylcarbamoyl)-2-fluorophenyl)-4'-chloro-3-methyl-1',2'-dihydrospiro[cyclopentane-1,3'-pyrrolo[2,3-b]pyridine]-3-carboxamide (1S,3R)-5'-(4-Amino-3-(dimethylcarbamoyl)-2-fluorophenyl)-4'-chloro-3-methyl-1',2'-dihydrospiro[cyclopentane-1,3'-pyrrolo[2,3-b]pyridine]-3-carboxamide |
| 155c 155d | | (1R,3R)-5'-(4-Amino-3-(dimethylcarbamoyl)-2-fluorophenyl)-4'-chloro-3-methyl-1',2'-dihydrospiro[cyclopentane-1,3'-pyrrolo[2,3-b]pyridine]-3-carboxamide (1S,3S)-5'-(4-Amino-3-(dimethylcarbamoyl)-2-fluorophenyl)-4'-chloro-3-methyl-1',2'-dihydrospiro[cyclopentane-1,3'-pyrrolo[2,3-b]pyridine]-3-carboxamide |
| 156 | 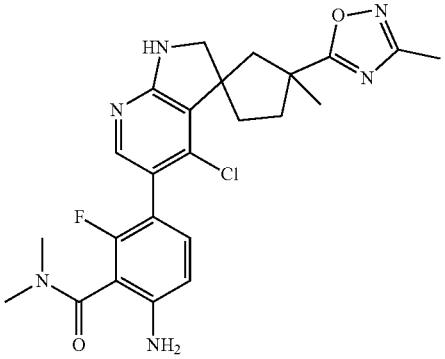 | 6-Amino-3-(4'-chloro-3-methyl-3-(3-methyl-1,2,4-oxadiazol-5-yl)-1',2'-dihydrospiro[cyclopentane-1,3'-pyrrolo[2,3-b]pyridin]-5'-yl)-2-fluoro-N,N-dimethylbenzamide |

TABLE 1-continued

| No. | Structure | Name |
|---|---|---|
| 156a 156b | | 6-Amino-3-((1R,3S)-4'-chloro-3-methyl-3-(3-methyl-1,2,4-oxadiazol-5-yl)-1',2'-dihydrospiro[cyclopentane-1,3'-pyrrolo[2,3-b]pyridin]-5'-yl)-2-fluoro-N,N-dimethylbenzamide 6-Amino-3-((1S,3R)-4'-chloro-3-methyl-3-(3-methyl-1,2,4-oxadiazol-5-yl)-1',2'-dihydrospiro[cyclopentane-1,3'-pyrrolo[2,3-b]pyridin]-5'-yl)-2-fluoro-N,N-dimethylbenzamide |
| 156c 156d | | 6-Amino-3-((1R,3R)-4'-chloro-3-methyl-3-(3-methyl-1,2,4-oxadiazol-5-yl)-1',2'-dihydrospiro[cyclopentane-1,3'-pyrrolo[2,3-b]pyridin]-5'-yl)-2-fluoro-N,N-dimethylbenzamide 6-Amino-3-((1S,3S)-4'-chloro-3-methyl-3-(3-methyl-1,2,4-oxadiazol-5-yl)-1',2'-dihydrospiro[cyclopentane-1,3'-pyrrolo[2,3-b]pyridin]-5'-yl)-2-fluoro-N,N-dimethylbenzamide |
| 157 | | 6-Amino-3-(3-(3-amino-5-methyl-1H-1,2,4-triazol-1-yl)-4'-chloro-1',2'-dihydrospiro[cyclopentane-1,3'-pyrrolo[2,3-b]pyridin]-5'-yl)-2-fluoro-N,N-dimethylbenzamide |
| 157a 157b | | 6-Amino-3-((1R,3S)-3-(3-amino-5-methyl-1H-1,2,4-triazol-1-yl)-4'-chloro-1',2'-dihydrospiro[cyclopentane-1,3'-pyrrolo[2,3-b]pyridin]-5'-yl)-2-fluoro-N,N-dimethylbenzamide 6-Amino-3-((1S,3R)-3-(3-amino-5-methyl-1H-1,2,4-triazol-1-yl)-4'-chloro-1',2'-dihydrospiro[cyclopentane-1,3'-pyrrolo[2,3-b]pyridin]-5'-yl)-2-fluoro-N,N-dimethylbenzamide |
| 157c 157d | | 6-Amino-3-((1R,3R)-3-(3-amino-5-methyl-1H-1,2,4-triazol-1-yl)-4'-chloro-1',2'-dihydrospiro[cyclopentane-1,3'-pyrrolo[2,3-b]pyridin]-5'-yl)-2-fluoro-N,N-dimethylbenzamide 6-Amino-3-((1S,3S)-3-(3-amino-5-methyl-1H-1,2,4-triazol-1-yl)-4'-chloro-1',2'-dihydrospiro[cyclopentane-1,3'-pyrrolo[2,3-b]pyridin]-5'-yl)-2-fluoro-N,N-dimethylbenzamide |
| 158 | | 6-Amino-3-(3-(5-amino-3-methyl-1H-1,2,4-triazol-1-yl)-4'-chloro-1',2'-dihydrospiro[cyclopentane-1,3'-pyrrolo[2,3-b]pyridin]-5'-yl)-2-fluoro-N,N-dimethylbenzamide |

TABLE 1-continued

| No. | Structure | Name |
|---|---|---|
| 158a 158b | | 6-Amino-3-((1R,3S)-3-(5-amino-3-methyl-1H-1,2,4-triazol-1-yl)-4'-chloro-1',2'-dihydrospiro[cyclopentane-1,3'-pyrrolo[2,3-b]pyridin]-5'-yl)-2-fluoro-N,N-dimethylbenzamide<br>6-Amino-3-((1S,3R)-3-(5-amino-3-methyl-1H-1,2,4-triazol-1-yl)-4'-chloro-1',2'-dihydrospiro[cyclopentane-1,3'-pyrrolo[2,3-b]pyridin]-5'-yl)-2-fluoro-N,N-dimethylbenzamide |
| 158c 158d | | 6-Amino-3-((1R,3R)-3-(5-amino-3-methyl-1H-1,2,4-triazol-1-yl)-4'-chloro-1',2'-dihydrospiro[cyclopentane-1,3'-pyrrolo[2,3-b]pyridin]-5'-yl)-2-fluoro-N,N-dimethylbenzamide<br>6-Amino-3-((1S,3S)-3-(5-amino-3-methyl-1H-1,2,4-triazol-1-yl)-4'-chloro-1',2'-dihydrospiro[cyclopentane-1,3'-pyrrolo[2,3-b]pyridin]-5'-yl)-2-fluoro-N,N-dimethylbenzamide |
| 159 | | 6-Amino-3-(4'-chloro-3-(3-methyl-1H-pyrazol-1-yl)-1',2'-dihydrospiro[cyclopentane-1,3'-pyrrolo[2,3-b]pyridin]-5'-yl)-2-fluoro-N,N-dimethylbenzamide |
| 159a 159b | | 6-Amino-3-((1R,3S)-4'-chloro-3-(3-methyl-1H-pyrazol-1-yl)-1',2'-dihydrospiro[cyclopentane-1,3'-pyrrolo[2,3-b]pyridin]-5'-yl)-2-fluoro-N,N-dimethylbenzamide<br>6-Amino-3-((1S,3R)-4'-chloro-3-(3-methyl-1H-pyrazol-1-yl)-1',2'-dihydrospiro[cyclopentane-1,3'-pyrrolo[2,3-b]pyridin]-5'-yl)-2-fluoro-N,N-dimethylbenzamide |
| 159c 159d | | 6-Amino-3-((1R,3R)-4'-chloro-3-(3-methyl-1H-pyrazol-1-yl)-1',2'-dihydrospiro[cyclopentane-1,3'-pyrrolo[2,3-b]pyridin]-5'-yl)-2-fluoro-N,N-dimethylbenzamide<br>6-Amino-3-((1S,3S)-4'-chloro-3-(3-methyl-1H-pyrazol-1-yl)-1',2'-dihydrospiro[cyclopentane-1,3'-pyrrolo[2,3-b]pyridin]-5'-yl)-2-fluoro-N,N-dimethylbenzamide |
| 160 | | 6-Amino-3-(4'-chloro-3-(5-methyl-1H-pyrazol-1-yl)-1',2'-dihydrospiro[cyclopentane-1,3'-pyrrolo[2,3-b]pyridin]-5'-yl)-2-fluoro-N,N-dimethylbenzamide |
| 160a 160b | | 6-Amino-3-((1R,3S)-4'-chloro-3-(5-methyl-1H-pyrazol-1-yl)-1',2'-dihydrospiro[cyclopentane-1,3'-pyrrolo[2,3-b]pyridin]-5'-yl)-2-fluoro-N,N-dimethylbenzamid<br>6-Amino-3-((1S,3R)-4'-chloro-3-(5-methyl-1H-pyrazol-1-yl)-1',2'-dihydrospiro[cyclopentane-1,3'-pyrrolo[2,3-b]pyridin]-5'-yl)-2-fluoro-N,N-dimethylbenzamide e |

TABLE 1-continued

| No. | Structure | Name |
|---|---|---|
| 160c 160d | | 6-Amino-3-((1R,3R)-4-chloro-3-(5-methyl-1H-pyrazol-1-yl)-1',2'-dihydrospiro[cyclopentane-1,3'-pyrrolo[2,3-b]pyridin]-5'-yl)-2-fluoro-N,N-dimethylbenzamid 6-Amino-3-((1S,3S)-4'-chloro-3-(5-methyl-1H-pyrazol-1-yl)-1',2'-dihydrospiro[cyclopentane-1,3'-pyrrolo[2,3-b]pyridin]-5'-yl)-2-fluoro-N,N-dimethylbenzamide e |
| 161 | | 6-Amino-3-(4'-chloro-3-(5-cyano-3-methyl-1H-pyrazol-1-yl)-1',2'-dihydrospiro[cyclopentane-1,3'-pyrrolo[2,3-b]pyridin]-5'-yl)-2-fluoro-N,N-dimethylbenzamide |
| 161a 161b | | 6-Amino-3-((1R,3S)-4-chloro-3-(5-cyano-3-methyl-1H-pyrazol-1-yl)-1',2'-dihydrospiro[cyclopentane-1,3'-pyrrolo[2,3-b]pyridin]-5'-yl)-2-fluoro-N,N-dimethylbenzamide 6-Amino-3-((1S,3R)-4'-chloro-3-(5-cyano-3-methyl-1H-pyrazol-1-yl)-1',2'-dihydrospiro[cyclopentane-1,3'-pyrrolo[2,3-b]pyridin]-5'-yl)-2-fluoro-N,N-dimethylbenzamide |
| 161c 161d | | 6-Amino-3-((1R,3R)-4'-chloro-3-(5-cyano-3-methyl-1H-pyrazol-1-yl)-1',2'-dihydrospiro[cyclopentane-1,3'-pyrrolo[2,3-b]pyridin]-5'-yl)-2-fluoro-N,N-dimethylbenzamide 6-Amino-3-((1S,3S)-4'-chloro-3-(5-cyano-3-methyl-1H-pyrazol-1-yl)-1',2'-dihydrospiro[cyclopentane-1,3'-pyrrolo[2,3-b]pyridin]-5'-yl)-2-fluoro-N,N-dimethylbenzamide |
| 162 | | 6-Amino-3-(4'-chloro-3-(3-cyano-5-methyl-1H-pyrazol-1-yl)-1',2'-dihydrospiro[cyclopentane-1,3'-pyrrolo[2,3-b]pyridin]-5'-yl)-2-fluoro-N,N-dimethylbenzamide |
| 162a 162b | | 6-Amino-3-((1R,3S)-4-chloro-3-(3-cyano-5-methyl-1H-pyrazol-1-yl)-1',2'-dihydrospiro[cyclopentane-1,3'-pyrrolo[2,3-b]pyridin]-5'-yl)-2-fluoro-N,N-dimethylbenzamide 6-Amino-3-((1S,3R)-4'-chloro-3-(3-cyano-5-methyl-1H-pyrazol-1-yl)-1',2'-dihydrospiro[cyclopentane-1,3'-pyrrolo[2,3-b]pyridin]-5'-yl)-2-fluoro-N,N-dimethylbenzamide |

TABLE 1-continued

| No. | Structure | Name |
| --- | --- | --- |
| 162c 162d | | 6-Amino-3-((1R,3R)-4'-chloro-3-(3-cyano-5-methyl-1H-pyrazol-1-yl)-1',2'-dihydrospiro[cyclopentane-1,3'-pyrrolo[2,3-b]pyridin]-5'-yl)-2-fluoro-N,N-dimethylbenzamide<br>6-Amino-3-((1S,3S)-4'-chloro-3-(3-cyano-5-methyl-1H-pyrazol-1-yl)-1',2'-dihydrospiro[cyclopentane-1,3'-pyrrolo[2,3-b]pyridin]-5'-yl)-2-fluoro-N,N-dimethylbenzamide |
| 163 | 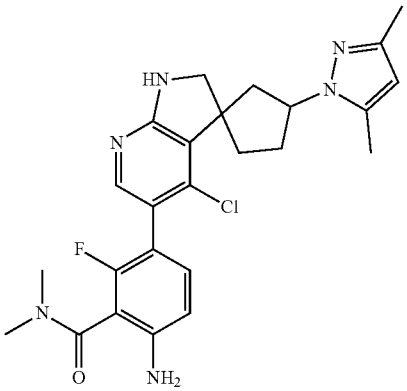 | 6-Amino-3-(4'-chloro-3-(3,5-dimethyl-1H-pyrazol-1-yl)-1',2'-dihydrospiro[cyclopentane-1,3'-pyrrolo[2,3-b]pyridin]-5'-yl)-2-fluoro-N,N-dimethylbenzamide |
| 163a 163b | | 6-Amino-3-((1R,3S)-4'-chloro-3-(3,5-dimethyl-1H-pyrazol-1-yl)-1',2'-dihydrospiro[cyclopentane-1,3'-pyrrolo[2,3-b]pyridin]-5'-yl)-2-fluoro-N,N-dimethylbenzamide<br>6-Amino-3-((1S,3R)-4'-chloro-3-(3,5-dimethyl-1H-pyrazol-1-yl)-1',2'-dihydrospiro[cyclopentane-1,3'-pyrrolo[2,3-b]pyridin]-5'-yl)-2-fluoro-N,N-dimethylbenzamide |
| 163c 163d | | 6-Amino-3-((1R,3R)-4'-chloro-3-(3,5-dimethyl-1H-pyrazol-1-yl)-1',2'-dihydrospiro[cyclopentane-1,3'-pyrrolo[2,3-b]pyridin]-5'-yl)-2-fluoro-N,N-dimethylbenzamide<br>6-Amino-3-((1S,3S)-4'-chloro-3-(3,5-dimethyl-1H-pyrazol-1-yl)-1',2'-dihydrospiro[cyclopentane-1,3'-pyrrolo[2,3-b]pyridin]-5'-yl)-2-fluoro-N,N-dimethylbenzamide |
| 164 | 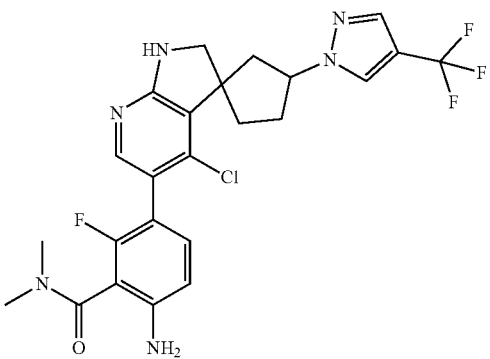 [SMILES: CN(C)C(=O)c1c(N)ccc(-c2cnc3c(c2Cl)C2(CCC(n4cc(C(F)(F)F)cn4)C2)CN3)c1F] | 6-Amino-3-(4'-chloro-3-(4-(trifluoromethyl)-1H-pyrazol-1-yl)-1',2'-dihydrospiro[cyclopentane-1,3'-pyrrolo[2,3-b]pyridin]-5'-yl)-2-fluoro-N,N-dimethylbenzamide |
| 164a 164b | | 6-Amino-3-((1R,3S)-4'-chloro-3-(4-(trifluoromethyl)-1H-pyrazol-1-yl)-1',2'-dihydrospiro[cyclopentane-1,3'-pyrrolo[2,3-b]pyridin]-5'-yl)-2-fluoro-N,N-dimethylbenzamide<br>6-Amino-3-((1S,3R)-4'-chloro-3-(4-(trifluoromethyl)-1H-pyrazol-1-yl)-1',2'-dihydrospiro[cyclopentane-1,3'-pyrrolo[2,3-b]pyridin]-5'-yl)-2-fluoro-N,N-dimethylbenzamide |

TABLE 1-continued

| No. | Structure | Name |
|---|---|---|
| 165 | 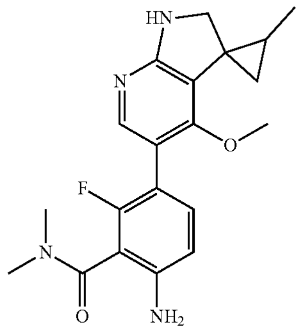 | 6-Amino-2-fluoro-3-(4'-methoxy-2-methyl-1',2'-dihydrospiro[cyclopropane-1,3'-pyrrolo[2,3-b]pyridin]-5'-yl)-N,N-dimethylbenzamide |
| 165a<br>165b | | 6-Amino-2-fluoro-3-((1R,2S)-4'-methoxy-2-methyl-1',2'-dihydrospiro[cyclopropane-1,3'-pyrrolo[2,3-b]pyridin]-5'-yl)-N,N-dimethylbenzamide<br>6-Amino-2-fluoro-3-((1S,2R)-4'-methoxy-2-methyl-1',2'-dihydrospiro[cyclopropane-1,3'-pyrrolo[2,3-b]pyridin]-5'-yl)-N,N-dimethylbenzamide |
| 166 | 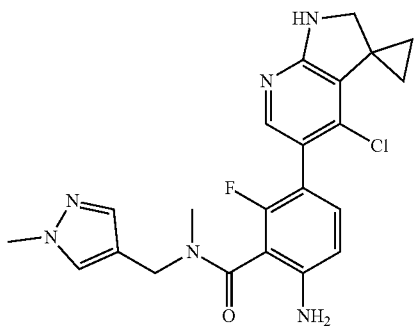 [SMILES: CN(Cc1cnn(C)c1)C(=O)c1c(N)ccc(-c2cnc3c(c2Cl)C2(CC2)CN3)c1F] | 6-Amino-3-(4'-chloro-1',2'-dihydrospiro[cyclopropane-1,3'-pyrrolo[2,3-b]pyridin]-5'-yl)-2-fluoro-N-methyl-N-((1-methyl-1H-pyrazol-4-yl)methyl)benzamide |
| 167 | 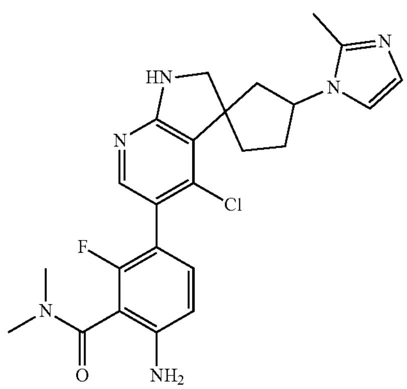 [SMILES: Cc1nccn1C1CCC2(CNc3ncc(-c4ccc(N)c(C(=O)N(C)C)c4F)c(Cl)c32)C1] | 6-Amino-3-(4'-chloro-3-(2-methyl-1H-imidazol-1-yl)-1',2'-dihydrospiro[cyclopentane-1,3'-pyrrolo[2,3-b]pyridin]-5'-yl)-2-fluoro-N,N-dimethylbenzamide |
| 167a<br>167b | | 6-Amino-3-((1R,3S)-4'-chloro-3-(2-methyl-1H-imidazol-1-yl)-1',2'-dihydrospiro[cyclopentane-1,3'-pyrrolo[2,3-b]pyridin]-5'-yl)-2-fluoro-N,N-dimethylbenzamide<br>6-Amino-3-((1S,3R)-4'-chloro-3-(2-methyl-1H-imidazol-1-yl)-1',2'-dihydrospiro[cyclopentane-1,3'-pyrrolo[2,3-b]pyridin]-5'-yl)-2-fluoro-N,N-dimethylbenzamide |
| 167c<br>167d | | 6-Amino-3-((1R,3R)-4'-chloro-3-(2-methyl-1H-imidazol-1-yl)-1',2'-dihydrospiro[cyclopentane-1,3'-pyrrolo[2,3-b]pyridin]-5'-yl)-2-fluoro-N,N-dimethylbenzamide<br>6-Amino-3-((1S,3S)-4'-chloro-3-(2-methyl-1H-imidazol-1-yl)-1',2'-dihydrospiro[cyclopentane-1,3'-pyrrolo[2,3-b]pyridin]-5'-yl)-2-fluoro-N,N-dimethylbenzamide |

TABLE 1-continued

| No. | Structure | Name |
|---|---|---|
| 168 | | 6-Amino-3-(4'-chloro-3-(3-(trifluoromethyl)-1H-pyrazol-1-yl)-1',2'-dihydrospiro[cyclopentane-1,3'-pyrrolo[2,3-b]pyridin]-5'-yl)-2-fluoro-N,N-dimethylbenzamide |
| 168a 168b | | 6-Amino-3-((1R,3S)-4'-chloro-3-(3-(trifluoromethyl)-1H-pyrazol-1-yl)-1',2'-dihydrospiro[cyclopentane-1,3'-pyrrolo[2,3-b]pyridin]-5'-yl)-2-fluoro-N,N-dimethylbenzamide 6-Amino-3-((1S,3R)-4'-chloro-3-(3-(trifluoromethyl)-1H-pyrazol-1-yl)-1',2'-dihydrospiro[cyclopentane-1,3'-pyrrolo[2,3-b]pyridin]-5'-yl)-2-fluoro-N,N-dimethylbenzamide |
| 168c 168d | | 6-Amino-3-((1R,3R)-4'-chloro-3-(3-(trifluoromethyl)-1H-pyrazol-1-yl)-1',2'-dihydrospiro[cyclopentane-1,3'-pyrrolo[2,3-b]pyridin]-5'-yl)-2-fluoro-N,N-dimethylbenzamide 6-Amino-3-((1S,3S)-4'-chloro-3-(3-(trifluoromethyl)-1H-pyrazol-1-yl)-1',2'-dihydrospiro[cyclopentane-1,3'-pyrrolo[2,3-b]pyridin]-5'-yl)-2-fluoro-N,N-dimethylbenzamide |
| 169 | | 6-Amino-3-(4'-chloro-3-(5-(trifluoromethyl)-1H-pyrazol-1-yl)-1',2'-dihydrospiro[cyclopentane-1,3'-pyrrolo[2,3-b]pyridin]-5'-yl)-2-fluoro-N,N-dimethylbenzamide |
| 169a 169b | | 6-Amino-3-((1R,3S)-4'-chloro-3-(5-(trifluoromethyl)-1H-pyrazol-1-yl)-1',2'-dihydrospiro[cyclopentane-1,3'-pyrrolo[2,3-b]pyridin]-5'-yl)-2-fluoro-N,N-dimethylbenzamide 6-Amino-3-((1S,3R)-4'-chloro-3-(5-(trifluoromethyl)-1H-pyrazol-1-yl)-1',2'-dihydrospiro[cyclopentane-1,3'-pyrrolo[2,3-b]pyridin]-5'-yl)-2-fluoro-N,N-dimethylbenzamide |
| 169c 169d | | 6-Amino-3-((1R,3R)-4'-chloro-3-(5-(trifluoromethyl)-1H-pyrazol-1-yl)-1',2'-dihydrospiro[cyclopentane-1,3'-pyrrolo[2,3-b]pyridin]-5'-yl)-2-fluoro-N,N-dimethylbenzamide 6-Amino-3-((1S,3S)-4'-chloro-3-(5-(trifluoromethyl)-1H-pyrazol-1-yl)-1',2'-dihydrospiro[cyclopentane-1,3'-pyrrolo[2,3-b]pyridin]-5'-yl)-2-fluoro-N,N-dimethylbenzamide |

TABLE 1-continued

| No. | Structure | Name |
|---|---|---|
| 170 | 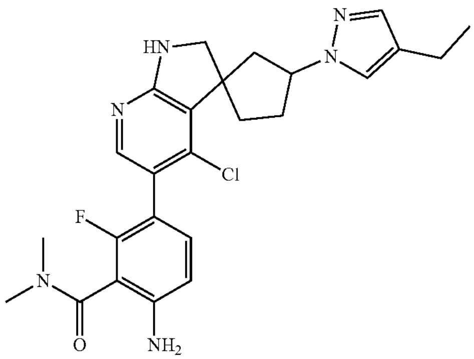 [SMILES: CCc1cnn(C2CCC3(CNc4ncc(-c5ccc(N)c(C(=O)N(C)C)c5F)c(Cl)c43)C2)c1] | 6-Amino-3-(4'-chloro-3-(4-ethyl-1H-pyrazol-1-yl)-1',2'-dihydrospiro[cyclopentane-1,3'-pyrrolo[2,3-b]pyridin]-5'-yl)-2-fluoro-N,N-dimethylbenzamide |
| 170a<br>170b | | 6-Amino-3-((1R,3S)-4'-chloro-3-(4-ethyl-1H-pyrazol-1-yl)-1',2'-dihydrospiro[cyclopentane-1,3'-pyrrolo[2,3-b]pyridin]-5'-yl)-2-fluoro-N,N-dimethylbenzamide<br>6-Amino-3-((1S,3R)-4'-chloro-3-(4-ethyl-1H-pyrazol-1-yl)-1',2'-dihydrospiro[cyclopentane-1,3'-pyrrolo[2,3-b]pyridin]-5'-yl)-2-fluoro-N,N-dimethylbenzamide |
| 170c<br>170d | | 6-Amino-3-((1R,3R)-4'-chloro-3-(4-ethyl-1H-pyrazol-1-yl)-1',2'-dihydrospiro[cyclopentane-1,3'-pyrrolo[2,3-b]pyridin]-5'-yl)-2-fluoro-N,N-dimethylbenzamide<br>6-Amino-3-((1S,3S)-4'-chloro-3-(4-ethyl-1H-pyrazol-1-yl)-1',2'-dihydrospiro[cyclopentane-1,3'-pyrrolo[2,3-b]pyridin]-5'-yl)-2-fluoro-N,N-dimethylbenzamide |
| 171 | 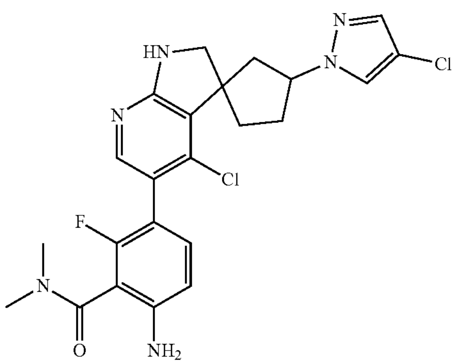 [SMILES: CN(C)C(=O)c1c(N)ccc(-c2cnc3c(c2Cl)C2(CCC(n4cc(Cl)cn4)C2)CN3)c1F] | 6-Amino-3-(4'-chloro-3-(4-chloro-1H-pyrazol-1-yl)-1',2'-dihydrospiro[cyclopentane-1,3'-pyrrolo[2,3-b]pyridin]-5'-yl)-2-fluoro-N,N-dimethylbenzamide |
| 171a<br>171b | | 6-Amino-3-((1R,3S)-4'-chloro-3-(4-chloro-1H-pyrazol-1-yl)-1',2'-dihydrospiro[cyclopentane-1,3'-pyrrolo[2,3-b]pyridin]-5'-yl)-2-fluoro-N,N-dimethylbenzamide<br>6-Amino-3-((1S,3R)-4'-chloro-3-(4-chloro-1H-pyrazol-1-yl)-1',2'-dihydrospiro[cyclopentane-1,3'-pyrrolo[2,3-b]pyridin]-5'-yl)-2-fluoro-N,N-dimethylbenzamide |
| 171c<br>171d | | 6-Amino-3-((1R,3R)-4'-chloro-3-(4-chloro-1H-pyrazol-1-yl)-1',2'-dihydrospiro[cyclopentane-1,3'-pyrrolo[2,3-b]pyridin]-5'-yl)-2-fluoro-N,N-dimethylbenzamide<br>6-Amino-3-((1S,3S)-4'-chloro-3-(4-chloro-1H-pyrazol-1-yl)-1',2'-dihydrospiro[cyclopentane-1,3'-pyrrolo[2,3-b]pyridin]-5'-yl)-2-fluoro-N,N-dimethylbenzamide |

TABLE 1-continued

| No. | Structure | Name |
|---|---|---|
| 172 | 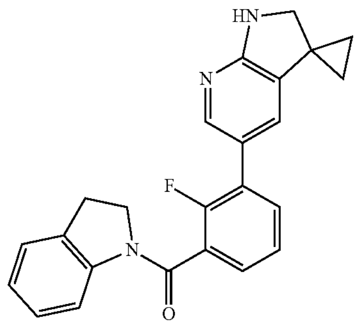 [SMILES: O=C(c1cccc(-c2cnc3c(c2)C2(CC2)CN3)c1F)N1CCc2ccccc21] | (3-(1',2'-dihydrospiro[cyclopropane-1,3'-pyrrolo[2,3-b]pyridin]-5'-yl)-2-fluorophenyl)(indolin-1-yl)methanone |
| 173 | 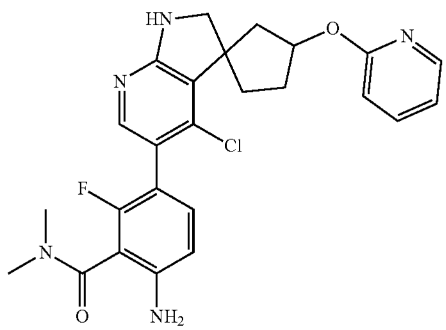 [SMILES: CN(C)C(=O)c1c(N)ccc(-c2cnc3c(c2Cl)C2(CCC(Oc4ccccn4)C2)CN3)c1F] | 6-Amino-3-(4'-chloro-3-(pyridin-2-yloxy)-1',2'-dihydrospiro[cyclopentane-1,3'-pyrrolo[2,3-b]pyridin]-5'-yl)-2-fluoro-N,N-dimethylbenzamide |
| 173a<br>173b | | 6-Amino-3-((1R,3S)-4'-chloro-3-(pyridin-2-yloxy)-1',2'-dihydrospiro[cyclopentane-1,3'-pyrrolo[2,3-b]pyridin]-5'-yl)-2-fluoro-N,N-dimethylbenzamide<br>6-Amino-3-((1R,3R)-4'-chloro-3-(pyridin-2-yloxy)-1',2'-dihydrospiro[cyclopentane-1,3'-pyrrolo[2,3-b]pyridin]-5'-yl)-2-fluoro-N,N-dimethylbenzamide |
| 173c<br>173d | | 6-Amino-3-((1R,3R)-4'-chloro-3-(pyridin-2-yloxy)-1',2'-dihydrospiro[cyclopentane-1,3'-pyrrolo[2,3-b]pyridin]-5'-yl)-2-fluoro-N,N-dimethylbenzamide<br>6-Amino-3-((1S,3S)-4'-chloro-3-(pyridin-2-yloxy)-1',2'-dihydrospiro[cyclopentane-1,3'-pyrrolo[2,3-b]pyridin]-5'-yl)-2-fluoro-N,N-dimethylbenzamide |
| 174 | 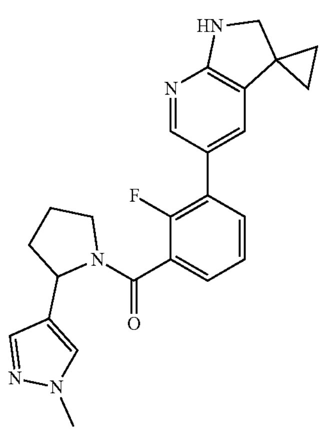 [SMILES: Cn1cc(C2CCCN2C(=O)c2cccc(-c3cnc4c(c3)C3(CC3)CN4)c2F)cn1] | (3-(1',2'-dihydrospiro[cyclopropane-1,3'-pyrrolo[2,3-b]pyridin]-5'-yl)-2-fluorophenyl)(2-(1-methyl-1H-pyrazol-4-yl)pyrrolidin-1-yl)methanone |
| 174a<br>174b | | (R)-(3-(1',2'-dihydrospiro[cyclopropane-1,3'-pyrrolo[2,3-6]pyridin]-5'-yl)-2-fluorophenyl)(2-(1-methyl-1H-pyrazol-4-yl)pyrrolidin-1-yl)methanone<br>(S)-(3-(1',2'-dihydrospiro[cyclopropane-1,3'-pyrrolo[2,3-6]pyridin]-5'-yl)-2-fluorophenyl)(2-(1-methyl-1H-pyrazol-4-yl)pyrrolidin-1-yl)methanone |

TABLE 1-continued

| No. | Structure | Name |
|---|---|---|
| 175 | 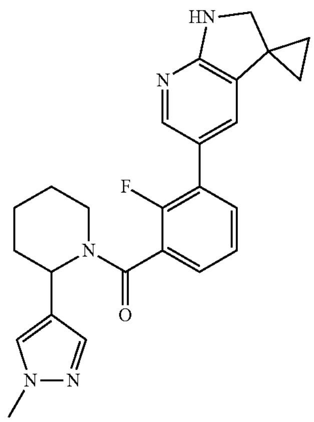 [SMILES: Cn1cc(C2CCCCN2C(=O)c2cccc(-c3cnc4c(c3)C3(CC3)CN4)c2F)cn1] | 3-(1',2'-dihydrospiro[cyclopropane-1,3'-pyrrolo[2,3-b]pyridin]-5'-yl)-2-fluorophenyl)(2-(1-methyl-1H-pyrazol-4-yl)piperidin-1-yl)methanone |
| 175a 175b | | (R)-(3-(1',2'-dihydrospiro[cyclopropane-1,3'-pyrrolo[2,3-b]pyridin]-5'-yl)-2-fluorophenyl)(2-(1-methyl-1H-pyrazol-4-yl)piperidin-1-yl)methanone (S)-(3-(1',2'-dihydrospiro[cyclopropane-1,3'-pyrrolo[2,3-b]pyridin]-5'-yl)-2-fluorophenyl)(2-(1-methyl-1H-pyrazol-4-yl)piperidin-1-yl)methanone |
| 176 | 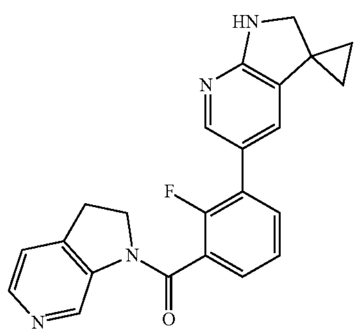 [SMILES: O=C(c1cccc(-c2cnc3c(c2)C2(CC2)CN3)c1F)N1CCc2ccncc21] | (2,3-dihydro-1H-pyrrolo[2,3-c]pyridin-1-yl)(3-(1',2'-dihydrospiro[cyclopropane-1,3'-pyrrolo[2,3-b]pyridin]-5'-yl)-2-fluorophenyl)methanone |
| 177 | 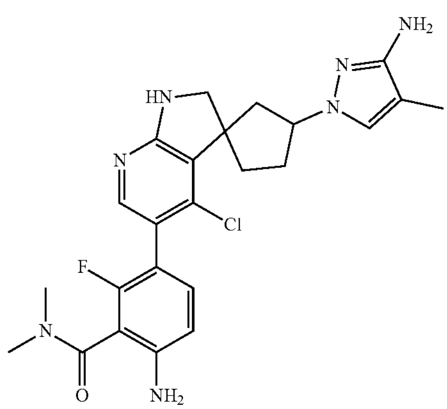 | 6-Amino-3-(3-(3-amino-4-methyl-1H-pyrazol-1-yl)-4'-chloro-1',2'-dihydrospiro[cyclopentane-1,3'-pyrrolo[2,3-b]pyridin]-5'-yl)-2-fluoro-N,N-dimethylbenzamide |
| 177a 177b | | 6-Amino-3-((1R,3S)-3-(3-amino-4-methyl-1H-pyrazol-1-yl)-4'-chloro-1',2'-dihydrospiro[cyclopentane-1,3'-pyrrolo[2,3-b]pyridin]-5'-yl)-2-fluoro-N,N-dimethylbenzamide 6-Amino-3-((1S,3R)-3-(3-amino-4-methyl-1H-pyrazol-1-yl)-4'-chloro-1',2'-dihydrospiro[cyclopentane-1,3'-pyrrolo[2,3-b]pyridin]-5'-yl)-2-fluoro-N,N-dimethylbenzamide |

TABLE 1-continued

| No. | Structure | Name |
|---|---|---|
| 177c 177d | | 6-Amino-3-((1R,3R)-3-(3-amino-4-methyl-1H-pyrazol-1-yl)-4'-chloro-1',2'-dihydrospiro[cyclopentane-1,3'-pyrrolo[2,3-b]pyridin]-5'-yl)-2-fluoro-N,N-dimethylbenzamide<br>6-Amino-3-((1S,3S)-3-(3-amino-4-methyl-1H-pyrazol-1-yl)-4'-chloro-1',2'-dihydrospiro[cyclopentane-1,3'-pyrrolo[2,3-b]pyridin]-5'-yl)-2-fluoro-N,N-dimethylbenzamide |
| 178 | (structure) | 6-Amino-3-(3-(5-amino-4-methyl-1H-pyrazol-1-yl)-4'-chloro-1',2'-dihydrospiro[cyclopentane-1,3'-pyrrolo[2,3-b]pyridin]-5'-yl)-2-fluoro-N,N-dimethylbenzamide |
| 178a 178b | | 6-Amino-3-((1R,3S)-3-(5-amino-4-methyl-1H-pyrazol-1-yl)-4'-chloro-1',2'-dihydrospiro[cyclopentane-1,3'-pyrrolo[2,3-b]pyridin]-5'-yl)-2-fluoro-N,N-dimethylbenzamide<br>6-Amino-3-((1S,3R)-3-(5-amino-4-methyl-1H-pyrazol-1-yl)-4'-chloro-1',2'-dihydrospiro[cyclopentane-1,3'-pyrrolo[2,3-b]pyridin]-5'-yl)-2-fluoro-N,N-dimethylbenzamide |
| 178c 178d | | 6-Amino-3-((1R,3R)-3-(5-amino-4-methyl-1H-pyrazol-1-yl)-4'-chloro-1',2'-dihydrospiro[cyclopentane-1,3'-pyrrolo[2,3-b]pyridin]-5'-yl)-2-fluoro-N,N-dimethylbenzamide<br>6-Amino-3-((1S,3S)-3-(5-amino-4-methyl-1H-pyrazol-1-yl)-4'-chloro-1',2'-dihydrospiro[cyclopentane-1,3'-pyrrolo[2,3-b]pyridin]-5'-yl)-2-fluoro-N,N-dimethylbenzamide |
| 179 | (structure) | 4'-Chloro-3-methyl-5'-(3-(1-methyl-2-oxo-1,2-dihydropyridin-3-yl)phenyl)-1',2'-dihydrospiro[cyclopentane-1,3'-pyrrolo[2,3-b]pyridine]-3-carboxamide |
| 179a 179b | | (1R,3S)-4'-Chloro-3-methyl-5'-(3-(1-methyl-2-oxo-1,2-dihydropyridin-3-yl)phenyl)-1',2'-dihydrospiro[cyclopentane-1,3'-pyrrolo[2,3-b]pyridine]-3-carboxamide<br>(1S,3R)-4'-Chloro-3-methyl-5'-(3-(1-methyl-2-oxo-1,2-dihydropyridin-3-yl)phenyl)-1',2'-dihydrospiro[cyclopentane-1,3'-pyrrolo[2,3-b]pyridine]-3-carboxamide |
| 179c 179d | | (1R,3R)-4'-Chloro-3-methyl-5'-(3-(1-methyl-2-oxo-1,2-dihydropyridin-3-yl)phenyl)-1',2'-dihydrospiro[cyclopentane-1,3'-pyrrolo[2,3-b]pyridine]-3-carboxamide<br>(1S,3S)-4'-Chloro-3-methyl-5'-(3-(1-methyl-2-oxo-1,2-dihydropyridin-3-yl)phenyl)-1',2'-dihydrospiro[cyclopentane-1,3'-pyrrolo[2,3-b]pyridine]-3-carboxamide |

TABLE 1-continued

| No. | Structure | Name |
|---|---|---|
| 180 | 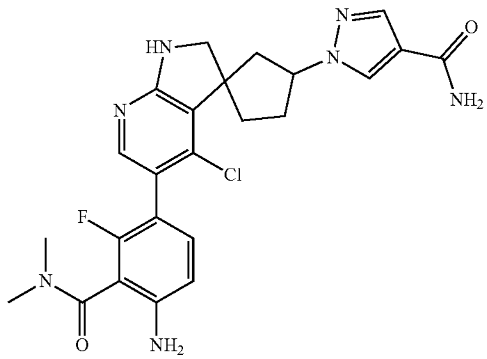 [SMILES: CN(C)C(=O)c1c(N)ccc(-c2cnc3c(c2Cl)C2(CCC(n4cc(C(N)=O)cn4)C2)CN3)c1F] | 1-(5'-(4-Amino-3-(dimethylcarbamoyl)-2-fluorophenyl)-4'-chloro-1',2'-dihydrospiro[cyclopentane-1,3'-pyrrolo[2,3-b]pyridin]-3-yl)-1H-pyrazole-4-carboxamide |
| 180a 180b | | 1-((1R,3S)-5'-(4-Amino-3-(dimethylcarbamoyl)-2-fluorophenyl)-4'-chloro-1',2'-dihydrospiro[cyclopentane-1,3'-pyrrolo[2,3-b]pyridin]-3-yl)-1H-pyrazole-4-carboxamide 1-((1S,3R)-5'-(4-Amino-3-(dimethylcarbamoyl)-2-fluorophenyl)-4'-chloro-1',2'-dihydrospiro[cyclopentane-1,3'-pyrrolo[2,3-b]pyridin]-3-yl)-1H-pyrazole-4-carboxamide |
| 180c 180d | | 1-((1R,3R)-5'-(4-Amino-3-(dimethylcarbamoyl)-2-fluorophenyl)-4'-chloro-1',2'-dihydrospiro[cyclopentane-1,3'-pyrrolo[2,3-b]pyridin]-3-yl)-1H-pyrazole-4-carboxamide 1-((1S,3S)-5'-(4-Amino-3-(dimethylcarbamoyl)-2-fluorophenyl)-4'-chloro-1',2'-dihydrospiro[cyclopentane-1,3'-pyrrolo[2,3-b]pyridin]-3-yl)-1H-pyrazole-4-carboxamide |
| 181 | 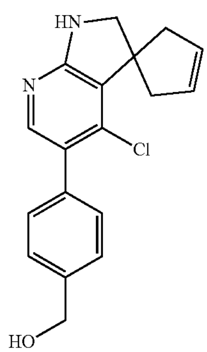 | (4-(4'-Chloro-1',2'-dihydrospiro[cyclopentane-1,3'-pyrrolo[2,3-b]pyridin]-3-en-5'-yl)phenyl)methanol |
| 182 | 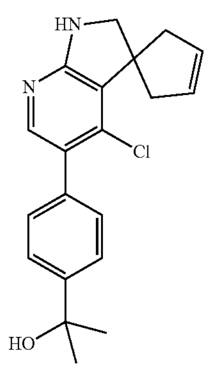 | 2-(4-(4'-Chloro-1',2'-dihydrospiro[cyclopentane-1,3'-pyrrolo[2,3-b]pyridin]-3-en-5'-yl)phenyl)propan-2-ol |

| No. | Structure | Name |
|---|---|---|
| 183 | 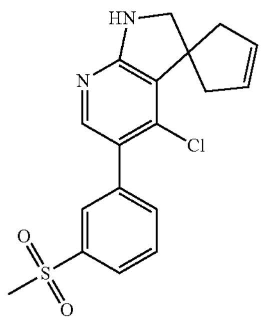 [SMILES: CS(=O)(=O)c1cccc(-c2cnc3c(c2Cl)C2(CC=CC2)CN3)c1] | 4-Chloro-5'-(3-(methylsulfonyl)phenyl)-1',2'-dihydrospiro[cyclopentane-1,3'-pyrrolo[2,3-b]pyridin]-3-ene |
| 184 | 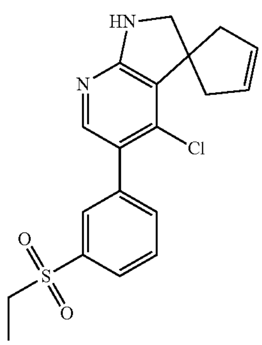 [SMILES: CCS(=O)(=O)c1cccc(-c2cnc3c(c2Cl)C2(CC=CC2)CN3)c1] | 4'-Chloro-5'-(3-(ethylsulfonyl)phenyl)-1',2'-dihydrospiro[cyclopentane-1,3'-pyrrolo[2,3-b]pyridin]-3-ene |
| 185 | 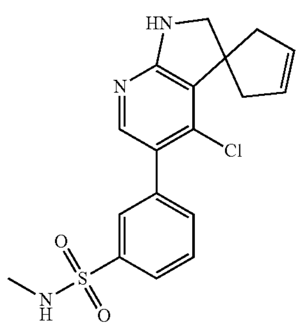 [SMILES: CNS(=O)(=O)c1cccc(-c2cnc3c(c2Cl)C2(CC=CC2)CN3)c1] | 3-(4'-Chloro-1',2'-dihydrospiro[cyclopentane-1,3'-pyrrolo[2,3-b]pyridin]-3-en-5'-yl)-N-methylbenzenesulfonamide |
| 186 | 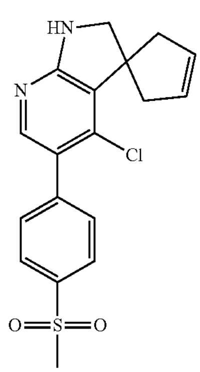 [SMILES: CS(=O)(=O)c1ccc(-c2cnc3c(c2Cl)C2(CC=CC2)CN3)cc1] | 4'-Chloro-5'-(4-(methylsulfonyl)phenyl)-1',2'-dihydrospiro[cyclopentane-1,3'-pyrrolo[2,3-b]pyridin]-3-ene |

TABLE 1-continued

| No. | Structure | Name |
|---|---|---|
| 187 | 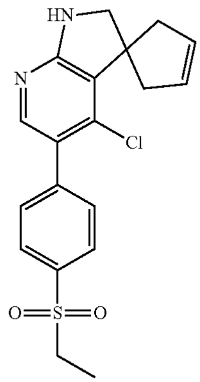 [SMILES: CCS(=O)(=O)c1ccc(-c2cnc3c(c2Cl)C2(CC=CC2)CN3)cc1] | 4'-Chloro-5'-(4-(ethylsulfonyl)phenyl)-1',2'-dihydrospiro[cyclopentane-1,3'-pyrrolo[2,3-b]pyridin]-3-ene |
| 188 | 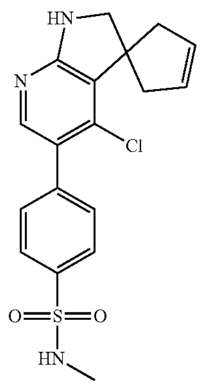 | 4-(4'-Chloro-1',2'-dihydrospiro[cyclopentane-1,3'-pyrrolo[2,3-b]pyridin]-3-en-5'-yl)-N-methylbenzenesulfonamide |
| 189 | 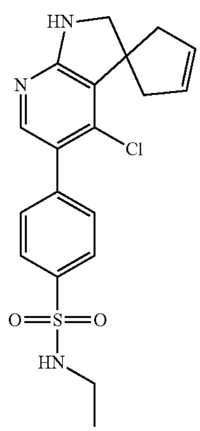 | 4-(4'-Chloro-1',2'-dihydrospiro[cyclopentane-1,3'-pyrrolo[2,3-b]pyridin]-3-en-5'-yl)-N-ethylbenzenesulfonamide |
| 190 | 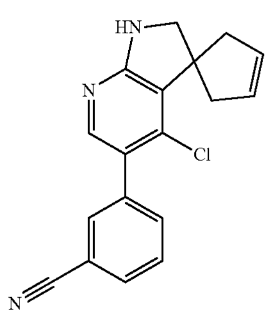 [SMILES: N#Cc1cccc(-c2cnc3c(c2Cl)C2(CC=CC2)CN3)c1] | 3-(4'-Chloro-1',2'-dihydrospiro[cyclopentane-1,3'-pyrrolo[2,3-b]pyridin]-3-en-5'-yl)benzonitrile |

TABLE 1-continued

| No. | Structure | Name |
|---|---|---|
| 191 | 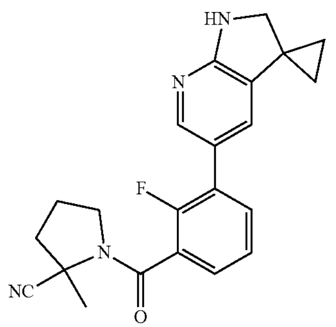 [SMILES: CC1(C#N)CCCN1C(=O)c1cccc(-c2cnc3c(c2)C2(CC2)CN3)c1F] | 1-(3-(1',2'-dihydrospiro[cyclopropane-1,3'-pyrrolo[2,3-b]pyridin]-5'-yl)-2-fluorobenzoyl)-2-methylpyrrolidine-2-carbonitrile |
| 191a 191b | | (R)-1-(3-(1',2'-dihydrospiro[cyclopropane-1,3'-pyrrolo[2,3-b]pyridin]-5'-yl)-2-fluorobenzoyl)-2-methylpyrrolidine-2-carbonitrile (S)-1-(3-(1',2'-dihydrospiro[cyclopropane-1,3'-pyrrolo[2,3-b]pyridin]-5'-yl)-2-fluorobenzoyl)-2-methylpyrrolidine-2-carbonitrile |
| 192 | 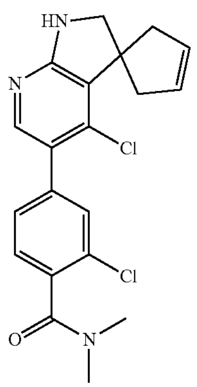 [SMILES: CN(C)C(=O)c1ccc(-c2cnc3c(c2Cl)C2(CC=CC2)CN3)cc1Cl] | 2-Chloro-4-(4'-chloro-1',2'-dihydrospiro[cyclopentane-1,3'-pyrrolo[2,3-b]pyridin]-3-en-5'-yl)-N,N-dimethylbenzamide |
| 193 | 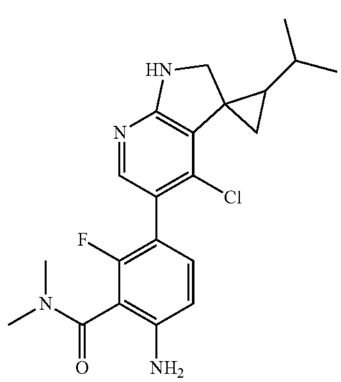 [SMILES: CC(C)C1CC12CNc1ncc(-c3ccc(N)c(C(=O)N(C)C)c3F)c(Cl)c12] | 6-Amino-3-(4'-chloro-2-isopropyl-1',2'-dihydrospiro[cyclopropane-1,3'-pyrrolo[2,3-b]pyridin]-5'-yl)-2-fluoro-N,N-dimethylbenzamide |
| 193a 193b | | 6-Amino-3-((1R,2R)-4'-chloro-2-isopropyl-1',2'-dihydrospiro[cyclopropane-1,3'-pyrrolo[2,3-b]pyridin]-5'-yl)-2-fluoro-N,N-dimethylbenzamide 6-Amino-3-((1S,2S)-4'-chloro-2-isopropyl-1',2'-dihydrospiro[cyclopropane-1,3'-pyrrolo[2,3-b]pyridin]-5'-yl)-2-fluoro-N,N-dimethylbenzamide |
| 193c 193d | | 6-Amino-3-((1R,2S)-4'-chloro-2-isopropyl-1',2'-dihydrospiro[cyclopropane-1,3'-pyrrolo[2,3-b]pyridin]-5'-yl)-2-fluoro-N,N-dimethylbenzamide 6-Amino-3-((1S,2R)-4'-chloro-2-isopropyl-1',2'-dihydrospiro[cyclopropane-1,3'-pyrrolo[2,3-b]pyridin]-5'-yl)-2-fluoro-N,N-dimethylbenzamide |

TABLE 1-continued

| No. | Structure | Name |
|---|---|---|
| 194 | 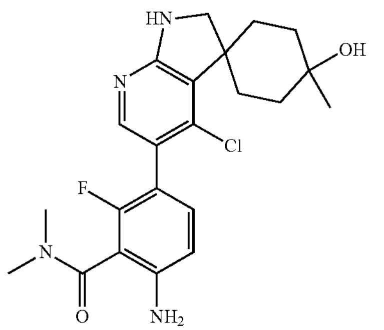 [SMILES: CN(C)C(=O)c1c(N)ccc(-c2cnc3c(c2Cl)C2(CCC(C)(O)CC2)CN3)c1F] | 6-Amino-3-(4'-chloro-4-hydroxy-4-methyl-1',2'-dihydrospiro[cyclohexane-1,3'-pyrrolo[2,3-b]pyridin]-5'-yl)-2-fluoro-N,N-dimethylbenzamide |
| 194a | | 6-Amino-3-((1r,4r)-4'-chloro-4-hydroxy-4-methyl-1',2'-dihydrospiro[cyclohexane-1,3'-pyrrolo[2,3-b]pyridin]-5'-yl)-2-fluoro-N,N-dimethylbenzamide |
| 194b | | 6-Amino-3-((1s,4s)-4'-chloro-4-hydroxy-4-methyl-1',2'-dihydrospiro[cyclohexane-1,3'-pyrrolo[2,3-b]pyridin]-5'-yl)-2-fluoro-N,N-dimethylbenzamide |
| 195 | 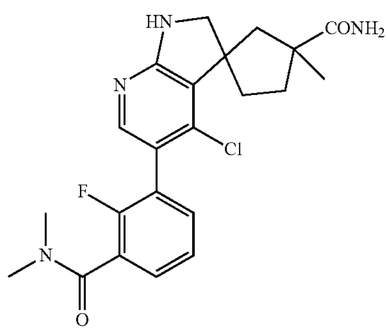 [SMILES: CN(C)C(=O)c1cccc(-c2cnc3c(c2Cl)C2(CCC(C)(C(N)=O)C2)CN3)c1F] | 4'-Chloro-5'-(3-(dimethylcarbamoyl)-2-fluorophenyl)-3-methyl-1',2'-dihydrospiro[cyclopentane-1,3'-pyrrolo[2,3-b]pyridine]-3-carboxamide |
| 195a 195b | | (1R,3S)-4'-Chloro-5'-(3-(dimethylcarbamoyl)-2-fluorophenyl)-3-methyl-1',2'-dihydrospiro[cyclopentane-1,3'-pyrrolo[2,3-b]pyridine]-3-carboxamide (1S,3R)-4'-Chloro-5'-(3-(dimethylcarbamoyl)-2-fluorophenyl)-3-methyl-1',2'-dihydrospiro[cyclopentane-1,3'-pyrrolo[2,3-b]pyridine]-3-carboxamide |
| 195c 195d | | (1R,3R)-4'-Chloro-5'-(3-(dimethylcarbamoyl)-2-fluorophenyl)-3-methyl-1',2'-dihydrospiro[cyclopentane-1,3'-pyrrolo[2,3-b]pyridine]-3-carboxamide (1S,3S)-4'-Chloro-5'-(3-(dimethylcarbamoyl)-2-fluorophenyl)-3-methyl-1',2'-dihydrospiro[cyclopentane-1,3'-pyrrolo[2,3-b]pyridine]-3-carboxamide |
| 196 | 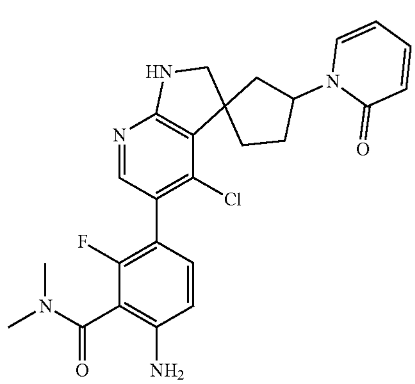 [SMILES: CN(C)C(=O)c1c(N)ccc(-c2cnc3c(c2Cl)C2(CCC(n4ccccc4=O)C2)CN3)c1F] | 6-Amino-3-(4'-chloro-3-(2-oxopyridin-1(2H)-yl)-1',2'-dihydrospiro[cyclopentane-1,3'-pyrrolo[2,3-b]pyridin]-5'-yl)-2-fluoro-N,N-dimethylbenzamide |

TABLE 1-continued

| No. | Structure | Name |
|---|---|---|
| 196a 196b | | 6-Amino-3-((1R,3S)-4'-chloro-3-(2-oxopyridin-1(2B)-yl)-1',2'-dihydrospiro[cyclopentane-1,3'-pyrrolo[2,3-b]pyridin]-5'-yl)-2-fluoro-N,N-dimethylbenzamide<br>6-Amino-3-((1S,3R)-4'-chloro-3-(2-oxopyridin-1(2B)-yl)-1',2'-dihydrospiro[cyclopentane-1,3'-pyrrolo[2,3-b]pyridin]-5'-yl)-2-fluoro-N,N-dimethylbenzamide |
| 196c 196d | | 6-Amino-3-((1R,3R)-4'-chloro-3-(2-oxopyridin-1(2H)-yl)-1',2'-dihydrospiro[cyclopentane-1,3'-pyrrolo[2,3-b]pyridin]-5'-yl)-2-fluoro-N,N-dimethylbenzamide<br>6-Amino-3-((1S,3S)-4'-chloro-3-(2-oxopyridin-1(2H)-yl)-1',2'-dihydrospiro[cyclopentane-1,3'-pyrrolo[2,3-b]pyridin]-5'-yl)-2-fluoro-N,N-dimethylbenzamide |
| 197 | | 6-Amino-3-(4'-chloro-2-propyl-1',2'-dihydrospiro[cyclopropane-1,3'-pyrrolo[2,3-b]pyridin]-5'-yl)-2-fluoro-N,N-dimethylbenzamide |
| 197a 197b | | 6-Amino-3-((1R,2S)-4'-chloro-2-propyl-1',2'-dihydrospiro[cyclopropane-1,3'-pyrrolo[2,3-b]pyridin]-5'-yl)-2-fluoro-N,N-dimethylbenzamide<br>6-Amino-3-((1S,2R)-4'-chloro-2-propyl-r,2'-dihydrospiro[cyclopropane-1,3'-pyrrolo[2,3-b]pyridin]-5'-yl)-2-fluoro-N,N-dimethylbenzamide |
| 197c 197d | | 6-Amino-3-((1R,2R)-4'-chloro-2-propyl-1',2'-dihydrospiro[cyclopropane-1,3'-pyrrolo[2,3-b]pyridin]-5'-yl)-2-fluoro-N,N-dimethylbenzamide<br>6-Amino-3-((1S,2S)-4'-chloro-2-propyl-1',2'-dihydrospiro[cyclopropane-1,3'-pyrrolo[2,3-b]pyridin]-5'-yl)-2-fluoro-N,N-dimethylbenzamide |
| 198 | | 6-Amino-3-(4'-chloro-2-(pyridin-4-yl)-1',2'-dihydrospiro[cyclopropane-1,3'-pyrrolo[2,3-b]pyridin]-5'-yl)-2-fluoro-N,N-dimethylbenzamide |
| 198a 198b | | 6-Amino-3-((1R,2R)-4'-chloro-2-(pyridin-4-yl)-1',2'-dihydrospiro[cyclopropane-1,3'-pyrrolo[2,3-b]pyridin]-5'-yl)-2-fluoro-N,N-dimethylbenzamide<br>6-Amino-3-((1S,2S)-4'-chloro-2-(pyridin-4-yl)-1',2'-dihydrospiro[cyclopropane-1,3'-pyrrolo[2,3-b]pyridin]-5'-yl)-2-fluoro-N,N-dimethylbenzamide |
| 198c 198d | | 6-Amino-3-((1R,2S)-4'-chloro-2-(pyridin-4-yl)-1',2'-dihydrospiro[cyclopropane-1,3'-pyrrolo[2,3-b]pyridin]-5'-yl)-2-fluoro-N,N-dimethylbenzamide<br>6-Amino-3-((1S,2R)-4'-chloro-2-(pyridin-4-yl)-1',2'-dihydrospiro[cyclopropane-1,3'-pyrrolo[2,3-b]pyridin]-5'-yl)-2-fluoro-N,N-dimethylbenzamide |

TABLE 1-continued

| No. | Structure | Name |
|---|---|---|
| 199 | 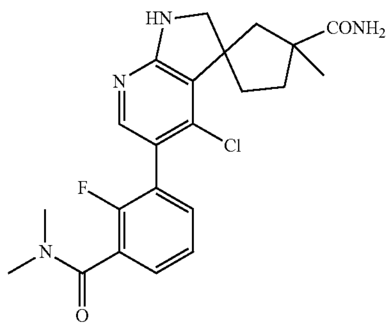 [SMILES: CN(C)C(=O)c1cccc(-c2cnc3c(c2Cl)C2(CCC(C)(C(N)=O)C2)CN3)c1F] | 5'-(3-(Dimethylcarbamoyl)-2-fluorophenyl)-3-methyl-1',2'-dihydrospiro[cyclopentane-1,3'-pyrrolo[2,3-b]pyridine]-3-carboxamide |
| 199a 199b | | (1R,3S)-5'-(3-(Dimethylcarbamoyl)-2-fluorophenyl)-3-methyl-1',2'-dihydrospiro[cyclopentane-1,3'-pyrrolo[2,3-b]pyridine]-3-carboxamide (1S,3R)-5'-(3-(Dimethylcarbamoyl)-2-fluorophenyl)-3-methyl-1',2'-dihydrospiro[cyclopentane-1,3'-pyrrolo[2,3-b]pyridine]-3-carboxamide |
| 199c 199d | | (1R,3R)-5'-(3-(Dimethylcarbamoyl)-2-fluorophenyl)-3-methyl-1',2'-dihydrospiro[cyclopentane-1,3'-pyrrolo[2,3-b]pyridine]-3-carboxamide (1S,3S)-5'-(3-(Dimethylcarbamoyl)-2-fluorophenyl)-3-methyl-1',2'-dihydrospiro[cyclopentane-1,3'-pyrrolo[2,3-b]pyridine]-3-carboxamide |
| 200 | 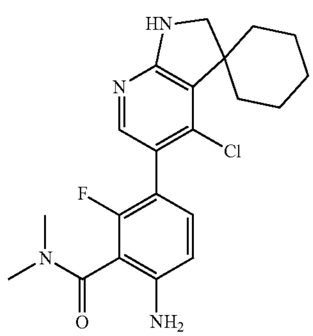 | 6-Amino-3-(4'-chloro-1',2'-dihydrospiro[cyclohexane-1,3'-pyrrolo[2,3-b]pyridin]-5'-yl)-2-fluoro-N,N-dimethylbenzamide |
| 201 | 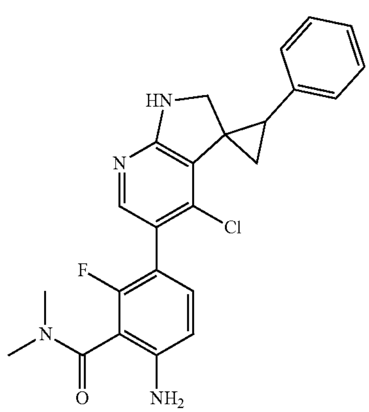 [SMILES: CN(C)C(=O)c1c(N)ccc(-c2cnc3c(c2Cl)C2(CN3)CC2c2ccccc2)c1F] | 6-Amino-3-(4'-chloro-2-phenyl-1',2'-dihydrospiro[cyclopropane-1,3'-pyrrolo[2,3-b]pyridin]-5'-yl)-2-fluoro-N,N-dimethylbenzamide |
| 201a 201b | | 6-Amino-3-((1R,2R)-4'-chloro-2-phenyl-1',2'-dihydrospiro[cyclopropane-1,3'-pyrrolo[2,3-b]pyridin]-5'-yl)-2-fluoro-N,N-dimethylbenzamide 6-Amino-3-((1S,2S)-4'-chloro-2-phenyl-1',2'-dihydrospiro[cyclopropane-1,3'-pyrrolo[2,3-b]pyridin]-5'-yl)-2-fluoro-N,N-dimethylbenzamide |

TABLE 1-continued

| No. | Structure | Name |
|---|---|---|
| 201c 201d | | 6-Amino-3-((1R,2S)-4'-chloro-2-phenyl-1',2'-dihydrospiro[cyclopropane-1,3'-pyrrolo[2,3-b]pyridin]-5'-yl)-2-fluoro-N,N-dimethylbenzamide 6-Amino-3-((1S,2R)-4'-chloro-2-phenyl-1',2'-dihydrospiro[cyclopropane-1,3'-pyrrolo[2,3-b]pyridin]-5'-yl)-2-fluoro-N,N-dimethylbenzamide |
| 202 | (structure) | 4'-Chloro-5'-(2-fluoro-3-(3-oxomorpholino)phenyl)-3-methyl-1',2'-dihydrospiro[cyclopentane-1,3'-pyrrolo[2,3-b]pyridine]-3-carboxamide |
| 202a 202b | | (1R,3S)-4'-Chloro-5'-(2-fluoro-3-(3-oxomorpholino)phenyl)-3-methyl-1',2'-dihydrospiro[cyclopentane-1,3'-pyrrolo[2,3-b]pyridine]-3-carboxamide (1S,3R)-4'-Chloro-5'-(2-fluoro-3-(3-oxomorpholino)phenyl)-3-methyl-1',2'-dihydrospiro[cyclopentane-1,3'-pyrrolo[2,3-b]pyridine]-3-carboxamide |
| 202c 202d | | (1R,3R)-4'-Chloro-5'-(2-fluoro-3-(3-oxomorpholino)phenyl)-3-methyl-1',2'-dihydrospiro[cyclopentane-1,3'-pyrrolo[2,3-b]pyridine]-3-carboxamide (1S,3S)-4'-Chloro-5'-(2-fluoro-3-(3-oxomorpholino)phenyl)-3-methyl-1',2'-dihydrospiro[cyclopentane-1,3'-pyrrolo[2,3-b]pyridine]-3-carboxamide |
| 203 | (structure) | 5'-(4-((1H-Pyrazol-1-yl)sulfonyl)phenyl)-4'-chloro-1',2'-dihydrospiro[cyclopentane-1,3'-pyrrolo[2,3-b]pyridin]-3-ene |
| 204 | (structure) | (1-(4-(4'-Chloro-1',2'-dihydrospiro[cyclopentane-1,3'-pyrrolo[2,3-b]pyridin]-3-en-5'-yl)phenyl)cyclopropyl)methanol |

TABLE 1-continued

| No. | Structure | Name |
|---|---|---|
| 205 | 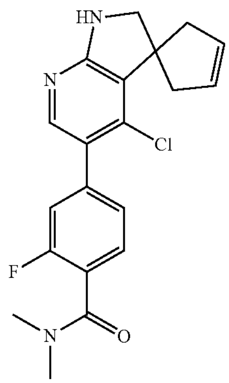 [SMILES: CN(C)C(=O)c1ccc(-c2cnc3c(c2Cl)C2(CC=CC2)CN3)cc1F] | 4-(4'-Chloro-1',2'-dihydrospiro[cyclopentane-1,3'-pyrrolo[2,3-b]pyridin]-3-en-5'-yl)-2-fluoro-N,N-dimethylbenzamide |
| 206 | 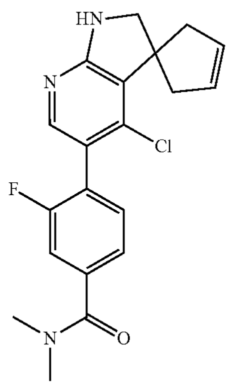 [SMILES: CN(C)C(=O)c1ccc(-c2cnc3c(c2Cl)C2(CC=CC2)CN3)c(F)c1] | 4-(4'-Chloro-1',2'-dihydrospiro[cyclopentane-1,3'-pyrrolo[2,3-b]pyridin]-3-en-5'-yl)-3-fluoro-N,N-dimethylbenzamide |
| 207 | 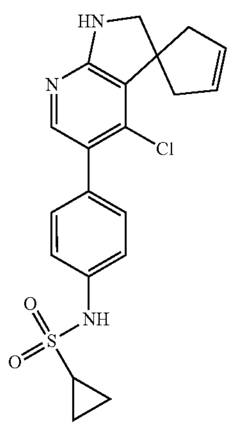 [SMILES: O=S(=O)(Nc1ccc(-c2cnc3c(c2Cl)C2(CC=CC2)CN3)cc1)C1CC1] | N-(4-(4'-Chloro-1',2'-dihydrospiro[cyclopentane-1,3'-pyrrolo[2,3-b]pyridin]-3-en-5'-yl)phenyl)cyclopropanesulfonamide |
| 208 | 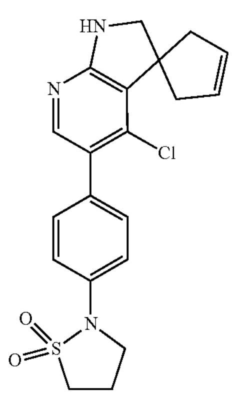 [SMILES: O=S1(=O)CCCN1c1ccc(-c2cnc3c(c2Cl)C2(CC=CC2)CN3)cc1] | 2-(4-(4'-Chloro-1',2'-dihydrospiro[cyclopentane-1,3'-pyrrolo[2,3-b]pyridin]-3-en-5'-yl)phenyl)isothiazolidine 1,1-dioxide |

TABLE 1-continued

| No. | Structure | Name |
|---|---|---|
| 209 | 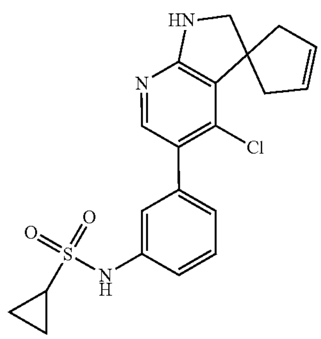 [SMILES: O=S(=O)(Nc1cccc(-c2cnc3c(c2Cl)C2(CC=CC2)CN3)c1)C1CC1] | N-(3-(4'-Chloro-1',2'-dihydrospiro[cyclopentane-1,3'-pyrrolo[2,3-b]pyridin]-3-en-5'-yl)phenyl)cyclopropanesulfonamide |
| 210 | 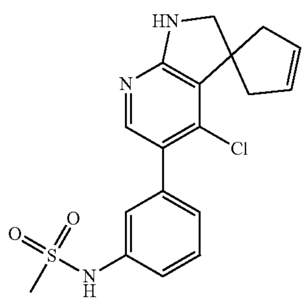 [SMILES: CS(=O)(=O)Nc1cccc(-c2cnc3c(c2Cl)C2(CC=CC2)CN3)c1] | N-(3-(4'-Chloro-1',2'-dihydrospiro[cyclopentane-1,3'-pyrrolo[2,3-b]pyridin]-3-en-5'-yl)phenyl)methanesulfonamide |
| 211 | 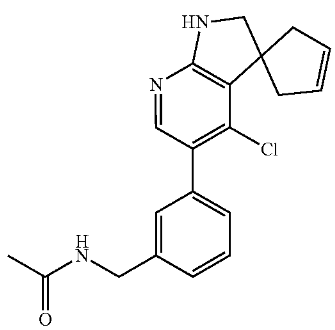 [SMILES: CC(=O)NCc1cccc(-c2cnc3c(c2Cl)C2(CC=CC2)CN3)c1] | N-(3-(4'-Chloro-1',2'-dihydrospiro[cyclopentane-1,3'-pyrrolo[2,3-b]pyridin]-3-en-5'-yl)benzyl)acetamide |
| 212 | 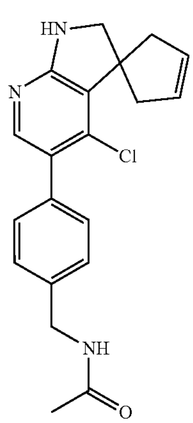 [SMILES: CC(=O)NCc1ccc(-c2cnc3c(c2Cl)C2(CC=CC2)CN3)cc1] | N-(4-(4'-Chloro-1',2'-dihydrospiro[cyclopentane-1,3'-pyrrolo[2,3-b]pyridin]-3-en-5'-yl)benzyl)acetamide |

TABLE 1-continued

| No. | Structure | Name |
|---|---|---|
| 213 | 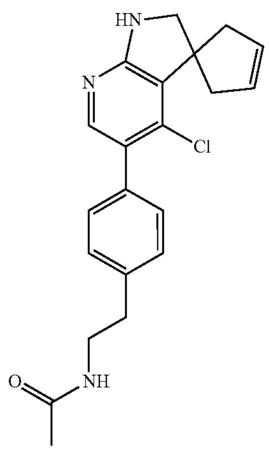 [SMILES: CC(=O)NCCc1ccc(-c2cnc3c(c2Cl)C2(CC=CC2)CN3)cc1] | N-(4-(4'-chloro-1',2'-dihydrospiro[cyclopentane-1,3'-pyrrolo[2,3-b]pyridin]-3-en-5'-yl)phenethyl)acetamide |
| 214 | 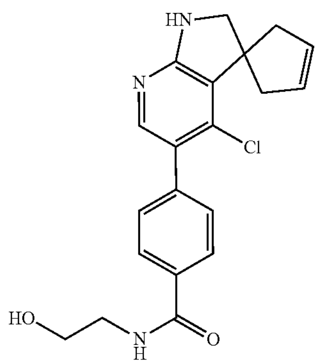 [SMILES: O=C(NCCO)c1ccc(-c2cnc3c(c2Cl)C2(CC=CC2)CN3)cc1] | 4-(4'-Chloro-1',2'-dihydrospiro[cyclopentane-1,3'-pyrrolo[2,3-6]pyridin]-3-en-5'-yl)-N-(2-hydroxyethyl)benzamide |
| 215 | 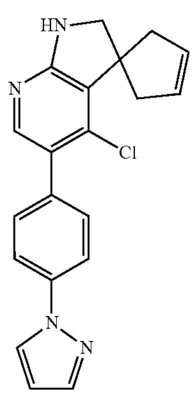 [SMILES: Clc1c(-c2ccc(-n3cccn3)cc2)cnc2c1C1(CC=CC1)CN2] | 5'-(4-(1H-Pyrazol-1-yl)phenyl)-4'-chloro-1',2'-dihydrospiro[cyclopentane-1,3'-pyrrolo[2,3-b]pyridin]-3-ene |
| 216 | 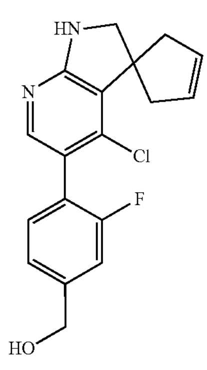 | (4-(4'-Chloro-1',2'-dihydrospiro[cyclopentane-1,3'-pyrrolo[2,3-b]pyridin]-3-en-5'-yl)-3-fluorophenyl)methanol |

TABLE 1-continued

| No. | Structure | Name |
|---|---|---|
| 217 | 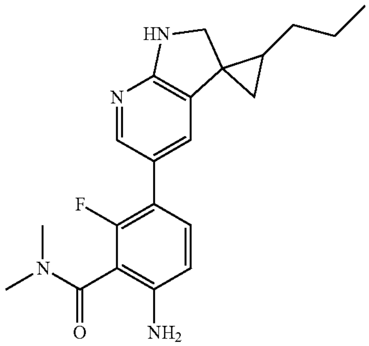 [SMILES: CCCC1CC12CNc1ncc(-c3ccc(N)c(C(=O)N(C)C)c3F)cc12] | 6-Amino-2-fluoro-N,N-dimethyl-3-(2-propyl-1',2'-dihydrospiro[cyclopropane-1,3'-pyrrolo[2,3-b]pyridin]-5'-yl)benzamide |
| 217a | | 6-Amino-2-fluoro-N,N-dimethyl-3-((1R,2S)-2-propyl-1',2'-dihydrospiro[cyclopropane-1,3'-pyrrolo[2,3-b]pyridin]-5'-yl)benzamide |
| 217b | | 6-Amino-2-fluoro-N,N-dimethyl-3-((1S,2R)-2-propyl-1',2'-dihydrospiro[cyclopropane-1,3'-pyrrolo[2,3-b]pyridin]-5'-yl)benzamide |
| 217c | | 6-Amino-2-fluoro-N,N-dimethyl-3-((1R,2R)-2-propyl-1',2'-dihydrospiro[cyclopropane-1,3'-pyrrolo[2,3-b]pyridin]-5'-yl)benzamide |
| 217d | | 6-Amino-2-fluoro-N,N-dimethyl-3-((1S,2S)-2-propyl-1',2'-dihydrospiro[cyclopropane-1,3'-pyrrolo[2,3-b]pyridin]-5'-yl)benzamide |
| 218 | 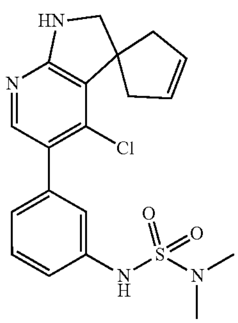 [SMILES: CN(C)S(=O)(=O)Nc1cccc(-c2cnc3c(c2Cl)C2(CC=CC2)CN3)c1] | N-(3-(4'-Chloro-1',2'-dihydrospiro[cyclopentane-1,3'-pyrrolo[2,3-b]pyridin]-3-en-5'-yl)phenyl)-N',N'-dimethylsulfamide |
| 219 | 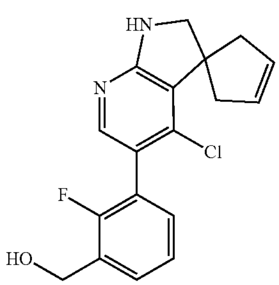 [SMILES: OCc1cccc(-c2cnc3c(c2Cl)C2(CC=CC2)CN3)c1F] | (3-(4'-Chloro-1',2'-dihydrospiro[cyclopentane-1,3'-pyrrolo[2,3-b]pyridin]-3-en-5'-yl)-2-fluorophenyl)methanol |
| 220 | 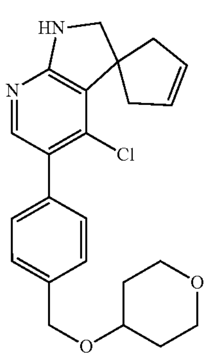 [SMILES: Clc1c(-c2ccc(COC3CCOCC3)cc2)cnc2c1C1(CC=CC1)CN2] | 4'-Chloro-5'-(4-(((tetrahydro-2H-pyran-4-yl)oxy)methyl)phenyl)-1',2'-dihydrospiro[cyclopentane-1,3'-pyrrolo[2,3-b]pyridin]-3-ene |

TABLE 1-continued

| No. | Structure | Name |
|---|---|---|
| 221 | 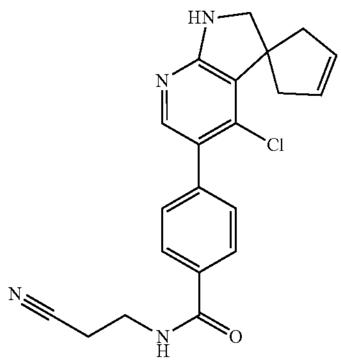 [SMILES: N#CCCNC(=O)c1ccc(-c2cnc3c(c2Cl)C2(CC=CC2)CN3)cc1] | 4-(4'-Chloro-1',2'-dihydrospiro[cyclopentane-1,3'-pyrrolo[2,3-b]pyridin]-3-en-5'-yl)-N-(2-cyanoethyl)benzamide |
| 222 | 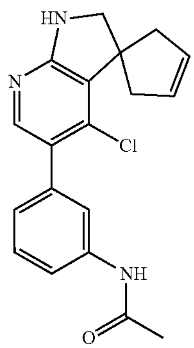 [SMILES: CC(=O)Nc1cccc(-c2cnc3c(c2Cl)C2(CC=CC2)CN3)c1] | N-(3-(4'-Chloro-1',2'-dihydrospiro[cyclopentane-1,3'-pyrrolo[2,3-b]pyridin]-3-en-5'-yl)phenyl)acetamide |
| 223 | 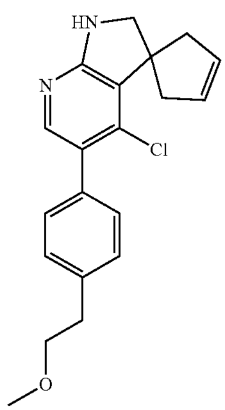 [SMILES: COCCc1ccc(-c2cnc3c(c2Cl)C2(CC=CC2)CN3)cc1] | 4'-Chloro-5'-(4-(2-methoxyethyl)phenyl)-1',2'-dihydrospiro[cyclopentane-1,3'-pyrrolo[2,3-b]pyridin]-3-ene |
| 224 | 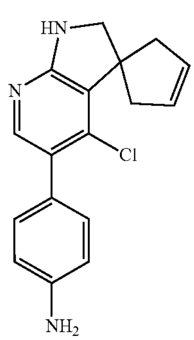 [SMILES: Nc1ccc(-c2cnc3c(c2Cl)C2(CC=CC2)CN3)cc1] | 4-(4'-Chloro-1',2'-dihydrospiro[cyclopentane-1,3'-pyrrolo[2,3-b]pyridin]-3-en-5'-yl)aniline |

TABLE 1-continued

| No. | Structure | Name |
|---|---|---|
| 225 | 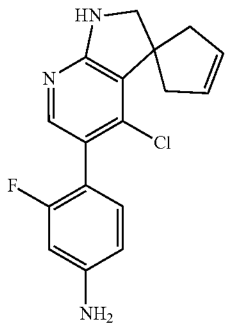 [SMILES: Nc1ccc(-c2cnc3c(c2Cl)C2(CC=CC2)CN3)c(F)c1] | 4-(4'-Chloro-1',2'-dihydrospiro[cyclopentane-1,3'-pyrrolo[2,3-b] pyridin]-3-en-5'-yl)-3-fluoroaniline |
| 226 | 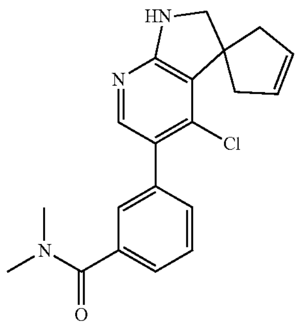 [SMILES: CN(C)C(=O)c1cccc(-c2cnc3c(c2Cl)C2(CC=CC2)CN3)c1] | 3-(4'-Chloro-1',2'-dihydrospiro[cyclopentane-1,3'-pyrrolo[2,3-b]pyridin]-3-en-5'-yl)-N,N-dimethylbenzamide |
| 227 | 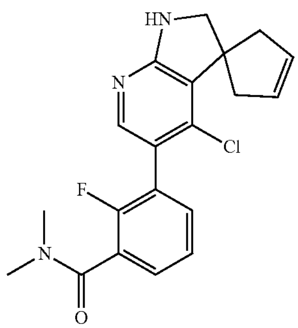 [SMILES: CN(C)C(=O)c1cccc(-c2cnc3c(c2Cl)C2(CC=CC2)CN3)c1F] | 3-(4'-Chloro-1',2'-dihydrospiro[cyclopentane-1,3'-pyrrolo[2,3-b]pyridin]-3-en-5'-yl)-2-fluoro-N,N-dimethylbenzamide |
| 228 | 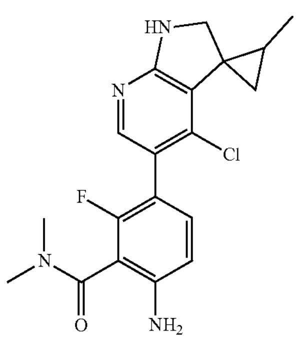 | 6-Amino-3-(4'-chloro-2-methyl-1',2'-dihydrospiro[cyclopropane-1,3'-pyrrolo[2,3-b]pyridin]-5'-yl)-2-fluoro-N,N-dimethylbenzamide |
| 228a | | 6-Amino-3-((1R,2S)-4'-chloro-2-methyl-1',2'-dihydrospiro[cyclopropane-1,3'-pyrrolo[2,3-b]pyridin]-5'-yl)-2-fluoro-N,N-dimethylbenzamide |
| 228b | | 6-Amino-3-((1S,2R)-4'-chloro-2-methyl-1',2'-dihydrospiro[cyclopropane-1,3'-pyrrolo[2,3-b]pyridin]-5'-yl)-2-fluoro-N,N-dimethylbenzamide |
| 228c | | 6-Amino-3-((1R,2R)-4'-chloro-2-methyl-1',2'-dihydrospiro[cyclopropane-1,3'-pyrrolo[2,3-b]pyridin]-5'-yl)-2-fluoro-N,N-dimethylbenzamide |
| 228d | | 6-Amino-3-((1S,2S)-4'-chloro-2-methyl-1',2'-dihydrospiro[cyclopropane-1,3'-pyrrolo[2,3-b]pyridin]-5'-yl)-2-fluoro-N,N-dimethylbenzamide |

| No. | Structure | Name |
|---|---|---|
| 229 | 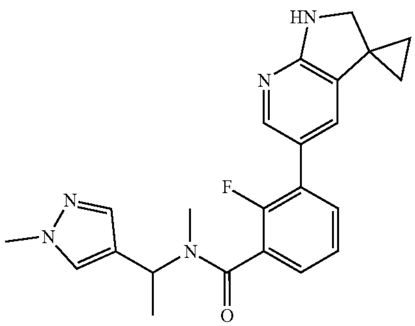 | 3-(1',2'-dihydrospiro[cyclopropane-1,3'-pyrrolo[2,3-b]pyridin]-5'-yl)-2-fluoro-N-methyl-N-(1-(1-methyl-1H-pyrazol-4-yl)ethyl)benzamide |
| 229a 229b | | (R)-3-(1',2'-dihydrospiro[cyclopropane-1,3'-pyrrolo[2,3-b]pyridin]-5'-yl)-2-fluoro-N-methyl-N-(1-(1-methyl-1H-pyrazol-4-yl)ethyl)benzamide (S)-3-(1',2'-dihydrospiro[cyclopropane-1,3'-pyrrolo[2,3-b]pyridin]-5'-yl)-2-fluoro-N-methyl-N-(1-(1-methyl-1H-pyrazol-4-yl)ethyl)benzamide |
| 230 | 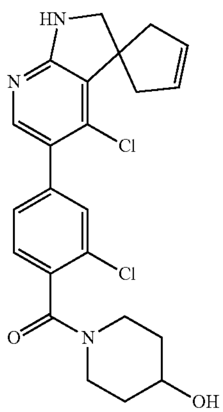 [SMILES: O=C(c1ccc(-c2cnc3c(c2Cl)C2(CC=CC2)CN3)cc1Cl)N1CCC(O)CC1] | (2-Chloro-4-(4'-chloro-1',2'-dihydrospiro[cyclopentane-1,3'-pyrrolo[2,3-b]pyridin]-3-en-5'-yl)phenyl)(4-hydroxypiperidin-1-yl)methanone |
| 231 | 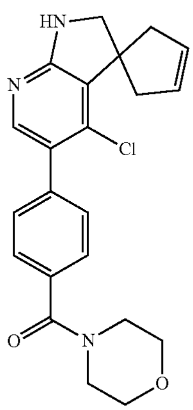 [SMILES: O=C(c1ccc(-c2cnc3c(c2Cl)C2(CC=CC2)CN3)cc1)N1CCOCC1] | (4-(4'-Chloro-1',2'-dihydrospiro[cyclopentane-1,3'-pyrrolo[2,3-b]pyridin]-3-en-5'-yl)phenyl)(morpholino)methanone |
| 232 | 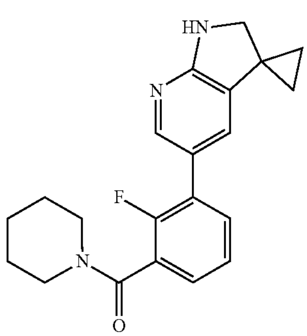 [SMILES: O=C(c1cccc(-c2cnc3c(c2)C2(CC2)CN3)c1F)N1CCCCC1] | (3-(1',2'-dihydrospiro[cyclopropane-1,3'-pyrrolo[2,3-b]pyridin]-5'-y1)-2-fluorophenyl)(piperidin-1-yl)methanone |

TABLE 1-continued

| No. | Structure | Name |
|---|---|---|
| 233 | 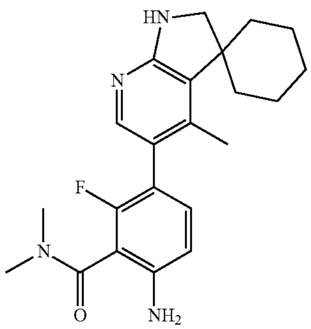 [SMILES: Cc1c(-c2ccc(N)c(C(=O)N(C)C)c2F)cnc2c1C1(CCCCC1)CN2] | 6-Amino-2-fluoro-N,N-dimethyl-3-(4'-methyl-1',2'-dihydrospiro[cyclohexane-1,3'-pyrrolo[2,3-b]pyridin]-5'-yl)benzamide |
| 234 | 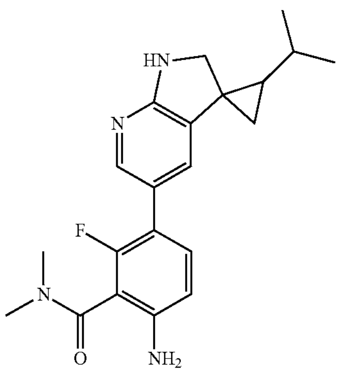 [SMILES: CC(C)C1CC12CNc1ncc(-c3ccc(N)c(C(=O)N(C)C)c3F)cc12] | 6-Amino-2-fluoro-3-(2-isopropyl-1',2'-dihydrospiro[cyclopropane-1,3'-pyrrolo[2,3-b]pyridin]-5'-yl)-N,N-dimethylbenzamide |
| 234a<br>234b | | 6-Amino-2-fluoro-3-((1R,2R)-2-isopropyl-1',2'-dihydrospiro[cyclopropane-1,3'-pyrrolo[2,3-b]pyridin]-5'-yl)-N,N-dimethylbenzamide<br>6-Amino-2-fluoro-3-((1S,2S)-2-isopropyl-1',2'-dihydrospiro[cyclopropane-1,3'-pyrrolo[2,3-b]pyridin]-5'-yl)-N,N-dimethylbenzamide |
| 234c<br>234d | | 6-Amino-2-fluoro-3-((1R, 2S)-2-isopropyl-1',2'-dihydrospiro[cyclopropane-1,3'-pyrrolo[2,3-b]pyridin]-5'-yl)-N,N-dimethylbenzamide<br>6-Amino-2-fluoro-3-((1S,2R)-2-isopropyl-1',2'-dihydrospiro[cyclopropane-1,3'-pyrrolo[2,3-b]pyridin]-5'-yl)-N,N-dimethylbenzamide |
| 235 | 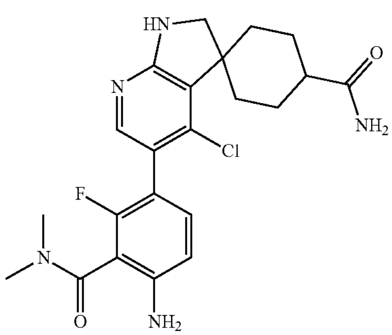 [SMILES: CN(C)C(=O)c1c(N)ccc(-c2cnc3c(c2Cl)C2(CCC(C(N)=O)CC2)CN3)c1F] | 5'-(4-Amino-3-(dimethylcarbamoyl)-2-fluorophenyl)-4'-chloro-1',2'-dihydrospiro[cyclohexane-1,3'-pyrrolo[2,3-b]pyridine]-4-carboxamide |
| 235a | | (1r,4r)-5'-(4-Amino-3-(dimethylcarbamoyl)-2-fluorophenyl)-4'-chloro-1',2'-dihydrospiro[cyclohexane-1,3'-pyrrolo[2,3-b]pyridine]-4-carboxamide |
| 235b | | (1s,4s)-5'-(4-Amino-3-(dimethylcarbamoyl)-2-fluorophenyl)-4'-chloro-1',2'-dihydrospiro[cyclohexane-1,3'-pyrrolo[2,3-b]pyridine]-4-carboxamide |

TABLE 1-continued

| No. | Structure | Name |
|---|---|---|
| 236 | 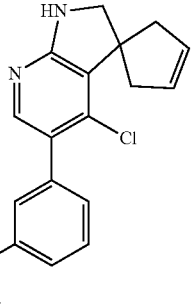 | 1-(3-(4'-Chloro-1',2'-dihydrospiro[cyclopentane-1,3'-pyrrolo[2,3-b]pyridin]-3-en-5'-yl)phenyl)cyclopropane-1-carboxamide |
| 237 | 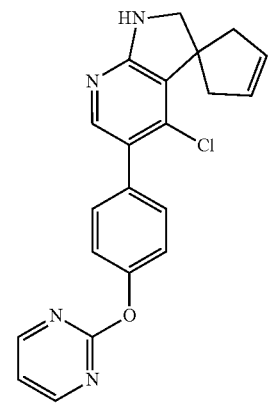 [SMILES: Clc1c(-c2ccc(Oc3ncccn3)cc2)cnc2c1C1(CC=CC1)CN2] | 4'-Chloro-5'-(4-(pyrimidin-2-yloxy)phenyl)-1',2'-dihydrospiro[cyclopentane-1,3'-pyrrolo[2,3-b]pyridin]-3-ene |
| 238 | 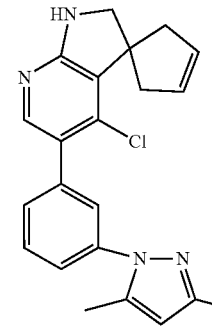 | 4'-Chloro-5'-(3-(3,5-dimethyl-1H-pyrazol-1-yl)phenyl)-1',2'-dihydrospiro[cyclopentane-1,3'-pyrrolo[2,3-b]pyridin]-3-ene |
| 239 | 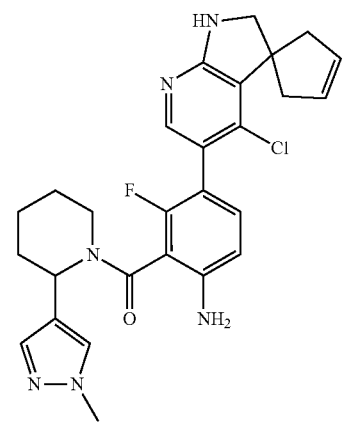 [SMILES: Cn1cc(C2CCCCN2C(=O)c2c(N)ccc(-c3cnc4c(c3Cl)C3(CC=CC3)CN4)c2F)cn1] | (6-Amino-3-(4'-chloro-1',2'-dihydrospiro[cyclopentane-1,3'-pyrrolo[2,3-b]pyridin]-3-en-5'-yl)-2-fluorophenyl)(2-(1-methyl-1H-pyrazol-4-yl)piperidin-1-yl)methanone |

TABLE 1-continued

| No. | Structure | Name |
|---|---|---|
| 239a 239b | | (R)-(6-Amino-3-(4'-chloro-1',2'-dihydrospiro[cyclopentane-1,3'-pyrrolo[2,3-b]pyridin]-3-en-5'-yl)-2-fluorophenyl)(2-(1-methyl-1H-pyrazol-4-yl)piperidin-1-yl)methanone (S)-(6-Amino-3-(4'-chloro-1',2'-dihydrospiro[cyclopentane-1,3'-pyrrolo[2,3-b]pyridin]-3-en-5'-yl)-2-fluorophenyl)(2-(1-methyl-1H-pyrazol-4-yl)piperidin-1-yl)methanone |
| 240 | 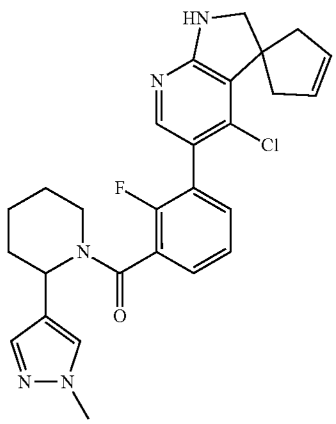 [SMILES: Cn1cc(C2CCCCN2C(=O)c2cccc(-c3cnc4c(c3Cl)C3(CC=CC3)CN4)c2F)cn1] | (3-(4'-Chloro-1',2'-dihydrospiro[cyclopentane-1,3'-pyrrolo[2,3-b]pyridin]-3-en-5'-yl)-2-fluorophenyl)(2-(1-methyl-1H-pyrazol-4-yl)piperidin-1-yl)methanone |
| 240a 240b | | (R)-(3-(4'-Chloro-1',2'-dihydrospiro[cyclopentane-1,3'-pyrrolo[2,3-b]pyridin]-3-en-5'-yl)-2-fluorophenyl)(2-(1-methyl-1H-pyrazol-4-yl)piperidin-1-yl)methanone (S)-(3-(4'-Chloro-1',2'-dihydrospiro[cyclopentane-1,3'-pyrrolo[2,3-b]pyridin]-3-en-5'-yl)-2-fluorophenyl)(2-(1-methyl-1H-pyrazol-4-yl)piperidin-1-yl)methanone |
| 241 | 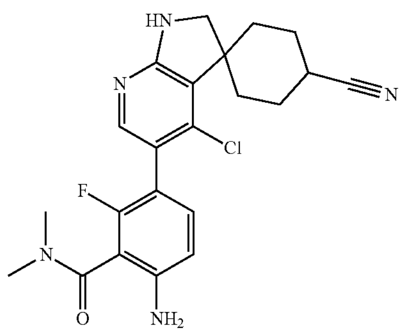 [SMILES: CN(C)C(=O)c1c(N)ccc(-c2cnc3c(c2Cl)C2(CCC(C#N)CC2)CN3)c1F] | 6-Amino-3-(4'-chloro-4-cyano-1',2'-dihydrospiro[cyclohexane-1,3'-pyrrolo[2,3-b]pyridin]-5'-yl)-2-fluoro-N,N-dimethylbenzamide |
| 241a 241b | | 6-Amino-3-((1r,4r)-4'-chloro-4-cyano-1',2'-dihydrospiro[cyclohexane-1,3'-pyrrolo[2,3-b]pyridin]-5'-yl)-2-fluoro-N,N-dimethylbenzamide 6-Amino-3-((1s,4s)-4'-chloro-4-cyano-1',2'-dihydrospiro[cyclohexane-1,3'-pyrrolo[2,3-b]pyridin]-5'-yl)-2-fluoro-N,N-dimethylbenzamide |
| 242 | 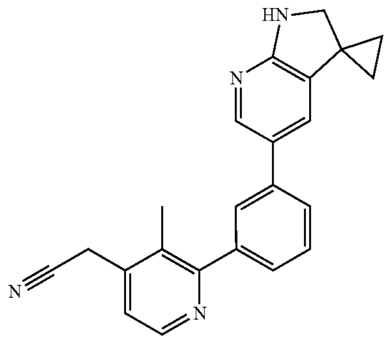 [SMILES: Cc1c(CC#N)ccnc1-c1cccc(-c2cnc3c(c2)C2(CC2)CN3)c1] | 2-(2-(3-(1',2'-Dihydrospiro[cyclopropane-1,3'-pyrrolo[2,3-b]pyridin]-5'-yl)phenyl)-3-methylpyridin-4-yl)acetonitrile |

TABLE 1-continued

| No. | Structure | Name |
|---|---|---|
| 243 | 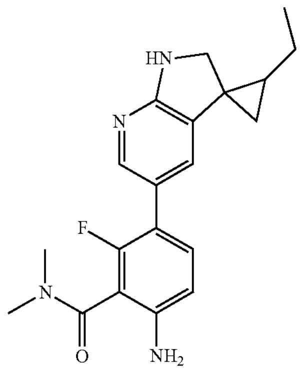 [SMILES: CCC1CC12CNc1ncc(-c3ccc(N)c(C(=O)N(C)C)c3F)cc12] | 6-Amino-3-(2-ethyl-1',2'-dihydrospiro[cyclopropane-1,3'-pyrrolo[2,3-b]pyridin]-5'-yl)-2-fluoro-N,N-dimethylbenzamide |
| 243a<br>243b | | 6-Amino-3-((1R,2S)-2-ethyl-1',2'-dihydrospiro[cyclopropane-1,3'-pyrrolo[2,3-b]pyridin]-5'-yl)-2-fluoro-N,N-dimethylbenzamide<br>6-Amino-3-((1S,2R)-2-ethyl-1',2'-dihydrospiro[cyclopropane-1,3'-pyrrolo[2,3-b]pyridin]-5'-yl)-2-fluoro-N,N-dimethylbenzamide |
| 243c<br>243d | | 6-Amino-3-((1R,2R)-2-ethyl-1',2'-dihydrospiro[cyclopropane-1,3'-pyrrolo[2,3-b]pyridin]-5'-yl)-2-fluoro-N,N-dimethylbenzamide<br>6-Amino-3-((1S,2S)-2-ethyl-1',2'-dihydrospiro[cyclopropane-1,3'-pyrrolo[2,3-b]pyridin]-5'-yl)-2-fluoro-N,N-dimethylbenzamide |
| 244 | 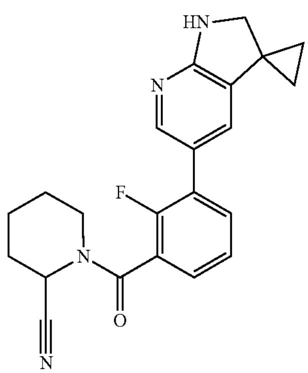 [SMILES: N#CC1CCCCN1C(=O)c1cccc(-c2cnc3c(c2)C2(CC2)CN3)c1F] | 1-(3-(1',2'-Dihydrospiro[cyclopropane-1,3'-pyrrolo[2,3-b]pyridin]-5'-yl)-2-fluorobenzoyl)piperidine-2-carbonitrile |
| 244a<br>244b | | (R)-1-(3-(1',2'-Dihydrospiro[cyclopropane-1,3'-pyrrolo[2,3-b]pyridin]-5'-yl)-2-fluorobenzoyl)piperidine-2-carbonitrile<br>(S)-1-(3-(1',2'-Dihydrospiro[cyclopropane-1,3'-pyrrolo[2,3-b]pyridin]-5'-yl)-2-fluorobenzoyl)piperidine-2-carbonitrile |
| 245 | 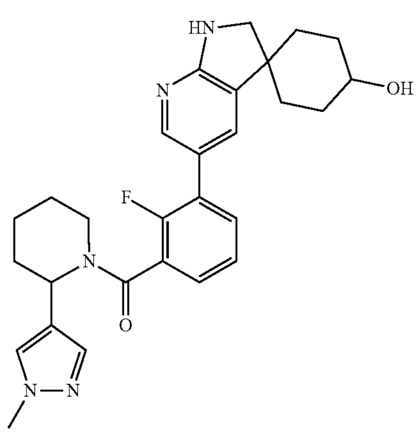 [SMILES: Cn1cc(C2CCCCN2C(=O)c2cccc(-c3cnc4c(c3)C3(CCC(O)CC3)CN4)c2F)cn1] | (2-Fluoro-3-(4-hydroxy-1',2'-dihydrospiro[cyclohexane-1,3'-pyrrolo[2,3-b]pyridin]-5'-yl)phenyl)(2-(1-methyl-1H-pyrazol-4-yl)piperidin-1-yl)methanone |

TABLE 1-continued

| No. | Structure | Name |
|---|---|---|
| 245a 245b | | (2-Fluoro-3-((1s,4s)-4-hydroxy-1',2'-dihydrospiro[cyclohexane-1,3'-pyrrolo[2,3-b]pyridin]-5'-yl)phenyl)((R)-2-(1-methyl-1H-pyrazol-4-yl)piperidin-1-yl)methanone (2-Fluoro-3-((1s,4s)-4-hydroxy-1',2'-dihydrospiro[cyclohexane-1,3'-pyrrolo[2,3-b]pyridin]-5'-yl)phenyl)((S)-2-(1-methyl-1H-pyrazol-4-yl)piperidin-1-yl)methanone |
| 245c 245d | | (2-Fluoro-3-((1r,4r)-4-hydroxy-1',2'-dihydrospiro[cyclohexane-1,3'-pyrrolo[2,3-b]pyridin]-5'-yl)phenyl)((R)-2-(1-methyl-1H-pyrazol-4-yl)piperidin-1-yl)methanone (2-Fluoro-3-((1r,4r)-4-hydroxy-1',2'-dihydrospiro[cyclohexane-1,3'-pyrrolo[2,3-b]pyridin]-5'-yl)phenyl)((S)-2-(1-methyl-1H-pyrazol-4-yl)piperidin-1-yl)methanone |
| 246 | | (3-(4'-Chloro-4-hydroxy-1',2'-dihydrospiro[cyclohexane-1,3'-pyrrolo[2,3-b]pyridin]-5'-yl)-2-fluorophenyl)(2-(1-methyl-1H-pyrazol-4-yl)piperidin-1-yl)methanone |
| 246a 246b | | (3-((1s,4s)-4'-Chloro-4-hydroxy-1',2'-dihydrospiro[cyclohexane-1,3'-pyrrolo[2,3-b]pyridin]-5'-yl)-2-fluorophenyl)((R)-2-(1-methyl-1H-pyrazol-4-yl)piperidin-1-yl)methanone (3-((1s,4s)-4'-Chloro-4-hydroxy-1',2'-dihydrospiro[cyclohexane-1,3'-pyrrolo[2,3-b]pyridin]-5'-yl)-2-fluorophenyl)((S)-2-(1-methyl-1H-pyrazol-4-yl)piperidin-1-yl)methanone |
| 246c 246d | | (3-((1r,4r)-4'-Chloro-4-hydroxy-1',2'-dihydrospiro[cyclohexane-1,3'-pyrrolo[2,3-b]pyridin]-5'-yl)-2-fluorophenyl)((R)-2-(1-methyl-1H-pyrazol-4-yl)piperidin-1-yl)methanone (3-((1r,4r)-4'-Chloro-4-hydroxy-1',2'-dihydrospiro[cyclohexane-1,3'-pyrrolo[2,3-b]pyridin]-5'-yl)-2-fluorophenyl)((S)-2-(1-methyl-1H-pyrazol-4-yl)piperidin-1-yl)methanone |
| 247 | | 2-(tert-Butyl)-5-(3-(4'-chloro-1',2'-dihydrospiro[cyclopentane-1,3'-pyrrolo[2,3-b]pyridin]-3-en-5'-yl)phenyl)-1,3,4-oxadiazole |

TABLE 1-continued

| No. | Structure | Name |
|---|---|---|
| 248 | 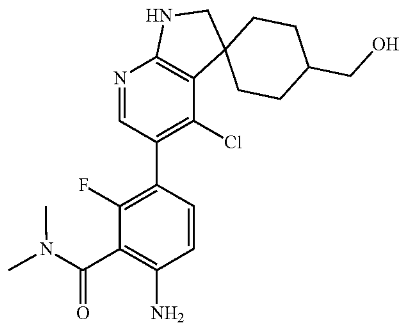 [SMILES: CN(C)C(=O)c1c(N)ccc(-c2cnc3c(c2Cl)C2(CCC(CO)CC2)CN3)c1F] | 6-Amino-3-(4'-chloro-4-(hydroxymethyl)-1',2'-dihydrospiro[cyclohexane-1,3'-pyrrolo[2,3-b]pyridin]-5'-yl)-2-fluoro-N,N-dimethylbenzamide |
| 248a | | 6-Amino-3-((1s,4s)-4'-chloro-4-(hydroxymethyl)-1',2'-dihydrospiro[cyclohexane-1,3'-pyrrolo[2,3-b]pyridin]-5'-yl)-2-fluoro-N,N-dimethylbenzamide |
| 248b | | 6-Amino-3-((1r,4r)-4'-chloro-4-(hydroxymethyl)-1',2'-dihydrospiro[cyclohexane-1,3'-pyrrolo[2,3-b]pyridin]-5'-yl)-2-fluoro-N,N-dimethylbenzamide |
| 249 | 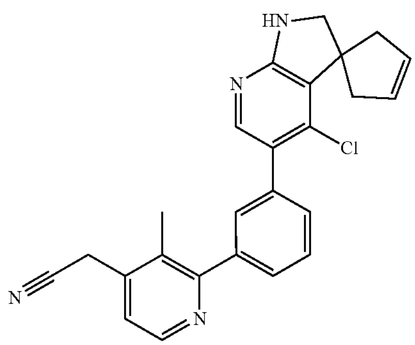 [SMILES: Cc1c(CC#N)ccnc1-c1cccc(-c2cnc3c(c2Cl)C2(CC=CC2)CN3)c1] | 2-(2-(3-(4'-Chloro-1',2'-dihydrospiro[cyclopentane-1,3'-pyrrolo[2,3-b]pyridin]-3-en-5'-yl)phenyl)-3-methylpyridin-4-yl)acetonitrile |
| 250 | 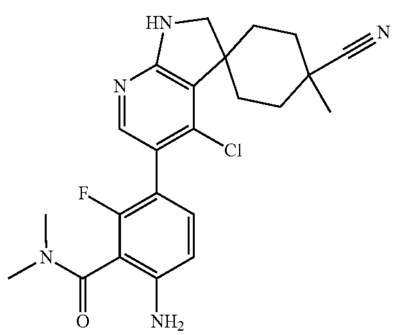 [SMILES: CN(C)C(=O)c1c(N)ccc(-c2cnc3c(c2Cl)C2(CCC(C)(C#N)CC2)CN3)c1F] | 6-Amino-3-(4'-chloro-4-cyano-4-methyl-1',2'-dihydrospiro[cyclohexane-1,3'-pyrrolo[2,3-b]pyridin]-5'-yl)-2-fluoro-N,N-dimethylbenzamide |
| 250a | | 6-Amino-3-((1s,4s)-4'-chloro-4-cyano-4-methyl-1',2'-dihydrospiro[cyclohexane-1,3'-pyrrolo[2,3-b]pyridin]-5'-yl)-2-fluoro-N,N-dimethylbenzamide |
| 250b | | 6-Amino-3-((1r,4r)-4'-chloro-4-cyano-4-methyl-1',2'-dihydrospiro[cyclohexane-1,3'-pyrrolo[2,3-b]pyridin]-5'-yl)-2-fluoro-N,N-dimethylbenzamide |
| 251 | 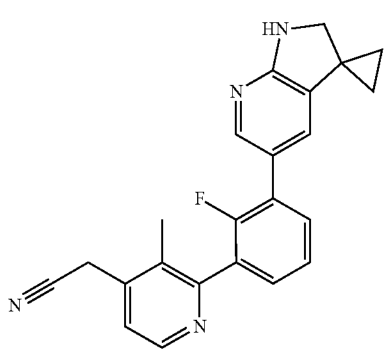 [SMILES: Cc1c(CC#N)ccnc1-c1cccc(-c2cnc3c(c2)C2(CC2)CN3)c1F] | 2-(2-(3-(1',2'-Dihydrospiro[cyclopropane-1,3'-pyrrolo[2,3-b]pyridin]-5'-yl)-2-fluorophenyl)-3-methylpyridin-4-yl)acetonitrile |

TABLE 1-continued

| No. | Name |
|---|---|
| 252 | 2-(2-(3-(4'-Chloro-1',2'-dihydrospiro[cyclopentane-1,3'-pyrrolo[2,3-b]pyridin]-3-en-5'-yl)-2-fluorophenyl)-3-methylpyridin-4-yl)acetonitrile |
| 253 | (6-Amino-2-fluoro-3-(4-hydroxy-1',2'-dihydrospiro[cyclohexane-1,3'-pyrrolo[2,3-b]pyridin]-5'-yl)phenyl)(2-(1-methyl-1H-pyrazol-4-yl)piperidin-1-yl)methanone |
| 253a | (6-Amino-2-fluoro-3-((1s,4s)-4-hydroxy-1',2'-dihydrospiro[cyclohexane-1,3'-pyrrolo[2,3-b]pyridin]-5'-yl)phenyl)((R)-2-(1-methyl-1H-pyrazol-4-yl)piperidin-1-yl)methanone |
| 253b | (6-Amino-2-fluoro-3-((1s,4s)-4-hydroxy-1',2'-dihydrospiro[cyclohexane-1,3'-pyrrolo[2,3-b]pyridin]-5'-yl)phenyl)((S)-2-(1-methyl-1H-pyrazol-4-yl)piperidin-1-yl)methanone |
| 253c | (6-Amino-2-fluoro-3-((1r,4r)-4-hydroxy-1',2'-dihydrospiro[cyclohexane-1,3'-pyrrolo[2,3-b]pyridin]-5'-yl)phenyl)((R)-2-(1-methyl-1H-pyrazol-4-yl)piperidin-1-yl)methanone |
| 253d | (6-Amino-2-fluoro-3-((1r,4r)-4-hydroxy-1',2'-dihydrospiro[cyclohexane-1,3'-pyrrolo[2,3-b]pyridin]-5'-yl)phenyl)((S)-2-(1-methyl-1H-pyrazol-4-yl)piperidin-1-yl)methanone |
| 254 | (6-Amino-3-(4'-chloro-4-hydroxy-1',2'-dihydrospiro[cyclohexane-1,3'-pyrrolo[2,3-b]pyridin]-5'-yl)-2-fluorophenyl)(2-(1-methyl-1H-pyrazol-4-yl)piperidin-1-yl)methanone |

TABLE 1-continued

| No. | Structure | Name |
|---|---|---|
| 254a 254b | | (6-Amino-3-((1s,4s)-4'-chloro-4-hydroxy-1',2'-dihydrospiro[cyclohexane-1,3'-pyrrolo[2,3-b]pyridin]-5'-yl)-2-fluorophenyl)((R)-2-(1-methyl-1H-pyrazol-4-yl)piperidin-1-yl)methanone (6-Amino-3-((1s,4s)-4'-chloro-4-hydroxy-1',2'-dihydrospiro[cyclohexane-1,3'-pyrrolo[2,3-b]pyridin]-5'-yl)-2-fluorophenyl)((S)-2-(1-methyl-1H-pyrazol-4-yl)piperidin-1-yl)methanone |
| 254c 254d | | (6-Amino-3-((1r,4r)-4'-chloro-4-hydroxy-1',2'-dihydrospiro[cyclohexane-1,3'-pyrrolo[2,3-b]pyridin]-5'-yl)-2-fluorophenyl)((R)-2-(1-methyl-1H-pyrazol-4-yl)piperidin-1-yl)methanone (6-Amino-3-((1r,4r)-4'-chloro-4-hydroxy-1',2'-dihydrospiro[cyclohexane-1,3'-pyrrolo[2,3-b]pyridin]-5'-yl)-2-fluorophenyl)((S)-2-(1-methyl-1H-pyrazol-4-yl)piperidin-1-yl)methanone |
| 255 | 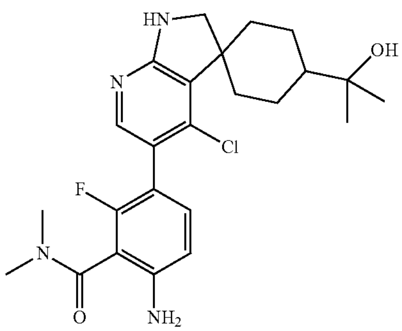 [SMILES: CN(C)C(=O)c1c(N)ccc(-c2cnc3c(c2Cl)C2(CCC(C(C)(C)O)CC2)CN3)c1F] | 6-Amino-3-(4'-chloro-4-(2-hydroxypropan-2-yl)-1',2'-dihydrospiro[cyclohexane-1,3'-pyrrolo[2,3-b]pyridin]-5'-yl)-2-fluoro-N,N-dimethylbenzamide |
| 255a | | 6-Amino-3-((1s,4s)-4'-chloro-4-(2-hydroxypropan-2-yl)-1',2'-dihydrospiro[cyclohexane-1,3'-pyrrolo[2,3-b]pyridin]-5'-yl)-2-fluoro-N,N-dimethylbenzamide |
| 255b | | 6-Amino-3-((1r,4r)-4'-chloro-4-(2-hydroxypropan-2-yl)-1',2'-dihydrospiro[cyclohexane-1,3'-pyrrolo[2,3-b]pyridin]-5'-yl)-2-fluoro-N,N-dimethylbenzamide |
| 256 | 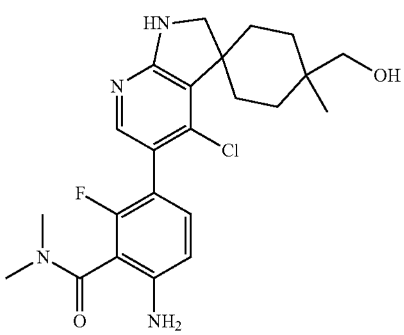 [SMILES: CN(C)C(=O)c1c(N)ccc(-c2cnc3c(c2Cl)C2(CCC(C)(CO)CC2)CN3)c1F] | 6-Amino-3-(4'-chloro-4-(hydroxymethyl)-4-methyl-1',2'-dihydrospiro[cyclohexane-1,3'-pyrrolo[2,3-b]pyridin]-5'-yl)-2-fluoro-N,N-dimethylbenzamide |
| 256a | | 6-Amino-3-((1r,4r)-4'-chloro-4-(hydroxymethyl)-4-methyl-1',2'-dihydrospiro[cyclohexane-1,3'-pyrrolo[2,3-b]pyridin]-5'-yl)-2-fluoro-N,N-dimethylbenzamide |
| 256b | | 6-Amino-3-((1s,4s)-4'-chloro-4-(hydroxymethyl)-4-methyl-1',2'-dihydrospiro[cyclohexane-1,3'-pyrrolo[2,3-b]pyridin]-5'-yl)-2-fluoro-N,N-dimethylbenzamide |

TABLE 1-continued

| No. | Structure | Name |
|---|---|---|
| 257 | 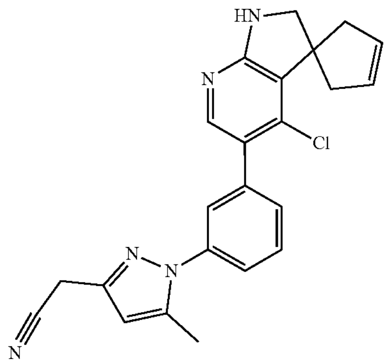 [SMILES: Cc1cc(CC#N)nn1-c1cccc(-c2cnc3c(c2Cl)C2(CC=CC2)CN3)c1] | 2-(1-(3-(4'-Chloro-1',2'-dihydrospiro[cyclopentane-1,3'-pyrrolo[2,3-b]pyridin]-3-en-5'-yl)phenyl)-5-methyl-1H-pyrazol-3-yl)acetonitrile |
| 258 | 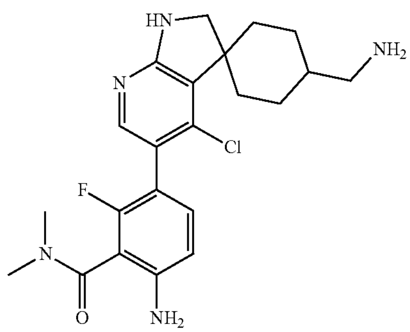 [SMILES: CN(C)C(=O)c1c(N)ccc(-c2cnc3c(c2Cl)C2(CCC(CN)CC2)CN3)c1F] | 6-Amino-3-(4-(aminomethyl)-4'-chloro-1',2'-dihydrospiro[cyclohexane-1,3'-pyrrolo[2,3-b]pyridin]-5'-yl)-2-fluoro-N,N-dimethylbenzamide |
| 258a | | 6-Amino-3-((1r,4r)-4-(aminomethyl)-4'-chloro-1',2'-dihydrospiro[cyclohexane-1,3'-pyrrolo[2,3-b]pyridin]-5'-yl)-2-fluoro-N,N-dimethylbenzamide |
| 258b | | 6-Amino-3-((1s,4s)-4-(aminomethyl)-4'-chloro-1',2'-dihydrospiro[cyclohexane-1,3'-pyrrolo[2,3-b]pyridin]-5'-yl)-2-fluoro-N,N-dimethylbenzamide |
| 259 | 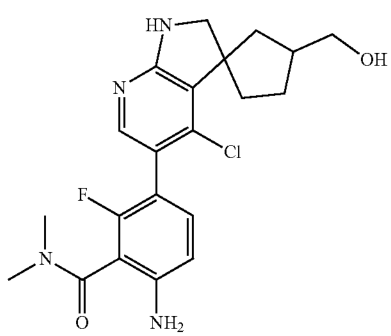 [SMILES: CN(C)C(=O)c1c(N)ccc(-c2cnc3c(c2Cl)C2(CCC(CO)C2)CN3)c1F] | 6-Amino-3-(4'-chloro-3-(hydroxymethyl)-1',2'-dihydrospiro[cyclopentane-1,3'-pyrrolo[2,3-b]pyridin]-5'-yl)-2-fluoro-N,N-dimethylbenzamide |
| 259a 259b | | 6-Amino-3-((1R,3S)-4'-chloro-3-(hydroxymethyl)-1',2'-dihydrospiro[cyclopentane-1,3'-pyrrolo[2,3-b]pyridin]-5'-yl)-2-fluoro-N,N-dimethylbenzamide<br>6-Amino-3-((1S,3R)-4'-chloro-3-(hydroxymethyl)-1',2'-dihydrospiro[cyclopentane-1,3'-pyrrolo[2,3-b]pyridin]-5'-yl)-2-fluoro-N,N-dimethylbenzamide |
| 259c 259d | | 6-Amino-3-((1R,3R)-4'-chloro-3-(hydroxymethyl)-1',2'-dihydrospiro[cyclopentane-1,3'-pyrrolo[2,3-b]pyridin]-5'-yl)-2-fluoro-N,N-dimethylbenzamide<br>6-Amino-3-((1S,3S)-4'-chloro-3-(hydroxymethyl)-1',2'-dihydrospiro[cyclopentane-1,3'-pyrrolo[2,3-b]pyridin]-5'-yl)-2-fluoro-N,N-dimethylbenzamide |

TABLE 1-continued

| No. | Structure | Name |
|---|---|---|
| 260 | 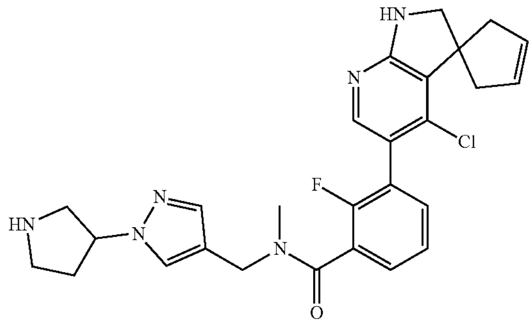 [SMILES: CN(Cc1cnn(C2CCNC2)c1)C(=O)c1cccc(-c2cnc3c(c2Cl)C2(CC=CC2)CN3)c1F] | 3-(4'-Chloro-1',2'-dihydrospiro[cyclopentane-1,3'-pyrrolo[2,3-b]pyridin]-3-en-5'-yl)-2-fluoro-N-methyl-N-((1-(pyrrolidin-3-yl)-1H-pyrazol-4-yl)methyl)benzamide |
| 261 | 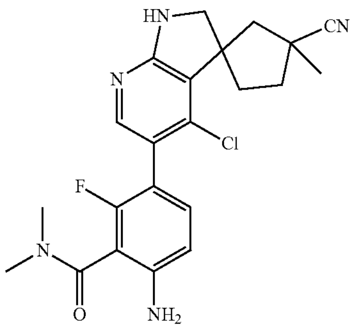 [SMILES: CN(C)C(=O)c1c(N)ccc(-c2cnc3c(c2Cl)C2(CCC(C)(C#N)C2)CN3)c1F] | 6-Amino-3-(4'-chloro-3-cyano-3-methyl-1',2'-dihydrospiro[cyclopentane-1,3'-pyrrolo[2,3-b]pyridin]-5'-yl)-2-fluoro-N,N-dimethylbenzamide |
| 261a 261b | | 6-Amino-3-((1R,3S)-4'-chloro-3-cyano-3-methyl-1',2'-dihydrospiro[cyclopentane-1,3'-pyrrolo[2,3-b]pyridin]-5'-yl)-2-fluoro-N,N-dimethylbenzamide 6-Amino-3-((1S,3R)-4'-chloro-3-cyano-3-methyl-1',2'-dihydrospiro[cyclopentane-1,3'-pyrrolo[2,3-b]pyridin]-5'-yl)-2-fluoro-N,N-dimethylbenzamide |
| 261c 261d | | 6-Amino-3-((1R,3R)-4'-chloro-3-cyano-3-methyl-1',2'-dihydrospiro[cyclopentane-1,3'-pyrrolo[2,3-b]pyridin]-5'-yl)-2-fluoro-N,N-dimethylbenzamide 6-Amino-3-((1S,3S)-4'-chloro-3-cyano-3-methyl-1',2'-dihydrospiro[cyclopentane-1,3'-pyrrolo[2,3-b]pyridin]-5'-yl)-2-fluoro-N,N-dimethylbenzamide |
| 262 | 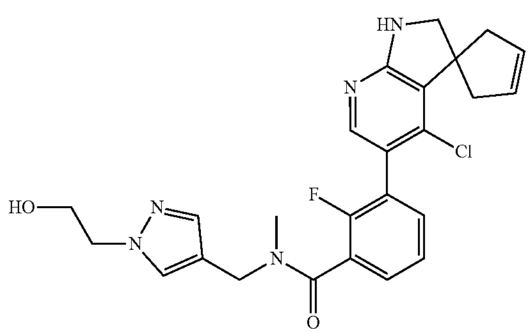 [SMILES: CN(Cc1cnn(CCO)c1)C(=O)c1cccc(-c2cnc3c(c2Cl)C2(CC=CC2)CN3)c1F] | 3-(4'-Chloro-1',2'-dihydrospiro[cyclopentane-1,3'-pyrrolo[2,3-b]pyridin]-3-en-5'-yl)-2-fluoro-N-((1-(2-hydroxyethyl)-1H-pyrazol-4-yl)methyl)-N-methylbenzamide |
| 263 | 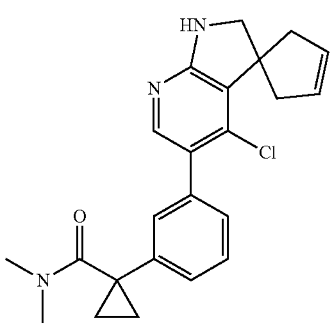 [SMILES: CN(C)C(=O)C1(c2cccc(-c3cnc4c(c3Cl)C3(CC=CC3)CN4)c2)CC1] | 1-(3-(4'-Chloro-1',2'-dihydrospiro[cyclopentane-1,3'-pyrrolo[2,3-b]pyridin]-3-en-5'-yl)phenyl)-N,N-dimethylcyclopropane-1-carboxamide |

TABLE 1-continued

| No. | Structure | Name |
|---|---|---|
| 264 | 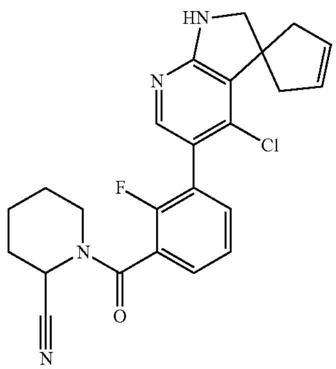 [SMILES: N#CC1CCCCN1C(=O)c1cccc(-c2cnc3c(c2Cl)C2(CC=CC2)CN3)c1F] | 1-(3-(4'-chloro-1',2'-dihydrospiro[cyclopentane-1,3'-pyrrolo[2,3-b]pyridin]-3-en-5'-yl)-2-fluorobenzoyl)piperidine-2-carbonitrile |
| 264a 264b | | (R)-1-(3-(4'-chloro-1',2'-dihydrospiro[cyclopentane-1,3'-pyrrolo[2,3-b]pyridin]-3-en-5'-yl)-2-fluorobenzoyl)piperidine-2-carbonitrile (S)-1-(3-(4'-chloro-1',2'-dihydrospiro[cyclopentane-1,3'-pyrrolo[2,3-b]pyridin]-3-en-5'-yl)-2-fluorobenzoyl)piperidine-2-carbonitrile |
| 265 | 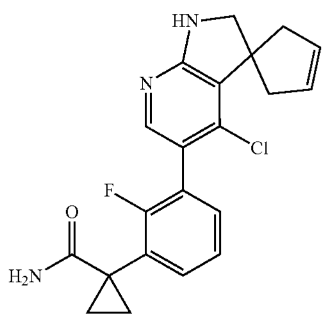 [SMILES: NC(=O)C1(c2cccc(-c3cnc4c(c3Cl)C3(CC=CC3)CN4)c2F)CC1] | 1-(3-(4'-Chloro-1',2'-dihydrospiro[cyclopentane-1,3'-pyrrolo[2,3-b]pyridin]-3-en-5'-yl)-2-fluorophenyl)cyclopropane-1-carboxamide |
| 266 | 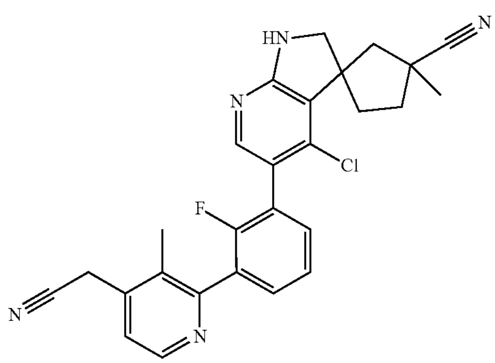 [SMILES: Cc1c(CC#N)ccnc1-c1cccc(-c2cnc3c(c2Cl)C2(CCC(C)(C#N)C2)CN3)c1F] | 4'-Chloro-5'-(3-(4-(cyanomethyl)-3-methylpyridin-2-yl)-2-fluorophenyl)-3-methyl-1',2'-dihydrospiro[cyclopentane-1,3'-pyrrolo[2,3-b]pyridine]-3-carbonitrile |
| 266a 266b | | (1R,3S)-4'-Chloro-5'-(3-(4-(cyanomethyl)-3-methylpyridin-2-yl)-2-fluorophenyl)-3-methyl-1',2'-dihydrospiro[cyclopentane-1,3'-pyrrolo[2,3-b]pyridine]-3-carbonitrile (1S,3R)-4'-Chloro-5'-(3-(4-(cyanomethyl)-3-methylpyridin-2-yl)-2-fluorophenyl)-3-methyl-1',2'-dihydrospiro[cyclopentane-1,3'-pyrrolo[2,3-b]pyridine]-3-carbonitrile |
| 266c 266d | | (1R,3R)-4'-Chloro-5'-(3-(4-(cyanomethyl)-3-methylpyridin-2-yl)-2-fluorophenyl)-3-methyl-1',2'-dihydrospiro[cyclopentane-1,3'-pyrrolo[2,3-b]pyridine]-3-carbonitrile (1S,3S)-4'-Chloro-5'-(3-(4-(cyanomethyl)-3-methylpyridin-2-yl)-2-fluorophenyl)-3-methyl-1',2'-dihydrospiro[cyclopentane-1,3'-pyrrolo[2,3-b]pyridine]-3-carbonitrile |

TABLE 1-continued

| No. | Structure | Name |
|---|---|---|
| 267 | 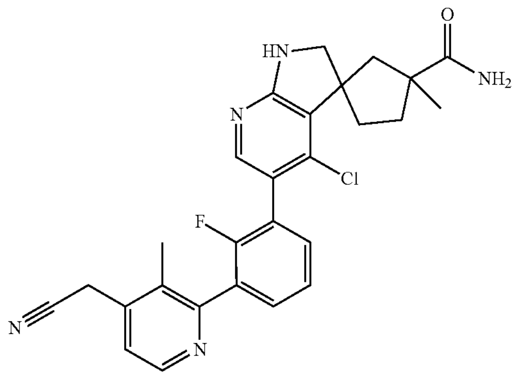 [SMILES: Cc1c(CC#N)ccnc1-c1cccc(-c2cnc3c(c2Cl)C2(CCC(C)(C(N)=O)C2)CN3)c1F] | 4'-Chloro-5'-(3-(4-(cyanomethyl)-3-methylpyridin-2-yl)-2-fluorophenyl)-3-methyl-1',2'-dihydrospiro[cyclopentane-1,3'-pyrrolo[2,3-b]pyridine]-3-carboxamide |
| 267a<br>267b | | (1R,3S)-4'-Chloro-5'-(3-(4-(cyanomethyl)-3-methylpyridin-2-yl)-2-fluorophenyl)-3-methyl-1',2'-dihydrospiro[cyclopentane-1,3'-pyrrolo[2,3-b]pyridine]-3-carboxamide<br>(1S,3R)-4'-Chloro-5'-(3-(4-(cyanomethyl)-3-methylpyridin-2-yl)-2-fluorophenyl)-3-methyl-1',2'-dihydrospiro[cyclopentane-1,3'-pyrrolo[2,3-b]pyridine]-3-carboxamide |
| 267c<br>267d | | (1R,3R)-4'-Chloro-5'-(3-(4-(cyanomethyl)-3-methylpyridin-2-yl)-2-fluorophenyl)-3-methyl-1',2'-dihydrospiro[cyclopentane-1,3'-pyrrolo[2,3-b]pyridine]-3-carboxamide<br>(1S,3S)-4'-Chloro-5'-(3-(4-(cyanomethyl)-3-methylpyridin-2-yl)-2-fluorophenyl)-3-methyl-1',2'-dihydrospiro[cyclopentane-1,3'-pyrrolo[2,3-b]pyridine]-3-carboxamide |
| 268 | 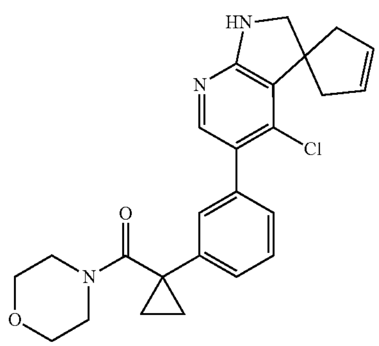 [SMILES: O=C(N1CCOCC1)C1(c2cccc(-c3cnc4c(c3Cl)C3(CC=CC3)CN4)c2)CC1] | (1-(3-(4'-Chloro-1',2'-dihydrospiro[cyclopentane-1,3'-pyrrolo[2,3-b]pyridin]-3-en-5'-yl)phenyl)cyclopropyl)(morpholino)methanone |
| 269 | 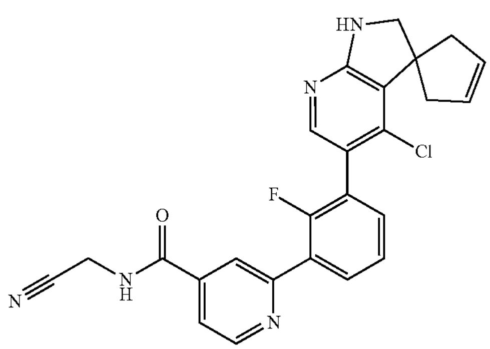 [SMILES: N#CCNC(=O)c1ccnc(-c2cccc(-c3cnc4c(c3Cl)C3(CC=CC3)CN4)c2F)c1] | 2-(3-(4'-Chloro-1',2'-dihydrospiro[cyclopentane-1,3'-pyrrolo[2,3-b]pyridin]-3-en-5'-yl)-2-fluorophenyl)-N-(cyanomethyl)isonicotinamide |

TABLE 1-continued

| No. | Structure | Name |
|---|---|---|
| 270 | 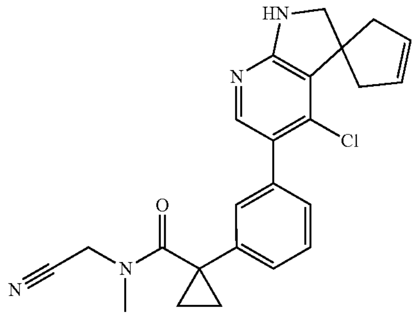 [SMILES: CN(CC#N)C(=O)C1(c2cccc(-c3cnc4c(c3Cl)C3(CC=CC3)CN4)c2)CC1] | 1-(3-(4'-Chloro-1',2'-dihydrospiro[cyclopentane-1,3'-pyrrolo[2,3-b]pyridin]-3-en-5'-yl)phenyl)-N-(cyanomethyl)-N-methylcyclopropane-1-carboxamide |
| 271 | 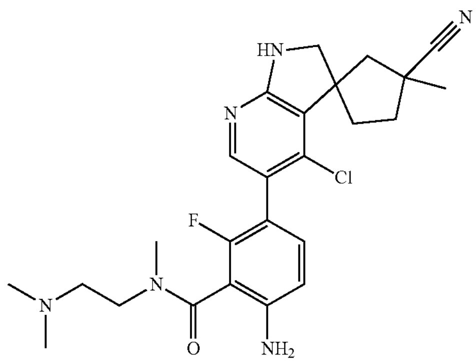 [SMILES: CN(C)CCN(C)C(=O)c1c(N)ccc(-c2cnc3c(c2Cl)C2(CCC(C)(C#N)C2)CN3)c1F] | 6-Amino-3-(4'-chloro-3-cyano-3-methyl-1',2'-dihydrospiro[cyclopentane-1,3'-pyrrolo[2,3-b]pyridin]-5'-yl)-N-(2-(dimethylamino)ethyl)-2-fluoro-N-methyl benzamide |
| 271a<br>271b | | 6-Amino-3-((1R,3R)-4'-chloro-3-cyano-3-methyl-1',2'-dihydrospiro[cyclopentane-1,3'-pyrrolo[2,3-b]pyridin]-5'-yl)-N-(2-(dimethylamino)ethyl)-2-fluoro-N-methyl benzamide<br>6-Amino-3-((1S,3R)-4'-chloro-3-cyano-3-methyl-1',2'-dihydrospiro[cyclopentane-1,3'-pyrrolo[2,3-b]pyridin]-5'-yl)-N-(2-(dimethylamino)ethyl)-2-fluoro-N-methyl benzamide |
| 271c<br>271d | | 6-Amino-3-((1R,3S)-4'-chloro-3-cyano-3-methyl-1',2'-dihydrospiro[cyclopentane-1,3'-pyrrolo[2,3-b]pyridin]-5'-yl)-N-(2-(dimethylamino)ethyl)-2-fluoro-N-methyl benzamide<br>6-Amino-3-((1S,3S)-4'-chloro-3-cyano-3-methyl-1',2'-dihydrospiro[cyclopentane-1,3'-pyrrolo[2,3-b]pyridin]-5'-yl)-N-(2-(dimethylamino)ethyl)-2-fluoro-N-methyl benzamide |
| 272 | 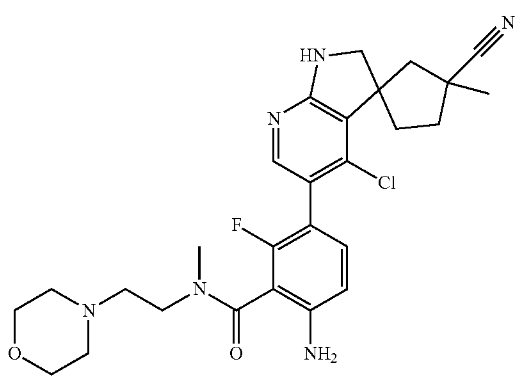 [SMILES: CN(CCN1CCOCC1)C(=O)c1c(N)ccc(-c2cnc3c(c2Cl)C2(CCC(C)(C#N)C2)CN3)c1F] | 6-Amino-3-(4'-chloro-3-cyano-3-methyl-1',2'-dihydrospiro[cyclopentane-1,3'-pyrrolo[2,3-b]pyridin]-5'-yl)-2-fluoro-N-methyl-N-(2-morpholinoethyl)benzamide |
| 272a<br>272b | | 6-Amino-3-((1R,3S)-4'-chloro-3-cyano-3-methyl-1',2'-dihydrospiro[cyclopentane-1,3'-pyrrolo[2,3-b]pyridin]-5'-yl)-2-fluoro-N-methyl-N-(2-morpholinoethyl)benzamide<br>6-Amino-3-((1S,3R)-4'-chloro-3-cyano-3-methyl-1',2'-dihydrospiro[cyclopentane-1,3'-pyrrolo[2,3-b]pyridin]-5'-yl)-2-fluoro-N-methyl-N-(2-morpholinoethyl)benzamide |

TABLE 1-continued

| No. | Structure | Name |
|---|---|---|
| 272c 272d | | 6-Amino-3-((1R,3R)-4'-chloro-3-cyano-3-methyl-1',2'-dihydrospiro[cyclopentane-1,3'-pyrrolo[2,3-b]pyridin]-5'-yl)-2-fluoro-N-methyl-N-(2-morpholinoethyl)benzamide<br>6-Amino-3-((1S,3S)-4'-chloro-3-cyano-3-methyl-1',2'-dihydrospiro[cyclopentane-1,3'-pyrrolo[2,3-b]pyridin]-5'-yl)-2-fluoro-N-methyl-N-(2-morpholinoethyl)benzamide |
| 273 | (structure) | 6-Amino-3-(4'-chloro-4-(methylsulfonyl)-1',2'-dihydrospiro[cyclohexane-1,3'-pyrrolo[2,3-b]pyridin]-5'-yl)-2-fluoro-N,N-dimethylbenzamide |
| 273a | | 6-Amino-3-((1r,4r)-4'-chloro-4-(methylsulfonyl)-1',2'-dihydrospiro[cyclohexane-1,3'-pyrrolo[2,3-b]pyridin]-5'-yl)-2-fluoro-N,N-dimethylbenzamide |
| 273b | | 6-Amino-3-((1s,4s)-4'-chloro-4-(methylsulfonyl)-1',2'-dihydrospiro[cyclohexane-1,3'-pyrrolo[2,3-b]pyridin]-5'-yl)-2-fluoro-N,N-dimethylbenzamide |
| 274 | (structure) | 5'-(3-Amino-5-(4-(cyanomethyl)-3-methylpyridin-2-yl)phenyl)-4'-chloro-3-methyl-1',2'-dihydrospiro[cyclopentane-1,3'-pyrrolo[2,3-b]pyridine]-3-carbonitrile |
| 274a 274b | | (1R,3S)-5'-(3-Amino-5-(4-(cyanomethyl)-3-methylpyridin-2-yl)phenyl)-4'-chloro-3-methyl-1',2'-dihydrospiro[cyclopentane-1,3'-pyrrolo[2,3-b]pyridine]-3-carbonitrile<br>(1S,3R)-5'-(3-Amino-5-(4-(cyanomethyl)-3-methylpyridin-2-yl)phenyl)-4'-chloro-3-methyl-1',2'-dihydrospiro[cyclopentane-1,3'-pyrrolo[2,3-b]pyridine]-3-carbonitrile |
| 274c 274d | | (1R,3R)-5'-(3-Amino-5-(4-(cyanomethyl)-3-methylpyridin-2-yl)phenyl)-4'-chloro-3-methyl-1',2'-dihydrospiro[cyclopentane-1,3'-pyrrolo[2,3-b]pyridine]-3-carbonitrile<br>(1S,3S)-5'-(3-Amino-5-(4-(cyanomethyl)-3-methylpyridin-2-yl)phenyl)-4'-chloro-3-methyl-1',2'-dihydrospiro[cyclopentane-1,3'-pyrrolo[2,3-b]pyridine]-3-carbonitrile |

TABLE 1-continued

| No. | Structure | Name |
|---|---|---|
| 275 | 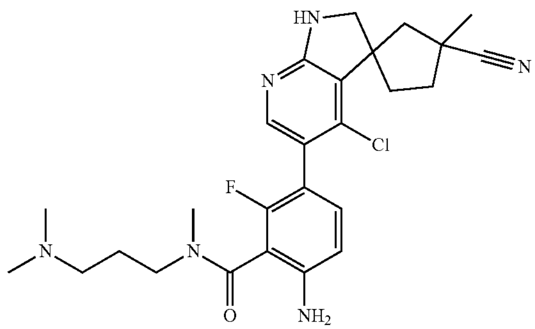 [SMILES: CN(C)CCCN(C)C(=O)c1c(N)ccc(-c2cnc3c(c2Cl)C2(CCC(C)(C#N)C2)CN3)c1F] | 6-Amino-3-(4'-chloro-3-cyano-3-methyl-1',2'-dihydrospiro[cyclopentane-1,3'-pyrrolo[2,3-b]pyridin]-5'-yl)-N-(3-(dimethylamino)propyl)-2-fluoro-N-methylbenzamide |
| 275a 275b | | 6-Amino-3-((1R,3S)-4'-chloro-3-cyano-3-methyl-1',2'-dihydrospiro[cyclopentane-1,3'-pyrrolo[2,3-b]pyridin]-5'-yl)-N-(3-(dimethylamino)propyl)-2-fluoro-N-methylbenzamide<br>6-Amino-3-((1S,3R)-4'-chloro-3-cyano-3-methyl-1',2'-dihydrospiro[cyclopentane-1,3'-pyrrolo[2,3-b]pyridin]-5'-yl)-N-(3-(dimethylamino)propyl)-2-fluoro-N-methylbenzamide |
| 275c 275d | | 6-Amino-3-((1R,3R)-4'-chloro-3-cyano-3-methyl-1',2'-dihydrospiro[cyclopentane-1,3'-pyrrolo[2,3-b]pyridin]-5'-yl)-N-(3-(dimethylamino)propyl)-2-fluoro-N-methyl benzamide<br>6-Amino-3-((1S,3S)-4'-chloro-3-cyano-3-methyl-1',2'-dihydrospiro[cyclopentane-1,3'-pyrrolo[2,3-b]pyridin]-5'-yl)-N-(3-(dimethylamino)propyl)-2-fluoro-N-methyl benzamide |
| 276 | 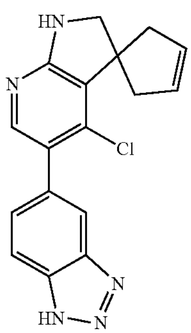 [SMILES: Clc1c(-c2ccc3[nH]nnc3c2)cnc2c1C1(CC=CC1)CN2] | 5'-(1H-Benzo[d][1,2,3]triazol-5-yl)-4'-chloro-1',2'-dihydrospiro[cyclopentane-1,3'-pyrrolo[2,3-b]pyridin]-3-ene |
| 277 | 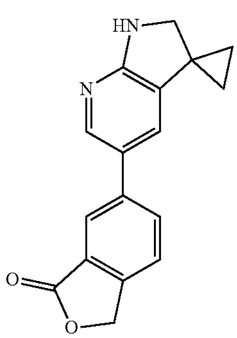 [SMILES: O=C1OCc2ccc(-c3cnc4c(c3)C3(CC3)CN4)cc21] | 6-(1',2'-dihydrospiro[cyclopropane-1,3'-pyrrolo[2,3-b]pyridin]-5'-yl)isobenzofuran-1(3H)-one |

TABLE 1-continued

| No. | Structure | Name |
|---|---|---|
| 278 | 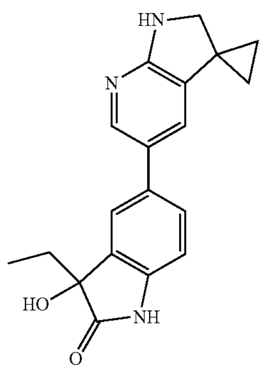 [SMILES: CCC1(O)C(=O)Nc2ccc(-c3cnc4c(c3)C3(CC3)CN4)cc21] | 5-(1',2'-dihydrospiro[cyclopropane-1,3'-pyrrolo[2,3-b]pyridin]-5'-yl)-3-ethyl-3-hydroxyindolin-2-one |
| 278a 278b | | (R)-5-(1',2'-dihydrospiro[cyclopropane-1,3'-pyrrolo[2,3-b]pyridin]-5'-yl)-3-ethyl-3-hydroxyindolin-2-one (S)-5-(1',2'-dihydrospiro[cyclopropane-1,3'-pyrrolo[2,3-b]pyridin]-5'-yl)-3-ethyl-3-hydroxyindolin-2-one |
| 279 | 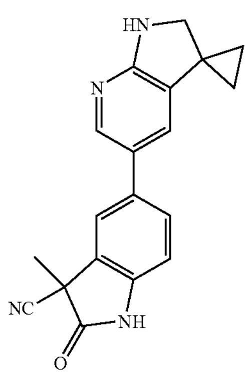 [SMILES: CC1(C#N)C(=O)Nc2ccc(-c3cnc4c(c3)C3(CC3)CN4)cc21] | 5-(1',2'-dihydrospiro[cyclopropane-1,3'-pyrrolo[2,3-b]pyridin]-5'-yl)-3-methyl-2-oxoindoline-3-carbonitrile |
| 279a 279b | | (R)-5-(1',2'-dihydrospiro[cyclopropane-1,3'-pyrrolo[2,3-b]pyridin]-5'-yl)-3-methyl-2-oxoindoline-3-carbonitrile (S)-5-(1',2'-dihydrospiro[cyclopropane-1,3'-pyrrolo[2,3-b]pyridin]-5'-yl)-3-methyl-2-oxoindoline-3-carbonitrile |
| 280 | 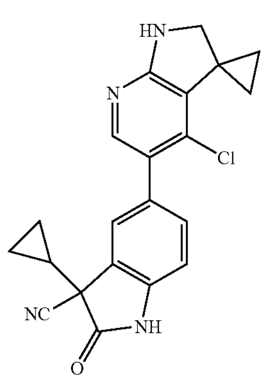 [SMILES: N#CC1(C2CC2)C(=O)Nc2ccc(-c3cnc4c(c3Cl)C3(CC3)CN4)cc21] | 5-(4'-chloro-1',2'-dihydrospiro[cyclopropane-1,3'-pyrrolo[2,3-b]pyridin]-5'-yl)-3-cyclopropyl-3-hydroxyindolin-2-one |
| 280a 280b | | (R)-5-(4'-chloro-1',2'-dihydrospiro[cyclopropane-1,3'-pyrrolo[2,3-b]pyridin]-5'-yl)-3-cyclopropyl-3-hydroxyindolin-2-one (S)-5-(4'-chloro-1',2'-dihydrospiro[cyclopropane-1,3'-pyrrolo[2,3-b]pyridin]-5'-yl)-3-cyclopropyl-3-hydroxyindolin-2-one |

TABLE 1-continued

| No. | Structure | Name |
|---|---|---|
| 281 | 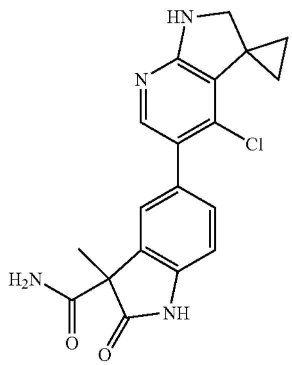 [SMILES: CC1(C(N)=O)C(=O)Nc2ccc(-c3cnc4c(c3Cl)C3(CC3)CN4)cc21] | 5-(4'-chloro-1',2'-dihydrospiro[cyclopropane-1,3'-pyrrolo[2,3-b]pyridin]-5'-yl)-3-methyl-2-oxoindoline-3-carboxamide |
| 281a<br>281b | | (R)-5-(4'-chloro-1',2'-dihydrospiro[cyclopropane-1,3'-pyrrolo[2,3-b]pyridin]-5'-yl)-3-methyl-2-oxoindoline-3-carboxamide<br>(S)-5-(4'-chloro-1',2'-dihydrospiro[cyclopropane-1,3'-pyrrolo[2,3-b]pyridin]-5'-yl)-3-methyl-2-oxoindoline-3-carboxamide |
| 282 | 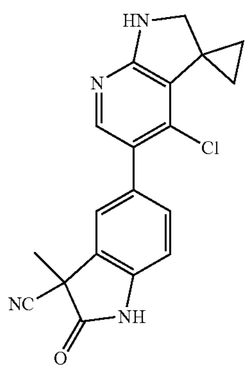 [SMILES: CC1(C#N)C(=O)Nc2ccc(-c3cnc4c(c3Cl)C3(CC3)CN4)cc21] | 5-(4'-chloro-1',2'-dihydrospiro[cyclopropane-1,3'-pyrrolo[2,3-b]pyridin]-5'-yl)-3-methyl-2-oxoindoline-3-carbonitrile |
| 282a<br>282b | | (R)-5-(4'-chloro-1',2'-dihydrospiro[cyclopropane-1,3'-pyrrolo[2,3-b]pyridin]-5'-yl)-3-methyl-2-oxoindoline-3-carbonitrile<br>(S)-5-(4'-chloro-1',2'-dihydrospiro[cyclopropane-1,3'-pyrrolo[2,3-b]pyridin]-5'-yl)-3-methyl-2-oxoindoline-3-carbonitrile |
| 283 | 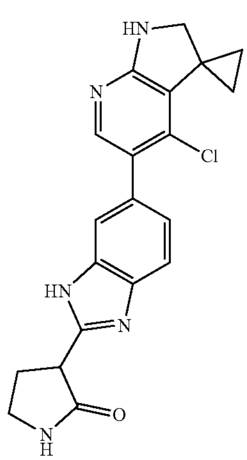 [SMILES: O=C1NCCC1c1nc2ccc(-c3cnc4c(c3Cl)C3(CC3)CN4)cc2[nH]1] | (±)-3-(6-(4'-Chloro-1',2'-dihydrospiro[cyclopropane-1,3'-pyrrolo[2,3-b]pyridin]-5'-yl)-1H-benzo[d]imidazol-2-yl)pyrrolidin-2-one |
| 283a<br>283b | | (R)-5-(4'-chloro-1',2'-dihydrospiro[cyclopropane-1,3'-pyrrolo[2,3-b]pyridin]-5'-yl)-3-cyclopropyl-3-hydroxyindolin-2-one<br>(S)-5-(4'-chloro-1',2'-dihydrospiro[cyclopropane-1,3'-pyrrolo[2,3-b]pyridin]-5'-yl)-3-cyclopropyl-3-hydroxyindolin-2-one |

TABLE 1-continued

| No. | Structure | Name |
|---|---|---|
| 284 | 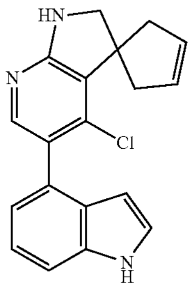 [SMILES: Clc1c(-c2cccc3[nH]ccc23)cnc2c1C1(CC=CC1)CN2] | 4-Chloro-5'-(1H-indol-4-yl)-1',2'-dihydrospiro[cyclopentane-1,3'-pyrrolo[2,3-b]pyridin]-3-ene |
| 285 | 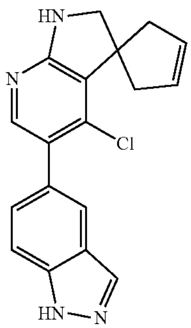 [SMILES: Clc1c(-c2ccc3[nH]ncc3c2)cnc2c1C1(CC=CC1)CN2] | 4-Chloro-5'-(1H-indazol-5-yl)-1',2'-dihydrospiro[cyclopentane-1,3'-pyrrolo[2,3-b]pyridin]-3-ene |
| 286 | 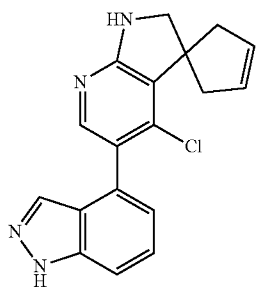 [SMILES: Clc1c(-c2cccc3[nH]ncc23)cnc2c1C1(CC=CC1)CN2] | 4-Chloro-5'-(1H-indazol-4-yl)-1',2'-dihydrospiro[cyclopentane-1,3'-pyrrolo[2,3-b]pyridin]-3-ene |
| 287 | 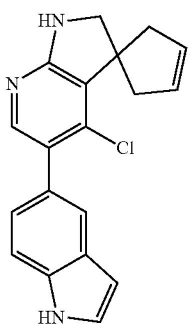 [SMILES: Clc1c(-c2ccc3[nH]ccc3c2)cnc2c1C1(CC=CC1)CN2] | 4-Chloro-5'-(1H-indol-5-yl)-1',2'-dihydrospiro[cyclopentane-1,3'-pyrrolo[2,3-b]pyridin]-3-ene |
| 288 | 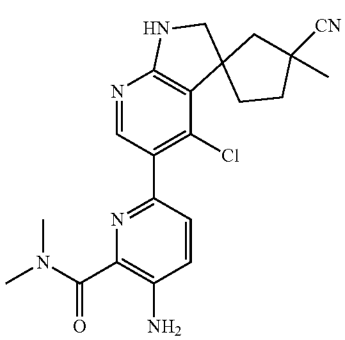 | 3-Amino-6-(4'-chloro-3-cyano-3-methyl-1',2'-dihydrospiro[cyclopentane-1,3'-pyrrolo[2,3-b]pyridin]-5'-yl)-N,N-dimethylpicolinamide |

TABLE 1-continued

| No. | Structure | Name |
|---|---|---|
| 288a 288b | | 1',2'-dihydrospiro[cyclopentane-1,3'-pyrrolo[2,3-b]pyridin]-5'-yl)-N,N-dimethylpicolinamide 3-Amino-6-((1S,3R)-4'-chloro-3-cyano-3-methyl-1',2'-dihydrospiro[cyclopentane-1,3'-pyrrolo[2,3-b]pyridin]-5'-yl)-N,N-dimethylpicolinamide |
| 288c 288d | | 3-Amino-6-((1R,3R)-4'-chloro-3-cyano-3-methyl-1',2'-dihydrospiro[cyclopentane-1,3'-pyrrolo[2,3-b]pyridin]-5'-yl)-N,N-dimethylpicolinamide 3-Amino-6-((1S,3S)-4'-chloro-3-cyano-3-methyl-1',2'-dihydrospiro[cyclopentane-1,3'-pyrrolo[2,3-b]pyridin]-5'-yl)-N,N-dimethylpicolinamide |
| 289 | 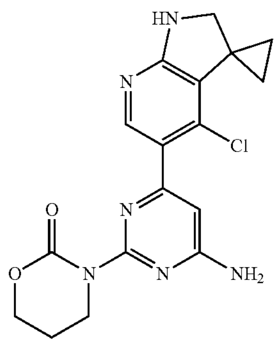 [SMILES: Nc1cc(-c2cnc3c(c2Cl)C2(CC2)CN3)nc(N2CCCOC2=O)n1] | 3-(4-amino-6-(1',2'-dihydrospiro[cyclopropane-1,3'-pyrrolo[2,3-b]pyridin]-5'-yl)pyrimidin-2-yl)-1,3-oxazinan-2-one |
| 290 | 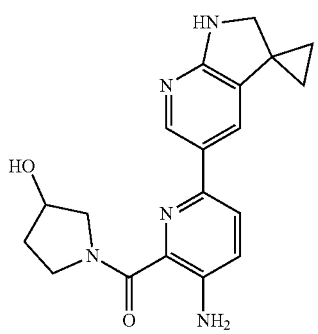 [SMILES: Nc1ccc(-c2cnc3c(c2)C2(CC2)CN3)nc1C(=O)N1CCC(O)C1] | (3-amino-6-(1',2'-dihydrospiro[cyclopropane-1,3'-pyrrolo[2,3-b]pyridin]-5'-yl)pyridin-2-yl)(3-hydroxypyrrolidin-1-yl)methanone |
| 290a | | (S)-(3-amino-6-(1',2'-dihydrospiro[cyclopropane-1,3'-pyrrolo[2,3-b]pyridin]-5'-yl)pyridin-2-yl)(3-hydroxypyrrolidin-1-yl)methanone |
| 290b | | (R)-(3-amino-6-(1',2'-dihydrospiro[cyclopropane-1,3'-pyrrolo[2,3-b]pyridin]-5'-yl)pyridin-2-yl)(3-hydroxypyrrolidin-1-yl)methanone |
| 291 | 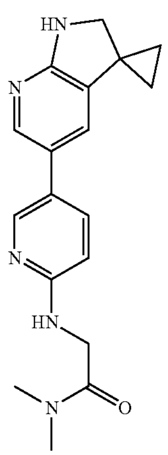 [SMILES: CN(C)C(=O)CNc1ccc(-c2cnc3c(c2)C2(CC2)CN3)cn1] | 2-((5-(1',2'-dihydrospiro[cyclopropane-1,3'-pyrrolo[2,3-b]pyridin]-5'-yl)pyridin-2-yl)amino)-N,N-dimethylacetamide |

TABLE 1-continued

| No. | Structure | Name |
|---|---|---|
| 292 | 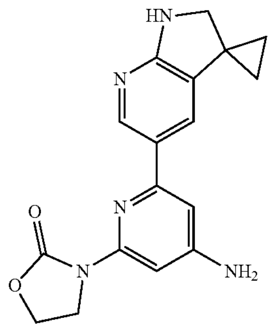 [SMILES: Nc1cc(-c2cnc3c(c2)C2(CC2)CN3)nc(N2CCOC2=O)c1] | 3-(4-amino-6-(1',2'-dihydrospiro[cyclopropane-1,3'-pyrrolo[2,3-b]pyridin]-5'-yl)pyridin-2-yl)oxazolidin-2-one |
| 293 | 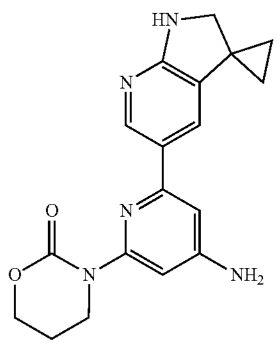 [SMILES: Nc1cc(-c2cnc3c(c2)C2(CC2)CN3)nc(N2CCCOC2=O)c1] | 3-(4-amino-6-(1',2'-dihydrospiro[cyclopropane-1,3'-pyrrolo[2,3-b]pyridin]-5'-yl)pyridin-2-yl)-1,3-oxazinan-2-one |
| 294 | 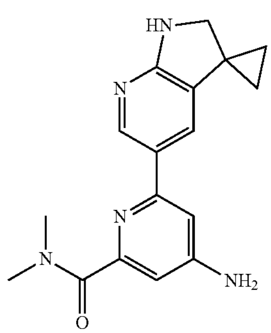 [SMILES: CN(C)C(=O)c1cc(N)cc(-c2cnc3c(c2)C2(CC2)CN3)n1] | 4-amino-6-(1',2'-dihydrospiro[cyclopropane-1,3'-pyrrolo[2,3-b]pyridin]-5'-yl)-N,N-dimethylpicolinamide |
| 295 | 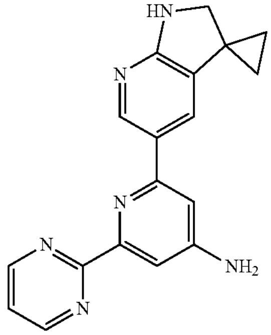 [SMILES: Nc1cc(-c2cnc3c(c2)C2(CC2)CN3)nc(-c2ncccn2)c1] | 2-(1',2'-dihydrospiro[cyclopropane-1,3'-pyrrolo[2,3-b]pyridin]-5'-yl)-6-(pyrimidin-2-yl)pyridin-4-amine |

TABLE 1-continued

| No. | Structure | Name |
|---|---|---|
| 296 | 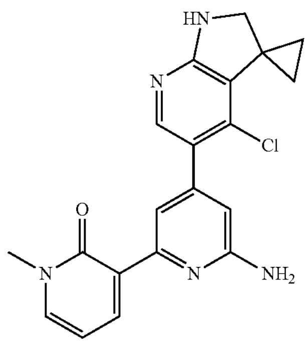 [SMILES: Cn1cccc(-c2cc(-c3cnc4c(c3Cl)C3(CC3)CN4)cc(N)n2)c1=O] | 6-amino-4-(4'-chloro-1',2'-dihydrospiro[cyclopropane-1,3'-pyrrolo[2,3-b]pyridin]-5'-yl)-1'-methyl-[2,3'-bipyridin]-2'(1'H)-one |
| 297 | 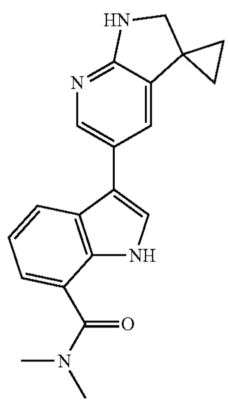 [SMILES: CN(C)C(=O)c1cccc2c(-c3cnc4c(c3)C3(CC3)CN4)c[nH]c12] | 3-(1',2'-Dihydrospiro[cyclopropane-1,3'-pyrrolo[2,3-b]pyridin]-5'-yl)-N,N-dimethyl-1H-indole-7-carboxamide |
| 298 | 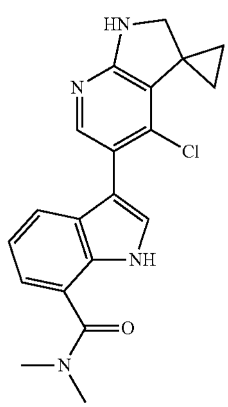 [SMILES: CN(C)C(=O)c1cccc2c(-c3cnc4c(c3Cl)C3(CC3)CN4)c[nH]c12] | 3-(4'-Chloro-1',2'-dihydrospiro[cyclopropane-1,3'-pyrrolo[2,3-b]pyridin]-5'-yl)-N,N-dimethyl-1H-indole-7-carboxamide |
| 299 | 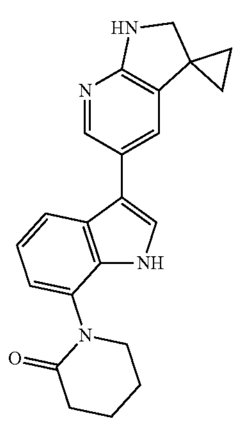 [SMILES: O=C1CCCCN1c1cccc2c(-c3cnc4c(c3)C3(CC3)CN4)c[nH]c12] | 1-(3-(1',2'-Dihydrospiro[cyclopropane-1,3'-pyrrolo[2,3-b]pyridin]-5'-yl)-1H-indol-7-yl)piperidin-2-one |

TABLE 1-continued

| No. | Structure | Name |
|---|---|---|
| 300 | 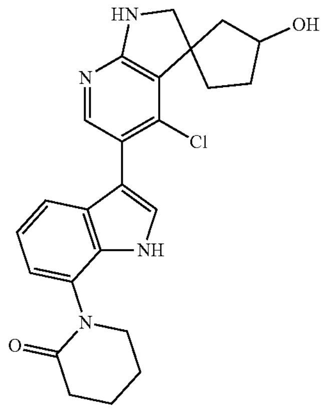 [SMILES: O=C1CCCCN1c1cccc2c(-c3cnc4c(c3Cl)C3(CCC(O)C3)CN4)c[nH]c12] | 1-(3-(4'-Chloro-3-hydroxy-1',2'-dihydrospiro[cyclopentane-1,3'-pyrrolo[2,3-b]pyridin]-5'-yl)-1H-indol-7-yl)piperidin-2-one |
| 300a<br>300b | | 1-(3-((1R,3S)-4'-Chloro-3-hydroxy-1',2'-dihydrospiro[cyclopentane-1,3'-pyrrolo[2,3-b]pyridin]-5'-yl)-1H-indol-7-yl)piperidin-2-one<br>1-(3-((1S,3R)-4'-Chloro-3-hydroxy-1',2'-dihydrospiro[cyclopentane-1,3'-pyrrolo[2,3-b]pyridin]-5'-yl)-1H-indol-7-yl)piperidin-2-one |
| 300c<br>300d | | 1-(3-((1R,3R)-4'-Chloro-3-hydroxy-1',2'-dihydrospiro[cyclopentane-1,3'-pyrrolo[2,3-b]pyridin]-5'-yl)-1H-indol-7-yl)piperidin-2-one<br>1-(3-((1S,3S)-4'-Chloro-3-hydroxy-1',2'-dihydrospiro[cyclopentane-1,3'-pyrrolo[2,3-b]pyridin]-5'-yl)-1H-indol-7-yl)piperidin-2-one |
| 301 | 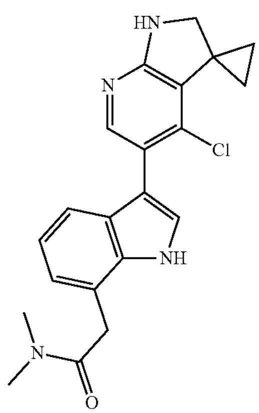 [SMILES: CN(C)C(=O)Cc1cccc2c(-c3cnc4c(c3Cl)C3(CC3)CN4)c[nH]c12] | 2-(3-(4'-Chloro-1',2'-dihydrospiro[cyclopropane-1,3'-pyrrolo[2,3-b]pyridin]-5'-yl)-1H-indol-7-yl)-N,N-dimethylacetamide |
| 302 | 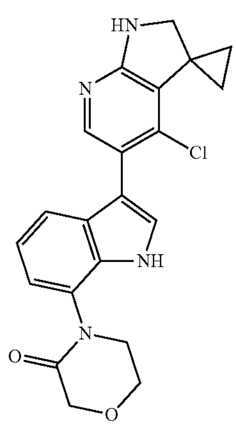 [SMILES: O=C1COCCN1c1cccc2c(-c3cnc4c(c3Cl)C3(CC3)CN4)c[nH]c12] | 4-(3-(4'-Chloro-1',2'-dihydrospiro[cyclopropane-1,3'-pyrrolo[2,3-b]pyridin]-5'-yl)-1H-indol-7-yl)morpholin-3-one |

TABLE 1-continued

| No. | Structure | Name |
|---|---|---|
| 303 | 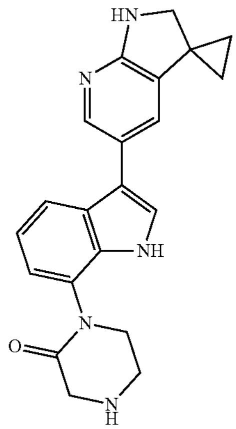 [SMILES: O=C1CNCCN1c1cccc2c(-c3cnc4c(c3)C3(CC3)CN4)c[nH]c12] | 1-(3-(1',2'-Dihydrospiro[cyclopropane-1,3'-pyrrolo[2,3-b]pyridin]-5'-yl)-1H-indol-7-yl)piperazin-2-one |
| 304 | 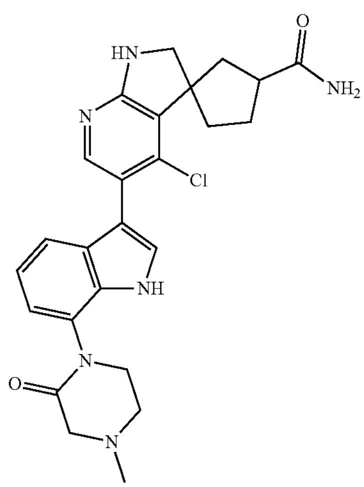 [SMILES: CN1CCN(c2cccc3c(-c4cnc5c(c4Cl)C4(CCC(C(N)=O)C4)CN5)c[nH]c23)C(=O)C1] | 4'-Chloro-5'-(7-(4-methyl-2-oxopiperazin-1-yl)-1H-indol-3-yl)-1',2'-dihydrospiro[cyclopentane-1,3'-pyrrolo[2,3-b]pyridine]-3-carboxamide |
| 304a 304b | | (1R,3S)-4'-Chloro-5'-(7-(4-methyl-2-oxopiperazin-1-yl)-1H-indol-3-yl)-1',2'-dihydrospiro[cyclopentane-1,3'-pyrrolo[2,3-b]pyridine]-3-carboxamide (1S,3R)-4'-Chloro-5'-(7-(4-methyl-2-oxopiperazin-1-yl)-1H-indol-3-yl)-1',2'-dihydrospiro[cyclopentane-1,3'-pyrrolo[2,3-b]pyridine]-3-carboxamide |
| 304c 304d | | (1R,3R)-4'-Chloro-5'-(7-(4-methyl-2-oxopiperazin-1-yl)-1H-indol-3-yl)-1',2'-dihydrospiro[cyclopentane-1,3'-pyrrolo[2,3-b]pyridine]-3-carboxamide (1S,3S)-4'-Chloro-5'-(7-(4-methyl-2-oxopiperazin-1-yl)-1H-indol-3-yl)-1',2'-dihydrospiro[cyclopentane-1,3'-pyrrolo[2,3-b]pyridine]-3-carboxamide |

TABLE 1-continued

| No. | Structure | Name |
|---|---|---|
| 305 | | 4'-Chloro-5'-(7-(2-oxopiperazin-1-yl)-1H-indol-3-yl)-1',2'-dihydrospiro[cyclopentane-1,3'-pyrrolo[2,3-b]pyridine]-3-carboxamide |
| 305a 305b | | (1R,3S)-4'-Chloro-5'-(7-(2-oxopiperazin-1-yl)-1H-indol-3-yl)-1',2'-dihydrospiro[cyclopentane-1,3'-pyrrolo[2,3-b]pyridine]-3-carboxamide (1S,3R)-4'-Chloro-5'-(7-(2-oxopiperazin-1-yl)-1H-indol-3-yl)-1',2'-dihydrospiro[cyclopentane-1,3'-pyrrolo[2,3-b]pyridine]-3-carboxamide |
| 305c 305d | | (1R,3R)-4'-Chloro-5'-(7-(2-oxopiperazin-1-yl)-1H-indol-3-yl)-1',2'-dihydrospiro[cyclopentane-1,3'-pyrrolo[2,3-b]pyridine]-3-carboxamide (1S,3S)-4'-Chloro-5'-(7-(2-oxopiperazin-1-yl)-1H-indol-3-yl)-1',2'-dihydrospiro[cyclopentane-1,3'-pyrrolo[2,3-b]pyridine]-3-carboxamide |
| 306 | | 1-(3-(2-methyl-1',2'-dihydrospiro[cyclopropane-1,3'-pyrrolo[2,3-b]pyridin]-5'-yl)-1H-indol-7-yl)piperazin-2-one |
| 306a 306b | | 1-(3-((1R,2R)-2-methyl-1',2'-dihydrospiro[cyclopropane-1,3'-pyrrolo[2,3-b]pyridin]-5'-yl)-1H-indol-7-yl)piperazin-2-one 1-(3-((1S,2S)-2-methyl-1',2'-dihydrospiro[cyclopropane-1,3'-pyrrolo[2,3-b]pyridin]-5'-yl)-1H-indol-7-yl)piperazin-2-one |
| 306c 306d | | 1-(3-((1R,2S)-2-methyl-1',2'-dihydrospiro[cyclopropane-1,3'-pyrrolo[2,3-b]pyridin]-5'-yl)-1H-indol-7-yl)piperazin-2-one 1-(3-((1S,2R)-2-methyl-1',2'-dihydrospiro[cyclopropane-1,3'-pyrrolo[2,3-b]pyridin]-5'-yl)-1H-indol-7-yl)piperazin-2-one |

TABLE 1-continued

| No. | Structure | Name |
|---|---|---|
| 307 | 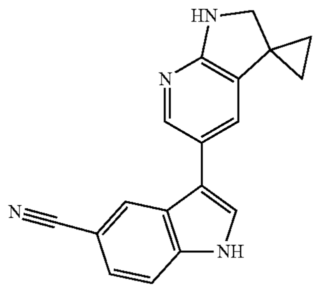 [SMILES: N#Cc1ccc2[nH]cc(-c3cnc4c(c3)C3(CC3)CN4)c2c1] | 3-(1',2'-Dihydrospiro[cyclopropane-1,3'-pyrrolo[2,3-b]pyridin]-5'-yl)-1H-indole-5-carbonitrile |
| 308 | 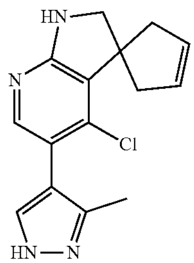 [SMILES: Cc1n[nH]cc1-c1cnc2c(c1Cl)C1(CC=CC1)CN2] | 4'-Chloro-5'-(3-methyl-1H-pyrazol-4-yl)-1',2'-dihydrospiro[cyclopentane-1,3'-pyrrolo[2,3-b]pyridin]-3-ene |
| 309 | 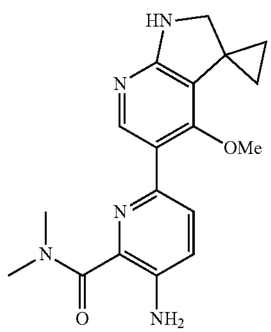 [SMILES: COc1c(-c2ccc(N)c(C(=O)N(C)C)n2)cnc2c1C1(CC1)CN2] | 3-Amino-6-(4'-methoxy-1',2'-dihydrospiro[cyclopropane-1,3'-pyrrolo[2,3-b]pyridin]-5'-yl)-N,N-dimethylpicolinamide |
| 310 | 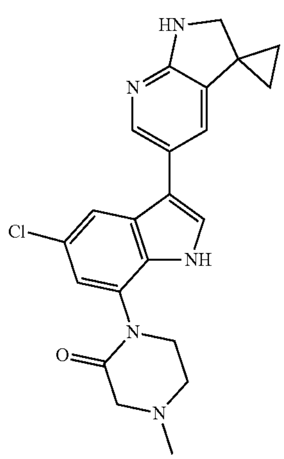 [SMILES: CN1CCN(c2cc(Cl)cc3c(-c4cnc5c(c4)C4(CC4)CN5)c[nH]c23)C(=O)C1] | 1-(5-Chloro-3-(1',2'-dihydrospiro[cyclopropane-1,3'-pyrrolo[2,3-b]pyridin]-5'-yl)-1H-indol-7-yl)-4-methylpiperazin-2-one |

TABLE 1-continued

| No. | Structure | Name |
|---|---|---|
| 311 | 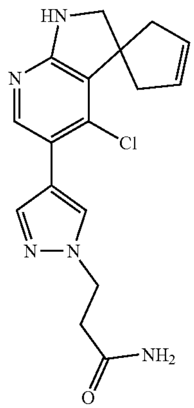 [SMILES: NC(=O)CCn1cc(-c2cnc3c(c2Cl)C2(CC=CC2)CN3)cn1] | 3-(4-(4'-Chloro-1',2'-dihydrospiro[cyclopentane-1,3'-pyrrolo[2,3-b]pyridin]-3-en-5'-yl)-1H-pyrazol-1-yl)propanamide |
| 312 | 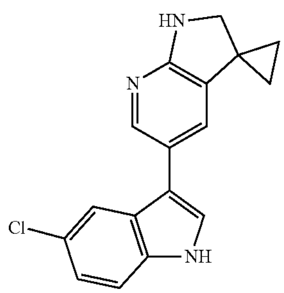 [SMILES: Clc1ccc2[nH]cc(-c3cnc4c(c3)C3(CC3)CN4)c2c1] | 5'-(5-Chloro-1H-indol-3-yl)-1',2'-dihydrospiro[cyclopropane-1,3'-pyrrolo[2,3-b]pyridine] |
| 313 | 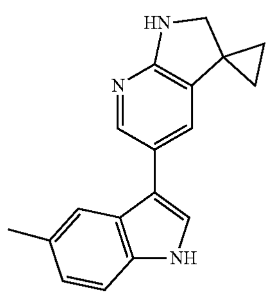 [SMILES: Cc1ccc2[nH]cc(-c3cnc4c(c3)C3(CC3)CN4)c2c1] | 5'-(5-Methyl-1H-indol-3-yl)-1',2'-dihydrospiro[cyclopropane-1,3'-pyrrolo[2,3-b]pyridine] |
| 314 | 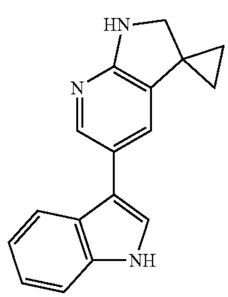 [SMILES: c1ccc2c(-c3cnc4c(c3)C3(CC3)CN4)c[nH]c2c1] | 5'-(1H-Indol-3-yl)-1',2'-dihydrospiro[cyclopropane-1,3'-pyrrolo[2,3-b]pyridine] |
| 315 | 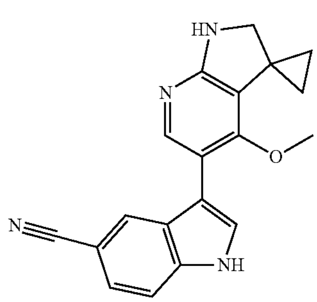 [SMILES: COc1c(-c2c[nH]c3ccc(C#N)cc23)cnc2c1C1(CC1)CN2] | 3-(4'-Methoxy-1',2'-dihydrospiro[cyclopropane-1,3'-pyrrolo[2,3-b]pyridin]-5'-yl)-1H-indole-5-carbonitrile |

TABLE 1-continued

| No. | Structure | Name |
|---|---|---|
| 316 | 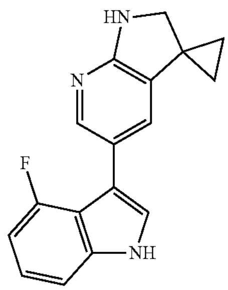 [SMILES: Fc1cccc2[nH]cc(-c3cnc4c(c3)C3(CC3)CN4)c12] | 5'-(4-Fluoro-1H-indol-3-yl)-1',2'-dihydrospiro[cyclopropane-1,3'-pyrrolo[2,3-b]pyridine] |
| 317 | 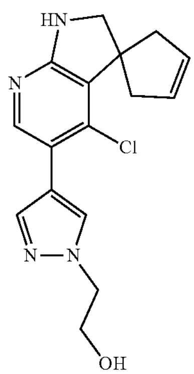 [SMILES: OCCn1cc(-c2cnc3c(c2Cl)C2(CC=CC2)CN3)cn1] | 2-(4-(4'-Chloro-1',2'-dihydrospiro[cyclopentane-1,3'-pyrrolo[2,3-b]pyridin]-3-en-5'-yl)-1H-pyrazol-1-yl)ethan-1-ol |
| 318 | 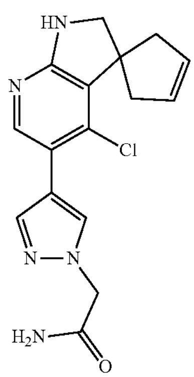 [SMILES: NC(=O)Cn1cc(-c2cnc3c(c2Cl)C2(CC=CC2)CN3)cn1] | 2-(4-(4'-Chloro-1',2'-dihydrospiro[cyclopentane-1,3'-pyrrolo[2,3-b]pyridin]-3-en-5'-yl)-1H-pyrazol-1-yl)acetamide |
| 319 | 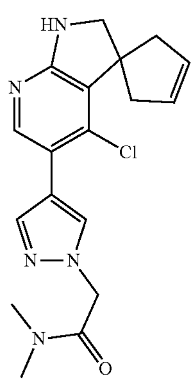 [SMILES: CN(C)C(=O)Cn1cc(-c2cnc3c(c2Cl)C2(CC=CC2)CN3)cn1] | 2-(4-(4'-Chloro-1',2'-dihydrospiro[cyclopentane-1,3'-pyrrolo[2,3-b]pyridin]-3-en-5'-yl)-1H-pyrazol-1-yl)-N,N-dimethylacetamide |

TABLE 1-continued

| No. | Structure | Name |
|---|---|---|
| 320 | 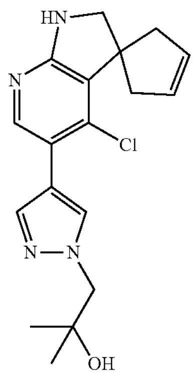 [SMILES: CC(C)(O)Cn1cc(-c2cnc3c(c2Cl)C2(CC=CC2)CN3)cn1] | 1-(4-(4'-Chloro-1',2'-dihydrospiro[cyclopentane-1,3'-pyrrolo[2,3-b]pyridin]-3-en-5'-yl)-1H-pyrazol-1-yl)-2-methylpropan-2-ol |
| 321 | 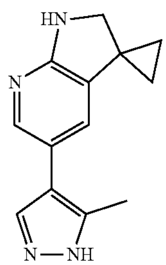 [SMILES: Cc1[nH]ncc1-c1cnc2c(c1)C1(CC1)CN2] | 5'-(5-Methyl-1H-pyrazol-4-yl)-1',2'-dihydrospiro[cyclopropane-1,3'-pyrrolo[2,3-b]pyridine] |
| 322 | 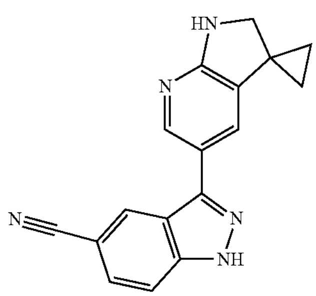 [SMILES: N#Cc1ccc2[nH]nc(-c3cnc4c(c3)C3(CC3)CN4)c2c1] | 3-(1',2'-Dihydrospiro[cyclopropane-1,3'-pyrrolo[2,3-b]pyridin]-5'-yl)-1H-indazole-5-carbonitrile |
| 323 | 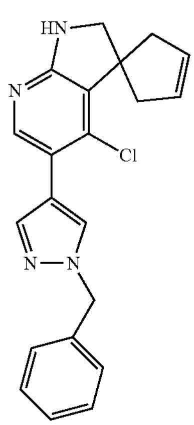 [SMILES: Clc1c(-c2cnn(Cc3ccccc3)c2)cnc2c1C1(CC=CC1)CN2] | 5'-(1-Benzyl-1H-pyrazol-4-yl)-4'-chloro-1',2'-dihydrospiro[cyclopentane-1,3'-pyrrolo[2,3-b]pyridin]-3-ene |

TABLE 1-continued

| No. | Structure | Name |
|---|---|---|
| 324 | 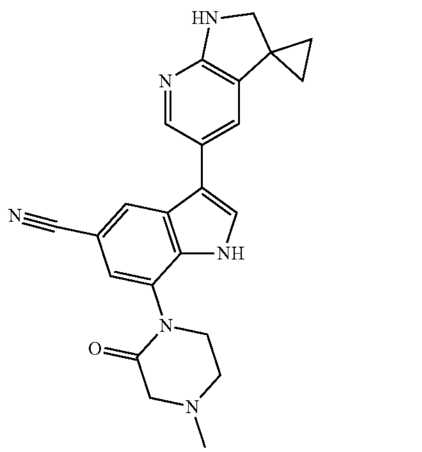 [SMILES: CN1CCN(c2cc(C#N)cc3c(-c4cnc5c(c4)C4(CC4)CN5)c[nH]c23)C(=O)C1] | 3-(1',2'-Dihydrospiro[cyclopropane-1,3'-pyrrolo[2,3-b]pyridin]-5'-yl)-7-(4-methyl-2-oxopiperazin-1-yl)-1H-indole-5-carbonitrile |
| 325 | 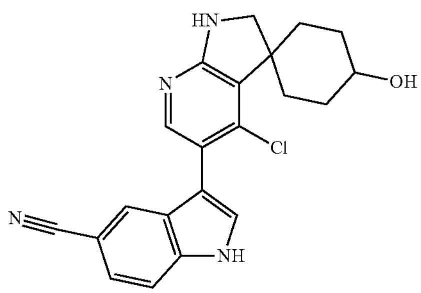 [SMILES: N#Cc1ccc2[nH]cc(-c3cnc4c(c3Cl)C3(CCC(O)CC3)CN4)c2c1] | 3-(4'-Chloro-4-hydroxy-1',2'-dihydrospiro[cyclohexane-1,3'-pyrrolo[2,3-b]pyridin]-5'-yl)-1H-indole-5-carbonitrile |
| 325a | | 3-((1s,4s)-4'-Chloro-4-hydroxy-1',2'-dihydrospiro[cyclohexane-1,3'-pyrrolo[2,3-b]pyridin]-5'-yl)-1H-indole-5-carbonitrile |
| 325b | | 3-((1r,4r)-4'-Chloro-4-hydroxy-1',2'-dihydrospiro[cyclohexane-1,3'-pyrrolo[2,3-b]pyridin]-5'-yl)-1H-indole-5-carbonitrile |
| 326 | 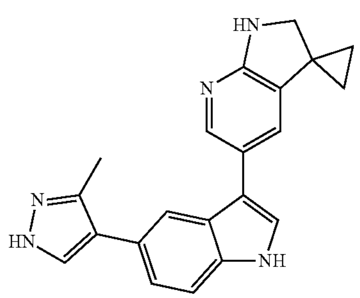 [SMILES: Cc1n[nH]cc1-c1ccc2[nH]cc(-c3cnc4c(c3)C3(CC3)CN4)c2c1] | 5'-(5-(3-Methyl-1H-pyrazol-4-yl)-1H-indol-3-yl)-1',2'-dihydrospiro[cyclopropane-1,3'-pyrrolo[2,3-b]pyridine] |
| 327 | 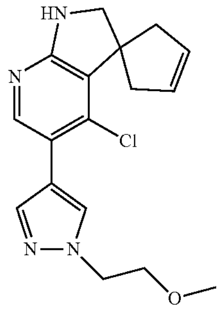 [SMILES: COCCn1cc(-c2cnc3c(c2Cl)C2(CC=CC2)CN3)cn1] | 4'-Chloro-5'-(1-(2-methoxyethyl)-1H-pyrazol-4-yl)-1',2'-dihydrospiro[cyclopentane-1,3'-pyrrolo[2,3-b]pyridin]-3-ene |

TABLE 1-continued

| No. | Structure | Name |
|---|---|---|
| 328 | 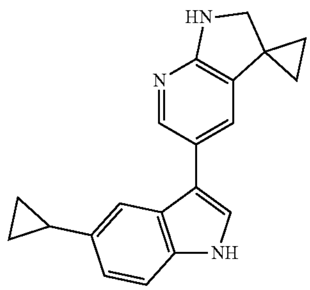 [SMILES: c1nc2c(cc1-c1c[nH]c3ccc(C4CC4)cc13)C1(CC1)CN2] | 5'-(5-Cyclopropyl-1H-indol-3-yl)-1',2'-dihydrospiro[cyclopropane-1,3'-pyrrolo[2,3-b]pyridine] |
| 329 | 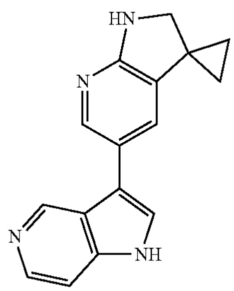 [SMILES: c1cc2[nH]cc(-c3cnc4c(c3)C3(CC3)CN4)c2cn1] | 5-(1H-Pyrrolo[3,2-c]pyridin-3-yl)spiro[1,2-dihydropyrrolo[2,3-b]pyridine-3,1'-cyclopropane] |
| 330 | 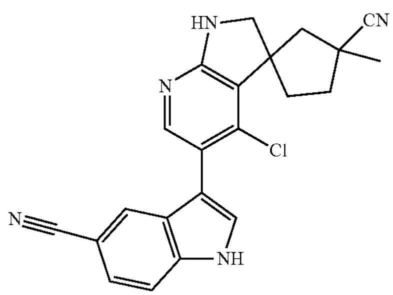 [SMILES: CC1(C#N)CCC2(CNc3ncc(-c4c[nH]c5ccc(C#N)cc45)c(Cl)c32)C1] | 4'-Chloro-5'-(5-cyano-1H-indol-3-yl)-3-methyl-1',2'-dihydrospiro[cyclopentane-1,3'-pyrrolo[2,3-b]pyridine]-3-carbonitrile |
| 330a 330b | | (1R,3S)-4'-Chloro-5'-(5-cyano-1H-indol-3-yl)-3-methyl-1',2'-dihydrospiro[cyclopentane-1,3'-pyrrolo[2,3-b]pyridine]-3-carbonitrile<br>(1S,3R)-4'-Chloro-5'-(5-cyano-1H-indol-3-yl)-3-methyl-1',2'-dihydrospiro[cyclopentane-1,3'-pyrrolo[2,3-b]pyridine]-3-carbonitrile |
| 330c 330d | | (1R,3R)-4'-Chloro-5'-(5-cyano-1H-indol-3-yl)-3-methyl-1',2'-dihydrospiro[cyclopentane-1,3'-pyrrolo[2,3-b]pyridine]-3-carbonitrile<br>(1S,3S)-4'-Chloro-5'-(5-cyano-1H-indol-3-yl)-3-methyl-1',2'-dihydrospiro[cyclopentane-1,3'-pyrrolo[2,3-b]pyridine]-3-carbonitrile |
| 331 | 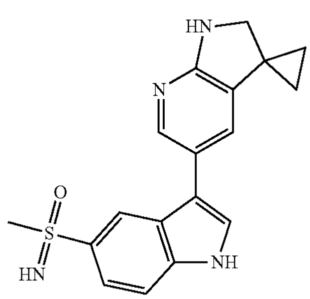 [SMILES: CS(=N)(=O)c1ccc2[nH]cc(-c3cnc4c(c3)C3(CC3)CN4)c2c1] | (3-(1',2'-Dihydrospiro[cyclopropane-1,3'-pyrrolo[2,3-b]pyridin]-5'-yl)-1H-indol-5-yl)(imino)(methyl)-λ6-sulfanone |

TABLE 1-continued

| No. | Structure | Name |
|---|---|---|
| 332 | 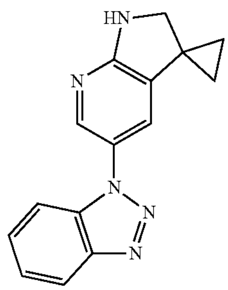 [SMILES: c1ccc2c(c1)nnn2-c1cnc2c(c1)C1(CC1)CN2] | 5-(Benzotriazol-1-yl)spiro[1,2-dihydropyrrolo[2,3-b]pyridine-3,1'-cyclopropane |
| 333 | 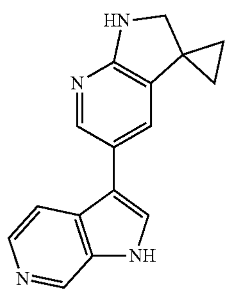 [SMILES: c1cc2c(-c3cnc4c(c3)C3(CC3)CN4)c[nH]c2cn1] | 5-(1H-Pyrrolo[2,3-c]pyridin-3-yl)spiro[1,2-dihydropyrrolo[2,3-b]pyridine-3,1'-cyclopropane] |
| 334 | 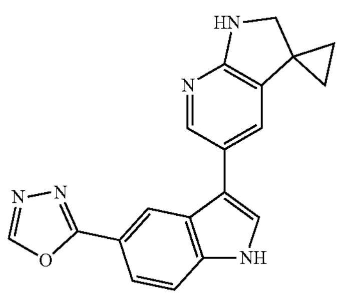 [SMILES: c1nnc(-c2ccc3[nH]cc(-c4cnc5c(c4)C4(CC4)CN5)c3c2)o1] | 2-(3-(1',2'-Dihydrospiro[cyclopropane-1,3'-pyrrolo[2,3-b]pyridin]-5'-yl)-1H-indol-5-yl)-1,3,4-oxadiazole |
| 335 | 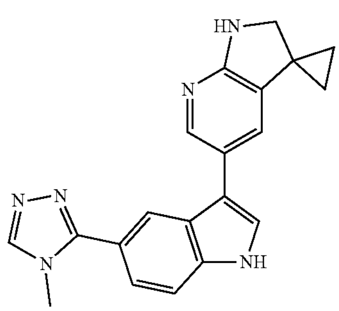 [SMILES: Cn1cnnc1-c1ccc2[nH]cc(-c3cnc4c(c3)C3(CC3)CN4)c2c1] | 5'-(5-(4-Methyl-4H-1,2,4-triazol-3-yl)-1H-indol-3-yl)-1',2'-dihydrospiro[cyclopropane-1,3'-pyrrolo[2,3-b]pyridine] |
| 336 | 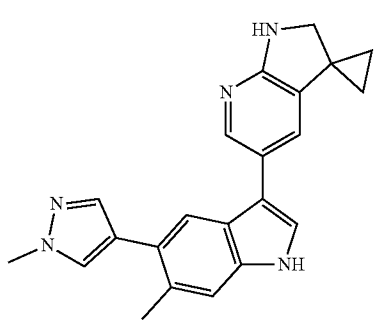 [SMILES: Cc1cc2[nH]cc(-c3cnc4c(c3)C3(CC3)CN4)c2cc1-c1cnn(C)c1] | 5'-(6-Methyl-5-(1-methyl-1H-pyrazol-4-yl)-1H-indol-3-yl)-1',2'-dihydrospiro[cyclopropane-1,3'-pyrrolo[2,3-b]pyridine] |

TABLE 1-continued

| No. | Structure | Name |
|---|---|---|
| 337 | 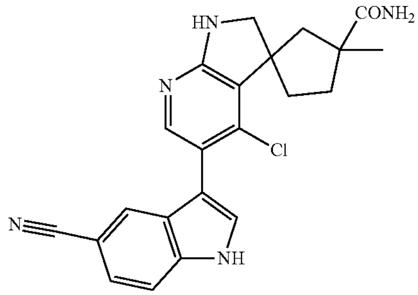 [SMILES: CC1(C(N)=O)CCC2(CNc3ncc(-c4c[nH]c5ccc(C#N)cc45)c(Cl)c32)C1] | 4'-Chloro-5'-(5-cyano-1H-indol-3-yl)-3-methyl-1',2'-dihydrospiro[cyclopentane-1,3'-pyrrolo[2,3-b]pyridine]-3-carboxamide |
| 337a 337b | | (1R,3S)-4'-Chloro-5'-(5-cyano-1H-indol-3-yl)-3-methyl-1',2'-dihydrospiro[cyclopentane-1,3'-pyrrolo[2,3-b]pyridine]-3-carboxamide (1S,3R)-4'-Chloro-5'-(5-cyano-1H-indol-3-yl)-3-methyl-1',2'-dihydrospiro[cyclopentane-1,3'-pyrrolo[2,3-b]pyridine]-3-carboxamide |
| 337c 337d | | (1R,3R)-4'-Chloro-5'-(5-cyano-1H-indol-3-yl)-3-methyl-1',2'-dihydrospiro[cyclopentane-1,3'-pyrrolo[2,3-b]pyridine]-3-carboxamide (1S,3S)-4'-Chloro-5'-(5-cyano-1H-indol-3-yl)-3-methyl-1',2'-dihydrospiro[cyclopentane-1,3'-pyrrolo[2,3-b]pyridine]-3-carboxamide |
| 338 | 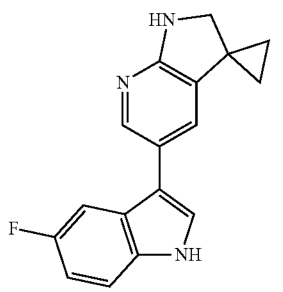 [SMILES: Fc1ccc2[nH]cc(-c3cnc4c(c3)C3(CC3)CN4)c2c1] | 5'-(5-Fluoro-1H-indol-3-yl)-1',2'-dihydrospiro[cyclopropane-1,3'-pyrrolo[2,3-b]pyridine] |
| 339 | 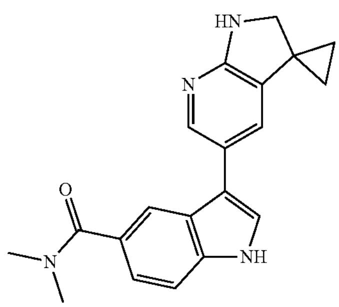 [SMILES: CN(C)C(=O)c1ccc2[nH]cc(-c3cnc4c(c3)C3(CC3)CN4)c2c1] | 3-(1',2'-Dihydrospiro[cyclopropane-1,3'-pyrrolo[2,3-b]pyridin]-5'-yl)-N,N-dimethyl-1H-indole-5-carboxamide |
| 340 | 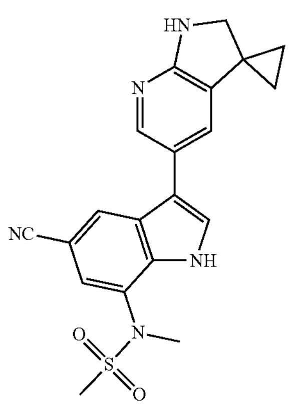 [SMILES: CN(c1cc(C#N)cc2c(-c3cnc4c(c3)C3(CC3)CN4)c[nH]c12)S(C)(=O)=O] | N-(5-Cyano-3-(1',2'-dihydrospiro[cyclopropane-1,3'-pyrrolo[2,3-b]pyridin]-5'-yl)-1H-indol-7-yl)-N-methylmethanesulfonamide |

TABLE 1-continued

| No. | Structure | Name |
| --- | --- | --- |
| 341 | 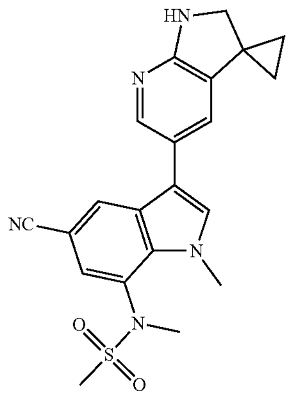 [SMILES: CN(c1cc(C#N)cc2c(-c3cnc4c(c3)C3(CC3)CN4)cn(C)c12)S(C)(=O)=O] | N-(5-Cyano-3-(1',2'-dihydrospiro[cyclopropane-1,3'-pyrrolo[2,3-b]pyridin]-5'-yl)-1-methyl-1H-indol-7-yl)-N-methylmethanesulfonamide |
| 342 | 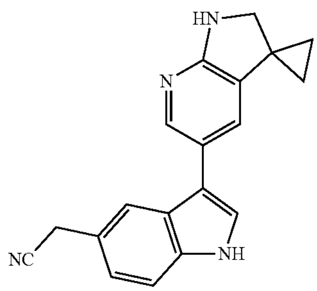 [SMILES: N#CCc1ccc2[nH]cc(-c3cnc4c(c3)C3(CC3)CN4)c2c1] | 2-(3-(1',2'-Dihydrospiro[cyclopropane-1,3'-pyrrolo[2,3-b]pyridin]-5'-yl)-1H-indol-5-yl)acetonitrile |
| 343 | 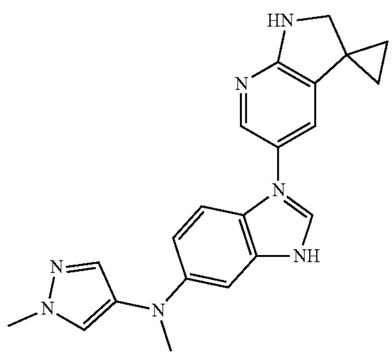 | 3-(1',2'-Dihydrospiro[cyclopropane-1,3'-pyrrolo[2,3-b]pyridin]-5'-yl)-N-methyl-N-(1-methyl-1H-pyrazol-4-yl)-1H-indol-6-amine |
| 344 | 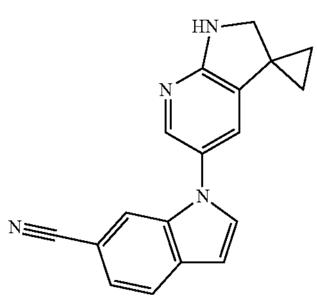 [SMILES: N#Cc1ccc2ccn(-c3cnc4c(c3)C3(CC3)CN4)c2c1] | 1-(1',2'-Dihydrospiro[cyclopropane-1,3'-pyrrolo[2,3-b]pyridin]-5'-yl)-1H-indole-6-carbonitrile |

TABLE 1-continued

| No. | Structure | Name |
|---|---|---|
| 345 | 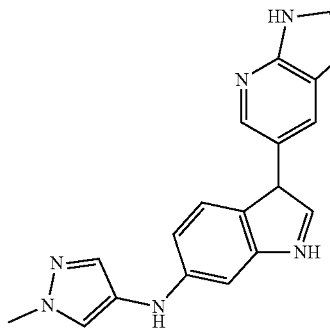 | 3-(1',2'-Dihydrospiro[cyclopropane-1,3'-pyrrolo[2,3-b]pyridin]-5'-yl)-N-(1-methyl-1H-pyrazol-4-yl)-1H-indol-6-amine |

In some embodiments, provided is a compound selected from Compound Nos. 1-345 in Table 1, or a salt (e.g., a pharmaceutically acceptable salt) thereof. In some embodiments, provided is a compound selected from Compound Nos. 1, 2, 3, 4, 5, 6, 7, 8, 9, 10, 11, 12, 13, 14, 15, 16, 17, 17a, 17b, 18, 19, 20, 21, 22, 23, 23a, 23b, 24, 24a, 24b, 25, 25a, 25b, 26, 27, 28, 29, 30, 31, 32, 33, 34, 35, 36, 37, 38, 38a, 38b, 38c, 38d, 39, 39a, 39b, 39c, 39d, 40, 40a, 40b, 41, 42, 43, 44, 45, 46, 47, 48, 49, 50, 51, 52, 53, 54, 55, 56, 57, 58, 59, 60, 61, 61a, 61b, 61c, 61d, 62, 63, 64, 65, 66, 67, 68, 68a, 68b, 68c, 68d, 69, 69a, 69b, 70, 71, 72, 73, 73a, 73b, 74, 75, 76, 77, 77a, 77b, 78, 78a, 78b, 79, 79a, 79b, 80, 80a, 80b, 81, 81a, 81b, 81c, 81d, 82, 82a, 82b, 82c, 82d, 83, 83a, 83b, 83c, 83d, 84, 84a, 84b, 84c, 84d, 85, 85a, 85b, 85c, 85d, 86, 86a, 86b, 86c, 86d, 87, 87a, 87b, 88, 88a, 88b, 89, 89a, 89b, 89c, 89d, 90, 90a, 90b, 90c, 90d, 91, 91a, 91b, 91c, 91d, 92, 92a, 92b, 93, 94, 94a, 94b, 95, 95a, 95b, 96, 96a, 96b, 97, 97a, 97b, 98, 98a, 98b, 98c, 98d, 99, 99a, 99b, 99c, 99d, 100, 100a 100b, 100c 100d, 101, 101a, 101b, 102, 102a, 102b, 103, 104, 104a, 104b, 104c, 104d, 105, 105a, 105b, 105c, 105d, 106, 106a, 106b, 106c, 106d, 107, 107a, 107b, 107c, 107d, 108, 108a, 108b, 108c, 108d, 109, 109a, 109b, 109c, 109d, 110, 110a, 110b, 110c, 110d, 111, 111a, 111b, 112, 112a, 112b, 113, 113a, 113b, 114, 114a, 114b, 114c, 114d, 115, 115a, 115b, 115c, 115d, 116, 116a, 116b, 116c, 116d, 117, 117a, 117b, 117c, 117d, 118, 118a, 118b, 118c, 118d, 119, 119a, 119b, 119c, 119d, 120, 120a, 120b, 120c, 120d, 121, 121a, 121b, 121c, 121d, 122, 122a, 122b, 123, 123a, 123b, 124, 124a, 124b, 124c, 124d, 125, 125a, 125b, 125c, 125d, 126, 126a, 126b, 126c, 126d, 127, 127a, 127b, 127c, 127d, 128, 128a, 128b, 129, 129a, 129b, 129c, 129d, 130, 130a, 130b, 130c, 130d, 131, 131a, 131b, 131c, 131d, 132, 132a, 132b, 132c, 132d, 133, 133a, 133b, 133c, 133d, 134, 134a, 134b, 134c, 134d, 135, 135a, 135b, 135c, 135d, 136, 137, 138, 139, 140, 140a, 140b, 140c, 140d, 140e, 140f, 140g, 140 h, 141, 142, 143, 143a, 143b, 143c, 143d, 144, 144a, 144b, 145, 145a, 145b, 145c, 145d, 146, 146a, 146b, 146c, 146d, 146e, 146f, 146g, 146 h, 147, 148, 148a, 148b, 149, 150, 150a, 150b, 150c, 150d, 151, 151a, 151b, 151c, 151d, 152, 152a, 152b, 152c, 152d, 153, 153a, 153b, 153c, 153d, 154, 154a, 154b, 155, 155a, 155b, 155c, 155d, 156, 156a, 156b, 156c, 156d, 157, 157a, 157b, 157c, 157d, 158, 158a, 158b, 158c, 158d, 159, 159a, 159b, 159c, 159d, 160, 160a, 160b, 160c, 160d, 161, 161a, 161b, 161c, 161d, 162, 162a, 162b, 162c, 162d, 163, 163a, 163b, 163c, 163d, 164, 164a, 164b, 165, 165a, 165b, 166, 167, 167a, 167b, 167c, 167d, 168, 168a, 168b, 168c, 168d, 169, 169a, 169b, 169c, 169d, 170, 170a, 170b, 170c, 170d, 171, 171a, 171b, 171c, 171d, 172, 173, 173a, 173b, 173c, 173d, 174, 174a, 174b, 175, 175a, 175b, 176, 177, 177a, 177b, 177c, 177d, 178, 178a, 178b, 178c, 178d, 179, 179a, 179b, 179c, 179d, 180, 180a, 180b, 180c, 180d, 181, 182, 183, 184, 185, 186, 187, 188, 189, 190, 191, 191a, 191b, 192, 193, 193a, 193b, 193c, 193d, 194, 194a, 194b, 195, 195a, 195b, 195c, 195d, 196, 196a, 196b, 196c, 196d, 197, 197a, 197b, 197c, 197d, 198, 198a, 198b, 198c, 198d, 199, 199a, 199b, 199c, 199d, 200, 201, 201a, 201b, 201c, 201d, 202, 202a, 202b, 202c, 202d, 203, 204, 205, 206, 207, 208, 209, 210, 211, 212, 213, 214, 215, 216, 217, 217a, 217b, 217c, 217d, 218, 219, 220, 221, 222, 223, 224, 225, 226, 227, 228, 228a, 228b, 228c, 228d, 229, 229a, 229b, 230, 231, 232, 233, 234, 234a, 234b, 234c, 234d, 235, 235a, 235b, 236, 237, 238, 239, 239a, 239b, 240, 240a, 240b, 241, 241a, 241b, 242, 243, 243a, 243b, 243c, 243d, 244, 244a, 244b, 245, 245a, 245b, 245c, 245d, 246, 246a, 246b, 246c, 246d, 247, 248, 248a, 248b, 249, 250, 250a, 250b, 251, 252, 253, 253a, 253b, 253c, 253d, 254, 254a, 254b, 254c, 254d, 255, 255a, 255b, 256, 256a, 256b, 257, 258, 258a, 258b, 259, 259a, 259b, 259c, 259d, 260, 261, 261a, 261b, 261c, 261d, 262, 263, 264, 264a, 264b, 265, 266, 266a, 266b, 266c, 266d, 267, 267a, 267b, 267c, 267d, 268, 269, 270, 271, 271a, 271b, 271c, 271d, 272, 272a, 272b, 272c, 272d, 273, 273a, 273b, 274, 274a, 274b, 274c, 274d, 275, 275a, 275b, 275c, 275d, 276, 277, 278, 278a, 278b, 279, 279a, 279b, 280, 280a, 280b, 281, 281a, 281b, 282, 282a, 282b, 283, 283a, 283b, 284, 285, 286, 287, 288, 288a, 288b, 288c, 288d, 289, 290, 290a, 290b, 291, 292, 293, 294, 295, 296, 297, 298, 299, 300, 300a, 300b, 300c, 300d, 301, 302, 303, 304, 304a, 304b, 304c, 304d, 305, 305a, 305b, 305c, 305d, 306, 306a, 306b, 306c, 306d, 307, 308, 309, 310, 311, 312, 313, 314, 315, 316, 317, 318, 319, 320, 321, 322, 323, 324, 325, 325a, 325b, 326, 327, 328, 329, 330, 330a, 330b, 330c, 330d, 331, 332, 333, 334, 335, 336, 337, 337a, 337b, 337c, 337d, 338, 339, 340, 341, 342, 343, 344, and 345 in Table 1, or a salt (e.g., a pharmaceutically acceptable salt) thereof. In some embodiments, provided is a compound selected from Compound Nos. 1, 2, 3, 4, 5, 6, 7, 8, 9, 10, 11, 12, 13, 14, 15, 16, 17, 17a, 17b, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, and 345 in Table 1, or a salt (e.g., a pharmaceutically acceptable salt) thereof. In some embodiments, provided is a compound selected from Compound Nos. 23a, 23b, 24a, 24b, 25a, 25b, 38a, 38b, 38c, 38d, 39a, 39b, 39c, 39d, 40a, 40b, 61a, 61b, 61c, 61d, 68a, 68b, 68c, 68d, 69a, 69b, 73a, 73b, 77a, 77b, 78a, 78b, 79a, 79b, 80a, 80b, 81a, 81b, 81c, 81d, 82a, 82b, 82c, 82d, 83a, 83b, 83c, 83d, 84a, 84b, 84c, 84d, 85a, 85b, 85c, 85d, 86a, 86b, 86c, 86d, 87a, 87b, 88a, 88b, 89a, 89b, 89c, 89d, 90a, 90b, 90c, 90d, 91a, 91b, 91c, 91d, 92a, 92b, 94a, 94b, 95a, 95b, 96a, 96b, 97a, 97b, 98a, 98b, 98c, 98d, 99a, 99b, 99c, 99d, 100a 100b, 100c 100d, 101a, 101b, 102a, 102b, 104a, 104b, 104c, 104d, 105a, 105b, 105c, 105d, 106a, 106b, 106c, 106d, 107a, 107b, 107c, 107d, 108a, 108b, 108c, 108d, 109a, 109b, 109c, 109d, 110a, 110b, 110c, 110d, 111a, 111b, 112a, 112b, 113a, 113b, 114a, 114b, 114c, 114d, 115a, 115b, 115c, 115d, 116a, 116b, 116c, 116d, 117a, 117b, 117c, 117d, 118a, 118b, 118c, 118d, 119a, 119b, 119c, 119d, 120a, 120b, 120c, 120d, 121a, 121b, 121c, 121d, 122a, 122b, 123a, 123b, 124a, 124b, 124c, 124d, 125a, 125b, 125c, 125d, 126a, 126b, 126c, 126d, 127a, 127b, 127c, 127d, 128a, 128b, 129a, 129b, 129c, 129d, 130a, 130b, 130c, 130d, 131a, 131b, 131c, 131d, 132a, 132b, 132c, 132d, 133a, 133b, 133c, 133d, 134a, 134b, 134c, 134d, 135a, 135b, 135c, 135d, 140a, 140b, 140c, 140d, 140e, 140f, 140g, 140 h, 143a, 143b, 143c, 143d, 144a, 144b, 145a, 145b, 145c, 145d, 146a, 146b, 146c, 146d, 146e, 146f, 146g, 146 h, 148a, 148b, 150a, 150b, 150c, 150d, 151a, 151b, 151c, 151d, 152a, 152b, 152c, 152d, 153a, 153b, 153c, 153d, 154a, 154b, 155a, 155b, 155c, 155d, 156a, 156b, 156c, 156d, 157a, 157b, 157c, 157d, 158a, 158b, 158c, 158d, 159a, 159b, 159c, 159d, 160a, 160b, 160c, 160d, 161a, 161b, 161c, 161d, 162a, 162b, 162c, 162d, 163a, 163b, 163c, 163d, 164a, 164b, 165a, 165b, 167a, 167b, 167c, 167d, 168a, 168b, 168c, 168d, 169a, 169b, 169c, 169d, 170a, 170b, 170c, 170d, 171a, 171b, 171c, 171d, 173a, 173b, 173c, 173d, 174a, 174b, 175a, 175b, 177a, 177b, 177c, 177d, 178a, 178b, 178c, 178d, 179a, 179b, 179c, 179d, 180a, 180b, 180c, 180d, 191a, 191b, 193a, 193b, 193c, 193d, 194a, 194b, 195a, 195b, 195c, 195d, 196a, 196b, 196c, 196d, 197a, 197b, 197c, 197d, 198a, 198b, 198c, 198d, 199a, 199b, 199c, 199d, 201a, 201b, 201c, 201d, 202a, 202b, 202c, 202d, 217a, 217b, 217c, 217d, 228a, 228b, 228c, 228d, 229a, 229b, 234a, 234b, 234c, 234d, 235a, 235b, 239a, 239b, 240a, 240b, 241a, 241b, 243a, 243b, 243c, 243d, 244a, 244b, 245a, 245b, 245c, 245d, 246a, 246b, 246c, 246d, 248a, 248b, 250a, 250b, 253a, 253b, 253c, 253d, 254a, 254b, 254c, 254d, 255a, 255b, 256a, 256b, 258a, 258b, 259a, 259b, 259c, 259d, 261a, 261b, 261c, 261d, 264a, 264b, 266a, 266b, 266c, 266d, 267a, 267b, 267c, 267d, 271a, 271b, 271c, 271d, 272a, 272b, 272c, 272d, 273a, 273b, 274a, 274b, 274c, 274d, 275a, 275b, 275c, 275d, 278a, 278b, 279a, 279b, 280a, 280b, 281a, 281b, 282a, 282b, 283a, 283b, 288a, 288b, 288c, 288d, 290a, 290b, 300a, 300b, 300c, 300d, 304a, 304b, 304c, 304d, 305a, 305b, 305c, 305d, 306a, 306b, 306c, 306d, 325a, 325b, 330a, 330b, 330c, 330d, 337a, 337b, 337c, and 337d in Table 1, or a salt (e.g., a pharmaceutically acceptable salt) thereof.

Compounds of Formula (I) described herein or a salt thereof may exist in stereoisomeric forms (e.g., it contains one or more asymmetric carbon atoms). The individual stereoisomers (enantiomers and diastereomers) and mixtures of these are included within the scope of the subject matter disclosed herein. Likewise, it is understood that a compound or salt of Formulas (I) may exist in tautomeric forms other than that shown in the formula and these are also included within the scope of the subject matter disclosed herein. It is to be understood that the subject matter disclosed herein includes combinations and subsets of the particular groups described herein. The scope of the subject matter disclosed herein includes mixtures of stereoisomers as well as purified enantiomers or enantiomerically/diastereomerically enriched mixtures. It is to be understood that the subject matter disclosed herein includes combinations and subsets of the particular groups defined herein.

The subject matter disclosed herein also includes isotopically-labelled forms of the compounds described herein, but for the fact that one or more atoms are replaced by an atom having an atomic mass or mass number different from the atomic mass or mass number usually found in nature. Examples of isotopes that can be incorporated into compounds described herein and pharmaceutically acceptable salts thereof include isotopes of hydrogen, carbon, nitrogen, oxygen, phosphorous, sulphur, fluorine, iodine, and chlorine, such as $^{2}H$, $^{3}H$, $^{11}C$, $^{13}C$, $^{14}C$, $^{15}N$, $^{17}O$, $^{18}O$, $^{31}P$, $^{32}P$, $^{35}S$, $^{18}F$, $^{36}Cl$, $^{123}I$ and $^{125}I$.

The subject matter disclosed herein includes prodrugs, metabolites, derivatives, and pharmaceutically acceptable salts of compounds of Formula (I). Metabolites of the compounds of Formula (I) include compounds produced by a process comprising contacting a compound of Formula (I) with a mammal for a period of time sufficient to yield a metabolic product thereof.

If the compound of Formula (I) is a base, the desired pharmaceutically acceptable salt may be prepared by any suitable method available in the art, for example, treatment of the free base with an inorganic acid, such as hydrochloric acid, hydrobromic acid, sulfuric acid, nitric acid, methanesulfonic acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

If the compound of Formula (I) is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include, but are not limited to, organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

A compound of Formula (I) can be in the form of a "prodrug," which includes compounds with moieties which can be metabolized in vivo. Generally, the prodrugs are metabolized in vivo by esterases or by other mechanisms to active drugs. Examples of prodrugs and their uses are well known in the art (See, e.g., Berge et al. (1977) "Pharmaceutical Salts", J. Pharm. Sci. 66:1-19). The prodrugs can be prepared in situ during the final isolation and purification of the compounds, or by separately reacting the purified compound in its free acid form or hydroxyl with a suitable esterifying agent. Hydroxyl groups can be converted into esters via treatment with a carboxylic acid. Examples of prodrug moieties include substituted and unsubstituted, branch or unbranched lower alkyl ester moieties, (e.g., propionoic acid esters), lower alkenyl esters, di-lower alkylamino lower-alkyl esters (e.g., dimethylaminoethyl ester), acylamino lower alkyl esters (e.g., acetyloxymethyl ester), acyloxy lower alkyl esters (e.g., pivaloyloxymethyl ester), aryl esters (phenyl ester), aryl-lower alkyl esters (e.g., benzyl ester), substituted (e.g., with methyl, halo, or methoxy substituents) aryl and aryl-lower alkyl esters, amides, lower-alkyl amides, di-lower alkyl amides, and hydroxy amides. Prodrugs which are converted to active forms through other mechanisms in vivo are also included. In aspects, the compounds of the invention are prodrugs of any of the formulae herein.

Compounds of Formula (I) can be prepared by procedures described in the general synthetic methods, and Examples as described herein, as well as methods known in the art.

Pharmaceutical Compositions and Formulations

The presently disclosed compounds can be formulated into pharmaceutical compositions along with a pharmaceutically acceptable carrier or excipient.

Compounds of Formula (I), or variations thereof such as Formula (IA), (IB) and (IC), can be formulated in accordance with standard pharmaceutical practice as a pharmaceutical composition. According to this aspect, there is provided a pharmaceutical composition comprising a compound of Formula (I), or variations thereof such as Formula (IA), (IB) and (IC), in association with a pharmaceutically acceptable excipient, diluent or carrier.

A typical formulation is prepared by mixing a compound of Formula (I), or variations thereof such as Formula (IA), (IB) and (IC), and a carrier, diluent or excipient. Suitable carriers, diluents and excipients are well known to those skilled in the art and include materials such as carbohydrates, waxes, water soluble and/or swellable polymers, hydrophilic or hydrophobic materials, gelatin, oils, solvents, water and the like. The particular carrier, diluent or excipient used will depend upon the means and purpose for which the compound of Formula (I), or variations thereof such as Formula (IA), (IB) and (IC), is being applied. Solvents are generally selected based on solvents recognized by persons skilled in the art as safe (GRAS) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG 400, PEG 300), etc. and mixtures thereof. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound of Formula (I), or variations thereof such as Formula (IA), (IB) and (IC), or pharmaceutical composition thereof) or aid in the manufacturing of the pharmaceutical product (i.e., medicament).

The formulations may be prepared using conventional dissolution and mixing procedures. For example, the bulk drug substance (i.e., compound of Formula (I), or variations thereof such as Formula (IA), (IB) and (IC), or stabilized form of the Compound of Formula (I), or variations thereof such as Formula (IA), (IB) and (IC), (e.g., complex with a cyclodextrin derivative or other known complexation agent) is dissolved in a suitable solvent in the presence of one or more of the excipients described above. The compound of Formula (I) is typically formulated into pharmaceutical dosage forms to provide an easily controllable dosage of the drug and to enable patient compliance with the prescribed regimen.

The pharmaceutical composition (or formulation) for application may be packaged in a variety of ways depending upon the method used for administering the drug. Generally, an article for distribution includes a container having deposited therein the pharmaceutical formulation in an appropriate form. Suitable containers are well known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

Pharmaceutical formulations may be prepared for various routes and types of administration. For example, a compound of Formula (I) having the desired degree of purity may optionally be mixed with pharmaceutically acceptable diluents, carriers, excipients or stabilizers (Remington's Pharmaceutical Sciences (1980) $16^{th}$ edition, Osol, A. Ed.), in the form of a lyophilized formulation, milled powder, or an aqueous solution. Formulation may be conducted by mixing at ambient temperature at the appropriate pH, and at the desired degree of purity, with physiologically acceptable excipients or carriers, i.e., excipients or carriers that are non-toxic to recipients at the dosages and concentrations employed. The pH of the formulation depends mainly on the particular use and the concentration of compound, but may range from about 3 to about 8. Formulation in an acetate buffer at pH 5 is a suitable embodiment.

The compounds of Formula (I) can be sterile. In particular, formulations to be used for in vivo administration should be sterile. Such sterilization is readily accomplished by filtration through sterile filtration membranes.

The compound ordinarily can be stored as a solid composition, a lyophilized formulation or as an aqueous solution.

The pharmaceutical compositions comprising a compound of Formula (I) can be formulated, dosed and administered in a fashion, i.e., amounts, concentrations, schedules, course, vehicles and route of administration, consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "therapeutically effective amount" of the compound to be administered will be governed by such considerations, and is the minimum amount necessary to prevent, ameliorate, or treat the coagulation factor mediated disorder. In some embodiments, the amount is below the amount that is toxic to the host or renders the host more susceptible to bleeding.

Acceptable diluents, carriers, excipients and stabilizers are nontoxic to recipients at the dosages and concentrations employed, and include buffers such as phosphate, citrate and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). The active pharmaceutical ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16$^{th}$ edition, Osol, A. Ed. (1980).

Sustained-release preparations of Formula (I) compounds may be prepared. Suitable examples of sustained-release preparations include semipermeable matrices of solid hydrophobic polymers containing a compound of Formula (I) or Ia, which matrices are in the form of shaped articles, e.g., films, or microcapsules. Examples of sustained-release matrices include polyesters, hydrogels (for example, poly (2-hydroxyethyl-methacrylate), or poly(vinyl alcohol)), polylactides (U.S. Pat. No. 3,773,919), copolymers of L-glutamic acid and gamma-ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate) and poly-D-(−)-3-hydroxybutyric acid.

The formulations include those suitable for the administration routes detailed herein. The formulations may conveniently be presented in unit dosage form and may be prepared by any of the methods well known in the art of pharmacy. Techniques and formulations generally are found in *Remington's Pharmaceutical Sciences* (Mack Publishing Co., Easton, PA). Such methods include the step of bringing into association the active ingredient with the excipient or carrier which constitutes one or more accessory ingredients. In general the formulations are prepared by uniformly and intimately bringing into association the active ingredient with liquid excipients or carriers or finely divided solid excipients or carriers or both, and then, if necessary, shaping the product.

Formulations of a compound of Formula (I) suitable for oral administration may be prepared as discrete units such as pills, capsules, cachets or tablets each containing a predetermined amount of a compound of Formula (I) or Ia.

Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered active ingredient moistened with an inert liquid diluent. The tablets may optionally be coated or scored and optionally are formulated so as to provide slow or controlled release of the active ingredient therefrom.

Tablets, troches, lozenges, aqueous or oil suspensions, dispersible powders or granules, emulsions, hard or soft capsules, e.g., gelatin capsules, syrups or elixirs may be prepared for oral use. Formulations of compounds of Formula (I) intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

For treatment of the eye or other external tissues, e.g., mouth and skin, the formulations are preferably applied as a topical ointment or cream containing the active ingredient (s) in an amount of, for example, 0.075 to 20% w/w. When formulated in an ointment, the active ingredients may be employed with either a paraffinic or a water-miscible ointment base. Alternatively, the active ingredients may be formulated in a cream with an oil-in-water cream base.

If desired, the aqueous phase of the cream base may include a polyhydric alcohol, i.e., an alcohol having two or more hydroxyl groups such as propylene glycol, butane 1,3-diol, mannitol, sorbitol, glycerol and polyethylene glycol (including PEG 400), and mixtures thereof. The topical formulations may desirably include a compound which enhances absorption or penetration of the active ingredient through the skin or other affected areas. Examples of such dermal penetration enhancers include dimethyl sulfoxide and related analogs.

The oily phase of the emulsions may be constituted from known ingredients in a known manner. While the phase may comprise solely an emulsifier, it may also comprise a mixture of at least one emulsifier and a fat or oil, or both a fat and an oil. A hydrophilic emulsifier included together with a lipophilic emulsifier may act as a stabilizer. Together, the emulsifier(s) with or without stabilizer(s) make up the so-called emulsifying wax, and the wax together with the oil and fat make up the so-called emulsifying ointment base which forms the oily dispersed phase of the cream formulations. Emulsifiers and emulsion stabilizers suitable for use in the formulation include Tween® 60, Span® 80, cetostearyl alcohol, benzyl alcohol, myristyl alcohol, glyceryl mono-stearate and sodium lauryl sulfate.

Aqueous suspensions of Formula (I) compounds contain the active materials in admixture with excipients suitable for the manufacture of aqueous suspensions. Such excipients include a suspending agent, such as sodium carboxymethylcellulose, croscarmellose, povidone, methylcellulose, hydroxypropyl methylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxybenzoate, one or more coloring agents, one or more flavoring agents and one or more sweetening agents, such as sucrose or saccharin.

The pharmaceutical compositions of compounds of Formula (I), or variations thereof such as Formula (IA), (IB) and (IC), may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such 1,3-butanediol. The sterile injectable preparation may also be prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the excipient or carrier material to produce a single dosage form will vary depending upon the host treated and the particular mode of administration. For example, a time-release formulation intended for oral administration to humans may contain approximately 1 to 1000 mg of active material compounded with an appropriate and convenient amount of excipient or carrier material which may vary from about 5 to about 95% of the total compositions (weight:weight). The pharmaceutical composition can be prepared to provide easily measurable amounts for administration. For example, an aqueous solution intended for intravenous infusion may contain from about 3 to 500 µg of the active ingredient per milliliter of solution in order that infusion of a suitable volume at a rate of about 30 mL/hr can occur.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

Formulations suitable for topical administration to the eye also include eye drops wherein the active ingredient is dissolved or suspended in a suitable excipient or carrier, especially an aqueous solvent for the active ingredient. The active ingredient is preferably present in such formulations in a concentration of about 0.5 to 20% w/w, for example about 0.5 to 10% w/w, for example about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid excipient or carrier.

Formulations for rectal administration may be presented as a suppository with a suitable base comprising for example cocoa butter or a salicylate.

Formulations suitable for intrapulmonary or nasal administration have a particle size for example in the range of 0.1 to 500 microns (including particle sizes in a range between 0.1 and 500 microns in increments microns such as 0.5, 1, 30 microns, 35 microns, etc.), which is administered by rapid inhalation through the nasal passage or by inhalation through the mouth so as to reach the alveolar sacs. Suitable formulations include aqueous or oily solutions of the active ingredient. Formulations suitable for aerosol or dry powder administration may be prepared according to conventional methods and may be delivered with other therapeutic agents such as compounds heretofore used in the treatment or prophylaxis of disorders as described below.

Formulations suitable for vaginal administration may be presented as pessaries, tampons, creams, gels, pastes, foams or spray formulations containing in addition to the active ingredient such excipients or carriers as are known in the art to be appropriate.

The formulations may be packaged in unit-dose or multi-dose containers, for example sealed ampoules and vials, and may be stored in a freeze-dried (lyophilized) condition requiring only the addition of the sterile liquid excipient or carrier, for example water, for injection immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

The subject matter further provides veterinary compositions comprising at least one active ingredient as above defined together with a veterinary excipient or carrier therefore. Veterinary excipients or carriers are materials useful for the purpose of administering the composition and may be solid, liquid or gaseous materials which are otherwise inert or acceptable in the veterinary art and are compatible with the active ingredient. These veterinary compositions may be administered parenterally, orally or by any other desired route.

In particular embodiments the pharmaceutical composition comprising the presently disclosed compounds further comprise a chemotherapeutic agent. In some of these embodiments, the chemotherapeutic agent is an immunotherapeutic agent.

Methods of Use

The presently disclosed compounds find use in inhibiting the activity of the enzyme HPK1. HPK1, also referred to as mitogen activated protein kinase kinase kinase kinase 1 or MAP4K1, is a member of the germinal center kinase subfamily of Ste20-related serine/threnonine kinases. HPK1 functions as a MAP4K by phosphorylating and activating MAP3K proteins, including MEKK1, MLK3 and TAK1, leading to the activation of the MAPK Jnk.

In an embodiment, the subject matter disclosed herein is directed to a method of inhibiting HPK1, the method comprising contacting HPK1 with an effective amount of a compound of Formula (I), or variations thereof such as Formula (IA), (IB) and (IC), or a pharmaceutical composition described herein.

In an embodiment, the subject matter disclosed herein is directed to a method for enhancing an immune response in a subject in need thereof, wherein the method comprises administering to said subject an effective amount of a compound of Formula (I), or variations thereof such as Formula (IA), (IB) and (IC), or a pharmaceutical composition described herein. In certain aspects of this embodiment, the T cells in the subject have at least one of enhanced priming, enhanced activation, enhanced migration, enhanced proliferation, enhanced survival, and enhanced cytolytic activity relative to prior to the administration of the compound or pharmaceutical composition. In certain aspects of this embodiment, the T cell activation is characterized by an elevated frequency of γ-IFN+ CD8 T cells, an elevated frequency of γ-IFN+ CD4 T cells, or enhanced levels of IL-2 or granzyme B production by T cells, relative to prior to administration of the compound or pharmaceutical composition. In certain aspects of this embodiment, the number of T cells is elevated relative to prior to administration of the compound or pharmaceutical composition. In certain aspects of this embodiment, the T cell is an antigen-specific CD8 T cell. In certain aspects of this embodiment, the T cell is an antigen-specific CD4 T cell. In certain aspects of this embodiment, the antigen presenting cells in the subject have enhanced maturation and activation relative prior to the administration of the compound or pharmaceutical composition. In certain aspects of this embodiment, the antigen presenting cells are dendritic cells. In certain aspects of this embodiment, the maturation of the antigen presenting cells is characterized by increased frequency of CD83+ dendritic cells. In certain aspects of this embodiment, the activation of the antigen presenting cells is characterized by elevated expression of CD80 and CD86 on dendritic cells. In some aspects, compounds of Formula (I), or variations thereof such as Formula (IA), (IB) and (IC), or a pharmaceutical composition thereof provides general priming of the immune response (i.e., vaccines) to tumors or viruses for boosting/generating anti-viral/tumor immunity.

In the methods described herein, a compound of Formula (I), or variations thereof such as Formula (IA), (IB) and (IC), or a pharmaceutical composition thereof is administered to a subject that has cancer as described elsewhere herein.

In an embodiment, the subject matter disclosed herein is directed to a method for treating a HPK1-dependent disorder, the method comprising administering to a subject in need thereof an effective amount of a compound of Formula (I), or variations thereof such as Formula (IA), (IB) and (IC), or a pharmaceutical composition described herein. In certain aspects of this embodiment, the HPK1-dependent disorder is a cancer. In certain aspects of this embodiment, the cancer comprises at least one cancer selected from the group consisting of colorectal cancer, melanoma, non-small cell lung cancer, ovarian cancer, breast cancer, pancreatic cancer, a hematological malignancy, and a renal cell carcinoma. In certain aspects of this embodiment, the cancer has elevated levels of T-cell infiltration. In certain aspects of this embodiment, the cancer cells in the subject selectively have elevated expression of MHC class I antigen expression relative to prior to the administration of the compound or composition.

In the methods described herein, the method can further comprise administering a chemotherapeutic agent to said subject. In certain aspects of this embodiment, the chemotherapeutic agent is administered to the subject simultaneously with the compound or the composition. In certain aspects of this embodiment, the chemotherapeutic agent is administered to the subject prior to administration of the compound or the composition. In certain aspects of this embodiment, the chemotherapeutic agent is administered to the subject after administration of the compound or said composition.

HPK1 polynucleotides and polypeptides are known in the art (Hu et al. (1996) *Genes Dev.* 10: 2251-2264, which is herein incorporated by reference in its entirety). Certain HPK1 polynucleotides and polypeptides comprise the human HPK1 polynucleotide are accessible and the sequences are known, for example, nucleotides 141-2642 of GenBank Accession No. NM_007181.5 and the encoded human HPK1 polypeptide (Accession No. NP_009112.1); and nucleotides 141-2606 of GenBank Accession No. NM_001042600.2 and the encoded human HPK1 polypeptide (Accession No. NP_001036065.1).

HPK1 polypeptides comprise a variety of conserved structural motifs. HPK1 polypeptides comprise an amino-terminal Ste20-like kinase domain, which includes the ATP-binding site. The kinase domain is followed by four proline-rich (PR) motifs that serve as binding sites for SH3-containing proteins, such as CrkL, Grb2, HIP-55, Gads, Nck, and Crk. HPK1 becomes phosphorylated and activated in response to TCR or BCR stimulation. TCR- and BCR-induced phosphorylation of a tyrosine residue located between PR1 and PR2, mediates binding to SLP-76 in T cells or BLNK in B cells via a SLP-76 or BLNK SH2 domain, and is required for activation of the kinase. A citron homology domain found in the C-terminus of HPK1 may act as a regulatory domain and may be involved in macromolecular interactions.

The presently disclosed compounds bind directly to HPK1 and inhibit its kinase activity. In some embodiments, the presently disclosed compounds reduce, inhibit, or otherwise diminish the HPK1-mediated phosphorylation of SLP76 and/or Gads.

The presently disclosed compounds may or may not be a specific HPK1 antagonist. A specific HPK1 antagonist reduces the biological activity of HPK1 by an amount that is statistically greater than the inhibitory effect of the antagonist on any other protein (e.g., other serine/threonine kinases). In certain embodiments, the presently disclosed compounds specifically inhibit the serine/threonine kinase activity of HPK1. In some of these embodiments, the $IC_{50}$ of the HPK1 antagonist for HPK1 is about 90%, 80%, 70%, 60%, 50%, 40%, 30%, 20%, 10%, 0.1%, 0.01%, 0.001%, or less of the $IC_{50}$ of the HPK1 antagonist for another serine/threonine kinase or other type of kinase (e.g., tyrosine kinase).

The presently disclosed compounds can be used in a method for inhibiting HPK1. Such methods comprise contacting HPK1 with an effective amount of a presently disclosed compound. By "contact" is intended bringing the compound within close enough proximity to an isolated HPK1 enzyme or a cell expressing HPK1 (e.g., T cell, B cell, dendritic cell) such that the compound is able to bind to and inhibit the activity of HPK1. The compound can be contacted with HPK1 in vitro or in vivo via administration of the compound to a subject.

Any method known in the art to measure the kinase activity of HPK1 may be used to determine if HPK1 has been inhibited, including in vitro kinase assays, immunoblots with antibodies specific for phosphorylated targets of HPK1, such as SLP76 and Gads, or the measurement of a downstream biological effect of HPK1 kinase activity, such as the recruitment of 14-3-3 proteins to phosphorylated SLP7 and Gads, release of the SLP76-Gads-14-3-3 complex from LAT-containing microclusters, or T or B cell activation.

The presently disclosed compounds can be used to treat a HPK1-dependent disorder. As used herein, a "HPK1-dependent disorder" is a pathological condition in which HPK1 activity is necessary for the genesis or maintenance of the pathological condition. In some embodiments, the HPK1-dependent disorder is cancer.

The presently disclosed compounds also find use in enhancing an immune response in a subject in need thereof. Such methods comprise administering an effective amount of a presently disclosed compound (i.e., compound of Formula (I), or variations thereof such as Formula (IA), (IB) and (IC), or a pharmaceutically acceptable salt, prodrug, metabolite, or derivative thereof).

As used herein, "enhancing an immune response" refers to an improvement in any immunogenic response to an antigen. Non-limiting examples of improvements in an immunogenic response to an antigen include enhanced maturation or migration of dendritic cells, enhanced activation of T cells (e.g., CD4 T cells, CD8 T cells), enhanced T cell (e.g., CD4 T cell, CD8 T cell) proliferation, enhanced B cell proliferation, increased survival of T cells and/or B cells, improved antigen presentation by antigen presenting cells (e.g., dendritic cells), improved antigen clearance, increase in production of cytokines by T cells (e.g., interleukin-2), increased resistance to prostaglandin E2-induced immune suppression, and enhanced priming and/or cytolytic activity of CD8 T cells.

In some embodiments, the CD8 T cells in the subject have enhanced priming, activation, proliferation and/or cytolytic activity relative to prior to the administration of the compound of Formula (I), or variations thereof such as Formula (IA), (IB) and (IC), or a pharmaceutically acceptable salt, prodrug, metabolite, or derivative thereof. In some embodiments, the CD8 T cell priming is characterized by elevated CD44 expression and/or enhanced cytolytic activity in CD8 T cells. In some embodiments, the CD8 T cell activation is characterized by an elevated frequency of γ-IFN$^+$ CD8 T cells. In some embodiments, the CD8 T cell is an antigen-specific T-cell.

In some embodiments, the CD4 T cells in the subject have enhanced priming, activation, proliferation and/or cytolytic activity relative to prior to the administration of the compound of Formula (I), or variations thereof such as Formula (IA), (IB) and (IC), or a pharmaceutically acceptable salt, prodrug, metabolite, or derivative thereof. In some embodiments, the CD4 T cell priming is characterized by elevated CD44 expression and/or enhanced cytolytic activity in CD4 T cells. In some embodiments, the CD4 T cell activation is characterized by an elevated frequency of γ-IFN$^+$ CD4 T cells. In some embodiments, the CD4 T cell is an antigen-specific T-cell.

In some embodiments, the antigen presenting cells in the subject have enhanced maturation and activation relative to prior to the administration of the compound of Formula (I), or variations thereof such as Formula (IA), (IB) and (IC), or a pharmaceutically acceptable salt, prodrug, metabolite, or derivative thereof. In some embodiments, the antigen presenting cells are dendritic cells. In some embodiments, the maturation of the antigen presenting cells is characterized by an increased frequency of CD83$^+$ dendritic cells. In some embodiments, the activation of the antigen presenting cells is characterized by elevated expression of CD80 and CD86 on dendritic cells.

In some embodiments, the serum levels of cytokine IL-10 and/or chemokine IL-8, a human homolog of murine KC, in the subject are reduced relative to prior to the administration of the compound of Formula (I), or variations thereof such as Formula (IA), (IB) and (IC), or a pharmaceutically acceptable salt, prodrug, metabolite, or derivative thereof.

Engagement of the TCR leads to HPK1 activation, which functions as a negative regulator of TCR-induced AP-1 response pathway. It is believed that HPK1 negatively regulates T cell activation by reducing the persistence of signaling microclusters by phosphorylating SLP76 at Ser376 (Di Bartolo et al. (2007) *JEM* 204:681-691) and Gads at Thr254, which leads to the recruitment of 14-3-3 proteins that bind to the phosphorylated SLP76 and Gads, releasing the SLP76-Gads-14-3-3 complex from LAT-containing microclusters, which leads to T cell dysfunction, including anergy and exhaustion (Lasserre et al. (2011) *J Cell Biol* 195(5):839-853).

The term "dysfunction" in the context of immune dysfunction, refers to a state of reduced immune responsiveness to antigenic stimulation. The term includes the common elements of both exhaustion and/or anergy in which antigen recognition may occur, but the ensuing immune response is ineffective to control infection or tumor growthours.

The term "dysfunctional", as used herein, also includes refractory or unresponsive to antigen recognition, specifically, impaired capacity to translate antigen recognition into downstream T-cell effector functions, such as proliferation, cytokine production (e.g., IL-2, γ-IFN) and/or target cell killing.

The term "anergy" refers to the state of unresponsiveness to antigen stimulation resulting from incomplete or insufficient signals delivered through the T-cell receptor (e.g. increase in intracellular Ca$^{+2}$ in the absence of ras-activation). T cell anergy can also result upon stimulation with antigen in the absence of co-stimulation, resulting in the cell becoming refractory to subsequent activation by the antigen even in the context of costimulation. The unresponsive state can often be overriden by the presence of Interleukin-2. Anergic T-cells do not undergo clonal expansion and/or acquire effector functions.

The term "exhaustion" refers to T cell exhaustion as a state of T cell dysfunction that arises from sustained TCR signaling that occurs during many chronic infections and cancer. It is distinguished from anergy in that it arises not through incomplete or deficient signaling, but from sustained signaling. It is defined by poor effector function, sustained expression of inhibitory receptors and a transcriptional state distinct from that of functional effector or memory T cells. Exhaustion prevents optimal control of infection and tumors. Exhaustion can result from both extrinsic negative regulatory pathways (e.g., immunoregulatory cytokines) as well as cell intrinsic negative regulatory (costimulatory) pathways (PD-1, B7-H3, B7-H4, etc.).

In some embodiments, administration of a compound of Formula (I), or variations thereof such as Formula (IA), (IB) and (IC), or a pharmaceutically acceptable salt, prodrug, metabolite, or derivative thereof to a subject results in an enhancement of T cell function. In some embodiments, administration of HPK1 inhibitors described herein may enhance/renew/reactivate immune response or activate de nove immune response.

"Enhancing T cell function" means to induce, cause or stimulate a T cell to have a sustained or amplified biological function, or renew or reactivate exhausted or inactive T cells. Examples of enhancing T cell function include: increased secretion of cytokines (e.g., γ-interferon, IL-2, IL-12, and TNFα), increased proliferation, increased antigen responsiveness (e.g., viral, pathogen, or tumor clearance) relative to such levels before the intervention, and increased effector granule production by CD8 T cells or CD4 T cells, such as granzyme B. In one embodiment, the level of enhancement is as least 50%, alternatively 60%, 70%, 80%, 90%, 100%, 120%, 150%, 200%. The manner of measuring this enhancement is known to one of ordinary skill in the art.

Accordingly, the presently disclosed compounds of Formula (I), or variations thereof such as Formula (IA), (IB) and (IC), or pharmaceutically acceptable salts, prodrugs, metabolites, or derivatives thereof are useful in treating T cell dysfunctional disorders. A "T cell dysfunctional disorder" is a disorder or condition of T cells characterized by decreased responsiveness to antigenic stimulation. In a particular embodiment, a T cell dysfunctional disorder is a disorder that is specifically associated with increased kinase activity of HPK1. In another embodiment, a T cell dysfunctional disorder is one in which T cells are anergic or have decreased ability to secrete cytokines, proliferate, or execute cytolytic activity. In a specific aspect, the decreased responsiveness results in ineffective control of a pathogen or tumor expressing an immunogen. Examples of T cell dysfunctional disorders characterized by T-cell dysfunction include unresolved acute infection, chronic infection and tumor immunity.

Thus, the presently disclosed compounds can be used in treating conditions where enhanced immunogenicity is desired, such as increasing tumor immunogenicity for the treatment of cancer.

"Immunogenecity" refers to the ability of a particular substance to provoke an immune response. Tumors are immunogenic and enhancing tumor immunogenicity aids in the clearance of the tumor cells by the immune response. Viruses may also be immunogenic and enhancing/activating immunogenicity may aid in clearance of viral particles by the immune response.

"Tumor immunity" refers to the process in which tumors evade immune recognition and clearance. Thus, as a therapeutic concept, tumor immunity is "treated" when such evasion is attenuated, and the tumors are recognized and attacked by the immune system. Examples of tumor recognition include tumor binding, tumor shrinkage and tumor clearance.

In one aspect, provided herein is a method for treating of cancer in a subject in need thereof comprising administering to the subject an effective amount of a compound of Formula (I), or variations thereof such as Formula (IA), (IB) and (IC), or a pharmaceutically acceptable salt, prodrug, metabolite, or derivative thereof. In some embodiments, the subject has melanoma. The melanoma may be at early stage or at late stage. In some embodiments, the subject has colorectal cancer. The colorectal cancer may be at early stage or at late stage. In some embodiments, the subject has non-small cell lung cancer. The non-small cell lung cancer may be at early stage or at late stage. In some embodiments, the subject has pancreatic cancer. The pancreatic cancer may be at early stage or late state. In some embodiments, the subject has a hematological malignancy. The hematological malignancy may be at early stage or late stage. In some embodiments, the subject has ovarian cancer. The ovarian cancer may be at early stage or at late stage. In some embodiments, the subject has breast cancer. The breast cancer may be at early stage or at late stage. In some embodiments, the subject has renal cell carcinoma. The renal cell carcinoma may be at early stage or at late stage. In some embodiments, the cancer has elevated levels of T-cell infiltration.

In one aspect, provided is a method for treating viral infection in a subject in need thereof comprising administering to the subject an effective amount of a compound of Formula (I), or variations thereof such as Formula (IA), (IB) and (IC), or a pharmaceutically acceptable salt, prodrug, metabolite, or derivative thereof. In one aspect, provided is a method for enhacing or boosting response to a vaccine (such as a cancer vaccine or a personalized cancer vaccine (PCV)) or a CAR-T cell therapy in a subject in need thereof comprising administering to the subject an effective amount of a compound of Formula (I), or variations thereof such as Formula (IA), (IB) and (IC), or a pharmaceutically acceptable salt, prodrug, metabolite, or derivative thereof.

The presently disclosed compounds may be administered in any suitable manner known in the art. In some embodiments, the compound of Formula (I), or variations thereof such as Formula (IA), (IB) and (IC), or a pharmaceutically acceptable salt, prodrug, metabolite, or derivative thereof is administered intravenously, intramuscularly, subcutaneously, topically, orally, transdermally, intraperitoneally, intraorbitally, by implantation, by inhalation, intrathecally, intraventricularly, intratumorally, or intranasally.

In some embodiments, the HPK1 antagonist is administered continuously. In other embodiments, the HPK1 antagonist is administered intermittently. Moreover, treatment of a subject with an effective amount of a HPK1 antagonist can include a single treatment or can include a series of treatments.

It is understood that appropriate doses of the active compound depends upon a number of factors within the knowledge of the ordinarily skilled physician or veterinarian. The dose(s) of the active compound will vary, for example, depending upon the age, body weight, general health, gender, and diet of the subject, the time of administration, the route of administration, the rate of excretion, and any drug combination.

It will also be appreciated that the effective dosage of a compound of Formula (I), or variations thereof such as Formula (IA), (IB) and (IC), or a pharmaceutically acceptable salt, prodrug, metabolite, or derivative thereof used for treatment may increase or decrease over the course of a particular treatment. Changes in dosage may result and become apparent from the results of diagnostic assays.

In some embodiments, the HPK1 antagonist is administered to the subject at a dose of between about 0.001 µg/kg and about 1000 mg/kg, including but not limited to about 0.001 µg/kg, about 0.01 µg/kg, about 0.05 µg/kg, about 0.1 µg/kg, about 0.5 µg/kg, about 1 µg/kg, about 10 µg/kg, about 25 µg/kg, about 50 µg/kg, about 100 µg/kg, about 250 µg/kg, about 500 µg/kg, about 1 mg/kg, about 5 mg/kg, about 10 mg/kg, about 25 mg/kg, about 50 mg/kg, about 100 mg/kg, and about 200 mg/kg.

In some embodiments, provided is a method for treating a cancer in a subject in need thereof comprising administering to the subject an effective amount of a compound of Formula (I), or variations thereof such as Formula (IA), (IB) and (IC), or a pharmaceutically acceptable salt, prodrug, metabolite, or derivative thereof, further comprising administering an additional therapy. The additional therapy may be radiation therapy, surgery (e.g., lumpectomy and a mastectomy), chemotherapy, gene therapy, DNA therapy, viral therapy, RNA therapy, immunotherapy, bone marrow transplantation, nanotherapy, monoclonal antibody therapy, or a combination of the foregoing. The additional therapy may be in the form of adjuvant or neoadjuvant therapy. In some embodiments, the additional therapy is the administration of an anti-metastatic agent. In some embodiments, the additional therapy is the administration of side-effect limiting agents (e.g., agents intended to lessen the occurrence and/or severity of side effects of treatment, such as anti-nausea agents, etc.). In some embodiments, the additional therapy is radiation therapy. In some embodiments, the additional therapy is surgery. In some embodiments, the additional therapy is a combination of radiation therapy and surgery. In some embodiments, the additional therapy is gamma irradiation. In some embodiments, the additional therapy is therapy targeting the PI3K/AKT/mTOR pathway, HSP90 inhibitor, tubulin inhibitor, apoptosis inhibitor, and/or chemopreventative agent.

The additional therapy may be one or more of a chemotherapeutic agent. Thus, the method of treating cancer can comprise administering the presently disclosed HPK1 antagonists in conjunction with at least one chemotherapeutic agent.

As used herein, "in conjunction with" refers to administration of one treatment modality in addition to another treatment modality. As such, "in conjunction with" refers to administration of one treatment modality before, during, or after administration of the other treatment modality to the subject.

For example, the HPK1 antagonist and chemotherapeutic agent may be administered sequentially (at different times) or concurrently (at the same time). The HPK1 antagonist and chemotherapeutic agent may be administered by the same route of administration or by different routes of administration.

In certain embodiments, the HPK1 antagonist is administered in conjunction with another immunotherapy. For example, the HPK1 antagonist can be combined with a chemotherapeutic agent or biologic that targets the PD-L1/PD-1 pathway. A known inhibitory checkpoint pathway involves signaling through PD-1 receptors. The programmed-death 1 (PD-1) receptor and its ligands PD-L1 and PD-L2 are part of the same family of coregulatory molecules as CTLA-4. —See more at: http://www.onclive.com/web-exclusives/the-role-of-anti-pd-11-immunotherapy-in-cancer/2#sthash.cGfYa1T1.dpuf. Chemotherapeutic agents or biologics that block PD-L1 binding to PD-1 and CD80 can prevent PD-L1-mediated inhibition/suppression of T-cell activation. Programmed cell death ligand-1 (PD-L1) is widely expressed on antigen-presenting cells (APC) and other immune cells. It is upregulated on tumor cells from a broad range of human cancers, and has been implicated with inhibition of antitumor T-cell immunity. PD-L1 is a cell surface protein that binds to the receptors PD-1 and CD80 on activated T cells, B cells, and other myeloid cells. PD-L1 binding to PD-1 on activated T-cells has been found to interfere with T-cell proliferation and inhibit immune responses. Overexpression of PD-L1 on cancer cells may allow these cells to avoid immune detection and elimination. High levels of PD-L1 expression on tumor cells have been associated with increased tumor aggressiveness and a poor prognosis. Chemotherapeutic agents or biologics that block PD-L1 binding to PD-1 include anti-PD-L1 antibodies, such as durvalumab, nivolumab, pidlizumab, MPDL3280A, MK-3475 and BMS-936559, among others. In some embodiments, the HPK1 antagonist is administered in conjunction with a PD-1 antagonist such as an anti-PD-1 antibody, a PD-L1 antagonist such as an anti-PD-L1 antibody, and/or a PD-L2 antagonist such as an anti-PD-L2 antibody. Examples of anti-PD-L1 antibodies include but are not limited to avelumab, atezolizumab (also known as MPDL3280A), pembrolizumab (also known as MK-3475), LY3300054 (Eli Lilly), STI-A1014 (Sorrento), KN035 (Suzhou Alphamab) and BMS-936559 (Bristol Myers Squibb). Examples of anti-PD-1 antibodies include but are not limited to nivolumab, pidlizumab, PDR001 (Novartis), REGN2810 (Regeneron), BGB-108 (BeiGene), BGB-A317 (BeiGene), JS-001 (Shanghai Junshi), STI-A1110 (Sorrento), INCSHR-1210 (Incyte), PF-06801591 (Pfizer), TSR-042 (also known as ANB011; Tesaro/AnaptysBio), AM0001 (ARMO Biosciences), and ENUM 244C8 (Enumeral Biomedical Holdings).

In another example, the HPK1 antagonist can be combined with a chemotherapeutic agent or biologic that targets OX40 and its ligand, OX40L, are members of the TNF superfamily. OX40 is expressed on activated CD4(+) and CD8(+) T cells as well as on a number of other lymphoid and non-lymphoid cells. Costimulatory signals from OX40 to a conventional T cell promote division and survival, augmenting the clonal expansion of effector and memory populations as they are being generated to antigen. OX40 additionally suppresses the differentiation and activity of T-regulatory cells, further amplifying this process. OX40 and OX40L also regulate cytokine production from T cells, antigen-presenting cells, natural killer cells, and natural killer T cells, and modulate cytokine receptor signaling. As one of the most prominent costimulatory molecules known to control T cells, stimulating OX40 has been shown be a target for therapeutic immunization strategies for cancer. Certain OX40 agonists include GBR 830, and those disclosed in Linch, et al., Frontiers in Oncology, v. 5, pp. 1-10 (2015), herein incorporated by reference in its entirety.

In other examples, the HPK1 antagonist can be combined with a chemotherapeutic agent or biologic that targets a CD28, OX40, GITR, CD137, CD27, CD40, ICOS, HVEM, NKG2D, MICA, 2B4, IL-2, IL-12, IFNγ, IFNα, TNFα, IL-1, CDN, HMGB1, TLR, PD-L1 axis, CTLA-4, TIM-3, BTLA, VISTA, LAG-3, B7H4, CD96, CD226, prostaglandin, VEGF, endothelin B, IDO, arginase, MICA/MICB, TIM-3, IL-10, IL-4, IL-13, TIGIT or TGFβ. In other examples, the HPK1 antagonist can be combined with an immunotherapy comprising a PD-L1 axis, CTLA-4, TIM-3, BTLA, VISTA, LAG-3, B7H4, CD96, TIGIT, CD226, prostaglandin, VEGF, endothelin B, IDO, arginase, MICA/MICB, TIM-3, IL-10, IL-4, or IL-13 antagonis. In other examples, the HPK1 antagonist can be combined with an immunotherapy comprising a CD28, OX40, GITR, CD137, CD27, CD40, ICOS, HVEM, NKG2D, MICA, 2B4, IL-2, IL-12, IFNγ, IFNα, TNFα, IL-1, CDN, HMGB1, or TLR agonist.

In another example, the HPK1 antagonist can be combined with a PCV. In another example, the HPK1 antagonist can be combined with an adoptive T cell therapy.

Provided is a method of inhibiting HPK1, said method comprising contacting HPK1 in a subject with an effective amount of a compound Formula (I), or variations thereof such as Formula (IA), (IB) and (IC), or a pharmaceutically acceptable salt thereof or a pharmaceutical composition comprising a compound Formula (I), or variations thereof such as Formula (IA), (IB) and (IC), or a pharmaceutically acceptable salt thereof.

A method for enhancing an immune response in a subject in need thereof, wherein the method comprises administering to said subject an effective amount of a compound Formula (I), or variations thereof such as Formula (IA), (IB) and (IC), or a pharmaceutically acceptable salt thereof or a pharmaceutical composition comprising a compound Formula (I), or variations thereof such as Formula (IA), (IB) and (IC), or a pharmaceutically acceptable salt thereof.

In some embodiments, said subject has cancer.

Also provided is a method for treating a HPK1-dependent disorder, said method comprising administering to a subject in need thereof an effective amount of a compound Formula (I), or variations thereof such as Formula (IA), (IB) and (IC), or a pharmaceutically acceptable salt thereof or a pharmaceutical composition comprising a compound Formula (I), or variations thereof such as Formula (IA), (IB) and (IC), or a pharmaceutically acceptable salt thereof.

In some embodiments, said HPK1-dependent disorder is a cancer.

In some embodiments, wherein the cancer comprises at least one cancer selected from the group consisting of colorectal cancer, melanoma, non-small cell lung cancer, ovarian cancer, breast cancer, pancreatic cancer, a hematological malignancy, and a renal cell carcinoma.

In some embodiments, said method further comprises administering a chemotherapeutic agent to said subject.

In some embodiments, the invention also provides compounds of Formula (I), or variations thereof such as Formula (IA), (IB) and (IC), described herein or pharmaceutical compositions described herein for use in a method for inhibiting HPK1 as described herein, in a method for enhancing an immune response in a subject in need thereof as described herein and/or in a method for treating a HPK1-dependent disorder as described herein.

In some embodiments, the invention also provides compounds of Formula (I), or variations thereof such as Formula (IA), (IB) and (IC), described herein or pharmaceutical compositions described herein for use in a method for inhibiting HPK1 as described herein.

In some embodiments, the invention also provides compounds of Formula (I), or variations thereof such as Formula (IA), (IB) and (IC), described herein or pharmaceutical compositions described herein for use in a method for enhancing an immune response in a subject in need thereof as described herein.

In some embodiments, the invention also provides compounds of Formula (I), or variations thereof such as Formula (IA), (IB) and (IC), described herein or pharmaceutical compositions described herein for use in a method for treating a HPK1-dependent disorder as described herein.

In some embodiments, the invention also provides the use of a compound of Formula (I), or variations thereof such as Formula (IA), (IB) and (IC), described herein or a pharmaceutical composition described herein for the manufacture of a medicament for inhibiting HPK1, a medicament for enhancing an immune response in a subject in need thereof and/or a medicament for treating a HPK1-dependent disorder.

In some embodiments, the invention also provides the use of a compound of Formula (I), or variations thereof such as Formula (IA), (IB) and (IC), described herein or a pharmaceutical composition described herein for the manufacture of a medicament for inhibiting HPK1.

In some embodiments, the invention also provides the use of a compound of Formula (I), or variations thereof such as Formula (IA), (IB) and (IC), described herein or a pharmaceutical composition described herein for the manufacture of a medicament for enhancing an immune response in a subject in need thereof.

In some embodiments, the invention also provides the use of a compound of Formula (I), or variations thereof such as Formula (IA), (IB) and (IC), described herein or a pharmaceutical composition described herein for the manufacture of a medicament treating a HPK1-dependent disorder.

In some embodiments, the invention also provides the use of compounds of Formula (I), or variations thereof such as Formula (IA), (IB) and (IC), described herein or pharmaceutical compositions described herein in a method for inhibiting HPK1 as described herein, in a method for enhancing an immune response in a subject in need thereof as described herein and/or in a method for treating a HPK1-dependent disorder as described herein.

In some embodiments, the invention also provides the use of compounds of Formula (I), or variations thereof such as Formula (IA), (IB) and (IC), described herein or pharmaceutical compositions described herein in a method for inhibiting HPK1 as described herein.

In some embodiments, the invention also provides the use of compounds of Formula (I), or variations thereof such as Formula (IA), (IB) and (IC), described herein or pharmaceutical compositions described herein in a method for enhancing an immune response in a subject in need thereof as described herein.

In some embodiments, the invention also provides the use of compounds of Formula (I), or variations thereof such as Formula (IA), (IB) and (IC), described herein or pharmaceutical compositions described herein in a method for treating a HPK1-dependent disorder as described herein.

In some embodiments, the treatment results in a sustained response in the subject after cessation of the treatment. "Sustained response" refers to the sustained effect on reducing tumor growth after cessation of a treatment. For example, the tumor size may remain the same or smaller as compared to the size at the beginning of the administration phase. In some embodiments, the sustained response has a duration at least the same as the treatment duration, at least 1.5×, 2.0×, 2.5×, or 3.0× length of the treatment duration.

The treatment methods disclosed herein may result in a partial or complete response. As used herein, "complete response" or "CR" refers to disappearance of all target lesions; "partial response" or "PR" refers to at least a 30% decrease in the sum of the longest diameters (SLD) of target lesions, taking as reference the baseline SLD; and "stable disease" or "SD" refers to neither sufficient shrinkage of target lesions to qualify for PR, nor sufficient increase to qualify for PD, taking as reference the smallest SLD since the treatment started. As used herein, "overall response rate" (ORR) refers to the sum of complete response (CR) rate and partial response (PR) rate.

The treatment methods disclosed herein can lead to an increase in progression free survival and overall survival of the subject administered the HPK1 antagonist. As used herein, "progression free survival" (PFS) refers to the length of time during and after treatment during which the disease being treated (e.g., cancer) does not get worse. Progression-free survival may include the amount of time patients have experienced a complete response or a partial response, as well as the amount of time patients have experienced stable disease.

As used herein, "overall survival" refers to the percentage of subjects in a group who are likely to be alive after a particular duration of time.

In some embodiments, the subject that is administered a HPK1 antagonist is a mammal, such as domesticated animals (e.g., cows, sheep, cats, dogs, and horses), primates (e.g., humans and non-human primates such as monkeys), rabbits, and rodents (e.g., mice and rats). In some embodiments, the subject treated is a human.

The subject in need of treatment for cancer may be a person demonstrating symptoms of cancer, one that has been diagnosed with cancer, a subject that is in remission from cancer, or a subject having an increased risk for developing cancer (e.g., a genetic predisposition, certain dietary or environmental exposures).

In any of the described methods, in one aspect the subject is a human, such as a human in need of the method. The subject may be a human who has been diagnosed with or is suspected of having an HPK1-dependent disorder such as cancer. The individual may be a human who does not have detectable disease but who has one or more risk factors for developing a cancer.

Further provided are kits for carrying out the methods detailed herein, which comprises one or more compounds described herein or a pharmaceutical composition comprising a compound described herein. The kits may employ any of the compounds disclosed herein. In one variation, the kit employs a compound described herein or a pharmaceutically acceptable salt thereof. The kits may be used for any one or more of the uses described herein, and, accordingly, may contain instructions for use in the treatment of an HPK1-dependent disorder such as cancer. In some embodiments, the kit contains instructions for use in the treatment of a cancer.

Kits generally comprise suitable packaging. The kits may comprise one or more containers comprising any compound described herein. Each component (if there is more than one component) can be packaged in separate containers or some components can be combined in one container where cross-reactivity and shelf life permit. One or more components of a kit may be sterile and/or may be contained within sterile packaging.

The kits may be in unit dosage forms, bulk packages (e.g., multi-dose packages) or sub-unit doses. For example, kits may be provided that contain sufficient dosages of a compound as disclosed herein (e.g., a therapeutically effective amount) and/or a second pharmaceutically active compound useful for an HPK1-dependent disorder (e.g., cancer) to provide effective treatment of an individual for an extended period, such as any of a week, 2 weeks, 3 weeks, 4 weeks, 6 weeks, 8 weeks, 3 months, 4 months, 5 months, 7 months, 8 months, 9 months, or more. Kits may also include multiple unit doses of the compounds and instructions for use and be packaged in quantities sufficient for storage and use in pharmacies (e.g., hospital pharmacies and compounding pharmacies).

The kits may optionally include a set of instructions, generally written instructions, although electronic storage media (e.g., magnetic diskette or optical disk) containing instructions are also acceptable, relating to the use of component(s) of the methods of the present invention. The instructions included with the kit generally include information as to the components and their administration to a subject.

The following examples are offered by way of illustration and not by way of limitation.

EXAMPLES

Abbreviations

| | |
|---|---|
| aq. | aqueous |
| n-BuLi | n-butyllithium solution |
| DCE | 1,2-dichloroethane |
| DCM | dichloromethane |
| DIBAL | diisobutylaluminum hydride |
| DIPEA | diisopropylethylamine |
| DMA | dimethylacetamide |
| DME | 1,2-dimethoxyethane |
| DMF | N,N-dimethylformamide |
| DMSO | dimethylsulfoxide |
| DMSO-$d_6$ | deuterated dimethylsulfoxide |
| EDCI•HCl | N-(3-dimethylaminopropyl)-N'-ethylcarbodiimide hydrochloride |
| ESI | electrospray ionization |
| EtOAc | ethyl acetate |
| Et$_2$O | diethyl ether |
| h | hours |
| HATU | O-(7-azabenzotriazol-1-yl)-N,N,N',N'-tetramethyluronium hexafluorophosphate |
| HCl | hydrochloric acid |
| HOBT | 1-hydroxybenzotriazole |
| IMS | industrial methylated spirits |
| LCMS | liquid chromatography-mass spectrometry |
| NaOH | sodium hydroxide |
| NMR | nuclear magnetic resonance |
| MeCN | acetonitrile |
| MeOH | methanol |
| MeOH•NH$_3$ | 2N methanolic ammonia |
| mg | milligram |
| mmol | millimole |
| MgSO$_4$ | magnesium sulfate |
| min | minutes |
| mL | millilitre |
| NaOH | sodium hydroxide |
| NBS | N-bromosuccinimide |
| NH$_3$ | ammonia |
| RT: | room temperature |
| R$_T$: | retention time |
| sat.: | saturated |
| SCX-2 | ISOLUTE ® Si-Propylsulfonic acid |
| SFC | supercritical fluid chromatography |
| TBAF | tetrabutylammonium fluoride |
| TFA | Trifluoroacetic acid |
| TMEDA | N,N,N',N'-tetramethylethylenediamine |
| THF | tetrahydrofuran |
| X-Phos | 2-Dicyclohexylphosphino-2',4',6'-triisopropylbiphenyl |
| X-Phos Pd G2 | Chloro(2-dicyclohexylphosphino-2',4',6'-triisopropyl-1,1'-biphenyl)[2-(2'-amino-1,1'-biphenyl)]palladium(II) |

General Chiral Purification Protocol

Compounds were purified using Supercritical Fluid Chromatography (SFC) used either Waters Thar Prep100 preparative SFC system or Waters Thar Investigator semi preparative system.

The compounds were purified using an appropriate column (from YMC Amylose-C, YMC Cellulose-C, YMC Cellulose-SC, Phenomenex LUX Cellulose-3 & Phenomenex LUX Cellulose-40.

Appropriate isocratic methods were selected based on methanol, ethanol or isopropanol solvent systems under un-modified or basic conditions. The standard method used was modifier/CO$_2$, 100 ml/min (or as appropriate), 120 Bar back pressure, 40° C. column temperature. The modifier used under basic conditions was diethyl amine (0.1% v/v).

Collected fractions were analysed by SFC (Waters/Thar SFC systems with Waters SQD or Waters UPCC with Waters QDa). The fractions that contained the desired product were concentrated by vacuum centrifugation.

All samples were pre-purified by achiral systems and purity checked before SFC chiral purification.

General Chromatrography and Anggalyncal Methods

Description of LCMS Methods referenced in the Tables and Experimental sections:

Method A: Experiments were performed on an Acquity UPLC (binary pump/PDA detector)+ZQ Mass Spectrometer using a reverse phase column (Acquity UPLC BEH C18 1.7 μm, 100×2.1 mm, column maintained at 40° C.). Detection UV, diode array 200-500 nm. Elution with solvent A: water+0.05% trifluoroacetic acid; solvent B: acetonitrile+0.05% trifluoroacetic acid. Gradient: 5%-95% B over 6.8 min Method B: Experiments were performed on an Acquity i-Class (quartemary pump/PDA detector)+Quattro Micro Mass Spectrometer using a reverse phase column (Acquity UPLC BEH C$_{18}$ 1.7 μm, 100×2.1 mm, column maintained at 40° C.). Detection UV, diode array 200-500 nm. Elution with solvent A: water+0.1% formic acid; solvent B: acetonitrile+0.1% formic acid. Gradient: 5%-95% B over 6.8 min Method C: Experiments were performed on an Agilent Technologies 1260 Infinity purification system and Agilent 6120 series Single Quadrupole Mass Spectrometer using a reverse phase column (XBridge Prep C18 Sum OBD, 19×250 mm, column at RT). Detection UV, diode array 200-500 nm. Elution with solvent A: 0.1% aqueous ammonia; solvent B: 0.1% ammonia in acetonitrile. Gradient: 10%-95% B over 22 min.

Method D: Experiments were performed on an Agilent Technologies 1260 Infinity purification system and Agilent 6120 series Single Quadrupole Mass Spectrometer using a reverse phase column (XSelect Prep C18 Sum OBD, 19×250 mm, column at RT). Detection UV, diode array 200-500 nm. Elution with solvent A: 0.1% formic acid in water; solvent B: 0.1% 0.1% formic acid in acetonitrile. Gradient: 10%-95% B over 22 min.

Synthetic Examples

The following are procedures to prepare the intermediates used to prepare the compounds described in the General Methods and in the Tables. Where the absolute stereo configuration (R)— or (S)— of a chiral center in a compound is undetermined or arbitrarily assigned, the stereo congaration in the name of the compound may be designated as (RS)— or (SR)—. In a compound where two chiral centers are present, the relative stereochemistry may be designated by the name although the absolute stereo configuration of each chiral center is undetermined or arbitrarily assigned. For example, where the compound name contains a (1RS,3RS)-designation, the compound may be (1R,3R)— and/or (1S,3S)—; where the compound name contains a (1RS,3SR)-designation, the compound may be (1R,3S)— and/or (1S,3R)—.

Example 1

5-Bromo-4-chloro-1-((2-(trimethylsilyl)ethoxy)methyl)-1,3-dihydro-2H-pyrrolo[2,3-b]pyridin-2-one

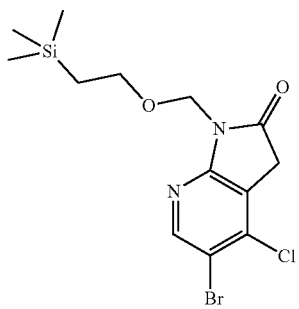 [SMILES: C[Si](C)(C)CCOCN1C(=O)Cc2c1ncc(Br)c2Cl]

Step 1: 5-Bromo-4-chloro-1-((2-(trimethylsilypethoxy)methyl)-1H-pyrrolo[2,3-b]pyridine

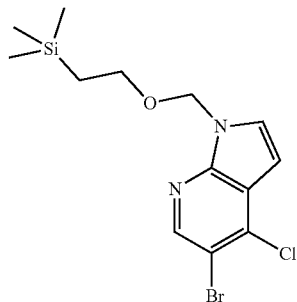 [SMILES: C[Si](C)(C)CCOCn1ccc2c(Cl)c(Br)cnc21]

To a solution of 5-bromo-4-chloro-1H-pyrrolo[2,3-b]pyridine (50 g, 216 mmol) in dry DMF (500 mL) at 0° C., was added sodium hydride (60% in oil, 17.3 g, 432 mmol). The reaction mixture was stirred at RT for 45 min, then cooled to −78° C. 2-(Trimethylsilyl)ethoxymethyl chloride (54 g, 324 mmol) was added, and the mixture was stirred at RT for 16 h. The reaction mixture was poured into ice water (200 mL), and then extracted with EtOAc (3×300 mL). The combined organic extracts were dried (Na$_2$SO$_4$) and concentrated. The residue was purified by chromatography on silica (solvent gradient 0-10% EtOAc in petroleum ether) to afford the title compound (70 g, 90%) as yellow oil. $^1$H NMR (400 MHz, CDCl$_3$) δ8.47 (s, 1H), 7.44 (d, J=3.6 Hz, 1H), 6.66 (d, J=3.6 Hz, 1H), 5.69 (s, 2H), 3.60-3.56 (m, 2H), 0.98-0.94 (m, 2H), 0.00 (s, 9H).

Step 2: 3,3,5-Tribromo-4-chloro-1-((2-(trimethylsilypethoxy)methyl)-1,3-dihydro-2H-pyrrolo[2,3-b]pyridin-2-one

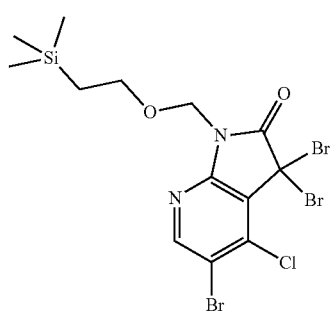 [SMILES: C[Si](C)(C)CCOCN1C(=O)C(Br)(Br)c2c1ncc(Br)c2Cl]

A mixture of 5-bromo-4-chloro-1-((2-(trimethylsilypethoxy)methyl)-1H-pyrrolo[2,3-b]pyridine (70.0 g, 193.5 mmol) and NBS (103.3 g, 580 mmol) in tert-butyl alcohol (1.5 L) was stirred at RT for 3 h. The reaction mixture was concentrated in vacuo to give the title compound (67g, 65%) as a yellow oil. LCMS (ESI) [M+H]$^+$ 533.0.

Step 3: 5-Bromo-4-chloro-1-((2-(trimethylsilyl)ethoxy)methyl)-1,3-dihydro-2H-pyrrolo[2,3-b]pyridin-2-one

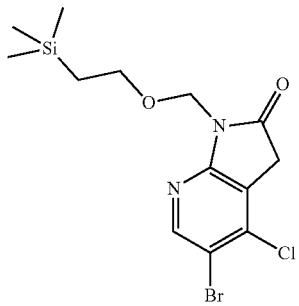 [SMILES: C[Si](C)(C)CCOCN1C(=O)Cc2c1ncc(Br)c2Cl]

A mixture of 3,3,5-tribromo-4-chloro-1-((2-(trimethylsilyl)ethoxy)methyl)-1,3-dihydro-2H-pyrrolo[2,3-b]pyridin-2-one (55 g, 102.7 mmol) and zinc powder (137.5 g, 2.1 mol) in THF (1 L) and sat. ammonium chloride (1 L) was stirred at RT for 20 min. The reaction mixture was filtered, and the filtrate was poured into water (500 mL) and extracted with EtOAc (3×1 L). The combined organic extracts were dried (Na$_2$SO$_4$) and concentrated. The residue was purified by chromatography on silica (solvent gradient 0-5% EtOAc in petroleum ether) to afford the title compound (30 g, 77%) as a brown solid. $^1$H NMR (CDCl$_3$) δ 8.39 (s, 1H), 5.22 (s, 2H), 3.70-3.65 (m, 4H), 1.00-0.95 (m, 2H), 0.00 (s, 9H).

Example 2

5-Bromo-4-methoxy-1-((2-(trimethylsilyl)ethoxy)methyl)-1,3-dihydro-2H-pyrrolo[2,3-b]pyridin-2-one

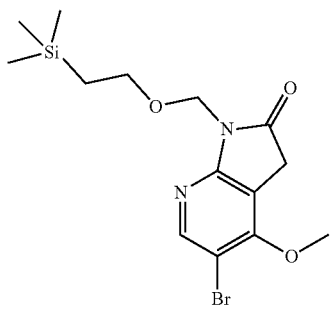

The title compound was prepared in an analogous manner as that described for 5-bromo-4-chloro-1-((2-(trimethylsilyl)ethoxy)methyl)-1,3-dihydro-2H-pyrrolo[2,3-b]pyrdin-2-one. LCMS [M+Na]$^+$ 394.9/396.9.

Example 3

5-Bromo-4-methyl-1-((2-(trimethylsilyl)ethoxy)methyl)-1,3-dihydro-2H-pyrrolo[2,3-b]pyridin-2-one

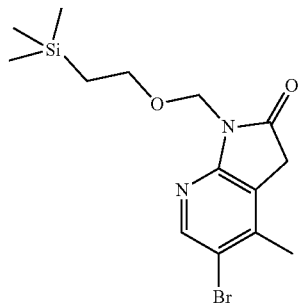

The title compound was prepared in an analogous manner as that described for 5-bromo-4-chloro-1-((2-(trimethylsilyl)ethoxy)methyl)-1,3-dihydro-2H-pyrrolo[2,3-b]pyrdin-2-one above. LCMS [M+Na]+ 379.0/381.0.

Example 4

5'-Bromo-1',2'-dihydrospiro[cyclopentane-1,3'-pyrrolo[2,3-b]pyridine]

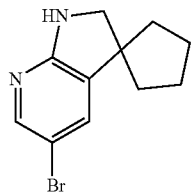 [SMILES: Brc1cnc2c(c1)C1(CCCC1)CN2]

Step 1: Spiro[cyclopentane-1,3'-pyrrolo[2,3-b]pyridin]-2'(1'H)-one

To a slurry of 7-azaoxindole (507 mg, 3.8 mmol) in THF (25 mL) at −78° C., were added dropwise n-BuLi (2.5N hexanes, 3.0 mL, 7.86 mmol) and TMEDA (1.1 mL, 7.6 mmol). The reaction mixture was stirred at −78° C. for 1 h, then was treated with 1,4-diiodobutane (0.5 mL, 3.8 mmol). The reaction mixture was stirred for 18 h, whilst the temperature was allowed to warm up to RT. The reaction was quenched with aq. sat. ammonium chloride and extracted with EtOAc. The combined organic extracts were dried (Na$_2$SO$_4$) and concentrated. The residue was purified by chromatography on silica (solvent gradient 33-100% EtOAc in cyclohexane), to afford the title compound (137 mg, 19%) as a colorless solid. LCMS (ESI) [M+H]$^+$ 189.1.

Step 2: 5'-Bromospiro[cyclopentane-1,3'-pyrrolo[2,3-b]pyridin]-2'(1'H)-one

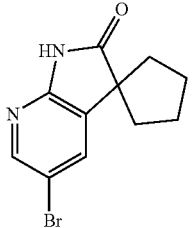 [SMILES: O=C1Nc2ncc(Br)cc2C12CCCC2]

A solution of spiro[cyclopentane-1,3'-pyrrolo[2,3-b]pyridin]-2'(1'H)-one (137 mg, 0.73 mmol) and NBS (130 mg, 0.73 mmol) in DMF (1.5 mL) was stirred at RT for 16 h. The reaction mixture was diluted with water, and extracted with EtOAc. The combined organic extracts were dried (Na$_2$SO$_4$) and concentrated. The residue was purified by chromatography on silica (solvent gradient 20-100% EtOAc in cyclohexane), to afford the title compound (149 mg, 76%) as a colorless solid. LCMS (ESI) [M+H]$^+$ 267.0/269.1.

Step 3: 5'-Bromo-1',2'-dihydrospiro[cyclopentane-1,3'-pyrrolo[2,3-b]pyridine]

To a solution of 5'-bromospiro[cyclopentane-1,3'-pyrrolo[2,3-b]pyridin]-2'(1'H)-one (149 mg, 0.56 mmol) in THF (1 mL) was added borane (1N in THF, 2 mL, 2 mmol). The reaction mixture was stirred at RT for 16 h. A further portion of borane (1N in THF, 2 mL, 2 mmol) was added, and the reaction mixture was stirred at RT for 16 h. The reaction was quenched with MeOH and concentrated. The residue was diluted in HCl (1.25 N, 20 mL), and refluxed for 2 h, then stirred at RT for 2 days. The mixture was concentrated, and the residue was purified by chromatography on silica (solvent gradient 1-10% MeOH·NH$_3$ in DCM), to afford the title compound (59 mg, 42%) as a white solid. LCMS (ESI) [M+H]$^+$ 253.1/255.1.

Example 5

5'-Chloro-1',2'-dihydrospiro[pyrrolidine-3,3'-pyrrolo[2,3-b]pyridin]-5-one

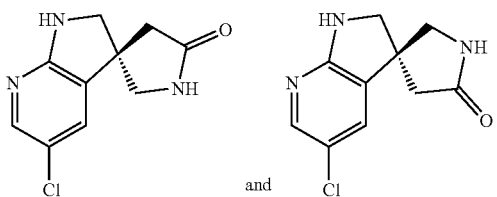 [SMILES: O=C1C[C@]2(CN1)CNc1ncc(Cl)cc12 ; O=C1C[C@@]2(CN1)CNc1ncc(Cl)cc12]

Step 1: 5'-Chloro-1'-(4-methoxybenzyl)-1',2'-dihydrospiro[cyclobutane-1,3'-pyrrolo[2,3-b]pyridin]-3-one oxime

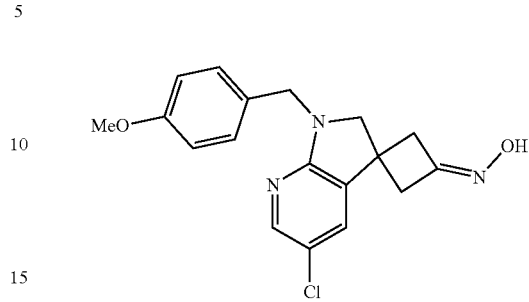

Hydroxylamine hydrochloride (720 mg, 10.36 mmol) was added to a solution of 5'-chloro-1'-(4-methoxybenzyl)-1',2'-dihydrospiro[cyclobutane-1,3'-pyrrolo[2,3-b]pyrdin]-3-one (340 mg, 1.036 mmol) in pyridine (10 mL). The reaction mixture was stirred at RT overnight then partitioned between Et$_2$O and water (30 mL). The aqueous layer was extracted with Et$_2$O. The combined organic extracts were washed with brine, dried (Na$_2$SO$_4$) and concentrated. The residue was triturated under Et$_2$O and filtered to give the title compound (263 mg, 74%) as a colorless solid. LCMS (ESI) [M+H]$^+$ 344.2/346.1.

Step 2: 5'-Chloro-1'-(4-methoxybenzyl)-1',2'-dihydrospiro[pyrrolidine-3,3'-pyrrolo[2,3-b]pyridin]-5-one

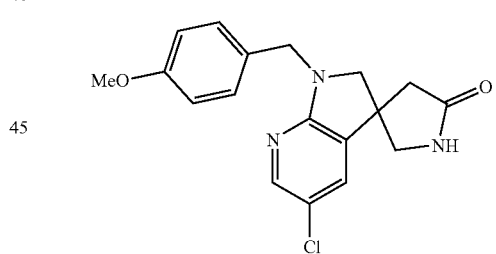

Methanesulphonyl chloride (0.088 mL, 1.143 mmol) was added dropwise to a solution of 5'-chloro-1'-(4-methoxybenzyl)-1',2'-dihydrospiro[cyclobutane-1,3'-pyrrolo[2,3-b]pyrdin]-3-one oxime (263 mg, 0.762 mmol) and triethylamine (0.16 mL, 1.143 mmol) in dry MeCN. The reaction mixture was stirred at RT for 3 h. Further triethylamine (0.16 mL, 1.143 mmol) and methanesulphonyl chloride (0.088 mL, 1.143 mmol) were added and stirring continued for a further 2 h. The mixture was partitioned between EtOAc and water (15 mL). The aqueous layer was extracted with EtOAc. The combined organic extracts were washed with brine, dried (Na$_2$SO$_4$) and concentrated. The residue was purified by chromatography on silica (solvent gradient 20-100% EtOAc in cyclohexane), to afford the title compound (54 mg, 20%). LCMS (ESI) [M+H]$^+$ 344.2/346.5.

Step 3: 5'-Chloro-1',2'-dihydrospiro[pyrrolidine-3,3'-pyrrolo[2,3-b]pyridin]-5-one

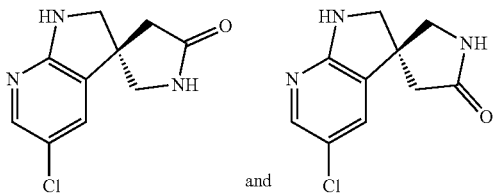 [SMILES: O=C1C[C@]2(CN1)CNc1ncc(Cl)cc12 ; O=C1C[C@@]2(CN1)CNc1ncc(Cl)cc12]

A solution of 5'-chloro-1'-(4-methoxybenzyl)-1',2'-dihydrospiro[pyrrolidine-3,3'-pyrrolo[2,3-b]pyridin]-5-one (110 mg, 0.32 mmol) in TFA/water (95:5; 2 mL) was heated in a sealed tube at 80° C. for 18 h. The cooled mixture was taken to dryness in vacuo, and azeotroped with DCM (2×5 mL). The residue was purified by chromatography on silica (solvent gradient 0-10% MeOH·NH₃ in DCM), to afford the title compounds (41 mg, 57%). LCMS (ESI) [M+H]⁺ 224.1/226.1.

Example 6

5'-Bromo-4'-chloro-1',2'-dihydrospiro[cyclopentane-1,3'-pyrrolo[2,3-b]pyridin]-3-ene

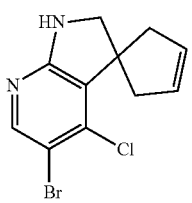 [SMILES: Clc1c(Br)cnc2c1C1(CC=CC1)CN2]

Step 1: 3,3-Diallyl-5-bromo-4-chloro-1-((2-(trimethylsilyl)ethoxy)methyl)-1,3-dihydro-2H-pyrrolo[2,3-b]pyridin-2-one

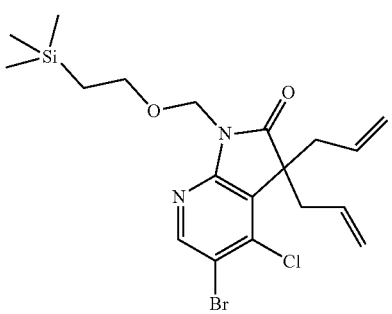 [SMILES: C=CCC1(CC=C)C(=O)N(COCC[Si](C)(C)C)c2ncc(Br)c(Cl)c21]

Allyl bromide (1.90 mL, 22.0 mmol) was added dropwise to a stirred mixture of 5-bromo-4-chloro-1-((2-(trimethylsilylpethoxy)methyl)-1,3-dihydro-2H-pyrrolo[2,3-b]pyridin-2-one (3.78 g, 10.0 mmol) and cesium carbonate (8.15 g, 25.0 mmol) in DMF (30 mL). The reaction mixture was stirred at RT for 3 h, then partitioned between EtOAc and water. The organic extract was washed with water (×2), brine, dried (Na₂SO₄) and concentrated. The residue was purified by chromatography on silica (solvent gradient 0-50% EtOAc in cyclohexane) to give the title compound (3.95 g, 86%) as a pale orange oil. LCMS (ESI) [M+H—CH₃CH₂OCH₂]⁺ 399.0.

Step 2: 5'-Bromo-4'-chloro-1'-((2-(trimethylsilyl)ethoxy)methyl)spiro[cyclopentane-1,3'-pyrrolo [2,3-b]pyrdin]-3-en-2'(1'H)-one

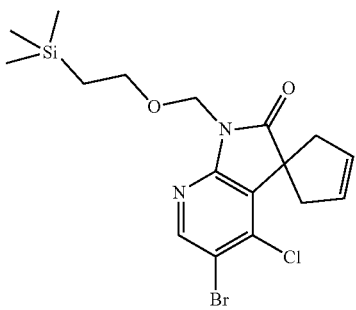 [SMILES: C[Si](C)(C)CCOCN1C(=O)C2(CC=CC2)c2c1ncc(Br)c2Cl]

A solution of 3,3-diallyl-5-bromo-4-chloro-1-((2-(trimethylsilyl)ethoxy)methyl)-1,3-dihydro-2H-pyrrolo[2,3-b]pyridin-2-one (3.95 g, 8.63 mmol) and Grubbs II catalyst (100 mg) in DCM was stirred at RT for 18 h. The mixture was concentrated. The residue was purified by chromatography on silica (solvent gradient 0-20% EtOAc in cyclohexane) to give the title compound (3.78 g, quant) as a pale yellow oil. LCMS (ESI) [M+H—CH₃CH₂OCH₂]⁺ 371.1.

Step 3: 5'-Bromo-4'-chlorospiro[cyclopentane-1,3'-pyrrolo[2,3-b]pyridin]-3-en-2'(1'H)-one

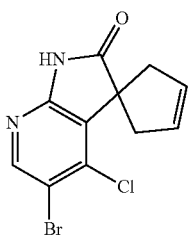 [SMILES: O=C1Nc2ncc(Br)c(Cl)c2C12CC=CC2]

A solution of 5'-bromo-4'-chloro-1'-((2-(trimethylsilypethoxy)methyl)spiro[cyclopentane-1,3'-pyrrolo[2,3-b]pyridin]-3-en-2'(1'H)-one (8.63 mmol) in TFA (12 mL) and DCM (36 mL) was stirred at RT for 1 h. The reaction mixture was partitioned between DCM and aq. sat. sodium bicarbonate. The organic extract was concentrated and taken up in MeOH·NH₃. The mixture was stirred at RT for 18 h and concentrated to afford the title compound (2.73 g, quant) as an off-white solid. LCMS (ESI) [M+H]⁺ 299.1.

Step 4: 5'-Bromo-4'-chloro-1',2'-dihydrospiro[cyclopentane-1,3'-pyrrolo[2,3-b]pyridin]-3-ene

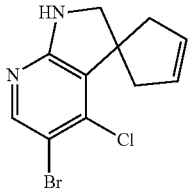 [SMILES: Clc1c(Br)cnc2c1C1(CC=CC1)CN2]

To a stirred suspension of 5'-bromo-4'-chlorospiro[cyclopentane-1,3'-pyrrolo[2,3-b]pyridin]-3-en-2'(1'H)-one (1.35 g, 4.51 mmol) in DCM (33 mL) at 0° C., was added DIBAL (1M in DCM, 21.0 mL, 21.0 mmol) dropwise. The reaction mixture was stirred at 0° C. for 5 min, then allowed to warm up to RT, and stirred for 18 h. The reaction was cooled to 0° C., water (7 mL) was added carefully with vigorous stirring and the resulting gelatinous mixture was allowed to warm to RT. EtOAc (~30 mL) and sodium bicarbonate (~7 g) were added. The resulting suspension was filtered through celite and washed with DCM/EtOAc. The residue was purified by chromatography on silica (solvent gradient 0-100% EtOAc in cyclohexane) to give the title compound (0.91 g, 71%) as a yellow solid. $^1$H NMR (CDCl$_3$) δ (ppm) 7.98 (s, 1H), 5.75 (s, 2H), 4.59 (br s, NH), 3.58 (s, 2H), 3.14 (m, 2H), 2.49 (m, 2H).

Example 7

(1RS,3SR)-5'-Bromo-4'-chloro-1'-(4-methoxybenzyl)-1',2'-dihydrospiro[cyclopentane-1,3'-pyrrolo[2,3-b]pyrdin]-3-ol and (1RS,3RS)-5'-bromo-4'-chloro-1'-(4-methoxybenzyl)-1',2'-dihydrospiro[cyclopentane-1,3'-pyrrolo[2,3-b]pyridin]-3-ol

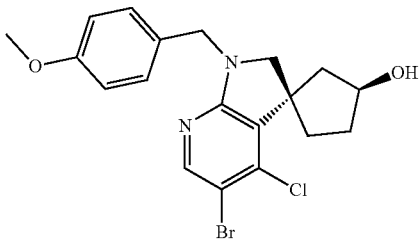

and

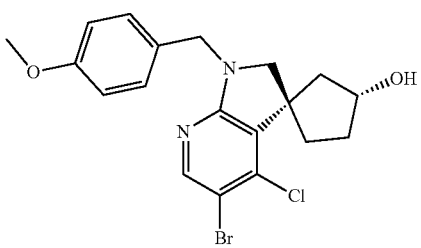

Step 1: 5'-Bromo-4'-chloro-1'-(4-methoxybenzyl)-1',2'-dihydrospiro[cyclopentane-1,3'-pyrrolo[2,3-b]pyridin]-3-ene

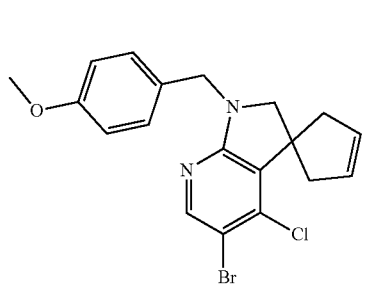 [SMILES: COc1ccc(CN2CC3(CC=CC3)c3c2ncc(Br)c3Cl)cc1]

Sodium hydride (60% in oil, 0.84 g, 21 mmol) was added portionwise to an ice-cooled solution of 5'-bromo-4'-chloro-1',2'-dihydrospiro[cyclopentane-1,3'-pyrrolo[2,3-b]pyrdin]-3-ene (5.0 g, 17.51 mmol) in THF (90 mL). After 10 min 1-(bromomethyl)-4-methoxybenzene (3.09 mL, 22.76 mmol) and 15-crown-5 (100 mg, 0.45 mmol) were added and the mixture was stirred at RT for 3 h. After cooling in an ice bath, aq. sat. ammonium chloride was added and the mixture extracted twice with EtOAc The organic extracts were washed with brine, dried (Na$_2$SO$_4$) and evaporated. The residue was purified by chromatography on silica (solvent gradient 0-20% EtOAc in cyclohexane) to afford the title compound (5.06 g, 71%) as a colorless oil. LCMS (ESI) [M+H]$^+$ 405/407/409.

Step 2: (1RS,3SR)-5'-Bromo-4'-chloro-1'-(4-methoxybenzyl)-1',2'-dihydrospiro[cyclopentane-1,3'-pyrrolo[2,3-b]pyridin]-3-ol and (1RS,3RS)-5'-Bromo-4'-chloro-1'-(4-methoxybenzyl)-1',2'-dihydrospiro[cyclopentane-1,3'-pyrrolo[2,3-b]pyridin]-3-ol

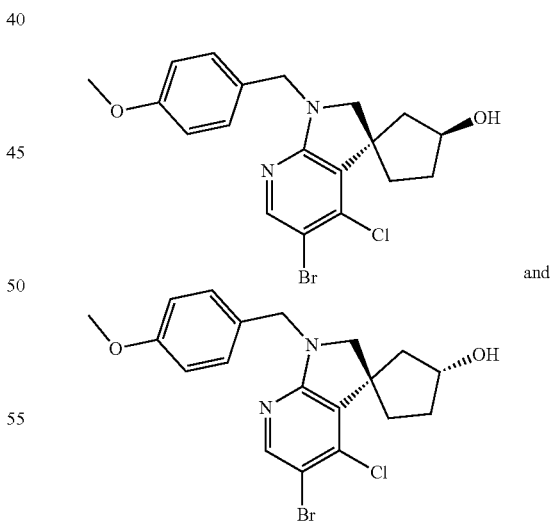

Borane dimethylsulfide complex (1.6 mL, 16.9 mmol) was added over 5 min. to an ice-cooled solution of 5'-bromo-4'-chloro-1'-(4-methoxybenzyl)-1',2'-dihydrospiro[cyclopentane-1,3'-pyrrolo[2,3-b]pyridin]-3-ene (4.57 g, 11.26 mmol) in THF (60 mL). The mixture was stirred at RT for 45 min, then recooled in an ice bath. NaOH (1N aq., 16.9 mL, 16.9 mmol) was added, very cautiously at first, then hydrogen peroxide (30%, 3.34 mL, 29.5 mmol) was added, and the mixture stirred at RT for 16 h. EtOAc and aq. sat. ammonium chloride were added. The aqueous phase was extracted with more EtOAc and the combined organic extracts were washed with 10% aq. sodium metabisulfite, then brine, dried (Na₂SO₄) and evaporated. The residue was purified by chromatography on silica (solvent gradient 20-50% EtOAc in cyclohexane) to afford (1RS,3SR)-5'-bromo-4'-chloro-1'-(4-methoxybenzyl)-1',2'-dihydrospiro [cyclopentane-1,3'-pyrrolo[2,3-b]pyridin]-3-ol (1.76 g, 37%). Later fractions gave a mixture of (1RS,3SR)-5'-bromo-4'-chloro-1'-(4-methoxybenzyl)-1',2'-dihydrospiro [cyclopentane-1,3'-pyrrolo[2,3-b]pyridin]-3-ol and (1RS,3RS)-5'-bromo-4'-chloro-1'-(4-methoxybenzyl)-1',2'-dihydrospiro[cyclopentane-1,3'-pyrrolo[2,3-b]pyridin]-3-ol (2.38 g, 50% yield). LCMS (ESI) [M+H]⁺ 423/425/427.

Step 3: (1RS,3RS)-5'-Bromo-4'-chloro-1'-(4-methoxybenzyl)-1',2'-dihydrospiro[cyclopentane-1,3'-pyrrolo[2,3-b]pyridin]-3-yl benzoate

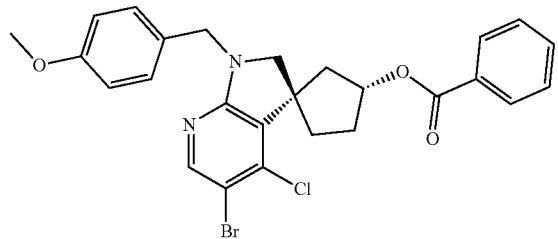 [SMILES: COc1ccc(CN2C[C@@]3(CC[C@@H](OC(=O)c4ccccc4)C3)c3c2ncc(Br)c3Cl)cc1]

To a ice-cooled solution of (1RS,3SR)-5'-bromo-4'-chloro-1'-(4-methoxybenzyl)-1',2'-dihydrospiro[cyclopentane-1,3'-pyrrolo[2,3-b]pyridin]-3-ol (1.54 g, 3.63 mmol), benzoic acid (0.53 g, 4.36 mmol) and triphenylphosphine (1.14 g, 4.36 mmol) in THF (24 mL) was added diisopropyl azodicarboxylate (0.86 mL, 4.36 mmol) dropwise over 5 min. The mixture was stirred at RT for 1 h. The solvent was evaporated, and the residue purified by chromatography on silica (solvent gradient 0-10% EtOAc in cyclohexane) to afford the title compound (1.92 g, 100%) as a colorless solid. LCMS (ESI) [M+H]⁺ 527/529/531.

Step 4: (1RS,3RS)-5'-Bromo-4'-chloro-1'-(4-methoxybenzyl)-1',2'-dihydrospiro[cyclopentane-1,3'-pyrrolo[2,3-b]pyridin]-3-ol

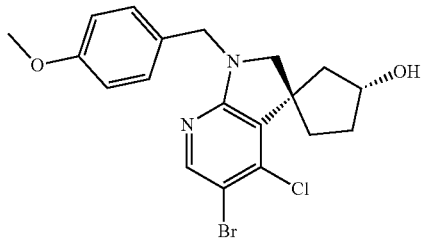 [SMILES: COc1ccc(CN2C[C@@]3(CC[C@@H](O)C3)c3c2ncc(Br)c3Cl)cc1]

To a solution of (1RS,3RS)-5'-bromo-4'-chloro-1'-(4-methoxybenzyl)-1',2'-dihydrospiro[cyclopentane-1,3'-pyrrolo[2,3-b]pyridin]-3-yl benzoate (1.91 g, 3.62 mmol) in THF (15 mL) and MeOH (5 mL) was added a solution of lithium hydroxide hydrate (0.311 g, 7.4 mmol) in water (15 mL). The mixture was stirred at RT for 16 h, then HCl (1N aq., 8 mL) was added. The mixture was concentrated, and the residue was partitioned between EtOAc and aq. sodium bicarbonate. The aqueous phase was extracted with more EtOAc and the combined organic extracts were washed with brine, dried (Na₂SO₄) and evaporated. The residue was purified by chromatography on silica (solvent gradient 20-50% EtOAc in cyclohexane) to afford the title compound as a yellow gum (1.43 g, 93%). LCMS (ESI) [M+H]⁺ 423/425/427.

Example 8

(1RS,3SR)-5'-Bromo-4'-chloro-1',2'-dihydrospiro [cyclopentane-1,3'-pyrrolo[2,3-b]pyridin]-3-ol and (1RS,3RS)-5'-bromo-4'-chloro-1',2'-dihydrospiro [cyclopentane-1,3'-pyrrolo[2,3-b]pyridin]-3-ol

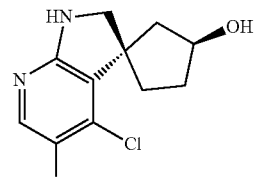

and

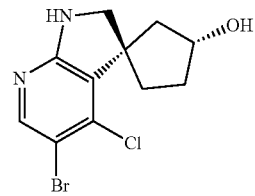

Borane dimethylsulfide complex (0.115 mL, 1.21 mmol) was added dropwise to an ice-cooled solution of 5'-bromo-4'-chloro-1',2'-dihydrospiro[cyclopentane-1,3'-pyrrolo[2,3-b]pyridin]-3-ene (230 mg, 0.805 mmol) in THF (4 mL). The mixture was stirred at 0° C. for 1 h then at RT for 2 h, then recooled in an ice bath. NaOH (1N. aq, 1 mL, 1 mmol) was added, very cautiously at first, then hydrogen peroxide (30%, 0.2 mL, 2 mmol) was added, and the mixture stirred at RT for 16 h. EtOAc and aq. sat. ammonium chloride were added. The aqueous layer was extracted with further EtOAc. The combined organic extracts were washed with 10% aqueous sodium metabisulfite, then with brine, were dried (Na₂SO₄) and evaporated. The residue was purified by chromatography on silica (solvent gradient 0-5% MeOH in DCM) to afford (1RS,3SR)-5'-bromo-4'-chloro-1',2'-dihydrospiro[cyclopentane-1,3'-pyrrolo[2,3-b]pyridin]-3-ol (55 mg, 22%). Later fractions afforded (1RS,3RS)-5'-bromo-4'-chloro-1',2'-dihydrospiro[cyclopentane-1,3'-pyrrolo[2,3-b] pyridin]-3-ol (55 mg, 22%). LCMS (ESI) [M+H]⁺ 303.0/305.0/307.0.

Example 9

(1RS,3RS)-5'-Bromo-4'-chloro-1'-(4-methoxybenzyl)-1',2'-dihydrospiro[cyclopentane-1,3'-pyrrolo[2,3-b]pyridin]-3-yl methanesulfonate

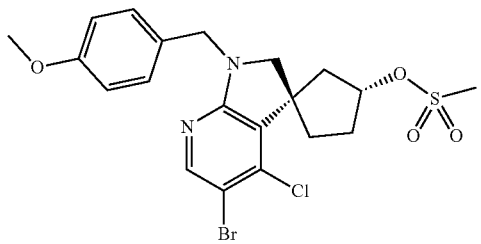

Methanesulfonyl chloride (0.35 mL, 4.53 mmol) was added over 5 min to solution of (1RS,3RS)-5'-bromo-4'-chloro-1'-(4-methoxybenzyl)-1',2'-dihydrospiro[cyclopentane-1,3'-pyrrolo[2,3-b]pyridin]-3-ol (1.279 g, 3.02 mmol) and triethylamine (0.84 mL, 6.04 mmol) in DCM (25 mL). The mixture was stirred at RT for 2 h and then diluted with DCM and washed with aq. sodium bicarbonate. The aqueous phase was extracted with DCM and the combined organic extracts were dried (Na$_2$SO$_4$), filtered and evaporated. The residue was purified by chromatography on silica (solvent gradient 20-50% EtOAc in cyclohexane) to afford the title compound as a colorless gum (1.449 g, 95%). LCMS (ESI) [M+H]$^+$ 501/503/505.

Example 10

(1RS,3SR)-5'-Bromo-4'-chloro-1'-(4-methoxybenzyl)-1',2'-dihydrospiro[cyclopentane-1,3'-pyrrolo[2,3-b]pyridine]-3-carbonitrile

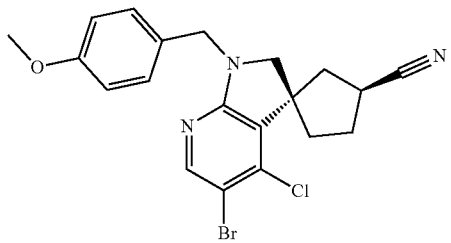 [SMILES: COc1ccc(CN2C[C@@]3(CC[C@H](C#N)C3)c3c2ncc(Br)c3Cl)cc1]

Sodium cyanide (0.342 g, 6.97 mmol) was added to solution of (1RS,3RS)-5'-bromo-4'-chloro-1'-(4-methoxybenzyl)-1',2'-dihydrospiro[cyclopentane-1,3'-pyrrolo[2,3-b]pyridin]-3-yl methanesulfonate (0.70 g, 1.39 mmol) and 15-crown-5 (0.083 mL, 0.42 mmol) in DMSO (10 mL). The mixture was stirred at 80° C. for 1.5 h. The cooled reaction mixture was partitioned between EtOAc and water. The aqueous phase was extracted with more EtOAc and the combined organic extracts were washed with water, then brine, dried (Na$_2$SO$_4$) and evaporated. The residue was purified by chromatography on silica (solvent gradient 10-30% EtOAc in cyclohexane) to afford the title compound as a colorless gum (0.489 g, 81%). LCMS (ESI) [M+H]$^+$ 432/434/436.

Example 11

(1RS,3SR)-5'-Bromo-4'-chloro-1',2'-dihydrospiro[cyclopentane-1,3'-pyrrolo[2,3-b]pyrdine]-3-carbonitrile and (1RS,3SR)-5'-bromo-4'-chloro-1',2'-dihydrospiro[cyclopentane-1,3'-pyrrolo[2,3-b]pyrdine]-3-carboxamide

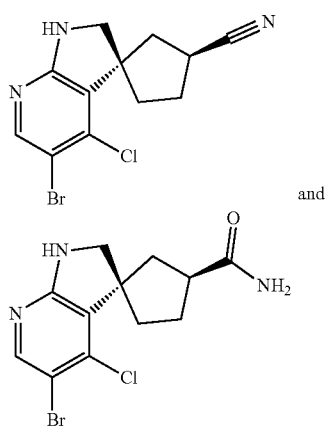

and

A mixture of (1RS,3SR)-5'-bromo-4'-chloro-1'-(4-methoxybenzyl)-1',2'-dihydrospiro[cyclopentane-1,3'-pyrrolo[2,3-b]pyridine]-3-carbonitrile (0.408 g, 0.944 mmol), anisole (1 mL) and TFA (10 mL) was stirred at 80° C. for 20 h. The cooled reaction mixture was evaporated. Toluene was added and evaporated. The residue was dissolved in MeOH/H$_2$O (9:1) and passed through a SCX-2 cartridge (eluting with MeOH then with MeOH·NH$_3$) The residue was purified by chromatography on silica (solvent gradient 2-10% MeOH·NH$_3$ in DCM) to afford (1RS,3SR)-5'-bromo-4'-chloro-1',2'-dihydrospiro[cyclopentane-1,3'-pyrrolo[2,3-b]pyridine]-3-carbonitrile as a colorless gum (0.08 g, 27%). LCMS (ESI) [M+H]$^+$ 312/314/316. Later fractions gave (1RS,3SR)-5'-bromo-4'-chloro-1',2'-dihydrospiro[cyclopentane-1,3'-pyrrolo[2,3-b]pyridine]-3-carboxamide as a white solid (0.192 g, 62%). LCMS (ESI) [M+H]$^+$ 330/332/334.

Example 12

(1RS,3SR)-5'-Bromo-4'-chloro-1',2'-dihydrospiro[cyclopentane-1,3'-pyrrolo[2,3-b]pyridine]-3-carboxylic Acid

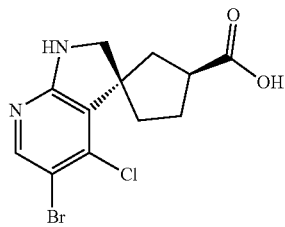 [SMILES: O=C(O)[C@H]1CC[C@@]2(CNc3ncc(Br)c(Cl)c32)C1]

A solution of (1RS,3SR)-5'-bromo-4'-chloro-1'-(4-methoxybenzyl)-1',2'-dihydrospiro[cyclopentane-1,3'-pyrrolo[2,3-b]pyridine]-3-carbonitrile (0.216 g, 0.50 mmol) in HCl (12N aq., 25 mL) was heated at 90° C. for 1.5 h. The cooled mixture was evaporated under reduced pressure.

Example 13

5'-Bromo-4'-chloro-1'-(4-methoxybenzyl)-1',2'-dihydrospiro[cyclopentane-1,3'-pyrrolo[2,3-b]pyridin]-3-one

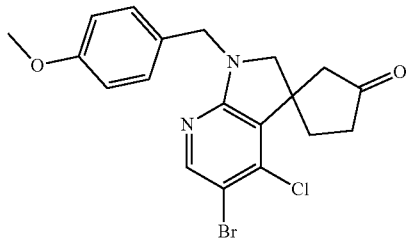 [SMILES: COc1ccc(CN2CC3(CCC(=O)C3)c3c2ncc(Br)c3Cl)cc1]

A solution of 5'-bromo-4'-chloro-1'-(4-methoxybenzyl)-1',2'-dihydrospiro[cyclopentane-1,3'-pyrrolo[2,3-b]pyridin]-3-ol (2.38 g, 5.62 mmol) in DCM (20 mL) was treated with Dess-Martin periodinane (2.86 g, 6.74 mmol). After stirring at RT for 1.5 h, the reaction mixture was partitioned between water and DCM. The aqueous layer was extracted with more DCM. The combined organic extracts were dried ($Na_2SO_4$) and evaporated. The residue was purified by chromatography on silica (solvent gradient 20-50% EtOAc in cyclohexane) to afford the title compound as a pale yellow gum (1.694 g, 72%). LCMS (ESI) $[M+H]^+$ 421/423/425.

Example 14

(1RS,3SR)-5'-Bromo-4'-chloro-1'-(4-methoxybenzyl)-1',2'-dihydrospiro[cyclopentane-1,3'-pyrrolo[2,3-b]pyridin]-3-yl methanesulfonate

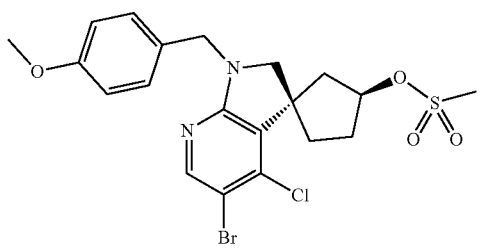

Methanesulfonyl chloride (0.53 mL, 6.89 mmol) was added over 5 min to a solution of (1RS,3SR)-5'-bromo-4'-chloro-1'-(4-methoxybenzyl)-1',2'-dihydrospiro[cyclopentane-1,3'-pyrrolo[2,3-b]pyridin]-3-ol (1.945 g, 4.59 mmol) and triethylamine (1.28 mL, 9.18 mmol) in DCM (30 mL). The mixture was stirred at RT for 30 min then was diluted with DCM and washed with aq. sodium bicarbonate. The aqueous phase was extracted with DCM and the combined organic extracts were dried ($Na_2SO_4$) and evaporated. The residue was purified by chromatography on silica (solvent gradient 20-50% EtOAc in cyclohexane) to afford the title compound (2.192 g, 95%) as a colorless gum. LCMS (ESI) $[M+H]^+$ 501/503/505.

Example 15

(1RS,3RS)-5'-Bromo-4'-chloro-1'-(4-methoxybenzyl)-1',2'-dihydrospiro[cyclopentane-1,3'-pyrrolo[2,3-b]pyridine]-3-carbonitrile

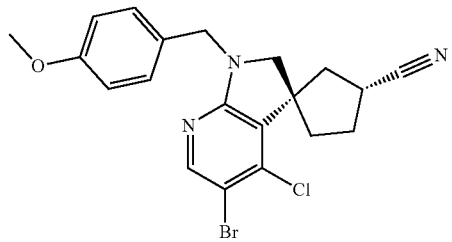 [SMILES: COc1ccc(CN2C[C@@]3(CC[C@@H](C#N)C3)c3c2ncc(Br)c3Cl)cc1]

Sodium cyanide (1.07 g, 6.97 mmol) was added to solution of (1RS,3SR)-5'-bromo-4'-chloro-1'-(4-methoxybenzyl)-1',2'-dihydrospiro[cyclopentane-1,3'-pyrrolo[2,3-b]pyridin]-3-yl methanesulfonate (2.19 g, 4.37 mmol) and 15-crown-5 (0.26 mL, 1.31 mmol) in DMSO (35 mL). The mixture was stirred at 60° C. for 1 h, then at 80° C. for 1 h. The cooled reaction mixture was partitioned between EtOAc and water. The aqueous phase was extracted with more EtOAc. The combined organic extracts were washed with water, brine, dried ($Na_2SO_4$) and evaporated. The residue was purified by chromatography on silica (solvent gradient 10-40% EtOAc in cyclohexane) to afford the title compound as a colorless solid (1.425 g, 75%). LCMS (ESI) $[M+H]^+$ 432/434/436.

Example 16

(1RS,3RS)-5'-Bromo-4'-chloro-1',2'-dihydrospiro[cyclopentane-1,3'-pyrrolo[2,3-b]pyridine]-3-carboxylic Acid

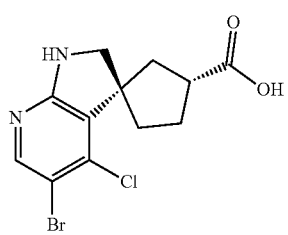 [SMILES: O=C(O)[C@@H]1CC[C@@]2(CNc3ncc(Br)c(Cl)c32)C1]

A mixture of (1RS,3RS)-5'-bromo-4'-chloro-1'-(4-methoxybenzyl)-1',2'-dihydrospiro[cyclopentane-1,3'-pyrrolo[2,3-b]pyridine]-3-carbonitrile (0.216 g, 0.50 mmol), dioxane (1 mL) and HCl (6N aq., 4 mL) was heated under microwave irradiation at 130° C. for 1.5 h. The cooled mixture was evaporated under reduced pressure. The residue was purified on SCX-2 cartridge (eluting with aq. MeCN, MeCN, 10% $NH_3$ in MeCN, MeOH·$NH_3$) to afford the title compound (0.17 g, 100%) as a colorless solid. LCMS (ESI) $[M+H]^+$ 331/333/335.

Example 17

(1RS,3SR)-5'-Bromo-4'-chloro-1'-(4-methoxybenzyl)-3-methyl-1',2'-dihydrospiro[cyclopentane-1,3'-pyrrolo[2,3-b]pyridine]-3-carbonitrile and (1RS,3RS)-5'-bromo-4'-chloro-1'-(4-methoxybenzyl)-3-methyl-1',2'-dihydrospiro[cyclopentane-1,3'-pyrrolo[2,3-b]pyridine]-3-carbonitrile

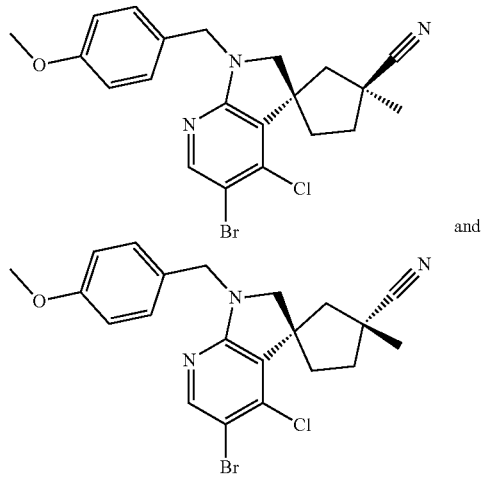

A solution of (1RS,3RS)-5'-bromo-4'-chloro-1'-(4-methoxybenzyl)-1',2'-dihydrospiro[cyclopentane-1,3'-pyrrolo[2,3-b]pyridine]-3-carbonitrile (0.40 g, 0.92 mmol) and iodomethane (0.075 mL, 1.2 mmol) in THF (5 mL) was cooled to −78° C. and lithium bis(trimethylsilyl)amide solution (1M in THF, 1.02 mL, 1.02 mmol) added over 5 min. The mixture was stirred at −78° C. for 30 min, then quenched with aq. sat. ammonium chloride, allowed to warm to RT and extracted with EtOAc (2×). The combined organic extracts were washed with brine, dried ($Na_2SO_4$) and evaporated. The residue was purified by chromatography on silica (solvent gradient 10-25% EtOAc in cyclohexane) to afford (1RS,3SR)-5'-bromo-4'-chloro-1'-(4-methoxybenzyl)-3-methyl-1',2'-dihydrospiro[cyclopentane-1,3'-pyrrolo[2,3-b]pyridine]-3-carbonitrile (0.3376 g, 82%) as a colorless gum. LCMS (ESI) [M+H]$^+$ 446/448/450. Later fractions gave (1RS,3RS)-5'-bromo-4'-chloro-1'-(4-methoxybenzyl)-3-methyl-1', 2'-dihydrospiro[cyclopentane-1,3'-pyrrolo[2,3-b]pyridine]-3-carbonitrile (0.0846 g, 20%) as a colorless gum. LCMS (ESI) [M+H]$^+$ 446/448/450.

Example 18

(1RS,3SR)-5'-Bromo-4'-chloro-3-methyl-1',2'-dihydrospiro[cyclopentane-1,3'-pyrrolo[2,3-b]pyridine]-3-carbonitrile and (1RS,3SR)-5'-bromo-4'-chloro-3-methyl-1',2'-dihydrospiro[cyclopentane-1,3'-pyrrolo[2,3-b]pyridine]-3-carboxamide

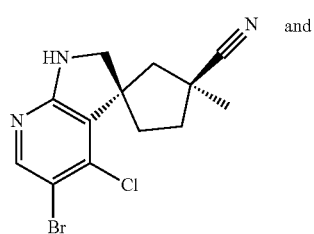

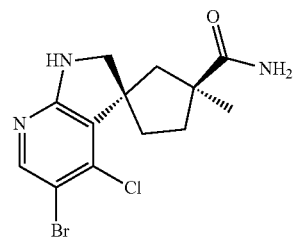

A mixture of (1RS,3SR)-5'-bromo-4'-chloro-1'-(4-methoxybenzyl)-3-methyl-1',2'-dihydrospiro[cyclopentane-1,3'-pyrrolo[2,3-b]pyridine]-3-carbonitrile (0.337 g, 0.75 mmol), anisole (0.5 mL) and TFA (5 mL) was stirred at 80° C. for 22 h. The cooled reaction mixture was evaporated. Toluene was added and evaporated. The residue was purified on SCX-2 cartridge (eluting with MeOH then 1N MeOH·$NH_3$ then a 1:1 mixture of 2N MeOH·$NH_3$ and DCM). The residue was purified by chromatography on silica (solvent gradient 2-10% MeOH·$NH_3$ in DCM) to afford (0.132 g, 54%) as a colorless gum. LCMS (ESI) [M+H]$^+$ 326/328/330. Later fractions gave (1RS,3SR)-5'-bromo-4'-chloro-3-methyl-1',2'-dihydrospiro[cyclopentane-1,3'-pyrrolo[2,3-b]pyridine]-3-carboxamide (0.0886 g, 34%) as a white solid. LCMS (ESI) [M+H]$^+$ 344/346/348.

Example 19

(1RS,3RS)-5'-Bromo-4'-chloro-3-methyl-1',2'-dihydrospiro[cyclopentane-1,3'-pyrrolo[2,3-b]pyridine]-3-carbonitrile and (1RS,3RS)-5'-bromo-4'-chloro-3-methyl-1',2'-dihydrospiro[cyclopentane-1,3'-pyrrolo[2,3-b]pyridine]-3-carboxamide

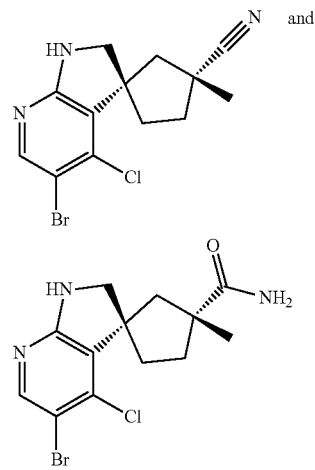

The title compounds were prepared in an analogous manner to that described for (1RS,3SR)-5'-bromo-4'-chloro-3-methyl-1',2'-dihydrospiro[cyclopentane-1,3'-pyrrolo[2,3-b]pyridine]-3-carbonitrile and (1RS,3SR)-5'-bromo-4'-chloro-3-methyl-1',2'-dihydrospiro[cyclopentane-1,3'-pyrrolo[2,3-b]pyridine]-3-carboxamide. LCMS (ESI) [M+H]$^+$ 344/346/348.

Example 20

(1RS,3SR)-5'-Bromo-4'-chloro-3-ethyl-1'-(4-methoxybenzyl)-1',2'-dihydrospiro[cyclopentane-1,3'-pyrrolo[2,3-b]pyridine]-3-carbonitrile

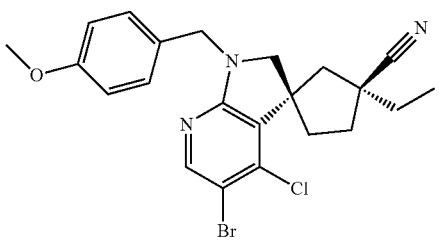 [SMILES: CC[C@]1(C#N)CC[C@@]2(CN(Cc3ccc(OC)cc3)c3ncc(Br)c(Cl)c32)C1]

A solution of (1RS,3RS)-5'-bromo-4'-chloro-1'-(4-methoxybenzyl)-1',2'-dihydrospiro[cyclopentane-1,3'-pyrrolo[2,3-b]pyridine]-3-carbonitrile (0.291 g, 0.67 mmol) and iodoethane (0.108 mL, 1.34 mmol) in THF (5 mL) was cooled to −78° C. and lithium bis(trimethylsilyl)amide solution (1M in THF, 0.81 mL, 0.81 mmol) added over 5 min. The mixture was stirred at −78° C. for 1 h, then quenched with aq. sat. ammonium chloride, allowed to warm to RT and extracted with EtOAc (2×). The combined organic extracts were washed with brine, dried ($Na_2SO_4$) and evaporated. The residue was purified by chromatography on silica (solvent gradient 5-30% EtOAc in cyclohexane) to afford (1RS,3SR)-5'-bromo-4'-chloro-1'-(4-methoxybenzyl)-3-methyl-1',2'-dihydrospiro[cyclopentane-1,3'-pyrrolo[2,3-b]pyridine]-3-carbonitrile as a colorless gum (0.173 g, 56%). LCMS (ESI) [M+H]$^+$ 460/462/464.

Example 21

(1RS,3SR)-5'-Bromo-4'-chloro-3-ethyl-1',2'-dihydrospiro[cyclopentane-1,3'-pyrrolo[2,3-b]pyridine]-3-carbonitrile and (1RS,3SR)-5'-bromo-4'-chloro-3-ethyl-1',2'-dihydrospiro[cyclopentane-1,3'-pyrrolo[2,3-b]pyridine]-3-carboxamide

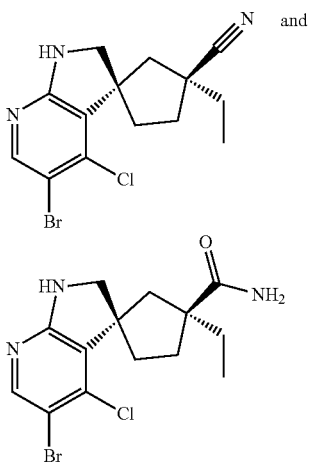

A mixture of (1RS,3SR)-5'-bromo-4'-chloro-3-ethyl-1'-(4-methoxybenzyl)-1',2'-dihydrospiro[cyclopentane-1,3'-pyrrolo[2,3-b]pyridine]-3-carbonitrile (0.221 g, 0.48 mmol), anisole (0.35 mL) and TFA (3.5 mL) was stirred at 80° C. for 22 h. The cooled reaction mixture was evaporated. Toluene was added and evaporated. The residue was purified on SCX-2 cartridge (eluting with MeOH then 1N MeOH·$NH_3$ then a 1:1 mixture of 2N MeOH·$NH_3$ and DCM). The residue was purified by chromatography on silica (solvent gradient 2-10% MeOH·$NH_3$ in DCM) to afford (1RS,3SR)-5'-bromo-4'-chloro-3-ethyl-1',2'-dihydrospiro[cyclopentane-1,3'-pyrrolo[2,3-b]pyridine]-3-carbonitrile (0.1179 g, 72%) as a white solid. LCMS (ESI) [M+H]$^+$ 340/342/344. Later fractions gave (1RS,3SR)-5'-bromo-4'-chloro-3-ethyl-1',2'-dihydrospiro[cyclopentane-1,3'-pyrrolo[2,3-b]pyridine]-3-carboxamide (0.0253 g, 15%) as a white solid. LCMS (ESI) [M+H]$^+$ 358/360/362.

Example 22

(1RS,3SR)-5'-Bromo-4'-chloro-3-methyl-1',2'-dihydrospiro[cyclopentane-1,3'-pyrrolo[2,3-b]pyridine]-3-carboxylic Acid

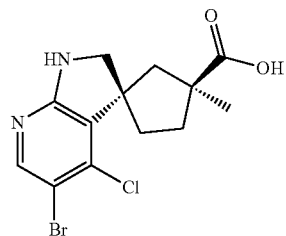 [SMILES: C[C@]1(C(=O)O)CC[C@@]2(CNc3ncc(Br)c(Cl)c32)C1]

A mixture of (1RS,3SR)-5'-bromo-4'-chloro-3-methyl-1',2'-dihydrospiro[cyclopentane-1,3'-pyrrolo[2,3-b]pyridine]-3-carbonitrile (0.132 g, 0.40 mmol) and HCl (12N, 5 mL) was stirred at 100° C. for 1.25 h. The cooled reaction mixture was evaporated under reduced pressure. Toluene was added and evaporated (2×) to give the title compound as the hydrochloride salt (163 mg, assume quantitative) as a white solid. LCMS (ESI) [M+H]$^+$ 345/347/349.

Example 23

(1RS,3SR)-5'-Bromo-4'-chloro-3-methoxy-1',2'-dihydrospiro[cyclopentane-1,3'-pyrrolo[2,3-b]pyridine] and (1RS,3RS)-5'-bromo-4'-chloro-3-methoxy-1',2'-dihydrospiro[cyclopentane-1,3'-pyrrolo[2,3-b]pyridine]

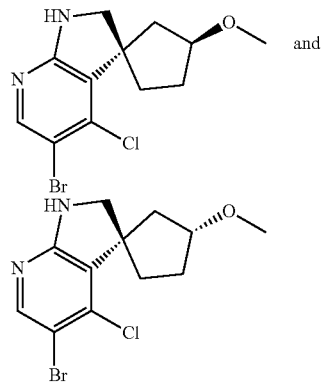

Step 1: (1RS,3SR)-5'-Bromo-4'-chloro-3-methoxy-1'-(4-methoxybenzyl)-1',2'-dihydrospiro [cyclopentane-1,3'-pyrrolo[2,3-b]pyrdine] and (1RS,3RS)-5'-bromo-4'-chloro-3-methoxy-1'-(4-methoxybenzyl)-1',2'-dihydrospiro[cyclopentane-1,3'-pyrrolo[2,3-b]pyrdine]

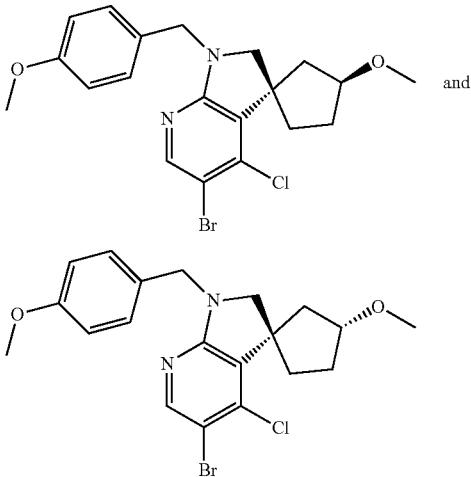
and

Sodium hydride (60% in oil, 13.5 mg, 0.34 mmol) was added to an ice-cooled solution of (1RS,3SR)-5'-bromo-4'-chloro-1'-(4-methoxybenzyl)-1',2'-dihydrospiro[cyclopentane-1,3'-pyrrolo[2,3-b]pyridin]-3-ol and (1RS,3RS)-5'-bromo-4'-chloro-1'-(4-methoxybenzyl)-1',2'-dihydrospiro [cyclopentane-1,3'-pyrrolo[2,3-b]pyridin]-3-ol (0.130 g, 0.306 mmol), iodomethane (0.038 mL, 0.612 mmol) and 15-crown-5 (0.02 mL) in THF (3 mL). The mixture was stirred at RT for 30 min then more sodium hydride (60% in oil, 5 mg, 0.13 mmol) and iodomethane (0.015 mL, 0.24 mmol) were added. Stirring was continued for 16 h. Aq. sat. ammonium chloride was added and the mixture extracted with EtOAc. The combined organic extracts were washed with water, brine, dried (Na₂SO₄) and evaporated. The residue was purified by chromatography on silica (solvent gradient 3-25% EtOAc in toluene) to afford a mixture of the title compounds (0.0864 g, 64%) as colorless gum. LCMS (ESI) [M+H]⁺ 437/439/441.

Step 2: (1RS,3SR)-5'-Bromo-4'-chloro-3-methoxy-1',2'-dihydrospiro[cyclopentane-1,3'-pyrrolo [2,3-b]pyridine] and (1RS,3RS)-5'-bromo-4'-chloro-3-methoxy-1',2'-dihydrospiro [cyclopentane-1,3'-pyrrolo[2,3-b]pyridine]

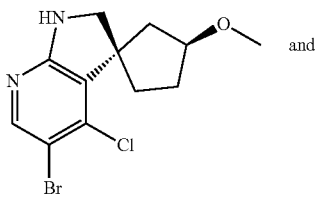
and

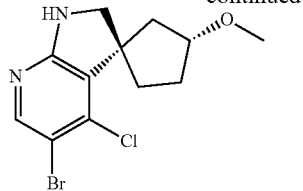

A mixture of (1RS,3SR)-5'-bromo-4'-chloro-3-methoxy-1'-(4-methoxybenzyl)-1',2'-dihydrospiro[cyclopentane-1,3'-pyrrolo[2,3-b]pyridine] and (1RS,3RS)-5'-bromo-4'-chloro-3-methoxy-1'-(4-methoxybenzyl)-1',2'-dihydrospiro [cyclopentane-1,3'-pyrrolo[2,3-b]pyridine](0.0864 g, 0.20 mmol) in TFA (4.3 mL) and water (0.23 mL) was stirred at 80 C for 16 h. Toluene was added and evaporated (2×). The residue was purified on SCX-2 cartridge (eluting with MeOH then 1N MeOH·NH₃/DCM (1:1)) to afford a mixture of the title compounds (0.061 g, 96%) as a yellow gum. LCMS (ESI) [M+H]⁺ 317/319/321.

Example 24

Methyl (1RS,3RS)-5'-bromo-4'-chloro-1',2'-dihydrospiro[cyclopentane-1,3'-pyrrolo[2,3-b]pyridine]-3-carboxylate

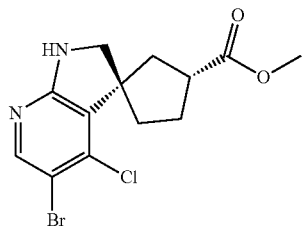 [SMILES: COC(=O)[C@@H]1CC[C@@]2(CNc3ncc(Br)c(Cl)c32)C1]

Concentrated sulfuric acid (1 mL) was added to a suspension of (1RS,3RS)-5'-bromo-4'-chloro-1',2'-dihydrospiro [cyclopentane-1,3'-pyrrolo[2,3-b]pyridine]-3-carboxylic acid (0.165 g, 0.50 mmol) in MeOH (10 mL). The resulting solution was stirred at RT for 2 h, then concentrated under reduced pressure. The residue was partitioned between EtOAc and aq. sodium bicarbonate. The aqueous phase was extracted with EtOAc and the combined extracts were washed with brine, dried (Na₂SO₄) and evaporated. The residue was purified by chromatography on silica (solvent gradient 25-75% EtOAc in diethyl ether) to afford the title compound (0.103 g, 60%) as a colorless gum. LCMS (ESI) [M+H]⁺ 345/347/349.

Example 25

((1RS,3RS)-5'-Bromo-4'-chloro-1',2'-dihydrospiro [cyclopentane-1,3'-pyrrolo[2,3-b]pyridin]-3-yl) methanol

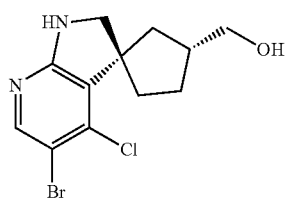

DIBAL (1N in DCM, 0.89 mL, 0.89 mmol) was added to solution of methyl (1RS,3RS)-5'-bromo-4'-chloro-1',2'-dihydrospiro[cyclopentane-1,3'-pyrrolo[2,3-b]pyridine]-3-carboxylate (0.103 g, 0.30 mmol) in DCM (2 mL) over 2 min. The mixture was stirred at RT for 30 min, then treated successively with water (0.035 mL), 15% NaOH (0.035 mL) and water (0.09 mL). The mixture was stirred for 1.5 h, then celite and Na$_2$SO$_4$ were added and stirring was continued for 30 min, before filtering and evaporating. The residue was purified by chromatography on silica (solvent gradient 1-5% MeOH·NH$_3$ in EtOAc) to afford the title compound (0.074 g, 78%) as a colorless gum. LCMS (ESI) [M+H]$^+$ 317/319/321.

Example 26

((1RS,3SR)-5'-Bromo-4'-chloro-1',2'-dihydrospiro[cyclopentane-1,3'-pyrrolo[2,3-b]pyridin]-3-yl)methanol

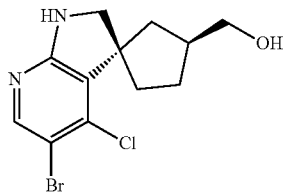 [SMILES: OC[C@H]1CC[C@@]2(CNc3ncc(Br)c(Cl)c32)C1]

The title compound was prepared by an analogous method to that described for ((1RS,3RS)-5'-bromo-4'-chloro-1',2'-dihydrospiro[cyclopentane-1,3'-pyrrolo[2,3-b]pyridine]-3-yl)methanol starting from (1RS,3SR)-5'-bromo-4'-chloro-1'-(4-methoxybenzyl)-1',2'-dihydrospiro[cyclopentane-1,3'-pyrrolo[2,3-b]pyridine]-3-carbonitrile. LCMS (ESI) [M+H]$^+$ 317/319/321.

Example 27

(5'-Bromo-4'-chloro-1',2'-dihydrospiro[cyclopentane-1,3'-pyrrolo[2,3-b]pyridin]-3-yl)methanamine

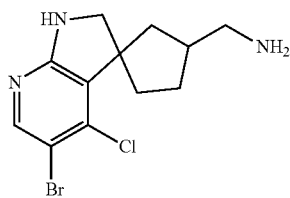 [SMILES: NCC1CCC2(CNc3ncc(Br)c(Cl)c32)C1]

Borane dimethylsulfide complex (0.1 mL, 1.07 mmol) was added to a suspension of (1'S, 3R)-5-bromo-4-chloro-spiro[1,2-dihydropyrrolo[2,3-b]pyridine-3,3'-cyclopentane]-1'-carboxamide (177 mg, 0.540 mmol) in THF (5 mL). The mixture was stirred at 70° C. for 4 h. TFA (0.5 mL) was added and the mixture was stirred for 15 min. The solvent was evaporated to dryness and the residue passed down a SCX-2 cartridge (eluting with MeOH followed by MeOH·NH$_3$) to afford the title compound (89 mg, 52%) as a brown foam. LCMS (ESI) [M+H]$^+$ 315.9/319.9.

Example 28 tert-Butyl 5'-bromo-4'-chlorospiro[cyclopentane-1,3'-pyrrolo[2,3-b]pyridin]-3-ene-1'(2'-1)-carboxylate

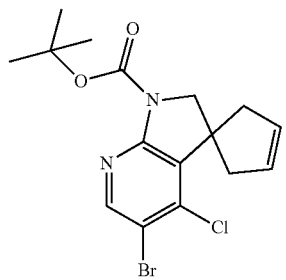 [SMILES: CC(C)(C)OC(=O)N1CC2(CC=CC2)c2c1ncc(Br)c2Cl]

Sodium hydride (60% in oil, 1.68 g, 42 mmol) was added portionwise to an ice-cooled solution of 5'-bromo-4'-chloro-1',2'-dihydrospiro[cyclopentane-1,3'-pyrrolo[2,3-b]pyridin]-3-ene (10.0 g, 35 mmol) in THF (60 mL). After 10 min a solution of di-tert-butyl dicarbonate (11.46 g, 52.53 mmol) in THF (40 mL) was added and the mixture was stirred at RT for 6 h. After cooling in an ice bath, aq. sat. ammonium chloride was added and the mixture extracted twice with EtOAc. A 10% aq. citric acid solution was added, followed by further extraction with EtOAc. The organic extracts were washed with brine, dried (Na$_2$SO$_4$) and evaporated. The residue was purified by chromatography on silica (solvent gradient 0-12% EtOAc in cyclohexane) to afford the title compound (12.06 g, 89%) as a pale yellow solid. LCMS (ESI) [M−tBu+2H]$^+$ 329/331/333.

Example 29 tert-Butyl (1RS,3RS)-5'-bromo-4'-chloro-3-hydroxyspiro[cyclopentane-1,3'-pyrrolo[2,3-b]pyridine]-1'(2'H)-carboxylate and tert-butyl (1RS,3SR)-5'-bromo-4'-chloro-3-hydroxyspiro[cyclopentane-1,3'-pyrrolo[2,3-b]pyridine]-1'(2'H)-carboxylate

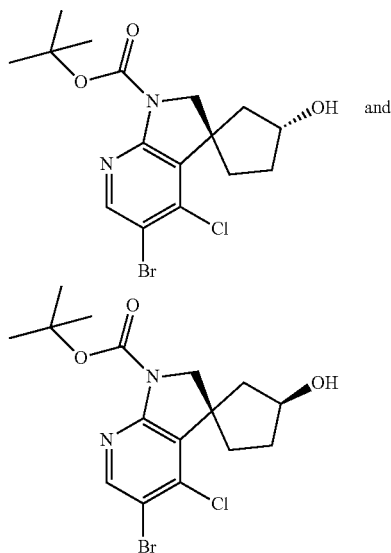

Borane dimethylsulfide complex (1 mL, 10.53 mmol) was added over 5 min to an ice-cooled solution of tert-butyl 5'-bromo-4'-chlorospiro[cyclopentane-1,3'-pyrrolo[2,3-b]pyridin]-3-ene-1'(2'H)-carboxylate (2.8 g, 7.26 mmol) in THF (30 mL). The mixture was stirred at RT for 1 h, then recooled in an ice bath. A further portion of borane dimethylsulfide complex (0.15 mL, 1.58 mmol) was added. The mixture was stirred at RT for 20 min, then recooled in an ice bath. Sodium hydroxide (1N aq., 10.7 mL, 10.7 mmol) was added, very cautiously at first, then hydrogen peroxide (30%, 2.14 mL, 20.93 mmol) was added, and the mixture stirred at RT for 18 h. EtOAc and aq. sat. ammonium chloride were added. The aqueous phase was extracted with more EtOAc and the combined organic extracts were washed with 10% aq. sodium metabisulfite, then brine, dried (MgSO$_4$) and evaporated. The residue was purified by chromatography on silica (solvent gradient 0-20% EtOAc in cyclohexane) to afford tert-butyl (1RS,3SR)-5'-bromo-4'-chloro-3-hydroxyspiro[cyclopentane-1,3'-pyrrolo[2,3-b]pyridine]-1'(2'H)-carboxylate (1.71 g, 58%) and tert-butyl (1RS,3RS)-5'-bromo-4'-chloro-3-hydroxyspiro[cyclopentane-1,3'-pyrrolo[2,3-b]pyridine]-1'(2'H)-carboxylate (0.52 g, 18%). LCMS (ESI) [M−tBu+2H]$^+$ 347/349/351.

Example 30 tert-Butyl 5'-bromo-4'-chloro-3-oxospiro[cyclopentane-1,3'-pyrrolo[2,3-b]pyridine]-1'(2'H)-carboxylate

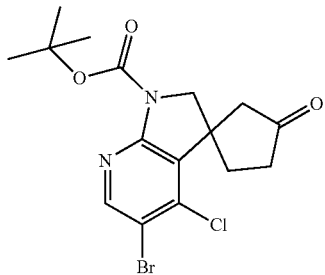 [SMILES: CC(C)(C)OC(=O)N1CC2(CCC(=O)C2)c2c1ncc(Br)c2Cl]

Dess-Martin periodinane (832 mg, 1.96 mmol) was added to a solution of tert-butyl (1RS,3RS)-5'-bromo-4'-chloro-3-hydroxyspiro[cyclopentane-1,3'-pyrrolo[2,3-b]pyridine]-P(27-1)-carboxylate and tert-butyl (1RS,3SR)-5'-bromo-4'-chloro-3-hydroxyspiro[cyclopentane-1,3'-pyrrolo[2,3-b]pyridine]-P(2'H)-carboxylate (660 mg, 1.63 mmol) in DCM (9 mL). The mixture was stirred at RT for 18 h, and then diluted with DCM and washed with water. The aqueous phase was extracted with DCM and the combined organic extracts were dried (MgSO$_4$) and evaporated, to afford the title compound (0.7 g, 100%) as a white solid. LCMS (ESI) [M+Na]$^+$ 423/425.

Example 31 tert-Butyl (1RS,3SR)-3,5'-dibromo-4'-chlorospiro[cyclopentane-1,3'-pyrrolo[2,3-b]pyridine]-1'(2'H)-carboxylate and tert-butyl (1RS,3RS)-3,5'-dibromo-4'-chlorospiro[cyclopentane-1,3'-pyrrolo[2,3-b]pyridine]-1'(2'H)-carboxylate

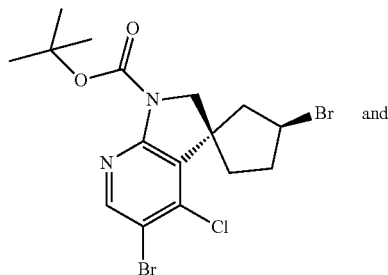

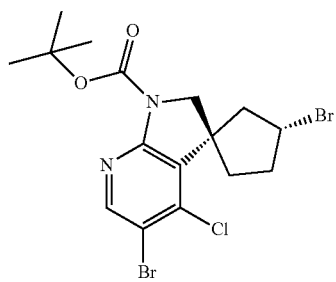

A solution of tert-butyl (1RS,3RS)-5'-bromo-4'-chloro-3-hydroxyspiro[cyclopentane-1,3'-pyrrolo[2,3-b]pyridine]-P(2'H)-carboxylate (523. mg, 1.3 mmol) in THF (8 mL) was treated with triphenylphosphine (441 mg, 1.68 mmol) followed by carbon tetrabromide (558 mg, 1.68 mmol). The mixture was stirred at RT for 2 h, then diluted with EtOAc and water. The aqueous layer was extracted with further EtOAc. The combined organic extracts were dried (MgSO$_4$) and concentrated. The residue was purified by chromatography on silica (solvent gradient 0-10% EtOAc in cyclohexane) to afford tert-butyl (1RS,3SR)-3,5'-dibromo-4'-chlorospiro[cyclopentane-1,3'-pyrrolo[2,3-b]pyridine]-1'(2'H)-carboxylate (316 mg, 52%) and tert-butyl (1RS,3RS)-3,5'-dibromo-4'-chlorospiro[cyclopentane-1,3'-pyrrolo[2,3-b]pyridine]-P(2'H)-carboxylate as a white solid (112 mg, 18%) as a white solid. LCMS (ESI) [M−tBu+2H]$^+$ 409/411/413.

Example 32 tert-Butyl (1RS,3RS)-5'-bromo-4'-chloro-3-((methylsulfonyl)oxy)spiro[cyclopentane-1,3'-pyrrolo[2,3-b]pyridine]-1'(2'H)-carboxylate

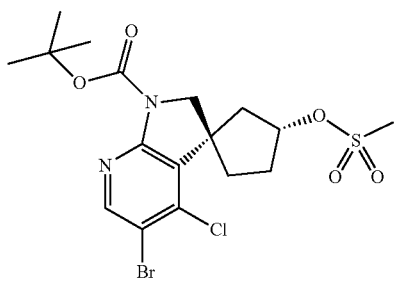 [SMILES: CC(C)(C)OC(=O)N1C[C@@]2(CC[C@@H](OS(C)(=O)=O)C2)c2c1ncc(Br)c2Cl]

Methanesulfonyl chloride (0.03 mL, 0.41 mmol) was added over 5 min to solution of tert-butyl (1R,3S)-5'-bromo-4'-chloro-3-hydroxyspiro[cyclopentane-1,3'-pyrrolo[2,3-b]pyridine]-1'(2'H)-carboxylate (111. mg, 0.27 mmol) and triethylamine (0.08 mL, 0.55 mmol) in DCM (5 mL). The mixture was stirred at RT for 1 h then was diluted with DCM and washed with aq. sodium bicarbonate. The aqueous phase was extracted with DCM and the combined organic extracts were dried (Na$_2$SO$_4$) and evaporated. The residue was purified by chromatography on silica (solvent gradient 20-50% EtOAc in cyclohexane) to afford the title compound (132 mg, 99%) as a colorless gum. LCMS (ESI) [M+Na]$^+$ 501/503/505.

Example 33

5'-Bromo-4'-chloro-3-methyl-1',2'-dihydrospiro[cyclopentane-1,3'-pyrrolo[2,3-b]pyridin]-3-ol

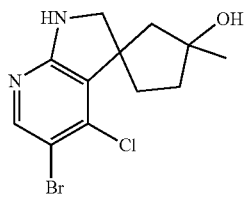 [SMILES: CC1(O)CCC2(CNc3ncc(Br)c(Cl)c32)C1]

To a solution of tert-butyl 5'-bromo-4'-chloro-3-oxospiro[cyclopentane-1,3'-pyrrolo[2,3-b]pyridine]-1'(2'H)-carboxylate (274 mg, 0.68 mmol) in THF (3 mL) at –50° C. was added methylmagnesium bromide (3M in Et$_2$O, 0.23 mL, 0.69 mmol). The reaction mixture was stirred at RT for 30 min., then was quenched by addition of aq. sat. ammonium chloride (5 mL). The mixture was extracted with EtOAc. The organic extracts were dried (Na$_2$SO$_4$) and evaporated. The residue was purified by chromatography on silica (solvent gradient 0-30% EtOAc in cyclohexane). The resulting residue was dissolved in DCM, and TFA (0.46 mL) was added. The resulting solution was stirred at RT for 30 min, then was passed through an SCX-2 cartridge (eluting with MeOH then MeOH·NH$_3$). The resulting residue was purified by chromatography on silica (solvent gradient 0-50% EtOAc in cyclohexane) to give the title compound (65 mg, 30%) as a solid. LCMS (ESI) [M+H]$^+$ 317/319/321.

Example 34

5'-Bromo-4'-chloro-3-(trifluoromethyl)-1',2'-dihydrospiro[cyclopentane-1,3'-pyrrolo[2,3-b]pyridin]-3-ol

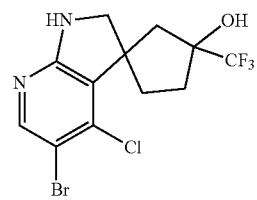 [SMILES: OC1(C(F)(F)F)CCC2(CNc3ncc(Br)c(Cl)c32)C1]

Step 1: tert-Butyl 5'-bromo-4'-chloro-3-hydroxy-3-(trifluoromethyl)spiro[cyclopentane-1,3'-pyrrolo[2,3-b]pyridine]-1'(2'H)-carboxylate

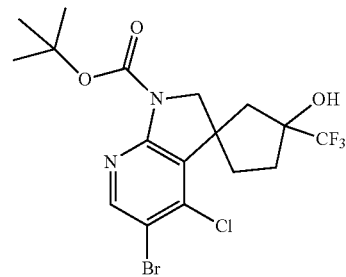 [SMILES: CC(C)(C)OC(=O)N1CC2(CCC(O)(C(F)(F)F)C2)c2c1ncc(Br)c2Cl]

To a solution of tert-butyl 5'-bromo-4'-chloro-3-oxospiro[cyclopentane-1,3'-pyrrolo[2,3-b]pyridine]-1'(2'H)-carboxylate (430 mg, 1.07 mmol) and cesium fluoride (10 mg, 0.066 mmol) in THF (3 mL) at 0° C. was added a solution of trifluoromethyltrimethylsilane (180 mg, 1.28 mmol) in THF (1 mL). The reaction mixture was allowed to warm up to RT and stirred for 16 h. Further trifluoromethyltrimethylsilane (90 mg, 0.633 mmol) and cesium fluoride (30 mg, 0.19 mmol) were added, and the reaction mixture was stirred for 16 h. The mixture was concentrated, and the residue purified by chromatography on silica (solvent gradient 0-20% EtOAc in cyclohexane) to afford the title compound (197 mg, 39%) as a white solid. $^1$H NMR (400 MHz, CDCl$_3$): δ ppm 8.40 (m, 1H), 3.89 (d, J=11.2 Hz, 1H), 3.79 (d, J=11.2 Hz, 1H), 2.87-2.74 (m, 2H), 2.31 (d, J=15.5 Hz, 1H), 2.13 (m, 1H), 2.03 (m, 1H), 1.86 (m, 1H), 1.54 (s, 9H).

Step 2: 5'-Bromo-4'-chloro-3-(trifluoromethyl)-1',2'-dihydrospiro[cyclopentane-1,3'-pyrrolo[2,3-b]pyridin]-3-ol

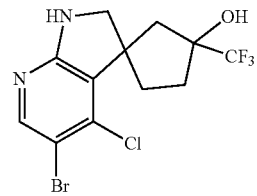 [SMILES: OC1(C(F)(F)F)CCC2(CNc3ncc(Br)c(Cl)c32)C1]

A solution of tert-butyl 5'-bromo-4'-chloro-3-hydroxy-3-(trifluoromethyl)spiro[cyclopentane-1,3'-pyrrolo[2,3-b]pyridine]-1'(2'H)-carboxylate (193 mg, 0.41 mmol) in TFA/DCM (1:2, 3 mL) was stirred at RT for 2 h, then diluted with DCM and washed with sat. aq. sodium bicarbonate. The organic extract was dried (MgSO₄) and concentrated. The residue was purified by chromatography on silica (solvent gradient 0-100% EtOAc in cyclohexane) to afford the title compound (128 mg, 84%) as a white solid. LCMS (ESI) [M+H]⁺ 372/374.

Example 35

(2RS,3'SR)-5"-Bromo-4"-chloro-1"-(4-methoxybenzyl)-1",2"-dihydrodispiro[oxirane-2,1'-cyclopentane-3',3"-pyrrolo[2,3-b]pyridine] and (2RS,3'RS)-5"-bromo-4"-chloro-1"-(4-methoxybenzyl)-1",2"-dihydrodispiro[oxirane-2,1'-cyclopentane-3',3"-pyrrolo[2,3-b]pyridine]

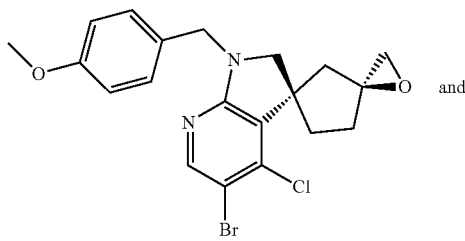

and

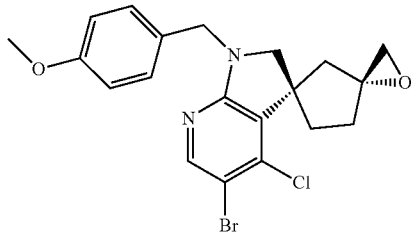

To a suspension of sodium hydride (60% oil, 91 mg, 2.28 mmol) in DMSO (1.5 mL), preheated at 70° C. for 30 min then cooled to RT, was added trimethylsulfoxonium iodide (0.6 g, 2.73 mmol). The reaction mixture was stirred for 20 min, and cooled to 0° C. A solution of 5-bromo-4-chloro-1-[(4-methoxyphenyl)methyl]spiro[2H-pyrrolo[2,3-b]pyridine-3,3'-cyclopentane]-1'-one (0.32 g, 0.76 mmol) in THF (3 mL) was added, and the mixture was stirred at RT for 16 h. The reaction mixture was concentrated, then diluted with EtOAc and water. The aqueous layer was extracted with further EtOAc. The combined organic extracts were dried (Na₂SO₄) and concentrated. The residue was purified by chromatography on silica (solvent gradient 0-50% EtOAc in cyclohexane) to afford (2RS,3'SR)-5"-bromo-4"-chloro-1"-(4-methoxybenzyl)-1",2"-dihydrodispiro[oxirane-2,1'-cyclopentane-3',3"-pyrrolo[2,3-b]pyridine](125 mg, 38%) and (2RS,3'RS)-5"-bromo-4"-chloro-1"-(4-methoxybenzyl)-1",2"-dihydrodispiro[oxirane-2,1'-cyclopentane-3',3"-pyrrolo[2,3-b]pyridine](18 mg, 5%). LCMS (ESI) [M+H]⁺ 435.1/437.1/439.0.

Example 36

5'-Bromo-4'-chloro-1'-(4-methoxybenzyl)-1',2'-dihydrospiro[cyclopentane-1,3'-pyrrolo[2,3-b]pyridin]-3-yl)methyl methanesulfonate

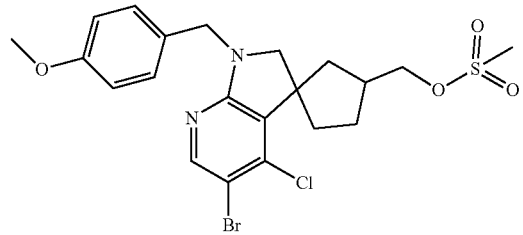 [SMILES: COc1ccc(CN2CC3(CCC(COS(C)(=O)=O)C3)c3c2ncc(Br)c3Cl)cc1]

Step 1: (5'-Bromo-4'-chloro-1'-(4-methoxybenzyl)-1',2'-dihydrospiro[cyclopentane-1,3'-pyrrolo[2,3-b]pyridin]-3-yl)methanol

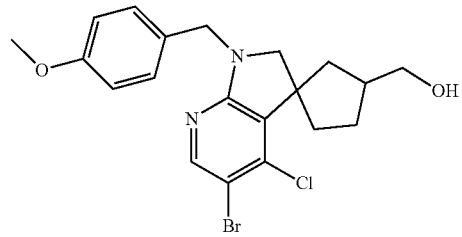 [SMILES: COc1ccc(CN2CC3(CCC(CO)C3)c3c2ncc(Br)c3Cl)cc1]

To a solution of 5"-bromo-4"-chloro-1"-(4-methoxybenzyl)-1",2"-dihydrodispiro[oxirane-2,1'-cyclopentane-3',3"-pyrrolo[2,3-b]pyridine](1.08 g, 2.48 mmol) in THF (20 mL) at RT were added sodium cyanoborohydride (0.38 g, 6.2 mmol) and followed by boron trifluoride diethyl etherate (0.31 mL, 2.48 mmol) as a solution in THF (5 mL). The reaction mixture was stirred for 2 h, then was diluted with EtOAc and brine. The aqueous layer was extracted with further EtOAc. The combined organic extracts were dried (Na₂SO₄) and concentrated. The residue was purified by chromatography on silica (solvent gradient 0-70% EtOAc in cyclohexane) to afford the title compound (426 mg, 39%) as a white solid. LCMS (ESI) [M+H]⁺ 437/439/441.

Step 2: 5'-Bromo-4'-chloro-1'-(4-methoxybenzyl)-1',2'-dihydrospiro[cyclopentane-1,3'-pyrrolo[2,3-b]pyridin]-3-yl)methyl methanesulfonate

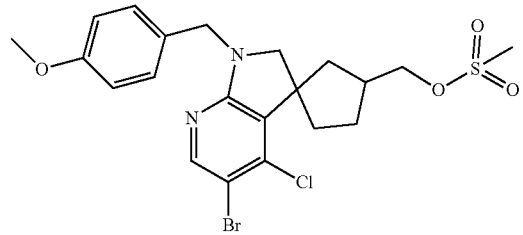 [SMILES: COc1ccc(CN2CC3(CCC(COS(C)(=O)=O)C3)c3c2ncc(Br)c3Cl)cc1]

To a solution of (5'-bromo-4'-chloro-1'-(4-methoxybenzyl)-1',2'-dihydrospiro[cyclopentane-1,3'-pyrrolo[2,3-b]pyridin]-3-yl)methanol (390 mg, 0.90 mmol) and triethylamine (0.25 mL, 1.8 mmol) in DCM (15 mL) was added methanesulfonyl chloride (0.1 mL, 1.35 mmol) as a solution in DCM (3 mL). The reaction mixture was stirred at RT for 20 min, then diluted with DCM and aq. sat. sodium bicarbonate. The aqueous layer was extracted with further DCM. The combined organic extracts were dried (Na$_2$SO$_4$) and concentrated. The residue was purified by chromatography on silica (solvent gradient 0-50% EtOAc in cyclohexane) to afford the title compound (460 mg, 99%). LCMS (ESI) [M+H]$^+$ 515/517/519.

Example 37

2-(-5'-Bromo-4'-chloro-1',2'-dihydrospiro[cyclopentane-1,3'-pyrrolo[2,3-b]pyridin]-3-yl)acedonitrile

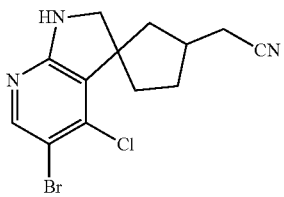 [SMILES: N#CCC1CCC2(CNc3ncc(Br)c(Cl)c32)C1]

Step 1: 2-(5'-Bromo-4'-chloro-1'-(4-methoxybenzyl)-1',2'-dihydrospiro[cyclopentane-1,3'-pyrrolo[2,3-b]pyridin]-3-yl)acetonitrile

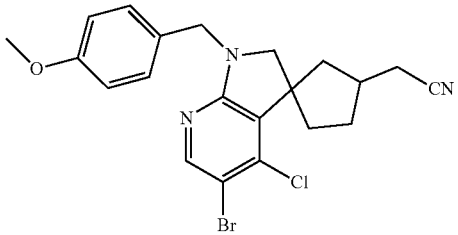 [SMILES: COc1ccc(CN2CC3(CCC(CC#N)C3)c3c2ncc(Br)c3Cl)cc1]

Sodium cyanide (90 mg, 1.81 mmol) was added to a solution of 5'-bromo-4'-chloro-1'-(4-methoxybenzyl)-1',2'-dihydrospiro[cyclopentane-1,3'-pyrrolo[2,3-b]pyridin]-3-yl methanesulfonate (310 mg, 0.60 mmol) and 15-crown-5 (0.04 mL, 0.18 mmol) in DMSO (3 mL). The reaction mixture was heated at 90° C. for 2 h. The reaction mixture was diluted with EtOAc and water. The aqueous layer was extracted with further EtOAc. The combined organic extracts were dried (Na$_2$SO$_4$) and concentrated. The residue was purified by chromatography on silica (solvent gradient 0-50% EtOAc in cyclohexane) to afford the title compound (242 mg, 83%) as a gum. LCMS (ESI) [M+H]$^+$ 446/448/450.

Step 2: 2-(-5'-Bromo-4'-chloro-1',2'-dihydrospiro[cyclopentane-1,3'-pyrrolo[2,3-b]pyridin]-3-yl)acedonitrile

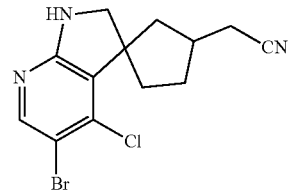 [SMILES: N#CCC1CCC2(CNc3ncc(Br)c(Cl)c32)C1]

A solution of 2-(5'-bromo-4'-chloro-1'-(4-methoxybenzyl)-1',2'-dihydrospiro[cyclopentane-1,3'-pyrrolo[2,3-b]pyridin]-3-yl)acetonitrile (90 mg, 0.21 mmol) in TFA/water (20:1, 2.1 mL) was heated at 80° C. in a sealed tube for 1.5 h. The reaction mixture was concentrated, then diluted with DCM and aq. sat. sodium bicarbonate. The aqueous layer was extracted with further DCM. The combined organic extracts were dried (Na$_2$SO$_4$) and concentrated. The residue was purified by chromatography on silica (solvent gradient 0-5% MeOH·NH$_3$ in DCM) to afford the title compound (71 mg, quant.) as a gum. LCMS (ESI) [M+H]$^+$ 326/328/330.

Example 38

2-(5'-Bromo-4'-chloro-1',2'-dihydrospiro[cyclopentane-1,3'-pyrrolo[2,3-b]pyridin]-3-yl)acetamide

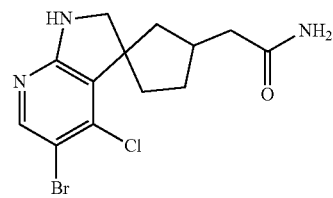 [SMILES: NC(=O)CC1CCC2(CNc3ncc(Br)c(Cl)c32)C1]

A solution of 2-(5'-bromo-4'-chloro-1'-(4-methoxybenzyl)-1',2'-dihydrospiro[cyclopentane-1,3'-pyrrolo[2,3-b]pyridin]-3-yl)acedonitrile (128 mg, 0.287 mmol) in TFA/water (10:1, 2.2 mL) was heated at 80° C. in a sealed tube for 16 h. The reaction mixture was concentrated, then diluted with DCM and aq. sat. sodium bicarbonate. The aqueous layer was extracted with further DCM. The combined organic extracts were dried (Na$_2$SO$_4$) and concentrated. The residue was purified by chromatography on silica (solvent gradient 0-10% MeOH·NH$_3$ in DCM) to afford the title compound (75 mg, 76%) as a gum. LCMS (ESI) [M+H]$^+$ 344/346/348.

Example 39

2-((1RS,3SR)-5'-Bromo-4'-chloro-3-hydroxy-1',2'-dihydrospiro[cyclopentane-1,3'-pyrrolo[2,3-b]pyridin]-3-yl)acetonitrile

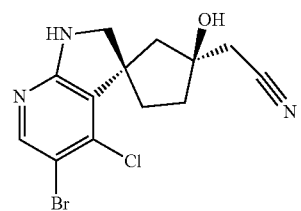 [SMILES: N#CC[C@]1(O)CC[C@@]2(CNc3ncc(Br)c(Cl)c32)C1]

Step 1: 2-((1RS,3SR)-5'-Bromo-4'-chloro-3-hydroxy-1'-(4-methoxybenzyl)-1',2'-dihydrospiro[cyclopentane-1,3'-pyrrolo[2,3-b]pyridin]-3-yl)acedonitrile and 2-((1RS,3RS)-5'-Bromo-4'-chloro-3-hydroxy-1'-(4-methoxybenzyl)-1',2'-dihydrospiro[cyclopentane-1,3'-pyrrolo[2,3-b]pyridin]-3-yl)acetonitrile

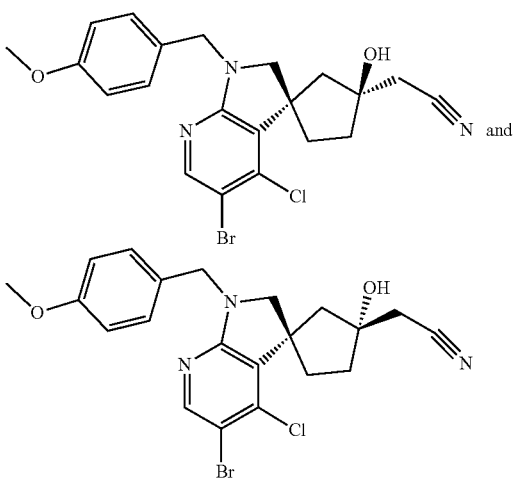

n-BuLi (1.6N, 0.39 mL, 0.63 mmol) was added to a solution of MeCN (1N in THF, 0.63 mL, 0.63 mmol) in THF (3 mL) at −78° C. The reaction mixture was stirred for 15 min, then a solution of 5'-bromo-4'-chloro-1'-(4-methoxybenzyl)-1',2'-dihydrospiro[cyclopentane-1,3'-pyrrolo[2,3-b]pyridin]-3-one (0.22 g, 0.52 mmol) in THF (2 mL) was added. The reaction mixture was stirred at −78° C. for 1 h, then was quenched by addition of aq. sat. ammonium chloride. The mixture was partitioned between EtOAc and water. The combined organic extracts were dried ($Na_2SO_4$) and concentrated. The residue was purified by chromatography on silica (solvent gradient 0-80% EtOAc in cyclohexane), then by Method C to afford 2-((1RS,3SR)-5'-bromo-4'-chloro-3-hydroxy-1'-(4-methoxybenzyl)-1',2'-dihydrospiro[cyclopentane-1,3'-pyrrolo[2,3-b]pyridin]-3-yl)acedonitrile (78 mg) and 2-((1RS,3RS)-5'-bromo-4'-chloro-3-hydroxy-1'-(4-methoxybenzyl)-1',2'-dihydrospiro[cyclopentane-1,3'-pyrrolo[2,3-b]pyridin]-3-yl)acetonitrile (66 mg) as white solids. LCMS (ESI) [M+H]$^+$ 462.1/464.0/466.0.

Step 2: 2-((1RS,3SR)-5'-Bromo-4'-chloro-3-hydroxy-1',2'-dihydrospiro[cyclopentane-1,3'-pyrrolo[2,3-b]pyridin]-3-yl)acetonitrile

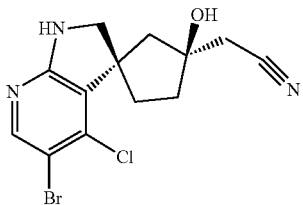 [SMILES: N#CC[C@]1(O)CC[C@@]2(CNc3ncc(Br)c(Cl)c32)C1]

A solution of 2-((1RS,3SR)-5'-bromo-4'-chloro-3-hydroxy-1'-(4-methoxybenzyl)-1',2'-dihydrospiro[cyclopentane-1,3'-pyrrolo[2,3-b]pyridin]-3-yl)acedonitrile (78 mg, 0.169 mmol) in TFA/water (20:1, 2.1 mL) was heated in a sealed tube at 80° C. for 3 h. The reaction mixture was concentrated, then diluted with DCM and aq. sat. sodium bicarbonate. The aqueous layer was extracted with further DCM. The combined organic extracts were dried ($Na_2SO_4$) and concentrated. The residue was purified by chromatography on silica (solvent gradient 0-100% EtOAc in cyclohexane) to afford the title compound (61 mg, assume quantitative) as a white solid. LCMS (ESI) [M+H]$^+$ 342.0/344.0/346.0.

Example 40

2-(1RS,3RS)-5'-Bromo-4'-chloro-3-hydroxy-1',2'-dihydrospiro[cyclopentane-1,3'-pyrrolo[2,3-b]pyridin]-3-yl)acetonitrile

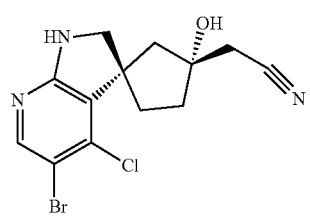 [SMILES: N#CC[C@@]1(O)CC[C@@]2(CNc3ncc(Br)c(Cl)c32)C1]

A solution of 2-((1RS,3RS)-5'-bromo-4'-chloro-3-hydroxy-1'-(4-methoxybenzyl)-1',2'-dihydrospiro[cyclopentane-1,3'-pyrrolo[2,3-b]pyridin]-3-yl)acedonitrile (70 mg, 0.140 mmol) in TFA/water (20:1, 2.1 mL) was heated in a sealed tube at 80° C. for 3 h. The reaction mixture was concentrated, then diluted with DCM and aq. sat. sodium bicarbonate. The aqueous layer was extracted with further DCM. The combined organic extracts were dried ($Na_2SO_4$) and concentrated. The residue was purified by chromatography on silica (solvent gradient 0-100% EtOAc in cyclohexane) to afford the title compound (66 mg, assume quantitative) as a gum. LCMS (ESI) [M+H]$^+$ 342.0/344.0/346.0.

Example 41

5'-Bromo-4'-chloro-3-((methylsulfonyl)methylene)-1',2'-dihydrospiro[cyclopentane-1,3'-pyrrolo[2,3-b]pyridine]

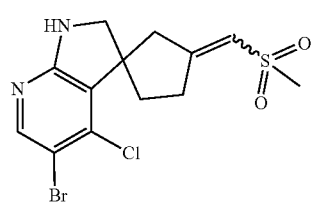 [SMILES: CS(=O)(=O)C=C1CCC2(CNc3ncc(Br)c(Cl)c32)C1]

303

Step 1: 5'-Bromo-4'-chloro-1'-(4-methoxybenzyl)-3-((methylsulfonyl)methylene)-1',2'-dihydrospiro[cyclopentane-1,3'-pyrrolo[2,3-b]pyridine]

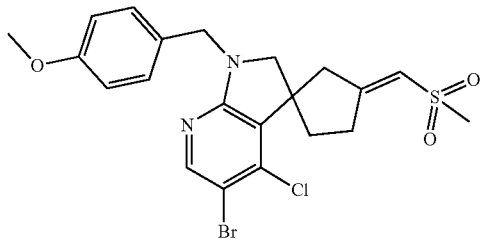 [SMILES: COc1ccc(CN2CC3(CC/C(=C\S(C)(=O)=O)C3)c3c2ncc(Br)c3Cl)cc1]

To a solution of diethyl (methylsulfonylmethyl)phosphonate (84 mg, 0.36 mmol) in THF (2 mL) at −78° C. was added n-BuLi (1.6N, 0.23 mL, 0.36 mmol). The reaction mixture was stirred for 30 min at −78° C., then a solution of 5'-bromo-4'-chloro-1'-(4-methoxybenzyl)-1',2'-dihydrospiro[cyclopentane-1,3'-pyrrolo[2,3-b]pyridin]-3-one (153 mg, 0.36 mmol) in THF (2 mL) was added. The reaction mixture was allowed to warm up to RT, stirred for 16 h, then diluted with EtOAc and aq. sat. ammonium chloride. The aqueous layer was extracted with further EtOAc. The combined organic extracts were dried ($Na_2SO_4$) and concentrated. The residue was purified by chromatography on silica (solvent gradient 0-100% EtOAc in cyclohexane) to afford the title compound (106 mg, 59%) as a gum. LCMS (ESI) $[M+H]^+$ 497.0/499.0/501.1.

Step 2: 5'-Bromo-4'-chloro-3-((methylsulfonyl)methylene)-1',2'-dihydrospiro[cyclopentane-1,3'-pyrrolo[2,3-b]pyridine]

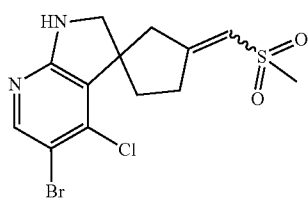 [SMILES: CS(=O)(=O)C=C1CCC2(CNc3ncc(Br)c(Cl)c32)C1]

A solution of 5'-bromo-4'-chloro-1'-(4-methoxybenzyl)-3-((methylsulfonyl)methylene)-1',2'-dihydrospiro[cyclopentane-1,3'-pyrrolo[2,3-b]pyridine](130 mg, 0.26 mmol) in TFA/water (20:1, 2.1 mL) was heated in a sealed tube at 80° C. for 5 h, then at RT for 3 days. The reaction mixture was concentrated, then diluted with DCM and aq. sat. sodium bicarbonate. The aqueous layer was extracted with further DCM. The combined organic extracts were dried ($Na_2SO_4$) and concentrated. The residue was purified by chromatography on silica (solvent gradient 0-100% EtOAc in cyclohexane) to afford the title compound (55 mg, 56%). LCMS (ESI) $[M+H]^+$ 377.0/379.0/381.0.

304

Example 42

2-(5'-Bromo-4'-chloro-1',2'-dihydrospiro[cyclopentane-1,3'-pyrrolo[2,3-b]pyridin]-3-ylidene)acetonitrile

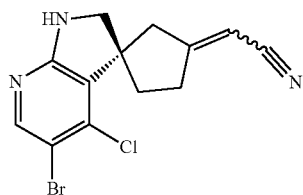 [SMILES: N#CC=C1CC[C@@]2(CNc3ncc(Br)c(Cl)c32)C1]

Step 1: 2-(5'-Bromo-4'-chloro-1'-(4-methoxybenzyl)-1',2'-dihydrospiro[cyclopentane-1,3'-pyrrolo[2,3-b]pyridin]-3-ylidene)acetonitrile To a solution of diethyl cyanomethylphosphonate (250 mg, 1.52 mmol) in THF (5 mL) at RT was added potassium tert-butoxide (1M in THF, 1.4 mL, 1.4 mmol). The reaction mixture was stirred for 30 min at −78° C., then a solution of 5'-bromo-4'-chloro-1'-(4-methoxybenzyl)-1',2'-dihydrospiro[cyclopentane-1,3'-pyrrolo[2,3-b]pyridin]-3-one (535 mg, 1.27 mmol) in THF (3 mL) was added. The reaction mixture was allowed to warm up to RT, stirred for 2 h, then diluted with EtOAc and aq. sat. ammonium chloride. The aqueous layer was extracted with further EtOAc. The combined organic extracts were dried ($Na_2SO_4$) and concentrated. The residue was purified by chromatography on silica (solvent gradient 0-50% EtOAc in cyclohexane) to afford the title compound (460 mg, 82%) as a gum. LCMS (ESI) $[M+H]^+$ 444/446/448.

Example 43

Step 2: 2-(5'-Bromo-4'-chloro-1',2'-dihydrospiro[cyclopentane-1,3'-pyrrolo[2,3-b]pyridin]-3-ylidene)acetonitrile

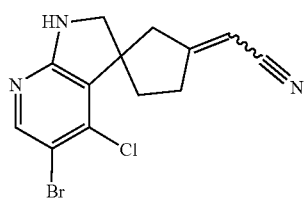 [SMILES: N#CC=C1CCC2(CNc3ncc(Br)c(Cl)c32)C1]

A solution of 2-(5'-bromo-4'-chloro-1'-(4-methoxybenzyl)-1',2'-dihydrospiro[cyclopentane-1,3'-pyrrolo[2,3-b]pyridin]-3-ylidene)acetonitrile (452 mg, 1.0 mmol) in TFA (3 mL) was heated in a sealed tube at 70° C. for 8 h, then at RT for 16 h. The reaction mixture was concentrated, then diluted with DCM and aq. sat. sodium bicarbonate. The aqueous layer was extracted with further DCM. The combined organic extracts were dried (Na$_2$SO$_4$) and concentrated. The residue was purified by chromatography on silica (solvent gradient 0-100% EtOAc in cyclohexane) to afford the title compound (235 mg, 71%) as a white solid. LCMS (ESI) [M+H]$^+$ 324/326/328.

Example 44

(1RS,3SR)-5'-Bromo-4'-chloro-3-(1H-1,2,4-triazol-5-yl)-1',2'-dihydrospiro[cyclopentane-1,3'-pyrrolo[2,3-b]pyridine]

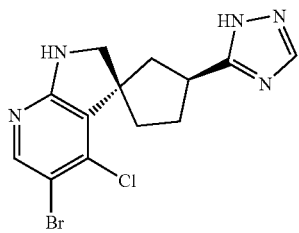 [SMILES: Clc1c(Br)cnc2c1[C@]1(CC[C@H](c3ncn[nH]3)C1)CN2]

A mixture of (1RS,3SR)-5'-bromo-4'-chloro-1',2'-dihydrospiro[cyclopentane-1,3'-pyrrolo[2,3-b]pyridine]-3-carboxamide (75 mg, 0.227 mmol) and N,N-dimethylformamide dimethyl acetal (1.25 mL) was stirred at 60° C. for 1 h. Toluene was added and evaporated (2×). To the residue was added acetic acid (2 mL) and hydrazine hydrate (0.5 mL). The mixture was stirred at 90° C. for 2 h and then evaporated. The residue was partitioned between EtOAc and aq. sodium bicarbonate. The aqueous phase was extracted with more EtOAc and the combined organic extracts were washed with water, then brine, and evaporated. The residue was purified by chromatography on silica (solvent gradient 2-12% MeOH·NH$_3$ in DCM) to afford the title compound (80 mg, 100%) as a colorless solid. LCMS (ESI) [M+H]$^+$ 354/356/358.

Example 45

5-((1RS,3SR)-5'-Bromo-4'-chloro-1',2'-dihydrospiro[cyclopentane-1,3'-pyrrolo[2,3-b]pyridin]-3-yl)-3-methyl-1,2,4-oxadiazole

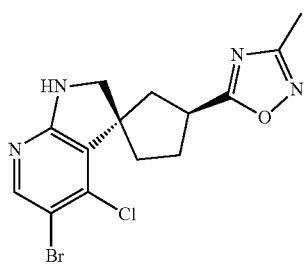 [SMILES: Cc1noc([C@H]2CC[C@@]3(CNc4ncc(Br)c(Cl)c43)C2)n1]

To a solution of (1RS,3SR)-5'-bromo-4'-chloro-1',2'-dihydrospiro[cyclopentane-1,3'-pyrrolo[2,3-b]pyridine]-3-carboxylic acid HCl salt (89 mg, 0.27 mmol) and N-hydroxyacetamidine (24 mg, 0.32 mmol) in DMF (1 mL) was added DIPEA (0.19 mL, 1.07 mmol). HATU (0.153 g, 0.40 mmol) was added portionwise over 5 min. The mixture was stirred at RT for 20 min, then partitioned between EtOAc and aq. sodium bicarbonate. The aqueous phase was extracted with more EtOAc and the combined organic extracts were washed with water, then brine, and evaporated. The residue was purified by chromatography on silica (solvent gradient 2-10% MeOH·NH$_3$ in DCM) to afford N-(4'RS,3SR)-5'-bromo-4'-chloro-1',2'-dihydrospiro[cyclopentane-1,3'-pyrrolo[2,3-b]pyridine]-3-carbonyl)oxy)acetimidamide (53.2 mg, 51%) as a colorless gum. LCMS (ESI) [M+H]$^+$ 387/389/391. This intermediate was suspended in toluene (30 mL) and refluxed under Dean-Stark conditions for 5 h. The cooled reaction mixture was purified by chromatography on silica (solvent gradient 25-100% EtOAc in toluene) to afford the title compound (26.8 mg, 53%) as colorless gum. LCMS (ESI) [M+H]$^+$ 369/371/373.

Example 46

(1RS,3SR)-5'-Bromo-4'-chloro-N-methyl-1',2'-dihydrospiro[cyclopentane-1,3'-pyrrolo[2,3-b]pyridine]-3-carboxamide

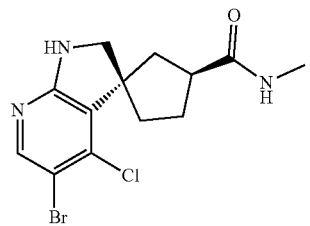 [SMILES: CNC(=O)[C@H]1CC[C@@]2(CNc3ncc(Br)c(Cl)c32)C1]

A mixture of (1RS,3SR)-5'-bromo-4'-chloro-1',2'-dihydrospiro[cyclopentane-1,3'-pyrrolo[2,3-b]pyridine]-3-carbonitrile (80 mg, 0.256 mmol) and HCl (6M aq., 6 mL) was heated in a sealed tube at 90° C. for 1.25 h. The cooled mixture was evaporated to dryness. Toluene was added and evaporated (2×) to give (1RS,3SR)-5'-bromo-4'-chloro-1',2'-dihydrospiro[cyclopentane-1,3'-pyrrolo[2,3-b]pyridine]-3-carboxylic acid as the HCl salt. To this salt was added methylamine hydrochloride (26 mg, 0.384 mmol), DMF (1 mL) and DIPEA (0.266 mL, 1.54 mmol). HATU (0.195 g, 0.512 mmol) was added portionwise over 5 min. The mixture was stirred at RT for 30 min, then partitioned between EtOAc and aq. sodium bicarbonate. The aqueous phase was extracted with more EtOAc and the combined organic extracts were washed with water, then brine, and evaporated. The residue was purified by chromatography on silica (solvent gradient 2-20% MeOH·NH$_3$ in DCM) to afford the title compound (75 mg, 85%) as a colorless solid. LCMS (ESI) [M+H]$^+$ 344/346/348.

Example 47

(1RS,3SR)-5'-Bromo-4'-chloro-N,N-dimethyl-1',2'-dihydrospiro[cyclopentane-1,3'-pyrrolo[2,3-b]pyridine]-3-carboxamide

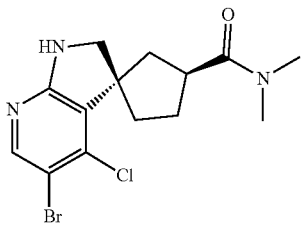 [SMILES: CN(C)C(=O)[C@H]1CC[C@@]2(CNc3ncc(Br)c(Cl)c32)C1]

To a solution of (1RS,3SR)-5'-bromo-4'-chloro-1',2'-dihydrospiro[cyclopentane-1,3'-pyrrolo[2,3-b]pyridine]-3-carboxylic acid HCl salt (80 mg, 0.24 mmol) in DMF (0.75 mL) was added DIPEA (0.25 mL, 1.45 mmol) and dimethylamine hydrochloride (29.5 mg, 0.36 mmol). HATU (0.183 g, 0.48 mmol) was added portionwise over 5 min. The mixture was stirred at RT for 20 min, then partitioned between EtOAc and aq. sodium bicarbonate. The aqueous phase was extracted with more EtOAc and the combined organic extracts were washed with water, then brine, and evaporated. The residue was purified by chromatography on silica (solvent gradient 2-10% MeOH·NH$_3$ in DCM) to afford the title compound (54.7 mg, 63%) as a yellow gum. LCMS (ESI) [M+H]$^+$ 358/360/362.

Example 48

(1RS,3SR)-5'-Bromo-4'-chloro-N-(2-hydroxyethyl)-1',2'-dihydrospiro[cyclopentane-1,3'-pyrrolo[2,3-b]pyridine]-3-carboxamide

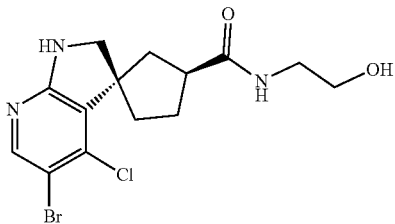 [SMILES: O=C(NCCO)[C@H]1CC[C@@]2(CNc3ncc(Br)c(Cl)c32)C1]

A mixture of tert-butyl (1RS,3SR)-5'-bromo-4'-chloro-3-cyanospiro[cyclopentane-1,3'-pyrrolo[2,3-b]pyridine]-1'(2'H)-carboxylate (0.746 g, 1.81 mmol) and HCl (6M aq., 25 mL) was stirred at 90° C. for 1.5 h. The cooled mixture was evaporated to dryness. Toluene was added and evaporated (2×) to give (1RS,3SR)-5'-bromo-4'-chloro-1',2'-dihydrospiro[cyclopentane-1,3'-pyrrolo[2,3-b]pyridine]-3-carboxylic acid as the HCl salt (0.749 g). To this acid (85.2 mg, 0.26 mmol) was added DMF (0.75 mL), DIPEA (0.18 mL, 1.03 mmol) and 2-aminoethanol (0.023 mL, 0.39 mmol). HATU (0.195 g, 0.512 mmol) was added portionwise over 5 min. The mixture was stirred at RT for 20 min, then partitioned between EtOAc and aq. sodium bicarbonate. The aqueous phase was extracted with more EtOAc and the combined organic extracts were washed with water, then brine, and evaporated. The residue was purified by chromatography on silica (solvent gradient 2-12% MeOH·NH$_3$ in DCM) to afford the title compound (58 mg, 60%) as a yellow foam. LCMS (ESI) [M+H]$^+$ 374/376/378.

Example 49

1-((1RS,3SR)-5'-Bromo-4'-chloro-1',2'-dihydrospiro[cyclopentane-1,3'-pyrrolo[2,3-b]pyridin]-3-yl)imidazolidin-2-one

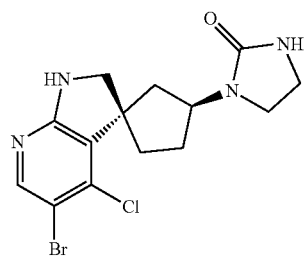 [SMILES: O=C1NCCN1[C@H]1CC[C@@]2(CNc3ncc(Br)c(Cl)c32)C1]

Step 1: N-1-((1RS,3SR)-5'-bromo-4'-chloro-1'-(4-methoxybenzyl)-1',2'-dihydrospiro [cyclopentane-1,3'-pyrrolo[2,3-b]pyrdin]-3-yl)ethane-1,2-diamine

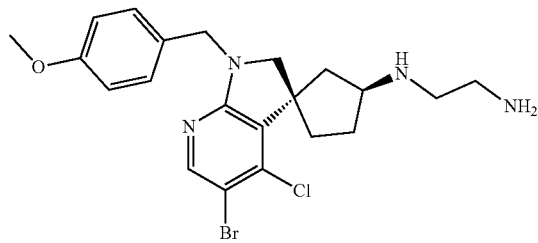 [SMILES: COc1ccc(CN2C[C@@]3(CC[C@H](NCCN)C3)c3c2ncc(Br)c3Cl)cc1]

A mixture of (1RS,3RS)-5'-bromo-4'-chloro-1'-(4-methoxybenzyl)-1',2'-dihydrospiro[cyclopentane-1,3'-pyrrolo[2,3-b]pyridin]-3-yl methanesulfonate (0.125 g, 0.25 mmol) and ethylenediamine (0.5 mL, 7.48 mmol) was stirred at 70° C. for 45 min. Toluene was added and evaporated (2×) and the residue was partitioned between chloroform and water. The aqueous phase was extracted with more chloroform. The combined organic extracts were dried (Na$_2$SO$_4$), and evaporated to afford the title compound (0.114 g, 98%) as pale yellow gum. LCMS (ESI) [M+H]$^+$ 465/467/469.

Step 2: 1-((1RS,3SR)-5'-Bromo-4'-chloro-1'-(4-methoxybenzyl)-1',2'-dihydrospiro[cyclopentane-1,3'-pyrrolo[2,3-b]pyridin]-3-yl)imidazolidin-2-one

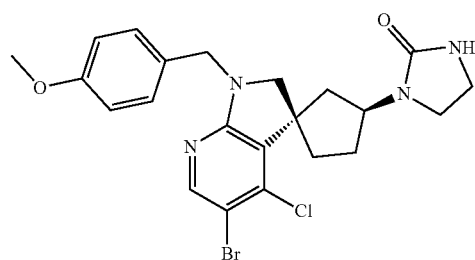 [SMILES: COc1ccc(CN2C[C@@]3(CC[C@H](N4CCNC4=O)C3)c3c2ncc(Br)c3Cl)cc1]

(1,1'-Carbonyldiimidazole (0.068 g, 0.42 mmol) was added to a solution of N-1-((1RS,3SR)-5'-bromo-4'-chloro-1'-(4-methoxybenzyl)-1',2'-dihydrospiro[cyclopentane-1,3'-pyrrolo[2,3-b]pyridin]-3-yl)ethane-1,2-diamine (0.13 g, 0.28 mmol) in MeCN (2 mL) at RT. The mixture was stirred at 60° C. for 1.5 h, then cooled to RT and partitioned between chloroform and water. The aqueous phase was extracted with more chloroform and the combined organic extracts were dried (Na$_2$SO$_4$) and evaporated. The residue was purified by chromatography on silica (solvent gradient 2-8% MeOH·NH$_3$ in DCM) to afford the title compound (0.1125 g, 82%) as colorless solid. LCMS (ESI) [M+H]$^+$ 491/493/495.

Step 3: 1-((1RS,3SR)-5'-Bromo-4'-chloro-1',2'-dihydrospiro[cyclopentane-1,3'-pyrrolo[2,3-b]pyridin]-3-yl)imidazolidin-2-one

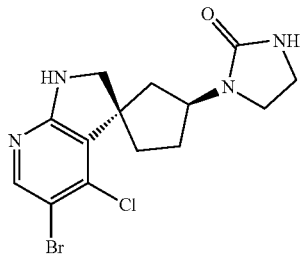 [SMILES: O=C1NCCN1[C@H]1CC[C@@]2(CNc3ncc(Br)c(Cl)c32)C1]

A mixture of 1-((1RS,3SR)-5'-bromo-4'-chloro-1'-(4-methoxybenzyl)-1',2'-dihydrospiro[cyclopentane-1,3'-pyrrolo[2,3-b]pyridin]-3-yl)imidazolidin-2-one (0.1125 g, 0.23 mmol) in TFA (2.5 mL) and anisole (0.25 mL) was stirred at 70° C. for 16 h. Toluene was added and evaporated (2×). The residue was purified on SCX-2 cartridge (eluting with MeOH then MeOH·NH$_3$). The residue was purified by chromatography on silica (solvent gradient 2-8% MeOH·NH$_3$ in DCM) to afford the title compound (0.061 g, 72%) as a white solid. LCMS (ESI) [M+H]$^+$ 371/373/375.

Example 50

3-((1RS,3SR)-5'-Bromo-4'-chloro-1',2'-dihydrospiro[cyclopentane-1,3'-pyrrolo[2,3-b]pyridin]-3-yl)oxazolidin-2-one

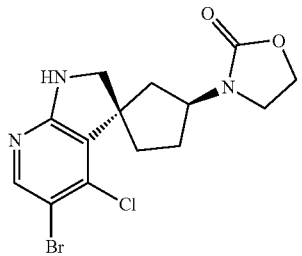 [SMILES: O=C1OCCN1[C@H]1CC[C@@]2(CNc3ncc(Br)c(Cl)c32)C1]

Step 1: 2-(((1RS,3SR)-5'-Bromo-4'-chloro-1'-(4-methoxybenzyl)-1',2'-dihydrospiro[cyclopentane-1,3'-pyrrolo[2,3-b]pyrdin]-3-yl)amino)ethan-1-ol

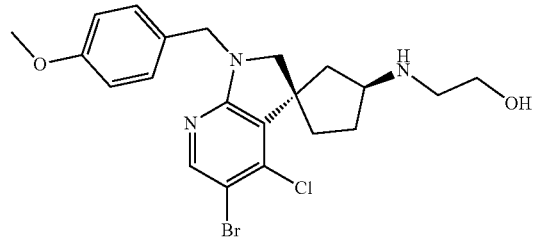 [SMILES: COc1ccc(CN2C[C@@]3(CC[C@H](NCCO)C3)c3c2ncc(Br)c3Cl)cc1]

A mixture of (1RS,3RS)-5'-bromo-4'-chloro-1'-(4-methoxybenzyl)-1',2'-dihydrospiro[cyclopentane-1,3'-pyrrolo[2,3-b]pyridin]-3-yl methanesulfonate (142 mg, 0.28 mmol) and 2-aminoethanol (0.75 mL, 12.4 mmol) was stirred at 80° C. for 2 h. The cooled reaction mixture was partitioned between EtOAc and aq. sodium bicarbonate. The aqueous phase was extracted with more EtOAc and the combined organic extracts were washed with water, brine, dried (Na$_2$SO$_4$) and evaporated to afford the title compound (125.5 mg, 95%) as pale yellow gum. LCMS (ESI) [M+H]$^+$ 466/468/470.

Step 2: 3-((1RS,3SR)-5'-Bromo-4'-chloro-1'-(4-methoxybenzyl)-1',2'-dihydrospiro[cyclopentane-1,3'-pyrrolo[2,3-b]pyridin]-3-yl)oxazolidin-2-one

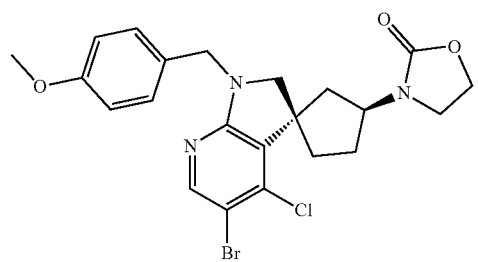 [SMILES: COc1ccc(CN2C[C@@]3(CC[C@H](N4CCOC4=O)C3)c3c2ncc(Br)c3Cl)cc1]

To an ice-cooled solution of 2-((1RS,3SR)-5'-bromo-4'-chloro-1'-(4-methoxybenzyl)-1',2'-dihydrospiro[cyclopentane-1,3'-pyrrolo[2,3-b]pyridin]-3-yl)amino)ethan-1-ol (125.5 mg, 0.27 mmol) in toluene (0.5 mL) was added 12.5% aq. potassium hydroxide (0.6 mL, 1.34 mmol). Phosgene solution (20% in toluene, 0.27 mL, 0.54 mmol) was added dropwise over 5 min. The mixture was stirred in the ice bath for a further 15 min, then partitioned between EtOAc and aq. sodium bicarbonate. The aqueous phase was extracted with more EtOAc and the combined organic extracts were washed with water, brine, dried (Na$_2$SO$_4$) and evaporated. The residue was purified by chromatography on silica (solvent gradient 1-5% MeOH in DCM) to afford the title compound (107 mg, 81%) as a white solid. LCMS (ESI) [M+H]$^+$ 492/494/496.

Step 3: 3-((1RS,3SR)-5'-Bromo-4'-chloro-1',2'-dihydrospiro[cyclopentane-1,3'-pyrrolo[2,3-b]pyridin]-3-yl)oxazolidin-2-one

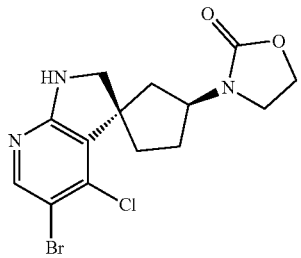 [SMILES: O=C1OCCN1[C@H]1CC[C@@]2(CNc3ncc(Br)c(Cl)c32)C1]

A mixture of 3-((1RS,3SR)-5'-bromo-4'-chloro-1'-(4-methoxybenzyl)-1',2'-dihydrospiro[cyclopentane-1,3'-pyrrolo[2,3-b]pyridin]-3-yl)oxazolidin-2-one (107 mg, 0.22 mmol) in TFA (3 mL) and anisole (0.3 mL) was stirred at 70° C. for 16 h. Toluene was added and evaporated (2×). The residue purified on SCX-2 cartridge (eluting with MeOH then MeOH·NH₃). The residue was purified by chromatography on silica (solvent gradient 2-6% MeOH·NH₃ in DCM) to afford the title compound (65.5 mg, 81%) as a white solid. LCMS (ESI) $[M+H]^+$ 372/374/376.

Example 51

5-((1RS,3SR)-5'-Bromo-4'-chloro-3-methyl-1',2'-dihydrospiro[cyclopentane-1,3'-pyrrolo[2,3-b]pyridin]-3-yl)-3-methyl-1,2,4-oxadiazole

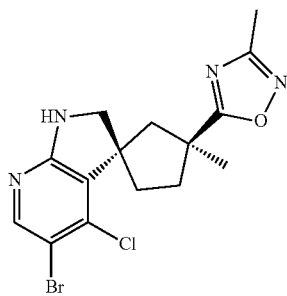 [SMILES: Cc1noc([C@@]2(C)CC[C@@]3(CNc4ncc(Br)c(Cl)c43)C2)n1]

To an ice-cooled solution of (1RS,3SR)-5'-bromo-4'-chloro-3-methyl-1',2'-dihydrospiro[cyclopentane-1,3'-pyrrolo[2,3-b]pyridine]-3-carboxylic acid HCl salt (0.14 g, 0.41 mmol) and N-hydroxyacetamidine (45 mg, 0.61 mmol) in DMF (2 mL) was added DIPEA (0.35 mL, 2.03 mmol). HATU (0.231 g, 0.61 mmol) was added portionwise over 5 min. The mixture was stirred at RT for 20 min, then partitioned between EtOAc and aq. sodium bicarbonate. The aqueous phase was extracted with more EtOAc and the combined organic extracts were washed with water, then brine, and evaporated. The residue was purified by chromatography on silica (solvent gradient 2-10% MeOH·NH₃ in DCM) to afford N-((1RS,3SR)-5'-bromo-4'-chloro-3-methyl-1',2'-dihydrospiro[cyclopentane-1,3'-pyrrolo[2,3-b]pyridine]-3-carbonyl)oxy)acetimidamide (168 mg, quantitative) as a colorless gum. LCMS (ESI) $[M+H]^+$ 401/403/405. This intermediate was suspended in toluene (35 mL) and refluxed under Dean-Stark conditions for 4.5 h. The cooled reaction mixture was purified by chromatography on silica (solvent gradient 25-100% EtOAc in toluene) to afford the title compound (73 mg, 47%) as colorless gum. LCMS (ESI) $[M+H]^+$ 383/385/387.

Example 52

(1RS,3RS,4RS)-5'-Bromo-4'-chloro-4-methoxy-1',2'-dihydrospiro[cyclopentane-1,3'-pyrrolo[2,3-b]pyridin]-3-ol and (1RS,3SR,4SR)-5'-bromo-4'-chloro-4-methoxy-1',2'-dihydrospiro[cyclopentane-1,3'-pyrrolo[2,3-b]pyridin]-3-ol

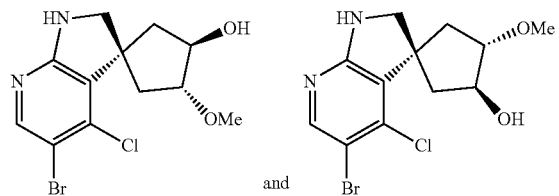 [SMILES: CO[C@@H]1C[C@@]2(CNc3ncc(Br)c(Cl)c32)C[C@H]1O ; CO[C@H]1C[C@]2(CNc3ncc(Br)c(Cl)c32)C[C@@H]1O]

Step 1: 5'-Bromo-4'-chloro-1'-(4-methoxybenzyl)-1',2'-dihydro-6-oxaspiro[bicyclo[3.1.0]hexane-3,3'-pyrrolo[2,3-b]pyridine]

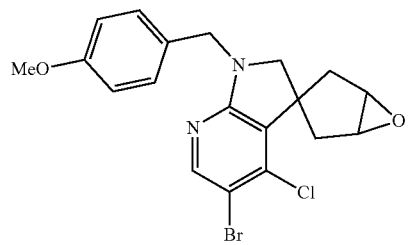 [SMILES: COc1ccc(CN2CC3(CC4OC4C3)c3c2ncc(Br)c3Cl)cc1]

TFA (1.52 mL, 19.72 mmol) was added to a solution of 5-bromo-4-chloro-1-[(4-methoxyphenyl)methyl]spiro[2H-pyrrolo[2,3-b]pyridine-3,4'-cyclopentene](4 g, 9.86 mmol) in DCM (30 mL). The mixture was stirred for 5 min at RT then 3-chloroperbenzoic acid (4.84 g, 19.63 mmol) was added and the mixture stirred for 3 h. The mixture was diluted with DCM (50 mL) and washed with aq. sodium carbonate (2×50 mL). The organic phase was washed with water (50 mL), dried (Na₂SO₄) and concentrated. The residue was purified by chromatography on silica (solvent gradient 0-40% EtOAc in cyclohexane), to afford the title compound (1.825 g, 43%). LCMS (ESI) $[M+H]^+$ 420.9/424.9.

Step 2: (1RS,3RS,4RS)-5'-Bromo-4'-chloro-4-methoxy-1'-(4-methoxybenzyl)-1',2'-dihydrospiro[cyclopentane-1,3'-pyrrolo[2,3-b]pyridin]-3-ol and (1RS,3SR,4SR)-5'-bromo-4'-chloro-4-methoxy-1'-(4-methoxybenzyl)-1',2'-dihydrospiro[cyclopentane-1,3'-pyrrolo[2,3-b]pyridin]-3-ol

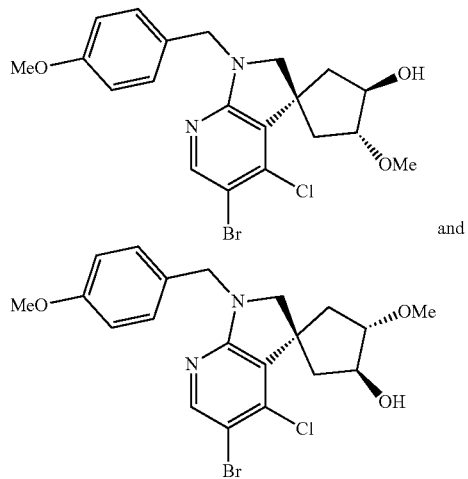

and

A mixture of 5'-bromo-4'-chloro-1',2'-dihydro-6-oxaspiro[bicyclo[3.1.0]hexane-3,3'-pyrrolo[2,3-b]pyridine](200 mg, 0.470 mmol) and sulfuric acid (4.7 mg, 0.05 mmol) in MeOH (3 mL) was stirred at 22° C. for 3 days, then heated under microwave irradiation at 80° C. for 10 min. The solvent was evaporated and the residue partitioned between EtOAc and aq. sat. sodium bicarbonate (20 mL). The aqueous layer was extracted with EtOAc. The combined organic extracts were washed with brine (15 mL) and dried (Na$_2$SO$_4$). The solvent was evaporated to dryness to give the title compounds (208 mg, 97% yield) as brown gum LCMS (ESI) [M+H]$^+$ 452.9/456.9.

Step 3: (1RS,3RS,4RS)-5'-Bromo-4'-chloro-4-methoxy-1',2'-dihydrospiro[cyclopentane-1,3'-pyrrolo[2,3-b]pyrdin]-3-ol and (1RS,3SR,4SR)-5'-bromo-4'-chloro-4-methoxy-1',2'-dihydrospiro[cyclopentane-1,3'-pyrrolo[2,3-b]pyridin]-3-ol

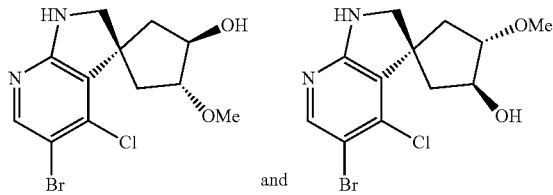 [SMILES: CO[C@@H]1C[C@@]2(CNc3ncc(Br)c(Cl)c32)C[C@H]1O ; CO[C@H]1C[C@]2(CNc3ncc(Br)c(Cl)c32)C[C@@H]1O]

and

A solution of (1RS,31'6, 4RS)-5'-Bromo-4'-chloro-4-methoxy-1'-(4-methoxybenzyl)-1',2'-dihydrospiro[cyclopentane-1,3'-pyrrolo[2,3-b]pyridin]-3-ol and (1RS,3SR,4SR)-5'-bromo-4'-chloro-4-methoxy-1'-(4-methoxybenzyl)-1',2'-dihydrospiro[cyclopentane-1,3'-pyrrolo[2,3-b]pyridin]-3-ol (208 mg, 0.46 mmol) in TFA (0.5 mL) was heated in a sealed tube at 80° C. for 18 h. The solvent was evaporated and the residue passed down a SCX-2 cartridge (eluting with MeOH followed MeOH·NH$_3$). The resulting brown gum was purified by chromatography on silica (solvent gradient 0-16% MeOH·NH$_3$ in DCM), to afford the title compounds (100 mg, 65%) as a colorless foam. LCMS (ESI) [M+H]$^+$ 332.8/336.8.

Example 53

(1RS,3RS,4RS)-5'-Bromo-4'-chloro-4-(1H-1,2,3-triazol-1-yl)-1',2'-dihydrospiro[cyclopentane-1,3'-pyrrolo[2,3-b]pyridin]-3-ol and (1RS,3SR,4SR)-5'-bromo-4'-chloro-4-(1H-1,2,3-triazol-1-yl)-1',2'-dihydrospiro[cyclopentane-1,3'-pyrrolo[2,3-b]pyridin]-3-ol

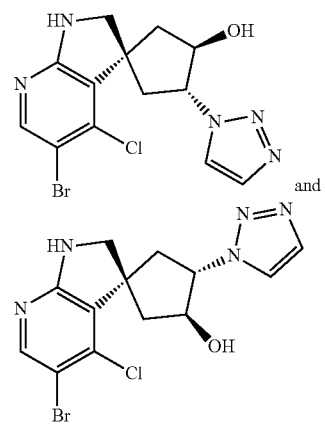

and

Step 1: (1RS,3RS,4RS)-3-Azido-5'-bromo-4'-chloro-1'-(4-methoxybenzyl)-1',2'-dihydrospiro[cyclopentane-1,3'-pyrrolo[2,3-b]pyridin]-4-ol and (1RS,3SR,4SR)-3-azido-5'-bromo-4'-chloro-1'-(4-methoxybenzyl)-1',2'-dihydrospiro[cyclopentane-1,3'-pyrrolo[2,3-b]pyridin]-4-ol

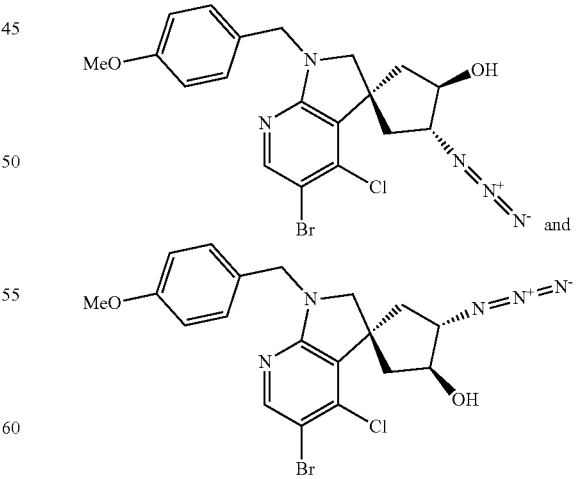

A mixture of 5'-bromo-4'-chloro-1'-(4-methoxybenzyl)-1',2'-dihydro-6-oxaspiro[bicyclo[3.1.0]hexane-3,3'-pyrrolo[2,3-b]pyridine](1.037 g, 2.46 mmol) and sodium azide (0.48 g, 7.38 mmol) in ethanol (20 mL) and water (2.5 mL)

was heated at 120° C. in a sealed vial for 2 days. The cooled mixture was evaporated and the residue partitioned between water (20 mL) and EtOAc. The aqueous layer was extracted with EtOAc. The combined organic extracts were washed with brine (30 mL), dried (Na₂SO₄), and concentrated. The residue was purified by chromatography on silica (solvent gradient 0-40% EtOAc in cyclohexane), to afford the title compounds (781 mg, 68%) as a pale yellow foam. LCMS (ESI) [M+H]⁺ 463.9/467.9.

Step 2: (1RS,3RS,4RS)-5'-Bromo-4'-chloro-1'-(4-methoxybenzyl)-4-(4-(trimethylsilyl)-1H-1,2,3-triazol-1-yl)-1',2'-dihydrospiro[cyclopentane-1,3'-pyrrolo[2,3-b]pyrdin]-3-ol and (1RS,3SR,4SR)-5'-bromo-4'-chloro-1'-(4-methoxybenzyl)-4-(4-(trimethylsilyl)-1H-1,2,3-triazol-1-yl)-1',2'-dihydrospiro[cyclopentane-1,3'-pyrrolo[2,3-b]pyridin]-3-ol

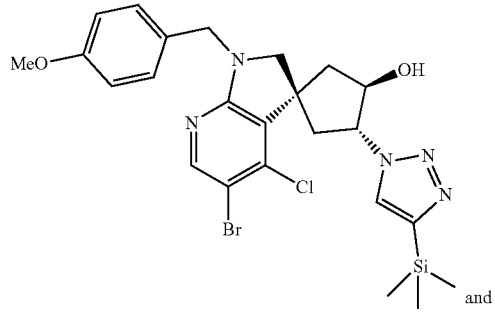

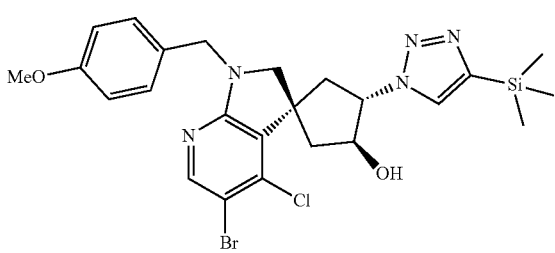

and

A mixture of (1RS,3RS,4RS)-3-azido-5'-bromo-4'-chloro-1'-(4-methoxybenzyl)-1',2'-dihydrospiro[cyclopentane-1,3'-pyrrolo[2,3-b]pyridin]-4-ol and (1RS,3SR,4SR)-3-azido-5'-bromo-4'-chloro-1'-(4-methoxybenzyl)-1',2'-dihydrospiro[cyclopentane-1,3'-pyrrolo[2,3-b]pyridin]-4-ol (200 mg, 0.43 mmol) and trimethylsilyl acetylene (0.3 mL, 2.15 mmol) in toluene (2 mL) was heated at 115° C. in a sealed vial for 18 h, resulting in the precipitation of a colorless solid. The cooled mixture was filtered. The solid was washed with Et₂O (5 mL) and dried to give the title compounds (181 mg, 75%). LCMS (ESI) [M+H]⁺ 562.0/565.0.

Step 3: (1RS,3RS,4RS)-5'-Bromo-4'-chloro-1'-(4-methoxybenzyl)-4-(1H-1,2,3-triazol-1-yl)-1',2'-dihydrospiro[cyclopentane-1,3'-pyrrolo[2,3-b]pyrdin]-3-ol and (1RS,3SR,4SR)-5'-bromo-4'-chloro-1'-(4-methoxybenzyl)-4-(1H-1,2,3-triazol-1-yl)-1',2'-dihydrospiro[cyclopentane-1,3'-pyrrolo[2,3-b]pyrdin]-3-ol

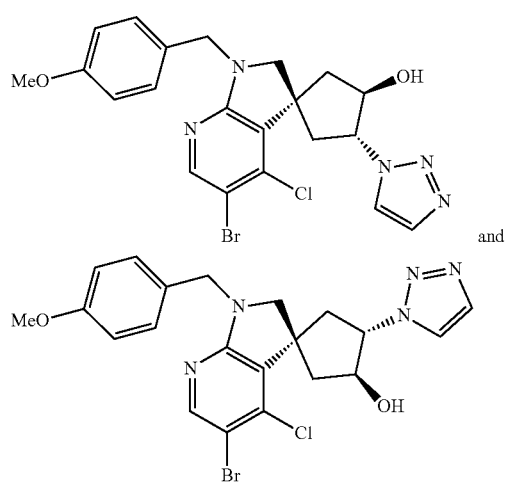

and

TBAF (1N in THF, 1.28 mL, 1.29 mmol) was added to a mixture of (1RS,3RS,4RS)-5'-bromo-4'-chloro-1'-(4-methoxybenzyl)-4-(4-(trimethylsilyl)-1H-1,2,3-triazol-1-yl)-1',2'-dihydrospiro[cyclopentane-1,3'-pyrrolo[2,3-b]pyridin]-3-ol and (1RS,3 SR,4SR)-5'-bromo-4'-chloro-1'-(4-methoxybenzyl)-4-(4-(trimethyl silyl)-1H-1,2,3-triazol-1-yl)-1',2'-dihydrospiro[cyclopentane-1,3'-pyrrolo[2,3-b]pyrdin]-3-ol (181 mg, 0.32 mmol) in THF (3 mL) at RT. The reaction mixture was stirred at RT for 18 h then at 50° C. for 18 h. The solvent was evaporated and the residue taken on to step 4 without further purification. LCMS (ESI) [M+H]⁺ 489.8/493.9.

Step 4: (1RS,3RS,4RS)-5'-Bromo-4'-chloro-4-(1H-1,2,3-triazol-1-yl)-1',2'-dihydrospiro[cyclopentane-1,3'-pyrrolo[2,3-b]pyridin]-3-ol and (1RS,3SR,4SR)-5'-bromo-4'-chloro-4-(1H-1,2,3-triazol-1-yl)-1',2'-dihydrospiro[cyclopentane-1,3'-pyrrolo[2,3-b]pyrdin]-3-ol

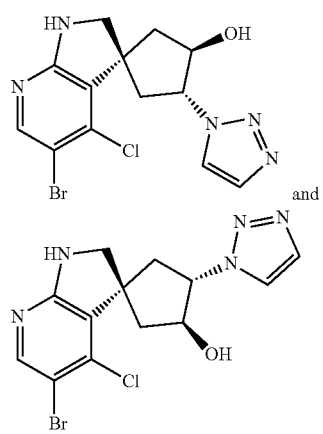

and

A mixture of (1RS,3RS,4RS)-5'-bromo-4'-chloro-1'-(4-methoxybenzyl)-4-(1H-1,2,3-triazol-1-yl)-1',2'-dihydrospiro[cyclopentane-1,3'-pyrrolo[2,3-b]pyridin]-3-ol and (1RS,3SR,4SR)-5'-bromo-4'-chloro-1'-(4-methoxybenzyl)-4-(1H-1,2,3-triazol-1-yl)-1',2'-dihydrospiro[cyclopentane-1,3'-pyrrolo[2,3-b]pyridin]-3-ol (157 mg, 0.32 mmol) in TFA (2 mL) was heated in a sealed tube at 75° C. for 18 h. The cooled mixture was concentrated in vacuo and the residue passed down a SCX-2 cartridge (eluting with MeOH followed by MeOH·NH₃). The resulting pale yellow gum was purified by chromatography on silica (solvent gradient 0-10% MeOH·NH₃ in DCM), to afford the title compounds (101 mg, 85% yield) as a pale yellow gum. LCMS (ESI) [M+H]⁺ 369.9/373.9.

Example 54 tert-Butyl 3-acetamido-5'-bromo-4'-chlorospiro[cyclopentane-1,3'-pyrrolo[2,3-b]pyridine]-1'(2'H)-carboxylate

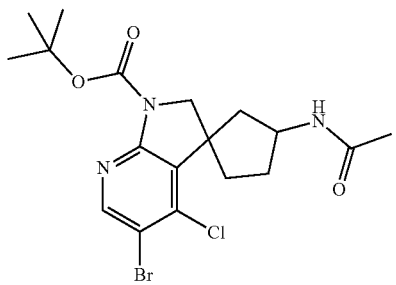 [SMILES: CC(=O)NC1CCC2(C1)CN(C(=O)OC(C)(C)C)c1ncc(Br)c(Cl)c12]

Step 1: tert-Butyl 3-azido-5'-bromo-4'-chlorospiro[cyclopentane-1,3'-pyrrolo[2,3-b]pyridine]-1'(2'H)-carboxylate

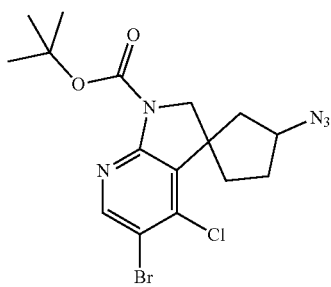 [SMILES: CC(C)(C)OC(=O)N1CC2(CCC(N=[N+]=[N-])C2)c2c1ncc(Br)c2Cl]

To a solution of ter t-butyl 5'-bromo-4'-chloro-3-hydroxyspiro[cyclopentane-1,3'-pyrrolo[2,3-b]pyridine]-1'(2'H)-carboxylate (81 mg, 0.2 mmol) and triphenylphosphine (66 mg, 0.25 mmol) in THF (2 mL) were added diisopropyl azodicarboxylate (0.053 mL, 0.27 mmoL) and, after 5 min, diphenylphosphoryl azide (0.06 mL, 0.28 mmol). The reaction mixture was stirred at RT for 24 h, then concentrated. The residue was purified by chromatography on silica (solvent gradient 0-50% EtOAc in cyclohexane) to afford the title compound (41 mg, 48%) as a pale yellow oil. LCMS (ESI) [M+H-tBu]⁺ 372/374/376.

Step 2: tert-Butyl 3-amino-5'-bromo-4'-chlorospiro[cyclopentane-1,3'-pyrrolo[2,3-b]pyridine]-1'(2'H)-carboxylate

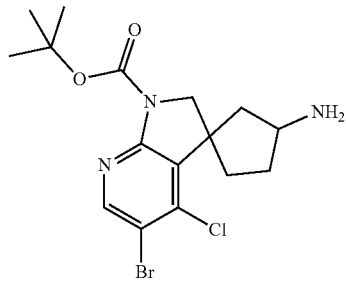 [SMILES: CC(C)(C)OC(=O)N1CC2(CCC(N)C2)c2c1ncc(Br)c2Cl]

To a solution of tert-butyl 3-azido-5'-bromo-4'-chlorospiro[cyclopentane-1,3'-pyrrolo[2,3-b]pyridine]-1'(2'H)-carboxylate (41 mg, 0.096 mmol) and triphenylphosphine (26 mg, 0.1 mmol) in THF/water (6:1, 3.5 mL) was added KOH (1N aq., 0.1 mL, 0.1 mmol). The reaction mixture was stirred at RT for 20 h, then diluted with MeOH. Purification on SCX-2 (eluting with MeOH then MeOH·NH₃) afforded the title compound (37 mg, 96%) as a colorless oil. LCMS (ESI) [M+H]⁺ 402.1/404.1/406.1.

Step 3: tert-Butyl 3-acetamido-5'-bromo-4'-chlorospiro[cyclopentane-1,3'-pyrrolo[2,3-b]pyridine]-1'(2'H)-carboxylate

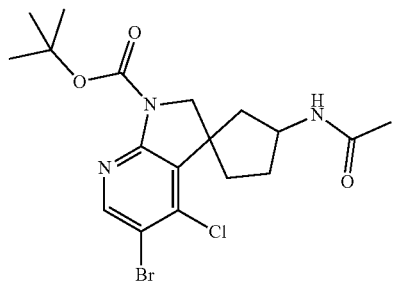 [SMILES: CC(=O)NC1CCC2(C1)CN(C(=O)OC(C)(C)C)c1ncc(Br)c(Cl)c12]

To a solution of tert-butyl 3-amino-5'-bromo-4'-chlorospiro[cyclopentane-1,3'-pyrrolo[2,3-b]pyridine]-1'(2'H)-carboxylate (37 mg, 0.092 mmol) and triethylamine (0.038 mL, 0.276 mmol) in DCM (2 mL) was added acetic anhydride (0.009 mL, 0.092 mmol). The reaction mixture was stirred at RT for 19 h, then diluted with DCM and washed with water. The organic extract was dried (MgSO₄) and concentrated. The residue was purified by chromatography on silica (solvent gradient 0-100% EtOAc in cyclohexane) to afford the title compound (21 mg, 51%) as a colorless oil. LCMS (ESI) [M+H]⁺ 446.1.

Example 55 tert-Butyl 3-((2-amino-2-oxoethyl)(methyl)amino)-5'-bromo-4'-chlorospiro[cyclopentane-1,3'-pyrrolo[2,3-b]pyridine]-1'(2'H)-carboxylate

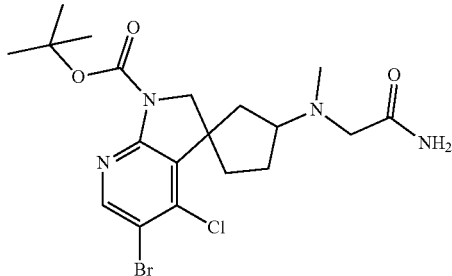 [SMILES: CN(CC(N)=O)C1CCC2(C1)CN(C(=O)OC(C)(C)C)c1ncc(Br)c(Cl)c12]

Sarcosinamide hydrochoride (32 mg, 0.26 mmol) was passed trough a SCX-2 cartridge (eluting with MeOH then MeOH·NH₃) to afford sarcosinamide (26 mg) after concentration. The residue was dissolved in DCE (2 mL) and the resulting solution treated with tert-butyl 5'-bromo-4'-chloro-3-oxospiro[cyclopentane-1,3'-pyrrolo[2,3-b]pyridine]-1' (2'H)-carboxylate (80 mg, 0.2 mmol) and acetic acid (0.011 mL, 0.2 mmol). The resulting solution was stirred with molecular sieves 4 Å (80 mg) for 30 min, then was treated with sodium triacetoxyborohydride (64 mg, 0.3 mmol). The resulting solution was stirred at RT for 18 h. Further portions of sarcosinamide hydrochloride (64 mg, 0.52 mmol) and sodium triacetoxyborohydride (128 mg, 0.6 mmol) were added, and the reaction mixture was stirred at RT for 18 h, then at 50° C. for 1 h. Further portions of sarcosinamide hydrochloride (105 mg, 0.84 mmol) and sodium triacetoxyborohydride (150 mg, 0.71 mmol) were added, and the reaction mixture was stirred at RT for 18 h. The mixture was passed trough a SCX-2 cartridge (eluting with MeOH then MeOH·NH₃). The resulting residue was purified by chromatography on silica (solvent gradient 0-10% MeOH in EtOAc) to afford the title compound (43 mg, 45%) as a white foam. LCMS (ESI) $[M+H]^+$ 473.1/475.1/477.1.

Example 56 tert-Butyl 5'-bromo-4'-chloro-3-(pyridin-3-yl)spiro[cyclopentane-1,3'-pyrrolo[2,3-b]pyridin]-2-ene-1'(2'H)-carboxylate

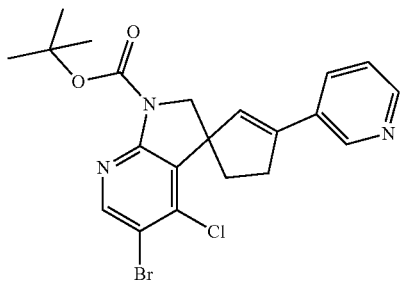 [SMILES: CC(C)(C)OC(=O)N1CC2(C=C(c3cccnc3)CC2)c2c1ncc(Br)c2Cl]

Step 1: tert-Butyl 5'-bromo-4'-chloro-3-(((trifluoromethyl)sulfonyl)oxy)spiro[cyclopentane-1,3'-pyrrolo[2,3-b]pyridin]-2-ene-1'(2'H)-carboxylate

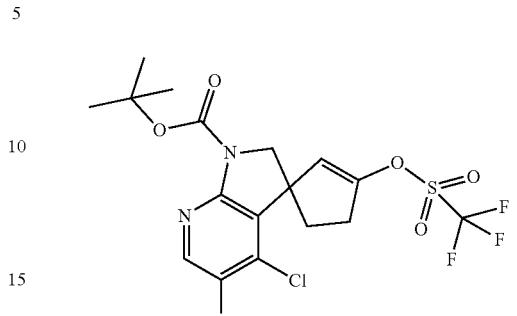

To a solution of tert-butyl 5'-bromo-4'-chloro-3-oxospiro[cyclopentane-1,3'-pyrrolo[2,3-b]pyridin]-1'(2'H)-carboxylate (656 mg, 1.63 mmol) in THF (11 mL) under argon at −78° C. was added a lithium bis(trimethylsilyl)amide solution (1N in THF, 1.99 mL, 1.99 mmol). The reaction mixture was stirred at 0° C. for 30 min, then treated with a solution of 2-[ATA-bis(trifluoromethanesulfonyl)amino] pyridine (761 mg, 2.13 mmol) in THF (3 mL). The reaction mixture was slowly left to reach RT, then stirred for 3 h. The reaction was quenched by the addition of aq. sat. ammonium chloride and extracted with EtOAc. The combined organic extracts were dried (MgSO₄) and concentrated. The residue was purified by chromatography on silica (solvent gradient 0-10% EtOAc in cyclohexane), to afford the title compound as a colorless oil (0.55 g, 63%), in a mixture with tert-butyl 5'-bromo-4'-chloro-3-(((trifluoromethyl)sulfonyl)oxy)spiro[cyclopentane-1,3'-pyrrolo[2,3-b]pyridin]-3-ene-1'(271)-carboxylate. $^1$H NMR (400 MHz, CDCl₃) δ ppm 8.41 (s, 1H-A), 8.40 (s, 1H-B), 5.73 (m, 1H-A), 5.58 (t, J=1.8 Hz, 1H-B), 4.04 (d, J=4.5 Hz, 2H-A), 3.94 (s, 2H-B), 3.49-3.42 (m, 1H-A), 3.25-3.17 (m, 1H-A), 2.90-2.83 (m, 2H-B), 2.70-2.62 (m, 1H-A), 2.61-2.54 (m, 1H-A) 2.57-2.49 (m, 1H-B), 2.26-2.18 (m, 1H-B), 1.56 (s, 9H-A, 9H-B).

Step 2: tert-Butyl 5'-bromo-4'-chloro-3-(pyridin-3-yl)spiro[cyclopentane-1,3'-pyrrolo[2,3-b]pyridin]-2-ene-1'(2'H)-carboxylate

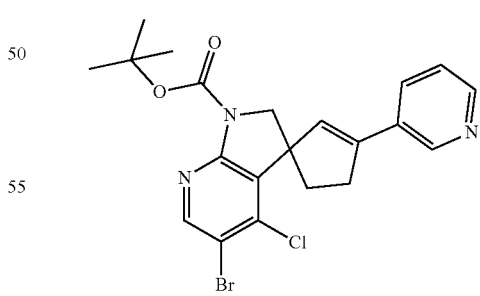

A sealed tube containing a degassed mixture of tert-butyl 5'-bromo-4'-chloro-3-(((trifluoromethyl)sulfonyl)oxy)spiro[cyclopentane-1,3'-pyrrolo[2,3-b]pyridin]-1'(TH)-carboxylate and tert-butyl 5'-bromo-4'-chloro-3-(((trifluoromethyl)sulfonyl)oxy)spiro[cyclopentane-1,3'-pyrrolo[2,3-b]pyridin]-3-ene-1'(2'H)-carboxylate (250 mg, 0.47 mmol), pyridine-3-boronic acid (86 mg, 0.70 mmol), 1,1-[1,1'-bis (diphenylphosphino)ferrocene]dichloropalladium(II) complex with DCM (18.6 mg, 0.03 mmol), sodium carbonate (2N aq., 0.45 mL, 0.90 mmol) in THF (4 mL) and water (1 mL) was stirred at RT for 4 days. The reaction mixture was diluted with EtOAc and washed with water. The aqueous layer was extracted with EtOAc. The combined organic extracts were washed with brine, dried (MgSO₄) and concentrated. The residue was purified by chromatography on silica (solvent gradient 0-50% EtOAc in cyclohexane), to afford the title compound as a colorless oil (135 mg, 62%) in a mixture with tert-butyl 5'-bromo-4'-chloro-3-(pyridin-3-yl)spiro[cyclopentane-1,3'-pyrrolo[2,3-b]pyridin]-3-ene-1'(2'H)-carboxylate. LCMS (ESI) [M+H]⁺ 462.1/463.1/465.1.

Example 57

5'-Bromo-4'-chloro-3-(pyridin-3-yl)-1',2'-dihydrospiro[cyclopentane-1,3'-pyrrolo[2,3-b]pyridine]

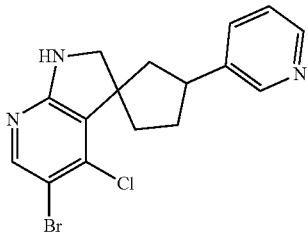 [SMILES: Clc1c(Br)cnc2c1C1(CCC(c3cccnc3)C1)CN2]

A solution of bis(cyclooctadiene)nickel(O) (29 mg, 0.11 mmol), bathophenanthroline (71 mg, 0.21 mmol), potassium tert-butoxide (120 mg, 1.07 mmol), pyridine-3-boronic acid (99 mg, 0.80 mmol) in anhydrous isobutyl alcohol (2 mL), was stirred at RT for 10 min. To the resulting dark purple mixture was added tert-butyl (1R,3R)-3,5'-dibromo-4'-chlorospiro[cyclopentane-1,3'-pyrrolo[2,3-b]pyridine]-P(2'H)-carboxylate (250 mg, 0.54 mmol). The mixture was degassed, placed under argon, and heated at 60° C. for 2 h. The mixture was diluted with EtOAc, and washed with water. The organic extract was dried (MgSO₄) and concentrated. The residue was dissolved in DCM (1 mL) and treated with TFA (0.5 mL). The solution was stirred at RT for 3 days, then concentrated. The mixture was diluted with EtOAc, and washed with aq. sodium carbonate. The aqueous layer was extracted with further EtOAc. The combined organic extracts were dried (MgSO₄) and concentrated. The residue was purified by chromatography on silica (solvent gradient 0-5% MeOH in DCM), to afford the title compound (63 mg, 32%) and some unreacted tert-butyl (1RS,3RS)-3,5'-dibromo-4'-chlorospiro[cyclopentane-1,3'-pyrrolo[2,3-b]pyridine]-1'(2'H)-carboxylate (90 mg, 46%). LCMS (ESI) [M+H]⁺ 363.9/365.9/367.9.

Example 58 tert-Butyl 4'-chloro-5'-(4,4,5,5-tetramethyl-1,3,2-dioxaborolan-2-yl)spiro[cyclopentane-1,3'-pyrrolo[2,3-b]pyridin]-3-ene-1'(2'H)-carboxylate

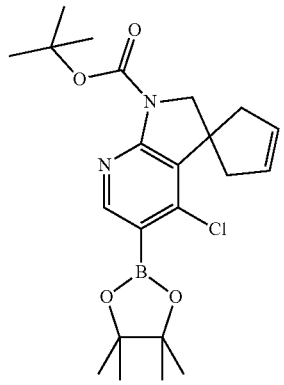 [SMILES: CC(C)(C)OC(=O)N1CC2(CC=CC2)c2c1ncc(B1OC(C)(C)C(C)(C)O1)c2Cl]

A degassed mixture of bis(pinacolato)diboron (2.47 g, 9.71 mmol), tert-butyl 5'-bromo-4'-chlorospiro[cyclopentane-1,3'-pyrrolo[2,3-b]pyridin]-3-ene-1'(27-1)-carboxylate (2.14 g, 5.55 mmol), [1,1'-bis(diphenylphosphino)ferrocene] dichloropalladium(II) complex with DCM (226 mg, 0.28 mmol) and potassium acetate (1.38 g, 13.87 mmol) in 1,4-dioxane (15 mL) was stirred at 100° C. for 20 h. The reaction mixture was diluted with water and extracted with EtOAc. The combined organic extracts were washed with brine, dried (MgSO₄) and concentrated. The residue was dissolved in hot MeOH and left to crystallise overnight. The precipitate was filtered and washed with cold MeOH to afford the title compound (1.5 g, 62%). LCMS (ESI) [M+H]⁺ 433.1.

Example 59

1-(3-(1'-(tert-Butoxycarbonyl)-4'-chloro-1',2'-dihydrospiro[cyclopentane-1,3'-pyrrolo[2,3-b]pyridin]-3-en-5'-yl)phenyl)cyclopropane-1-carboxylic Acid

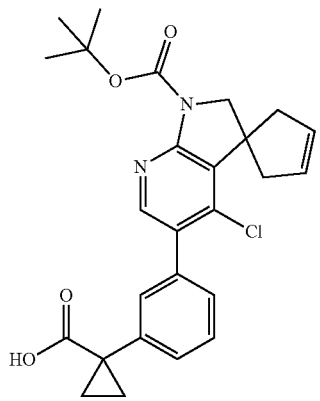 [SMILES: CC(C)(C)OC(=O)N1CC2(CC=CC2)c2c1ncc(-c1cccc(C3(C(=O)O)CC3)c1)c2Cl]

A degassed mixture of tert-butyl 4'-chloro-5'-(4,4,5,5-tetramethyl-1,3,2-dioxaborolan-2-yl)spiro[cyclopentane-1,3'-pyrrolo[2,3-b]pyridin]-3-ene-1'(2'H)-carboxylate (200 mg, 0.46 mmol), 1-(3-bromophenyl)cyclopropanecarboxylic acid (145 mg, 0.60 mmol), tetrakis(triphenylphosphine) palladium(O) (22 mg, 0.02 mmol), cesium carbonate (0.92 mL, 0.92 mmol) in 1,4-dioxane (1.5 mL) was irradiated in the microwave at 125° C. for 20 min. The reaction mixture was partitioned between EtOAc and water. The aqueous layer was acidified and extracted with EtOAc (×2). The combined organic layers were dried (MgSO$_4$) and concentrated.

The residue was purified by chromatography on silica (solvent gradient from 0-3% MeOH in DCM) to afford the title compound (153 mg, 71%). LCMS (ESI) [M−tBu+H]$^+$ 411.0/413.0.

Example 60

1-(3-(4'-Chloro-1',2'-dihydrospiro[cyclopentane-1,3'-pyrrolo[2,3-b]pyrdin]-3-en-5'-yl)phenyl)cyclopropane-1-carboxylic Acid

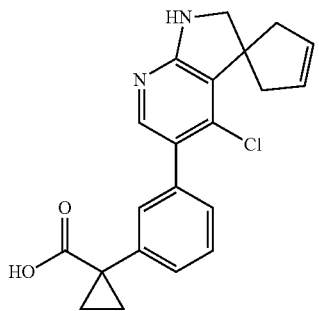 [SMILES: O=C(O)C1(c2cccc(-c3cnc4c(c3Cl)C3(CC=CC3)CN4)c2)CC1]

A solution of 1-(3-(1'-(tert-butoxycarbonyl)-4'-chloro-1',2'-dihydrospiro[cyclopentane-1,3'-pyrrolo[2,3-b]pyridin]-3-en-5'-yl)phenyl)cyclopropane-1-carboxylic acid (90 mg, 0.19 mmol) in DCM (0.8 mL) was treated with TFA (0.5 mL). The reaction mixture was stirred at RT for 4 h. The volatiles were removed by blowing nitrogen then the residue was coevaporated with NH$_3$/MeOH, to afford the title compound (90 mg, 100%). LCMS (ESI) [M+H]$^+$ 367.0/369.0.

Example 61

5'-Bromo-1',2'-dihydrospiro[cyclobutane-1,3'-pyrrolo[2,3-b]pyridine]

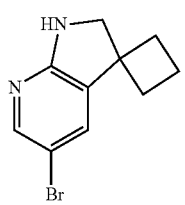

Step 1: Spiro[cyclobutane-1,3'-pyrrolo[2,3-b]pyridin]-2'(1'H)-one

n-BuLi (1.6N in hexanes; 9.3 mL, 14.9 mmol) was added dropwise to a solution of 1,3-dihydro-2H-pyrrolo[2,3-b]pyridin-2-one (1 g, 7.50 mmol) in dry THF (50 mL) at −78° C. TMEDA (2.2 mL, 15 mmol) was then added and the mixture stirred for 1 h at −78° C. 1,3-Dibromopropane (0.76 mL, 7.5 mmol) was added in one portion and the mixture allowed to warm up to RT overnight. The mixture was quenched with aq. sat. ammonium chloride (100 mL) then extracted with EtOAc (2×50 mL). The combined organic extracts were washed with brine (50 mL), dried (Na$_2$SO$_4$) and evaporated. The residue was purified by chromatography on silica (solvent gradient 33-100% EtOAc in cyclohexane), to afford the title compound (255 mg, 20%). LCMS (ESI) [M+H]$^+$ 175.1.

Step 2: 5'-Bromospiro[cyclobutane-1,3'-pyrrolo[2,3-b]pyridin]-2'(1'H)-one

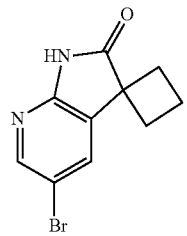 [SMILES: O=C1Nc2ncc(Br)cc2C12CCC2]

NBS (338 mg, 1.90 mmol) was added portionwise to a solution of spiro[cyclobutane-1,3'-pyrrolo[2,3-b]pyridin]-2'(1'H)-one (304 mg, 1.90 mmol) in dry DMF (3 mL). The reaction mixture was stirred for 18 h at RT. Further NBS (85 mg, 0.475 mmol) was added and the mixture stirred for 4 h. The mixture was partitioned between EtOAc and water (30 mL). The aqueous layer was extracted with EtOAc. The combined organic extracts were washed with brine, dried (Na$_2$SO$_4$) and concentrated. The residue was suspended in 2-propanol (10 mL) and heated under microwave irradiation at 150° C. for 5 min. The slurry was allowed to cool down to RT and filtered to give the title compound (296 mg, 65%) as a pale pink solid. LCMS (ESI) [M+H]$^+$ 239.0/241.0.

Step 3: 5'-Bromo-1',2'-dihydrospiro[cyclobutane-1,3'-pyrrolo[2,3-b]pyridine]

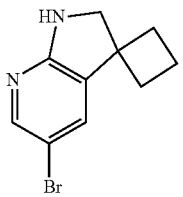 [SMILES: Brc1cnc2c(c1)C1(CCC1)CN2]

Borane THF complex (1.0M in THF, 5 mL, 5.0 mmol) was added to a suspension of 5'-bromospiro[cyclobutane-1,3'-pyrrolo[2,3-b]pyridin]-2'(1'H)-one (271 mg, 1.07 mmol) in THF (5 mL). The reaction mixture was stirred at RT overnight, then was quenched with MeOH (1 mL). HCl (1.25N aq., 2 mL) was added. The mixture was heated under reflux for 2 h, then taken to dryness in vacuo. The residue was purified by chromatography on silica (solvent gradient MeOH·NH$_3$ in DCM), to afford the title compound (158 mg, 58%). LCMS (ESI) [M+H]$^+$ 239.0/241.0.

Example 62

5'-Chloro-1'-(4-methoxybenzyl)-1',2'-dihydrospiro[cyclobutane-1,3'-pyrrolo[2,3-b]pyridin]-3-one

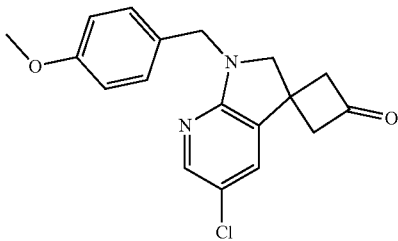 [SMILES: COc1ccc(CN2CC3(CC(=O)C3)c3cc(Cl)cnc32)cc1]

Step 1: N-(3-Bromo-5-chloropyridin-2-yl)-N-(4-methoxybenzyl)-3-oxocyclobutane-1-carboxamide

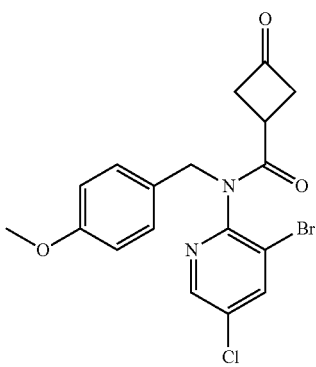 [SMILES: COc1ccc(CN(C(=O)C2CC(=O)C2)c2ncc(Cl)cc2Br)cc1]

3-Oxocyclobutane-1-carbonyl chloride (1.62 g, 12.2 mmol) was added dropwise to a solution of 3-bromo-5-chloro-N-(4-methoxybenzyl)pyridin-2-amine (2 g, 6.10 mmol) and DIPEA (3.2 mL, 18.3 mmol) in dry THF (15 mL). The reaction mixture was stirred for 64 h at RT. Further 3-oxocyclobutane-1-carbonyl chloride (2.0 g, 15.1 mmol) was added and the mixture was stirred for 18 h, then was evaporated to dryness. The residue was partitioned between EtOAc and aq. sodium bicarbonate (8%, 50 mL). The aqueous layer was extracted with EtOAc. The organic extract was washed with brine, dried (Na$_2$SO$_4$) and concentrated. The residue was purified by chromatography on silica (solvent gradient 0-60% EtOAc in pentane), to afford the title compound (2.6 g, 100%) as a pale yellow gum. LCMS (ESI) [M+H]$^+$ 445/449.

Step 2: N-(3-Bromo-5-chloropyridin-2-yl)-3,3-dimethoxy-N-(4-methoxybenzyl)cyclobutane-1-carboxamide

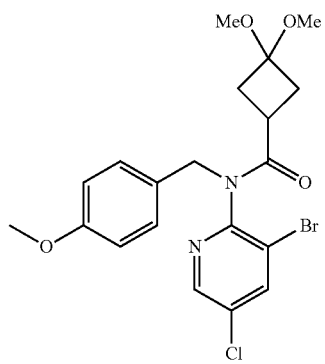 [SMILES: COc1ccc(CN(C(=O)C2CC(OC)(OC)C2)c2ncc(Cl)cc2Br)cc1]

A solution of N-(3-bromo-5-chloropyridin-2-yl)-N-(4-methoxybenzyl)-3-oxocyclobutane-1-carboxamide (2.58 g, 6.08 mmol), trimethylorthoformate (15 mL, 137 mmol) and 4-toluenesulphonic acid (10 mg) in methanol (30 mL) was heated at 75° C. for 18 h. The mixture was taken to dryness in vacuo and the residue partitioned between EtOAc and aq. sodium bicarbonate (8%, 100 mL). The aqueous layer was extracted with EtOAc. The combined organic extracts were washed with brine, dried (Na$_2$SO$_4$) and concentrated. The residue was purified by chromatography on silica (solvent gradient 0-50% EtOAc in pentane), to afford the title compound (2.87 g, 100%) as a pale yellow gum. LCMS (ESI) [M+Na]$^+$ 491/493/495.

Step 3: 5'-Chloro-3,3-dimethoxy-1'-(4-methoxybenzyl)spiro[cyclobutane-1,3'-pyrrolo[2,3-b]pyridin]-2'(1'H)-one

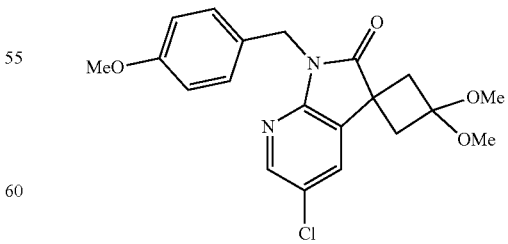

A degassed mixture of N-(3-bromo-5-chloropyridin-2-yl)-3,3-dimethoxy-N-(4-methoxybenzyl)cyclobutane-1-carboxamide (1.52 g, 3.236 mmol), [1,3-bis(2,6-diisopropylphenyl)imidazol-2-ylidene](3-chloropyridyl)palladium(II)

dichloride (PEPPSI-iPr; 220 mg, 0.324 mmol) and sodium tert-butoxide (932 mg, 9.71 mmol) in dry toluene (20 mL) was heated at 115° C. for 2.5 h in a sealed tube. The solvent was evaporated and the residue partitioned between EtOAc and water (30 mL). The aqueous layer was extracted with EtOAc. The combined organic extracts were washed with brine (30 mL), dried (Na$_2$SO$_4$) and concentrated. The residue was purified by chromatography on silica (solvent gradient 0-30% EtOAc in cyclohexane), to afford the title compound (115 mg, 43%) as a pale yellow gum. LCMS (ESI) [M+H]$^+$ 389.2/391.2.

Step 4: 5'-Chloro-1'-(4-methoxybenzyl)-1',2'-dihydrospiro[cyclobutane-1,3'-pyrrolo[2,3-b]pyridin]-3-one

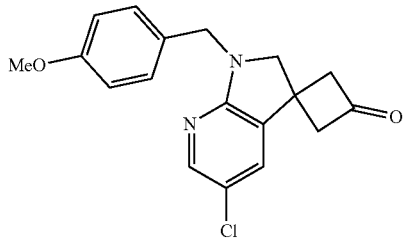 [SMILES: COc1ccc(CN2CC3(CC(=O)C3)c3cc(Cl)cnc32)cc1]

Borane-dimethylsulphide complex (0.29 mL, 3.055 mmol) was added dropwise to a solution of 5'-chloro-3,3-dimethoxy-1'-(4-methoxybenzyl)spiro[cyclobutane-1,3'-pyrrolo[2,3-b]pyridin]-2'(1'H)-one (594 mg, 1.528 mmol) in dry THF (15 mL) at RT. The mixture was heated at 75° C. for 3 h, cooled to 0° C. and MeOH (ca 5 mL) cautiously added dropwise. The reaction mixture was stirred for 30 min, then was filtered and evaporated to give a colorless gum which was dissolved in DCM (1 mL). TFA/water (95:5; 1 mL) was added and the mixture was stirred overnight. The mixture was concentrated and the residue partitioned between EtOAc and aq. sodium bicarbonate (8%; 15 mL). The aqueous layer was extracted with EtOAc. The combined organic extracts were washed with brine (30 mL), dried (Na$_2$SO$_4$) and concentrated. The residue was purified by chromatography on silica (solvent gradient 0-30% EtOAc in cyclohexane), to afford the title compound (384 mg, 66%) LCMS (ESI) [M+H]$^+$ 329.2/331.2.

Example 63

5'-Chloro-1',2'-dihydrospiro[cyclobutane-1,3'-pyrrolo[2,3-b]pyridin]-3-ol

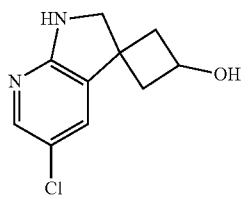

Step 1: 5'-Chloro-1'-(4-methoxybenzyl)-1',2'-dihydrospiro[cyclobutane-1,3'-pyrrolo[2,3-b]pyridin]-3-ol

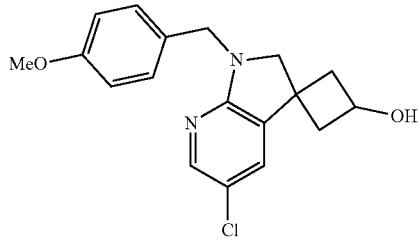 [SMILES: COc1ccc(CN2CC3(CC(O)C3)c3cc(Cl)cnc32)cc1]

Sodium borohydride (49 mg, 1.288 mmol) was added portionwise to a solution of 5'-chloro-1'-(4-methoxybenzyl)-1',2'-dihydrospiro[cyclobutane-1,3'-pyrrolo[2,3-b]pyrdin]-3-one (384 mg, 1.17 mmol) in MeOH/DCM (1:1, 8 mL). The reaction mixture was stirred for 3 h at RT, then was carefully quenched with water (2 mL), and partitioned between DCM and water (20 mL). The aqueous layer was extracted with DCM. The combined organic extracts were washed with water (20 mL), dried (Na$_2$SO$_4$) and concentrated. The residue was purified by chromatography on silica (solvent gradient 0-60% EtOAc in cyclohexane), to afford the title compound (330 mg, 85%) LCMS (ESI) [M+H]$^+$ 331.2/333.1.

Step 2: 5'-Chloro-1',2'-dihydrospiro[cyclobutane-1,3'-pyrrolo[2,3-b]pyridin]-3-ol

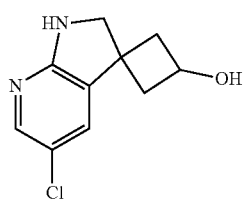 [SMILES: OC1CC2(CNc3ncc(Cl)cc32)C1]

5'-Chloro-1'-(4-methoxybenzyl)-1',2'-dihydrospiro[cyclobutane-1,3'-pyrrolo[2,3-b]pyridin]-3-ol (330 mg, 1.00 mmol) in TFA/water (95:5, 3 mL) was heated in a sealed tube at 70° C. for 18 h. The mixture was evaporated and the residue suspended in MeOH (10 mL). NaOH (2N aq., 2 mL) was added and the mixture stirred vigorously for 1 h. The mixture was partitioned between EtOAc and water (15 mL). The aqueous layer was extracted with EtOAc. The combined organic extracts were washed with brine (15 mL), dried (Na$_2$SO$_4$) and concentrated. The residue was purified by chromatography on silica (solvent gradient 20-100% EtOAc in cyclohexane), to afford the title compound (143 mg, 68%) as a colorless foam. LCMS (ESI) [M+H]$^+$ 211.2/213.2.

Example 64

5'-Chloro-3-methoxy-1',2'-dihydrospiro[cyclobutane-1,3'-pyrrolo[2,3-b]pyridine]

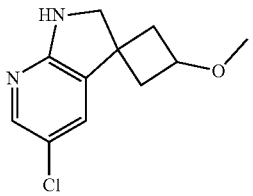

Step 1: N-(3-Bromo-5-chloropyridin-2-yl)-3-methoxy-N-(4-methoxybenzyl)cyclobutane-1-carboxamide

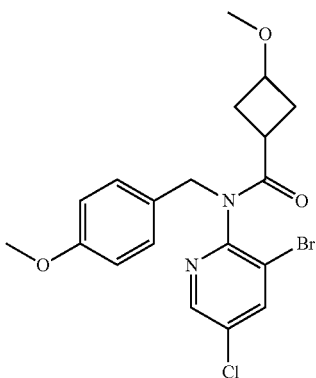 [SMILES: COc1ccc(CN(C(=O)C2CC(OC)C2)c2ncc(Cl)cc2Br)cc1]

To a solution of oxalyl bromide (0.35 mL, 6.9 mmol) in DCM (5 mL) at 0° C., was added dropwise a solution of 3-methoxy-cyclobutane carboxylic acid (1.5 g, 4.6 mmol) in DCM (5 mL) containing a drop of DMF. The reaction mixture was stirred at 0° C. for 30 min, then at RT for 30 min. The reaction mixture was cooled to 0° C. and treated with a solution of 5-chloro-N-(4-methoxybenzyl)pyridin-2-amine (0.9 g, 6.9 mmol) and DIPEA (3.8 mL, 22.7 mmol) in DCM (10 mL). The reaction was left to warm up to RT and stirred for 16 h. The mixture was partitioned between DCM and water. The aqueous layer was extracted with further DCM. The combined organic extracts were dried (Na$_2$SO$_4$) and concentrated. The residue was purified by chromatography on silica (solvent gradient 0-50% EtOAc in cyclohexane), to afford the title compound (1.28 g, 64%) as a pale yellow oil LCMS (ESI) [M+H]$^+$ 439.0/441.0/443.0.

Step 2: 5'-Chloro-3-methoxy-1'-(4-methoxybenzyl)spiro[cyclobutane-1,3'-pyrrolo[2,3-b]pyridin]-2'(1'H)-one

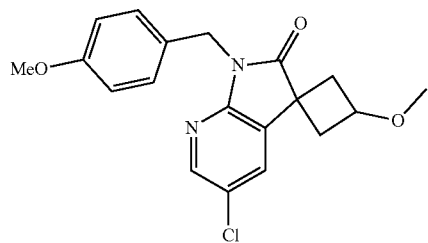 [SMILES: COc1ccc(CN2C(=O)C3(CC(OC)C3)c3cc(Cl)cnc32)cc1]

The title compound was prepared in an analogous manner to that described for 5'-chloro-3,3-dimethoxy-1'-(4-methoxybenzyl)spiro[cyclobutane-1,3'-pyrrolo[2,3-b]pyridin]-2'(1'H)-one, starting from N-(3-bromo-5-chloropyridin-2-yl)-3-methoxy-N-(4-methoxybenzyl)cyclobutane-1-carboxamide. LCMS (ESI) [M+H]$^+$ 359.1/361.1.

Step 3: 5'-Chloro-3-methoxy-1',2'-dihydrospiro[cyclobutane-1,3'-pyrrolo[2,3-b]pyridine]

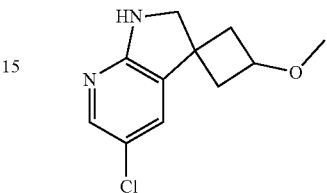

Borane-dimethylsulphide complex (0.3 mL, 3.22 mmol) was added dropwise to a solution of 5'-chloro-3-methoxy-1'-(4-methoxybenzyl)spiro[cyclobutane-1,3'-pyrrolo[2,3-b]pyridin]-2'(1'H)-one (580 mg, 1.61 mmol) in dry THF (10 mL) at RT. The mixture was heated at 70° C. for 2 h, then cooled to RT. The mixture was evaporated, dissolved in TFA (2 mL) and stirred at 80° C. overnight. The mixture was concentrated and the residue partitioned between DCM and sat. aq. sodium bicarbonate. The aqueous layer was extracted with further DCM. The combined organic extracts were washed with brine (30 mL), dried (Na$_2$SO$_4$) and concentrated. The residue was purified by chromatography on silica (solvent gradient 0-100% EtOAc in cyclohexane), to afford the title compound (270 mg, 75%) as a tan solid. LCMS (ESI) [M+H]$^+$ 225.1/227.1.

Example 65

(1r,3r)-5'-Chloro-1'-(4-methoxybenzyl)-1',2'-dihydrospiro[cyclobutane-1,3'-pyrrolo[2,3-b]pyridin]-3-yl methanesulfonate

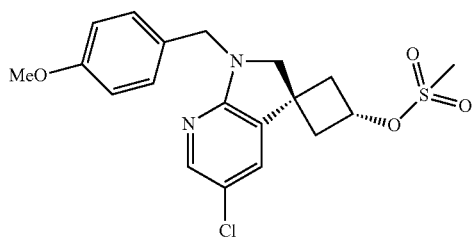 [SMILES: COc1ccc(CN2C[C@]3(C[C@H](OS(C)(=O)=O)C3)c3cc(Cl)cnc32)cc1]

To a solution of 5'-chloro-1',2'-dihydrospiro[cyclobutane-1,3'-pyrrolo[2,3-b]pyridin]-3-ol (1.5 g, 4.5 mmol) and triethylamine (1.6 mL, 11.6 mmol) in DCM (15 mL) at 0° C. was added methanesulfonyl chloride (0.45 mL, 5.8 mmol). The reaction mixture was stirred at 0° C. for 1 h, then was diluted with water. The organic extract was dried (Na$_2$SO$_4$) and concentrated. The residue was purified by chromatography on silica (solvent gradient 0-50% EtOAc in cyclohexane), and the residue recrystallized from cyclohexane/EtOAc, to afford the title compound (0.5 g, 27%). LCMS (ESI) [M+H]$^+$ 409.

Example 66

(1s,3s)-5'-Chloro-1',2'-dihydrospiro[cyclobutane-1,3'-pyrrolo[2,3-b]pyridine]-3-carbonitrile and (1s,3s)-5'-chloro-1',2'-dihydrospiro[cyclobutane-1,3'-pyrrolo[2,3-b]pyridine]-3-carboxamide

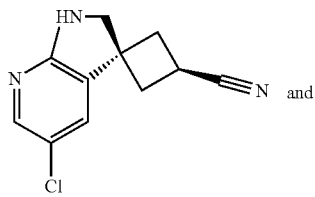

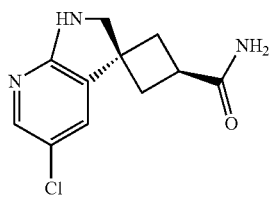

Step 1: (is, 3s)-5'-Chloro-1'-(4-methoxybenzyl)-1',2'-dihydrospiro[cyclobutane-1,3'-pyrrolo[2,3-b]pyridine]-3-carbonitrile

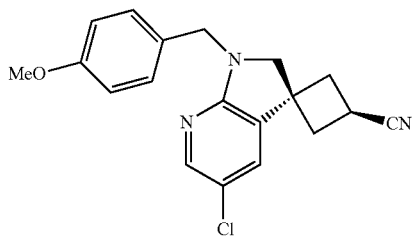 [SMILES: COc1ccc(CN2C[C@]3(C[C@@H](C#N)C3)c3cc(Cl)cnc32)cc1]

A solution of (1r,3O-5'-chloro-P-(4-methoxybenzyl)-1',2'-dihydrospiro[cyclobutane-1,3'-pyrrolo[2,3-b]pyridin]-3-yl methanesulfonate (609 mg, 1.5 mmol), potassium cyanide (487 mg, 7.5 mmol) and 18-crown-6 (396 mg, 1.5 mmol) in DMSO (1.5 mL) was stirred at 90° C. for 1 h then at 100° C. for 3 h. The reaction mixture was diluted with water and the aqueous layer was extracted with EtOAc. The combined organic extracts were dried (Na$_2$SO$_4$) and concentrated. The residue was purified by chromatography on silica (solvent gradient 0-30% EtOAc in cyclohexane), to afford the title compound (375 mg, 74%) as a colorless oil. $^1$H NMR (400 MHz, CDCl$_3$): δ ppm 7.91 (d, J=2.2 Hz, 1H), 7.25 (d, J=2.3 Hz, 1H), 7.19 (d, J=8.6 Hz, 2H), 6.85 (m, 2H), 4.48 (s, 2H), 3.80 (s, 3H), 3.52 (s, 2H), 3.24-3.15 (m, 1H), 2.75-2.68 (m, 2H), 2.59-2.52 (m, 2H).

Step 2: (1s,3s)-5'-Chloro-1',2'-dihydrospiro[cyclobutane-1,3'-pyrrolo[2,3-b]pyridine]-3-carbonitrile and (1s,3s)-5'-chloro-1',2'-dihydrospiro[cyclobutane-1,3'-pyrrolo[2,3-b]pyridine]-3-carboxamide

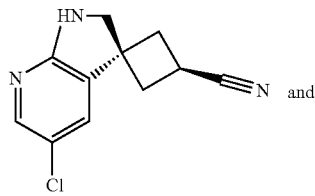

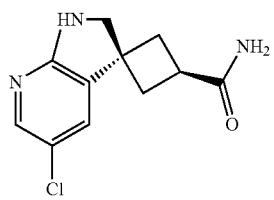

A solution of (1s,3s)-5'-chloro-1'-(4-methoxybenzyl)-1',2'-dihydrospiro[cyclobutane-1,3'-pyrrolo[2,3-b]pyridine]-3-carbonitrile (367 mg, 1.08 mmol) in TFA (2 mL) with 2 drops of anisole was heated in a sealed vial at 65° C. for 6 h. The reaction mixture was diluted with DCM, and passed trough a SCX-2 cartridge (eluting with MeOH then MeOH·NH$_3$). The residue was purified by chromatography on silica (solvent gradient 0-30% EtOAc in cyclohexane to afford (1s,3s)-5'-chloro-1',2'-dihydrospiro[cyclobutane-1,3'-pyrrolo[2,3-b]pyridine]-3-carbonitrile (100 mg, 42%) as a yellow powder. LCMS (ESI) [M+H]$^+$ 220. Further elution with 0-10% MeOH in EtOAc afforded (1s,3s)-5'-chloro-1',2'-dihydrospiro[cyclobutane-1,3'-pyrrolo[2,3-b]pyridine]-3-carboxamide (100 mg, 39%) as a beige solid. LCMS (ESI) [M+H]$^+$ 238.

Example 67

(R)-1-(5'-Chloro-1',2'-dihydrospiro[cyclobutane-1,3'-pyrrolo[2,3-b]pyridin]-3-yl)pyrrolidin-3-ol

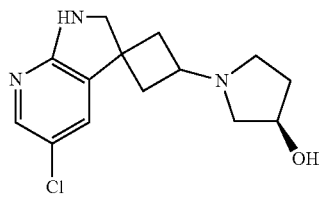 [SMILES: O[C@@H]1CCN(C2CC3(CNc4ncc(Cl)cc43)C2)C1]

333

Step 1: (R)-1-(5'-Chloro-1'-(4-methoxybenzyl)-1',2'-dihydrospiro[cyclobutane-1,3'-pyrrolo[2,3-b]pyridin]-3-yl)pyrrolidin-3-ol

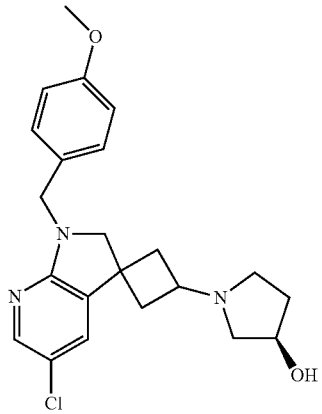 [SMILES: COc1ccc(CN2CC3(CC(N4CC[C@@H](O)C4)C3)c3cc(Cl)cnc32)cc1]

To a mixture of 5'-chloro-1'-(4-methoxybenzyl)-1',2'-dihydrospiro[cyclobutane-1,3'-pyrrolo[2,3-b]pyridin]-3-one (132 mg, 0.402 mmol), (R)-pyrrolidinol (46 mg, 0.523 mmol) and acetic acid (0.04 mL) in dry THF (1 mL) was added sodium cyanoborohydride (33 mg, 0.523 mmol). The reaction mixture was stirred for 1 h at RT then was partitioned between water (15 mL) and EtOAc. The aqueous layer was further extracted with EtOAc. The combined organic extracts were washed with brine (20 mL), dried ($Na_2SO_4$), and concentrated. The residue was purified by chromatography on silica (solvent gradient 0-8% MeOH·$NH_3$ in DCM), to give the title compound (168 mg, 59%) as a colorless gum. LCMS (ESI) [M+H]$^+$ 400.3/402.3.

Step 2: (R)-1-(5'-Chloro-1',2'-dihydrospiro[cyclobutane-1,3'-pyrrolo[2,3-b]pyridin]-3-yl)pyrrolidin-3-ol

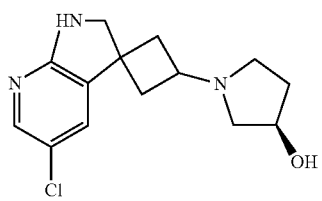 [SMILES: O[C@@H]1CCN(C2CC3(CNc4ncc(Cl)cc43)C2)C1]

A solution of (R)-1-(5'-chloro-1'-(4-methoxybenzyl)-1',2'-dihydrospiro[cyclobutane-1,3'-pyrrolo[2,3-b]pyridin]-3-yl)pyrrolidin-3-ol (168 mg, 0.42 mmol) in TFA (2 mL) containing water (0.1 mL) was heated in a sealed tube at 80° C. for 18 h. The cooled mixture was evaporated and then passed down a SCX-2 cartridge (eluting with MeOH then MeOH·$NH_3$) to give the title compound (106 mg, 90%) as a pale yellow gum. LCMS (ESI) [M+H]$^+$ 280.1/282.1.

334

Example 68

(1s,3s)-5'-Chloro-3-methyl-1',2'-dihydrospiro[cyclobutane-1,3'-pyrrolo[2,3-b]pyridin]-3-ol

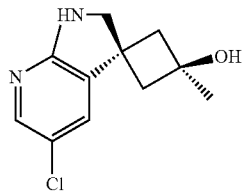

Step 1: (1s,3s)-5'-Chloro-1'-(4-methoxybenzyl)-3-methyl-1',2'-dihydrospiro[cyclobutane-1,3'-pyrrolo[2,3-b]pyrdin]-3-ol and (1r,3r)-5'-chloro-1'-(4-methoxybenzyl)-3-methyl-1',2'-dihydrospiro[cyclobutane-1,3'-pyrrolo[2,3-b]pyrdin]-3-ol

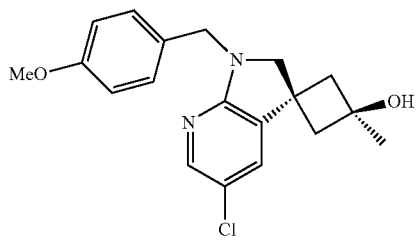

Methyl magnesium bromide (1.4N in THF, 1.74 mL, 2.432 mmol) was added dropwise to a solution of 5'-chloro-1'-(4-methoxybenzyl)-1',2'-dihydrospiro[cyclobutane-1,3'-pyrrolo[2,3-b]pyridin]-3-one (400 mg, 1.216 mmol) in dry THF (5 mL) at −20° C. The reaction mixture was stirred for 30 min then allowed to warm up to RT over 1 h, re-cooled to −10° C. and quenched with aq. sat. ammonium chloride (ca 5 mL). The mixture was partitioned between EtOAc and water (15 mL) with brine (15 mL). The aqueous layer was extracted with EtOAc. The combined organic extracts were washed with brine, dried ($Na_2SO_4$) and concentrated. The residue was purified by chromatography on silica (solvent gradient 0-30% EtOAc in cyclohexane), to afford (1s,3s)-5'-chloro-1'-(4-methoxybenzyl)-3-methyl-1',2'-dihydrospiro [cyclobutane-1,3'-pyrrolo[2,3-b]pyridin]-3-ol (87 mg, 20%) and (1r,3r)-5'-chloro-1'-(4-methoxybenzyl)-3-methyl-1',2'-dihydrospiro[cyclobutane-1,3'-pyrrolo[2,3-b]pyridin]-3-ol (279 mg, 66%). LCMS (ESI) [M+H]$^+$ 345.2/347.2.

Step 2: (1s,3s)-5'-Chloro-3-methyl-1',2'-dihydrospiro[cyclobutane-1,3'-pyrrolo[2,3-b]pyridin]-3-ol

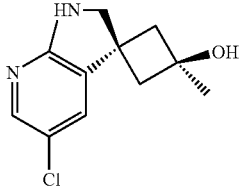

(1s,3s)-5'-Chloro-1'-(4-methoxybenzyl)-3-methyl-1',2'-dihydrospiro[cyclobutane-1,3'-pyrrolo[2,3-b]pyridin]-3-ol (87 mg, 0.252 mmol) in TFA/water (95:5, 0.5 mL) was heated in a sealed tube at 70° C. for 18 h. The cooled mixture was evaporated and the residue purified by SCX-2 (eluting with MeOH followed by MeOH·NH$_3$) to afford the title compound (67 mg, 100%). LCMS (ESI) [M+H]$^+$ 225.1/227.1.

Example 69

(1r,3r)-5'-Chloro-3-(trifluoromethyl)-1',2'-dihydrospiro[cyclobutane-1,3'-pyrrolo[2,3-b]pyridin]-3-ol

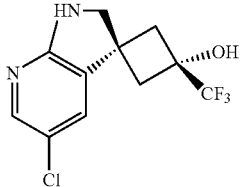

Step 1: (1r,30-5'-Chloro-1'-(4-methoxybenzyl)-3-(trifluoromethyl)-1',2'-dihydrospiro[cyclobutane-1,3'-pyrrolo[2,3-b]pyridin]-3-ol

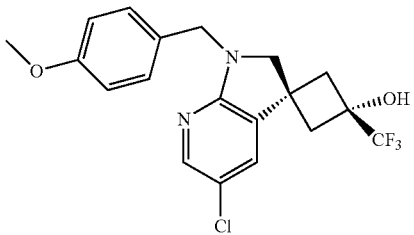 [SMILES: COc1ccc(CN2C[C@]3(C[C@@](O)(C(F)(F)F)C3)c3cc(Cl)cnc32)cc1]

To a solution of 5'-chloro-1'-(4-methoxybenzyl)-1',2'-dihydrospiro[cyclobutane-1,3'-pyrrolo[2,3-b]pyridin]-3-one (500 mg, 1.5 mmol) and cesium fluoride (9 mg, 0.06 mmol) in THF (3 mL) at 0° C. was added a solution of trifluoromethyltrimethylsilane (260 mg, 1.8 mmol) in THF (2 mL). The reaction mixture was stirred at 0° C. for 16 h, then was concentrated. The residue was purified by chromatography on silica (solvent gradient 0-30% EtOAc in cyclohexane) to afford the title compound (230 mg, 38%). LCMS (ESI) [M+H]$^+$ 399.

Step 2: (1r, 30-5'-Chloro-3-(trifluoromethyl)-1',2'-dihydrospiro[cyclobutane-1,3'-pyrrolo[2,3-b]pyridin]-3-ol

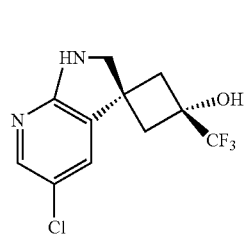 [SMILES: O[C@]1(C(F)(F)F)C[C@@]2(CNc3ncc(Cl)cc32)C1]

A solution of (1r,30-5'-chloro-1'-(4-methoxybenzyl)-3-(trifluoromethyl)-1',2'-dihydrospiro[cyclobutane-1,3'-pyrrolo[2,3-b]pyridin]-3-ol (230 mg, 0.57 mmol) in TFA (2 mL) containing a drop of water was stirred at 85° C. for 16 h. The solution was purified on SCX-2 (eluting with MeOH then MeOH·NH$_3$) to afford the title compound (144 mg, 90%) as a beige solid. LCMS (ESI) [M+H]$^+$ 279.

Example 70

2-(5'-Chloro-1',2'-dihydrospiro[cyclobutane-1,3'-pyrrolo[2,3-b]pyridin]-3-ylidene)acetonitrile

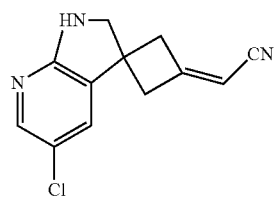 [SMILES: N#CC=C1CC2(CNc3ncc(Cl)cc32)C1]

Step 1: 2-(5'-Chloro-1'-(4-methoxybenzyl)-1',2'-dihydrospiro[cyclobutane-1,3'-pyrrolo[2,3-b]pyridin]-3-ylidene)acetonitrile

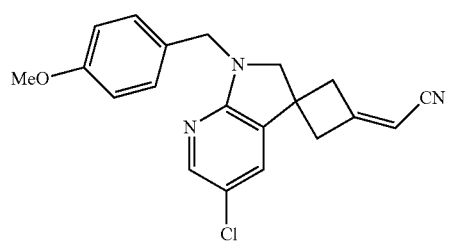 [SMILES: COc1ccc(CN2CC3(CC(=CC#N)C3)c3cc(Cl)cnc32)cc1]

Potassium tert-butoxide (187 mg, 1.663 mmol) was added portionwise to a solution of diethyl cyanomethylphosphonate (284 mg, 1.742 mmol) in dry THF (7 mL) and the mixture stirred for 15 min. 5'-Chloro-1'-(4-methoxybenzyl)-1',2'-dihydrospiro[cyclobutane-1,3'-pyrrolo[2,3-b]pyridin]-3-one (521 mg, 1.584 mmol) was then added and the mixture stirred for 3 h. The solvent was evaporated and the residue partitioned between EtOAc (3×10 mL) and aq. sat. ammonium chloride (15 mL). The aqueous layer was extracted with EtOAc. The combined organic extracts were washed with brine (20 mL), dried (Na$_2$SO$_4$) and evaporated. The residue was purified by chromatography on silica (solvent

Example 71

Step 2: 2-(5'-Chloro-1',2'-dihydrospiro[cyclobutane-1,3'-pyrrolo[2,3-b]pyridin]-3-ylidene)acetonitrile

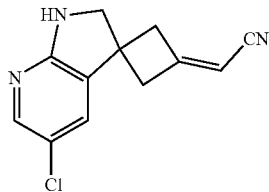 [SMILES: N#CC=C1CC2(CNc3ncc(Cl)cc32)C1]

2-(5'-Chloro-1'-(4-methoxybenzyl)-1',2'-dihydrospiro[cyclobutane-1,3'-pyrrolo[2,3-b]pyridin]-3-ylidene)acetonitrile (444 mg, 1.265 mmol) in TFA (0.5 mL) was heated at 70° C. for 2 h. The cooled mixture was evaporated and the residue purified by SCX-2 (eluting with MeOH followed by MeOH·NH$_3$) to afford the title compound (284 mg, 97%). LCMS (ESI) [M+H]$^+$ 232.0/234.0.

Example 72

2-(5'-Chloro-1',2'-dihydrospiro[cyclobutane-1,3'-pyrrolo[2,3-b]pyridin]-3-ylidene)acetamide

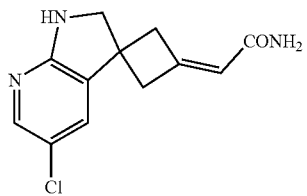 [SMILES: NC(=O)C=C1CC2(CNc3ncc(Cl)cc32)C1]

A solution of 2-(5'-Chloro-1',2'-dihydrospiro[cyclobutane-1,3'-pyrrolo[2,3-b]pyridin]-3-ylidene)acetonitrile (184 mg, 0.794 mmol) in TFA (1.0 mL) and water (0.25 mL) was heated at 85° C. for 18 h. The cooled mixture was evaporated and the residue purified by SCX-2 (eluting with MeOH followed by MeOH·NH$_3$) to afford the title compound (198 mg, 100%). LCMS (ESI) [M+H]$^+$ 250.0/252.0.

Example 73

1-(5'-Chloro-1',2'-dihydrospiro[azetidine-3,3'-pyrrolo[2,3-b]pyridin]-1-yl)ethan-1-one

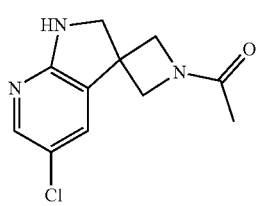

gradient 0-30% EtOAc in cyclohexane), to afford the title compound (478 mg, 86%) as a pale yellow gum. LCMS (ESI) [M+H]$^+$ 352.0/354.0.

Step 1: tert-Butyl 3-((3-bromo-5-chloropyridin-2-yl)(4-methoxybenzyl)carbamoyl)azetidine-1-carboxylate

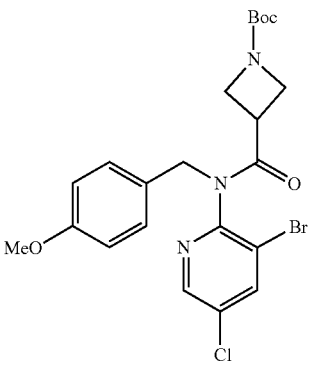 [SMILES: COc1ccc(CN(C(=O)C2CN(C(=O)OC(C)(C)C)C2)c2ncc(Cl)cc2Br)cc1]

Sodium methoxide (540 mg, 10.0 mmol) was added portionwise to a suspension of 1-(tert-butoxycarbonyl)azetidine-3-carboxylic acid (2.0 g, 10.0 mmol) in dry THF (20 mL). The reaction mixture was stirred for 1 h at RT. The solvent was evaporated and the residue dissolved in DCM (20 mL). DMF (1 drop) was added followed by oxalyl chloride (0.85 mL, 10.0 mmol) dropwise. When gas evolution had subsided, 3-bromo-5-chloro-N-(4-methoxybenzyl)pyridin-2-amine (1.0 g, 1.96 mmol) was added and the mixture stirred overnight. The mixture was quenched with water (15 mL) and extracted with DCM (3×15 mL). The combined organic extracts were passed through a PTFE cartridge and concentrated. The residue was purified by chromatography on silica (solvent gradient 0-40% EtOAc in cyclohexane), to afford the title compound (1.2 g, 66%). LCMS (ESI) [M+Na]$^+$ 532.1/534.1/536.0.

Example 74

Step 2: tert-Butyl 5'-chloro-1'-(4-methoxybenzyl)-2'-oxo-1',2'-dihydrospiro[azetidine-3,3'-pyrrolo[2,3-b]pyridine]-1-carboxylate

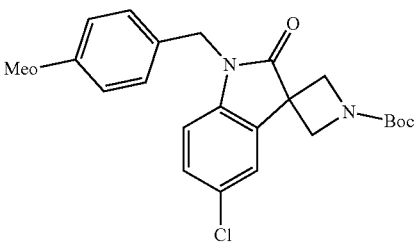

A degassed mixture of tert-butyl 3-((3-bromo-5-chloropyridin-2-yl)(4-methoxybenzyl)carbamoyl)azetidine-1-carboxylate (944 mg, 1.848 mmol), [1,3-bis(2,6-diisopropylphenyl)imidazol-2-ylidene](3-chloropyridyl)palladium(II) dichloride (PEPPSI-iPr; 125 mg, 0.185 mmol) and sodium tert-butoxide (533 mg, 5.544 mmol) in dry toluene (15 mL) was heated at 115° C. for 4 h in a sealed tube. The solvent was evaporated and the residue partitioned between EtOAc and water (20 mL). The aqueous layer was extracted with EtOAc. The combined organic extracts were washed with brine (20 mL), dried (Na₂SO₄) and concentrated. The residue was purified by chromatography on silica (solvent gradient 0-30% EtOAc in cyclohexane), to afford the title compound (235 mg, 29%). LCMS (ESI) [M+Na]+452.2/454.1.

Step 3: 5'-Chloro-1'-(4-methoxybenzyl)spiro[azetidine-3,3'-pyrrolo[2,3-b]pyridin]-2'(1'H)-one

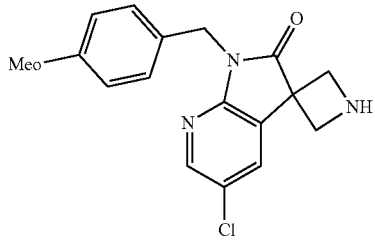

TFA (0.5 mL) was added to a solution of tert-butyl 5'-chloro-1'-(4-methoxybenzyl)-2'-oxo-1', 2'-dihydrospiro[azetidine-3,3'-pyrrolo[2,3-b]pyridine]-1-carboxylate (248 mg, 0.577 mmol) in dry DCM (5 mL). The reaction mixture was stirred at RT for 3 h, then was evaporated.

The residue was purified by SCX-2 (eluting with MeOH followed by MeOH·NH₃) to afford the title compound (160 mg, 84%). LCMS (ESI) [M+H]+ 330.1/332.1.

Step 4: 5'-Chloro-1'-(4-methoxybenzyl)-1',2'-dihydrospiro[azetidine-3,3'-pyrrolo[2,3-b]pyridine]

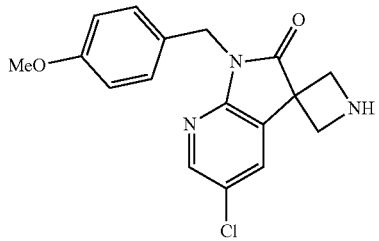

Borane-dimethylsulphide complex (0.092 mL, 0.973 mmol) was added dropwise to a solution of 5'-chloro-1'-(4-methoxybenzyl)spiro[azetidine-3,3'-pyrrolo[2,3-b]pyridin]-2'(1'H)-one (160 mg, 0.486 mmol) in dry THF (5 mL) at RT. The mixture was heated at 75° C. for 2 h then cooled to 0° C. MeOH (ca 3 mL) was cautiously added dropwise then the reaction was stirred for 30 min. The mixture was evaporated to give a colorless gum which was dissolved in DCM (5 mL) and TFA (0.5 mL). The mixture was stirred for 1 h then concentrated. The residue was purified by SCX-2 (eluting with MeOH followed by MeOH·NH₃) to afford the title compound (153 mg, 100%). LCMS (ESI) [M+H]+ 316.1/318.1.

Step 5: 1-(5'-Chloro-1'-(4-methoxybenzyl)-1',2'-dihydrospiro[azetidine-3,3'-pyrrolo[2,3-b]pyridin]-1-yl)ethan-1-one

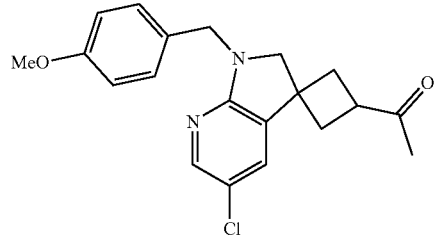 [SMILES: COc1ccc(CN2CC3(CC(C(C)=O)C3)c3cc(Cl)cnc32)cc1]

Acetic anhydride (0.025 mL, 0.266 mmol) was added to a solution of 5'-chloro-1'-(4-methoxybenzyl)-1',2'-dihydrospiro[azetidine-3,3'-pyrrolo[2,3-b]pyridine](70 mg, 0.222 mmol) and DIPEA (0.114 mL, 0.666 mmol) in dry DCM (1 mL). The reaction mixture was stirred at RT for 2 h. The solvent was evaporated in vacuo resulting in the precipitation of the title compound (79 mg, 100%) which was filtered off as a colorless solid. LCMS (ESI) [M+H]+ 358.2/360.2.

Step 6: 1-(5'-Chloro-1',2'-dihydrospiro[azetidine-3,3'-pyrrolo[2,3-b]pyridin]-1-yl)ethan-1-one

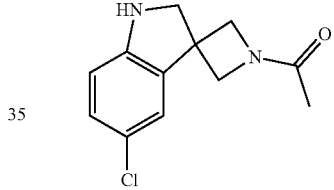

1-(5'-Chloro-1'-(4-methoxybenzyl)-1',2'-dihydrospiro[azetidine-3,3'-pyrrolo[2,3 b]pyridin]-1-yl)ethan-1-one (79 mg, 0.221 mmol) in TFA (0.5 mL) was heated in a sealed tube at 70° C. for 3 h. The cooled mixture was evaporated and the residue purified by SCX-2 (eluting with MeOH followed by MeOH·NH₃) to afford the title compound (52 mg, 99%). LCMS (ESI) [M+H]+ 238.0/240.0.

Example 75

3-(4'-Chloro-1',2'-dihydrospiro[cyclopropane-1,3'-pyrrolo[2,3-b]pyridin]-5'-yl)-2-fluorobenzoic acid

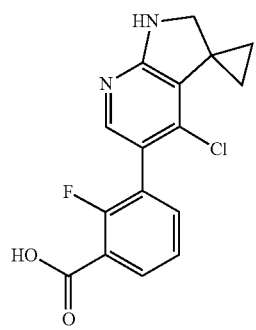 [SMILES: O=C(O)c1cccc(-c2cnc3c(c2Cl)C2(CC2)CN3)c1F]

341

Step 1: Ethyl 3-(4'-chloro-1',2'-dihydrospiro[cyclopropane-1,3'-pyrrolo[2,3-b]pyridin]-5'-yl)-2-fluorobenzoate

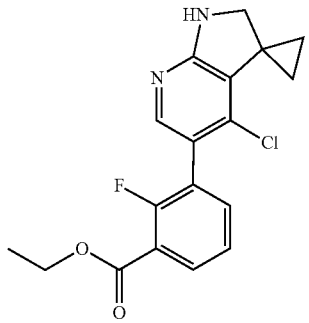 [SMILES: CCOC(=O)c1cccc(-c2cnc3c(c2Cl)C2(CC2)CN3)c1F]

The title compound was prepared according to general Method L (see below), starting from (2-fluoro-3-(ethoxycarbonyl)phenyl)boronic acid and 5'-bromo-4'-chloro-1',2'-dihydrospiro[cyclopropane-1,3'-pyrrolo[2,3-b]pyridine]. $^1$H NMR (400 MHz, DMSO-$d_6$): δ ppm 7.90-7.85 (m, 1H), 7.58 (s, 1H), 7.54 (dt, J=1.8, 7.2 Hz, 1H), 7.36 (t, J=7.7 Hz, 1H), 7.15 (s, 1H), 4.32 (q, J=7.1 Hz, 2H), 3.55 (s, 2H), 1.66-1.61 (m, 2H), 1.31 (t, J=7.1 Hz, 3H), 0.92-0.90 (m, 2H).

Step 2: 3-(4'-Chloro-1',2'-dihydrospiro[cyclopropane-1,3'-pyrrolo[2,3-b]pyridin]-5'-yl)-2-fluorobenzoic acid

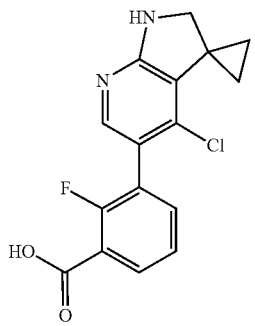 [SMILES: O=C(O)c1cccc(-c2cnc3c(c2Cl)C2(CC2)CN3)c1F]

To a solution of methyl 3-(4'-chloro-1',2'-dihydrospiro[cyclopropane-1,3'-pyrrolo[2,3-b]pyridin]-5'-yl)-2-fluorobenzoate (850 mg, 2.45 mmol) in THF/IMS (1:1, 20 mL) was added lithium hydroxide (1N aq., 3 mL, 3 mmol). The reaction mixture was stirred at RT for 16 h, then was concentrated. The residue was dissolved in water (2 mL) and triturated with acetic acid (0.2 mL). The precipitate was collected by filtration and dried to afford the title compound (906 mg, 96%) as a beige solid. $^1$H NMR (400 MHz, DMSO-$d_6$): δ ppm 7.85-7.80 (m, 1H), 7.57 (s, 1H), 7.48-7.44 (m, 1H), 7.30 (t, J=7.6 Hz, 1H), 7.12 (s, 1H), 3.55 (s, 2H), 1.66-1.62 (m, 2H), 0.92-0.90 (m, 2H).

342

Example 76

1-(3-Bromophenyl)imidazolidin-2-one

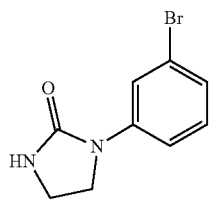 [SMILES: O=C1NCCN1c1cccc(Br)c1]

Step 1: 1-(3-Bromophenyl)-3-(2-chloroethyl)urea

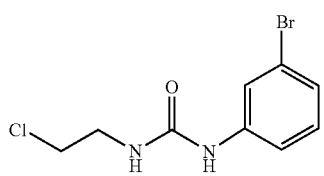 [SMILES: O=C(NCCCl)Nc1cccc(Br)c1]

To an ice-cooled solution of 3-bromoaniline (2.0 g, 11.63 mmol) in toluene (20 mL) was added a solution of 2-chloroethylisocyanate (1.84 g, 17.44 mmol) in toluene (5 mL). The mixture was stirred at RT for 64 h. The resultant solid was collected by filtration, washed with toluene and dried in vacuo to give the title compound (2.9 g, 90%) as a white solid. LCMS (ESI) [M+H]$^+$ 277/279/281.

Step 2: 1-(3-Bromophenyl)imidazolidin-2-one

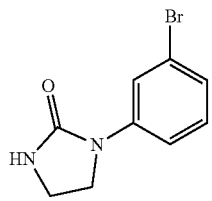 [SMILES: O=C1NCCN1c1cccc(Br)c1]

1-(3-Bromophenyl)-3-(2-chloroethyl)urea (1.0 g, 3.6 mmol) in THF (7.5 mL) was added over 10 min to an ice-cooled suspension of sodium hydride (60% in oil, 0.288 g, 7.2 mmol) in THF (5 mL). The mixture was stirred at RT for 2 h then quenched with MeOH. After concentration in vacuo, the residue was partitioned between DCM and aq. HCl. The aqueous phase was extracted with more DCM and the combined organic extracts were washed with water, dried (Na$_2$SO$_4$), filtered and evaporated. The residue was purified by chromatography on silica (solvent gradient 10-70% EtOAc in DCM) to afford the title compound (0.825 g, 95%) as a colorless solid. $^1$H NMR (400 MHz, CDCl$_3$): δ 7.72 (s, 1H), 7.52 (dt, J=7.5, 2.0 Hz, 1H), 7.21-7.16 (m, 2H), 5.20 (brs, 1H), 3.93-3.89 (m, 2H), 3.61-3.57 (m, 2H).

Example 77

1-(3-Bromophenyl)tetrahydropyrimidin-2(1H)-one

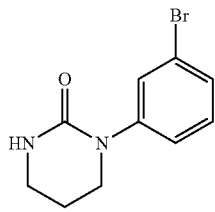 [SMILES: O=C1NCCCN1c1cccc(Br)c1]

Step 1: 1-(3-Bromophenyl)-3-(3-chloropropyl)urea

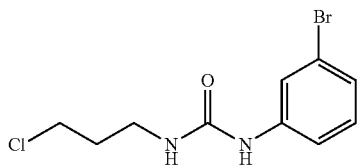 [SMILES: O=C(NCCCCl)Nc1cccc(Br)c1]

To an ice-cooled solution of 3-bromoaniline (1.637 g, 9.52 mmol) in toluene (15 mL) was added a solution of 3-chloropropylisocyanate (1.48 g, 12.37 mmol) in toluene (5 mL). The mixture was stirred at RT for 10 days. The resultant solid was collected by filtration, washed with toluene and dried in vacuo to give the title compound (2.68 g, 97%) as a white solid. LCMS (ESI) [M+H]$^+$ 291/293/295.

Step 2: 1-(3-Bromophenyl)tetrahydropyrimidin-2(1H)-one

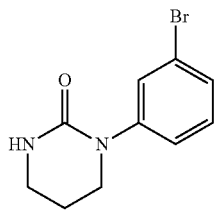 [SMILES: O=C1NCCCN1c1cccc(Br)c1]

1-(3-Bromophenyl)-3-(3-chloropropyl)urea (1 g, 3.4 mmol) in THF (7.5 mL) was added over 10 min to an ice-cooled suspension of sodium hydride (60% in oil, 0.274 g, 6.86 mmol) in THF (5 mL). The mixture was stirred at RT for 2 h then quenched with MeOH. After concentration in vacuo, the residue was partitioned between DCM and aq. HCl. The aqueous phase was extracted with more DCM and the combined organic extracts were washed with water, dried (Na$_2$SO$_4$) and evaporated. The residue was purified by chromatography on silica (solvent gradient 2-10% MeOH in DCM) to afford the title compound (0.853 g, 97%) as a colorless solid. $^1$H NMR (400 MHz, DMSO-d$_6$): δ 7.55 (s, 1H), 7.31-7.25 (m, 3H), 6.71 (brs, 1H), 3.64-3.61 (m, 2H), 3.23-3.20 (m, 2H), 1.96-1.91 (m, 2H).

1-(3-Bromophenyl)piperidin-2-one

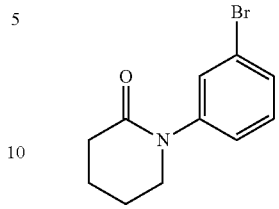

To an ice-cooled solution of 3-bromoaniline (2.0 g, 11.63 mmol) and triethylamine (2.27 mL, 16.3 mmol) in DCM (45 mL) was added a solution of 5-bromopentanoyl chloride (2.78 g, 14.0 mmol) in DCM (5 mL) over 5 min. The mixture was stirred in the ice bath for 1.5 h. The reaction mixture was diluted with DCM, washed successively with 10% aq. citric acid, aq. sodium bicarbonate and water, then dried (Na$_2$SO$_4$) and evaporated to afford 5-bromo-N-(3-bromophenyl)pentanamide (4.22 g, assume quantitative). This was dissolved in THF (100 mL), cooled in an ice bath and potassium tert-butoxide (1.95 g, 17.4 mmol) was added portionwise over 10 min. The mixture was stirred in the ice bath for 1 h, then concentrated under reduced pressure. The residue was partitioned between EtOAc and water. The aqueous phase was extracted with more EtOAc and the combined organic extracts were washed with brine, dried (Na$_2$SO$_4$) and evaporated. The residue was purified by chromatography on silica (solvent gradient 20-100% EtOAc in cyclohexane) to afford the title compound (2.33 g, 79%) as an orange solid. LCMS (ESI) [M+H]$^+$ 254/256.

Example 78 tert-Butyl 4-(3-bromophenyl)-3-oxopiperazine-1-carboxylate

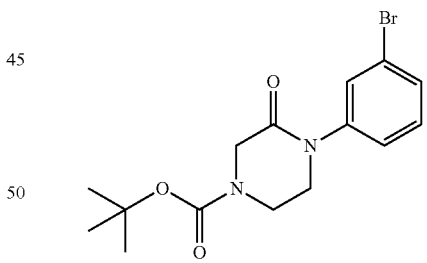

A degassed mixture of 3-bromoiodobenzene (849 mg, 3.00 mmol), tert-butyl 3-oxopiperazine-1-carboxylate (660 mg, 3.30 mmol), copper acetate (109 mg, 0.60 mmol), 3,4,7,8-tetramethyl-1,10-phenanthroline (212 mg, 0.90 mmol), cesium carbonate (1.95 g, 6.00 mmol) and 1,4-dioxane (10 mL) was stirred in a sealed tube at 100° C. for 18 h. The cooled reaction mixture was filtered through a pad of celite eluting with EtOAc. The filtrate was washed with water, brine, dried (Na$_2$SO$_4$) and concentrated in vacuo. The residue was purified by chromatography on silica (solvent gradient 20-30% EtOAc in cyclohexane) to afford the title compound (794 mg, 75%) as a white solid. LCMS (ESI) [M−tBu+H]$^+$ 299/301.

Example 79

(R)-1-(3-Bromophenyl)-5-methylimidazolidin-2-one

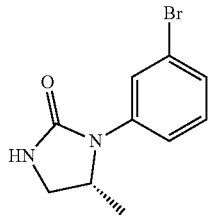

A mixture of 3-bromoiodobenzene (0.60 g, 2.12 mmol), (R)-3-aminobutanoic acid (0.218 g, 2.12 mmol), copper(I) iodide (0.080 g, 0.42 mmol), potassium phosphate (1.8 g, 8.48 mmol) and DMSO (3.5 mL) was stirred in a sealed tube at 120° C. for 2.5 h. The cooled reaction mixture was diluted with DCM (70 mL) and loaded on to a 25 g silica cartridge (solvent gradient 5-50% MeOH·NH$_3$ in DCM. After evaporation, the crude (R)-3-((3-bromophenyl)amino)butanoic acid was suspended in toluene (10 mL) and triethylamine (1 mL) was added and evaporated. The residue was suspended in toluene (18 mL), triethylamine (1 mL) and a solution of diphenyl phosphoryl azide (1.71 g, 6.21 mmol) in toluene (2 mL) was added. After stirring at RT for 5 min the mixture was heated at 100° C. for 1 h. The cooled reaction mixture was partitioned between EtOAc and sat. sodium bicarbonate. The aqueous phase was extracted with more EtOAc and the combined organic extracts were washed with brine, dried (Na$_2$SO$_4$) and evaporated. The residue was purified by chromatography on silica (solvent gradient 50-100% EtOAc in cyclohexane) to afford the title compound (0.3618 g, 67%) as a colorless gum. LCMS (ESI) [M+H]$^+$ 255/257.

Example 80

(S)-1-(3-Bromophenyl)-5-methylimidazolidin-2-one

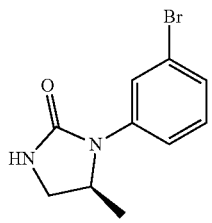

(S)-1-(3-Bromophenyl)-5-methylimidazolidin-2-one was prepared from (S)-3-aminobutanoic acid by an analogous method to that described for (R)-1-(3-bromophenyl)-5-methylimidazolidin-2-one. LCMS (ESI) [M+H]$^+$ 255/257.

Example 81

3-(3-Bromophenyl)piperidin-2-one

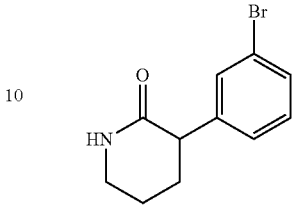

A solution of methyl 2-(3-bromophenyl)acetate (0.58 g, 2.53 mmol) in DMSO (1.5 mL) was added over 2 min to a suspension of sodium hydride (60% in oil, 102 mg, 2.54 mmol) in DMSO (0.5 mL). The mixture was stirred at RT for 5 min, then a solution of tert-butyl (3-bromopropyl)carbamate (0.50 g, 2.10 mmol) in DMSO (1.5 mL) was added. The mixture was stirred at 50° C. for 1 h. The cooled reaction mixture was partitioned between EtOAc and aq. ammonium chloride. The aqueous phase was extracted with more EtOAc and the combined organic extracts were washed with water, brine, dried (Na$_2$SO$_4$) and evaporated. The residue was purified by chromatography on silica (solvent gradient 0-20% MeOH in EtOAc) to afford the title compound (0.171 g, 32%) as a colorless solid. LCMS (ESI) [M+H]$^+$ 254/256.

Example 82

3-(3-Bromophenyl)pyrrolidin-2-one

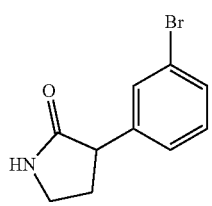

Step 1: Methyl 2-(3-bromophenyl)-3-cyanopropanoate

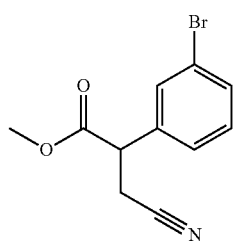

n-BuLi (2.5N in hexanes, 1.75 mL, 4.36 mmol) was added to a solution of diisopropylamine (0.68 mL, 1.8 mmol) in THF (10 mL) at −40° C. The mixture was allowed to warm to −20° C. over 15 min, then cooled to −78° C. when a solution of methyl 2-(3-bromophenyl)acetate (1.0 g, 4.36 mmol) in THF (4 mL) was added over 5 min. The mixture was stirred at −78° C. for 1 h, then a solution of bromoacetonitrile (0.574 g, 4.8 mmol) in THF (2 mL) was added over 5 min. The mixture was stirred at −78° C. for 1 h, then allowed to warm to 5° C. over 1.5 h. Sat. aq. ammonium chloride was added and the mixture extracted with EtOAc (2×). The combined organic extracts were washed with brine, dried (Na₂SO₄) and evaporated. The residue was purified by chromatography on silica (solvent gradient 2-25% EtOAc in cyclohexane) to afford the title compound (609 mg, 52%) as a colorless oil. LCMS (ESI) [M+H]⁺ 268/270.

Step 2: 3-(3-Bromophenyl)pyrrolidin-2-one

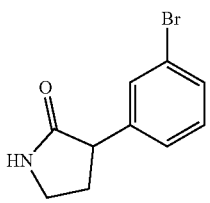

Raney nickel (0.1 g) was added to a solution of methyl 2-(3-bromophenyl)-3-cyanopropanoate (0.50 g, 1.865 mmol) in MeOH (15 mL) and concentrated aq. ammonia (5 mL). The mixture was stirred under 1 atmosphere of hydrogen for 5.5 h, then filtered through celite. The filtrate was evaporated and the residue purified by chromatography on silica (solvent gradient 2-10% MeOH in EtOAc) to afford the title compound (0.165 g, 37%) as a colorless solid. LCMS (ESI) [M+H]⁺ 240/242.

Example 83

1-(6-Bromopyridin-2-yl)imidazolidin-2-one

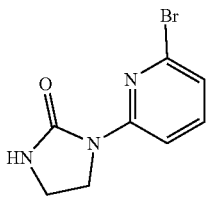

Step 1: 1-(6-Bromopyridin-2-yl)-3-(2-chloroethyl)urea

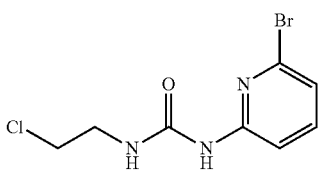 [SMILES: O=C(NCCCl)Nc1cccc(Br)n1]

A solution of 2-amino-6-bromopyridine (1.10 g, 6.358 mmol) and 2-chloroethylisocyanate (1.0 g, 9.54 mmol) in toluene (10 mL) was stirred at RT for 12 days. The resultant solid was collected by filtration, washed with toluene and dried in vacuo to give the title compound (1.73 g, 98%) as a white solid. LCMS (ESI) [M+H]⁺ 278/280/282.

Step 2: 1-(6-Bromopyridin-2-yl)imidazolidin-2-one

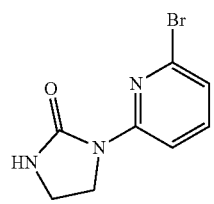

A suspension of 1-(6-bromopyridin-2-yl)-3-(2-chloroethyl)urea (0.50 g, 1.8 mmol) in THF (4 mL) was added over 5 min to an ice-cooled suspension of sodium hydride (60% in oil, 0.144 g, 3.6 mmol) in THF (3 mL). The mixture was stirred at RT for 3 h then quenched with MeOH. After concentration in vacuo the residue was partitioned between aq. sodium bicarbonate and DCM. The aqueous phase was extracted with more DCM and the combined organic extracts were washed with water, dried (Na₂SO₄) and evaporated. The residue was purified by chromatography on silica (solvent gradient 2-10% MeOH in DCM) to afford the title compound (0.225 g, 52%) as a colorless solid. ¹H NMR (400 MHz, DMSO-d₆): δ 8.17 (d, J=8.4 Hz, 1H), 7.63 (dd, J=8.4, 7.6 Hz, 1H), 7.36 (brs, 1H), 7.18 (d, J=7.6 Hz, 1H), 3.96-3.91 (m, 2H), 3.42-3.38 (m, 2H).

Example 84

1-(6-Bromopyridin-2-yl)tetrahydropyrimidin-2(1H)-one

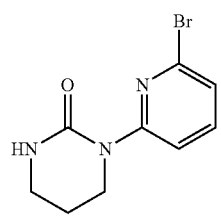 [SMILES: O=C1NCCCN1c1cccc(Br)n1]

Step 1: 1-(6-Bromopyridin-2-yl)-3-(3-chloropropyl)urea

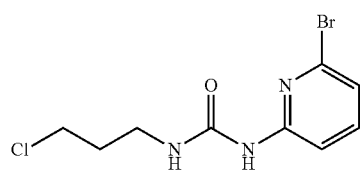 [SMILES: O=C(NCCCCl)Nc1cccc(Br)n1]

A solution of 2-amino-6-bromopyridine (880 mg, 5.09 mmol) and 3-chloropropylisocyanate (730 mg, 6.1 mmol) in toluene (8 mL) was stirred at RT for 9 days. The resultant solid was collected by filtration, washed with toluene and dried in vacuo to give the title compound (795 mg, 53%) as a white solid. LCMS (ESI) [M+H]⁺ 292/294/296.

Step 2: 1-(6-Bromopyridin-2-yl)tetrahydropyrimidin-2(1H)-one

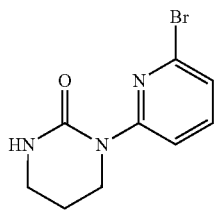 [SMILES: O=C1NCCCN1c1cccc(Br)n1]

A suspension of 1-(6-bromopyridin-2-yl)-3-(3-chloropropyl)urea (0.78 g, 2.67 mmol) in THF (5 mL) was added over 5 min to an ice-cooled suspension of sodium hydride (60% in oil, 0.144 g, 3.6 mmol) in THF (3 mL). The mixture was stirred at RT for 2 h then at 40° C. for a further 16 h. The reaction mixture was quenched with MeOH. After concentration in vauo the residue was partitioned between aq. sodium bicarbonate and DCM. The aqueous phase was extracted with more DCM and the combined organic extracts were washed with water, dried ($Na_2SO_4$) and evaporated. The residue was purified by chromatography on silica (solvent gradient 2-8% MeOH in DCM), then crystallised from EtOAc to afford the title compound (0.345 g, 50%) as a colorless solid. $^1$H NMR (400 MHz, DMSO-$d_6$): δ 7.94 (d, J=8.3 Hz, 1H), 7.61 (dd, J=8.3, 7.6 Hz, 1H), 7.24 (d, J=7.6 Hz, 1H), 7.06 (brs, 1H), 3.84-3.81 (m, 2H), 3.22-3.19 (m, 2H), 1.95-1.89 (m, 2H).

Example 85

3-(6-Bromo-1H-benzo[d]imidazol-2-yl)pyrrolidin-2-one

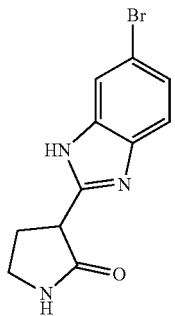 [SMILES: O=C1NCCC1c1nc2ccc(Br)cc2[nH]1]

Step 1: N-(2-Amino-4-bromophenyl)-2-oxopyrrolidine-3-carboxamide

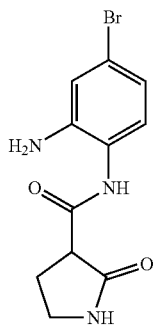

To a solution of ethyl 2-oxopyrrolidine-3-carboxylate (0.50 g, 3.18 mmol) in MeOH (10 mL) was added 1M NaOH (5 mL). The mixture was stirred at RT for 1 h, then HCl (1N aq., 5 mL) was added and evaporated to dryness. DMF (3 mL) was added and evaporated to give 2-oxopyrrolidine-3-carboxylic acid. To this acid was added DMF (10 mL), 4-bromobenzene-1,2-diamine (0.595 g, 3.18 mmol) and DIPEA (2.2 mL, 12.7 mmol). The mixture was cooled in an ice bath and HATU (2.42 g, 6.36 mmol) was added over 10 min. The mixture was stirred at RT for 30 min then partitioned between EtOAc and water. The aqueous phase was extracted with more EtOAc and the combined organic extracts were washed with water, brine, dried ($Na_2SO_4$) and evaporated. The residue was purified by chromatography on silica (solvent gradient 2-10% MeOH in DCM) to afford the title compound (0.652 g, 69%) as a brown solid. LCMS (ESI) [M+H]+298/300.

Step 2: 3-(6-Bromo-1H-benzo[d]imidazol-2-yl)pyrrolidin-2-one

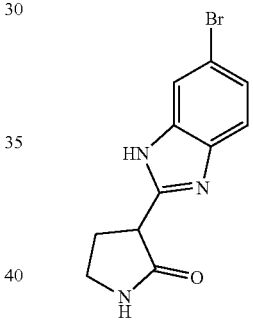

A solution of N-(2-amino-4-bromophenyl)-2-oxopyrrolidine-3-carboxamide (0.65 g, 2.18 mmol) in acetic acid (10 mL) was stirred at 90° C. for 1 h. The cooled mixture was evaporated. Toluene was added and evaporated. The residue was partitioned between sat. aq. sodium bicarbonate and EtOAc. The organic phase was washed with brine, dried ($Na_2SO_4$), filtered and evaporated. The residue was purified by chromatography on silica (solvent gradient 3-20% MeOH in EtOAc) to afford the title compound (0.448 g, 73%) as a light brown foam. LCMS (ESI) [M+H]$^+$ 280/282.

Example 86 tert-Butyl 3-(3-(4,4,5,5-tetramethyl-1,3,2-dioxaborolan-2-yl)phenyl)-6,7-dihydro-[1,2,3]triazolo[1,5-a]pyrazine-5(4H)-carboxylate

Step 1: tert-Butyl 3-(3-aminophenyl)-6,7-dihydro-[1,2,3]triazolo[1,5-a]pyrazine-5(4H)-carboxylate

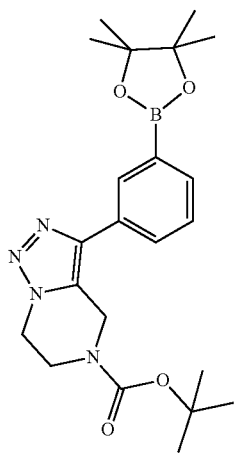 [SMILES: CC(C)(C)OC(=O)N1CCn2nnc(-c3cccc(B4OC(C)(C)C(C)(C)O4)c3)c2C1]

A degassed solution of tert-butyl 3-bromo-6,7-dihydro-[1,2,3]triazolo[1,5-a]pyrazine-5(4H)-carboxylate (120 mg, 0.396 mmol), (3-aminophenyl)boronic acid (65 mg, 0.475 mmol), tetrakis(triphenylphosphine)palladium(O) (46 mg, 0.039 mmol) and potassium carbonate (1.8N aq., 0.5 mL) in 1,4-dioxane (3 mL), was heated at 100° C. for 18 h. The reaction mixture was diluted with EtOAc, washed with brine, dried (Na₂SO₄) and concentrated. The residue was purified by chromatography on silica (solvent gradient 0-10% EtOAc in cyclohexane) to afford the title compound (33 mg, 26%) as a yellow oil. LCMS (ESI) [M+H]⁺ 316.2.

Step 2: tert-Butyl 3-(3-(4,4,5,5-tetramethyl-1,3,2-dioxaborolan-2-yl)phenyl)-6,7-dihydro-[1,2,3]triazolo[1,5-a]pyrazine-5(4H)-carboxylate To a suspension of tert-butyl 3-(3-aminophenyl)-6,7-dihydro-[1,2,3]triazolo[1,5-a]pyrazine-5(1H)-carboxylate (33 mg, 0.105 mmol) in MeOH (1 mL) cooled to 0° C., were added successively HCl (1N, 0.314 mL, 0.314 mmol) and sodium nitrite (8 mg, 0.115 mmol) in water (0.05 mL). The reaction mixture was stirred for 30 min at 0° C., then treated with a solution of bis(pinacolato)diboron (80 mg, 0.314 mmol) in MeOH (0.5 mL). The reaction mixture was stirred for 30 min at 0° C., then allowed to warm up to RT, and stirred for a further 18 h. The mixture was diluted with DCM and washed with water. The organic extract was dried (Na₂SO₄), filtered and evaporated. The residue was purified by chromatography on silica (solvent gradient 0-100% EtOAc in cyclohexane) to afford the title compound as a yellow solid. LCMS (ESI) [M+H]⁺ 427.3.

Example 87

(2-(3-Bromophenyl)pyridin-3-yl)methanol

Step 1: (2-Bromopyridin-3-yl)methanol

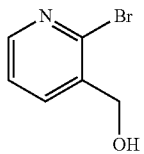

To a solution of 2-bromonicotinaldehyde (1.86 g, 10 mmol) in MeOH (20 mL) at 0° C., was added sodium borohydride (380 mg, 10 mmol) portionwise over 10 min. The reaction mixture was stirred for a further 1 h at 0° C. The reaction was quenched with water and the volatiles were evaporated in vacuo. The residual suspension was diluted with EtOAc. The organic solution was washed with water, brine, dried (Na$_2$SO$_4$) and concentrated in vacuo to afford the title compound (1.82 g, 96%) as white solid. $^1$H NMR (400 MHz, DMSO-d$_6$) δ 8.27 (dd, J=1.9, 4.6 Hz, 1H), 7.90 (dd, J=1.0, 7.6 Hz, 1H), 7.48 (dd, J=4.7, 7.6 Hz, 1H), 5.60 (t, J=5.6 Hz, 1H), 4.49 (d, J=5.6 Hz, 2H).

Step 2: (2-(3-Aminophenyl)pyridin-3-yl)methanol

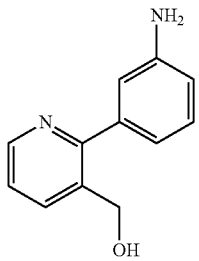 [SMILES: Nc1cccc(-c2ncccc2CO)c1]

A degassed solution of (2-bromopyridin-3-yl)methanol (940 mg, 5.00 mmol), (3-aminophenyl)boronic acid (822 mg, 6.0 mmol), tetrakis(triphenylphosphine)palladium(O) (289 mg, 0.25 mmol), cesium carbonate (3.26 g, 10.00 mmol) in 1,4-dioxane (15 mL) and water (5 mL), was heated at 80° C. for 18 h. The reaction mixture was partitioned between EtOAc and water. The organic extract was washed with brine, dried (Na$_2$SO$_4$) and concentrated. The residue was purified by chromatography on silica (solvent EtOAc) to afford the title compound (846 mg, 85%) as a yellow solid. LCMS (ESI) [M+H]$^+$ 201.1.

Step 3: (2-(3-Bromophenyl)pyridin-3-yl)methanol

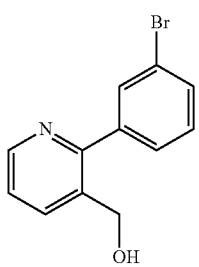 [SMILES: OCc1cccnc1-c1cccc(Br)c1]

To a suspension of copper (II) bromide (536 mg, 2.4 mmol) in MeCN (3 mL) at 0° C., were added successively tert-butyl nitrite (0.357 mL, 3.00 mmol) and (2-(3-aminophenyl)pyridin-3-yl)methanol (400 mg, 2.00 mmol) in MeCN (4 mL). The reaction mixture was stirred for 3 h at 0° C., then was partitioned between EtOAc and water. The organic extract was washed with brine, dried (Na$_2$SO$_4$), and concentrated. The residue was purified by chromatography on silica (solvent gradient 30-40% EtOAc in cyclohexane) to afford the title compound as a white solid. LCMS (ESI) [M+H]$^+$ 264.1/266.1.

Example 88

2-(1-(3-Bromophenyl)-5-methyl-1H-pyrazol-3-yl)acedonitrile

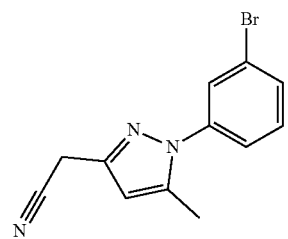 [SMILES: Cc1cc(CC#N)nn1-c1cccc(Br)c1]

Step 1: (1-(3-Bromophenyl)-5-methyl-1H-pyrazol-3-yl)methyl methanesulfonate

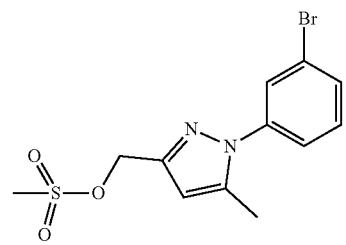 [SMILES: Cc1cc(COS(C)(=O)=O)nn1-c1cccc(Br)c1]

To a solution of [1-(3-bromophenyl)-5-methylpyrazol-3-yl]methanol (804 mg, 3.01 mmol) and triethylamine (0.55 mL, 3.91 mmol) in DCM (10 mL) at 0° C. was added methanesulfonyl chloride (0.28 mL, 3.61 mmol). The reaction mixture was stirred at 0° C. for 10 min, then was diluted with water and extracted with DCM. The combined organic extracts were washed with brine, dried (MgSO$_4$) and concentrated in vacuo to give the title product (1.2 g, 115%) as an off-white solid. $^1$H NMR (400 MHz, CDCl$_3$) δ 7.65-7.61 (m, 1H), 7.54 (dt, J=7.4, 1.8 Hz, 1H), 7.40-7.32 (m, 2H), 6.36 (s, 1H), 5.27 (s, 2H), 3.03 (s, 3H), 2.36 (s, 3H).

Step 2: 2-(1-(3-Bromophenyl)-5-methyl-1H-pyrazol-3-yl)acedonitrile

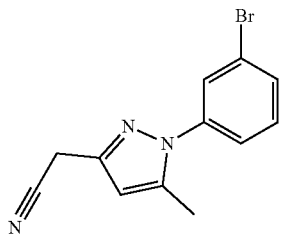 [SMILES: Cc1cc(CC#N)nn1-c1cccc(Br)c1]

To a solution of [1-(3-bromophenyl)-5-methyl-pyrazol-3-yl]methyl methanesulfonate (1.04 g, 3.01 mmol) in DMF (10 mL) was added sodium cyanide (221 mg, 4.52 mmol). The reaction mixture was stirred at 60° C. for 48 h, then was diluted with water and extracted with EtOAc. The combined organic extracts were washed with brine, dried (MgSO$_4$) and concentrated in vacuo. The residue was purified by chromatography on silica (solvent gradient 0-100% EtOAc in cyclohexane) to give the title product (544 mg, 65%) as an off-white solid. LCMS (ESI) [M+H]$^+$ 276/278.

Example 89

2-(3-Methyl-2-(3-(4,4,5,5-tetramethyl-1,3,2-dioxaborolan-2-yl)phenyl)pyridin-4-yl)acedonitrile

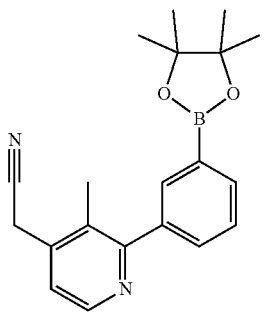 [SMILES: Cc1c(CC#N)ccnc1-c1cccc(B2OC(C)(C)C(C)(C)O2)c1]

Step 1: tert-Butyl 2-(2-chloro-3-methylpyridin-4-yl)-2-cyanoacetate

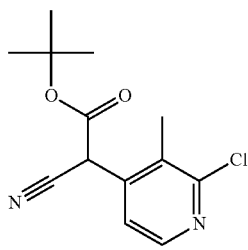 [SMILES: Cc1c(C(C#N)C(=O)OC(C)(C)C)ccnc1Cl]

A degassed mixture of copper(I) iodide (30 mg, 0.16 mmol), tert-butyl cyanoacetate, (4.51 mL, 31.56 mmol), 2-chloro-4-iodo-3-methylpyridine (4 g, 15.78 mmol) and potassium carbonate (8.72 g, 63.12 mmol) in DMF (35 mL) was heated at 120° C. for 48 h. The reaction mixture was diluted with water and acidified with 10% aq. citric acid. The product was extracted with EtOAc. The combined organic fractions were washed with brine, dried (MgSO$_4$) and concentrated in vacuo. The residue was purified by chromatography on silica (solvent gradient 0-100% EtOAc in cyclohexane) to give the title compound (2.37 g, 56%) as an orange oil. LCMS (ESI) [M+H]$^+$ 267.

Step 2: 2-(2-Chloro-3-methylpyridin-4-yl)acetonitrile

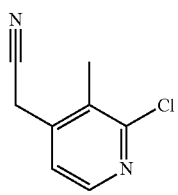

A solution of tert-butyl 2-(2-chloro-3-methylpyridin-4-yl)-2-cyanoacetate (2.37 g, 8.89 mmol) and TFA (5 mL) in DCM (5 mL) was stirred at 40° C. for 3.5 h. The reaction mixture was concentrated in vacuo, the residue dissolved in DCM and washed with sat. aq. sodium bicarbonate. The combined organic fractions were washed with brine, dried (MgSO$_4$) and concentrated in vacuo. The residue was purified by chromatography on silica (solvent gradient 0-50% EtOAc in cyclohexane) to give the title compound (1.1 g, 74%) as a beige solid. LCMS (ESI) [M+H]$^+$ 167.

Step 3: 2-(2-(3-Chlorophenyl)-3-methylpyridin-4-yl)acetonitrile

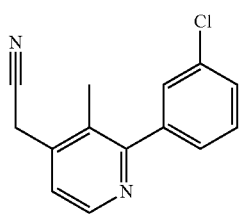 [SMILES: Cc1c(CC#N)ccnc1-c1cccc(Cl)c1]

A degassed mixture of 2-(2-chloro-3-methylpyridin-4-yl)acetonitrile (250 mg, 1.5 mmol), 3-chlorophenylboronic acid (469 mg, 3.0 mmol), tetrakis(triphenylphosphine)palladium(O) (104 mg, 0.09 mmol) and potassium carbonate (2N aq., 3.75 mL, 7.5 mmol) in 1,4-dioxane (5 mL) was heated at 100° C. for 30 min. The reaction mixture was diluted with water and extracted with EtOAc. The combined organic extracts were washed with brine, dried (MgSO$_4$) and concentrated in vacuo. The residue was purified twice by chromatography on silica (solvent gradient 0-100% EtOAc in cyclohexane) to give the title compound (410 mg, 113%) as a yellow oil. $^1$H NMR (400 MHz, CDCl$_3$) δ 8.57 (d, J=4.6 Hz, 1H), 7.48-7.45 (m, 1H), 7.42-7.37 (m, 3H), 7.36-7.31 (m, 1H), 3.76 (s, 2H), 2.31 (s, 3H).

Step 4: 2-(3-Methyl-2-(3-(4,4,5,5-tetramethyl-1,3,2-dioxaborolan-2-yl)phenyl)pyridin-4-yl)acedonitrile

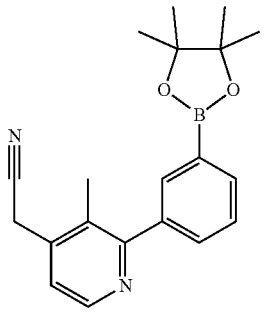 [SMILES: Cc1c(CC#N)ccnc1-c1cccc(B2OC(C)(C)C(C)(C)O2)c1]

A degassed mixture of 2-(2-(3-chlorophenyl)-3-methylpyridin-4-yl)acetonitrile (280 mg, 1.15 mmol), bis(pinacolato)diboron (380 mg, 1.5 mmol), Xphos-Pd-G2 (91 mg, 0.12 mmol) and potassium acetate (343 mg, 3 mmol) in 1,4-dioxane (5 mL) was heated at 100° C. for 8 h. The reaction mixture was diluted with water and extracted with EtOAc. The combined organic extracts were washed with brine, dried (MgSO$_4$) and concentrated in vacuo. The residue was purified by chromatography on silica (solvent gradient 0-100% EtOAc in cyclohexane) to give the title compound (320 mg, 83%) as a yellow oil. LCMS (ESI) [M+H]$^+$ 335.

Example 90

1-(3-Bromophenyl)-N,N-dimethylcyclopropane-1-carboxamide

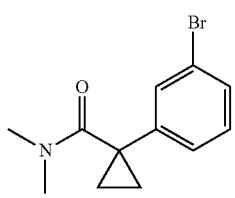

To a solution of 1-(3-Bromophenyl)cyclopropanecarboxylic acid (480 mg, 1.99 mmol) in DCM (10 mL) was added oxalyl chloride (0.51 mL, 5.97 mmol) and immediate effervescence was observed. The reaction mixture was stirred for 1 h, then was evaporated and azeotroped with toluene to remove excess oxalyl chloride. The crude was re-dissolved in DCM (5 mL) and dimethylamine (2M in THF, 2.99 mL, 5.97 mmol) was added. The mixture was stirred for 1 h, then was diluted with DCM and water. The organic layer was separated and dried by passage through a PTFE filter. The solvent was removed and the resultant crude residue was purified by chromatography on silica (solvent gradient 0-50% EtOAc in cyclohexane) to afford the title compound (400 mg 75%) as a pale yellow oil. LCMS (ESI) [M+H]$^+$ 268/270.

Example 91

3-Amino-N,N-dimethyl-6-(tributylstannyl)picolinamide

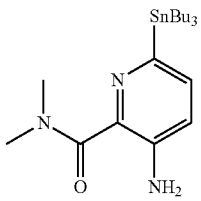

Step 1:
3-Amino-6-bromo-N,N-dimethylpicolinamide

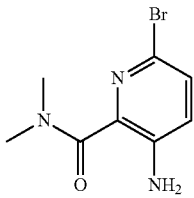

NBS (0.44 g, 2.46 mmol) was added portionwise to a solution of 3-amino-N,N-dimethyl-pyridine-2-carboxamide (4.51 g, 8.19 mmol) in chloroform (100 mL) at RT. The reaction mixture was stirred for 5 mins, then was washed with aq. sodium bicarbonate (100 mL). The aqueous phase was extracted with DCM (3×50 mL). The combined organic extracts were washed with water (20 mL), dried (Na$_2$SO$_4$) and concentrated. The residue was triturated under Et$_2$O and filtered to give the title compound (1.81 g, 90% yield) as a pale yellow solid. LCMS (ESI) [M+H]$^+$ 244.0/246.0.

Step 2: 3-Amino-N,N-dimethyl-6-(tributylstannyl)picolinamide

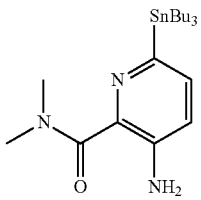

A degassed mixture of 3-amino-6-bromo-N,N-dimethylpicolinamide (371 mg, 1.52 mmol), hexabutylditin (0.77 mL, 1.52 mmol) and tetrakis(triphenylphosphine)palladium (O) (175 mg, 0.150 mmol) in 1,4-dioxane (2 mL) was irradiated in a sealed tube at 115° C. under microwave irradiation for 5 h. The solvent was evaporated and the residue purified by chromatography on silica (solvent gradient 0-3% MeOH·NH$_3$ in DCM) to afford the title compound (326 mg, 47%) as a pale yellow gum. LCMS (ESI) [M+H]$^+$ 452.4/460.5.

Example 92

2-(2-(3-Amino-5-(4,4,5,5-tetramethyl-1,3,2-dioxaborolan-2-yl)phenyl)-3-methylpyridin-4-yl)acetonitrile

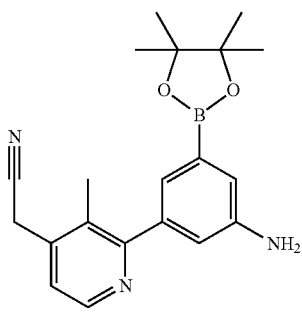 [SMILES: Cc1c(CC#N)ccnc1-c1cc(N)cc(B2OC(C)(C)C(C)(C)O2)c1]

Step 1: 2-(2-(3-Chloro-5-nitrophenyl)-3-methylpyridin-4-yl)acetonitrile

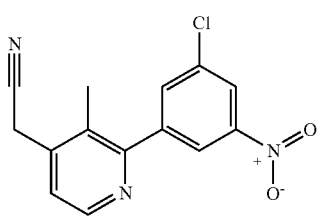

A degassed mixture of 2-(2-chloro-3-methylpyridin-4-yl)acetonitrile (350 mg, 2.1 mmol), 2-(3-chloro-5-nitrophenyl)-4,4,5,5-tetramethyl-1,3,2-dioxaborolane (700 mg, 2.47 mmol), tetrakis(triphenylphosphine)palladium (O) (145 mg, 0.13 mmol) and potassium carbonate (1.45 g, 10.5 mmol) in 1,4-dioxane (6 mL) was heated at 100° C. for 3 h. The reaction mixture was diluted with water and extracted with EtOAc. The combined organic fractions were washed with brine, dried (MgSO$_4$) and concentrated in vacuo. The residue was purified by chromatography on silica (solvent gradient 0-60% EtOAc in iso-hexane) to give the title product (604 mg, 99%) as a yellow oil. LCMS (ESI) [M+H]$^+$ 288.

Step 2: 2-(2-(3-Amino-5-chlorophenyl)-3-methylpyridin-4-yl)acetonitrile

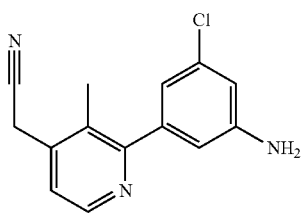 [SMILES: Cc1c(CC#N)ccnc1-c1cc(N)cc(Cl)c1]

To a solution of 2-(2-(3-chloro-5-nitrophenyl)-3-methylpyridin-4-yl)acetonitrile (604 mg, 2.1 mmol) in MeOH (5 mL) and water (0.5 mL) were added iron powder (234 mg, 4.2 mmol) and ammonium chloride (224 mg, 4.2 mmol). The reaction mixture was heated at reflux for 5 h, then was filtered through celite and concentrated in vacuo. The residue was purified by chromatography on silica (solvent gradient 0-5% MeOH·NH$_3$ in EtOAc). to give the title product (270 mg, 50%, ~80% pure) as a brown solid. LCMS (ESI) [M+H]$^+$ 258.

Step 3: 2-(2-(3-Amino-5-(4,4,5,5-tetramethyl-1,3,2-dioxaborolan-2-yl)phenyl)-3-methylpyridin-4-yl)acedonitrile

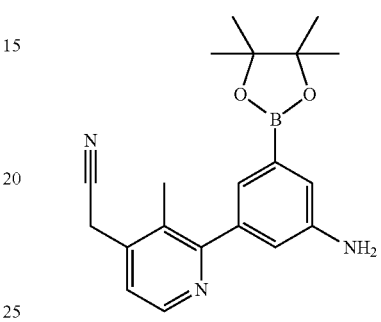

A degassed mixture of 2-(2-(3-amino-5-chlorophenyl)-3-methylpyridin-4-yl)acetonitrile (369 mg, 1.43 mmol), bis(pinacolato)diboron (545 mg, 2.15 mmol), Xphos-Pd-G2 (112 mg, 0.14 mmol) and potassium acetate (426 mg, 4.3 mmol) in 1,4-dioxane (5 mL) was heated at 100° C. for 1.5 h, then was diluted with water and extracted with EtOAc. The combined organic fractions were washed with brine, dried (MgSO$_4$) and concentrated in vacuo. The residue was purified by chromatography on silica (solvent gradient 0-2% MeOH in EtOAc) to give the title product (340 mg, 68%) as a colorless oil. LCMS (ESI) [M+H]$^+$ 350.

Example 93

1-(3-Bromo-2-fluorophenyl)cyclopropane-1-carboxamide

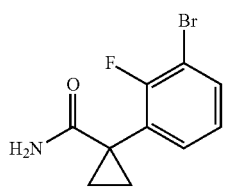 [SMILES: NC(=O)C1(c2cccc(Br)c2F)CC1]

Step 1: 1-(3-Bromo-2-fluorophenyl)cyclopropane-1-carbonitrile

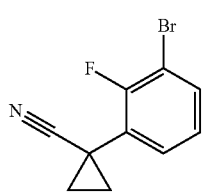 [SMILES: N#CC1(c2cccc(Br)c2F)CC1]

To a solution of 2-(3-bromo-2-fluoro-phenyl)acetonitrile (1 g, 4.67 mmol) in DMF (8 mL) at 0° C., were added successively sodium hydride (60% in oil, 0.22 g, 5.61 mmol) and 1,2-dibromoethane (0.48 mL, 5.61 mmol). The reaction mixture was stirred at 0° C. for 1 h then at RT for 1 h. The reaction mixture was cooled again to 0° C., and treated with further sodium hydride (60% in oil, 0.22 g, 5.61 mmol). The mixture was stirred at RT for 10 min then quenched with water and diluted with EtOAc. The aqueous layer was extracted with further EtOAc. The combined organic extracts were washed with brine, dried (MgSO$_4$) and concentrated. The residue was purified by chromatography on silica (solvent gradient 0-5% EtOAc in cyclohexane) to afford the title compound (900 mg, 80%). $^1$H NMR (400 MHz, CDCl$_3$) δ 7.55 (ddd, J=1.6, 6.4, 8.1 Hz, 1H), 7.29 (ddd, J=1.5, 6.5, 7.9 Hz, 1H), 7.02 (dt, J=1.2, 7.9 Hz, 1H), 1.72 (q, J=4.3 Hz, 2H), 1.40 (q, J=4.3 Hz, 2H).

Step 2: 1-(3-Bromo-2-fluorophenyl)cyclopropane-1-carboxamide

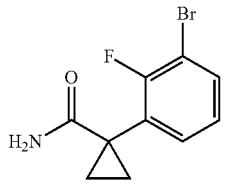 [SMILES: NC(=O)C1(c2cccc(Br)c2F)CC1]

A solution of 1-(3-bromo-2-fluorophenyl)cyclopropane-1-carbonitrile (239 mg, 1 mmol) and potassium hydroxide (167 mg, 2.99 mmol) in IMS (0.5 mL) and water (1.5 mL) was heated at 90° C. for 2 h. The reaction mixture was concentrated, then partitioned between water and EtOAc. The organic extract was dried (MgSO$_4$) and concentrated, to afford the title compound (130 mg, 50%) as a yellow solid. $^1$H NMR (400 MHz, DMSO-d$_6$) δ 7.61 (ddd, J=1.6, 6.6, 8.1 Hz, 1H), 7.38-7.33 (m, 1H), 7.11 (dt, J=0.9, 7.9 Hz, 1H), 6.98 (s, 1H), 6.57 (s, 1H), 1.42-1.38 (m, 2H), 1.01-0.98 (m, 2H).

Example 94

2-Fluoro-N,N-dimethyl-3-(4,4,5,5-tetramethyl-1,3,2-dioxaborolan-2-yl)benzamide

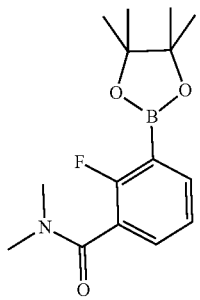

To a solution of 2-fluoro-3-(4,4,5,5-tetramethyl-1,3,2-dioxaborolan-2-yl)benzoic acid (300 mg, 1.13 mmol) in DCM (5 mL) was added oxalyl chloride (0.15 mL, 1.69 mmol), followed by 1 drop of DMF. The reaction mixture was stirred at RT for 30 min until all effervescence subsided, then was diluted with toluene and coevaporated (×2). The resultant oil was dissolved in DCM, cooled 0° C., and treated with dimethylamine (2N in THF, 1.69 mL, 3.38 mmol) dropwise. The reaction mixture was stirred for 1 h, then diluted with DCM and washed with water. The DCM extract was isolated by passage through a PTFE filter and concentrated to afford the title compound (300 mg, 91%) as a clear oil. $^1$H NMR (400 MHz, CDCl$_3$) δ 7.80-7.76 (m, 1H), 7.47 (dt, J=1.7, 7.1 Hz, 1H), 7.19 (t, J=7.4 Hz, 1H), 3.12 (s, 3H), 2.94 (s, 3H), 1.36 (s, 12H).

Example 95

3-Bromo-2-fluoro-N-(2-hydroxyethyl)-N-methyl-benzamide

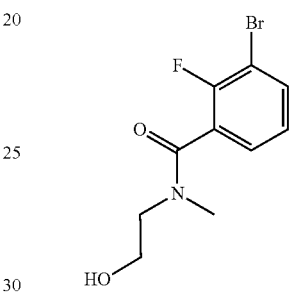

To a suspension of 3-bromo-2-fluorobenzoic acid (438 mg, 2.00 mmol) and 2-(methylamino)ethanol (240 µL, 3.0 mmol) in DCM (6 mL) was added DIPEA (1 mL, 6.00 mmol) followed by HATU (1.15 g, 3.00 mmol). The reaction mixture was stirred at RT for 18 h, then partitioned between DCM and sat. aq sodium bicarbonate. The aqueous phase was extracted with more DCM and the combined organic extracts were passed through a hydrophobic filter and evaporated in vacuo. The residue was purified by chromatography on silica (solvent gradient 0-80% EtOAc in cyclohexane) to afford the title compound (602 mg, >100%) as a colorless oil. LCMS (ESI) [M+H]$^+$ 276/278.

Example 96

1-(2-Fluoro-3-(4,4,5,5-tetramethyl-1,3,2-dioxaborolan-2-yl)benzoyl)piperidine-2-carbonitrile

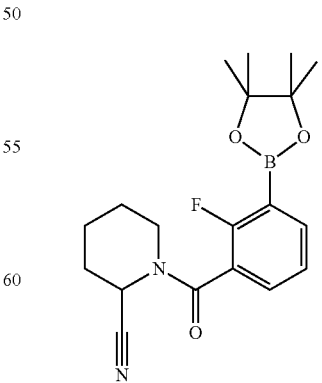

Piperidine-2-carbonitrile oxalate salt (660. mg, 2.13 mmol) was dissolved in water and diluted with methanol.

The mixture was basified by passage through an SCX cartridge (20 g) (pre-washed with methanol); the cartridge was washed thoroughly with methanol and the compound, as the free base was eluted with MeOH·NH₃. The product fractions were concentrated to give a yellow oil. 2-Fluoro-3-(4,4,5,5-tetramethyl-1,3,2-dioxaborolan-2-yl)benzoic acid (565 mg, 2.13 mmol) was dissolved in DCM (7 mL) and oxalyl chloride (0.55 mL, 6.38 mmol) was added dropwise leading to immediate effervescence. The mixture was stirred for 1 h until all gas evolution ceased and the solvent was removed in vacuo and the residue was then diluted with toluene and evaporated to remove any excess oxalyl chloride. The crude acid chloride was dissolved in DCM (anhydrous, 7 mL) and piperidine-2-carbonitrile (crude free base) in DCM (2 mL) and Et₃N (0.44 mL, 3.19 mmol) was added to the stirred solution. The mixture was stirred at RT for 1 h, then diluted with DCM (10 mL) and washed with water. The organic layer was separated and dried by passage through a PTFE filter. The solvent was removed in vacuo and the crude residue was purified by chromatography on silica (solvent gradient 0-100% EtOAc in cyclohexane) to afford the title compound as a white solid (560 mg, 73%). LCMS (ESI) [M+H]⁺ 359.

Example 97

(2-Fluoro-3-(4,4,5,5-tetramethyl-1,3,2-dioxaborolan-2-yl)phenyl)(2-(1-methyl-1H-pyrazol-4-yl)piperidin-1-yl)methanone

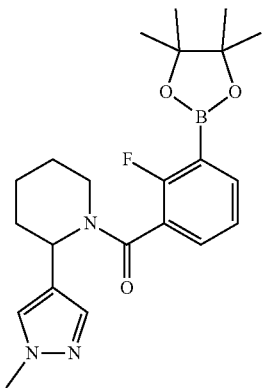

To a solution of 2-fluoro-3-(4,4,5,5-tetramethyl-1,3,2-dioxaborolan-2-yl)benzoic acid (1.05 g, 3.93 mmol) in DCM (15 mL) was added oxalyl chloride (0.51 mL, 5.9 mmol) dropwise, followed by 1 drop of DMF. The reaction mixture was stirred for 30 min until all gas evolution had ceased. The solution was diluted with toluene, evaporated and dried in vacuo. The resulting residue was dissolved in DCM (15 mL), cooled to 0° C., and treated with a solution of triethylamine (0.82 mL, 5.9 mmol) and 2-(1-methylpyrazol-4-yl)piperidine (650 mg, 3.93 mmol) in DCM (2 mL). The resulting mixture was stirred for 30 min, then was diluted with water, filtered through a PTFE filter and concentrated. The residue was purified by chromatography on silica (solvent gradient 0-100% EtOAc in cyclohexane), then crystallised from Et₂O to give the title compound (1.4 g, 86%) as a white solid. LCMS (ESI) [M+H-pinacol]⁺ 332.

Example 98

2-(2-(2-Fluoro-3-(4,4,5,5-tetramethyl-1,3,2-dioxaborolan-2-yl)phenyl)-3-methylpyridin-4-yl)acetonitrile

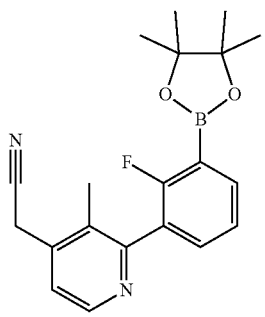 [SMILES: Cc1c(CC#N)ccnc1-c1cccc(B2OC(C)(C)C(C)(C)O2)c1F]

Step 1: 2-(2-(3-Chloro-2-fluorophenyl)-3-methylpyridin-4-yl)acetonitrile

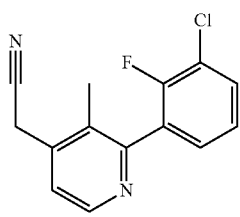 [SMILES: Cc1c(CC#N)ccnc1-c1cccc(Cl)c1F]

A degassed mixture of 2-(2-chloro-3-methylpyridin-4-yl)acetonitrile (336 mg, 2.02 mmol), 3-chloro-2-fluorophenylboronicacid (703 mg, 4.03 mmol), tetrakis(triphenylphosphine)palladium (O) (139 mg, 0.12 mmol), and potassium carbonate (2N aq., 5.04 mL, 10.08 mmol) in 1,4-dioxane (6 mL) was heated at 100° C. for 45 min. The reaction mixture was diluted with water and extracted with EtOAc. The combined organic extracts were washed with brine, dried (MgSO₄) and concentrated in vacuo. The residue was purified by chromatography on silica (solvent gradient 0-50% EtOAc in cyclohexane) to give the title product (350 mg, 66%) as a yellow oil. LCMS (ESI) [M+H]⁺ 261.

Step 2: 2-(2-(2-Fluoro-3-(4,4,5,5-tetramethyl-1,3,2-dioxaborolan-2-yl)phenyl)-3-methylpyridin-4-yl)acedonitrile

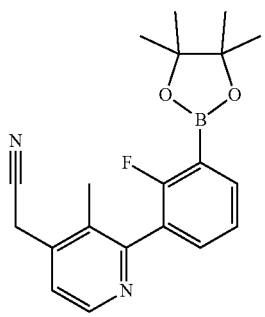

A degassed mixture of 2-[2-(3-chloro-2-fluoro-phenyl)-3-methyl-4-pyridyl]acetonitrile (350 mg, 1.34 mmol), bis(pinacolato)diboron (443 mg, 1.75 mmol), Xphos-Pd-G2 (105 mg, 0.13 mmol) and potassium acetate (399 mg, 4.03 mmol) in 1,4-dioxane (6 mL) was heated at 100° C. for 1 h. The reaction mixture was diluted with water and extracted with EtOAc. The combined organic extracts were washed with brine, dried (MgSO$_4$) and concentrated in vacuo. The residue was purified by chromatography on silica (solvent gradient 0-100% EtOAc in cyclohexane) to give the title compound (~70% pure, 608 mg, 129%) as a yellow oil. LCMS (ESI) [M+H]$^+$ 353.

Example 99

N-(Cyanomethyl)-2-(2-fluoro-3-(4,4,5,5-tetramethyl-1,3,2-dioxaborolan-2-yl)phenyl)isonicotinamide

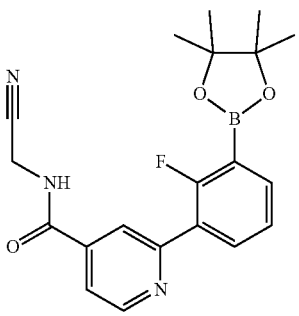 [SMILES: CC1(C)OB(c2cccc(-c3cc(C(=O)NCC#N)ccn3)c2F)OC1(C)C]

Step 1: Methyl 2-(3-chloro-2-fluorophenyl)isonicotinate

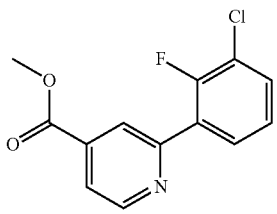 [SMILES: COC(=O)c1ccnc(-c2cccc(Cl)c2F)c1]

A degassed mixture of methyl 2-chloropyridine-4-carboxylate (500 mg, 2.91 mmol), 3-chloro-2-fluorophenylboronicacid (1.01 g, 5.83 mmol), tetrakis(triphenylphosphine)palladium (O) (202 mg, 0.17 mmol) and potassium carbonate (2.01 g, 14.57 mmol) in 1,4-dioxane (8 mL) was heated at 100° C. for 1 h. The reaction mixture was diluted with water and extracted with EtOAc. The combined organic extracts were washed with brine, dried (MgSO$_4$) and concentrated in vacuo. The residue was purified by chromatography on silica (solvent gradient 0-50% EtOAc in cyclohexane) to give the title product (704 mg, 91%) as a yellow oil. LCMS (ESI) [M+H]$^+$ 266.0.

Step 2: 2-(3-Chloro-2-fluorophenyl)isonicotinic Acid

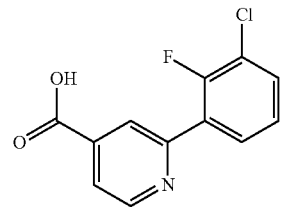 [SMILES: O=C(O)c1ccnc(-c2cccc(Cl)c2F)c1]

To a suspension of methyl 2-(3-chloro-2-fluorophenyl)isonicotinate (704 mg, 2.65 mmol) in MeOH (5 mL) and water (0.5 mL) was added lithium hydrxide monohydrate (130 mg, 3.18 mmol). The reaction mixture was stirred at RT for 16 h, then diluted with water and concentrated in vacuo. The suspension was acidified to ~pH3 with 1N HCl causing a thick white precipitate to form. The precipitate was collected by filtration and dried in vacuo to give the title compound (630 mg, 94%) as a white solid. LCMS (ESI) [M+H]$^+$ 252.

Step 3: 2-(3-Chloro-2-fluorophenyl)-N-(cyanomethyl)isonicotinamide

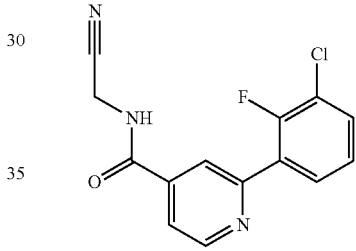

To a suspension of 2-(3-chloro-2-fluorophenyl)isonicotinic acid (630 mg, 2.5 mmol), aminoacetonitrile hydrochloride (301 mg, 3.25 mmol) and triethylamine (0.87 mL, 6.26 mmol) in DMF (10 mL) was added HATU (1.33 g, 3.51 mmol). The reaction mixture was stirred at RT for 15 min, then was diluted with water and extracted with EtOAc. The combined organic extracts were washed with brine, dried (MgSO$_4$) and concentrated in vacuo to give the title compound (706 mg, 97%) as a yellow oil. LCMS (ESI) [M+H]$^+$ 290.

Step 4: N-(Cyanomethyl)-2-(2-fluoro-3-(4,4,5,5-tetramethyl-1,3,2-dioxaborolan-2-yl)phenyl)isonicotinamide

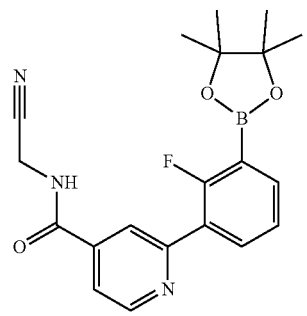 [SMILES: CC1(C)OB(c2cccc(-c3cc(C(=O)NCC#N)ccn3)c2F)OC1(C)C]

A degassed mixture of 2-(3-chloro-2-fluorophenyl)-N-(cyanomethyl)isonicotinamide (760 mg, 2.62 mmol), bis(pinacolato)diboron (732 mg, 2.89 mmol), Xphos-Pd-G2 (206 mg, 0.26 mmol) and potassium acetate (780 mg, 7.87 mmol) in 1,4-dioxane (15 mL) was heated at 100° C. for 1 h. The reaction mixture was diluted with water and extracted with EtOAc. The combined organic extracts were washed with brine, dried (MgSO$_4$) and concentrated in vacuo. The residue was purified by chromatography on silica (solvent gradient 0-100% EtOAc in cyclohexane) to give the title product (494 mg, 49%) as an oil. $^1$H NMR (400 MHz, CDCl$_3$) δ 8.87 (d, J=4.2 Hz, 1H), 8.16 (td, J=7.7, 2.1 Hz, 1H), 8.13-8.11 (m, 1H), 7.84 (ddd, J=7.4, 5.1, 1.8 Hz, 1H), 7.67 (dd, J=5.1, 1.6 Hz, 1H), 7.31 t, J=7.6 Hz, 1H), 6.76 (t, J=5.7 Hz, 1H), 4.42 (d, J=5.8 Hz, 2H), 1.39 (s, 12H).

Example 100

3-Bromo-N-((1-(2-((tert-butyldimethylsilyl)oxy)ethyl)-1H-pyrazol-4-yl)methyl)-2-fluoro-N-methylbenzamide

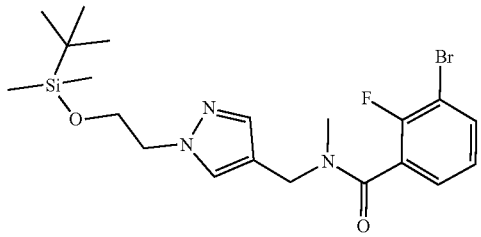 [SMILES: CN(Cc1cnn(CCO[Si](C)(C)C(C)(C)C)c1)C(=O)c1cccc(Br)c1F]

Step 1: N-((1H-Pyrazol-4-yl)methyl)-3-bromo-2-fluoro-N-methylbenzamide

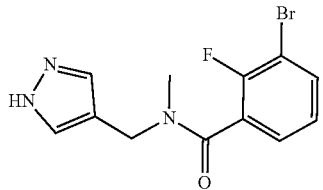 [SMILES: CN(Cc1cn[nH]c1)C(=O)c1cccc(Br)c1F]

To a suspension of 3-bromo-2-fluorobenzoic acid (678 mg, 3.1 mmol), N-methyl-1-(1H-pyrazol-4-yl)methanamine dihydrochloride (600 mg, 3.26 mmol) and triethylamine (1.59 mL, 11.41 mmol) in DMF (15 mL) was added HATU (1.48 g, 3.91 mmol). The reaction mixture was stirred at RT for 30 min then was diluted with water and extracted with EtOAc. The combined organic extracts were washed with brine, dried (MgSO$_4$) and concentrated in vacuo. The residue was purified by chromatography on silica (solvent gradient 0-5% MeOH in EtOAc) to afford the title compound (487 mg, 48%). LCMS (ESI) [M+H]$^+$ 312/314.

Step 2: 3-Bromo-N-(1-(2-((tert-butyldimethylsilyl)oxy)ethyl)-1H-pyrazol-4-yl)methyl)-2-fluoro-N-methylbenzamide

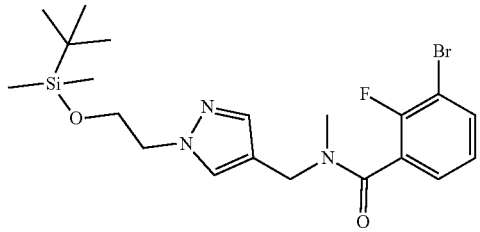 [SMILES: CN(Cc1cnn(CCO[Si](C)(C)C(C)(C)C)c1)C(=O)c1cccc(Br)c1F]

To a solution of N-((1H-pyrazol-4-yl)methyl)-3-bromo-2-fluoro-N-methylbenzamide (100 mg, 0.32 mmol) and (2-bromoethoxy)-tert-butyldimethylsilane (0.1 mL, 0.48 mmol) in DMF (3 mL) was added cesium carbonate (189 mg, 0.58 mmol). The reaction mixture was stirred at RT for 16 h, then diluted with water and extracted with EtOAc. The combined organic extracts were washed with brine, dried (MgSO$_4$) and concentrated in vacuo. The residue was purified by chromatography on silica (solvent gradient 0-100% EtOAc in cyclohexane) to afford the title compound (122 mg, 81%) as a yellow oil. LCMS (ESI) [M+H]$^+$ 470.2/472.2.

Example 101 tert-Butyl 3-(4-((3-bromo-2-fluoro-N-methylbenzamido)methyl)-1H-pyrazol-1-yl)pyrrolidine-1-carboxylate

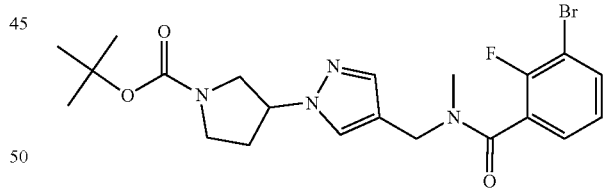

A solution of N-((1H-pyrazol-4-yl)methyl)-3-bromo-2-fluoro-N-methylbenzamide (100 mg, 0.32 mmol), tert-butyl 3-bromopyrrolidine-1-carboxylate (120 mg, 0.48 mmol) and cesium carbonate (189 mg, 0.58 mmol) in DMF (2 mL) was stirred at RT for 72 h. Further tert-butyl 3-bromopyrrolidine-1-carboxylate (120 mg, 0.48 mmol) was added and the reaction was stirred for a further 24 h. The reaction mixture was diluted with water and extracted with EtOAc. The combined organic extracts were washed with brine, dried (MgSO$_4$) and concentrated in vacuo. The residue was purified by chromatography on silica (solvent gradient 0-100% EtOAc in cyclohexane) to afford the title compound (91 mg, 59%) as an off-white gum. LCMS (ESI) [M+Na]$^+$ 503.2/505.2.

Example 102

6-Amino-2-fluoro-N,N-dimethyl-3-(4,4,5,5-tetramethyl-1,3,2-dioxaborolan-2-yl)benzamide

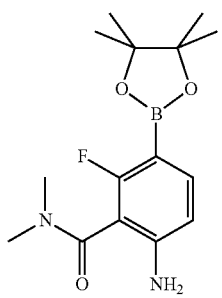

Step 1: 6-Amino-3-bromo-2-fluorobenzoic Acid

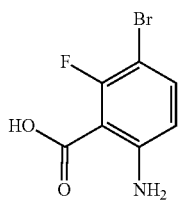 [SMILES: Nc1ccc(Br)c(F)c1C(=O)O]

A suspension of 2-amino-6-fluorobenzoic acid (6 g, 38.7 mmol) in chloroform (80 mL) was cooled in ice. Bromine (2.19 mL, 42.6 mmol) was added dropwise and the mixture was stirred at 0° C. for 0.5 h, then at room temperature for 16 h. The solid was isolated by filtration, washed with a little DCM and dried under vacuum at 40° C. to give the title compound (12.29 g). Analysis by LCMS showed some residual starting material, dibromo product and a minor bromo isomer in addition to the desired product as the major component ~80% pure. LCMS (ESI) [MH–H$_2$O]$^+$ 216/218). The material was used without further purification.

Step 2:
6-Amino-3-bromo-2-fluoro-N,N-dimethylbenzamide

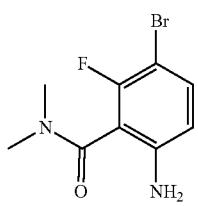

N,N-Diisopropylethylamine (16.4 mL, 96 mmol) was added to a suspension of crude product from Step 1 (10.28 g) in dry DCM (100 mL) to give a solution. HATU (18.2 g, 48 mmol) was added and the mixture was stirred for 5 min before addition of dimethylamine (2M in THF, 24.0 mL, 48 mmol), with gentle cooling in a cold water-bath. The mixture was stirred at room temperature for 3 h, and then washed with 1M sodium hydroxide and brine. The aqueous phases were re-extracted twice with DCM. Combined organic phases were dried (Na$_2$SO$_4$) and evaporated. The residue was purified by chromatography on 300 g silica eluting with 0-50% ethyl acetate/cyclohexane to give an impure solid. This material was re-purified by chromatography (200 g silica, 0-50% ethyl acetate/cyclohexane) to give a 1.5:1 mixture of title compound and unbrominated analogue (3.55 g). LCMS (acidic): title compound (ESI) [MI-1]+261.

Step 3: 6-Amino-2-fluoro-N,N-dimethyl-3-(4,4,5,5-tetramethyl-1,3,2-dioxaborolan-2-yl)benzamide

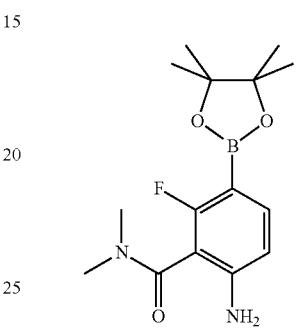

A mixture of the product mixture from Step 2 (3.47 g), bis(pinacolato)diboron (6.76 g, 26.6 mmol), [1,1'-bis(diphenylphosphino)ferrocene]dichloropalladium (II) chloride (DCM complex, 1.09 g, 1.33 mmol) and potassium acetate (3.86 g, 39.9 mmol) in DMF (25 mL) was purged with argon and heated at 100° C. for 3 h. The cooled mixture was filtered through Celite, washed through with ethyl acetate and evaporated to a small volume. The residue was dissolved in ethyl acetate and water, filtered through Celite again and phases separated. The aqueous phase was extracted with ethyl acetate (3×). Organic fractions were dried (Na$_2$SO$_4$) and evaporated. The residue was purified by chromatography on 200 g silica eluting with 50-100% ethyl acetate/cyclohexane to give a 2.8:1 mixture of the title compound and unbrominated material (carried through from Step 2) (2.12 g). LCMS (acidic): title compound (ESI) [MH]$^+$ 309.0.

Example 103

6-Amino-N-(2-((tert-butyldimethylsilyl)oxy)ethyl)-2-fluoro-N-methyl-3-(4,4,5,5-tetramethyl-1,3,2-dioxaborolan-2-yl)benzamide

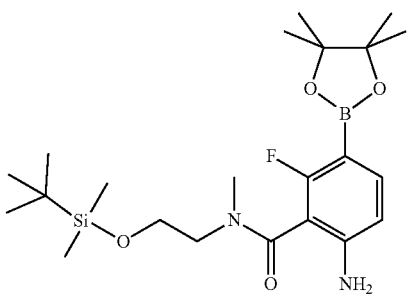 [SMILES: CN(CCO[Si](C)(C)C(C)(C)C)C(=O)c1c(N)ccc(B2OC(C)(C)C(C)(C)O2)c1F]

The title compound was prepared in a fashion analoguous to 6-Amino-2-fluoro-N,N-dimethyl-3-(4,4,5,5-tetramethyl-1,3,2-dioxaborolan-2-yl)benzamide. LCMS (ESI) [M+H]+ 453.0.

Example 104

3-Bromo-N,N-dimethyl-1H-indole-7-carboxamide

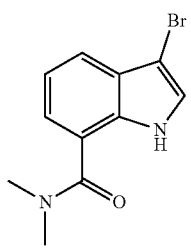

To a suspension of 1H-indole-7-carboxylic acid (2.0 g, 12.4 mmol) in DCM (50 mL) were added DIPEA (10.75 mL, 62 mmol) and HATU (9.43 g, 24.8 mmol). The reaction mixture was stirred at RT for 5 min, then dimethylamine hydrochloride (1.518 g, 18.6 mmol) was added. Stirring was pursued for 1 h. The mixture was diluted with DCM, washed with aq. sodium bicarbonate, water, dried (Na$_2$SO$_4$) and evaporated. The residue was purified by chromatography on silica (solvent gradient 50-100% EtOAc in cyclohexane) to afford N,N-dimethyl-1H-indole-7-carboxamide (5.0 g). LCMS (ESI) [M+H]+ 189. The amide was dissolved in DCM (120 mL) and NBS (2.207 g, 12.4 mmol) was added over 5 min. The mixture was stirred at RT for 15 min, then washed with 10% aqueous sodium metabisulfite, water, dried (Na$_2$SO$_4$) and evaporated. The residue was purified by chromatography on silica (solvent gradient 50-100% EtOAc in cyclohexane) to afford the title compound (2.888 g, 87%) as a colorless solid. LCMS (ESI) [M+H]+ 267/269.

Example 105

3-Bromo-N,N-dimethyl-1-tosyl-1H-indole-7-carboxamide

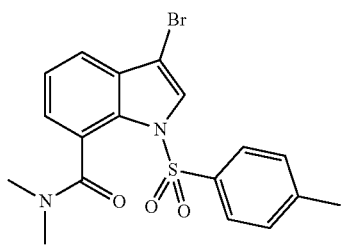

Sodium hydride (0.082 g, 60% in oil, 2.06 mmol) was added over 10 min to an ice-cooled solution of 3-bromo-N,N-dimethyl-1H-indole-7-carboxamide (0.50 g, 1.87 mmol) and tosyl chloride (0.375 g, 1.96 mmol) in THF (10 mL). The mixture was allowed to warm to RT overnight. Sat. aq. ammonium chloride was added and the mixture extracted with EtOAc (2×). The combined organic extracts were washed with brine, dried (Na$_2$SO$_4$) and evaporated. The residue was purified by chromatography on silica (solvent gradient 20-50% EtOAc in cyclohexane) to afford the title compound (0.759 g, 96%) as a pale yellow gum. LCMS (ESI) [M+H]+ 421/423.

2-(3-Bromo-1-tosyl-1H-indol-7-yl)-N,N-dimethylacetamide

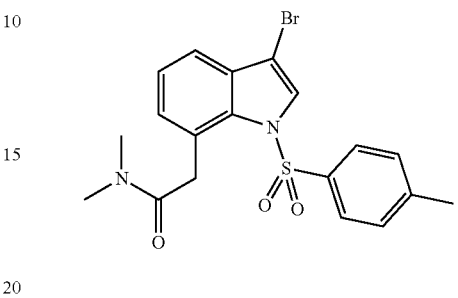

Step 1: 2-(1H-Indol-7-yl)-N,N-dimethylacetamide

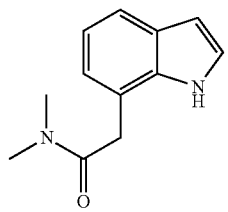

To a solution of 2-(1H-indol-7-yl)acetic acid (109 mg, 0.622 mmol) in DMF (2.5 mL) were added dimethylamine hydrochloride (101 mg, 1.24 mmol) and DIPEA (0.54 mL, 3.11 mmol). The reaction mixture was cooled to 15° C., treated with HATU (476 mg, 1.24 mmol), then stirred at RT for 30 min. The mixture was diluted with EtOAc and HCl (1N). The aqueous layer was extracted with further EtOAc. The combined organic extracts were washed with water, brine, dried (Na$_2$SO$_4$) and concentrated. The residue was purified by chromatography on silica (solvent gradient 30-85% EtOAc in cyclohexane) to afford the title compound (151 mg, >100%). LCMS (ESI) [M+H]+ 203.

Step 2:
2-(3-Bromo-1H-indol-7-yl)-N,N-dimethylacetamide

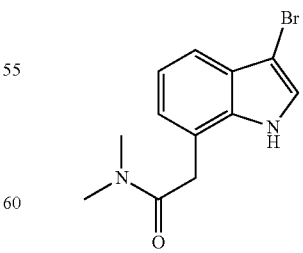

NBS (111 mg, 0.622 mmol) was added portionwise to a solution of 2-(1H-indol-7-yl)-N,N-dimethylacetamide (126 mg, 0.622 mmol) in DCM (10 mL). The mixture was stirred at RT for 30 min, then was washed with aq. sodium bisulfite, water, dried (Na₂SO₄) and concentrated. The residue was purified by chromatography on silica (solvent gradient 30-85% EtOAc in cyclohexane) to afford the title compound (123 mg, 70%) as a colorless gum. LCMS (ESI) [M+H]⁺ 281/283.

Step 3: 2-(3-Bromo-1-tosyl-1H-indol-7-yl)-N,N-dimethylacetamide

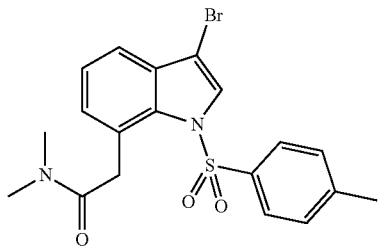

Sodium hydride (60% in oil, 18.6 mg, 0.464 mmol) was added portionwise to a solution of 2-(3-bromo-1H-indol-7-yl)-N,N-dimethylacetamide (119 mg, 0.422 mmol) and 4-toluenesulfonyl chloride (84.5 mg, 0.443 mmol) in THF (3 mL) at 0° C. The mixture was stirred for 30 min, quenched with aq. ammonium chloride and extracted with EtOAc. The combined organic extracts were washed with brine, dried (Na₂SO₄) and concentrated. The residue was purified by chromatography on silica (solvent gradient 30-85% EtOAc in cyclohexane) to afford the title compound (181 mg, 99% yield). LCMS (ESI) [M+H]⁺ 435/437.

Example 106

3-Bromo-1-tosyl-1H-indole-5-carbonitrile

Step 1: 3-Bromo-1H-indole-5-carbonitrile

NBS (689 mg, 3.87 mmol) was added portionwise to a solution of 5-cyanoindole (500 mg, 3.52 mmol) in DMF (10 mL) at RT, resulting in an immediate dark purple coloration. The mixture was stirred for 1 h, then was partitioned between NaOH solution (1M, 10 mL) and EtOAc (3×15 mL). The combined organic extracts were washed with brine, dried (Na₂SO₄) and concentrated. The residue was triturated with DCM and filtered to give the title compound (535 mg, 68%) as a pale yellow solid. LCMS (ESI) [M+H]⁺ 219.0/221.0.

Step 2: 3-Bromo-1-tosyl-1H-indole-5-carbonitrile

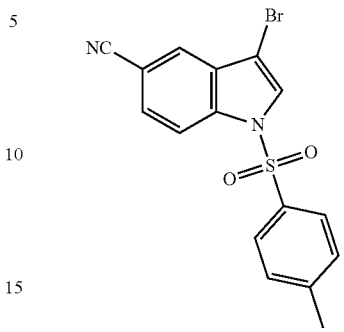

Sodium hydride (60% in oil, 116 mg, 2.90 mmol) was added portionwise to a solution of 3-bromo-1H-indole-5-carbonitrile (535 mg, 2.42 mmol) at 0° C. The mixture was stirred for 5 min, then 4-toluenesulfonyl chloride (507 mg, 2.66 mmol) was added. The ice-bath was removed and the mixture was allowed to warm to RT and stirred for 1 h. The cooled mixture was quenched with aq. ammonium chloride and extracted with EtOAc. The combined organic extracts where washed with brine, dried (Na₂SO₄) and concentrated. The residue was triturated with Et₂O and filtered to give the title compound (908 mg, 100% yield) as a buff-colored solid. ¹H NMR (400 MHz, CDCl₃) δ 8.09 (d, J=8.6 Hz, 1H), 7.85 (d, J=1.3 Hz, 1H), 7.80-7.77 (m, 2H), 7.74 (s, 1H), 7.62 (dd, J=8.6, 1.5 Hz, 1H), 7.29 (d, J=8.2 Hz, 2H), 2.38 (s, 3H).

Example 107

3-Bromo-1-tosyl-1H-indole-5-carboxylic Acid

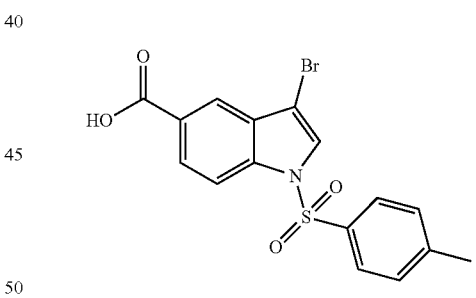

To a solution of 3-bromo-1H-indole-5-carboxylic acid (2.4 g, 10 mmol) in DMF (30 mL) at 0° C. was added sodium hydride (60% in oil, 999 mg, 25 mmol). The reaction mixture was stirred at 0° C. for 15 min, then p-toluenesulfonyl chloride (2.09 g, 11 mmol) was added. The reaction mixture was stirred at 0° C. for 30 min, then was diluted with water, acidified with 1N HCl and extracted with EtOAc. The combined organic extracts were washed with brine, dried (MgSO₄) and concentrated in vacuo. The solid was triturated with DCM/MeOH (~20:1) to give the title product (2.36 g, 60%) as a buff colored solid. ¹H NMR (400 MHz, DMSO-d₆) δ 8.27 (s, 1H), 8.13-8.08 (m, 1H), 8.04-7.99 (m, 2H), 7.96 (d, J=8.3 Hz, 2H), 7.43 (d, J=8.0 Hz, 2H), 2.33 (s, 3H).

Example 108

3-Bromo-N,N-dimethyl-1-tosyl-1H-indole-5-carboxamide

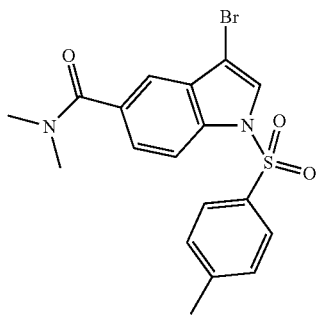 [SMILES: Cc1ccc(S(=O)(=O)n2cc(Br)c3cc(C(=O)N(C)C)ccc32)cc1]

To a solution of 3-bromo-1-tosyl-1H-indole-5-carboxylic acid (335 mg, 0.85 mmol), dimethylamine hydrochloride (208 mg, 2.55 mmol), triethylamine (0.59 mL, 4.25 mmol) and 4-dimethylaminopyridine (21 mg, 0.17 mmol) in DCM (8.5 mL), was added N-(3-dimethylaminopropyl)-N-ethylcarbodiimide hydrochloride (195 mg, 1.02 mmol). The reaction mixture was stirred at RT for 2 days. Further portions of dimethylamine hydrochloride (69 mg, 0.85 mmol), N-(3-dimethylaminopropyl)-N'-ethylcarbodiimide hydrochloride (97 mg, 0.51 mmol), triethylamine (0.19 mL, 1.41 mmol) and 4-dimethylaminopyridine (21 mg, 0.17 mmol) were added, and stirring was pursued for 24 h. The reaction mixture was poured into 1N HCl and this mixture was extracted with EtOAc. The combined organic extracts were washed with a sat. aq. sodium bicarbonate, brine, dried ($Na_2SO_4$) and concentrated. The residue was purified by chromatography on silica (solvent gradient 0-30% EtOAc in cyclohexane) to give afford the title compound (210 mg, 59% yield) as a white foam. LCMS (ESI) $[M+H]^+$ 421.2.

Example 109

(3-Bromo-1-tosyl-1H-indol-5-yl)(imino)(methyl)-$\lambda^6$-sulfanone

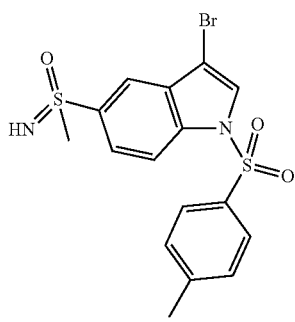 [SMILES: Cc1ccc(S(=O)(=O)n2cc(Br)c3cc(S(C)(=N)=O)ccc32)cc1]

Step 1: 5-(Methylthio)-1-tosyl-1H-indole

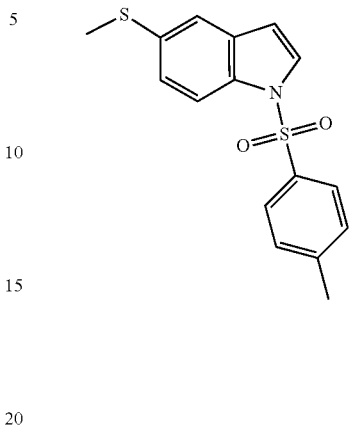

Sodium hydride (60% oil, 294 mg, 7.35 mmol) was added portionwise to a solution of 5-methylsulfanyl-1H-indole (1.0 g, 6.13 mmol) in DMF (15 mL) at 0 C. The reaction mixture was stirred for 5 min, then 4-toluenesulfonyl chloride (1.28 g, 6.74 mmol) was added at 0° C. The ice-bath was removed and the mixture was allowed to warm to RT and stirred for 1 h. The cooled mixture was quenched with aq. ammonium chloride and extracted with EtOAc. The combined organic extracts were washed with brine, dried ($Na_2SO_4$) and concentrated. The residue was purified by chromatography on silica (solvent gradient 0-30% EtOAc in cyclohexane), and the resulting residue triturated in $Et_2O$ to afford the title compound (1.48 g, 76% yield) as a colorless solid. LCMS (ESI) $[M+H]^+$ 318.0.

Step 2: Imino(methyl)(1-tosyl-1H-indol-5-yl)-$\lambda^6$-sulfanone

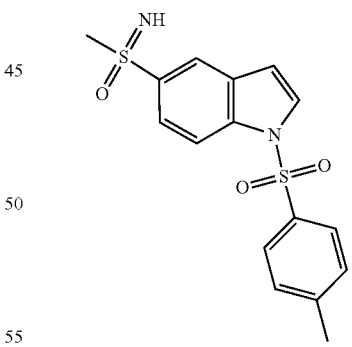

Ammonium carbamate (197 mg, 2.52 mmol) was added to a mixture of 5-(methylthio)-1-tosyl-1H-indole (200 mg, 0.63 mmol) and iodobenzene diacetate (406 mg, 1.26 mmol) in MeOH (15 mL). The mixture was stirred for 1 h at RT. The solvent was evaporated and the residue was partitioned between water (20 mL) and EtOAc. The aqueous layer was extracted with further EtOAc. The combined organic extracts were washed with brine, dried ($Na_2SO_4$) and concentrated to afford the title compound (220 mg, 100%) as a colorless solid. LCMS (ESI) $[M+H]^+$ 349.1.

Step 3: (3-Bromo-1-tosyl-1H-indol-5-yl)(imino)(methyl)-λ⁶-sulfanone

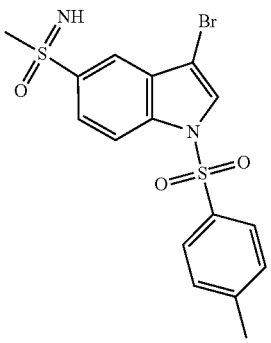 [SMILES: Cc1ccc(S(=O)(=O)n2cc(Br)c3cc(S(C)(=N)=O)ccc32)cc1]

Copper (II) bromide (460 mg, 2.04 mmol) was added portionwise to a solution of imino(methyl)(1-tosyl-1H-indol-5-yl)-λ⁶-sulfanone (237 mg, 0.68 mmol) in MeCN (15 mL). The reaction mixture was stirred at RT for 1 h then at 50° C. for 18 h. Further copper (II) bromide (460 mg, 2.04 mmol) was added and heating was continued at 50° C. for 1 h. The reaction mixture was quenched with 2N MeOH·NH₃ (15 mL) and the resulting blue precipitate stirred for 30 min. The solvent was evaporated and the residue partitioned between water (50 mL) and EtOAc. The aqueous layer was extracted with further EtOAc. The combined organic extracts were washed with brine, dried (Na₂SO₄) and concentrated. The residue was purified by chromatography on silica (solvent gradient 20-100% EtOAc in cyclohexane) to afford the title compound (106 mg, 36%) as a colorless solid. LCMS (ESI) [M+H]⁺ 427.0/429.0.

Example 110

3-Bromo-5-cyclopropyl-1-tosyl-1H-indole

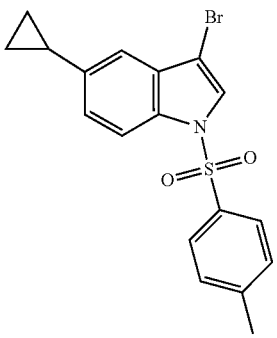 [SMILES: Cc1ccc(S(=O)(=O)n2cc(Br)c3cc(C4CC4)ccc32)cc1]

Step 1: 3-Bromo-5-cyclopropyl-1H-indole

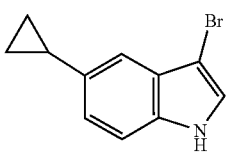 [SMILES: Brc1c[nH]c2ccc(C3CC3)cc12]

NBS (623 mg, 3.5 mmol) was added portionwise to a solution of 5-cyclopropyl-1H-indole (500 mg, 3.18 mmol) in DMF (7 mL). The reaction mixture was stirred at RT for 1 h, then was partitioned between NaOH solution (1N, 20 mL) and EtOAc (3×15 mL). The combined organic extracts were washed with brine, dried (Na₂SO₄) and concentrated to afford the title compound (685 mg, 91% yield) as a brown solid. LCMS (ESI) [M+H]⁺ 234.2/236.2.

Step 2: 3-Bromo-5-cyclopropyl-1-tosyl-1H-indole

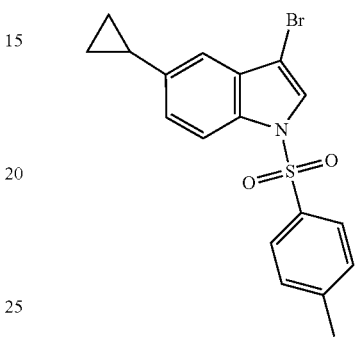

Sodium hydride (60% in oil, 139 mg, 3.48 mmol) was added portionwise to a solution of 3-bromo-5-cyclopropyl-1H-indole (685 mg, 2.9 mmol) in DMF (12 mL) at 0° C. The reaction mixture was stirred for 5 min, then 4-toluenesulfonyl chloride (608 mg, 3.19 mmol) was added at 0° C. The ice-bath was removed and the mixture allowed to warm up to RT and stirred for 1 h. The cooled mixture was quenched with aq. ammonium chloride and then extracted with EtOAc (3×15 mL). The combined organic extracts were washed with brine, dried (Na₂SO₄) and concentrated. The residue was purified by chromatography on silica (solvent gradient 0-20% EtOAc in cyclohexane) to afford the title compound (914 mg, 81%) as an amber colored glass. LCMS (ESI) [M+H]⁺ not detected.

2-(3-Bromo-1H-indol-5-yl)acetonitrile

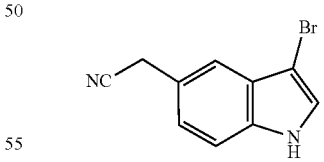

NBS (251 mg, 1.41 mmol) was added portionwise to a solution of 2-(1H-indol-5-yl)acetonitrile (200 mg, 1.28 mmol) in DMF (5 mL). The reaction mixture was stirred for 0.25 h at RT, then was partitioned between water and EtOAc. The aqueous layer was extracted with further EtOAc. The combined organic extracts were washed with brine, dried (Na₂SO₄) and concentrated. The residue was purified by chromatography on silica (solvent gradient 0-30% EtOAc in cyclohexane) to afford the title compound (123 mg, 41%) as a buff-colored solid. LCMS (ESI) [M−H]⁻ 232.9/234.9.

Example 111

3-Bromo-5-(4-methyl-4H-1,2,4-triazol-3-yl)-1-tosyl-1H-indole and 2-(3-bromo-1-tosyl-1H-indol-5-yl)-1,3,4-oxadiazole

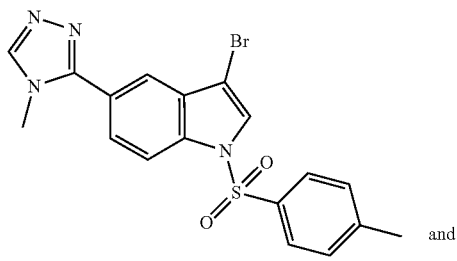

and

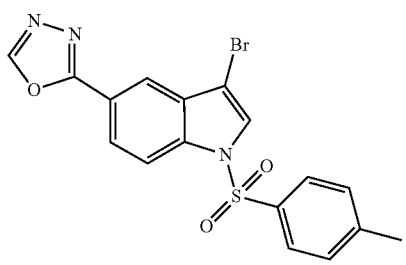

Step 1: 3-Bromo-1-tosyl-1H-indole-5-carbohydrazide

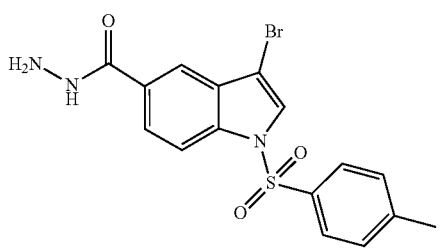 [SMILES: Cc1ccc(S(=O)(=O)n2cc(Br)c3cc(C(=O)NN)ccc32)cc1]

3-Bromo-1-tosyl-1H-indole-5-carboxylic acid (1 g, 2.54 mmol), EDCI·HCl (583 mg, 3.04 mmol) and HOBT hydrate (466.14 mg, 3.04 mmol) were suspended in DMF (15 mL). The reaction was stirred at RT for 30 min, during which the solids dissolved. Hydrazine hydrate (25 mL, 25.37 mmol) was added and the reaction stirred at RT for 15 min. The reaction mixture was poured into water (~100 mL), the precipitated solid collected by filtration and dried in vacuo at 40° C. overnight to yield the title product (891 mg, 86%) as a white solid. LCMS (ESI) [M+H]+ 408/410.

Step 2: (E)-N'-(3-Bromo-1-tosyl-1H-indole-5-carbonyl)-N,N-dimethylformohydrazonamide

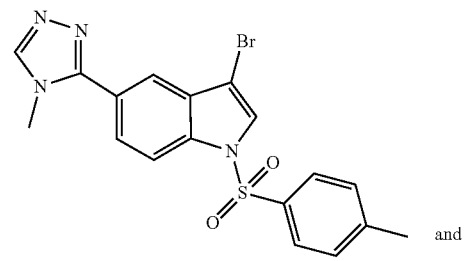

A suspension of 3-bromo-1-tosyl-1H-indole-5-carbohydrazide (500 mg, 1.22 mmol) and N,N-dimethylformamide dimethyl acetal (0.33 mL, 2.45 mmol) in MeCN (6 mL) was heated at reflux for 30 min, during which the solids dissolved. The reaction mixture was concentrated in vacuo to give the product as an off-white solid. (567 mg, 100%) $^1$H NMR (400 MHz, DMSO-$d_6$) δ 8.21 (s, 1H), 8.04 (d, J=8.3 Hz, 1H), 7.97-7.85 (m, 5H), 7.42 (d, J=8.6 Hz, 2H), 2.84 (s, 6H), 2.33 (s, 3H).

Step 3: 3-Bromo-5-(4-methyl-4H-1,2,4-triazol-3-yl)-1-tosyl-1H-indole and 2-(3-bromo-1-tosyl-1H-indol-5-yl)-1,3,4-oxadiazole

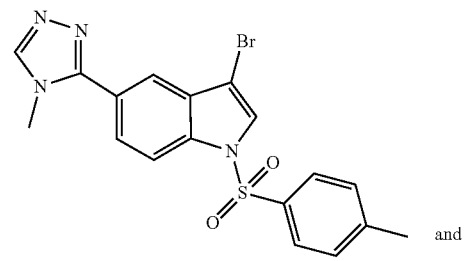

and

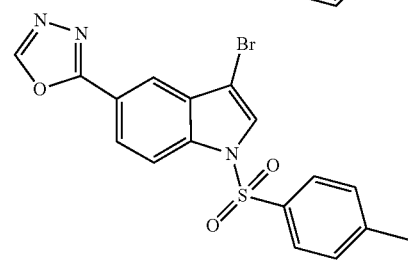

(E)-N'-(3-bromo-1-tosyl-1H-indole-5-carbonyl)-N,N-dimethylformohydrazonamide (1.6 g, 3.48 mmol) and methylamine (2N in THF, 17.4 mL, 34.77 mmol) were dissolved in acetic acid (16 mL) and heated at 65° C. for 1.5 h. The reaction mixture was diluted with water and extracted with EtOAc. The combined organic extracts were washed with brine, dried (MgSO$_4$) and concentrated in vacuo. The residue was purified by chromatography on silica (solvent gradient 0-6% MeOH in DCM) to afford 2-(3-bromo-1-tosyl-1H-indol-5-yl)-1,3,4-oxadiazole (378 mg, 39%). LCMS (ESI) [M+H]+ 418/420. The impure fractions were re-purified by chromatography on silica (solvent gradient 0-10% MeOH in EtOAc) to afford 3-bromo-5-(4-methyl-4H-1,2,4-triazol-3-yl)-1-tosyl-1H-indole (317 mg, 21%). LCMS (ESI) [M+H]+ 431/433.

Example 112 tert-Butyl 3-bromo-5-(3-methyl-1H-pyrazol-4-yl)-1H-indole-1-carboxylate

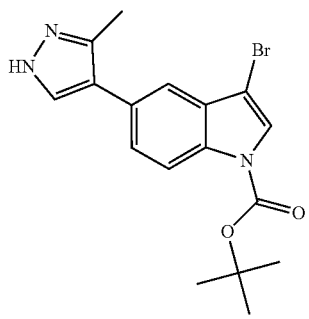 [SMILES: Cc1n[nH]cc1-c1ccc2c(c1)c(Br)cn2C(=O)OC(C)(C)C]

Step 1: tert-Butyl 3-bromo-5-iodo-1H-indole-1-carboxylate

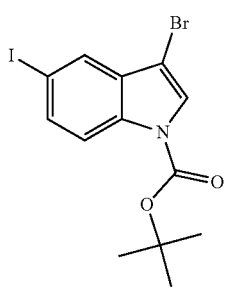 [SMILES: CC(C)(C)OC(=O)n1cc(Br)c2cc(I)ccc21]

To a solution of tert-butyl 5-iodoindole-1-carboxylate (2 g, 5.83 mmol) in DCM (20 mL) at 0° C. was added NBS (1.24 g, 6.99 mmol). The reaction mixture was stirred at 0° C. to RT over 48 h, then was diluted with water and extracted with DCM. The combined organic extracts were washed with brine, dried (MgSO$_4$) and concentrated in vacuo. The residue was purified by chromatography on silica (solvent gradient 0-30% DCM in cyclohexane), to afford the title compound (1.31 g, 53%) as a beige solid. $^1$H NMR (400 MHz, CDCl$_3$) δ 7.94-7.88 (m, 1H), 7.87-7.85 (m, 1H), 7.64 (dd, J=8.8, 1.6 Hz, 1H), 7.59 (s, 1H), 1.65 (s, 9H).

Step 2: tert-Butyl 3-bromo-5-(3-methyl-1H-pyrazol-4-yl)-1H-indole-1-carboxylate

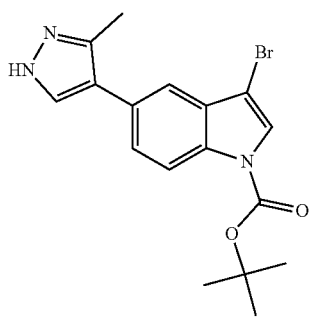 [SMILES: Cc1n[nH]cc1-c1ccc2c(c1)c(Br)cn2C(=O)OC(C)(C)C]

A degassed mixture of tert-butyl 3-bromo-5-iodoindole-1-carboxylate (500 mg, 1.18 mmol), 3-methyl-4-(4,4,5,5-tetramethyl-1,3,2-dioxaborolan-2-yl)-1H-pyrazole (320 mg, 1.54 mmol), tetrakis(triphenylphosphine)palladium(O) (137 mg, 0.12 mmol) and cesium carbonate (582 mg, 1.78 mmol) in 1,4-dioxane (9 mL) and water (1 mL) was heated at 100° C. for 3 h. The reaction mixture was diluted with water and extracted with EtOAc. The combined organic extracts were washed with brine, dried (MgSO$_4$) and concentrated in vacuo. The residue was purified by chromatography on silica (solvent gradient 0-100% EtOAc in cyclohexane), then re-purified (solvent gradient 0-4% MeOH in DCM), to afford the title compound (186 mg, 41%) as an oil. LCMS (ESI) [M+H]$^+$ 376/378.

Example 113 tert-Butyl 5-cyano-3-iodo-1H-pyrrolo[2,3-c]pyridine-1-carboxylate

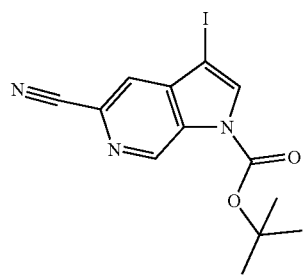 [SMILES: CC(C)(C)OC(=O)n1cc(I)c2cc(C#N)ncc21]

Step 1: 1H-Pyrrolo[2,3-c]pyridine-5-carbonitrile

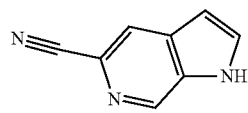

A degassed mixture of 5-chloro-1H-pyrrolo[2,3-c]pyridine (225 mg, 1.47 mmol), anhydrous DMA (13.5 mL), zinc cyanide (0.29 mL, 3.39 mmol) and tetrakis(triphenylphosphine)palladium(O) (170 mg, 0.15 mmol) was heated under microwave irradiation at 145° C. for 3 h. The cooled reaction mixture was then passed onto a SCX-2 cartridge (eluting with DCM/MeOH 1:1 then MeOH·NH$_3$) to give the title compound (218 mg, ~100%) as a yellowish solid. LCMS (ESI) [M+H]$^+$ 144.1.

Step 2: tert-Butyl 5-cyano-1H-pyrrolo[2,3-c]pyridine-1-carboxylate

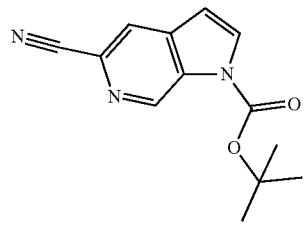 [SMILES: CC(C)(C)OC(=O)n1ccc2cc(C#N)ncc21]

To a solution of 1H-pyrrolo[2,3-c]pyridine-5-carbonitrile (210 mg, 1.47 mmol) in MeCN (6.5 mL) and DMF (5 mL) were added 4-dimethylaminopyridine (18 mg, 0.15 mmol) and tert-butyl dicarbonate (368 mg, 1.69 mmol). The mixture was stirred for 1 h. The solvents were removed in vacuo and the residue was purified by chromatography on silica (solvent gradient 0-20% EtOAc in cyclohexane), to afford the title compound (160 mg, 44.7%) as a white solid. LCMS (ESI) [M+H-tBu]$^+$ 188.1.

Step 3: tert-Butyl 5-cyano-3-iodo-1H-pyrrolo[2,3-c]pyridine-1-carboxylate

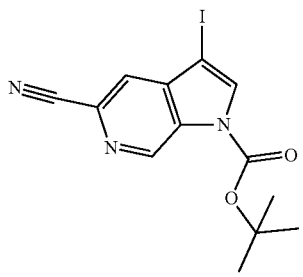 [SMILES: CC(C)(C)OC(=O)n1cc(I)c2cc(C#N)ncc21]

To a solution of 1H-pyrrolo[2,3-c]pyridine-5-carbonitrile (84 mg, 0.59 mmol) in DMF (2.5 mL) were added iodine (298 mg, 1.17 mmol) and potassium hydroxide (99 mg, 1.76 mmol). The reaction mixture was stirred at RT for 2 h. The solvent was then removed in vacuo. The residue was dissolved into THF (5 mL) and treated with tert-butyl dicarbonate (153.5 mg, 0.70 mmol) and 4-dimethylaminopyridine (14 mg, 0.12 mmol). The mixture was stirred for 1 h. The reaction mixture was diluted with EtOAc, then poured onto ice with 10% aq. sodium metabisulfite. The organic extract was washed with water, brine, dried (Na$_2$SO$_4$) and concentrated in vacuo. The residue was purified by chromatography on silica (solvent gradient 0-20% EtOAc in cyclohexane), to afford the title compound (148 mg, 68.3%) as a light brown solid. $^1$H NMR (400 MHz, CDCl$_3$) δ9.42 (s, 1H), 7.97 (s, 1H), 7.81 (s, 1H), 1.71 (s, 9H).

Example 114

1-(3-Bromo-1-tosyl-1H-indol-7-yl)piperidin-2-one

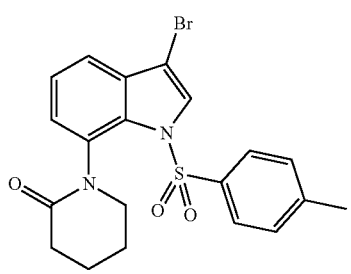 [SMILES: Cc1ccc(S(=O)(=O)n2cc(Br)c3cccc(N4CCCCC4=O)c32)cc1]

Step 1: 5-Bromo-N-(1H-indol-7-yl)pentanamide

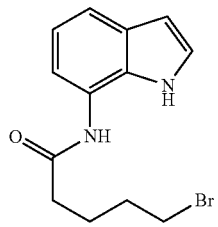 [SMILES: O=C(CCCCBr)Nc1cccc2cc[nH]c12]

A solution of 5-bromopentanoyl chloride (0.906 g, 4.54 mmol) in DCM (5 mL) was added over 15 min to a solution of 1H-indol-7-amine (0.50 g, 3.78 mmol) and triethylamine (0.74 mL, 5.3 mmol) in DCM (15 mL). The mixture was stirred for 1 h, then washed with aq. sodium bicarbonate, water, dried (Na$_2$SO$_4$) and evaporated. The residue was purified by chromatography on silica (solvent gradient 5-30% EtOAc in cyclohexane) to afford the title compound (1.0 g, 90%) as a buff solid. LCMS (ESI) [M+H]$^+$ 295/297.

Step 2: 1-(1H-Indol-7-yl)piperidin-2-one

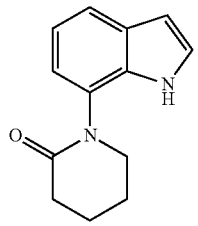 [SMILES: O=C1CCCCN1c1cccc2cc[nH]c12]

To an ice-cooled solution of 5-bromo-N-(1H-indol-7-yl)pentanamide (0.90 g, 3.05 mmol) in THF (10 mL) was added potassium tert-butoxide (0.41 g, 3.65 mmol) portionwise over 5 min. The mixture was stirred in the ice bath for 30 min, then partitioned between sat. aq. ammonium chloride and EtOAc. The aqueous phase was extracted with more EtOAc and the combined organic extracts were washed with brine, dried (Na$_2$SO$_4$) and evaporated. The residue was purified by chromatography on silica (solvent gradient 50-100% EtOAc in cyclohexane, then 5-10% MeOH in EtOAc) to afford the title compound (0.679 g, 94%) as a buff solid. LCMS (ESI) [M+H]$^+$ 215.

Step 3: 1-(3-Bromo-1H-indol-7-yl)piperidin-2-one

1-(1H-Indol-7-yl)piperidin-2-one (0.676 g, 3.15 mmol) was dissolved in DCM (25 mL) and NBS (0.562 g, 3.15 mmol) was added over 5 min. The mixture was stirred at RT for 10 min, then was washed with 10% aq. sodium metabisulfite, then water, dried (Na$_2$SO$_4$) and evaporated. The residue was purified by chromatography on silica (solvent gradient 2-8% MeOH in DCM) to afford the title compound (0.91 g, 98%) as a buff solid. LCMS (ESI) [M+H]$^+$ 293/295.

Step 4: 1-(3-Bromo-1-tosyl-1H-indol-7-yl)piperidin-2-one

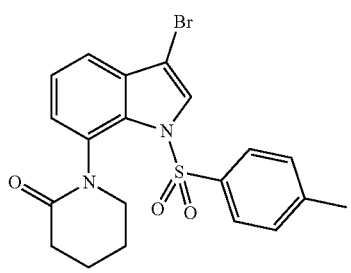 [SMILES: Cc1ccc(S(=O)(=O)n2cc(Br)c3cccc(N4CCCCC4=O)c32)cc1]

Sodium hydride (60% in oil, 0.075 g, 1.88 mmol) was added over 5 min to an ice-cooled solution of 1-(3-bromo-1H-indol-7-yl)piperidin-2-one (0.50 g, 1.7 mmol) and tosyl chloride (0.341 g, 1.79 mmol) in THF (10 mL). The mixture was allowed to warm to RT overnight. Sat. aq. ammonium chloride was added and the mixture extracted with EtOAc (2×). The combined organic extracts were washed with brine, dried (Na$_2$SO$_4$) and evaporated. The residue was purified by chromatography on silica (solvent gradient 50-100% EtOAc in cyclohexane) to afford the title compound (0.681 g, 89%) as a pale brown foam. LCMS (ESI) [M+H]$^+$ 447/449.

Example 115

4-(3-Bromo-1-tosyl-1H-indol-7-yl)morpholin-3-one

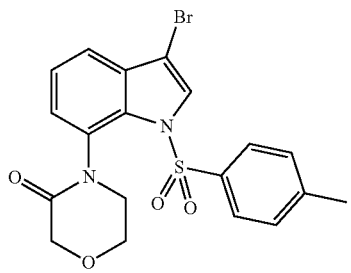 [SMILES: Cc1ccc(S(=O)(=O)n2cc(Br)c3cccc(N4CCOCC4=O)c32)cc1]

Step 1: 2-(2-Chloroethoxy)-N-(1H-indol-7-yl)acetamide

To a solution of 1H-indol-7-amine (0.10 g, 0.756 mmol) and (2-chloroethoxy)acetic acid (0.115 g, 0.832 mmol) in DMF (2.5 mL) were added DIPEA (0.524 mL, 3.03 mmol) and HATU (0.575 g, 1.51 mmol). The reaction mixture was stirred at RT for 1 h, then was partitioned between EtOAc and aq. sodium bicarbonate. The aqueous phase was extracted with more EtOAc and the combined organic extracts were washed with water, dried (Na$_2$SO$_4$) and evaporated. The residue was purified by chromatography on silica (solvent gradient 30-70% EtOAc in cyclohexane) to afford the title compound (0.18 g, 94%) as an off-white solid. LCMS (ESI) [M+H]$^+$ 253/255.

Step 2: 4-(1H-Indol-7-yl)morpholin-3-one

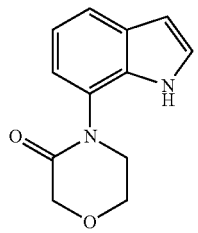 [SMILES: O=C1COCCN1c1cccc2cc[nH]c12]

To an ice-cooled solution of 2-(2-chloroethoxy)-N-(1H-indol-7-yl)acetamide (0.177 g, 0.70 mmol) in THF (5 mL) was added potassium tert-butoxide (0.094 g, 0.84 mmol) portionwise over 5 min. The mixture was stirred at RT for 1 h, then was partitioned between sat. aq ammonium chloride and EtOAc. The aqueous phase was extracted with more EtOAc and the combined organic extracts were washed with brine, dried (Na$_2$SO$_4$) and evaporated. The residue was purified by chromatography on silica (solvent gradient 50-100% EtOAc in cyclohexane) to afford the title compound (0.144 g, 95%) as a colorless solid. LCMS (ESI) [M+H]$^+$ 217.

387
Step 3: 4-(3-Bromo-1H-indol-7-yl)morpholin-3-one

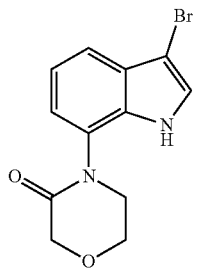 [SMILES: O=C1COCCN1c1cccc2c(Br)c[nH]c12]

4-(1H-Indol-7-yl)morpholin-3-one (0.144 g, 0.666 mmol) was dissolved in DCM (20 mL) and NBS (0.118 g, 0.666 mmol) was added over 5 min. The reaction mixture was stirred at RT for 15 min, then was washed with 10% aq. sodium metabisulfite, water, dried (Na$_2$SO$_4$) and evaporated. The residue was purified by chromatography on silica (solvent gradient 50-100% EtOAc in cyclohexane) to afford the title compound (0.18 g, 92%) as a colorless gum. LCMS (ESI) [M+H]$^+$ 295/297.

Step 4: 4-(3-Bromo-1-tosyl-1H-indol-7-yl)morpholin-3-one

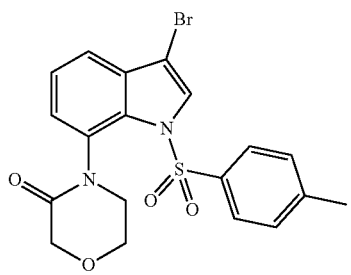 [SMILES: Cc1ccc(S(=O)(=O)n2cc(Br)c3cccc(N4CCOCC4=O)c32)cc1]

Sodium hydride (60% in oil, 27 mg, 0.67 mmol) was added over 5 min to an ice-cooled solution of 4-(3-bromo-1H-indol-7-yl)morpholin-3-one (180 mg, 0.61 mmol) and tosyl chloride (122 mg, 0.64 mmol) in THF (4 mL). The mixture was stirred at RT for 1.5 h. Sat. aq. ammonium chloride was added and the mixture extracted with EtOAc (2×). The combined organic extracts were washed with brine, dried (Na$_2$SO$_4$) and evaporated. The residue was purified by chromatography on silica (solvent gradient 50-90% EtOAc in cyclohexane) to afford the title compound (193 mg, 70%) as a colorless gum. LCMS (ESI) [M+H]$^+$ 449/451.

388
Example 116 tert-Butyl 4-(3-bromo-1-tosyl-1H-indol-7-yl)-3-oxopiperazine-1-carboxylate

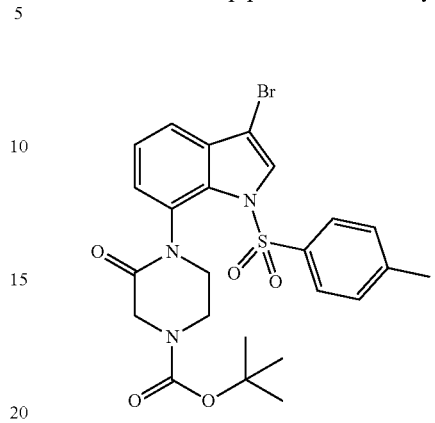

Step 1: 2-Bromo-N-(1H-indol-7-yl)acetamide

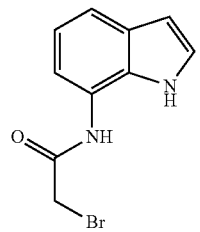 [SMILES: O=C(CBr)Nc1cccc2cc[nH]c12]

To an ice-cooled solution of 1H-indol-7-amine (0.20 g, 1.51 mmol) and triethylamine (0.316 mL, 2.27 mmol) in THF (9 mL) was added a solution of bromoacetyl bromide (0.145 mL, 1.66 mmol) in THF (1 mL). The mixture was stirred at RT for 1.5 h. The reaction mixture was diluted with DCM, washed with 1N HCl, then aq. sodium bicarbonate, dried (Na$_2$SO$_4$) and evaporated. The residue was purified by chromatography on silica (solvent gradient 10-30% EtOAc in DCM) to afford the title compound (0.237 g, 62%) as an off-white solid. LCMS (ESI) [M+H]$^+$ 253/255.

Step 2: 2-((2-Hydroxyethyl)amino)-N-(1H-indol-7-yl)acetamide

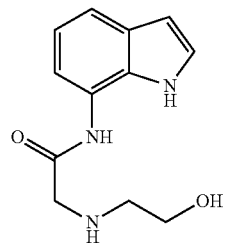 [SMILES: O=C(CNCCO)Nc1cccc2cc[nH]c12]

A mixture of 2-bromo-N-(1H-indol-7-yl)acetamide (0.237 g, 0.936 mmol) and ethanolamine (0.20 mL, 3.34 mmol) in EtOAc (10 mL) was stirred at 60° C. for 45 min. The cooled reaction mixture was diluted with EtOAc,

Step 3: 1-(1H-Indol-7-yl)piperazin-2-one

Tributylphosphine was added to a suspension of 2-((2-hydroxyethyl)amino)-N-(1H-indol-7-yl)acetamide (0.204 g, 0.87 mmol) in EtOAc (6 mL) at 0° C. Di-tert-butyl azodicarboxylate (0.20 g, 0.87 mmol) was added portionwise over 30 min. After a further 30 min the reaction mixture was heated at 40° C. for 1 h. The reaction mixture was cooled in an ice bath, then was treated with EtOH (2 mL) and HCl in dioxane (4M, 0.5 mL). The reaction mixture was stirred for 20 min at 0° C., then for 30 min at RT, then evaporated to dryness. The residue was dissolved in a mixture of MeOH (0.2 mL), water (20 mL) and 1N HCl (3 mL), and purified by chromatography on C18 silica (solvent gradient 1-20% MeOH in 0.025M aq. HCl). The residue was passed through a SCX-2 cartridge (eluting with MeOH then with MeOH·NH₃). The resulting residue was purified by chromatography on silica (solvent gradient 2-14% MeOH·NH₃ in DCM) to afford the title compound (0.134 g, 71%) as a colorless solid. LCMS (ESI) [M+H]$^+$ 216.

Step 4: tert-Butyl 4-(1H-indol-7-yl)-3-oxopiperazine-1-carboxylate

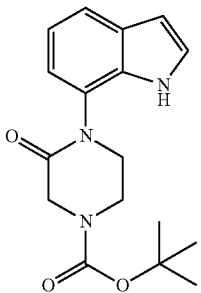 [SMILES: CC(C)(C)OC(=O)N1CCN(c2cccc3cc[nH]c23)C(=O)C1]

A solution of di-tert-butyl dicarbonate (0.149 g, 0.685 mmol) in DCM (2 mL) was added over 3 min to a solution of 1-(1H-indol-7-yl)piperazin-2-one (0.134 g, 0.622 mmol) and triethylamine (0.13 mL, 0.934 mmol) in DCM (8 mL). The mixture was stirred at RT for 1 h, then more di-tert-butyl dicarbonate (0.015 g, 0.069 mmol) in DCM (0.5 mL) was added and stirring continued for 15 min. The mixture was diluted with cyclohexane (10 mL) and purified chromatography on silica (solvent gradient 20-80% EtOAc in cyclohexane) to afford the title compound (0.17 g, 87%) as a colorless gum. LCMS (ESI) [M+H]$^+$ 316.

Step 5: tert-Butyl 4-(3-bromo-1H-indol-7-yl)-3-oxopiperazine-1-carboxylate

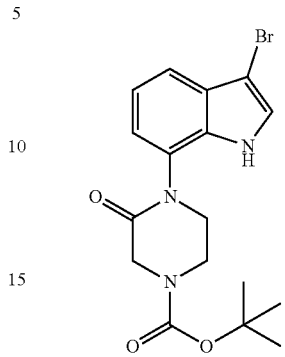

tert-Butyl 4-(1H-indol-7-yl)-3-oxopiperazine-1-carboxylate (0.169 g, 0.536 mmol) was dissolved in DCM (15 mL) and NBS (0.095 g, 0.536 mmol) was added over 5 min. The reaction mixture was stirred at RT for 15 min, then was washed with 10% aq. sodium metabisulfite, water, dried (Na₂SO₄) and evaporated. The residue was purified by chromatography on silica (solvent gradient 20-80% EtOAc in cyclohexane) to afford the title compound (0.185 g, 88%) as a colorless gum. LCMS (ESI) [M+H]$^+$ 416/418.

Step 6: tert-Butyl 4-(3-bromo-1-tosyl-1H-indol-7-yl)-3-oxopiperazine-1-carboxylate

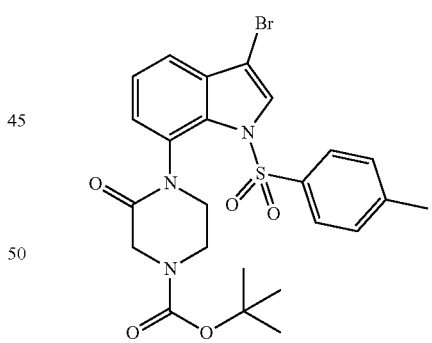

Sodium hydride (60% in oil, 21 mg, 0.518 mmol) was added to an ice-cooled solution of tert-butyl 4-(3-bromo-1H-indol-7-yl)-3-oxopiperazine-1-carboxylate (0.185 g, 0.47 mmol) and tosyl chloride (0.094 g, 0.49 mmol) in THF (4 mL). The mixture was stirred at RT for 5 h. Sat. aq. ammonium chloride was added and the mixture was extracted with EtOAc (2×). The combined organic extracts were washed with brine, dried (Na₂SO₄), filtered and evaporated. The residue was purified by chromatography on silica (solvent gradient 20-50% EtOAc in cyclohexane) to afford the title compound (0.19 g, 74%) as a pale yellow solid. LCMS (ESI) [M+H]$^+$ 570/572.

Example 117

1-(3-Bromo-1-tosyl-1H-indol-7-yl)-4-methylpiperazin-2-one

Step 1: 2-((2-Hydroxyethyl)(methyl)amino)-N-(1H-indol-7-yl)acetamide

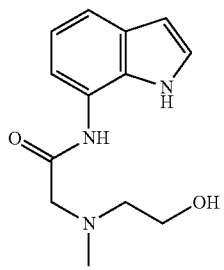 [SMILES: CN(CCO)CC(=O)Nc1cccc2cc[nH]c12]

1-(Methylamino)ethanol (0.69 mL, 8.53 mmol) was added to a suspension of 2-bromo-N-(1H-indol-7-yl)acetamide (617 mg, 2.44 mmol) in EtOAc (20 mL). The reaction mixture was heated at 60° C. for 20 min, then was diluted with EtOAc (20 mL). The solution was washed with sat. sodium bicarbonate (2×20 mL), dried (Na$_2$SO$_4$) and concentrated. The residue was triturated with Et$_2$O (10 mL) and filtered to give the title compound (430 mg, 71%) as a buff-colored solid. LCMS (ESI) [M+H]$^+$ 248.1.

Step 2: 1-(1H-Indol-7-yl)-4-methylpiperazin-2-one

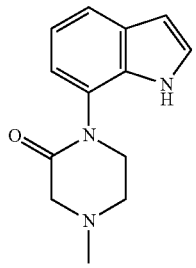 [SMILES: CN1CCN(c2cccc3cc[nH]c23)C(=O)C1]

Di-tert-butyl azodicarboxylate (397 mg, 1.72 mmol) was added portionwise to a suspension of 2 μl-hydroxyethyl (methyl)aminol-N-(1H-indol-7-yl)acetamide (426 mg, 1.72 mmol) and tributylphosphine (0.43 mL, 1.72 mmol) in EtOAc (10 mL) at 0° C. over 5 mins. The ice-bath was removed and the homogeneous mixture was allowed to warm up to RT over 1 h, resulting in the precipitation of a colorless solid. The mixture was concentrated in vacuo. The residue was triturated with Et$_2$O (5 mL) and filtered to give the title compound (253 mg, 64%) as a colorless solid. LCMS (ESI) [M+H]$^+$ 230.1.

Step 3: 1-(3-Bromo-1H-indol-7-yl)-4-methylpiperazin-2-one

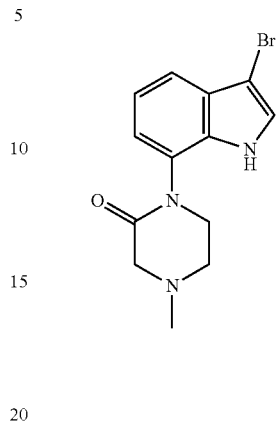

NBS (223 mg, 1.25 mmol) was added portionwise to a solution of 1-(1H-indol-7-yl)-4-methyl-piperazin-2-one (287 mg, 1.25 mmol) in DCM (15 mL). The reaction mixture was stirred at RT for 20 min and diluted with DCM (20 mL). The solution was washed with aq. sodium bicarbonate (20 mL) and sodium metabisulphite (1M, 30 mL), dried (Na$_2$SO$_4$) and concentrated. The residue was purified by chromatography on silica (solvent gradient 0-15% MeOH·NH$_3$ in DCM) to afford the title compound (250 mg, 64%) as a colorless solid. LCMS (ESI) [M+H]$^+$ 308.0/310.0.

Step 4: 1-(3-bromo-1-tosyl-1H-indol-7-yl)-4-methylpiperazin-2-one

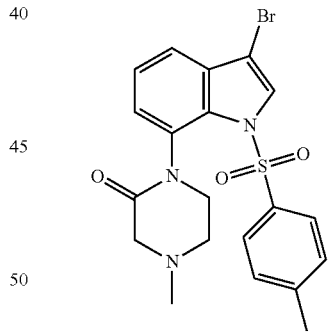

Sodium hydride (60% oil, 39 mg, 0.970 mmol) was added portionwise to a solution of 1-(3-bromo-1H-indol-7-yl)-4-methyl-piperazin-2-one (250 mg, 0.810 mmol) at 0° C. The mixture was stirred for 5 min, then p-toluenesulfonyl chloride (170 mg, 0.890 mmol) was added at 0° C. The ice-bath was removed and the mixture allowed to warm up to RT and stirred for 1 h. The cooled mixture was quenched with aq. ammonium chloride and extracted with EtOAc (3×15 mL). The combined organic extracts were washed with brine (20 mL), dried (Na$_2$SO$_4$) and concentrated. The residue was purified by chromatography on silica (solvent gradient 0-5% MeOH·NH$_3$ in DCM) to afford the title compound (355 mg, 94%). LCMS (ESI) [M+H]$^+$ 462.1/464.0.

Example 118

1-(3-Bromo-5-chloro-1-tosyl-1H-indol-7-yl)-4-methylpiperazin-2-one

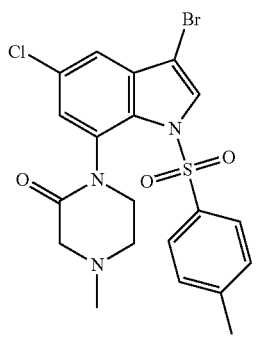 [SMILES: Cc1ccc(S(=O)(=O)n2cc(Br)c3cc(Cl)cc(N4CCN(C)CC4=O)c32)cc1]

Step 1: 2-Bromo-N-(5-chloro-1H-indol-7-yl)acetamide

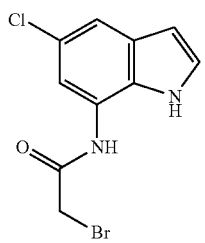 [SMILES: O=C(CBr)Nc1cc(Cl)cc2cc[nH]c12]

Bromoacetyl bromide (0.63 mL, 7.2 mmol) was added dropwise to a solution of 5-chloro-1H-indol-7-amine (1.0 g, 6.0 mmol) and triethylamine (1.0 mL, 7.2 mmol) in DCM (25 mL) at 0° C. The ice-bath was removed and the reaction mixture was stirred at RT for 1 h, then was diluted with DCM (30 mL), and washed successively with 1N HCl (30 mL) and aq. sodium bicarbonate (30 mL). The organic extract was dried (Na₂SO₄) and concentrated to give the title compound (1.21 g, 70%) as a buff-colored solid (1.25 g). LCMS (ESI) [M+H]⁺ 286.8/288.8.

Step 2: N-(5-Chloro-1H-indol-7-yl)-2-((2-hydroxyethyl)(methyl)amino)acetamide

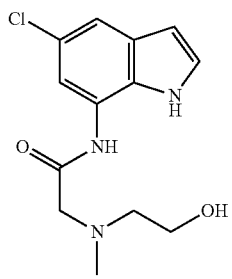 [SMILES: CN(CCO)CC(=O)Nc1cc(Cl)cc2cc[nH]c12]

2-(Methylamino)ethanol (1.18 mL, 14.73 mmol) was added to a suspension of 2-bromo-N-(5-chloro-1H-indol-7-yl)acetamide (1.21 g, 4.21 mmol) in EtOAc (50 mL). The reaction mixture was stirred at 22° C. for 20 mins, then diluted with EtOAc (20 mL), washed with aq. sodium bicarbonate (2×20 mL), dried (Na₂SO₄) and concentrated. The residue was triturated with Et₂O (10 mL) and filtered to give the title compound (1.147 g, 96%) as a buff-colored solid. LCMS (ESI) [M+H]⁺ 281.9/283.9.

Step 3: 1-(5-Chloro-1H-indol-7-yl)-4-methylpiperazin-2-one

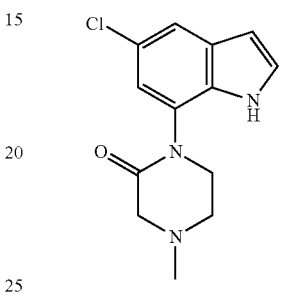

Di-tert-butyl azodicarboxylate (0.92 g, 3.98 mmol) was added portionwise to a suspension of N-(5-chloro-1H-indol-7-yl)-2-[2-hydroxyethyl(methyl)amino]acetamide (1.12 g, 3.98 mmol) and tributylphosphine (0.99 mL, 3.98 mmol) in EtOAc (30 mL) at 0° C. The ice-bath was removed and the homogeneous mixture allowed to warm up to RT over 1 h, resulting in the precipitation of a colorless solid. The mixture was concentrated in vacuo. The residue was triturated in Et₂O (5 mL) and filtered to give the title compound (880 mg, 83%) as a colorless solid. LCMS (ESI) [M+H]⁺ 263.9/265.9.

Step 4: 1-(3-Bromo-5-chloro-1H-indol-7-yl)-4-methylpiperazin-2-one

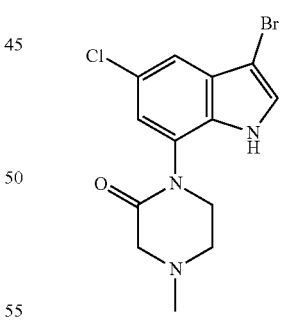

NBS (319 mg, 1.79 mmol) was added portionwise to a solution of 1-(5-chloro-1H-indol-7-yl)-4-methyl-piperazin-2-one (430 mg, 1.63 mmol) in chloroform (25 mL). The mixture was stirred for 20 min at RT, diluted with DCM (20 mL) and washed with aq. sodium bicarbonate (20 mL). The organic extract was dried (Na₂SO₄), concentrated, then purified by chromatography on silica (solvent gradient 0-15% MeOH·NH₃ in DCM) to afford the title compound (348 mg, 62%) as a pale yellow solid. LCMS (ESI) [M+H]⁺ 341.9/345.9.

Step 5: 1-(3-Bromo-5-chloro-1-tosyl-1H-indol-7-yl)-4-methylpiperazin-2-one

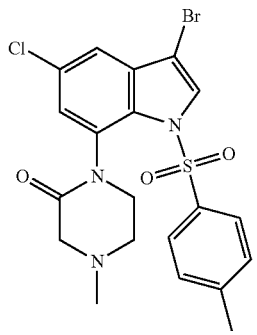 [SMILES: Cc1ccc(S(=O)(=O)n2cc(Br)c3cc(Cl)cc(N4CCN(C)CC4=O)c32)cc1]

Sodium hydride (60% in oil, 37 mg, 0.930 mmol) was added portionwise to a solution of 1-(3-bromo-5-chloro-1H-indol-7-yl)-4-methyl-piperazin-2-one (265 mg, 0.770 mmol) at 0° C. The mixture was stirred for 5 min, then 4-toluenesulfonyl chloride (162 mg, 0.850 mmol) was added. The ice-bath was removed and the mixture was allowed to warm up to RT and stirred for 1 h. The cooled mixture was quenched with aq. ammonium chloride extracted with EtOAc (3×15 mL). The combined organic extracts were washed with brine, dried (Na$_2$SO$_4$) and concentrated. The residue was purified by chromatography on silica (solvent gradient 0-5% MeOH·NH$_3$ in DCM) to afford the title compound (377 mg, 98%). LCMS (ESI) [M+H]$^+$ 496.0/500.0.

Example 119

3-Bromo-7-(4-methyl-2-oxopiperazin-1-yl)-1-tosyl-1H-indole-5-carbonitrile

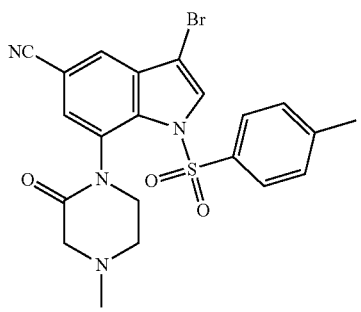 [SMILES: Cc1ccc(S(=O)(=O)n2cc(Br)c3cc(C#N)cc(N4CCN(C)CC4=O)c32)cc1]

Step 1: 7-Amino-1H-indole-5-carbonitrile

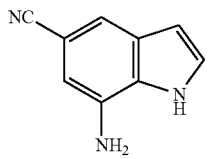 [SMILES: N#Cc1cc(N)c2[nH]ccc2c1]

Trimethylphosphine (1N in toluene, 13 mL, 12.62 mmol) was added dropwise to a solution of 1H-pyrrole-3-carbaldehyde (1.0 g, 10.52 mmol) and (E)-but-2-enedinitrile (1.03 g, 13.14 mmol) in THF (15 mL) at RT [slight exotherm to 30° C.—cooling was required]. The mixture was stirred for 5 h at RT. The mixture was evaporated in vacuo and the residue dissolved in DCE (10 mL). Boron trifluoride diethyl etherate (3.3 mL, 26.29 mmol) was then added and the mixture was heated at 90° C. overnight. The cooled mixture was partitioned between aq. sodium bicarbonate (30 mL) and EtOAc (3×50 mL). The combined organic extracts were washed with brine, dried (Na$_2$SO$_4$), and concentrated. The residue was purified by chromatography on silica (solvent gradient 0-80% EtOAc in cyclohexane) to afford the title compound (970 mg, 59%). LCMS (ESI) [M+H]$^+$ 158.1.

Step 2: 2-Bromo-N-(5-cyano-1H-indol-7-yl)acetamide

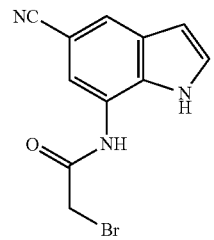 [SMILES: N#Cc1cc(NC(=O)CBr)c2[nH]ccc2c1]

Bromoacetyl bromide (0.64 mL, 7.37 mmol) was added dropwise to a solution of 7-amino-1H-indole-5-carbonitrile (965 mg, 6.14 mmol) and triethylamine (1.03 mL, 7.37 mmol) in DCM (15 mL) at 0° C. over 5 mins. The ice-bath was removed and the mixture stirred for 1 h. The mixture was diluted with DCM (30 mL) and washed with 1N HCl (30 mL), then with aq. sodium bicarbonate (30 mL). The organic extract was dried (Na$_2$SO$_4$) and concentrated to give the title compound (953 mg, 56%) as a buff colored solid (1.25 g). LCMS (ESI) [M+H]$^+$ 276.0/277.9.

Step 3: N-(5-Cyano-1H-indol-7-yl)-2-((2-hydroxyethyl)(methy)amino)acetamide

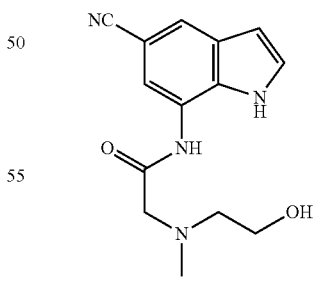

2-(Methylamino)ethanol (0.96 mL, 11.99 mmol) was added to a suspension of 2-bromo-N-(5-cyano-1H-indol-7-yl)acetamide (953 mg, 3.43 mmol) in EtOAc (15 mL). The reaction mixture was stirred at RT for 20 min, then was diluted with EtOAc (20 mL), washed with aq. sodium bicarbonate solution (2×20 mL), dried (Na$_2$SO$_4$), and concentrated. The residue was triturated under Et$_2$O (15 mL)

and filtered to give the title compound (809 mg, 87%) as a buff-colored solid. LCMS (ESI) [M+H]+ 273.2.

Step 4: 7-(4-Methyl-2-oxopiperazin-1-yl)-1H-indole-5-carbonitrile

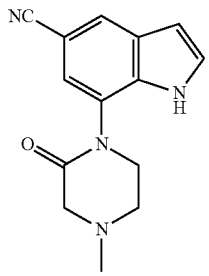 [SMILES: CN1CCN(c2cc(C#N)cc3cc[nH]c23)C(=O)C1]

Di-tert-butyl azodicarboxylate (744 mg, 3.23 mmol) was added portionwise to a suspension of N-(5-cyano-1H-indol-7-yl)-2-[2-hydroxyethyl(methyl)amino]acetamide (800 mg, 2.94 mmol) and tributylphosphine (0.81 mL, 3.23 mmol) in EtOAc (15 mL) at 0° C. over 5 mins. The ice-bath was removed and the homogeneous mixture was allowed to warm up to RT over 1 h, then was concentrated in vacuo. The residue was purified by chromatography on silica (solvent gradient 0-15% MeOH·NH₃ in DCM) to afford the title compound (725 mg, 97% yield) as a brown solid. LCMS (ESI) [M+H]+ 255.2.

Step 5: 3-Bromo-7-(4-methyl-2-oxopiperazin-1-yl)-1H-indole-5-carbonitrile

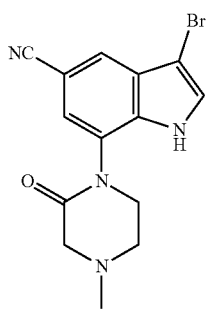 [SMILES: CN1CCN(c2cc(C#N)cc3c(Br)c[nH]c23)C(=O)C1]

NBS (558 mg, 3.14 mmol) was added portionwise to a solution of 7-(4-methyl-2-oxo-piperazin-1-yl)-1H-indole-5-carbonitrile (725 mg, 2.85 mmol) in DMF (15 mL) at RT. The reaction mixture was stirred for 1 h, then was partitioned between aq. NaOH (1N, 20 mL) and EtOAc (3×15 mL). The combined organic extracts were washed with brine (20 mL), dried (Na₂SO₄) and concentrated. The residue was triturated under Et₂O and filtered to give the title compound (512 mg, 54% yield) as a buff-colored solid. LCMS (ESI) [M+H]+ 333.0/335.0.

Step 6: 3-Bromo-7-(4-methyl-2-oxopiperazin-1-yl)-1-tosyl-1H-indole-5-carbonitrile

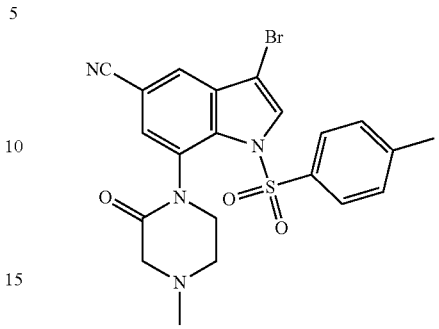

Sodium hydride (60% in oil, 74 mg, 1.84 mmol) was added portionwise to a solution of 3-bromo-7-(4-methyl-2-oxo-piperazin-1-yl)-1H-indole-5-carbonitrile (512 mg, 1.54 mmol). The mixture was stirred for 5 min at RT then 4-toluenesulfonyl chloride (322 mg, 1.69 mmol) was added. The reaction mixture was stirred for 1 h, then the reaction was quenched with aq. ammonium chloride and extracted with EtOAc (3×15 mL). The combined organic extracts were washed with brine (20 mL), dried (Na₂SO₄) and concentrated. The residue was triturated under Et₂O and filtered to give the title compound (555 mg, 74% yield) as a buff-colored solid. LCMS (ESI) [M+H]+ 487.0/489.0.

Example 120

N-(3-Bromo-5-cyano-1-methyl-1H-indol-7-yl)acetamide

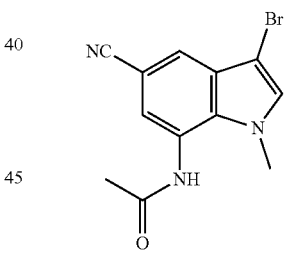

Step 1: N-(5-Cyano-1H-indol-7-yl)acetamide

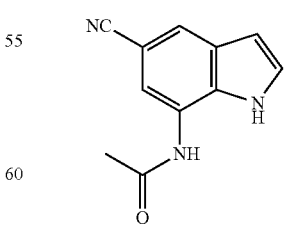

Acetyl chloride (0.11 mL, 1.53 mmol) was added dropwise to a solution of 7-amino-1H-indole-5-carbonitrile (200 mg, 1.27 mmol) and triethylamine (0.53 mL, 3.82 mmol) in DCM (5 mL). The reaction mixture was stirred for 10 min at RT, then was partitioned between water (10 mL) and DCM. The aqueous layer was extracted with further DCM. The combined organic extracts were washed with water (2×10 mL), dried (Na$_2$SO$_4$) and concentrated. The residue purified by chromatography on silica (solvent gradient 0-80% EtOAc in cyclohexane) to afford the title compound (207 mg, 81%). LCMS (ESI) [M+H]$^+$ 198.1.

Step 2: N-(5-Cyano-1-methyl-1H-indol-7-yl)acetamide and N-(5-cyano-1-methyl-1H-indol-7-yl)-N-methylacetamide

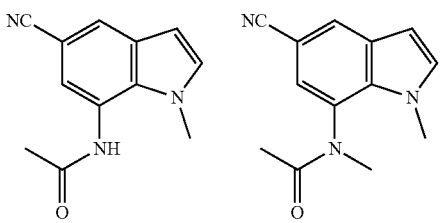 [SMILES: CC(=O)Nc1cc(C#N)cc2ccn(C)c12 ; CC(=O)N(C)c1cc(C#N)cc2ccn(C)c12]

Iodomethane (0.06 mL, 0.99 mmol) was added dropwise to a mixture of N-(5-cyano-1H-indol-7-yl)acetamide (198 mg, 0.990 mmol) and potassium carbonate (137 mg, 0.990 mmol) in DMF (0.5 mL). The reaction mixture was stirred at RT for 3 h, then was partitioned between water (10 mL) and EtOAc. The aqueous layer was extracted with further EtOAc. The combined organic extracts were washed with brine (20 mL), dried (Na$_2$SO$_4$) and concentrated. The residue was purified by chromatography on silica (solvent gradient 0-100% EtOAc in cyclohexane) to afford N-(5-cyano-1-methyl-indol-7-yl)acetamide (40.3 mg, 19%). LCMS (ESI) [M+H]$^+$ 214.3. Further fractions afforded N-(5-cyano-1-methyl-indol-7-yl)-N-methyl-acetamide (108 mg, 48%). LCMS (ESI) [M+H]$^+$ 228.2.

Step 3: N-(3-Bromo-5-cyano-1-methyl-1H-indol-7-yl)acetamide

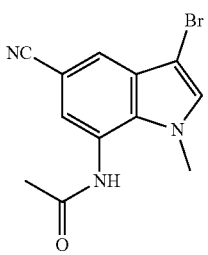 [SMILES: CC(=O)Nc1cc(C#N)cc2c(Br)cn(C)c12]

NBS (37 mg, 0.210 mmol) was added to a solution of N-(5-cyano-1-methyl-indol-7-yl)acetamide (40 mg, 0.190 mmol) in DMF (2 mL). The reaction mixture was stirred at RT for 30 min. Water (ca 5 mL) was added to the vigorously stirred mixture, resulting in formation of a precipitate. Filtration afforded the title compound (54 mg, 98%) as a colorless solid. LCMS (ESI) [M+H]$^+$ 292.0/294.0.

Example 121

N-(3-bromo-5-cyano-1H-indol-7-yl)-N-methylmethanesulfonamide and N-(3-bromo-5-cyano-1-methyl-1H-indol-7-yl)-N-methylmethanesulfonamide

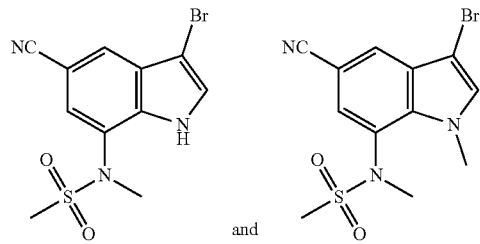 [SMILES: CN(c1cc(C#N)cc2c(Br)c[nH]c12)S(C)(=O)=O ; CN(c1cc(C#N)cc2c(Br)cn(C)c12)S(C)(=O)=O]

Step 1:
N-(5-Cyano-1H-indol-7-yl)methanesulfonamide

Methanesulfonyl chloride (0.12 mL, 1.53 mmol) was added dropwise to a mixture of 7-amino-1H-indole-5-carbonitrile (200 mg, 1.27 mmol) and triethylamine (0.2 mL, 1.53 mmol) in DCM (3 mL). The reaction mixture was stirred for 2 h at RT. Further triethylamine (0.2 mL, 1.53 mmol) and methanesulfonyl chloride (0.12 mL, 1.53 mmol) were added, and stirring was pursued for 15 min. The reaction mixture was diluted with DCM (15 mL) and filtered to give the title compound (163 mg, 54%) as a buff-colored solid. The filtrate was washed with water (2×15 mL), dried (Na$_2$SO$_4$), and concentrated to give a second crop of title compound (117 mg, 39%). LCMS (ESI) [M+H]$^+$ 234.0.

Step 2: N-(5-cyano-1H-indol-7-yl)-N-methylmethanesulfonamide and N-(5-cyano-1-methyl-1H-indol-7-yl)-N-methylmethanesulfonamide

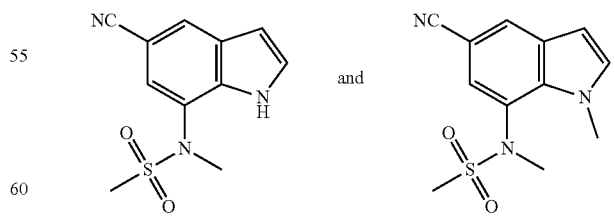

Iodomethane (0.05 mL, 0.830 mmol) was added dropwise to a mixture of N-(5-cyano-1H-indol-7-yl)methanesulfonamide (163 mg, 0.690 mmol) and potassium carbonate (287 mg, 2.08 mmol) in DMF (2 mL). The reaction mixture was stirred at RT for 18 h, then was partitioned between water (20 mL) and EtOAc. The aqueous layer was extracted with further EtOAc. The combined organic extracts were washed with water (2×15 mL), dried (Na$_2$SO$_4$) and concentrated. The residue was triturated under DCM (3 mL) and filtered to give a mixture of N-(5-cyano-1H-indol-7-yl)-N-methyl-methanesulfonamide and N-(5-cyano-1-methyl-1H-indol-7-yl)-N-methylmethanesulfonamide as a colorless solid (57 mg, 33%) LCMS (ESI) [M−H]$^-$ 248.0 and [M−H]$^-$ 234.0.

Step 3: N-(3-Bromo-5-cyano-1H-indol-7-yl)-N-methylmethanesulfonamide and N-(3-bromo-5-cyano-1-methyl-1H-indol-7-yl)-N-methylmethanesulfonamide

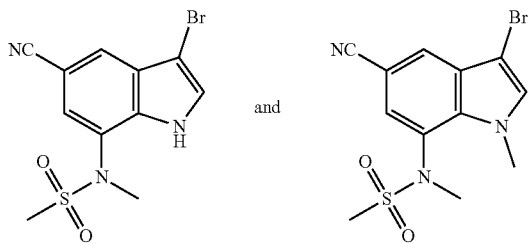 [SMILES: CN(c1cc(C#N)cc2c(Br)c[nH]c12)S(C)(=O)=O ; CN(c1cc(C#N)cc2c(Br)cn(C)c12)S(C)(=O)=O]

NBS (44 mg, 0.25 mmol) was added portionwise to a solution of a mixture of N-(5-cyano-1H-indol-7-yl)-N-methylmethanesulfonamide and N-(5-cyano-1-methyl-1H-indol-7-yl)-N-methylmethanesulfonamide (124 mg, 0.50 mmol) in DMF (1.5 mL). The reaction mixture was stirred at RT for 1 h, then was partitioned between water (10 mL) and EtOAc (3×10 mL). The combined organic extracts were washed with brine (30 mL), dried (Na$_2$SO$_4$) and concentrated to afford a mixture of N-(3-bromo-5-cyano-1H-indol-7-yl)-N-methylmethanesulfonamide and N-(3-bromo-5-cyano-1-methyl-1H-indol-7-yl)-N-methylmethanesulfonamide (150 mg, 92%) LCMS (ESI) [M−H]$^-$ 325.9/327.9 and [M−H]$^-$ 339.9/342.1.

Example 122

6-Fluoro-3-iodo-1H-indole-5-carbonitrile

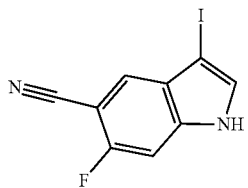 [SMILES: N#Cc1cc2c(I)c[nH]c2cc1F]

To a solution of 6-fluoro-1H-indole-5-carbonitrile (250 mg, 1.56 mmol) in MeOH (5.5 mL) was added sodium hydroxide (62 mg, 1.56 mmol) in water (0.27 mL), iodine (396 mg, 1.56 mmol), and potassium iodide (261 mg, 1.56 mmol) in water (80 μL). The reaction mixture was stirred at RT for 3 h, then poured onto ice with 10% aq. sodium metabisulfite. The precipitate was collected and washed with water, then co-evaporated with toluene, to give the title compound (421 ng, 91%) as a brown powder. LCMS (ESI) [M−H]$^-$ 285.0.

Example 123

5-Bromo-3-iodo-6-methyl-1H-indole

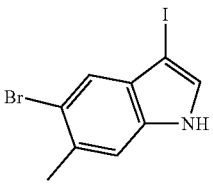

To a solution of 5-bromo-6-methyl-1H-indole (200 mg, 0.95 mmol) in MeOH (3 mL) was added sodium hydroxide (38 mg, 0.95 mmol) in water (0.5 mL), iodine (242 mg, 0.95 mmol) and potassium iodide (159 mg, 0.95 mmol) in water (1 mL). The reaction mixture was stirred at RT for 2 h, then poured onto ice with 10% aq. sodium metabisulfite. The precipitate was collected and washed with water, then co-evaporated with toluene, to give the title compound (320 mg, 100%) as a brown powder. $^1$H NMR (400 MHz, DMSO-d$_6$) δ ppm 11.57 (s, 1H), 7.53 (s, 1H), 7.43 (s, 1H), 7.41 (s, 1H), 2.44 (s, 3H).

Example 124 tert-Butyl 5'-(5-bromo-6-methyl-1H-indol-3-yl)spiro[cyclopropane-1,3'-pyrrolo[2,3-b]pyridine]-1'(2'H)-carboxylate

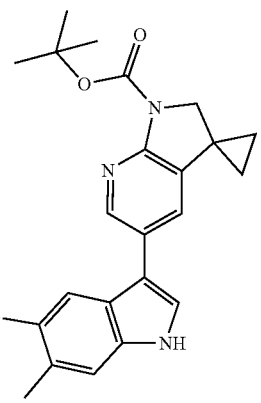

A degassed mixture of (1'-(tert-butoxycarbonyl)-1',2'-dihydrospiro[cyclopropane-1,3'-pyrrolo[2,3-b]pyridin]-5'-yl) boronic acid (80 mg, 0.28 mmol), [1,1'-bis(diphenylphosphino)ferrocene]dichloropalladium(II) complex with dichloromethane (11 mg, 0.01 mmol), cesium carbonate (1N aq., 0.55 mL, 0.55 mmol), 5-bromo-3-iodo-6-methyl-1H-indole (93 mg, 0.28 mmol) in 1,4-dioxane (2.5 mL) and water (0.5 mL) was heated at 50° C. for 2 h. The reaction mixture was diluted with EtOAc and washed with water. The aqueous layer was extracted with EtOAc. The combined organic extracts were dried (MgSO$_4$) and concentrated. The residue was purified by chromatography on silica (solvent gradient 0-50% EtOAc in cyclohexane) to afford the title compound (50 mg, 40%). LCMS (ESI) [M+H]$^+$ 454.2/456.1.

Example 125

5'-Bromo-1',2'-dihydrospiro[cyclopropane-1,3'-pyrrolo[2,3-b]pyridine]

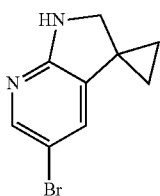 [SMILES: Brc1cnc2c(c1)C1(CC1)CN2]

Step 1: 5'-Bromospiro[cyclopropane-1,3'-pyrrolo[2,3-b]pyridin]-2'(1'H)-one

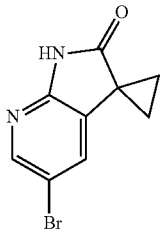 [SMILES: O=C1Nc2ncc(Br)cc2C12CC2]

To a solution of 5-bromo-1,3-dihydro-2H-pyrrolo[2,3-b]pyridin-2-one (10 g, 50 mmol) and di-isopropylamine (14.2 mL, 100 mmol) in THF (200 mL) at −30° C. was added dropwise n-BuLi (2.5N, 80 mL, 200 mmol) over 35 min. The reaction mixture was stirred at −30° C. for 10 min, then allowed to warm to 0° C., and treated with 1,2-dibromoethane (12.8 mL, 150 mmol). The reaction mixture was allowed to warm up to RT, then stirred for 16 h. The mixture was diluted with EtOAc and water. The organic extract was washed with brine, dried (Na$_2$SO$_4$) and concentrated. The residue was triturated with Et$_2$O, filtered and dried in vacuo, to afford the title compound (4.54 g, 36%) as a light brown solid. $^1$H NMR (400 MHz, DMSO-d$_6$) δ ppm 11.31 (s, 1H), 8.15 (d, J=2.3 Hz, 1H), 7.66 (d, J=2.3 Hz, 1H), 1.76-1.70 (m, 2H), 1.58-1.52 (m, 2H).

Step 2: 5'-Bromo-1',2'-dihydrospiro[cyclopropane-1,3'-pyrrolo[2,3-b]pyridine]

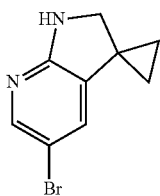

To a suspension of 5'-bromospiro[cyclopropane-1,3'-pyrrolo[2,3-b]pyridin]-2'(1'H)-one (4.34 g, 18.1 mmol) in DCM (90 mL) at 0° C. was added DIBAL (1N in DCM, 90 mL, 90 mmol) dropwise over 45 min. The reaction mixture was allowed to warm up to RT, stirred for 16 h, then cooled to 0° C. Water (30 mL) was added dropwise to the mixture, followed by EtOAc and solid sodium bicarbonate. The mixture was filtered and concentrated. The residue was purified by chromatography on silica (solvent gradient 1-4% MeOH in DCM), to afford the title compound (2.94 g, 72%) as an off-white solid. $^1$H NMR (400 MHz, DMSO-d$_6$) δ ppm 7.66 (d, J=2.2 Hz, 1H), 6.99 (d, J=2.0 Hz, 1H), 6.77 (s, 1H), 3.51 (d, J=1.2 Hz, 2H), 1.06-1.02 (m, 2H), 0.97-0.93 (m, 2H).

Example 126 tert-Butyl 5'-bromospiro[cyclopropane-1,3'-pyrrolo[2,3-b]pyridine]-1'(2'H)-carboxylate

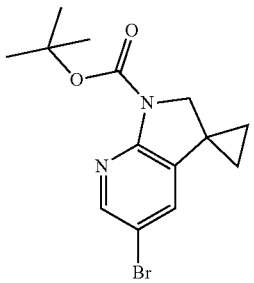 [SMILES: CC(C)(C)OC(=O)N1CC2(CC2)c2cc(Br)cnc21]

To a solution of 5'-bromo-1',2'-dihydrospiro[cyclopropane-1,3'-pyrrolo[2,3-b]pyridine] (1.63 g, 7.24 mmol) in THF (20 mL) were added DIPEA (1.7 mL, 9.78 mmol), 4-dimethylaminopyridine (0.88 g, 7.24 mmol) and di-tert-butyl dicarbonate (2.51 g, 11.5 mmol). The mixture was heated to 65° C. for 1.5 h, then was diluted with EtOAc and washed with water. The aqueous layer was extracted with EtOAc. The combined organic extracts were dried (MgSO$_4$) and concentrated. The residue was purified by chromatography on silica (solvent gradient 0-20% EtOAc in cyclohexane), to afford the title compound (2.16 g, 92%). $^1$H NMR (300 MHz, CDCl$_3$) δ ppm 8.20 (d, J=2.1 Hz, 1H), 6.95 (d, J=2.2 Hz, 1H), 3.96 (s, 2H), 1.55 (s, 9H), 1.10-1.07 (m, 4H).

Example 127

(1RS,2RS)-5'-chloro-2-methyl-1',2'-dihydrospiro[cyclopropane-1,3'-pyrrolo[2,3-b]pyridine]

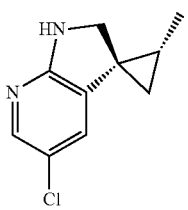

Step 1: 3-Bromo-5-chloro-N-(4-methoxybenzyl) pyridin-2-amine

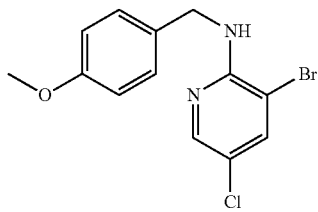 [SMILES: COc1ccc(CNc2ncc(Cl)cc2Br)cc1]

A mixture of 2-fluoro-3-bromo-5-chloropyridine (5.74 g; 27 28 mmol), 4-methoxybenzylamine (7.1 mL, 54.34 mmol) and DIPEA (5.6 mL, 43.92 mmol) in 2-propanol (30 mL) was heated in a microwave at 150° C. for 1 h. The cooled mixture was partitioned between EtOAc (200 mL) and aq. sodium bicarbonate (8%; 150 mL). The organic extract was washed with brine (150 mL), dried (Na$_2$SO$_4$) and concentrated. The residue was purified by chromatography on silica (solvent gradient 0-10% EtOAc in pentane), to afford the title compound (8.85 g, 99%) as a colorless oil which solidified on standing. LCMS (ESI) [M+H]$^+$ 327.0/330.9.

Step 2: N-(3-Bromo-5-chloropyridin-2-yl)-N-(4-methoxybenzyl)-2-methylcyclopropane-1-carboxamide

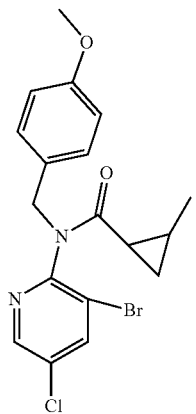 [SMILES: COc1ccc(CN(C(=O)C2CC2C)c2ncc(Cl)cc2Br)cc1]

To a solution of oxalyl bromide (0.28 mL, 3 mmol) in DCM (1.5 mL) was added 2-methylcyclopropane-1-carboxylic acid (0.292 mL, 3 mmol). The reaction mixture was stirred at RT for 1.25 h, then was treated with a solution of 3-bromo-5-chloro-N-(4-methoxybenzyl)pyridin-2-amine (354 mg, 2 mmol) and DIPEA (0.68 mL, 4 mmol) in DCM (1.5 mL). The reaction mixture was stirred at RT for 18 h, then was diluted with DCM and water. The aqueous layer was extracted with further DCM. The combined organic extracts were dried (MgSO$_4$) and concentrated. The residue was purified by chromatography on silica (solvent gradient 0-10% EtOAc in cyclohexane) to afford the title compound (0.49 g, 59%) as a white solid. LCMS (ESI) [M+Na]$^+$ 431/433.

Step 3: (1RS,2RS)-5'-Chloro-1'-(4-methoxybenzyl)-2-methylspiro[cyclopropane-1,3'-pyrrolo[2,3-b]pyridin]-2'(1'H)-one and (1RS,2SR)-5'-Chloro-1'-(4-methoxybenzyl)-2-methylspiro[cyclopropane-1,3'-pyrrolo[2,3-b]pyrdin]-2'(1'H)-one

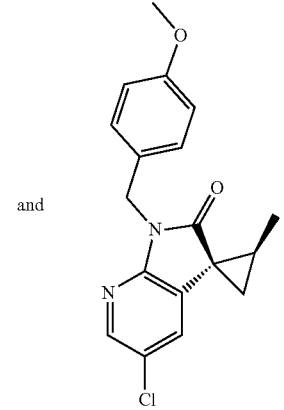

A degassed mixture of N-(3-bromo-5-chloropyridin-2-yl)-N-(4-methoxybenzyl)-2-methylcyclopropane-1-carboxamide (120 mg, 0.287 mmol), tricyclohexylphosphine (8 mg, 0.058 mmol), palladium(II) acetate (6.5 mg, 0.028 mmol), silver phosphate (40 mg, 0.096 mmol) and potassium carbonate (79 mg, 0.574 mmol) in toluene (0.7 mL) was heated at 130° C. in a sealed tube for 3.5 h. The reaction mixture was diluted with EtOAc and water. The aqueous layer was extracted with further EtOAc. The combined organic extracts were dried (MgSO$_4$) and concentrated. The residue was purified by chromatography on silica (solvent gradient 0-20% EtOAc in cyclohexane), to afford (1RS,2RS)-5'-chloro-1'-(4-methoxybenzyl)-2-methylspiro[cyclopropane-1,3'-pyrrolo[2,3-b]pyridin]-2'(1'H)-one (60 mg, 64%) as a clear oil and (1RS,2SR)-5'-chloro-1'-(4-methoxybenzyl)-2-methylspiro[cyclopropane-1,3'-pyrrolo[2,3-b]pyridin]-2'(1'H)-one (20 mg, 21%) as a clear oil. LCMS (ESI) [M+H]$^+$ 329.1.

Step 4: (1RS,2RS)-5'-Chloro-2-methyl-1',2'-dihydrospiro[cyclopropane-1,3'-pyrrolo[2,3-b]pyridine]

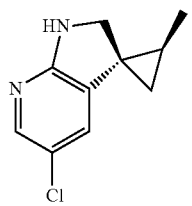

A solution of (1RS,2RS)-5'-chloro-1'-(4-methoxybenzyl)-2-methylspiro[cyclopropane-1,3'-pyrrolo[2,3-b]pyridin]-2'(1'H)-one (470 mg, 1.43 mmol) and borane dimethyl sulfide complex (0.271 mL, 2.88 mmol) in THF (3 mL) was heated at 70° C. for 5 h. The reaction mixture was concentrated. The residue was dissolved in TFA (3 mL) and water (1 drop), and the reaction mixture was heated at 80° C. for 18 h in a sealed vial. The reaction mixture was diluted with EtOAc and sat. aq. sodium bicarbonate. The aqueous layer was extracted with further EtOAc. The combined organic extracts were dried (MgSO₄) and concentrated. The residue was purified by chromatography on silica (solvent gradient 0-50% EtOAc in cyclohexane) to afford the title compound (236 mg, 85%) as a white solid. LCMS (ESI) [M+H]⁺ 195.2.

Example 128

(1RS,2SR)-5'-chloro-2-methyl-1',2'-dihydrospiro[cyclopropane-1,3'-pyrrolo[2,3-b]pyridine]

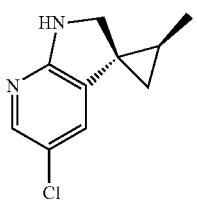

The title compound was prepared in a similar manner as described for (1RS,2RS)-5'-chloro-2-methyl-1',2'-dihydrospiro[cyclopropane-1,3'-pyrrolo[2,3-b]pyridine](step 4 above) starting from (1RS,2SR)-5'-chloro-1'-(4-methoxybenzyl)-2-methylspiro[cyclopropane-1,3'-pyrrolo[2,3-b]pyridin]-2'(1'H)-one. LCMS (ESI) [M+H]⁺ 195.2.

Example 129

5'-Bromo-2,2-dimethyl-1',2'-dihydrospiro[cyclopropane-1,3'-pyrrolo[2,3-b]pyridine]

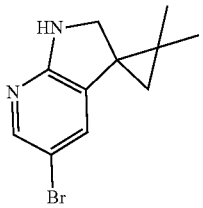

Step 1: 3-(Propan-2-ylidene)-1,3-dihydro-2H-pyrrolo[2,3-b]pyridin-2-one

A mixture of 1,3-dihydro-2H-pyrrolo[2,3-b]pyridin-2-one (1.0 g, 7.5 mmol), piperidine (4 mL, 40.5 mmol) and acetone (10 mL) in MeOH (10 mL) was stirred at 40° C. for 3 h. The mixture was evaporated and the residue azeotroped with toluene. The residue was dried under high vacuum to give the title compound (1.3 g, 100%). LCMS (ESI) [M+H]⁺ 175.1.

Step 2: 2,2-Dimethylspiro[cyclopropane-1,3'-pyrrolo[2,3-b]pyridin]-2'(1'H)-one

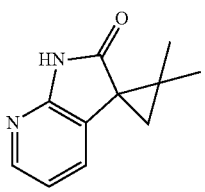

Sodium hydride (60% in oil, 388 mg, 9.7 mmol) was added portion wise to a solution of trimethylsulphoxonium iodide (1.8 g, 8.2 mmol) in DMSO (20 mL). The reaction mixture was stirred at RT for 30 min. 3-(Propan-2-ylidene)-1,3-dihydro-2H-pyrrolo[2,3-b]pyridin-2-one (1.3 g, 7.5 mmol) was added portionwise over 5 min, and the mixture was stirred for 18 h. The mixture was quenched with sat. aq. ammonium chloride (150 mL), and extracted with EtOAc (2×100 mL). The combined organic extracts were washed with brine (30 mL), dried (Na₂SO₄) and concentrated. The residue was purified by chromatography on silica (solvent gradient 0-10% MeOH·NH₃ in DCM), to afford the title compound (1.17 g, 83%). LCMS (ESI) [M+H]⁺ 189.1.

Step 3: 5'-Bromo-2,2-dimethylspiro[cyclopropane-1,3'-pyrrolo[2,3-b]pyridin]-2'(1'H)-one

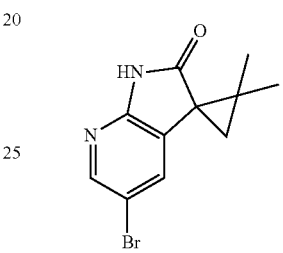

NBS (1.11 g, 6.2 mmol) was added portionwise to a solution of 2,2-dimethylspiro[cyclopropane-1,3'-pyrrolo[2,3-b]pyridin]-2'(1'H)-one (1.17 g, 6.2 mmol) in dry DMF (19 mL). The reaction mixture was stirred for 64 h at RT, then was partitioned between EtOAc and water (200 mL). The aqueous layer was extracted with further EtOAc. The combined organic extracts were washed with brine (50 mL), dried (Na₂SO₄) and concentrated. The residue was purified by chromatography on silica (solvent gradient 0-70% EtOAc in cyclohexane), to afford the title compound (1.18 g, 71%) as an off-white solid. LCMS (ESI) [M+H]⁺ 267.0/269.0.

Step 4: 5'-Bromo-2,2-dimethyl-1',2'-dihydrospiro[cyclopropane-1,3'-pyrrolo[2,3-b]pyridine]

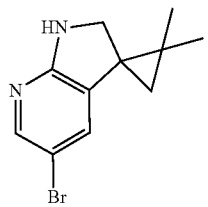

DIBAL (1N in DCM; 2.8 mL, 2.8 mmol) was added dropwise to a suspension of 5'-bromo-2,2-dimethylspiro[cyclopropane-1,3'-pyrrolo[2,3-b]pyridin]-2'(1'H)-one (150 mg, 0.56 mmol) in dry DCM (2.8 mL) at 0° C. The reaction mixture was stirred for 5 h at RT, then was quenched with aq. Rochelle salt (25 mL) and extracted with DCM (25 mL). The organic extract was dried (Na₂SO₄) and concentrated. The residue was purified by chromatography on silica (solvent gradient 0-20% DCM·NH₃ in EtOAc), to afford the title compound (32 mg, 23%) as an off-white solid. LCMS (ESI) [M+H]⁺ 253.1/255.0.

Example 130

5'-Chloro-2'-methyl-1',2'-dihydrospiro[cyclopropane-1,3'-pyrrolo[2,3-b]pyridine]

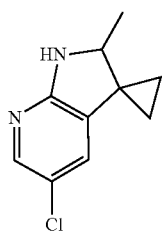

Step 1: 2-(5-Chloro-2-(trimethylsilyl)-1H-pyrrolo[2,3-b]pyridin-3-yl)ethan-1-ol

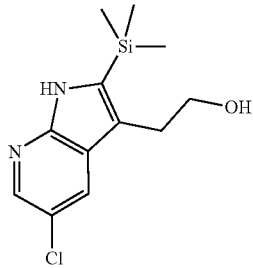 [SMILES: C[Si](C)(C)c1[nH]c2ncc(Cl)cc2c1CCO]

A degassed mixture of 5-chloro-3-iodopyridin-2-amine (3.11 g, 12.24 mmol), 4-(trimethylsilyl)but-3-yn-1-ol (7.72 mL, 36.79 mmol), [1,1'-bis(diphenylphosphino)ferrocene]dichloropalladium(II) complex with DCM (503 mg, 0.62 mmol), lithium chloride (520 mg, 12.4 mmol) and sodium carbonate (2.6 g, 24.4 mmol) in DMF (90 mL) was heated at 100° C. for 18 h. The cooled reaction mixture was concentrated, then diluted with EtOAc and water. The aqueous layer was further extracted with EtOAc. The combined organic extracts were washed with brine, dried (Na$_2$SO$_4$) and concentrated. The residue was purified by chromatography on silica (solvent gradient 0-20% EtOAc in cyclohexane) to afford the title compound (3.35 g, 88%) as a brown oil. LCMS (ESI) [M+H]$^+$ 311.1.

Step 2: 2-(5-Chloro-1H-pyrrolo[2,3-b]pyridin-3-yl)ethan-1-ol

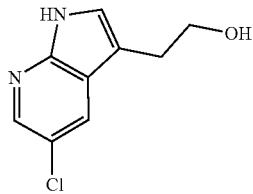 [SMILES: OCCc1c[nH]c2ncc(Cl)cc12]

A solution of 2-(5-chloro-2-(trimethylsilyl)-1H-pyrrolo[2,3-b]pyridin-3-yl)ethan-1-ol (3.35 g, 10.8 mmol) in TBAF (1N in THF, 30 mL, 30 mmol) was stirred at RT for 18 h. The solvent was evaporated, and the residue diluted with EtOAc and water. The aqueous layer was further extracted with EtOAc. The combined organic extracts were washed with brine, dried (Na$_2$SO$_4$) and concentrated. The residue was purified by chromatography on silica (solvent gradient 50-100% EtOAc in cyclohexane) to afford the title compound (1.54 g, 73%). LCMS (ESI) [M+H]$^+$ 197.2.

Step 3: 3-(2-Bromoethyl)-5-chloro-1H-pyrrolo[2,3-b]pyridine

To a solution of 2-(5-chloro-1H-pyrrolo[2,3-b]pyridin-3-yl)ethan-1-ol (1.1 g, 5.61 mmol) in DCM (30 mL) cooled to 0° C., were added triphenylphosphine (1.62 g, 6.17 mmol) and carbon tetrabromide (2.04 g, 6.17 mmol). The reaction mixture was stirred at 0° C. for 3.5 h then at RT for 3 h, then concentrated. The residue was purified by chromatography on silica (solvent gradient 0-50% EtOAc in cyclohexane) to afford the title compound (1.25 g, 86%). LCMS (ESI) [M+H]$^+$ 259.2/261.2.

Step 4: 5'-Chlorospiro[cyclopropane-1,3'-pyrrolo[2,3-b]pyridine]

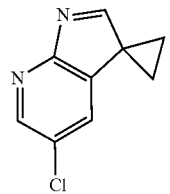 [SMILES: Clc1cnc2c(c1)C1(C=N2)CC1]

To a solution of 3-(2-bromoethyl)-5-chloro-1H-pyrrolo[2,3-b]pyridine (942 mg, 3.67 mmol) in MeCN/THF (1:1, 30 mL) was added 2-tert-butylimino-2-diethylamino-1,3-dimethylperhydro-1,3,2-diazaphosphorine-polymer-bound (1.88 g, 4.14 mmol). The reaction mixture was stirred at RT for 3.5 h, then was filtered through Celite, washed with MeCN/THF (1:1) and concentrated. The residue was dried in vacuo to afford the title compound (678 mg, 100%). LCMS (ESI) [M+H+H$_2$O]$^+$ 197.1. $^1$H NMR (400 MHz, DMSO-d$_6$) δ ppm 8.43 (d, J=2.4 Hz, 1H), 8.40 (s, 1H), 7.93 (d, J=2.4 Hz, 1H), 2.23-2.20 (m, 2H), 2.11-2.07 (m, 2H).

Step 5: 5'-Chloro-2'-methyl-1',2'-dihydrospiro[cyclopropane-1,3'-pyrrolo[2,3-b]pyridine]

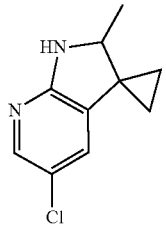

To a solution of 5'-chlorospiro[cyclopropane-1,3'-pyrrolo[2,3-b]pyridine](470 mg, 2.64 mmol) in toluene (10 mL), previously stirred with 4 Å molecular sieves for 16 h, were added successively cuprous chloride (47 mg, 0.47 mmol) and methyl magnesium bromide (3N in $Et_2O$, 4.4 mL, 13.2 mmol) dropwise. The reaction mixture was stirred at 120° C. for 3 h, then cooled to 0° C. and quenched with aq. sat. ammonium chloride. The mixture was diluted with EtOAc and water. The aqueous layer was extracted with further EtOAc. The combined organic extracts were dried ($Na_2SO_4$), and concentrated. The residue was purified by chromatography on silica (solvent gradient 0-50% EtOAc in cyclohexane) to afford the title compound (259 mg, 51%). LCMS (ESI) [M+H]$^+$ 195.

Example 131

(1'-(tert-Butoxycarbonyl)-1',2'-dihydrospiro[cyclopropane-1,3'-pyrrolo[2,3-b]pyridin-5'-yl)boronic Acid

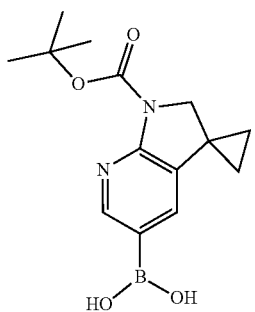 [SMILES: CC(C)(C)OC(=O)N1CC2(CC2)c2cc(B(O)O)cnc21]

A degassed mixture of tert-butyl 5'-bromospiro[cyclopropane-1,3'-pyrrolo[2,3-b]pyridine]-1'(2'H)-carboxylate (500 mg, 1.54 mmol), bis(pinacolato)diboron (683 mg, 2.69 mmol), potassium acetate (0.24 mL, 3.84 mmol) and [1,1'-bis(diphenylphosphino)ferrocene]dichloropalladium(II) complex with dichloromethane (125 mg, 0.15 mmol) in 1,4-dioxane (5 mL) was heated in a sealed tube at 80° C. for 20 h. The reaction mixture was filtered through a pad of celite and the solvent was evaporated in vacuo. The residue was purified by chromatography on a C18 cartridge (solvent gradient 5-80% $CH_3CN$ in water with 0.1% $NH_4OH$) to afford the title compound (438 mg, 98%) as a white fluffy solid. LCMS (ESI) [M+H]$^+$ 291.1.

Example 132

(1r,4r)-5'-Bromo-1',2'-dihydrospiro[cyclohexane-1,3'-pyrrolo[2,3-b]pyridin]-4-ol and (1s,4s)-5'-bromo-1',2'-dihydrospiro[cyclohexane-1,3'-pyrrolo[2,3-b]pyridin]-4-ol

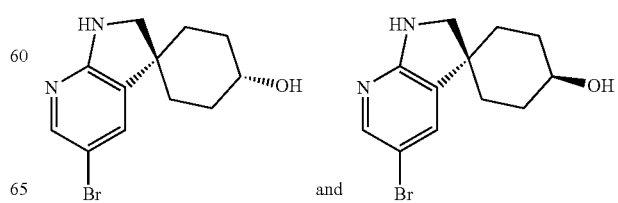

Step 1: 5'-Bromospiro[cyclohexane-1,3'-pyrrolo[2,3-b]pyridine]-2',4(1'H)-dione Potassium tert-butoxide (14.2 mg, 0.126 mmol) was added to a suspension of 5-bromo-1,3-dihydro-2H-pyrrolo[2,3-b]pyridin-2-one (0.408 g, 1.92 mmol) in DMSO (2 mL). After stirring at RT for 10 min the mixture was heated to 45° C. and methyl acrylate (0.535 mL, 5.94 mmol) was added dropwise over 1 h. Stirring was continued at 45° C. for 1 h, then potassium tert-butoxide (0.666 g, 5.94 mmol) was added portionwise over 30 min at 45° C. The mixture was then heated at 100° C. for 20 min, then cooled to 20° C. Water (10 mL) was added and the mixture stirred at 85° C. for 30 min. After cooling to RT the reaction mixture was partitioned between EtOAc and water. The aqueous phase was extracted with more EtOAc and the combined organic extracts were washed with water, brine, dried ($Na_2SO_4$) and evaporated. The residue was purified by chromatography on silica (solvent gradient 30-100% EtOAc in cyclohexane) to afford the title compound (0.252 g, 45%) as a colorless solid. LCMS (ESI) [M+H]$^+$ 295/297.

Step 2: (1r,4r)-5'-Bromo-1',2'-dihydrospiro[cyclohexane-1,3'-pyrrolo[2,3-b]pyridin]-4-ol and (1s,4s)-5'-bromo-1',2'-dihydrospiro[cyclohexane-1,3'-pyrrolo[2,3-b]pyridin]-4-ol To an ice-cooled suspension of 5'-bromospiro[cyclohexane-1,3'-pyrrolo[2,3-b]pyridine]-2',4(1'H)-dione (0.25 g, 0.85 mmol) in DCM (3 mL) was added DIBAL (1M in DCM, 5.93 mL, 5.93 mmol) over 5 min. The mixture was stirred in the ice bath for 20 min, then at RT for 3 h. More DIBAL (1M in DCM, 2.0 mL, 2.0 mmol) was added and stirring continued at RT for 1 h. The reaction mixture was cooled in an ice bath and MeOH (3 mL) was added dropwise. The mixture was diluted with DCM, washed with sat. aq. potassium sodium tartrate, then water, dried (Na$_2$SO$_4$) and evaporated. The residue was purified by chromatography on silica (solvent gradient 50-100% EtOAc in cyclohexane, then 50-100% MeOAc in EtOAc, then 5-10% MeOH in MeOAc) to afford (1r,4r)-5'-bromo-1',2'-dihydrospiro[cyclohexane-1,3'-pyrrolo[2,3-b]pyridin]-4-ol (0.0554 g, 23%) as a colorless gum. LCMS (ESI) [M+H]$^+$ 283/285. Later fractions gave (1s,4s)-5'-bromo-1',2'-dihydrospiro[cyclohexane-1,3'-pyrrolo[2,3-b]pyridin]-4-ol (0.0821 g, 34%) as a white solid. LCMS (ESI) [M+H]$^+$ 283/285.

Example 133

5'-Bromo-4'-chloro-1',2'-dihydrospiro[cyclohexane-1,3'-pyrrolo[2,3-b]pyridine]

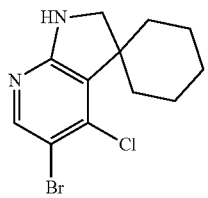 [SMILES: Clc1c(Br)cnc2c1C1(CCCCC1)CN2]

Step 1: 5'-Bromo-4'-chloro-1'-((2-(trimethylsilyl)ethoxy)methyl)spiro[cyclohexane-1,3'-pyrrolo[2,3-b]pyridine]-2" (1'H)-one

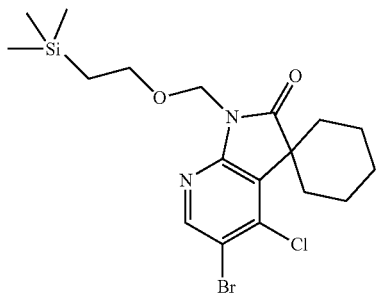 [SMILES: C[Si](C)(C)CCOCN1C(=O)C2(CCCCC2)c2c1ncc(Br)c2Cl]

Sodium hydride (60% in oil, 0.0617 g, 1.54 mmol) was added over 5 min. to an ice-cooled solution of 5-bromo-4-chloro-1-((2-(trimethylsilyl)ethoxy)methyl)-1,3-dihydro-2H-pyrrolo[2,3-b]pyridine-2-one (0.265 g, 0.70 mmol) and 1,5-dibromopentane (0.11 mL, 0.84 mmol) in DMF (3 mL). The mixture was stirred at RT for 5 h then quenched with aq. sat. ammonium chloride. The mixture was diluted with water and extracted twice with EtOAc. The combined organic extracts were washed with water, brine, dried (Na$_2$SO$_4$) and evaporated. The residue was purified by chromatography on silica (solvent gradient 2-10% EtOAc in cyclohexane) to afford the title compound (0.186 g, 59%) as a colorless gum. LCMS (ESI) [M−57]$^+$ 387/389/391.

Step 2: 5'-Bromo-4'-chlorospiro[cyclohexane-1,3'-pyrrolo[2,3-b]pyridine]-2'(1'H)-one

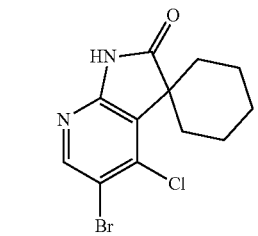 [SMILES: O=C1Nc2ncc(Br)c(Cl)c2C12CCCCC2]

To a solution of 5'-bromo-4'-chloro-1'-((2-(trimethylsilyl)ethoxy)methyl)spiro[cyclohexane-1,3'-pyrrolo[2,3-b]pyridine]-2'(1'H)-one (0.186 g, 0.42 mmol) in DCM (5 mL) was added TFA (3 mL). The mixture was stirred at RT for 16 h then toluene was added and evaporated (2×). The residue was dissolved in MeOH (2 mL) and 2N NH$_3$ in MeOH (5 mL) and concentrated aqueous NH$_3$ (5 mL) were added. The reaction mixture was stirred at RT for 4 h, then was concentrated and partitioned between EtOAc and water. The aqueous phase was extracted with more EtOAc and the combined organic extracts were washed with brine, dried (Na$_2$SO$_4$) and evaporated. The residue was purified by chromatography on silica (solvent gradient 10-50% EtOAc in cyclohexane) to afford the title compound (0.0927 g, 70%) as a colorless solid. LCMS (ESI) [M+H]$^+$ 315/315/319.

Step 3: 5'-Bromo-4'-chloro-1',2'-dihydrospiro[cyclohexane-1,3'-pyrrolo[2,3-b]pyridine]

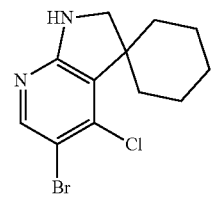

DIBAL (1M in DCM, 2.94 mL, 2.94 mmol) was added over 15 min to an ice-cooled suspension of 5'-bromo-4'-chlorospiro[cyclohexane-1,3'-pyrrolo[2,3-b]pyridine]-2'(1'H)-one (0.116 g, 0.37 mmol) in DCM (3 mL). The mixture was stirred at RT for 2 h then cooled in an ice bath. Water (0.11 mL), 15% NaOH (0.11 mL) and water (0.3 mL) were added successively. The mixture was stirred at RT for 1 h. then celite and Na$_2$SO$_4$ were added. Stirring was continued for 30 min. The solution was filtered through celite and evaporated. The residue was purified by chromatography on silica (solvent gradient 20-40% EtOAc in cyclohexane) to afford the title compound (0.0697 g, 63%) as a colorless solid. LCMS (ESI) [M+H]$^+$ 301/303/305.

Example 134

5'-Bromo-4'-chloro-1',2'-dihydrospiro[cyclohexane-1,3'-pyrrolo[2,3-b]pyridine]-4-carboxylic acid

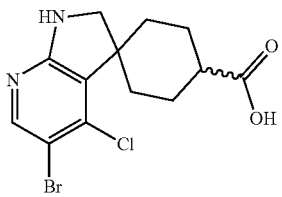 [SMILES: O=C(O)C1CCC2(CC1)CNc1ncc(Br)c(Cl)c12]

Step 1: tert-Butyl 5-bromo-4-chloro-3,3-bis(2-hydroxyethyl)-2,3-dihydro-1H-pyrrolo[2,3-b]pyridine-1-carboxylate

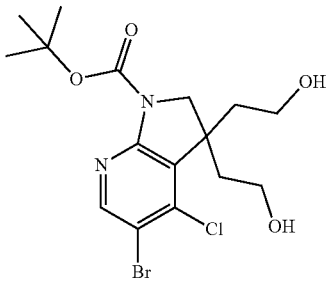 [SMILES: CC(C)(C)OC(=O)N1CC(CCO)(CCO)c2c1ncc(Br)c2Cl]

Ozone was passed into a solution of tert-butyl 5'-bromo-4'-chlorospiro[cyclopentane-1,3'-pyrrolo[2,3-b]pyridine]-3-ene-1'(2'H)-carboxylate (3.0 g, 7.78 mmol) in DCM (20 mL) and MeOH (65 mL) at −78° C. for 1.5 h. Air, then nitrogen, was passed through the solution. Sodium borohydride (1.47 g, 38.9 mmol) was then added portionwise over 10 min at −78° C. The reaction mixture was allowed to warm to −15° C. when more sodium borohydride (0.3 g, 7.9 mmol) was added. Warming was continued to RT when more sodium borohydride (0.3 g, 7.9 mmol) was added. Stirring was continued for a further 30 min at RT. The reaction mixture was cooled in an ice bath and sat.aq. sodium carbonate (50 g in 55 mL water) was added. The mixture was stirred at RT for 10 min, then concentrated. The residual suspension was extracted with EtOAc (2×). The combined extracts were washed with water, brine, dried (Na$_2$SO$_4$) and evaporated. The residue was purified by chromatography on silica (solvent gradient 50-100% EtOAc in DCM, then MeOAc) to afford the title compound (2.754 g, 84%) as white solid. LCMS (ESI) [M+H−$^t$Bu]$^+$ 365/367/369.

Step 2: tert-Butyl 5-bromo-4-chloro-3,3-bis(2-iodoethyl)-2,3-dihydro-1H-pyrrolo[2,3-b]pyridine-1-carboxylate

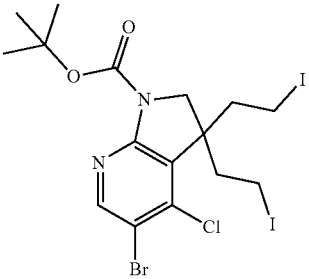 [SMILES: CC(C)(C)OC(=O)N1CC(CCI)(CCI)c2c1ncc(Br)c2Cl]

Methanesulfonyl chloride (1.11 mL, 14.36 mmol) was added over 15 min to an ice-cooled mixture of ter t-butyl 5-bromo-4-chloro-3,3-bis(2-hydroxyethyl)-2,3-dihydro-1H-pyrrolo[2,3-b]pyridine-1-carboxylate (2.75 g, 6.53 mmol) and triethylamine (2.18 mL, 15.67 mmol) in DCM (50 mL). The mixture was stirred at RT for 1.5 h then diluted with DCM, washed successively with 1M HCl, water and aq. sodium bicarbonate, dried (Na$_2$SO$_4$), and evaporated to give crude tert-butyl 5-bromo-4-chloro-3,3-bis(2-methylsulfonyloxyethyl)-2,3-dihydro-1H-pyrrolo[2,3-b]pyridine-1-carboxylate (4.02 g, quantitative) as a colorless foam. LCMS (ESI) [M+Na]$^+$ 599/601/603. This was dissolved in acetone (65 mL) and sodium iodide (4.89 g, 32.6 mmol) was added. The mixture was heated under reflux for 3 h. The cooled reaction mixture was filtered, the solid was washed with acetone and the filtrate concentrated. The residue was taken up in DCM, washed successively with water, aq. sodium thiosulfate, water, dried (Na$_2$SO$_4$) and evaporated to give the title compound (4.16 g, 99%) as a colorless solid. LCMS (ESI) [M+Na]$^+$ 663/665/667.

Step 3: Di-tert-butyl 5'-bromo-4'-chloro-4-cyanospiro[cyclohexane-1,3'-pyrrolo[2,3-b]pyridine]-1',4(2'H)-dicarboxylate

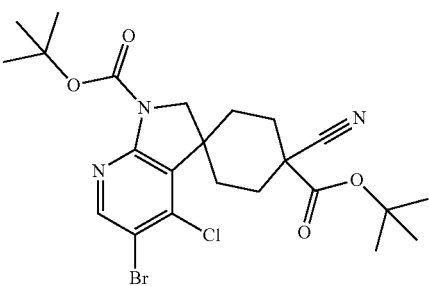 [SMILES: CC(C)(C)OC(=O)N1CC2(CCC(C#N)(C(=O)OC(C)(C)C)CC2)c2c1ncc(Br)c2Cl]

To a suspension of tert-butyl 5-bromo-4-chloro-3,3-bis(2-iodoethyl)-2,3-dihydro-1H-pyrrolo[2,3-b]pyridine-1-carboxylate (1.544 g, 2.41 mmol) in DMF (15 mL) was added tert-butyl cyanoacetate (0.407 g, 2.89 mmol). Sodium hydride (60% in oil, 0.211 g, 5.3 mmol) was added portionwise over 15 min. The mixture was stirred at RT for 1 h then poured into EtOAc and aq. ammonium chloride. The aqueous phase was extracted with more EtOAc and the combined extracts were washed with water, brine, dried (Na$_2$SO$_4$) and evaporated. The residue was purified by chromatography on silica (solvent gradient 5-25% EtOAc in cyclohexane) to afford the title compound (1.054 g, 83%) as a colorless solid. LCMS (ESI) [M+Na]⁺ 548/550/552.

Step 4: 5'-Bromo-4'-chloro-1',2'-dihydrospiro[cyclohexane-1,3'-pyrrolo[2,3-b]pyridine]-4-carboxylic Acid

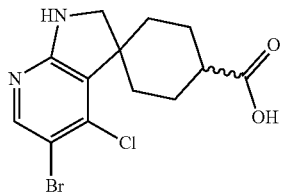 [SMILES: O=C(O)C1CCC2(CC1)CNc1ncc(Br)c(Cl)c12]

A mixture of di-tert-butyl 5'-bromo-4'-chloro-4-cyanospiro[cyclohexane-1,3'-pyrrolo[2,3-b]pyridine]-1',4(2'H)-dicarboxylate (0.974. g, 1.85 mmol), dioxane (4 mL) and HCl (6M aq., 14 mL) was stirred on a hotplate at 100° C. for 20 min, then heated at 150° C. under microwave irradiation for 1 h. The cooled reaction mixture was evaporated and the residue on SCX-2 cartridge (eluting with aq. MeCN, MeCN, 5% NH₃ in MeCN, 1N MeOH·NH₃) to afford the title compound as a mixture of isomers (0.639 g, quantitative). LCMS (ESI) [M+H]⁺ 345/347/349.

Example 135

(1r,4r)-5'-Bromo-4'-chloro-1',2"-dihydrospiro[cyclohexane-1,3'-pyrrolo[2,3-b]pyrdine]-4-carboxamide and (1 s,4s)-5'-bromo-4'-chloro-1',2'-dihydrospiro [cyclohexane-1,3'-pyrrolo[2,3-b]pyridine]-4-carboxamide

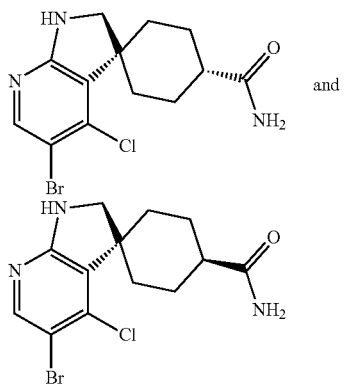

To a solution of 5'-bromo-4'-chloro-1',2'-dihydrospiro[cyclohexane-1,3'-pyrrolo[2,3-b]pyridine]-4-carboxylic acid (0.291 g, 0.84 mmol) in DMF (3 mL) was added ammonium chloride (0.09 g, 1.68 mmol) and DIPEA (0.73 mL, 4.21 mmol). HATU (0.48 g, 1.26 mmol) was added portionwise over 5 min. The mixture was stirred at RT for 20 min, then partitioned between EtOAc and aq. sodium bicarbonate. The aqueous phase was extracted with more EtOAc and the combined organic extracts were washed with water, then brine, and evaporated. The residue was purified by chromatography on silica (solvent gradient 2-20% MeOH·NH₃ in DCM) to afford (1r,4r)-5'-bromo-4'-chloro-1',2'-dihydrospiro[cyclohexane-1,3'-pyrrolo[2,3-b]pyridine]-4-carboxamide (0.10 g, 34%) as a colorless solid. LCMS (ESI) [M+H]⁺ 344/346/348. Later fractions gave (1s,4s)-5'-bromo-4'-chloro-1',2'-dihydrospiro[cyclohexane-1,3'-pyrrolo[2,3-b]pyridine]-4-carboxamide (0.17 g, 59%) as a colorless solid. LCMS (ESI) [M+H]⁺ 344/346/348.

Example 136

(1r,4r)-5'-Bromo-4'-chloro-1',2'-dihydrospiro[cyclohexane-1,3'-pyrrolo[2,3-b]pyridine]-4-carbonitrile

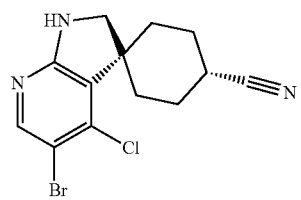

To a suspension of (1r,4r)-5'-bromo-4'-chloro-1',2'-dihydrospiro[cyclohexane-1,3'-pyrrolo[2,3-b]pyridine]-4-carboxamide (0.10 g, 0.29 mmol) in DCM (7 mL) was added triethylamine (0.2 mL, 1.45 mmol). The mixture was cooled to −20° C. and trifluoroacetic anhydride (0.1 mL, 0.72 mmol) was added over 5 min. The resulting solution was allowed to warm to 5° C. over 30 min, then diluted with DCM, washed with water, dried (Na₂SO₄) and evaporated. The residue was dissolved in MeOH (5 mL). MeOH·NH₃ (5 mL) was added and the mixture stirred for 10 min, then evaporated to dryness. The residue was purified by chromatography on silica (solvent gradient 1-4% MeOH·NH₃ in DCM) to afford the title compound (0.086 g, 91%) as a colorless solid. LCMS (ESI) [M+H]⁺ 326/328/330.

Example 137

(1s,4s)-5'-Bromo-4'-chloro-1',2'-dihydrospiro[cyclohexane-1,3'-pyrrolo[2,3-b]pyridine]-4-carbonitrile

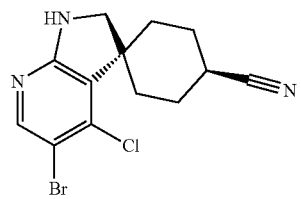

The title compound was prepared in an analogous manner as that described for (1r,4r)-5'-bromo-4'-chloro-1',2'-dihydrospiro[cyclohexane-1,3'-pyrrolo[2,3-b]pyridine]-4-carbonitrile, starting from (1s,4s)-5'-bromo-4'-chloro-1',2'-dihydrospiro[cyclohexane-1,3'-pyrrolo[2,3-b]pyridine]-4-carboxamide. LCMS (ESI) [M+H]⁺ 326/328/330.

Example 138

(1r,4r)-5'-Bromo-4'-chloro-4-methyl-1',2'-dihydrospiro[cyclohexane-1,3'-pyrrolo[2,3-b]pyridine]-4-carbonitrile and (1s,4s)-5'-bromo-4'-chloro-4-methyl-1',2'-dihydrospiro[cyclohexane-1,3'-pyrrolo[2,3-b]pyridine]-4-carbonitrile

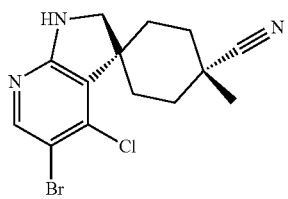

and

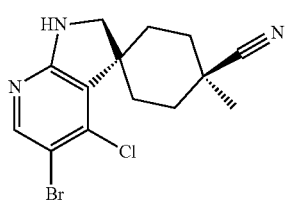

Step 1: tert-Butyl (1r,4r)-5'-Bromo-4'-chloro-4-cyanospiro[cyclohexane-1,3'-pyrrolo[2,3-b]pyridine]-1'(2'H)-carboxylate

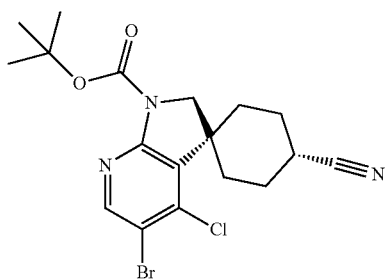

Sodium hydride (60% in oil, 13.2 mg, 0.33 mmol) was added to a solution of (1r,4r)-5'-bromo-4'-chloro-1',2'-dihydrospiro[cyclohexane-1,3'-pyrrolo[2,3-b]pyridine]-4-carbonitrile (90 mg, 0.27 mmol) and di-tert-butyl dicarbonate (78 mg, 0.36 mmol) in THF (2 mL). The mixture was stirred at RT for 2 days, and then partitioned between EtOAc and 10% aq. citric acid. The organic phase was washed with water, brine, dried (Na$_2$SO$_4$) and evaporated. The residue was purified by chromatography on silica (solvent gradient 20-50% EtOAc in cyclohexane) to afford the title compound (0.117 g, quantitative) as a white solid. LCMS (ESI) [M+Na]$^+$ 448/450/452.

Step 2: tert-Butyl (1r,4r)-5'-bromo-4'-chloro-4-cyano-4-methylspiro[cyclohexane-1,3'-pyrrolo[2,3-b]pyridine]-1'(2'H)-carboxylate and tert-butyl (1s,4s)-5'-bromo-4'-chloro-4-cyano-4-methylspiro[cyclohexane-1,3'-pyrrolo[2,3-b]pyridine]-1'(2'H)-carboxylate

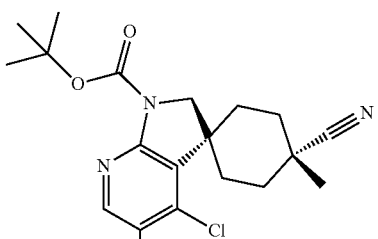

and

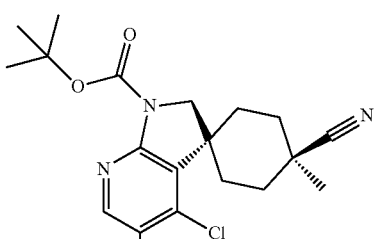

A solution of tert-butyl (1r,4r)-5'-bromo-4'-chloro-4-cyanospiro[cyclohexane-1,3'-pyrrolo[2,3-b]pyridine]-1'(2'H)-carboxylate (0.0805 g, 0.567 mmol) and iodomethane (0.035 mL, 0.57 mmol) in THF (2 mL) was cooled to −78° C. and lithium bis(trimethylsilyl)amide solution (1M in THF, 0.34 mL, 0.34 mmol) added. The mixture was stirred at −78° C. for 20 min, then quenched with aq. sat. ammonium chloride, allowed to warm to RT and extracted with EtOAc (2×). The combined organic extracts were washed with brine, dried (Na$_2$SO$_4$) and evaporated. The residue was purified by chromatography on silica (solvent gradient 10-30% EtOAc in cyclohexane) to afford a mixture of the title compounds (0.058 g, 48%) as a white solid. LCMS (ESI) [M+Na]$^+$ 462/464/466.

Step 3: (1r,4r)-5'-Bromo-4'-chloro-4-methyl-1',2'-dihydrospiro[cyclohexane-1,3'-pyrrolo[2,3-b]pyridine]-4-carbonitrile and (1s,4s)-5'-bromo-4'-chloro-4-methyl-1',2'-dihydrospiro[cyclohexane-1,3'-pyrrolo[2,3-b]pyridine]-4-carbonitrile

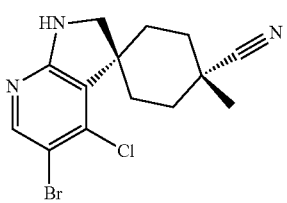

and

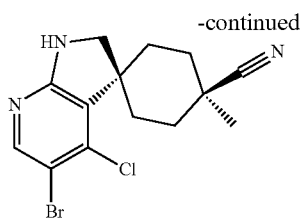

TFA (1 mL) was added to a solution of tert-butyl (1r,4r)-5'-bromo-4'-chloro-4-cyano-4-methylspiro[cyclohexane-1,3'-pyrrolo[2,3-b]pyridine]-1'(2'H)-carboxylate and tert-butyl (1s,4s)-5'-bromo-4'-chloro-4-cyano-4-methylspiro[cyclohexane-1,3'-pyrrolo[2,3-b]pyridine]-1'(2'H)-carboxylate (0.058 g, 0.13 mmol) in DCM (2 mL). The mixture was stirred at RT for 1 h, then more TFA (1 mL) was added. Stirring was continued for a further 1.5 h. Toluene was added and the mixture evaporated (2×). The residue was dissolved in MeOH and purified on SCX-2 cartridge (eluting with MeOH then 1N MeOH·NH₃). The residue was purified by chromatography on silica (solvent gradient 30-100% EtOAc in cyclohexane) to afford (1r,4r)-5'-bromo-4'-chloro-4-methyl-1',2'-dihydrospiro[cyclohexane-1,3'-pyrrolo[2,3-b]pyridine]-4-carbonitrile (0.0228 g, 51%) as a colorless solid. LCMS (ESI) [M+H]⁺ 340/342/344. Later fractions gave (1s,4s)-5'-bromo-4'-chloro-4-methyl-1',2'-dihydrospiro[cyclohexane-1,3'-pyrrolo[2,3-b]pyridine]-4-carbonitrile (0.0124 g, 28%) as a colorless solid. LCMS (ESI) [M+H]⁺ 340/342/344.

Example 139

Methyl (1r,4r)-5'-bromo-4'-chloro-1',2'-dihydrospiro[cyclohexane-1,3'-pyrrolo[2,3-b]pyridine]-4-carboxylate and methyl (1s,4s)-5'-bromo-4'-chloro-1',2'-dihydrospiro[cyclohexane-1,3'-pyrrolo[2,3-b]pyridine]-4-carboxylate

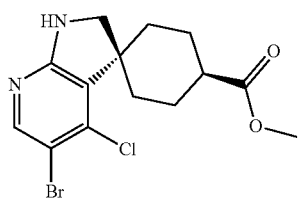

and

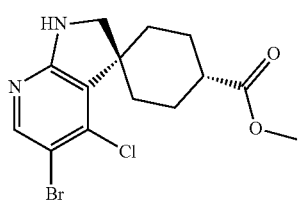

Sulfuric acid (0.5 mL) was added to a solution of 5'-bromo-4'-chloro-1',2'-dihydrospiro[cyclohexane-1,3'-pyrrolo[2,3-b]pyridine]-4-carboxylic acid (0.125 mg, 0.36 mmol) in MeOH (12 mL). The reaction mixture was stirred at RT for 4 h. After concentration under reduced pressure, the residue was partitioned between EtOAc and aq. sodium bicarbonate. The aqueous phase was extracted with more EtOAc and the combined extracts were washed with brine, dried (Na₂SO₄) and evaporated. The residue was purified by chromatography on silica (i-PrOAc). Earlier fractions contained predominantly methyl (1'-bromo-4'-chloro-1',2'-dihydrospiro[cyclohexane-1,3'-pyrrolo[2,3-b]pyridine]-4-carboxylate (0.07 g, 54%). LCMS (ESI) [M+Na]⁺ 359/361/363. Later fractions contained predominantly methyl (1s,4s)-5'-bromo-4'-chloro-1',2'-dihydrospiro[cyclohexane-1,3'-pyrrolo[2,3-b]pyridine]-4-carboxylate (0.061 g, 46%). LCMS (ESI) [M+Na]⁺ 359/361/363.

Example 140

((1 r,4r)-5'-Bromo-4'-chloro-1',2''-dihydrospiro[cyclohexane-1,3'-pyrrolo[2,3-b]pyrdine]-4-yl)methanol and ((1s,4s)-5'-bromo-4''-chloro-1',2'-dihydrospiro[cyclohexane-1,3''-pyrrolo[2,3-b]pyridine]-4-yl)methanol

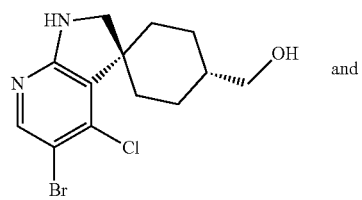

and

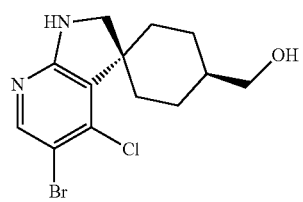

DIBAL (1M in DCM, 0.54 mL, 0.54 mmol) was added to a solution of methyl (1r,4r)-5'-bromo-4'-chloro-1',2'-dihydrospiro[cyclohexane-1,3'-pyrrolo[2,3-b]pyridine]-4-carboxylate and methyl (1s,4s)-5'-bromo-4'-chloro-1'',2'-dihydrospiro[cyclohexane-1,3'-pyrrolo[2,3-b]pyridine]-4-carboxylate (0.065 g, 0.18 mmol) in DCM (2 mL). The mixture was stirred at RT for 30 min, then treated successively with water (0.02 mL), 15% aq NaOH (0.02 mL) and water (0.05 mL). The mixture was stirred for 1 h, then diluted with DCM. Celite and Na₂SO₄ were added and stirring continued for a further 1 h. After filtration and evaporation, the residue was purified by chromatography on silica (solvent gradient 0-100% EtOAc in diethyl ether). Earlier fractions gave ((1r,4r)-5'-bromo-4'-chloro-1',2''-dihydrospiro[cyclohexane-1,3'-pyrrolo[2,3-b]pyridine]-4-yl)methanol (0.03 g, 50%). LCMS (ESI) [M+Na]⁺ 331/333/335. Later fractions gave methyl ((1s,4s)-5'-bromo-4'-chloro-1',2'-dihydrospiro[cyclohexane-1,3'-pyrrolo[2,3-b]pyridine]-4-yl)methanol (0.021 g, 35%). LCMS (ESI) [M+Na]⁺ 331/333/335.

Example 141

1'-(tert-Butyl) 4-methyl (1s,4s)-5'-bromo-4'-chlorospiro[cyclohexane-1,3'-pyrrolo[2,3-b]pyridine]-1',4(2'H)-dicarboxylate and 1'-(tert-butyl) 4-methyl (1r,4r)-5'-bromo-4'-chlorospiro[cyclohexane-1,3'-pyrrolo[2,3-b]pyridine]-1',4(2'H)-dicarboxylate

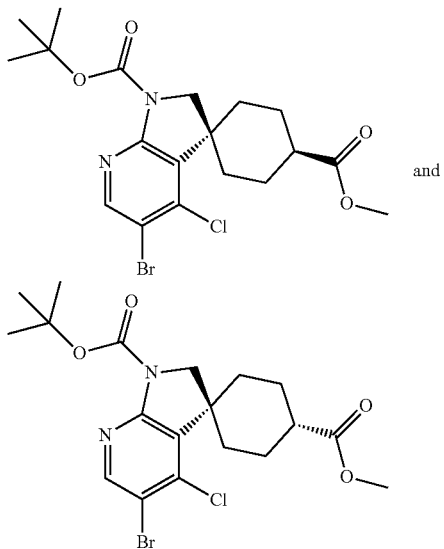

and

Sodium hydride (60% in oil, 53.1 mg, 1.33 mmol) was added to a solution of methyl (1r,4r)-5'-bromo-4'-chloro-1',2'-dihydrospiro[cyclohexane-1,3'-pyrrolo[2,3-b]pyridine]-4-carboxylate and methyl (1s,4s)-5'-bromo-4'-chloro-1',2'-dihydrospiro[cyclohexane-1,3'-pyrrolo[2,3-b]pyridine]-4-carboxylate (0.319 g, 0.886 mmol) and di-tert-butyl dicarbonate (0.967 g, 4.43 mmol) in THF (3 mL). The mixture was stirred at RT for 3 days, then quenched with aq. sat. ammonium chloride and extracted with EtOAc (2×). The combined extracts were washed with brine, dried (Na$_2$SO$_4$) and evaporated. The residue was purified by chromatography on silica (solvent gradient 10-30% EtOAc in cyclohexane) to afford a mixture of the title compounds (0.38 g, 93%) as a colorless gum. LCMS (ESI) [M+H–$^t$Bu]$^+$ 403/405/407.

Example 142

Methyl (1r,4r)-5'-bromo-4'-chloro-1',2'-dihydrospiro[cyclohexane-1,3'-pyrrolo[2,3-b]pyridine]-4-carboxylate and 2-((1s,4s)-5'-bromo-4'-chloro-1',2'-dihydrospiro[cyclohexane-1,3'-pyrrolo[2,3-b]pyridine]-4-yl)propan-2-ol

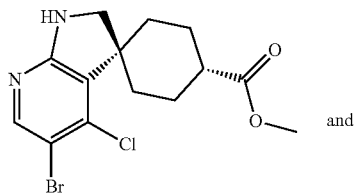

and

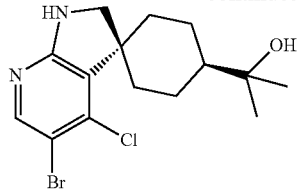

To a solution of 1'-(tert-butyl) 4-methyl (1s,4s)-5'-bromo-4'-chlorospiro[cyclohexane-1,3'-pyrrolo[2,3-b]pyridine]-1',4(2'H)-dicarboxylate and 1'-(tert-butyl) 4-methyl (1r,4r)-5'-bromo-4'-chlorospiro[cyclohexane-1,3'-pyrrolo[2,3-b]pyridine]-1',4(2'H)-dicarboxylate (0.0927 g, 0.20 mmol) in THF (2 mL), cooled to –78° C. was added methylmagnesium chloride (3M in THF, 0.54 mL, 1.62 mmol) over 5 min. The mixture was stirred at –78° C. for 10 min, then allowed to warm to 0° C. over 1 h. The reaction was quenched with aq. sat. ammonium chloride, then extracted twice with EtOAc. The combined extracts were washed with brine, dried (Na$_2$SO$_4$) and evaporated. The residue was purified by chromatography on silica (solvent gradient 0-100% EtOAc in diethyl ether). Earlier fractions gave methyl (1r,4r)-5'-bromo-4'-chloro-1',2'-dihydrospiro[cyclohexane-1,3'-pyrrolo[2,3-b]pyridine]-4-carboxylate (0.0308 g, 42%). LCMS (ESI) [M+H]$^+$ 359/361/363. Later fractions gave 2-((1s,4s)-5'-bromo-4'-chloro-1',2'-dihydrospiro[cyclohexane-1,3'-pyrrolo[2,3-b]pyridine]-4-yl)propan-2-ol (0.0253 g, 35%). LCMS (ESI) [M+H]$^+$ 359/361/363.

Example 143

2-((1r,4r)-5'-Bromo-4'-chloro-1',2'-dihydrospiro[cyclohexane-1,3'-pyrrolo[2,3-b]pyridine]-4-yl)propan-2-ol

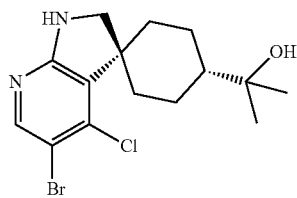 [SMILES: CC(C)(O)[C@H]1CC[C@@]2(CC1)CNc1ncc(Br)c(Cl)c12]

To an ice-cooled solution of methyl (1r,4r)-5'-bromo-4'-chloro-1',2'-dihydrospiro[cyclohexane-1,3'-pyrrolo[2,3-b]pyridine]-4-carboxylate (0.054 g, 0.15 mmol) in THF (2 mL) was added methylmagnesium chloride (3M in THF, 0.4 mL, 1.2 mmol). The mixture was stirred at RT for 1 h, then further methylmagnesium chloride (3M in THF, 0.4 mL, 1.2 mmol) was added and the mixture stirred for 4 h. The reaction was quenched with aq. sat. ammonium chloride, and then extracted twice with EtOAc. The combined extracts were washed with brine, dried (Na$_2$SO$_4$), filtered and evaporated. The residue was purified by chromatography on silica (solvent gradient 0-100% EtOAc in diethyl ether) to afford the title compound (0.036 g, 67%) as a colorless gum. LCMS (ESI) [M+H]$^+$ 359/361/363.

Example 144

Methyl (1r,4r)-5'-bromo-4'-chloro-4-methyl-1',2'-dihydrospiro[cyclohexane-1,3'-pyrrolo[2,3-b]pyridine]-4-carboxylate

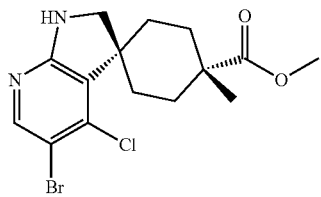 [SMILES: COC(=O)[C@]1(C)CC[C@]2(CC1)CNc1ncc(Br)c(Cl)c12]

Step 1: 1'-(tert-Butyl) 4-methyl (1r,4r)-5'-bromo-4'-chloro-4-methylspiro[cyclohexane-1,3'-pyrrolo[2,3-b]pyridine]-1',4(2'H)-dicarboxylate

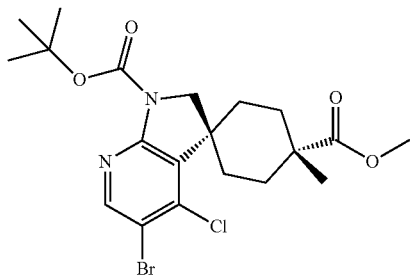 [SMILES: COC(=O)[C@]1(C)CC[C@]2(CC1)CN(C(=O)OC(C)(C)C)c1ncc(Br)c(Cl)c12]

A solution of 1'-(tert-butyl) 4-methyl (1s,4s)-5'-bromo-4'-chlorospiro[cyclohexane-1,3'-pyrrolo[2,3-b]pyridine]-1',4(2'H)-dicarboxylate and 1'-(tert-butyl) 4-methyl (1r,4r)-5'-bromo-4'-chlorospiro[cyclohexane-1,3'-pyrrolo[2,3-b]pyridine]-1',4(2'H)-dicarboxylate (0.145 g, 0.315 mmol) and iodomethane (0.137 mL, 2.21 mmol) in THF (2 mL) was cooled to −78° C. Lithium bis(trimethylsilyl)amide solution (1M in THF, 1.58 mL, 1.58 mmol) was added over 5 min. The mixture was stirred at −78° C. for 10 min, then allowed to warm to 0° C. over 30 min. After stirring at 0° C. for 30 min, the reaction was quenched with aq. sat. ammonium chloride, extracted with EtOAc (2×). The combined organic extracts were washed with brine, dried (Na₂SO₄) and evaporated. The residue was purified by chromatography on silica (solvent gradient 5-30% EtOAc in cyclohexane) to afford the title compound (0.0626 g, 42%) as a colorless gum. LCMS (ESI) [M+Na]⁺ 495/497/499.

Step 2: Methyl (1r,4r)-5'-bromo-4'-chloro-4-methyl-1',2'-dihydrospiro[cyclohexane-1,3'-pyrrolo[2,3-b]pyridine]-4-carboxylate

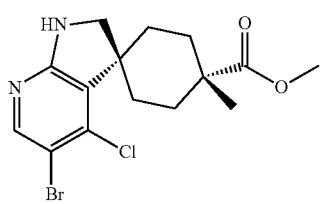 [SMILES: COC(=O)[C@]1(C)CC[C@]2(CC1)CNc1ncc(Br)c(Cl)c12]

TFA (1.5 mL) was added to a solution of 1'-(tert-butyl) 4-methyl (1r,4r)-5'-bromo-4'-chloro-4-methylspiro[cyclohexane-1,3'-pyrrolo[2,3-b]pyridine]-1',4(2'H)-dicarboxylate (0.0864 g, 0.18 mmol) in DCM (1.5 mL). The mixture was stirred at RT for 2 h. Toluene was added and evaporated (2×). The residue was purified on SCX-2 cartridge (eluting with MeOH then 1N MeOH·NH₃). The residue was purified by chromatography on silica (solvent gradient 30-50% EtOAc in cyclohexane) to afford the title compound (0.0555 g, 81%) as a colorless solid. LCMS (ESI) [M+H]⁺ 373/375/377.

Example 145

((1r,4r)-5'-Bromo-4'-chloro-4-methyl-1',2'-dihydrospiro[cyclohexane-1,3'-pyrrolo[2,3-b]pyridine]-4-yl)methanol

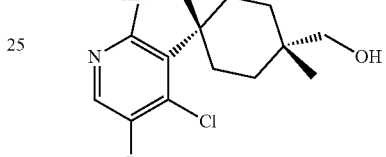

DIBAL (1M in DCM, 0.45 mL, 0.45 mmol) was added to a solution of methyl (1r,4r)-5'-bromo-4'-chloro-4-methyl-1',2'-dihydrospiro[cyclohexane-1,3'-pyrrolo[2,3-b]pyridine]-4-carboxylate (0.0555 g, 0.15 mmol) in DCM (2.5 mL). The mixture was stirred at RT for 30 min, then treated successively with water (0.018 mL), 15% NaOH (0.018 mL) and water (0.045 mL) and stirred for 1 h. The mixture was diluted with DCM. Celite and Na₂SO₄ were added and stirring continued for 30 min. The mixture was filtered and evaporated. The residue was purified by chromatography on silica (solvent gradient 30-100% EtOAc in cyclohexane) to afford the title compound (0.0372 g, 72%) as a colorless solid. LCMS (ESI) [M+H]⁺ 345/347/349.

Example 146

5'-Bromo-4'-chlorospiro[cyclohexane-1,3'-pyrrolo[2,3-b]pyridine]-2',4(1'H)-dione

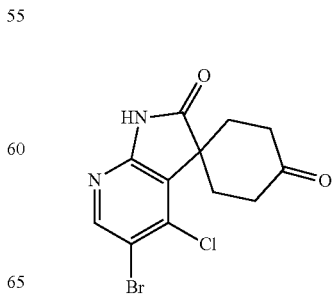

Step 1: Dimethyl 3,3'-(5-bromo-4-chloro-2-oxo-1-((2-(trimethylsilyl)ethoxy)methyl)-2,3-dihydro-1H-pyrrolo[2,3-b]pyridine-3,3-diyl)dipropionate

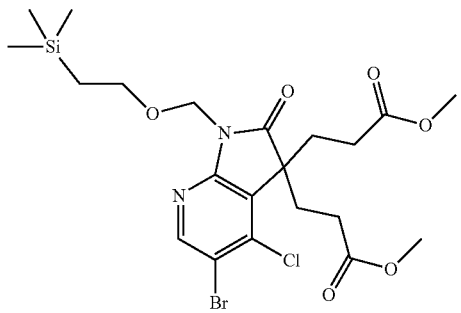

Potassium tert-butoxide (39 mg, 0.35 mmol) was added to a suspension of 5-bromo-4-chloro-1-((2-(trimethylsilypethoxy)methyl)-1,3-dihydro-2H-pyrrolo[2,3-b]pyridine-2-one (2.0 g, 5.29 mmol) in DMSO (8 mL). After stirring at RT for 10 min the mixture was heated to 45° C. and methyl acrylate (1.48 mL, 16.4 mmol) was added dropwise over 10 min. The reaction mixture was stirred at 45° C. for 1 h then was partitioned between EtOAc and water. The aqueous phase was extracted with more EtOAc. The combined organic extracts were washed with water, brine, dried (Na$_2$SO$_4$) and evaporated. The residue was purified by chromatography on silica (solvent gradient 10-30% EtOAc in cyclohexane) to afford the title compound (2.56 g, 88%) as a pink gum. LCMS (ESI) [M+Na]$^+$ 571/573/575.

Step 2: Dimethyl 3,3'-(5-bromo-4-chloro-2-oxo-2,3-dihydro-1H-pyrrolo[2,3-b]pyridine-3,3-diyl)dipropionate

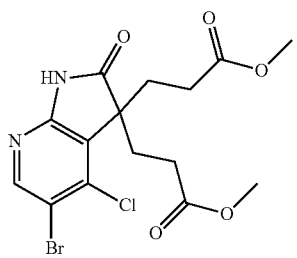 [SMILES: COC(=O)CCC1(CCC(=O)OC)C(=O)Nc2ncc(Br)c(Cl)c21]

To an ice-cooled solution of dimethyl 3,3'-(5-bromo-4-chloro-2-oxo-1-((2-(trimethylsilypethoxy)methyl)-2,3-dihydro-1H-pyrrolo[2,3-b]pyridine-3,3-diyl)dipropionate (2.56 g, 4.66 mmol) in DCM (40 mL) was added TFA (12 mL). The mixture was stirred at RT for 1 h then toluene was added and evaporated (2×). The residue was dissolved in MeOH (10 mL), cooled in an ice bath and MeOH·NH$_3$ (30 mL) was added. The mixture was stirred at RT for 1 h, then concentrated aq. NH$_3$ (5 mL) was added. Stirring was continued for h. The mixture was concentrated under reduced pressure and then partitioned between EtOAc and water. The aqueous phase was extracted with more EtOAc. The combined organic extracts were washed with brine, dried (Na$_2$SO$_4$) and evaporated. The residue was purified by chromatography on silica (solvent gradient 30-70% EtOAc in cyclohexane) to afford the title compound (1.5 g, 77%) as a colorless gum. LCMS (ESI) [M+Na]$^+$ 441/443/445.

Step 3: Methyl 5'-bromo-4'-chloro-2',4-dioxo-1',2'-dihydrospiro[cyclohexane-1,3'-pyrrolo[2,3-b]pyridine]-3-carboxylate

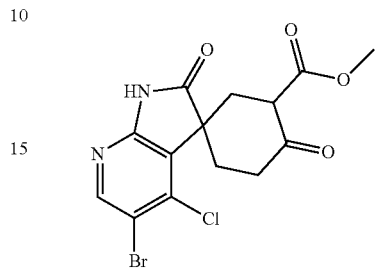

Sodium tert-butoxide (2M in THF, 4.45 mL, 8.9 mmol) was added over 20 min to a solution of dimethyl 3,3'-(5-bromo-4-chloro-2-oxo-2,3-dihydro-1H-pyrrolo[2,3-b]pyridine-3,3-diyl)dipropionate (1.21 g, 2.87 mmol) in DMSO (12 mL). The mixture was stirred at RT for 10 min. then was partitioned between EtOAc and aq. sat. ammonium chloride. The aqueous phase was extracted with more EtOAc. The combined organic extracts were washed with water, brine, dried (Na$_2$SO$_4$) and evaporated. The residue was purified by chromatography on silica (solvent gradient 1-5% MeOH in DCM) to afford the title compound (0.943 g, 77%) as a light brown foam. LCMS (ESI) [M+H]$^+$ 387/389/391.

Step 4: 5'-Bromo-4'-chlorospiro[cyclohexane-1,3'-pyrrolo[2,3-b]pyridine]-2',4(1'H)-dione

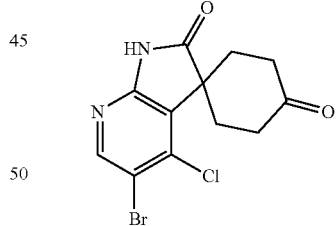

A mixture of methyl 5'-bromo-4'-chloro-2',4-dioxo-1',2'-dihydrospiro[cyclohexane-1,3'-pyrrolo[2,3-b]pyridine]-3-carboxylate (1.01 g, 2.61 mmol), HCl (3N aq., 50 mL), MeOH (5 mL) and 1,4-dioxane (10 mL) was stirred at 100° C. for 1 h. After cooling to RT and concentration under reduced pressure, EtOAc was added. The mixture was neutralised by addition of sat. aq. sodium bicarbonate. The aqueous phase was extracted with more EtOAc and the combined organic extracts were washed with brine, dried (Na$_2$SO$_4$), filtered and evaporated. The residue was purified by chromatography on silica (solvent gradient 1-5% MeOH in DCM) to afford the title compound (0.655 g, 76%) as an off-white solid. LCMS (ESI) [M+H]$^+$ 329/331/333.

429

(1r,4r)-5'-Bromo-4'-chloro-1',2'-dihydrospiro[cyclohexane-1,3'-pyrrolo[2,3-b]pyridin]-4-ol and (1s,4s)-5'-bromo-4'-chloro-1',2'-dihydrospiro[cyclohexane-1,3'-pyrrolo[2,3-b]pyridin]-4-ol

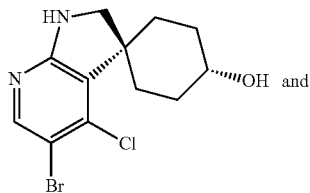 and

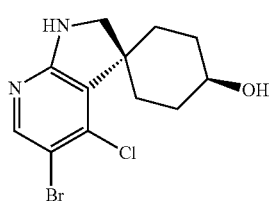

To an ice-cooled suspension of 5'-bromo-4'-chlorospiro[cyclohexane-1,3'-pyrrolo[2,3-b]pyridine]-2',4(1'H)-dione (0.651 g, 1.98 mmol) in DCM (10 mL) was added DIBAL (1 M in DCM, 19.8 mL, 19.8 mmol) over 15 min. The mixture was stirred at RT for 16 h, then cooled in an ice bath. Water (0.8 mL), 15% NaOH (0.8 mL) and water (2.0 mL) were successively added. The mixture was stirred at RT for 15 min. Celite and Na$_2$SO$_4$ were added and the mixture was stirred for a further 10 min before filtration and evaporation. The residue was purified by chromatography on silica (solvent gradient 50-100% EtOAc in cyclohexane, then MeOAc with 0-5% MeOH) to afford (1r,4r)-5'-bromo-4'-chloro-1',2'-dihydrospiro[cyclohexane-1,3'-pyrrolo[2,3-b]pyridin]-4-ol (0.102 g, 16%) as a colorless gum. LCMS (ESI) [M+H]$^+$ 317/319/321. Later fractions gave (1s,4s)-5'-bromo-4'-chloro-1',2'-dihydrospiro[cyclohexane-1,3'-pyrrolo[2,3-b]pyridin]-4-ol (0.213 g, 34%) as a colorless foam. LCMS (ESI) [M+H]$^+$ 317/319/321.

Example 147

(1r,4r)-5'-Bromo-4'-chloro-1',2'-dihydrospiro[cyclohexane-1,3'-pyrrolo[2,3-b]pyridine]-4-yl methanesulfonate

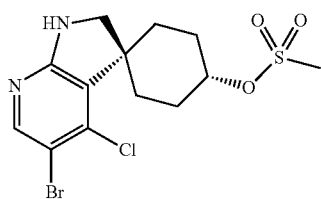 [SMILES: CS(=O)(=O)O[C@H]1CC[C@@]2(CC1)CNc1ncc(Br)c(Cl)c12]

430

Step 1: (1r,4r)-5'-Bromo-4'-chloro-1',2'-dihydrospiro[cyclohexane-1,3'-pyrrolo[2,3-b]pyridine]-4-yl benzoate

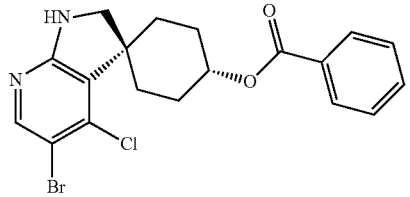 [SMILES: O=C(O[C@H]1CC[C@@]2(CC1)CNc1ncc(Br)c(Cl)c12)c1ccccc1]

Diisopropyl azodicarboxylate (0.14 mL, 0.70 mmol) was added to an ice-cooled solution of (1s,4s)-5'-bromo-4'-chloro-1',2'-dihydrospiro[cyclohexane-1,3'-pyrrolo[2,3-b]pyridin]-4-ol (0.148 g, 0.47 mmol), benzoic acid (0.0854 g, 0.70 mmol) and triphenylphosphine (0.183 g, 0.70 mmol) in THF (5 mL). The mixture was stirred at RT for 1 h, then concentrated under reduced pressure. The residue was purified by chromatography on silica (solvent gradient 0-100% EtOAc in toluene) to afford the title compound contaminated with triphenylphosphine oxide (0.391 g, assume quantitative). LCMS (ESI) [M+H]$^+$ 421/423/425.

Step 2: (1r,4r)-5'-Bromo-4'-chloro-1'-(4-methoxybenzyl)-1',2'-dihydrospiro[cyclohexane-1,3'-pyrrolo[2,3-b]pyridine]-4-yl benzoate

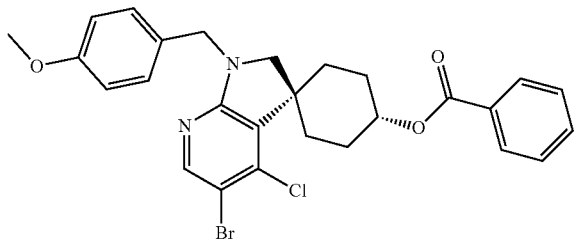 [SMILES: COc1ccc(CN2C[C@]3(CC[C@H](OC(=O)c4ccccc4)CC3)c3c2ncc(Br)c3Cl)cc1]

Sodium hydride (60% in oil, 22.3 mg, 0.56 mmol) was added over 5 min to a solution of the impure (1r,4r)-5'-bromo-4'-chloro-1',2'-dihydrospiro[cyclohexane-1,3'-pyrrolo[2,3-b]pyridine]-4-yl benzoate (assumed 0.46 mmol), 4-methoxybenzyl chloride (0.082 mL, 0.604 mmol) and 15-crown-5 (0.01 mL, 0.05 mmol) in THF (5 mL). The mixture was stirred at RT for 4 h, then more sodium hydride (60% in oil, 22.3 mg, 0.56 mmol) and 4-methoxybenzyl chloride (0.082 mL, 0.604 mmol) were added. Stirring was continued for a further 2 h. The reaction mixture was quenched with aq. sat. ammonium chloride and extracted with EtOAc (2×). The combined organic extracts were washed with brine, dried (Na$_2$SO$_4$) and evaporated. The residue was purified by chromatography on silica (solvent gradient 5-20% EtOAc in toluene) to afford the title compound (0.151 g, 60% over 2 steps) as a colorless gum. LCMS (ESI) [M+H]$^+$ 541/543/545.

431

Step 3: (1r,4r)-5'-Bromo-4'-chloro-1'-(4-methoxy-benzyl)-1',2'-dihydrospiro[cyclohexane-1,3'-pyrrolo[2,3-b]pyridine]-4-ol

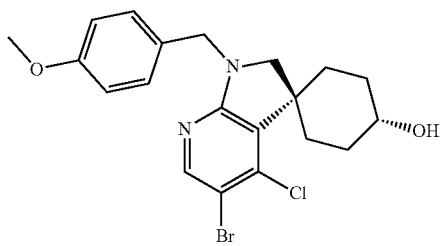 [SMILES: COc1ccc(CN2C[C@]3(CC[C@H](O)CC3)c3c2ncc(Br)c3Cl)cc1]

To a solution of (1r,4r)-5'-bromo-4'-chloro-1'-(4-methoxybenzyl)-1',2'-dihydrospiro[cyclohexane-1,3'-pyrrolo[2,3-b]pyridine]-4-yl benzoate (0.151 mg, 0.28 mmol) in THF (2 mL) and MeOH (1 mL) was added a solution of lithium hydroxide monohydrate (0.024 g, 0.56 mmol) in water (1 mL). The mixture was stirred at RT for 16 h. A further portion of lithium hydroxide monohydrate (0.024 g, 0.56 mmol) in water (1 mL) was added and stirring continued for 6.5 h. The reaction mixture was partitioned between aq. sodium bicarbonate and EtOAc. The aqueous phase was extracted with more EtOAc. The combined extracts were washed with brine, dried (Na$_2$SO$_4$) and evaporated. The residue was purified by chromatography on silica (solvent gradient 20-50% EtOAc in cyclohexane) to afford the title compound as a colorless gum (0.0865 g, 71%). LCMS (ESI) [M+H]$^+$ 437/439/441.

Step 4: (1r,4r)-5'-Bromo-4'-chloro-1',2'-dihydrospiro[cyclohexane-1,3'-pyrrolo[2,3-b]pyridine]-4-yl methanesulfonate

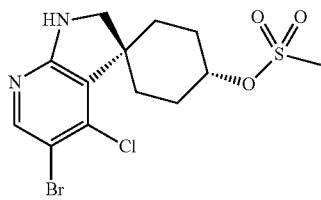

Methanesulfonyl chloride (0.023 mL, 0.30 mmol) was added over 2 min to solution of (1r,4r)-5'-bromo-4'-chloro-1'-(4-methoxybenzyl)-1',2'-dihydrospiro[cyclohexane-1,3'-pyrrolo[2,3-b]pyridine]-4-ol (0.0865 g, 0.20 mmol) and triethylamine (0.055 mL, 0.40 mmol) in DCM (3 mL). The mixture was stirred at RT for 2 h, then was diluted with DCM and washed with aq. sodium bicarbonate 3. The aqueous phase was extracted with more DCM. The combined organic extracts were dried (Na$_2$SO$_4$) and evaporated. The residue was purified by chromatography on silica (solvent gradient 20-50% EtOAc in cyclohexane) to afford the title compound (0.10 g, 98%) as a colorless gum. LCMS (ESI) [M+H]$^+$ 515/517/519.

432

Example 148

(1r,4r)-5'-Bromo-4'-chloro-4-methyl-1',2'-dihydrospiro[cyclohexane-1,3'-pyrrolo[2,3-b]pyridine]-4-ol

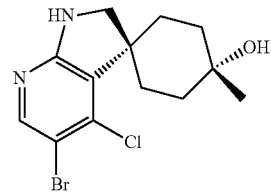 [SMILES: C[C@]1(O)CC[C@@]2(CC1)CNc1ncc(Br)c(Cl)c12]

Step 1: (1r,4r)-5'-Bromo-4'-chloro-4-hydroxy-4-methyl spiro[cyclohexane-1,3'-pyrrolo[2,3-b]pyridine]-2"(1'H)-one and (1s,4s)-5'-bromo-4'-chloro-4-hydroxy-4-methylspiro[cyclohexane-1,3'-pyrrolo[2,3-b]pyrdine]-2'(1'H)-one

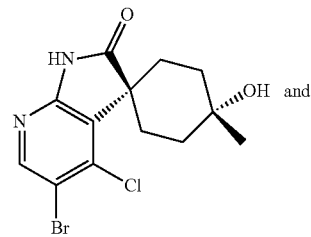 and

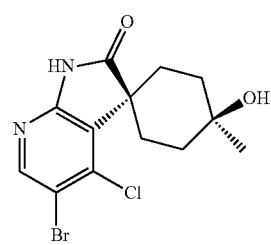

To an ice-cooled solution of 5'-bromo-4'-chlorospiro[cyclohexane-1,3'-pyrrolo[2,3-b]pyridine]-2',4(1'H)-dione (0.115 g, 0.35 mmol) in THF (3 mL) was added methylmagnesium chloride (3M in THF, 0.5 mL, 1.5 mmol) over 5 min. The mixture was stirred at 0° C. for 30 min then was quenched with aq. sat. ammonium chloride and extracted with EtOAc (2×). The combined organic extracts were washed with brine, dried (Na$_2$SO$_4$) and evaporated. The residue was purified by chromatography on silica (solvent gradient 2-10% MeOH in DCM) to afford (1r,4r)-5'-bromo-4'-chloro-4-hydroxy-4-methylspiro[cyclohexane-1,3'-pyrrolo[2,3-b]pyrdine]-2'(1'H)-one (0.0319 g, 26%). LCMS (ESI) [M+H]$^+$ 345/347/349. Later fractions gave (1s,4s)-5'-bromo-4'-chloro-4-hydroxy-4-methylspiro[cyclohexane-1,3'-pyrrolo[2,3-b]pyrdine]-2'(1'H)-one (0.0543 g, 45%). LCMS (ESI) [M–H]$^-$ 343/345/347.

Step 2: (1r,4r)-5'-Bromo-4'-chloro-4-methyl-1',2'-dihydrospiro[cyclohexane-1,3'-pyrrolo[2,3-b]pyridine]-4-ol

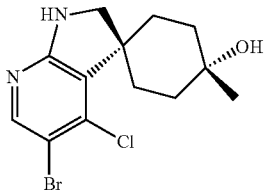 [SMILES: C[C@]1(O)CC[C@@]2(CC1)CNc1ncc(Br)c(Cl)c12]

To an ice-cooled suspension of (1r,4r)-5'-bromo-4'-chloro-4-hydroxy-4-methylspiro[cyclohexane-1,3'-pyrrolo[2,3-b]pyridine]-2'(1H)-one (0.0319 g, 0.092 mmol) in DCM (2 mL) was added DIBAL (1.0 M in DCM 0.65 mL, 0.65 mmol) over 5 min. The mixture was stirred in the ice bath for 10 min, then at RT for 16 h. More DIBAL (1M in DCM, 0.65 mL, 0.65 mmol) was added. The reaction mixture was stirred at RT for a further 3 h, then was cooled in an ice bath. Water (0.052 mL) was added cautiously, then 15% NaOH (0.052 mL) and water (0.13 mL) were added. Stirring was pursued at RT for 1 h. Celite and $Na_2SO_4$ were added and the mixture was stirred for a further 30 min, then filtered and evaporated. The residue was purified by chromatography on silica (solvent gradient 2-6% MeOH in DCM) to afford the title compound (0.0157 g, 51%) as a colorless gum. LCMS (ESI) [M+H]+ 331/333/335.

Example 149

(1s,4s)-5'-Bromo-4'-chloro-4-methyl-1',2'-dihydrospiro[cyclohexane-1,3'-pyrrolo[2,3-b]pyridine]-4-ol

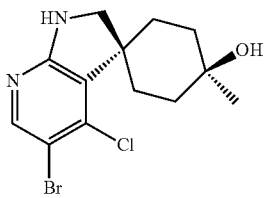 [SMILES: C[C@]1(O)CC[C@]2(CC1)CNc1ncc(Br)c(Cl)c12]

The title compound (0.0223 g, 43%) was prepared by an analogous method to that described for (1r,4r)-5'-bromo-4'-chloro-4-methyl-1',2'-dihydrospiro[cyclohexane-1,3'-pyrrolo[2,3-b]pyridine]-4-ol. LCMS (ESI) [M+H]+ 331/333/335.

Example 150

(1r,4r)-5'-Bromo-4'-chloro-4-(methylsulfonyl)-1',2'-dihydrospiro[cyclohexane-1,3'-pyrrolo[2,3-b]pyridine]

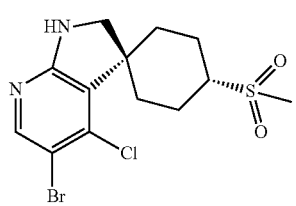 [SMILES: CS(=O)(=O)[C@H]1CC[C@@]2(CC1)CNc1ncc(Br)c(Cl)c12]

Step 1: Di-tert-butyl 5'-bromo-4'-chloro-4-(methylsulfonyl)spiro[cyclohexane-1,3'-pyrrolo[2,3-b]pyridine]-1',4(2'H)-dicarboxylate

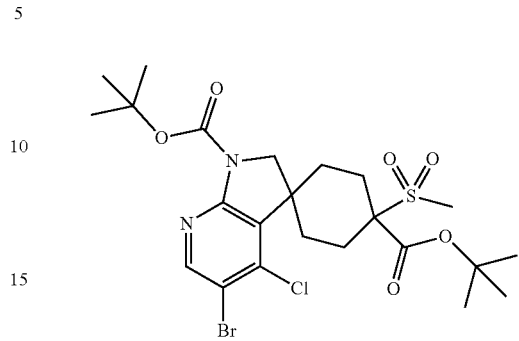

To a suspension of tert-butyl 5-bromo-4-chloro-3,3-bis(2-iodoethyl)-2,3-dihydro-1H-pyrrolo[2,3-b]pyridine-1-carboxylate (0.268 g, 0.42 mmol) in DMF (2.5 mL) was added potassium carbonate (0.144 g, 1.04 mmol) and tert-butyl 2-(methylsulfonyl)acetate (0.097 g, 0.50 mmol). The mixture was stirred at 60° C. for 6.5 h. then poured into EtOAc and water. The aqueous phase was extracted with more EtOAc and the combined extracts were washed with water, brine, dried ($Na_2SO_4$), filtered and evaporated. The residue was purified by chromatography on silica (solvent gradient 20-40% EtOAc in cyclohexane) to afford the title compound as a mixture of isomers as a colorless solid (0.238 g, 98%). LCMS (ESI) [M+Na]+ 601/603/605.

Step 2: 5'-Bromo-4'-chloro-4-(methylsulfonyl)-1',2'-dihydrospiro[cyclohexane-1,3'-pyrrolo[2,3-b]pyridine]-4-carboxylic Acid

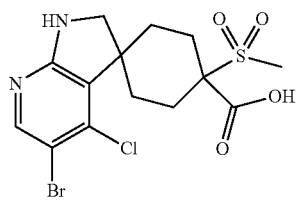 [SMILES: CS(=O)(=O)C1(C(=O)O)CCC2(CC1)CNc1ncc(Br)c(Cl)c12]

A mixture of di-tert-butyl 5'-bromo-4'-chloro-4-(methylsulfonyl)spiro[cyclohexane-1,3'-pyrrolo[2,3-b]pyridine]-1',4(2'H)-dicarboxylate (0.238 g, 0.41 mmol), DCM (3 mL) and TFA (3 mL) was stirred at RT for 16 h, then evaporated and the residue in MeCN was loaded on to a 2 g SCX cartridge, washed with MeCN. 10% Concentrated aqueous $NH_3$ in MeCN was passed through, then eluted with 1N $NH_3$/MeOH. Evaporation gave the title compound as a mixture of isomers as a white solid (0.10 g, 57%). LCMS (ESI) [M+H]+ 423/425/427.

Step 3: (1r,4r)-5'-Bromo-4'-chloro-4-(methylsulfonyl)-1',2'-dihydrospiro[cyclohexane-1,3'-pyrrolo[2,3-b]pyridine]

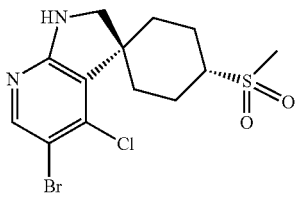

A mixture of 5'-bromo-4'-chloro-4-(methylsulfonyl)-1',2'-dihydrospiro[cyclohexane-1,3'-pyrrolo[2,3-b]pyridine]-4-carboxylic acid (0.10 g, 0.235 mmol), DMSO (2.2 mL), water (1.1 mL) and saturated brine (1.1 mL) was refluxed (bath at 130° C.) for 16 h, then poured into EtOAc and water. The aqueous phase was extracted with more EtOAc and the combined extracts were washed with water, brine, dried (Na$_2$SO$_4$), filtered and evaporated. The residue was purified by chromatography on silica (solvent gradient 3-15% 2N NH$_3$/MeOH in EtOAc) to afford the title compound as a colorless solid (0.0294 g, 33%). LCMS (ESI) [M+H]$^+$ 379/381/383.

Example 151

5'-Bromo-4'-chloro-1',2'-dihydrospiro[piperidine-4,3'-pyrrolo[2,3-b]pyridin]-2-one and 5'-bromo-4'-chloro-1',2'-dihydrospiro[piperidine-3,3'-pyrrolo[2,3-b]pyridin]-6-one

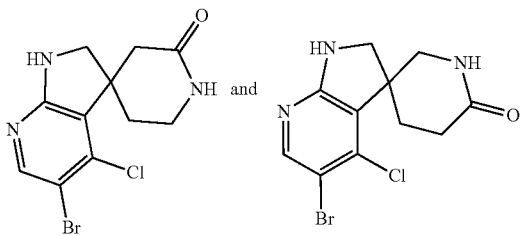 [SMILES: O=C1CC2(CCN1)CNc1ncc(Br)c(Cl)c12 ; O=C1CCC2(CN1)CNc1ncc(Br)c(Cl)c12]

Step 1: 5'-Bromo-4'-chloro-1'-(4-methoxybenzyl)-1',2'-dihydrospiro[cyclopentane-1,3'-pyrrolo[2,3-b]pyridin]-3-one oxime

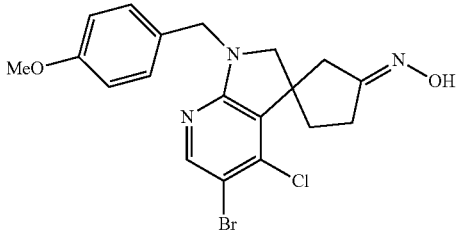 [SMILES: COc1ccc(CN2CC3(CC/C(=N\O)C3)c3c2ncc(Br)c3Cl)cc1]

Hydroxylamine hydrochloride (873 mg, 12.57 mmol) was added to a solution of 5-bromo-4-chloro-1-[(4-methoxyphenyl)methyl]spiro[2H-pyrrolo[2,3-b]pyridine-3,3'-cyclopentane]-1'-one (530 mg, 1.26 mmol) in pyridine (5 mL). The reaction mixture was stirred for 1 h at RT, then was taken up in Et$_2$O (100 mL), and washed with water (2×100 mL) then brine (100 mL). The organic extract was dried (Na$_2$SO$_4$) and concentrated to dryness to give the title compound (548 mg, 100%) as a colorless solid. LCMS (ESI) [M+H]$^+$ 436.0/440.0.

Step 2: 5'-Bromo-4'-chloro-1'-(4-methoxybenzyl)-1',2'-dihydrospiro[cyclopentane-1,3'-pyrrolo[2,3-b]pyridin]-3-one O-tosyloxime

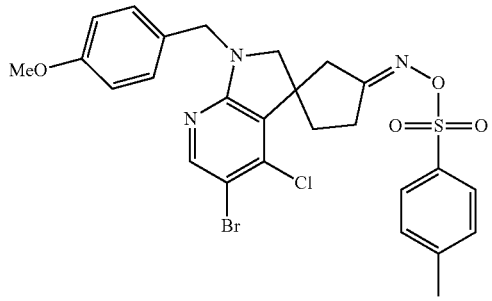 [SMILES: COc1ccc(CN2CC3(CC/C(=N\OS(=O)(=O)c4ccc(C)cc4)C3)c3c2ncc(Br)c3Cl)cc1]

4-Toluenesulfonyl chloride (478.42 mg, 2.51 mmol) was added to a mixture of 5'-bromo-4'-chloro-1'-(4-methoxybenzyl)-1',2'-dihydrospiro[cyclopentane-1,3'-pyrrolo[2,3-b]pyridin]-3-one oxime (548 mg, 1.25 mmol) and sodium carbonate (633 mg, 5.02 mmol) in acetone (20 mL) and water (20 mL). The reaction mixture was stirred at RT overnight, then was partitioned between water (20 mL) and EtOAc. The aqueous layer was extracted with EtOAc. The combined organic extracts were washed with brine (30 mL), dried (Na$_2$SO$_4$) and concentrated. The residue was purified by chromatography on silica (solvent gradient 0-40% EtOAc in cyclohexane) to afford the title compound (387 mg, 52%) as a colorless foam. LCMS (ESI) [M+H]$^+$ 590.0/593.9.

Step 3: 5'-Bromo-4'-chloro-1'-(4-methoxybenzyl)-1',2'-dihydrospiro[piperidine-4,3'-pyrrolo[2,3-b]pyridin]-2-one and 5'-bromo-4'-chloro-1'-(4-methoxybenzyl)-1',2'-dihydrospiro[piperidine-3,3'-pyrrolo[2,3-b]pyridin]-6-one

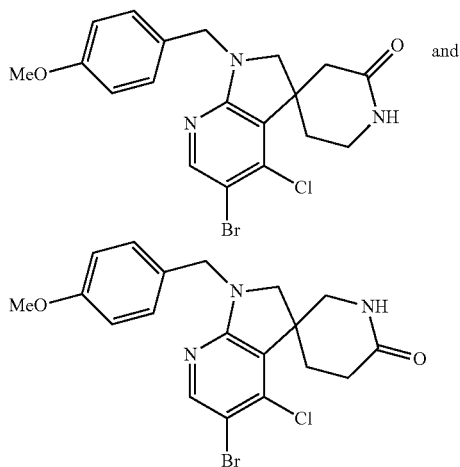

Sodium carbonate (326 mg, 2.59 mmol) in water (7 mL) was added to a solution of 5'-bromo-4'-chloro-1'-(4-methoxybenzyl)-1',2'-dihydrospiro[cyclopentane-1,3'-pyrrolo[2,3-b]pyridin]-3-one O-tosyl oxime (382 mg, 0.65 mmol) in acetone (7 mL). The reaction mixture was vigorously stirred and heated at 70° C. for 18 h. The cooled mixture was partitioned between water (20 mL) and EtOAc. The aqueous layer was extracted with EtOAc. The combined organic extracts were washed with brine, dried (Na₂SO₄) and concentrated. The residue was purified by chromatography on silica (solvent gradient 0-5% MeOH·NH₃ in DCM) to afford the title compounds (232 mg, 82%) as a brown foam. LCMS (ESI) [M+H]⁺ 435.9/439.9.

Step 4: 5'-Bromo-4'-chloro-1',2'-dihydrospiro[piperidine-4,3'-pyrrolo[2,3-b]pyridin]-2-one and 5'-bromo-4'-chloro-1',2'-dihydrospiro[piperidine-3,3'-pyrrolo[2,3-b]pyridin]-6-one

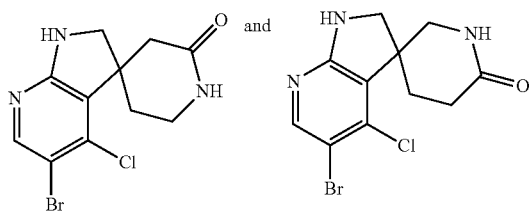 [SMILES: O=C1CC2(CCN1)CNc1ncc(Br)c(Cl)c12 ; "and" ; O=C1CCC2(CN1)CNc1ncc(Br)c(Cl)c12]

A mixture of 5'-bromo-4'-chloro-1'-(4-methoxybenzyl)-1',2'-dihydrospiro[piperidine-4,3'-pyrrolo[2,3-b]pyridin]-2-one and 5'-bromo-4'-chloro-1'-(4-methoxybenzyl)-1',2'-dihydrospiro[piperidine-3,3'-pyrrolo[2,3-b]pyridin]-6-one (232 mg, 0.530 mmol) in TFA (1 mL) was heated in a sealed tube at 75° C. for 18 h. The cooled mixture was dried in vacuo and the residue passed down a SCX-2 cartridge (eluting with MeOH followed by MeOH·NH₃). The resulting brown gum was purified by chromatography on silica (solvent gradient 0-10% MeOH·NH₃ in DCM) to afford the title compounds (67 mg, 40%) as a colorless solid. LCMS (ESI) [M+H]⁺ 315.9/319.8.

Example 152

(1r,4r)-5'-Bromo-4'-methoxy-1',2'-dihydrospiro[cyclohexane-1,3'-pyrrolo[2,3-b]pyrdin]-4-ol and (1s,4s)-5"-bromo-4'-methoxy-1',2'-dihydrospiro[cyclohexane-1,3'-pyrrolo[2,3-b]pyrdin]-4-ol

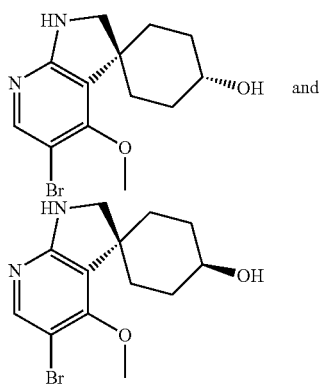

Step 1: Dimethyl 3,3'-(5-bromo-4-methoxy-2-oxo-1-((2-(trimethylsilyl)ethoxy)methyl)-2,3-dihydro-1H-pyrrolo[2,3-b]pyridine-3,3-diyl)dipropionate

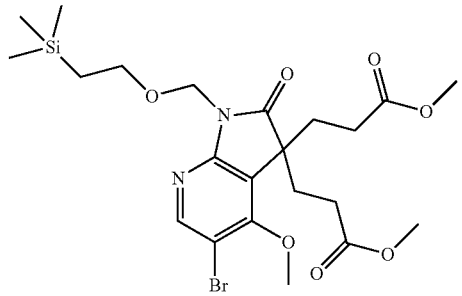

The title compound was prepared by an analogous method to that described for the preparation of dimethyl 3,3'-(5-bromo-4-chloro-2-oxo-1-((2-(trimethylsilypethoxy)methyl)-2,3-dihydro-1H-pyrrolo[2,3-b]pyridine-3,3-diyl)dipropionate. LCMS (ESI) [M+Na]⁺ 567/569.

Step 2: Dimethyl 3,3'-(5-bromo-4-methoxy-2-oxo-2,3-dihydro-1H-pyrrolo[2,3-b]pyridine-3,3-diyl)dipropionate

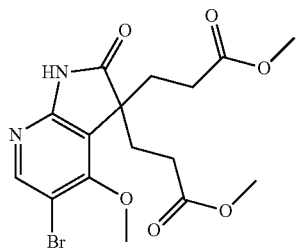 [SMILES: COC(=O)CCC1(CCC(=O)OC)C(=O)Nc2ncc(Br)c(OC)c21]

The title compound was prepared by a method analogous to that described for the preparation of dimethyl 3,3'-(5-bromo-4-chloro-2-oxo-2,3-dihydro-1H-pyrrolo[2,3-b]pyridine-3,3-diyl)dipropionate. LCMS (ESI) [M+Na]⁺ 437/439.

Step 3: 5'-Bromo-4'-methoxyspiro[cyclohexane-1,3'-pyrrolo[2,3-b]pyridine]-2',4(1'H)-dione

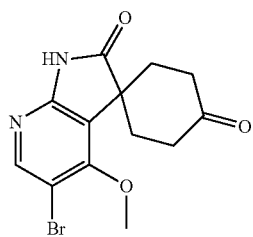 [SMILES: COc1c(Br)cnc2c1C1(CCC(=O)CC1)C(=O)N2]

Potassium tert-butoxide (0.614 g, 5.47 mmol) was added to a solution of dimethyl 3,3'-(5-bromo-4-methoxy-2-oxo-2,3-dihydro-1H-pyrrolo[2,3-b]pyridine-3,3-diyl)dipropionate (0.733 g, 1.77 mmol) in DMSO (3 mL). The reaction mixture was stirred at RT for 30 min then heated to 80° C. for 10 min. After recooling to RT, water (15 mL) was added and the mixture stirred at 85° C. for 30 min. The cooled mixture was partitioned between EtOAc and water. The aqueous phase was extracted with more EtOAc. The combined organic extracts were washed with water, brine, dried (Na₂SO₄) and evaporated. The residue was purified by chromatography on silica (solvent gradient 2-10% MeOH in DCM) to afford the title compound (0.062 g, 11%) as a colorless gum. LCMS (ESI) [M+H]⁺ 325/327.

Step 4: (1r,4r)-5'-Bromo-4'-methoxy-1',2'-dihydrospiro[cyclohexane-1,3'-pyrrolo[2,3-b]pyrdin]-4-ol and (1s,4s)-5'-bromo-4'-methoxy-1',2'-dihydrospiro[cyclohexane-1,3'-pyrrolo[2,3-b]pyridin]-4-ol

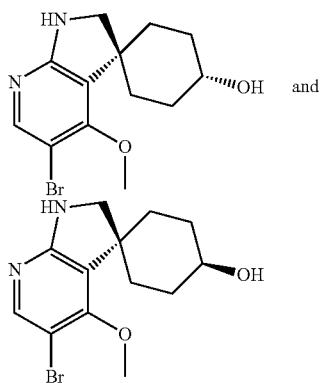

To an ice-cooled suspension of 5'-bromo-4'-methoxyspiro[cyclohexane-1,3'-pyrrolo[2,3-b]pyridine]-2',4(1'H)-dione (0.282 g, 0.87 mmol) in DCM (4 mL) was added DIBAL (1N in DCM, 8.67 mL, 8.67 mmol) over 15 min. The mixture was stirred at RT for 16 h. After cooling in an ice bath, MeOH (3 mL) was added dropwise. The mixture was diluted with DCM, then filtered through a silica cartridge (eluting with 2-15% MeOH in DCM). The residue was purified by chromatography on silica (solvent gradient 0-100% MeOAc in EtOAc, then 0-5% MeOH in MeOAc) to afford (1r,4r)-5'-bromo-4'-methoxy-1',2'-dihydrospiro[cyclohexane-1,3'-pyrrolo[2,3-b]pyridin]-4-ol (0.064 g, 24%) as a colorless gum. LCMS (ESI) [M+H]⁺ 313/315. Later fractions gave (1s,4s)-5'-bromo-4'-methoxy-1',2'-dihydrospiro[cyclohexane-1,3'-pyrrolo[2,3-b]pyridin]-4-ol (0.103 g, 38%) as a white solid. LCMS (ESI) [M+H]⁺ 313/315.

Example 153: General Method E

5'-Bromo-4'-chloro-2-propyl-1',2'-dihydrospiro[cyclopropane-1,3'-pyrrolo[2,3-b]pyridine]

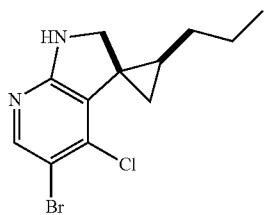 [SMILES: CCC[C@H]1C[C@@]12CNc1ncc(Br)c(Cl)c12]

Step 1: 5'-Bromo-4'-chloro-2-propyl-1'-((2-(trimethylsilyl)ethoxy)methyl)spiro[cyclopropane-1,3'-pyrrolo[2,3-b]pyridin]-2'(1'H)-one

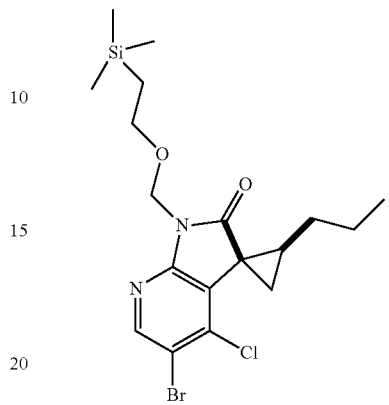

A mixture of 5-bromo-4-chloro-1-(2-trimethylsilylethoxymethyl)-3H-pyrrolo[2,3-b]pyridin-2-one (1 g, 2.65 mmol), trimethylsulfoxonium iodide (640 mg, 2.91 mmol), 1,3,4,6,7,8-hexahydro-1-methyl-2H-pyrimidol[1,2-a]pyrimidine (0.76 mL, 5.29 mmol) and butyraldehyde (0.36 mL, 3.97 mmol) in MeCN (9 mL) were stirred under argon in a sealed tube. 1-Methylpiperazine (0.03 mL, 0.26 mmol) was added and the reaction was stirred at RT for 30 min then at 60° C. for 1.5 h. The reaction mixture was diluted with water and extracted with EtOAc. The combined organic fractions were washed with brine, dried (MgSO₄) and concentrated. The residue was purified by chromatography on silica (solvent gradient 0-30% EtOAc in cyclohexane) to afford the title compound (630 mg, 53%) as a red oil. LCMS (ESI) [M+Na]⁺ 467/469.

Step 2: 5'-Bromo-4'-chloro-2-propylspiro[cyclopropane-1,3'-pyrrolo[2,3-b]pyridin]-2'(1'H)-one

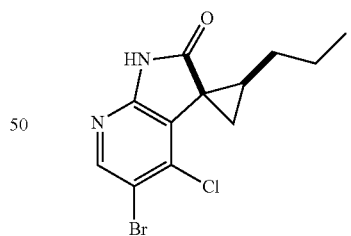

To a solution of 5'-bromo-4'-chloro-2-propyl-1'-((2-(trimethylsilyl)ethoxy)methyl)spiro[cyclopropane-1,3'-pyrrolo[2,3-b]pyridin]-2'(1'H)-one (630 mg, 1.41 mmol) in DCM (3 mL) was added TFA (2 mL). The reaction mixture was stirred at RT for 1 h, then was concentrated in vacuo. The residue was azeotroped with toluene (×3), dissolved in 2N MeOH·NH₃ (2 mL) and stirred at RT for 1 h. The reaction mixture was concentrated to give the product as an off-white solid, which was used crude in the next step (499 mg, assume quantitative) LCMS (ESI) [M+H]⁺ 315/319.

Step 3: 5'-Bromo-4'-chloro-2-propyl-1',2'-dihy-
drospiro[cyclopropane-1,3'-pyrrolo[2,3-b]pyridine]

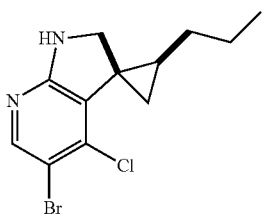 [SMILES: CCC[C@H]1C[C@@]12CNc1ncc(Br)c(Cl)c12]

To a suspension of 5'-bromo-4'-chloro-2-propylspiro[cy-clopropane-1,3'-pyrrolo[2,3-b]pyridin]-2'(1'H)-one (1.41 mmol) in DCM (5 mL) at 0° C. was slowly added DIBAL 1M in DCM (15.81 mL, 15.81 mmol) causing the solids to dissolve and effervescence to occur. The yellow solution was stirred at RT for 16 h. The reaction was cooled to 0° C. and water (0.7 mL) carefully added, followed by 15% aq. NaOH (0.7 mL) and water (1 mL). The reaction was stirred at RT for 30 min then MgSO$_4$ added and the mixture stirred for 30 min. The mixture was filtered and the filtrate concentrated in vacuo. The residue was purified by chromatography on silica (solvent gradient 0-50% EtOAc in cyclohexane) to afford the title compound (245 mg, 58%) as a colorless oil which solidified on standing. LCMS (ESI) [M+H]$^+$ 301/303.

The following intermediates were prepared using procedures described in Method E:

Example 153b

5'-Bromo-2-ethyl-1',2'-dihydrospiro[cyclopropane-1,3'-pyrrolo[2,3-b]pyridine]

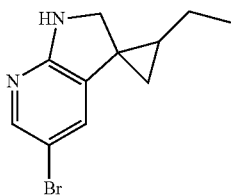

The title compound was prepared according to General Method E, starting from 5-bromo-1,3-dihydro-1-[[2-(trimethyl silyl)ethoxy]methyl]-2H-pyrrolo[2,3-b]pyrdin-2-one and propionaldehyde. LCMS (ESI) [M+H]$^+$ 253/255.

Example 153c (1RS,2SR)-5'-Bromo-2-propyl-1',2'-dihydrospiro
[cyclopropane-1,3'-pyrrolo[2,3-b]pyridine] and
(1RS,2RS)-5'-bromo-2-propyl-1',2'-dihydrospiro
[cyclopropane-1,3'-pyrrolo[2,3-b]pyridine]

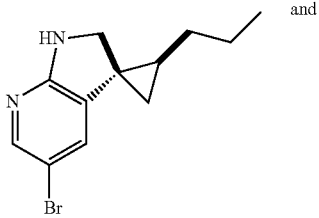

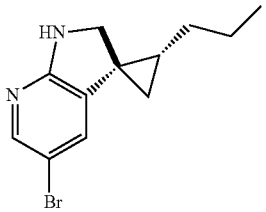

The title compounds were prepared according the General Method E, starting from 5-bromo-1,3-dihydro-1-[ [2-(trimethyl silyl)ethoxy]methyl]-2H-pyrrolo[2,3-b]pyrdin-2-one and butyraldehyde. LCMS (ESI) [M+H]$^+$ 267/269.

Example 153d (1RS,2RS)-5'-Bromo-2-isopropyl-1',2'-dihydrospiro
[cyclopropane-1,3'-pyrrolo[2,3-b]pyridine] and
(1RS,2SR)-5'-bromo-2-isopropyl-1',2'-dihydrospiro
[cyclopropane-1,3'-pyrrolo[2,3-b]pyridine]

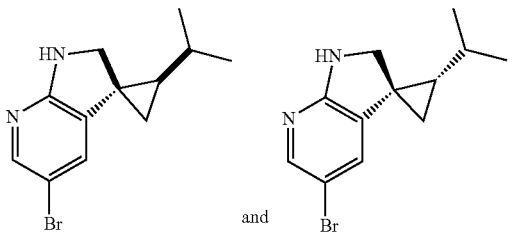

The title compounds were prepared according the General Method E, starting from 5-bromo-1,3-dihydro-1-[[2-(trimethyl silyl)ethoxy]methyl]-2H-pyrrolo[2,3-b]pyrdin-2-one and isobutyraldehyde. LCMS (ESI) [M+H]$^+$ 267/269.

Example 153e (1RS,2SR)-5'-Bromo-4'-chloro-2-methyl-1',2'-dihydrospiro[cyclopropane-1,3'-pyrrolo[2,3-b]pyridine]

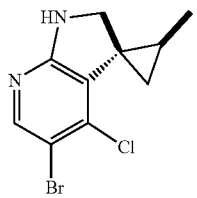

The title compound was prepared according the General Method E, starting from 5-bromo-4-chloro-1-(2-trimethylsilylethoxymethyl)-3H-pyrrolo[2,3-b]pyridin-2-one and acetaldehyde. ¹H NMR (400 MHz, CDCl₃) δ ppm 7.84 (s, 1H), 3.76 (dd, J=9.0, 1.6 Hz, 1H), 3.47 (dd, J=9.0, 1.0 Hz, 1H), 2.15-2.06 (m, 1H), 1.95 (dd, J=9.3, 4.9 Hz, 1H), 1.13 (d, J=6.3 Hz, 3H), 0.40 (t, J=5.5 Hz, 1H).

Example 153f (1RS,2SR)-5'-Bromo-4'-chloro-2-ethyl-1',2'-dihydrospiro[cyclopropane-1,3'-pyrrolo[2,3-b]pyrdine] and (1RS,2RS)-5'-bromo-4'-chloro-2-ethyl-1',2'-dihydrospiro[cyclopropane-1,3'-pyrrolo[2,3-b]pyridine]

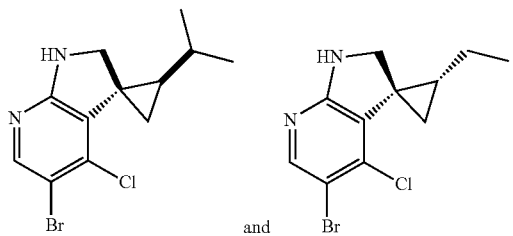 [SMILES: CC(C)[C@H]1C[C@@]12CNc1ncc(Br)c(Cl)c12 ; CC[C@@H]1C[C@@]12CNc1ncc(Br)c(Cl)c12]

The title compounds were prepared according to General Method E, starting from 5-bromo-4-chloro-1-((2-(trimethylsilylypethoxy)methyl)-1,3-dihydro-2H-pyrrolo[2,3-b]pyridin-2-one and propionaldehyde. LCMS (ESI) [M+H]⁺ 287.0/289.0/291.0.

Example 153g (1RS,2RS)-5'-Bromo-4'-chloro-2-isopropyl-1',2'-dihydrospiro[cyclopropane-1,3'-pyrrolo[2,3-b]pyridine]

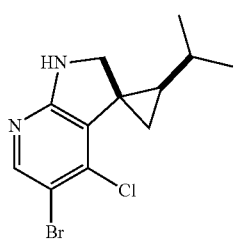

The title compound was prepared according the General Method E, starting from 5-bromo-4-chloro-1-((2-(trimethylsilylypethoxy)methyl)-1,3-dihydro-2H-pyrrolo[2,3-b]pyridin-2-one and isobutyraldehyde. LCMS (ESI) [M+Na]⁺ 301/303.

Example 153h (1RS,2SR)-5'-Bromo-4'-methoxy-2-methyl-1',2'-dihydrospiro[cyclopropane-1,3'-pyrrolo[2,3-b]pyridine]

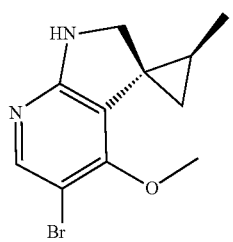

The title compound was prepared according to General Method E, starting from 5-bromo-4-methoxy-1-((2-(trimethyl silyl)ethoxy)methyl)-1,3-dihydro-2H-pyrrolo[2,3-b]pyrdin-2-one and acetaldehyde. LCMS (ESI) [M+H]⁺ 269.0/271.0.

Example 154: General Method F (1RS,2RS)-5'-Bromo-4'-chloro-2-phenyl-1',2'-dihydrospiro[cyclopropane-1,3'-pyrrolo[2,3-b]pyridine]

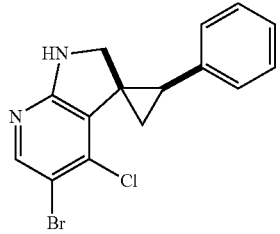

Step 1: (Z)-3-Benzylidene-5-bromo-4-chloro-1-((2-(trimethylsilyl)ethoxy)methyl)-1,3-dihydro-2H-pyrrolo[2,3-b]pyridin-2-one

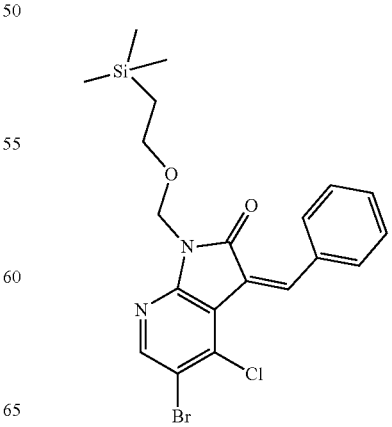

A solution of 5-bromo-4-chloro-1-((2-(trimethylsilypethoxy)methyl)-1,3-dihydro-2H-pyrrolo[2,3-b]pyridin-2-one (600 mg, 1.59 mmol), benzaldehyde (0.32 mL, 3.18 mmol) and 1-methylpiperazine (0.07 mL, 0.64 mmol) in toluene (10 mL) was stirred at RT for 2 days. The reaction mixture was concentrated in vacuo and the residue was purified by chromatography on silica (solvent gradient 0-30% EtOAc in cyclohexane) to afford the title compound. $^1$H NMR (400 MHz, CDCl$_3$) δ8.61 (s, 1H), 8.38 (s, 1H), 8.20-8.12 (m, 2H), 7.54-7.45 (m, 3H), 5.33 (s, 2H), 3.73-3.65 (m, 2H), 1.02-0.94 (m, 2H), 0.00 (s, 9H).

Step 2: (1RS,2RS)-5'-Bromo-4'-chloro-2-phenyl-1'-((2-(trimethylsilyl)ethoxy)methyl)spiro[cyclopropane-1,3'-pyrrolo[2,3-b]pyrdin]-2'(1'H)-one

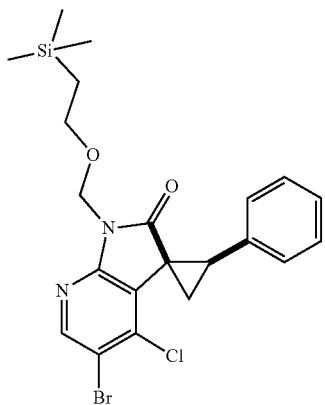 [SMILES: C[Si](C)(C)CCOCN1C(=O)[C@@]2(C[C@@H]2c2ccccc2)c2c1ncc(Br)c2Cl]

To a solution of trimethylsulfoxonium iodide (358 mg, 1.63 mmol) in DMF (8 mL) was added sodium hydride (60% in oil, 77 mg, 1.93 mmol). The reaction mixture was stirred at RT for 20 min then cooled to 0° C. A solution of ((Z)-3-benzylidene-5-bromo-4-chloro-1-((2-(trimethylsilypethoxy)methyl)-1,3-dihydro-2H-pyrrolo[2,3-b]pyridin-2-one (690 mg, 1.48 mmol) in THF (16 mL) was added, causing a precipitate to form. The reaction mixture was stirred at 0° C. for 10 min, then diluted with water and extracted with EtOAc. The combined organic extracts were washed with brine, dried (MgSO$_4$) and concentrated. The residue was purified by chromatography on silica (solvent gradient 0-50% Et$_2$O in cyclohexane) to afford the title compound (458 mg, 64%). LCMS (ESI) [M+Na]$^+$ 501/503.

Step 3: (1RS,2RS)-5'-Bromo-4'-chloro-2-phenylspiro[cyclopropane-1,3'-pyrrolo[2,3-b]pyridin]-ol

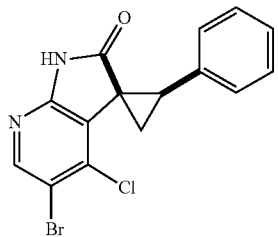 [SMILES: O=C1Nc2ncc(Br)c(Cl)c2[C@]12C[C@@H]2c1ccccc1]

To a solution of (1RS,2RS)-5'-bromo-4'-chloro-2-phenyl-1-1'-((2-(trimethylsilypethoxy)methyl)spiro[cyclopropane-1,3'-pyrrolo[2,3-b]pyridin]-2'(1'H)-one (1.01 g, 2.1 mmol) in DCM (10 mL) was added TFA (2 mL). The reaction mixture was stirred at RT for 30 min, then concentrated in vacuo. The residue was azeotroped with toluene, dissolved in MeOH·NH$_3$ (3 mL), and stirred at RT for 30 min, during which a precipitate formed. The reaction mixture was concentrated in vacuo and the residue triturated with MeOH to give the title compound (315 mg, 42%) as an off white solid. LCMS (ESI) [M+H]$^+$ 349/351.

Step 4: (1RS,2RS)-5'-Bromo-4'-chloro-2-phenyl-1',2'-dihydrospiro[cyclopropane-1,3'-pyrrolo[2,3-b]pyridine]

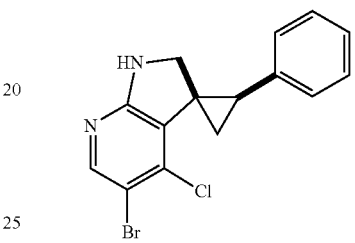

To a suspension of (1RS,2RS)-5'-bromo-4'-chloro-2-phenylspiro[cyclopropane-1,3'-pyrrolo[2,3-b]pyridin]-2'(1'H)-one (315 mg, 0.90 mmol) in DCM (10 mL) at 0° C. was added DIBAL (1M in DCM, 9.01 mL, 9.01 mmol). The reaction mixture was stirred whilst warming from 0° C. to RT over 16 h, then cooled to 0° C., diluted with Et$_2$O and quenched with water (0.4 mL), 15% aq NaOH (0.4 mL) and water (0.9 mL). MgSO$_4$ was added and the reaction mixture filtered. The filtrate was concentrated in vacuo and purified by chromatography on silica (solvent gradient 0-50% EtOAc in cyclohexane) to afford the title product (180 mg, 59%) as a white solid. LCMS (ESI) [M+H]$^+$ 335/337.

The following intermediates were prepared using procedures described in Method F:

Example 154b (1RS,2RS)-5'-Bromo-4'-chloro-2-(pyridin-4-yl)-1',2'-dihydrospiro[cyclopropane-1,3'-pyrrolo[2,3-b]pyridine]

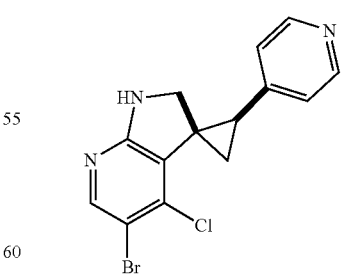

The title compound was prepared according the general Method F, starting from 5-bromo-4-chloro-1-((2-(trimethylsilypethoxy)methyl)-1,3-dihydro-2H-pyrrolo[2,3-b]pyrdin-2-one and isonicotinaldehyde. LCMS (ESI) [M+H]$^+$ 336/338.

Example 155: General Method G 1-((1RS,3SR)-5'-Bromo-4'-chloro-1',2'-dihydrospiro[cyclopentane-1,3'-pyrrolo[2,3-b]pyridin]-3-yl)-1H-1,2,4-triazol-5-amine and 1-((1RS,3SR)-5'-bromo-4'-chloro-1',2'-dihydrospiro[cyclopentane-1,3'-pyrrolo[2,3-b]pyridin]-3-yl)-1H-1,2,4-triazol-3-amine

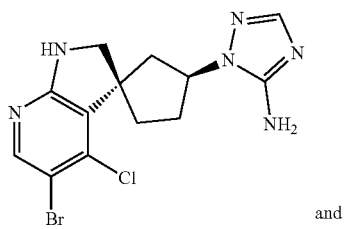

and

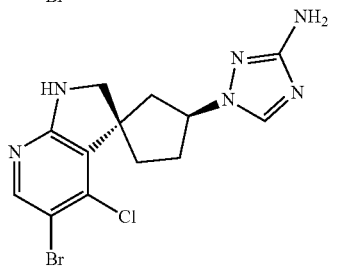

Step 1: 1-((1RS,3SR)-5'-Bromo-4'-chloro-1'-(4-methoxybenzyl)-1',2'-dihydrospiro[cyclopentane-1,3'-pyrrolo[2,3-b]pyridin]-3-yl)-1H-1,2,4-triazol-5-amine and 1-((1RS,3SR)-5'-bromo-4'-chloro-1'-(4-methoxybenzyl)-1',2'-dihydrospiro[cyclopentane-1,3'-pyrrolo[2,3-b]pyrdin]-3-yl)-1H-1,2,4-triazol-3-amine

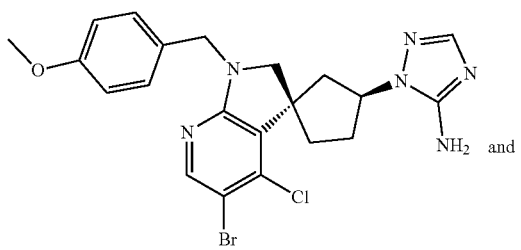

and

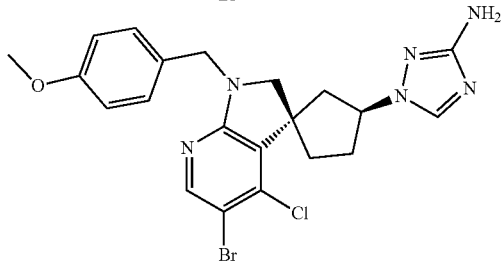

Sodium hydride (60% in oil, 19.6 mg, 0.49 mmol) was added to a solution of 1H-1,2,4-triazol-5-amine (41 mg, 0.49 mmol) in DMF (1 mL). The mixture was stirred at RT for 15 min then a solution of (1RS,3RS)-5'-bromo-4'-chloro-1'-(4-methoxybenzyl)-1',2'-dihydrospiro[cyclopentane-1,3'-pyrrolo[2,3-b]pyridin]-3-yl methanesulfonate (0.123 g, 0.25 mmol) in DMF (1 mL) was added. The mixture was heated at 100° C. for 1 h, then allowed to cool and partitioned between EtOAc and aq. sodium bicarbonate. The aqueous phase was extracted with more EtOAc and the combined organic extracts were washed with water, brine, dried (Na$_2$SO$_4$) and evaporated. The residue was purified by chromatography on silica (solvent gradient 2-10% MeOH·NH$_3$ in DCM) to afford a mixture of the title compounds (0.102 g, 85%) as colorless gum. LCMS (ESI) [M+H]$^+$ 489/491/493.

Step 2: 1-((1RS,3SR)-5'-Bromo-4'-chloro-1',2'-dihydrospiro[cyclopentane-1,3'-pyrrolo[2,3-b]pyridin]-3-yl)-1H-1,2,4-triazol-5-amine and 1-((1RS,3SR)-5'-bromo-4'-chloro-1',2'-dihydrospiro[cyclopentane-1,3'-pyrrolo[2,3-b]pyrdin]-3-yl)-1H-1,2,4-triazol-3-amine

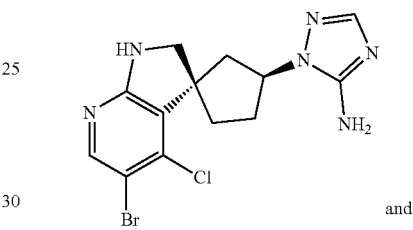

and

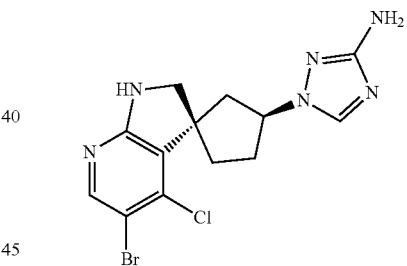

A mixture of 1-((1RS,3SR)-5'-bromo-4'-chloro-1'-(4-methoxybenzyl)-1',2'-dihydrospiro[cyclopentane-1,3'-pyrrolo[2,3-b]pyridin]-3-yl)-1H-1,2,4-triazol-5-amine and 1-((1RS,3SR)-5'-bromo-4'-chloro-1'-(4-methoxybenzyl)-1',2'-dihydrospiro[cyclopentane-1,3'-pyrrolo[2,3-b]pyridin]-3-yl)-1H-1,2,4-triazol-3-amine (0.16 g, 0.33 mmol) in TFA (3 mL) and anisole (0.3 mL) was stirred at 80° C. for 16 h. Toluene was added and evaporated (2×). The residue was passed through a SCX-2 cartridge (eluting with MeOH then MeOH·NH$_3$). The resulting residue was purified by chromatography on silica (solvent gradient 2-10% MeOH·NH$_3$ in DCM) to afford a mixture of the title compounds (0.101 g, 84%) as a colorless foam. LCMS (ESI) [M+H]$^+$ 369/371/373.

Example 155b (1s,3s)-5'-Chloro-3-(1H-1,2,4-triazol-1-yl)-1',2'-dihydrospiro[cyclobutane-1,3'-pyrrolo[2,3-b]pyridine]

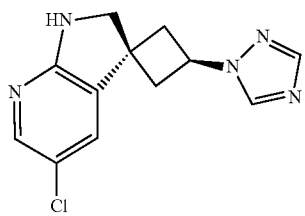 [SMILES: Clc1cnc2c(c1)[C@]1(CN2)C[C@@H](n2cncn2)C1]

The title compound was prepared according to general Method G, starting from (1r,3r)-5'-chloro-1'-(4-methoxybenzyl)-1',2'-dihydrospiro[cyclobutane-1,3'-pyrrolo[2,3-b]pyridin]-3-yl methanesulfonate and 1,2,4-triazole. LCMS (ESI) [M+H]$^+$ 261.

Example 155c 3-((1H-1,2,4-Triazol-1-yl)methyl)-5'-bromo-4'-chloro-1', 2'-dihydrospiro[cyclopentane-1,3'-pyrrolo[2,3-b]pyridine]

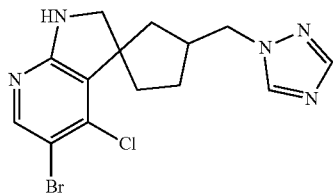 [SMILES: Clc1c(Br)cnc2c1C1(CCC(Cn3cncn3)C1)CN2]

The title compound was prepared according to general Method G, starting from 5'-bromo-4'-chloro-1'-(4-methoxybenzyl)-1',2'-dihydrospiro[cyclopentane-1,3'-pyrrolo[2,3-b]pyridin]-3-yl)methyl methanesulfonate and 1,2,4-triazole. LCMS (ESI) [M+H]$^+$ 368/370/372.

Example 155d (1RS,3SR)-3-((1H-1,2,4-Triazol-1-yl)methyl)-5'-bromo-4'-chloro-1',2'-dihydrospiro[cyclopentane-1,3'-pyrrolo[2,3-b]pyridin]-3-ol

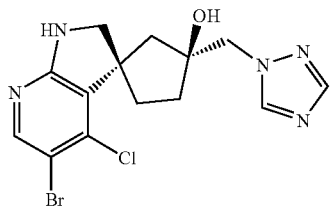 [SMILES: O[C@@]1(Cn2cncn2)CC[C@@]2(CNc3ncc(Br)c(Cl)c32)C1]

The title compound was prepared according to general Method G, starting from (2RS,3'SR)-5''-bromo-4''-chloro-1''-(4-methoxybenzyl)-1'',2''-dihydrodispiro[oxirane-2,1'-cyclopentane-3',3''-pyrrolo[2,3-b]pyridine] and 1,2,4-triazole. LCMS (ESI) [M+H]$^+$ 384/386/388.

Example 155e (1RS,3RS)-3-((1H-1,2,4-Triazol-1-yl)methyl)-5'-bromo-4'-chloro-1',2'-dihydrospiro[cyclopentane-1,3'-pyrrolo[2,3-b]pyridin]-3-ol

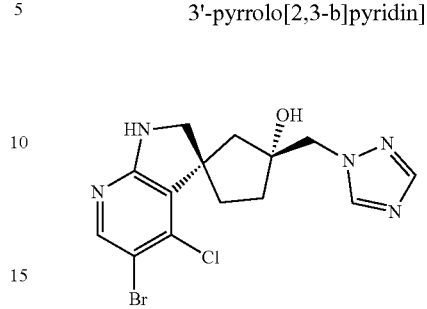

The title compound was prepared according to general Method G, starting from (2RS,3'RR)-5''-bromo-4''-chloro-1''-(4-methoxybenzyl)-1'',2''-dihydrodispiro[oxirane-2,1'-cyclopentane-3',3''-pyrrolo[2,3-b]pyridine] and 1,2,4-triazole. LCMS (ESI) [M+H]$^+$ 384/386/388.

Example 155f (1RS,3SR)-3-((1H-Imidazol-1-yl)methyl)-5'-bromo-4'-chloro-1',2'-dihydrospiro[cyclopentane-1,3'-pyrrolo[2,3-b]pyridin]-3-ol

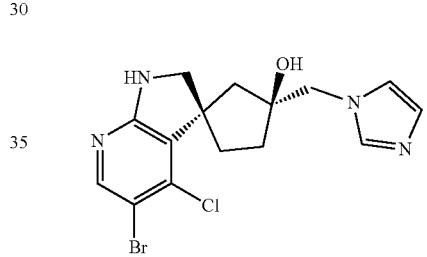

The title compound was prepared according to general Method G, starting from (2RS,3'SR)-5''-bromo-4''-chloro-1''-(4-methoxybenzyl)-1'',2''-dihydrodispiro[oxirane-2,1'-cyclopentane-3',3''-pyrrolo[2,3-b]pyridine] and Boc-imidazole. LCMS (ESI) [M+H]$^+$ 383/385/387.

Example 155g (1RS,3SR)-5'-Bromo-4'-chloro-3-(1H-1,2,4-triazol-1-yl)-1',2'-dihydrospiro[cyclopentane-1,3'-pyrrolo[2,3-b]pyridine]

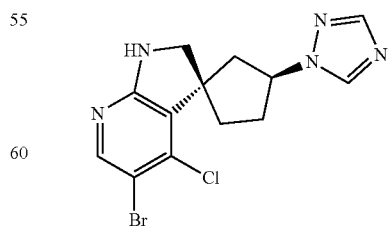

The compound was prepared according to general Method G, starting from (1RS,3RS)-5'-bromo-4'-chloro-1'-(4-methoxybenzyl)-1',2'-dihydrospiro[cyclopentane-1,3'-pyrrolo[2,3-b]pyridin]-3-yl methanesulfonate and 1,2,4-triazole. LCMS (ESI) [M+H]+ 354/356/358.

Example 155h (1RS,3SR)-5'-Bromo-4'-chloro-3-(2H-1,2,3-triazol-2-yl)-1',2'-dihydrospiro[cyclopentane-1,3'-pyrrolo[2,3-b]pyridine], (1RS,3RS)-5'-Bromo-4'-chloro-3-(2H-1,2,3-triazol-2-yl)-1',2'-dihydrospiro[cyclopentane-1,3'-pyrrolo[2,3-b]pyridine], (1RS,3SR)-5'-bromo-4'-chloro-3-(1H-1,2,3-triazol-1-yl)-1',2'-dihydrospiro[cyclopentane-1,3'-pyrrolo[2,3-b]pyridine] and (1RS,3RS)-5'-bromo-4'-chloro-3-(1H-1,2,3-triazol-1-yl)-1',2'-dihydrospiro[cyclopentane-1,3'-pyrrolo[2,3-b]pyridine]

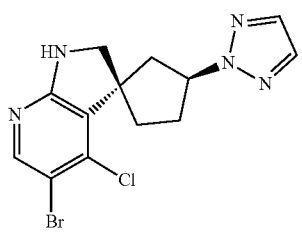

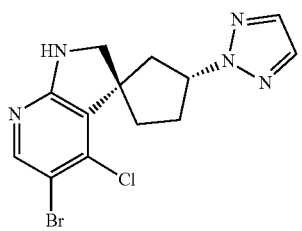

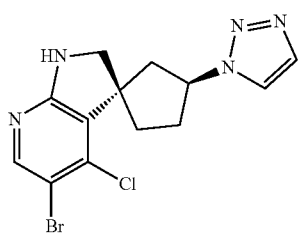

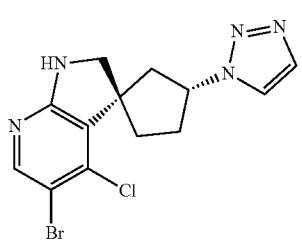

The title compounds were prepared according to general Method G, starting from 5'-bromo-4'-chloro-1'-(4-methoxybenzyl)-1',2'-dihydrospiro[cyclopentane-1,3'-pyrrolo[2,3-b]pyridin]-3-yl methanesulfonate and 1H-1,2,3-triazole. LCMS (ESI) [M+H]+ 354/356/358.

Example 155i (1RS,3SR)-5'-Bromo-4'-chloro-3-(4-methyl-2H-1,2,3-triazol-2-yl)-1',2'-dihydrospiro[cyclopentane-1,3'-pyrrolo[2,3-b]pyridine]

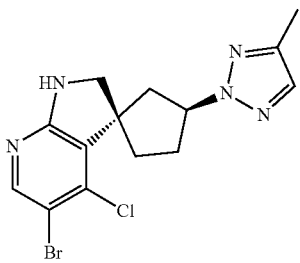 [SMILES: Cc1cnn([C@H]2CC[C@@]3(CNc4ncc(Br)c(Cl)c43)C2)n1]

The title compound was prepared according to general Method G, starting from (1RS,3RS)-5'-bromo-4'-chloro-1'-(4-methoxybenzyl)-1',2'-dihydrospiro[cyclopentane-1,3'-pyrrolo[2,3-b]pyridin]-3-yl methanesulfonate and 4-methyl 1H-1,2,3-triazole. LCMS (ESI) [M+H]+ 368/370/370.

Example 155j (1RS,3SR)-5'-Bromo-4'-chloro-3-(4-methyl-1H-pyrazol-1-yl)-1',2'-dihydrospiro[cyclopentane-1,3'-pyrrolo[2,3-b]pyridine]

The title compound was prepared according to general Method G, starting from (1RS,3RS)-5'-bromo-4'-chloro-1'-(4-methoxybenzyl)-1',2'-dihydrospiro[cyclopentane-1,3'-pyrrolo[2,3-b]pyridin]-3-yl methanesulfonate and 4-methylpyrazole. LCMS (ESI) [M+H]+ 367/369/371.

Example 155k (1RS,3SR)-5'-Bromo-4'-chloro-3-(1H-pyrazol-1-yl)-1',2'-dihydrospiro[cyclopentane-1,3'-pyrrolo[2,3-b]pyridine]

The title compound was prepared according to general Method G, starting from (1RS,3RS)-5'-bromo-4'-chloro-1'-(4-methoxybenzyl)-1',2'-dihydrospiro[cyclopentane-1,3'-pyrrolo[2,3-b]pyridin]-3-yl methanesulfonate and pyrazole. LCMS (ESI) [M+H]+ 353/355/357.

Example 155l 1-((1RS,3SR)-5'-Bromo-4'-chloro-1',2'-dihydrospiro[cyclopentane-1,3'-pyrrolo[2,3-b]pyrdin]-3-yl)-1H-pyrazol-3-amine and 1-((1RS,3SR)-5'-bromo-4'-chloro-1',2'-dihydrospiro[cyclopentane-1,3'-pyrrolo[2,3-b]pyridin]-3-yl)-1H-pyrazol-5-amine

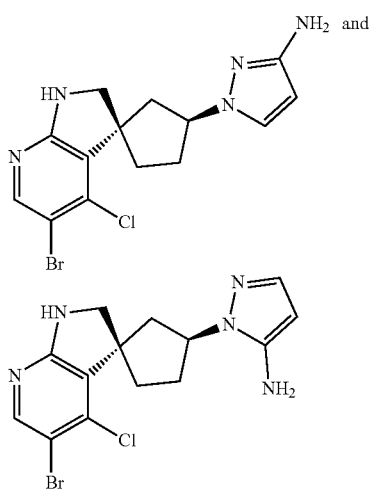

The title compounds were prepared according to general Method G, starting from (1RS,3RS)-5'-bromo-4'-chloro-1'-(4-methoxybenzyl)-1',2'-dihydrospiro[cyclopentane-1,3'-pyrrolo[2,3-b]pyridin]-3-yl methanesulfonate and 3-aminopyrazole. LCMS (ESI) [M+H]+ 368/370/372.

Example 155m 1-((1RS,3SR)-5'-Bromo-4'-chloro-1',2'-dihydrospiro[cyclopentane-1,3'-pyrrolo[2,3-b]pyridin]-3-yl)pyrrolidin-2-one

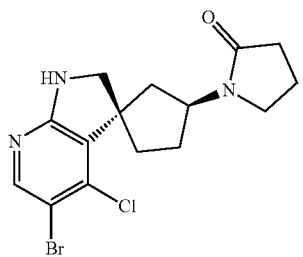 [SMILES: O=C1CCCN1[C@H]1CC[C@@]2(CNc3ncc(Br)c(Cl)c32)C1]

The title compound was prepared according to general Method G, starting from (1RS,3RS)-5'-bromo-4'-chloro-1'-(4-methoxybenzyl)-1',2'-dihydrospiro[cyclopentane-1,3'-pyrrolo[2,3-b]pyridin]-3-yl methanesulfonate and 2-pyrrolidinone. LCMS (ESI) [M+H]+ 370/372/374.

Example 155n 1-((1RS,3SR)-5'-Bromo-4'-chloro-1',2'-dihydrospiro[cyclopentane-1,3'-pyrrolo[2,3-b]pyrdin]-3-yl)-3-methyl-1H-1,2,4-triazol-5-amine and 1-((1RS,3SR)-5'-bromo-4'-chloro-1',2'-dihydrospiro[cyclopentane-1,3'-pyrrolo[2,3-b]pyrdin]-3-yl)-5-methyl-1H-1,2,4-triazol-3-amine

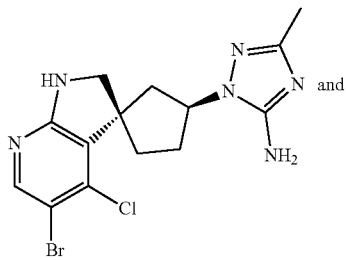

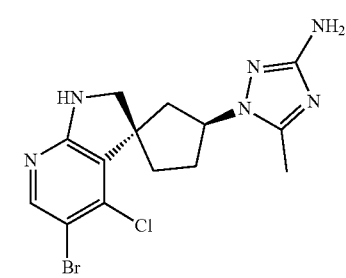

The title compounds were prepared according to general Method G, starting from (1RS,3RS)-5'-bromo-4'-chloro-1'-(4-methoxybenzyl)-1',2'-dihydrospiro[cyclopentane-1,3'-pyrrolo[2,3-b]pyridin]-3-yl methanesulfonate and 3-methyl-1,2,4-triazol-5-amine. LCMS (ESI) [M+H]+ 383/385/387.

Example 155o (1RS,3SR)-5'-Bromo-4'-chloro-3-(3-methyl-1H-pyrazol-1-yl)-1',2'-dihydrospiro[cyclopentane-1,3'-pyrrolo[2,3-130]pyridine] and (1RS,3SR)-5'-bromo-4'-chloro-3-(5-methyl-1H-pyrazol-1-yl)-1',2'-dihydrospiro[cyclopentane-1,3'-pyrrolo[2,3-b]pyridine]

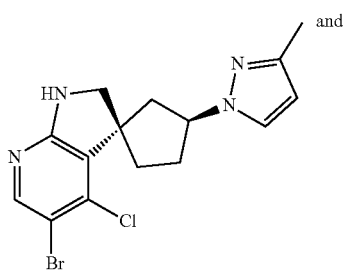

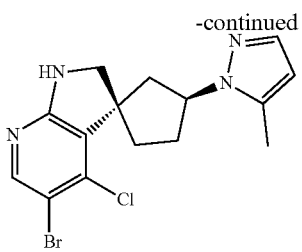

The title compounds were prepared according to general Method G, starting from (1RS,3RS)-5'-bromo-4'-chloro-1'-(4-methoxybenzyl)-1',2'-dihydrospiro[cyclopentane-1,3'-pyrrolo[2,3-b]pyridin]-3-yl methanesulfonate and 3-methylpyrazole. LCMS (ESI) [M+H]⁺ 367/369/371.

Example 155p (1RS,3SR)-5'-Bromo-4'-chloro-3-(3,5-dimethyl-1H-pyrazol-1-yl)-1',2'-dihydrospiro[cyclopentane-1,3'-pyrrolo[2,3-b]pyridine]

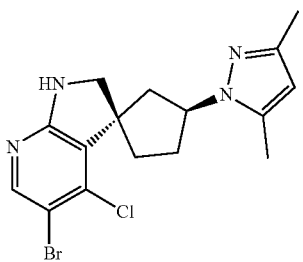 [SMILES: Cc1cc(C)n([C@H]2CC[C@@]3(CNc4ncc(Br)c(Cl)c43)C2)n1]

The title compound was prepared according to general Method G, starting from (1RS,3RS)-5'-bromo-4'-chloro-1'-(4-methoxybenzyl)-1',2'-dihydrospiro[cyclopentane-1,3'-pyrrolo[2,3-b]pyridin]-3-yl methanesulfonate and 3,5-dimethyl-1H-pyrazole. LCMS (ESI) [M+H]⁺ 381/383/385.

Example 155q (1RS,3SR)-5'-Bromo-4'-chloro-3-(4-(trifluoromethyl)-1H-pyrazol-1-yl)-1',2'-dihydrospiro[cyclopentane-1,3'-pyrrolo[2,3-b]pyridine]

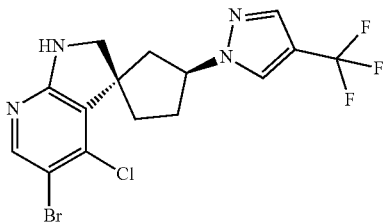 [SMILES: FC(F)(F)c1cnn([C@H]2CC[C@@]3(CNc4ncc(Br)c(Cl)c43)C2)c1]

The title compound was prepared according to general Method G, starting from (1RS,3RS)-5'-bromo-4'-chloro-1'-(4-methoxybenzyl)-1',2'-dihydrospiro[cyclopentane-1,3'-pyrrolo[2,3-b]pyridin]-3-yl methanesulfonate and 4-(trifluoromethyl)-1H-pyrazole. LCMS (ESI) [M+H]⁺ 421/423/425.

Example 155r 1-((1RS,3SR)-5'-Bromo-4'-chloro-1',2'-dihydrospiro[cyclopentane-1,3'-pyrrolo[2,3-b]pyridin]-3-yl)-3-methyl-1H-pyrazole-5-carbonitrile and 1-((1RS,3SR)-5'-bromo-4'-chloro-1',2'-dihydrospiro[cyclopentane-1,3'-pyrrolo[2,3-b]pyridin]-3-yl)-5-methyl-1H-pyrazole-3-carbonitrile

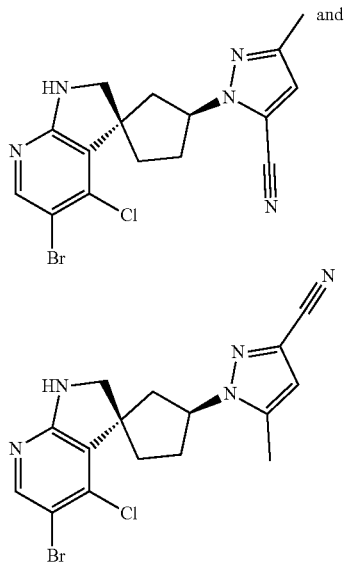

The title compounds were prepared according to general Method G, starting from tert-butyl (1RS,3RS)-5'-bromo-4'-chloro-3-((methylsulfonyl)oxy)spiro[cyclopentane-1,3'-pyrrolo[2,3-b]pyridine]-1'(2'H)-carboxylate and 3-cyano-5-methylpyrazole. The second step was performed in 25% TFA in DCM at RT for 3 h. LCMS (ESI) [M+H]⁺ 392/394/396.

Example 155s (1RS,3SR)-5'-Bromo-4'-chloro-3-(2-methyl-1H-imidazol-1-yl)-1',2'-dihydrospiro[cyclopentane-1,3'-pyrrolo[2,3-b]pyridine]

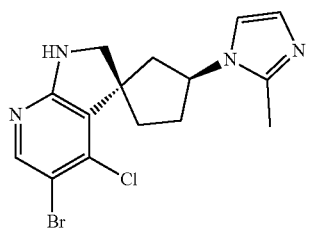 [SMILES: Cc1nccn1[C@H]1CC[C@@]2(CNc3ncc(Br)c(Cl)c32)C1]

The title compound was prepared according to general Method G, starting from (1RS,3RS)-5'-bromo-4'-chloro-1'-(4-methoxybenzyl)-1',2'-dihydrospiro[cyclopentane-1,3'-pyrrolo[2,3-b]pyridin]-3-yl methanesulfonate and 2-methylimidazole. LCMS (ESI) [M+H]⁺ 367/369/371.

Example 155t (1RS,3SR)-5'-Bromo-4'-chloro-3-(3-(trifluoromethyl)-1H-pyrazol-1-yl)-1',2'-dihydrospiro[cyclopentane-1,3'-pyrrolo[2,3-b]pyridine] and (1RS,3SR)-5'-bromo-4'-chloro-3-(5-(trifluoromethyl)-1H-pyrazol-1-yl)-1',2'-dihydrospiro[cyclopentane-1,3'-pyrrolo[2,3-b]pyridine]

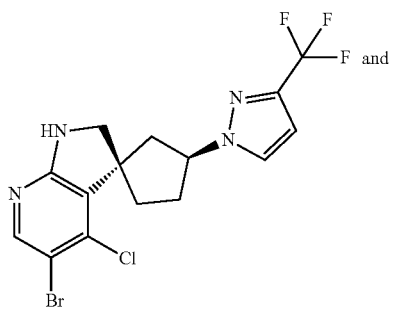

The title compounds were prepared according to general Method G, starting from (1RS,3RS)-5'-bromo-4'-chloro-1'-(4-methoxybenzyl)-1',2'-dihydrospiro[cyclopentane-1,3'-pyrrolo[2,3-b]pyridin]-3-yl methanesulfonate and 3-(trifluoromethyl)-pyrazole. LCMS (ESI) [M+H]⁺ 421/423/425.

Example 155u (1RS,3SR)-5'-Bromo-4'-chloro-3-(4-ethyl-1H-pyrazol-1-yl)-1',2'-dihydrospiro[cyclopentane-1,3'-pyrrolo[2,3-b]pyridine]

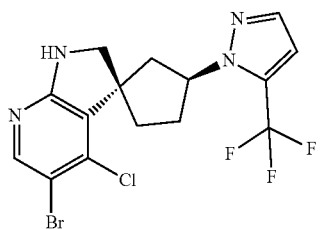

The title compound was prepared according to general Method G, starting from (1RS,3RS)-5'-bromo-4'-chloro-1'-(4-methoxybenzyl)-1',2'-dihydrospiro[cyclopentane-1,3'-pyrrolo[2,3-b]pyridin]-3-yl methanesulfonate and 4-ethylpyrazole. LCMS (ESI) [M+H]⁺ 381/383/385.

Example 155v (1RS,3SR)-5'-Bromo-4'-chloro-3-(4-chloro-1H-pyrazol-1-yl)-1',2'-dihydrospiro[cyclopentane-1,3'-pyrrolo[2,3-b]pyridine]

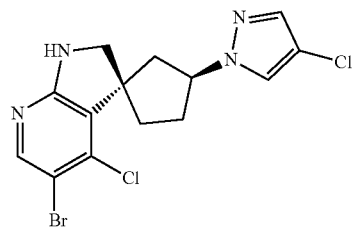 [SMILES: Clc1cnn([C@H]2CC[C@@]3(CNc4ncc(Br)c(Cl)c43)C2)c1]

The title compound was prepared according to general Method G, starting from (1RS,3RS)-5'-bromo-4'-chloro-1'-(4-methoxybenzyl)-1',2'-dihydrospiro[cyclopentane-1,3'-pyrrolo[2,3-b]pyridin]-3-yl methanesulfonate and 4-chloropyrazole. LCMS (ESI) [M+H]⁺ 387/389/391/393.

Example 155w 1-((1RS,3SR)-5'-Bromo-4'-chloro-1',2'-dihydrospiro[cyclopentane-1,3'-pyrrolo[2,3-b]pyridin]-3-yl)-4-methyl-1H-pyrazol-3-amine and 1-((1RS,3SR)-5'-bromo-4'-chloro-1',2'-dihydrospiro[cyclopentane-1,3'-pyrrolo[2,3-b]pyridin]-3-yl)-4-methyl-1H-pyrazol-5-amine

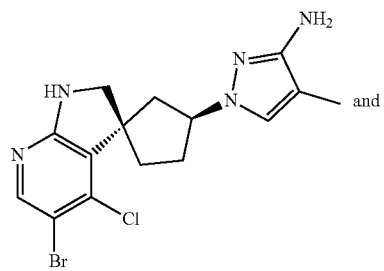

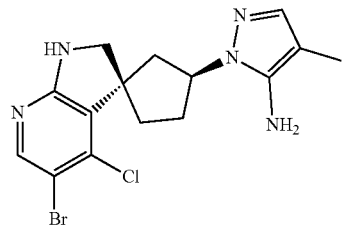

The title compounds were prepared according to general Method G, starting from (1RS,3RS)-5'-bromo-4'-chloro-1'-(4-methoxybenzyl)-1',2'-dihydrospiro[cyclopentane-1,3'-pyrrolo[2,3-b]pyridin]-3-yl methanesulfonate and 3-amino-4-methylpyrazole. LCMS (ESI) [M+H]⁺ 382/384/386.

Example 155x 1-((1RS,3SR)-5'-Bromo-4'-chloro-1',2'-dihydrospiro[cyclopentane-1,3'-pyrrolo[2,3-b]pyridin]-3-yl)-1H-pyrazole-4-carboxamide

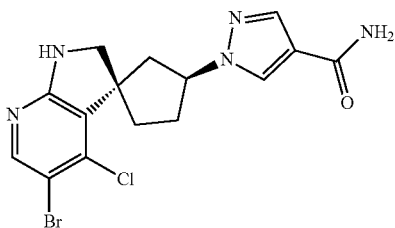 [SMILES: NC(=O)c1cnn([C@H]2CC[C@@]3(CNc4ncc(Br)c(Cl)c43)C2)c1]

The title compound was prepared according to general Method G, starting from (1RS,3RS)-5'-bromo-4'-chloro-1'-(4-methoxybenzyl)-1',2'-dihydrospiro[cyclopentane-1,3'-pyrrolo[2,3-b]pyridin]-3-yl methanesulfonate and 1H-pyrazole-4-carboxamide. LCMS (ESI) [M+H]$^+$ 396/398/400.

Example 155y (1r,4r)-5'-Bromo-4'-chloro-4-(4-methyl-1H-pyrazol-1-yl)-1',2'-dihydrospiro[cyclohexane-1,3'-pyrrolo[2,3-b]pyridine]

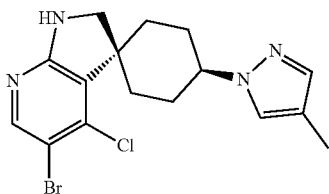 [SMILES: Cc1cnn([C@H]2CC[C@]3(CC2)CNc2ncc(Br)c(Cl)c23)c1]

The title compound was prepared according to general Method G, starting from (1r,4r)-5'-bromo-4'-chloro-1',2'-dihydrospiro[cyclohexane-1,3'-pyrrolo[2,3-b]pyrdin]-4-yl methanesulfonate and 4-methylpyrazole. LCMS (ESI) [M+H]$^+$ 381/383/385.

Example 156: General Method H 4-((1RS,3SR)-5'-Bromo-4'-chloro-1',2'-dihydrospiro[cyclopentane-1,3'-pyrrolo[2,3-b]pyridin]-3-yl)morpholine

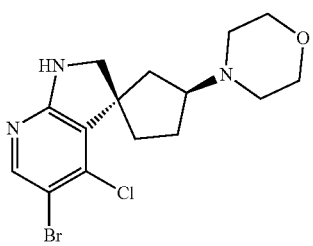

Step 1: 4-((1RS,3SR)-5'-Bromo-4'-chloro-1'-(4-methoxybenzyl)-1',2'-dihydrospiro[cyclopentane-1,3'-pyrrolo[2,3-b]pyridin]-3-yl)morpholine

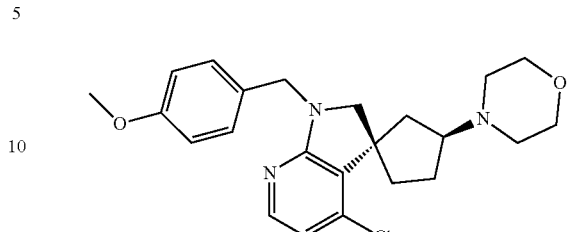

A mixture of (1RS,3RS)-5'-bromo-4'-chloro-1'-(4-methoxybenzyl)-1',2'-dihydrospiro[cyclopentane-1,3'-pyrrolo[2,3-b]pyridin]-3-yl methanesulfonate (0.10 g, 0.20 mmol) and morpholine (0.5 mL, 5.7 mmol) was stirred at 70° C. for 45 min, then heated at 110° C. for 1.5 h. Toluene was added and evaporated (2×). The residue was partitioned between EtOAc and aq. sodium bicarbonate. The aqueous phase was extracted with more EtOAc and the combined organic extracts were washed with brine, dried (Na$_2$SO$_4$), filtered and evaporated. The residue was purified by chromatography on silica (solvent gradient 0-100% MeOH in EtOAc, then 5% MeOH in EtOAc) to afford the title compound (61.5 mg, 63%) as a colorless gum. LCMS (ESI) [M+H]$^+$ 492/494/496.

Step 2: 4-((1RS,3SR)-5'-Bromo-4'-chloro-1',2'-dihydrospiro[cyclopentane-1,3'-pyrrolo[2,3-b]pyridin]-3-yl)morpholine

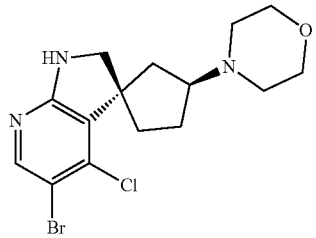 [SMILES: Clc1c(Br)cnc2c1[C@]1(CC[C@H](N3CCOCC3)C1)CN2]

A mixture of 4-(1RS,3SR)-5'-bromo-4'-chloro-1'-(4-methoxybenzyl)-1',2'-dihydrospiro[cyclopentane-1,3'-pyrrolo[2,3-b]pyridin]-3-yl)morpholine (61.5 mg, 0.12 mmol) in TFA (2.5 mL) and anisole (0.25 mL) was stirred at 80° C. for 16 h. Toluene was added and evaporated (2×). The residue was dissolved in MeOH then passed through a SCX-2 cartridge (eluting with MeOH then MeOH·NH$_3$). The resulting residue was purified by chromatography on silica (solvent gradient 2-10% MeOH·NH$_3$ in DCM) to afford the title compound (42.3 mg, 91%) as a colorless gum. LCMS (ESI) [M+H]$^+$ 372/374/376.

Example 156b (1RS,3SR)-5'-Bromo-4'-chloro-3-(pyridin-2-yloxy)-1',2'-dihydrospiro[cyclopentane-1,3'-pyrrolo[2,3-b]pyridine]

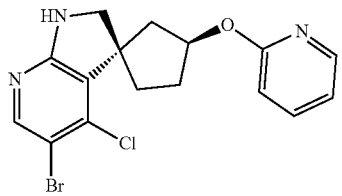 [SMILES: Clc1c(Br)cnc2c1[C@]1(CC[C@H](Oc3ccccn3)C1)CN2]

The title compound was prepared according to general Method H, starting from (1RS,3RS)-5'-bromo-4'-chloro-1'-(4-methoxybenzyl)-1',2'-dihydrospiro[cyclopentane-1,3'-pyrrolo[2,3-b]pyridin]-3-yl methanesulfonate and 2-hydroxypyridine. LCMS (ESI) [M+H]$^+$ 380/382/384.

Example 156c 1-((1RS,3SR)-5'-Bromo-4'-chloro-1',2'-dihydrospiro[cyclopentane-1,3'-pyrrolo[2,3-b]pyridin]-3-yl)pyridin-2(1H)-one

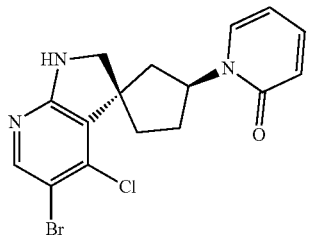 [SMILES: O=c1ccccn1[C@H]1CC[C@@]2(CNc3ncc(Br)c(Cl)c32)C1]

The title compound was prepared according to general Method H, starting from (1RS,3RS)-5'-bromo-4'-chloro-1'-(4-methoxybenzyl)-1',2'-dihydrospiro[cyclopentane-1,3'-pyrrolo[2,3-b]pyridin]-3-yl methanesulfonate and 2-hydroxypyridine. LCMS (ESI) [M+H]$^+$ 380/382/384.

Example 156d (1RS,3SR)-5'-Bromo-4'-chloro-3-(pyrrolidin-1-yl)-1',2'-dihydrospiro[cyclopentane-1,3'-pyrrolo[2,3-b]pyridine]

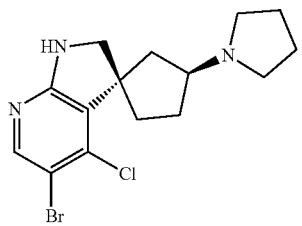 [SMILES: Clc1c(Br)cnc2c1[C@]1(CC[C@H](N3CCCC3)C1)CN2]

The title compound was prepared according to general Method H, using (1RS,3RS)-5'-bromo-4'-chloro-1'-(4-methoxybenzyl)-1',2'-dihydrospiro[cyclopentane-1,3'-pyrrolo[2,3-b]pyridin]-3-yl methanesulfonate and pyrrolidine. LCMS (ESI) [M+H]$^+$ 356/358/360.

Example 157: General Method J

5'-Bromo-4'-methyl-1',2'-dihydrospiro[cyclobutane-1,3'-pyrrolo[2,3-b]pyridine]

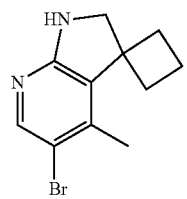

Step 1: 5'-Bromo-4'-methyl-1'-((2-(trimethylsilyl)ethoxy)methyl)spiro[cyclobutane-1,3'-pyrrolo[2,3-b]pyridine]-2'(1'H)-one

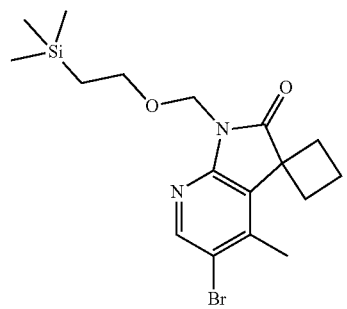 [SMILES: Cc1c(Br)cnc2c1C1(CCC1)C(=O)N2COCC[Si](C)(C)C]

Sodium hydride (60% in oil, 0.672 g, 16.8 mmol) was added over 5 min to an ice-cooled solution of 5-bromo-4-methyl-1-((2-(trimethylsilyl)ethoxy)methyl)-1,3-dihydro-2H-pyrrolo[2,3-b]pyridine-2-one (2.0 g, 5.6 mmol) in DMF (37 mL). After stirring for 20 min a solution of 1,3-diiodopropane (2.15 g, 7.28 mmol) in DMF (3 mL) was added. The mixture was stirred at RT for 1.5 h. then quenched with sat. aq. ammonium chloride. The mixture was diluted with water and extracted twice with EtOAc. The combined organic extracts were washed with water, brine, dried (Na$_2$SO$_4$), filtered and evaporated. The residue was purified by chromatography on silica (solvent gradient 2-12% EtOAc in cyclohexane) to afford the title compound (1.18 g, 53%) as a colorless oil. LCMS (ESI) [M−57]$^+$ 339/341.

Step 2: 5'-Bromo-4'-methylspiro[cyclobutane-1,3'-pyrrolo[2,3-b]pyridine]-2'(1'H)-one

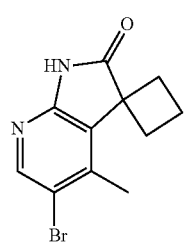

To an ice-cooled solution of 5'-bromo-4'-methyl-1'-((2-(trimethylsilyl)ethoxy)methyl)spiro[cyclobutane-1,3'-pyrrolo[2,3-b]pyridine]-2'(1'H)-one (1.18 g, 2.97 mmol) in DCM (20 mL) was added TFA (5 mL). The mixture was stirred at RT for 1.5 h then toluene was added and evaporated (2x). The residue was partitioned between EtOAc and sat. sodium bicarbonate. The aqueous phase extracted with more EtOAc and the combined extracts were washed with brine, dried (Na₂SO₄), filtered and evaporated. The residue was dissolved in MeOH·NH₃ (15 mL) and stirred at RT for 16 h. The mixture was evaporated and the residue purified by chromatography on silica (solvent gradient 1-6% MeOH·NH₃ in DCM) to afford the title compound (0.605 g, 76%) as a white solid. LCMS (ESI) [M+H]⁺ 267/269.

Step 3: 5'-Bromo-4'-methyl-1',2'-dihydrospiro[cyclobutane-1,3'-pyrrolo[2,3-b]pyridine]

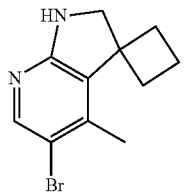

DIBAL (1M in DCM, 11.2 mL, 11.2 mmol) was added over 10 min to an ice-cooled suspension of 5'-bromo-4'-methylspiro[cyclobutane-1,3'-pyrrolo[2,3-b]pyridine]-2'(1'H)-one (0.60 g, 2.246 mmol) in DCM (20 mL). The mixture was stirred at RT for 4 h then cooled in an ice bath and MeOH (7 mL) added cautiously. The mixture was passed through a silica column, eluting with 10-20% MeOH in DCM and then purified by chromatography on silica (solvent gradient 20-60% EtOAc in cyclohexane) to afford the title compound (0.288 g, 51%) as a white solid. LCMS (ESI) [M+H]⁺ 253/255.

Example 157b

5'-Bromo-4'-chloro-1',2'-dihydrospiro[cyclopropane-1,3'-pyrrolo[2,3-b]pyridine]

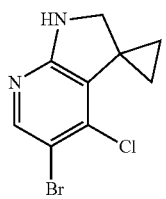

The title compound was prepared according to general Method J, starting from 5-bromo-4-chloro-1-((2-(trimethylsilypethoxy)methyl)-1,3-dihydro-2H-pyrrolo[2,3-b]pyridin-2-one and 1-chloro-2-iodoethane, and using cesium carbonate as the base in step 1. ¹H NMR (400 MHz, DMSO-d₆) δ ppm 7.82 (s, 1H), 7.14 (s, 1H), 3.51 (m, 2H), 1.61 (dd, J=4.3, 6.7 Hz, 2H), 0.89 (dd, J=4.5, 6.9 Hz, 2H).

Example 157c ((1RS,2RS)-5'-Bromo-4'-chloro-1',2'-dihydrospiro[cyclopropane-1,3'-pyrrolo[2,3-b]pyridin]-2-yl)methanol and ((1RS,2SR)-5'-bromo-4'-chloro-1',2'-dihydrospiro[cyclopropane-1,3'-pyrrolo[2,3-b]pyrdin]-2-yl)methanol

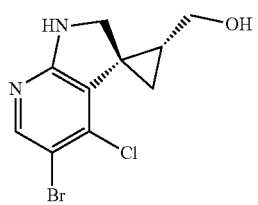

and

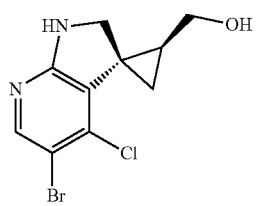

The title compounds were prepared according to general Method J, starting from 5-bromo-4-chloro-1-((2-(trimethylsilypethoxy)methyl)-2,3-dihydro-1H-pyrrolo[2,3-b]pyridine and methyl 2,3-dibromopropionate, and using cesium carbonate as the base in step 1. LCMS (ESI) [M+H]⁺ 288.9/290.9/292.9.

Example 157d

5'-Bromo-4'-methoxy-1',2'-dihydrospiro[cyclopropane-1,3'-pyrrolo[2,3-b]pyridine]

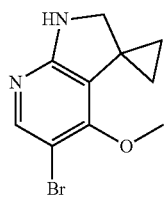

The title compound was prepared according to general Method J, starting from 5-bromo-4-methoxy-1-((2-(trimethylsilyl)ethoxy)methyl)-2,3-dihydro-1H-pyrrolo[2,3-b]pyridin-2-one and 1-chloro-2-iodoethane, using cesium carbonate as the base in step 1. LCMS (ESI) [M+H]⁺ 254.9/256.9.

Example 157e

5'-Bromo-4'-methyl-1',2'-dihydrospiro[cyclopropane-1,3'-pyrrolo[2,3-b]pyridine]

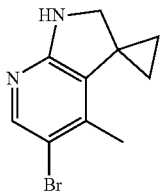

The title compound was prepared according to general Method J, starting from 5-bromo-4-methyl-1-((2-(trimethylsilyl)ethoxy)methyl)-2,3-dihydro-1H-pyrrolo[2,3-b]pyridin-2-one and 1-chloro-2-iodoethane, using cesium carbonate as the base in step 1. $^1$H NMR (400 MHz, CDCl$_3$) δ ppm 7.85 (s, 1H), 4.46 (s, 1H), 3.53 (d, J=1.6 Hz, 2H), 2.05 (s, 3H), 1.45 (dd, J=5.4, 6.7 Hz, 2H), 0.86 (dd, J=5.4, 6.6 Hz, 2H).

Example 157f

5'-Bromo-4'-chloro-1',2'-dihydrospiro[cyclobutane-1,3'-pyrrolo[2,3-b]pyridine]

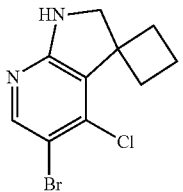

The title compound was prepared according to general Method J, starting from 5-bromo-4-chloro-1-((2-(trimethylsilyl)ethoxy)methyl)-1,3-dihydro-2H-pyrrolo[2,3-b]pyridin-2-one and 1,3-diiodopropane, and using sodium hydride as the base in step 1. LCMS (ESI) [M+H]$^+$ 273/275.

Example 157g

5'-Bromo-4'-methoxy-1',2'-dihydrospiro[cyclobutane-1,3'-pyrrolo[2,3-b]pyridine]

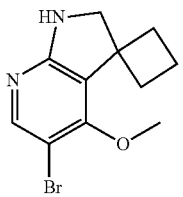

The title compound was prepared according to general Method J, starting from 5-bromo-4-methoxy-1-((2-(trimethyl silyl)ethoxy)methyl)-1,3-dihydro-2H-pyrrolo[2,3-b]pyrdin-2-one and 1,3-diiodopropane using sodium hydride as the base in step 1. LCMS (ESI) [M+H]$^+$ 269.0/271.0.

Example 157h

5'-Bromo-4'-chloro-1',2'-dihydrospiro[cyclopentane-1,3'-pyrrolo[2,3-b]pyridine]

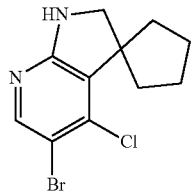 [SMILES: Clc1c(Br)cnc2c1C1(CCCC1)CN2]

The title compound was prepared according to general Method J, starting from 5-bromo-4-chloro-1-((2-(trimethylsilyl)ethoxy)methyl)-1,3-dihydro-2H-pyrrolo[2,3-b]pyridin-2-one and 1,4-diiodobutane, using cesium carbonate as the base in step 1. LCMS (ESI) [M+H]$^+$ 287/289.

Example 157i (RS)-5'-Bromo-4'-chloro-1',2',5,7-tetrahydrospiro[cyclopenta[c]pyridine-6,3'-pyrrolo[2,3-b]pyridine]

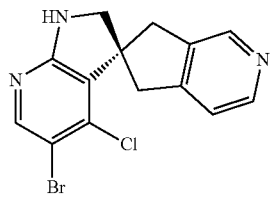 [SMILES: Clc1c(Br)cnc2c1[C@@]1(CN2)Cc2ccncc2C1]

The title compound was prepared according to general Method J, starting from 5-bromo-4-chloro-1-((2-(trimethylsilyl)ethoxy)methyl)-1,3-dihydro-2H-pyrrolo[2,3-b]pyridin-2-one and 3,4-bis(chloromethyl)pyridine HCl salt, using cesium carbonate as the base in step 1. LCMS (ESI) [M+H]$^+$ 336.0/338.0/340.0.

Example 157j

5'-bromo-4'-methyl-1',2'-dihydrospiro[cyclohexane-1,3'-pyrrolo[2,3-b]pyridine]

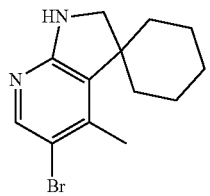 [SMILES: Cc1c(Br)cnc2c1C1(CCCCC1)CN2]

The title compound was prepared according to general Method J, starting from 5-bromo-4-methyl-1-((2-(trimethylsilyl)ethoxy)methyl)-1,3-dihydro-2H-pyrrolo[2,3-b]pyridin-2-one and 1,5-diiodopentane, using sodium hydride as the base in step 1. LCMS (ESI) [M+H]$^+$ 281.1/283.1.

Example 158: General Method K tert-Butyl 3-oxo-4-(3-(4,4,5,5-tetramethyl-1,3,2-dioxaborolan-2-yl)phenyl)piperazine-1-carboxylate

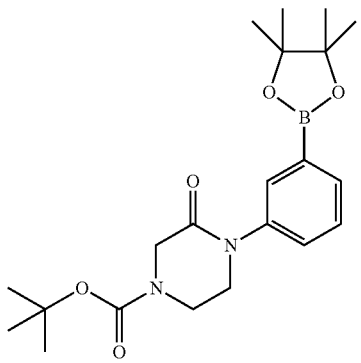 [SMILES: CC(C)(C)OC(=O)N1CCN(c2cccc(B3OC(C)(C)C(C)(C)O3)c2)C(=O)C1]

A degassed mixture of tert-butyl 4-(3-bromophenyl)-3-oxopiperazine-1-carboxylate (529 mg, 1.5 mmol), bis(pinacolato)diboron (457 mg, 1.8 mmol), [1,1'-bis(diphenylphosphino)ferrocene]dichloropalladium(II), complex with DCM (61 mg, 0.075 mmol), potassium acetate (300 mg, 3 mmol) in 1,4-dioxane (10 mL) was heated in a sealed vial at 110° C. for 16 h. The reaction mixture was diluted with DCM and filtered. The filtrate was concentrated then purified by chromatography on silica (solvent gradient 0-50% EtOAc in cyclohexane) to afford the title compound (650 mg, 100%) as a colorless oil which solidified on standing. LCMS (ESI) [M+H]$^+$ 403.3.

Example 158b

1-Methyl-3-(3-(4,4,5,5-tetramethyl-1,3,2-dioxaborolan-2-yl)phenyl)pyridin-2(1H)-one

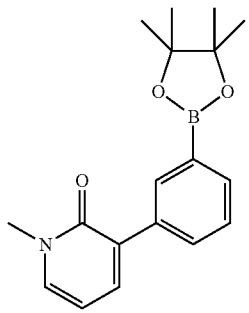

Step 1:
3-(3-Bromophenyl)-1-methylpyridin-2(1H)-one

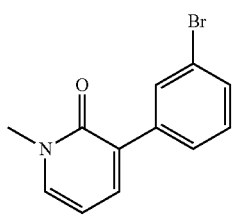

A degassed mixture of 3-bromo-1-methylpyridin-2(1H)-one (800 mg, 4.25 mmol), (3-bromophenyl)boronic acid (854 mg, 4.27 mmol), tetrakis(triphenylphosphine)palladium(O) (230 mg, 0.2 mmol), sodium carbonate (2.6 g, 8 mmol) in 1,4-dioxane/water (5:1, 12 mL) was irradiated in the microwave at 100° C. for 45 min. The cooled mixture was evaporated. The residue was partitioned between water and EtOAc. The organic phase was washed with brine, dried (Na$_2$SO$_4$) and evaporated. The residue was purified by chromatography on silica (solvent gradient 0-100% EtOAc in cyclohexane) to afford the title compound (563 mg, 56%) as a white solid. $^1$H NMR (400 MHz, CDCl$_3$): δ7.86 (t, J=1.8 Hz, 1H), 7.66-7.63 (m, 1H), 7.48 (dd, J=2.1, 7.0 Hz, 1H), 7.45 (ddd, J=1.0, 1.9, 8.0 Hz, 1H), 7.33 (dd, J=2.1, 6.7 Hz, 1H), 7.29-7.24 (m, 1H), 6.26 (t, J=6.9 Hz, 1H), 3.62 (s, 3H).

Step 2: 1-Methyl-3-(3-(4,4,5,5-tetramethyl-1,3,2-dioxaborolan-2-yl)phenyl)pyridin-2(1H)-one

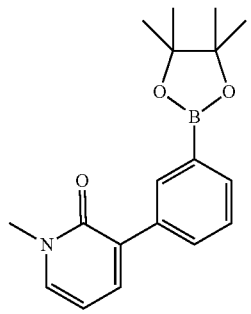

The title compound was prepared according to general Method K, starting from 3-(3-bromophenyl)-1-methylpyridin-2(1H)-one. $^1$H NMR (400 MHz, CDCl$_3$): δ8.2 (s, 1H), 7.89 (td, J=1.6, 7.7 Hz, 1H), 7.77 (td, J=1.2, 7.4 Hz, 1H), 7.52 (dd, J=2.1, 7.0 Hz, 2H), 7.40 (t, J=7.6 Hz, 1H), 6.23 (t, J=6.8 Hz, 1H), 3.61 (s, 3H), 1.34 (s, 12H).

Example 158c (2-Amino-5-(4,4,5,5-tetramethyl-1,3,2-dioxaborolan-2-yl)phenyl)(7-azabicyclo[2.2.1]heptan-7-yl)methanone

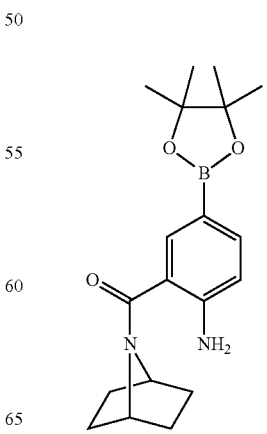

Step 1: (2-Amino-5-bromophenyl)(7-azabicyclo[2.2.1]heptan-7-yl)methanone

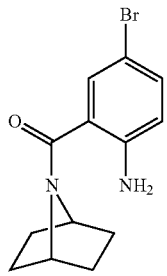 [SMILES: Nc1ccc(Br)cc1C(=O)N1C2CCC1CC2]

To a suspension of 2-amino-5-bromobenzoic acid (430 mg, 2.00 mmol) and 7-azabicyclo[2.2.1]heptane, hydrochloride (300 mg, 2.24 mmol) in DCM (5.0 mL) was added DIPEA (1.75 mL, 10.0 mmol) followed by HATU (800 mg, 2.10 mmol). The reaction mixture was stirred at RT for 1 h, then partitioned between DCM and a sat. aq. sodium bicarbonate. The aqueous phase was extracted with more DCM and the combined organic extracts were passed through a hydrophobic filter and evaporated in vacuo. The residue was purified by chromatography on silica (solvent gradient 0-40% EtOAc in DCM) to afford the title compound (528 mg, 89%) as an off-white solid. LCMS (ESI) [M+H]$^+$ 295/297.

Step 2: (2-Amino-5-(4,4,5,5-tetramethyl-1,3,2-dioxaborolan-2-yl)phenyl)(7-azabicyclo[2.2.1]heptan-7-yl)methanone

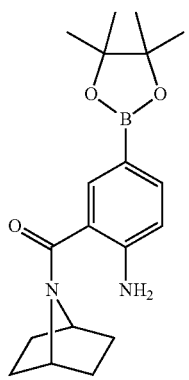 [SMILES: CC1(C)OB(c2ccc(N)c(C(=O)N3C4CCC3CC4)c2)OC1(C)C]

The title compound was prepared according to the general Method K, starting from (2-amino-5-bromophenyl)(7-azabicyclo[2.2.1]heptan-7-yl)methanone. LCMS (ESI) [M+H]$^+$ 343.

Example 158d (2-(3-Amino-5-bromophenyl)pyridin-3-yl)methanol

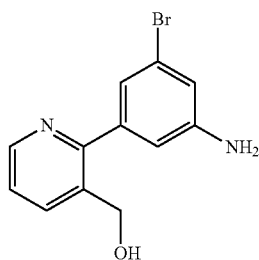 [SMILES: Nc1cc(Br)cc(-c2ncccc2CO)c1]

Step 1: 3-Bromo-5-(4,4,5,5-tetramethyl-1,3,2-dioxaborolan-2-yl)aniline

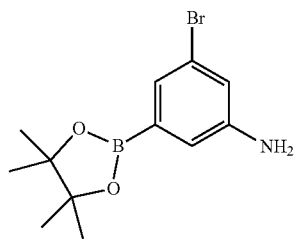 [SMILES: CC1(C)OB(c2cc(N)cc(Br)c2)OC1(C)C]

A degassed mixture of 3,5-dibromoaniline (28 g, 0.11 mol), bis(pinacolato)diboron (16.5 g, 65.0 mmol), potassium acetate (19.0 g, 0.19 mol) and [1,1'-bis(diphenylphosphino)ferrocene]dichloropalladium(II), complex with DCM (2.4 g, 0.30 mmol) in 1,4-dioxane (300 mL) was heated at 90° C. for 16 h. The reaction mixture was filtered and the filtrate concentrated in vacuo. The residue was purified by chromatography on silica (solvent gradient 0-100% DCM in cyclohexane) to give the title product (9.92 g, 30%) as an oil which crystallised on standing. $^1$H NMR (400 MHz, CDCl$_3$) δ7.30 (s, 1H), 7.01 (s, 1H), 6.92 (s, 1H), 3.69 (s, 2H), 1.32 (s, 12H).

Step 2: (2-(3-Amino-5-bromophenyl)pyridin-3-yl)methanol

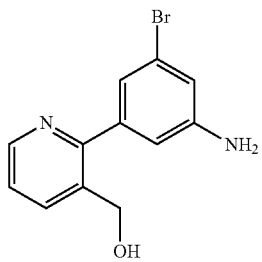 [SMILES: Nc1cc(Br)cc(-c2ncccc2CO)c1]

A degassed mixture of 3-bromo-5-(4,4,5,5-tetramethyl-1,3,2-dioxaborolan-2-yl)aniline (25 g, 83.0 mmol), (2-bromopyridin-3-yl)methanol (17.3 g, 92.1 mmol), tetrakis(triphenylphosphine)palladium(O) (4.7 g, 4.2 mmol) and cesium carbonate (54 g, 166 mmol) in 1,4-dioxane (300 mL)

Example 158e (2-(3-Amino-5-(4,4,5,5-tetramethyl-1,3,2-dioxaborolan-2-yl)phenyl)pyridin-3-yl)methanol

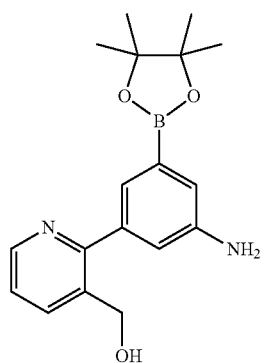 [SMILES: CC1(C)OB(c2cc(N)cc(-c3ncccc3CO)c2)OC1(C)C]

The title compound was prepared according to general Method K starting from (2-(3-amino-5-bromophenyl)pyridin-3-yl)methanol (288 mg, 1.03 mmol). LCMS (ESI) [M+H]+ 327.

4-(3-Bromo-2-fluorophenyl)morpholin-3-one

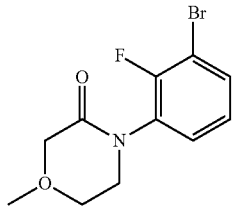

Step 1:
4-(3-Amino-2-fluorophenyl)morpholin-3-one

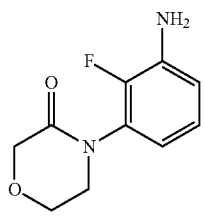 [SMILES: Nc1cccc(N2CCOCC2=O)c1F]

A degassed mixture of 3-bromo-2-fluoroaniline (1.9 g, 10 mmol), morpholin-3-one (847 mg, 11 mmol) copper iodide (476 mg, 2.5 mmol), trans-N,N'-dimethyl-1,2-cyclohexanediamine (710 mg, 5 mmol), potassium phosphate (3.2 g, 15 mmol) in 1,4-dioxane (50 mL) was stirred at 100° C. for 16 h. The cooled reaction mixture was filtered and concentrated. The residue was partitioned between EtOAc and water. The organic extract was washed with brine, dried (Na$_2$SO$_4$) and concentrated. The residue was purified by chromatography on silica (solvent gradient 80-100% EtOAc in cyclohexane) to afford the title compound (1.2 g, 58%) as a pale brown solid. $^1$H NMR (300 MHz, DMSO-d$_6$) δ6.89 (t, J=7.9 Hz, 1H), 6.72 (dt, J=1.6, 8.1 Hz, 1H), 6.49 (dt, J=1.4, 7.2 Hz, 1H), 5.24 (s, 2H), 4.19 (s, 2H), 3.95 (t, J=5.1 Hz, 2H), 3.60 (t, J=5.1 Hz, 2H).

Step 2:
4-(3-Bromo-2-fluorophenyl)morpholin-3-one

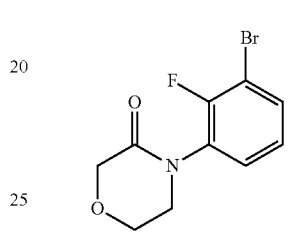

To a solution of copper (II) bromide (892 mg, 4 mmol) and tert-butyl nitrite (0.512 mL, 4.8 mmol) in MeCN (16 mL) at 0° C., was added a solution of 4-(3-amino-2-fluorophenyl)morpholin-3-one (630 mg, 3 mmol) in MeCN (16 mL). The reaction mixture was stirred for 4 h at 0° C., then was quenched with HCl N, diluted with water, and extracted with EtOAc. The combined organic extracts were washed with brine, dried (Na$_2$SO$_4$) and concentrated. The residue was purified by chromatography on silica (solvent gradient 40-60% EtOAc in cyclohexane) to afford the title compound (405 mg, 41%) as a yellow solid. $^1$H NMR (400 MHz, DMSO-d$_6$) δ 7.73-7.68 (m, 1H), 7.54-7.49 (m, 1H), 7.25 (dt, J=1.2, 8.0 Hz, 1H), 4.25 (s, 2H), 3.99 (t, J=5.1 Hz, 2H), 3.70 (t, J=5.0 Hz, 2H).

Example 158f 4-(2-Fluoro-3-(4,4,5,5-tetramethyl-1,3,2-dioxaborolan-2-yl)phenyl)morpholin-3-one

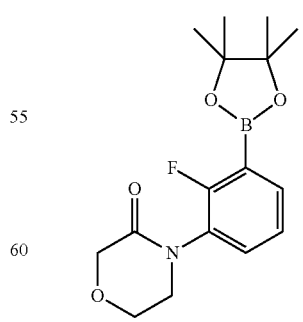

The title compound was prepared according to general Method K, starting from 4-(3-bromo-2-fluoro-phenyl)morpholin-3-one. LCMS (ESI) [M+H]+ 321.2.

Example 158g (6-Amino-2-fluoro-3-(4,4,5,5-tetramethyl-1,3,2-dioxaborolan-2-yl)phenyl)(2-(1-methyl-1H-pyrazol-4-yl)piperidin-1-yl)methanone

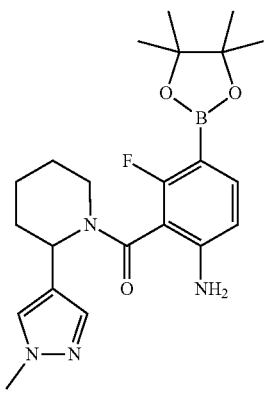

Step 1: (6-Amino-3-bromo-2-fluorophenyl)(2-(1-methyl-1H-pyrazol-4-yl)piperidin-1-yl)methanone

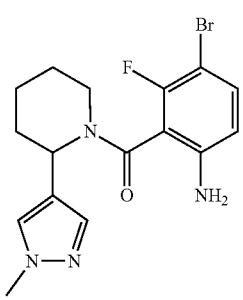

To a solution of 6-amino-3-bromo-2-fluorobenzoic acid (364 mg, 1.56 mmol), HATU (650 mg, 1.71 mmol) and triethylamine (0.3 mL, 2.18 mmol) in DMF (10 mL) was added 2-(1-methylpyrazol-4-yl)piperidine (283 mg, 1.71 mmol). The reaction mixture was stirred at RT for 30 min, then was partitioned between water (100 mL) and EtOAc. The aqueous layer was extracted with further EtOAc. The combined organic extracts were washed with brine, dried (Na$_2$SO$_4$) and concentrated. The residue was purified by chromatography on silica (solvent gradient 0-100% EtOAc in cyclohexane) to afford the title compound (590 mg, 100%), as a pale yellow gum. LCMS (ESI) [M+H]$^+$ 381.1/383.1.

Step 2: (6-Amino-2-fluoro-3-(4,4,5,5-tetramethyl-1,3,2-dioxaborolan-2-yl)phenyl)(2-(1-methyl-1H-pyrazol-4-yl)piperidin-1-yl)methanone

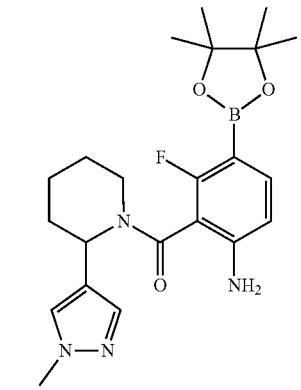

The title compound was prepared according the general Method K, starting from (6-amino-3-bromo-2-fluorophenyl)(2-(1-methyl-1H-pyrazol-4-yl)piperidin-1-yl)methanone LCMS (ESI) [M+H]$^+$ 429.3.

Example 158h

6-Amino-2-fluoro-N-methyl-N-((1-methyl-1H-pyrazol-4-yl)methyl)-3-(4,4,5,5-tetramethyl-1,3,2-dioxaborolan-2-yl)benzamide

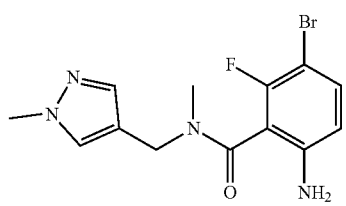

Step 1: 6-Amino-3-bromo-2-fluoro-N-methyl-N-[(1-methylpyrazol-4-yl)methyl]benzamide N-Methyl-1-(1-methylpyrazol-4-yl)methanamine (294 mg, 2.35 mmol) in DMF (0.5 mL) was added to a solution of 6-amino-3-bromo-2-fluorobenzoic acid (500 mg, 2.14 mmol), HATU (894 mg, 2.35 mmol) and triethylamine (0.42 mL, 2.99 mmol) in DMF (15 mL) at RT. The reaction mixture was stirred for 30 min, then was partitioned between water (50 mL) and EtOAc. The aqueous layer was extracted with further EtOAc. The combined organic extracts were washed with brine, dried (Na₂SO₄) and concentrated. The residue was purified by chromatography on silica (solvent gradient 0-4% MeOH·NH₃ in DCM) to give the title compound (720 mg, 99% yield) as a pale yellow gum. LCMS (ESI) [M+Na]⁺ 362.9/364.9.

Step 2: 6-Amino-2-fluoro-N-methyl-N-((1-methyl-1H-pyrazol-4-yl)methyl)-3-(4,4,5,5-tetramethyl-1,3,2-dioxaborolan-2-yl)benzamide

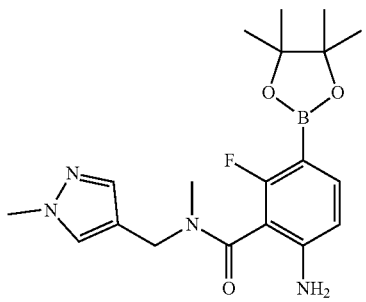

The title compound was prepared according to general Method K, starting from 6-amino-3-bromo-2-fluoro-N-methyl-N-[(1-methylpyrazol-4-yl)methyl]benzamide. LCMS (ESI) [M+H]⁺ 389.2.

Example 158i

6-Amino-N-(2-(dimethylamino)ethyl)-2-fluoro-N-methyl-3-(4,4,5,5-tetramethyl-1,3,2-dioxaborolan-2-yl)benzamide

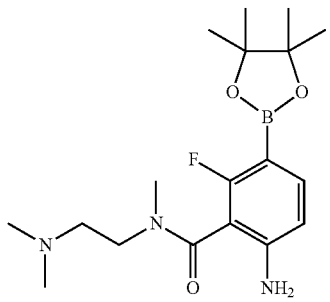

Step 1: 6-Amino-3-bromo-N-(2-(dimethylamino)ethyl)-2-fluoro-N-methylbenzamide

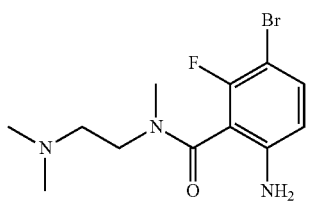

To an ice-cooled solution of 6-amino-3-bromo-2-fluorobenzoic acid (200 mg, 0.8500 mmol), DIPEA (0.45 mL, 2.56 mmol) and N,N,N'-trimethylethylenediamine (0.13 mL, 1.03 mmol) in DMF (2.5 mL), was added HATU (487 mg, 1.28 mmol) portionwise over 5 min. The reaction mixture was stirred at RT for 10 min, then was partitioned between EtOAc and water. The aqueous layer was extracted with further EtOAc. The combined organic extracts were washed with water, brine, dried (Na₂SO₄), and concentrated. The residue was purified by chromatography on silica (solvent gradient 0-10% MeOH·NH₃ in DCM) to afford the title compound (157 mg, 58%) as a colorless solid. LCMS (ESI) [M+H]⁺ 318/320.

Step 2: 6-Amino-N-(2-(dimethylamino)ethyl)-2-fluoro-N-methyl-3-(4,4,5,5-tetramethyl-1,3,2-dioxaborolan-2-yl)benzamide

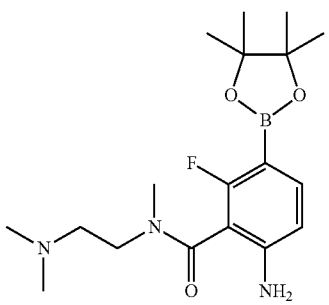

The title compound was prepared according to general Method K, starting from 6-amino-3-bromo-N-(2-(dimethylamino)ethyl)-2-fluoro-N-methylbenzamide. LCMS (ESI) [M+H]⁺ 366.

Example 158j

6-Amino-2-fluoro-N-methyl-N-(2-morpholinoethyl)-3-(4,4,5,5-tetramethyl-1,3,2-dioxaborolan-2-yl)benzamide

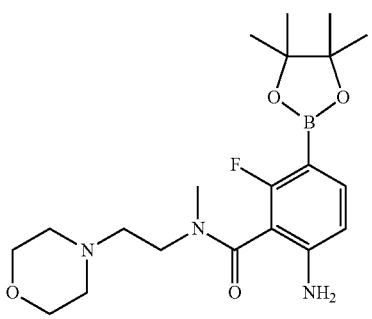 [SMILES: CN(CCN1CCOCC1)C(=O)c1c(N)ccc(B2OC(C)(C)C(C)(C)O2)c1F]

The title compound was prepared in an analogous manner as that described above for 6-amino-N-(2-(dimethylamino)ethyl)-2-fluoro-N-methyl-3-(4,4,5,5-tetramethyl-1,3,2-dioxaborolan-2-yl)benzamide, using morpholine in place of N,N,N'-trimethylethylenediamine in step 1. LCMS (ESI) [M+H]⁺ 408.

Example 159: General Method L

2-Amino-5-(1',2'-dihydrospiro[cyclopentane-1,3'-pyrrolo[2,3-b]pyridin]-5'-yl)-N,N-dimethylbenzamide (Compound 1)

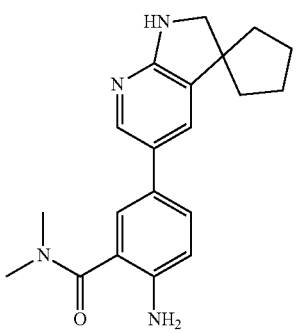 [SMILES: CN(C)C(=O)c1cc(-c2cnc3c(c2)C2(CCCC2)CN3)ccc1N]

A degassed mixture of 5'-bromo-1',2'-dihydrospiro[cyclopentane-1,3'-pyrrolo[2,3-b]pyridine](59 mg, 0.23 mmol), 2-amino-N,N-dimethyl-5-(4,4,5,5-tetramethyl-1,3,2-dioxaborolan-2-yl)benzamide (68 mg, 0.23 mmol), X-Phos (7 mg, 0.014 mmol), X-Phos Pd G2 (11 mg, 0.014 mmol), potassium phosphate tribasic (99 mg, 0.47 mmol) in 1,4-dioxane (1.7 mL) and water (0.3 mL) was heated in a sealed tube at 100° C. for 16 h. The cooled mixture was concentrated and then passed down a SCX-2 cartridge (eluting with MeOH followed by MeOH. $NH_3$). The resulting brown gum was purified by Method C to afford the title compound (35 mg, 45%) as a colorless solid (characterisation in Table A1).

Example 160: General Method M 4-(3-(1',2'-Dihydrospiro[cyclopropane-1,3'-pyrrolo[2,3-b]pyridin]-5'-yl)-2-fluorophenyl)morpholin-3-one (Compound 9)

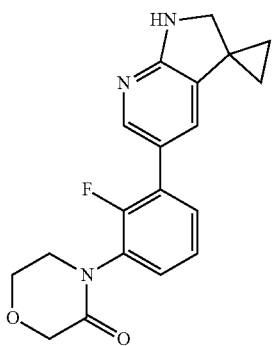 [SMILES: O=C1COCCN1c1cccc(-c2cnc3c(c2)C2(CC2)CN3)c1F]

A degassed solution of S-bromo-1',2'-dihydrospiro[cyclopropane-1,3'-pyrrolo[2,3-b]pyridine](112 mg, 0.5 mmol), XPhos-Pd-G2 (4 mg, 0.005 mmol), Xphos (5 mg, 0.01 mmol), potassium acetate (147 mg, 1.5 mmol) and tetrahydroxydiboron (135 mg, 1.5 mmol) in IMS (5 mL) was heated at 80° C. for 2 h. 4-(3-Bromo-2-fluorophenyl)morpholin-3-one (137 mg, 0.5 mmol) and potassium carbonate (1.8 M aq., 0.83 mL, 1.5 mmol) were added and the reaction was stirred at 80° C. for 16 h. The reaction mixture was diluted with water and extracted with EtOAc. The combined organic fractions were washed with brine, dried ($Na_2SO_4$) and concentrated in vacuo. The resulting residue was purified by Method C to give the title compound (18 mg, 11%) as a white solid (characterisation in table).

Example 161: General Method N 1-(3-(1',2'-Dihydrospiro[cyclopropane-1,3'-pyrrolo[2,3-b]pyridin]-5'-yl)phenyl)tetrahydropyrimidin-2(1H)-one (Compound 67)

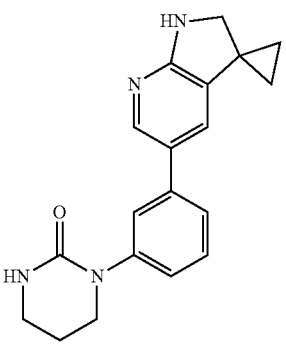

A degassed mixture of 5'-bromo-1',2'-dihydrospiro[cyclopropane-1,3'-pyrrolo[2,3-b]pyridine](120 mg, 0.533 mmol), bis(pinacolato)diboron (187 mg, 0.736 mmol), potassium acetate (0.157 g, 1.60 mmol), [1,1'-bis(diphenylphosphino)ferrocene]dichloropalladium(II), complex with DCM (44 mg, 0.053 mmol) and DME (2.5 mL) was heated in a sealed vial under nitrogen at 110° C. for 2.25 h. The cooled reaction mixture was added to a mixture of 1-(6-bromopyridin-2-yl)tetrahydropyrimidin-2(1R)-one (113 mg, 0.444 mmol), XPhos (21 mg, 0.044 mmol), XPhos Pd G2 (0.0352 g. 0.044 mmol) and dioxane (1 mL). $K_3PO_4$ (1N aq., 0.8 mL) was added and the mixture was heated in a sealed vial under nitrogen at 100° C. for 30 min. MeOH (30 mL) and HCl (0.5N, 10 mL) were added to the cooled reaction mixture. This was passed through a SCX-2 cartridge (eluting with aqueous MeOH, then MeOH then MeOH·$NH_3$). The resulting residue was purified by chromatography on silica (solvent gradient 3-30% MeOH in EtOAc). Trituration from MeOH gave the title compound (53 mg, 37%) as a buff solid (characterisation in table).

Example 162: General Method P 3-(1',2'-Dihydrospiro[cyclopropane-1,3'-pyrrolo[2,3-b]pyridin]-5'-yl)-1H-indole-5-carbonitrile (Compound 307)

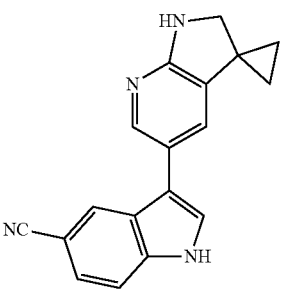 [SMILES: N#Cc1ccc2[nH]cc(-c3cnc4c(c3)C3(CC3)CN4)c2c1]

Step 1: 3-(4,4,5,5-Tetramethyl-1,3,2-dioxaborolan-2-yl)-1-tosyl-1H-indole-5-carbonitrile

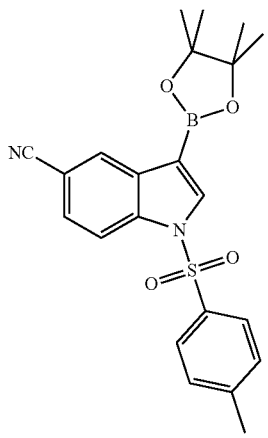 [SMILES: Cc1ccc(S(=O)(=O)n2cc(B3OC(C)(C)C(C)(C)O3)c3cc(C#N)ccc32)cc1]

A degassed mixture of 3-bromo-1-(p-tolylsulfonyl)indole-5-carbonitrile (167 mg, 0.45 mmol), bis(pinacolato) diboron (135 mg, 0.53 mmol), potassium acetate (132 mg, 1.34 mmol) and [1,1'-bis(diphenylphosphino)ferrocene]dichloropalladium(II), complex with DCM (33 mg, 0.040 mmol) in DME (2 mL) was heated in a sealed tube at 110° C. for 1.5 h. The reaction mixture was used in step 2 without work-up or purification. LCMS (ESI) [2M+Na]$^+$ 467.1.

Step 2: 3-(1',2'-Dihydrospiro[cyclopropane-1,3'-pyrrolo[2,3-b]pyridin]-5'-yl)-1-tosyl-1H-indole-5-carbonitrile

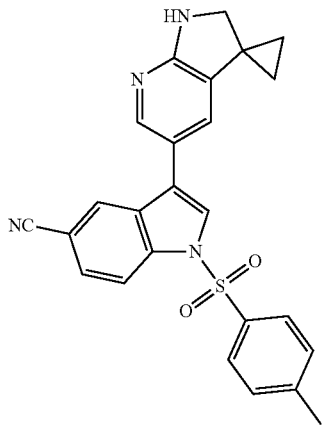 [SMILES: Cc1ccc(S(=O)(=O)n2cc(-c3cnc4c(c3)C3(CC3)CN4)c3cc(C#N)ccc32)cc1]

To the cooled reaction mixture from step 1 was added 5-bromospiro[1,2-dihydropyrrolo[2,3-b]pyridine-3,1'-cyclopropane](45 mg, 0.20 mmol), X-Phos (9.5 mg, 0.020 mmol), X-Phos Pd G2 (16 mg, 0.020 mmol), potassium phosphate (94 mg, 0.44 mmol) and water (1 mL) in 1,4-dioxane (2 mL). The mixture degassed (vacuum/argon x3), then heated in a sealed tube at 100° C. for 3 h. The cooled mixture was concentrated and then passed down a SCX-2 cartridge (eluting with MeOH then MeOH·NH$_3$). The resulting brown gum was purified by chromatography on silica (solvent gradient 0-3.5% MeOH·NH$_3$ in DCM), to afford the title compound (70 mg, 79%) as a buff-colored solid. LCMS (ESI) [M+H]$^+$ 441.1.

Step 3: 3-(1',2'-Dihydrospiro[cyclopropane-1,3'-pyrrolo[2,3-b]pyridin]-5'-yl)-1H-indole-5-carbonitrile

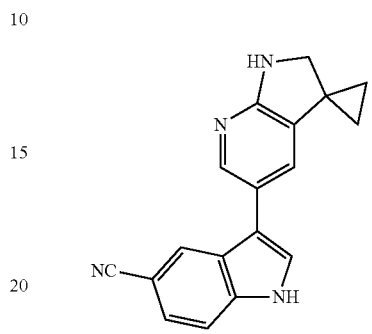

TBAF 1.0 M in THF (1.63 mL, 1.63 mmol) was added dropwise to a solution of 1-(p-tolylsulfonyl)-3-spiro[1,2-dihydropyrrolo[2,3-b]pyridine-3,1'-cyclopropane]-5-yl-indole-5-carbonitrile (144. mg, 0.3300 mmol) and piperidine (0.16 mL, 1.63 mmol) in THF (5 mL) at RT. The mixture was stirred for 4 h, then was concentrated in vacuo and passed down a SCX-2 cartridge (eluting with MeOH then MeOH·NH$_3$). The residue was purified by chromatography on silica (solvent gradient 0-5% MeOH·NH$_3$ in DCM). Further purification by HPLC (solvent gradient 5-75% MeCN in water (0.1% NH$_3$)) gave the title compound (53 mg, 57%) as a colorless powder (characterisation in table).

Example 163: General Method Q (1RS,3SR)-4'-Chloro-5'-(7-(2-oxopiperazin-1-yl)-1H-indol-3-yl)-1',2'-dihydrospiro[cyclopentane-1,3'-pyrrolo[2,3-b]pyrdine]-3-carboxamide (Compound 305a)

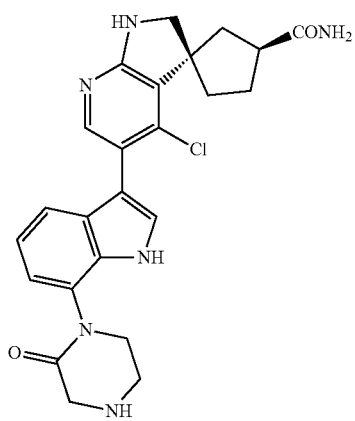 [SMILES: NC(=O)[C@H]1CC[C@@]2(CNc3ncc(-c4c[nH]c5c(N6CCNCC6=O)cccc45)c(Cl)c32)C1]

Step 1: tert-Butyl 3-oxo-4-(3-(4,4,5,5-tetramethyl-1,3,2-dioxaborolan-2-yl)-1-tosyl-1H-indol-7-yl)piperazine-1-carboxylate

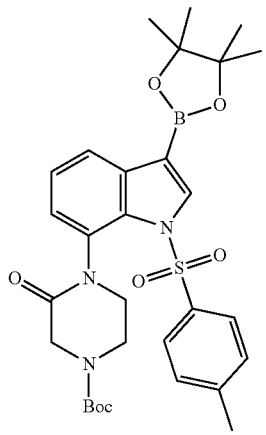 [SMILES: Cc1ccc(S(=O)(=O)n2cc(B3OC(C)(C)C(C)(C)O3)c3cccc(N4CCN(C(=O)OC(C)(C)C)CC4=O)c32)cc1]

A degassed mixture of tert-butyl 4-[3-bromo-1-(p-tolylsulfonyindol-7-yl]-3-oxo-piperazine-1-carboxylate (190 mg, 0.35 mmol), bis(pinacolato)diboron (132 mg, 0.520 mmol), potassium acetate (103 mg, 1.04 mmol) and [1,1'-bis(diphenylphosphino)ferrocene]dichloropalladium (II), complex with DCM (26 mg, 0.030 mmol) in DME (1.5 mL) was heated in a sealed tube at 110° C. for 1.5 h. The mixture was cooled to RT and used in step 2 without further purification. LCMS (ESI) [M+Na]$^+$ 618.3.

Step 2: tert-Butyl 4-(3-((1RS,3SR)-3-carbamoyl-4'-chloro-1',2'-dihydrospiro[cyclopentane-1,3'-pyrrolo[2,3-b]pyridin]-5'-yl)-1-tosyl-1H-indol-7-yl)-3-oxopiperazine-1-carboxylate

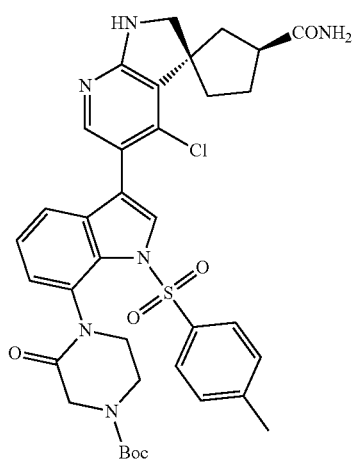 [SMILES: Cc1ccc(S(=O)(=O)n2cc(-c3cnc4c(c3Cl)[C@]3(CC[C@H](C(N)=O)C3)CN4)c3cccc(N4CCN(C(=O)OC(C)(C)C)CC4=O)c32)cc1]

To the cooled reaction mixture from step 1 was added (1RS,3SR)-5'-bromo-4'-chloro-1',2'-dihydrospiro[cyclopentane-1,3'-pyrrolo[2,3-b]pyridine]-3-carboxamide (114.5 mg, 0.35 mmol), 2-dicyclohexylphosphino-2',4',6'-triisopropylbiphenyl (16.5 mg, 0.030 mmol), X-Phos Pd G2 (28 mg, 0.030 mmol), potassium phosphate tribasic (1N, 0.06 mL, 0.690 mmol), 1,4-dioxane (1 mL) and water (0.1 mL). The mixture was degassed (vacuum/argon x3) and heated in a sealed tube at 100° C. for 3.5 h. The cooled mixture was concentrated in vacuo and then passed down a SCX-2 cartridge (eluting with MeOH then MeOH·NH$_3$). The residue was purified by chromatography on silica (solvent gradient 0-6.25% MeOH·NH$_3$ in DCM), to afford the title compound (117 mg, 47% yield) as a pale yellow solid. LCMS (ESI) [M+H]$^+$ 719.4/721.1.

Step 3: tert-Butyl 4-(3-((1RS,3SR)-3-carbamoyl-4'-chloro-1',2'-dihydrospiro[cyclopentane-1,3'-pyrrolo[2,3-b]pyridin]-5'-yl)-1H-indol-7-yl)-3-oxopiperazine-1-carboxylate

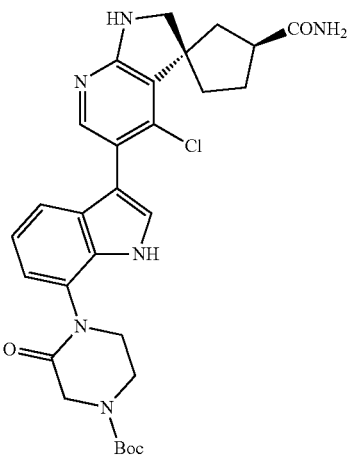 [SMILES: CC(C)(C)OC(=O)N1CCN(c2cccc3c(-c4cnc5c(c4Cl)[C@]4(CC[C@H](C(N)=O)C4)CN5)c[nH]c23)C(=O)C1]

TBAF (1N in THF, 0.23 mL, 0.2300 mmol) was added dropwise to a solution of tert-butyl 4-[3-[(1RS,3SR)-3'-carbamoyl-4-chloro-spiro[1,2-dihydropyrrolo[2,3-b]pyridine-3,1'-cyclopentane]-5-yl]-1-(p-tolylsulfonyindol-7-yl]-3-oxo-piperazine-1-carboxylate (33.4 mg, 0.050 mmol) and piperidine (0.02 mL, 0.2300 mmol) in THF (0.5 mL) at RT. The mixture was stirred for 18 h, then concentrated and passed down a SCX-2 cartridge (eluting with MeOH then MeOH·NH$_3$), to afford the title compound (26 mg, 99%) as a colorless gum. LCMS (ESI) [M+H]$^+$ 563.1/565.1.

Step 4: (1RS,3SR)-4'-Chloro-5'-(7-(2-oxopiperazin-1-yl)-1H-indol-3-yl)-1',2'-dihydrospiro[cyclopentane-1,3'-pyrrolo[2,3-b]pyridine]-3-carboxamide

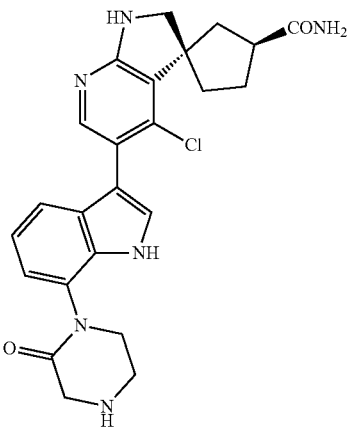 [SMILES: NC(=O)[C@H]1CC[C@@]2(CNc3ncc(-c4c[nH]c5c(N6CCNCC6=O)cccc45)c(Cl)c32)C1]

A solution of tert-butyl 4-[3-[(1RS,3SR)-3'-carbamoyl-4-chloro-spiro[1,2-dihydropyrrolo[2,3-b]pyridine-3,1'-cyclopentane]-5-yl]-1H-indol-7-yl]-3-oxo-piperazine-1-carboxylate (90 mg, 0.160 mmol) and TFA (0.18 mL) in DCM (2 mL) was stirred at RT for 16 h. The reaction mixture was taken to dryness and the residue passed down a SCX-2 cartridge (eluting with MeOH then MeOH·NH₃). The resulting light brown gum was purified by chromatography on silica (solvent gradient 6-20% MeOH·NH₃ in DCM). The resulting residue was triturated with Et₂O (1 mL) and filtered to give the title compound (49 mg, 66%) as a colorless solid (characterisation in table).

Example 164: General Method R 3-(4'-Chloro-1',2'-dihydrospiro[cyclopropane-1,3'-pyrrolo[2,3-b]pyridin]-5'-yl)-2-fluoro-N-(2-hydroxyethyl)-N-methylbenzamide (Compound 45)

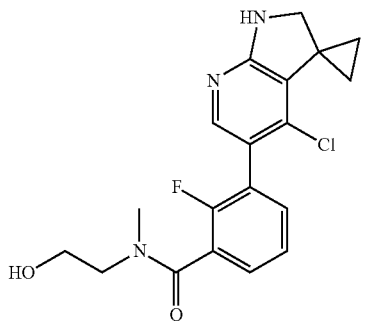 [SMILES: CN(CCO)C(=O)c1cccc(-c2cnc3c(c2Cl)C2(CC2)CN3)c1F]

To a suspension of 3-(4'-chloro-1',2'-dihydrospiro[cyclopropane-1,3'-pyrrolo[2,3-I]pyridin]-5'-yl)-2-fluorobenzoate (130 mg, 0.4 mmol) in DCM (5 mL) were added DIPEA (0.21 mL, 1.2 mmol) and HATU (190 mg, 0.5 mmol). The reaction mixture was stirred at RT for 10 min, then 2-(methylamino)ethan-1-ol (36 mg, 0.48 mmol) was added. The reaction mixture was stirred at RT for 16 h, then diluted with DCM and washed with brine. The organic extract was dried (MgSO₄) and concentrated. The residue was purified by Method C to afford the title compound (50 mg, 33%) as a white solid (characterization in table).

Example 165: General Method S 5-(1H-Pyrrolo[2,3-c]pyridin-3-yl)spiro[1,2-dihydropyrrolo[2,3-b]pyridine-3,1'-cyclopropane](Compound 333)

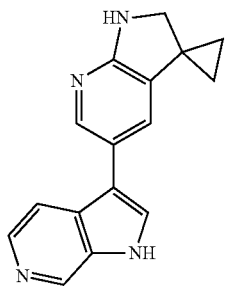

Step 1: tert-Butyl 5'-(1H-pyrrolo[2,3-c]pyridin-3-yl) spiro[cyclopropane-1,3'-pyrrolo[2,3-b]pyridine]-1' (2'H)-carboxylate

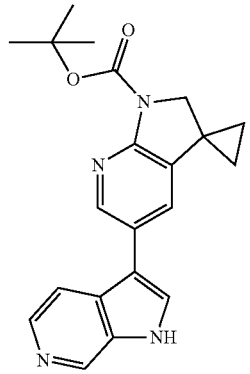 [SMILES: CC(C)(C)OC(=O)N1CC2(CC2)c2cc(-c3c[nH]c4cnccc34)cnc21]

A degassed mixture of (1'-(tert-butoxycarbonyl)-1',2'-dihydrospiro[cyclopropane-1,3'-pyrrolo[2,3-b]pyridin]-5'-yl) boronic acid (50 mg, 0.17 mmol), X-Phos-Pd G2 (13.6 mg, 0.017 mmol), X-Phos (8.2 mg, 0.017 mmol), 3-bromo-1H-pyrrolo[2,3-c]pyridine (41 mg, 0.21 mmol), potassium phosphate tribasic (1N aq., 0.38 mL, 0.38 mmol) and 1,4-dioxane (2.4 mL) was heated at 100° C. for 1 h. The reaction mixture was diluted with EtOAc and washed with water. The aqueous layer was extracted with EtOAc. The combined organic extracts were dried (Na₂SO₄) and concentrated. The residue was purified by chromatography on silica (solvent gradient 0-10% MeOH in DCM), to afford the title compound (37 mg, 59.2%) as a pale yellow solid. LCMS (ESI) [M+H]⁺ 363.2.

Step 2: 5-(1H-Pyrrolo[2,3-c]pyridin-3-yl)spiro[1,2-dihydropyrrolo[2,3-b]pyridine-3,1'-cyclopropane]

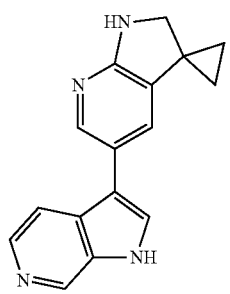

tert-Butyl 5-(1H-pyrrolo[2,3-c]pyridin-3-yl)spiro[2H-pyrrolo[2,3-b]pyridine-3,1'-cyclopropane]-1-carboxylate (37 mg, 0.10 mmol) was treated with TFA/DCM (1/4, 1 mL) and purified by chromatography on silica (solvent gradient 0-10% MeOH·NH₃ in DCM) to afford the title compound (21 mg, 78% yield) as a light brown solid (characterisation in table).

Example 166: General Method T

5'-(3-(4,5,6,7-Tetrahydro-[1,2,3]triazolo[1,5-a]pyrazin-3-yl)phenyl)-1',2'-dihydrospiro[cyclopropane-1,3'-pyrrolo[2,3-b]pyridine](Compound 72)

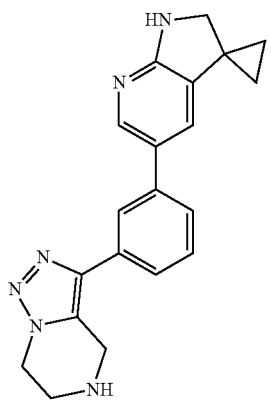 [SMILES: c1cc(-c2cnc3c(c2)C2(CC2)CN3)cc(-c2nnn3c2CNCC3)c1]

Step 1: tert-Butyl 3-(3-(1',2'-dihydrospiro[cyclopropane-1,3'-pyrrolo[2,3-b]pyridin]-5'-yl)phenyl)-6,7-dihydro-[1,2,3]triazolo[1,5-a]pyrazine-5(4H)-carboxylate

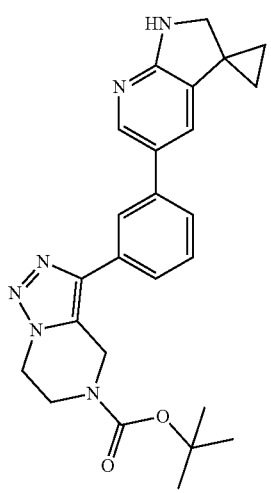 [SMILES: CC(C)(C)OC(=O)N1CCn2nnc(-c3cccc(-c4cnc5c(c4)C4(CC4)CN5)c3)c2C1]

The title compound was prepared according general Method L, using 5'-bromo-1',2'-dihydrospiro[cyclopropane-1,3'-pyrrolo[2,3-b]pyridine] and tert-butyl 3-(3-(4,4,5,5-tetramethyl-1,3,2-dioxaborolan-2-yl)phenyl)-6,7-dihydro-[1,2,3]triazolo[1,5-a]pyrazine-5(4H)-carboxylate. LCMS (ESI) [M+H]+ 445.2.

Step 2: 5'-(3-(4,5,6,7-Tetrahydro-[1,2,3]triazolo[1,5-a]pyrazin-3-yl)phenyl)-1',2'-dihydrospiro[cyclopropane-1,3'-pyrrolo[2,3-b]pyridine]

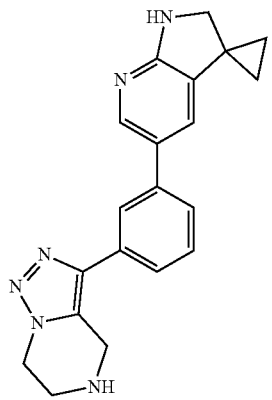 [SMILES: c1cc(-c2cnc3c(c2)C2(CC2)CN3)cc(-c2nnn3c2CNCC3)c1]

To a solution of tert-butyl 3-(3-(1',2'-dihydrospiro[cyclopropane-1,3'-pyrrolo[2,3-b]pyridin]-5'-yl)phenyl)-6,7-dihydro-[1,2,3]triazolo[1,5-a]pyrazine-5(4H)-carboxylate (38 mg, 0.085 mmol) in DCM (1 mL) was added TFA (1 mL). The reaction mixture was stirred at RT for 1 h, then purified on Isolute SCX-2 cartridge (eluting with MeOH then MeOH·NH₃). The residue was purified by chromatography on silica (solvent gradient 0-20% MeOH·NH₃ in DCM) to afford the title compound (22.3 mg, 76%) as a yellow solid (characterisation in table).

Example 167: General Method V (3-(4'-Chloro-1',2'-dihydrospiro[cyclopropane-1,3'-pyrrolo[2,3-b]pyridin]-5'-yl)-2-fluorophenyl)(piperazin-1-yl)methanone (Compound 48)

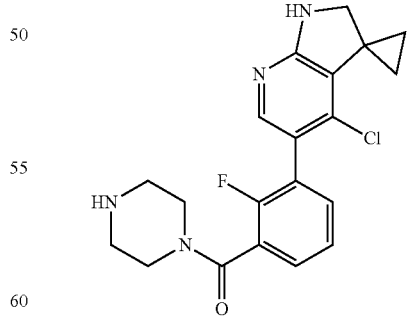

The title compound was prepared according to general Method R, starting from 3-(4'-chloro-1',2'-dihydrospiro[cyclopropane-1,3'-pyrrolo[2,3-b]pyrdin]-5'-yl)-2-fluorobenzoate and tert-butylpiperazine-1-carboxylate, followed by treatment with TFA/DCM, and purification by Method C.

Example 168: General Method W

6-Amino-3-((1s,4s)-4-(aminomethyl)-4'-chloro-1',2'-dihydrospiro[cyclohexane-1,3'-pyrrolo[2,3-b]pyridin]-5'-yl)-2-fluoro-N,N-dimethylbenzamide (Compound 258b)

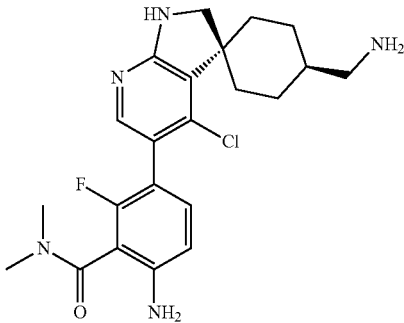

6-Amino-3-((1s,4s)-4'-chloro-4-cyano-1',2'-dihydrospiro[cyclohexane-1,3'-pyrrolo[2,3-b]pyridin]-5'-yl)-2-fluoro-N,N-dimethylbenzamide (0.111 g, 0.26 mmol) was dissolved in ethanol (8 mL). HCl (4M in dioxane, 0.39 mL, 1.55 mmol) and platinum (IV) oxide (20 mg) were added and the mixture stirred under 1 atmosphere of hydrogen for 2 days at RT. Water was added and the mixture was filtered through celite. The filtrate was evaporated under reduced pressure. The residue was purified on C18 cartridge (eluting with 2-14% MeCN in 0.5% TFA in water). The residue was passed through a SCX-2 cartridge (eluting with MeOH then 1N MeOH·NH$_3$) to afford the title compound (0.0306 g, 27%) as a white solid. $^1$H NMR (400 MHz, DMSO-d$_6$): δ ppm 7.57 (s, 1H), 6.95 (t, J=8.5 Hz, 1H), 6.88 (brs, 1H), 6.54 (d, J=8.4 Hz, 1H), 5.37 (brs, 2H), 3.39 (brs, 2H), 2.99 (s, 3H), 2.88 (s, 3H), 2.21-2.11 (m, 2H), 1.72-1.62 (m, 3H), 1.30-1.21 (m, 1H), 1.06-0.94 (m, 2H). LCMS (Method A) (ESI) R$_T$ 1.67 min, [M+H]$^+$ 432.3.

Example 169: 6-Amino-3-((1r,4r)-4-(aminomethyl)-4'-chloro-1',2'-dihydrospiro[cyclohexane-1,3'-pyrrolo[2,3-b]pyridin]-5'-yl)-2-fluoro-N,N-dimethylbenzamide (Compound 258a)

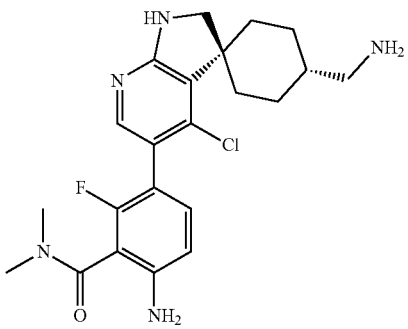 [SMILES: CN(C)C(=O)c1c(N)ccc(-c2cnc3c(c2Cl)[C@]2(CC[C@@H](CN)CC2)CN3)c1F]

The title compound was prepared in an analogous manner to that described for 6-amino-3-((1s,4s)-4-(aminomethyl)-4'-chloro-1',2'-dihydrospiro[cyclohexane-1,3'-pyrrolo[2,3-b]pyridin]-5'-yl)-2-fluoro-N,N-dimethylbenzamide. $^1$H NMR (400 MHz, DMSO-d$_6$): δ ppm 7.56 (s, 1H), 6.95 (t, J=8.5 Hz, 1H), 6.89 (brs, 1H), 6.54 (d, J=8.4 Hz, 1H), 5.37 (brs, 2H), 3.46 (brs, 2H), 2.99 (s, 3H), 2.88 (s, 3H), 2.29-2.18 (m, 2H), 1.68-1.50 (m, 4H), 1.41-1.34 (m, 2H). LCMS (Method A) (ESI) R$_T$ 1.64 min, [M+H]$^+$ 432.3.

Example 170: 1-(3-(1',2'-Dihydrospiro[cyclopropane-1,3'-pyrrolo[2,3-b]pyridin]-5'-yl)phenyl)piperazin-2-one (Compound 41)

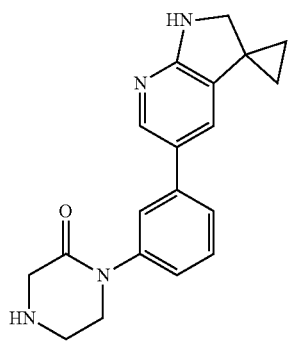

The title compound was prepared according to general Method M, starting from 5'-bromo-1',2'-dihydrospiro[cyclopropane-1,3'-pyrrolo[2,3-b]pyridine] and tert-butyl 4-(3-bromophenyl)-3-oxopiperazine-1-carboxylate, followed by treatment with TFA/DCM, and purified by chromatography on silica (solvent gradient 5-6% MeOH·NH$_3$ in DCM). $^1$H NMR (400 MHz, DMSO-d$_6$): δ ppm 7.96 (d, J=2.1 Hz, 1H), 7.45-7.42 (m, 2H), 7.38 (t, J=7.8 Hz, 1H), 7.17 (td, J=1.6, 7.8 Hz, 1H), 7.14 (d, J=2.1 Hz, 1H), 6.71 (s, 1H), 3.63 (t, J=5.4 Hz, 2H), 3.55 (s, 2H), 3.39 (s, 2H), 3.02 (t, J=5.4 Hz, 2H), 1.13-1.08 (m, 2H), 1.00-0.95 (m, 2H). LCMS (Method A) (ESI) R$_T$ 1.72 min, [M+H]$^+$ 321.2.

Example 171: 6-Amino-3-(4'-chloro-1',2'-dihydrospiro[cyclopropane-1,3'-pyrrolo[2,3-b]pyridin]-5'-yl)-2-fluoro-N-(2-hydroxyethyl)-N-methylbenzamide (Compound 36)

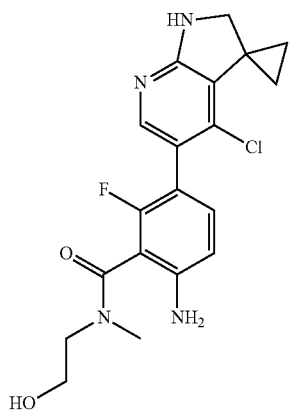 [SMILES: CN(CCO)C(=O)c1c(N)ccc(-c2cnc3c(c2Cl)C2(CC2)CN3)c1F]

Step 1: 6-Amino-N-(2-((tert-butyldimethylsilyl)oxy)ethyl)-3-(4'-chloro-1',2'-dihydrospiro[cyclopropane-1,3'-pyrrolo[2,3-b]pyridin]-5'-yl)-2-fluoro-N-methylbenzamide

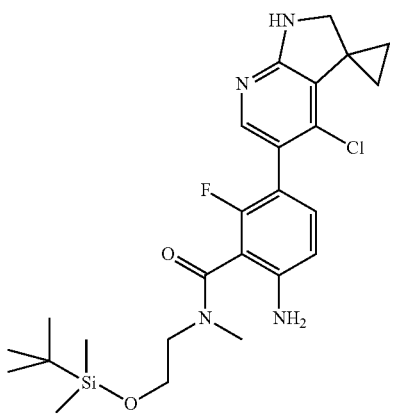 [SMILES: CN(CCO[Si](C)(C)C(C)(C)C)C(=O)c1c(N)ccc(-c2cnc3c(c2Cl)C2(CC2)CN3)c1F]

The title compound was prepared according to general Method L, starting from 2-amino-N-(2-((tert-butyldimethylsilyl)oxy)ethyl)-6-fluoro-N-methyl-4-(4,4,5,5-tetramethyl-1,3,2-dioxaborolan-2-yl)benzamide and 5'-bromo-4'-chloro-1',2'-dihydrospiro[cyclopropane-1,3'-pyrrolo[2,3-b]pyridine]. LCMS (ESI) [M+H]+ 505.1.

Step 2: 6-Amino-3-(4'-chloro-1',2'-dihydrospiro[cyclopropane-1,3'-pyrrolo[2,3-b]pyridin]-5'-yl)-2-fluoro-N-(2-hydroxyethyl)-N-methylbenzamide

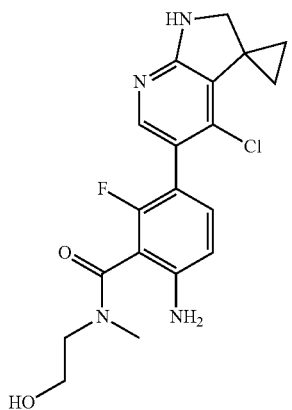 [SMILES: CN(CCO)C(=O)c1c(N)ccc(-c2cnc3c(c2Cl)C2(CC2)CN3)c1F]

To a solution of 6-amino-N-(2-((tert-butyldimethylsilyl)oxy)ethyl)-3-(4'-chloro-1',2'-dihydrospiro[cyclopropane-1,3'-pyrrolo[2,3-b]pyridin]-5'-yl)-2-fluoro-N-methylbenzamide (150 mg, 0.3 mmol) in THF (3 mL) was added TBAF (1N in THF, 2 mL). The reaction mixture was stirred at RT for 16 h then was diluted with water and extracted with EtOAc. The combined organic extracts were washed with brine, dried (Na$_2$SO$_4$) and concentrated in vacuo. The residue was purified by chromatography on silica (solvent gradient 0-3% MeOH in DCM) to yield the title compound (30 mg, 26%) as an off-white solid. $^1$H NMR (400 MHz, DMSO-d$_6$) δ ppm 7.50 (d, J=3.5 Hz, 1H), 6.98-6.87 (m, 2H), 6.53 (dd, J=8.3, 6.6 Hz, 1H), 5.37 (s, 1H), 5.32 (s, 1H), 4.84 (t, J=5.3 Hz, 0.5 H), 4.74 (t, J=5.3 Hz, 0.5 H), 3.74-3.64 (m, 0.5H), 3.62-3.57 (m, 1H), 3.51 (s, 2H), 3.47-3.34 (m, 1.5 H), 3.28-3.18 (m, 1H), 3.00 (s, 1.5H), 2.90 (s, 1.5H), 1.64-1.57 (m, 2H), 0.91-0.83 (m, 2H). LCMS (Method A) (ESI), RT 2.46 min, [M+H]+ 391.1.

Example 172: 5'-(5-(3-Methyl-1H-pyrazol-4-yl)-1H-indol-3-yl)-1',2'-dihydrospiro[cyclopropane-1,3'-pyrrolo[2,3-b]pyridine](Compound 326)

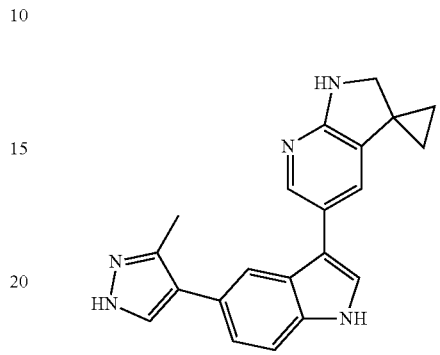

Step 1: tert-Butyl 3-(1',2'-dihydrospiro[cyclopropane-1,3'-pyrrolo[2,3-b]pyridin]-5'-yl)-5-(3-methyl-1H-pyrazol-4-yl)-1H-indole-1-carboxylate

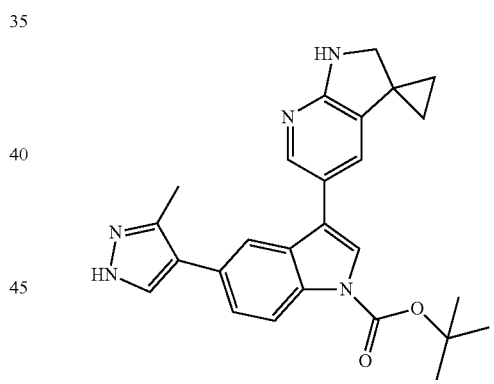

A degassed mixture of tert-butyl 3-bromo-5-(3-methyl-1H-pyrazol-4-yl)-1H-indole-1-carboxylate (180 mg, 0.48 mmol), bis(pinacolato)diboron (146 mg, 0.58 mmol), potassium acetate (0.1 mL, 1.6 mmol) and [1,1'-bis(diphenylphosphino)ferrocene]dichloropalladium(II) complex with DCM (39 mg, 0.05 mmol) in DME (2 mL) was heated at 100° C. for 1.5 h. To the reaction were added potassium phosphate tribasic (1N aq., 0.98 mL, 0.98 mmol), 5-bromo-spiro[1,2-dihydropyrrolo[2,3-b]pyridine-3,1'-cyclopropane] (100 mg, 0.44 mmol), Xphos (21 mg, 0.04 mmol) and Xphos Pd G2 (35 mg, 0.04 mmol). The reaction mixture was heated at 100° C. for 1 h, then diluted with water and extracted with EtOAc. The combined organic extracts were washed with brine, dried (MgSO$_4$) and concentrated. The residue was purified by chromatography on silica (solvent gradient 0-10% MeOH in DCM), to give the product as an off-white solid. LCMS (ESI) [M+H]+ 442.

Step 2: 5'-(5-(3-Methyl-1H-pyrazol-4-yl)-1H-indol-3-yl)-1',2'-dihydrospiro[cyclopropane-1,3'-pyrrolo[2,3-b]pyridine]

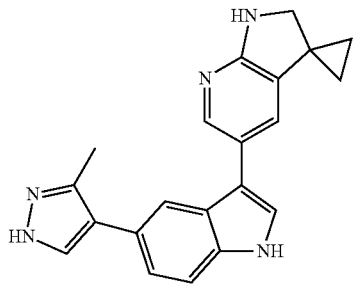 [SMILES: Cc1n[nH]cc1-c1ccc2[nH]cc(-c3cnc4c(c3)C3(CC3)CN4)c2c1]

To a solution of tert-butyl 3-(1',2'-dihydrospiro[cyclopropane-1,3'-pyrrolo[2,3-b]pyridin]-5'-yl)-5-(3-methyl-1H-pyrazol-4-yl)-1H-indole-1-carboxylate (60 mg, 0.14 mmol) in MeOH (1 mL) was added HCl (4N in dioxane, 3 mL, 12 mmol). The reaction mixture was stirred at RT for 3 h, then was concentrated in vacuo and the residue purified according to Method D to give the title compound (12 mg, 26%) as a white solid. $^1$H NMR (400 MHz, CDCl$_3$) δ ppm 8.43 (s, 1H), 8.31 (s, 1H), 7.84 (d, J=1.9 Hz, 1H), 7.69 (s, 1H), 7.67 (s, 1H), 7.46 (d, J=8.6 Hz, 1H), 7.30 (dd, J=8.3, 1.5 Hz, 1H), 7.27 (s, 1H), 7.04 (d, J=1.8 Hz, 1H), 3.79 (s, 2H), 2.46 (s, 3H), 1.15-1.07 (m, 4H). LCMS (Method A) (ESI) R$_T$ 2.57 min, [M+H]$^+$ 342.1.

Example 173: 5'-(5-(4-Methyl-4H-1,2,4-triazol-3-yl)-1H-indol-3-yl)-1',2'-dihydrospiro[cyclopropane-1,3'-pyrrolo[2,3-b]pyridine](Compound 335)

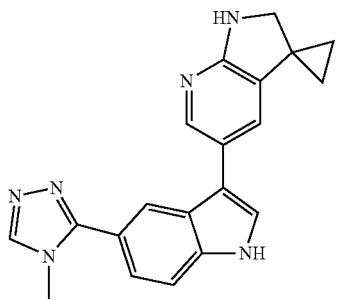 [SMILES: Cn1cnnc1-c1ccc2[nH]cc(-c3cnc4c(c3)C3(CC3)CN4)c2c1]

Step 1: tert-Butyl 5'-(5-(4-methyl-4H-1,2,4-triazol-3-yl)-1-tosyl-1H-indol-3-yl)spiro[cyclopropane-1,3'-pyrrolo[2,3-b]pyridine]-1'(2'H)-carboxylate

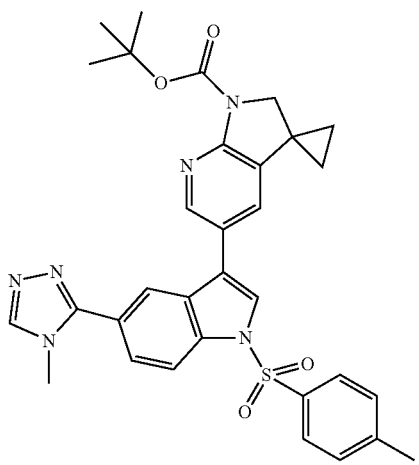 [SMILES: Cc1ccc(S(=O)(=O)n2cc(-c3cnc4c(c3)C3(CC3)CN4C(=O)OC(C)(C)C)c3cc(-c4nncn4C)ccc32)cc1]

The title compound was prepared according to general Method N, using 3-bromo-5-(4-methyl-4H-1,2,4-triazol-3-yl)-1-tosyl-1H-indole and (1'-(tert-butoxycarbonyl)-1',2'-dihydrospiro[cyclopropane-1,3'-pyrrolo[2,3-b]pyridin]-5'-yl)boronic acid. LCMS (ESI) [M+H]$^+$ 597.4.

Step 2: tert-Butyl 5'-(5-(4-Methyl-4H-1,2,4-triazol-3-yl)-1H-indol-3-yl)spiro[cyclopropane-1,3'-pyrrolo[2,3-b]pyridine]-1'(2'H)-carboxylate

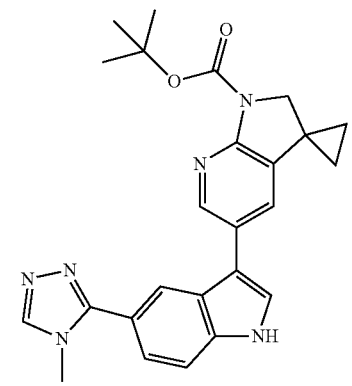 [SMILES: Cn1cnnc1-c1ccc2[nH]cc(-c3cnc4c(c3)C3(CC3)CN4C(=O)OC(C)(C)C)c2c1]

To a solution of tert-butyl 5'-(5-(4-methyl-4H-1,2,4-triazol-3-yl)-1-tosyl-1H-indol-3-yl)spiro[cyclopropane-1,3'-pyrrolo[2,3-b]pyridine]-1'(2'H)-carboxylate (61 mg, 0.10 mmol) in THF (1 mL) was added TBAF (1N in THF, 0.51 mL, 0.51 mmol) and piperidine (0.05 mL, 0.51 mmol). The reaction mixture was stirred at RT for 4 days, then was diluted with water and extracted with EtOAc. The combined organic extracts were washed with brine, dried (MgSO$_4$) and concentrated in vacuo to give the title product (60 mg) as a 2:1 mix of product and starting material, which was used crude in the next reaction. LCMS (ESI) [M+H]$^+$ 443.2.

Step 3: 5'-(5-(4-Methyl-4H-1,2,4-triazol-3-yl)-1H-indol-3-yl)-1',2'-dihydrospiro[cyclopropane-1,3'-pyrrolo[2,3-b]pyridine]

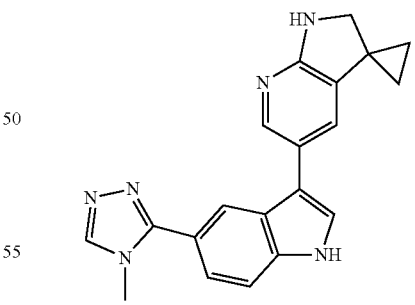

tert-Butyl 5'-(5-(4-methyl-4H-1,2,4-triazol-3-yl)-1H-indol-3-yl)spiro[cyclopropane-1,3'-pyrrolo[2,3-b]pyridine]-1'(2'H)-carboxylate (0.10 mmol) was dissolved in HCl (4N in dioxane, 1 mL, 4 mmol). The reaction mixture was stirred at RT for 3 h, then was concentrated in vacuo. The residue was purified by Method C to afford the title compound (26 mg, 74%). $^1$H NMR (400 MHz, DMSO-d$_6$) δ ppm 11.95 (s, 1H), 8.98 (s, 1H), 8.80 (s, 1H), 8.18 (s, 1H), 7.97 (d, J=2.4 Hz, 1H), 7.89 (d, J=1.4 Hz, 1H), 7.68 (d, J=8.4 Hz, 1H), 7.64 (d, J=1.6 Hz, 1H), 7.58 (dd, J=8.4, 1.6 Hz, 1H), 3.96 (s, 2H), 2.54 (s, 3H), 1.37-1.31 (m, 2H), 1.26-1.22 (m, 2H). LCMS (Method B) (ESI) $R_T$ 2.16 min, [M+H]$^+$ 343.1.

Example 174: 2-(3-(1',2'-Dihydrospiro[cyclopropane-1,3'-pyrrolo[2,3-b]pyridin]-5'-yl)-1H-indol-5-yl)-1,3,4-oxadiazole Formate Salt (Compound 334)

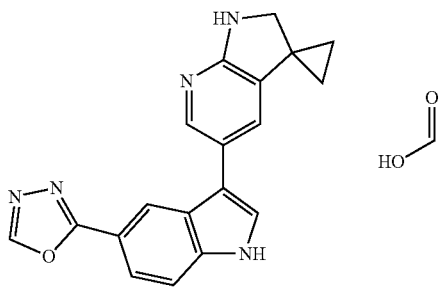 [SMILES: c1nnc(-c2ccc3[nH]cc(-c4cnc5c(c4)C4(CC4)CN5)c3c2)o1 ; O=CO]

The title compound was prepared as described above for 2-(3-(1',2'-dihydrospiro[cyclopropane-1,3'-pyrrolo[2,3-b]pyridin]-5'-yl)-1H-indol-5-yl)-1,3,4-oxadiazole (steps 1-3), starting from 2-(3-bromo-1-tosyl-1H-indol-5-yl)-1,3,4-oxadiazole in place of 3-bromo-5-(4-methyl-4H-1,2,4-triazol-3-yl)-1-tosyl-1H-indole in step 1. $^1$H NMR (400 MHz, DMSO-d$_6$) δ ppm 9.25 (s, 1H), 8.33 (s, 1H), 8.16 (s, 1H), 7.99 (d, J=1.5 Hz, 1H), 7.80 (d, J=8.6 Hz, 1H), 7.65 (d, J=2.1 Hz, 1H), 7.60 (d, J=8.6 Hz, 1H), 7.14 (d, J=1.8 Hz, 1H), 6.56 (s, 1H), 3.55 (s, 2H), 1.11-1.04 (m, 2H), 1.02-0.98 (m, 2H). LCMS (Method B) (ESI) $R_T$ 2.46 min, [M+H]$^+$ 330.0.

Example 175: 3-Amino-6-(4'-methoxy-1',2'-dihydrospiro[cyclopropane-1,3'-pyrrolo[2,3-b]pyridin]-5'-yl)-N,N-dimethylpicolinamide (Compound 309)

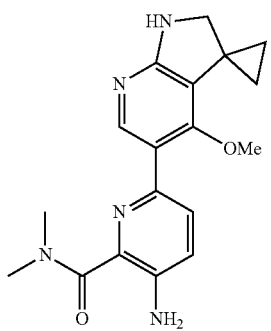 [SMILES: COc1c(-c2ccc(N)c(C(=O)N(C)C)n2)cnc2c1C1(CC1)CN2]

A degassed mixture of 3-amino-N,N-dimethyl-6-(tributylstannyl)picolinamide (163 mg, 0.36 mmol), 5'-bromo-4'-methoxy-1',2'-dihydrospiro[cyclopropane-1,3'-pyrrolo[2,3-b]pyridine](91 mg, 0.360 mmol), copper (I) iodide (21 mg, 0.11 mmol), lithium chloride (76 mg, 1.79 mmol) and tetrakis(triphenylphosphine)palladium (O) (41.5 mg, 0.040 mmol) in 1,4-dioxane (1.5 mL) was heated in a sealed tube under microwave irradiation at 115° C. for 4 h. The cooled mixture was passed down a SCX-2 cartridge (eluting with MeOH followed by MeOH·NH$_3$). The resulting pale yellow gum was purified by chromatography on silica (solvent gradient with 0-6% MeOH·NH$_3$ in DCM), followed by further purification by Method C to afford the title compound as a pale yellow solid. $^1$H NMR (400 MHz, DMSO-d$_6$) δ ppm 7.77 (s, 1H), 7.29 (d, J=8.6 Hz, 1H), 7.14 (d, J=8.6 Hz, 1H), 6.60 (s, 1H), 5.52 (s, 2H), 3.45 (d, J=0.9 Hz, 2H), 3.29 (s, 3H), 3.01 (s, 3H), 3.00 (s, 3H), 1.33-1.28 (m, 2H), 0.87-0.83 (m, 2H). LCMS (Method B) (ESI) $R_T$ 2.25 min, [M+H]$^+$ 340.2.

Example 176: 3-Amino-6-((1R,3 S)-4'-chloro-3-cyano-3-methyl-1',2'-dihydrospiro[cyclopentane-1,3'-pyrrolo[2,3-b]pyridin]-5'-yl)-N,N-dimethylpicolinamide (Compound 288)

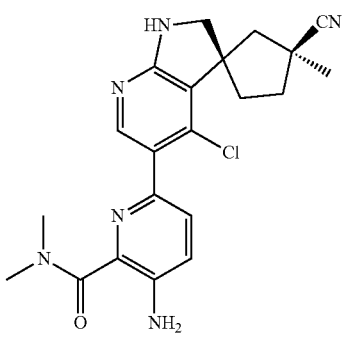

A mixture of 3-amino-N,N-dimethyl-6-(tributylstannyl)picolinamide (166 mg, 0.37 mmol), (1RS,3SR)-5'-bromo-4'-chloro-3-methyl-1',2'-dihydrospiro[cyclopentane-1,3'-pyrrolo[2,3-b]pyridine]-3-carbonitrile (100 mg, 0.31 mmol) and tetrakis(triphenylphosphine)palladium(O) (35 mg, 0.03 mmol) in 1,4-dioxane (2 mL) were degassed with argon and the reaction mixture heated at 100° C. for 16 h. The reaction mixture was concentrated in vacuo and the residue purified on silica (solvent gradient 0-6% MeOH·NH$_3$ in EtOAc). The product was crystallised from MeCN and further purified by rpHPLC (Method D) to give the product as a white solid (19 mg, 15%). $^1$H NMR (400 MHz, DMSO-d$_6$) δ7.79 (s, 1H), 7.26 (d, J=8.2 Hz, 1H), 7.15 (d, J=8.7 Hz, 1H), 6.99 (s, 1H), 5.57 (s, 2H), 3.64 (d, J=9.3 Hz, 1H), 3.52 (d, J=9.3 Hz, 1H), 2.99 (s, 3H), 2.98 (s, 3H), 2.60-2.51 (m, 1H), 2.38 (d, J=13.1 Hz, 1H), 2.29-2.21 (m, 1H), 2.15 (d, J=13.2 Hz, 1H), 2.06-1.88 (m, 2H), 1.48 (s, 3H). LCMS (Method B) (ESI) $R_T$ 2.60 min, [M+H]$^+$ 411.2.

Example 177: 1-(1',2'-Dihydrospiro[cyclopropane-1,3'-pyrrolo[2,3-b]pyridin]-5'-yl)-1H-indole-6-carbonitrile (Compound 344)

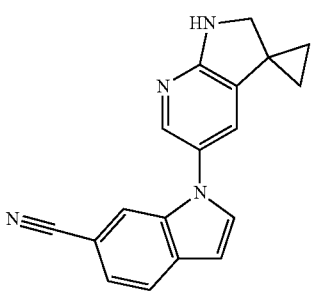 [SMILES: N#Cc1ccc2ccn(-c3cnc4c(c3)C3(CC3)CN4)c2c1]

A degassed mixture of tert-butyl 5'-bromospiro[cyclopropane-1,3'-pyrrolo[2,3-b]pyridine]-1'(2'H)-carboxylate (100 mg, 0.31 mmol), 5-cyanoindole (52 mg, 0.37 mmol), copper iodide (2.9 mg, 0.02 mmol), (+)-trans-1,2-diaminocyclohexane (7 mg, 0.06 mmol) and potassium phosphate (137 mg, 0.65 mmol) in DMF (1 mL) was heated in a sealed vial at 130° C. for 16 h. The cooled mixture was passed through a plug of celite, eluting with EtOAc, and concentrated. The residue was taken up in DCM (2 mL) and stirred with TFA (2 mL) at RT for 16 h. The mixture was concentrated and purified by Method C to afford the title compound (22 mg, 25%) as a white solid. $^1$H NMR (400 MHz, DMSO-d$_6$) δ ppm 7.80 (m, 1H), 7.77 (m, 3H), 7.42 (dd, J=1.4, 8.2 Hz, 1H), 7.08 (d, J=2.3 Hz, 1H), 6.93 (s, 1H), 6.77 (d, J=2.6 Hz, 1H), 3.61 (s, 2H), 1.16-1.11 (m, 2H), 1.03-0.98 (m, 2H). LCMS (Method B) (ESI) R$_T$ 3.22 min, [M+H]$^+$ 287.3.

Example 178: 5-(Benzotriazol-1-yl)spiro[1,2-dihydropyrrolo[2,3-b]pyridine-3,1'-cyclopropane](Compound 332)

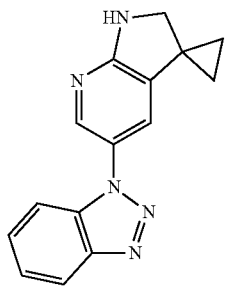 [SMILES: c1ccc2c(c1)nnn2-c1cnc2c(c1)C1(CC1)CN2]

A degassed mixture of tert-butyl 5-bromospiro[2H-pyrrolo[2,3-b]pyridine-3,1'-cyclopropane]-1-carboxylate (100 mg, 0.31 mmol), benzotriazole (44 mg, 0.37 mmol), copper iodide (2.9 mg, 0.02 mmol), potassium phosphate (137 mg, 0.65 mmol) and (±)-trans-1,2-diaminocyclohexane (7 mg, 0.06 mmol) in DMF (2 mL) was heated to 130° C. for 16 h with vigorous stirring, then was cooled and passed through a silica cartridge (eluting with EtOAc). The relevant combined fractions were washed with a 5% aq LiCl solution. The organic extract was dried (Na$_2$SO$_4$), filtered and concentrated in vacuo. The resulting residue was dissolved in HCl (4N in 1,4-dioxane, 1 mL), and the reaction mixture was stirred for 16 h, then concentrated in vacuo. The residue was purified by Method D to give the title compound (40 mg, 49.4%) as a grey/brown powder. $^1$H NMR (400 MHz, CDCl$_3$) δ ppm 8.13-8.09 (m, 2H), 7.63-7.60 (m, 1H), 7.55-7.50 (m, 1H), 7.44-7.39 (m, 1H), 7.08 (d, J=2.3 Hz, 1H), 4.96 (s, 1H), 3.79 (s, 2H), 1.18-1.07 (m, 4H). LCMS (Method B) (ESI) R$_T$ 2.84 min, [M+H]$^+$ 264.

Example 179: 5-(1H-Pyrrolo[3,2-c]pyridin-3-yl)spiro[1,2-dihydropyrrolo[2,3-b]pyridine-3,1'-cyclopropane](Compound 329)

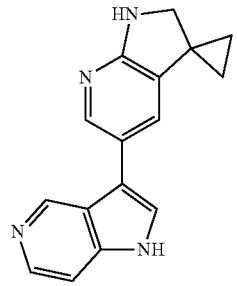

Step 1: tert-Butyl 3-(1',2'-dihydrospiro[cyclopropane-1,3'-pyrrolo[2,3-b]pyridin]-5'-yl)-1H-pyrrolo[3,2-c]pyridine-1-carboxylate

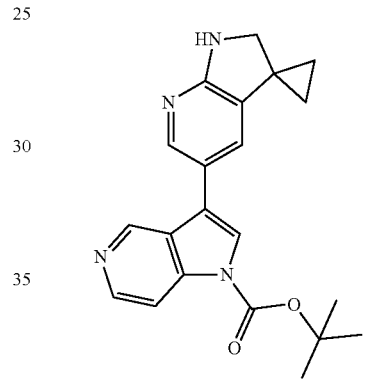

The title compound was prepared according to general Method N, using 5-bromospiro[1,2-dihydropyrrolo[2,3-b]pyridine-3,1'-cyclopropane]and tert-butyl 3-(4,4,5,5-tetramethyl-1,3,2-dioxaborolan-2-yl)pyrrolo[3,2-c]pyridine-1-carboxylate. LCMS (ESI) [M+H]$^+$ 363.3.

Step 2: 5-(1H-)Pyrrolo[3,2-c]pyridin-3-yl)spiro[1,2-dihydropyrrolo[2,3-b]pyridine-3,1'-cyclopropane]

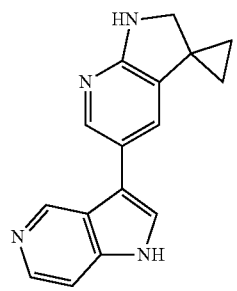 [SMILES: c1cc2[nH]cc(-c3cnc4c(c3)C3(CC3)CN4)c2cn1]

A solution of tert-butyl 3-spiro[1,2-dihydropyrrolo[2,3-b]pyridine-3,1'-cyclopropane]-5-ylpyrrolo[3,2-c]pyridine-1-carboxylate (100 mg, 0.28 mmol) in trifluoroethanol (7.7 mL) was heated under microwave irradiation at 140° C. for 1 h. The solvent was removed in vacuo and the residue was purified by chromatography on silica (solvent gradient 0-8% MeOH·NH₃ in DCM) to afford the title compound (49 mg, 68%) as a light brown solid. ¹H NMR (400 MHz, DMSO-d₆) δ ppm 11.58 (s, 1H), 9.00 (s, 1H), 8.18 (d, J=5.6 Hz, 1H), 8.02 (d, J=2.1 Hz, 1H), 7.59 (d, J=2.2 Hz, 1H), 7.38 (dd, J=0.9, 5.7 Hz, 1H), 7.17 (d, J=1.9 Hz, 1H), 6.52 (s, 1H), 3.54 (d, J=1.3 Hz, 2H), 1.12 (q, J=3.5 Hz, 2H), 0.98 (q, J=3.7 Hz, 2H). LCMS (Method A) (ESI): R_T 2.99 min, [M+H]⁺ 262.9.

Example 180: 3-(1',2'-Dihydrospiro[cyclopropane-1, 3'-pyrrolo[2,3-b]pyridin]-5'-yl)-6-fluoro-1H-indole-5-carbonitrile (Compound 348)

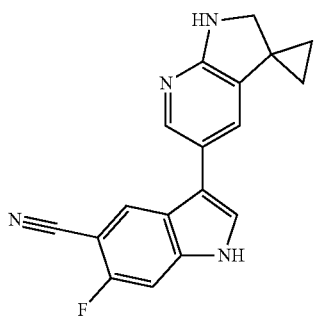 [SMILES: N#Cc1cc2c(-c3cnc4c(c3)C3(CC3)CN4)c[nH]c2cc1F]

Step 1: tert-Butyl 5'-(5-cyano-6-fluoro-1H-indol-3-yl)spiro[cyclopropane-1,3'-pyrrolo[2,3-b]pyridine]-1'(2'H)-carboxylate

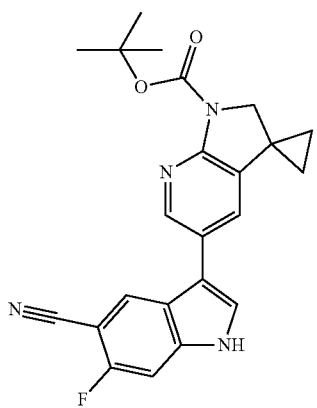 [SMILES: CC(C)(C)OC(=O)N1CC2(CC2)c2cc(-c3c[nH]c4cc(F)c(C#N)cc34)cnc21]

A degassed mixture of (1-tert-butoxycarbonylspiro[2H-pyrrolo[2,3-b]pyridine-3,1'-cyclopropane]-5-yl)boronic acid (142 mg, 0.49 mmol), [1,1'-bis(diphenylphosphino) ferrocene]dichloropalladium(II) complex with dichloromethane (26 mg, 0.03 mmol), cesium carbonate (298 mg, 0.91 mmol), 6-fluoro-3-iodo-1H-indole-5-carbonitrile (130 mg, 0.45 mmol) in 1,4-dioxane (4.3 mL) and water (0.85 mL) was heated at 100° C. for 1.5 h. The reaction mixture was diluted with EtOAc and washed with water. The aqueous layer was extracted with EtOAc. The combined organic extracts were dried (Na₂SO₄) and concentrated. The residue was purified by chromatography on silica (solvent gradient 0-5% MeOH in DCM), to afford the title compound (60 mg, 32.6%) as a brown solid. LCMS (ESI) [M+H]⁺ 405.3.

Step 2: 3-(1',2'-Dihydrospiro[cyclopropane-1,3'-pyrrolo[2,3-b]pyridin]-5'-yl)-6-fluoro-1H-indole-5-carbonitrile

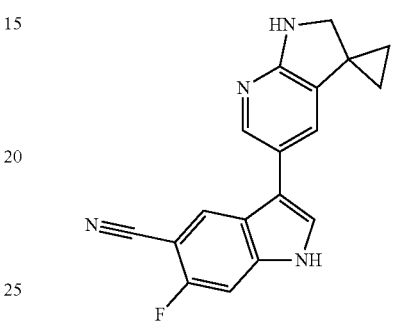

A solution of tert-butyl 5-(5-cyano-6-fluoro-1H-indol-3-yl)spiro[2H-pyrrolo[2,3-b]pyridine-3,1'-cyclopropane]-1-carboxylate (54 mg, 0.13 mmol) in trifluoroethanol (2 mL) was heated under microwave irradiation at 140° C. for 1 h. The solvent was removed in vacuo and the residue was purified by chromatography on silica (solvent gradient 0-5% MeOH·NH₃ in DCM) to afford the title compound (25.5 mg, 62.7% yield) as a light brown solid. ¹H NMR (400 MHz, DMSO-d₆) δ ppm 11.83 (s, 1H), 8.22 (d, J=6.2 Hz, 1H), 7.97-7.96 (m, 1H), 7.68 (s, 1H), 7.46 (d, J=10.4 Hz, 1H), 7.13 (d, J=1.9 Hz, 1H), 6.57-6.55 (m, 1H), 3.53 (d, J=1.1 Hz, 2H), 1.14 (dd, J=4.2, 6.8 Hz, 2H), 0.97 (dd, J=4.3, 6.7 Hz, 2H). LCMS (Method A) (ESI) R_T 2.87 min, [M+H]⁺ 305.2.

Example 181: 3-(1',2'-Dihydrospiro[cyclopropane-1, 3'-pyrrolo[2,3-b]pyridin]-5'-yl)-N-(1-methyl-1H-pyrazol-4-yl)-1H-indol-6-amine (Compound 345)

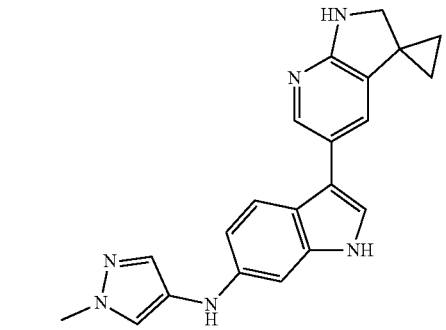 [SMILES: Cn1cc(Nc2ccc3c(-c4cnc5c(c4)C4(CC4)CN5)c[nH]c3c2)cn1]

Step 1: tert-Butyl 5'-(6-bromo-1-(phenylsulfonyl)-1H-indol-3-yl)spiro[cyclopropane-1,3'-pyrrolo[2,3-b]pyridine]-1'(2'H)-carboxylate

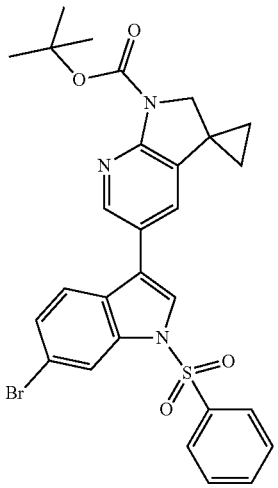 [SMILES: CC(C)(C)OC(=O)N1CC2(CC2)c2cc(-c3cn(S(=O)(=O)c4ccccc4)c4cc(Br)ccc34)cnc21]

A degassed mixture of (1-tert-butoxycarbonylspiro[2H-pyrrolo[2,3-b]pyridine-3,1'-cyclopropane]-5-yl)boronic acid (35 mg, 1.21 mmol), [1,1'-bis(diphenylphosphino)ferrocene]dichloropalladium(II) complex with DCM (69 mg, 0.08 mmol), cesium carbonate (796 mg, 2.43 mmol), 1-(benzenesulfonyl)-6-bromo-3-iodo-indole (561 mg, 1.21 mmol) in 1,4-dioxane (2.8 mL) and water (0.56 mL) was heated at 50° C. for 1 h.
The reaction mixture was diluted with EtOAc and washed with water. The aqueous layer was extracted with EtOAc. The combined organic extracts were dried (Na$_2$SO$_4$) and concentrated in vacuo. The residue was purified by chromatography on silica (solvent gradient 0-60% Et$_2$O in cyclohexane) to afford the title compound (363 mg, 51.4%) as a pale yellow solid. LCMS (ESI) [M+H]$^+$ 580.2.

Step 2: tert-Butyl 5'-(6-((1-methyl-1H-pyrazol-4-yl)amino)-1-(phenylsulfonyl)-1H-indol-3-yl)spiro[cyclopropane-1,3'-pyrrolo[2,3-b]pyridine]-1'(2'H)-carboxylate

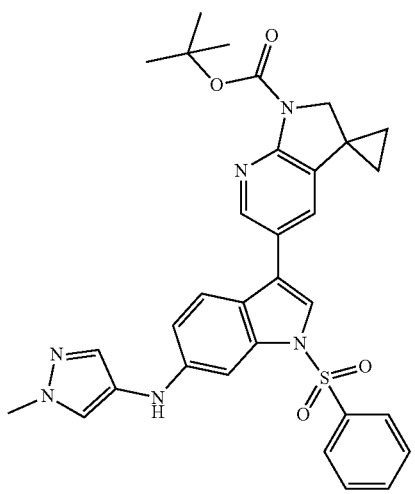 [SMILES: Cn1cc(Nc2ccc3c(-c4cnc5c(c4)C4(CC4)CN5C(=O)OC(C)(C)C)cn(S(=O)(=O)c4ccccc4)c3c2)cn1]

A degassed mixture of tert-butyl 5'-(6-bromo-1-(phenylsulfonyl)-1H-indol-3-yl)spiro[cyclopropane-1,3'-pyrrolo[2,3-b]pyridine]-1'(2'H)-carboxylate (360 mg, 0.62 mmol), tris(dibenzylideneacetone)dipalladium(O) (40 mg, 0.04 mmol), XantPhos (50 mg, 0.09 mmol), cesium carbonate (813 mg, 2.48 mmol), 1-methylpyrazol-4-amine (78 mg, 0.80 mmol) and 1,4-dioxane (10.5 mL) was heated at 100° C. for 1 h. The reaction mixture was allowed to cool to RT and filtered onto a pad of Celite®, rinsing with 1,4-dioxane. The solvent was evaporated in vacuo. The residue was purified by chromatography on silica (solvent gradient 0-6% MeOH in DCM), to afford the title compound (159 mg, 43%) as a brown solid. LCMS (ESI) [M+H]$^+$ 597.4.

Step 3: tert-Butyl 5'-(6-((1-methyl-1H-pyrazol-4-yl)amino)-1H-indol-3-yl)spiro[cyclopropane-1,3'-pyrrolo[2,3-b]pyridine]-1'(2'H)-carboxylate

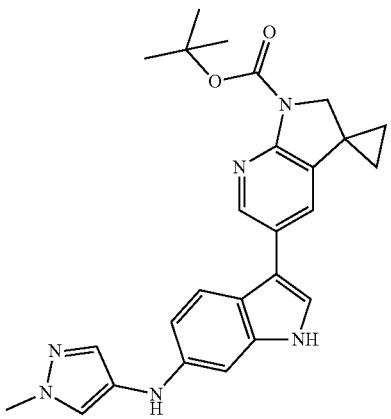 [SMILES: Cn1cc(Nc2ccc3c(-c4cnc5c(c4)C4(CC4)CN5C(=O)OC(C)(C)C)c[nH]c3c2)cn1]

To a solution of tert-butyl 5'-(6-((1-methyl-1H-pyrazol-4-yl)amino)-1-(phenylsulfonyl)-1H-indol-3-yl)spiro[cyclopropane-1,3'-pyrrolo[2,3-b]pyridine]-1'(27-1)-carboxylate (77 mg, 0.13 mmol) in THF (0.61 mL) at RT were added successively piperidine (0.07 mL, 0.68 mmol) and TBAF (1N in THF, 0.645 mL, 0.65 mmol). The reaction mixture was heated to 70° C. for 18 h, then treated with further portions of piperidine (10 eq.) and tetrabutylammonium fluoride (10 eq.). After stirring at 70° C. for another 6 h, the mixture was allowed to cool to RT and a mixture of water/brine/EtOAc was added. The aqueous phase was re-extracted with further EtOAc and the combined organic extracts were washed with brine, dried (Na$_2$SO$_4$) and concentrated. The residue was purified by chromatography on silica (solvent gradient 0-7% MeOH·NH$_3$ in DCM) to afford the title compound (14 mg, 23.7%) as a light yellow oil. LCMS (ESI) [M+H]$^+$ 457.4.

501

Step 4: 3-(1',2'-Dihydrospiro[cyclopropane-1,3'-pyrrolo[2,3-b]pyridin]-5'-yl)-N-(1-methyl-1H-pyrazol-4-yl)-1H-indol-6-amine

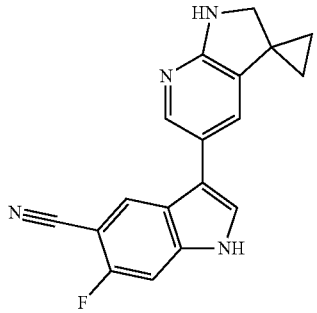 [SMILES: N#Cc1cc2c(-c3cnc4c(c3)C3(CC3)CN4)c[nH]c2cc1F]

tert-Butyl 5'-(6-((1-methyl-1H-pyrazol-4-yl)amino)-1H-indol-3-yl)spiro[cyclopropane-1,3'-pyrrolo[2,3-b]pyridine]-1'(2'H)-carboxylate (14 mg, 0.03 mmol) was treated with TFA/DCM and purified by chromatography on silica (solvent gradient 0-10% MeOH·NH$_3$ in DCM) to afford the title compound (3.4 mg, 31.1%) as a light brown solid. $^1$H NMR (400 MHz, CDCl$_3$) δ ppm 8.07 (d, J=1.9 Hz, 1H), 7.94 (s, 1H), 7.56 (d, J=8.3 Hz, 1H), 7.45 (s, 1H), 7.34 (s, 1H), 7.03 (dd, J=2.1, 18.6 Hz, 2H), 6.76 (d, J=1.8 Hz, 1H), 6.69 (dd, J=2.1, 8.5 Hz, 1H), 5.06 (s, 1H), 4.57 (s, 1H), 3.90 (s, 3H), 3.67 (s, 2H), 1.12-0.98 (m, 4H). LCMS (Method A) (ESI): R$_T$ 2.57 min, [M+H]$^+$ 357.2.

Example 182: 3-(1',2'-Dihydrospiro[cyclopropane-1,3'-pyrrolo[2,3-b]pyridin]-5'-yl)-N-methyl-N-(1-methyl-1H-pyrazol-4-yl)-1H-indol-6-amine (Compound 343)

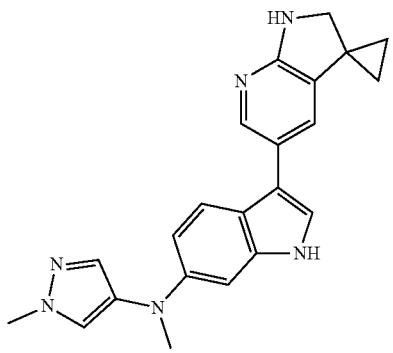 [SMILES: CN(c1ccc2c(-c3cnc4c(c3)C3(CC3)CN4)c[nH]c2c1)c1cnn(C)c1]

502

Step 1: tert-Butyl 5'-(6-(methyl(1-methyl-1H-pyrazol-4-yl)amino)-1-(phenylsulfonyl)-1H-indol-3-yl)spiro[cyclopropane-1,3'-pyrrolo[2,3-b]pyridine]-1'(2'H)-carboxylate

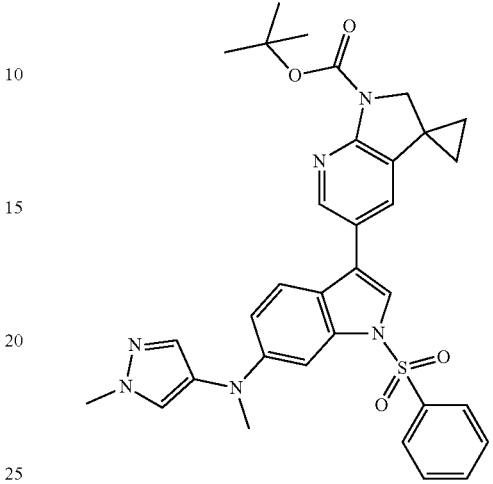

Sodium hydride (60% in oil, 9.7 mg, 0.24 mmol) was added to a solution of tert-butyl 5-[1-(benzenesulfonyl)-6-[(1-methylpyrazol-4-yl)amino]indol-3-yl]spiro[2H-pyrrolo[2,3-b]pyridine-3,1'-cyclopropane]-1-carboxylate (131 mg, 0.22 mmol) in THF (3.8 mL) at 0° C. Iodomethane (0.016 mL, 0.25 mmol) was then added dropwise, and the reaction mixture was stirred for 1 h at RT. Further portions of sodium hydride (1 eq.) and iodomethane (1 eq.) were added at 0° C. The reaction was stirred at RT for 1.5 h. Further portions of sodium hydride (1 eq.) and iodomethane (1 eq.) were added at 0° C. The reaction was stirred at RT for 18 h. Water was carefully added, followed by EtOAc. The aqueous phase was further extracted with EtOAc. The combined organic extracts were washed with sat. aq. sodium chloride, dried (Na$_2$SO$_4$) and concentrated. The residue was purified by chromatography on silica (solvent gradient 0-7% MeOH·NH$_3$ in DCM) to afford the title compound (78 mg, 58.2%) as a white solid. LCMS (ESI) [M+H]$^+$ 611.4.

Step 2: tert-Butyl 5'-(6-(methyl(1-methyl-1H-pyrazol-4-yl)amino)-1H-indol-3-yl)spiro[cyclopropane-1,3'-pyrrolo[2,3-b]pyridine]-1'(2'H)-carboxylate

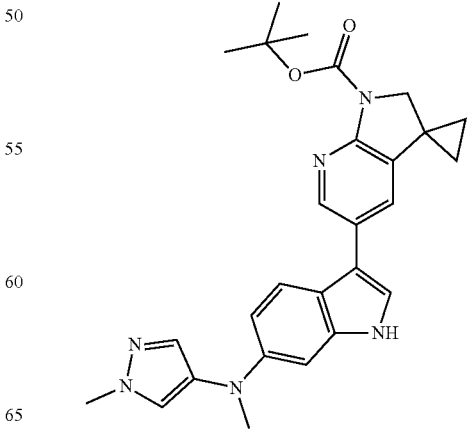

A solution of tert-butyl 5'-(6-(methyl(1-methyl-1H-pyrazol-4-yl)amino)-1-(phenylsulfonyl)-1H-indol-3-yl)spiro[cyclopropane-1,3'-pyrrolo[2,3-b]pyridine]-1'(2'H)-carboxylate (78 mg, 0.13 mmol) in TBAF (1N in THF, 1.92 mL, 1.92 mmol) was heated to 60° C. for 18 h. The mixture was allowed to cool to RT and a mixture of water/brine/EtOAc was added. The aqueous phase was re-extracted with EtOAc and the combined organic extracts were washed with brine, dried (Na$_2$SO$_4$) and concentrated. The residue was purified by chromatography on silica (solvent gradient 0-7% MeOH·NH$_3$ in DCM) to afford the title compound (44 mg, 73.2%) as a white solid. LCMS (ESI) [M+H]$^+$ 471.3.

Step 3: 3-(1',2'-Dihydrospiro[cyclopropane-1,3'-pyrrolo[2,3-b]pyridin]-5'-yl)-N-methyl-N-(1-methyl-1H-pyrazol-4-yl)-1H-indol-6-amine

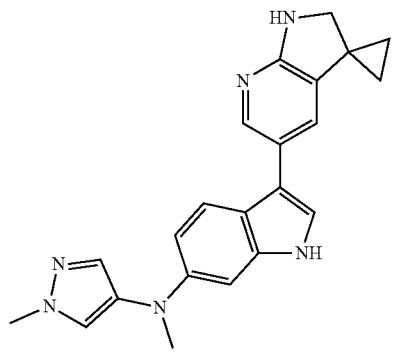 [SMILES: CN(c1ccc2c(-c3cnc4c(c3)C3(CC3)CN4)c[nH]c2c1)c1cnn(C)c1]

tert-Butyl 5'-(6-(methyl(1-methyl-1H-pyrazol-4-yl)amino)-1H-indol-3-yl)spiro[cyclopropane-1,3'-pyrrolo[2,3-b]pyridine]-1'(2'H)-carboxylate (44 mg, 0.09 mmol) was treated with TFA/DCM and purified by chromatography on silica (solvent gradient 0-10% MeOH·NH$_3$ in DCM) to afford the title compound (32 mg, 92.4%) as a light brown solid. $^1$H NMR (400 MHz, CDCl$_3$) δ ppm 8.07 (d, J=2.0 Hz, 1H), 7.97 (s, 1H), 7.58 (d, J=8.6 Hz, 1H), 7.38 (d, J=0.6 Hz, 1H), 7.22 (d, J=0.8 Hz, 1H), 7.10 (d, J=2.3 Hz, 1H), 7.01 (d, J=2.0 Hz, 1H), 6.92-6.86 (m, 2H), 4.59 (s, 1H), 3.88 (s, 3H), 3.68 (s, 2H), 3.25 (s, 3H), 1.11-0.99 (m, 4H). LCMS (Method A) (ESI): R$_T$ 2.87 min, [M+H]$^+$ 371.3.

Example 183: 6-Amino-3-(4'-chloro-1',2'-dihydrospiro[cyclobutane-1,3'-pyrrolo[2,3-b]pyridin]-5'-yl)-2-fluoro-N-(2-hydroxyethyl)-N-methylbenzamide (Compound 44)

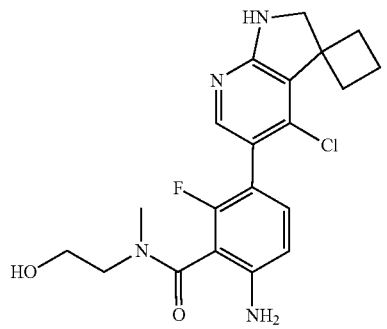

Step 1: 6-Amino-N-(2-((tert-butyldimethylsilyl)oxy)ethyl)-3-(4'-chloro-1',2'-dihydrospiro[cyclobutane-1,3'-pyrrolo[2,3-b]pyrdin]-5'-yl)-2-fluoro-N-methylbenzamide

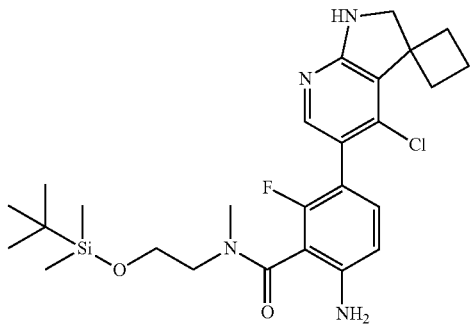 [SMILES: CN(CCO[Si](C)(C)C(C)(C)C)C(=O)c1c(N)ccc(-c2cnc3c(c2Cl)C2(CCC2)CN3)c1F]

The title compound was prepared according to general Method L, starting from 5'-bromo-4'-chloro-1',2'-dihydrospiro[cyclobutane-1,3'-pyrrolo[2,3-b]pyridine] and 6-amino-N-(2-((tert-butyldimethylsilyl)oxy)ethyl)-2-fluoro-N-methyl-3-(4,4,5,5-tetramethyl-1,3,2-dioxaborolan-2-yl)benzamide. LCMS (ESI) [M+H]$^+$ 519.3.

Step 2: 6-Amino-3-(4'-chloro-1',2'-dihydrospiro[cyclobutane-1,3'-pyrrolo[2,3-b]pyridin]-5'-yl)-2-fluoro-N-(2-hydroxyethyl)-N-methylbenzamide

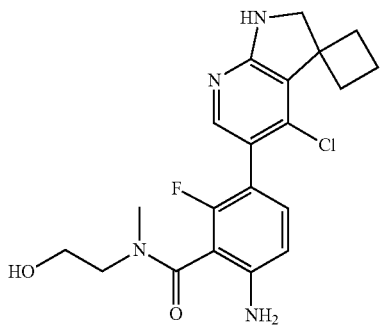 [SMILES: CN(CCO)C(=O)c1c(N)ccc(-c2cnc3c(c2Cl)C2(CCC2)CN3)c1F]

TBAF (1.0N in THF, 0.34 mL, 0.34 mmol) was added dropwise to a suspension of 6-amino-N-(2-((tert-butyldimethylsilyl)oxy)ethyl)-3-(4'-chloro-1',2'-dihydrospiro[cyclobutane-1,3'-pyrrolo[2,3-b]pyridin]-5'-yl)-2-fluoro-N-methylbenzamide (146 mg, 0.282 mmol) in THF (1 mL). The mixture was stirred for 2 h at RT, then was partitioned between ice-water (15 mL) and EtOAc (3×15 mL). The combined organic extracts were washed with brine (20 mL), dried (Na$_2$SO$_4$) and concentrated. The residue was passed down a SCX-2 cartridge (eluting with MeOH followed by MeOH·NH$_3$). The resulting brown gum was triturated under DCM and filtered. The filtered solid was purified by HPLC (solvent gradient 10-50% MeCN in H$_2$O (HCO$_2$H 0.1%)) to afford the title compound (25 mg, 22%) as a colorless powder after freeze drying. $^1$H NMR (400 MHz, DMSO-d$_6$): δ ppm 7.59 (d, J=3.82 Hz, 1H), 6.97 (m, 1H), 6.85 (s, 1H), 6.55 (dd, 1H), 5.37 (d, J=19.7 Hz, 1H), 3.70 (s, 2H), 3.61 (m, 1H), 3.52-3.21 (m, 4H), 3.02 (s, 1H), 2.92 (s, 1H), 2.82 (m, 1H), 2.50 (m, 3H), 2.08-1.96 (m, 3H). LCMS (Method A) (ESI) R$_T$ 2.66 min, [M+H]$^+$ 405.2.

Example 184: 6-Amino-2-fluoro-N-(2-hydroxyethyl)-3-(4'-methoxy-1',2'-dihydrospiro[cyclobutane-1,3'-pyrrolo[2,3-b]pyridin]-5'-yl)-N-methylbenzamide (Compound 52)

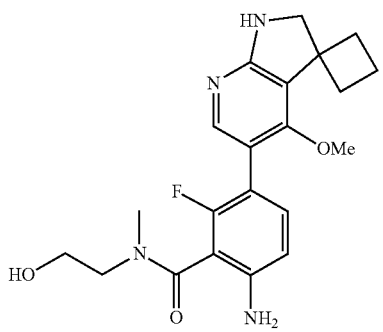

Step 1: 6-Amino-N-(2-((tert-butyldimethylsilyl)oxy)ethyl)-2-fluoro-3-(4'-methoxy-1',2'-dihydrospiro[cyclobutane-1,3'-pyrrolo[2,3-b]pyridin]-5'-yl)-N-methylbenzamide

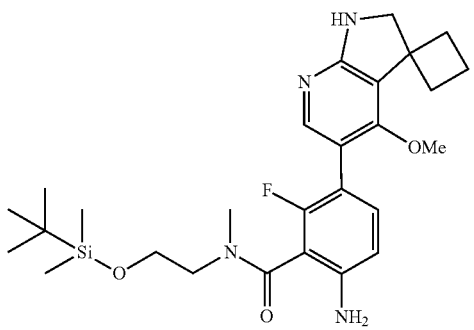 [SMILES: COc1c(-c2ccc(N)c(C(=O)N(C)CCO[Si](C)(C)C(C)(C)C)c2F)cnc2c1C1(CCC1)CN2]

The title compound was prepared according to general Method L starting from 5'-bromo-4'-methoxy-1',2'-dihydrospiro[cyclobutane-1,3'-pyrrolo[2,3-b]pyridine] and 6-amino-N-(2-((tert-butyldimethylsilyl)oxy)ethyl)-2-fluoro-N-methyl-3-(4,4,5,5-tetramethyl-1,3,2-dioxaborolan-2-yl)benzamide. LCMS (ESI) [M+H]$^+$ 515.3.

Step 2: 6-Amino-2-fluoro-N-(2-hydroxyethyl)-3-(4'-methoxy-1',2'-dihydrospiro[cyclobutane-1,3'-pyrrolo[2,3-b]pyridin]-5'-yl)-N-methylbenzamide

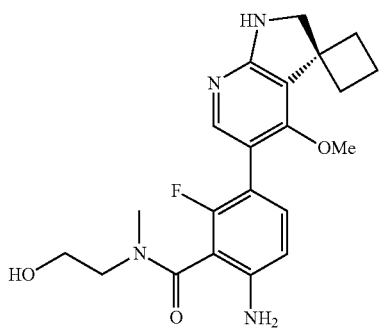

TBAF (1.0N in THF, 0.43 mL, 0.43 mmol) was added dropwise to a suspension of 6-amino-N-(2-((tert-butyldimethylsilyl)oxy)ethyl)-2-fluoro-3-(4'-methoxy-1',2'-dihydrospiro[cyclobutane-1,3'-pyrrolo[2,3-b]pyridin]-5'-yl)-N-methylbenzamide (146 mg, 0.282 mmol) in THF (2 mL). The mixture was stirred for 2 h at RT, then was partitioned between ice-water (15 mL) and EtOAc (3×15 mL). The combined organic extracts were washed with brine, dried (Na$_2$SO$_4$) and concentrated. The residue was passed down a SCX-2 cartridge (eluting with MeOH followed by MeOH·NH$_3$). The resulting brown gum was triturated under DCM and filtered. The filtered solid was purified by HPLC (solvent gradient 10-50% MeCN in H$_2$O (HCO$_2$H 0.1%)) to afford the title compound (38 mg, 26%) as a colorless powder after freeze drying. $^1$H NMR (400 MHz, DMSO-d$_6$): δ ppm 7.51 (d, J=3.1 Hz, 1H), 7-06-7.01 (dt, J=6.0 Hz, 1H), 6.59-6.27 (dd, J=6.3 Hz, 1H), 6.40 (s, 1H), 5.37 (s, 1H), 5.30 s, 1H), 4.87-4.75 (dt, 1H), 3.74-3.67 (m, 1H), 3.61 (m, 1H), 3.56 (s, 2H), 3.51-3.36 (m, 2H), 3.43 (d, 2H), 3.27-3.23 (m, 1H), 3.01, 2.92 (2xs, 3H), 2.56-2.49 (m, 2H, obscured by water), 2.12-1.89 (m, 4H). LCMS (Method A) (ESI) R$_T$ 2.61 min, [M+H]$^+$ 401.2.

Example 185: 6-Amino-3-((1r,3r)-3-(cyanomethyl)-1',2'-dihydrospiro[cyclobutane-1,3'-pyrrolo[2,3-b]pyridin]-5'-yl)-2-fluoro-N,N-dimethylbenzamide (Compound 95)

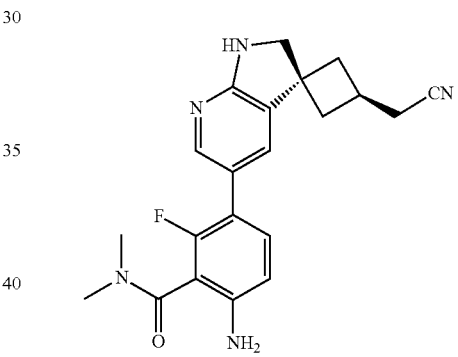

Step 1: 6-Amino-3-(3-(cyanomethylene)-1',2'-dihydrospiro[cyclobutane-1,3'-pyrrolo[2,3-b]pyridin]-5'-yl)-2-fluoro-N,N-dimethylbenzamide

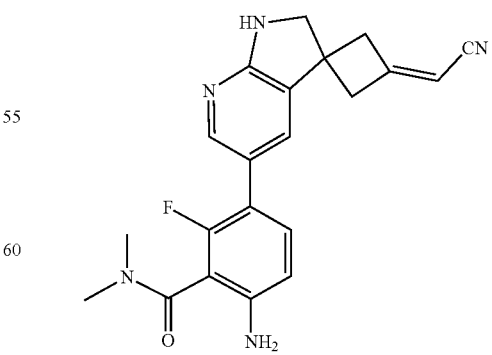

The title compound was prepared according to general Method L, starting from 2-(5'-chloro-1',2'-dihydrospiro[cyclobutane-1,3'-pyrrolo[2,3-b]pyrdin]-3-ylidene)acetonitrile and 6-amino-2-fluoro-N,N-dimethyl-3-(4,4,5,5-tetramethyl-1,3,2-dioxaborolan-2-yl)benzamide. LCMS (ESI) [M+H]⁺ 378.2.

Step 2: 6-Amino-3-((1r,3r)-3-(cyanomethyl)-1',2'-dihydrospiro[cyclobutane-1,3'-pyrrolo[2,3-b]pyridin]-5'-yl)-2-fluoro-N,N-dimethylbenzamide

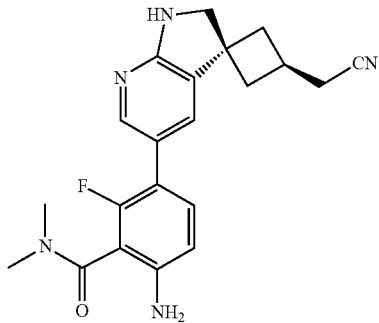 [SMILES: CN(C)C(=O)c1c(N)ccc(-c2cnc3c(c2)[C@]2(CN3)C[C@@H](CC#N)C2)c1F]

A solution of 6-amino-3-(3-(cyanomethylene)-1',2'-dihydrospiro[cyclobutane-1,3'-pyrrolo[2,3-b]pyridin]-5'-yl)-2-fluoro-N,N-dimethylbenzamide (110 mg, 0.291 mmol) in EtOAc/MeOH (1:1, 2 mL) was hydrogenated over palladium (10% on carbon) at RT for 4 h. The catalyst was filtered off and the filtrate evaporated. The residue was purified by HPLC (solvent gradient 0-98% MeCN in H$_2$O (NH$_4$OH 0.1%)) to afford the title compound (48 mg, 43%) as a colorless powder after freeze drying. $^1$H NMR (400 MHz, DMSO) δ ppm 7.79 (t, J=1.7 Hz, 1H), 7.57 (s, 1H), 7.17 (t, J=8.8 Hz, 1H), 6.58 (d, J=8.4 Hz, 1H), 6.48 (s, 1H), 5.31 (s, 2H), 3.63 (s, 2H), 3.00 (s, 3H), 2.88 (s, 3H), 2.74-2.71 (m, 3H), 2.33-2.24 (m, 2H), 2.16-2.08 (m, 2H). LCMS (Method A) (ESI) R$_T$ 2.30 min, [M+H]⁺ 380.2.

Example 186

6-Amino-3-((1r,3r)-3-(2-amino-2-oxoethyl)-1',2'-dihydrospiro[cyclobutane-1,3'-pyrrolo[2,3-b]pyridin]-5'-yl)-2-fluoro-N,N-dimethylbenzamide (Compound 102a)

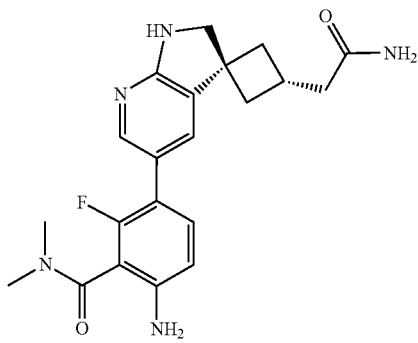 [SMILES: CN(C)C(=O)c1c(N)ccc(-c2cnc3c(c2)[C@]2(CN3)C[C@H](CC(N)=O)C2)c1F]

Step 1: 6-Amino-3-(3-(2-amino-2-oxoethylidene)-1',2'-dihydrospiro[cyclobutane-1,3'-pyrrolo[2,3-b]pyridin]-5'-yl)-2-fluoro-N,N-dimethylbenzamide

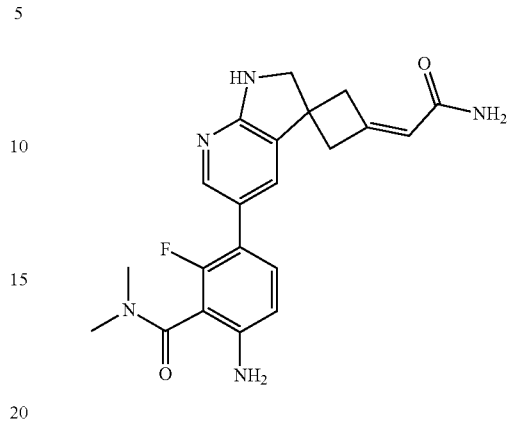

The title compound was prepared according to general Method L starting from 2-(5'-chloro-1',2'-dihydrospiro[cyclobutane-1,3'-pyrrolo[2,3-b]pyrdin]-3-ylidene)acetamide and 6-amino-2-fluoro-N,N-dimethyl-3-(4,4,5,5-tetramethyl-1,3,2-dioxaborolan-2-yl)benzamide. LCMS (ESI) [M+H]⁺ 396.2.

Step 2: 6-Amino-3-((1r,3r)-3-(2-amino-2-oxoethyl) 4,2'-dihydrospiro[cyclobutane-1,3'-pyrrolo[2,3-b] pyridin]-5'-yl)-2-fluoro-N,N-dimethylbenzamide

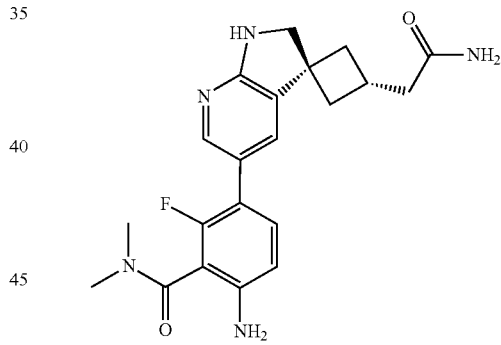

A solution of 6-amino-3-(3-(2-amino-2-oxoethylidene)-1',2'-dihydrospiro[cyclobutane-1,3'-pyrrolo[2,3-b]pyridin]-5'-yl)-2-fluoro-N,N-dimethylbenzamide (193 mg, 0.489 mmol) in EtOAc/MeOH (1:1, 4 mL) was hydrogenated over palladium (10% on carbon) at RT for 18 h. The catalyst was filtered off and the filtrate evaporated. The residue was purified by chromatography on silica (solvent gradient 0-10% MeOH·NH$_3$ in DCM) to afford the title compound (134 mg, 69%) as a colorless powder. $^1$H NMR (400 MHz, DMSO-d$_6$) δ ppm 7.77 (t, J=1.7 Hz, 1H), 7.45 (s, 1H), 7.22 (s, 1H), 7.18 (t, J=8.9 Hz, 1H), 6.74-6.68 (m, 1H), 6.58 (d, J=8.4 Hz, 1H), 6.45 (s, 1H), 5.31 (s, 2H), 3.62-3.62 (m, 2H), 3.17 (d, J=5.3 Hz, 1H), 3.00 (s, 3H), 2.89 (s, 3H), 2.68-2.54 (m, 1H), 2.26-2.17 (m, 3H), 2.05-1.97 (m, 2H). LCMS (Method A) (ESI) R$_T$ 1.92 min, [M+H]⁺ 398.3.

Example 187: 6-Amino-3-(3-((2-amino-2-oxoethyl)amino)-4'-chloro-1',2'-dihydrospiro[cyclopentane-1,3'-pyrrolo[2,3-b]pyridin]-5'-yl)-2-fluoro-N,N-dimethylbenzamide (Compound 76)

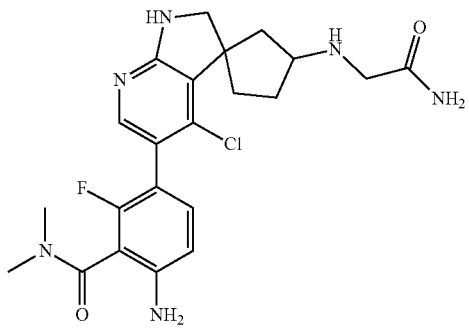 [SMILES: CN(C)C(=O)c1c(N)ccc(-c2cnc3c(c2Cl)C2(CCC(NCC(N)=O)C2)CN3)c1F]

Step 1: tert-Butyl 5'-(4-amino-3-(dimethylcarbamoyl)-2-fluorophenyl)-4'-chloro-3-oxospiro[cyclopentane-1,3'-pyrrolo[2,3-b]pyridine]-1'(2'H)-carboxylate

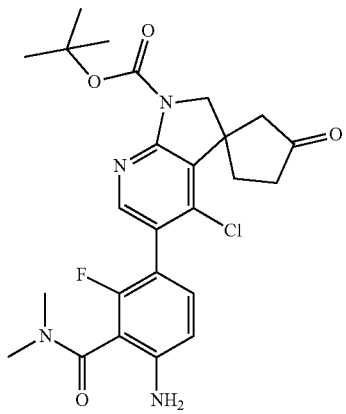 [SMILES: CN(C)C(=O)c1c(N)ccc(-c2cnc3c(c2Cl)C2(CCC(=O)C2)CN3C(=O)OC(C)(C)C)c1F]

The title compound was prepared according to general Method L, starting from tert-butyl 5'-bromo-4'-chloro-3-oxospiro[cyclopentane-1,3'-pyrrolo[2,3-b]pyridine]-1' (2'H)-carboxylate and 6-amino-2-fluoro-N,N-dimethyl-3-(4,4,5,5-tetramethyl-1,3,2-dioxaborolan-2-yl)benzamide. LCMS (ESI) [M+H]$^+$ 503.2.

Step 2: tert-Butyl 3-((2-amino-2-oxoethyl)amino)-5'-(4-amino-3-(dimethylcarbamoyl)-2-fluorophenyl)-4'-chlorospiro[cyclopentane-1,3'-pyrrolo[2,3-b]pyridine]-1'(2'H)-carboxylate

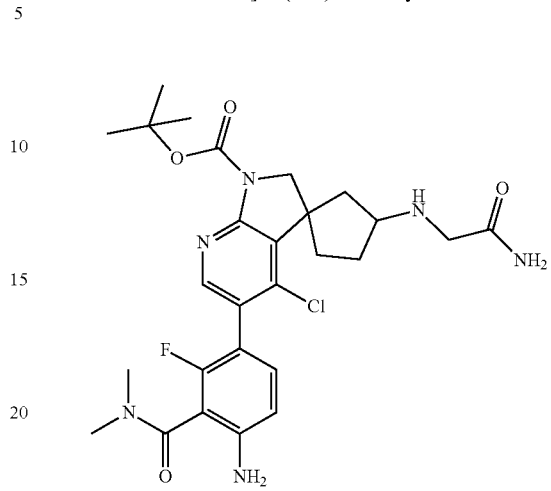

To as solution of tert-butyl 5'-(4-amino-3-(dimethylcarbamoyl)-2-fluorophenyl)-4'-chloro-3-oxospiro[cyclopentane-1,3'-pyrrolo[2,3-b]pyridine]-1'(2'H)-carboxylate (72 mg, 0.143 mmol) in MeOH (2 mL) were added successively glycinamide·HCl (21 mg, 0.186 mmol) and sodium cyanoborohydride (10.8 mg, 0.172 mmol). The reaction mixture was stirred at RT for 18 h, then was concentrated. The residue was purified by chromatography on silica (solvent gradient 0-10% MeOH·NH$_3$ in DCM) to afford the title compound as a colorless oil (50 mg, 62%). LCMS (ESI) [M+H]$^+$ 561.3.

Step 3: 6-Amino-3-(3-((2-amino-2-oxoethyl)amino)-4'-chloro-1',2'-dihydrospiro[cyclopentane-1,3'-pyrrolo[2,3-b]pyridin]-5'-yl)-2-fluoro-N,N-dimethylbenzamide

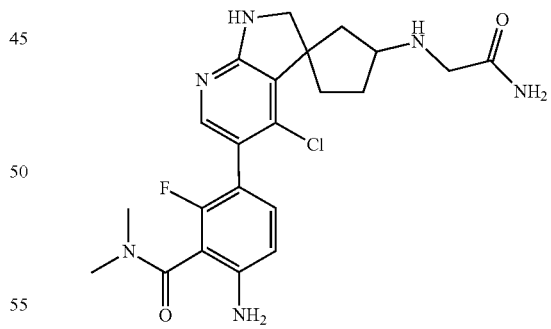

To a solution of tert-butyl 3-((2-amino-2-oxoethyl)amino)-5'-(4-amino-3-(dimethylcarbamoyl)-2-fluorophenyl)-4'-chlorospiro[cyclopentane-1,3'-pyrrolo[2,3-b]pyridine]-1'(2'H)-carboxylate (50 mg, 0.089 mmol) in DCM (3 mL) was added TFA (1 mL). The reaction mixture was stirred at RT for 1 h, then purified on SCX-2 cartridge (eluting with MeOH then MeOH·NH$_3$) to afford the title compound (41 mg, 100%) as a colorless oil. $^1$H NMR (400 MHz, CDCl$_3$) δ ppm 7.71 (d, J=1.3 Hz, 1H), 7.03 (dt, J=1.3, 8.3 Hz, 2H), 6.90 (s, 1H), 6.55 (d, J=8.3 Hz, 1H), 5.46 (bs, 1H), 4.64 (s, 1H), 4.40 (s, 2H), 3.56 (s, 1H), 3.44 (m, 1H), 3.14 (s, 3H), 3.04 (s, 3H), 2.86-2.75 (m, 1H), 2.68-2.57 (m, 1H), 2.21-2.13 (m, 1H), 2.02-1.94 (m, 1H), 1.77-1.69 (m, 1H), 1.52-1.43 (m, 1H). LCMS (Method A) $R_T$ 1.57 min, [M+H]$^+$ 461.2.

Example 188

3-(4'-Chloro-1',2'-dihydrospiro[cyclopentane-1,3'-pyrrolo[2,3-b]pyridin]-3-en-5'-yl)-2-fluoro-N-((1-(2-hydroxyethyl)-1H-pyrazol-4-yl)methyl)-N-methyl-benzamide (Compound 262)

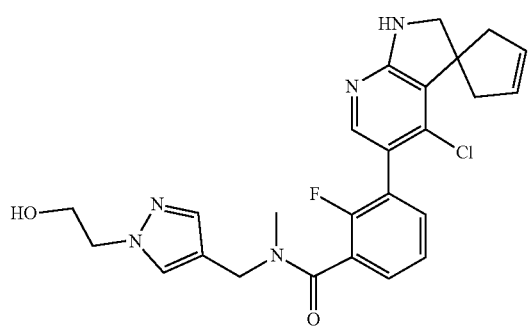 [SMILES: CN(Cc1cnn(CCO)c1)C(=O)c1cccc(-c2cnc3c(c2Cl)C2(CC=CC2)CN3)c1F]

Step 1: tert-Butyl 5'-(3-(((1-(2-((tert-butyldimethylsilyl)oxy)ethyl)-1H-pyrazol-4-yl)methyl)(methyl)carbamoyl)-2-fluorophenyl)-4'-chlorospiro[cyclopentane-1,3'-pyrrolo[2,3-b]pyrdin]-3-ene-1'(2'H)-carboxylate

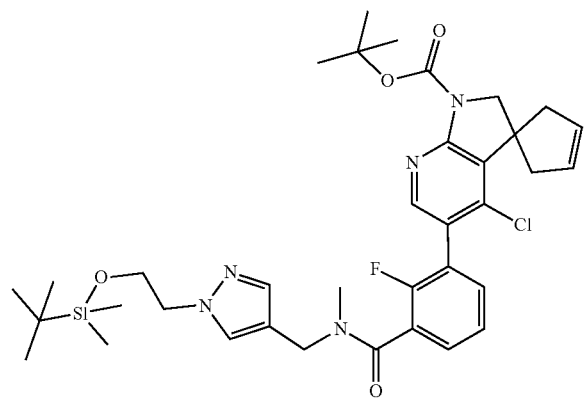

The title compound was prepared according to general Method N, using 3-bromo-N-((1-(2-((tert-butyldimethylsilyl)oxy)ethyl)-1H-pyrazol-4-yl)methyl)-2-fluoro-N-methyl-benzamide and tert-butyl 4'-chloro-5'-(4,4,5,5-tetramethyl-1,3-dioxolan-2-yl)spiro[cyclopentane-1,3'-pyrrolo[2,3-b]pyridin]-3-ene-1'(2'H)-carboxylate. LCMS (ESI) [M+H]$^+$ 696.4.

Step 2: 3-(4'-Chloro-1',2'-dihydrospiro[cyclopentane-1,3'-pyrrolo[2,3-b]pyridin]-3-en-5'-yl)-2-fluoro-N-((1-(2-hydroxyethyl)-1H-pyrazol-4-yl)methyl)-N-methylbenzamide

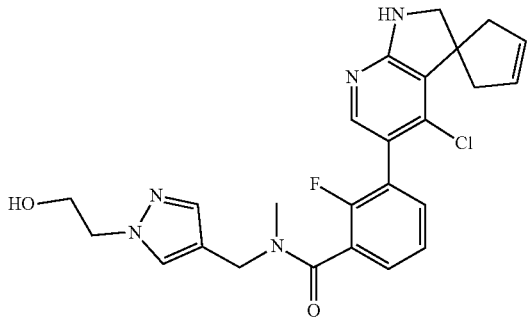 [SMILES: CN(Cc1cnn(CCO)c1)C(=O)c1cccc(-c2cnc3c(c2Cl)C2(CC=CC2)CN3)c1F]

To a solution of tert-butyl 5'-(3-((1-(2-((tert-butyldimethylsilyl)oxy)ethyl)-1H-pyrazol-4-yl)methyl)(methyl)carbamoyl)-2-fluorophenyl)-4'-chlorospiro[cyclopentane-1,3'-pyrrolo[2,3-b]pyrdin]-3-ene-1'(2'H)-carboxylate (53 mg, 0.08 mmol) in MeOH (1 mL) was added HCl (4N in dioxane, 1 mL, 4 mmol). The reaction mixture was stirred at RT for 3 days, then was concentrated in vacuo. The residue was purified by Method C (18 mg, 49%). $^1$H NMR (400 MHz, CDCl$_3$) δ ppm 7.76-7.72 (m, 1H), 7.56-7.49 (m, 1H), 7.44-7.37 (m, 1H), 7.36-7.21 (m, 3H), 5.75 (s, 2H), 4.67 (s, 1H), 4.60 (s, 1H), 4.32 (s, 1H), 4.24-4.16 (m, 2H), 4.03-3.95 (m, 2H), 3.61 (s, 2H), 3.25-3.15 (m, 2H), 3.05 (s, 1H), 2.90 (s, 2H), 2.58-2.48 (m, 2H). LCMS (Method A) (ESI) $R_T$ 2.99 min, [M+H]$^+$ 482.1.

Example 189

3-(4'-Chloro-1',2'-dihydrospiro[cyclopentane-1,3'-pyrrolo[2,3-b]pyridin]-3-en-5'-yl)-2-fluoro-N-methyl-N-((1-(pyrrolidin-3-yl)-1H-pyrazol-4-yl)methyl)benzamide (Compound 260)

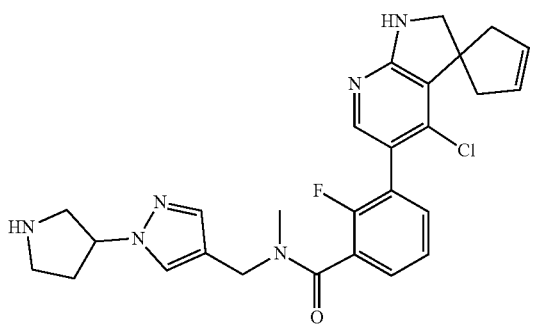 [SMILES: CN(Cc1cnn(C2CCNC2)c1)C(=O)c1cccc(-c2cnc3c(c2Cl)C2(CC=CC2)CN3)c1F]

Step 1: tert-Butyl 5'-(3-((1-(1-(tert-butoxycarbonyl)pyrrolidin-3-yl)-1H-pyrazol-4-yl)methyl)(methyl)carbamoyl)-2-fluorophenyl)-4'-chlorospiro[cyclopentane-1,3'-pyrrolo[2,3-b]pyridin]-3-ene-1'(2'H)-carboxylate

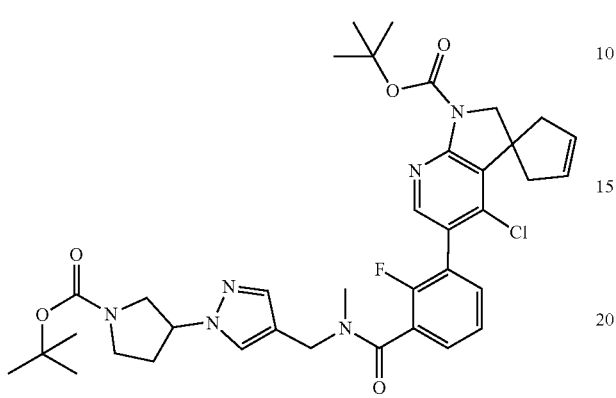

The title compound was prepared according to general Method M, starting from tert-butyl 3-(4-((3-bromo-2-fluoro-N-methylbenzamido)methyl)-1H-pyrazol-1-yl)pyrrolidine-1-carboxylate and tert-butyl 4'-chloro-5'-(4,4,5,5-tetramethyl-1,3-dioxolan-2-yl)spiro[cyclopentane-1,3'-pyrrolo[2,3-b]pyridin]-3-ene-1'(2'H)-carboxylate. LCMS (ESI) [M+H]+ 707.5.

Step 2: 3-(4'-Chloro-1',2'-dihydrospiro[cyclopentane-1,3'-pyrrolo[2,3-b]pyridin]-3-en-5'-yl)-2-fluoro-N-methyl-N-41-(pyrrolidin-3-yl)-1H-pyrazol-4-yl)methyl)benzamide

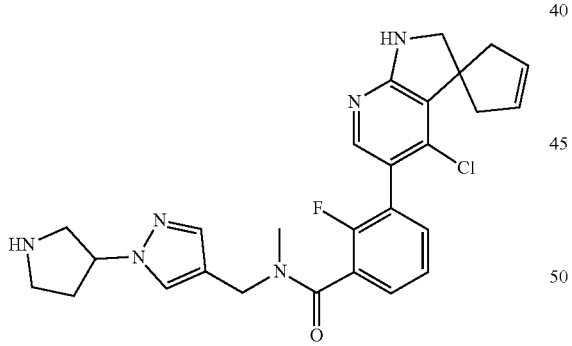

To a solution tert-butyl 5'-(3-(((1-(1-(tert-butoxycarbonyl)pyrrolidin-3-yl)-1H-pyrazol-4-yl)methyl)(methyl)carbamoyl)-2-fluorophenyl)-4'-chlorospiro[cyclopentane-1,3'-pyrrolo[2,3-b]pyridin]-3-ene-1'(27-1)-carboxylate (226 mg, 0.32 mmol) in MeOH (2 mL) was added HCl (4N in dioxane, 2 mL, 8 mmol). The reaction mixture was stirred at RT for 1 h, then was concentrated in vacuo and the residue purified by Method C. $^1$H NMR (400 MHz, CDCl$_3$) δ ppm 7.74 (s, 1H), 7.53-7.49 (m, 1H), 7.44-7.22 (m, 4H), 5.75 (s, 2H), 4.85-4.73 (m, 2H), 4.58 (s, 2H), 4.30 (1H, s), 3.66-3.59 (m, 2H), 3.38-3.13 (m, 2H), 3.17-3.04 (m, 3H), 2.89 (s, 3H), 2.57-2.48 (m, 2H), 2.41-2.26 (m, 2H), 2.25-2.14 (m, 1H). LCMS (Method B) (ESI) R$_T$ 2.66 min, [M+H]+ 507.2.

Example 190: 6-Amino-3-(3-(2-amino-2-oxoethylidene)-4'-chloro-1',2'-dihydrospiro[cyclopentane-1,3'-pyrrolo[2,3-b]pyridin]-5'-yl)-2-fluoro-N,N-dimethylbenzamide (Compound 110)

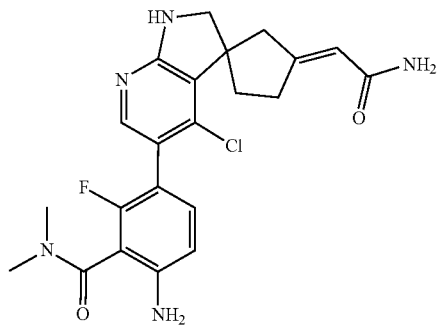 [SMILES: CN(C)C(=O)c1c(N)ccc(-c2cnc3c(c2Cl)C2(CC/C(=C\C(N)=O)C2)CN3)c1F]

Step 1: (3-(3-(2-Amino-2-oxoethylidene)-4'-chloro-1',2'-dihydrospiro[cyclopentane-1,3'-pyrrolo[2,3-b]pyridin]-5'-yl)-2-fluoro-N,N-dimethyl-6-(2,2,2-trifluoroacetamido)benzamide

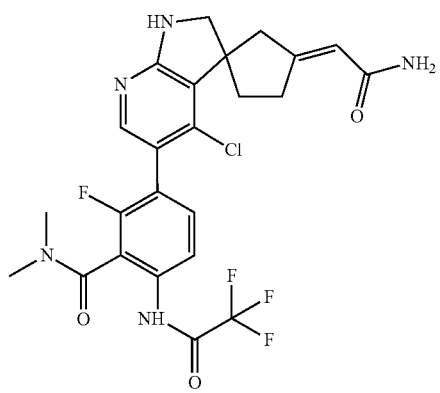 [SMILES: CN(C)C(=O)c1c(NC(=O)C(F)(F)F)ccc(-c2cnc3c(c2Cl)C2(CC/C(=C\C(N)=O)C2)CN3)c1F]

6-Amino-3-(4'-chloro-3-(cyanomethylene)-1',2'-dihydrospiro[cyclopentane-1,3'-pyrrolo[2,3-b]pyridin]-5'-yl)-2-fluoro-N,N-dimethylbenzamide (0.12 g, 0.28 mmol) was dissolved in TFA (1 mL) and heated in a sealed tube at 80° C. for 7 h. The reaction mixture was concentrated in vacuo and the residue partitioned between DCM and aq. sodium bicarbonate. The combined organic extracts were dried (Na$_2$SO$_4$) and concentrated in vacuo. The residue was purified by chromatography on silica (solvent gradient 0-20% MeOH·NH$_3$ in DCM), to afford the title compound (105 mg, 84%) as a white solid. LCMS (ESI) [M+H]+ 540/542.

Step 2: 6-Amino-3-(3-(2-amino-2-oxoethylidene)-4'-chloro-1',2'-dihydrospiro[cyclopentane-1,3'-pyrrolo[2,3-b]pyridin]-5'-yl)-2-fluoro-N,N-dimethylbenzamide

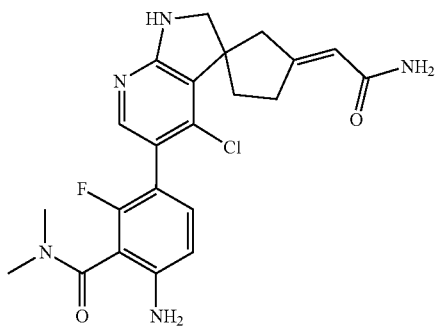 [SMILES: CN(C)C(=O)c1c(N)ccc(-c2cnc3c(c2Cl)C2(CC/C(=C\C(N)=O)C2)CN3)c1F]

A mixture of (3-(3-(2-amino-2-oxoethylidene)-4'-chloro-1',2'-dihydrospiro[cyclopentane-1,3'-pyrrolo[2,3-b]pyridin]-5'-yl)-2-fluoro-N,N-dimethyl-6-(2,2,2-trifluoroacetamido)benzamide (0.11 g, 0.19 mmol) and potassium carbonate (0.08 g, 0.58 mmol) in MeOH (2 mL) and water (0.2 mL) was heated at 50° C. for 17 h. The reaction mixture was partitioned between DCM and brine. The combined organic extracts were dried ($Na_2SO_4$) and concentrated in vacuo. The residue was purified by Method C to give the title product (50 mg, 58%) as a white solid. $^1$H NMR (400 MHz, DMSO-$d_6$) δ ppm 7.64-7.59 (m, 1H), 7.29-7.18 (m, 1H), 7.00-6.91 (m, 1H), 6.85-6.77 (m, 2H), 6.55 (dd, J=8.6, 3.3 Hz, 1H), 5.48-5.34 (m, 3H), 3.32 (s, 6H), 2.99 (s, 2H), 2.92-2.85 (m, 4H), 2.54 (s, 2H). LCMS (Method A) (ESI) RT 2.15 min, [M+H]$^+$ 444.1.

Example 191

Additional compounds were synthesized according to the General Synthetic Methods descried herein and following procedures similar to those described above. Chemical analytical data (LC/MS and NMR) are provided in Table A1.

TABLE A1

| No. | Structure/Name | LCMS R$_T$ (min) m/z Method | Prep Mtd | $^1$H NMR δ (ppm) |
|---|---|---|---|---|
| 1 | 2-Amino-5-(1',2'-dihydrospiro[cyclopentane-1,3'-pyrrolo[2,3-b]pyridin]-5'-yl)-N,N-dimethylbenzamide | 2.65 337.2 A | L | (400 MHz, DMSO-d$_6$) δ 7.84 (d, J = 2.0 Hz, 1H), 7.44 (d, J = 2.0 Hz, 1H), 7.31 (dd, J = 2.2, 8.6 Hz, 1H), 7.18, (d, J = 2.0 Hz, 1H), 6.74 (d, J = 8.8 Hz, 1H), 6.30 (bs, 1H), 5.10 (bs, 2H), 3.28 (d, J = 1.0 Hz, 2H), 2.95 (s, 6H), 1.87-1.66 (m, 8H) |
| 2 | 2-Amino-5-(1',2'-dihydrospiro[cyclopropane-1,3'-pyrrolo[2,3-b]pyridin]-5'-yl)-N,N-dimethylbenzamide | 2.25 309.2 B | L | (400 MHz, DMSO-d$_6$) δ 7.84 (d, J = 2.0 Hz, 1H), 7.28 (dd, J = 2.2, 8.6 Hz, 1H), 7.15 (d, J = 2.0 Hz, 1H), 7.05 (d, J = 2.0 Hz, 1H), 6.72 (d, J = 8.8 Hz, 1H), 6.46 (bs, 1H), 5.13 (bs, 2H), 3.50 (d, J = 1.0 Hz, 2H), 2.94 (s, 6H), 1.10-1.06 (m, 2H), 0.96-0.91 (m, 2H) |

TABLE A1-continued

| No. | Structure/Name | LCMS R_T (min) m/z Method | Prep Mtd | $^1$H NMR δ (ppm) |
|---|---|---|---|---|
| 3 | 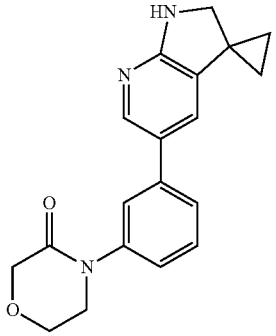<br>4-(3-(1′,2′-Dihydrospiro[cyclopropane-1,3′-pyrrolo[2,3-b]pyridin]-5′-yl)phenyl)morpholin-3-one | 2.37<br>322.2<br>B | L | (400 MHz, DMSO-d$_6$) δ 7.98 (d, J = 2.4 Hz, 1H), 7.54 (app t, J = 1.7 Hz, 1H), 7.49-7.44 (m, 1H), 7.40 (app t, J = 7.8 Hz, 1H), 7.27-7.23 (m, 1H), 7.16 (d, J = 2.0 Hz, 1H), 6.72 (bs, 1H), 4.21 (s, 2H), 4.01-3.96 (m, 2H), 3.79-3.75 (m, 2H), 3.54 (d, J = 1.0 Hz, 2H), 1.13-1.08 (m, 2H), 1.00-0.95 (m, 2H) |
| 4 | 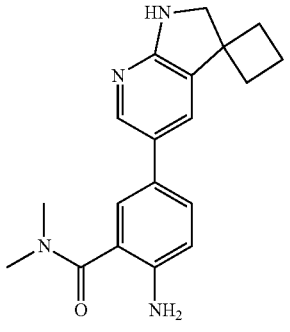<br>2-Amino-5-(1′,2′-dihydrospiro[cyclobutane-1,3′-pyrrolo[2,3-b]pyridin]-5′-yl)-N,N-dimethylbenzamide | 2.49<br>323.2<br>B | L | (400 MHz, DMSO-d$_6$) δ 7.92 (d, J = 2.0 Hz, 1H), 7.70 (d, J = 2.0 Hz, 1H), 7.35 (dd, J = 2.2, 8.6 Hz, 1H), 7.23 (d, J = 2.4 Hz, 1H), 6.76 (d, J = 8.3 Hz, 1H), 6.31 (bs, 1H), 5.15 (bs, 2H), 3.55 (d, J = 1.0 Hz, 2H), 2.96 (s, 6H), 2.38-2.28 (m, 2H), 2.18-2.09 (m, 2H), 2.07-1.89 (m, 2H) |
| 5 | 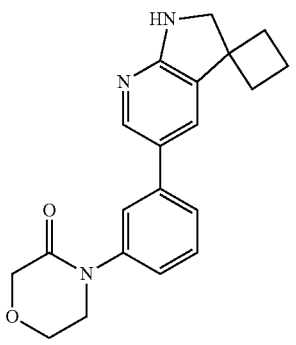<br>4-(3-(1′,2′-Dihydrospiro[cyclobutane-1,3′-pyrrolo[2,3-b]pyridin]-5′-yl)phenyl)morpholin-3-one | 2.60<br>336.2<br>B | L | (400 MHz, DMSO-d$_6$) δ 8.06 (d, J = 2.0 Hz, 1H), 7.82 (d, J = 2.4 Hz, 1H), 7.63 (t, J = 1.7 Hz, 1H), 7.55-7.51 (m, 1H), 7.44 (t, J = 7.8 Hz, 1H), 7.30-7.26 (m, 1H), 6.57 (s, 1H), 4.22 (s, 2H), 4.02-3.98 (m, 2H), 3.82-3.78 (m, 2H), 3.60 (d, J = 1.0 Hz, 2H), 2.40-2.31 (m, 2H), 2.21-2.11 (m, 2H), 2.07-1.93 (m, 2H) |

TABLE A1-continued

| No. | Structure/Name | LCMS R_T (min) m/z Method | Prep Mtd | $^1$H NMR δ (ppm) |
|---|---|---|---|---|
| 6 | 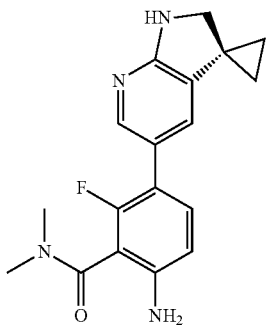<br>6-Amino-3-(1',2'-dihydrospiro[cyclopropane-1,3'-pyrrolo[2,3-b]pyridin]-5'-yl)-2-fluoro-N,N-dimethylbenzamide | 2.32<br>327.2<br>B | L | (400 MHz, DMSO-d$_6$) δ 7.70 (t, J = 1.8 Hz, 1H), 7.12 (t, J = 8.8 Hz, 1H), 6.89 (s, 1H), 6.58-6.53 (m, 2H), 5.28 (s, 2H), 3.51 (d, J = 1.0 Hz, 2H), 2.99 (s, 3H), 2.87 (s, 3H), 1.03-1.00 (m, 2H), 0.98-0.94 (m, 2H). |
| 7 | 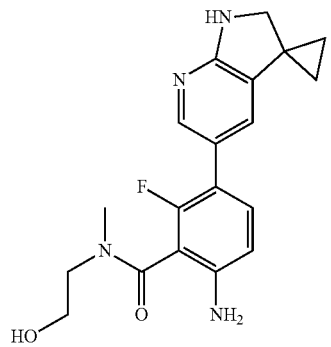<br>6-amino-3-(1',2'-dihydrospiro[cyclopropane-1,3'-pyrrolo[2,3-b]pyridin]-5'-yl)-2-fluoro-N-(2-hydroxyethyl)-N-methylbenzamide | 357.2 | L | |
| 8 | 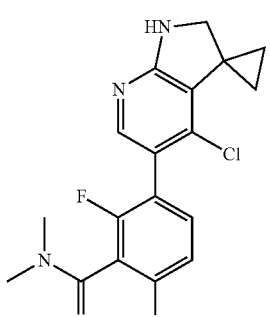<br>6-Amino-3-(4'-chloro-1',2'-dihydrospiro[cyclopropane-1,3'-pyrrolo[2,3-b]pyridin]-5'-yl)-2-fluoro-N,N-dimethylbenzamide | 2.71<br>361.1<br>A | L | (400 MHz, DMSO-d$_6$) δ 7.51 (bs, 1H), 6.95 (s, 1H), 6.93 (app t, J = 8.5 Hz, 1H), 6.54 (d, J = 8.4 Hz, 1H), 5.37 (s, 2H), 3.51 (s, 2H), 2.98 (s, 3H), 2.87 (d, J = 1.0 Hz, 3H), 1.63-1.59 (m, 2H), 0.90-0.85 (m, 2H) |

TABLE A1-continued

| No. | Structure/Name | LCMS R$_T$ (min) m/z Method | Prep Mtd | $^1$H NMR δ (ppm) |
|---|---|---|---|---|
| 9 | 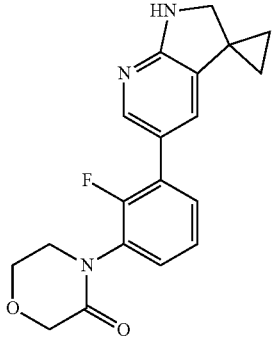  4-(3-(1',2'-Dihydrospiro[cyclopropane-1,3'-pyrrolo[2,3-b]pyridin]-5'-yl)-2-fluorophenyl)morpholin-3-one | 2.36 340.1 B | M | (400 MHz, DMSO-d$_6$) δ 7.83 (t, J = 1.8 Hz, 1H), 7.43 (td, J = 7.4, 1.8 Hz, 1H), 7.35 (td, J = 7.4, 1.6 Hz, 1H), 7.27 (t, J = 7.9 Hz, 1H), 7.01-6.98 (m, 1H), 6.81 (s, 1H), 4.23 (s, 2H), 4.02-3.95 (m, 2H), 3.71-3.66 (m, 2H), 3.55 (s, 2H), 1.08-1.02 (m, 2H), 1.01-0.95 (m, 2H). |
| 10 | 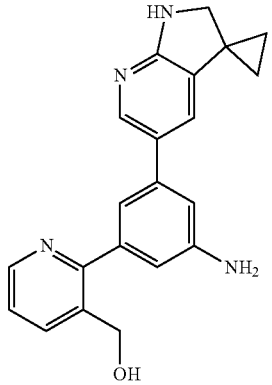  (2-(3-Amino-5-(1',2'-dihydrospiro[cyclopropane-1,3'-pyrrolo[2,3-b]pyridin]-5'-yl)phenyl)pyridin-3-yl)methanol | 1.68 345.1 B | M | (400 MHz, DMSO-d$_6$) δ 8.50 (dd, J = 4.6, 1.8 Hz, 1H), 7.94 (dd, J = 7.8, 1.7 Hz, 1H), 7.90 (d, J = 2.2 Hz, 1H), 7.37 (dd, J = 7.8, 4.7 Hz, 1H), 7.06 (d, J = 2.0 Hz, 1H), 6.81 (t, J = 1.6 Hz, 1H), 6.78 (t, J = 1.9 Hz, 1H), 6.62 (t, J = 1.7 Hz, 1H), 6.60 (s, 1H), 5.16 (s, 2H), 5.30 (br s, 1H), 4.52 (s, 2H), 3.53 (s, 2H), 1.08-1.04 (m, 2H), 0.98-0.93 (m, 2H). |
| 11 | 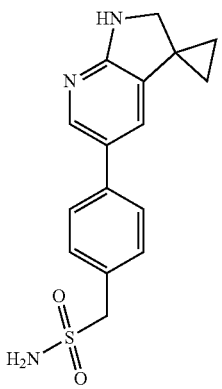  (4-(1',2'-Dihydrospiro[cyclopropane-1,3'-pyrrolo[2,3-b]pyridin]-5'-yl)phenyl)methanesulfonamide | 2.25 316.1 B | M | (400 MHz, DMSO-d$_6$) δ 7.98 (d, J = 2.2 Hz, 1H), 7.55 (d, J = 8.3 Hz, 2H), 7.36 (d, J = 8.3 Hz, 2H), 7.15 (d, J = 1.9 Hz, 1H), 6.82 (s, 2H), 6.69 (s, 1H), 4.26 (s, 2H), 3.54 (s, 2H), 1.12-1.07 (m, 2H), 1.00-0.95 (m, 2H). |

TABLE A1-continued

| No. | Structure/Name | LCMS $R_T$ (min) m/z Method | Prep Mtd | $^1$H NMR δ (ppm) |
|---|---|---|---|---|
| 12 | 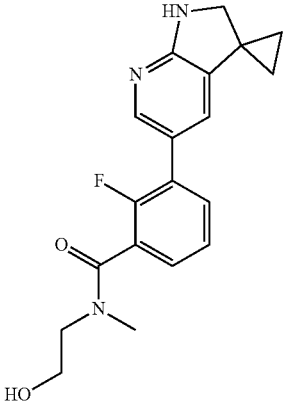<br>3-(1',2'-Dihydrospiro[cyclopropane-1,3'-pyrrolo[2,3-b]pyridin]-5'-yl)-2-fluoro-N-(2-hydroxyethyl)-N-methylbenzamide | 2.15 342.1 B | M | (400 MHz, DMSO-d$_6$) δ 7.85-7.81 (m, 1H), 7.53-7.44 (m, 1H), 7.32-721 (m, 2H), 7.04-6.99 (m, 1H), 6.80 (s, 1H), 4.77 (dt, J = 16.3, 11.0 Hz, 1H), 3.62 (q, J = 5.9 Hz, 1H), 3.55 (s, 2H), 3.53 (q, J = 5.9 Hz, 1H), 3.48-3.41 (m, 1H), 3.25-3.18 (mm, 1H), 3.01 (s, 1.8H), 2.89 (s, 1.2 H), 1.08-1.02 (m, 2H), 1.01-0.95 (m, 2H). |
| 13 | 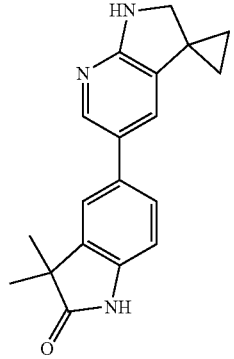<br>5-(1',2'-dihydrospiro[cyclopropane-1,3'-pyrrolo[2,3-b]pyridin]-5'-yl)-3,3-dimethylindolin-2-one | 306.1 | L | (400 MHz, DMSO-d$_6$) δ 10.32 (s, 1H), 7.91 (d, J = 2.2 Hz, 1H), 7.49 (d, J = 1.8 Hz, 1H), 7.32 (dd, J = 8.1, 1.9 Hz, 1H), 7.10 (d, J = 2.0 Hz, 1H), 6.84 (d, J = 8.0 Hz, 1H), 6.58 (s, 1H), 3.53 (s, 2H), 1.28 (s, 6H), 1.09 (dd, J = 6.7, 4.3 Hz, 2H), 0.97 (dd, J = 6.6, 4.3 Hz, 2H). |
| 14 | 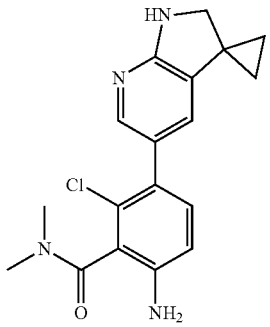<br>6-amino-2-chloro-3-(1',2'-dihydrospiro[cyclopropane-1,3'-pyrrolo[2,3-b]pyridin]-5'-yl)-N,N-dimethylbenzamide | 343.1 | L | |

TABLE A1-continued

| No. | Structure/Name | LCMS $R_T$ (min) m/z Method | Prep Mtd | $^1$H NMR δ (ppm) |
|---|---|---|---|---|
| 15 | 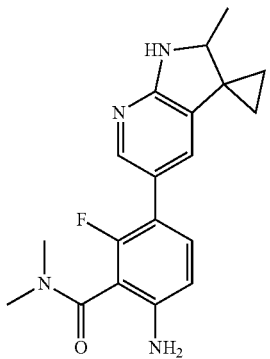<br>6-Amino-2-fluoro-N,N-dimethyl-3-(2'-methyl-1',2'-dihydrospiro[cyclopropane-1,3'-pyrrolo[2,3-b]pyridin]-5'-yl)benzamide | 2.43<br>341.1<br>B | L | (400 MHz, CDCl$_3$) δ 7.86 (t, J = 1.6 Hz, 1H), 6.84 (t, J = 2.0 Hz, 1H), 6.55-6.53 (m, 1H), 4.76 (s, 1H), 4.25 (s, 1H), 4.12 (q, J = 7.1 Hz, 1H), 3.91 (q, J = 6.3 Hz, 1H), 3.14-3.14 (m, 3H), 3.00-2.99 (m, 3H), 1.28-1.14 (m, 5H), 1.07-1.00 (m, 1H), 0.88-0.78 (m, 2H). |
| 16 | 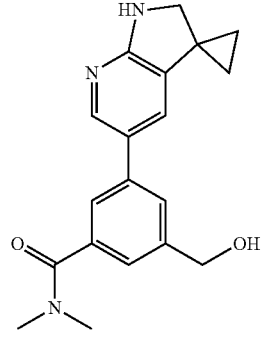<br>3-(1',2'-dihydrospiro[cyclopropane-1,3'-pyrrolo[2,3-b]pyridin]-5'-yl)-5-(hydroxymethyl)-N,N-dimethylbenzamide | 324.2 | L | |
| 17 | 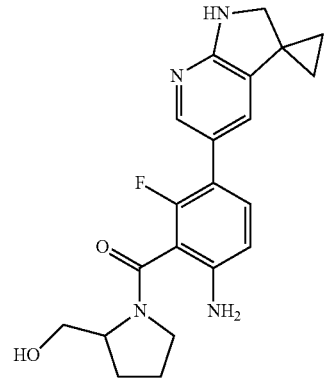<br>(RS)-(6-amino-3-(1',2'-dihydrospiro[cyclopropane-1,3'-pyrrolo[2,3-b]pyridin]-5'-yl)-2-fluorophenyl)(2-(hydroxymethyl)pyrrolidin-1-yl)methanone | 383.2 | L | |

TABLE A1-continued

| No. | Structure/Name | LCMS $R_T$ (min) m/z Method | Prep Mtd | $^1$H NMR δ (ppm) |
|---|---|---|---|---|
| 18 | 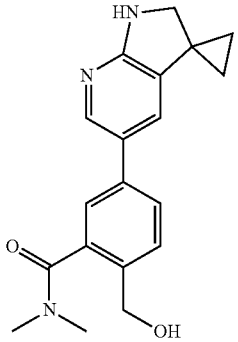 5-(1',2'-dihydrospiro[cyclopropane-1,3'-pyrrolo[2,3-b]pyridin]-5'-yl)-2-(hydroxymethyl)-N,N-dimethylbenzamide | 324.2 | L | |
| 19 | 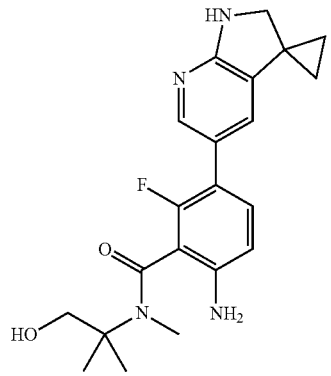 6-amino-3-(1',2'-dihydrospiro[cyclopropane-1,3'-pyrrolo[2,3-b]pyridin]-5'-yl)-2-fluoro-N-(1-hydroxy-2-methylpropan-2-yl)-N-methylbenzamide | 385.2 | L | |
| 20 | 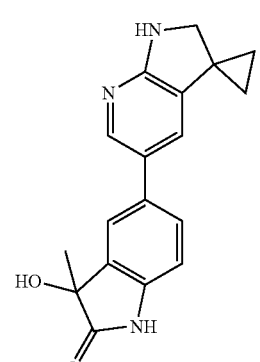 5-(1',2'-dihydrospiro[cyclopropane-1,3'-pyrrolo[2,3-b]pyridin]-5'-yl)-3-hydroxy-3-methylindolin-2-one | 308.1 | L | |

TABLE A1-continued

| No. | Structure/Name | LCMS R_T (min) m/z Method | Prep Mtd | $^1$H NMR δ (ppm) |
|---|---|---|---|---|
| 21 | 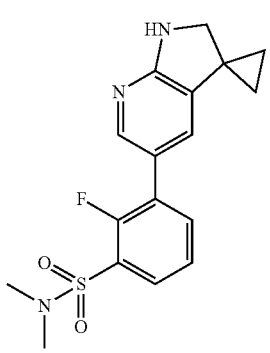<br>3-(1',2'-dihydrospiro[cyclopropane-1,3'-pyrrolo[2,3-b]pyridin-5'-yl)-2-fluoro-N,N-dimethylbenzenesulfonamide | 348.1 | L | |
| 22 | 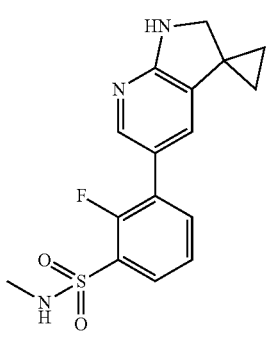<br>3-(1',2'-dihydrospiro[cyclopropane-1,3'-pyrrolo[2,3-b]pyridin]-5'-yl)-2-fluoro-N-methylbenzenesulfonamide | 334.1 | L | |
| 23 | 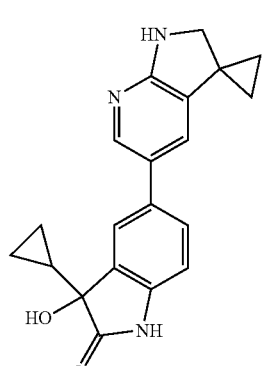<br>(RS)-3-cyclopropyl-5-(1',2'-dihydrospiro[cyclopropane-1,3'-pyrrolo[2,3-b]pyridin]-5'-yl)-3-hydroxyindolin-2-one | 334.1 | L | |

TABLE A1-continued

| No. | Structure/Name | LCMS R$_T$ (min) m/z Method | Prep Mtd | $^1$H NMR δ (ppm) |
|---|---|---|---|---|
| 24 | 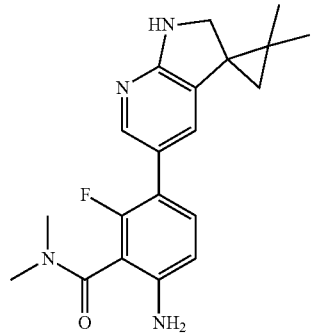<br>(RS)-6-Amino-3-(2,2-dimethyl-1′,2′-dihydrospiro[cyclopropane-1,3′-pyrrolo[2,3-b]pyridin]-5′-yl)-2-fluoro-N,N-dimethylbenzamide | 2.74<br>355.1<br>A | L | (400 MHz, DMSO-d$_6$) δ 7.71-7.69 (m, 1H), 7.15-7.09 (m, 1H), 7.02-6.99 (m, 1H), 6.56 (bs, 1H), 6.56 (d, J = 8.4 Hz, 1H), 5.27 (bs, 2H), 3.58 (d, J = 9.7 Hz, 1H), 3.45 (dd, J = 1.5, 9.7 Hz, 1H), 2.99 (2 × s, 3H), 2.87 (2 × s, 3H), 1.14 (s, 6H), 1.00 (t, J = 4.2 Hz, 1H), 0.72 (t, J = 4.3 Hz, 1H). |
| 25 | 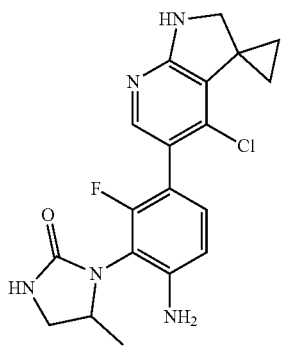<br>(RS)-1-(6-amino-3-(4′-chloro-1′,2′-dihydrospiro[cyclopropane-1,3′-pyrrolo[2,3-b]pyridin]-5′-yl)-2-fluorophenyl)-5-methylimidazolidin-2-one | 354.1 | L | |
| 26 | 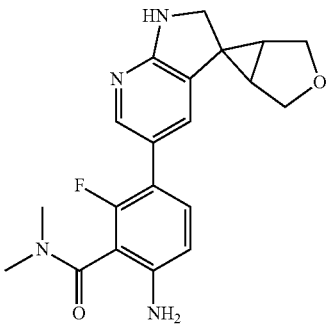<br>6-amino-3-(1′,2′-dihydro-3-oxaspiro[bicyclo[3.1.0]hexane-6,3′-pyrrolo[2,3-b]pyridin-5′-yl)-2-fluoro-N,N-dimethylbenzamide | 369.2 | L | |

TABLE A1-continued

| No. | Structure/Name | LCMS R$_T$ (min) m/z Method | Prep Mtd | $^1$H NMR δ (ppm) |
|---|---|---|---|---|
| 27 | 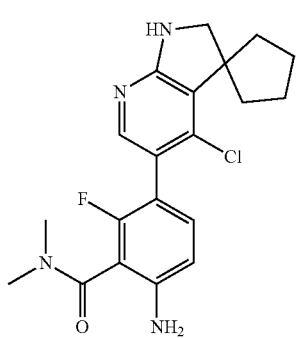<br>6-Amino-3-(4'-chloro-1',2'-dihydrospiro[cyclopentane-1,3'-pyrrolo[2,3-b]pyridin]-5'-yl)-2-fluoro-N,N-dimethylbenzamide | 308, 389.1 A | L | (400 MHz, DMSO-d$_6$) δ 7.60 (s, 1H), 6.97 (t, J = 8.5 Hz, 1H), 6.83 (brs, 1H), 6.55 (d, J = 8.4 Hz, 1H), 5.37 (s, 2H), 2.99 (s, 3H), 2.88 (s, 3H), 2.21-2.10 (m, 2H), 1.81-1.63 (m, 6H). |
| 28 | 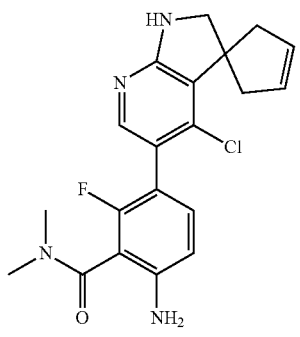<br>6-Amino-3-(4'-chloro-1',2'-dihydrospiro[cyclopentane-1,3'-pyrrolo[2,3-b]pyridin]-3-en-5'-yl)-2-fluoro-N,N-dimethylbenzamide | 2.96 387.1 A | L | (400 MHz, DMSO-d$_6$) δ 7.62 (s, 1H), 6.97 (t, J = 8.8 Hz, 1H), 6.87 (s, 1H), 6.55 (d, J = 8.4 Hz, 1H), 5.75 (s, 2H), 5.38 (s, 2H), 3.48 (s, 2H), 3.07-2.96 (m, 4H), 2.99 (s, 3H), 2.87 (s, 3H). |
| 29 | 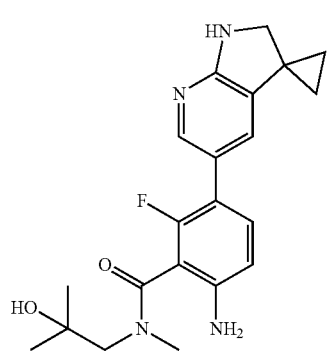<br>6-amino-3-(1',2'-dihydrospiro[cyclopropane-1,3'-pyrrolo[2,3-b]pyridin]-5'-yl)-2-fluoro-N-(2-hydroxy-2-methylpropyl)-N-benzamide | 385.2 | L | |

| No. | Structure/Name | LCMS R$_T$ (min) m/z Method | Prep Mtd | $^1$H NMR δ (ppm) |
|---|---|---|---|---|
| 30 | 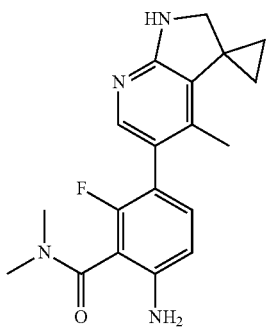<br>6-Amino-2-fluoro-N,N-dimethyl-3-(4'-methyl-1',2'-dihydrospiro[cyclopropane-1,3'-pyrrolo[2,3-b]pyridin]-5'-yl)benzamide | 2.53<br>341.2<br>A | L | (400 MHz, DMSO-d$_6$) δ 7.39 (s, 1H), 6.89 (t, J = 8.5 Hz, 1H), 6.54 (d, J = 8.2 Hz, 1H), 6.42 (s, 1H), 5.31 (s, 2H), 3.40 (s, 2H), 2.98 (s, 3H), 2.87 (s, 3H), 1.75 (s, 3H), 1.45-1.37 (m, 2H), 0.85-0.77 (m, 2H). |
| 31 | 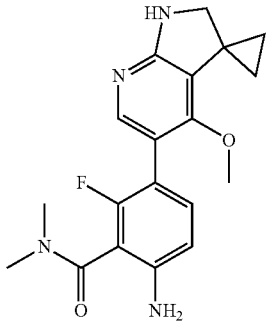<br>6-Amino-2-fluoro-3-(4'-methoxy-1',2'-dihydrospiro[cyclopropane-1,3'-pyrrolo[2,3-b]pyridin]-5'-yl)-N,N-dimethylbenzamide | 2.59<br>357.2<br>A | L | (400 MHz, DMSO-d$_6$) δ 7.44 (s, 1H), 6.99 (t, J = 8.3 Hz, 1H), 6.55 (d, J = 8.6 Hz, 1H), 6.52 (s, 1H), 5.33 (s, 2H), 3.44 (s, 2H), 3.23 (s, 3H), 2.99 (s, 3H), 2.86 (s, 3H), 1.30-1.22 (m, 2H), 0.85-0.78 (m, 2H). |
| 32 | 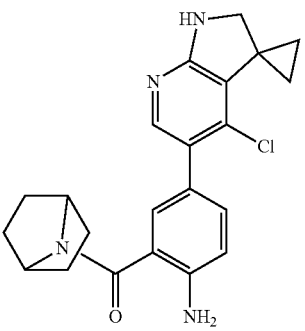<br>(2-Amino-5-(4'-chloro-1',2'-dihydrospiro[cyclopropane-1,3'-pyrrolo[2,3-b]pyridin]-5'-yl)phenyl)(7-azabicyclo[2.2.1]heptan-7-yl)methanone | 3.22<br>395.2<br>B | L | (400 MHz, DMSO-d$_6$) δ 7.55 (s, 1H), 7.10-7.05 (2H, s), 6.87 (s, 1H), 6.74 (dd, J = 7.6, 1.1 Hz, 1H), 5.64 (s, 2H), 4.27 (brs, 2H), 3.50 (s, 2H), 1.77-1.67 (m, 4H), 1.64 (dd, J = 6.6, 4.4 Hz, 2H), 1.49-1.40 (m, 4H), 0.87 (dd, J = 6.6, 4.5 Hz, 2H). |

TABLE A1-continued

| No. | Structure/Name | LCMS R_T (min) m/z Method | Prep Mtd | $^1$H NMR δ (ppm) |
|---|---|---|---|---|
| 33 | 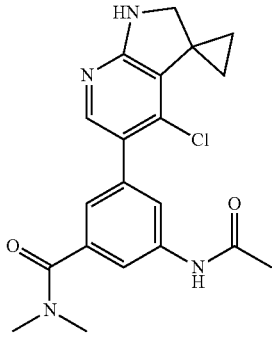<br>3-acetamido-5-(4'-chloro-1',2'-dihydrospiro[cyclopropane-1,3'-pyrrolo[2,3-b]pyridin]-5'-yl)-N,N-dimethylbenzamide | 351.1 | L | |
| 34 | 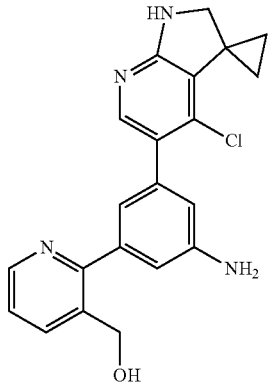<br>(2-(3-Amino-5-(4'-chloro-1',2'-dihydrospiro[cyclopropane-1,3'-pyrrolo[2,3-b]pyridin]-5'-yl)phenyl)pyridin-3-yl)methanol | 2.04<br>379.1<br>B | L | (400 MHz, DMSO-d$_6$) δ 8.49 (dd, J = 4.7, 1.7 Hz, 1H), 7.93 (dd, J = 7.8, 1.7 Hz, 1H), 7.57 (s, 1H), 7.36 (dd, J = 7.8, .47 Hz, 1H), 6.92 (s, 1H), 6.71 (dd, J = 2.0, 1.7 Hz, 1H), 6.57 (t, J = 1.5 Hz, 1H), 6.54 (t, J = 3.7 Hz, 1H), 5.29 (br s, 1H), 5.23 (br s, 2H), 4.52 (s, 2H), 3.52 (s, 2H), 1.66 (dd, J = 6.6, 4.3 Hz, 2H), 0.88 (dd, J = 6.6, 4.5 Hz, 2H). |
| 35 | 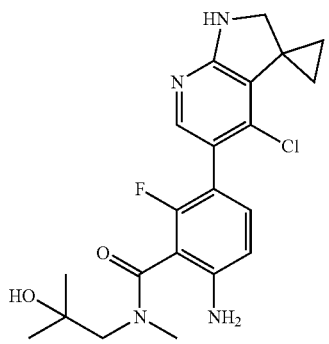<br>6-amino-3-(4'-chloro-1',2'-dihydrospiro[cyclopropane-1,3'-pyrrolo[2,3-b]pyridin]-5'-yl)-2-fluoro-N-(2-hydroxy-2-methylpropyl)-N-methylbenzamide | 420.2 | L | |

TABLE A1-continued

| No. | Structure/Name | LCMS R_T (min) m/z Method | Prep Mtd | $^1$H NMR δ (ppm) |
|---|---|---|---|---|
| 36 | 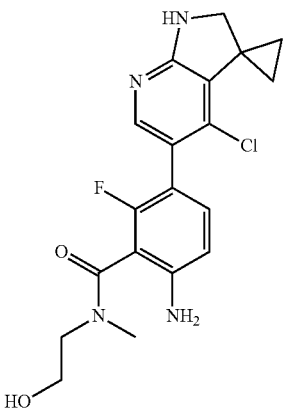<br>6-Amino-3-(4'-chloro-1',2'-dihydrospiro[cyclopropane-1,3'-pyrrolo[2,3-b]pyridin]-5'-yl)-2-fluoro-N-(2-hydroxyethyl)-N-methylbenzamide | 2.46<br>391.1<br>A | L | (400 MHz, DMSO-d$_6$) δ ppm 7.50 (d, J = 3.5 Hz, 1H), 6.98-6.87 (m, 2H), 6.53 (dd, J = 8.3, 6.6 Hz, 1H), 5.37 (s, 1H), 5.32 (s, 1H), 4.84 (t, J = 5.3 Hz, 0.5 H), 4.74 (t, J = 5.3 Hz, 0.5 H), 3.74-3.64 (m 0.5H), 3.62-3.57 (m, 1H), 3.51 (s, 2H), 3.47-3.34 (m, 1.5 H), 3.28-3.18 (m, 1H), 3.00 (s, 1.5H), 2.90 (s, 1.5H), 1.64-1.57 (m, 2H), 0.91-0.83 (m, 2H). |
| 37 | 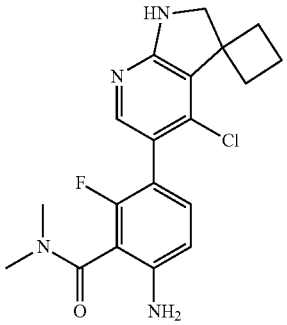<br>6-Amino-3-(4'-chloro-1',2'-dihydrospiro[cyclobutane-1,3'-pyrrolo[2,3-b]pyridin]-5'-yl)-2-fluoro-N,N-dimethylbenzamide | 3.01<br>375.1<br>B | L | (400 MHz, DMSO-d$_6$) δ 7.60 (s, 1H), 6.98 (t, J = 8.5 Hz, 1H), 6.85 (s, 1H), 6.56 (d, J = 8.4 Hz, 1H), 5.39 (s, 2H), 3.70 (s, 2H), 2.99 (s, 3H), 2.90 (s, 3H), 2.89-2.75 (m, 2H), 2.09-1.92 (m, 4H). |
| 38a | 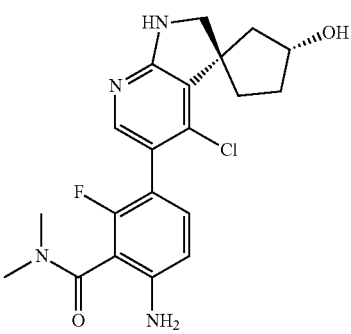<br>6-Amino-3-((1R,3RS)-4'-chloro-3-hydroxy-1',2'-dihydrospiro[cyclopentane-1,3'-pyrrolo[2,3-b]pyridin]-5'-yl)-2-fluoro-N,N-dimethylbenzamide | 2.11<br>405.2<br>A | L | (400 MHz, DMSO-d$_6$) δ 7.59 (s, 1H), 6.97 (t, J = 8.5 Hz, 1H), 6.82 (s, 1H), 6.55 (d, J = 8.4 Hz, 1H), 5.38 (s, 2H), 4.74 (d, J = 4.5 Hz, 1H), 4.21-4.12 (m, 1H), 3.31 (s, 2H), 3.17 (d, J = 5.2 Hz, 1H), 2.99 (s, 3H), 2.88 (s, 3H), 2.46-2.37 (m, 1H), 2.10-1.86 (m, 2H), 1.69-1.55 (m, 2H). |

TABLE A1-continued

| No. | Structure/Name | LCMS $R_T$ (min) m/z Method | Prep Mtd | $^1$H NMR δ (ppm) |
|---|---|---|---|---|
| 38c | <br>6-Amino-3-((1RS,3SR)-4'-chloro-3-hydroxy-1',2'-dihydrospiro[cyclopentane-1,3'-pyrrolo[2,3-b]pyridin]-5'-yl)-2-fluoro-N,N-dimethylbenzamide | 2.29<br>405.2<br>A | L | (400 MHz, DMSO-d$_6$) δ 7.59 (s, 1H), 6.96 (t, J = 8.5 Hz, 1H), 6.79 (s, 1H), 6.54 (d, J = 8.4 Hz, 1H), 5.38 (s, 2H), 4.64 (d, J = 3.2 Hz, 1H), 3.59 (d, J = 9.5 Hz, 1H), 3.42 (d, J = 9.4 Hz, 1H), 3.17 (d, J = 5.2 Hz, 1H), 2.99 (s, 3H), 2.88 (s, 3H), 2.29 (td, J = 13.0, 5.7 Hz, 1H), 2.19-2.06 (m, 1H), 2.05-1.94 (m, 1H), 1.90-1.79 (m, 1H), 1.71 (d, J = 14.6 Hz, 1H), 1.70-1.59 (m, 1H). |
| 39 | 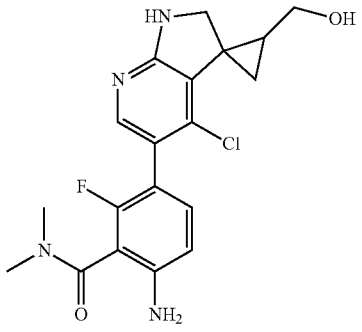<br>6-Amino-3-(4'-chloro-2-(hydroxymethyl)-1',2'-dihydrospiro[cyclopropane-1,3'-pyrrolo[2,3-b]pyridin]-5'-yl)-2-fluoro-N,N-dimethylbenzamide<br>Mixture of isomers | 2.26<br>391.1<br>A | L | (400 MHz, DMSO-d$_6$) δ 7.49 (s, 1H), 6.98 (s, 1H), 6.92 (t, J = 8.3 Hz, 1H), 6.54 (d, J = 8.3 Hz, 1H), 5.37 (s, 2H), 4.74-4.66 (m, 1H), 3.75 (d, J = 9.5 Hz, 1H), 3.72-3.63 (m, 1H), 3.42 (d, J = 9.4 Hz, 1H), 3.25-3.14 (m, 1H), 2.99 (s, 3H), 2.87 (s, 3H), 2.24-2.12 (m, 1H), 1.72-1.63 (m, 1H), 0.67 (t, J = 5.5 Hz, 1H). |
| 39a | 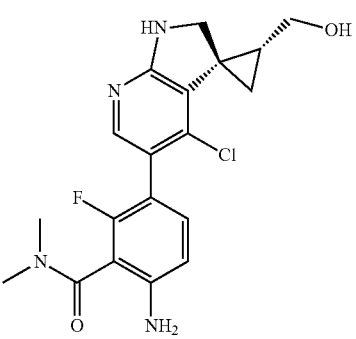<br>6-Amino-3-((1R,2R)-4'-chloro-2-(hydroxymethyl)-1',2'-dihydrospiro[cyclopropane-1,3'-pyrrolo[2,3-b]pyridin]-5'-yl)-2-fluoro-N,N-dimethylbenzamide<br>isomer A on SFC; absolute configuration arbitrarily assigned | 2.27<br>391.2<br>A | L | (400 MHz, DMSO-d$_6$) δ 7.54 (s, 1H), 6.94 (dt, J = 8.6, 3.4 Hz, 1H), 6.86 (brs, 1H), 6.54 (d, J = 8.4 Hz, 1H), 5.38 (brs, 2H), 4.51 (q, J = 5.7 Hz, 1H), 3.67 (dd, J = 8.9, 2.1 Hz, 1H), 3.55-3.41 (m, 2H), 3.08 (d, J = 9.0 Hz, 1H), 2.99 (s, 3H), 2.88 & 2.86 (2 × s, 3H), 1.93 (t, J = 6.0 Hz, 1H), 1.43-1.35 (m, 1H), 1.03-1.00 (m, 1H). |

TABLE A1-continued

| No. | Structure/Name | LCMS R$_T$ (min) m/z Method | Prep Mtd | $^1$H NMR δ (ppm) |
|---|---|---|---|---|
| 39b | 6-Amino-3-((1S,2S)-4'-chloro-2-(hydroxymethyl)-1',2'-dihydrospiro[cyclopropane-1,3'-pyrrolo[2,3-b]pyridin]-5'-yl)-2-fluoro-N,N-dimethylbenzamide isomer B SFC; absolute configuration arbitrarily assigned | 2.27 391.2 A | L | (400 MHz, DMSO-d$_6$) δ 7.54 (s, 1H), 6.94 (dt, J = 8.5, 3.3 Hz, 1H), 6.86 (brs, 1H), 6.54 (d, J = 8.4 Hz, 1H), 5.38 (brs, 2H), 4.51 (q, J = 5.7 Hz, 1H), 3.67 (dd, J = 8.9, 2.0 Hz, 1H), 3.55-3.41 (m, 2H), 3.08 (d, J = 8.9 Hz, 1H), 2.99 (s, 3H), 2.88 & 2.86 (2 × s, 3H), 1.93 (t, J = 6.0 Hz, 1H), 1.43-1.35 (m, 1H), 1.03-1.00 (m, 1H). |
| 39c | 6-Amino-3-((1R,2S)-4'-chloro-2-(hydroxymethyl)-1',2'-dihydrospiro[cyclopropane-1,3'-pyrrolo[2,3-b]pyridin]-5'-yl)-2-fluoro-N,N-dimethylbenzamide isomer C from SFC; absolute configuration arbitrarily assigned | 2.25 391.2 A | L | (400 MHz, DMSO-d$_6$) δ 7.49 (s, 1H), 6.99 (s, 1H), 6.92 (t, J = 8.0 Hz, 1H), 6.54 (d, J = 8.4 Hz, 1H), 5.37 (s, 2H), 4.71 (t, J = 5.2 Hz, 1H), 3.76 (d, J = 9.1 Hz, 1H), 3.72-3.66 (m, 1H), 3.43 (d, J = 8.4 Hz, 1H), 3.25-3.15 (m, 1H), 2.98 (s, 3H), 2.87 (s, 3H), 2.24-2.11 (m, 1H), 1.72-1.64 (m, 1H), 0.69-0.65 (m, 1H). |
| 39d | 6-Amino-3-((1S,2R)-4'-chloro-2-(hydroxymethyl)-1',2'-dihydrospiro[cyclopropane-1,3'-pyrrolo[2,3-b]pyridin]-5'-yl)-2-fluoro-N,N-dimethylbenzamide isomer D from SFC; absolute configuration arbitrarily assigned | 2.25 391.2 A | L | (400 MHz, DMSO-d$_6$) δ 7.49 (s, 1H), 6.99 (s, 1H), 6.92 (t, J = 8.0 Hz, 1H), 6.54 (d, J = 8.4 Hz, 1H), 5.37 (s, 2H), 4.70 (t, J = 5.2 Hz, 1H), 3.76 (d, J = 9.9 Hz, 1H), 3.72-3.66 (m, 1H), 3.42 (d, J = 9.2 Hz, 1H), 3.24-3.18 (m, 1H), 2.98 (s, 3H), 2.87 (s, 3H), 2.23-2.08 (m, 1H), 1.72-1.64 (m, 1H), 0.69-0.64 (m, 1H). |

TABLE A1-continued

| No. | Structure/Name | LCMS $R_T$ (min) m/z Method | Prep Mtd | $^1$H NMR δ (ppm) |
|---|---|---|---|---|
| 40 | 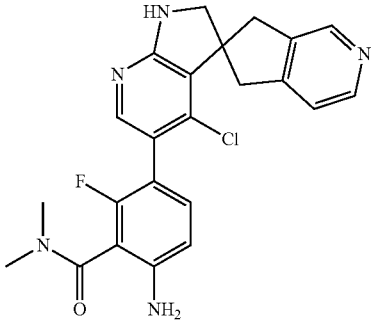<br>6-Amino-3-(RS)-(4′-chloro-1′,2′,5,7-tetrahydrospiro[cyclopenta[c]pyridine-6,3′-pyrrolo[2,3-b]pyridin]-5′-yl)-2-fluoro-N,N-dimethylbenzamide | 1.75<br>438.2<br>A | L | (400 MHz, DMSO-d$_6$) δ 8.46 (s, 1H), 8.37 (d, J = 5.0 Hz, 1H), 7.69 (s, 1H), 7.31 (d, J = 4.2 Hz, 1H), 7.01-6.96 (m, 2H), 6.55 (d, J = 8.4 Hz, 1H), 5.39 (bs, 2H), 3.71-3.57 (m, 2H), 3.52 (d, J = 11.1 Hz, 1H), 3.49 (d, J = 10.5 Hz, 1H), 3.16 (dd, J = 8.8, 16.5 Hz, 2H), 2.98 (s, 3H), 2.86 (s, 3H) |
| 41 | 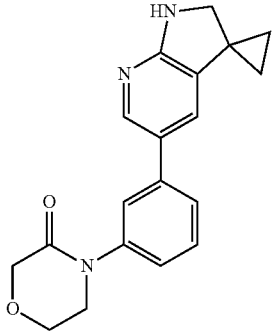<br>4-(3-(1′,2′-Dihydrospiro[cyclopropane-1,3′-pyrrolo[2,3-b]pyridin]-5′-yl)phenyl)morpholin-3-one | 1.67<br>321.3<br>A | M | (400 MHz, DMSO-d$_6$) δ 7.96 (d, J = 2.1 Hz, 1H), 7.46-7.36 (m, 3H), 7.19-7.13 (m, 2H), 6.71 (s, 1H), 3.63 (t, J = 5.4 Hz, 2H), 3.55 (s, 2H), 3.39 (s, 2H), 3.02 (t, J = 5.4 Hz, 2H), 1.13-1.08 (m, 2H), 1.00-0.95 (m, 2H). |
| 42 | 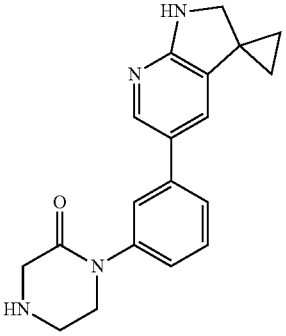<br>1-(3-(1′,2′-Dihydrospiro[cyclopropane-1,3′-pyrrolo[2,3-b]pyridin]-5′-yl)phenyl)piperazin-2-one | 1.72<br>321.2<br>A | L | (400 MHz, DMSO-d$_6$): δ ppm 7.96 (d, J = 2.1 Hz, 1H), 7.45-7.42 (m, 2H), 7.38 (t, J = 7.8 Hz, 1H), 7.17 (td, J = 1.6, 7.8 Hz, 1H), 7.14 (d, J = 2.1 Hz, 1H), 6.71 (s, 1H), 3.63 (t, J = 5.4 Hz, 2H), 3.55 (s, 2H), 3.39 (s, 2H), 3.02 (t, J = 5.4 Hz, 2H), 1.13-1.08 (m, 2H), 1.00-0.95 (m, 2H). |

TABLE A1-continued

| No. | Structure/Name | LCMS R_T (min) m/z Method | Prep Mtd | $^1$H NMR δ (ppm) |
|---|---|---|---|---|
| 43 | 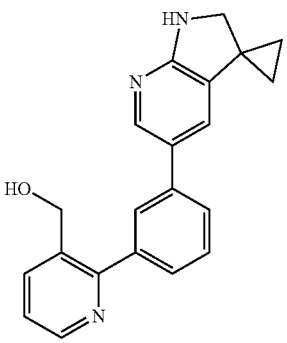<br>(2-(3-(1',2'-Dihydrospiro[cyclopropane-1,3'-pyrrolo[2,3-b]pyridin]-5'-yl)phenyl)pyridin-3-yl)methanol | 2.03<br>330.2<br>A | M | (400 MHz, DMSO-d$_6$) δ 8.56 (dd, J = 1.7, 4.7 Hz, 1H), 8.01 (d, J = 2.3 Hz, 1H), 7.98 (dd, J = 1.9, 8.0 Hz, 1H), 7.72 (s, 1H), 7.63-7.59 (m, 1H), 7.49-7.40 (m, 3H), 7.20 (d, J = 2.1 Hz, 1H), 6.70 (s, 1H), 5.37 (s, 1H), 4.51 (d, J = 3.3 Hz, 2H), 3.54 (s, 2H), 1.13-1.08 (m, 2H), 0.99-0.94 (m, 2H). |
| 44 | 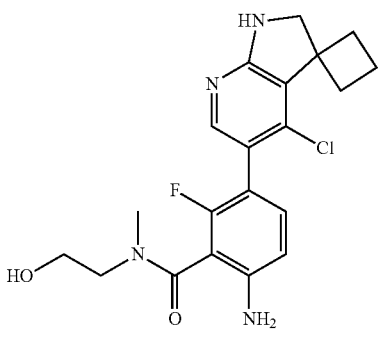<br>6-Amino-3-(4'-chloro-1',2'-dihydrospiro[cyclobutane-1,3'-pyrrolo[2,3-b]pyridin]-5'-yl)-2-fluoro-N-(2-hydroxyethyl)-N-methylbenzamide | 2.66<br>405.2<br>A | L | 1H NMR (400 MHz, DMSO-d$_6$): δ ppm 7.59 (d, J = 3.82 Hz, 1H), 6.97 (m, 1H), 6.85 (s, 1H), 6.55 (dd, 1H), 5.37 (d, J = 19.7 Hz, 1H), 3.70 (s, 2H), 3.61 (m, 1H), 3.52-3.21 (m, 4H), 3.02 (s, 1H), 2.92 (s, 1H), 2.82 (m, 1H), 2.50 (m, 3H), 2.08-1.96 (m, 3H) |
| 45 | 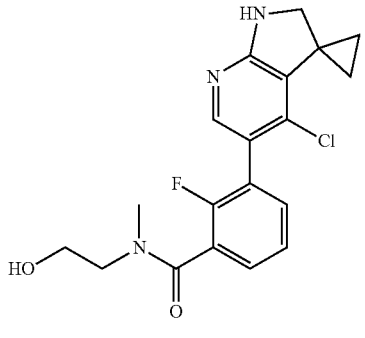<br>3-(4'-Chloro-1',2'-dihydrospiro[cyclopropane-1,3'-pyrrolo[2,3-b]pyridin]-5'-yl)-2-fluoro-N-(2-hydroxyethyl)-N-methylbenzamide | 2.54<br>376.2<br>A | L | (400 MHz, DMSO-d$_6$) δ 7.60 & 7.59 (2 × s, 1H), 7.40-7.27 (m, 3H), 7.14 (s, 1H), 4.78 & 4.72 (2 × t, J = 5.4 Hz, 1H), 3.62-3.50 (m, 4H), 3.46-3.42 (m, 1H), 3.23-3.20 (m, 1H), 3.01 & 2.98 (2 × s, 3H), 1.65-1.62 (m, 2H), 0.92-0.89 (m, 2H). |

TABLE A1-continued

| No. | Structure/Name | LCMS R_T (min) m/z Method | Prep Mtd | $^1$H NMR δ (ppm) |
|---|---|---|---|---|
| 46 | 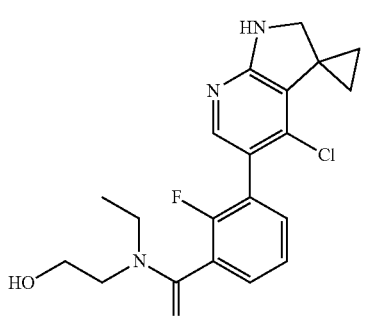<br>3-(4'-Chloro-1',2'-dihydrospiro[cyclopropane-1,3'-pyrrolo[2,3-b]pyridin]-5'-yl)-N-ethyl-2-fluoro-N-(2-hydroxyethyl)benzamide | 2.73<br>390.2<br>A | R | (400 MHz, DMSO-d$_6$) δ 7.59 (2 × s, 1H), 7.39-7.26 (m, 3H), 7.14 (brs, 1H), 4.78 & 4.73 (2 × t, J = 5.4 Hz, 1H), 3.61-3.57 (m, 1H), 3.55 (s, 2H), 3.51-3.48 (m, 1H), 3.43-3.39 (m, 1H), 3.25-3.18 (m, 2H), 1.65-1.62 (m, 2H), 1.13 & 0.99 (2 × t, J = 7.1 Hz, 3H), 0.92-0.89 (m, 2H). |
| 47 | 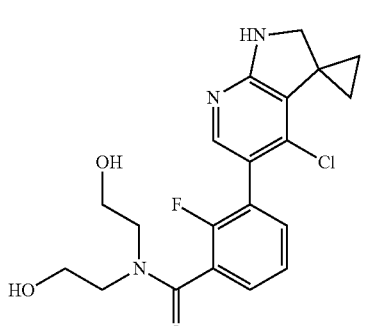<br>3-(4'-Chloro-1',2'-dihydrospiro[cyclopropane-1,3'-pyrrolo[2,3-b]pyridin]-5'-yl)-2-fluoro-N,N-bis(2-hydroxyethyl)benzamide | 2.30<br>406.1<br>A | R | (400 MHz, DMSO-d$_6$) δ 7.58 (s, 1H), 7.39-7.27 (m, 3H), 7.14 (brs, 1H), 4.80-4.74 (m, 2H), 3.62-3.55 (m, 6H), 3.43-3.39 (m, 2H), 3.28-3.25 (m, 2H), 1.65-1.62 (m, 2H), 0.92-0.89 (m, 2H). |
| 48 | 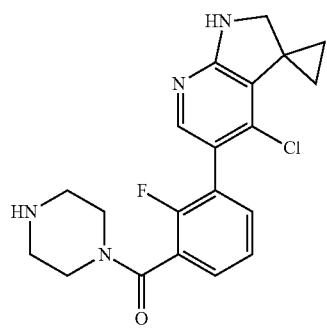<br>(3-(4'-Chloro-1',2'-dihydrospiro[cyclopropane-1,3'-pyrrolo[2,3-b]pyridin]-5'-yl)-2-fluorophenyl)(piperazin-1-yl)methanone | 2.06<br>387.1<br>A | V | (400 MHz, DMSO-d$_6$) δ 7.60 (s, 1H), 7.40-7.29 (m, 3H), 7.15 (brs, 1H), 3.60-3.54 (m, 4H), 3.15-3.12 (m, 2H), 2.72-2.70 (m, 2H), 2.62-2.59 (m, 2H), 2.43 (brs, 1H), 1.65-1.62 (m, 2H), 0.92-0.89 (m, 2H). |

TABLE A1-continued

| No. | Structure/Name | LCMS R_T (min) m/z Method | Prep Mtd | $^1$H NMR δ (ppm) |
|---|---|---|---|---|
| 49 | 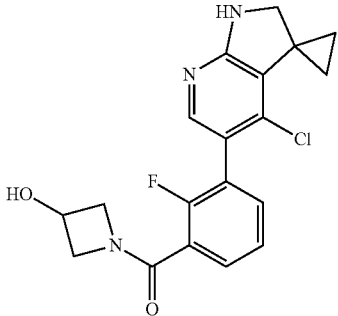<br>((3-(4'-Chloro-1',2'-dihydrospiro[cyclopropane-1,3'-pyrrolo[2,3-b]pyridin]-5'-yl)-2-fluorophenyl)(3-hydroxyazetidin-1-yl)methanone | 2.47 374.2 A | R | (400 MHz, DMSO-d$_6$) δ 7.59 (s, 1H), 7.50-7.46 (m, 1H), 7.39 (dt, J = 7.4, 1.2 Hz, 1H), 7.31 (t, J = 7.6 Hz, 1H), 7.15 (brs, 1H), 5.78 (brs, 1H), 4.49 (brs, 1H), 4.26-4.21 (m, 1H), 4.16-4.11 (m, 1H), 3.78-3.74 (m, 2H), 3.55 (s, 2H), 1.65-1.62 (m, 2H), 0.92-0.90 (m, 2H). |
| 50 | 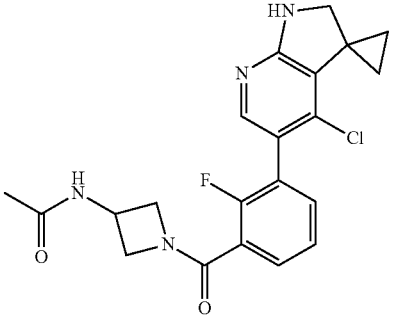<br>N-(1-(3-(4'-Chloro-1',2'-dihydrospiro[cyclopropane-1,3'-pyrrolo[2,3-b]pyridin]-5'-yl)-2-fluorobenzoyl)azetidin-3-yl)acetamide | 2.47 415.2 A | R | (400 MHz, DMSO-d$_6$) δ 8.54 (d, J = 6.9 Hz, 1H), 7.59 (s, 1H), 7.51-7.48 (m, 1H), 7.41 (dt, J = 7.4, 1.9 Hz, 1H), 7.30 (t, J = 7.5 Hz, 1H), 7.15 (s, 1H), 4.52-4.40 (m, 1H), 4.30-4.19 (m, 2H), 3.86-3.82 (m, 2H), 3.55 (s, 2H), 1.81 (s, 3H), 1.65-1.62 (m, 2H), 0.93-0.90 (m, 2H). |
| 51 | 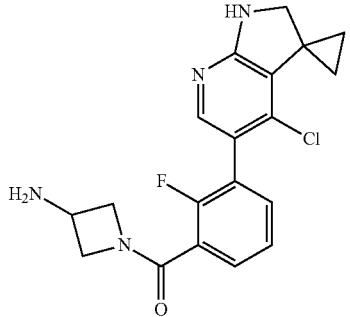<br>(3-Aminoazetidin-1-yl)(3-(4'-chloro-1',2'-dihydrospiro[cyclopropane-1,3'-pyrrolo[2,3-b]pyridin]-5'-yl)-2-fluorophenyl)methanone | 2.00 373.1 A | V | (400 MHz, DMSO-d$_6$) δ 7.58 (s, 1H), 7.49-7.45 (m, 1H), 7.38 (dt, J = 7.5, 1.9 Hz, 1H), 7.30 (t, J = 7.5 Hz, 1H), 7.15 (brs, 1H), 4.19-4.15 (m, 1H), 4.09-4.05 (m, 1H), 3.75-3.69 (m, 1H), 3.65-3.61 (m, 2H), 3.55 (s, 2H), 2.10 (brs, 2H), 1.65-1.62 (m, 2H), 0.92-0.90 (m, 2H). |

TABLE A1-continued

| No. | Structure/Name | LCMS R_T (min) m/z Method | Prep Mtd | $^1$H NMR δ (ppm) |
|---|---|---|---|---|
| 52 | 6-Amino-2-fluoro-N-(2-hydroxyethyl)-3-(4'-methoxy-1',2'-dihydrospiro[cyclobutane-1,3'-pyrrolo[2,3-b]pyridin]-5'-yl)-N-methylbenzamide | 2.61 401.2 A | L | (400 MHz, DMSO-d$_6$): δ ppm 7.51 (d, J = 3.1 Hz, 1H), 7.06-7.01 (dt, J = 6.0 Hz, 1H), 6.59-6.27 (dd, J = 6.3 Hz, 1H), 6.40 (s, 1H), 5.37 (s, 1H), 5.30 (s, 1H), 4.87-4.75 (dt, 1H), 3.74-3.67 (m, 1H), 3.61 (m, 1H), 3.56 (s, 2H), 3.51-3.36 (m, 2H), 3.43 (d, 2H), 3.27-3.23 (m, 1H), 3.01, 2.92 (m, 3H), 2.56-2.49 (m, 2H, obscured by water), 2.12-1.89 (m, 4H). |
| 53 | 6-Amino-2-fluoro-N,N-dimethyl-3-(4'-methyl-1',2'-dihydrospiro[cyclobutane-1,3'-pyrrolo[2,3-b]pyridin]-5'-yl)benzamide | 2.67 355.3 A | L | (400 MHz, DMSO-d$_6$) δ 7.47 (s, 1H), 6.93 (t, J = 8.5 Hz, 1H), 6.57 (d, J = 8.3 Hz, 1H), 6.30 (brs, 1H), 5.32 (brs, 2H), 3.60 (s, 2H), 2.99 (s, 3H), 2.89 (s, 3H), 2.68-2.59 (m, 2H), 2.22 (s, 3H), 2.09-2.00 (m, 4H). |
| 54 | N-(5-Cyano-3-(1',2'-dihydrospiro[cyclopropane-1,3'-pyrrolo[2,3-b]pyridin]-5'-yl)-1-methyl-1H-indol-7-yl)acetamide | 2.37 358.2 A | S | (400 MHz, DMSO-d$_6$) δ 9.93 (s, 1H), 8.05 (d, J = 1.4 Hz, 1H), 7.91 (d, J = 2.1 Hz, 1H), 7.59 (s, 1H), 7.24 (d, J = 1.3 Hz, 1H), 7.08 (d, J = 1.9 Hz, 1H), 6.59 (s, 1H), 3.93-3.92 (m, 3H), 3.54 (d, J = 1.0 Hz, 2H), 2.12 (s, 3H), 1.14-1.09 (m, 2H), 1.01-0.96 (m, 2H). |

TABLE A1-continued

| No. | Structure/Name | LCMS R_T (min) m/z Method | Prep Mtd | $^1$H NMR δ (ppm) |
|---|---|---|---|---|
| 55 | 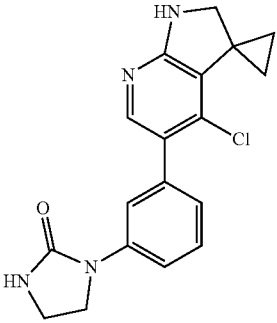<br>1-(3-(4'-Chloro-1',2'-dihydrospiro[cyclopropane-1,3'-pyrrolo[2,3-b]pyridin]-5'-yl)phenyl)imidazolidin-2-one | 2.85<br>341.1<br>A | L | (400 MHz, DMSO-d$_6$) δ 7.58 (s, 1H), 7.52-7.49 (m, 2H), 7.34-7.29 (m, 1H), 6.98 (s, 1H), 6.96 (s, 1H), 6.93-6.90 (m, 1H), 3.88-3.84 (m, 2H), 3.52 (s, 2H), 3.42-3.38 (m, 2H), 1.67-1.64 (m, 2H), 0.90-0.87 (m, 2H). |
| 56 | 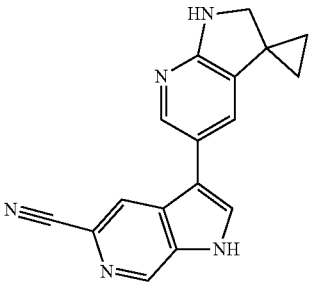<br>3-(1',2'-Dihydrospiro[cyclopropane-1,3'-pyrrolo[2,3-b]pyridin]-5'-yl)-1H-pyrrolo[2,3-b]pyridine-5-carbonitrile | 2.30<br>288.2<br>A | S | (400 MHz, DMSO-d$_6$) δ 12.34 (s, 1H), 8.86 (d, J = 0.9 Hz, 1H), 8.42 (d, J = 0.9 Hz, 1H), 8.04-7.99 (m, 2H), 7.19 (d, J = 2.0 Hz, 1H), 6.61 (s, 1H), 3.55 (s, 2H), 1.16 (dd, J = 4.4, 7.0 Hz, 2H), 0.98 (dd, J = 4.2, 7.0 Hz, 2H). |
| 57 | 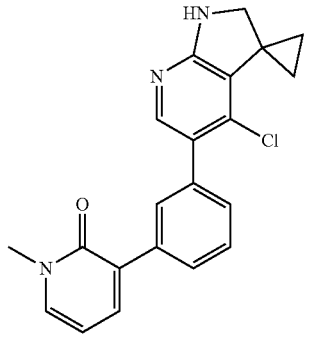<br>3-(3-(4'-Chloro-1',2'-dihydrospiro[cyclopropane-1,3'-pyrrolo[2,3-b]pyridin]-5'-yl)phenyl)-1-methylpyridin-2(1H)-one | 3.10<br>364.2<br>A | L | (400 MHz, DMSO-d$_6$) δ 7.75 (dd, J = 2.0, 6.7 Hz, 1H), 7.68-7.63 (m, 4H), 7.40 (t, J = 7.7 Hz, 1H), 7.28-7.24 (m, 1H), 7.00 (s, 1H), 6.32 (t, J = 6.8 Hz, 1H), 3.53 (s, 2H), 3.51 (s, 3H), 3.17 (d, J = 4.7 Hz, 1H), 1.67 (dd, J = 4.3, 6.5 Hz, 2H), 0.89 (dd, J = 4.5, 6.7 Hz, 2H). |

TABLE A1-continued

| No. | Structure/Name | LCMS R$_T$ (min) m/z Method | Prep Mtd | $^1$H NMR δ (ppm) |
|---|---|---|---|---|
| 58 | 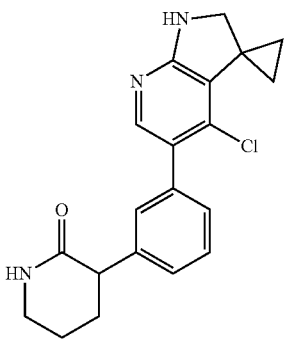<br>3-(3-(4'-Chloro-1',2'-dihydrospiro[cyclopropane-1,3'-pyrrolo[2,3-b]pyridin-5'-yl)phenyl)piperidin-2-one | 2.91<br>354.2<br>B | L | (400 MHz, DMSO-d$_6$) δ 7.64 (brs, 1H), 7.57 (s, 1H), 7.31 (t, J = 7.7 Hz, 1H), 7.17-7.11 (m, 3H), 6.98 (s, 1H), 3.55-3.51 (m, 3H), 3.30-3.19 (m, 2H), 2.09-2.02 (m, 1H), 1.87-1.63 (m, 5H), 0.90-0.87 (m, 2H). |
| 59 | 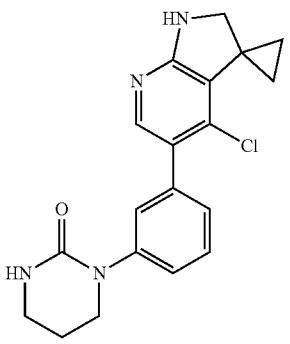<br>1-(3-(4'-Chloro-1',2'-dihydrospiro[cyclopropane-1,3'-pyrrolo[2,3-b]pyridin]-5'-yl)phenyl)tetrahydropyrimidin-2(1H)-one | 2.84<br>355.2<br>A | L | (400 MHz, DMSO-d$_6$) δ 7.58 (s, 1H), 7.33-7.25 (m, 2H), 7.22 (t, J = 1.8 Hz, 1H), 7.05 (dt, J = 7.2, 1.5 Hz, 1H), 6.99 (brs, 1H), 6.59 (brs, 1H), 3.66-3.63 (m, 2H), 3.52 (s, 2H), 3.24-3.21 (m, 2H), 1.97-1.91 (m, 2H), 1.67-1.65 (m, 2H), 0.90-0.87 (m, 2H). |
| 60 | 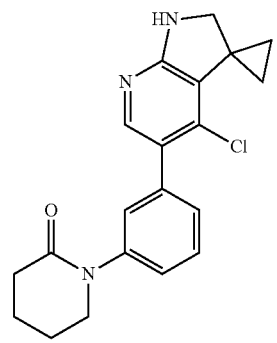<br>1-(3-(4'-Chloro-1',2'-dihydrospiro[cyclopropane-1,3'-pyrrolo[2,3-b]pyridin]-5'-yl)phenyl)piperidin-2-one | 3.05<br>354.2<br>A | L | (400 MHz, DMSO-d$_6$) δ 7.59 (s, 1H), 7.39 (t, J = 7.7 Hz, 1H), 7.25-7.21 (m, 2H), 7.20-7.17 (m, 1H), 7.02 (brs, 1H), 3.64-3.61 (m, 2H), 3.53 (s, 2H), 2.39 (t, J = 6.5 Hz, 2H), 1.90-1.79 (m, 4H), 1.67-1.65 (m, 2H), 0.90-0.88 (m, 2H). |

TABLE A1-continued

| No. | Structure/Name | LCMS R_T (min) m/z Method | Prep Mtd | $^1$H NMR δ (ppm) |
|---|---|---|---|---|
| 61 | (1RS,3SR)-5'-(3-Amino-5-(3-(hydroxymethyl)pyridin-2-yl)phenyl)-4'-chloro-1',2'-dihydrospiro[cyclopentane-1,3'-pyrrolo[2,3-b]pyridin-3-ol | 1.71 423.2 A | L | 1H NMR (400 MHz, CDCl3 + MeOD-d4): δ 8.52 (dd, J = 4.8, 1.4 Hz, 1H), 7.99 (d, J = 7.8 Hz, 1H), 7.70 (s, 1H), 7.34 (dd, J = 7.7, 4.9 Hz, 1H), 6.87-6.85 (m, 1H), 6.84-6.82 (m, 1H), 6.75-6.74 (m, 1H), 4.56-4.52 (m, 1H), 3.73 (d, J = 9.3 Hz, 1H), 3.58 (d, J = 9.3 Hz, 1H), 2.55 (dd, J = 13.9, 5.9 Hz, 1H), 2.38-2.30 (m, 1H), 2.22-2.14 (m, 1H), 2.02-1.95 (m, 1H), 1.86-1.74 (m, 2H). |
| 61a | (1R,3S)-5'-(3-Amino-5-(3-(hydroxymethyl)pyridin-2-yl)phenyl)-4'-chloro-1',2'-dihydrospiro[cyclopentane-1,3'-pyrrolo[2,3-b]pyridin-3-ol first peak on SFC; absolute configuration arbitrarily assigned | 1.72 423.2 B | L | (400 MHz, DMSO-d$_6$) δ 8.50 (dd, J = 4.7, 1.8 Hz, 1H), 7.95-7.92 (m, 1H), 7.66 (s, 1H), 7.36 (dd, J = 7.8, 4.7 Hz, 1H), 6.76 (s, 1H), 6.72 (dd, J = 2.1, 1.6 Hz, 1H), 6.60 (t, J = 1.5 Hz, 1H), 6.58 (dd, J = 2.1, 1.6 Hz, 1H), 5.24 (brs, 3H), 4.54 (brs, 2H), 4.37-4.33 (m, 1H), 3.60 (d, J = 9.4 Hz, 1H), 2.36-2.31 (m, 1H), 2.21-2.14 (m, 1H), 2.06-1.96 (m, 1H), 1.89-1.83 (m, 1H), 1.75-1.63 (m, 2H). |

TABLE A1-continued

| No. | Structure/Name | LCMS R$_T$ (min) m/z Method | Prep Mtd | $^1$H NMR δ (ppm) |
|---|---|---|---|---|
| 61b | 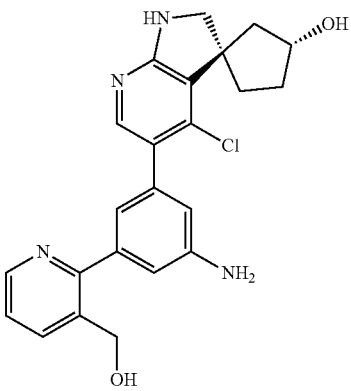<br>(1S,3R)-5'-(3-Amino-5-(3-(hydroxymethyl)pyridin-2-yl)phenyl)-4'-chloro-1',2'-dihydrospiro[cyclopentane-1,3'-pyrrolo[2,3-b]pyridin]-3-ol second peak on SFC; absolute configuration arbitrarily assigned | 1.71<br>423.2<br>A | L | (400 MHz, DMSO-d$_6$) δ 8.50 (dd, J = 4.7, 1.8 Hz, 1H), 7.95-7.92 (m, 1H), 7.66 (s, 1H), 7.36 (dd, J = 7.8, 4.7 Hz, 1H), 6.76 (s, 1H), 6.72 (dd, J = 2.1, 1.6 Hz, 1H), 6.60 (t, J = 1.5 Hz, 1H), 6.58 (dd, J = 2.1, 1.6 Hz, 1H), 5.30 (t, J = 5.3 Hz, 1H), 5.23 (brs, 2H), 4.65 (d, J = 3.2 Hz, 1H), 4.54 (d, J = 4.9 Hz, 2H), 4.35 (brs, 1H), 3.60 (d, J = 9.4 Hz, 1H), 3.43 (d, J = 9.4 Hz, 1H), 2.36-2.31 (m, 1H), 2.21-2.14 (m, 1H), 2.06-1.97 (m, 1H), 1.89-1.83 (m, 1H), 1.74-1.62 (m, 2H). |
| 62 | 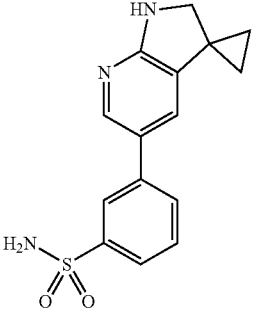<br>3-(1',2'-Dihydrospiro[cyclopropane-1,3'-pyrrolo[2,3-b]pyridin]-5'-yl)benzenesulfonamide | 2.21<br>302.1<br>A | M | (400 MHz, DMSO-d$_6$) δ 8.02 (d, J = 2.2 Hz, 1H), 7.98 (t, J = 1.7 Hz, 1H), 7.78 (ddd, J = 7.8, 1.8, 1.1 Hz, 1H), 7.68 (ddd, J = 7.8, 1.7, 1.1 Hz, 1H), 7.56 (t, J = 7.8 Hz, 1H), 7.34 (s, 2H), 7.18 (d, J = 2.2 Hz, 1H), 6.85 (s, 1H), 3.57 (s, 2H), 1.12-1.10 (m, 2H), 1.02-0.99 (m, 2H). |
| 63 | 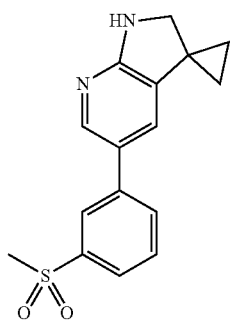<br>5'-(3-(Methylsulfonyl)phenyl)-1',2'-dihydrospiro[cyclopropane-1,3'-pyrrolo[2,3-b]pyridine] | 2.42<br>301.1<br>A | M | (400 MHz, DMSO-d$_6$) δ 8.07 (d, J = 2.3 Hz, 1H), 8.03 (t, J = 1.7 Hz, 1H), 7.91 (ddd, J = 7.9, 1.9, 1.1 Hz, 1H), 7.77 (ddd, J = 7.8, 1.8, 1.1 Hz, 1H), 7.64 (t, J = 7.8 Hz, 1H), 7.26 (d, J = 2.2 Hz, 1H), 6.87 (s, 1H), 3.57 (s, 2H), 3.27 (s, 3H), 1.15-1.12 (m, 2H), 1.01-0.99 (m, 2H). |

TABLE A1-continued

| No. | Structure/Name | LCMS R_T (min) m/z Method | Prep Mtd | $^1$H NMR δ (ppm) |
|---|---|---|---|---|
| 64 | 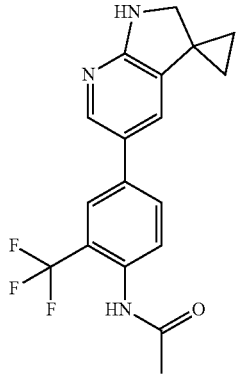<br>N-(4-(1',2'-Dihydrospiro[cyclopropane-1,3'-pyrrolo[2,3-b]pyridin]-5'-yl)-2-(trifluoromethyl)phenyl)acetamide | 2.63<br>348.2<br>A | M | (400 MHz, DMSO-d$_6$) δ 9.53 (s, 1H), 8.03 (d, J = 2.2 Hz, 1H), 7.83-7.80 (m, 2H), 7.46 (d, J = 8.1 Hz, 1H), 7.24 (d, J = 2.1 Hz, 1H), 6.82 (s, 1H), 3.55 (s, 2H), 2.05 (s, 3H), 1.14-1.12 (m, 2H), 0.99-0.97 (m, 2H). |
| 65 | 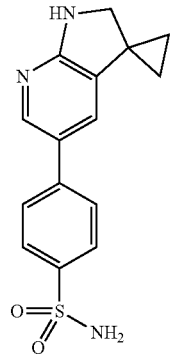<br>4-(1',2'-Dihydrospiro[cyclopropane-1,3'-pyrrolo[2,3-b]pyridin]-5'-yl)benzenesulfonamide | 2.13<br>302.2<br>A | L | (400 MHz, DMSO-d$_6$) δ 8.06 (d, J = 2.2 Hz, 1H), 7.79 & 7.74 (ABq, J = 8.6 Hz, 4H), 7.31 (s, 2H), 7.23 (d, J = 2.2 Hz, 1H), 6.87 (s, 1H), 3.56 (s, 2H), 1.13-1.10 (m, 2H), 1.01-0.98 (m, 2H). |
| 66 | 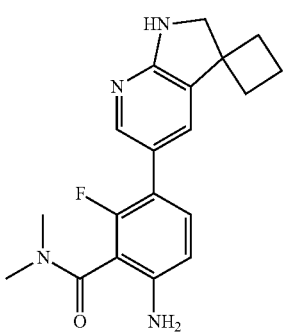<br>6-Amino-3-(1',2'-dihydrospiro[cyclobutane-1,3'-pyrrolo[2,3-b]pyridin]-5'-yl)-2-fluoro-N,N-dimethylbenzamide | 2.56<br>341.2<br>A | L | (400 MHz, DMSO-d$_6$) δ 7.79 (t, J = 1.8 Hz, 1H), 7.55 (t, J = 1.7 Hz, 1H), 7.19 (t, J = 8.7 Hz, 1H), 6.58 (d, J = 8.4 Hz, 1H), 6.41 (s, 1H), 5.31 (s, 2H), 3.57 (s, 2H), 3.00 (s, 3H), 2.89 (s, 3H), 2.33-2.24 (m, 2H), 2.17-2.11 (m, 2H), 2.00-1.92 (m, 2H). |

TABLE A1-continued

| No. | Structure/Name | LCMS R$_T$ (min) m/z Method | Prep Mtd | $^1$H NMR δ (ppm) |
|---|---|---|---|---|
| 67 | 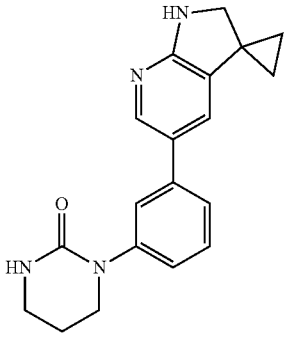<br>1-(3-(1',2'-Dihydrospiro[cyclopropane-1,3'-pyrrolo[2,3-b]pyridin]-5'-yl)phenyl)tetrahydropyrimidin-2(1H)-one | 2.48<br>321.1<br>A | N | (400 MHz, DMSO-d$_6$) δ 7.94 (d, J = 2.2 Hz, 1H), 7.41-7.40 (m, 1H), 7.32-7.27 (m, 2H), 7.17-7.14 (m, 1H), 7.13-7.11 (m, 1H), 6.67 (brs, 1H), 6.56 (brs, 1H), 3.67-3.64 (m, 2H), 3.54 (s, 2H), 3.25-3.22 (m, 2H), 1.98-1.93 (m, 2H), 1.11-1.09 (m, 2H), 0.98-0.96 (m, 2H). |
| 68a | 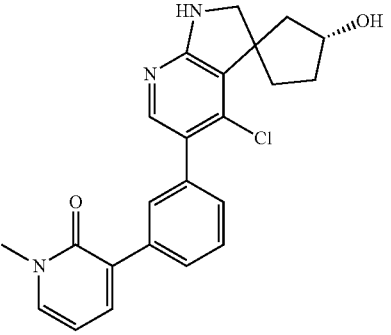<br>3-(3-((3R*)-4'-chloro-3-hydroxy-1',2'-dihydrospiro[cyclopentane-1,3'-pyrrolo[2,3-b]pyridin]-5'-yl)phenyl)-1-methylpyridin-2(1H)-one<br>Peak 1 SFC; absolute configuration arbitrarily assigned | 408.1 | L | |
| 68b | 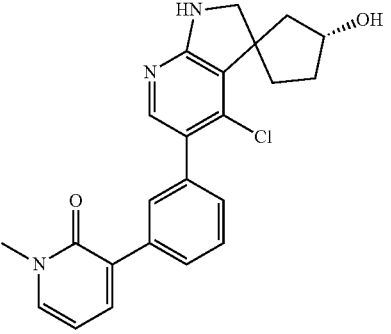<br>3-(3-((3R*)-4'-chloro-3-hydroxy-1',2'-dihydrospiro[cyclopentane-1,3'-pyrrolo[2,3-b]pyridin]-5'-yl)phenyl)-1-methylpyridin-2(1H)-one<br>Peak 2 SFC; absolute configuration arbitrarily assigned | 408.1 | L | |

| No. | Structure/Name | LCMS R$_T$ (min) m/z Method | Prep Mtd | $^1$H NMR δ (ppm) |
|---|---|---|---|---|
| 68c | 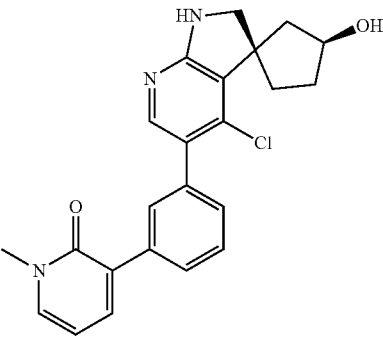<br>3-(3-((1RS,3SR)-4'-chloro-3-hydroxy-1',2'-dihydrospiro[cyclopentane-1,3'-pyrrolo[2,3-b]pyridin]-5'-yl)phenyl)-1-methylpyridin-2(1H)-one | 2.76<br>408.2<br>A | L | (400 MHz, DMSO-d$_6$) δ 7.75 (dd, J = 2.1, 6.7 Hz, 1H), 7.71 (s, 1H), 7.69-7.65 (m, 3H), 7.44-7.39 (m, 1H), 7.30 (td, J = 1.5, 7.7 Hz, 1H), 6.84 (s, 1H), 6.33 (t, J = 6.8 Hz, 1H), 4.66 (d, J = 3.2 Hz, 1H), 4.37-4.32 (m, 1H), 3.62 (d, J = 8.9 Hz, 1H), 3.51 (s, 3H), 3.44 (d, J = 9.5 Hz, 1H), 2.34 (dd, J = 5.9, 13.5 Hz, 1H), 2.24-2.14 (m, 1H), 2.08-1.97 (m, 1H), 1.91-1.82 (m, 1H), 1.77-1.62 (m, 2H). |
| 69a | 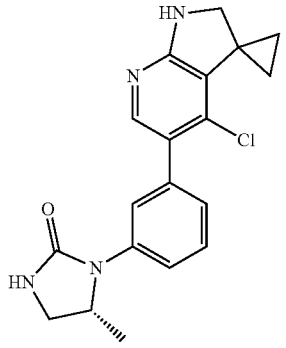<br>(R)-1-(3-(4'-Chloro-1',2'-dihydrospiro[cyclopropane-1,3'-pyrrolo[2,3-b]pyridin]-5'-yl)phenyl)-5-methylimidazolidin-2-one | 2.99<br>355.1<br>A | L | (400 MHz, DMSO-d$_6$) δ 7.58 (s, 1H), 7.47 (ddd, J = 8.3, 2.3, 1.0 Hz, 1H), 7.39 (t, J = 1.9 Hz, 1H), 7.33 (t, J = 7.9 Hz, 1H), 6.99 (s, 1H), 6.95 (ddd, J = 7.6, 1.6, 1.0 Hz, 1H), 6.88 (brs, 1H), 4.52-4.44 (m, 1H), 3.56 (dt, J = 8.6, 1.0 Hz, 1H), 3.53 (s, 2H), 2.98 (ddd, J = 8.8, 5.3, 1.0 Hz, 1H), 1.67-1.64 (m, 2H), 1.21 (d, J = 6.1 Hz, 3H), 0.90-0.87 (m, 2H). |
| 69b | 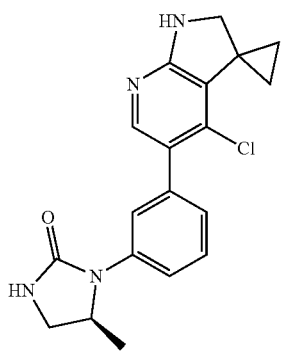<br>(S)-1-(3-(4'-Chloro-1',2'-dihydrospiro[cyclopropane-1,3'-pyrrolo[2,3-b]pyridin]-5'-yl)phenyl)-5-methylimidazolidin-2-one | 2.98<br>355.2<br>A | L | (400 MHz, DMSO-d$_6$) δ 7.58 (s, 1H), 7.47 (ddd, J = 8.3, 2.3, 1.0 Hz, 1H), 7.39 (t, J = 1.9 Hz, 1H), 7.33 (t, J = 7.9 Hz, 1H), 6.99 (s, 1H), 6.95 (ddd, J = 7.6, 1.6, 1.0 Hz, 1H), 6.88 (brs, 1H), 4.52-4.44 (m, 1H), 3.56 (dt, J = 8.6, 1.0 Hz, 1H), 3.53 (s, 2H), 2.98 (ddd, J = 8.8, 5.3, 1.0 Hz, 1H), 1.67-1.64 (m, 2H), 1.21 (d, J = 6.1 Hz, 3H), 0.90-0.87 (m, 2H). |

TABLE A1-continued

| No. | Structure/Name | LCMS R$_T$ (min) m/z Method | Prep Mtd | $^1$H NMR δ (ppm) |
|---|---|---|---|---|
| 70 | 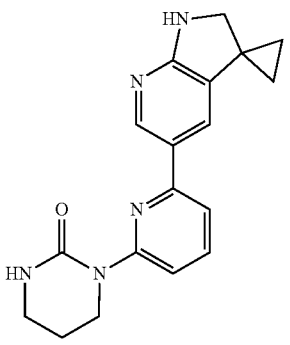 | 2.32 322.2 A | N | (400 MHz, DMSO-d$_6$) δ 8.43 (d, J = 2.0 Hz, 1H), 7.68 (dd, J = 8.3, 0.8 Hz, 1H), 7.62 (dd, J = 8.2, 7.5 Hz, 1H), 7.45 (brd, J = 2.0 Hz, 1H), 7.40 (dd, J = 7.5, 0.8 Hz, 1H), 6.88 (brs, 1H), 6.86 (brs, 1H), 3.98-3.95 (m, 2H), 3.56 (s, 2H), 3.25-3.21 (m, 2H), 1.98-1.93 (m, 2H), 1.10-1.07 (m, 2H), 1.01-0.98 (m, 2H). |
| 71 | 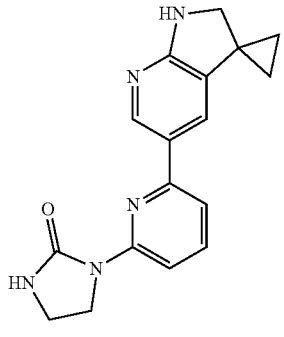<br>1-(6-(1',2'-Dihydrospiro[cyclopropane-1,3'-pyrrolo[2,3-b]pyridin]-5'-yl)pyridin-2-yl)imidazolidin-2-one | 2.40 308.1 A | N | (400 MHz, DMSO-d$_6$) δ 8.44 (d, J = 2.1 Hz, 1H), 7.98 (dd, J = 8.3, 0.6 Hz, 1H), 7.65 (dd, J = 8.3, 7.7 Hz, 1H), 7.46 (brd, J = 2.0 Hz, 1H), 7.36 (dd, J = 7.6, 0.7 Hz, 1H), 7.15 (brs, 1H), 6.89 (brs, 1H), 4.12-4.08 (m, 2H), 3.56 (s, 2H), 3.44-3.40 (m, 2H), 1.09-1.06 (m, 2H), 1.01-0.98 (m, 2H). |
| 72 | 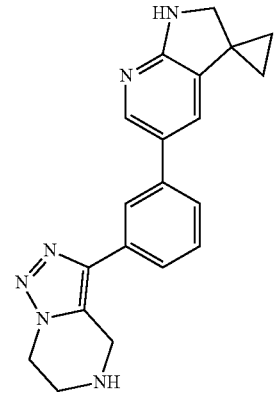<br>5'-(3-(4,5,6,7-Tetrahydro-[1,2,3]triazolo[1,5-a]pyrazin-3-yl)phenyl)-1',2'-dihydrospiro[cyclopropane-1,3'-pyrrolo[2,3-b]pyridine] | 1.84 345.2 A | T | (400 MHz, DMSO-d$_6$) δ 8.00 (d, J = 2.2 Hz, 1H), 7.76 (s, 1H), 7.54 (td, J = 1.7, 7.0 Hz, 1H), 7.52-7.43 (m, 2H), 7.18 (d, J = 1.9 Hz, 1H), 6.72 (s, 1H), 4.30 (t, J = 5.4 Hz, 2H), 4.23 (s, 2H), 3.56 (s, 2H), 3.17 (d, J = 5.3 Hz, 2H), 3.15 (bs, 1H), 1.15-1.10 (m, 2H), 1.01-0.96 (m, 2H) |

TABLE A1-continued

| No. | Structure/Name | LCMS R_T (min) m/z Method | Prep Mtd | $^1$H NMR δ (ppm) |
|---|---|---|---|---|
| 73 | 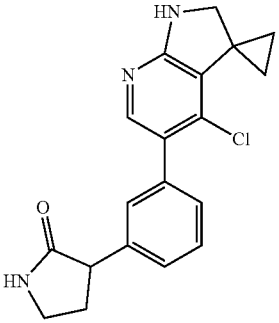<br>(±)-3-(3-(4'-Chloro-1',2'-dihydrospiro[cyclopropane-1,3'-pyrrolo[2,3-b]pyridin]-5'-yl)phenyl)piperidin-2-one | 2.82<br>340.1<br>A | L | (400 MHz, DMSO-d$_6$) δ 7.82 (brs, 1H), 7.57 (s, 1H), 7.34 (t, J = 7.6 Hz, 1H), 7.22-7.16 (m, 3H), 6.99 (s, 1H), 3.56 (t, J = 8.9 Hz, 1H), 3.53 (s, 2H), 3.31-3.25 (m, 2H), 2.49-2.45 (m, 1H), 2.14-2.05 (m, 1H), 1.67-1.65 (m, 2H), 0.90-0.87 (m, 2H). |
| 74 | 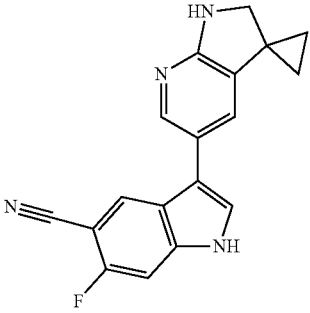<br>3-(1',2'-Dihydrospiro[cyclopropane-1,3'-pyrrolo[2,3-b]pyridin]-5'-yl)-6-fluoro-1H-indole-5-carbonitrile | 2.87<br>305.2<br>A | See text | (400 MHz, DMSO-d$_6$) δ ppm 11.83 (s, 1H), 8.22 (d, J = 6.2 Hz, 1H), 7.97-7.96 (m, 1H), 7.68 (s, 1H), 7.46 (d, J = 10.4 Hz, 1H), 7.13 (d, J = 1.9 Hz, 1H), 6.57-6.55 (m, 1H), 3.53 (d, J = 1.1 Hz, 2H), 1.14 (dd, J = 4.2, 6.8 Hz, 2H), 0.97 (dd, J = 4.3, 6.7 Hz, 2H). |
| 75 | 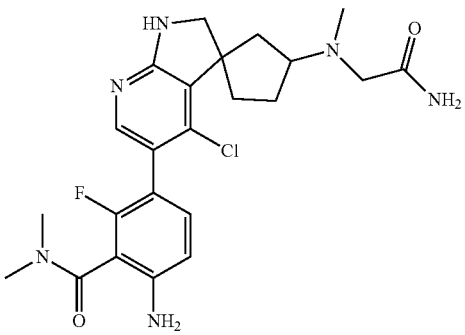<br>6-Amino-3-(3-((2-amino-2-oxoethyl)(methyl)amino)-4'-chloro-1',2'-dihydrospiro[cyclopentane-1,3'-pyrrolo[2,3-b]pyridin]-5'-yl)-2-fluoro-N,N-dimethylbenzamide | 1.63<br>475.3<br>A | T | (400 MHz, CDCl3) δ 7.71 (s, 1H), 7.16-7.09 (m, 1H), 7.03 (t, J = 8.5 Hz, 1H), 6.55 (d, J = 8.3 Hz, 1H), 5.64-5.53 (m, 1H), 4.74 (s, 1H), 4.41 (s, 2H), 3.54-3.45 (m, 2H), 3.15-3.02 (m, 9H), 2.34 (s, 3H), 2.18-1.94 (m, 3H) |

TABLE A1-continued

| No. | Structure/Name | LCMS R_T (min) m/z Method | Prep Mtd | $^1$H NMR δ (ppm) |
|---|---|---|---|---|
| 76 | 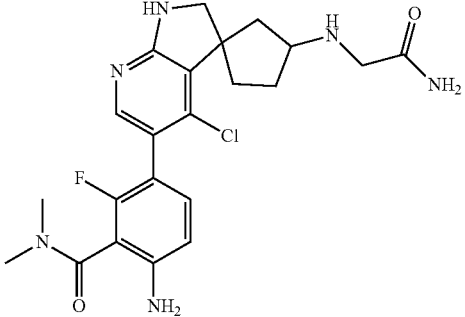<br>6-Amino-3-(3-((2-amino-2-oxoethyl)amino)-4'-chloro-1',2'-dihydrospiro[cyclopentane-1,3'-pyrrolo[2,3-b]pyridin]-5'-yl)-2-fluoro-N,N-dimethylbenzamide | 1.57<br>461.2<br>A | L | (400 MHz, CDCl3) δ ppm 7.71 (d, J = 1.3 Hz, 1H), 7.03 (dt, J = 1.3, 8.3 Hz, 2H), 6.90 (s, 1H), 6.55 (d, J = 8.3 Hz, 1H), 5.46 (bs, 1H), 4.64 (s, 1H), 4.40 (s, 2H), 3.56 (s, 1H), 3.44 (m, 1H), 3.14 (s, 3H), 3.04 (s, 3H), 2.86-2.75 (m, 1H), 2.68-2.57 (m, 1H), 2.21-2.13 (m, 1H), 2.02-1.94 (m, 1H), 1.77-1.69 (m, 1H), 1.52-1.43 (m, 1H) |
| 77a | 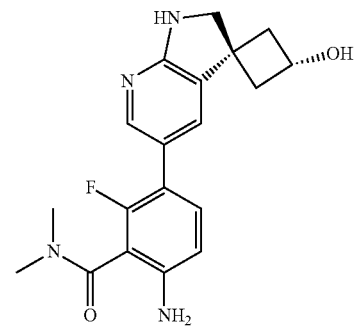<br>6-Amino-2-fluoro-3-((1r,3r)-3-hydroxy-1',2'-dihydrospiro[cyclobutane-1,3'-pyrrolo[2,3-b]pyridin]-5'-yl)-N,N-dimethylbenzamide | 1.86<br>357.2<br>A | L | (400 MHz, DMSO-d$_6$) δ 7.77 (s, 1H), 7.40 (s, 1H), 7.19 (t, J = 8.8 Hz, 1H), 6.59-6.56 (m, 1H), 6.39 (s, 1H), 5.31 (s, 2H), 5.14 (d, J = 5.9 Hz, 1H), 4.44-4.36 (m, 1H), 3.49 (s, 2H), 3.00 (s, 3H), 2.89 (s, 3H), 2.52-2.47 (m, 2H), 2.54-2.45 (m, 2H), 2.12-2.04 (m, 2H). |
| 77b | 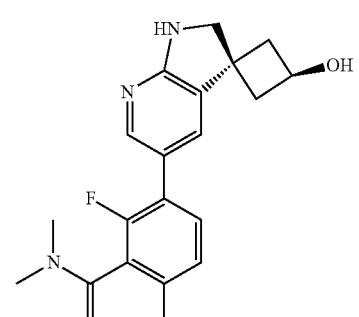<br>6-Amino-2-fluoro-3-((1s,3s)-3-hydroxy-1',2'-dihydrospiro[cyclobutane-1,3'-pyrrolo[2,3-b]pyridin-5'-yl)-N,N-dimethylbenzamide | 1.87<br>357.2<br>A | L | (400 MHz, DMSO-d$_6$) δ 7.78 (s, 1H), 7.45 (s, 1H), 7.18 (t, J = 8.9 Hz, 1H), 6.58 (d, J = 8.4 Hz, 1H), 6.45 (s, 1H), 5.31 (s, 2H), 5.14 (d, J = 6.8 Hz, 1H), 4.18-4.11 (m, 1H), 3.51 (s, 2H), 3.00 (s, 3H), 2.89 (s, 3H), 2.46-2.37 (m, 2H), 2.17-2.07 (m, 2H). |

TABLE A1-continued

| No. | Structure/Name | LCMS R$_T$ (min) m/z Method | Prep Mtd | $^1$H NMR δ (ppm) |
|---|---|---|---|---|
| 78a | 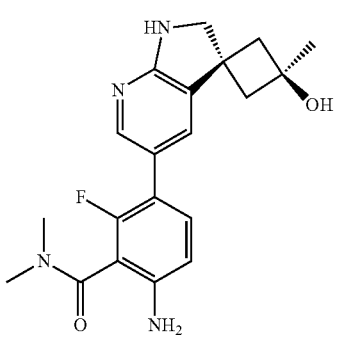<br>6-Amino-2-fluoro-3-((1r,3r)-3-hydroxy-3-methyl-1',2'-dihydrospiro[cyclobutane-1,3'-pyrrolo[2,3-b]pyridin]-5'-yl)-N,N-dimethylbenzamide | 1.99<br>371.2<br>A | L | (400 MHz, DMSO-d$_6$) δ 7.76 (s, 1H), 7.60 (s, 1H), 7.16 (t, 1H), 6.58 (d, J = 7.9 Hz, 1H), 6.44 (s, 1H), 5.31 (s, 1H), 5.09 (s, 1H), 3.58 (s, 2H), 3.00 (s, 3H), 2.88 (s, 3H), 2.35 (d, J = 12.1 Hz, 2H), 2.22 (d, J = 12.7 Hz, 2H), 1.30 (s, 3H), |
| 78b | 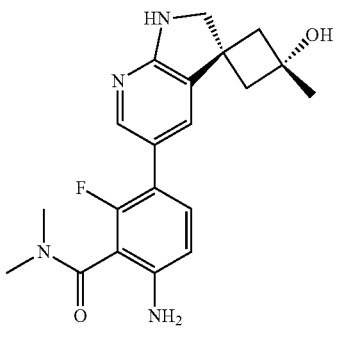<br>6-Amino-2-fluoro-3-((1s,3s)-3-hydroxy-3-methyl-1',2'-dihydrospiro[cyclobutane-1,3'-pyrrolo[2,3-b]pyridin]-5'-yl)-N,N-dimethylbenzamide | 2.08<br>371.2<br>A | L | (400 MHz, DMSO-d$_6$) δ 7.77 (s, 1H), 7.44 (s, 1H), 7.17 (t, 1H), 6.58 (d, J = 8.2 Hz, 1H), 6.38 (s, 1H), 5.30 (s, 1H), 4.90 (s, 1H), 3.63 (s, 2H), 3.00 (s, 3H), 2.88 (s, 3H), 2.31 (d, J = 10.7 Hz, 2H), 2.16 (d, J = 12.4 Hz, 2H), 1.34 (s, 3H), |
| 79 | 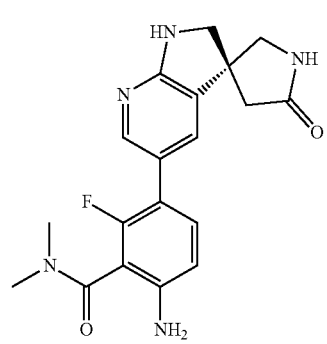<br>(RS)-6-Amino-2-fluoro-N,N-dimethyl-3-(5-oxo-1',2'-dihydrospiro[pyrrolidine-3,3'-pyrrolo[2,3-b]pyridin]-5'-yl)benzamide | 1.60<br>370.2<br>A | L | (400 MHz, DMSO-d$_6$) δ 7.84 (s, 1H), 7.76 (s, 1H), 7.50 (s, 1H), 7.15 (t, 1H), 6.58 (s, 1H), 6.55 (s, 1H), 5.32 (s, 2H), 3.53-3.45 (q, 2H), 3.38 (s, 2H), 2.99 (s, 3H), 2.88 (s, 3H), 2.6-2.54 (dd, J = 16.5, 7.5 Hz, 1H), 2.38-2.33 (dd, J = 16.8, 3.4 Hz, 1H). |

TABLE A1-continued

| No. | Structure/Name | LCMS R$_T$ (min) m/z Method | Prep Mtd | $^1$H NMR δ (ppm) |
|---|---|---|---|---|
| 80a | 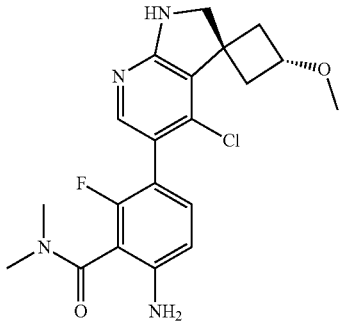<br>6-Amino-3-((1r,3r)-4'-chloro-3-methoxy-1',2'-dihydrospiro[cyclobutane-1,3'-pyrrolo[2,3-b]pyridin]-5'-yl)-2-fluoro-N,N-dimethylbenzamide | 2.28 371.3 A | L | (400 MHz, DMSO-d$_6$) δ 7.80-7.78 (m, 1H), 7.45-7.45 (m, 1H), 7.19 (t, J = 8.8 Hz, 1H), 6.58 (d, J = 8.3 Hz, 1H), 6.49 (s, 1H), 5.31 (s, 2H), 3.98-3.89 (m, 1H), 3.53 (d, J = 0.9 Hz, 2H), 3.17 (s, 3H), 3.00 (s, 3H), 2.90-2.88 (m, 3H), 2.48-2.39 (m, 2H), 2.18-2.07 (m, 2H). |
| 80b | 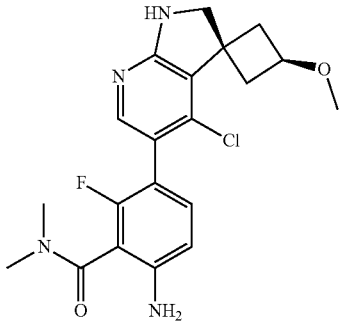<br>6-Amino-3-((1s,3s)-4'-chloro-3-methoxy-1',2'-dihydrospiro[cyclobutane-1,3'-pyrrolo[2,3-b]pyridin]-5'-yl)-2-fluoro-N,N-dimethylbenzamide | 2.30 371.2 A | L | (400 MHz, DMSO-d$_6$) δ 7.79 (t, J = 1.8 Hz, 1H), 7.46-7.45 (m, 1H), 7.19 (t, J = 8.8 Hz, 1H), 6.58 (d, J = 8.4 Hz, 1H), 6.42 (s, 1H), 5.31 (s, 2H), 4.21-4.13 (m, 1H), 3.50 (d, J = 0.9 Hz, 2H), 3.17 (s, 3H), 3.00 (s, 3H), 2.89 (s, 3H), 2.46-2.52 (m, 2H), 2.15-2.07 (m, 2H). |
| 81a | 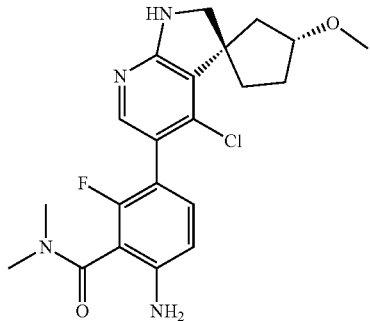<br>6-Amino-3-((1RS,3RS)-4'-chloro-3-methoxy-1',2'-dihydrospiro[cyclopentane-1,3'-pyrrolo[2,3-b]pyridin]-5'-yl)-2-fluoro-N,N-dimethylbenzamide | 2.68 419.3 A | L | (400 MHz, DMSO-d$_6$) δ 7.60 (s, 1H), 6.97 (t, J = 8.5 Hz, 1H), 6.86 (s, 1H), 6.55 (d, J = 8.4 Hz, 1H), 5.38 (brs, 2H), 3.92-3.86 (m, 1H), 3.21 (d, J = 2.4 Hz, 3H), 2.99 (s, 3H), 2.88 (s, 3H), 2.44-2.33 (m, 1H), 2.15-2.11 (m, 2H), 1.99-1.90 (m, 1H), 1.78-1.62 (m, 2H). |

TABLE A1-continued

| No. | Structure/Name | LCMS R$_T$ (min) m/z Method | Prep Mtd | $^1$H NMR δ (ppm) |
|---|---|---|---|---|
| 81c | 6-Amino-3-((1RS,3SR)-4'-chloro-3-methoxy-1',2'-dihydrospiro[cyclopentane-1,3'-pyrrolo[2,3-b]pyridin]-5'-yl)-2-fluoro-N,N-dimethylbenzamide | 2.82 419.2 A | L | (400 MHz, DMSO-d$_6$) δ 7.60 (s, 1H), 6.96 (t, J = 8.5 Hz, 1H), 6.81 (s, 1H), 6.55 (d, J =8.3 Hz, 1H), 5.37 (brs, 2H), 3.99-3.95 (m, 1H), 3.47 (d, J = 9.6 Hz, 1H), 3.39 (d, J = 9.6 Hz, 1H), 3.21 (s, 3H), 2.99 (s, 3H), 2.88 (s, 3H), 2.35-2.27 (m, 1H), 2.19-2.03 (m, 2H), 1.90-1.70 (m, 3H). |
| 82a | 6-Amino-3-((1RS,3SR)-4'-chloro-3-hydroxy-3-methyl-1',2'-dihydrospiro[cyclopentane-1,3'-pyrrolo[2,3-b]pyridin]-5'-yl)-2-fluoro-N,N-dimethylbenzamide | 2.47 419.2 A | L | (400 MHz, DMSO-d$_6$) δ 7.58 (s, 1H), 6.96 (t, J = 8.5 Hz, 1H), 6.76 (s, 1H), 6.55 (d, J = 8.3 Hz, 1H), 5.39-5.36 (m, 2H), 4.38 (s, 1H), 3.72 (d, J = 9.6 Hz, 1H), 3.42 (d, J = 9.6 Hz, 1H), 2.99 (s, 3H), 2.88 (s, 3H), 2.41-2.29 (m, 1H), 2.06-1.74 (m, 6H), 1.28 (d, J = 4.1 Hz, 3H). |
| 83 | 3-(3-Acetamido-4'-chloro-1',2'-dihydrospiro[cyclopentane-1,3'-pyrrolo[2,3-b]pyridin]-5'-yl)-6-amino-2-fluoro-N,N-dimethylbenzamide 7:3 Mixture of cis/trans isomers | 2.19 446.2 A | T | (400 MHz, CDCl3) δ 7.71 (2xs, 1H), 7.05-6.99 (2xt, 1H), 6.57-6.53 (2xd, 1H), 5.56 (d, J = 7.2 Hz), 5.45 (d, J = 7.3 Hz, 1H), 4.83-4.80 (m, 1H), 4.44-4.33 (m, 3H), 3.57-3.45 (m, 2H), 3.14-3.14 (m, 4H), 3.04-3.01 (m, 4H), 2.64-2.53 (m, 1H), 2.29-2.17 (m, 2H), 1.80-1.65 (m, 2H), 1.57-1.43 (m, 1H). |

TABLE A1-continued

| No. | Structure/Name | LCMS R$_T$ (min) m/z Method | Prep Mtd | $^1$H NMR δ (ppm) |
|---|---|---|---|---|
| 84a | 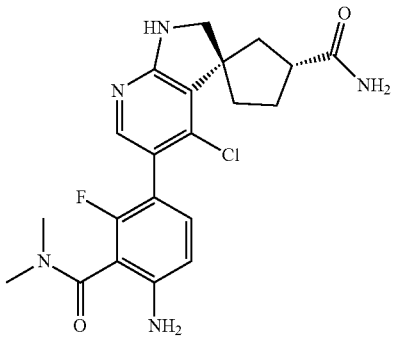<br>(1RS,3RS)-5'-(4-amino-3-(dimethylcarbamoyl)-2-fluorophenyl)-4'-chloro-1',2'-dihydrospiro[cyclopentane-1,3'-pyrrolo[2,3-b]pyridine]-3-carboxamide | 2.04<br>432.2<br>A | L | (400 MHz, DMSO-d$_6$) δ 7.60 (s, 1H), 7.26 (brs, 1H), 6.97 (t, J = 8.5 Hz, 1H), 6.86 (s, 1H), 6.87 (brs, 1H), 6.55 (d, J = 8.2 Hz, 1H), 5.38 (brs, 2H), 2.99 (s, 3H), 2.89 (s, 3H), 2.77-2.68 (m, 1H), 2.48-2.38 (m, 1H), 2.27-2.18 (m, 1H), 1.98-1.83 (m, 3H), 1.71-1.63 (m, 1H). |
| 84c | 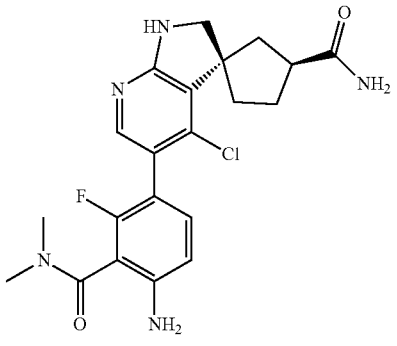<br>(1RS,3SR)-5'-(4-amino-3-(dimethylcarbamoyl)-2-fluorophenyl)-4'-chloro-1',2'-dihydrospiro[cyclopentane-1,3'-pyrrolo[2,3-b]pyridine]-3-carboxamide | 2.11<br>432.2<br>A | L | (400 MHz, DMSO-d$_6$) δ 7.61 (s, 1H), 7.34 (brs, 1H), 6.97 (t, J = 8.5 Hz, 1H), 6.83 (s, 1H), 6.79 (brs, 1H), 6.55 (d, J = 8.2 Hz, 1H), 5.39 (brs, 2H), 3.46-3.34 (m, 2H), 2.99 (s, 3H), 2.95-2.89 (m, 1H), 2.89 (s, 3H), 2.08-1.92 (m, 2H), 1.87-1.81 (m, 2H), 1.77-1.67 (m, 1H). |
| 85a | 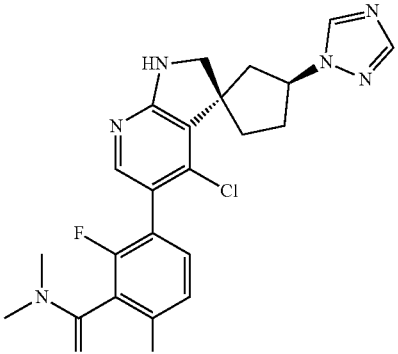<br>6-Amino-3-((1RS,3RS)-4'-chloro-3-(1H-1,2,4-triazol-1-yl)-1',2'-dihydrospiro[cyclopentane-1,3'-pyrrolo[2,3-b]pyridin]-5'-yl)-2-fluoro-N,N-dimethylbenzamide | 2.32<br>456.2<br>A | L | (400 MHz, DMSO-d$_6$) δ 8.62 (s, 1H), 8.00 (s, 1H), 7.64 (s, 1H), 6.99 (t, J = 8.5 Hz, 1H), 6.990 (brs, 1H), 6.56 (d, J = 8.3 Hz, 1H), 5.41 (brs, 2H), 5.13 (quintet, J = 7.7 Hz, 1H), 3.53-3.47 (m, 2H), 2.99 (s, 3H), 2.96-2.89 (m, 1H), 2.89 (s, 3H), 2.35-2.28 (m, 1H), 2.26-1.98 (m, 4H). |

TABLE A1-continued

| No. | Structure/Name | LCMS R_T (min) m/z Method | Prep Mtd | $^1$H NMR δ (ppm) |
|---|---|---|---|---|
| 85c | 6-Amino-3-((1RS,3RS)-4'-chloro-3-(1H-1,2,4-triazol-1-yl)-1',2'-dihydrospiro[cyclopentane-1,3'-pyrrolo[2,3-b]pyridin]-5'-yl)-2-fluoro-N,N-dimethylbenzamide | 2.29 456.2 A | L | (400 MHz, DMSO-d$_6$) δ 8.56 (d, J = 2.9 Hz, 1H), 7.98 (d, J = 4.0 Hz, 1H), 7.64 (s, 1H), 6.97 (t, J = 8.5 Hz, 1H), 6.94 (brs, 1H), 6.55 (d, J = 8.4 Hz, 1H), 5.40 (brs, 2H), 5.01-4.93 (m, 1H), 3.53 (d, J = 9.6 Hz, 1H), 3.45 (d, J = 9.4 Hz, 1H), 2.99 (s, 3H), 2.89 (s, 3H), 2.68-2.52 (m, 2H), 2.36-2.28 (m, 2H), 2.25-2.15 (m, 1H), 1.88-1.81 (m, 1H). |
| 86a | 6-Amino-2-fluoro-N,N-dimethyl-3-((1RS,2SR)-2-methyl-1',2'-dihydrospiro[cyclopropane-1,3'-pyrrolo[2,3-b]pyridin]-5'-yl)benzamide | 2.49 341.2 A | L | (400 MHz, DMSO-d$_6$) δ 7.72 (d, J = 1.3 Hz, 1H), 7.17-7.10 (m, 1H), 6.98 (d, J = 1.5 Hz, 1H), 6.56 (d, J = 8.5 Hz, 1H), 6.53 (s, 1H), 5.29 (s, 2H), 3.60 (dd, J = 2.1, 9.0 Hz, 1H), 3.33 (m, 1H assumed under water peak), 2.99 (s, 3H), 2.87 (d, J = 8.3 Hz, 3H), 1.15-1.11 (m, 1H), 1.10-1.02 (m, 4H), 0.88-0.82 (m, 1H). |
| 86c | 6-Amino-2-fluoro-N,N-dimethyl-3-((1RS,2RS)-2-methyl-1',2'-dihydrospiro[cyclopropane-1,3'-pyrrolo[2,3-b]pyridin]-5'-yl)benzamide | 2.56 341.2 B | L | (400 MHz, DMSO-d$_6$) δ 7.68 (s, 1H), 7.10 (t, J = 8.8 Hz, 1H), 6.83 (s, 1H), 6.60 (s, 1H), 6.55 (d, J = 8.2 Hz, 1H), 5.28 (s, 2H), 3.60 (d, J = 9.4 Hz, 1H), 3.42 (d, J = 9.9 Hz, 1H), 2.99 (s, 3H), 2.87 (m, 3H), 1.33-1.21 (m, 1H), 1.17-1.11 (m, 1H), 1.10-1.07 (m, 3H), 0.58 (t, J = 4.3 Hz, 1H). |

TABLE A1-continued

| No. | Structure/Name | LCMS R_T (min) m/z Method | Prep Mtd | $^1$H NMR δ (ppm) |
|---|---|---|---|---|
| 87a | 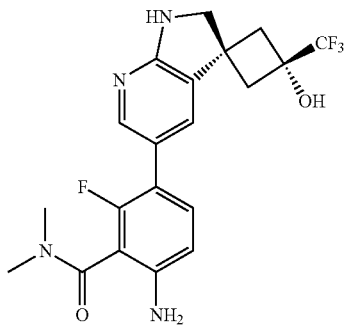<br>6-Amino-3-((1r,3r)-4'-chloro-3-hydroxy-3-(trifluoromethyl)-1',2'-dihydrospiro[cyclobutane-1,3'-pyrrolo[2,3-b]pyridin]-5'-yl)-2-fluoro-N,N-dimethylbenzamide | 2.39<br>425.2<br>A | L | (400 MHz, DMSO-d$_6$) δ 7.83 (t, J = 1.7 Hz, 1H), 7.71 (s, 1H), 7.18 (t, J = 8.8 Hz, 1H), 6.74 (s, 1H), 6.59 (d, J = 8.5 Hz, 1H), 6.51 (s, 1H), 5.34 (s, 2H), 3.56 (s, 2H), 3.01 (s, 3H), 2.89 (s, 3H), 2.70 (d, J = 14.7 Hz, 2H), 2.41 (d, J = 14.3 Hz, 2H). |
| 88a | 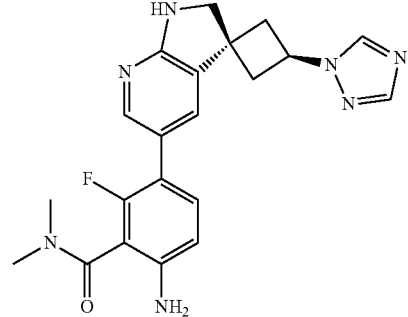<br>6-Amino-3-((1s,3s)-4'-chloro-3-(1H-1,2,4-triazol-1-yl)-1',2'-dihydrospiro[cyclobutane-1,3'-pyrrolo[2,3-b]pyridin]-5'-yl)-2-fluoro-N,N-dimethylbenzamide | 2.01<br>408.2<br>A | L | (400 MHz, DMSO-d$_6$) δ 8.60 (s, 1H), 8.03 (s, 1H), 7.85 (t, J = 1.8 Hz, 1H), 7.75-7.73 (br s, 1H), 7.24 (t, J = 8.8 Hz, 1H), 6.61 (d, J = 8.4 Hz, 1H), 6.50 (s, 1H), 5.47-5.38 (qn, J = 8.3Hz), 5.33 (s, 2H), 3.60 (s, 2H), 3.01 (s, 3H), 2.89 (s, 3H), 2.90 (s, 3H), 2.77 (d, J = 8.3 Hz, 4H). |
| 89a | 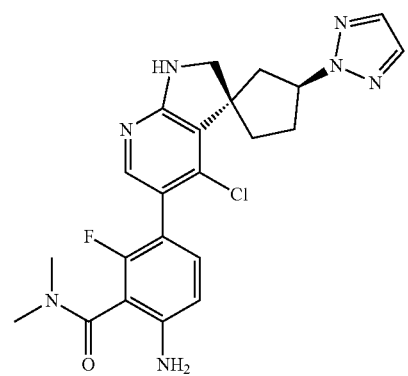<br>6-Amino-3-((1RS,3SR)-4'-chloro-3-(2H-1,2,3-triazol-2-yl)-1',2'-dihydrospiro[cyclopentane-1,3'-pyrrolo[2,3-b]pyridin]-5'-yl)-2-fluoro-N,N-dimethylbenzamide | 2.85<br>456.2<br>A | L | (400 MHz, DMSO-d$_6$) δ 7.81 (s, 2H), 7.64 (s, 1H), 6.99 (t, J = 8.5 Hz, 1H), 6.88 (brs, 1H), 6.56 (d, J = 8.4 Hz, 1H), 5.40 (brs, 2H), 5.29 (quintet, J = 7.3 Hz, 1H), 3.46 (d, J = 9.5 Hz, 1H), 3.39 (d, J = 9.7 Hz, 1H), 2.99 (s, 3H), 2.96-2.88 (m, 1H), 2.90 (s, 3H), 2.45-2.30 (m, 2H), 2.28-2.17 (m, 2H), 2.06-1.99 (m, 1H). |

TABLE A1-continued

| No. | Structure/Name | LCMS R$_T$ (min) m/z Method | Prep Mtd | $^1$H NMR δ (ppm) |
|---|---|---|---|---|
| 89c | 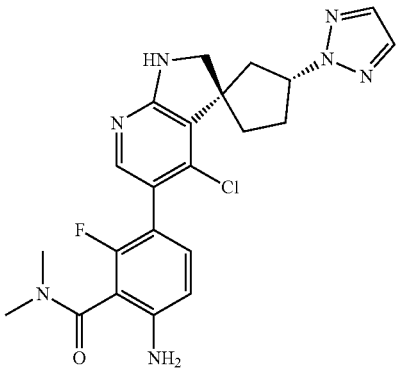<br>6-Amino-3-((1RS,3RS)-4'-chloro-3-(2H-1,2,3-triazol-2-yl)-1',2'-dihydrospiro[cyclopentane-1,3'-pyrrolo[2,3-b]pyridin]-5'-yl)-2-fluoro-N,N-dimethylbenzamide | 2.79<br>456.2<br>A | L | (400 MHz, DMSO-d$_6$) δ 7.78 (d, J = 3.6 Hz, 2H), 7.63 (s, 1H), 6.97 (t, J = 8.5 Hz, 1H), 6.95 (brs, 1H), 6.55 (d, J = 8.4 Hz, 1H), 5.39 (brs, 2H), 5.21 (quintet, J = 8.0 Hz, 1H), 3.56 (d, J = 9.5 Hz, 1H), 3.46 (d, J = 9.5 Hz, 1H), 2.99 (s, 3H), 2.88 (s, 3H), 2.81-2.72 (m, 1H), 2.68-2.56 (m, 1H), 2.43-2.23 (m, 3H), 1.90-1.83 (m, 1H). |
| 90a | 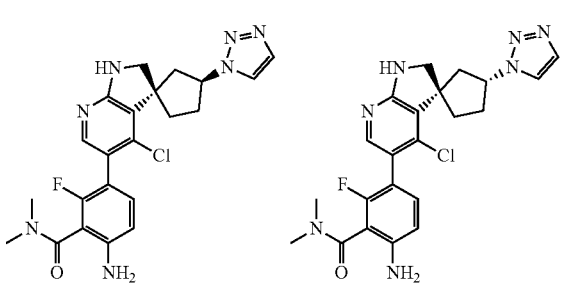<br>1.5: 1 Mixture of 6-amino-3-((1RS,3SR)-4'-chloro-3-(1H-1,2,3-triazol-1-yl)-1',2'-dihydrospiro[cyclopentane-1,3'-pyrrolo[2,3-b]pyridin]-5'-yl)-2-fluoro-N,N-dimethylbenzamide and 6-amino-3-((1RS,3RS)-4'-chloro-3-(1H-1,2,3-triazol-1-yl)-1',2'-dihydrospiro[cyclopentane-1,3'-pyrrolo[2,3-b]pyridin]-5'-yl)-2-fluoro-N,N-dimethylbenzamide | Major isomer:<br>2.42<br>456.2<br>A | L | Data for major isomer. (400 MHz, DMSO-d$_6$) δ 8.27 (s, 1H), 7.75 (s, 1H), 7.65 (s, 1H), 6.99 (t, J = 8.5 Hz, 1H), 6.91 (brs, 1H), 6.57 (d, J = 8.4 Hz, 1H), 5.41 (brs, 2H), 5.26 (quintet, J = 7.9 Hz, 1H), 3.53 (d, J = 9.5 Hz, 1H), 3.42 (d, J = 9.7 Hz, 1H), 3.05-3.01 (m, 1H), 3.00 (s, 3H), 2.90 (s, 3H), 2.46-2.24 (m, 2H), 2.18-2.03 (m, 3H). |
| 90c | 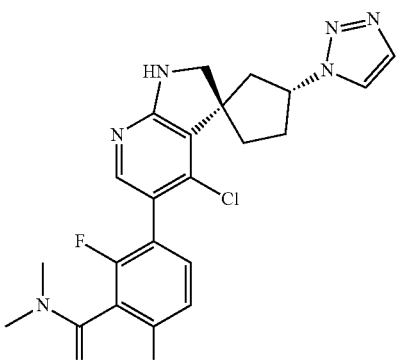<br>6-Amino-3-((1RS,3RS)-4'-chloro-3-(1H-1,2,3-triazol-1-yl)-1',2'-dihydrospiro[cyclopentane-1,3'-pyrrolo[2,3-b]pyridin]-5'-yl)-2-fluoro-N,N-dimethylbenzamide | 2.36<br>456.2<br>A | L | (400 MHz, DMSO-d$_6$) δ 8.19 (dd, J = 3.1, 0.9 Hz, 1H), 7.73 (dd, J = 3.2, 0.9 Hz, 1H), 7.64 (s, 1H), 6.97 (t, J = 8.5 Hz, 1H), 6.96 (brs, 1H), 6.55 (d, J = 8.4 Hz, 1H), 5.39 (brs, 2H), 5.18-5.09 (m, 1H), 3.57 (d, J = 9.5 Hz, 1H), 3.47 (d, J = 9.5 Hz, 1H), 2.99 (s, 3H), 2.88 (s, 3H), 2.70-2.55 (m, 2H), 2.48-2.38 (m, 2H), 2.31-2.21 (m, 1H), 1.92-1.85 (m, 1H). |

TABLE A1-continued

| No. | Structure/Name | LCMS $R_T$ (min) m/z Method | Prep Mtd | $^1$H NMR δ (ppm) |
|---|---|---|---|---|
| 91a | 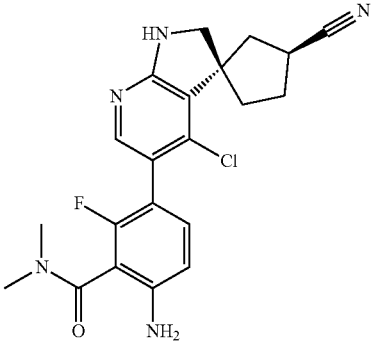<br>6-Amino-3-((1RS,3SR)-4'-chloro-3-cyano-1',2'-dihydrospiro[cyclopentane-1,3'-pyrrolo[2,3-b]pyridin]-5'-yl)-2-fluoro-N,N-dimethylbenzamide | 2.64<br>414.2<br>A | L | (400 MHz, DMSO-d$_6$) δ 7.64 (s, 1H), 6.97 (t, J = 8.5 Hz, 1H), 6.94 (brs, 1H), 6.55 (d, J = 8.4 Hz, 1H), 5.40 (brs, 2H), 3.51-3.46 (m, 2H), 2.99 (s, 3H), 2.88 (s, 3H), 2.74-2.66 (m, 1H), 2.29-2.23 (m, 1H), 2.05-1.90 (m, 4H). |
| 92 | 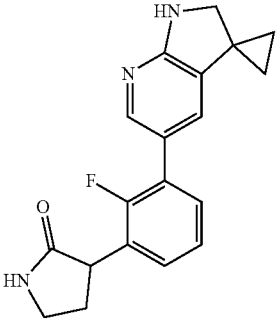<br>(RS)-3-(3-(1',2'-dihydrospiro[cyclopropane-1,3'-pyrrolo[2,3-b]pyridin]-5'-yl)-2-fluorophenyl)pyrrolidin-2-one | 340.1<br>L | L | n/a |
| 93 | 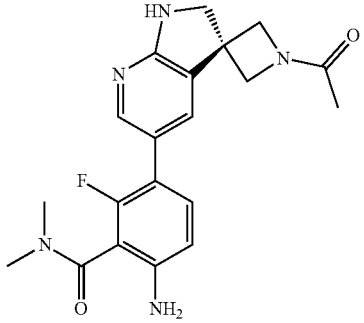<br>3-(1-Acetyl-1',2'-dihydrospiro[azetidine-3,3'-pyrrolo[2,3-b]pyridin]-5'-yl)-6-amino-2-fluoro-N,N-dimethylbenzamide | 1.81<br>384.2<br>A | L | (400 MHz, DMSO-d$_6$) δ 7.87 (s, 1H), 7.69 (s, 1H), 7.21 (t, 1H), 6.60-6.57 (m, 2H), 5.32 (s, 2H), 4.32-4.29 (dd, J = 8.3, 4.8 Hz, 1H), 4.23-4.21 (m, 1H), 4.00-3.94 (m, 2H), 3.73 (s, 2H), 3.00 (s, 3H), 2.88 (s, 3H), 1.80 (s, 3H), |

| No. | Structure/Name | LCMS R_T (min) m/z Method | Prep Mtd | $^1$H NMR δ (ppm) |
|---|---|---|---|---|
| 94a | (s,E)-6-Amino-3-(3-(cyanomethylene)-1',2'-dihydrospiro[cyclobutane-1,3'-pyrrolo[2,3-b]pyridin]-5'-yl)-2-fluoro-N,N-dimethylbenzamide and (r,Z)-6-amino-3-(3-(cyanomethylene)-1',2'-dihydrospiro[cyclobutane-1,3'-pyrrolo[2,3-b]pyridin]-5'-yl)-2-fluoro-N,N-dimethylbenzamide Mixture of enantiomers | 2.29 378.2 A | L | (400 MHz, DMSO-d$_6$) δ 7.84 (t, J = 1.8 Hz, 1H), 7.56 (d, J = 1.4 Hz, 1H), 7.19 (t, J = 8.8 Hz, 1H), 6.60-6.55 (m, 2H), 5.68 (t, J = 2.2 Hz, 1H), 5.32 (s, 2H), 3.64-3.61 (m, 2H), 3.25-3.08 (m, 4H), 3.00 (s, 3H), 2.88 (s, 3H). |
| 95a | 6-Amino-3-((1r,3r)-3-(cyanomethyl)-1',2'-dihydrospiro[cyclobutane-1,3'-pyrrolo[2,3-b]pyridin]-5'-yl)-2-fluoro-N,N-dimethylbenzamide | 2.30 380.2 A | L | (400 MHz, DMSO-d$_6$) δ ppm 7.79 (t, J = 1.7 Hz, 1H), 7.57 (s, 1H), 7.17 (t, J = 8.8 Hz, 1H), 6.58 (d, J = 8.4 Hz, 1H), 6.48 (s, 1H), 5.31 (s, 2H), 3.63 (s, 2H), 3.00 (s, 3H), 2.88 (s, 3H), 2.74-2.71 (m, 3H), 2.33-2.24 (m, 2H), 2.16-2.08 (m, 2H) |
| 96a | 6-Amino-3-((1s,3s)-4'-chloro-3-cyano-1',2'-dihydrospiro[cyclobutane-1,3'-pyrrolo[2,3-b]pyridin]-5'-yl)-2-fluoro-N,N-dimethylbenzamide | 2.17 366.1 A | L | (400 MHz, DMSO-d$_6$) δ 7.83 (t, J = 1.8 Hz, 1H), 7.70-7.68 (m, 1H), 7.20 (t, J = 8.8 Hz, 1H), 6.59 (d, J = 8.4 Hz, 1H), 6.48 (s, 1H), 5.32 (s, 2H), 3.69-3.58 (m, 1H), 3.60 (s, 2H), 3.00 (s, 3H), 2.89 (s, 3H), 2.71-2.61 (m, 2H), 2.60-2.53 (m, 2H). |

TABLE A1-continued

| No. | Structure/Name | LCMS $R_T$ (min) m/z Method | Prep Mtd | $^1$H NMR δ (ppm) |
|---|---|---|---|---|
| 97a | 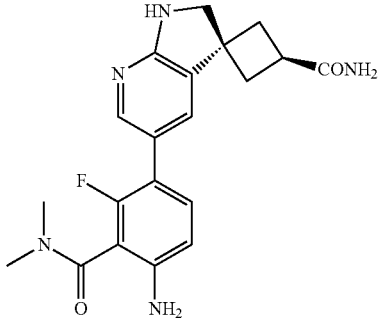<br>(1s,3s)-5'-(4-Amino-3-(dimethylcarbamoyl)-2-fluorophenyl)-4'-chloro-1',2'-dihydrospiro[cyclobutane-1,3'-pyrrolo[2,3-b]pyridine]-3-carboxamide | 1.83<br>384.2<br>A | L | (400 MHz, DMSO-$d_6$) δ 7.81 (t, J = 1.7 Hz, 1H), 7.58 (t, J = 1.9 Hz, 1H), 7.24 (s, 1H), ,7.20 (t, J = 8.9 Hz, 1H), 6.78 (s, 1H), 6.59 (d, J = 8.5 Hz, 1H), 6.40 (s, 1H), 5.32 (s, 2H), 3.47 (s, 2H), 3.23-3.15 (m, 1H), 3.00 (s, 3H), 2.89 (s, 3H), 2.37-2.28 (m, 4H). |
| 98a | 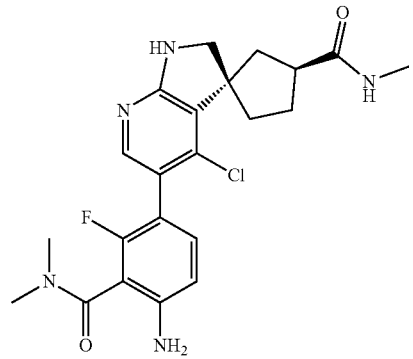<br>(1RS,3SR)-5'-(4-Amino-3-(dimethylcarbamoyl)-2-fluorophenyl)-4'-chloro-N-methyl-1',2'-dihydrospiro[cyclopentane-1,3'-pyrrolo[2,3-b]pyridine]-3-carboxamide | 2.25<br>446.2<br>A | L | (400 MHz, DMSO-$d_6$) δ 7.82 (q, J = 4.6 Hz, 1H), 7.61 (s, 1H), 6.97 (t, J = 8.5 Hz, 1H), 6.84 (brs, 1H), 6.55 (d, J = 8.5 Hz, 1H), 5.39 (brs, 2H), 3.47 (d, J = 9.5 Hz, 1H), 3.36 (d, J = 9.4 Hz, 1H), 2.99 (s, 3H), 2.94-2.88 (m, 1H), 2.88 (s, 3H), 2.58 (d, J = 4.5 Hz, 3H), 2.06-1.89 (m, 2H), 1.86-1.67 (m, 3H). |
| 99a | 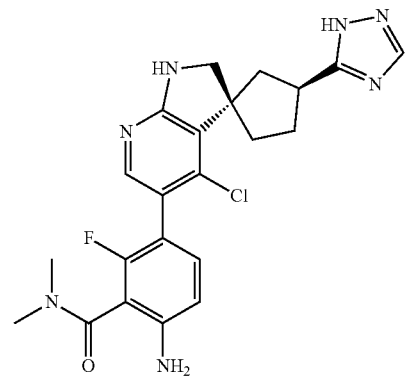<br>6-Amino-3-((1RS,3SR)-4'-chloro-3-(1H-1,2,4-triazol-5-yl)-1',2'-dihydrospiro[cyclopentane-1,3'-pyrrolo[2,3-b]pyridin]-5'-yl)-2-fluoro-N,N-dimethylbenzamide | 2.15<br>456.2<br>A | | (400 MHz, DMSO-$d_6$) δ 13.67 (brs, 1H), 7.84 (brs, 1H), 7.63 (s, 1H), 6.99 (t, J = 8.5 Hz, 1H), 6.85 (brs, 1H), 6.56 (d, J = 8.3 Hz, 1H), 5.40 (brs, 2H), 3.60-3.50 (m, 1H), 3.42 (brs, 1H), 2.99 (s, 3H), 2.89 (s, 3H), 2.84-2.72 (m, 1H), 2.22-2.03 (m, 3H), 1.98-1.89 (m, 3H). |

TABLE A1-continued

| No. | Structure/Name | LCMS R_T (min) m/z Method | Prep Mtd | $^1$H NMR δ (ppm) |
|---|---|---|---|---|
| 100a | 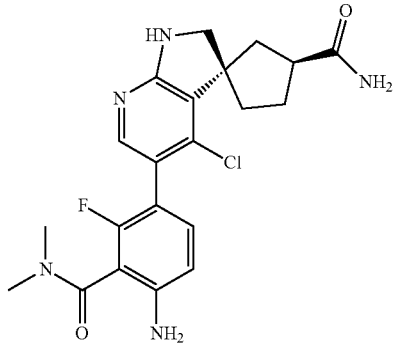<br>(1R,3S)-5'-(4-Amino-3-(dimethylcarbamoyl)-2-fluorophenyl)-4'-chloro-1',2'-dihydrospiro[cyclopentane-1,3'-pyrrolo[2,3-b]pyridine]-3-carboxamide<br>first peak on SFC; absolute configuration arbitrarily assigned | 2.11 432.2 A | L | (400 MHz, DMSO-d$_6$) δ 7.61 (s, 1H), 7.34 (brs, 1H), 6.97 (t, J = 8.5 Hz, 1H), 6.83 (s, 1H), 6.79 (brs, 1H), 6.55 (d, J = 8.2 Hz, 1H), 5.39 (brs, 2H), 3.46-3.34 (m, 2H), 2.99 (s, 3H), 2.95-2.89 (m, 1H), 2.89 (s, 3H), 2.08-1.92 (m, 2H), 1.87-1.81 (m, 2H), 1.77-1.67 (m, 1H). |
| 100b | 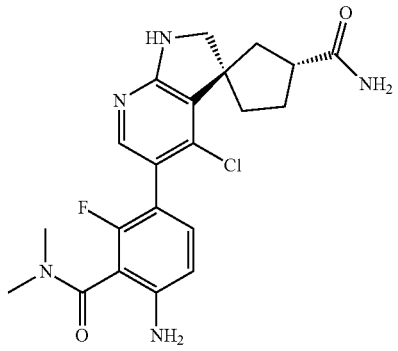<br>(1S,3R)-5'-(4-Amino-3-(dimethylcarbamoyl)-2-fluorophenyl)-4'-chloro-1',2'-dihydrospiro[cyclopentane-1,3'-pyrrolo[2,3-b]pyridine]-3-carboxamide<br>second peak on SFC; absolute configuration arbitrarily assigned | 2.12 432.2 A | L | (400 MHz, DMSO-d$_6$) δ 7.61 (s, 1H), 7.34 (brs, 1H), 6.97 (t, J = 8.5 Hz, 1H), 6.83 (s, 1H), 6.79 (brs, 1H), 6.55 (d, J = 8.2 Hz, 1H), 5.39 (brs, 2H), 3.46-3.34 (m, 2H), 2.99 (s, 3H), 2.95-2.89 (m, 1H), 2.89 (s, 3H), 2.08-1.92 (m, 2H), 1.87-1.81 (m, 2H), 1.77-1.67 (m, 1H). |
| 101 | 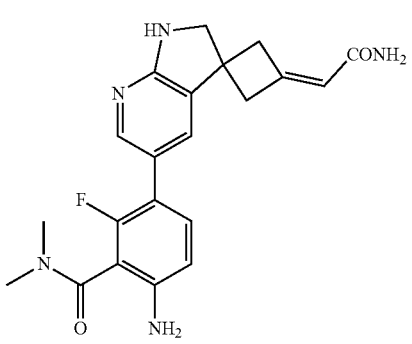<br>(±)-6-Amino-3-(3-(2-amino-2-oxoethylidene)-1',2'-dihydrospiro[cyclobutane-1,3'-pyrrolo[2,3-b]pyridin]-5'-yl)-2-fluoro-N,N-dimethylbenzamide<br>Mixture of enantiomers | 1.85 396.2 A | L | (400 MHz, DMSO-d$_6$) δ 7.81 (s, 1H), 7.47 (d, J = 5.5 Hz, 1H), 7.18 (m, 2H), 6.77 (s, 1H), 6.57 (d, J = 8.5 Hz, 1H), 6.50 (s, 1H), 5.74 (m, 1H), 5.30 (s, 2H), 3.59 (s, 2H), 3.35-3.21 (m, 3H), 3.00 (s, 3H), 3.02-2.94 (m, 1H), 2.88 (s, 3H) |

| No. | Structure/Name | LCMS R_T (min) m/z Method | Prep Mtd | $^1$H NMR δ (ppm) |
|---|---|---|---|---|
| 102a | 6-Amino-3-((1r,3r)-3-(2-amino-2-oxoethyl)-1',2'-dihydrospiro[cyclobutane-1,3'-pyrrolo[2,3-b]pyridin]-5'-yl)-2-fluoro-N,N-dimethylbenzamide | 1.92<br>398.3<br>A | L | (400 MHz, DMSO-d$_6$) δ ppm 7.77 (t, J = 1.7 Hz, 1H), 7.45 (s, 1H), 7.22 (s, 1H), 7.18 (t, J = 8.9 Hz, 1H), 6.74-6.68 (m, 1H), 6.58 (d, J = 8.4 Hz, 1H), 6.45 (s, 1H), 5.31 (s, 2H), 3.62-3.62 (m, 2H), 3.17 (d, J = 5.3 Hz, 1H), 3.00 (s, 3H), 2.89 (s, 3H), 2.68-2.54 (m, 1H), 2.26-2.17 (m, 3H), 2.05-1.97 (m, 2H). |
| 103 | 6-Amino-3-(4'-chloro-3-((methylsulfonyl)methylene)-1',2'-dihydrospiro[cyclopentane-1,3'-pyrrolo[2,3-b]pyridin]-5'-yl)-2-fluoro-N,N-dimethylbenzamide<br>60:40 Mix of isomers | 2.39<br>&<br>2.45<br>479.2<br>A | L | |
| 104 | 6-Amino-3-(4'-chloro-3-(cyanomethylene)-1',2'-dihydrospiro[cyclopentane-1,3'-pyrrolo[2,3-b]pyridin]-5'-yl)-2-fluoro-N,N-dimethylbenzamide<br>50:50 Mix of isomers | 2.85<br>&<br>2.88<br>426.2<br>A | L | (400 MHz, DMSO-d$_6$) δ 7.65 (d, J = 4.2 Hz, 1H), 7.01-6.94 (m, 2H), 6.55 (dd, J = 1.7, 8.3 Hz, 1H), 5.69-5.64 (m, 1H), 5.42-5.38 (m, 2H), 3.49-3.42 (m, 3H), 2.99-2.99 (m, 3H), 2.90-2.87 (m, 3H), 2.80-2.67 (m, 3H), 2.44-2.28 (m, 1H), 2.03-1.96 (m, 1H). |

TABLE A1-continued

| No. | Structure/Name | LCMS R_T (min) m/z Method | Prep Mtd | $^1$H NMR δ (ppm) |
|---|---|---|---|---|
| 105a | 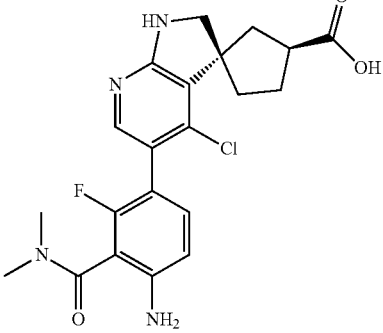<br>(1RS,3SR)-5'-(4-Amino-3-(dimethylcarbamoyl)-2-fluorophenyl)-4'-chloro-1',2'-dihydrospiro[cyclopentane-1,3'-pyrrolo[2,3-b]pyridine]-3-carboxylic acid | 2.40<br>433.1<br>A | L | (400 MHz, DMSO-d$_6$) δ 7.61 (s, 1H), 6.97 (t, J = 8.5 Hz, 1H), 6.85 (brs, 1H), 6.55 (d, J = 8.3 Hz, 1H), 5.39 (brs, 2H), 3.40 (d, J = 9.4 Hz, 1H), 3.36 (d, J = 9.4 Hz, 1H), 3.02-2.96 & 2.99 (m, 1H & s, 3H), 2.88 (s, 3H), 2.60-2.52 (m, 1H), 2.09-2.00 (m, 2H), 1.95-1.89 (m, 1H), 1.86-1.75 (m, 2H). |
| 106a | 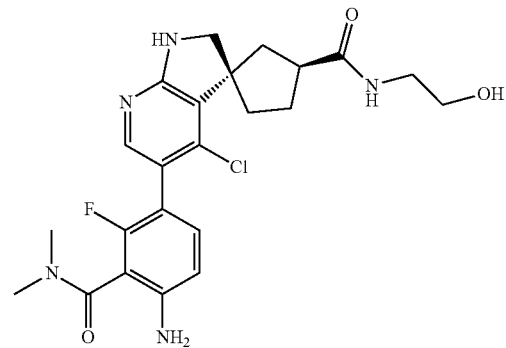<br>(1RS,3SR)-5'-(4-Amino-3-(dimethylcarbamoyl)-2-fluorophenyl)-4'-chloro-N-(2-hydroxyethyl)-1',2'-dihydrospiro[cyclopentane-1,3'-pyrrolo[2,3-b]pyridine]-3-carboxamide | 2.11<br>476.2<br>A | L | (400 MHz, DMSO-d$_6$) δ 7.88 (t, J = 5.6 Hz, 1H), 7.61 (s, 1H), 6.97 (t, J = 8.5 Hz, 1H), 6.83 (brs, 1H), 6.55 (d, J = 8.3 Hz, 1H), 5.39 (brs, 2H), 4.64 (t, J = 5.4 Hz, 1H), 3.49-3.35 (m, 4H), 3.16-3.07 (m, 2H), 2.99 (s, 3H), 2.98-2.91 (m, 1H), 2.89 (s, 3H), 2.06-1.89 (m, 2H), 1.87-1.68 (m, 3H). |
| 107a | 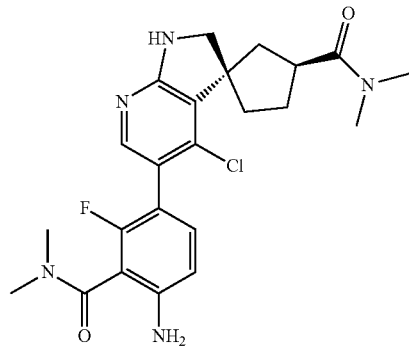<br>(1RS,3SR)-5'-(4-Amino-3-(dimethylcarbamoyl)-2-fluorophenyl)-4'-chloro-N,N-dimethyl-1',2'-dihydrospiro[cyclopentane-1,3'-pyrrolo[2,3-b]pyridine]-3-carboxamide | 2.54<br>460.2<br>A | L | (400 MHz, DMSO-d$_6$) δ 7.61 (s, 1H), 6.97 (t, J = 8.5 Hz, 1H), 6.84 (brs, 1H), 6.55 (d, J = 8.5 Hz, 1H), 5.39 (brs, 2H), 3.45 (d, J = 9.5 Hz, 1H), 3.33 (d, J = 9.5 Hz, 1H), 3.01 (s, 3H), 2.99 (s, 3H), 2.88 (s, 3H), 2.83 (s, 3H), 2.58-2.51 (m, 1H), 2.15-2.05 (m, 1H), 2.00-1.94 (m, 1H), 1.88-1.72 (m, 3H). |

TABLE A1-continued

| No. | Structure/Name | LCMS R_T (min) m/z Method | Prep Mtd | $^1$H NMR δ (ppm) |
|---|---|---|---|---|
| 108a | 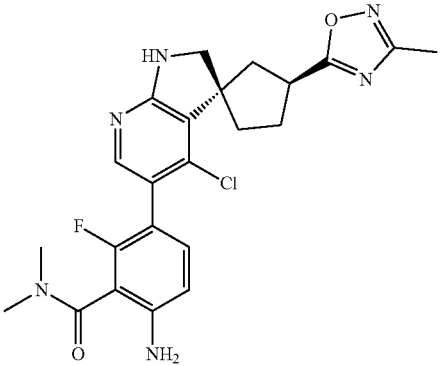<br>6-Amino-3-((1RS,3SR)-4'-chloro-3-(3-methyl-1,2,4-oxadiazol-5-yl)-1',2'-dihydrospiro[cyclopentane-1,3'-pyrrolo[2,3-b]pyridin]-5'-yl)-2-fluoro-N,N-dimethylbenzamide | 2.87<br>471.1<br>A | L | (400 MHz, DMSO-d$_6$) δ 7.64 (s, 1H), 6.98 (t, J = 8.5 Hz, 1H), 6.90 (brs, 1H), 6.56 (d, J = 8.4 Hz, 1H), 5.40 (brs, 2H), 3.78-3.69 (m, 1H), 3.45 (d, J = 9.3 Hz, 1H), 3.39 (d, J = 9.5 Hz, 1H), 2.99 (s, 3H), 2.92-2.84 & 2.89 (m, 1H & s, 3H), 2.34-2.28 & 2.32 (m, 1H & s, 3H), 2.17-2.07 (m, 1H), 2.06-1.93 (m, 3H). |
| 109a | 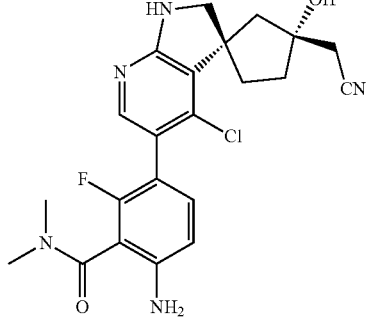<br>6-Amino-3-((1RS,3RS)-4'-chloro-3-(cyanomethyl)-3-hydroxy-1',2'-dihydrospiro[cyclopentane-1,3'-pyrrolo[2,3-b]pyridin]-5'-yl)-2-fluoro-N,N-dimethylbenzamide | 2.16<br>444.0<br>A | L | (400 MHz, DMSO-d$_6$) δ 7.61 (s, 1H), 6.97 (t, J = 8.5 Hz, 1H), 6.87 (s, 1H), 6.57-6.54 (m, 1H), 5.39 (s, 2H), 5.21-5.21 (m, 1H), 3.44-3.37 (m, 2H), 3.00-2.99 (m, 3H), 2.90-2.88 (m, 3H), 2.78 (s, 2H), 2.52-2.49 (m, 2H, obscured by DMSO), 2.50 (d, J = 15.6 Hz, 2H), 1.98-1.86 (m, 2H), 1.82-1.70 (m, 2H). |
| 109c | 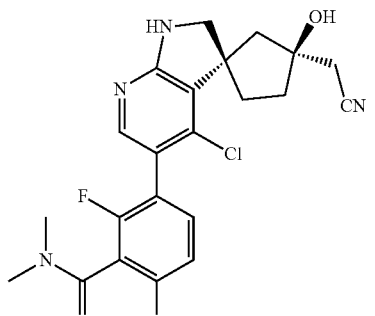<br>6-Amino-3-((1RS,3SR)-4'-chloro-3-(cyanomethyl)-3-hydroxy-1',2'-dihydrospiro[cyclopentane-1,3'-pyrrolo[2,3-b]pyridin]-5'-yl)-2-fluoro-N,N-dimethylbenzamide | 2.32<br>444.1<br>A | L | (400 MHz, DMSO-d$_6$) δ 7.61 (s, 1H), 6.96 (t, J = 8.5 Hz, 1H), 6.82 (s, 1H), 6.55 (d, J = 8.4 Hz, 1H), 5.39 (s, 2H), 5.19-5.15 (m, 1H), 3.70 (d, J = 9.6 Hz, 1H), 3.44 (d, J = 9.6 Hz, 1H), 2.99-2.98 (m, 3H), 2.88 (s, 3H), 2.80-2.77 (m, 2H), 2.43-2.33 (m, 1H), 2.17 (dd, J = 13.3, 22.0 Hz, 1H), 2.04-1.83 (m, 4H). |

TABLE A1-continued

| No. | Structure/Name | LCMS $R_T$ (min) m/z Method | Prep Mtd | $^1$H NMR δ (ppm) |
|---|---|---|---|---|
| 110 | 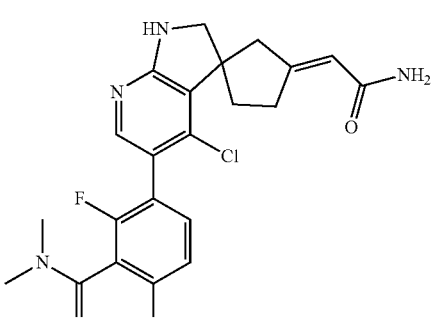<br>6-Amino-3-(3-(2-amino-2-oxoethylidene)-4'-chloro-1',2'-dihydrospiro[cyclopentane-1,3'-pyrrolo[2,3-b]pyridin]-5'-yl)-2-fluoro-N,N-dimethylbenzamide | 2.15 444.1 A | See text | (400 MHz, DMSO-$d_6$) δ 7.64-7.59 (m, 1H), 7.29-7.18 (m, 1H), 7.00-6.91 (m, 1H), 6.85-6.77 (m, 2H), 6.55 (dd, J = 8.6, 3.3 Hz, 1H), 5.48-5.34 (m, 3H), 3.32 (s, 6H), 2.99 (s, 2H), 2.92-2.85 (m, 4H), 2.54 (s, 2H) |
| 111a | 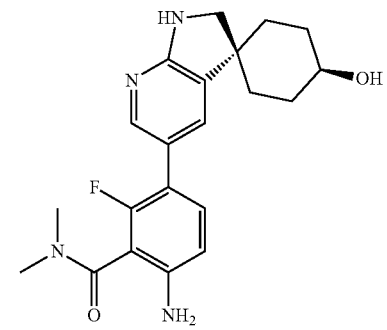<br>6-Amino-2-fluoro-3-((1s,4s)-4-hydroxy-1',2'-dihydrospiro[cyclohexane-1,3'-pyrrolo[2,3-b]pyridin]-5'-yl)-N,N-dimethylbenzamide | 2.02 385.1 A | L | (400 MHz, DMSO-$d_6$) δ 7.76 (t, J = 1.8 Hz, 1H), 7.27 (t, J = 1.8 Hz, 1H), 7.13 (t, J = 8.8 Hz, 1H), 6.56 (d, J = 8.4 Hz, 1H), 6.44 (s, 1H), 5.28 (s, 2H), 4.58 (d, J = 4.4 Hz, 1H), 3.53-3.45 (m, 1H), 3.35 (s, 2H), 3.00 (s, 3H), 2.87 (s, 3H), 1.79-1.74 (m, 2H), 1.68-1.58 (m, 4H), 1.32-1.22 (m, 2H). |
| 111b | 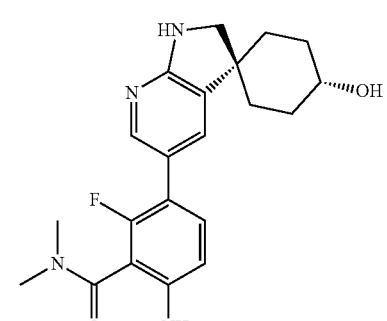<br>6-Amino-2-fluoro-3-((1r,4r)-4-hydroxy-1',2'-dihydrospiro[cyclohexane-1,3'-pyrrolo[2,3-b]pyridin]-5'-yl)-N,N-dimethylbenzamide | 2.02 385.1 A | L | (400 MHz, DMSO-$d_6$) δ 7.78 (t, J = 1.7 Hz, 1H), 7.34 (brs, 1H), 7.15 (t, J = 8.8 Hz, 1H), 6.58 (d, J = 8.4 Hz, 1H), 6.42 (s, 1H), 5.29 (brs, 2H), 4.47 (d, J = 4.3 Hz, 1H), 3.77-3.72 (m, 1H), 3.31 (obscured by water peak, 2H), 3.00 (s, 3H), 2.88 (s, 3H), 1.95-1.88 (m, 2H), 1.65-1.57 (m, 4H), 1.45-1.39 (m, 2H). |

TABLE A1-continued

| No. | Structure/Name | LCMS R$_T$ (min) m/z Method | Prep Mtd | $^1$H NMR δ (ppm) |
|---|---|---|---|---|
| 112 | 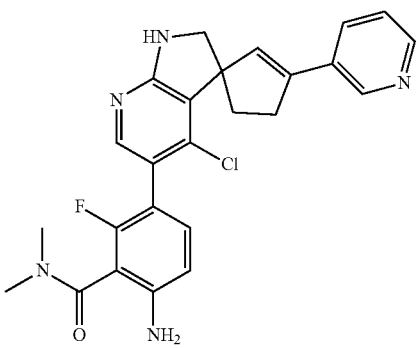<br>6-Amino-3-(4'-chloro-3-(pyridin-3-yl)-1',2'-dihydrospiro[cyclopentane-1,3'-pyrrolo[2,3-b]pyridin]-2-en-5'-yl)-2-fluoro-N,N-dimethylbenzamide | 2.27<br>464.0<br>A | T | (400 MHz, DMSO-d$_6$) δ 8.74 (dd, J = 1.9, 4.9 Hz, 1H), 8.46 (m, 1H), 7.93-7.88 (m, 1H), 7.66 (s, 1H), 7.40-7.34 (m, 1H), 6.7 (t, J = 8.5 Hz, 1H), 6.92 (s, 1H), 6.54 (d, J = 8.4 Hz, 1H), 6.43 (d, J = 13.6 Hz, 1H), 5.37 (s, 2H), 3.52-3.49 (m, 2H), 2.97 (d, J = 2.6 Hz, 3H), 2.92 (t, J = 7.2 Hz, 2H), 2.85 (d, J = 2.8 Hz, 3H), 2.43-2.34 (m, 1H), 2.28-2.21 (m, 1H) |
| 113a | 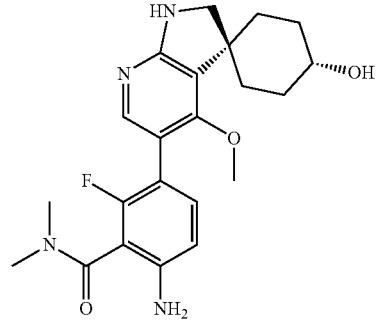<br>6-Amino-2-fluoro-3-((1r,4r)-4-hydroxy-4'-methoxy-1',2'-dihydrospiro[cyclohexane-1,3'-pyrrolo[2,3-b]pyridin]-5'-yl)-N,N-dimethylbenzamide | 2.06<br>415.0<br>A | L | (400 MHz, DMSO-d$_6$) δ 7.51 (s, 1H), 7.03 (t, J = 8.5 Hz, 1H), 6.57 (d, J = 8.3 Hz, 1H), 6.50 (brs, 1H), 5.34 (brs, 2H), 4.29 (d, J = 2.3 Hz, 1H), 3.85 (brs, 1H), 3.34 (s, 2H), 3.31 (obscured by water peak, 3H), 2.99 (s, 3H), 2.88 (s, 3H), 2.38-2.32 (m, 2H), 1.61-1.48 (m, 4H), 1.38-1.33 (m, 2H). |
| 113b | 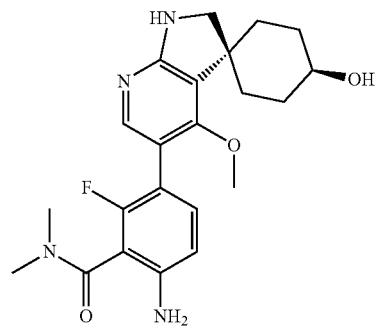<br>6-Amino-2-fluoro-3-((1s,4s)-4-hydroxy-4'-methoxy-1',2'-dihydrospiro[cyclohexane-1,3'-pyrrolo[2,3-b]pyridin]-5'-yl)-N,N-dimethylbenzamide | 2.08<br>415.0<br>A | L | (400 MHz, DMSO-d$_6$) δ 7.52 (s, 1H), 7.02 (t, J = 8.5 Hz, 1H), 6.81 (brs, 1H), 6.57 (d, J = 8.4 Hz, 1H), 5.38 (brs, 2H), 4.60 (brs, 1H), 3.37 (s, 2H), 3.32 (obscured by water peak, 3H), 2.99 (s, 3H), 2.88 (s, 3H), 1.98-1.88 (m, 2H), 1.78-1.72 (m, 2H), 1.67-1.63 (m, 2H), 1.29-1.19 (m, 2H). |

| No. | Structure/Name | LCMS R_T (min) m/z Method | Prep Mtd | $^1$H NMR δ (ppm) |
|---|---|---|---|---|
| 114a | 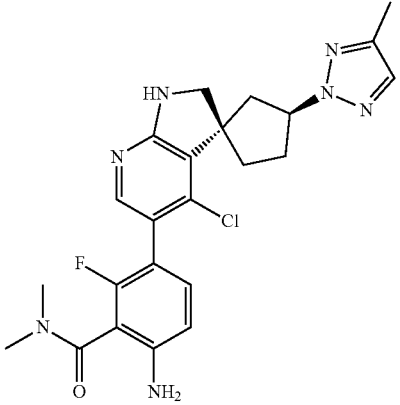<br>6-Amino-3-((1RS,3SR)-4'-chloro-3-(4-methyl-2H-1,2,3-triazol-2-yl)-1',2'-dihydrospiro[cyclopentane-1,3'-pyrrolo[2,3-b]pyridin]-5'-yl)-2-fluoro-N,N-dimethylbenzamide | 3.04<br>470.1<br>A | L | (400 MHz, DMSO-$d_6$) δ 7.64 (s, 1H), 7.55 (s, 1H), 6.99 (t, J = 8.5 Hz, 1H), 6.90 (s, 1H), 6.56 (d, J = 8.3 Hz, 1H), 5.42 (brs, 2H), 5.22-5.15 (m, 1H), 3.46 (d, J = 9.4 Hz, 1H), 3.40 (d, J = 9.5 Hz, 1H), 2.99 (s, 3H), 2.92-2.84 & 2.89 (m, 1H & s, 3H), 2.39-2.26 (m, 2H), 2.24 (s, 3H), 2.21-2.14 (m, 2H), 2.04-1.97 (m, 1H). |
| 115a | 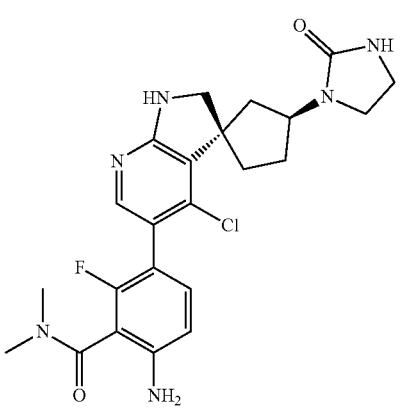<br>6-Amino-3-((1RS,3SR)-4'-chloro-3-(2-oxoimidazolidin-1-yl)-1',2'-dihydrospiro[cyclopentane-1,3'-pyrrolo[2,3-b]pyridin]-5'-yl)-2-fluoro-N,N-dimethylbenzamide | 2.25<br>473.0<br>A | L | (400 MHz, DMSO-$d_6$) δ 7.62 (s, 1H), 6.98 (t, J = 8.4 Hz, 1H), 6.87 (s, 1H), 6.56 (d, J = 8.4 Hz, 1H), 6.28 (brs, 1H), 5.39 (brs, 2H), 4.39 (quintet, J = 8.6 Hz, 1H), 3.47 (d, J = 9.4 Hz, 1H), 3.42 (d, J = 9.4 Hz, 1H), 3.36-3.29 (obscured by water peak, 2H), 3.25-3.21 (m, 2H), 2.99 (s, 3H), 2.89 (d, J = 4.6 Hz, 3H), 2.62-2.54 (m, 1H), 1.88-1.72 (m, 4H), 1.65-1.60 (m, 1H). |

TABLE A1-continued

| No. | Structure/Name | LCMS R$_T$ (min) m/z Method | Prep Mtd | $^1$H NMR δ (ppm) |
|---|---|---|---|---|
| 116a | 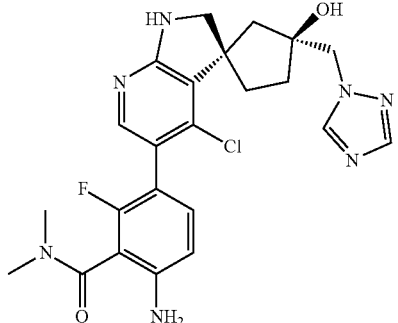<br>3-((1RS,3SR)-3-((1H-1,2,4-Triazol-1-yl)methyl)-4'-chloro-3-hydroxy-1',2'-dihydrospiro[cyclopentane-1,3'-pyrrolo[2,3-b]pyridin]-5'-yl)-6-amino-2-fluoro-N,N-dimethylbenzamide | 2.14<br>486.0<br>A | L | (400 MHz, DMSO-d$_6$) δ 8.42 (d, J = 1.6 Hz, 1H), 7.91 (s, 1H), 7.59-7.58 (m, 1H), 6.96 (t, J = 8.5 Hz, 1H), 6.78 (s, 1H), 6.55 (d, J = 8.4 Hz, 1H), 5.39 (s, 2H), 4.27 (d, J = 3.6 Hz, 2H), 3.69-3.64 (m, 1H), 3.41 (d, J = 9.2 Hz, 1H), 3.40 (d, J = 9.6 Hz, 1H), 3.00-2.99 (m, 3H), 2.90-2.88 (m, 3H), 2.37-2.27 (m, 1H), 2.23-2.03 (m, 2H), 1.94-1.84 (m, 1H), 1.79-1.67 (m, 2H). |
| 116c | 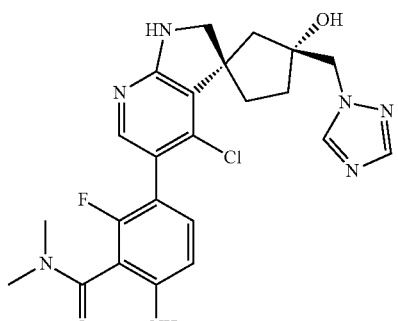<br>3-((1RS,3RS)-3-((1H-1,2,4-Triazol-1-yl)methyl)-4'-chloro-3-hydroxy-1',2'-dihydrospiro[cyclopentane-1,3'-pyrrolo[2,3-b]pyridin]-5'-yl)-6-amino-2-fluoro-N,N-dimethylbenzamide | 2.04<br>486.0<br>A | L | (400 MHz, DMSO-d$_6$) δ 8.43 (s, 1H), 7.96 (s, 1H), 7.60 (s, 1H), 6.96 (t, J = 8.5 Hz, 1H), 6.85 (s, 1H), 6.55 (d, J = 8.4 Hz, 1H), 5.38 (s, 2H), 4.97 (s, 1H), 4.26 (s, 2H), 3.37-3.33 (m, 2H), 2.99-2.97 (m, 3H), 2.88 (s, 3H), 2.34-2.24 (m, 1H), 2.09-2.08 (m, 2H), 1.88-1.68 (m, 3H). |
| 117a | 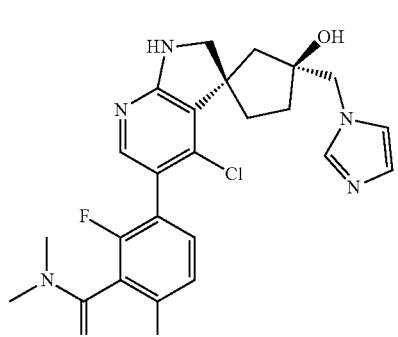<br>3-((1RS,3SR)-3-((1H-Imidazol-1-yl)methyl)-4'-chloro-3-hydroxy-1',2'-dihydrospiro[cyclopentane-1,3'-pyrrolo[2,3-b]pyridin]-5'-yl)-6-amino-2-fluoro-N,N-dimethylbenzamide | 1.74<br>485.0<br>A | L | (400 MHz, DMSO-d$_6$) δ 7.59 (s, 1H), 7.57 (d, J = 3.3 Hz, 1H), 7.14 (d, J = 3.9 Hz, 1H), 6.96 (t, J = 8.5 Hz, 1H), 6.82 (s, 1H), 6.77 (s, 1H), 6.57-6.53 (m, 1H), 5.39 (s, 2H), 4.87-4.81 (m, 1H), 4.06-4.02 (m, 2H), 3.68 (d, J = 9.5 Hz, 1H), 3.40 (d, J = 9.5 Hz, 1H), 3.00-2.99 (m, 3H), 2.90-2.88 (m, 3H), 2.40-2.30 (m, 1H), 2.09-1.85 (m, 3H), 1.77-1.63 (m, 2H). |

TABLE A1-continued

| No. | Structure/Name | LCMS R_T (min) m/z Method | Prep Mtd | $^1$H NMR δ (ppm) |
|---|---|---|---|---|
| 118a | 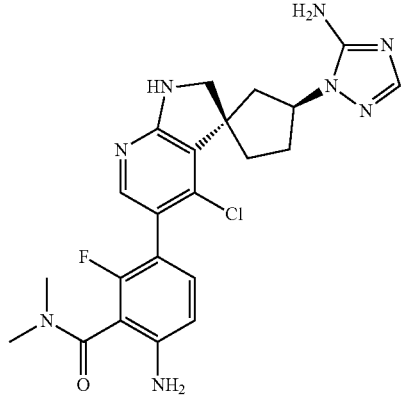<br>6-Amino-3-((1RS,3SR)-3-(5-amino-1H-1,2,4-triazol-1-yl)-4'-chloro-1',2'-dihydrospiro[cyclopentane-1,3'-pyrrolo[2,3-b]pyridin]-5'-yl)-2-fluoro-N,N-dimethylbenzamide | 2.01<br>471.0<br>A | L | (400 MHz, DMSO-d$_6$) δ 7.63 (s, 1H), 7.37 (s, 1H), 6.99 (t, J = 8.5 Hz, 1H), 6.88 (s, 1H), 6.56 (d, J = 8.5 Hz, 1H), 6.18 (brs, 2H), 5.40 (brs, 2H), 4.88-4.81 (m, 1H), 3.60 (d, J = 9.5 Hz, 1H), 3.50 (d, J = 9.5 Hz, 1H), 2.99 (s, 3H), 2.89 (s, 3H), 2.81-2.72 (m, 1H), 2.20-1.92 (m, 5H). |
| 119a | 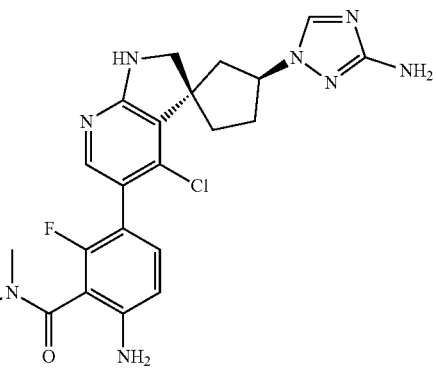<br>6-Amino-3-((1RS,3SR)-3-(3-amino-1H-1,2,4-triazol-1-yl)-4'-chloro-1',2'-dihydrospiro[cyclopentane-1,3'-pyrrolo[2,3-b]pyridin]-5'-yl)-2-fluoro-N,N-dimethylbenzamide | 2.12<br>471.0<br>A | L | (400 MHz, DMSO-d$_6$) δ 8.04 (s, 1H), 7.64 (s, 1H), 6.98 (t, J = 8.5 Hz, 1H), 6.89 (s, 1H), 6.56 (d, J = 8.4 Hz, 1H), 5.40 (brs, 2H), 5.28 (brs, 2H), 4.84 (quintet, J = 7.7 Hz, 1H), 3.50 & 3.45 (ABq, J = 9.5 Hz, 2H), 2.99 (s, 3H), 2.89 (s, 3H), 2.83-2.74 (m, 1H), 2.20-1.93 (m, 5H). |

TABLE A1-continued

| No. | Structure/Name | LCMS R_T (min) m/z Method | Prep Mtd | $^1$H NMR δ (ppm) |
|---|---|---|---|---|
| 120a | 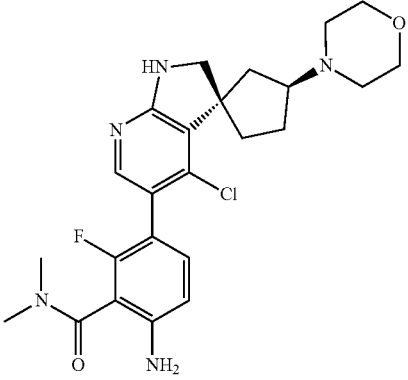<br>6-Amino-3-((1RS,3SR)-4'-chloro-3-morpholino-1',2'-dihydrospiro[cyclopentane-1,3'-pyrrolo[2,3-b]pyridin]-5'-yl)-2-fluoro-N,N-dimethylbenzamide | 1.75<br>474.0<br>A | L | (400 MHz, DMSO-d$_6$) δ 7.61 (s, 1H), 6.97 (t, J = 8.5 Hz, 1H), 6.83 (s, 1H), 6.55 (d, J = 8.3 Hz, 1H), 5.39 (brs, 2H), 3.57 (brs, 4H), 3.43 (d, J = 9.3 Hz, 1H), 3.37 (d, J = 9.4 Hz, 1H), 2.99 (s, 3H), 2.88 (d, J = 4.8 Hz, 3H), 2.81-2.75 (m, 1H), 2.65-2.57 (m, 1H), 2.39 (brs, 4H), 1.98-1.79 (m, 3H), 1.57-1.44 (m, 2H). |
| 121a | 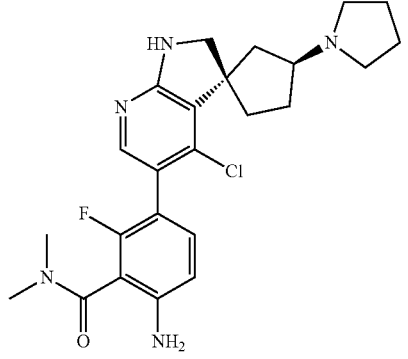<br>6-Amino-3-((1RS,3SR)-4'-chloro-3-(pyrrolidin-1-yl)-1',2'-dihydrospiro[cyclopentane-1,3'-pyrrolo[2,3-b]pyridin]-5'-yl)-2-fluoro-N,N-dimethylbenzamide | 1.85<br>458.0<br>A | L | (400 MHz, DMSO-d$_6$, 80° C.) δ 7.60 (s, 1H), 6.95 (t, J = 8.5 Hz, 1H), 6.57 (d, J = 8.4 Hz, 1H), 6.56 (brs, 1H), 5.16 (brs, 2H), 3.48 & 3.44 (ABq, J = 9.5 Hz, 2H), 2.99 (s, 3H), 2.88 (s, 3H), 2.59 (brs, 6H), 2.08-1.99 (m, 2H), 1.87-1.65 (m, 7H). |
| 122a | 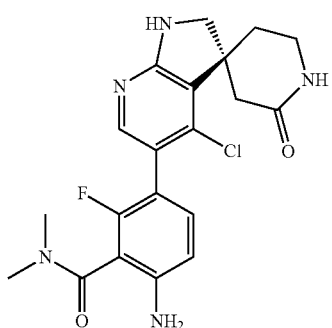<br>(R)-6-Amino-3-(4'-chloro-2-oxo-1',2'-dihydrospiro[piperidine-4,3'-pyrrolo[2,3-b]pyridin]-5'-yl)-2-fluoro-N,N-dimethylbenzamide; absolute configuration arbitrarily assigned | 1.96<br>418.0<br>A | L | (400 MHz, DMSO-d$_6$) δ 7.68-7.65 (m, 2H), 6.98 (t, J = 8.5 Hz, 2H), 6.57-6.54 (m, 1H), 5.40 (s, 2H), 3.52 (d, J = 9.3 Hz, 1H), 3.30-3.21 (m, 4H), 2.99 (s, 3H), 2.88 (d, J = 2.4 Hz, 3H), 2.70 (dd, J = 13.9, 17.0 Hz, 1H), 2.32-2.24 (m, 1H), 1.86-1.80 (m, 1H). |

TABLE A1-continued

| No. | Structure/Name | LCMS R$_T$ (min) m/z Method | Prep Mtd | $^1$H NMR δ (ppm) |
|---|---|---|---|---|
| 122b | 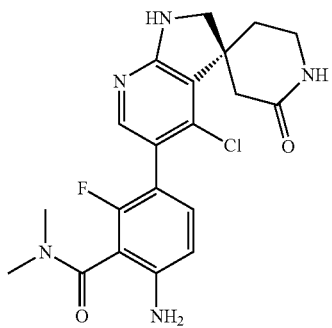<br>(S)-6-Amino-3-(4'-chloro-2-oxo-1',2'-dihydrospiro[piperidine-4,3'-pyrrolo[2,3-b]pyridin]-5'-yl)-2-fluoro-N,N-dimethylbenzamide; absolute configuration arbitrarily assigned | 1.95<br>418.0<br>A | L | (400 MHz, DMSO-d$_6$) δ 7.68-7.63 (s + br s, 2H), 7.01-6.95 (m, 2H), 6.55 (d, J = 8.4 Hz, 1H), 5.40 (s, 2H), 3.52 (d, J = 9.5 Hz, 1H), 3.30-3.19 (m, 4H), 2.99 (s, 3H), 2.88 (d, J = 2.3 Hz, 3H), 2.70 (dd, J = 13.9, 16.9 Hz, 1H), 2.34-2.23 (m, 1H), 1.91-1.80 (m, 1H). |
| 123a | 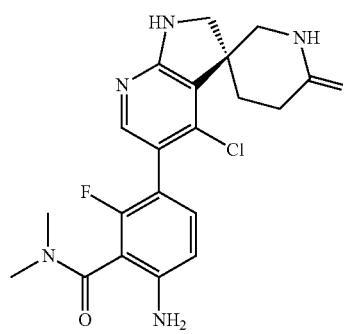<br>(S)-6-Amino-3-(4'-chloro-6-oxo-1',2'-dihydrospiro[piperidine-3,3'-pyrrolo[2,3-b]pyridin]-5'-yl)-2-fluoro-N,N-dimethylbenzamide; absolute configuration arbitrarily assigned | 1.97<br>418.0<br>A | L | (400 MHz, DMSO-d$_6$) δ 7.66 (s, 1H), 7.52 (d, J = 3.5 Hz, 1H), 7.05 (s, 1H), 6.99-6.94 (m, 1H), 6.55 (d, J = 8.4 Hz, 1H), 5.40 (s, 2H), 3.64-3.57 (m, 1H), 3.54-3.44 (m, 2H), 3.11-3.06 (m, 1H), 2.99 (s, 3H), 2.88 (s, 3H), 2.76-2.65 (m, 1H), 2.34-2.26 (m, 2H), 1.91-1.83 (m, 1H). |
| 123b | 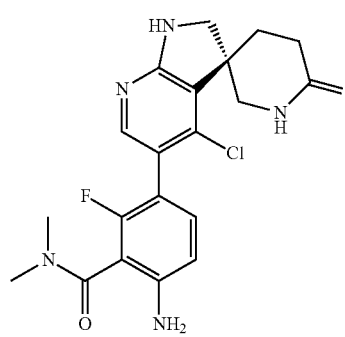<br>(R)-6-Amino-3-(4'-chloro-6-oxo-1',2'-dihydrospiro[piperidine-3,3'-pyrrolo[2,3-b]pyridin]-5'-yl)-2-fluoro-N,N-dimethylbenzamide; absolute configuration arbitrarily assigned | 1.98<br>418.0<br>A | L | (400 MHz, DMSO-d$_6$) δ 7.66 (s, 1H), 7.53 (d, J = 3.8 Hz, 1H), 7.04 (s, 1H), 6.97 (t, J = 8.5 Hz, 1H), 6.55 (d, J = 8.5 Hz, 1H), 5.40 (s, 2H), 3.61 (t, J = 11.9 Hz, 1H), 3.54-3.46 (m, 2H), 3.11-3.06 (m, 1H), 2.99 (s, 3H), 2.88 (s, 3H), 2.82-2.66 (m, 2H), 2.33-2.26 (m, 2H), 1.91-1.83 (m, 1H), 1.26-1.22 (m, 1H). |

TABLE A1-continued

| No. | Structure/Name | LCMS $R_T$ (min) m/z Method | Prep Mtd | $^1$H NMR δ (ppm) |
|---|---|---|---|---|
| 124a | 6-Amino-3-((1RS,3SR)-4'-chloro-3-(2-oxooxazolidin-3-yl)-1',2'-dihydrospiro[cyclopentane-1,3'-pyrrolo[2,3-b]pyridin]-5'-yl)-2-fluoro-N,N-dimethylbenzamide | 2.37 474.0 A | L | (400 MHz, DMSO-$d_6$) δ 7.63 (s, 1H), 6.98 (t, J = 8.5 Hz, 1H), 6.89 (s, 1H), 6.56 (d, J = 8.4 Hz, 1H), 5.39 (s, 2H), 4.40-4.30 (m, 1H), 4.27 (t, J = 8.2 Hz, 2H), 3.61-3.52 (m, 2H), 3.49 (d, J = 9.4 Hz, 1H), 3.43 (d, J = 9.4 Hz, 1H), 2.99 (s, 3H), 2.89 (d, J = 4.3 Hz, 3H), 2.70-2.62 (m, 1H), 1.91-1.76 (m, 4H), 1.73-1.68 (m, 1H). |
| 125a | 6-Amino-3-((1RS,3SR)-4'-chloro-3-(4-methyl-1H-pyrazol-1-yl)-1',2'-dihydrospiro[cyclopentane-1,3'-pyrrolo[2,3-b]pyridin]-5'-yl)-2-fluoro-N,N-dimethylbenzamide | 3.09 469.1 A | L | (400 MHz, DMSO-$d_6$) δ 7.63 (s, 1H), 7.58 (s, 1H), 7.26 (s, 1H), 6.98 (t, J = 8.5 Hz, 1H), 6.86 (s, 1H), 6.56 (d, J = 8.4 Hz, 1H), 5.40 (s, 2H), 4.90 (quintet, J = 7.7 Hz, 1H), 3.48 & 3.46 (ABq, J = 9.6 Hz, 2H), 2.99 (s, 3H), 2.89 (s, 3H), 2.87-2.79 (m, 1H), 2.24-1.93 & 2.00 (m, 5H, & s, 3H). |
| 126a | 6-Amino-3-((1RS,3SR)-4'-chloro-3-(1H-pyrazol-1-yl)-1',2'-dihydrospiro[cyclopentane-1,3'-pyrrolo[2,3-b]pyridin]-5'-yl)-2-fluoro-N,N-dimethylbenzamide | 2.84 455.0 A | L | (400 MHz, DMSO-$d_6$) δ 7.83 (d, J = 2.0 Hz, 1H), 7.64 (s, 1H), 7.47 (d, J = 1.7 Hz, 1H), 6.99 (t, J = 8.5 Hz, 1H), 6.87 (s, 1H), 6.56 (d, J = 8.3 Hz, 1H), 6.24 (t, J = 1.9 Hz, 1H), 5.40 (s, 2H), 5.00 (quintet, J = 7.8 Hz, 1H), 3.50 & 3.47 (ABq, J = 9.7 Hz, 2H), 3.00 (s, 3H), 2.90 (s, 3H), 2.89-2.82 (m, 1H), 2.28-2.06 (m, 4H), 2.02-1.96 (m, 1H). |

TABLE A1-continued

| No. | Structure/Name | LCMS R_T (min) m/z Method | Prep Mtd | $^1$H NMR δ (ppm) |
|---|---|---|---|---|
| 127a | 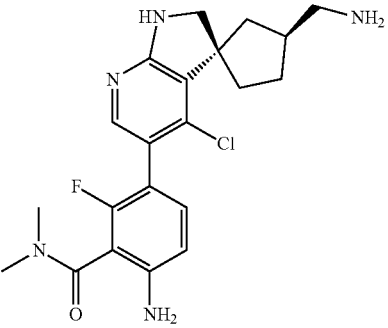<br>6-Amino-3-((1RS,3SR)-3-(aminomethyl)-4'-chloro-1',2'-dihydrospiro[cyclopentane-1,3'-pyrrolo[2,3-b]pyridin]-5'-yl)-2-fluoro-N,N-dimethylbenzamide | 1.69<br>418.0<br>A | L | (400 MHz, DMSO-d$_6$) δ 7.59 (s, 1H), 6.97 (t, J = 8.5 Hz, 1H), 6.81 (s, 1H), 6.55 (d, J = 8.4 Hz, 1H), 5.38 (s, 2H), 3.00-2.98 (m, 4H), 2.89 (d, J = 3.4 Hz, 3H), 2.53 (s, 4H), 2.34-2.31 (m, 1H), 2.20 (t, J = 16.3 Hz, 1H), 1.98-1.86 (m, 2H), 1.80-1.76 (m, 1H), 1.41-1.23 (m, 3H). |
| 128a | 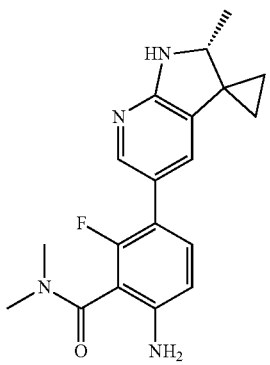<br>(R)-6-Amino-2-fluoro-N,N-dimethyl-3-(2'-methyl-1',2'-dihydrospiro[cyclopropane-1,3'-pyrrolo[2,3-b]pyridin]-5'-yl)benzamide<br>first peak on SFC; absolute configuration arbitrarily assigned | 2.43<br>341.1<br>B | L | (400 MHz, CDCl3) δ 7.86 (t, J = 1.6 Hz, 1H), 6.84 (t, J = 2.0 Hz, 1H), 6.55-6.53 (m, 1H), 4.76 (s, 1H), 4.25 (s, 1H), 4.12 (q, J = 7.1 Hz, 1H), 3.91 (q, J = 6.3 Hz, 1H), 3.14-3.14 (m, 3H), 3.00-2.99 (m, 3H), 1.28-1.14 (m, 5H), 1.07-1.00 (m, 1H), 0.88-0.78 (m, 2H). |
| 128b | 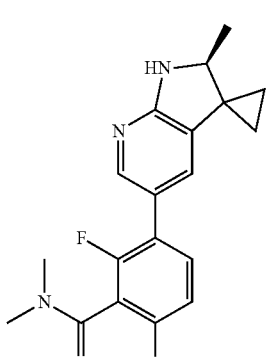<br>(S)-6-Amino-2-fluoro-N,N-dimethyl-3-(2'-methyl-1',2'-dihydrospiro[cyclopropane-1,3'-pyrrolo[2,3-b]pyridin]-5'-yl)benzamide<br>second peak on SFC; absolute configuration arbitrarily assigned | 2.43<br>341.1<br>B | L | (400 MHz, CDCl3) δ 7.86 (t, J = 1.6 Hz, 1H), 6.84 (t, J = 2.0 Hz, 1H), 6.55-6.53 (m, 1H), 4.76 (s, 1H), 4.25 (s, 1H), 4.12 (q, J = 7.1 Hz, 1H), 3.91 (q, J = 6.3 Hz, 1H), 3.14-3.14 (m, 3H), 3.00-2.99 (m, 3H), 1.28-1.14 (m, 5H), 1.07-1.00 (m, 1H), 0.88-0.78 (m, 2H). |

TABLE A1-continued

| No. | Structure/Name | LCMS R$_T$ (min) m/z Method | Prep Mtd | $^1$H NMR δ (ppm) |
|---|---|---|---|---|
| 129 | 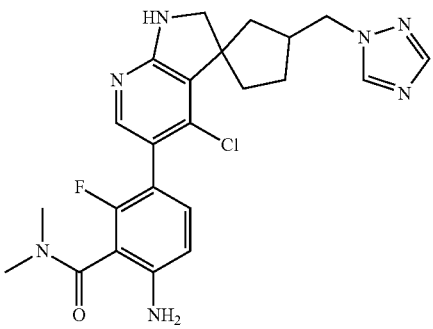<br>3-(3-((1H-1,2,4-Triazol-1-yl)methyl)-4'-chloro-1',2'-dihydrospiro[cyclopentane-1,3'-pyrrolo[2,3-b]pyridin]-5'-yl)-6-amino-2-fluoro-N,N-dimethylbenzamide | 2.41<br>470.1<br>A | L | (400 MHz, DMSO-d$_6$) δ 8.54 (s, 1H), 7.95 (d, J = 3.8 Hz, 1H), 7.60 (s, 1H), 6.96 (t, J = 8.3 Hz, 1H), 6.84 (s, 1H), 6.57-6.53 (m, 1H), 5.39 (s, 2H), 4.22 (d, J = 7.3 Hz, 2H), 3.42-3.30 (m, 2H), 3.00-2.98 (m, 3H), 2.90-2.86 (m, 3H), 2.73-2.67 (m, 1H), 1.98-1.36 (m, 6H). |
| 130 | 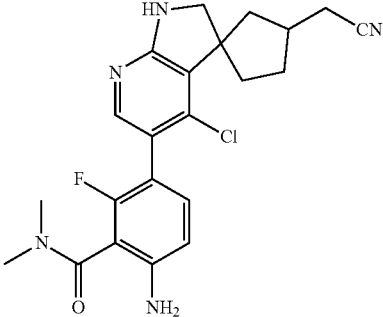<br>6-Amino-3-(4'-chloro-3-(cyanomethyl)-1',2'-dihydrospiro[cyclopentane-1,3'-pyrrolo[2,3-b]pyridin]-5'-yl)-2-fluoro-N,N-dimethylbenzamide | 2.73<br>428.0<br>A | L | (400 MHz, DMSO-d$_6$) δ 7.62 (s, 1H), 7.00-6.93 (m, 1H), 6.84 (d, J = 7.2 Hz, 1H), 6.55 (d, J = 8.4 Hz, 1H), 5.38 (s, 2H), 3.44-3.37 (m, 2H), 2.99 (s, 3H), 2.88 (d, J = 0.9 Hz, 3H), 2.66-2.62 (m, 3H), 2.34-2.27 (m, 1H), 1.98-1.87 (m, 4H), 1.45-1.37 (m, 2H). |
| 131a | 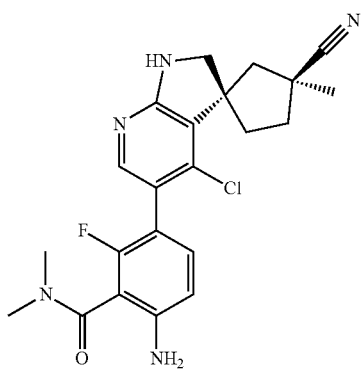<br>6-Amino-3-((1RS,3SR)-4'-chloro-3-cyano-3-methyl-1',2'-dihydrospiro[cyclopentane-1,3'-pyrrolo[2,3-b]pyridin]-5'-yl)-2-fluoro-N,N-dimethylbenzamide | 2.94<br>428.0<br>A | L | (400 MHz, DMSO-d$_6$, 80° C.): δ 7.64 (s, 1H), 6.95 (t, J = 8.5 Hz, 1H), 6.67 (s, 1H), 6.57 (d, J = 8.4 Hz, 1H), 5.17 (brs, 2H), 3.66 (d, J = 9.6 Hz, 1H), 3.52 (d, J = 9.7 Hz, 1H), 2.99 (s, 3H), 2.88 (s, 3H), 2.56-2.50 (m, 1H), 2.37 (d, J = 13.8 Hz, 1H), 2.28-2.17 (m, 2H), 2.05-1.91 (m, 2H), 1.48 (s, 3H). |

TABLE A1-continued

| No. | Structure/Name | LCMS R$_T$ (min) m/z Method | Prep Mtd | $^1$H NMR δ (ppm) |
|---|---|---|---|---|
| 132a | 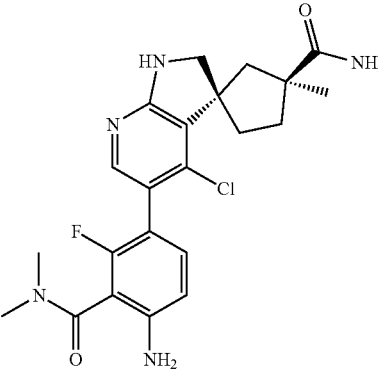<br>(1RS,3SR)-5′-(4-Amino-3-(dimethylcarbamoyl)-2-fluorophenyl)-4′-chloro-3-methyl-1′,2′-dihydrospiro[cyclopentane-1,3′-pyrrolo[2,3-b]pyridine]-3-carboxamide | 2.36<br>446.0<br>A | L | (400 MHz, DMSO-d$_6$) δ 7.59 (s, 1H), 7.22 (brs, 1H), 6.97 (t, J = 8.5 Hz, 1H), 6.87 (brs, 1H), 6.80 (s, 1H), 6.55 (d, J = 8.3 Hz, 1H), 5.38 (brs, 2H), 3.45 (d, J = 9.4 Hz, 1H), 3.24 (d, J = 9.4 Hz, 1H), 2.99 (s, 3H), 2.88 (s, 3H), 2.48-2.39 (m, 2H), 2.23-2.15 (m, 1H), 1.94-1.85 (m, 1H), 1.72-1.61 (m, 2H), 1.29 (d, J = 3.9 Hz, 3H). |
| 133a | 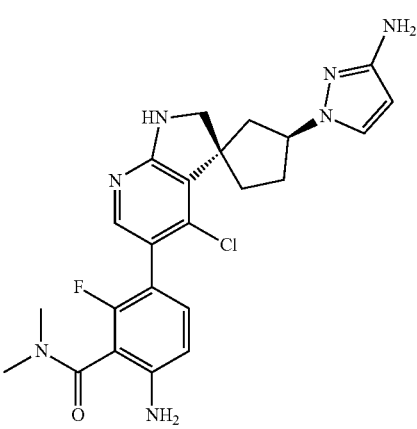<br>6-Amino-3-((1RS,3SR)-3-(3-amino-1H-pyrazol-1-yl)-4′-chloro-1′,2′-dihydrospiro[cyclopentane-1,3′-pyrrolo[2,3-b]pyridin]-5′-yl)-2-fluoro-N,N-dimethylbenzamide | 2.28<br>470.0<br>A | L | (400 MHz, DMSO-d$_6$) δ 7.63 (s, 1H), 7.40 (d, J = 1.8 Hz, 1H), 6.98 (t, J = 8.5 Hz, 1H), 6.86 (s, 1H), 6.56 (d, J = 8.4 Hz, 1H), 5.40 (brs, 2H), 5.36 (d, J = 2.1 Hz, 1H), 4.70 (quintet, J = 7.8 Hz, 1H), 4.58 (brs, 2H), 3.48 & 3.45 (ABq, J = 9.5 Hz, 2H), 2.99 (s, 3H), 2.89 (s, 3H), 2.77-2.69 (m, 1H), 2.16-2.00 (m, 4H), 1.96-1.90 (m, 1H). |

TABLE A1-continued

| No. | Structure/Name | LCMS R$_T$ (min) m/z Method | Prep Mtd | $^1$H NMR δ (ppm) |
|---|---|---|---|---|
| 134a | 6-Amino-3-((1RS,3SR)-3-(5-amino-1H-pyrazol-1-yl)-4'-chloro-1',2'-dihydrospiro[cyclopentane-1,3'-pyrrolo[2,3-b]pyridin]-5'-yl)-2-fluoro-N,N-dimethylbenzamide | 2.24 470.0 A | L | (400 MHz, DMSO-d$_6$) δ 7.62 (s, 1H), 7.08 (d, J = 1.7 Hz, 1H), 6.99 (t, J = 8.5 Hz, 1H), 6.86 (s, 1H), 6.56 (d, J = 8.4 Hz, 1H), 5.39 (brs, 2H), 5.26 (d, J = 1.7 Hz, 1H), 5.14 (brs, 2H), 4.88-4.80 (m, 1H), 3.60 (d, J = 9.4 Hz, 1H), 3.47 (d, J = 9.5 Hz, 1H), 3.00 (s, 3H), 2.89 (s, 3H), 2.77-2.67 (m, 1H), 2.19-2.02 (m, 4H), 1.97-1.91 (m, 1H). |
| 135a | 6-Amino-3-((1RS,3SR)-3-(2-amino-2-oxoethyl)-4'-chloro-1',2'-dihydrospiro[cyclopentane-1,3'-pyrrolo[2,3-b]pyridin]-5'-yl)-2-fluoro-N,N-dimethylbenzamide | 2.16 446.0 A | L | (400 MHz, DMSO-d$_6$) δ 7.60 (s, 1H), 7.26 (s, 1H), 6.97 (t, J = 8.5 Hz, 1H), 6.82 (s, 1H), 6.71 (s, 1H), 6.55 (d, J = 8.4 Hz, 1H), 5.38 (s, 2H), 3.42-3.28 (m, 2H), 2.99 (s, 3H), 2.90-2.87 (m, 3H), 2.60-2.54 (m, 2H), 2.15-2.10 (m, 2H), 1.91-1.77 (m, 3H), 1.35-1.22 (m, 2H). |
| 135c | 6-Amino-3-((1RS,3RS)-3-(2-amino-2-oxoethyl)-4'-chloro-1',2'-dihydrospiro[cyclopentane-1,3'-pyrrolo[2,3-b]pyridin]-5'-yl)-2-fluoro-N,N-dimethylbenzamide | 2.21 446.0 A | L | (400 MHz, DMSO-d$_6$) δ 7.59 (s, 1H), 7.24 (s, 1H), 6.96 (t, J = 8.4 Hz, 1H), 6.83 (s, 1H), 6.71 (s, 1H), 6.55 (d, J = 8.4 Hz, 1H), 5.38 (s, 2H), 3.36-3.35 (m, 2H), 2.99 (s, 3H), 2.88 (s, 3H), 2.46-2.37 (m, 1H), 2.34-2.26 (m, 1H), 2.16-2.11 (m, 2H), 1.90-1.84 (m, 2H), 1.76-1.60 (m, 2H), 1.50-1.39 (m, 1H). |

TABLE A1-continued

| No. | Structure/Name | LCMS R_T (min) m/z Method | Prep Mtd | $^1$H NMR δ (ppm) |
|---|---|---|---|---|
| 136 | 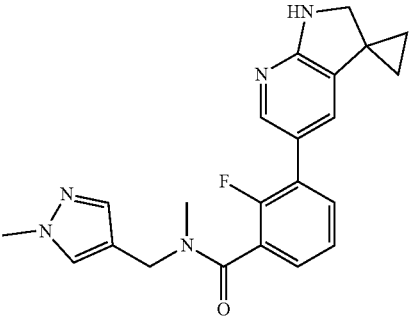<br>3-(1',2'-dihydrospiro[cyclopropane-1,3'-pyrrolo[2,3-b]pyridin]-5'-yl)-2-fluoro-N-methyl-N-((1-methyl-1H-pyrazol-4-yl)methyl)benzamide | 392.2 | L | (300 MHz, DMSO-d$_6$) δ 7.83 (t, J = 1.8 Hz, 1H), 7.68 & 7.57 (2 × s, 1H), 7.55-7.48 (m, 1H), 7.40 & 7.21 (2 × s, 1H), 7.34-7.23 (m, 2H), 7.02 (s, 1H), 6.84 (s, 1H), 4.49 & 4.21 (2 × s, 2H), 3.28 & 3.78 ((2 × s, 3H), 3.55 (s, 2H), 2.92 & 2.77 (s, 3H), 1.08-0.94 (m, 4H). |
| 137 | 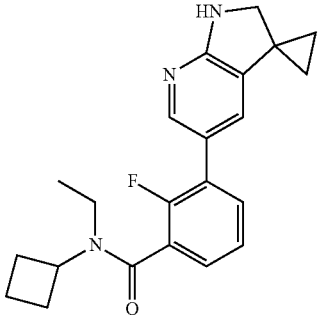<br>N-cyclobutyl-3-(1',2'-dihydrospiro[cyclopropane-1,3'-pyrrolo[2,3-b]pyridin]-5'-yl)-N-ethyl-2-fluorobenzamide | 366.2 | L | (300 MHz, DMSO-d$_6$) δ 7.84 (s, 1H), 7.53-7.78 (m, 1H), 7.27 (t, J = 7.5 Hz, 1H), 7.23-7.14 (m, 1H), 7.02 (s, 1H), 6.85 (s, 1H), 4.63-3.92 (m, 1H), 3.55-3.18 (m, 4H), 2.20-1.89 (m, 4H), 1.70-1.37 (m, 2H), 1.15 & 0.92 (2 × t, J = 7.2 Hz, 3H), 1.08-0.95 (m, 4H). |
| 138 | 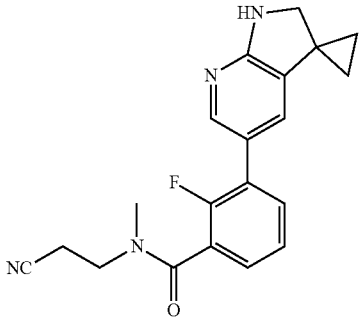<br>N-(2-cyanoethyl)-3-(1',2'-dihydrospiro[cyclopropane-1,3'-pyrrolo[2,3-b]pyridin]-5'-yl)-2-fluoro-N-methylbenzamide | 351.2 | L | (300 MHz, DMSO-d$_6$) δ 7.85-7.83 (m, 1H), 7.55-7.49 (m, 1H), 7.33-7.22 (m, 2H), 7.03 (s, 1H), 6.85 (s, 1H), 3.73 & 3.48 (2 × t, J = 6.6 Hz, 2H), 3.55 (s, 2H), 3.02 & 2.91 (2 × s, 3H), 2.87 & 2.78 (2 × t, J = 6.6 Hz, 2H), 1.07-0.95 (m, 4H) |

| No. | Structure/Name | LCMS R_T (min) m/z Method | Prep Mtd | $^1$H NMR δ (ppm) |
|---|---|---|---|---|
| 139 | 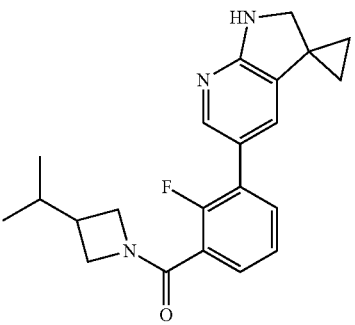<br>(3-(1',2'-dihydrospiro[cyclopropane-1,3'-pyrrolo[2,3-b]pyridin]-5'-yl)-2-fluorophenyl)(3-isopropylazetidin-1-yl)methanone | 366.2 | L | (300 MHz, DMSO-$d_6$) δ 7.84 (t, J = 1.8 Hz, 1H), 7.522 (dt, J = 1.8 Hz, 7.5 Hz, 1H), 7.37-7.24 (m, 2H), 7.01 (s, 1H), 6.81 (s, 1H), 4.08-3.98 (m, 2H), 3.73-3.64 (m, 2H), 3.56 (s, 2H), 2.32-2.29 (m, 1H), 1.74-1.71 (m, 1H), 1.08-0.96 (m, 4H), 0.85 (d, J = 6.6 Hz, 3H), 0.80 (d, J = 6.6 Hz, 3H). |
| 140a | 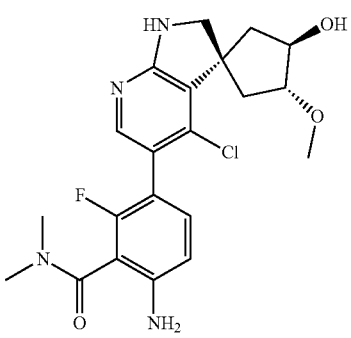<br>6-Amino-3-((1RS,3SR,4SR)-4'-chloro-3-hydroxy-4-methoxy-1',2'-dihydrospiro[cyclopentane-1,3'-pyrrolo[2,3-b]pyridin]-5'-yl)-2-fluoro-N,N-dimethylbenzamide | 2.16<br>435.0<br>A | L | (400 MHz, DMSO-$d_6$) δ 7.61 (s, 1H), 6.97 (t, J = 8.5 Hz, 1H), 6.57-6.54 (m, 1H), 5.45-5.37 (m, 1H), 5.03-4.99 (m, 1H), 4.15-4.09 (m, 1H), 3.65-3.59 (m, 2H), 3.55 (d, J = 9.7 Hz, 1H), 3.44 (d, J = 9.7 Hz, 1H), 3.29 (d, J = 2.8 Hz, 4H), 2.99 (s, 3H), 2.88 (s, 3H), 2.67-2.58 (m, 1H), 2.24-2.15 (m, 1H), 2.08-1.95 (m, 1H), 1.62 (d, J = 13.6 Hz, 1H). |
| 140b | 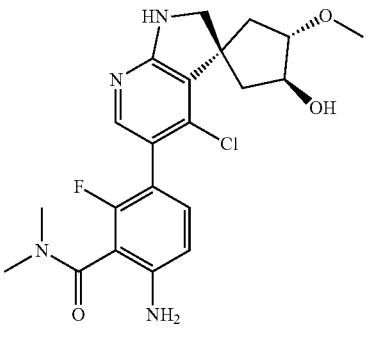<br>6-Amino-3-((1RS,3SR,4SR)-4'-chloro-3-hydroxy-4-methoxy-1',2'-dihydrospiro[cyclopentane-1,3'-pyrrolo[2,3-b]pyridin]-5'-yl)-2-fluoro-N,N-dimethylbenzamide | 2.16<br>435.0<br>A | L | (400 MHz, DMSO-$d_6$) δ 7.61 (s, 1H), 6.97 (t, J = 8.7 Hz, 1H), 7.00-6.94 (m, 1H), 6.57-6.54 (m, 1H), 5.41 (s, 1H), 5.08-4.94 (m, 1H), 4.15-4.09 (m, 1H), 3.66-3.59 (m, 1H), 3.56 (d, J = 9.6 Hz, 1H), 3.45 (d, J = 9.7 Hz, 1H), 3.29 (d, J = 3.0 Hz, 4H), 2.99-2.98 (m, 3H), 2.88 (s, 3H), 2.68-2.59 (m, 1H), 2.23-2.16 (m, 1H), 2.05-1.96 (m, 1H), 1.62 (d, J = 13.6 Hz, 1H). |

TABLE A1-continued

| No. | Structure/Name | LCMS R_T (min) m/z Method | Prep Mtd | $^1$H NMR δ (ppm) |
|---|---|---|---|---|
| 141 | 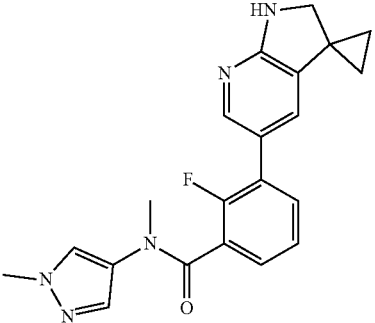<br>3-(1′,2′-dihydrospiro[cyclopropane-1,3′-pyrrolo[2,3-b]pyridin]-5′-yl)-2-fluoro-N-methyl-N-(1-methyl-1H-pyrazol-4-yl)benzamide | 378.2 | L | (300 MHz, DMSO-d$_6$) δ 8.16 & 7.86 (2 × s, 1H), 7.72-7.54 (m, 2H), 7.39-7.11 (m, 3H), 7.05-6.82 (m, 2H), 3.85 & 3.65 (2 × s, 3H), 3.55 (d, J = 4.5 Hz, 2H), 3.33 & 3.28 & 3.19 (3 × s, 3H), 1.08-0.98 (m, 4H). |
| 142 | 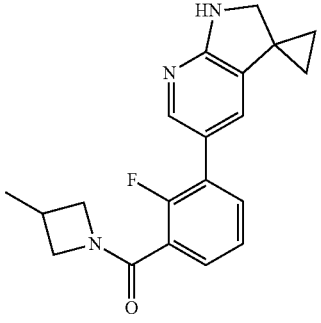<br>3-(1′,2′-dihydrospiro[cyclopropane-1,3′-pyrrolo[2,3-b]pyridin]-5′-yl)-2-fluorophenyl)(3-methylazetidin-1-yl)methanone | 338.2 | L | (300 MHz, DMSO-d$_6$) δ 7.82 (t, J = 1.8 Hz, 1H), 7.52 (dt, J = 1.8 Hz, 7.5 Hz, 1H), 7.38-7.24 (m, 2H), 7.02 (s, 1H), 6.84 (s, 1H), 4.17-4.06 (m, 2H), 3.61-3.53 (m, 4H), 2.74-2.68 (m, 1H), 1.20 (d, J = 6.9 Hz, 3H), 1.09-0.96 (m, 4H). |
| 143a | 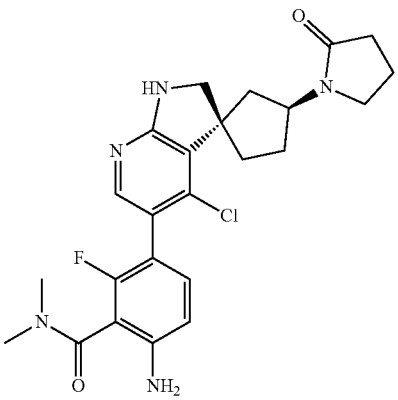<br>6-Amino-3-((1RS,3SR)-4′-chloro-3-(2-oxopyrrolidin-1-yl)-1′,2′-dihydrospiro[cyclopentane-1,3′-pyrrolo[2,3-b]pyridin]-5′-yl)-2-fluoro-N,N-dimethylbenzamide | 2.41<br>472.1<br>A | L | (400 MHz, DMSO-d$_6$) δ 7.62 (s, 1H), 6.98 (dt, J = 1.8, 8.5 Hz, 1H), 6.88 (s, 1H), 6.56 (d, J = 8.4 Hz, 1H), 5.39 (brs, 2H), 4.63 (quintet, J = 8.5 Hz, 1H), 3.50 (d, J = 9.5 Hz, 1H), 3.43 (d, J = 9.5 Hz, 1H), 3.40-3.30 (m, 3H), 2.99 (s, 3H), 2.89 (d, J = 3.8 Hz, 3H), 2.64-2.56 (m, 1H), 2.22 (t, J = 7.9 Hz, 2H), 1.96-1.74 (m, 5H), 1.63 (dd, J = 14.2, 8.9 Hz, 1H). |

TABLE A1-continued

| No. | Structure/Name | LCMS R_T (min) m/z Method | Prep Mtd | $^1$H NMR δ (ppm) |
|---|---|---|---|---|
| 144a | 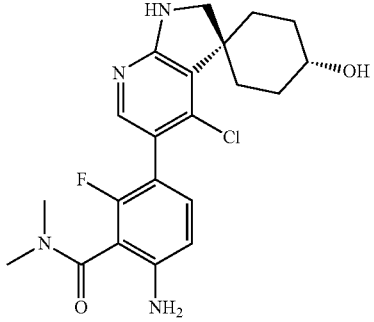<br>6-Amino-3-((1r,4r)-4'-chloro-4-hydroxy-1',2'-dihydrospiro[cyclohexane-1,3'-pyrrolo[2,3-b]pyridin]-5'-yl)-2-fluoro-N,N-dimethylbenzamide | 2.09<br>418.9<br>A | L | (400 MHz, DMSO-d$_6$) δ 7.56 (s, 1H), 6.96 (t, J = 8.5 Hz, 1H), 6.85 (brs, 1H), 6.55 (d, J = 8.4 Hz, 1H), 5.37 (brs, 2H), 4.33 (d, J = 2.3 Hz, 1H), 3.87-3.85 (m, 1H), 3.43 (brs, 2H), 2.99 (s, 3H), 2.89 (brs, 3H), 2.65-2.53 (m, 2H), 1.62-1.51 (m, 4H), 1.35-1.28 (m, 2H). |
| 144b | 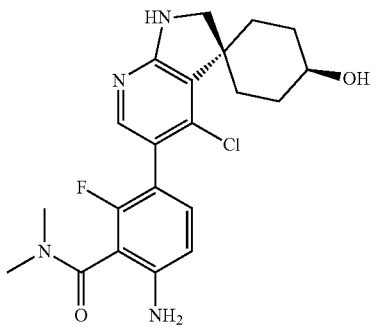<br>6-Amino-3-((1s,4s)-4'-chloro-4-hydroxy-1',2'-dihydrospiro[cyclohexane-1,3'-pyrrolo[2,3-b]pyridin]-5'-yl)-2-fluoro-N,N-dimethylbenzamide | 2.17<br>418.9<br>A | L | (400 MHz, DMSO-d$_6$) δ 7.57 (s, 1H), 6.95 (t, J = 8.5 Hz, 1H), 6.90 (brs, 1H), 6.54 (d, J = 8.4 Hz, 1H), 5.37 (brs, 2H), 4.63 (d, J = 4.3 Hz, 1H), 3.46-3.38 (m, 3H), 2.99 (s, 3H), 2.88 (brs, 3H), 2.24-2.21 (m, 2H), 1.79-1.75 (m, 2H), 1.66-1.58 (m, 2H), 1.32-1.21 (m, 2H). |
| 145 | 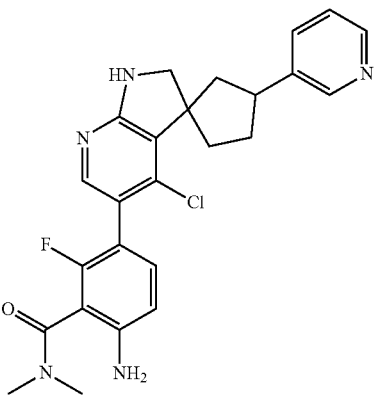<br>6-Amino-3-(4'-chloro-3-(pyridin-3-yl)-1',2'-dihydrospiro[cyclopentane-1,3'-pyrrolo[2,3-b]pyridin]-5'-yl)-2-fluoro-N,N-dimethylbenzamide<br>Mixture of isomers | 2.1<br>466.1<br>A | L | (400 MHz, DMSO-d$_6$) δ 8.52 (m, 1H), 8.41 (m, 1H), 7.76-7.68 (m, 1H), 7.63 (m, 1H), 7.36-7.30 (m, 1H), 7.01-6.95 (m, 1H), 6.89 (m, 1H), 6.58-6.54 (m, 1H), 5.39 (s, 2H), 3.56 (m, 1H), 3.45 (m, 1H), 2.99 (s, 3H), 2.90 (s, 3H), 2.65-2.60 (m, 1H), 2.21-2.07 (m, 6H). |

TABLE A1-continued

| No. | Structure/Name | LCMS R$_T$ (min) m/z Method | Prep Mtd | $^1$H NMR δ (ppm) |
|---|---|---|---|---|
| 145a | 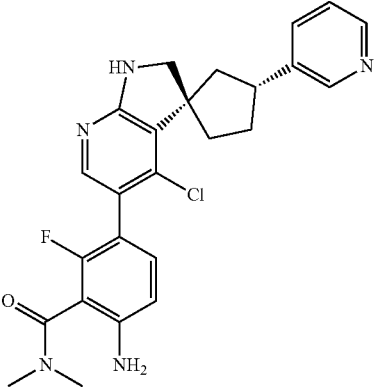<br>6-Amino-3-((1RS,3RS)-4'-chloro-3-(pyridin-3-yl)-1',2'-dihydrospiro[cyclopentane-1,3'-pyrrolo[2,3-b]pyridin]-5'-yl)-2-fluoro-N,N-dimethylbenzamide | 2.11<br>466.1<br>A | L | (400 MHz, DMSO-d$_6$) δ 8.51 (d, J = 2.4 Hz, 1H), 8.40 (m, 1H), 7.73-7.68 (m, 1H), 7.63 (s, 1H), 7.35-7.30 (m, 1H), 6.98 (t, J = 8.5 Hz, 1H), 6.91 (s, 1H), 6.56 (d, J = 8.4 Hz, 1H), 5.39 (s, 2H), 3.58 (d, J = 9.3 Hz, 1H), 3.45 (1H, d, J = 10.3 Hz), 3.29-3.19 (m, 1H), 2.99 (s, 3H), 2.88 (s, 3H), 2.69-2.58 (m, 1H), 2.21-2.07 (m, 3H), 1.98-1.79 (m, 2H). |
| 145c | 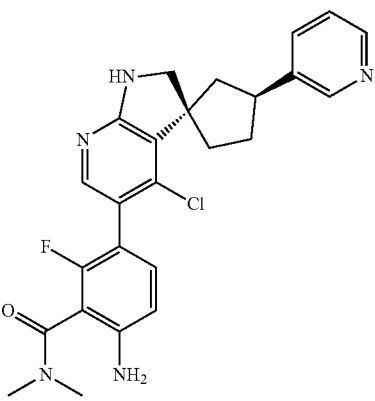<br>6-Amino-3-((1R,3S)-4'-chloro-3-(pyridin-3-yl)-1',2'-dihydrospiro[cyclopentane-1,3'-pyrrolo[2,3-b]pyridin]-5'-yl)-2-fluoro-N,N-dimethylbenzamide first peak on SFC; absolute configuration arbitrarily assigned | 2.09<br>466.1<br>A | L | (400 MHz, DMSO-d$_6$) δ 8.54 (s, 1H), 8.41 (d, J = 4.5 Hz, 1H), 7.74 (dd, J = 1.1, 7.7 Hz, 1H), 7.64 (s, 1H), 7.33 (dd, J = 4.7, 7.9 Hz, 1H), 6.99 (dt, J = 2.1, 8.6 Hz, 1H), 6.88 (s, 1H), 6.56 (d, J = 8.6 Hz, 1H), 5.40 (s, 2H), 3.56 (d, J = 9.1 Hz, 1H), 3.50-3.40 (m, 2H), 2.99 (m, 3H), 2.90 (m, 3H), 2.18-2.11 (m, 1H), 2.07 (s, 2H), 2.03-1.94 (m, 1H), 1.88-1.79 (m, 1H), 1.71-1.64 (m, 1H). |

TABLE A1-continued

| No. | Structure/Name | LCMS R_T (min) m/z Method | Prep Mtd | $^1$H NMR δ (ppm) |
|---|---|---|---|---|
| 145d | 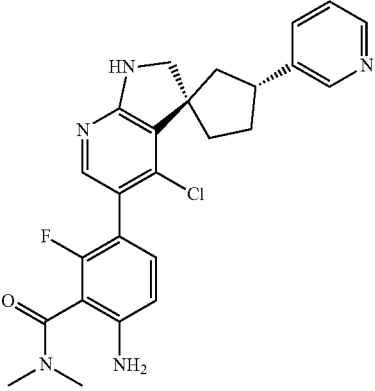<br>6-Amino-3-((1S,3R)-4'-chloro-3-(pyridin-3-yl)-1',2'-dihydrospiro[cyclopentane-1,3'-pyrrolo[2,3-b]pyridin]-5'-yl)-2-fluoro-N,N-dimethylbenzamide second peak on SFC; absolute configuration arbitrarily assigned | 2.09 466.1 A | L | (400 MHz, DMSO-d$_6$) δ 8.54 (s, 1H), 8.41 (d, J = 4.5 Hz, 1H), 7.74 (dd, J = 1.1, 7.7 Hz, 1H), 7.64 (s, 1H), 7.33 (dd, J = 4.7, 7.9 Hz, 1H), 6.99 (dt, J = 2.1, 8.6 Hz, 1H), 6.88 (s, 1H), 6.56 (d, J = 8.6 Hz, 1H), 5.40 (s, 2H), 3.56 (d, J = 9.1 Hz, 1H), 3.50-3.40 (m, 2H), 2.99 (m, 3H), 2.90 (m, 3H), 2.18-2.11 (m, 1H), 2.07 (s, 2H), 2.03-1.94 (m, 1H), 1.88-1.79 (m, 1H), 1.71-1.64 (m, 1H). |
| 146a | 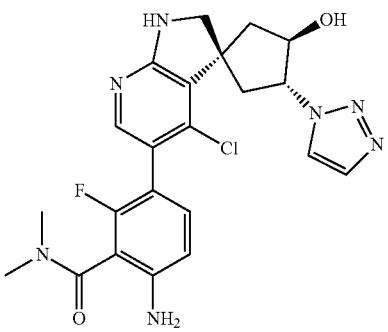<br>6-Amino-3-((1RS,3SR,4SR)-4'-chloro-3-hydroxy-4-(1H-1,2,3-triazol-1-yl)-1',2'-dihydrospiro[cyclopentane-1,3'-pyrrolo[2,3-b]pyridin]-5'-yl)-2-fluoro-N,N-dimethylbenzamide | 2.04 472.0 A | L | (400 MHz, DMSO-d$_6$) δ 8.16 (d, J = 1.3 Hz, 1H), 7.75-7.73 (m, 1H), 7.65 (s, 1H), 6.99 (t, J = 8.5 Hz, 1H), 6.95 (s, 1H), 6.58-6.55 (m, 1H), 5.50-5.46 (m, 1H), 5.40 (s, 2H), 4.87-4.78 (m, 1H), 4.64-4.57 (m, 1H), 3.70 (d, J = 9.5 Hz, 1H), 3.56 (d, J = 9.3 Hz, 1H), 2.99 (s, 3H), 2.96-2.91 (m, 1H), 2.90-2.88 (m, 3H), 2.64-2.54 (m, 1H), 2.43-2.36 (m, 1H), 1.78-1.73 (m, 1H). |

TABLE A1-continued

| No. | Structure/Name | LCMS R$_T$ (min) m/z Method | Prep Mtd | $^1$H NMR δ (ppm) |
|---|---|---|---|---|
| 146c | 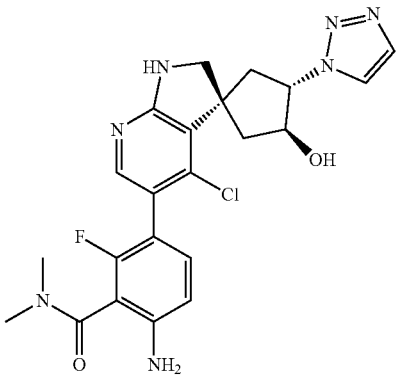<br>6-Amino-3-((1RS,3RS,4RS)-4'-chloro-3-hydroxy-4-(1H-1,2,3-triazol-1-yl)-1',2'-dihydrospiro[cyclopentane-1,3'-pyrrolo[2,3-b]pyridin]-5'-yl)-2-fluoro-N,N-dimethylbenzamide | 2.04<br>472.0<br>A | L | (400 MHz, DMSO-d$_6$) δ 8.16 (d, J = 1.3 Hz, 1H), 7.74 (d, J = 2.3 Hz, 1H), 7.65 (s, 1H), 6.99 (t, J = 8.5 Hz, 1H), 6.95 (s, 1H), 6.58-6.55 (m, 1H), 5.48 (dd, J = 3.9, 5.4 Hz, 1H), 5.40 (s, 2H), 4.87-4.79 (m, 1H), 4.65-4.57 (m, 1H), 3.70 (d, J = 9.5 Hz, 1H), 3.56 (d, J = 9.3 Hz, 1H), 2.99 (s, 3H), 2.95-2.91 (m, 1H), 2.89 (s, 3H), 2.64-2.56 (m, 1H), 2.43-2.35 (m, 1H), 1.80-1.72 (m, 1H). |
| 147 | 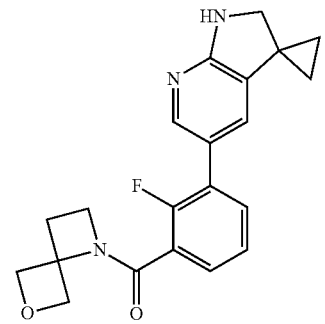<br>(3-(1',2'-dihydrospiro[cyclopropane-1,3'-pyrrolo[2,3-b]pyridin]-5'-yl)-2-fluorophenyl)(6-oxa-1-azaspiro[3.3]heptan-1-yl)methanone | 366.2 | L | (300 MHz, CD3OD) δ 7.77 (t, J = 1.8 Hz, 1H), 7.52 (dt, J = 2.1 Hz, 7.8 Hz, 1H), 7.40-7.35 (m, 1H), 7.30 (t, J = 7.5 Hz, 1H), 7.03 (t, J = 1.8 Hz, 1H), 5.53 (d, J = 7.5 Hz, 2H), 4.75 (d, J = 7.5 Hz, 2H), 3.90 (t, J = 7.5 Hz, 2H), 3.67 (s, 2H), 2.60 (t, J = 7.5 Hz, 2H), 1.13-1.02 (m, 4H) |
| 148a | 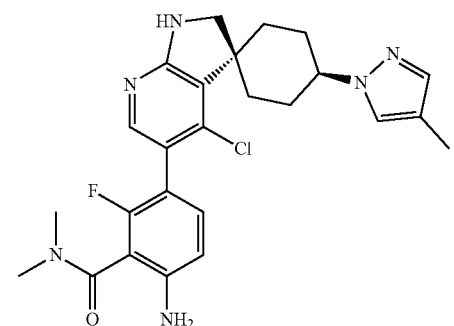<br>6-Amino-3-((1s,4s)-4'-chloro-4-(4-methyl-1H-pyrazol-1-yl)-1',2'-dihydrospiro[cyclohexane-1,3'-pyrrolo[2,3-b]pyridin]-5'-yl)-2-fluoro-N,N-dimethylbenzamide | 3.13<br>483.1<br>A | L | (400 MHz, DMSO-d$_6$) δ 7.60 (s, 1H), 7.55 (t, J = 0.7 Hz, 1H), 7.21 (s, 1H), 6.97 (s & t, J = 8.5 Hz, 2H), 6.55 (d, J = 8.4 Hz, 1H), 5.39 (brs, 2H), 4.18-4.10 (m, 1H), 3.52 (s, 2H), 2.99 (s, 3H), 2.89 (s, 3H), 2.41-2.31 (m, 2H), 2.00 (s, 3H), 1.96-1.75 (m, 6H). |

TABLE A1-continued

| No. | Structure/Name | LCMS R_T (min) m/z Method | Prep Mtd | $^1$H NMR δ (ppm) |
|---|---|---|---|---|
| 149 | 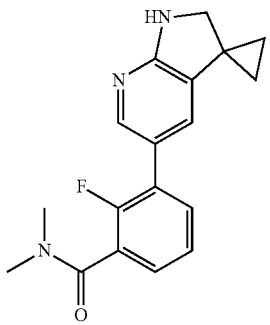<br>3-(1',2'-dihydrospiro[cyclopropane-1,3'-pyrrolo[2,3-b]pyridin]-5'-yl)-2-fluoro-N,N-dimethylbenzamide | 312.2 | L | (400 MHz, DMSO-d$_6$) δ 7.84 (t, J = 1.6 Hz, 1H), 7.53-7.49 (m, 1H), 7.31-7.24 (m, 2H), 7.03 (t, J = 1.6 Hz, 1H), 6.85 (s, 1H), 3.56 (s, 2H), 3.01 (s, 3H), 2.86 (s, 3H), 1.07-0.97 (m, 4H). |
| 150a | 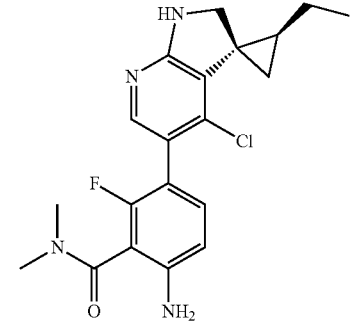<br>6-Amino-3-((1RS,2SR)-4'-chloro-2-ethyl-1',2'-dihydrospiro[cyclopropane-1,3'-pyrrolo[2,3-b]pyridin]-5'-yl)-2-fluoro-N,N-dimethylbenzamide | 3.16<br>389.0<br>A | L | (400 MHz, DMSO-d$_6$) δ 7.48 (s, 1H), 6.98 (s, 1H), 6.92 (t, J = 8.5 Hz, 1H), 6.53 (d, J = 8.4 Hz, 1H), 5.37 (s, 2H), 3.58 (dd, J = 2.9, 9.5 Hz, 1H), 3.42 (dd, J = 1.8, 9.1 Hz, 1H), 2.98 (s, 3H), 2.86 (s, 3H), 1.89-1.70 (m, 2H), 1.46-1.35 (m, 1H), 1.32-1.21 (m, 1H), 0.99 (dt, J = 2.9, 7.3 Hz, 3H), 0.50 (t, J = 5.3 Hz, 1H). |
| 150c | 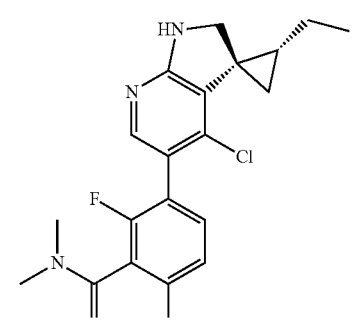<br>6-Amino-3-((1RS,2RS)-4'-chloro-2-ethyl-1',2'-dihydrospiro[cyclopropane-1,3'-pyrrolo[2,3-b]pyridin]-5'-yl)-2-fluoro-N,N-dimethylbenzamide | 3.17<br>389.0<br>A | L | (400 MHz, DMSO-d$_6$) δ 7.54-7.53 (m, 1H), 6.94 (dt, J = 1.7, 8.5 Hz, 1H), 6.86 (s, 1H), 6.54 (d, J = 8.6 Hz, 1H), 5.37 (s, 2H), 3.67 (dd, J = 2.1, 8.8 Hz, 1H), 3.03 (d, J = 9.4 Hz, 1H), 2.99 (d, J = 1.9 Hz, 3H), 2.89-2.85 (m, 3H), 1.85-1.80 (m, 1H), 1.55-1.32 (m, 2H), 1.17-1.08 (m, 1H), 1.04-0.99 (m, 1H), 0.83-0.78 (m, 3H). |

TABLE A1-continued

| No. | Structure/Name | LCMS R_T (min) m/z Method | Prep Mtd | $^1$H NMR δ (ppm) |
|---|---|---|---|---|
| 151a | 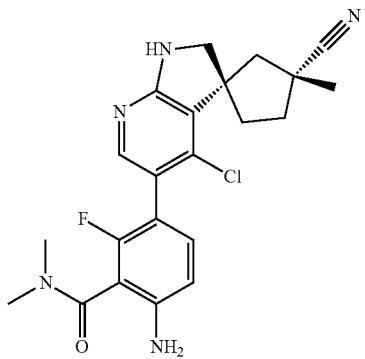<br>6-Amino-3-((1RS,3RS)-4'-chloro-3-cyano-3-methyl-1',2'-dihydrospiro[cyclopentane-1,3'-pyrrolo[2,3-b]pyridin]-5'-yl)-2-fluoro-N,N-dimethylbenzamide | 2.80<br>428.0<br>A | L | (400 MHz, DMSO-d$_6$) δ 7.64 (s, 1H), 6.98 (s & t, J = 8.5 Hz, 2H), 6.56 (d, J = 8.4 Hz, 1H), 5.40 (brs, 2H), 3.49 & 3.43 (ABq, J = 9.5 Hz, 2H), 2.99 (s, 3H), 2.91-2.84 (m & brs, 4H), 2.41-2.27 (m, 2H), 2.00-1.83 (m, 3H), 1.46 (s, 3H). |
| 152a | 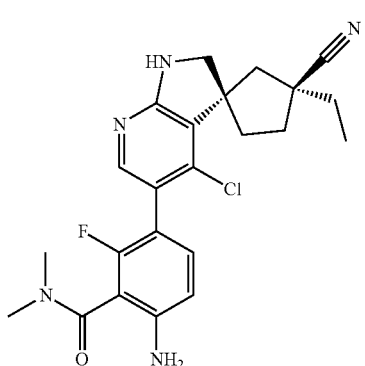<br>6-Amino-3-((1RS,3SR)-4'-chloro-3-cyano-3-ethyl-1',2'-dihydrospiro[cyclopentane-1,3'-pyrrolo[2,3-b]pyridin]-5'-yl)-2-fluoro-N,N-dimethylbenzamide | 3.24<br>442.0<br>A | L | (400 MHz, DMSO-d$_6$) δ 7.65 (s, 1H), 6.96 (s & t, J = 8.5 Hz, 2H), 6.55 (d, J = 8.4 Hz, 1H), 5.40 (brs, 2H), 3.64 (d, J = 9.5 Hz, 1H), 3.52 (d, J = 9.5 Hz, 1H), 2.99 (s, 3H), 2.88 (s, 3H), 2.52-2.44 (m, 1H), 2.38-2.34 (m, 1H), 2.26-2.19 (m, 1H), 2.15-1.89 (m, 3H), 1.75-1.69 (m, 2H), 1.03 (dt, J = 3.2, 7.3 Hz, 3H). |
| 153a | 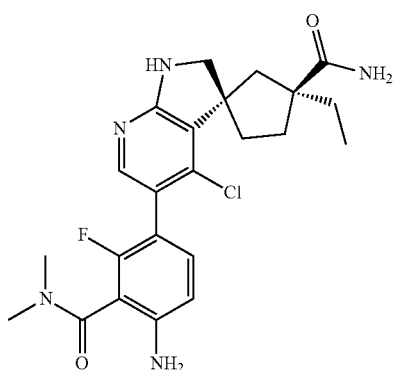<br>(1RS,3SR)-5'-(4-Amino-3-(dimethylcarbamoyl)-2-fluorophenyl)-4'-chloro-3-ethyl-1',2'-dihydrospiro[cyclopentane-1,3'-pyrrolo[2,3-b]pyridine]-3-carboxamide | 2.52<br>460.0<br>A | L | (400 MHz, DMSO-d$_6$) δ 7.59 (s, 1H), 7.23 (brs, 1H), 6.97 (dt, J = 1.3, 8.5 Hz, 1H), 6.90 (brs, 1H), 6.79 (brs, 1H), 6.55 (d, J = 8.3 Hz, 1H), 5.38 (brs, 2H), 3.42 (d, J = 9.4 Hz, 1H), 3.21 (d, J = 9.2 Hz, 1H), 2.99 (s, 3H), 2.88 (s, 3H), 2.47-2.35 (m, 2H), 2.21-2.13 (m, 1H), 1.92-1.84 (m, 1H), 1.74-1.85 (m, 4H), 0.77 (dt, J = 3.0, 7.2 Hz, 3H). |

TABLE A1-continued

| No. | Structure/Name | LCMS R_T (min) m/z Method | Prep Mtd | $^1$H NMR δ (ppm) |
|---|---|---|---|---|
| 154a | (R)-1-(3-(1',2'-dihydrospiro[cyclopropane-1,3'-pyrrolo[2,3-b]pyridin]-5'-yl)-2-fluorobenzoyl)pyrrolidine-2-carbonitrile | 363.2 | L | (300 MHz, DMSO-d$_6$) δ 7.89-7.85 (m, 1H), 7.57 (dt, J = 1.8 Hz, 7.5 Hz, 1H), 7.38-7.30 (m, 2H), 7.05 (s, 1H), 6.86 (s, 1H), 4.96-4.75 (m, 1H), 3.65-3.42 (m, 1H), 3.56 (s, 2H), 3.34-3.28 (m, 1H partially under H2O peak), 2.34-2.30 (m, 1H), 2.24-2.20 (m, 1H), 2.10-1.95 (m, 2H), 1.08-0.97 (m, 4H). |
| 155a | (1R,3S)-5'-(4-Amino-3-(dimethylcarbamoyl)-2-fluorophenyl)-4'-chloro-3-methyl-1',2'-dihydrospiro[cyclopentane-1,3'-pyrrolo[2,3-b]pyridine]-3-carboxamide<br>first peak on SFC; absolute configuration arbitrarily assigned | 2.34<br>446.0<br>A | L | (400 MHz, DMSO-d$_6$) δ 7.59 (s, 1H), 7.23 (brs, 1H), 6.97 (t, J = 8.5 Hz, 1H), 6.88 (brs, 1H), 6.80 (s, 1H), 6.55 (d, J = 8.4 Hz, 1H), 5.38 (brs, 2H), 3.45 (d, J = 9.3 Hz, 1H), 3.24 (d, J = 9.3 Hz, 1H), 2.99 (s, 3H), 2.89 (s, 3H), 2.47-2.39 (m, 2H), 2.23-2.15 (m, 1H), 1.94-1.85 (m, 1H), 1.73-1.61 (m, 2H), 1.30 (d, J = 3.9 Hz, 3H). |

TABLE A1-continued

| No. | Structure/Name | LCMS $R_T$ (min) m/z Method | Prep Mtd | $^1$H NMR δ (ppm) |
|---|---|---|---|---|
| 155b | (1S,3R)-5'-(4-Amino-3-(dimethylcarbamoyl)-2-fluorophenyl)-4'-chloro-3-methyl-1',2'-dihydrospiro[cyclopentane-1,3'-pyrrolo[2,3-b]pyridine]-3-carboxamide<br>second peak on SFC; absolute configuration arbitrarily assigned | 2.35<br>446.0<br>A | L | (400 MHz, DMSO-d$_6$) δ 7.59 (s, 1H), 7.23 (brs, 1H), 6.97 (t, J = 8.5 Hz, 1H), 6.88 (brs, 1H), 6.80 (s, 1H), 6.55 (d, J = 8.4 Hz, 1H), 5.38 (brs, 2H), 3.45 (d, J = 9.4 Hz, 1H), 3.24 (d, J = 9.4 Hz, 1H), 2.99 (s, 3H), 2.88 (s, 3H), 2.48-2.39 (m, 2H), 2.23-2.15 (m, 1H), 1.94-1.85 (m, 1H), 1.72-1.62 (m, 2H), 1.30 (d, J = 3.8 Hz, 3H). |
| 156a | 6-Amino-3-((1RS,3SR)-4'-chloro-3-methyl-3-(3-methyl-1,2,4-oxadiazol-5-yl)-1',2'-dihydrospiro[cyclopentane-1,3'-pyrrolo[2,3-b]pyridin]-5'-yl)-2-fluoro-N,N-dimethylbenzamide | 3.18<br>485.0<br>A | A | (400 MHz, DMSO-d$_6$) δ 7.63 (s, 1H), 6.98 (t, J = 8.5 Hz, 1H), 6.87 (s, 1H), 6.56 (d, J = 8.4 Hz, 1H), 5.40 (brs, 2H), 3.33-3.26 (m, 2H), 2.99 (s, 3H), 2.89 (s, 3H), 2.63-2.54 (m, 2H), 2.41-2.32 & 2.34 (m, 2H & s, 3H), 2.06-1.99 (m, 1H), 1.91-1.84 (m, 1H), 1.53 (d, J = 3.6 Hz, 3H). |

TABLE A1-continued

| No. | Structure/Name | LCMS R$_T$ (min) m/z Method | Prep Mtd | $^1$H NMR δ (ppm) |
|---|---|---|---|---|
| 157a | 6-Amino-3-((1RS,3SR)-3-(3-amino-5-methyl-1H-1,2,4-triazol-1-yl)-4'-chloro-1',2'-dihydrospiro[cyclopentane-1,3'-pyrrolo[2,3-b]pyridin]-5'-yl)-2-fluoro-N,N-dimethylbenzamide | 2.10 485.0 A | L | (400 MHz, DMSO-d$_6$) δ 7.63 (s, 1H), 6.98 (t, J = 8.5 Hz, 1H), 6.91 (s, 1H), 6.56 (d, J = 8.4 Hz, 1H), 5.40 (brs, 2H), 5.11 (brs, 2H), 4.84-4.76 (m, 1H), 3.64 (d, J = 9.4 Hz, 1H), 3.50 (d, J = 9.4 Hz, 1H), 2.99 (s, 3H), 2.89 (s, 3H), 2.81-2.72 (m, 1H), 2.23 (s, 3H), 2.16-2.05 (m, 3H), 2.01-1.92 (m, 2H). |
| 158a | 6-Amino-3-((1RS,3SR)-3-(5-amino-3-methyl-1H-1,2,4-triazol-1-yl)-4'-chloro-1',2'-dihydrospiro[cyclopentane-1,3'-pyrrolo[2,3-b]pyridin]-5'-yl)-2-fluoro-N,N-dimethylbenzamide | 2.02 485.0 A | L | (400 MHz, DMSO-d$_6$) δ 7.63 (s, 1H), 6.99 (t, J = 8.5 Hz, 1H), 6.87 (s, 1H), 6.56 (d, J = 8.3 Hz, 1H), 6.02 (brs, 2H), 5.40 (brs, 2H), 4.79-4.71 (m, 1H), 3.60 (d, J = 9.4 Hz, 1H), 3.50 (d, J = 9.4 Hz, 1H), 2.99 (s, 3H), 2.89 (s, 3H), 2.78-2.67 (m, 1H), 2.14-1.90 & 2.03 (m & s, 8H). |

TABLE A1-continued

| No. | Structure/Name | LCMS R_T (min) m/z Method | Prep Mtd | $^1$H NMR δ (ppm) |
|---|---|---|---|---|
| 159a | 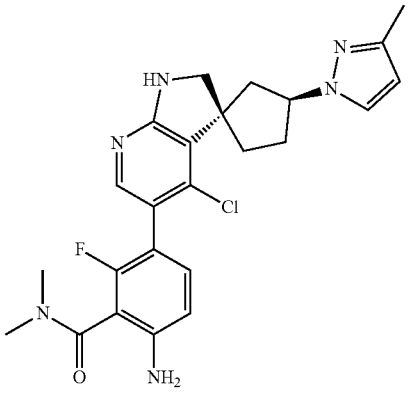<br>6-Amino-3-((1RS,3SR)-4'-chloro-3-(3-methyl-1H-pyrazol-1-yl)-1',2'-dihydrospiro[cyclopentane-1,3'-pyrrolo[2,3-b]pyridin]-5'-yl)-2-fluoro-N,N-dimethylbenzamide | 2.97<br>469.0<br>A | L | (400 MHz, DMSO-d$_6$) δ 7.68 (d, J = 1.8 Hz, 1H), 7.63 (s, 1H), 6.99 (t, J = 8.5 Hz, 1H), 6.87 (s, 1H), 6.56 (d, J = 8.4 Hz, 1H), 5.99 (d, J = 2.0 Hz, 1H), 5.40 (s, 2H), 4.89 (quintet, J = 7.9 Hz, 1H), 3.50 & 3.47 (ABq, J = 9.5 Hz, 2H), 3.00 (s, 3H), 2.89 (s, 3H), 2.87-2.79 (m, 1H), 2.22-2.17 (m, 2H), 2.16 (s, 3H), 2.09-1.94 (m, 3H). |
| 160a | 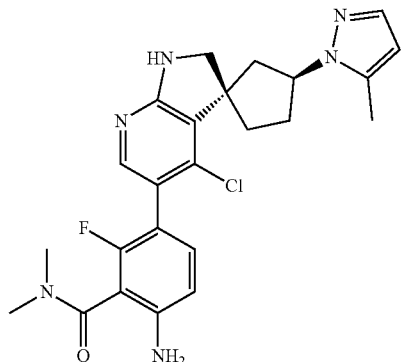<br>6-Amino-3-((1RS,3RS)-4'-chloro-3-(5-methyl-1H-pyrazol-1-yl)-1',2'-dihydrospiro[cyclopentane-1,3'-pyrrolo[2,3-b]pyridin]-5'-yl)-2-fluoro-N,N-dimethylbenzamide | 3.04<br>469.0<br>A | L | (400 MHz, DMSO-d$_6$) δ 7.63 (s, 1H), 7.34 (d, J = 1.6 Hz, 1H), 6.99 (t, J = 8.5 Hz, 1H), 6.88 (s, 1H), 6.56 (d, J = 8.4 Hz, 1H), 6.01 (brs, 1H), 5.40 (brs, 2H), 4.93 (quintet, J = 7.7 Hz, 1H), 3.60 & 3.51 (AB, J = 9.5 Hz, 2H), 3.00 (s, 3H), 2.89 (s, 3H), 2.85-2.77 (m, 1H), 2.27 (s, 3H), 2.23-2.10 (m, 3H), 2.05-1.97 (m, 2H). |

TABLE A1-continued

| No. | Structure/Name | LCMS R_T (min) m/z Method | Prep Mtd | $^1$H NMR δ (ppm) |
|---|---|---|---|---|
| 161a | 6-Amino-3-((1RS,3SR)-4'-chloro-3-(5-cyano-3-methyl-1H-pyrazol-1-yl)-1',2'-dihydrospiro[cyclopentane-1,3'-pyrrolo[2,3-b]pyridin-5'-yl)-2-fluoro-N,N-dimethylbenzamide | 3.54 494.1 A | L | (400 MHz, DMSO-d$_6$) δ 7.65 (s, 1H), 6.99 (t, J = 8.5 Hz, 1H), 6.94 (s, 1H), 6.92 (s, 1H), 6.56 (d, J = 8.3 Hz, 1H), 5.41 (brs, 2H), 5.19-5.11 (m, 1H), 3.55 (s, 2H), 2.99 (s, 3H), 2.98-2.91 (m, 1H), 2.89 (s, 3H), 2.35-2.20 & 2.25 (m & s, 5H), 2.15-2.02 (m, 3H). |
| 162a | 6-Amino-3-((1RS,3SR)-4'-chloro-3-(3-cyano-5-methyl-1H-pyrazol-1-yl)-1',2'-dihydrospiro[cyclopentane-1,3'-pyrrolo[2,3-b]pyridin]-5'-yl)-2-fluoro-N,N-dimethylbenzamide | 3.45 494.1 A | L | (400 MHz, DMSO-d$_6$) δ 7.64 (s, 1H), 6.99 (t, J = 8.5 Hz, 1H), 6.91 (s, 1H), 6.75 (s, 1H), 6.56 (d, J = 8.4 Hz, 1H), 5.41 (brs, 2H), 5.11-5.03 (m, 1H), 3.54 (s, 2H), 2.99 (s, 3H), 2.94-2.86 & 2.89 (m & s, 4H), 2.35 (s, 3H), 2.33-2.27 (m, 1H), 2.23-2.10 (m, 2H), 2.07-1.97 (m, 2H). |

TABLE A1-continued

| No. | Structure/Name | LCMS R_T (min) m/z Method | Prep Mtd | $^1$H NMR δ (ppm) |
|---|---|---|---|---|
| 163a | 6-Amino-3-((1RS,3SR)-4'-chloro-3-(3,5-dimethyl-1H-pyrazol-1-yl)-1',2'-dihydrospiro[cyclopentane-1,3'-pyrrolo[2,3-b]pyridin]-5'-yl)-2-fluoro-N,N-dimethylbenzamide | 3.32 483.1 A | L | (400 MHz, DMSO-d$_6$) δ 7.63 (s, 1H), 6.99 (t, J = 8.5 Hz, 1H), 6.88 (s, 1H), 6.56 (d, J = 8.4 Hz, 1H), 5.78 (s, 1H), 5.40 (brs, 2H), 4.83 (quintet, J = 8.0 Hz, 1H), 3.60 (d, J = 9.5 Hz, 1H), 3.52 (d, J = 9.5 Hz, 1H), 2.99 (s, 3H), 2.89 (s, 3H), 2.81-2.73 (m, 1H), 2.21 (d, J = 1.6 Hz, 3H), 2.17-2.05 & 2.10 (m & s, 6H), 2.01-1.95 (m, 2H). |
| 164a | 6-Amino-3-((1RS,3SR)-4'-chloro-3-(4-(trifluoromethyl)-1H-pyrazol-1-yl)-1',2'-dihydrospiro[cyclopentane-1,3'-pyrrolo[2,3-b]pyridin]-5'-yl)-2-fluoro-N,N-dimethylbenzamide | 3.74 523.1 A | L | (400 MHz, DMSO-d$_6$) δ 8.53 (s, 1H), 7.93 (s, 1H), 7.64 (s, 1H), 6.99 (t, J = 8.5 Hz, 1H), 6.90 (s, 1H), 6.56 (d, J = 8.3 Hz, 1H), 5.41 (s, 2H), 5.07 (quintet, J = 7.9 Hz, 1H), 3.52 & 3.48 (ABq, J = 9.4 Hz, 2H), 3.00 (s, 3H), 2.97-2.91 (m, 1H), 2.89 (s, 3H), 2.35-2.18 (m, 2H), 2.15-1.99 (m, 3H). |
| 165a | 6-Amino-2-fluoro-3-((1RS,2SR)-4'-methoxy-2-methyl-1',2'-dihydrospiro[cyclopropane-1,3'-pyrrolo[2,3-b]pyridin]-5'-yl)-N,N-dimethylbenzamide | 2.77 371.1 A | L | (400 MHz, DMSO-d$_6$) δ 7.42 (s, 1H), 6.98 (t, J = 8.4 Hz, 1H), 6.56 (s, 1H), 6.54 (s, 1H), 5.33 (s, 2H), 3.56 (dd, J = 1.7, 9.5 Hz, 1H), 3.33-3.28 (m, 1H), 3.22 (s, 3H), 2.99 (s, 3H), 2.86 (s, 3H), 1.65-1.56 (m, 1H), 1.42-1.35 (m, 1H), 1.08-1.05 (m, 3H), 0.44-0.40 (m, 1H). |

TABLE A1-continued

| No. | Structure/Name | LCMS $R_T$ (min) m/z Method | Prep Mtd | $^1$H NMR δ (ppm) |
|---|---|---|---|---|
| 166 | 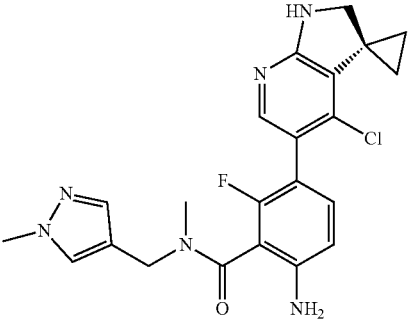<br>6-Amino-3-(4'-chloro-1',2'-dihydrospiro[cyclopropane-1,3'-pyrrolo[2,3-b]pyridin]-5'-yl)-2-fluoro-N-methyl-N-((1-methyl-1H-pyrazole-4-yl)methyl)benzamide<br>Mixture of conformers | 2.73<br>441.1<br>A | L | (400 MHz, DMSO-d$_6$) δ 7.65, 7.51, 7.50 (3xs, 2H), 7.38, 7.21 (2xs, 1H), 6.96-6.91 (m, 2H), 6.58-6.54 (m, 1H), 5.44-5.34 (2xs, 2H), 4.61 (d, J = 14.5 Hz), 4.33 (d, J = 14.5 Hz), 4.23 (s, 2H), 3.80, 3.76 (2xs, 3H), 3.50 (s, 2H), 2.87, 2.77 (2xs, 3H), 1.63-1.58 (m, 2H), 0.89-0.85 (m, 2H). |
| 167a | 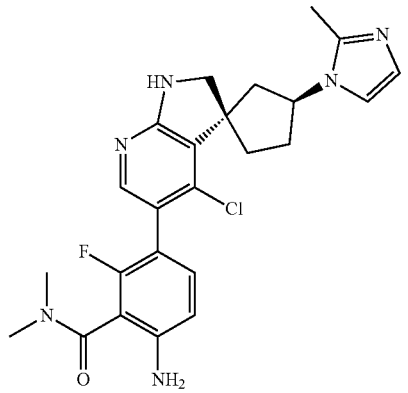<br>6-Amino-3-((1RS,3SR)-4'-chloro-3-(2-methyl-1H-imidazol-1-yl)-1',2'-dihydrospiro[cyclopentane-1,3'-pyrrolo[2,3-b]pyridin]-5'-yl)-2-fluoro-N,N-dimethylbenzamide | 1.88<br>469.1<br>A | L | (400 MHz, DMSO-d$_6$) δ 7.65 (s, 1H), 7.23 (d, J = 1.4 Hz, 1H), 6.99 (dt, J = 2.7, 8.6 Hz, 1H), 6.90 (s, 1H), 6.78 (s, 1H), 6.56 (d, J = 8.4 Hz, 1H), 5.41 (brs, 2H), 4.80-4.71 (m, 1H), 3.59 (d, J = 9.5 Hz, 1H), 3.44 (d, J = 9.5 Hz, 1H), 2.99 (s, 3H), 2.98-2.92 (m, 1H), 2.89 (s, 3H), 2.30 (d, J = 3.0 Hz, 3H), 2.23-2.17 (m, 1H), 2.10-1.90 (m, 3H), 1.73-1.66 (m, 1H). |

TABLE A1-continued

| No. | Structure/Name | LCMS R_T (min) m/z Method | Prep Mtd | $^1$H NMR δ (ppm) |
|---|---|---|---|---|
| 168a | 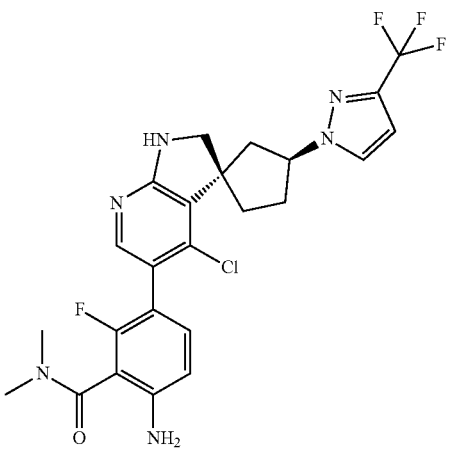 6-Amino-3-((1RS,3RS)-4'-chloro-3-(3-(trifluoromethyl)-1H-pyrazol-1-yl)-1',2'-dihydrospiro[cyclopentane-1,3'-pyrrolo[2,3-b]pyridine-5'-yl)-2-fluoro-N,N-dimethylbenzamide | 3.71 523.1 A | L | (400 MHz, DMSO-d$_6$) δ 8.12 (brs, 1H), 7.65 (s, 1H), 6.99 (t, J = 8.5 Hz, 1H), 6.90 (s, 1H), 6.73 (d, J = 2.2 Hz, 1H), 6.56 (d, J = 8.4 Hz, 1H), 5.41 (s, 2H), 5.11 (quintet, J = 7.9 Hz, 1H), 3.53 (d, J = 9.4 Hz, 1H), 3.46 (d, J = 9.3 Hz, 1H), 3.00 (s, 3H), 2.96-2.92 (m, 1H), 2.90 (brs, 3H), 2.36-2.30 (m, 1H), 2.28-2.18 (m, 1H), 2.15-2.00 (m, 3H). |
| 169a | 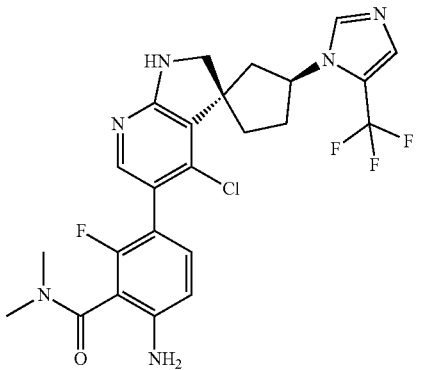 6-Amino-3-((1RS,3RS)-4'-chloro-3-(5-(trifluoromethyl)-1H-pyrazol-1-yl)-1',2'-dihydrospiro[cyclopentane-1,3'-pyrrolo[2,3-b]pyridin]-5'-yl)-2-fluoro-N,N-dimethylbenzamide | 3.77 523.1 A | L | (400 MHz, DMSO-d$_6$) δ 7.74 (d, J = 1.7 Hz, 1H), 7.65 (s, 1H), 6.99 (dt, J = 1.3, 8.5 Hz, 1H), 6.93 (s, 1H), 6.89 (d, J = 1.8 Hz, 1H), 6.56 (d, J = 8.3 Hz, 1H), 5.41 (brs, 2H), 5.08 (quintet, J = 7.9 Hz, 1H), 3.58 (s, 2H), 2.99 (s, 3H), 2.95-2.90 (m, 1H), 2.89 (brs, 3H), 2.36-2.25 (m, 2H), 2.16-2.03 (m, 3H). |

TABLE A1-continued

| No. | Structure/Name | LCMS R$_T$ (min) m/z Method | Prep Mtd | $^1$H NMR δ (ppm) |
|---|---|---|---|---|
| 170a | 6-Amino-3-((1RS,3SR)-4'-chloro-3-(4-ethyl-1H-pyrazol-1-yl)-1',2'-dihydrospiro[cyclopentane-1,3'-pyrrolo[2,3-b]pyridin]-5'-yl)-2-fluoro-N,N-dimethylbenzamide | 3.38 483.0 A | L | (400 MHz, DMSO-d$_6$) δ 7.63 (s, 1H), 7.61 (s, 1H), 7.30 (s, 1H), 6.99 (t, J = 8.5 Hz, 1H), 6.87 (s, 1H), 6.56 (d, J = 8.4 Hz, 1H), 5.40 (brs, 2H), 4.95-4.87 (m, 1H), 3.48 (s, 2H), 2.99 (s, 3H), 2.89 (s, 3H), 2.88-2.79 (m, 1H), 2.42 (q, J = 7.6 Hz, 2H), 2.24-2.04 (m, 4H), 2.00-1.94 (m, 1H), 1.13 (t, J = 7.6 Hz, 3H). |
| 171a | 6-Amino-3-((1RS,3SR)-4'-chloro-3-(4-chloro-1H-pyrazol-1-yl)-1',2'-dihydrospiro[cyclopentane-1,3'-pyrrolo[2,3-b]pyridin]-5'-yl)-2-fluoro-N,N-dimetylbenzamide | 3.40 489.0 A | L | (400 MHz, DMSO-d$_6$) δ 8.12 (s, 1H), 7.64 (s, 1H), 7.58 (d, J = 0.7 Hz, 1H), 6.99 (t, J = 8.5 Hz, 1H), 6.88 (s, 1H), 6.56 (d, J = 8.4 Hz, 1H), 5.40 (brs, 2H), 5.00-4.92 (m, 1H), 3.49 & 3.44 (ABq, J = 9.5 Hz, 2H), 2.99 (s, 3H), 2.91-2.83 & 2.89 (m & s, 4H), 2.30-2.05 (m, 4H), 2.02-1.95 (m, 1H). |
| 172 | (3-(1',2'-dihydrospiro[cyclopropane-1,3'-pyrrolo[2,3-b]pyridin]-5'-yl)-2-fluorophenyl)(indolin-1-yl)methanone | 386.2 | L | (300 MHz, DMSO-d$_6$) δ 8.16 (d, J = 8.1 Hz, 1H), 7.88 (s, 1H), 7.61-7.57 (m, 1H), 7.48-7.23 (m, 4H), 7.12-7.06 (m, 2H), 6.85 (s, 1H), 3.88 (t, J = 8.1 Hz, 2H), 3.55 (s, 2H), 3.11 (t, J = 8.1 Hz, 1H), 1.05-0.96 (m, 4H) |

TABLE A1-continued

| No. | Structure/Name | LCMS R_T (min) m/z Method | Prep Mtd | $^1$H NMR δ (ppm) |
|---|---|---|---|---|
| 173a | 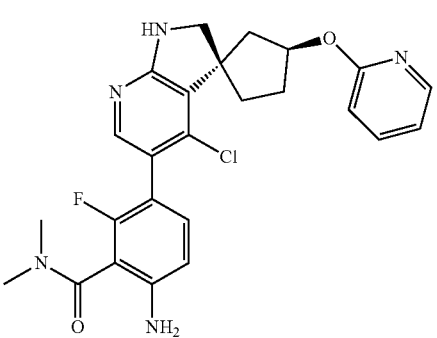<br>6-Amino-3-((1RS,3SR)-4'-chloro-3-(pyridin-2-yloxy)-1',2'-dihydrospiro[cyclopentane-1,3'-pyrrolo[2,3-b]pyridin]-5'-yl)-2-fluoro-N,N-dimethylbenzamide | 3.27<br>482.1<br>A | L | (400 MHz, DMSO-d$_6$) δ 8.17-8.15 (m, 1H), 7.70 (ddd, J = 8.4, 7.1, 2.0 Hz, 1H), 7.62 (s, 1H), 6.98 (t, J = 8.5 Hz, 1H), 6.97-6.94 (m, 1H), 6.86 (s, 1H), 6.79 (dt, J = 8.3, 0.8 Hz, 1H), 6.56 (d, J = 8.3 Hz, 1H), 5.57-5.52 (m, 1H), 5.40 (brs, 2H), 3.54 & 3.51 (ABq, J = 9.4 Hz, 2H), 2.99 (s, 3H), 2.89 (s, 3H), 2.69-2.60 (m, 1H), 2.37-2.20 (m, 2H), 1.97-1.88 (m, 3H). |
| 174a | 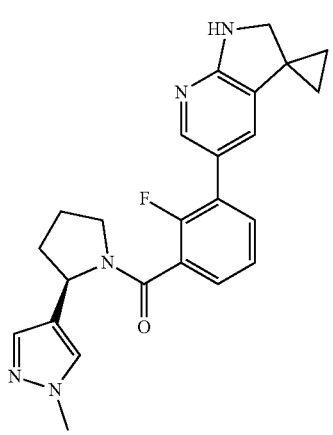<br>(R)-(3-(1',2'-dihydrospiro[cyclopropane-1,3'-pyrrolo[2,3-b]pyridin]-5'-yl)-2-fluorophenyl)(2-(1-methyl-1H-pyrazol-4-yl)pyrrolidin-1-yl)methanone<br>Peak 1 on SFC; absolute configuration arbitrarily assigned | 418.3 | L | (400 MHz, DMSO-d$_6$) δ 7.85 & 7.70 (2 × s, 1H), 7.60 (s, 1H), 7.53-7.48 (m, 1H), 7.41-7.37 (m, 1H), 7.33-7.27 (m, 1H), 7.19-7.10 (m, 1H), 7.04 & 6.99 (2 × s, 1H), 6.85 (t, J = 7.2 Hz, 1H), 5.20-4.67 (m, 1H), 3.80 (s, 2H), 3.66-3.63 (m, 2H), 3.56 (2, 2H), 3.44-3.22 (m, 1H partially under H2O peak), 2.26-2.15 (m, 1H), 1.98-1.76 (m, 3H), 1.09-0.97 (m, 4H). |

TABLE A1-continued

| No. | Structure/Name | LCMS R_T (min) m/z Method | Prep Mtd | $^1$H NMR δ (ppm) |
|---|---|---|---|---|
| 174b | 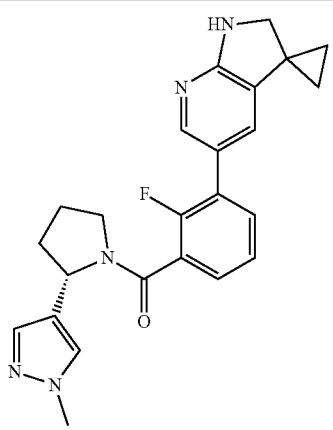<br>(S)-(3-(1',2'-dihydrospiro[cyclopropane-1,3'-pyrrolo[2,3-b]pyridin]-5'-yl)-2-fluorophenyl)(2-(1-methyl-1H-pyrazol-4-yl)pyrrolidin-1-yl)methanone<br>Peak 2 on SFC; absolute configuration arbitrarily assigned | 418.3 | L | (400 MHz, DMSO-d$_6$) δ 7.85 & 7.70 (2 × s, 1H), 7.60 (s, 1H), 7.53-7.48 (m, 1H), 7.41-7.37 (m, 1H), 7.33-7.27 (m, 1H), 7.19-7.10 (m, 1H), 7.04 & 6.99 (2 × s, 1H), 6.85 (t, J = 7.2 Hz, 1H), 5.20-4.67 (m, 1H), 3.80 (s, 2H), 3.66-3.63 (m, 2H), 3.56 (s, 2H), 3.44-3.22 (m, 1H, partially under H2O peak), 2.26-2.15 (m, 1H), 1.98-1.76 (m, 3H), 1.09-0.97 (m, 4H). |
| 175a | 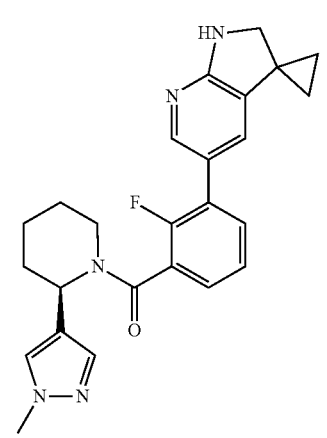<br>(R)-(3-(1',2'-dihydrospiro[cyclopropane-1,3'-pyrrolo[2,3-b]pyridin]-5'-yl)-2-fluorophenyl)(2-(1-methyl-1H-pyrazol-4-yl)piperidin-1-yl)methanone<br>Peak 1 on SFC; absolute configuration arbitrarily assigned | 432.2 | L | (300 MHz, DMSO-d$_6$) δ 7.85 (s, 1H), 7.76-7.45 (m, 2H), 7.32-7.18 (m, 3H), 7.04 (s, 1H), 6.85 (s, 1H), 5.83-4.41 (m, 1H), 3.82 & 3.78 (2 × s, 3H), 3.56 (s, 2H), 3.43-3.21 (m, 1H partially under DMSO peak), 3.02-2.72 (m, 1H), 2.15-1.95 (m, 1H), 1.90-1.42 (m, 5H), 1.06-0.98 (m, 4H). |

TABLE A1-continued

| No. | Structure/Name | LCMS R_T (min) m/z Method | Prep Mtd | $^1$H NMR δ (ppm) |
|---|---|---|---|---|
| 175b | 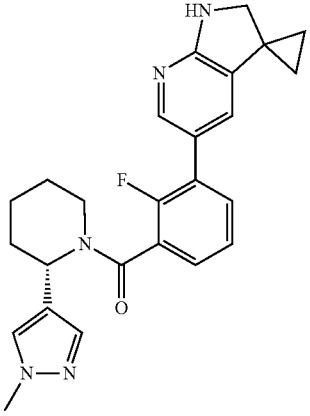<br>(S)-(3-(1',2'-dihydrospiro[cyclopropane-1,3'-pyrrolo[2,3-b]pyridin]-5'-yl)-2-fluorophenyl)(2-(1-methyl-1H-pyrazol-4-yl)piperidin-1-yl)methanone<br>Peak 2 on SFC; absolute configuration arbitrarily assigned | 432.2 | L | (300 MHz, DMSO-d$_6$) δ 7.85 (s, 1H), 7.76-7.45 (m, 2H), 7.32-7.18 (m, 3H), 7.04 (s, 1H), 6.85 (s, 1H), 5.83-4.41 (m, 1H), 3.82 & 3.78 (2 × s, 3H), 3.56 (s, 2H), 3.43-3.21 (m, 1H, partially under DMSO peak), 3.02-2.72 (m, 1H), 2.15-1.95 (m, 1H), 1.90-1.42 (m, 5H), 1.06-0.98 (m, 4H). |
| 176 | 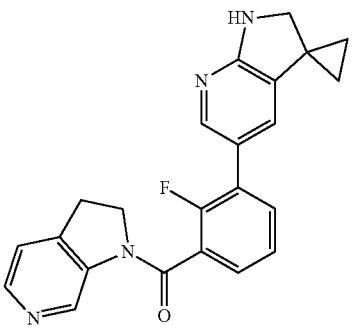<br>(2,3-dihydro-1H-pyrrolo[2,3-c]pyridin-1-yl)(3-(1',2'-dihydrospiro[cyclopropane-1,3'-pyrrolo[2,3-b]pyridin]-5'-yl)-2-fluorophenyl)methanone | 387.2 | L | (400 MHz, DMSO-d$_6$) δ 9.28 (s, 1H), 8.32 (d, J = 4.8 Hz, 1H), 7.89 (s, 1H), 7.62-7.58 (m, 1H), 7.49-7.35 (m, 3H), 7.07 (s, 1H), 6.87 (s, 1H), 3.92 (t, J = 8.4 Hz, 2H), 3.56 (s, 2H), 3.19 (t, J = 8.4 Hz, 2H), 1.06-0.99 (m, 4H). |

| No. | Structure/Name | LCMS R$_T$ (min) m/z Method | Prep Mtd | $^1$H NMR δ (ppm) |
|---|---|---|---|---|
| 177a | 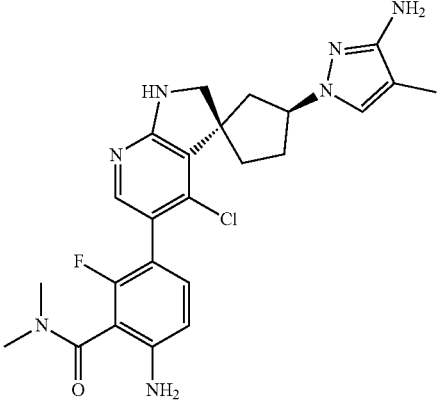<br>6-Amino-3-((1RS,3SR)-3-(3-amino-4-methyl-1H-pyrazol-1-yl)-4'-chloro-1',2'-dihydrospiro[cyclopentane-1,3'-pyrrolo[2,3-b]pyridin]-5'-yl)-2-fluoro-N,N-dimethylbenzamide | 2.31<br>484.1<br>A | L | (400 MHz, DMSO-d$_6$) δ 7.62 (s, 1H), 6.99 (t, J = 8.4 Hz, 1H), 6.96 (s, 1H), 6.85 (s, 1H), 6.56 (d, J = 8.4 Hz, 1H), 5.39 (brs, 2H), 4.88-4.81 (m, 1H), 4.81 (brs, 2H), 3.59 (d, J = 9.5 Hz, 1H), 3.45 (d, J = 9.5 Hz, 1H), 2.99 (s, 3H), 2.89 (s, 3H), 2.74-2.65 (m, 1H), 2.19-2.00 (m, 4H), 1.96-1.90 (m, 1H), 1.80 (s, 3H). |
| 178a | 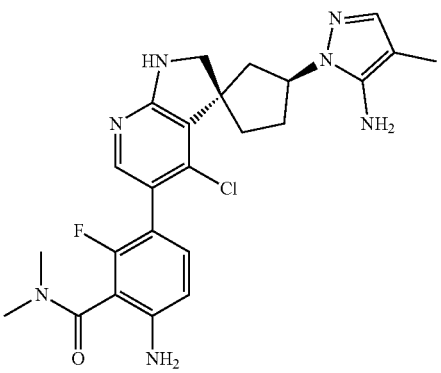<br>6-Amino-3-((1RS,3SR)-3-(5-amino-4-methyl-1H-pyrazol-1-yl)-4'-chloro-1',2'-dihydrospiro[cyclopentane-1,3'-pyrrolo[2,3-b]pyridin]-5'-yl)-2-fluoro-N,N-dimethylbenzamide | 2.44<br>484.1<br>A | L | (400 MHz, DMSO-d$_6$) δ 7.62 (s, 1H), 7.22 (s, 1H), 6.98 (t, J = 8.5 Hz, 1H), 6.85 (s, 1H), 6.56 (d, J = 8.4 Hz, 1H), 5.40 (brs, 2H), 4.67-4.59 (m, 1H), 4.39 (brs, 2H), 3.47 & 3.44 (ABq, J = 9.5 Hz, 2H), 2.99 (s, 3H), 2.89 (s, 3H), 2.74-2.66 (m, 1H), 2.12-2.04 (m, 3H), 2.02-1.97 (m, 1H), 1.94-1.89 (m, 1H), 1.80 (s, 3H). |

TABLE A1-continued

| No. | Structure/Name | LCMS R$_T$ (min) m/z Method | Prep Mtd | $^1$H NMR δ (ppm) |
|---|---|---|---|---|
| 179a | (1R,3S)-4'-Chloro-3-methyl-5'-(3-(1-methyl-2-oxo-1,2-dihydropyridin-3-yl)phenyl)-1',2'-dihydrospiro[cyclopentane-1,3'-pyrrolo[2,3-b]pyridine]-3-carboxamide<br>first peak from SFC; absolute configuration arbitrarily assigned | 2.81<br>449.3<br>B | L | (400 MHz, DMSO-d$_6$) δ 7.78-7.73 (m, 1H), 7.72 (s, 1H), 7.70-7.65 (m, 3H), 7.45-7.40 (m, 1H), 7.33-7.28 (m, 1H), 7.23 (s, 1H), 6.89 (s, 1H), 6.85 (s, 1H), 6.33 (t, J = 6.8 Hz, 1H), 3.51-3.50 (m, 3H), 3.47 (d, J = 9.3 Hz, 1H), 3.26 (d, J = 9.3 Hz, 1H), 2.48-2.54 (m, 1H), 2.46 (d, J = 13.4 Hz, 1H), 2.25-2.16 (m, 1H), 1.96 (d, J = 13.4 Hz, 1H), 1.75-1.63 (m, 2H), 1.32-1.30 (m, 3H). |
| 179b | (1S,3R)-4'-Chloro-3-methyl-5'-(3-(1-methyl-2-oxo-1,2-dihydropyridin-3-yl)phenyl)-1',2'-dihydrospiro[cyclopentane-1,3'-pyrrolo[2,3-b]pyridine]-3-carboxamide<br>second peak from SFC; absolute configuration arbitrarily assigned | 2.81<br>449.3<br>B | L | (400 MHz, DMSO-d$_6$) δ 7.78-7.73 (m, 1H), 7.72 (s, 1H), 7.70-7.65 (m, 3H), 7.45-7.40 (m, 1H), 7.33-7.28 (m, 1H), 7.23 (s, 1H), 6.89 (s, 1H), 6.85 (s, 1H), 6.33 (t, J = 6.8 Hz, 1H), 3.51-3.50 (m, 3H), 3.47 (d, J = 9.3 Hz, 1H), 3.26 (d, J = 9.3 Hz, 1H), 2.48-2.54 (m, 1H), 2.46 (d, J = 13.4 Hz, 1H), 2.25-2.16 (m, 1H), 1.96 (d, J = 13.4 Hz, 1H), 1.75-1.63 (m, 2H), 1.32-1.30 (m, 3H). |
| 180a | 1-((1RS,3SR)-5'-(4-Amino-3-(dimethylcarbamoyl)-2-fluorophenyl)-4'-chloro-1',2'-dihydrospiro[cyclopentane-1,3'-pyrrolo[2,3-b]pyridin]-3-yl)-1H-pyrazole-4-carboxamide | 2.27<br>498.3<br>B | L | (400 MHz, DMSO-d$_6$) δ 8.26 (s, 1H), 7.88 (s, 1H), 7.64 (s, 1H), 7.52 (brs, 1H), 6.99 (t, J = 8.5 Hz, 1H), 6.97 (brs, 1H), 6.88 (s, 1H), 6.56 (d, J = 8.4 Hz, 1H), 5.40 (brs, 2H), 5.04-4.96 (m, 1H), 3.50 & 3.46 (ABq, J = 9.4 Hz, 2H), 3.00 (s, 3H), 2.93-2.85 & 2.90 (m & s, 4H), 2.33-2.07 (m, 4H), 2.03-1.97 (m, 1H). |

TABLE A1-continued

| No. | Structure/Name | LCMS R_T (min) m/z Method | Prep Mtd | $^1$H NMR δ (ppm) |
|---|---|---|---|---|
| 181 | 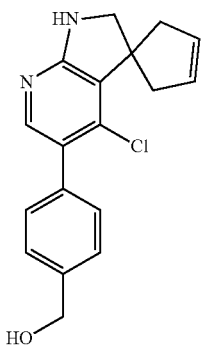<br>(4-(4'-Chloro-1',2'-dihydrospiro[cyclopentane-1,3'-pyrrolo[2,3-b]pyridin]-3-en-5'-yl)phenyl)methanol | 3.00<br>313.2<br>B | L | (400 MHz, DMSO-d$_6$) δ 7.68 (s, 1H), 7.36 (d, J = 8.4 Hz, 1H), 7.31 (d, J = 8.2 Hz, 2H), 6.89 (s, 1H), 5.76 (s, 2H), 5.19 (t, J = 5.6 Hz, 1H), 4.52 (d, J = 5.3 Hz, 2H), 3.49 (d, J = 0.8 Hz, 2H), 3.06 (d, J = 15.1 Hz, 2H), 2.50 (m, 2H assumed under DMSO peak) |
| 182 | 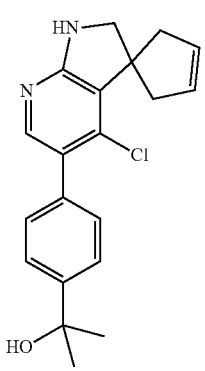<br>2-(4-(4-Chloro-1',2'-dihydrospiro[cyclopentane-1,3'-pyrrolo[2,3-b]pyridin]-3-en-5'-yl)phenyl)propan-2-ol | 3.4<br>341.2<br>B | L | (400 MHz, DMSO-d$_6$) δ 7.69 (s, 1H), 7.50 (d, J = 7.9 Hz, 1H), 7.29 (d, J = 7.5 Hz, 2H), 6.88 (s, 1H), 5.77 (s, 2H), 5.02 (s, 1H), 3.49 (s, 2H), 3.06 (d, J = 15.0 Hz, 2H), 2.53 (m, 2H partially under DMSO peak), 1.45 (s, 6H). |
| 183 | 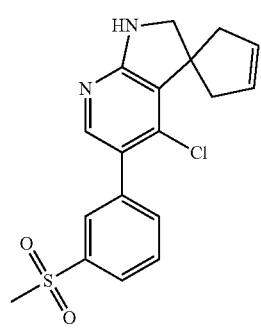<br>4'-Chloro-5'-(3-(methylsulfonyl)phenyl)-1',2'-dihydrospiro[cyclopentane-1,3'-pyrrolo[2,3-b]pyridin]-3-ene | 3.39<br>361.2<br>B | L | (400 MHz, DMSO-d$_6$) δ 7.91-7.88 (m, 2H), 7.80 (s, 1H), 7.77-7.69 (m, 2H), 7.09 (s, 1H), 5.77 (s, 2H), 3.53 (s, 2H), 3.26 (s, 3H), 3.07 (d, J = 15.1 Hz, 2H), 2.54 (d, J = 1.5 Hz, 2H) |

TABLE A1-continued

| No. | Structure/Name | LCMS R_T (min) m/z Method | Prep Mtd | $^1$H NMR δ (ppm) |
|---|---|---|---|---|
| 184 | 4'-Chloro-5'-(3-(ethylsulfonyl)phenyl)-1',2'-dihydrospiro[cyclopentane-1,3'-pyrrolo[2,3-b]pyridin]-3-ene | 3.63 375.2 B | L | (400 MHz, DMSO-d$_6$) δ 7.88-7.84 (m, 2H), 7.80 (s, 1H), 7.78-7.68 (m, 2H), 7.09 (s, 1H), 5.77 (s, 2H), 3.53 (s, 2H), 3.34 (q, J = 7.1 Hz, 2H), 3.07 (d, J = 15.2 Hz, 2H), 2.54 (d, J = 15.2 Hz, 2H), 1.12 (t, J = 7.3 Hz, 3H) |
| 185 | 3-(4'-Chloro-1',2'-dihydrospiro[cyclopentane-1,3'-pyrrolo[2,3-b]pyridin]-3-en-5'-yl)-N-methylbenzenesulfonamide | 3.28 376.2 B | L | (400 MHz, DMSO-d$_6$) δ 9.80 (bs, 1H), 7.70 (s, 1H), 7.39-7.34 (m, 1H), 7.19-7.16 (m, 2H), 7.09-7.07 (m, 1H), 6.96 (bs, 1H), 5.77 (s, 2H), 3.50 (s, 2H), 3.06 (d, J = 15.4 Hz, 2H), 3.01 (s, 3H), 2.52 (d, J = 15.4 Hz, 2H) |
| 186 | 4'-Chloro-5'-(4-(methylsulfonyl)phenyl)-1',2'-dihydrospiro[cyclopentane-1,3'-pyrrolo[2,3-b]pyridin]-3-ene | 3.36 361.1 B | L | (400 MHz, DMSO-d$_6$) δ 7.95 (td, J = 1.9, 8.6 Hz, 2H), 7.77 (s, 1H), 7.66 (td, J = 2.0, 8.6 Hz, 2H), 7.12 (s, 1H), 5.77 (s, 2H), 3.52 (s, 2H), 3.27 (s, 3H), 3.07 (d, J = 15.1 Hz, 2H), 2.56-2.54 (m, 2H, partially under DMSO peak). |

TABLE A1-continued

| No. | Structure/Name | LCMS R_T (min) m/z Method | Prep Mtd | $^1$H NMR δ (ppm) |
|---|---|---|---|---|
| 187 | 4'-Chloro-5'-(4-(ethylsulfonyl)phenyl)-1',2'-dihydrospiro[cyclopentane-1,3'-pyrrolo[2,3-b]pyridin]-3-ene | 3.61 375.2 B | L | (400 MHz, DMSO-d$_6$) δ 7.91 (td, J = 2.0, 8.6 Hz, 2H), 7.78 (s, 1H), 7.67 (td, J = 2.0, 8.6 Hz, 2H), 7.13 (s, 1H), 5.77 (s, 2H), 3.53 (s, 2H), 3.38-3.34 (m, 2H, partially under water peak), 3.07 (d, J = 15.2 Hz, 2H), 2.56-2.54 (m, 2H, partially under DMSO peak), 1.14 (t, J = 7.3 Hz, 3H). |
| 188 | 4-(4'-Chloro-1',2'-dihydrospiro[cyclopentane-1,3'-pyrrolo[2,3-b]pyridin]-3-en-5'-yl)-N-methyl-benzamide sulfonamide | 3.43 376.2 B | L | (400 MHz, DMSO-d$_6$) δ 7.82-7.78 (m, 2H), 7.77 (s, 1H), 7.64-7.60 (m, 2H), 7.49 (bs, 1H), 7.09 (bs, 1H), 5.77 (s, 2H), 3.52 (s, 2H), 3.07 (d, J = 15.1 Hz, 2H), 2.54 (d, J = 15.1 Hz, 2H), 2.46 (s, 3H) |

TABLE A1-continued

| No. | Structure/Name | LCMS R_T (min) m/z Method | Prep Mtd | $^1$H NMR δ (ppm) |
|---|---|---|---|---|
| 189 | 4-(4'-Chloro-1',2'-dihydrospiro[cyclopentane-1,3'-pyrrolo[2,3-b]pyridin]-3-en-5'-yl)-N-ethyl-benzenesulfonamide | 3.69 390.2 B | L | (400 MHz, DMSO-d$_6$) δ 7.82-7.79 (m, 2H), 7.76 (s, 1H), 7.62-7.56 (m, 3H), 7.08 (s, 1H), 5.77 (bs, 2H), 3.52 (s, 2H), 3.07 (d, J = 15.1 Hz, 2H), 2.82 (q, J = 7.2 Hz, 2H), 2.53 (d, J = 13.0 Hz, 2H), 1.01 (t, J = 7.2 Hz, 3H) |
| 190 | 3-(4'-Chloro-1',2'-dihydrospiro[cyclopentane-1,3'-pyrrolo[2,3-b]pyridin-3-en-5'-yl)benzonitrile | 4.01 308.2 B | L | (400 MHz, DMSO-d$_6$) δ 7.86-7.80 (m, 2H), 7.75 (s, 1H), 7.74-7.72 (m, 1H), 7.63 (dd, J = 7.8, 7.8 Hz, 1H), 7.08 (bs, 1H), 5.77 (s, 2H), 3.52 (s, 2H), 3.06 (d, J = 15.2 Hz, 2H), 2.53 (d, J = 15.2 Hz, 2H) |
| 191 | (RS)-1-(3-(1',2'-dihydrospiro[cyclopropane-1,3'-pyrrolo[2,3-b]pyridin]-5'-yl)-2-fluorobenzyl)-2-methylpyrrolidine-2-carbonitrile | n/a | L | (400 MHz, CDCl3) δ 7.79 (s, 1H), 7.46-7.41 (m, 2H), 7.31-7.28 (m, 1H partially under CDCl3 peak), 6.96 (s, 1H), 6.31 (brs, 1H), 3.82 (s, 2H), 3.55-3.47 (m, 2H), 2.69-2.64 (m, 1H), 2.20-1.96 (m, 3H partially under H2O peak), 1.94 (s, 3H partially under H2O peak), 1.18-1.11 (m, 4H) |

TABLE A1-continued

| No. | Structure/Name | LCMS R$_T$ (min) m/z Method | Prep Mtd | $^1$H NMR δ (ppm) |
|---|---|---|---|---|
| 192 | 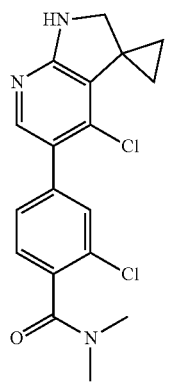<br>2-Chloro-4-(4'-chloro-1,2-dihydrospiro[cyclopentane-1,3'-pyrrolo[2,3-b]pyridin]-3-en-5'-yl)-N,N-dimethylbenzamide | 3.55<br>389.1<br>B | L | (400 MHz, DMSO-d$_6$) δ 7.76 (s, 1H), 7.52 (d, J = 1.2 Hz, 1H), 7.41-7.36 (m, 2H), 7.06 (s, 1H), 5.77 (s, 2H), 3.51 (s, 2H), 3.07 (d, J = 15.0 Hz, 2H), 3.02 (s, 3H), 2.82 (s, 3H), 2.56-2.50 (m, 2H, partially under the DMSO peak). |
| 193a | 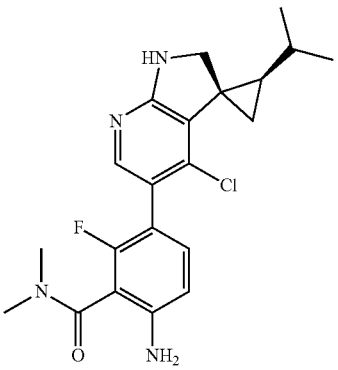<br>6-Amino-3-((1R,2R)-4'-chloro-2-isopropyl-1',2'-dihydrospiro[cyclopropane-1,3'-pyrrolo[2,3-b]pyridin]-5'-yl)-2-fluoro-N,N-dimethylbenzamide<br>first peak on SFC; absolute configuration arbitrarily assigned | 3.48<br>403.2<br>B | L | (400 MHz, CDCl3) δ 7.58 (s, 1H), 7.00 (t, J = 8.4 Hz, 1H), 6.52 (d, J = 7.8 Hz,, 1H), 4.68 (s, 1H), 4.38 (s, 2H), 3.76-3.69 (m, 1H), 3.57-3.50 (m, 1H), 3.12 (s, 3H), 3.01 (s, 3H), 2.00-1.92 (m, 1H), 1.81-1.69 (m, 1H), 1.65-1.55 (m, 1H), 1.07 (d, J = 7.1 Hz, 6H), 0.43 (dd, J = 6.2, 5.1 Hz, 1H). |

TABLE A1-continued

| No. | Structure/Name | LCMS R$_T$ (min) m/z Method | Prep Mtd | $^1$H NMR δ (ppm) |
|---|---|---|---|---|
| 193b | 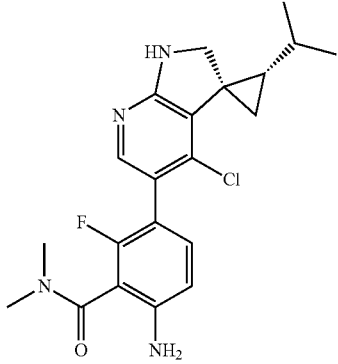<br>6-Amino-3-((1S,2S)-4'-chloro-2-isopropyl-1',2'-dihydrospiro[cyclopropane-1,3'-pyrrolo[2,3-b]pyridin]-5'-yl)-2-fluoro-N,N-dimethylbenzamide second peak on SFC; absolute configuration arbitrarily assigned | 3.48<br>403.2<br>B | L | (400 MHz, CDCl$_3$) δ 7.58 (s, 1H), 7.00 (t, J = 8.4 Hz, 1H), 6.52 (d, J = 7.8 Hz, 1H), 4.68 (s, 1H), 4.38 (s, 2H), 3.76-3.69 (m, 1H), 3.57-3.50 (m, 1H), 3.12 (s, 3H), 3.01 (s, 3H), 2.00-1.92 (m, 1H), 1.81-1.69 (m, 1H), 1.65-1.55 (m, 1H), 1.07 (d, J = 7.1 Hz, 6H), 0.43 (dd, J = 6.2, 5.1 Hz, 1H). |
| 194a | 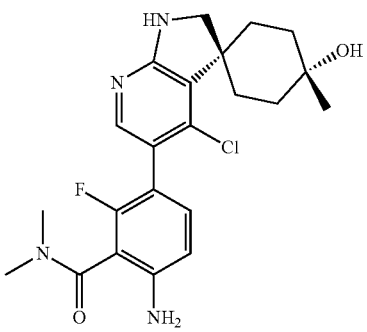<br>6-Amino-3-((1r,4r)-4'-chloro-4-hydroxy-4-methyl-1',2'-dihydrospiro[cyclohexane-1,3'-pyrrolo[2,3-b]pyridin]-5'-yl)-2-fluoro-N,N-dimethylbenzamide | 2.35<br>433.2<br>B | L | (400 MHz, DMSO-d$_6$) δ 7.56 (s, 1H), 6.96 (t, J = 8.5 Hz, 1H), 6.84 (s, 1H), 6.54 (d, J = 8.3 Hz, 1H), 5.37 (brs, 2H), 4.01 (s, 1H), 3.40 (s, 2H), 2.99 (s, 3H), 2.89 (s, 3H), 2.63-2.53 (m, 2H), 1.50-1.31 (m, 6H), 1.12 (s, 3H). |
| 194b | 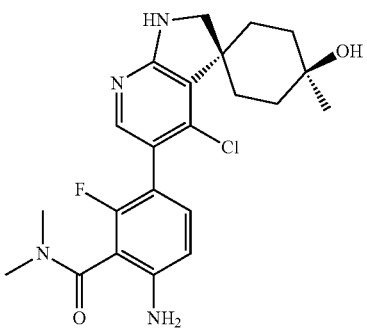<br>6-Amino-3-((1s,4s)-4'-chloro-4-hydroxy-4-methyl-1',2'-dihydrospiro[cyclohexane-1,3'-pyrrolo[2,3-b]pyridin]-5'-yl)-2-fluoro-N,N-dimethylbenzamide | 2.37<br>433.2<br>B | L | (400 MHz, DMSO-d$_6$) δ 7.58 (s, 1H), 6.95 (t, J = 8.5 Hz, 1H), 6.90 (s, 1H), 6.54 (d, J = 8.4 Hz, 1H), 5.37 (brs, 2H), 4.40 (s, 1H), 3.43 (s, 2H), 2.99 (s, 3H), 2.88 (s, 3H), 2.32-2.20 (m, 2H), 1.59-1.48 (m, 6H), 1.21 (s, 3H). |

TABLE A1-continued

| No. | Structure/Name | LCMS R$_T$ (min) m/z Method | Prep Mtd | $^1$H NMR δ (ppm) |
|---|---|---|---|---|
| 195b | 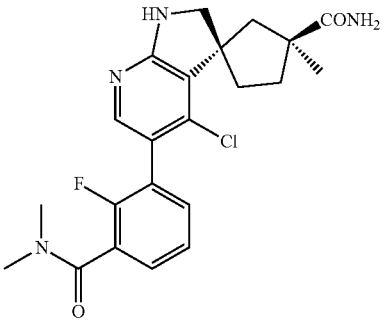<br>(1R*,3S*)-4'-Chloro-5'-(3-(dimethylcarbamoyl)-2-fluorophenyl)-3-methyl-1',2'-dihydrospiro[cyclopentane-1,3'-pyrrolo[2,3-b]pyridine]-3-carboxamide<br>second peak from SFC; absolute configuration arbitrarily assigned | 2.62<br>431.2<br>B | L | (400 MHz, DMSO-d$_6$) δ 7.69 (s, 1H), 7.42-7.30 (m, 3H), 7.24 (s, 1H), 6.99 (s, 1H), 6.89 (s, 1H), 3.49 (d, J = 9.4 Hz, 1H), 3.28 (d, J = 9.6 Hz, 1H), 3.01 (s, 3H), 2.87 (s, 3H), 2.48-2.40 (m, 2H), 2.24-2.15 (m, 1H), 1.91 (d, J = 13.3 Hz, 1H), 1.76-1.62 (m, 2H), 1.30 (s, 3H). |
| 196a | 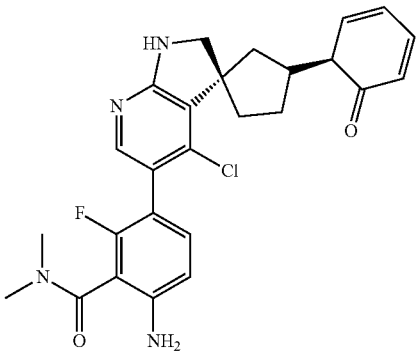<br>6-Amino-3-((1RS,3SR)-4'-chloro-3-(2-oxopyridin-1(2H)-yl)-1',2'-dihydrospiro[cyclopentane-1,3'-pyrrolo[2,3-b]pyridin-5'-yl)-2-fluoro-N,N-dimethylbenzamide | 2.48<br>482.1<br>A | L | (400 MHz, DMSO-d$_6$) δ 7.78 (d, J = 7.8 Hz, 1H), 7.64 (s, 1H), 7.41-7.36 (m, 1H), 6.99 (dt, J = 2.7, 8.5 Hz, 1H), 6.91 (s, 1H), 6.57 (d, J = 8.4 Hz, 1H), 6.36 (d, J = 9.1 Hz, 1H), 6.27 (t, J = 6.7 Hz, 1H), 5.42-5.33 & 5.40 (m & brs, 3H), 3.62 & 3.52 (ABq, J = 9.6 Hz, 2H), 3.00 (s, 3H), 2.97-2.91 (m, 1H), 2.90 (d, J = 4.8 Hz, 3H), 2.21-2.10 (m, 1H), 2.03-1.87 (m, 3H), 1.78-1.71 (m, 1H). |
| 197a | 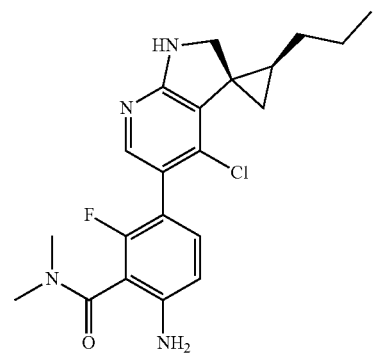<br>6-Amino-3-((1R,2S)-4'-chloro-2-propyl-1',2'-dihydrospiro[cyclopropane-1,3'-pyrrolo[2,3-b]pyridin]-5'-yl)-2-fluoro-N,N-dimethylbenzamide<br>first peak on SFC; absolute configuration arbitrarily assigned | 3.49<br>403.1<br>A | L | (400 MHz, DMSO-d$_6$) δ 7.48 (s, 1H), 6.97 (s, 1H), 6.92 (t, J = 8.5 Hz, 1H), 6.53 (d, J = 8.2 Hz, 1H), 5.37 (s, 2H), 3.58 (dd, J = 9.8, 2.7 Hz, 1H), 3.41 (d, J = 9.9 Hz, 1H), 2.98 (s, 3H), 2.86 (s, 3H), 1.94-1.84 (m, 1H), 1.79-1.70 (m, 1H), 1.48-1.34 (m, 3H), 1.26-1.13 (m, 1H), 0.92 (t, J = 6.8 Hz, 3H), 0.51 (t, J = 5.4 Hz, 1H). |

TABLE A1-continued

| No. | Structure/Name | LCMS R$_T$ (min) m/z Method | Prep Mtd | $^1$H NMR δ (ppm) |
|---|---|---|---|---|
| 197b | 6-Amino-3-((1S,2R)-4'-chloro-2-propyl-1',2'-dihydospiro[cyclopropane-1,3'-pyrrolo[2,3-b]pyridin]-5'-yl)-2-fluoro-N,N-dimethylbenzamide<br>second peak on SFC; absolute configuration arbitrarily assigned | 3.49<br>403.1<br>A | L | (400 MHz, DMSO-d$_6$) δ 7.48 (s, 1H), 6.97 (s, 1H), 6.92 (t, J = 8.5 Hz, 1H), 6.53 (d, J = 8.2 Hz, 1H), 5.37 (s, 2H), 3.58 (dd, J = 9.8, 2.7 Hz, 1H), 3.41 (d, J = 9.9 Hz, 1H), 2.98 (s, 3H), 2.86 (s, 3H), 1.94-1.84 (m, 1H), 1.79-1.70 (m, 1H), 1.48-1.34 (m, 3H), 1.26-1.13 (m, 1H), 0.92 (t, J = 6.8 Hz, 3H), 0.51 (t, J = 5.4 Hz, 1H). |
| 198a | 6-Amino-3-((1RS,2RS)-4'-chloro-2-(pyridin-4-yl)-1',2'-dihydrospiro[cyclopropane-1,3'-pyrrolo[2,3-b]pyridin]-5'-yl)-2-fluoro-N,N-dimethylbenzamide | 2.10<br>438.1<br>A | L | 1H NMR (400 MHz, CDCl3) δ 8.54 (d, J = 6.16 Hz, 2H), 7.67 (s, 1H), 7.10-7.05 (2H, m), 7.03 (t, J = 8.2 Hz, 1H), 6.56 (d, J = 8.2 Hz, 1H), 4.65 (s, 1H), 4.41 (s, 2H), 3.49 (dd, J = 9.8, 4.9 Hz, 1H), 3.29 (q, J = 7.2 Hz, 1H), 3.21 (d, J = 9.4 Hz, 1H), 3.15 (s, 3H), 3.03 (s, 3H), 2.54-2.45 (m, 1H), 1.36 (t, J = 6.4 Hz, 1H). |
| 199a | (1R,3S)-5'-(3-(Dimethylcarbamoyl)-2-fluorophenyl)-3-methyl-1',2'-dihydrospiro[cyclopentane-1,3'-pyrrolo[2,3-b]pyridine]-3-carboxamide<br>first peak on SFC; absolute configuration arbitrarily assigned | 2.32<br>397.3<br>B | L | (400 MHz, DMSO-d$_6$) δ 7.91 (t, J = 1.8 Hz, 1H), 7.55 (dt, J = 2.3, 7.6 Hz, 1H), 7.48 (t, J = 1.7 Hz, 1H), 7.33-7.25 (m, 2H), 7.19 (s, 1H), 6.84 (s, 1H), 6.62 (s, 1H), 3.41 (d, J = 9.3 Hz, 1H), 3.25 (d, J = 9.5 Hz, 1H), 3.01 (s, 3H), 2.87 (s, 3H), 2.5 (m, 1H, under DMSO), 2.24-2.15 (m, 1H), 1.96-1.87 (m, 1H), 1.84-1.76 (m, 1H), 1.66-1.58 (m, 2H), 1.32-1.31 (m, 3H), 1.27-1.21 (m, 1H). |

TABLE A1-continued

| No. | Structure/Name | LCMS R$_T$ (min) m/z Method | Prep Mtd | $^1$H NMR δ (ppm) |
|---|---|---|---|---|
| 199b | 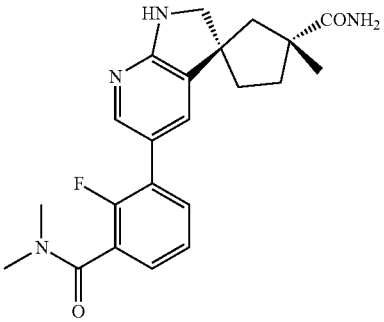<br>(1S,3R)-5'-(3-(Dimethylcarbamoyl)-2-fluorophenyl)-3-methyl-1',2'-dihydrospiro[cyclopentane-1,3'-pyrrolo[2,3-b]pyridine]-3-carboxamide<br>second peak on SFC; absolute configuration arbitrarily assigned | 2.32<br>397.3<br>B | L | (400 MHz, DMSO-d$_6$) δ 7.91 (t, J = 1.8 Hz, 1H), 7.55 (dt, J = 2.3, 7.6 Hz, 1H), 7.48 (t, J = 1.7 Hz, 1H), 7.33-7.25 (m, 2H), 7.19 (s, 1H), 6.84 (s, 1H), 6.62 (s, 1H), 3.41 (d, J = 9.3 Hz, 1H), 3.25 (d, J = 9.5 Hz, 1H), 3.01 (s, 3H), 2.87 (s, 3H), 2.5 (m, 1H, under DMSO), 2.24-2.15 (m, 1H), 1.96-1.87 (m, 1H), 1.84-1.76 (m, 1H), 1.66-1.58 (m, 2H), 1.32-1.31 (m, 3H), 1.27-1.21 (m, 1H). |
| 200 | 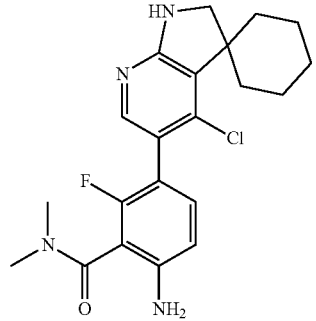<br>6-Amino-3-(4'-chloro-1',2'-dihydrospiro[cyclohexane-1,3'-pyrrolo[2,3-b]pyridin]-5'-yl)-2-fluoro-N,N-dimethylbenzamide | 3.34<br>403.2<br>B | L | (400 MHz, DMSO-d$_6$) δ δ 7.57 (s, 1H), 6.95 (t, J = 8.5 Hz, 1H), 6.89 (s, 1H), 6.54 (d, J = 8.3 Hz, 1H), 5.37 (brs, 2H), 3.42 (s, 2H), 2.99 (s, 3H), 2.88 (s, 3H), 2.18-2.08 (m, 2H), 1.66-1.59 (m, 5H), 1.41-1.31 (m, 2H), 1.25-1.15 (m, 1H). |
| 201a | 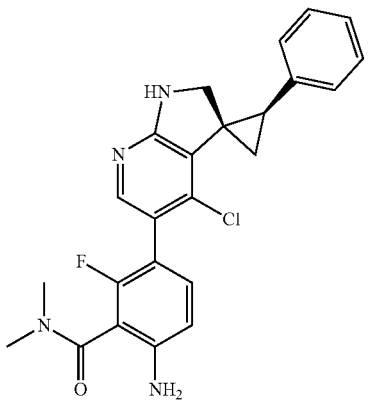<br>6-Amino-3-((1RS,2RS)-4'-chloro-2-phenyl-1',2'-dihydrospiro[cyclopropane-1,3'-pyrrolo[2,3-b]pyridin]-5'-yl)-2-fluoro-N,N-dimethylbenzamide | 3.65<br>437.2<br>B | L | 1H NMR (400 MHz, CDCl3) δ 7.62 (s, 1H), 7.33 (t, J = 7.4 Hz, 2H), 7.24 (t, J = 4.5 Hz, 1H), 7.20-7.15 (m, 2H), 7.03 (t, J = 8.2 Hz, 1H), 6.55 (d, J = 8.2 Hz, 1H), 4.72 (s, 1H), 4.40 (s, 2H), 3.41 (dd, J = 9.4, 6.6 Hz, 1H), 3.33 (q, J = 7.5 Hz, 1H), 3.22 (d, J = 9.0 Hz, 1H), 3.14 (s, 3H), 3.03 (d, J = 2.2 Hz, 3H), 2.45-2.38 (m, 1H), 1.29 (t, J = 6.7 Hz, 1H). |

| No. | Structure/Name | LCMS $R_T$ (min) m/z Method | Prep Mtd | $^1$H NMR δ (ppm) |
|---|---|---|---|---|
| 202b | 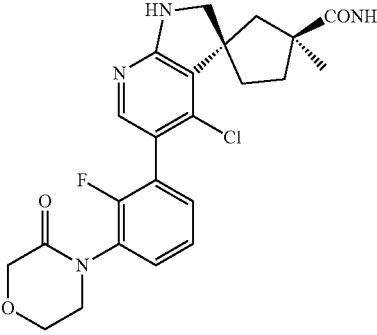<br>(1R,3S)-4'-Chloro-5'-(2-fluoro-3-(3-oxomorpholino)phenyl)-3-methyl-1',2'-dihydrospiro[cyclopentane-1,3'-pyrrolo[2,3-b]pyridine]-3-carboxamide<br>second peak on SFC; absolute configuration arbitrarily assigned | 2.56<br>459.2<br>B | L | (400 MHz, DMSO-$d_6$) δ 7.67 (s, 1H), 7.50-7.45 (m, 1H), 7.36-7.28 (m, 2H), 7.22 (s, 1H), 6.98 (s, 1H), 6.89 (s, 1H), 4.23 (s, 2H), 3.99 (t, J = 5.1 Hz, 2H), 3.69 (t, J = 5.0 Hz, 2H), 3.49 (d, J = 9.3 Hz, 1H), 3.28 (d, J = 9.4 Hz, 1H), 2.43-2.5 (m, 1H, under DMSO), 2.46 (d, J = 13.6 Hz, 1H), 2.25-2.15 (m, 1H), 1.95-1.89 (m, 1H), 1.75-1.62 (m, 2H), 1.30 (s, 3H). |
| 203 | 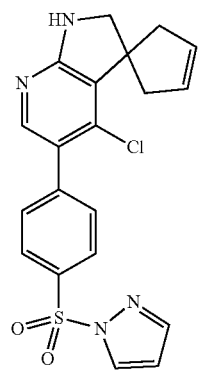<br>5'-(4-((1H-Pyrazol-1-yl)sulfonyl)phenyl)-4'-chloro-1',2'-dihydrospiro[cyclopentane-1,3'-pyrrolo[2,3-b]pyridin]-3-ene | 4.18<br>413.1<br>B | L | (400 MHz, DMSO-$d_6$) δ 8.52 (d, J = 2.6 Hz, 1H), 7.99 (d, J = 9.0 Hz, 2H), 7.93 (d, J = 1.2 Hz, 1H), 7.76 (s, 1H), 7.68 (d, J = 9.0 Hz, 2H), 7.18 (s, 1H), 6.64 (dd, J = 1.6, 2.8 Hz, 1H), 5.77 (s, 2H), 3.52 (s, 2H), 3.05 (d, J = 15.1 Hz, 2H), 2.53 (m, 2H partially under DMSO peak). |
| 204 | 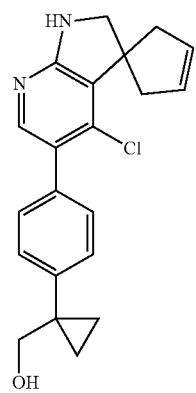<br>(1-(4-(4'-Chloro-1',2'-dihydrospiro[cyclopentane-1,3'-pyrrolo[2,3-b]pyridin]-3-en-5'-yl)phenyl)cyclopropyl)methanol | 3.53<br>353.2<br>B | L | (400 MHz, DMSO-$d_6$) δ 7.67 (s, 1H), 7.33 (d, J = 8.2 Hz, 2H), 7.26 (d, J = 8.2 Hz, 2H), 6.87 (s, 1H), 5.76 (s, 2H), 4.69 (t, J = 5.4 Hz, 1H), 3.55 (d, J = 5.0 Hz, 2H), 3.49 (s, 2H), 3.06 (d, J = 15.1 Hz, 2H), 2.52 (m, 2H assumed under DMSO peak), 0.85 (m, 2H), 0.76 (m, 2H). |

TABLE A1-continued

| No. | Structure/Name | LCMS R$_T$ (min) m/z Method | Prep Mtd | $^1$H NMR δ (ppm) |
|---|---|---|---|---|
| 205 | 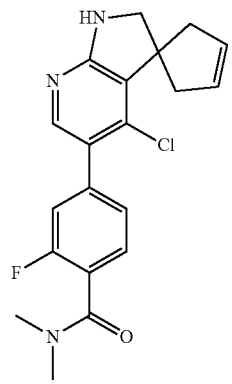<br>4-(4'-Chloro-1',2'-dihydrospiro[cyclopentane-1,3'-pyrrolo[2,3-b]pyridin]-3-en-5'-yl)-2-fluoro-N,N-dimethylbenzamide | 3.49<br>372.2<br>B | L | (400 MHz, DMSO-d$_6$) δ 7.76 (s, 1H), 7.41 (dd, J = 7.7, 7.7 Hz, 1H), 7.32 (dd, J = 1.4, 10.8 Hz, 1H), 7.28 (dd, J = 1.6, 7.8 Hz, 1H), 7.06 (bs, 1H), 5.77 (s, 2H), 3.51 (s, 2H), 3.08 (d, J = 15.2 Hz, 2H), 3.02 (s, 3H), 2.89 (d, J = 0.9 Hz, 3H), 2.52 (d, J = 15.2 Hz, 2H) |
| 206 | 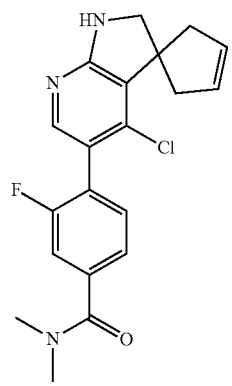<br>4-(4'-Chloro-1',2'-dihydrospiro[cyclopentane-1,3'-pyrrolo[2,3-b]pyridin]-3-en-5'-yl)-3-fluoro-N,N-dimethylbenzamide | 3.45<br>372.2<br>B | L | (400 MHz, DMSO-d$_6$) δ 7.71 (s, 1H), 7.40 (dd, J = 7.6, 7.6 Hz, 1H), 7.33 (dd, J = 1.4, 10.1 Hz, 1H), 7.28 (dd, J = 1.6, 7.7 Hz, 1H), 7.07 (bs, 1H), 5.77 (s, 2H), 3.52 (s, 2H), 3.05 (d, J = 15.4 Hz, 2H), 2.98 (s, 3H), 2.95 (s, 3H), 2.53 (d, J = 15.4 Hz, 2H) |

| No. | Structure/Name | LCMS R_T (min) m/z Method | Prep Mtd | $^1$H NMR δ (ppm) |
|---|---|---|---|---|
| 207 | 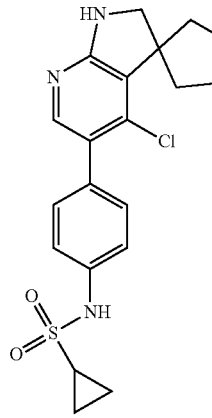<br>N-(4-(4'-Chloro-1',2'-dihydrospiro[cyclopentane-1,3'-pyrrolo[2,3-b]pyridin]-3-en-5'-yl)phenyl)cyclopropanesulfonamide | 3.50<br>402.2<br>B | L | (400 MHz, DMSO-d$_6$) δ 9.80 (bs, 1H), 7.68 (s, 1H), 7.31 (ddd, J = 2.2, 2.2, 8.7 Hz, 2H), 7.25 (ddd, J = 2.2, 2.2, 8.7 Hz, 2H), 6.89 (bs, 1H), 5.76 (s, 2H), 3.48 (s, 2H), 3.06 (d, J = 15.1 Hz, 2H), 2.70-2.62 (m, 1H), 2.52 (d, J = 15.1 Hz, 2H), 0.97-0.94 (m, 4H) |
| 208 | 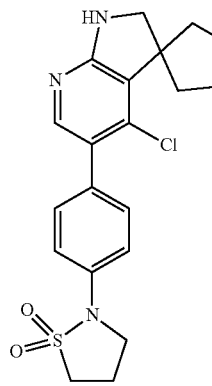<br>2-(4-(4'-Chloro-1',2'-dihydrospiro[cyclopentane-1,3'-pyrrolo[2,3-b]pyridin]-3-en-5'-yl)phenyl)isothiazolidine 1,1-dioxide | 3.44<br>402.2<br>B | L | (400 MHz, DMSO-d$_6$) δ 7.69 (s, 1H), 7.37 (ddd, J = 2.3, 2.3, 9.0 Hz, 2H), 7.24 (ddd, J = 2.4, 2.4, 9.1 Hz, 2H), 6.91 (bs, 1H), 5.76 (s, 2H), 3.78 (app t, J = 6.5 Hz, 2H), 3.53 (app t, J = 7.4 Hz, 2H), 3.50 (d, J = 0.9 Hz, 2H), 3.06 (d, J = 15.1 Hz, 2H), 2.51 (d, J = 15.1 Hz, 2H), 2.46-2.37 (m, 2H) |
| 209 | 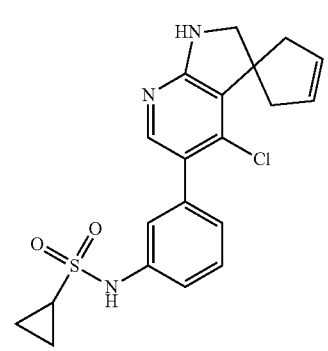<br>N-(3-(4'-Chloro-1',2'-dihydrospiro[cyclopentane-1,3'-pyrrolo[2,3-b]pyridin]-3-en-5'-yl)phenyl)cyclopropanesulfonamide | 3.58<br>402.2<br>B | L | (400 MHz, DMSO-d$_6$) δ 9.76 (bs, 1H), 7.69 (s, 1H), 7.34 (dd, J = 7.8, 7.8 Hz, 1H), 7.21-7.17 (m, 2H), 7.05 (ddd, J = 1.2, 1.2, 7.7 Hz, 1H), 6.95 (bs, 1H), 5.77 (s, 2H), 3.50 (s, 2H), 3.06 (d, J = 15.0 Hz, 2H), 2.68-2.58 (m, 1H), 2.52 (d, J = 15.1 Hz, 2H), 0.93-0.90 (m, 4H) |

TABLE A1-continued

| No. | Structure/Name | LCMS R_T (min) m/z Method | Prep Mtd | $^1$H NMR δ (ppm) |
|---|---|---|---|---|
| 210 | N-(3-(4'-Chloro-1',2'-dihydrospiro[cyclopentane-1,3'-pyrrolo[2,3-b]pyridin]-3-en-5'-yl)phenyl)methanesulfonamide | 3.32 376.1 B | L | (400 MHz, DMSO-d$_6$) δ 9.82 (bs, 1H), 7.70 (s, 1H), 7.36 (dd, J = 7.9, 7.9 Hz, 1H), 7.19-7.16 (m, 2H), 7.07 (ddd, J = 1.2, 1.2, 7.7 Hz, 1H), 6.96 (bs, 1H), 5.77 (s, 2H), 3.50 (s, 2H), 3.06 (d, J = 15.2 Hz, 2H), 3.00 (s, 3H), 2.52 (d, J = 15.2 Hz, 2H) |
| 211 | N-(3-(4'-Chloro-1',2'-dihydrospiro[cyclopentane-1,3'-pyrrolo[2,3-b]pyridin]-3-en-5'-yl)benzyl)acetamide | 3.09 354.2 B | L | (400 MHz, DMSO-d$_6$) δ 8.35 (bt, J = 5.6 Hz, 1H), 7.68 (s, 1H), 7.38-7.33 (m, 1H), 7.24-7.20 (m, 3H), 6.92 (bs, 1H), 5.77 (s, 2H), 4.28 (d, J = 5.9 Hz, 2H), 3.50 (s, 2H), 3.06 (d, J = 15.1 Hz, 2H), 2.51 (d, J = 15.2 Hz, 2H), 1.87 (s, 3H) |
| 212 | N-(4-(4'-Chloro-1',2'-dihydrospiro[cyclopentane-1,3'-pyrrolo[2,3-b]pyridin]-3-en-5'-yl)benzyl)acetamide | 3.02 354.2 B | L | (400 MHz, DMSO-d$_6$) δ 8.37 (bt, J = 5.8 Hz, 1H), 7.68 (s, 1H), 7.30-7.28 (m, 4H), 6.90 (bs, 1H), 5.76 (s, 2H), 4.27 (d, J = 5.9 Hz, 2H), 3.49 (s, 2H), 3.06 (d, J = 15.1 Hz, 2H), 2.52 (d, J = 15.1 Hz, 2H), 1.88 (s, 3H) |

TABLE A1-continued

| No. | Structure/Name | LCMS R_T (min) m/z Method | Prep Mtd | $^1$H NMR δ (ppm) |
|---|---|---|---|---|
| 213 | 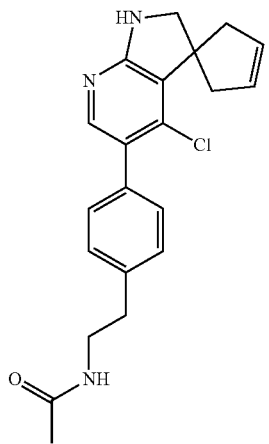<br>N-(4-(4'-chloro-1',2'-dihydrospiro[cyclopentane-1,3'-pyrrolo[2,3-b]pyridin-3-en-5'-yl)phenethyl)acetamide | 3.1<br>368.2<br>B | L | (400 MHz, DMSO-d$_6$) δ 7.96 (t, J = 5.4 Hz, 1H), 7.68 (s, 1H), 7.29 (d, J = 8.3 Hz, 2H), 7.24 (d, J = 8.3 Hz, 2H), 6.89 (s, 1H), 5.76 (s, 2H), 3.49 (s, 2H), 3.28 (dd, J = 7.2, 13.4 Hz, 2H), 3.06 (d, J = 15.1 Hz, 2H), 2.73 (t, J = 7.5 Hz, 2H), 2.52 (m, 2H assumed under DMSO peak), 1.80 (s, 3H). |
| 214 | 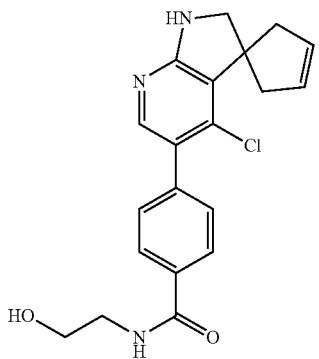<br>4-(4'-Chloro-1',2'-dihydrospiro[cyclopentane-1,3-pyrrolo[2,3-b]pyridin]-3'-en-5'-yl)-N-(2-hydroxyethyl)benzamide | 2.78<br>370.2<br>B | L | (400 MHz, DMSO-d$_6$) δ 8.46 (t, J = 5.6 Hz, 1H), 7.88 (td, J = 2.0, 8.5 Hz, 2H), 7.74-7.73 (s, 1H), 7.45 (td, J = 1.8, 8.5 Hz, 2H), 7.01 (s, 1H), 5.77 (s, 2H), 4.73 (t, J = 5.6 Hz, 1H), 3.53-3.50 (m, 4H), 3.07 (d, J = 15.1 Hz, 2H), 2.53 (m, 2H assumed under DMSO peak). |

TABLE A1-continued

| No. | Structure/Name | LCMS R_T (min) m/z Method | Prep Mtd | $^1$H NMR δ (ppm) |
|---|---|---|---|---|
| 215 | 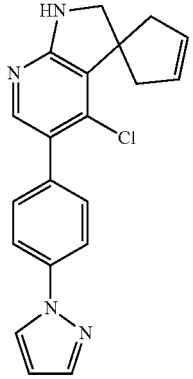<br>5'-(4-(1H-Pyrazol-1-yl)phenyl)-4'-chloro-1',2'-dihydro-spiro[cyclopentane-1,3'-pyrrolo[2,3-b]pyridin]-3-ene | 3.89<br>349.2<br>B | L | (400 MHz, DMSO-d$_6$) δ 8.54 (d, J = 2.3 Hz, 1H), 7.88 (td, J = 2.3, 9.3 Hz, 2H), 7.76 (d, J = 2.6 Hz, 2H), 7.49 (td, J = 2.3, 9.2 Hz, 2H), 6.97 (s, 1H), 6.56 (dd, J = 1.9, 2.4 Hz, 1H), 5.77 (s, 2H), 3.51 (s, 2H), 3.08 (d, J = 15.2 Hz, 2H), 2.53 (m, 2H partially under DMSO peak). |
| 216 | 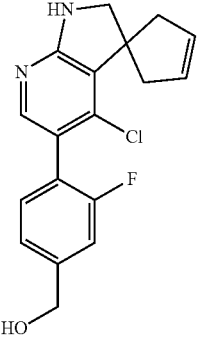<br>(4-(4'-Chloro-1',2'-dihydrospiro[cyclo-pentane-1,3'-pyrrolo[2,3-b]pyridin]-3-en-5'-yl)-3-fluorophenyl)methanol | 3.19<br>330.9<br>A | L | (400 MHz, DMSO-d$_6$) δ 7.67 (s, 1H), 7.27 (t, J = 7.7 Hz, 1H), 7.18 (d, J = 9.2 Hz, 2H), 6.99 (s, 1H), 5.76 (s, 2H), 5.34 (s, 1H), 4.54 (s, 2H), 3.50 (s, 2H), 3.03 (d, J = 15.2 Hz, 2H), 2.52 (m, 2H partially under DMSO peak). |
| 217a | 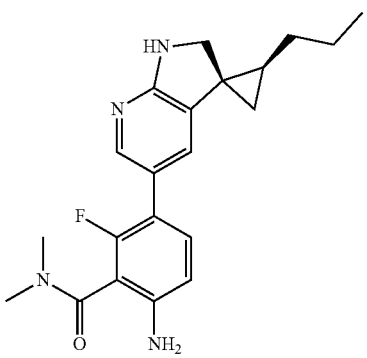<br>6-Amino-2-fluoro-N,N-dimethyl-3-((1R,2S)-2-propyl-1',2'-dihydrospiro[cyclopropane-1,3'-pyrrolo[2,3-b]pyridin]-5'-yl)benzamide<br>first peak on SFC; absolute configuration arbitrarily assigned | 3.07<br>369.1<br>A | L | 1H NMR (400 MHz, CDCl3) δ 7.84 (t, J = 1.5 Hz, 1H), 7.14 (t, J = 8.5 Hz, 1H), 6.81 (t, J = 1.9 Hz, 1H), 6.54 (d, J = 8.6 Hz, 1H), 4.59 (s, 1H), 4.25 (s, 2H), 3.75 (d, J = 9.2 Hz, 1H), 3.54 (d, J = 8.8 Hz, 1H), 3.14 (s, 3H), 2.99 (d, J = 1.9 Hz, 3H), 1.53-1.40 (m, 3H), 1.22-1.14 (m, 3H), 0.99-0.92 (m, 3H), 0.64-0.58 (m, 1H). |

TABLE A1-continued

| No. | Structure/Name | LCMS R$_T$ (min) m/z Method | Prep Mtd | $^1$H NMR δ (ppm) |
|---|---|---|---|---|
| 217b | 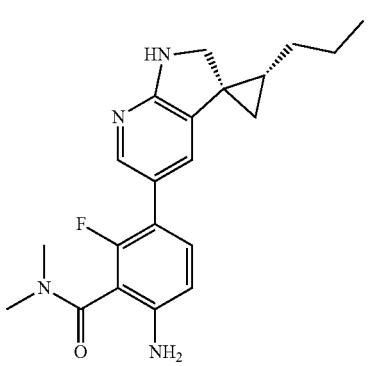<br>6-Amino-2-fluoro-N,N-dimethyl-3-((1S,2R)-2-propyl-1′,2′-dihydrospiro[cyclopropane-1,3′-pyrrolo[2,3-b]pyridin]-5′-yl)benzamide<br>second peak on SFC; absolute configuration arbitrarily assigned | 3.07<br>369.1<br>A | L | 1H NMR (400 MHz, CDCl3) δ 7.84 (t, J = 1.5 Hz, 1H), 7.14 (t, J = 8.5 Hz, 1H), 6.81 (t, J = 1.9 Hz, 1H), 6.54 (d, J = 8.6 Hz, 1H), 4.59 (s, 1H), 4.25 (s, 2H), 3.75 (d, J = 9.2 Hz, 1H), 3.54 (d, J = 8.8 Hz, 1H), 3.14 (s, 3H), 2.99 (d, J = 1.9 Hz, 3H), 1.53-1.40 (m, 3H), 1.22-1.14 (m, 3H), 0.99-0.92 (m, 3H), 0.64-0.58 (m, 1H). |
| 217c | 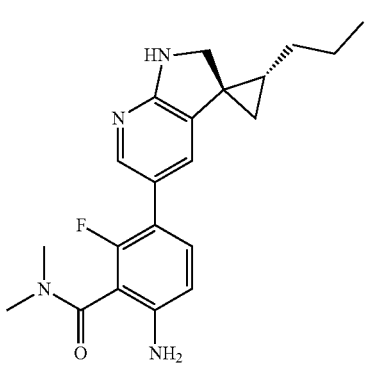<br>6-Amino-2-fluoro-N,N-dimethyl-3-((1R,2R)-2-propyl-1′,2′-dihydrospiro[cyclopropane-1,3′-pyrrolo[2,3-b]pyridin]-5′-yl)benzamide<br>first peak on SFC; absolute configuration arbitrarily assigned | 2.96<br>369.2<br>A | L | (400 MHz, CDCl3) δ 7.86 (s, 1H), 7.19-7.10 (m, 1H), 6.97 (s, 1H), 6.55 (d, J = 8.7 Hz, 1H), 4.57 (s, 1H), 4.25 (s, 2H), 3.77 (dd, J = 8.6, 1.9 Hz, 1H), 3.43 (d, J = 8.64 Hz, 1H), 3.15 (s, 3H), 3.00 (dd, J = 7.1, 1.8 Hz, 3H), 1.48-1.19 (m, 4H), 1.16-1.06 (m, 2H), 0.90-0.78 (m, 4H). |

TABLE A1-continued

| No. | Structure/Name | LCMS R$_T$ (min) m/z Method | Prep Mtd | $^1$H NMR δ (ppm) |
|---|---|---|---|---|
| 217d | 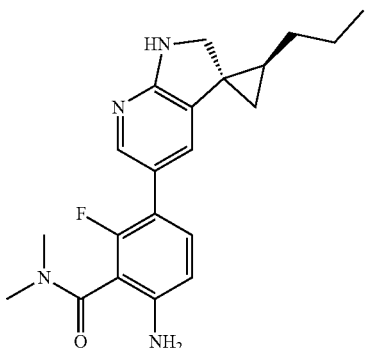<br>6-Amino-2-fluoro-N,N-dimethyl-3-((1S,2S)-2-propyl-1',2'-dihydrospiro[cyclopropane-1,3'-pyrrolo[2,3-b]pyridin]-5'-yl)benzamide<br>second peak on SFC; absolute configuration arbitrarily assigned | 2.96<br>369.2<br>A | L | (400 MHz, CDCl3) δ 7.86 (s, 1H), 7.19-7.10 (m, 1H), 6.97 (s, 1H), 6.55 (d, J = 8.7 Hz, 1H), 4.57 (s, 1H), 4.25 (s, 2H), 3.77 (dd, J = 8.6, 1.9 Hz, 1H), 3.43 (d, J = 8.64 Hz, 1H), 3.15 (s, 3H), 3.00 (dd, J = 7.1, 1.8 Hz, 3H), 1.48-1.19 (m, 4H), 1.16-1.06 (m, 2H), 0.90-0.78 (m, 4H). |
| 218 | 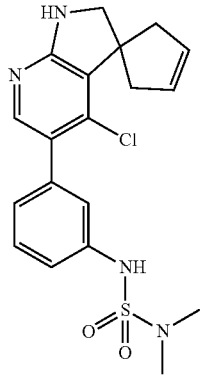<br>N-(3-(4'-Chloro-1',2'-dihydrospiro[cyclo-pentane-1,3'-pyrrolo[2,3-b]pyridin]-3-en-5'-yl)phenyl)-N',N'-dimethylsulfamide | 3.51<br>405.1<br>A | L | (400 MHz, DMSO-d$_6$) δ 9.94 (bs, 1H), 7.67 (s, 1H), 7.35-7.30 (m, 1H), 7.18 (m, 2H), 7.02 (d, J = 7.7 Hz, 1H), 6.94 (s, 1H), 5.76 (s, 2H), 3.50 (s, 2H), 3.05 (d, J = 15.1 Hz, 2H), 2.71-2.70 (m, 6H), 2.52 (m, 2H partially under DMSO peak). |
| 219 | 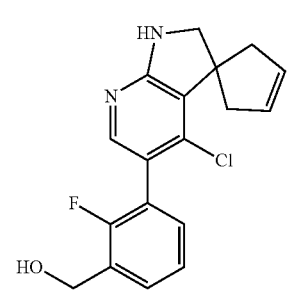<br>(3-(4'-Chloro-1',2'-dihydrospiro[cyclopentane-1,3'-pyrrolo[2,3-b]pyridin]-3-en-5'-yl)-2-fluorophenyl)methanol | 3.18<br>331<br>A | L | (400 MHz, DMSO-d$_6$) δ 7.66 (s, 1H), 7.49 (dt, J = 2.5, 6.9 Hz, 1H), 7.26-7.17 (m, 2H), 6.98 (s, 1H), 5.77 (s, 2H), 5.29 (t, J = 5.5 Hz, 1H), 4.57 (d, J = 5.0 Hz, 2H), 3.51 (s, 2H), 3.03 (d, J = 15.3 Hz, 2H), 2.53 (m, 2H partially under DMSO peak). |

TABLE A1-continued

| No. | Structure/Name | LCMS R_T (min) m/z Method | Prep Mtd | $^1$H NMR δ (ppm) |
|---|---|---|---|---|
| 220 | 4'-Chloro-5'-(4-(((tetrahydro-2H-pyran-4-yl)oxy)methyl)phenyl)-1',2'-dihydro-spiro[cyclopentane-1,3'-pyrrolo[2,3-b]pyridin]-3-ene | 3.82 397.1 A | L | (400 MHz, DMSO-d$_6$) δ 7.69 (s, 1H), 7.37 (d, J = 8.2 Hz, 2H), 7.33 (d, J = 8.2 Hz, 2H), 6.90 (s, 1H), 5.76 (s, 2H), 4.55 (s, 2H), 3.86-3.79 (m, 2H), 3.65-3.57 (m, 1H), 3.49 (s, 2H), 3.40-3.33 (m, 2H), 3.06 (d, J = 15.1 Hz, 2H), 2.53 (m, 2H partially under DMSO peak), 1.94-1.88 (m, 2H), 1.53-1.43 (m, 2H). |
| 221 | 4-(4'-Chloro-1',2'-dihydrospiro[cyclopentane-1,3'-pyrrolo[2,3-b]pyridin]-3-en-5'-yl)-N-(2-cyanoethyl)benzamide | 3.07 379.1 A | L | (400 MHz, DMSO-d$_6$) δ 8.87 (t, J = 5.7 Hz, 1H), 7.89 (d, J = 8.5 Hz, 2H), 7.74 (s, 1H), 7.49 (d, J = 8.2 Hz, 2H), 7.01 (s, 1H), 5.77 (s, 2H), 3.53-3.49 (m, 4H), 3.07 (d, J = 15.1 Hz, 2H), 2.79 (t, J = 6.5 Hz, 2H), 2.53 (m, 2H partially under DMSO peak). |

TABLE A1-continued

| No. | Structure/Name | LCMS R$_T$ (min) m/z Method | Prep Mtd | $^1$H NMR δ (ppm) |
|---|---|---|---|---|
| 222 | 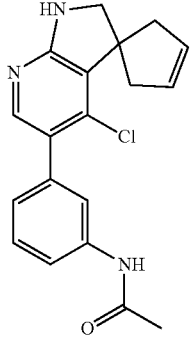<br>N-(3-(4'-Chloro-1',2'-dihydrospiro[cyclopentane-1,3'-pyrrolo[2,3-b]pyridin]-3-en-5'-yl)phenyl)acetamide | 3.09<br>340<br>A | L | (400 MHz, DMSO-d$_6$) δ 9.97 (s, 1H), 7.67 (s, 1H), 7.59-7.54 (m, 2H), 7.32 (t, J = 7.9 Hz, 1H), 7.00 (d, J = 7.8 Hz, 1H), 6.91 (s, 1H), 5.77 (s, 2H), 3.50 (s, 2H), 3.06 (d, J = 15.1 Hz, 2H), 2.52 (m, 2H partially under DMSO peak), 2.04 (s, 3H). |
| 223 | 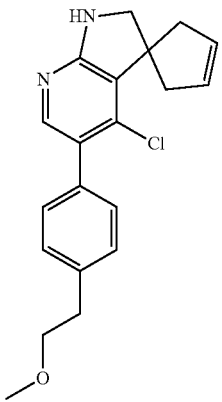<br>4'-Chloro-5'-(4-(2-methoxyethyl)phenyl)-1',2'-dihydrospiro[cyclopentane-1,3'-pyrrolo[2,3-b]pyridin]-3-ene | 3.85<br>341.1<br>A | L | (400 MHz, DMSO-d$_6$) δ 7.69 (s, 1H), 7.27 (s, 4H), 6.87 (s, 1H), 5.77 (s, 2H), 3.57 (t, J = 6.8 Hz, 2H), 3.49 (s, 2H), 3.26 (s, 3H), 3.06 (d, J = 15.1 Hz, 2H), 2.83 (t, J = 6.8 Hz, 2H), 2.50 (m, 2H assumed under DMSO peak). |
| 224 | 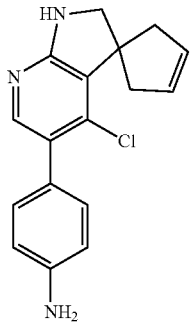<br>4-(4'-Chloro-1',2'-dihydrospiro[cyclopentane-1,3'-pyrrolo[2,3-b]pyridin]-3-en-5'-yl)aniline | 2.77<br>298<br>A | L | (400 MHz, DMSO-d$_6$) δ 7.62 (s, 1H), 6.99 (d, J = 8.9 Hz, 2H), 6.69 (s, 1H), 6.58 (d, J = 8.6 Hz, 2H), 5.76 (s, 2H), 5.13 (s, 2H), 3.46 (s, 2H), 3.05 (d, J = 15.1 Hz, 2H), 2.48 (m, 2H partially under DMSO peak). |

TABLE A1-continued

| No. | Structure/Name | LCMS R_T (min) m/z Method | Prep Mtd | $^1$H NMR δ (ppm) |
|---|---|---|---|---|
| 225 | 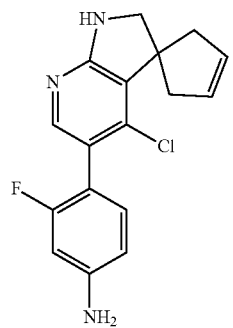<br>4-(4'-Chloro-1',2'-dihydrospiro[cyclopentane-1,3'-pyrrolo[2,3-b]pyridin]-3-en-5'-yl)-3-fluoroaniline | 3.17<br>316<br>A | L | (400 MHz, DMSO-d$_6$) δ 7.59 (s, 1H), 6.89 (t, J = 8.5 Hz, 1H), 6.80 (s, 1H), 6.42-6.33 (m, 2H), 5.76 (s, 2H), 5.47 (s, 2H), 3.48 (s, 2H), 3.02 (d, J = 15.1 Hz, 2H), 2.47 (m, 2H partially under DMSO peak). |
| 226 | 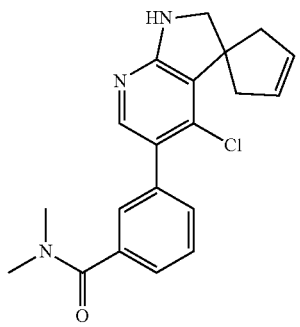<br>3-(4'-Chloro-1',2'-dihydrospiro[cyclopentane-1,3'-pyrrolo[2,3-b]pyridin]-3-en-5'-yl)-N,N-dimethylbenzamide | 3.19<br>354<br>A | L | (400 MHz, DMSO-d$_6$) δ 7.73 (s, 1H), 7.51-7.45 (m, 1H), 7.43 (td, J = 1.6, 7.7 Hz, 1H), 7.39-7.35 (m, 2H), 6.96 (s, 1H), 5.76 (s, 2H), 3.50 (s, 2H), 3.06 (d, J = 15.1 Hz, 2H), 2.98 (s, 3H), 2.94 (s, 3H), 2.53 (m, 2H partially under DMSO peak). |
| 227 | 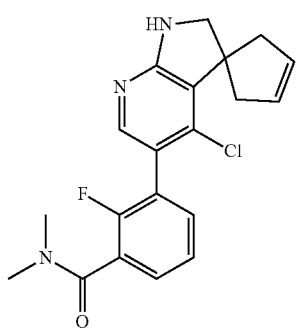<br>3-(4'-Chloro-1',2'-dihydrospiro[cyclopentane-1,3'-pyrrolo[2,3-b]pyridin]-3-en-5'-yl)-2-fluoro-N,N-dimethylbenzamide | 3.42<br>372.2<br>B | L | (400 MHz, DMSO-d$_6$) δ 7.72 (s, 1H), 7.42-7.38 (m, 2H), 7.32 (t, J = 7.5 Hz, 1H), 7.06 (s, 1H), 5.76 (s, 2H), 3.52 (s, 2H), 3.04 (d, J = 15.1 Hz, 2H), 3.00 (s, 3H), 2.86 (s, 3H), 2.53 (m, 2H partially under DMSO peak). |

TABLE A1-continued

| No. | Structure/Name | LCMS R_T (min) m/z Method | Prep Mtd | $^1$H NMR δ (ppm) |
|---|---|---|---|---|
| 228a | 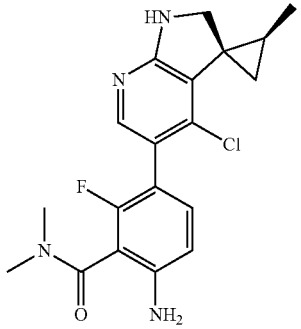<br>6-Amino-3-((1R,2S)-4'-chloro-2-methyl-1',2'-dihydrospiro[cyclopropane-1,3'-pyrrolo[2,3-b]pyridin]-5'-yl)-2-fluoro-N,N-dimethylbenzamide first peak on SFC; absolute configuration arbitrarily assigned | 2.95 375.0 A | L | 1H NMR (400 MHz, CDCl3) δ 7.59 (s, 1H), 6.99 (t, J = 8.0 Hz, 1H), 6.52 (d, J = 8.2 Hz, 1H), 4.69 (s, 1H), 4.38 (s, 2H), 3.77 (d, J = 8.6 Hz, 1H), 3.48 (d, J = 8.6 Hz, 1H), 3.13 (s, 3H), 3.01 (d, J = 2.2 Hz, 3H), 2.19-2.06 (m, 1H), 2.01-1.92 (m, 1H), 1.14 (d, J = 6.3 Hz, 3H), 0.39 (t, J = 5.5 Hz, 1H). |
| 228b | 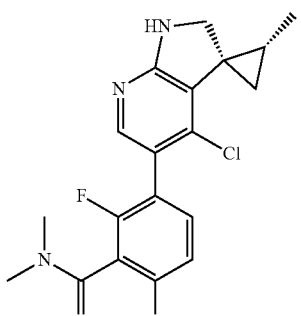<br>6-Amino-3-((1S,2R)-4'-chloro-2-methyl-1',2'-dihydrospiro[cyclopropane-1,3'-pyrrolo[2,3-b]pyridin]-5'-yl)-2-fluoro-N,N-dimethylbenzamide second peak on SFC; absolute configuration arbitrarily assigned | 2.95 375.0 A | L | 1H NMR (400 MHz, CDCl3) δ 7.59 (s, 1H), 6.99 (t, J = 8.0 Hz, 1H), 6.52 (d, J = 8.2 Hz, 1H), 4.69 (s, 1H), 4.38 (s, 2H), 3.77 (d, J = 8.6 Hz, 1H), 3.48 (d, J = 8.6 Hz, 1H), 3.13 (s, 3H), 3.01 (d, J = 2.2 Hz, 3H), 2.19-2.06 (m, 1H), 2.01-1.92 (m, 1H), 1.14 (d, J = 6.3 Hz, 3H), 0.39 (t, J = 5.5 Hz, 1H). |
| 229a | 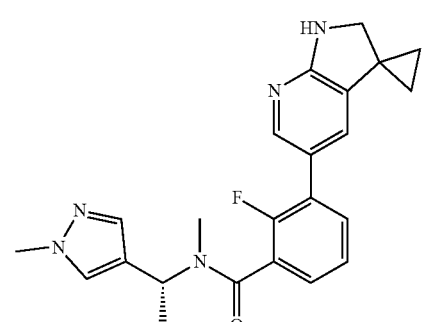<br>(R)-3-(1',2'-dihydrospiro[cyclopropane-1,3'-pyrrolo[2,3-b]pyridin]-5'-yl)-2-fluoro-N-methyl-N-(1-(1-methyl-1H-pyrazol-4-yl)ethyl)benzamide 1st peak SFC; absolute configuration arbitrarily assigned | 2.78 406.2, E | L | |

TABLE A1-continued

| No. | Structure/Name | LCMS R$_T$ (min) m/z Method | Prep Mtd | $^1$H NMR δ (ppm) |
|---|---|---|---|---|
| 229b | 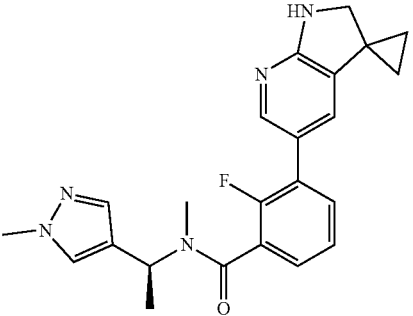<br>(S)-3-(1',2'-dihydrospiro[cyclopropane-1,3'-pyrrolo[2,3-b]pyridin]-5'-yl)-2-fluoro-N-methyl-N-(1-(1-methyl-1H-pyrazol-4-yl)ethyl)benzamide 2nd peak SFC; absolute configuration arbitrarily assigned | 3.02, 406.2 E | L | |
| 230 | 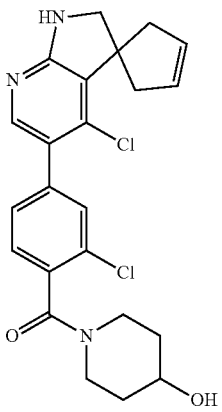<br>(2-Chloro-4-(4'-chloro-1',2'-dihydrospiro[cyclopentane-1,3'-pyrrolo[2,3-b]pyridin]-3-en-5'-yl)phenyl)(4-hydroxypiperidin-1-yl)methanone | 3.14 444.1 A | L | (400 MHz, DMSO-d$_6$) δ 7.76 (s, 1H), 7.52 (d, J = 1.4 Hz, 1H), 7.41-7.34 (m, 2H), 7.06 (s, 1H), 5.77 (s, 2H), 4.81 (d, J = 2.0 Hz, 1H), 4.12-4.03 (m, 2H), 3.76-3.72 (m, 1H), 3.52 (s, 2H), 3.17 (m, 1H), 3.11-3.02 (m, 3H), 2.53 (m, 2H partially under DMSO peak), 1.86-1.69 (m, 2H), 1.45-1.22 (m, 2H). |

TABLE A1-continued

| No. | Structure/Name | LCMS R_T (min) m/z Method | Prep Mtd | $^1$H NMR δ (ppm) |
|---|---|---|---|---|
| 231 | 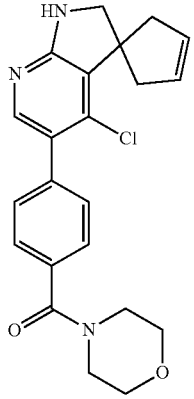<br>(4-(4'-Chloro-1',2'-dihydrospiro[cyclopentane-1,3'-pyrrolo[2,3-b]pyridin]-3-en-5'-yl)phenyl)(morpholino)methanone | 3.17 396 A | L | (400 MHz, DMSO-d$_6$) δ 7.73 (s, 1H), 7.45 (s, 4H), 6.99 (s, 1H), 5.78 (s, 2H), 3.51-3.41 (m, 8H), 3.07 (d, J = 15.1 Hz, 2H), 2.53 (m, 2H partially under DMSO peak). |
| 232 | 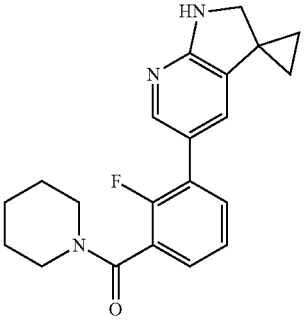<br>(3-(1',2'-dihydrospiro[cyclopropane-1,3'-pyrrolo[2,3-b]pyridin]-5'-yl)-2-fluorophenyl)(piperidin-1-yl)methanone | 3.27, 352.2, E | L | |
| 233 | 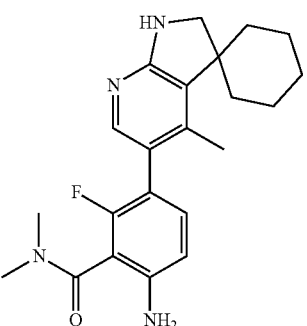<br>6-Amino-2-fluoro-N,N-dimethyl-3-(4'-methyl-1',2'-dihydrospiro[cyclohexane-1,3'-pyrrolo[2,3-b]pyridin]-5'-yl)benzamide | 3.11 383.1 A | L | (400 MHz, DMSO-d$_6$) δ 7.44 (s, 1H), 6.91 (t, J = 8.6 Hz, 1H), 6.55 (d, J = 8.3 Hz, 1H), 6.31 (s, 1H), 5.29 (s, 2H), 3.34 (m, 1H, partially under water peak), 3.17 (d, J = 5.3 Hz, 1H), 2.99 (s, 3H), 2.88 (s, 3H), 2.05 (s, 3H), 1.89 (d, J = 11.3 Hz, 2H), 1.69-1.60 (m, 5H), 1.39-1.25 (m, 3H). |

TABLE A1-continued

| No. | Structure/Name | LCMS R$_T$ (min) m/z Method | Prep Mtd | $^1$H NMR δ (ppm) |
|---|---|---|---|---|
| 234a | 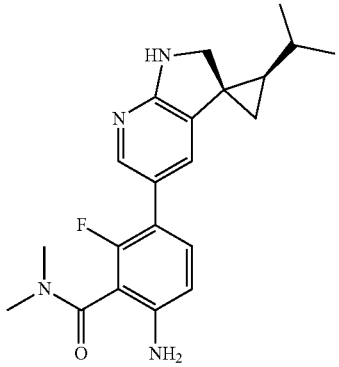<br>6-Amino-2-fluoro-3-((1R,2R)-2-isopropyl-1',2'-dihydrospiro[cyclopropane-1,3'-pyrrolo[2,3-b]pyridin]-5'-yl)-N,N-dimethylbenzamide<br>first peak on SFC; absolute configuration arbitrarily assigned | 2.94<br>369.0<br>A | L | (400 MHz, CDCl3) δ 7.85 (s, 1H), 7.14 (t, J = 8.7 Hz, 1H), 6.82 (s, 1H), 6.54 (d, J = 8.2 Hz, 1H), 4.66 (s, 1H), 4.26 (s, 2H), 3.76 (d, J = 9.0 Hz, 1H), 3.57 (d, J = 9.0 Hz, 1H), 3.14 (s, 3H), 3.00 (d, J = 2.1 Hz, 3H), 1.79-1.68 (m, 1H), 1.19-1.18 (m, 1H), 1.06 (d, J = 11.5 Hz, 6H), 1.00-0.91 (m, 1H), 0.66-0.60 (m, 1H). |
| 234b | 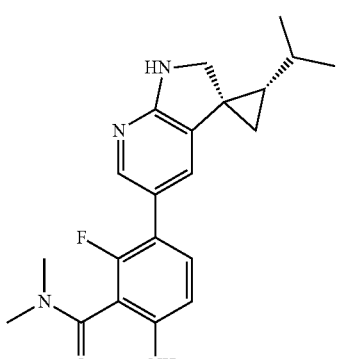<br>6-Amino-2-fluoro-3-((1S,2S)-2-isopropyl-1',2'-dihydrospiro[cyclopropane-1,3'-pyrrolo[2,3-b]pyridin]-5'-yl)-N,N-dimethylbenzamide<br>second peak on SFC; absolute configuration arbitrarily assigned | 2.97<br>369.0<br>A | L | (400 MHz, CDCl3) δ 7.85 (s, 1H), 7.14 (t, J = 8.7 Hz, 1H), 6.82 (s, 1H), 6.54 (d, J = 8.2 Hz, 1H), 4.66 (s, 1H), 4.26 (s, 2H), 3.76 (d, J = 9.0 Hz, 1H), 3.57 (d, J = 9.0 Hz, 1H), 3.14 (s, 3H), 3.00 (d, J = 2.1 Hz, 3H), 1.79-1.68 (m, 1H), 1.19-1.18 (m, 1H), 1.06 (d, J = 11.5 Hz, 6H), 1.00-0.91 (m, 1H), 0.66-0.60 (m, 1H). |

| No. | Structure/Name | LCMS R$_T$ (min) m/z Method | Prep Mtd | $^1$H NMR δ (ppm) |
|---|---|---|---|---|
| 234c | 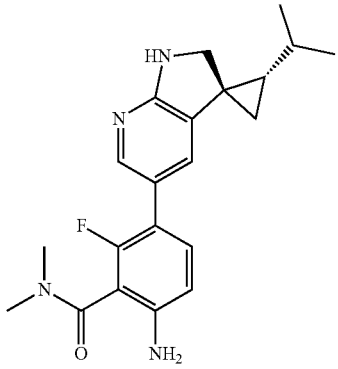<br>6-Amino-2-fluoro-3-((1R,2S)-2-isopropyl-1',2'-dihydrospiro[cyclopropane-1,3'-pyrrolo[2,3-b]pyridin]-5'-yl)-N,N-dimethylbenzamide<br>first peak on SFC; absolute configuration arbitrarily assigned | 2.87<br>369.0<br>A | L | (400 MHz, CDCl3) δ 7.87 (d, J = 6.2 Hz, 1H), 7.15 (q, J = 9.0 Hz, 1H), 6.99 (d, J = 12.2 Hz, 1H), 6.55 (d, J = 7.0 Hz, 1H), 4.58 (s, 1H), 4.24 (d, J = 6.2 Hz, 2H), 3.74 (dd, J = 8.6, 2.0 Hz, 1H), 3.42 (d, J = 8.2 Hz, 1H), 3.16 (s, 3H), 3.00 (s, 3H), 1.38-1.24 (m, 1H), 1.11-1.01 (m, 4H), 0.92-0.81 (m, 2H), 0.77 (dd, J = 10.6, 6.6 Hz, 3H). |
| 234d | 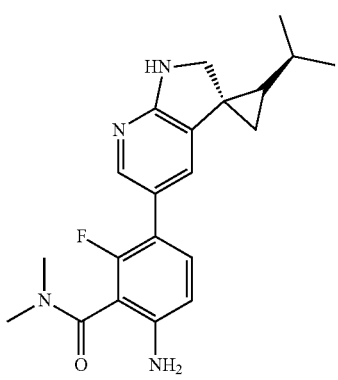<br>6-Amino-2-fluoro-3-((1S,2R)-2-isopropyl-1',2'-dihydrospiro[cyclopropane-1,3'-pyrrolo[2,3-b]pyridin]-5'-yl)-N,N-dimethylbenzamide<br>second peak on SFC; absolute configuration arbitrarily assigned | 2.87<br>369.0<br>A | L | (400 MHz, CDCl3) δ 7.87 (d, J = 6.2 Hz, 1H), 7.15 (q, J = 9.0 Hz, 1H), 6.99 (d, J = 12.2 Hz, 1H), 6.55 (d, J = 7.0 Hz, 1H), 4.58 (s, 1H), 4.24 (d, J = 6.2 Hz, 2H), 3.74 (dd, J = 8.6, 2.0 Hz, 1H), 3.42 (d, J = 8.2 Hz, 1H), 3.16 (s, 3H), 3.00 (s, 3H), 1.38-1.24 (m, 1H), 1.11-1.01 (m, 4H), 0.92-0.81 (m, 2H), 0.77 (dd, J = 10.6, 6.6 Hz, 3H). |
| 235a | 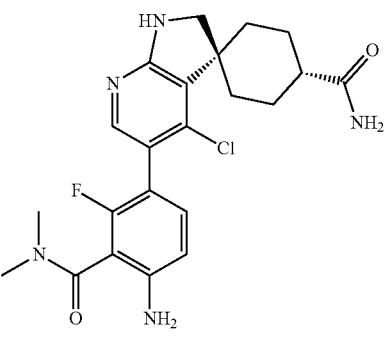<br>(1r,4r)-5'-(4-Amino-3-(dimethylcarbamoyl)-2-fluorophenyl)-4'-chloro-1',2'-dihydrospiro[cyclohexane-1,3'-pyrrolo[2,3-b]pyridine]-4-carboxamide | 1.93<br>446.1<br>A | L | (400 MHz, DMSO-d$_6$) δ 7.56 (s, 1H), 7.19 (brs, 1H), 6.94 (t, J = 8.5 Hz, 1H), 6.86 (s, 1H), 6.81 (brs, 1H), 6.54 (d, J = 8.4 Hz, 1H), 5.36 (brs, 2H), 3.44 (s, 2H), 2.99 (s, 3H), 2.88 (s, 3H), 2.46-2.36 (m, 3H), 1.99 (brd, J = 13.4 Hz, 2H), 1.61-1.52 (m, 2H), 1.45-1.38 (m, 2H). |

TABLE A1-continued

| No. | Structure/Name | LCMS R_T (min) m/z Method | Prep Mtd | $^1$H NMR δ (ppm) |
|---|---|---|---|---|
| 235b | 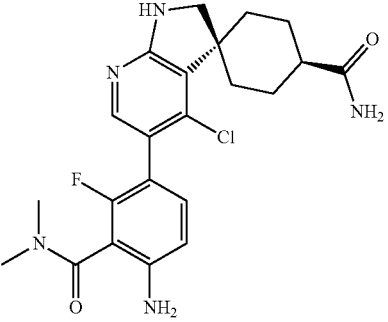<br>(1s,4s)-5'-(4-Amino-3-(dimethylcarbamoyl)-2-fluorophenyl)-4'-chloro-1',2'-dihydrospiro[cyclohexane-1,3'-pyrrolo[2,3-b]pyridine]-4-carboxamide | 2.09 446.1 A | L | (400 MHz, DMSO-d$_6$) δ 7.58 (s, 1H), 7.24 (brs, 1H), 6.96 (t, J = 8.5 Hz, 1H), 6.90 (s, 1H), 6.71 (brs, 1H), 6.54 (d, J = 8.4 Hz, 1H), 5.38 (brs, 2H), 3.42 (s, 2H), 2.99 (s, 3H), 2.88 (s, 3H), 2.24-2.10 (m, 3H), 1.73-1.65 (m, 4H), 1.51-1.40 (m, 2H). |
| 236 | 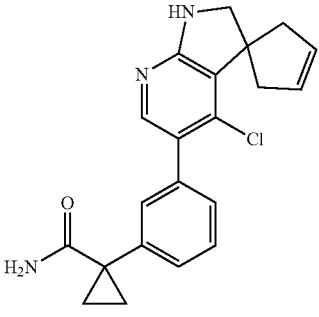<br>1-(3-(4'-Chloro-1',2'-dihydrospiro[cyclopentane-1,3'-pyrrolo[2,3-b]pyridin]-3-en-5'-yl)phenyl)cyclopropane-1-carboxamide | 3.24 366.1 A | L | (400 MHz, DMSO-d$_6$) δ 7.75 (s, 1H), 7.41-7.36 (m, 1H), 7.33-7.27 (m, 3H), 7.06 (s, 1H), 6.92 (s, 1H), 6.17 (s, 1H), 5.77 (s, 2H), 3.50 (s, 2H), 3.07 (d, J = 15.1 Hz, 2H), 2.51 (m, 2H, partially under DMSO peak), 1.33 (dd, J = 3.8, 6.6 Hz, 2H), 1.00 (dd, J = 3.8, 6.7 Hz, 2H). |
| 237 | 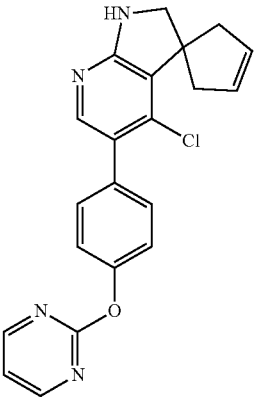<br>4'-Chloro-5'-(4-(pyrimidin-2-yloxy)phenyl)-1',2'-dihydrospiro[cyclopentane-1,3'-pyrrolo[2,3-b]pyridin]-3-ene | 3.42 377.1 A | L | (400 MHz, DMSO-d$_6$) δ 8.67 (d, J = 4.8 Hz, 2H), 7.75 (s, 1H), 7.45-7.39 (m, 2H), 7.28 (t, J = 4.8 Hz, 1H), 7.27-7.22 (m, 2H), 6.93 (s, 1H), 5.78 (s, 2H), 3.51 (s, 2H), 3.08 (d, J = 15.1 Hz, 2H) 2.51 (m, 2H partially under DMSO peak). |

TABLE A1-continued

| No. | Structure/Name | LCMS R$_T$ (min) m/z Method | Prep Mtd | $^1$H NMR δ (ppm) |
|---|---|---|---|---|
| 238 | 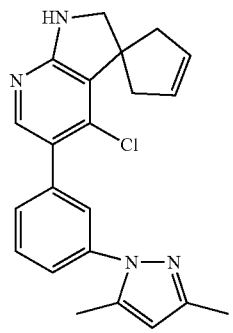<br>4'-Chloro-5'-(3-(3,5-dimethyl-1H-pyrazol-1-yl)phenyl)-1',2'-dihydrospiro[cyclopentane-1,3'-pyrrolo[2,3-b]pyridin]-3-ene | 4.06<br>376.9<br>A | L | (400 MHz, DMSO-d$_6$) δ 7.76 (s, 1H), 7.52 (t, J = 7.7 Hz, 1H), 7.49-7.45 (m, 2H), 7.37-7.33 (m, 1H), 6.99 (s, 1H), 6.07 (s, 1H), 5.78 (m, 2H), 3.51 (s, 2H), 3.08 (d, J = 15.0 Hz, 2H), 2.51 (m, 2H partially under DMSO peak), 2.33 (s, 3H), 2.18 (s, 3H). |
| 239a | 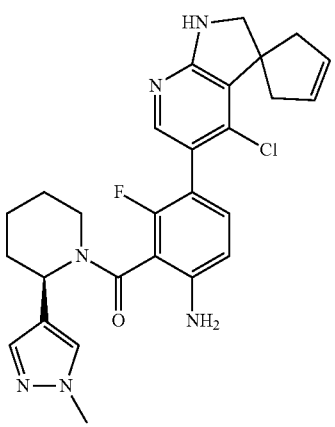<br>(R)-(6-Amino-3-(4'-chloro-1',2'-dihydrospiro[cyclopentane-1,3'-pyrrolo[2,3-b]pyridin]-3-en-5'-yl)-2-fluorophenyl)(2-(1-methyl-1H-pyrazol-4-yl)piperidin-1-yl)methanone<br>first peak on SFC; absolute configuration arbitrarily assigned | 3.33<br>507.2<br>A | L | (400 MHz, DMSO-d$_6$) mixture of conformers: δ 7.67-7.45 (m, 2H), 7.15-7.4 (4 x s, 1H), 7.03-6.84 (m, 2H), 6.64-6.51 (m, 1H), 5.80-5.90 (m, 0.5H), 5.76 (s, 2H), 5.48-5.27 (m, 2H), 4.90-4.75 (m, 0.5H), 4.46-4.42 (m, 0.5H), 3.82-3.73 (4 x s, 3H), 3.49-3.44 (m, 2H), 3.38-3.35 (m, 0.5H), 3.08-2.87 (m, 2.5H), 2.73-2.62 (m, 0.5H), 2.53-2.48 (m, 2H), 2.15-1.38 (m, 6H). |

TABLE A1-continued

| No. | Structure/Name | LCMS R$_T$ (min) m/z Method | Prep Mtd | $^1$H NMR δ (ppm) |
|---|---|---|---|---|
| 239b | 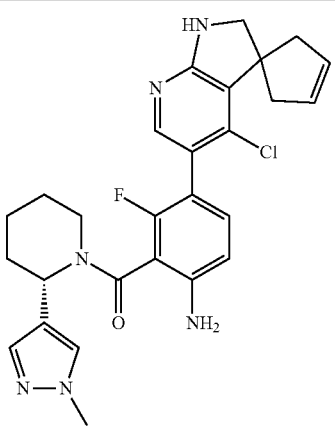<br>(S)-(6-Amino-3-(4'-chloro-1',2'-dihydrospiro[cyclopentane-1,3'-pyrrolo[2,3-b]pyridin]-3-en-5'-yl)-2-fluorophenyl)(2-(1-methyl-1H-pyrazol-4-yl)piperidin-1-yl)methanone<br>second peak on SFC; absolute configuration arbitrarily assigned | 3.33<br>507.2<br>A | L | (400 MHz, DMSO-d$_6$) mixture of conformers: δ 7.67-7.45 (m, 2H), 7.15-7.4 (4 x s, 1H), 7.03-6.84 (m, 2H), 6.64-6.51 (m, 1H), 5.80-5.90 (m, 0.5H), 5.76 (s, 2H), 5.48-5.27 (m, 2H), 4.90-4.75 (m, 0.5H), 4.46-4.42 (m, 0.5H), 3.82-3.73 (4 x s, 3H), 3.49-3.44 (m, 2H), 3.38-3.35 (m, 0.5H), 3.08-2.87 (m, 2.5H), 2.73-2.62 (m, 0.5H), 2.53-2.48 (m, 2H), 2.15-1.38 (m, 6H). |
| 240a | 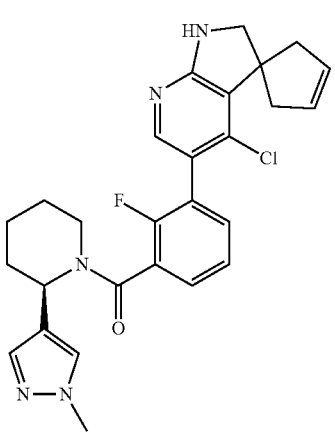<br>(R)-(3-(4'-Chloro-1',2'-dihydrospiro[cyclopentane-1,3'-pyrrolo[2,3-b]pyridin]-3-en-5'-yl)-2-fluorophenyl)(2-(1-methyl-1H-pyrazol-4-yl)piperidin-1-yl)methanone<br>first speak on SFC; absolute configuration arbitrarily assigned | 3.66<br>492.2<br>A | L | (400 MHz, DMSO-d$_6$) mixture of conformers: δ 7.73 (s, 1H), 7.66-7.17 (m, 5H), 7.07 (s, 1H), 5.84-5.77 (m, 2.5H), 4.70 (d, J = 16.1 Hz, 0.5H), 4.42 (d, J = 12.1 Hz, 0.5H), 3.79 (d, J = 14.2 Hz, 3H), 3.51 (s, 2H), 3.30-3.24 (m, 0.5H), 3.02-2.98 (m, 2.5H), 2.74-2.66 (m, 0.5H), 2.55 (s, 2H), 2.14-2.05 (m, 1H), 1.77-1.75 (m, 1H), 1.68-1.50 (m, 3H), 1.40-1.34 (m, 1H). |

TABLE A1-continued

| No. | Structure/Name | LCMS R_T (min) m/z Method | Prep Mtd | $^1$H NMR δ (ppm) |
|---|---|---|---|---|
| 240b | (S)-(3-(4'-Chloro-1',2'-dihydrospiro[cyclopentane-1,3'-pyrrolo[2,3-b]pyridin]-3-en-5'-yl)-2-fluorophenyl)(2-(1-methyl-1H-pyrazol-4-yl)piperidin-1-yl)methanone<br>second peak on SFC; absolute configuration arbitrarily assigned | 3.66<br>492.2<br>A | L | (400 MHz, DMSO-d$_6$) mixture of conformers: δ 7.73 (s, 1H), 7.66-7.17 (m, 5H), 7.07 (s, 1H), 5.84-5.77 (m, 2.5H), 4.70 (d, J = 16.1 Hz, 0.5H), 4.42 (d, J = 12.1 Hz, 0.5H), 3.79 (d, J = 14.2 Hz, 3H), 3.51 (s, 2H), 3.30-3.24 (m, 0.5H), 3.02-2.98 (m, 2.5H), 2.74-2.66 (m, 0.5H), 2.55 (s, 2H), 2.14-2.05 (m, 1H), 1.77-1.75 (m, 1H), 1.68-1.50 (m, 3H), 1.40-1.34 (m, 1H). |
| 241a | 6-Amino-3-((1r,4r)-4'-chloro-4-cyano-1',2'-dihydrospiro[cyclohexane-1,3'-pyrrolo[2,3-b]pyridin]-5'-yl)-2-fluoro-N,N-dimethylbenzamide | 2.61<br>428.0<br>A | L | (400 MHz, DMSO-d$_6$) δ 7.61 (s, 1H), 6.97 (t, J = 8.5 Hz, 1H), 6.96 (s, 1H), 6.55 (d, J = 8.4 Hz, 1H), 5.38 (brs, 2H), 3.43 (s, 2H), 3.16 (brs, 1H), 2.99 (s, 3H), 2.89 (s, 3H), 2.48-2.36 (m, 2H), 1.85-1.82 (m, 2H), 1.76-1.62 (m, 4H). |
| 241b | 6-Amino-3-((1s,4s)-4'-chloro-4-cyano-1',2'-dihydrospiro[cyclohexane-1,3'-pyrrolo[2,3-b]pyridin]-5'-yl)-2-fluoro-N,N-dimethylbenzamide | 2.72<br>428.3<br>B | L | (400 MHz, DMSO-d$_6$) δ 7.59 (s, 1H), 6.96 (s, 1H), 6.95 (t, J = 8.5 Hz, 1H), 6.54 (d, J = 8.4 Hz, 1H), 5.38 (brs, 2H), 3.45 (s, 2H), 2.99 (s, 3H), 2.88 (s, 3H), 2.78-2.70 (m, 1H), 2.21-2.11 (m, 2H), 2.00-1.94 (m, 2H), 1.72-1.63 (m, 4H). |

TABLE A1-continued

| No. | Structure/Name | LCMS R_T (min) m/z Method | Prep Mtd | $^1$H NMR δ (ppm) |
|---|---|---|---|---|
| 242 | 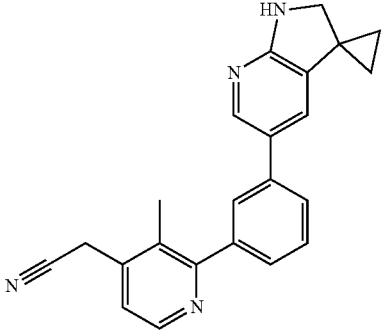<br>2-(2-(3-(1',2'-Dihydrospiro[cyclopropane-1,3'-pyrrolo[2,3-b]pyridin-5'-yl)phenyl)-3-methylpyridin-4-yl)acetonitrile | 2.64<br>353.4<br>B | L | (400 MHz, CDCl3) δ 8.58 (d, J = 5.1 Hz, 1H), 8.06 (d, J = 2.3 Hz, 1H), 7.57-7.45 (m, 3H), 7.39-7.33 (m, 2H), 7.00 (d, J = 2.3 Hz, 1H), 4.64 (s, 1H), 3.77 (s, 2H), 3.68 (s, 2H), 2.33 (s, 3H), 1.12-1.05 (m, 2H), 1.05-0.98 (m, 2H). |
| 243a | 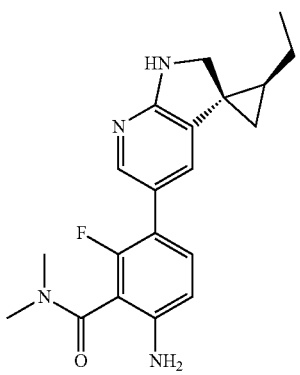<br>6-Amino-3-((1R,2S)-3-ethyl-1',2'-dihydrospiro[cyclopropane-1,3'-pyrrolo[2,3-b]pyridin]-5'-yl)-2-fluoro-N,N-dimethylbenzamide first peak SFC; absolute configuration arbitrarily assigned | 2.77<br>355.1<br>A | L | (400 MHz, DMSO-d$_6$) δ 7.68 (s, 1H), 7.12 (t, J = 8.4 Hz, 1H), 6.85 (d, J = 1.4 Hz, 1H), 6.63 (s, 1H), 6.55 (d, J = 8.5 Hz, 1H), 5.28 (s, 2H), 3.57 (d, J = 9.8 Hz, 1H), 3.42 (d, J = 9.8 Hz, 1H), 2.99 (s, 3H), 2.87 (s, 3H), 1.42-1.11 (m, 4H), 0.99 (t, J = 7.2 Hz, 3H), 0.64-0.59 (m, 1H). |
| 243b | 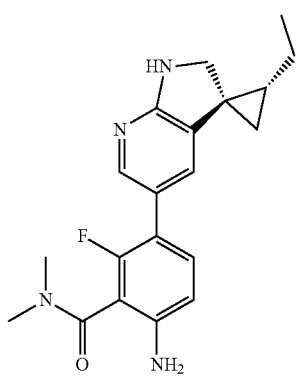<br>6-Amino-3-((1S,2R)-2-ethyl-1',2'-dihydrospiro[cyclopropane-1,3'-pyrrolo[2,3-b]pyridin]-5'-yl)-2-fluoro-N,N-dimethylbenzamide second peak SFC; absolute configuration arbitrarily assigned | 2.78<br>355.1<br>A | L | (400 MHz, DMSO-d$_6$) δ 7.68 (s, 1H), 7.12 (t, J = 8.5 Hz, 1H), 6.84 (d, J = 1.5 Hz, 1H), 6.59 (s, 1H), 6.55 (d, J = 8.5 Hz, 1H), 5.28 (s, 2H), 3.56 (d, J = 9.6 Hz, 1H), 3.43 (d, J = 9.7 Hz, 1H), 2.99 (s, 3H), 2.86 (s, 3H), 1.42-1.11 (m, 4H), 0.99 (t, J = 7.2 Hz, 3H), 0.64-0.58 (m, 1H). |

TABLE A1-continued

| No. | Structure/Name | LCMS R$_T$ (min) m/z Method | Prep Mtd | $^1$H NMR δ (ppm) |
|---|---|---|---|---|
| 243c | 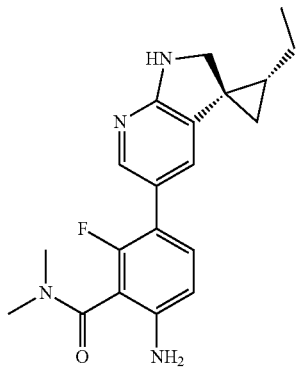<br>6-Amino-3-((1R,2R)-2-ethyl-1',2'-dihydrospiro[cyclopropane-1,3'-pyrrolo[2,3-b]pyridin]-5'-yl)-2-fluoro-N,N-dimethylbenzamide<br>first peak SFC; absolute configuration arbitrarily assigned | 2.68<br>355.2<br>A | L | (400 MHz, DMSO-d$_6$) δ 7.73-7.70 (m, 1H), 7.16-7.09 (m, 1H), 6.99 (d, J = 5.6 Hz, 1H), 6.56 (d, J = 8.4 Hz, 1H), 6.52 (s, 1H), 5.29 (s, 2H), 3.60 (dd, J = 2.1, 9.0 Hz, 1H), 3.30 (d, J = 9.1 Hz, 1H), 2.99 (s, 3H), 2.87 (app d, J = 6.3 Hz, 3H), 1.47-1.17 (m, 2H), 1.11-1.03 (m, 2H), 0.93-0.90 (m, 1H), 0.81 (dt, J = 1.6, 7.3 Hz, 3H). |
| 243d | 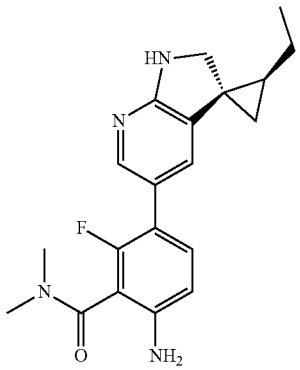<br>6-Amino-3-((1S,2S)-2-ethyl-1',2'-dihydrospiro[cyclopropane-1,3'-pyrrolo[2,3-b]pyridin]-5'-yl)-2-fluoro-N,N-dimethylbenzamide<br>second peak SFC; absolute configuration arbitrarily assigned | 2.69<br>355.2<br>A | L | (400 MHz, DMSO-d$_6$) δ 7.72 (d, J = 4.9 Hz, 1H), 7.16-7.09 (m, 1H), 6.99 (d, J = 5.6 Hz, 1H), 6.56 (d, J = 8.5 Hz, 1H), 6.52 (s, 1H), 5.29 (s, 2H), 3.60 (dd, J = 2.2, 9.0 Hz, 1H), 2.99 (s, 3H), 2.87 (d, J = 6.3 Hz, 3H), 1.47-1.13 (m, 2H), 1.11-1.03 (m, 3H), 0.93-0.90 (m, 1H), 0.81 (dt, J = 1.6, 7.3 Hz, 3H). |
| 244 | 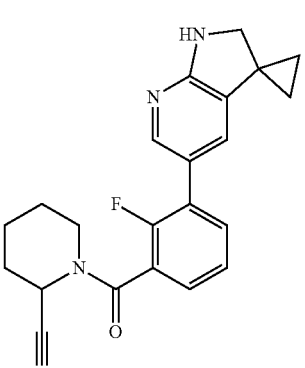<br>(±)-1-(3-(1',2'-Dihydrospiro[cyclopropane-1,3'-pyrrolo[2,3-b]pyridin]-5'-yl)-2-fluorobenzyl)piperidine-2-carbonitrile | 2.95<br>377.2<br>A | L | (400 MHz, DMSO-d$_6$) δ 7.86 (s, 1H), 7.61-7.54 (m, 1H), 7.35-7.29 (m, 2H), 7.04 (s, 1H), 6.85 (s, 1H), 5.03-4.49 (m, 1H), 3.56 (s, 2H), 3.50-3.43 (m, 1H), 3.21-3.08 (m 1H), 2.05-1.97 (m, 1H), 1.88-1.56 (m, 4H), 1.43-1.36 (m, 1H), 1.10-0.96 (m, 4H). |

TABLE A1-continued

| No. | Structure/Name | LCMS R_T (min) m/z Method | Prep Mtd | $^1$H NMR δ (ppm) |
|---|---|---|---|---|
| 245a | 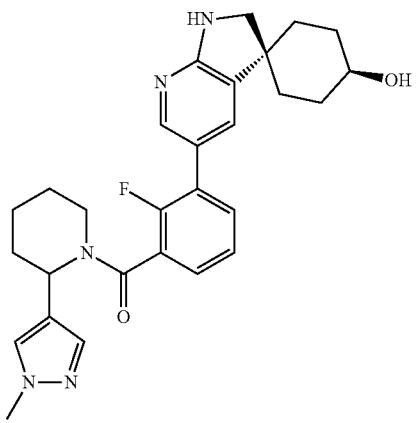<br>(2-Fluoro-3-((1s,4s)-4-hydroxy-1′,2′-dihydrospiro[cyclohexane-1,3′-pyrrolo[2,3-b]pyridin]-5′-yl)phenyl)((RS)-2-(1-methyl-1H-pyrazol-4-yl)piperidin-1-yl)methanone | 2.64<br>490.4<br>A | L | (400 MHz, DMSO-d$_6$) δ 7.92-7.89 (m, 1H), 7.66-7.17 (m, 6H), 6.73-6.71 (m, 1H), 5.84 (bs, 1H), 4.72-4.42 (m, 2H), 3.82-3.77 (m, 3H), 3.54-3.46 (m, 1H), 3.41-3.36 (m, 2H), 3.07-2.67 (m, 1H), 2.13-1.22 (m, 14H) |
| 246a | 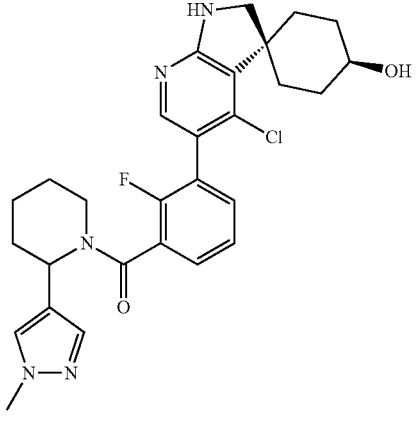<br>(3-((1s,4s)-4′-Chloro-4-hydroxy-1′,2′-dihydrospiro[cyclohexane-1,3′-pyrrolo[2,3-b]pyridin]-5′-yl)-2-fluorophenyl)((R)-2-(1-methyl-1H-pyrazol-4-yl)piperidin-1-yl)methanone<br>first peak on SFC; absolute configuration arbitrarily assigned | 2.89<br>524.4<br>A | L | (400 MHz, DMSO-d$_6$) δ 7.69-7.16 (6H, m), 7.11 (1H, s), 5.84-5.81 (1H, m), 4.71-4.41 (2H, m), 3.84-3.77 (3H, m), 3.47-3.42 (1H, m), 3.29-3.24 (2H, m), 3.10-2.65 (1H, m), 2.19-1.06 (14H, m) |

TABLE A1-continued

| No. | Structure/Name | LCMS R_T (min) m/z Method | Prep Mtd | $^1$H NMR δ (ppm) |
|---|---|---|---|---|
| 246b | (3-((1s,4s)-4'-Chloro-4-hydroxy-1',2'-dihydrospiro[cyclohexane-1,3'-pyrrolo[2,3-b]pyridin]-5'-yl)-2-fluorophenyl)((S)-2-(1-methyl-1H-pyrazol-4-yl)piperidin-1-yl)methanone<br>second peak on SFC; absolute configuration arbitrarily assigned | 2.89<br>524.4<br>A | L | (400 MHz, DMSO-d$_6$) δ 7.69-7.16 (6H, m), 7.11 (1H, s), 5.84-5.81 (1H, m), 4.71-4.41 (2H, m), 3.84-3.77 (3H, m), 3.47-3.42 (1H, m), 3.29-3.24 (2H, m), 3.10-2.65 (1H, m), 2.19-1.06 (14H, m) |
| 247 | 2-(tert-Butyl)-5-(3-(4'-chloro-1',2'-dihydrospiro[cyclopentane-1,3'-pyrrolo[2,3-b]pyridin]-3-en-5'-yl)phenyl)-1,3,4-oxadiazole | 4.38<br>407.2<br>A | L | (400 MHz, DMSO-d$_6$) δ 8.00-7.96 (m, 2H), 7.78 (s, 1H), 7.66-7.59 (m, 2H), 7.05 (s, 1H), 5.78 (s, 2H), 3.53 (s, 2H), 3.05 (d, J = 15.1 Hz, 3H), 2.51 (m, 2H partially under DMSO peak), 1.43 (s, 9H). |
| 248a | 6-Amino-3-((1s,4s)-4'-chloro-4-(hydroxymethyl)-1',2'-dihydrospiro[cyclohexane-1,3'-pyrrolo[2,3-b]pyridin]-5'-yl)-2-fluoro-N,N-dimethylbenzamide | 2.39<br>433.4<br>B | L | (400 MHz, DMSO-d$_6$) δ 7.57 (s, 1H), 6.95 (t, J = 8.5 Hz, 1H), 6.88 (s, 1H), 6.54 (d, J = 8.3 Hz, 1H), 5.37 (brs, 2H), 4.39 (t, J = 5.3 Hz, 1H), 3.38 (s, 2H), 3.24 (t, J = 5.7 Hz, 2H), 2.99 (s, 3H), 2.88 (s, 3H), 2.23-2.11 (m, 2H), 1.69-1.63 (m, 4H), 1.38 (brs, 1H), 1.08-0.98 (m, 2H). |

TABLE A1-continued

| No. | Structure/Name | LCMS R$_T$ (min) m/z Method | Prep Mtd | $^1$H NMR δ (ppm) |
|---|---|---|---|---|
| 248b | 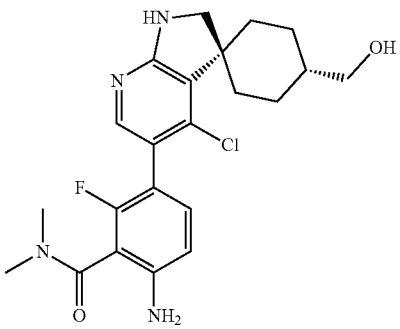 6-Amino-3-((1r,4r)-4'-chloro-4-(hydroxymethyl)-1',2'-dihydrospiro[cyclohexane-1,3'-pyrrolo[2,3-b]pyridin-5'-yl)-2-fluoro-N,N-dimethylbenzamide | 2.29 433.4 B | L | (400 MHz, DMSO-d$_6$) δ 7.57 (s, 1H), 6.96 (t, J = 8.5 Hz, 1H), 6.89 (s, 1H), 6.54 (d, J = 8.4 Hz, 1H), 5.37 (brs, 2H), 4.47 (t, J = 5.3 Hz, 1H), 3.53 (dd, J = 7.6, 5.4 Hz, 2H), 3.46 (s, 2H), 2.99 (s, 3H), 2.89 (s, 3H), 2.30-2.19 (m, 2H), 1.74 (brs, 1H), 1.68-1.61 (m, 2H), 1.58-1.48 (m, 2H), 1.42-1.35 (m, 2H). |
| 249 | 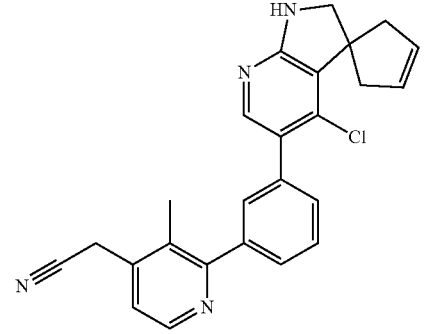 2-(2-(3-(4'-Chloro-1',2'-dihydrospiro[cyclopentane-1,3'-pyrrolo[2,3-b]pyridin-3-en-5'-yl)phenyl)-3-methylpyridin-4-yl)acetonitrile | 3.48 413.3 B | L | (400 MHz, CDCl3) δ 8.57 (d, J = 4.7 Hz, 1H), 7.84 (s, 1H), 7.54-7.45 (m, 3H), 7.43 (dt, J = 7.4, 1.7 Hz, 1H), 7.36 (d, J = 5.1 Hz, 1H), 5.76 (s, 2H), 4.61 (s, 1H), 3.76 (s, 2H), 3.61 (d, J = 1.1 Hz, 2H), 3.27-3.18 (m, 2H), 2.57-2.49 (m, 2H), 2.36 (s, 3H). |
| 250a | 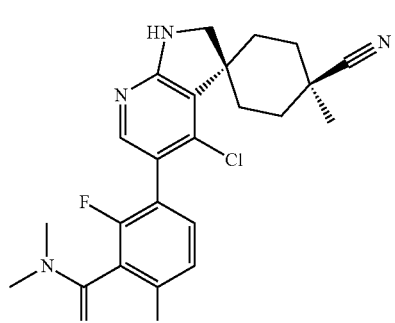 6-Amino-3-((1s,4s)-4'-chloro-4-cyano-4-methyl-1',2'-dihydrospiro[cyclohexane-1,3'-pyrrolo[2,3-b]pyridin]-5'-yl)-2-fluoro-N,N-dimethylbenzamide | 2.94 442.4 B | L | (400 MHz, DMSO-d$_6$) δ 7.60 (s, 1H), 6.98 (s, 1H), 6.96 (t, J = 8.5 Hz, 1H), 6.54 (d, J = 8.4 Hz, 1H), 5.38 (brs, 2H), 3.48 (s, 2H), 2.99 (s, 3H), 2.88 (s, 3H), 2.35-2.24 (m, 2H), 1.97-1.89 (m, 2H), 1.83-1.77 (m, 2H), 1.59-1.51 (m, 2H), 1.44 (s, 3H). |

TABLE A1-continued

| No. | Structure/Name | LCMS R_T (min) m/z Method | Prep Mtd | $^1$H NMR δ (ppm) |
|---|---|---|---|---|
| 250b | 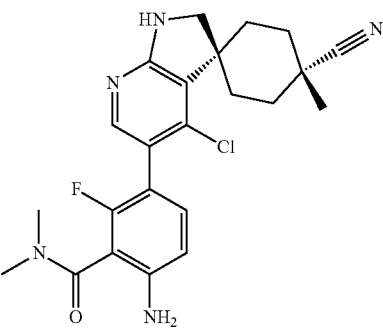<br>6-Amino-3-((1r,4r)-4'-chloro-4-cyano-4-methyl-1',2'-dihydrospiro[cyclohexane-1,3'-pyrrolo[2,3-b]pyridin]-5'-yl)-2-fluoro-N,N-dimethylbenzamide | 2.88<br>442.4<br>B | L | (400 MHz, DMSO-d$_6$) δ 7.61 (s, 1H), 6.97 (s & t, J = 8.5 Hz, 2H), 6.55 (d, J = 8.4 Hz, 1H), 5.38 (brs, 2H), 3.42 (s, 2H), 2.99 (s, 3H), 2.89 (s, 3H), 2.51-2.39 (m, 2H), 1.88-1.83 (m, 2H), 1.71-1.64 (m, 2H), 1.56-1.48 (m, 2H), 1.35 (s, 3H). |
| 251 | 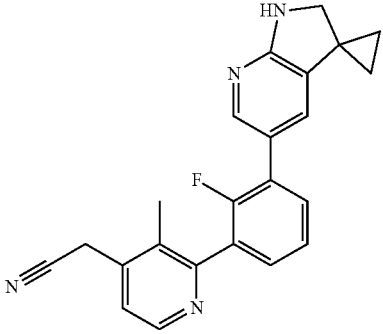<br>2-(2-(3-(1',2'-Dihydrospiro[cyclopropane-1,3'-pyrrolo[2,3-b]pyridin]-5'-yl)-2-fluorophenyl)-3-methylpyridin-4-yl)acetonitrile | 2.76<br>371.0<br>B | L | (400 MHz, CDCl3) δ 8.60 (d, J = 4.9 Hz, 1H), 7.97 (s, 1H), 7.74-7.40 (m, 2H), 7.35-7.27 (m, 2H), 6.97-6.94 (m, 1H), 4.74 (s, 1H), 3.77 (s, 2H), 3.69 (s, 2H), 2.23 (s, 3H), 1.09-1.03 (m, 2H), 1.03-0.97 (m, 2H). |
| 252 | 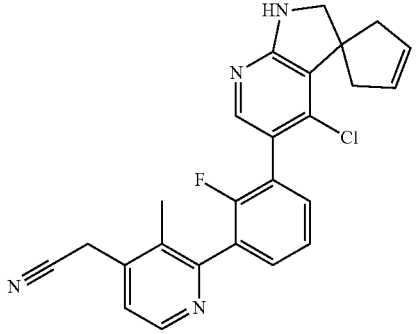<br>2-(2-(3-(4'-Chloro-1',2'-dihydrospiro[cyclopentane-1,3'-pyrrolo[2,3-b]pyridin]-3-en-5'-yl)-2-fluorophenyl)-3-methylpyridin-4-yl)acetonitrile | 3.53<br>431.2<br>A | L | (400 MHz, CDCl3) δ 8.60 (d, J = 5.2 Hz, 1H), 7.79 (s, 1H), 7.47 (td, J = 6.8, 2.5 Hz, 1H), 7.42 (d, J = 5.2 Hz, 1H), 7.38-7.29 (m, 2H), 5.75 (s, 2H), 4.68 (s, 1H), 3.77 (s, 2H), 3.62 (s, 2H), 3.22 (d, J = 16.3 Hz, 2H), 2.53 (d, J = 15.1 Hz, 2H), 2.25 (d, J = 1.8 Hz, 3H). |

TABLE A1-continued

| No. | Structure/Name | LCMS $R_T$ (min) m/z Method | Prep Mtd | $^1$H NMR δ (ppm) |
|---|---|---|---|---|
| 253a | 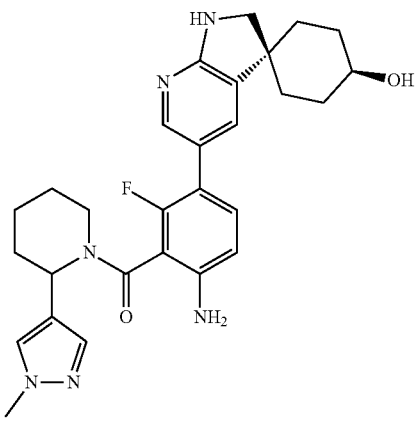<br>(6-Amino-2-fluoro-3-((1s,4s)-4-hydroxy-1',2'-dihydrospiro[cyclohexane-1,3'-pyrrolo[2,3-b]pyridin]-5'-yl)phenyl)((RS)-2-(1-methyl-1H-pyrazol-4-yl)piperidin-1-yl)methanone | 2.55<br>505.3<br>A | L | (400 MHz, DMSO-$d_6$) δ 7.79-7.05 (m, 5H), 6.61-6.44 (m, 2H), 5.89-5.82 (m, 1H), 5.38-5.13 (m, 2H), 4.83-4.44 (m, 2H), 3.83-3.75 (m, 3H), 3.54-3.44 (m, 1H), 3.39-3.34 (m, 2H), 3.06-2.63 (m, 1H), 2.16-1.21 (m, 14H) |
| 254a | 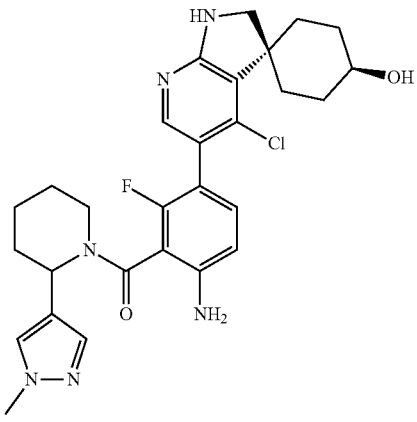<br>(6-Amino-3-((1s,4s)-4'-chloro-4-hydroxy-1',2'-dihydroxyspiro[cyclohexane-1,3'-pyrrolo[2,3-b]pyridin]-5'-yl)-2-fluorophenyl)((R)-2-(1-methyl-1H-pyraol-4-yl)piperidin-1-yl)methanone<br>first peak on SFC; absolute configuration arbitrarily assigned | 2.68<br>539.3<br>A | L | (400 MHz, DMSO-$d_6$) δ 7.73-7.15 (m, 3H), 7.01-6.88 (m, 2H), 6.63-6.51 (m, 1H), 5.89-5.80 (m, 1H), 5.48-5.28 (m, 2H), 4.89-4.44 (m, 2H), 3.82-3.76 (m, 3H), 3.46-3.38 (m, 3H), 3.02-2.64 (m, 1H), 2.27-0.84 (m, 14H) |

TABLE A1-continued

| No. | Structure/Name | LCMS R$_T$ (min) m/z Method | Prep Mtd | $^1$H NMR δ (ppm) |
|---|---|---|---|---|
| 254b | (6-Amino-3-((1s,4s)-4'-chloro-4-hydroxy-1',2'-dihydrospiro[cyclohexane-1,3'-pyrrolo[2,3-b]pyridin]-5'-yl)-2-fluorophenyl)((S)-2-(1-methyl-1H-pyrazol-4-yl)piperidin-1-yl)methanone<br>second peak on SFC; absolute configuration arbitrarily assigned | 2.68<br>539.3<br>A | L | (400 MHz, DMSO-d$_6$) δ 7.73-7.15 (m, 3H), 7.01-6.88 (m, 2H), 6.63-6.51 (m, 1H), 5.89-5.80 (m, 1H), 5.48-5.28 (m, 2H), 4.89-4.44 (m, 2H), 3.82-3.76 (m, 3H), 3.46-3.38 (m, 3H), 3.02-2.64 (m, 1H), 2.27-0.84 (m, 14H) |
| 255a | 6-Amino-3-((1s,4s)-4'-chloro-4-(2-hydroxypropan-2-yl)-1',2'-dihydrospiro[cyclohexane-1,3'-pyrrolo[2,3-b]pyridin]-5'-yl)-2-fluoro-N,N-dimethylbenzamide | 2.77<br>461.3<br>A | L | (400 MHz, DMSO-d$_6$) δ 7.57 (s, 1H), 6.95 (t, J = 8.5 Hz, 1H), 6.88 (s, 1H), 6.54 (d, J = 8.3 Hz, 1H), 5.37 (brs, 2H), 4.04 (s, 1H), 3.38 (s, 2H), 2.99 (s, 3H), 2.88 (s, 3H), 2.20-2.10 (m, 2H), 1.76-1.66 (m, 4H), 1.27-1.17 (m, 3H), 1.05 (s, 6H). |
| 255b | 6-Amino-3-((1r,4r)-4'-chloro-4-(2-hydroxypropan-2-yl)-1',2'-dihydrospiro[cyclohexane-1,3'-pyrrolo[2,3-b]pyridin]-5'-yl)-2-fluoro-N,N-dimethylbenzamide | 2.72<br>461.3<br>A | L | (400 MHz, DMSO-d$_6$) δ 7.57 (s, 1H), 6.95 (t, J = 8.5 Hz, 1H), 6.82 (s, 1H), 6.54 (d, J = 8.3 Hz, 1H), 5.37 (brs, 2H), 4.07 (s, 1H), 3.40 (s, 2H), 2.99 (s, 3H), 2.88 (s, 3H), 2.38-2.27 (m, 2H), 1.81-1.70 (m, 2H), 1.62-1.53 (m, 2H), 1.45-1.37 (m, 3H), 1.12 (s, 6H). |

TABLE A1-continued

| No. | Structure/Name | LCMS R$_T$ (min) m/z Method | Prep Mtd | $^1$H NMR δ (ppm) |
|---|---|---|---|---|
| 256a | 6-Amino-3-((1r,4r)-4'-chloro-4-(hydroxymethyl)-4-methyl-1',2'-dihydrospiro[cyclohexane-1,3'-pyrrolo[2,3-b]pyridin]-5'-yl)-2-fluoro-N,N-dimethylbenzamide | 2.52 447.2 A | L | (400 MHz, DMSO-d$_6$) δ 7.57 (s, 1H), 6.96 (t, J = 8.5 Hz, 1H), 6.89 (s, 1H), 6.54 (d, J = 8.3 Hz, 1H), 5.38 (brs, 2H), 4.44 (t, J = 5.3 Hz, 1H), 3.43 (s, 2H), 3.41-3.39 (m, 2H), 2.99 (s, 3H), 2.89 (s, 3H), 2.34-2.23 (m, 2H), 1.53-1.47 (m, 2H), 1.42-1.35 (m, 2H), 1.23-1.14 (m, 2H), 0.85 (s, 3H). |
| 257 | 2-(1-(3-(4'-Chloro-1',2'-dihydrospiro[cyclopentane-1,3'-pyrrolo[2,3-b]pyridin]-3-en-5'-yl)phenyl)-5-methyl-1H-pyrazol-3-yl)acetonitrile | 3.92 402.3 A | M | (400 MHz, CDCl3) δ 7.82 (s, 1H), 7.52 (t, J = 7.7 Hz, 1H), 7.45-7.39 (m, 3H), 6.27 (s, 1H), 5.76 (s, 2H), 4.65 (s, 1H), 3.77 (s, 2H), 3.62 (s, 2H), 3.27 (d, J = 14.7 Hz, 2H), 2.53 (d, J = 14.8 Hz, 2H), 2.38 (s, 3H). |
| 258a | 6-Amino-3-((1r,4r)-4-(aminomethyl)-4'-chloro-1',2'-dihydrospiro[cyclohexane-1,3'-pyrrolo[2,3-b]pyridin]-5'-yl)-2-fluoro-N,N-dimethylbenzamide | 1.64 432.3 A | L | (400 MHz, DMSO-d$_6$): δ ppm 7.56 (s, 1H), 6.95 (t, J = 8.5 Hz, 1H), 6.89 (brs, 1H), 6.54 (d, J = 8.4 Hz, 1H), 5.37 (brs, 2H), 3.46 (brs, 2H), 2.99 (s, 3H), 2.88 (s, 3H), 2.29-2.18 (m, 2H), 1.68-1.50 (m, 4H), 1.41-1.34 (m, 2H). |

TABLE A1-continued

| No. | Structure/Name | LCMS R_T (min) m/z Method | Prep Mtd | $^1$H NMR δ (ppm) |
|---|---|---|---|---|
| 258b | 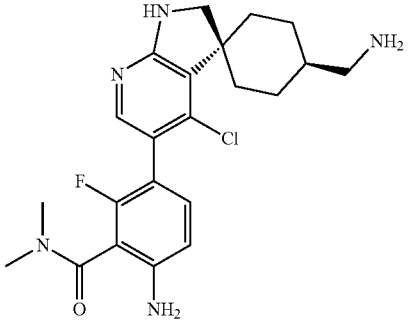<br>6-Amino-3-((1s,4s)-4-(aminomethyl)-4'-chloro-1',2'-dihydrospiro[cyclohexane-1,3'-pyrrolo[2,3-b]pyridin]-5'-yl)-2-fluoro-N,N-dimethylbenzamide | 1.67<br>432.3<br>A | L | (400 MHz, DMSO-d$_6$): δ ppm 7.57 (s, 1H), 6.95 (t, J = 8.5 Hz, 1H), 6.88 (brs, 1H), 6.54 (d, J = 8.4 Hz, 1H), 5.37 (brs, 2H), 3.39 (brs, 2H), 2.99 (s, 3H), 2.88 (s, 3H), 2.21-2.11 (m, 2H), 1.72-1.62 (m, 3H), 1.30-1.21 (m, 1H), 1.06-0.94 (m, 2H). |
| 259a | 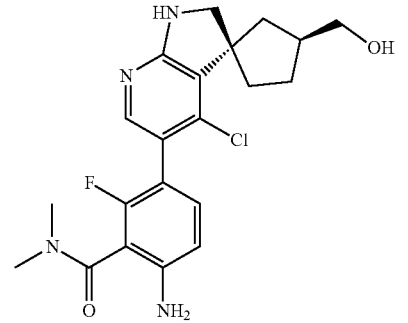<br>6-Amino-3-((1RS,3SR)-4'-chloro-3-(hydroxymethyl)-1',2'-dihydrospiro[cyclopentane-1,3'-pyrrolo[2,3-b]pyridin]-5'-yl)-2-fluoro-N,N-dimethylbenzamide | 2.33<br>419.3<br>A | L | (400 MHz, DMSO-d$_6$) δ 7.59 (s, 1H), 6.97 (t, J = 8.5 Hz, 1H), 6.81 (brs, 1H), 6.55 (d, J = 8.4 Hz, 1H), 5.38 (brs, 2H), 4.53 (t, J = 5.2 Hz, 1H), 3.38-3.35 (m, 4H), 2.99 (s, 3H), 2.88 (brs, 3H), 2.36-2.26 (m, 1H), 2.04-1.93 (m, 1H), 1.87-1.76 (m, 2H), 1.46-1.29 (m, 2H). |
| 259c | 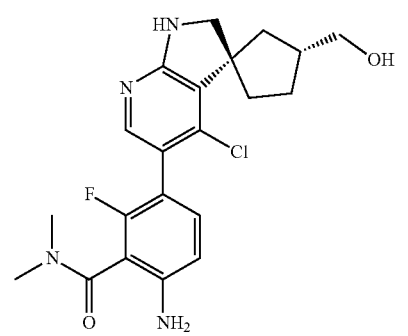<br>6-Amino-3-((1RS,3RS)-4'-chloro-3-(hydroxymethyl)-1',2'-dihydrospiro[cyclopentane-1,3'-pyrrolo[2,3-b]pyridin]-5'-yl)-2-fluoro-N,N-dimethylbenzamide | 2.29<br>419.2<br>A | L | (400 MHz, DMSO-d$_6$) δ 7.59 (s, 1H), 6.96 (t, J = 8.5 Hz, 1H), 6.84 (brs, 1H), 6.55 (d, J = 8.4 Hz, 1H), 5.38 (brs, 2H), 4.52 (dt, J = 5.1, 3.1 Hz, 1H), 3.39-3.35 (m, 2H), 3.35 (brs, 2H), 2.99 (s, 3H), 2.88 (s, 3H), 2.40-2.30 (m, 1H), 2.19-2.11 (m, 1H), 1.89-1.74 (m, 3H), 1.67-1.61 (m, 1H), 1.58-1.49 (m, 1H). |

TABLE A1-continued

| No. | Structure/Name | LCMS R$_T$ (min) m/z Method | Prep Mtd | $^1$H NMR δ (ppm) |
|---|---|---|---|---|
| 260 | 3-(4'-Chloro-1',2'-dihydrospiro[cyclopentane-1,3'-pyrrolo[2,3-b]pyridin]-3-en-5'-yl)-2-fluoro-N-methyl-N-((1-(pyrrolidin-3-yl)-1H-pyrazol-4-yl)methyl)benzamide | 2.66 507.2 B | M | (400 MHz, CDCl3) δ 7.74 (s, 1H), 7.53-7.49 (m, 1H), 7.44-7.22 (m, 4H), 5.75 (s, 2H), 4.85-4.73 (m, 2H), 4.58 (s, 2H), 4.30 (1H, s), 3.66-3.59 (m, 2H), 3.38-3.13 (m, 2H), 3.17-3.04 (m, 3H), 2.89 (s, 3H), 2.57-2.48 (m, 2H), 2.41-2.26 (m, 2H), 2.25-2.14 (m, 1H). |
| 261a | 6-Amino-2-((1R,3S)-4'-chloro-3-cyano-3-methyl-1',2'-dihydrospiro[cyclopentane-1,3'-pyrrolo[2,3-b]pyridin]-5'-yl)-2-fluoro-N,N-dimethylbenzamide first peak on SFC; absolute configuration arbitrarily assigned | 2.93 428.1 A | L | (400 MHz, DMSO-d$_6$) δ 7.64 (s, 1H), 6.99-6.94 (m, 2H), 6.55 (d, J = 8.4 Hz, 1H), 5.40 (s, 2H), 3.63 (d, J = 9.5 Hz, 1H), 3.52 (d, J = 8.7 Hz, 1H), 2.99 (s, 3H), 2.88 (s, 3H), 2.46-2.56 (m, 1H, under DMSO), 2.39 (d, J = 13.6 Hz, 1H), 2.29-2.20 (m, 1H), 2.17-1.89 (m, 3H), 1.47 (d, J = 3.9 Hz, 3H). |
| 261b | 6-Amino-3-((1S,3R)-4'-chloro-3-cyano-3-methyl-1',2'-dihydrospiro[cyclopentane-1,3'-pyrrolo[2,3-b]pyridin]-5'-yl)-2-fluoro-N,N-dimethylbenzamide second peak on SFC; absolute configuration arbitrarily assigned | 2.93 428.2 A | L | (400 MHz, DMSO-d$_6$) δ 7.65 (s, 1H), 7.00-6.94 (m, 2H), 6.55 (d, J = 8.4 Hz, 1H), 5.40 (s, 2H), 3.65-3.61 (m, 1H), 3.52 (d, J =8.7 Hz, 1H), 2.99 (s, 3H), 2.88 (s, 3H), 2.46-2.56 (m, 1H, under DMSO), 2.39 (d, J = 13.5 Hz, 1H), 2.29-2.20 (m, 1H), 2.17-1.88 (m, 3H), 1.49-1.46 (m, 3H). |

TABLE A1-continued

| No. | Structure/Name | LCMS R_T (min) m/z Method | Prep Mtd | ¹H NMR δ (ppm) |
|---|---|---|---|---|
| 262 | 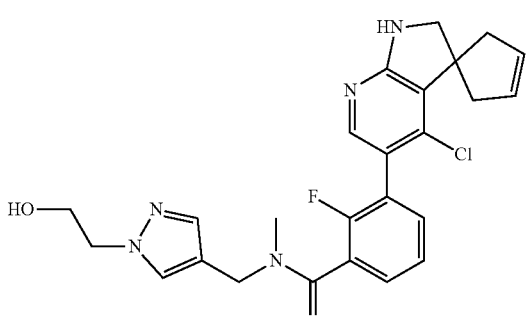<br>3-(4'-Chloro-1',2'-dihydrospiro[cyclopentane-1,3'-pyrrolo[2,3-b]pyridin]-3-en-5'-yl)-2-fluoro-N-((1-(2-hydroxyethyl)-1H-pyrazol-4-yl)methyl)-N-methylbenzamide | 2.99 482.1 A | N | (400 MHz, CDCl3) δ ppm 7.76-7.72 (m, 1H), 7.56-7.49 (m, 1H), 7.44-7.37 (m, 1H), 7.36-7.21 (m, 3H), 5.75 (s, 2H), 4.67 (s, 1H), 4.60 (s, 1H), 4.32 (s, 1H), 4.24-4.16 (m, 2H), 4.03-3.95 (m, 2H), 3.61 (s, 2H), 3.25-3.15 (m, 2H), 3.05 (s, 1H), 2.90 (s, 2H), 2.58-2.48 (m, 2H). |
| 263 | 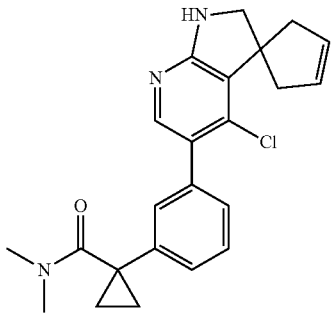<br>1-(3-(4'-Chloro-1',2'-dihydrospiro[cyclopentane-1,3'-pyrrolo[2,3-b]pyridin]-3-en-5'-yl)phenyl)-N,N-dimethylcyclopropane-1-carboxamide | 3.44 394.2 A | S | (400 MHz, DMSO-d$_6$) δ 7.69 (s, 1H), 7.35 (t, J = 7.6 Hz, 1H), 7.19 (d, J = 7.8 Hz, 1H), 7.12-7.07 (m, 2H), 6.93 (s, 1H), 5.76 (s, 2H), 3.49 (s, 2H), 3.06 (d, J = 15.2 Hz, 2H), 2.50 (m, 2H, assumed under DMSO peak), 2.86 (s, 6H), 1.30-1.15 (m, 4H) |
| 264 | 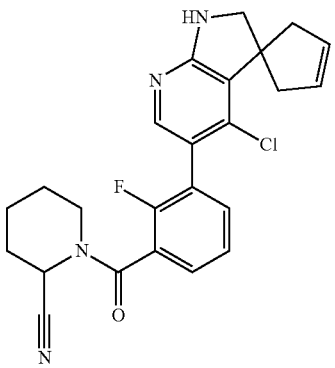<br>1-(3-(4'-chloro-1',2'-dihydrospiro[cyclopentane-1,3'-pyrrolo[2,3-b]pyridin]-3-en-5'-yl)-2-fluorobenzoyl)piperidine-2-carbonitrile | 2.95 377.2 A | L | (400 MHz, DMSO-d$_6$) δ 1.32-2.10 (m, 7H), 2.56 (s, 1H), 2.79-3.22 (m, 3H), 3.48-3.55 (m, 0.8H), 3.51 (s, 2H), 4.51-4.61 (m, 0.2H), 4.90 (br s, 0.2H), 5.76 (s, 2H), 5.88 (br s, 0.8H), 7.12 (s, 1H), 7.35-7.52 (m, 3H), 7.75 (br s, 1H). |

TABLE A1-continued

| No. | Structure/Name | LCMS R_T (min) m/z Method | Prep Mtd | $^1$H NMR δ (ppm) |
|---|---|---|---|---|
| 265 | 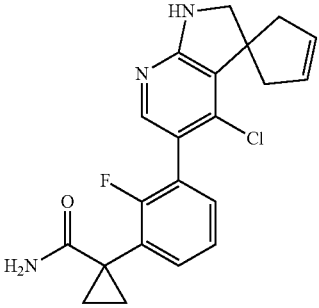<br>1-(3-(4'-Chloro-1',2'-dihydrospiro[cyclopentane-1,3'-pyrrolo[2,3-b]pyridin]-3-en-5'-yl)-2-fluorophenyl)cyclopropane-1-carboxamide | 3.29<br>384.2<br>A | S | (400 MHz, DMSO-d$_6$) δ 7.72 (s, 1H), 7.38 (dt, J = 1.9, 7.2 Hz, 1H), 7.26 (dt, J = 1.8, 7.2 Hz, 1H), 7.20 (t, J = 7.5 Hz, 1H), 7.00 (s, 2H), 6.28 (s, 1H), 5.76 (s, 2H), 3.51 (s, 2H), 3.03 (d, J = 15.4 Hz, 2H), 2.56-2.50 (m, 2H, partially under DMSO peak), 1.42-1.38 (m, 2H), 1.02-0.96 (m, 2H) |
| 266a | 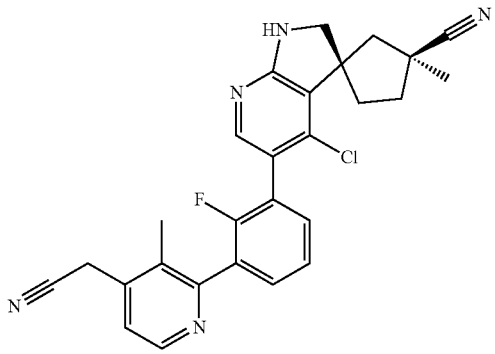<br>(1R,3S)-4'-Chloro-5'-(3-(4-(cyanomethyl)-3-methylpyridin-2-yl)-2-fluorophenyl)-3-methyl-1',2'-dihydrospiro[cyclopentane-1,3'-pyrrolo[2,3-b]pyridine]-3-carbonitrile<br>first speak SFC; absolute configuration arbitrarily assigned | 3.72<br>472.1<br>A | L | (400 MHz, CDCl3) δ 8.60 (d, J = 5.2 H, 1H), 7.82 (s, 1H), 7.51-7.44 (m, 1H), 7.42 (d, J = 4.8 Hz, 1H), 7.36-7.30 (m, 2H), 4.74 (s, 1H), 3.92 (d, J = 9.4 Hz, 1H), 3.76 (s, 2H), 3.64 (dd, J = 9.6, 1.7 Hz, 1H), 2.81-2.68 (m, 1H), 2.49 (d, J = 13.1 Hz, 1H), 2.35-2.89 (m, 1H), 2.26 (d, J = 1.9 Hz, 3H), 2.21-2.13 (m, 1H), 2.12-2.00 (m, 2H), 1.54 (s, 3H). |
| 266b | 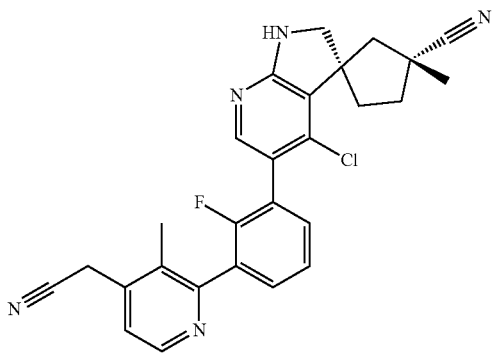<br>(1S,3R)-4'-Chloro-5'-(3-(4-(cyanomethyl)-3-methylpyridin-2-yl)-2-fluorophenyl)-3-methyl-1',2'-dihydrospiro[cyclopentane-1,3'-pyrrolo[2,3-b]pyridine]-3-carbonitrile<br>second peak SFC; absolute configuration arbitrarily assigned | 3.72<br>472.1<br>A | L | (400 MHz, CDCl3) δ 8.60 (d, J = 5.2 H, 1H), 7.82 (s, 1H), 7.51-7.44 (m, 1H), 7.42 (d, J = 4.8 Hz, 1H), 7.36-7.30 (m, 2H), 4.74 (s, 1H), 3.92 (d, J = 9.4 Hz, 1H), 3.76 (s, 2H), 3.64 (dd, J = 9.6, 1.7 Hz, 1H), 2.81-2.68 (m, 1H), 2.49 (d, J = 13.1 Hz, 1H), 2.35-2.89 (m, 1H), 2.26 (d, J = 1.9 Hz, 3H), 2.21-2.13 (m, 1H), 2.12-2.00 (m, 2H), 1.54 (s, 3H). |

TABLE A1-continued

| No. | Structure/Name | LCMS $R_T$ (min) m/z Method | Prep Mtd | $^1$H NMR δ (ppm) |
|---|---|---|---|---|
| 267a | 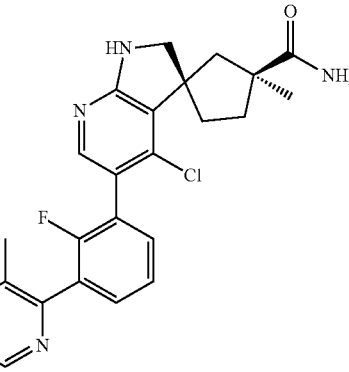<br>(1R,3S)-4'-Chloro-5'-(3-(4-(cyanomethyl)-3-methylpyridin-2-yl)-2-fluorophenyl)-3-methyl-1',2'-dihydrospiro[cyclopentane-1,3'-pyrrolo[2,3-b]pyridine]-3-carboxamide<br>first peak of SFC; absolute configuration arbitrarily assigned | 2.99<br>490.2<br>B | L | (400 MHz, CDCl3) δ 8.60 (d, J = 5.0 Hz, 1H), 7.77 (s, 1H), 7.47 (td, J = 6.3, 3.4 Hz, 1H), 7.42 (d, J = 4.9 Hz, 1H), 7.37-7.30 (m, 2H), 5.63 (s, 1H), 5.32 (s, 1H), 4.78 (s, 1H), 3.77 (s, 2H), 3.75 (d, J = 9.6 Hz, 1H), 3.49 (d, J = 9.3 Hz, 1H), 2.71-2.59 (m, 1H), 2.51 (d, J = 13.3 Hz, 1H), 2.35-2.22 (m, 5H), 1.94-1.86 (m, 1H), 1.86-1.78 (m, 1H), 1.44 (s, 3H). |
| 267b | 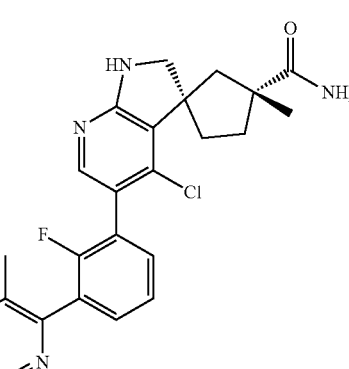<br>(1S,3R)-4'-Chloro-5'-(3-(4-(cyanomethyl)-3-methylpyridin-2-yl)-2-fluorophenyl)-3-methyl-1',2'-dihydrospiro[cyclopentane-1,3'-pyrrolo[2,3-b]pyridine]-3-carboxamide<br>second peak on SFC; absolute configuration arbitrarily assigned | 2.99<br>490.2<br>B | L | (400 MHz, CDCl3) δ 8.60 (d, J = 5.0 Hz, 1H), 7.77 (s, 1H), 7.47 (td, J = 6.3, 3.4 Hz, 1H), 7.42 (d, J = 4.9 Hz, 1H), 7.37-7.30 (m, 2H), 5.63 (s, 1H), 5.32 (s, 1H), 4.78 (s, 1H), 3.77 (s, 2H), 3.75 (d, J = 9.6 Hz, 1H), 3.49 (d, J = 9.3 Hz, 1H), 2.71-2.59 (m, 1H), 2.51 (d, J = 13.3 Hz, 1H), 2.35-2.22 (m, 5H), 1.94-1.86 (m, 1H), 1.86-1.78 (m, 1H), 1.44 (s, 3H). |

TABLE A1-continued

| No. | Structure/Name | LCMS $R_T$ (min) m/z Method | Prep Mtd | $^1$H NMR δ (ppm) |
|---|---|---|---|---|
| 268 | 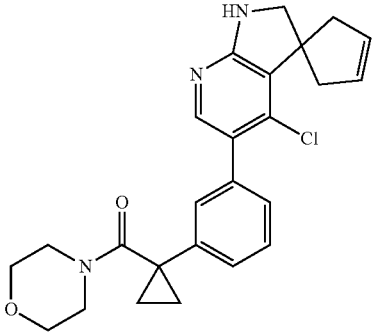<br>(1-(3-(4'-Chloro-1',2'-dihydrospiro[cyclopentane-1,3'-pyrrolo[2,3-b]pyridin]-3-en-5'-yl)phenyl)cyclopropyl)(morpholino)methanone | 3.37<br>436.2<br>A | V | (400 MHz, DMSO-d$_6$) δ 7.69 (s, 1H), 7.36 (t, J = 7.7 Hz, 1H), 7.20 (d, J = 7.7 Hz, 1H), 7.14 (d, J = 8.3 Hz, 1H), 7.10 (m, 1H), 6.93 (s, 1H), 5.77 (s, 2H), 3.45 (d, J = 24.1 Hz, 7H), 3.57-3.38 (m, 8H), 3.06 (d, J = 15.1 Hz, 2H), 2.53 (d, J = 4.4 Hz, 2H), 1.34-1.28 (m, 2H), 1.24-1.19 (m, 2H) |
| 269 | 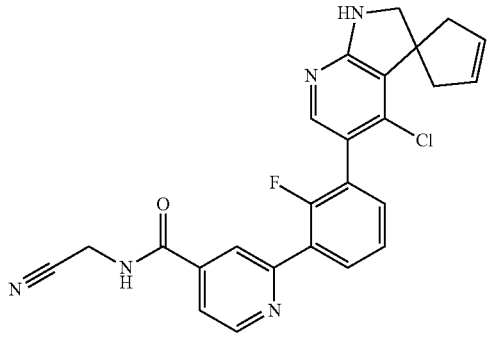<br>2-(3-(4'-Chloro-1',2'-dihydrospiro[cyclopentane-1,3'-pyrrolo[2,3-b]pyridin]-3-en-5'-yl)-2-fluorophenyl)-N-(cyanomethyl)isonicotinamide | 3.54<br>460.2<br>A | L | (400 MHz, CDCl3) δ 8.88 (d, J = 5.0 Hz, 1H), 8.08 (s, 1H), 7.97 (td, J = 6.0, 2.5 Hz, 1H), 7.74 (s, 1H), 7.66 (dd, J = 5.0, 1.6 Hz, 1H), 7.47 (t, J = 5.2 Hz, 1H), 7.38-7.28 (m, 2H), 5.76 (s, 2H), 4.72 (s, 1H), 4.39 (d, J = 5.7 Hz, 2H), 3.62 (s, 2H), 3.22 (d, J = 15.4 Hz, 2H), 2.53 (d, J = 15.0 Hz, 2H). |
| 270 | 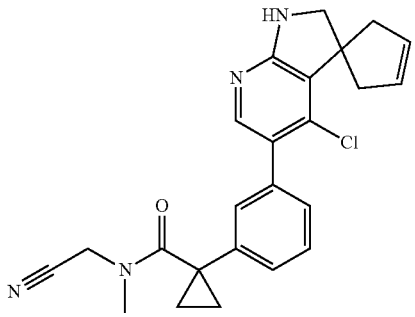<br>1-(3-(4'-Chloro-1',2'-dihydrospiro[cyclopentane-1,3'-pyrrolo[2,3-b]pyridin]-3-en-5'-yl)phenyl)-N-(cyanomethyl)-N-methylcyclopropane-1-carboxamide | 3.49<br>419.2<br>A | R | (400 MHz, DMSO-d$_6$) δ 7.70 (s, 1H), 7.38 (t, J = 7.9 Hz, 1H), 7.22 (d, J = 7.7 Hz, 1H), 7.11 (m, 2H), 6.93 (s, 1H), 5.76 (s, 2H), 4.43 (s, 2H), 3.49 (s, 2H), 3.06 (d, J = 15.2 Hz, 2H), 2.92 (s, 3H), 2.50-2.47 (m, 2H, partially under DMSO peak), 1.35-1.25 (m, 4H). |

TABLE A1-continued

| No. | Structure/Name | LCMS R_T (min) m/z Method | Prep Mtd | $^1$H NMR δ (ppm) |
|---|---|---|---|---|
| 271a | 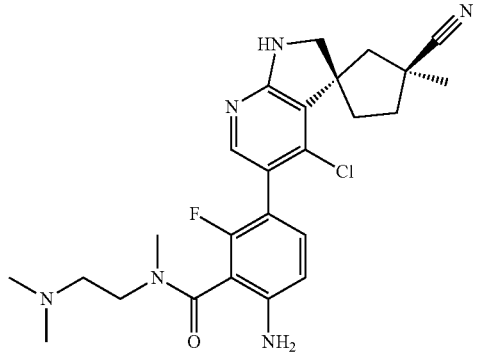<br>6-Amino-3-((1RS,3SR)-4'-chloro-3-cyano-3-methyl-1',2'-dihydrospiro[cyclopentane-1,3'-pyrrolo[2,3-b]pyridin]-5'-yl)-N-(2-(dimethylamino)ethyl)-2-fluoro-N-methylbenzamide | 2.25<br>485.2<br>A | L | (400 MHz, DMSO-d$_6$) δ 7.64 & 7.61 (2 × s, 1H), 6.98-6.92 (m, 2H), 6.55 & 6.52 (2 × d, J = 8.4 Hz, 1H), 5.71 & 5.37 (2 × brs, 2H), 4.10-4.02 (m, 1H), 3.63 & 3.52 (ABq, J = 9.6 Hz, 2H), 3.28-3.11 (m, 2H), 2.99 & 2.86 (2 × s, 3H), 2.69-2.61 (m, 1H), 2.40-1.89 (m, 12H), 1.48 & 1.47 (2 × s, 3H). |
| 272a | 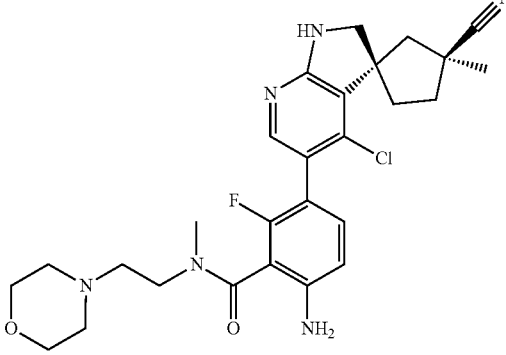<br>6-Amino-3-((1RS,3SR)-4'-chloro-3-cyano-3-methyl-1',2'-dihydrospiro[cyclopentane-1,3'-pyrrolo[2,3-b]pyridin]-5'-yl)-2-fluoro-N-methyl-N-(2-morpholinoethyl)benzamide | 2.31<br>527.2<br>A | L | (400 MHz, DMSO-d$_6$) δ 7.65 & 7.61 (2 × s, 1H), 6.98-6.94 (m, 2H), 6.54 & 6.52 (2 × d, J = 8.3 Hz, 1H), 5.72 & 5.40 (2 × brs, 2H), 4.25-4.17 (m, 1H), 3.63 (d, J = 9.5 Hz, 2H), 3.57-3.45 (m, 5H), 3.11-3.05 (m, 1H), 2.99 & 2.88 (2 × s, 3H), 2.76-2.55 (m, 2H), 2.44-1.89 (m, 10H), 1.47 (2 × s, 3H). |
| 273a | 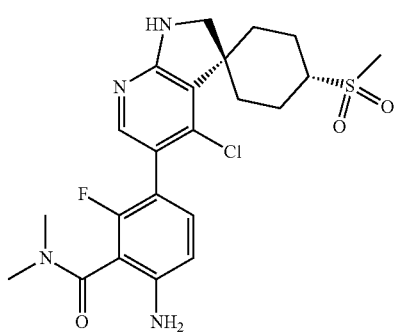<br>6-Amino-3-((1r,4r)-4'-chloro-4-(methylsulfonyl)-1',2'-dihydrospiro[cyclohexane-1,3'-pyrrolo[2,3-b]pyridin]-5'-yl)-2-fluoro-N,N-dimethylbenzamide | 2.21<br>481.1<br>A | L | (400 MHz, DMSO-d$_6$) δ 7.58 (s, 1H), 6.95 (t, J = 8.5 Hz, 1H), 6.91 (s, 1H), 6.54 (d, J = 8.4 Hz, 1H), 5.37 (brs, 2H), 3.47 (s, 2H), 3.27-3.24 (m, 1H), 3.01 (s, 3H), 2.99 (s, 3H), 2.88 (s, 3H), 2.72-2.62 (m, 2H), 2.29-2.24 (m, 2H), 1.93-1.84 (m, 2H), 1.50-1.44 (m, 2H). |

TABLE A1-continued

| No. | Structure/Name | LCMS R_T (min) m/z Method | Prep Mtd | $^1$H NMR δ (ppm) |
|---|---|---|---|---|
| 274a | 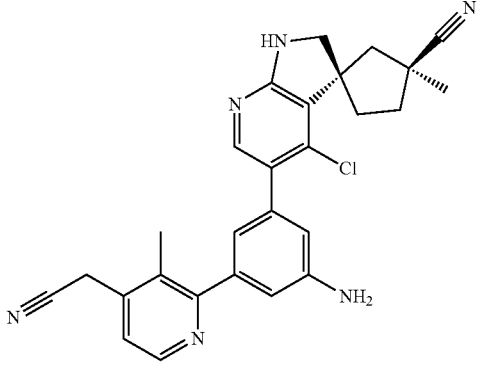<br>(1R,3S)-5'-(3-Amino-5-(4-(cyanomethyl)-3-methylpyridin-2-yl)phenyl)-4'-chloro-3-methyl-1',2'-dihydrospiro[cyclopentane-1,3'-pyrrolo[2,3-b]pyridine]-3-carbonitrile<br>first peak on SFC; absolute configuration arbitrarily assigned | 2.76 469.1 A | L | (400 MHz, CDCl3) δ 8.55 (d, J = 4.9 Hz, 1H), 7.84 (s, 1H), 7.34 (d, J = 4.9 Hz, 1H), 6.82-6.76 (m, 2H), 6.73-6.69 (m, 1H), 4.65 (s, 1H), 3.90 (d, J = 9.4 Hz, 1H), 3.89 (s, 2H), 3.75 (s, 2H), 3.62 (dd, J = 9.4, 1.7 Hz, 1H), 2.80-2.71 (m, 1H), 2.47 (d, J = 13.9 Hz, 1H), 2.36 (s, 3H), 2.33-2.26 (m, 2H), 2.16 (d, J = 13.7 Hz, 1H), 2.13-1.99 (m, 1H), 1.53 (s, 3H). |
| 274b | 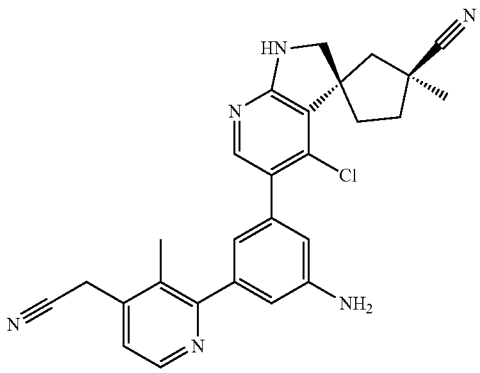<br>(1S,3R)-5'-(3-Amino-5-(4-(cyanomethyl)-3-methylpyridin-2-yl)phenyl)-4'-chloro-3-methyl-1',2'-dihydrospiro[cyclopentane-1,3'-pyrrolo[2,3-b]pyridine]-3-carbonitrile<br>second peak on SFC; absolute configuration arbitrarily assigned | 2.76 469.1 A | L | (400 MHz, CDCl3) δ 8.55 (d, J = 4.9 Hz, 1H), 7.84 (s, 1H), 7.34 (d, J = 4.9 Hz, 1H), 6.82-6.76 (m, 2H), 6.73-6.69 (m, 1H), 4.65 (s, 1H), 3.90 (d, J = 9.4 Hz, 1H), 3.89 (s, 2H), 3.75 (s, 2H), 3.62 (dd, J = 9.4, 1.7 Hz, 1H), 2.80-2.71 (m, 1H), 2.47 (d, J = 13.9 Hz, 1H), 2.36 (s, 3H), 2.33-2.26 (m, 2H), 2.16 (d, J = 13.7 Hz, 1H), 2.13-1.99 (m, 1H), 1.53 (s, 3H). |

TABLE A1-continued

| No. | Structure/Name | LCMS R_T (min) m/z Method | Prep Mtd | $^1$H NMR δ (ppm) |
|---|---|---|---|---|
| 275a | 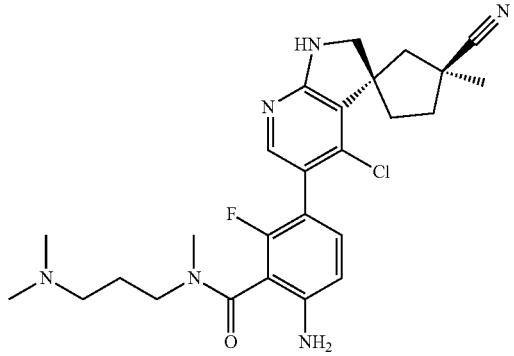<br>6-Amino-3-((1R,3SR)-4'-chloro-3-cyano-3-methyl-1',2'-dihydrospiro[cyclopentane-1,3'-pyrrolo[2,3-b]pyridin]-5'-yl)-N-(3-(dimethylamino)propyl)-2-fluoro-N-methylbenzamide | 2.26<br>499.2<br>A | L | (400 MHz, DMSO-d$_6$) δ 7.64 & 7.60 (2 × s, 1H), 6.99-6.93 (m, 2H), 6.56 & 6.53 (2 × d, J = 8.4 Hz, 1H), 5.37 & 5.36 (2 × brs, 2H), 3.63 & 3.52 (ABq, J = 9.6 Hz, 2H), 3.60-3.54 (m, 0.5H), 3.38-3.34 (m, 0.5H), 3.19 (t, J = 7.6 Hz, 1H), 2.97 & 2.86 (2 × s, 3H), 2.41-2.36 (m, 1H), 2.28-2.22 (m, 2H), 2.16-1.89 (m, 10H), 1.78-1.49 (m, 2H), 1.47 (s, 3H). |
| 276 | 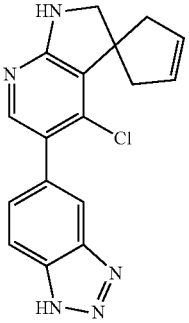<br>5'-(1H-Benzo[d][1,2,3]triazol-5-yl)-4'-chloro-1',2'-dihydrospiro[cyclopentane-1,3'-pyrrolo[2,3-b]pyridin]-3-ene | 2.91<br>324.2<br>B | L | (400 MHz, DMSO-d$_6$) δ 7.89 (d, J = 8.6 Hz, 1H), 7.80 (m, 1H), 7.79 (s, 1H), 7.36 (dd, J = 1.5, 8.6 Hz, 1H), 6.95 (s, 1H), 5.77 (s, 2H), 3.52 (s, 2H), 3.08 (d, J = 15.2 Hz, 2H), 2.54-2.50 (m, 2H, partially under the DMSO peak). |
| 277 | 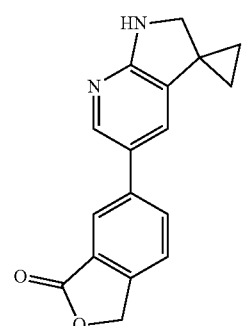<br>6-(1',2'-dihydrospiro[cyclopropane-1,3'-pyrrolo[2,3-b]pyridin]-5'-yl)isobenzofuran-1(3H)-one | 279.1 | L | |

TABLE A1-continued

| No. | Structure/Name | LCMS R$_T$ (min) m/z Method | Prep Mtd | $^1$H NMR δ (ppm) |
|---|---|---|---|---|
| 278 | 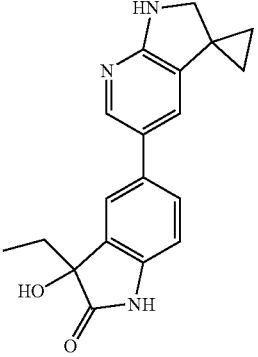<br>(RS)-5-(1',2'-dihydrospiro[cyclopropane-1,3'-pyrrolo[2,3-b]pyridin]-5'-yl)-3-ethyl-3-hydroxyindolin-2-one | 322.1 | L | |
| 279 | 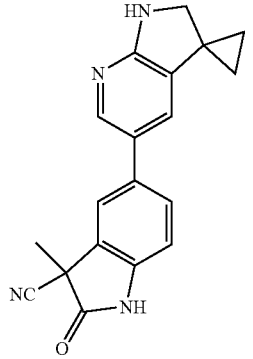<br>(RS)-5-(1',2'-dihydrospiro[cyclopropane-1,3'-pyrrolo[2,3-b]pyridin]-5'-yl)-3-methyl-2-oxoindoline-3-carbonitrile | 317.1 | L | |
| 280 | 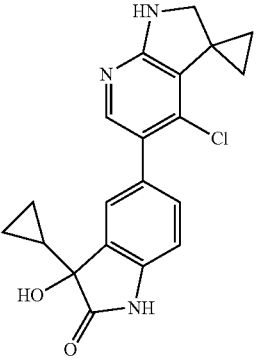<br>(RS)-5-(4'-chloro-1',2'-dihydrospiro[cyclopropane-1,3'-pyrrolo[2,3-b]pyridin]-5'-yl)-3-cyclopropyl-3-hydroxyindolin-2-one | 368.2 | L | |

TABLE A1-continued

| No. | Structure/Name | LCMS R_T (min) m/z Method | Prep Mtd | $^1$H NMR δ (ppm) |
|---|---|---|---|---|
| 281 | 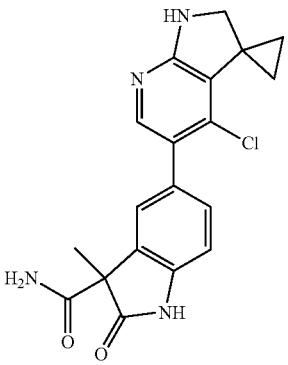<br>(RS)-5-(4'-chloro-1',2'-dihydrospiro[cyclopropane-1,3'-pyrrolo[2,3-b]pyridin]-5'-yl)-3-methyl-2-oxoindoline-3-carboxamide | 369.1 | L | |
| 282 | 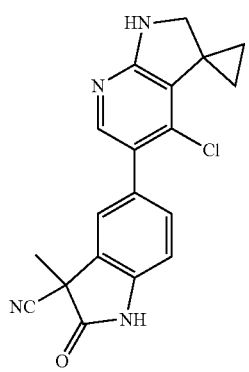<br>(RS)-5-(4'-chloro-1',2'-dihydrospiro[cyclopropane-1,3'-pyrrolo[2,3-b]pyridin]-5'-yl)-3-methyl-2-oxoindoline-3-carbonitrile | 351.2 | L | |
| 283 | 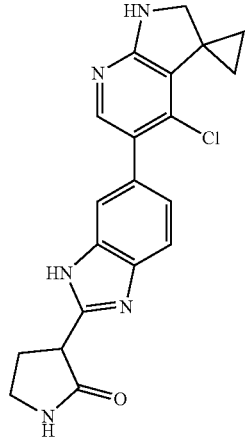<br>(±)-3-(6-(4'-Chloro-1',2'-dihydrospiro[cyclopropane-1,3'-pyrrolo[2,3-b]pyridin]-5'-yl)-1H-benzo[d]imidazol-2-yl)pyrrolidin-2-one | 2.11<br>380.1<br>A | L | (400 MHz, DMSO-d$_6$) δ 12.42 (brs, 1H), 7.96 (s, 1H), 7.61 (s, 1H), 7.50 (d, J = 8.1 Hz, 1H), 7.39 (s, 1H), 7.06 (dd, J = 8.2, 1.6 Hz, 1H), 6.92 (s, 1H), 3.84 (t, J = 9.0 Hz, 1H), 3.53 (s, 2H), 3.45-3.40 (m, 1H), 3.38-3.32 (m, 1H), 2.64-2.57 (m, 1H), 1.68-1.65 (m, 2H), 0.90-0.87 (m, 2H). |

TABLE A1-continued

| No. | Structure/Name | LCMS R_T (min) m/z Method | Prep Mtd | $^1$H NMR δ (ppm) |
|---|---|---|---|---|
| 284 | 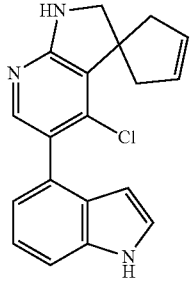<br>4'-Chloro-5'-(1H-indol-4-yl)-1',2'-dihydrospiro[cyclopentane-1,3'-pyrrolo[2,3-b]pyridin]-3-ene | 3.41<br>322.2<br>B | L | (400 MHz, DMSO-d$_6$) δ 11.17 (s, 1H), 7.74 (s, 1H), 7.39 (d, J = 8.1 Hz, 1H), 7.33 (t, J = 2.7 Hz, 1H), 7.12 (t, J = 7.7 Hz, 1H), 6.89 (dd, J = 0.9, 7.2 Hz, 1H), 6.84 (s, 1H), 6.14 (s, 1H), 5.77 (s, 2H), 3.52 (d, J = 1.0 Hz, 2H), 3.09 (d, J = 15.1 Hz, 2H), 2.54 (d, J = 15.0 Hz, 2H). |
| 285 | 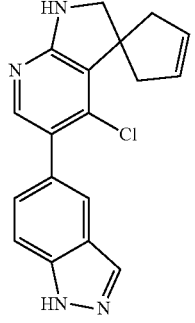<br>4'-Chloro-5'-(1H-indazol-5-yl)-1',2'-dihydrospiro[cyclopentane-1,3'-pyrrolo[2,3-b]pyridin]-3-ene | 3.0<br>323.2<br>B | L | (400 MHz, DMSO-d$_6$) δ 13.10 (bs, 1H), 8.09 (d, J = 0.9 Hz, 1H, 7.74 (s, 1H), 7.70 (s, 1H), 7.56 (d, J = 8.9 Hz, 1H), 7.33 (dd, J = 1.6, 8.6 Hz, 1H), 6.86 (s, 1H), 5.77 (s, 2H), 3.50 (s, 2H), 3.08 (d, J = 15.1 Hz, 2H), 2.52 (m, 2H, partially under DMSO peak). |
| 286 | 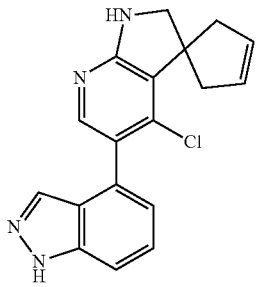<br>4'-Chloro-5'-(1H-indazol-4-yl)-1',2'-dihydrospiro[cyclopentane-1,3'-pyrrolo[2,3-b]pyridin]-3-ene | 3.19<br>323.2<br>B | L | (400 MHz, DMSO-d$_6$) δ 13.14 (bs, 1H), 7.82 (d, J = 0.9 Hz, 1H), 7.79 (s, 1H), 7.55-7.51 (m, 1H), 7.38 (dd, J = 7.0, 8.4 Hz, 1H), 7.02 (dd, J = 0.6, 7.0 Hz, 1H), 6.99 (bs, 1H), 5.77 (s, 2H), 3.54 (s, 2H), 3.10 (d, J = 15.3 Hz, 2H), 2.55 (d, J = 15.0 Hz, 2H) |

TABLE A1-continued

| No. | Structure/Name | LCMS R$_T$ (min) m/z Method | Prep Mtd | $^1$H NMR δ (ppm) |
|---|---|---|---|---|
| 287 | 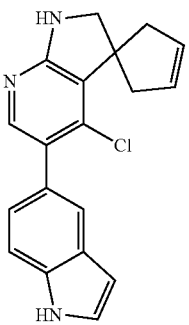<br>4'-Chloro-5'-(1H-indol-5-yl)-1',2'-dihydrospiro[cyclopropane-1,3'-pyrrolo[2,3-b]pyridin]-3-ene | 3.45<br>322.3<br>B | L | (400 MHz, DMSO-d$_6$) δ 11.13 (s, 1H), 7.71 (s, 1H), 7.48 (m, 1H), 7.41 (d, J = 8.4 Hz, 1H), 7.37 (t, J = 2.7 Hz, 1H), 7.05 (dd, J = 1.7, 8.3 Hz, 1H), 6.76 (s, 1H), 6.45 (m, 1H), 5.77 (s, 2H), 3.49 (s, 2H), 3.08 (d, J = 15.1 Hz, 2H), 2.53-2.52 (m, 2H, partially under the DMSO peak). |
| 288 | 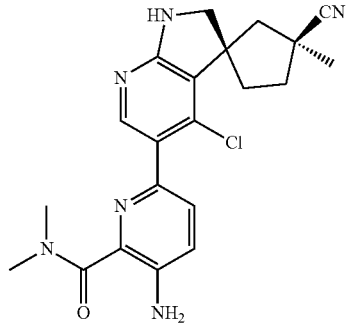<br>3-Amino-6-((1R,3S)-4'-chloro-3-cyano-3-methyl-1',2'-dihydrospiro[cyclopentane-1,3'-pyrrolo[2,3-b]pyridin]-5-yl)-N,N-dimethylpicolinamide | 2.60<br>411.2<br>B | See text | (400 MHz, DMSO-d$_6$) δ 7.79 (s, 1H), 7.26 (d, J = 8.2 Hz, 1H), 7.15 (d, J = 8.7 Hz, 1H), 6.99 (s, 1H), 5.57 (s, 2H), 3.64 (d, J = 9.3 Hz, 1H), 3.52 (d, J = 9.3 Hz, 1H), 2.99 (s, 3H), 2.98 (s, 3H), 2.60-2.51 (m, 1H), 2.38 (d, J = 13.1 Hz, 1H), 2.29-2.21 (m, 1H), 2.15 (d, J = 13.2 Hz, 1H), 2.06-1.88 (m, 2H), 1.48 (s, 3H). |
| 289 | 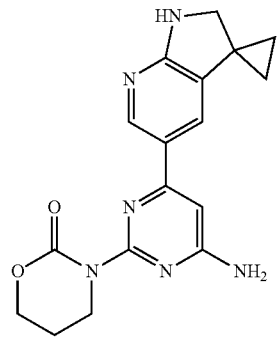<br>3-(4-amino-6-(1',2'-dihydrospiro[cyclopropane-1,3'-pyrrolo[2,3-b]pyridin]-5'-yl)pyrimidin-2-yl)-1,3-oxazinan-2-one | 339.2 | L | |

| No. | Structure/Name | LCMS R_T (min) m/z Method | Prep Mtd | $^1$H NMR δ (ppm) |
|---|---|---|---|---|
| 290a | 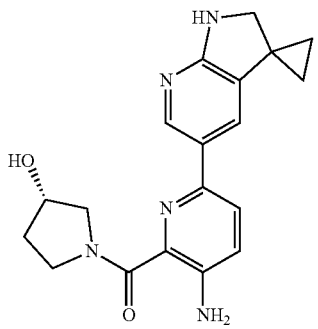<br>(S)-(3-amino-6-(1′,2′-dihydrospiro[cyclopropane-1,3′-pyrrolo[2,3-b]pyridin]-5′-yl)pyridin-2-yl)(3-hydroxypyrrolidin-1-yl)methanone | 352.2 | L | |
| 290b | 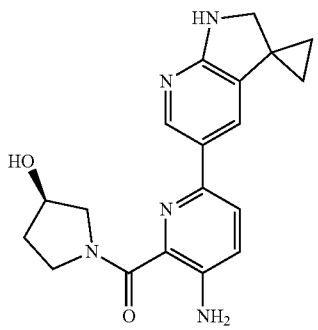<br>(R)-(3-amino-6-(1′,2′-dihydrospiro[cyclopropane-1,3′-pyrrolo[2,3-b]pyridin]-5′-yl)pyridin-2-yl)(3-hydroxypyrrolidin-1-yl)methanone | 352.2 | L | |

TABLE A1-continued
| No. | Structure/Name | LCMS R_T (min) m/z Method | Prep Mtd | ¹H NMR δ (ppm) |
|---|---|---|---|---|
| 291 | 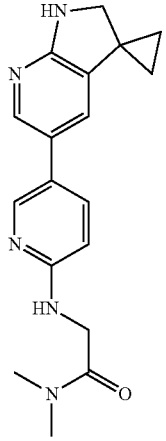 2-((5-(1',2'-dihydrospiro[cyclopropane-1,3'-pyrrolo[2,3-b]pyridin]-5'-yl)pyridin-2-yl)amino)-N,N-dimethyl-acetamide | 324.2 | L | |
| 292 | 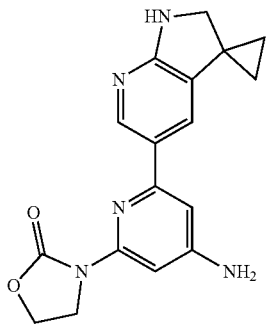 3-(4-amino-6-(1',2'-dihydrospiro[cyclopropane-1,3'-pyrrolo[2,3-b]pyridin]-5'-yl)pyridin-2-yl)oxazolidin-2-one | 324.2 | L | |
| 293 | 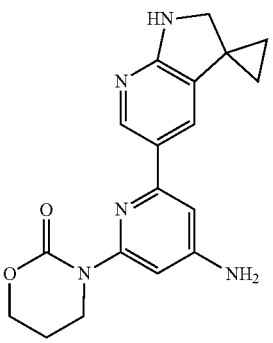 3-(4-amino-6-(1',2'-dihydrospiro[cyclopropane-1,3'-pyrrolo[2,3-b]pyridin]-5'-yl)pyridin-2-yl)-1,3-oxazinan-2-one | 338.1 | L | |

| No. | Structure/Name | LCMS R_T (min) m/z Method | Prep Mtd | $^1$H NMR δ (ppm) |
|---|---|---|---|---|
| 294 | 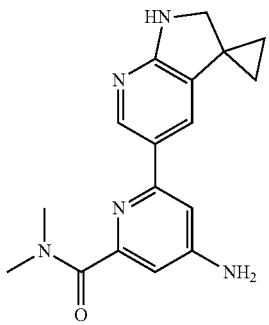<br>4-amino-6-(1',2'-dihydrospiro[cyclopropane-1,3'-pyrrolo[2,3-b]pyridin]-5'-yl)-N,N-dimethylpiconlinamide | 310.1 | L | |
| 295 | 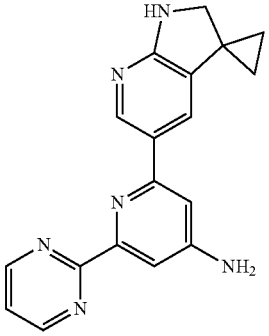 [SMILES: Nc1cc(-c2cnc3c(c2)C2(CC2)CN3)nc(-c2ncccn2)c1] | 317.2 | L | |
| 296 | 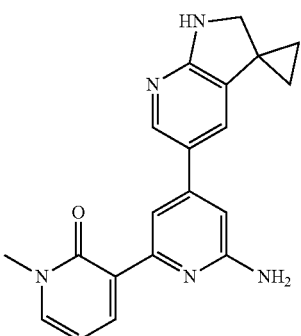<br>6-amino-4-(4'-chloro-1',2'-dihydrospiro[cyclopropane-1,3'-pyrrolo[2,3-b]pyridin]-5'-yl)-1-methyl-[2,3'-bipyridin]-2'(1'H)-one | 380.1 | L | |

| No. | Structure/Name | LCMS R$_T$ (min) m/z Method | Prep Mtd | $^1$H NMR δ (ppm) |
|---|---|---|---|---|
| 297 | 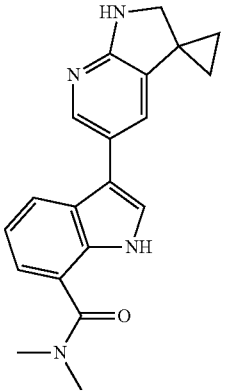<br>3-(1',2'-Dihydrospiro[cyclopropane-1,3'-pyrrolo[2,3-b]pyridin]-5'-yl)-N,N-dimethyl-1H-indole-7-carboxamide | 2.64<br>333.2<br>A | N | (400 MHz, DMSO-d$_6$) δ 11.15 (s, 1H), 7.97 (d, J = 2.0 Hz, 1H), 7.77 (d, J = 7.3, 1.8 Hz, 1H), 7.49 (s, 1H), 7.14-7.06 (m, 2H), 6.46 (s, 1H), 3.53 (d, J = 1.3 Hz, 2H), 3.17 (s, 1H), 3.11-2.82 (m, 6H), 1.11-1.06 (m, 2H), 1.00-0.95 (m, 2H). |
| 298 | 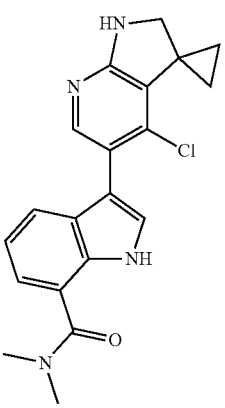<br>3-(4'-Chloro-1',2'-dihydrospiro[cyclopropane-1,3'-pyrrolo[2,3-b]pyridin]-5'-yl)-N,N-dimethyl-1H-indole-7-carboxamide | 2.95<br>367.2<br>A | P | (400 MHz, DMSO-d$_6$) δ 11.22 (brs, 1H), 7.69 (s, 1H), 7.41 (d, J = 7.7 Hz, 1H), 7.34 (d, J = 2.6 Hz, 1H), 7.12 (dd, J = 7.2, 1.1 Hz, 1H), 7.05 (dd, J = 7.8, 7.4 Hz, 1H), 6.88 (s, 1H), 3.54 (s, 2H), 3.00 (brs, 6H), 1.68-1.66 (m, 2H), 0.91-0.88 (m, 2H). |

TABLE A1-continued

| No. | Structure/Name | LCMS R_T (min) m/z Method | Prep Mtd | $^1$H NMR δ (ppm) |
|---|---|---|---|---|
| 299 | 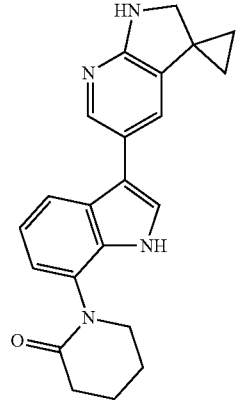<br>1-(3-(1',2'-Dihydrospiro[cyclopropane-1,3'-pyrrolo[2,3-b]pyridin]-5'-yl)-1H-indol-7-yl)piperidin-2-one | 2.81<br>359.2<br>A | P | (400 MHz, DMSO-d$_6$) δ 11.05 (brs, 1H), 7.96 (d, J = 2.0 Hz, 1H), 7.62 (brd, J = 7.9 Hz, 1H), 7.48 (d, J = 2.6 Hz, 1H), 7.10 (d, J = 2.0 Hz, 1H), 7.05 (t, J = 7.6 Hz, 1H), 6.97 (dd, J = 7.4, 1.0 Hz, 1H), 6.45 (brs, 1H), 3.60-3.57 (m, 2H), 3.53 (d, J = 1.4 Hz, 2H), 2.46-2.43 (m, 2H), 1.96-1.91 (m, 4H), 1.10-1.07 (m, 2H), 1.00-0.97 (m, 2H). |
| 300 | 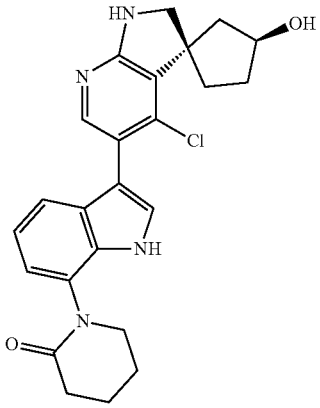<br>1-(3-((1R,3SR)-4'-Chloro-3-hydroxy-1',2'-dihydrospiro[cyclopentane-1,3'-pyrrolo[2,3-b]pyridin]-5'-yl)-1H-indol-7-yl)piperidin-2-one | 2.75<br>437.2<br>A | P | (400 MHz, DMSO-d$_6$) δ 11.16 (brs, 1H), 7.77 (s, 1H), 7.40 (d, J = 2.6 Hz, 1H), 7.30 (brd, J = 7.7 Hz, 1H), 7.02 (t, J = 7.6 Hz, 1H), 6.97 (dd, J = 7.4, 1.0 Hz, 1H), 6.71 (s, 1H), 4.66 (d, J = 3.2 Hz, 1H), 4.39-4.33 (m, 1H), 3.63-3.60 (m, 3H), 3.46-3.43 (m, 1H), 2.47-2.44 (m, 2H), 2.37 (dd, J = 13.5, 5.9 Hz, 1H), 2.24-2.17 (m, 1H), 2.07-1.98 (m, 1H), 1.95-1.85 (m, 5H), 1.77-1.63 (m, 2H). |

TABLE A1-continued

| No. | Structure/Name | LCMS $R_T$ (min) m/z Method | Prep Mtd | $^1$H NMR δ (ppm) |
|---|---|---|---|---|
| 300a | 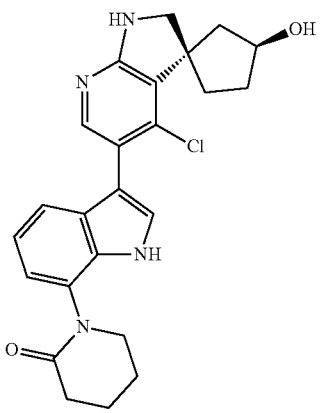<br>1-(3-((1R,3S)-4'-Chloro-3-hydroxy-1',2'-dihydrospiro[cyclopentane-1,3'-pyrrolo[2,3-b]pyridin]-5'-yl)-1H-indol-7-yl)piperidin-2-one<br>first peak on SFC; absolute configuration arbitrarily assigned | 2.73<br>437.2<br>A | P | (400 MHz, DMSO-d$_6$) δ 11.16 (brs, 1H), 7.77 (s, 1H), 7.40 (d, J = 2.6 Hz, 1H), 7.30 (brd, J = 7.7 Hz, 1H), 7.02 (t, J = 7.6 Hz, 1H), 6.97 (dd, J = 7.4, 1.0 Hz, 1H), 6.71 (s, 1H), 4.66 (d, J = 2.8 Hz, 1H), 4.39-4.33 (m, 1H), 3.63-3.60 (m, 3H), 3.46-3.43 (m, 1H), 2.47-2.44 (m, 2H), 2.37 (dd, J = 13.5, 6.0 Hz, 1H), 2.24-2.17 (m, 1H), 2.07-1.98 (m, 1H), 1.95-1.85 (m, 5H), 1.77-1.63 (m, 2H). |
| 300b | 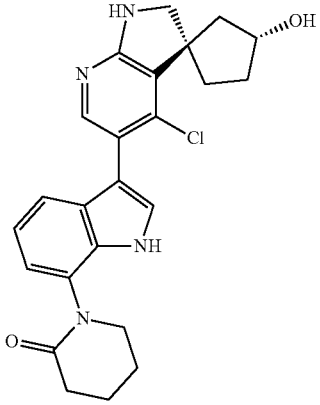<br>1-(3-((1S,3R)-4'-Chloro-3-hydroxy-1',2'-dihydrospiro[cyclopentane-1,3'-pyrrolo[2,3-b]pyridin]-5'-yl)-1H-indol-7-yl)piperidin-2-one<br>second peak on SFC; absolute configuration arbitrarily assigned | 2.73<br>437.2<br>A | P | (400 MHz, DMSO-d$_6$) δ 11.16 (brs, 1H), 7.77 (s, 1H), 7.40 (s, 1H), 7.30 (dd, J = 7.7, 1.1 Hz, 1H), 7.02 (t, J = 7.6 Hz, 1H), 6.97 (dd, J = 7.4, 1.0 Hz, 1H), 6.71 (s, 1H), 4.67 (brs, 1H), 4.39-4.33 (m, 1H), 3.63-3.60 (m, 3H), 3.46-3.43 (m, 1H), 2.47-2.44 (m, 2H), 2.37 (dd, J = 13.5, 5.9 Hz, 1H), 2.24-2.17 (m, 1H), 2.07-1.98 (m, 1H), 1.95-1.85 (m, 5H), 1.77-1.63 (m, 2H). |

TABLE A1-continued

| No. | Structure/Name | LCMS R$_T$ (min) m/z Method | Prep Mtd | $^1$H NMR δ (ppm) |
|---|---|---|---|---|
| 301 | 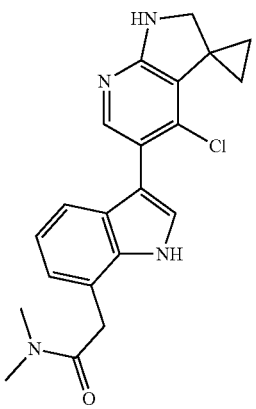<br>2-(3-(4'-Chloro-1',2'-dihydrospiro[cyclopropane-1,3'-pyrrolo[2,3-b]pyridin]-5'-yl)-1H-indol-7-yl)-N,N-dimethylacetamide | 3.02<br>381.2<br>A | P | (400 MHz, DMSO-d$_6$) δ 11.04 (brs, 1H), 7.68 (s, 1H), 7.35 (d, J = 2.6 Hz, 1H), 7.23 (brd, J = 7.7 Hz, 1H), 6.96 (t, J = 7.3 Hz, 1H), 6.90 (brd, J = 7.1 Hz, 1H), 6.85 (brs, 1H), 3.93 (s, 2H), 3.53 (s, 2H), 3.06 (s, 3H), 2.87 (s, 3H), 1.68-1.65 (m, 2H), 0.90-0.87 (m, 2H). |
| 302 | 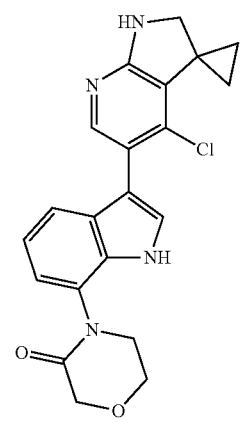<br>4-(3-(4'-Chloro-1',2'-dihydrospiro[cyclopropane-1,3'-pyrrolo[2,3-b]pyridin]-5'-yl)-1H-indol-7-yl)morpholin-3-one | 2.81<br>395.2<br>A | P | (400 MHz, DMSO-d$_6$) δ 11.27 (brs, 1H), 7.69 (s, 1H), 7.39 (d, J = 2.5 Hz, 1H), 7.32 (dd, J = 6.9, 2.1 Hz, 1H), 7.08-7.02 (m, 2H), 6.88 (s, 1H), 4.27 (s, 2H), 4.07-4.05 (m, 2H), 3.75-3.72 (m, 2H), 3.54 (s, 2H), 1.69-1.66 (m, 2H), 0.91-0.88 (m, 2H). |

| No. | Structure/Name | LCMS R$_T$ (min) m/z Method | Prep Mtd | $^1$H NMR δ (ppm) |
|---|---|---|---|---|
| 303 | 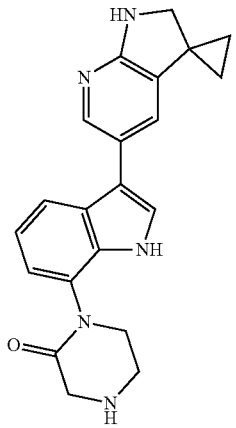<br>1-(3-(1',2'-Dihydrospiro[cyclopropane-1,3'-pyrrolo[2,3-b]pyridin]-5'-yl)-1H-indol-7-yl)piperazin-2-one | 1.81<br>360.2<br>A | Q | (400 MHz, DMSO-d$_6$) δ 11.05 (brs, 1H), 7.97 (d, J = 2.0 Hz, 1H), 7.64 (d, J = 7.8 Hz, 1H), 7.50 (d, J = 2.6 Hz, 1H), 7.10 (d, J = 2.0 Hz, 1H), 7.06 (t, J = 7.6 Hz, 1H), 6.99 (dd, J = 7.4, 1.0 Hz, 1H), 6.46 (s, 1H), 3.58 (t, J = 5.4 Hz, 2H), 3.53 (s, 2H), 3.44 (s, 2H), 3.10 (t, J = 5.4 Hz, 2H), 2.74 (brs, 1H), 1.10-1.07 (m, 2H), 1.00-0.97 (m, 2H). |
| 304a | 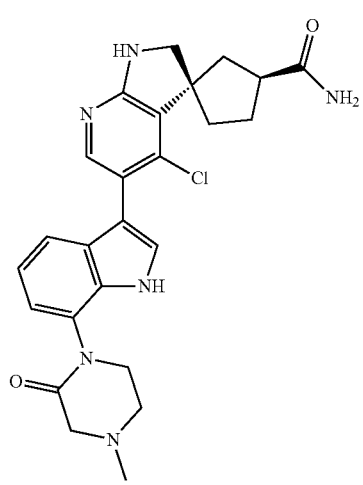<br>(1RS,3SR)-4'-Chloro-5'-(7-(4-methyl-2-oxopiperazin-1-yl)-1H-indol-3-yl)-1',2'-dihydrospiro[cyclopentane-1,3'-pyrrolo[2,3-b]pyridine-3-carboxamide | 1.83<br>479.2<br>A | P | (400 MHz, DMSO-d$_6$) δ 11.17 (d, J = 2.1 Hz, 1H), 7.79 (s, 1H), 7.39 (d, J = 2.6 Hz, 1H), 7.37-7.31 (m, 2H), 7.05-7.01 (m, 2H), 6.79 (s, 1H), 6.74 (s, 1H), 3.70-3.65 (m, 2H), 3.48 (dd, J = 1.1, 9.4 Hz, 1H), 3.42-3.35 (m, 2H), 3.01-2.90 (m, 1H), 2.82 (t, J = 5.3 Hz, 2H), 2.60 (dd, J = 10.0, 13.5 Hz, 1H), 2.34 (s, 3H), 2.14-2.04 (m, 1H), 2.02-1.94 (m, 1H), 1.92-1.83 (m, 2H), 1.81-1.69 (m, 1H), 1.09 (t, J = 7.0 Hz, 1H). |

TABLE A1-continued

| No. | Structure/Name | LCMS R$_T$ (min) m/z Method | Prep Mtd | $^1$H NMR δ (ppm) |
|---|---|---|---|---|
| 305a | 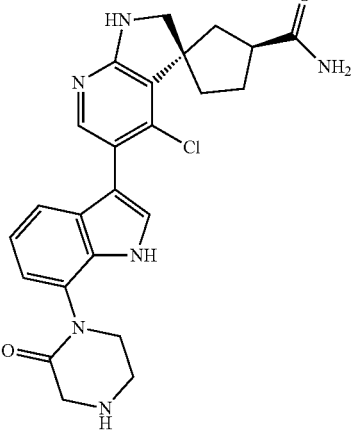<br>(1RS,3SR)-4'-Chloro-5'-(7-(2-oxopiperazin-1-yl)-1H-indol-3-yl)-1',2'-dihydrospiro[cyclopentane-1,3'-pyrrolo[2,3-b]pyridine]-3-carboxamide | 1.76<br>465.1<br>A | Q | (400 MHz, DMSO-d$_6$) δ 11.17-11.13 (m, 1H), 7.79 (s, 1H), 7.43 (d, J = 2.6 Hz, 1H), 7.37-7.32 (m, 2H), 7.07-7.02 (m, 1H), 7.00 (dd, J = 1.1, 7.4 Hz, 1H), 6.80 (s, 1H), 6.75 (s, 1H), 3.64-3.58 (m, 2H), 3.48-3.44 (m, 3H), 3.39 (d, J = 9.2 Hz, 2H), 3.10 (t, J = 5.4 Hz, 2H), 3.01-2.91 (m, 1H), 2.60 (dd, J = 10.0, 13.5 Hz, 1H), 2.15-2.03 (m, 1H), 2.03-1.94 (m, 1H), 1.92-1.82 (m, 2H), 1.82-1.68 (m, 1H). |
| 306a | 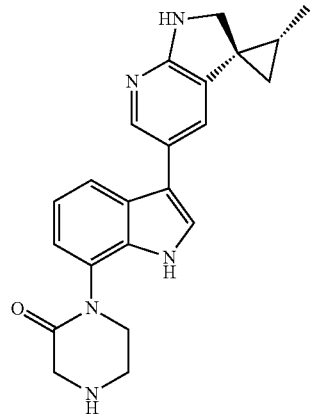<br>1-(3-((1RS,2RS)-2-methyl-1',2'-dihydrospiro[cyclopropane-1,3'-pyrrolo[2,3-b]pyridin-5'-yl)-1H-indol-7-yl)piperazin-2-one | 2.1<br>373.9<br>A | Q | (400 MHz, DMSO-d$_6$) δ 11.06 (1H, bs), 7.97 (1H, d, J = 1.9 Hz), 7.62 (1H, d, J = 7.8 Hz), 7.52 (1H, d, J = 2.5 Hz), 7.19 (1H, d, J = 2.0 Hz), 7.07 (1H, t, J = 7.7 Hz), 7.00 (1H, d, J = 6.7 Hz), 6.42 (d, J = 1.3 Hz, 1H), 3.65-3.56 (3H, m), 3.45 (2H, s), 3.14-3.09 (2H, m), 3.03-2.98 (1H, m), 1.25-1.15 (1H, m), 1.12-1.09 (4H, m), 0.93-0.89 (1H, m). |
| 307 | 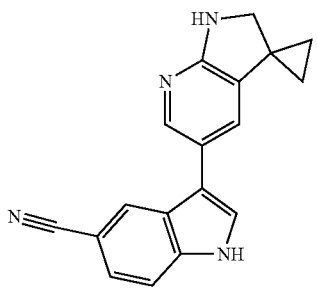<br>3-(1',2'-Dihydrospiro[cyclopropane-1,3'-pyrrolo[2,3-b]pyridin]-5'-yl)-1H-indole-5-carbonitrile | 2.68<br>287.0<br>A | P | (400 MHz, DMSO-d$_6$) δ 11.78 (s, 1H), 8.19 (s, 1H), 7.97 (d, J = 2.0 Hz, 1H), 7.70 (d, J = 2.4 Hz, 1H), 7.57 (dd, J = 0.5, 8.3 Hz, 1H), 7.46 (dd, J = 1.5, 8.4 Hz, 1H), 7.14 (d, J = 1.9 Hz, 1H), 6.54 (s, 1H), 3.54 (d, J = 1.2 Hz, 2H), 1.16-1.11 (m, 2H), 1.00-0.95 (m, 2H). |

TABLE A1-continued

| No. | Structure/Name | LCMS R_T (min) m/z Method | Prep Mtd | $^1$H NMR δ (ppm) |
|---|---|---|---|---|
| 308 | 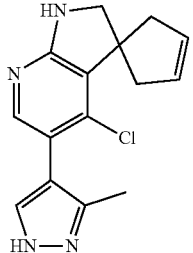<br>4'-Chloro-5'-(3-methyl-1H-pyrazol 4-yl)-1',2'-dihydro-spiro[cyclopentane-1,3'-pyrrolo[2,3-b]pyridin]-3-ene | 2.62<br>287.2<br>B | L | (400 MHz, DMSO-d$_6$) δ 8.25 (s, 1H), 7.63 (s, 1H), 7.48 (s, 1H), 6.78 (s, 1H), 5.77 (s, 2H), 3.46 (s, 2H), 3.03 (d, J = 15.1 Hz, 2H), 2.47 (m, 2H partially under DMSO peak), 2.12 (s, 3H). |
| 309 | 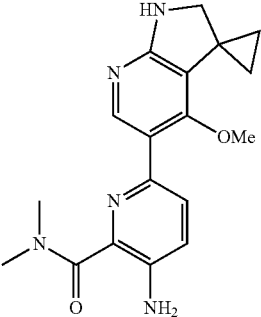<br>3-Amino-6-(4'-methoxy-1',2'-dihydrospiro[cyclopropane-1,3'-pyrrolo[2,3-b]pyridin]-5'-yl)-N,N-dimethylpicolinamide | 2.25<br>340.2<br>B | See text | (400 MHz, DMSO-d$_6$) δ 7.77 (s, 1H), 7.29 (d, J = 8.6 Hz, 1H), 7.14 (d, J = 8.6 Hz, 1H), 6.60 (s, 1H), 5.52 (s, 2H), 3.45 (d, J = 0.9 Hz, 2H), 3.29 (s, 3H), 3.01 (s, 3H), 3.00 (s, 3H), 1.33-1.28 (m, 2H), 0.87-0.83 (m, 2H). |
| 310 | 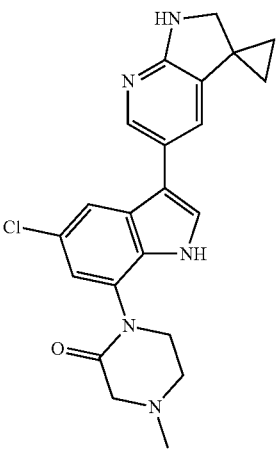<br>1-(5-Chloro-3-(1',2'-dihydrospiro[cyclopropane-1,3'-pyrrolo[2,3-b]pyridin]-5'-yl)-1H-indol-7-yl)-4-methylpiperazin-2-one | 2.19<br>408.2<br>B | P | (400 MHz, DMSO-d$_6$) δ 11.34-11.30 (m, 1H), 7.92 (d, J = 2.0 Hz, 1H), 7.61 (d, J = 1.8 Hz, 1H), 7.55 (s, 1H), 7.10 (dd, J = 1.9, 13.4 Hz, 2H), 6.51 (s, 1H), 3.69-3.64 (m, 2H), 3.53 (d, J = 1.1 Hz, 2H), 3.19 (s, 2H), 2.84-2.78 (m, 2H), 2.34-2.33 (m, 3H), 1.12-1.07 (m, 2H), 1.00-0.96 (m, 2H). |

TABLE A1-continued

| No. | Structure/Name | LCMS R$_T$ (min) m/z Method | Prep Mtd | $^1$H NMR δ (ppm) |
|---|---|---|---|---|
| 311 | 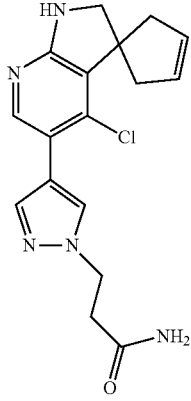<br>3-(4-(4'-Chloro-1',2'-dihydrospiro[cyclopentane-1,3'-pyrrolo[2,3-b]pyridin]-3-en-5'-yl)-1H-pyrazol-1-yl)propanamide | 2.47<br>344.2<br>B | L | (400 MHz, DMSO-d$_6$) δ 7.88 (s, 1H), 7.84 (s, 1H), 7.63 (s, 1H), 7.40 (s, 1H), 6.91 (s, 1H), 6.78 (s, 1H), 5.77 (s, 2H), 4.31 (t, J = 7.0 Hz, 2H), 3.46 (s, 2H), 3.04 (d, J = 15.0 Hz, 2H), 2.63 (t, J = 7.0 Hz, 2H), 2.47 (m, 2H partially under DMSO peak). |
| 312 | 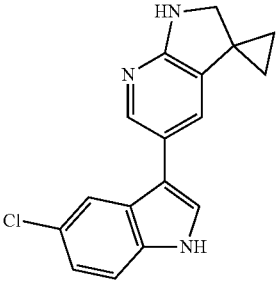<br>5'-(5-Chloro-1H-indol-3-yl)-1',2'-dihydrospiro[cyclopropane-1,3'-pyrrolo[2,3-b]pyridine] | 3.21<br>296.2<br>B | P | (400 MHz, DMSO-d$_6$) δ 11.39 (s, 1H), 7.92 (d, J = 2.1 Hz, 1H), 7.65 (d, J = 2.0 Hz, 1H), 7.56 (d, J = 2.5 Hz, 1H), 7.42 (d, J = 8.6 Hz, 1H), 7.12 (dd, J = 2.0, 8.5 Hz, 1H), 7.09 (d, J = 1.9 Hz, 1H), 6.48 (s, 1H), 3.53 (d, J = 1.3 Hz, 2H), 1.11-1.07 (m, 2H), 1.00-0.95 (m, 2H). |
| 313 | 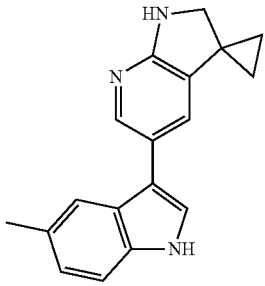<br>5'-(5-Methyl-1H-indol-3-yl)-1',2'-dihydrospiro[cyclopropane-1,3'-pyrrolo[2,3-b]pyridine] | 3.03<br>276.1<br>A | P | (400 MHz, DMSO-d$_6$) δ 11.04 (s, 1H), 7.95 (d, J = 2.0 Hz, 1H), 7.48 (s, 1H), 7.42 (d, J = 2.5 Hz, 1H), 7.28 (d, J = 8.3 Hz, 1H), 7.08 (d, J = 1.8 Hz, 1H), 6.93 (dd, J = 1.4, 8.3 Hz, 1H), 6.41 (s, 1H), 3.52 (d, J = 1.4 Hz, 2H), 2.39 (s, 3H), 1.10-1.05 (m, 2H), 1.00-0.95 (m, 2H). |

TABLE A1-continued

| No. | Structure/Name | LCMS R$_T$ (min) m/z Method | Prep Mtd | $^1$H NMR δ (ppm) |
|---|---|---|---|---|
| 314 | 5'-(1H-Indol-3-yl)-1',2'-dihydrospiro[cyclopropane-1,3'-pyrrolo[2,3-b]pyridine] | 2.91 262.2 B | P | (400 MHz, DMSO-d$_6$) δ 11.18 (s, 1H), 7.95 (d, J = 2.0 Hz, 1H), 7.72-7.69 (m, 1H), 7.49 (d, J = 2.5 Hz, 1H), 7.40 (d, J = 8.0 Hz, 1H), 7.14-7.02 (m, 3H), 6.53 (s, 1H), 3.54 (s, 2H), 1.12-1.07 (m, 2H), 1.01-0.96 (m, 2H). |
| 315 | 3-(4'-Methoxy-1',2'-dihydrospiro[cyclopropane-1,3'-pyrrolo[2,3-b]pyridin]-5'-yl)-1H-indole-5-carbonitrile | 2.98 317.2 B | P | (400 MHz, DMSO-d$_6$) δ 11.81 (s, 1H), 7.88 (d, J = 0.9 Hz, 1H), 7.70 (s, 1H), 7.61 (s, 1H), 7.58 (dd, J = 0.5, 8.5 Hz, 1H), 7.48-7.44 (m, 1H), 6.56 (s, 1H), 3.48 (d, J = 1.1 Hz, 2H), 3.15 (s, 3H), 1.38-1.33 (m, 2H), 0.91-0.87 (m, 2H). |
| 316 | 5'-(4-Fluoro-1H-indol-3-yl)-1',2'-dihydrospiro[cyclopropane-1,3'-pyrrolo[2,3-b]pyridine] | 3.05 280.2 B | P | (400 MHz, DMSO-d$_6$) δ 11.48 (s, 1H), 7.84 (t, J = 2.1 Hz, 1H), 7.40 (d, J = 2.5 Hz, 1H), 7.24-7.21 (m, 1H), 7.10-7.04 (m, 1H), 7.00 (t, J = 2.3 Hz, 1H), 6.78-6.73 (m, 1H), 6.43 (s, 1H), 3.52 (d, J = 1.4 Hz, 2H), 1.02-0.96 (m, 4H). |

TABLE A1-continued

| No. | Structure/Name | LCMS $R_T$ (min) m/z Method | Prep Mtd | $^1$H NMR δ (ppm) |
|---|---|---|---|---|
| 317 | 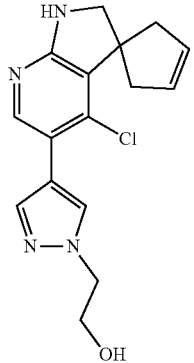<br>2-(4-(4'-Chloro-1',2'-dihydrospiro[cyclopentane-1,3'-pyrrolo[2,3-b]pyridin]-3-en-5'-yl)-1H-pyrazol-1-yl)ethan-1-ol | 2.59<br>317.2<br>B | L | (400 MHz, DMSO-$d_6$) δ 7.92 (s, 1H), 7.85 (s, 1H), 7.64 (s, 1H), 6.78 (s, 1H), 5.77 (s, 2H), 4.91 (s, 1H), 4.15 (t, J = 5.7 Hz, 2H), 3.75 (t, J = 5.6 Hz, 2H), 3.47 (d, J = 1.0 Hz, 2H), 3.04 (d, J = 15.0 Hz, 2H), 2.48 (m, 2H partially under DMSO peak). |
| 318 | 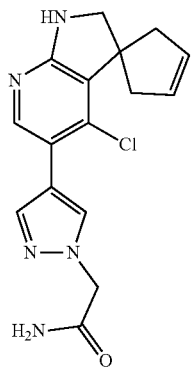<br>2-(4-(4'-Chloro-1',2'-dihydrospiro[cyclopentane-1,3'-pyrrolo[2,3-b]pyridin]-3-en-5'-yl)-1H-pyrazol-1-yl)acetamide | 2.39<br>330<br>A | L | (400 MHz, DMSO-$d_6$) δ 7.93 (s, 1H), 7.87 (s, 1H), 7.66 (s, 1H), 7.47 (s, 1H), 7.26 (s, 1H), 6.79 (s, 1H), 5.77 (s, 2H), 4.77 (s, 2H), 3.47 (s, 2H), 3.05 (d, J = 15.0 Hz, 2H), 2.48 (m, 2H partially under DMSO peak). |
| 319 | 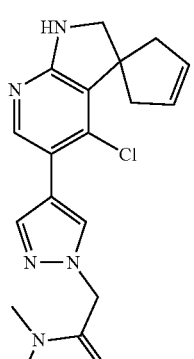<br>2-(4-(4'-Chloro-1',2'-dihydrospiro[cyclopentane-1,3'-pyrrolo[2,3-b]pyridin]-3-en-5'-yl)-1H-pyrazol-1-yl)-N,N-dimethylacetamide | 2.7<br>358.2<br>B | L | (400 MHz, DMSO-$d_6$) δ 7.87 (d, J = 1.8 Hz, 2H), 7.64 (s, 1H), 6.78 (s, 1H), 5.77 (s, 2H), 5.11 (s, 2H), 3.47 (d, J = 0.9 Hz, 2H), 3.04 (d, J = 15.1 Hz, 2H), 3.03 (s, 3H), 2.86 (s, 3H), 2.48 (m, 2H partially under DMSO peak). |

TABLE A1-continued

| No. | Structure/Name | LCMS R_T (min) m/z Method | Prep Mtd | $^1$H NMR δ (ppm) |
|---|---|---|---|---|
| 320 | 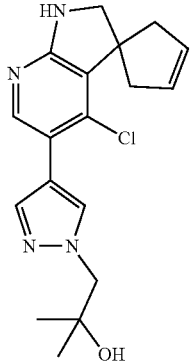<br>1-(4-(4'-Chloro-1',2'-dihydrospiro[cyclopentane-1,3'-pyrrolo[2,3-b]pyridin]-3-en-5'-yl)-1H-pyrazol-1-yl)-2-methylpropan-2-ol | 2.91<br>345.2<br>B | L | (400 MHz, DMSO-d$_6$) δ 7.88 (d, J = 9.1 Hz, 2H), 7.63 (s, 1H), 6.78 (s, 1H), 5.78 (s, 2H), 4.69 (s, 1H), 4.03 (s, 2H), 3.47 (s, 2H), 3.05 (d, J = 15.1 Hz, 2H), 2.48 (m, 2H partially under DMSO peak), 1.08 (s, 6H). |
| 321 | 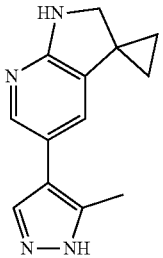<br>5'-(5-Methyl-1H-pyrazol-4-yl)-1',2'-dihydrospiro[cyclopropane-1,3'-pyrrolo[2,3-b]pyridine] | 1.93<br>227.1<br>A | L | (400 MHz, DMSO-d$_6$) δ 12.47-12.43 (m, 1H), 7.69 (d, J = 2.0 Hz, 1H), 7.51 (s, 1H), 6.89 (d, J = 1.8 Hz, 1H), 6.44-6.41 (m, 1H), 3.49 (d, J = 1.4 Hz, 2H), 2.26 (s, 3H), 1.05-1.00 (m, 2H), 0.98-0.94 (m, 2H). |
| 322 | 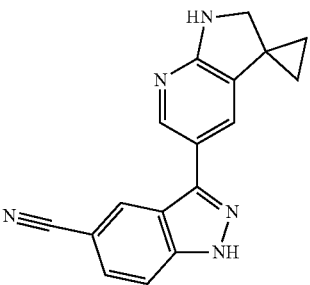<br>3-(1',2'-Dihydrospiro[cyclopropane-1,3'-pyrrolo[2,3-b]pyridin]-5'-yl)-1H-indazole-5-carbonitrile | 2.55<br>288.1<br>A | N | (400 MHz, DMSO-d$_6$) δ 13.51 (s, 1H), 8.60 (s, 1H), 8.31 (d, J = 2.0 Hz, 1H), 7.69-7.68 (m, 2H), 7.37 (d, J = 1.8 Hz, 1H), 6.89 (s, 1H), 3.58 (s, 2H), 1.20-1.15 (m, 2H), 1.03-0.98 (m, 2H). |

TABLE A1-continued

| No. | Structure/Name | LCMS R_T (min) m/z Method | Prep Mtd | $^1$H NMR δ (ppm) |
|---|---|---|---|---|
| 323 | 5′-(1-Benzyl-1H-pyrazol-4-yl)-4′-chloro-1′,2′-dihydrospiro[cyclopentane-1,3′-pyrrolo[2,3-b]pyridin]-3-ene | 3.79 363.1 A | L | (400 MHz, DMSO-d$_6$) δ 8.08 (s, 1H), 7.86 (s, 1H), 7.67 (s, 1H), 7.38-7.33 (m, 2H), 7.31-7.25 (m, 3H), 6.80 (s, 1H), 5.76 (s, 2H), 5.35 (s, 2H), 3.46 (d, J = 1.0 Hz, 2H), 3.04 (d, J = 15.1, Hz, 2H), 2.46 (s, 2H partially under DMSO peak). |
| 324 | 3-(1′,2′-Dihydrospiro[cyclopropane-1,3′-pyrrolo[2,3-b]pyridin]-5′-yl)-7-(4-methyl-2-oxopiperazin-1-yl)-1H-indole-5-carbonitrile | 1.94 399.1 A | P | (400 MHz, DMSO-d$_6$) δ 11.68 (s, 1H), 8.14 (d, J = 1.3 Hz, 1H), 7.97 (d, J = 2.0 Hz, 1H), 7.68 (s, 1H), 7.50 (d, J = 1.3 Hz, 1H), 7.14 (d, J = 1.9 Hz, 1H), 6.56 (s, 1H), 3.72-3.67 (m, 2H), 3.54 (s, 2H), 3.20 (s, 2H), 2.82 (t, J = 5.3 Hz, 2H), 2.34 (s, 3H), 1.16-1.11 (m, 2H), 1.01-0.96 (m, 2H). |
| 325a | 3-((1s,4s)-4′-Chloro-4-hydroxy-1′,2′-dihydrospiro[cyclohexane-1,3′-pyrrolo[2,3-b]pyridin]-5′-yl)-1H-indole-5-carbonitrile | 2.66 379.0 A | P | (400 MHz, DMSO-d$_6$) δ 11.84-11.81 (m, 1H), 7.78 (d, J = 0.9 Hz, 1H), 7.60-7.58 (m, 2H), 7.46 (dd, J = 1.6, 8.4 Hz, 1H), 6.91 (s, 1H), 4.64 (d, J = 4.3 Hz, 1H), 3.18-3.16 (m, 1H), 2.33-2.21 (m, 2H), 1.80 (d, J = 10.0 Hz, 2H), 1.71-1.64 (m, 2H), 1.36-1.22 (m, 2H). |

TABLE A1-continued

| No. | Structure/Name | LCMS R_T (min) m/z Method | Prep Mtd | $^1$H NMR δ (ppm) |
|---|---|---|---|---|
| 326 | 5'-(5-(3-Methyl-1H-pyrazol-4-yl)-1H-indol-3-yl)-1',2'-dihydrospiro[cyclopropane-1,3'-pyrrolo[2,3-b]pyridine] | 2.57 342.1 A | See text | (400 MHz, CDCl3) δ ppm 8.43 (s, 1H), 8.31 (s, 1H), 7.84 (d, J = 1.9 Hz, 1H), 7.69 (s, 1H), 7.67 (s, 1H), 7.46 (d, J = 8.6 Hz, 1H), 7.30 (dd, J = 8.3, 1.5 Hz, 1H), 7.27 (s, 1H), 7.04 (d, J = 2.8 Hz, 1H), 3.79 (s, 2H), 2.46 (s, 3H), 1.15-1.07 (m, 4H). |
| 327 | 4'-Chloro-5'-(1-(2-methoxy-ethyl)-1H-pyrazol-4-yl)-1',2'-dihydrospiro[cyclopentane-1,3'-pyrrolo[2,3-b]pyridin]-3-ene | 2.9 331 A | L | (400 MHz, DMSO-d$_6$) δ 7.92 (s, 1H), 7.85 (s, 1H), 7.64 (d, J = 1.0 Hz, 1H), 6.78 (s, 1H), 5.77 (s, 2H), 4.27 (t, J = 5.4 Hz, 2H), 3.70 (t, J = 5.4 Hz, 2H), 3.47 (d, J = 1.1 Hz, 2H), 3.24 (s, 3H), 3.04 (d, J = 15.0 Hz, 2H), 2.49 (m, 2H partially under DMSO peak). |
| 328 | 5'-(5-Cyclopropyl-1H-indol-3-yl)-1',2'-dihydrospiro[cyclopropane-1,3'-pyrrolo[2,3-b]pyridine] | 3.32 302.1 A | P | (400 MHz, CDCl3) δ 8.12 (s, 1H), 8.09 (d, J = 1.7 Hz, 1H), 7.49-7.48 (m, 1H), 7.30 (d, J = 8.4 Hz, 1H), 7.19 (d, J = 2.2 Hz, 1H), 7.01-6.97 (m, 2H), 4.53 (s, 1H), 3.68 (d, J = 1.2 Hz, 2H), 2.06-1.98 (m, 1H), 1.11-1.07 (m, 2H), 1.06-0.99 (m, 2H), 0.96-0.92 (m, 2H), 0.72-0.66 (m, 2H). |

TABLE A1-continued

| No. | Structure/Name | LCMS R_T (min) m/z Method | Prep Mtd | $^1$H NMR δ (ppm) |
|---|---|---|---|---|
| 329 | 5-(1H-Pyrrolo[3,2-c]pyridin-3-yl)spiro[1,2-dihydropyrrolo[2,3-b]pyridine-3,1'-cyclopropane] | 2.99 262.9 A | N | (400 MHz, DMSO-d$_6$) δ 11.58 (s, 1H), 9.00 (s, 1H), 8.18 (d, J = 5.6 Hz, 1H), 8.02 (d, J = 2.1 Hz, 1H), 7.59 (d, J = 2.2 Hz, 1H), 7.38 (dd, J = 0.9, 5.7 Hz, 1H), 7.17 (d, J = 1.9 Hz, 1H), 6.52 (s, 1H), 3.54 (d, J = 1.3 Hz, 2H), 1.12 (q, J = 3.5 Hz, 2H), 0.98 (q, J = 3.7 Hz, 2H). |
| 330a | (1RS,3SR)-4'-Chloro-5'-(5-cyano-1H-indol-3-yl)-3-methyl-1',2'-dihydrospiro[cyclopentane-1,3'-pyrrolo[2,3-b]pyridine]-3-carbonitrile | 3.38 388.2 B | P | (400 MHz, CDCl3) δ 8.67 (s, 1H), 7.92 (s, 1H), 7.88 (s, 1H), 7.50-7.48 (m, 2H), 7.37 (d, J = 2.4 Hz, 1H), 4.78-4.75 (m, 1H), 3.95 (d, J = 9.4 Hz, 1H), 3.67 (dd, J = 1.7, 9.4 Hz, 1H), 2.84-2.74 (m, 1H), 2.55-2.50 (m, 1H), 2.39-2.29 (m, 1H), 2.22 (d, J = 13.8 Hz, 1H), 2.14-2.04 (m, 2H), 1.57 (s, 3H). |
| 331 | (3-(1',2'-Dihydrospiro[cyclopropane-1,3'-pyrrolo[2,3-b]pyridin-5'-yl)-1H-indol-5-yl)(imino)(methyl)-γ6-sulfanone | 1.98 339.3 B | | (400 MHz, DMSO-d$_6$) δ 11.67 (s, 1H), 8.29 (d, J = 1.6 Hz, 1H), 8.00 (d, J = 2.0 Hz, 1H), 7.68 (d, J = 2.4 Hz, 1H), 7.67 (d, J = 1.8 Hz, 1H), 7.56 (d, J = 8.6 Hz, 1H), 7.11 (d, J = 1.9 Hz, 1H), 6.56 (s, 1H), 3.99 (s, 1H), 3.54 (d, J = 1.0 Hz, 2H), 3.05 (s, 3H), 1.09-1.04 (m, 2H), 1.03-0.97 (m, 2H). |

TABLE A1-continued

| No. | Structure/Name | LCMS R_T (min) m/z Method | Prep Mtd | $^1$H NMR δ (ppm) |
|---|---|---|---|---|
| 332 | 5-(Benzotriazol-1-yl)spiro[1,2-dihydropyrrolo[2,3-b]pyridine-3,1'-cyclopropane | 2.84 264 B | See text | (400 MHz, CDCl3) δ 8.13-8.09 (m, 2H), 7.63-7.60 (m, 1H), 7.55-7.50 (m, 1H), 7.44-7.39 (m, 1H), 7.08 (d, J = 2.3 Hz, 1H), 4.96 (s, 1H), 3.79 (s, 2H), 1.18-1.07 (m, 4H) |
| 333 | 5-(1H-Pyrrolo[2,3-c]pyridin-3-yl)spiro[1,2-dihydropyrrolo[2,3-b]pyridine-3,1'-cyclopropane] | 3.06 263.2 A | S | (400 MHz, CD3OD) δ 8.70 (s, 1H), 8.11 (d, J = 5.7 Hz, 1H), 7.92 (d, J = 1.8 Hz, 1H), 7.73 (dd, J = 1.0, 5.8 Hz, 1H), 7.68 (s, 1H), 7.14 (d, J = 2.0 Hz, 3H), 3.66 (s, 2H), 1.17-1.13 (m, 2H), 1.07-1.03 (m, 2H). |
| 334 | 2-(3-(1',2'-Dihydrospiro[cyclopropane-1,3'-pyrrolo[2,3-b]pyridin]-5'-yl)-1H-indol-5-yl)-1,3,4-oxadiazole formate salt | 2.46 330 B | N | (400 MHz, DMSO-d_6) δ ppm 9.25 (s, 1H), 8.33 (s, 1H), 8.16 (s, 1H), 7.99 (d, J = 1.5 Hz, 1H), 7.80 (d, J = 8.6 Hz, 1H), 7.65 (d, J = 2.1 Hz, 1H), 7.60 (d, J = 8.6 Hz, 1H), 7.14 (d, J = 1.8 Hz, 1H), 6.56 (s, 1H), 3.55 (s, 2H), 1.11-1.04 (m, 2H), 1.02-0.98 (m, 2H). |

TABLE A1-continued

| No. | Structure/Name | LCMS R$_T$ (min) m/z Method | Prep Mtd | $^1$H NMR δ (ppm) |
|---|---|---|---|---|
| 335 | 5'-(5-(4-Methyl-4H-1,2,4-triazol-3-yl)-1H-indol-3-yl)-1',2'-dihydrospiro[cyclopropane-1,3'-pyrrolo[2,3-b]pyridine] | 2.16 343.1 B | N | (400 MHz, DMSO-d$_6$) δ ppm 11.95 (s, 1H), 8.98 (s, 1H), 8.80 (s, 1H), 8.18 (s, 1H), 7.97 (d, J = 2.4 Hz, 1H), 7.89 (d, J = 1.4 Hz, 1H), 7.68 (d, J = 8.4 Hz, 1H), 7.64 (d, J = 1.6 Hz, 1H), 7.58 (dd, J = 8.4, 1.6 Hz, 1H), 3.96 (s, 2H), 2.54 (s, 3H), 1.37-1.31 (m, 2H), 1.26-1.22 (m, 2H). |
| 336 | 5'-(6-Methyl-5-(1-methyl-1H-pyrazol-4-yl)-1H-indol-3-yl)-1',2'-dihydrospiro[cyclopropane-1,3'-pyrrolo[2,3-b]pyridine] | 2.94 356.3 A | T | (400 MHz, DMSO-d$_6$) δ 11.01 (s, 1H), 7.97 (d, J = 2.0 Hz, 1H), 7.86 (s, 1H), 7.57 (d, J = 7.4 Hz, 2H), 7.40 (s, 1H), 7.26 (s, 1H), 7.09 (d, J = 1.9 Hz, 1H), 6.41 (s, 1H), 3.88 (s, 3H), 3.51 (d, J = 1.2 Hz, 2H), 2.41 (s, 3H), 1.08-1.04 (m, 2H), 1.00-0.95 (m, 2H). |
| 337a | (1RS,3SR)-4'-Chloro-5'-(5-cyano-1H-indol-3-yl)-3-methyl-1',2'-dihydrospiro[cyclopentane-1,3'-pyrrolo[2,3-b]pyridine]-3-carboxamide | 2.80 406.3 A | P | (400 MHz, DMSO-d$_6$) δ 11.86 (s, 1H), 7.83 (d, J = 0.9 Hz, 1H), 7.77 (s, 1H), 7.62 (s, 1H), 7.60 (d, J = 8.7 Hz, 1H), 7.47 (dd, J = 1.5, 8.4 Hz, 1H), 7.24 (s, 1H), 6.88 (s, 1H), 6.81 (s, 1H), 3.49 (d, J = 9.1 Hz, 1H), 3.27 (d, J = 9.3 Hz, 1H), 2.56-2.44 (m, 2H), 2.25-2.17 (m, 1H), 1.99 (d, J = 13.4 Hz, 1H), 1.77-1.63 (m, 2H), 1.32-1.31 (m, 3H). |

TABLE A1-continued

| No. | Structure/Name | LCMS R$_T$ (min) m/z Method | Prep Mtd | $^1$H NMR δ (ppm) |
|---|---|---|---|---|
| 338 | 5'-(5-Fluoro-1H-indol-3-yl)-1',2'-dihydrospiro[cyclopropane-1,3'-pyrrolo[2,3-b]pyridine] | 2.96 280.2 A | P | (400 MHz, DMSO-d$_6$) δ 11.29 (s, 1H), 7.92 (d, J = 2.0 Hz, 1H), 7.57 (d, J = 2.6 Hz, 1H), 7.42-7.37 (m, 2H), 7.09 (d, J = 2.0 Hz, 1H), 6.99-6.93 (m, 1H), 6.45 (s, 1H), 3.52 (d, J = 1.3 Hz, 2H), 1.12-1.08 (m, 2H), 0.99-0.95 (m, 2H). |
| 339 | 3-(1',2'-Dihydrospiro[cyclopropane-1,3'-pyrrolo[2,3-b]pyridin]-5'-yl)-N,N-dimethyl-1H-indole-5-carboxamide | 2.51 333.3 A | P | (400 MHz, CD3OD) δ 7.89 (d, J = 1.9 Hz, 1H), 7.80 (s, 1H), 7.48-7.42 (m, 2H), 7.26-7.22 (m, 1H), 7.13-7.11 (m, 1H), 3.64 (s, 2H), 3.10 (s, 6H), 1.15-1.10 (m, 2H), 1.06-1.01 (m, 2H). |
| 340 | N-(5-Cyano-3-(1',2'-dihydrospiro[cyclopropane-1,3'-pyrrolo[2,3-b]pyridin]-5'-yl)-1H-indol-7-yl)-N-methylmethanesulfonamide | 2.71 394.2 A | S | (400 MHz, DMSO-d$_6$) δ 11.87 (br s, 1H), 8.18 (d, J = 1.3 Hz, 1H), 7.97 (d, J = 2.1 Hz, 1H), 7.72 (d, J = 1.3 Hz, 1H), 7.67 (s, 2H), 7.14 (d, J = 2.0 Hz, 1H), 6.57 (s, 1H), 5.76 (s, 2H), 3.54 (d, J = 0.9 Hz, 2H), 3.13 (s, 3H), 1.16-1.11 (m, 2H), 1.00-0.95 (m, 2H). |

TABLE A1-continued

| No. | Structure/Name | LCMS R_T (min) m/z Method | Prep Mtd | $^1$H NMR δ (ppm) |
|---|---|---|---|---|
| 341 | 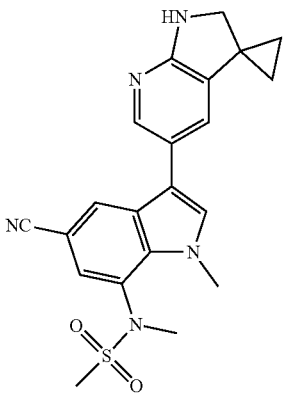<br>N-(5-Cyano-3-(1′,2′-dihydrospiro[cyclopropane-1,3′-pyrrolo[2,3-b]pyridin]-5′-yl)-1-methyl-1H-indol-7-yl)-N-methylmethanesulfonamide | 2.87<br>408.2<br>A | S | (400 MHz, DMSO-$d_6$) δ 8.18 (d, J = 1.3 Hz, 1H), 7.91 (d, J = 2.0 Hz, 1H), 7.81 (d, J = 1.3 Hz, 1H), 7.66 (s, 1H), 7.08 (d, J = 2.0 Hz, 1H), 6.61 (s, 1H), 4.03 (s, 3H), 3.55-3.54 (m, 2H), 3.33 (s, 3H), 3.19 (s, 3H), 1.14-1.07 (m, 2H), 1.01-0.93 (m, 2H). |
| 342 | 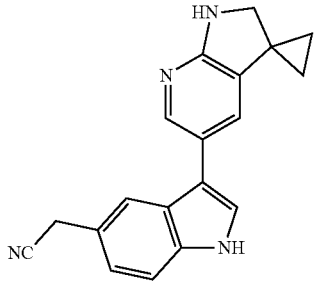<br>2-(3-(1′,2′-Dihydrospiro[cyclopropane-1,3′-pyrrolo[2,3-b]pyridin]-5′-yl)-1H-indol-5-yl)acetonitrile | 2.70<br>301.2<br>A | S | (400 MHz, DMSO-$d_6$) δ 11.26 (s, 1H), 7.97 (d, J = 2.0 Hz, 1H), 7.70 (s, 1H), 7.53 (d, J = 2.4 Hz, 1H), 7.42 (d, J = 8.3 Hz, 1H), 7.10-7.06 (m, 2H), 6.46 (s, 1H), 4.07 (s, 2H), 3.53 (d, J = 1.2 Hz, 2H), 1.11-1.06 (m, 2H), 1.01-0.96 (m, 2H). |
| 343 | 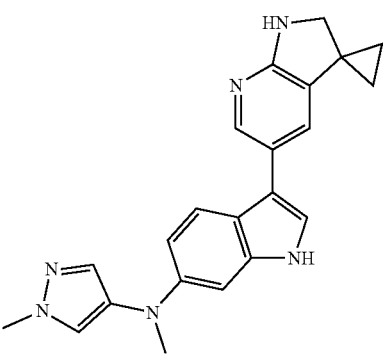<br>3-(1′,2′-Dihydrospiro[cyclopropane-1,3′-pyrrolo[2,3-b]pyridin]-5′-yl)-N-methyl-N-(1-methyl-1H-pyrazol-4-yl)-1H-indol-6-amine | 2.87<br>371.3<br>A | See text | (400 MHz, CDCl3) δ 8.07 (d, J = 2.0 Hz, 1H), 7.97 (s, 1H), 7.58 (d, J = 8.6 Hz, 1H), 7.38 (d, J = 0.6 Hz, 1H), 7.22 (d, J = 0.8 Hz, 1H), 7.10 (d, J = 2.3 Hz, 1H), 7.01 (d, J = 2.0 Hz, 1H), 6.92-6.86 (m, 2H), 4.59 (s, 1H), 3.88 (s, 3H), 3.68 (s, 2H), 3.25 (s, 3H), 1.11-0.99 (m, 4H). |

| No. | Structure/Name | LCMS R$_T$ (min) m/z Method | Prep Mtd | $^1$H NMR δ (ppm) |
|---|---|---|---|---|
| 344 | 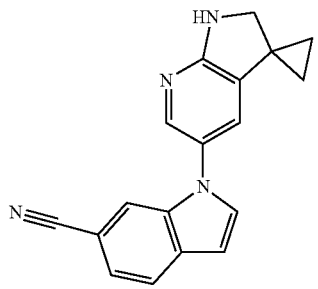<br>1-(1',2'-Dihydrospiro[cyclopropane-1,3'-pyrrolo[2,3-b]pyridin]-5'-yl)-1H-indole-6-carbonitrile | 3.22<br>287.3<br>B | See text | (400 MHz, DMSO-d$_6$) δ 7.80 (m, 1H), 7.77 (m, 3H), 7.42 (dd, J = 1.4, 8.2 Hz, 1H), 7.08 (d, J = 2.3 Hz, 1H), 6.93 (s, 1H), 6.77 (d, J = 2.6 Hz, 1H), 3.61 (s, 2H), 1.16-1.11 (m, 2H), 1.03-0.98 (m, 2H). |
| 345 | 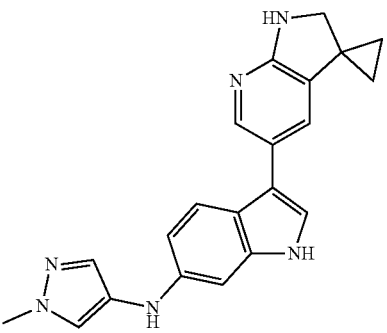<br>3-(1',2'-Dihydrospiro[cyclopropane-1,3'-pyrrolo[2,3-b]pyridin]-5'-yl)-N-(1-methyl-1H-pyrazol-4-yl)-1H-indol-6-amine | 2.57<br>357.2<br>A | See text | (400 MHz, CDCl3) δ ppm 8.07 (d, J = 1.9 Hz, 1H), 7.94 (s, 1H), 7.56 (d, J = 8.3 Hz, 1H), 7.45 (s, 1H), 7.34 (s, 1H), 7.03 (dd, J = 2.1, 18.6 Hz, 2H), 6.76 (d, J = 1.8 Hz, 1H), 6.69 (dd, J = 2.1, 8.5 Hz, 1H), 5.06 (s, 1H), 4.57 (s, 1H), 3.90 (s, 3H), 3.67 (s, 2H), 1.12-0.98 (m, 4H). |

BIOLOGICAL EXAMPLES

Exemplary compounds of Formula (I) were tested to assess compound inhibition of HPK-1. The K$_i$ for each exemplary compound was determined

Example B1

HPK1-FL HTRF Enzymatic Assay ("HTRF")

Assay Principle:

HPK-FL enzyme phosphorylates Biotin-SLP-76 substrate in the presence of ATP at 1 mM and varying concentrations of test compound. Product is detected by FRET using Eu-anti-pSLP76 Ab and SA-XL665. Also see www.cisbio.com/HTRF for additional HTRF technology information.

Instrumentation:
Echo555 compound dispenser
Agilent Bravo
Perkin Elmer Envision
Final Assay Conditions:

| HPK full length, T165E S171E: | 0.125 nM |
|---|---|
| Biotin-SLP76: | 100 nM |
| ATP: | 1 mM (ATP Km = 20 μM) |
| Eu-anti-pSLP76: | 2 nM |
| SA-XL665: | 8.3 nM |
| Preincubation time: | 30 min |
| Kinase reaction time: | 60 min |
| Temperature: | ambient |
| Total volume: | 12 μl |
| ATP$^{app}$ Km: | 17.7 μM |

Materials:
Assay plate: White ProxiPlate 384 F (PerkinElmer cat #6008289)
Kinase: HPK full length double mutant
Substrate: Biotin-SLP76
ATP: 100 mM ATP
BSG: 2% BSG
DMSO: DMSO (Sigma cat #34869-100ML)
Reaction Buffer: H$_2$O/50 mM HEPES, pH 7.5/10 mM MgCl$_2$/2 mM TCEP/0.01% Brij-35/0.01% BSG
Detection mix:Eu-anti-pSLP76/SA-XL665 (Cisbio, #610SAXAC)

Assay Procedure Ki Determination:

To a 384 well Proxiplate with 80 nL compound or DMSO spotted on was added 4 kinase mix. The mixture was preincubated for 30 minutes and then 4 μl/well substrate mix was added. The solution was incubated for 60 min and then 4 μl/well detection mix was added. The solution was incubated for another 60 min. The plates were then loaded onto a Perkin Elmer Envision and the TR-FRET signal was measured at 615 and 665 nm. A ratio of 665/620 was used to calculate the % activity at each concentration of compound.

Example B2: HPK1 Lantha Binding Assay ("Lanth")

Materials:

| Reagent | Vender-Cat# |
|---|---|
| white ProxiPlate 384 F(assay plate) | PerkinElmer-6008289 |
| 384-well Microplate(compound plate) | Labcyte-LP-0200 |
| HPK1 enzyme | Signalchem-M23-11G |
| Tracer-222 | Invitrogen-PV6121 |
| Eu-Anti-GST Ab | Invitrogen-PV5594 |
| Assay Buffer | 2 mM DTT(Sigma-43815), 0.01% BRIJ-35(Sigma-B4184), 10 mM MgCl$_2$, 50 mM HEPES(Invitrogen-15630130) |

Procedure:
I. Compound Dilution:
The compounds to be tested were diluted by preparing 12.5 uL/well of 5 mM compound (100×) in columns 2 and 13 and 10 ul/well of DMSO in columns 3-12, 14-23, and wells A1-H1 and I24-P24 of the compound plate using a Bravo liquid handling platform. For the reference compound, the top concentration was 1 mM. To the plate was added 10 ul 2 mM staurosporine in wells J1-P1 and A24-H24. A 11 point 5-fold compound serial dilution was performed using the Bravo liquid handling platform. From the plate were transferred 2.5 ul of the solutions from column 2 and column 13 to the 10 ul of DMSO in columns 3 and 14 & so on. The compound plate was centrifuged at 2500 rpm for 1 min. From the compound plate was transferred 80 nl of the compounds into an assay plate using the Echo liquid handler system. One compound plate makes two assay plates. Each assay plate is sealed and stored in an N$_2$ cabinet.
II. Assay Condition:
The following assay concentrations and times were used: 2 nM HPK1, 2 nM Eu-Anti-GST Ab, and 15 nM Tracer222, with 60 min incubation time.
III. HPK Lantha Binding Assay:
For the binding assay, 4 ul 2×HPK1 and Eu-anti-GST antibody were added to each well of the assay plate using a Multidrop reagent dispenser. The solutions were incubated in a 23 C incubator for 1 h. To each well of the assay plate was added 4 ul 2× Tracer-222 using a Multidrop reagent dispenser. The solutions were again incubated in a 23 C incubator for 1 h. The results of the assay were read using an Envision plate reader with the following parameters: TR_FRET, 340 ex/615 and 665em; 100 usec Delay; and 200 usec integration.
IV. Analysis:
Compound Ki was analyzed using Morrison ki fit model in XL-fit
  a. fit=(1−(((((E+x)+(Ki*(1+(S/Kd))))−(((((E+x)+(Ki*(1+(S/Kd))))^2)−((4*E)*x)^0.5))/(2*E)))
     res=(y−fit)
  b. Parameters:
     E=enzyme concentration
     S=Tracer222 concentration, Kd=Tracer222 Kd
     All measurements reported using the same units (uM)

Exemplary compounds were tested in the binding assays. The Ki values determined are listed in Table B1.

TABLE B1

| Compound No. | HPK1 Ki (μM) |
|---|---|
| 1 | 0.02879 |
| 2 | 0.03556 |
| 3 | 0.04031 |
| 4 | 0.07166 |
| 5 | 0.09872 |
| 6 | 0.02267 |
| 7 | 0.0216 |
| 8 | 0.00771 |
| 9 | 0.0389 |
| 10 | 0.0127 |
| 11 | 0.0912 |
| 12 | 0.0376 |
| 13 | 0.0216 |
| 14 | 0.8631 |
| 15 | 0.12196 |
| 16 | 0.5210 |
| 17 | 0.0328 |
| 18 | 0.2589 |
| 19 | 0.0208 |
| 20 | 0.2124 |
| 21 | 0.2966 |
| 22 | 0.8687 |
| 23 | 0.1838 |
| 24 | 0.08866 |
| 25 | 0.0439 |
| 26 | 0.4461 |
| 27 | 0.00671 |
| 28 | 0.00695 |
| 29 | 0.0300 |
| 30 | 0.05386 |
| 31 | 0.02857 |
| 32 | 0.01279 |
| 33 | 0.7709 |
| 34 | 0.00615 |
| 35 | 0.0228 |
| 36 | 0.0047 |
| 37 | 0.00220 |
| 38a | 0.02419 |
| 38c | 0.00847 |
| 39 | 0.01723 |
| 39a | 0.02766 |
| 39b | 0.04053 |
| 39c | 0.01161 |
| 39d | 0.01872 |
| 40 | 0.01532 |
| 41 | 0.1026 |
| 42 | 0.100 |
| 43 | 0.0815 |
| 44 | 0.0044 |
| 45 | 0.04369 |
| 46 | 0.03864 |
| 47 | 0.08847 |
| 48 | 0.151364 |
| 49 | 0.05529 |
| 50 | 0.13924 |
| 51 | 0.068211 |
| 52 | 0.019 |
| 53 | 0.02886 |
| 54 | 0.06437 |
| 55 | 0.08471 |
| 56 | 0.035314 |
| 57 | 0.00906 |
| 58 | 0.04371 |
| 59 | 0.01425 |
| 60 | 0.01601 |
| 61 | 0.01284 |
| 61a | 0.03912 |
| 61b | 0.01209 |
| 62 | 0.0664 |
| 63 | 0.0849 |
| 64 | 0.0891 |
| 65 | 0.13467 |
| 66 | 0.05313 |
| 67 | 0.0275 |

TABLE B1-continued

| Compound No. | HPK1 Ki (μM) |
|---|---|
| 68a | 0.0179 |
| 68b | 0.0077 |
| 68c | 0.00540 |
| 69a | 0.03562 |
| 69b | 0.01604 |
| 70 | 0.1017 |
| 71 | 0.1148 |
| 72 | 0.278559 |
| 73 | 0.02607 |
| 74 | 0.031 |
| 75 | 0.25107 |
| 76 | 0.49 |
| 77a | 0.15968 |
| 77b | 0.21711 |
| 78a | 0.92698 |
| 78b | 0.16503 |
| 79 | 0.65891 |
| 80a | 0.09759 |
| 80b | 0.12906 |
| 81a | 0.03960 |
| 81c | 0.01768 |
| 82a | 0.00812 |
| 83 | 0.20761 |
| 84a | 0.02587 |
| 84c | 0.00207 |
| 85a | 0.04805 |
| 85c | 0.14858 |
| 86a | 0.00790 |
| 86c | 0.00325 |
| 87a | 0.35833 |
| 88a | 0.12575 |
| 89a | 0.0060 |
| 89c | 0.02306 |
| 90a | 0.05179 |
| 90c | 0.08043 |
| 91a | 0.00553 |
| 92 | 0.0284 |
| 93 | 0.91573 |
| 94a | 0.07361 |
| 95a | 0.12 |
| 96a | 0.12397 |
| 97a | 0.05068 |
| 98a | 0.07561 |
| 99a | 0.01454 |
| 100a | 0.06352 |
| 100b | 0.00174 |
| 101 | 0.05584 |
| 102a | 0.067 |
| 103 | 0.02414 |
| 104 | 0.01309 |
| 105a | 0.00985 |
| 106a | 0.02357 |
| 107a | 0.05010 |
| 108a | 0.00827 |
| 109a | 0.02526 |
| 109c | 0.03249 |
| 110 | 0.0045 |
| 111a | 0.04829 |
| 111b | 0.17249 |
| 112 | 0.0066 |
| 113a | 0.03895 |
| 113b | 0.01506 |
| 114a | 0.00284 |
| 115a | 0.02298 |
| 116a | 0.15333 |
| 116c | 0.14039 |
| 117a | 0.24686 |
| 118a | 0.00849 |
| 119a | 0.07677 |
| 120a | 0.47949 |
| 121a | 0.38143 |
| 122a | 0.30430 |
| 122b | 0.02600 |
| 123a | 0.03764 |
| 123b | 0.77085 |
| 124a | 0.03505 |
| 125a | 0.00356 |
| 126a | 0.01847 |
| 127a | 0.16460 |
| 128a | 0.04658 |
| 128b | 0.04215 |
| 129 | 0.02343 |
| 130 | 0.00400 |
| 131a | 0.00393 |
| 132a | 0.00208 |
| 133a | 0.03400 |
| 134a | 0.01607 |
| 135a | 0.00716 |
| 135c | 0.00295 |
| 136 | 0.0159 |
| 137 | 0.0341 |
| 138 | 0.0386 |
| 139 | 0.1202 |
| 140a | 0.33908 |
| 140b | 0.06251 |
| 141 | 0.1255 |
| 142 | 0.1157 |
| 143a | 0.15719 |
| 144a | 0.03963 |
| 144b | 0.00998 |
| 145 | 0.00937 |
| 145a | 0.00994 |
| 145c | 0.01039 |
| 145d | 0.01991 |
| 146a | 0.49387 |
| 146c | 0.07456 |
| 147 | 0.0613 |
| 148a | 0.00221 |
| 149 | 0.0335 |
| 150a | 0.00330 |
| 150c | 0.00251 |
| 151a | 0.04203 |
| 152a | 0.00435 |
| 153a | 0.00716 |
| 154a | 0.0142 |
| 155a | 0.00081 |
| 155b | 0.08478 |
| 156a | 0.00263 |
| 157a | 0.10903 |
| 158a | 0.13242 |
| 159a | 0.03219 |
| 160a | 0.05654 |
| 161a | 0.05104 |
| 162a | 0.10346 |
| 163a | 0.06930 |
| 164a | 0.00665 |
| 165a | 0.00641 |
| 166 | 0.00439 |
| 167a | 0.16258 |
| 168a | 0.02631 |
| 169a | 0.05402 |
| 170a | 0.00554 |
| 171a | 0.00658 |
| 172 | 0.319 |
| 173a | 0.00675 |
| 174a | 0.0742 |
| 174b | 0.582 |
| 175a | 0.0042 |
| 175b | 0.945 |
| 176 | 0.127 |
| 177a | 0.01472 |
| 178a | 0.01591 |
| 179a | 0.19404 |
| 179b | 0.00091 |
| 180a | 0.04613 |
| 181 | 0.19773 |
| 182 | 0.82929 |
| 183 | 0.03028 |
| 184 | 0.05026 |
| 185 | 0.07581 |
| 186 | 0.27640 |
| 187 | 0.29952 |
| 188 | 0.21017 |
| 189 | 0.31513 |
| 190 | 0.35883 |
| 191a | 0.0347 |

TABLE B1-continued

| Compound No. | HPK1 Ki (μM) |
|---|---|
| 192 | 0.16310 |
| 193a | 0.00364 |
| 193b | 0.00141 |
| 194a | 0.03040 |
| 194b | 0.00836 |
| 195b | 0.00623 |
| 196a | 0.09761 |
| 197a | 0.00513 |
| 197b | 0.00364 |
| 198a | 0.01524 |
| 199a | 0.94095 |
| 199b | 0.10478 |
| 200 | 0.00476 |
| 201a | 0.00358 |
| 202b | 0.02189 |
| 203 | 0.88467 |
| 204 | 0.28498 |
| 205 | 0.26739 |
| 206 | 0.43623 |
| 207 | 0.08696 |
| 208 | 0.20136 |
| 209 | 0.19871 |
| 210 | 0.07085 |
| 211 | 0.14522 |
| 212 | 0.11217 |
| 213 | 0.28600 |
| 214 | 0.33992 |
| 215 | 0.67640 |
| 216 | 0.33032 |
| 217a | 0.00940 |
| 217b | 0.00905 |
| 217c | 0.06791 |
| 217d | 0.02337 |
| 218 | 0.22983 |
| 219 | 0.47782 |
| 220 | 0.30842 |
| 221 | 0.30283 |
| 222 | 0.27494 |
| 223 | 0.43564 |
| 224 | 0.12585 |
| 225 | 0.36315 |
| 226 | 0.01396 |
| 227 | 0.01117 |
| 228a | 0.00476 |
| 228b | 0.00173 |
| 229a | 0.0110 |
| 229b | 0.0130 |
| 230 | 0.17272 |
| 231 | 0.44703 |
| 232 | 0.0337 |
| 233 | 0.02606 |
| 234a | 0.00392 |
| 234b | 0.03803 |
| 234c | 0.10281 |
| 234d | 0.05186 |
| 235a | 0.04673 |
| 235b | 0.01190 |
| 236 | 0.03316 |
| 237 | 0.28259 |
| 238 | 0.02289 |
| 239a | 0.00089 |
| 239b | 0.02101 |
| 240a | 0.00387 |
| 240b | 0.11195 |
| 241a | 0.04480 |
| 241b | 0.01250 |
| 242 | 0.01170 |
| 243a | 0.00578 |
| 243b | 0.01043 |
| 243c | 0.06310 |
| 243d | 0.02510 |
| 244 | 0.00825 |
| 245a | 0.04204 |
| 246a | 0.01028 |
| 246b | 0.31633 |
| 247 | 0.25307 |
| 248a | 0.00601 |
| 248b | 0.00489 |

TABLE B1-continued

| Compound No. | HPK1 Ki (μM) |
|---|---|
| 249 | 0.00430 |
| 250a | 0.00849 |
| 250b | 0.04132 |
| 251 | 0.00315 |
| 252 | 0.00594 |
| 253a | 0.02307 |
| 254a | 0.00520 |
| 254b | 0.10871 |
| 255a | 0.01989 |
| 255b | 0.01195 |
| 256a | 0.01114 |
| 257 | 0.0532 |
| 258a | 0.19 |
| 258b | 0.15 |
| 259a | 0.0061 |
| 259c | 0.0030 |
| 260 | 0.038 |
| 261a | 0.0042 |
| 261b | 0.0371 |
| 262 | 0.012 |
| 263 | 0.283239 |
| 264 | 0.01153 |
| 265 | 0.108179 |
| 266a | 0.0653 |
| 266b | 0.0039 |
| 267a | 0.1095 |
| 267b | 0.00039 |
| 268 | 0.4842 |
| 269 | 0.1911 |
| 270 | 0.3314 |
| 271a | 0.0249 |
| 272a | 0.0308 |
| 273a | 0.0448 |
| 274a | 0.0133 |
| 274b | 0.0009 |
| 275a | 0.041 |
| 276 | 0.25158 |
| 277 | 0.3423 |
| 278 | 0.2807 |
| 279 | 0.0418 |
| 280 | 0.1789 |
| 281 | 0.1436 |
| 282 | 0.2166 |
| 283 | 0.07423 |
| 284 | 0.62923 |
| 285 | 0.37539 |
| 286 | 0.11983 |
| 287 | 0.63825 |
| 288 | 0.016 |
| 289 | 0.2152 |
| 290a | 0.5587 |
| 290b | 0.8949 |
| 291 | 0.2362 |
| 292 | 0.1269 |
| 293 | 0.0474 |
| 294 | 0.3087 |
| 295 | 0.3866 |
| 296 | 0.0114 |
| 297 | 0.0576 |
| 298 | 0.0523 |
| 299 | 0.0889 |
| 300 | 0.0506 |
| 300a | 0.027 |
| 300b | 0.2699 |
| 301 | 0.0682 |
| 302 | 0.0463 |
| 303 | 0.0326 |
| 304a | 0.0439 |
| 305a | 0.0386 |
| 306a | 0.0432 |
| 307 | 0.0172 |
| 308 | 0.18640 |
| 309 | 0.029 |
| 310 | 0.0106 |
| 311 | 0.16059 |
| 312 | 0.0459 |
| 313 | 0.0731 |
| 314 | 0.125 |

TABLE B1-continued

| Compound No. | HPK1 Ki (μM) |
|---|---|
| 315 | 0.0344 |
| 316 | 0.4924 |
| 317 | 0.20877 |
| 318 | 0.23556 |
| 319 | 0.30574 |
| 320 | 0.33730 |
| 321 | 0.32096 |
| 322 | 0.0373 |
| 323 | 0.60335 |
| 324 | 0.0304 |
| 325a | 0.0407 |
| 326 | 0.076 |
| 327 | 0.39696 |
| 328 | 0.2893 |
| 329 | 0.09 |
| 330a | 0.0739 |
| 331 | 0.2432 |
| 332 | 0.57 |
| 333 | 0.042277 |
| 334 | 0.048 |
| 335 | 0.13 |
| 336 | 0.04662 |
| 337a | 0.0284 |
| 338 | 0.0797 |
| 339 | 0.3734 |
| 340 | 0.0147735 |
| 341 | 0.012419 |
| 342 | 0.0734 |
| 343 | 0.074 |
| 344 | 0.59 |
| 345 | 0.094 |

Example B3: Human T-Cell IL2 Induction Assay

Assay Principle

Anti-CD3 and anti-CD28 activates TCR signaling in primary human pan T cells leading to IL-2 promoter induction. Secreted IL-2 in cell culture supernatant is detected by electrochemiluminescence using a capture antibody against IL-2 and an anti-IL-2 antibody labeled with SULFO-tag.

Literature:

See www.mesoscale.com for additional electrochemiluminescence technology information.

Assay Procedure:

Incubate primary human pan T cells with varying concentrations of test compounds for 30 minutes in a humidified incubator at 37° C. and 5% $CO_2$. Transfer cells to a plate pre-coated with a fixed concentration of anti-human CD3 (determined separately for each donor lot) and add soluble anti-human CD28 (final concentration=1 μg/ml). Stimulate cells in a humidified incubator at 37° C. and 5% $CO_2$ for 4 hours. Transfer 25 μl of supernatant to a MSD single spot plate pre-coated with an anti-human IL-2 antibody. Incubate MSD plate overnight at 4° C. with gentle shaking. Wash MSD plate 4× with wash buffer. Add SULFO-tagged detection antibody at a 1:50 dilution and incubate at room temperature shaking for 2 hours. Wash MSD plate 4× with wash buffer and add 1500 μl 2×MSD read buffer. Read on an MSD instrument. Normalize data to stimulated/untreated controls to calculate % activity at each concentration of compound.

Materials:

Frozen Primary Human Pan-T Cells (StemCell Technologies #70024)
anti-human CD3 (OKT3 clone) (eBioscience #16-0037-81)
anti-human CD28 (CD28.2 clone) (BD #555725)
96-well Human IL-2 tissue culture kit (MSD #K151AHB-4)

Instrumentation:

Biomek FX for liquid handling (Beckman Coulter)
MSD SECTOR S 600 (Meso Scale Discovery)

Exemplary compounds of Formula (I) were tested in the human T-cell IL-2 induction assays. The % increase measured for IL-2 in cells treated by the test compounds relative to untreated cells are provided in Table B2 for certain compounds.

TABLE B2

| Cmpd No. | % IL relative to untreated cells | Assayed concentration (μM) |
|---|---|---|
| 243a | 111% | 2.8 |
| 250a | 504% | 25 |
| 259c | 604% | 8.3 |
| 267b | 298% | 0.926 |
| 274b | 564% | 0.926 |

It is to be noted that the term "a" or "an" entity refers to one or more of that entity; for example, "a polypeptide" is understood to represent one or more polypeptides. As such, the terms "a" (or "an"), "one or more," and "at least one" can be used interchangeably herein.

All technical and scientific terms used herein have the same meaning. Efforts have been made to ensure accuracy with respect to numbers used (e.g. amounts, temperature, etc.) but some experimental errors and deviations should be accounted for.

Throughout this specification and the claims, the words "comprise," "comprises," and "comprising" are used in a non-exclusive sense, except where the context requires otherwise. It is understood that embodiments described herein include "consisting of" and/or "consisting essentially of" embodiments.

As used herein, the term "about," when referring to a value is meant to encompass variations of, in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Where a range of values is provided, it is understood that each intervening value, to the tenth of the unit of the lower limit, unless the context clearly dictates otherwise, between the upper and lower limit of the range and any other stated or intervening value in that stated range, is encompassed within the invention. The upper and lower limits of these small ranges which may independently be included in the smaller rangers is also encompassed within the invention, subject to any specifically excluded limit in the stated range. Where the stated range includes one or both of the limits, ranges excluding either or both of those included limits are also included in the invention.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed

The invention claimed is:
1. A compound of Formula (I)

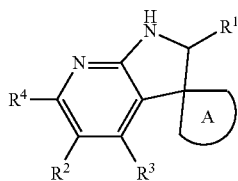

or a pharmaceutically acceptable salt thereof, wherein:
R$^1$ is hydrogen or C$_{1-6}$ alkyl;
A is C$_{3-12}$ cycloalkyl, 3- to 14-membered heterocyclyl, C$_{6-14}$ aryl or 5- to 14-membered heteroaryl, wherein the C$_{3-12}$ cycloalkyl, 3- to 14-membered heterocyclyl, C$_{6-14}$ aryl and 5- to 14-membered heteroaryl of A are each optionally substituted with 1, 2, 3, 4 or 5 substituents independently selected from R$^9$;
R$^2$ is C$_{6-14}$ aryl optionally substituted with 1, 2, 3, 4 or 5 substituents independently selected from R$^{10}$, or 5- to 14-membered heteroaryl optionally substituted with 1, 2, 3, 4 or 5 substituents independently selected from R$^{10}$;
R$^3$ is hydrogen, halogen, cyano, C$_{1-6}$ alkyl, C$_{1-6}$ haloalkyl, C$_{3-6}$ cycloalkyl, —OR$^7$, or —NR$^{8a}$R$^{8b}$;
R$^4$ is hydrogen, halogen, cyano, C$_{1-6}$ alkyl, or C$_{3-6}$ cycloalkyl;
R$^7$ is hydrogen or C$_{1-6}$ alkyl optionally substituted with 1, 2, 3, 4 or 5 substituents independently selected from R$^{10}$;
each R$^{8a}$ and R$^{8b}$ is independently hydrogen or C$_{1-6}$ alkyl optionally substituted with 1, 2, 3, 4 or 5 substituents independently selected from R$^{10}$;
each R$^9$ is independently R$^{10}$, or C$_{1-6}$ alkylidene optionally substituted with 1, 2, 3 or 4 substituents independently selected from R$^{11}$;
each R$^{10}$ is independently oxo, C$_{1-6}$ alkyl, C$_{2-6}$ alkenyl, C$_{2-6}$ alkynyl, C$_{3-8}$ cycloalkyl, C$_{6-10}$ aryl, 5- to 10-membered heteroaryl, 3- to 12-membered heterocyclyl, halogen, cyano, —C(O)R$^a$, —C(O)OR$^b$, —C(O)NR$^c$R$^d$, —OR$^b$, —OC(O)R$^a$, —OC(O)NR$^c$R$^d$, —SR$^b$, —S(O)R$^e$, —S(O)$_2$R$^e$, —S(O)(=NH)R$^e$, —S(O)$_2$NR$^c$R$^d$, —NR$^c$R$^d$, —N(R$^f$)C(O)R$^a$, —N(R$^f$)C(O)OR$^b$, —N(R$^f$)C(O)NR$^c$R$^d$, —N(R$^f$)S(O)$_2$R$^e$, —N(R$^f$)S(O)$_2$NR$^c$R$^d$, or —P(O)R$^g$R$^h$; wherein the C$_{1-6}$ alkylidene, C$_{1-6}$ alkyl, C$_{2-6}$ alkenyl, C$_{2-6}$ alkynyl, C$_{3-8}$ cycloalkyl, C$_{6-14}$ aryl, 5- to 14-membered heteroaryl and 3- to 14-membered heterocyclyl of R$^{10}$ are each optionally substituted with 1, 2, 3 or 4 substituents independently selected from R$^{11}$;
each R$^a$ is independently hydrogen, C$_{1-6}$ alkyl, C$_{2-6}$ alkenyl, C$_{2-6}$ alkynyl, C$_{3-8}$ cycloalkyl, C$_{6-10}$ aryl, 5- to 10-membered heteroaryl or 3- to 12-membered heterocyclyl; wherein the C$_{1-6}$ alkyl, C$_{2-6}$ alkenyl, C$_{2-6}$ alkynyl, C$_{3-8}$ cycloalkyl, C$_{6-10}$ aryl, 5- to 10-membered heteroaryl and 3- to 12-membered heterocyclyl of R$^a$ are each optionally substituted with 1, 2, 3 or 4 substituents independently selected from R$^{11}$;
each R$^b$ is independently hydrogen, C$_{1-6}$ alkyl, C$_{3-8}$ cycloalkyl, C$_{6-10}$ aryl, 5- to 10-membered heteroaryl or 3- to 12-membered heterocyclyl; wherein the C$_{1-6}$ alkyl, C$_{3-8}$ cycloalkyl, C$_{6-10}$ aryl, 5- to 10-membered heteroaryl and 3- to 12-membered heterocyclyl of R$^b$ are each optionally substituted with 1, 2, 3 or 4 substituents independently selected from R$^{11}$;
each R$^c$ and R$^d$ is independently hydrogen, C$_{1-6}$ alkyl, C$_{3-8}$ cycloalkyl, C$_{6-10}$ aryl, 5- to 10-membered heteroaryl or 3- to 12-membered heterocyclyl; wherein the C$_{1-6}$ alkyl, C$_{3-8}$ cycloalkyl, C$_{6-10}$ aryl, 5- to 10-membered heteroaryl and 3- to 12-membered heterocyclyl of R$^c$ and R$^d$ are each optionally substituted with 1, 2, 3 or 4 substituents independently selected from R$^{11}$;
or R$^c$ and R$^d$ are taken together with the nitrogen atom to which they are attached to form a 4- to 12-membered heterocyclyl optionally substituted with 1, 2, 3 or 4 substituents independently selected from R$^{11}$;
each R$^e$ is independently C$_{1-6}$ alkyl, C$_{3-8}$ cycloalkyl, C$_{6-10}$ aryl, 5- to 10-membered heteroaryl or 3- to 12-membered heterocyclyl; wherein the C$_{1-6}$ alkyl, C$_{3-8}$ cycloalkyl, C$_{6-10}$ aryl, 5- to 10-membered heteroaryl and 3- to 12-membered heterocyclyl of R$^e$ are each optionally substituted with 1, 2, 3 or 4 substituents independently selected from R$^{11}$;
each R$^f$ is independently hydrogen or C$_{1-6}$ alkyl;
each R$^g$ and R$^h$ is independently C$_{1-6}$ alkyl, C$_{3-8}$ cycloalkyl, C$_{6-10}$ aryl, 5- to 10-membered heteroaryl, 3- to 12-membered heterocyclyl, or —O—C$_{1-6}$ alkyl; wherein the C$_{1-6}$ alkyl, C$_{3-8}$ cycloalkyl, C$_{6-10}$ aryl, 5- to 10-membered heteroaryl and 3- to 12-membered heterocyclyl of R$^g$ and R$^h$ are each optionally substituted with 1, 2, 3 or 4 substituents independently selected from R$^{11}$;
or R$^g$ and R$^h$ are taken together with the phosphorus atom to which they are attached to form a 4- to 12-membered heterocyclyl optionally substituted with 1, 2, 3 or 4 substituents independently selected from R$^{11}$;
each R$^{11}$ is independently oxo, C$_{1-6}$ alkyl, C$_{2-6}$ alkenyl, C$_{2-6}$ alkynyl, C$_{3-6}$ cycloalkyl, C$_{6-10}$ aryl, 5- to 10-membered heteroaryl, 3- to 8-membered heterocyclyl, halogen, cyano, —C(O)R$^{a1}$, —C(O)OR$^{b1}$, —C(O)NR$^{c1}$R$^{d1}$, —OR$^{b1}$, —OC(O)R$^{a1}$, —OC(O)NR$^{c1}$R$^{d1}$, —SR$^{b1}$, —S(O)R$^{e1}$, —S(O)$_2$R$^{e1}$, —S(O)$_2$NR$^{c1}$R$^{d1}$, —NR$^{c1}$R$^{d1}$, —N(R$^{f1}$)C(O)R$^{a1}$, —N(R$^{f1}$)C(O)OR$^{b1}$, —N(R$^{f1}$)C(O)NR$^{c1}$R$^{d1}$, —N(R$^{f1}$)S(O)$_2$R$^{e1}$, —N(R$^{f1}$)S(O)$_2$NR$^{c1}$R$^{d1}$, or —P(O)R$^{g1}$R$^{h1}$; wherein the C$_{1-6}$ alkyl, C$_{2-6}$ alkenyl, C$_{2-6}$ alkynyl, C$_{3-6}$ cycloalkyl, C$_{6-14}$ aryl, 5- to 14-membered heteroaryl and 3- to 14-membered heterocyclyl of R$^{11}$ are each optionally substituted with 1, 2, 3 or 4 substituents independently selected from R$^{12}$;
each R$^{a1}$ is independently hydrogen, C$_{1-6}$ alkyl, C$_{2-6}$ alkenyl, C$_{2-6}$ alkynyl, C$_{3-6}$ cycloalkyl, C$_{6-10}$ aryl, 5- to 10-membered heteroaryl or 3- to 8-membered heterocyclyl; wherein the C$_{1-6}$ alkyl, C$_{2-6}$ alkenyl, C$_{2-6}$ alkynyl, C$_{3-6}$ cycloalkyl, C$_{6-10}$ aryl, 5- to 10-membered heteroaryl and 3- to 8-membered heterocyclyl of R$^{a1}$ are each optionally substituted with 1, 2, 3 or 4 substituents independently selected from R$^{12}$;
each R$^{b1}$ is independently hydrogen, C$_{1-6}$ alkyl, C$_{3-6}$ cycloalkyl, C$_{6-10}$ aryl, 5- to 10-membered heteroaryl or 3- to 8-membered heterocyclyl; wherein the C$_{1-6}$ alkyl, C$_{3-6}$ cycloalkyl, C$_{6-10}$ aryl, 5- to 10-membered heteroaryl and 3- to 8-membered heterocyclyl of R$^{b1}$ are each optionally substituted with 1, 2, 3 or 4 substituents independently selected from R$^{12}$;
each R$^{c1}$ and R$^{d1}$ is independently hydrogen, C$_{1-6}$ alkyl, C$_{3-6}$ cycloalkyl, C$_{6-10}$ aryl, 5- to 10-membered heteroaryl or 3- to 8-membered heterocyclyl; wherein the $C_{1-6}$ alkyl, $C_{3-6}$ cycloalkyl, $C_{6-10}$ aryl, 5- to 10-membered heteroaryl and 3- to 8-membered heterocyclyl of $R^{c1}$ and $R^{d1}$ are each optionally substituted with 1, 2, 3 or 4 substituents independently selected from $R^{12}$;

or $R^{c1}$ and $R^{d1}$ are taken together with the nitrogen atom to which they are attached to form a 4- to 8-membered heterocyclyl optionally substituted with 1, 2, 3 or 4 substituents independently selected from $R^{12}$;

each $R^{e1}$ is independently $C_{1-6}$ alkyl, $C_{3-6}$ cycloalkyl, $C_{6-10}$ aryl, 5- to 10-membered heteroaryl or 3- to 8-membered heterocyclyl; wherein the $C_{1-6}$ alkyl, $C_{3-6}$ cycloalkyl, $C_{6-10}$ aryl, 5- to 10-membered heteroaryl and 3- to 8-membered heterocyclyl of $R^{e1}$ are each optionally substituted with 1, 2, 3 or 4 substituents independently selected from $R^{12}$;

each $R^{f1}$ is independently hydrogen or $C_{1-6}$ alkyl;

each $R^{g1}$ and $R^{h1}$ is independently $C_{1-6}$ alkyl, $C_{3-6}$ cycloalkyl, $C_{6-10}$ aryl, 5- to 10-membered heteroaryl, 3- to 8-membered heterocyclyl, or —O—$C_{1-6}$ alkyl; wherein the $C_{1-6}$ alkyl, $C_{3-6}$ cycloalkyl, $C_{6-10}$ aryl, 5- to 10-membered heteroaryl and 3- to 8-membered heterocyclyl of $R^{g1}$ and $R^{h1}$ are each optionally substituted with 1, 2, 3 or 4 substituents independently selected from $R^{12}$;

or $R^{g1}$ and $R^{h1}$ are taken together with the phosphorus atom to which they are attached to form a 4- to 8-membered heterocyclyl optionally substituted with 1, 2, 3 or 4 substituents independently selected from $R^{12}$;

each $R^{12}$ is independently oxo, $C_{1-6}$ alkyl, $C_{3-6}$ cycloalkyl, $C_6$ aryl, 5- to 6-membered heteroaryl, 3- to 6-membered heterocyclyl, halogen, cyano, —C(O)$R^{a2}$, —C(O)O$R^{b2}$, —C(O)N$R^{c2}R^{d2}$, —O$R^{b2}$, —OC(O)$R^{a2}$, —OC(O)N$R^{c2}R^{d2}$, —S(O)$_2R^{e2}$, —S(O)$_2$N$R^{c2}R^{d2}$, —N$R^{c2}R^{d2}$, —N($R^{f2}$)C(O)$R^{a2}$, —N($R^{f2}$)C(O)O$R^{b2}$, —N($R^{f2}$)C(O)N$R^{c2}R^{d2}$, —N($R^{f2}$)S(O)$_2R^{e2}$, —N($R^{f2}$)S(O)$_2$N$R^{c2}R^{d2}$, or —P(O)$R^{g2}R^{h2}$; wherein the $C_{1-6}$ alkyl, $C_{3-6}$ cycloalkyl, $C_6$ aryl, 5- to 6-membered heteroaryl and 3- to 6-membered heterocyclyl of $R^{12}$ are each optionally substituted with 1, 2, 3 or 4 substituents independently selected from $R^{13}$;

each $R^{a2}$ is independently hydrogen, $C_{1-6}$ alkyl, $C_{3-6}$ cycloalkyl, $C_6$ aryl, 5- to 6-membered heteroaryl or 3- to 6-membered heterocyclyl; wherein the $C_{1-6}$ alkyl, $C_{3-6}$ cycloalkyl, $C_6$ aryl, 5- to 6-membered heteroaryl and 3- to 6-membered heterocyclyl of $R^2$ are each optionally substituted with 1, 2, 3 or 4 substituents independently selected from $R^{13}$;

each $R^{b2}$ is independently hydrogen, $C_{1-6}$ alkyl, $C_{3-6}$ cycloalkyl or 3- to 6-membered heterocyclyl; wherein the $C_{1-6}$ alkyl, $C_{3-6}$ cycloalkyl and 3- to 6-membered heterocyclyl of $R^2$ are each optionally substituted with 1, 2, 3 or 4 substituents independently selected from $R^{13}$;

each $R^{c2}$ and $R^{d2}$ is independently hydrogen, $C_{1-6}$ alkyl, $C_{3-6}$ cycloalkyl or 3- to 8-membered heterocyclyl; wherein the $C_{1-6}$ alkyl, $C_{3-6}$ cycloalkyl and 3- to 8-membered heterocyclyl of $R^{c2}$ and $R^{d2}$ are each optionally substituted with 1, 2, 3 or 4 substituents independently selected from $R^{13}$;

or $R^{c2}$ and $R^{d2}$ are taken together with the nitrogen atom to which they are attached to form a 4- to 6-membered heterocyclyl optionally substituted with 1, 2, 3 or 4 substituents independently selected from $R^{13}$;

each $R^{e2}$ is independently $C_{1-6}$ alkyl, $C_{3-6}$ cycloalkyl, $C_6$ aryl, 5- to 6-membered heteroaryl or 3- to 6-membered heterocyclyl; wherein the $C_{1-6}$ alkyl, $C_{3-6}$ cycloalkyl, $C_6$ aryl, 5- to 6-membered heteroaryl and 3- to 6-membered heterocyclyl of $R^{e2}$ are each optionally substituted with 1, 2, 3 or 4 substituents independently selected from $R^{13}$;

each $R^{f2}$ is independently hydrogen or $C_{1-6}$ alkyl;

each $R^{g2}$ and $R^{h2}$ is independently $C_{1-6}$ alkyl, $C_{3-6}$ cycloalkyl, 3- to 8-membered heterocyclyl, or —O—$C_{1-6}$ alkyl; wherein the $C_{1-6}$ alkyl, $C_{3-6}$ cycloalkyl, and 3- to 8-membered heterocyclyl of $R^{g2}$ and $R^h$ are each optionally substituted with 1, 2, 3 or 4 substituents independently selected from $R^{13}$;

or $R^{g2}$ and $R^{h2}$ are taken together with the phosphorus atom to which they are attached to form a 4- to 6-membered heterocyclyl optionally substituted with 1, 2, 3 or 4 substituents independently selected from $R^{13}$; and each $R^{13}$ is independently oxo, halogen, hydroxyl, —O($C_{1-6}$ alkyl), cyano, $C_{1-6}$ alkyl or $C_{1-6}$ haloalkyl;

provided that the compound is other than Compound Nos. 1x-4x in Table 1X and salts thereof.

2. The compound of claim 1, wherein $R^3$ is hydrogen, halogen, $C_{1-6}$ alkyl or —O$R^7$.

3. The compound of claim 2, wherein $R^3$ is hydrogen, chloro, methyl or methoxy.

4. The compound of claim 1, wherein $R^4$ is hydrogen.

5. The compound of claim 1, wherein A is

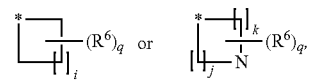

wherein the * indicates the point of attachment;
i is 0, 1, 2 or 3;
j is 1, 2 or 3;
k is 1 or 2;
each q is independently 0, 1, 2, 3, 4 or 5; and
each $R^6$, where present, is independently selected from $R^9$; wherein optionally two $R^6$ groups are taken together to form a spiro, fused or bridged ring which is optionally substituted with 1, 2, 3 or 4 substituents independently selected from $R^{10}$, or two vicinal $R^6$ groups are taken together to form a bond.

6. The compound of claim 1, wherein A is selected from the group consisting of:

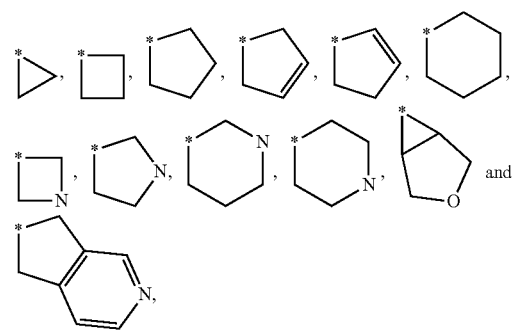

each of which is optionally substituted with 1, 2, 3, 4 or 5 substituents independently selected from $R^9$; wherein the * indicates the point of attachment.

7. The compound of claim 1, wherein A is:

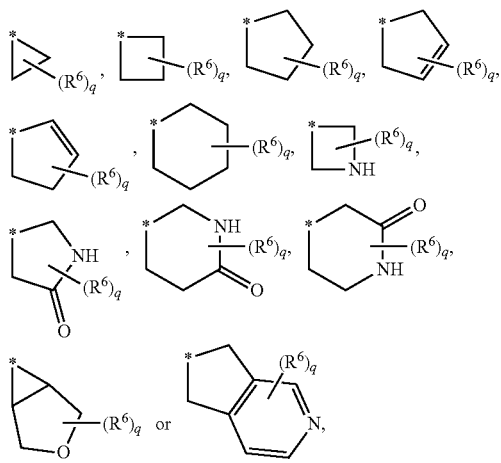

wherein the * indicates the point of attachment, each q is independently 0, 1, 2, 3, or 4; and each $R^6$, where present, is independently selected from $R^9$.

8. The compound of claim 5, wherein q is 0.

9. The compound of claim 5, wherein each $R^6$, where present, is independently oxo, $C_{1-6}$ alkyl, $C_{1-6}$ alkylidene, $C_{3-8}$ cycloalkyl, $C_{6-10}$ aryl, 5- to 10-membered heteroaryl, 3- to 12-membered heterocyclyl, halogen, cyano, —C(O)R$^a$, —C(O)OR$^b$, —C(O)NR$^c$R$^d$, —OR$^b$, —S(O)$_2$R$^e$, —S(O) (=NH)R$^e$, —S(O)$_2$NR$^c$R$^d$, —NR$^c$R$^d$, —N(R$^f$)C(O)R$^a$, —N(R$^f$)S(O)$_2$R$^e$, or —N(R$^f$)S(O)$_2$NR$^c$R$^d$; wherein the $C_{1-6}$ alkyl, $C_{1-6}$ alkylidene, $C_{3-8}$ cycloalkyl, $C_{6-10}$ aryl, 5- to 10-membered heteroaryl and 3- to 12-membered heterocyclyl of $R^6$ are optionally substituted with 1, 2, 3 or 4 substituents independently selected from $R^{11}$.

10. The compound of claim 5, wherein each q is independently 1, 2, 3, or 4; and at least one $R^6$ is oxo, or $C_{1-6}$ alkylidene optionally substituted with 1, 2, 3 or 4 substituents independently selected from $R^{11}$.

11. The compound of claim 5, wherein each q is independently 1, 2, 3, or 4; and at least one $R^6$ is 3- to 12-membered heterocyclyl optionally substituted with 1, 2, 3 or 4 substituents independently selected from $R^{11}$, 5- to 10-membered heteroaryl optionally substituted with 1, 2, 3 or 4 substituents independently selected from $R^{11}$, or $C_{6-10}$ aryl optionally substituted with 1, 2, 3 or 4 substituents independently selected from $R^{11}$.

12. The compound of claim 5, wherein each q is independently 1, 2 or 3; and each $R^6$ is independently selected from the group consisting of halogen, cyano, —C(O)R$^a$, —C(O)OR$^b$, —C(O)NR$^c$R$^d$, —OR$^b$, —S(O)$_2$R$^e$, —NR$^c$R$^d$, —N(R$^f$)C(O)R$^a$, and $C_{1-6}$ alkyl optionally substituted with 1, 2, 3 or 4 substituents independently selected from $R^{11}$.

13. The compound of claim 1, wherein $R^2$ is $C_{6-14}$ aryl optionally substituted with 1, 2, 3, 4 or 5 substituents independently selected from $R^{10}$.

14. The compound of claim 13, wherein $R^2$ is phenyl optionally substituted with 1, 2, 3, 4 or 5 substituents independently selected from $R^{10}$.

15. The compound of claim 1, wherein $R^2$ is 5- to 14-membered heteroaryl optionally substituted with 1, 2, 3, 4 or 5 substituents independently selected from $R^{10}$.

16. The compound of claim 15, wherein $R^2$ is 5- to 10-membered heteroaryl optionally substituted with 1, 2, 3, 4 or 5 substituents independently selected from $R^{10}$, and wherein the 5- to 10-membered heteroaryl contains 1, 2 or 3 heteroatoms independently selected from the group consisting of N and O.

17. The compound of claim 16, wherein $R^2$ is pyrazolyl, pyridinyl, pyrimidinyl, indolyl, indolinyl, indazolyl, benzo[d]imidazolyl, benzo[d][1,2,3]triazolyl, or pyrrolo[2,3-b]pyridinyl; each is optionally substituted with 1, 2, 3, 4 or 5 substituents independently selected from $R^{10}$.

18. The compound of claim 1, wherein the compound is of the formula (IA):

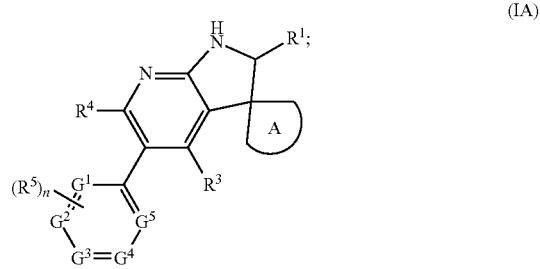

(IA)

or a pharmaceutically acceptable salt thereof, wherein:

$G^1$, $G^2$, $G^3$, $G^4$ and $G^5$ are independently N, CH or CR$^5$, provided that no more than two of $G^1$, $G^2$, $G^3$, $G^4$ and $G^5$ are N;

n is 0, 1, 2, 3, 4 or 5;

each $R^5$ is independently selected from $R^{10}$, optionally two vicinal $R^5$ groups are taken together with the carbon atoms to which they are attached to form a ring which is optionally substituted with 1, 2, 3 or 4 substituents independently selected from $R^{10}$; and A, $R^1$, $R^3$, $R^4$ and $R^{10}$ are as defined in claim 1.

19. The compound of claim 1, wherein the compound is of the formula (IB):

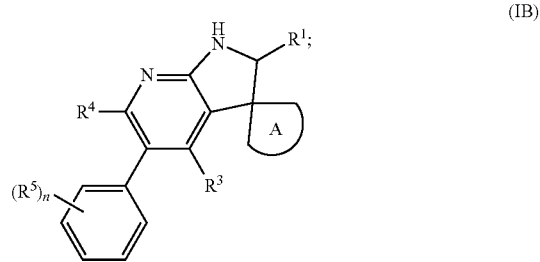

(IB)

or a pharmaceutically acceptable salt thereof, wherein n is 0, 1, 2, 3, 4 or 5; each $R^5$ is independently selected from $R^{10}$; and A, $R^1$, $R^3$, $R^4$ and $R^{10}$ are as defined in claim 1.

20. The compound of claim 1, wherein the compound is of the formula (IC):

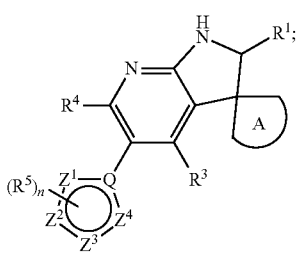

(IC)

or a pharmaceutically acceptable salt thereof, wherein:
Q is C or N, $Z^1$, $Z^2$, $Z^3$ and $Z^4$ are independently N, NH, $NR^5$, CH or $CR^5$, provided that at least one of Q, $Z^1$, $Z^2$, $Z^3$ and $Z^4$ is N, NH or $NR^5$;
n is 0, 1, 2, 3 or 4;
each $R^5$ is independently selected from $R^{10}$, optionally two vicinal $R^5$ groups are taken together with the atoms to which they are attached to form a ring which is optionally substituted with 1, 2, 3 or 4 substituents independently selected from $R^{10}$; and
A, $R^1$, $R^3$, $R^4$ and $R^{10}$ are as defined in claim 1.

21. The compound of claim 18, wherein each $R^5$, where present, is independently oxo, $C_{1-6}$ alkyl, $C_{3-8}$ cycloalkyl, $C_{6-10}$ aryl, 5- to 10-membered heteroaryl, 3- to 12-membered heterocyclyl, halogen, cyano, —C(O)$R^a$, —C(O)O$R^b$, —C(O)N$R^cR^d$, —O$R^b$, —S(O)$_2R^e$, —S(O)(=NH)$R^e$, —S(O)$_2$N$R^cR^d$, —N$R^cR^d$, —N($R^f$)C(O)$R^a$, —N($R^f$)S(O)$_2R^e$, or —N($R^f$)S(O)$_2$N$R^cR^d$; wherein the $C_{1-6}$ alkyl, $C_{3-8}$ cycloalkyl, $C_{6-10}$ aryl, 5- to 10-membered heteroaryl and 3- to 12-membered heterocyclyl of $R^5$ are optionally substituted with 1, 2, 3 or 4 substituents independently selected from $R^{11}$.

22. The compound of claim 18, wherein n is 1, 2, 3 or 4; at least one $R^5$ is —C(O)N$R^cR^d$ or —N$R^cR^d$.

23. The compound of claim 18, wherein n is 1, 2, 3 or 4; and at least one $R^5$ is 3- to 12-membered heterocyclyl optionally substituted with 1, 2, 3 or 4 substituents independently selected from $R^{11}$; 5- to 10-membered heteroaryl optionally substituted with 1, 2, 3 or 4 substituents independently selected from $R^{11}$; or $C_{3-8}$ cycloalkyl optionally substituted with 1, 2, 3 or 4 substituents independently selected from $R^{11}$.

24. The compound of claim 22, wherein n is 2, 3 or 4; and one $R^5$ is halogen, cyano, or $C_{1-6}$ alkyl optionally substituted with 1, 2, 3 or 4 substituents independently selected from $R^{11}$.

25. The compound of claim 18, wherein n is 1, 2, 3 or 4; and at least one $R^5$ is halogen, cyano, —C(O)$R^a$, —C(O)O$R^b$, —C(O)N$R^cR^d$, —O$R^b$, —S(O)$_2R^e$, —S(O)(=NH)$R^e$, —S(O)$_2$N$R^cR^d$, —N$R^cR^d$, —N($R^f$)C(O)$R^a$, —N($R^f$)S(O)$_2R^e$, or —N($R^f$)S(O)$_2$N$R^cR^d$.

26. The compound of claim 18, wherein n is 1, 2, 3 or 4; and at least one $R^5$ is $C_{1-6}$ alkyl optionally substituted with 1, 2, 3 or 4 substituents independently selected from $R^{11}$.

27. The compound of claim 1, wherein the compound is selected from the group consisting of Compound Nos. 1-345 in Table 1, or a pharmaceutically acceptable salt thereof:

TABLE 1

| No. | Structure | Name |
| --- | --- | --- |
| 1 | 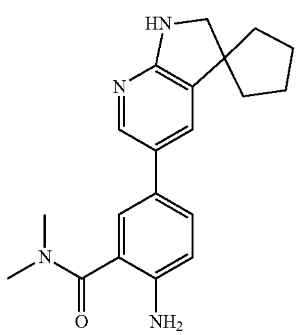 [SMILES: CN(C)C(=O)c1cc(-c2cnc3c(c2)C2(CCCC2)CN3)ccc1N] | 2-Amino-5-(1',2'-dihydrospiro[cyclopentane-1,3'-pyrrolo[2,3-b]pyridin]-5'-yl)-N,N-dimethylbenzamide |
| 2 | 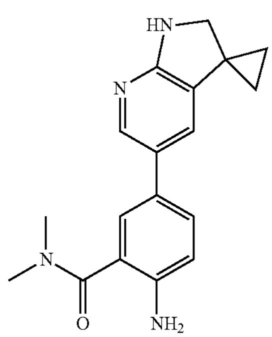 [SMILES: CN(C)C(=O)c1cc(-c2cnc3c(c2)C2(CC2)CN3)ccc1N] | 2-Amino-5-(1',2'-dihydrospiro[cyclopropane-1,3'-pyrrolo[2,3-b]pyridin]-5'-yl)-N,N-dimethylbenzamide |

TABLE 1-continued

| No. | Structure | Name |
| --- | --- | --- |
| 3 | 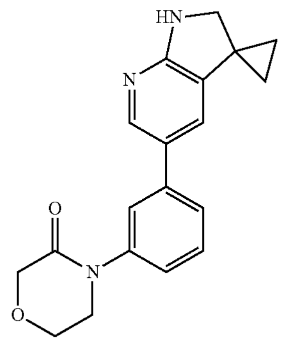 [SMILES: O=C1COCCN1c1cccc(-c2cnc3c(c2)C2(CC2)CN3)c1] | 4-(3-(1',2'-Dihydrospiro[cyclopropane-1,3'-pyrrolo[2,3-b]pyridin]-5'-yl)phenyl)morpholin-3-one |
| 4 | 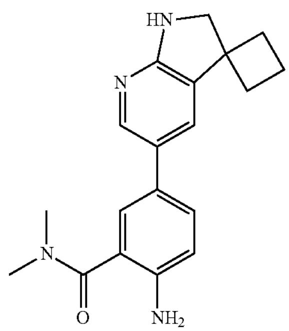 [SMILES: CN(C)C(=O)c1cc(-c2cnc3c(c2)C2(CCC2)CN3)ccc1N] | 2-Amino-5-(1',2'-dihydrospiro[cyclobutane-1,3'-pyrrolo[2,3-b]pyridin]-5'-yl)-N,N-dimethylbenzamide |
| 5 | 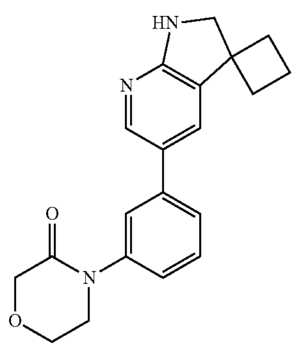 [SMILES: O=C1COCCN1c1cccc(-c2cnc3c(c2)C2(CCC2)CN3)c1] | 4-(3-(1'2'-Dihydrospiro[cyclobutane-1,3'-pyrrolo[2,3-b]pyridin]-5'-yl)phenyl)morpholin-3-one |
| 6 | 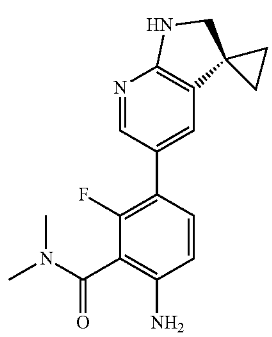 | 6-Amino-3-(1',2'-dihydrospiro[cyclopropane-1,3'-pyrrolo[2,3-b]pyridin]-5'-yl)-2-fluoro-N,N-dimethylbenzamide |

TABLE 1-continued

| No. | Structure | Name |
|---|---|---|
| 7 | 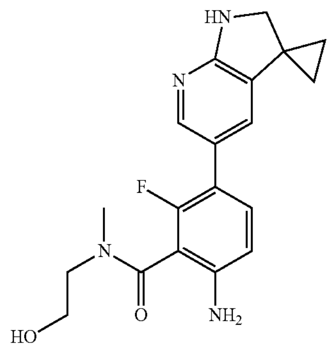 [SMILES: CN(CCO)C(=O)c1c(N)ccc(-c2cnc3c(c2)C2(CC2)CN3)c1F] | 6-amino-3-(1',2'-dihydrospiro[cyclopropane-1,3'-pyrrolo[2,3-b]pyridin]-5'-yl)-2-fluoro-N-(2-hydroxyethyl)-N-methylbenzamide |
| 8 | 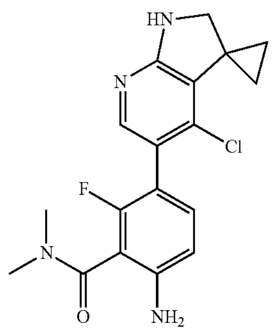 [SMILES: CN(C)C(=O)c1c(N)ccc(-c2cnc3c(c2Cl)C2(CC2)CN3)c1F] | 6-Amino-3-(4'-chloro-1',2'-dihydrospiro[cyclopropane-1,3'-pyrrolo[2,3-b]pyridin]-5'-yl)-2-fluoro-N,N-dimethylbenzamide |
| 9 | 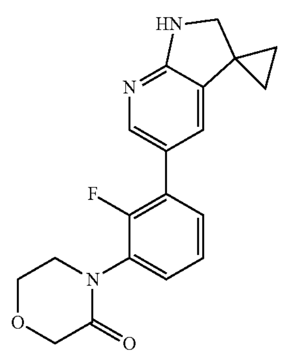 [SMILES: O=C1COCCN1c1cccc(-c2cnc3c(c2)C2(CC2)CN3)c1F] | 4-(3-(1',2'-Dihydrospiro[cyclopropane-1,3'-pyrrolo[2,3-b]pyridin]-5'-yl)-2-fluorophenyl)morpholin-3-one |
| 10 | 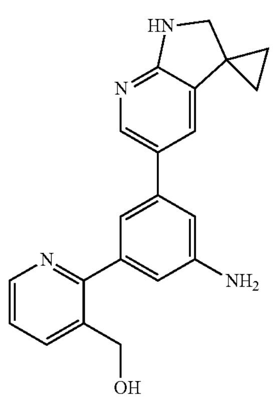 [SMILES: Nc1cc(-c2cnc3c(c2)C2(CC2)CN3)cc(-c2ncccc2CO)c1] | (2-(3-Amino-5-(1',2'-dihydrospiro[cyclopropane-1,3'-pyrrolo[2,3-b]pyridin]-5'-yl)phenyl)pyridin-3-yl)methanol |

TABLE 1-continued

| No. | Structure | Name |
| --- | --- | --- |
| 11 | 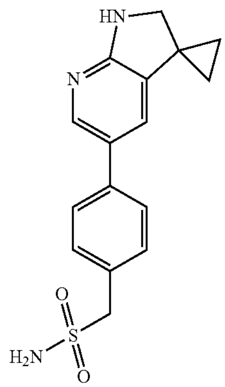 [SMILES: NS(=O)(=O)Cc1ccc(-c2cnc3c(c2)C2(CC2)CN3)cc1] | (4-(1',2'-Dihydrospiro[cyclopropane-1,3'-pyrrolo[2,3-b]pyridin]-5'-yl)phenyl)methanesulfonamide |
| 12 | 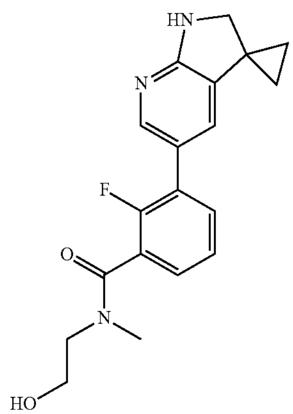 [SMILES: CN(CCO)C(=O)c1cccc(-c2cnc3c(c2)C2(CC2)CN3)c1F] | 3-(1',2'-Dihydrospiro[cyclopropane-1,3'-pyrrolo[2,3-b]pyridin]-5'-yl)-2-fluoro-N-(2-hydroxyethyl)-N-methylbenzamide |
| 13 | 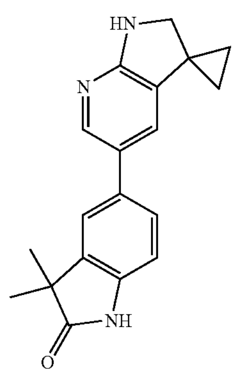 [SMILES: CC1(C)C(=O)Nc2ccc(-c3cnc4c(c3)C3(CC3)CN4)cc21] | 5-(1',2'-dihydrospiro[cyclopropane-1,3'-pyrrolo[2,3-b]pyridin]-5'-yl)-3,3-dimethylindolin-2-one |
| 14 | 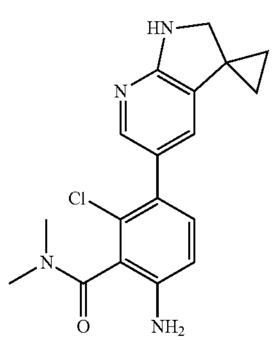 [SMILES: CN(C)C(=O)c1c(N)ccc(-c2cnc3c(c2)C2(CC2)CN3)c1Cl] | 6-amino-2-chloro-3-(1',2'-dihydrospiro[cyclopropane-1,3'-pyrrolo[2,3-b]pyridin]-5'-yl)-N,N-dimethylbenzamide |

TABLE 1-continued

| No. | Structure | Name |
|---|---|---|
| 15 | 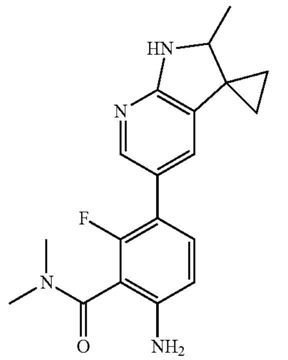 [SMILES: CC1Nc2ncc(-c3ccc(N)c(C(=O)N(C)C)c3F)cc2C12CC2] | 6-Amino-2-fluoro-N,N-dimethyl-3-(2'-methyl-1',2'-dihydrospiro[cyclopropane-1,3'-pyrrolo[2,3-b]pyridin]-5'-yl)benzamide |
| 16 | 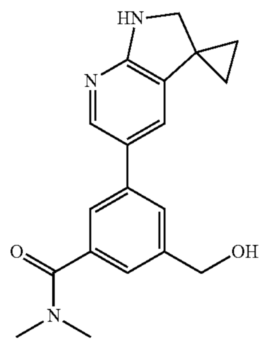 [SMILES: CN(C)C(=O)c1cc(CO)cc(-c2cnc3c(c2)C2(CC2)CN3)c1] | 3-(1',2'-dihydrospiro[cyclopropane-1,3'-pyrrolo[2,3-b]pyridin]-5'-yl)-5-(hydroxymethyl)-N,N-dimethylbenzamide |
| 17 | 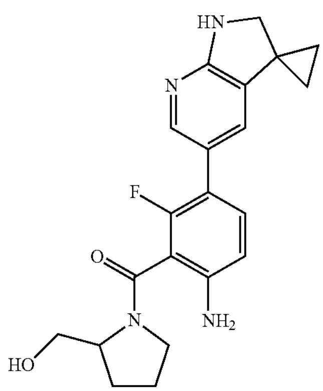 [SMILES: Nc1ccc(-c2cnc3c(c2)C2(CC2)CN3)c(F)c1C(=O)N1CCCC1CO] | (6-amino-3-(1',2'-dihydrospiro[cyclopropane-1,3'-pyrrolo[2,3-b]pyridin]-5'-yl)-2-fluorophenyl)(2-(hydroxymethyl)pyrrolidin-1-yl)methanone |
| 17a | | (R)-(6-amino-3-(1',2'-dihydrospiro[cyclopropane-1,3'-pyrrolo[2,3-b]pyridin]-5'-yl)-2-fluorophenyl)(2-(hydroxymethyl)pyrrolidin-1-yl)methanone |
| 17b | | (S)-(6-amino-3-(1',2'-dihydrospiro[cyclopropane-1,3'-pyrrolo[2,3-b]pyridin]-5'-yl)-2-fluorophenyl)(2-(hydroxymethyl)pyrrolidin-1-yl)methanone |
| 18 | 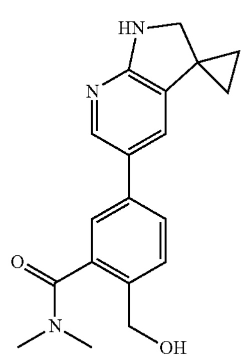 [SMILES: CN(C)C(=O)c1cc(-c2cnc3c(c2)C2(CC2)CN3)ccc1CO] | 5-(1',2'-dihydrospiro[cyclopropane-1,3'-pyrrolo[2,3-b]pyridin]-5'-yl)-2-(hydroxymethyl)-N,N-dimethylbenzamide |

TABLE 1-continued

| No. | Structure | Name |
|---|---|---|
| 19 | 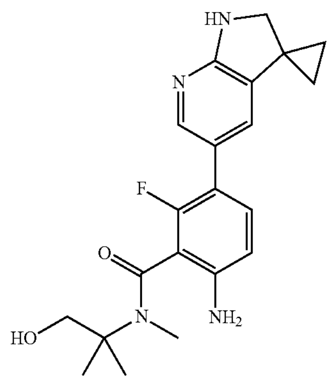 [SMILES: CN(C(=O)c1c(N)ccc(-c2cnc3c(c2)C2(CC2)CN3)c1F)C(C)(C)CO] | 6-amino-3-(1'2'-dihydrospiro[cyclopropane-1,3'-pyrrolo[2,3-b]pyridin]-5'-yl)-2-fluoro-N-(1-hydroxy-2-methylpropan-2-yl)-N-methylbenzamide |
| 20 | 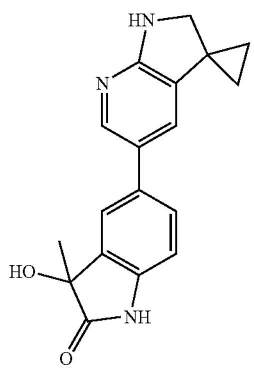 [SMILES: CC1(O)C(=O)Nc2ccc(-c3cnc4c(c3)C3(CC3)CN4)cc21] | 5-(1',2'-dihydrospiro[cyclopropane-1,3'-pyrrolo[2,3-b]pyridin]-5'-yl)-3-hydroxy-3-methylindolin-2-one |
| 21 | 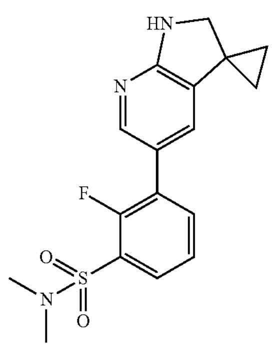 [SMILES: CN(C)S(=O)(=O)c1cccc(-c2cnc3c(c2)C2(CC2)CN3)c1F] | 3-(1'2'-dihydrospiro[cyclopropane-1,3'-pyrrolo[2,3-b]pyridin]-5'-yl)-2-fluoro-N,N-dimethylbenzenesulfonamide |
| 22 | 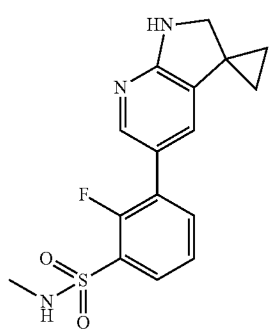 [SMILES: CNS(=O)(=O)c1cccc(-c2cnc3c(c2)C2(CC2)CN3)c1F] | 3-(1',2'-dihydrospiro[cyclopropane-1,3'-pyrrolo[2,3-b]pyridin]-5'-yl)-2-fluoro-N-methylbenzenesulfonamide |

TABLE 1-continued

| No. | Structure | Name |
|---|---|---|
| 23 | 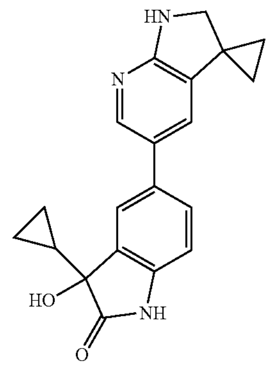 [SMILES: O=C1Nc2ccc(-c3cnc4c(c3)C3(CC3)CN4)cc2C1(O)C1CC1] | 3-cyclopropyl-5-(1',2'-dihydrospiro[cyclopropane-1,3'-pyrrolo[2,3-b]pyridin]-5'-yl)-3-hydroxyindolin-2-one |
| 23a | | (R)-3-cyclopropyl-5-(1',2'-dihydrospiro[cyclopropane-1,3'-pyrrolo[2,3-b]pyridin]-5'-yl)-3-hydroxyindolin-2-one |
| 23b | | (S)-3-cyclopropyl-5-(1'2'-dihydrospiro[cyclopropane-1,3'-pyrrolo[2,3-b]pyridin]-5'-yl)-3-hydroxyindolin-2-one |
| 24 | 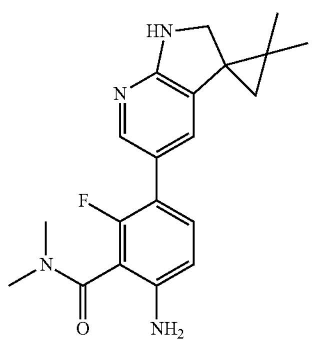 | 6-Amino-3-(2,2-dimethyl-1',2'-dihydrospiro[cyclopropane-1,3'-pyrrolo[2,3-b]pyridin]-5'-yl)-2-fluoro-N,N-dimethylbenzamide |
| 24a | | (R)-6-Amino-3-(2,2-dimethyl-1',2'-dihydrospiro[cyclopropane-1,3'-pyrrolo[2,3-b]pyridin]-5'-yl)-2-fluoro-N,N-dimethylbenzamide |
| 24b | | (S)-6-Amino-3-(2,2-dimethyl-1',2'-dihydrospiro[cyclopropane-1,3'-pyrrolo[2,3-b]pyridin]-5'-yl)-2-fluoro-N,N-dimethylbenzamide |
| 25 | 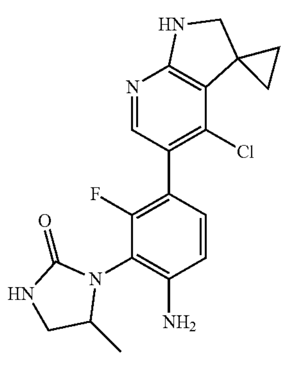 [SMILES: CC1CNC(=O)N1c1c(N)ccc(-c2cnc3c(c2Cl)C2(CC2)CN3)c1F] | 1-(6-amino-3-(4'-chloro-1',2'-dihydrospiro[cyclopropane-1,3'-pyrrolo[2,3-b]pyridin]-5'-yl)-2-fluorophenyl)-5-methylimidazolidin-2-one |
| 25a | | (R)-1-(6-amino-3-(4'-chloro-1',2'-dihydrospiro[cyclopropane-1,3'-pyrrolo[2,3-b]pyridin]-5'-yl)-2-fluorophenyl)-5-methylimidazolidin-2-one |
| 25b | | (S)-1-(6-amino-3-(4'-chloro-1',2'-dihydrospiro[cyclopropane-1,3'-pyrrolo[2,3-b]pyridin]-5'-yl)-2-fluorophenyl)-5-methylimidazolidin-2-one |

TABLE 1-continued

| No. | Structure | Name |
|---|---|---|
| 26 | 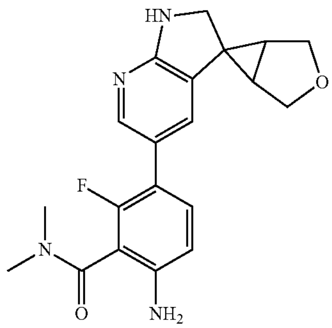 [SMILES: CN(C)C(=O)c1c(N)ccc(-c2cnc3c(c2)C2(CN3)C3COCC32)c1F] | 6-amino-3-(1',2'-dihydro-3-oxaspiro[bicyclo[3.1.0]hexane-6,3'-pyrrolo[2,3-b]pyridin]-5'-yl)-2-fluoro-N,N-dimethylbenzamide |
| 27 | 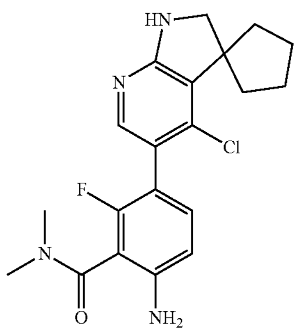 [SMILES: CN(C)C(=O)c1c(N)ccc(-c2cnc3c(c2Cl)C2(CCCC2)CN3)c1F] | 6-Amino-3-(4'-chloro-1',2'-dihydrospiro[cyclopentane-1,3'-pyrrolo[2,3-b]pyridin]-5'-yl)-2-fluoro-N,N-dimethylbenzamide |
| 28 | 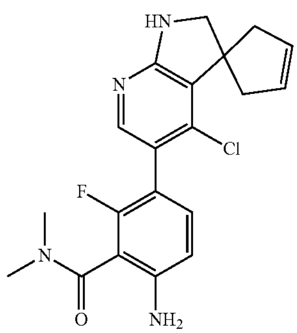 [SMILES: CN(C)C(=O)c1c(N)ccc(-c2cnc3c(c2Cl)C2(CC=CC2)CN3)c1F] | 6-Amino-3-(4'-chloro-1',2'-dihydrospiro[cyclopentane-1,3'-pyrrolo[2,3-b]pyridin]-3-en-5'-yl)-2-fluoro-N,N-dimethylbenzamide |
| 29 | 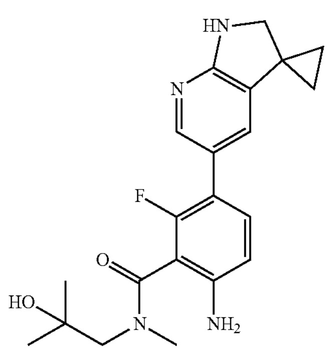 [SMILES: CN(CC(C)(C)O)C(=O)c1c(N)ccc(-c2cnc3c(c2)C2(CC2)CN3)c1F] | 6-amino-3-(1',2'-dihydrospiro[cyclopropane-1,3'-pyrrolo[2,3-b]pyridin]-5'-yl)-2-fluoro-N-(2-hydroxy-2-methylpropyl)-N-methylbenzamide |

TABLE 1-continued

| No. | Structure | Name |
|---|---|---|
| 30 | 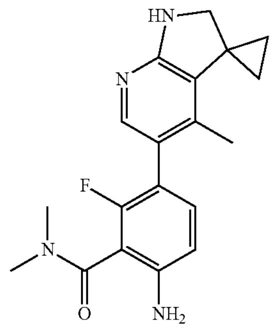 [SMILES: Cc1c(-c2ccc(N)c(C(=O)N(C)C)c2F)cnc2c1C1(CC1)CN2] | 6-Amino-2-fluoro-N,N-dimethyl-3-(4'-methyl-1',2'-dihydrospiro[cyclopropane-1,3'-pyrrolo[2,3-b]pyridin]-5'-yl)benzamide |
| 31 | 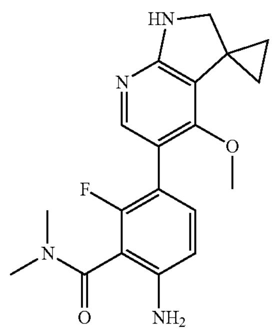 [SMILES: COc1c(-c2ccc(N)c(C(=O)N(C)C)c2F)cnc2c1C1(CC1)CN2] | 6-Amino-2-fluoro-3-(4'-methoxy-1',2'-dihydrospiro[cyclopropane-1,3'-pyrrolo[2,3-b]pyridin]-5'-yl)-N,N-dimethylbenzamide |
| 32 | 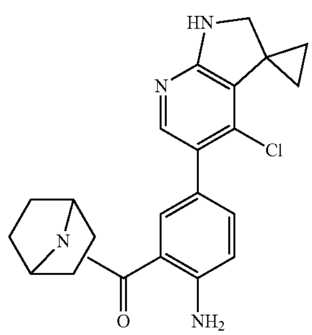 | (2-Amino-5-(4'-chloro-1',2'-dihydrospiro[cyclopropane-1,3'-pyrrolo[2,3-b]pyridin]-5'-yl)phenyl)(7-azabicyclo[2.2.1]heptan-7-yl)methanone |
| 33 | 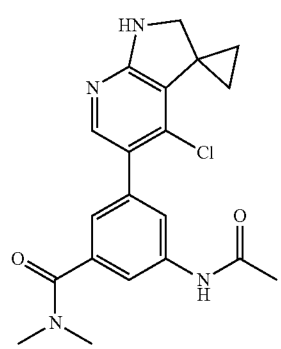 [SMILES: CC(=O)Nc1cc(C(=O)N(C)C)cc(-c2cnc3c(c2Cl)C2(CC2)CN3)c1] | 3-acetamido-5-(4'-chloro-1',2'-dihydrospiro[cyclopropane-1,3'-pyrrolo[2,3-b]pyridin]-5'-yl)-N,N-dimethylbenzamide |

TABLE 1-continued

| No. | Structure | Name |
|---|---|---|
| 34 | 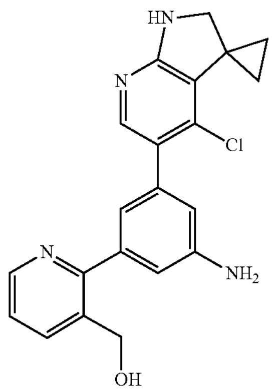 [SMILES: Nc1cc(-c2cnc3c(c2Cl)C2(CC2)CN3)cc(-c2ncccc2CO)c1] | (2-(3-Amino-5-(4'-chloro-1',2'-dihydrospiro[cyclopropane-1,3'-pyrrolo[2,3-b]pyridin]-5'-yl)phenyl)pyridin-3-yl)methanol |
| 35 | 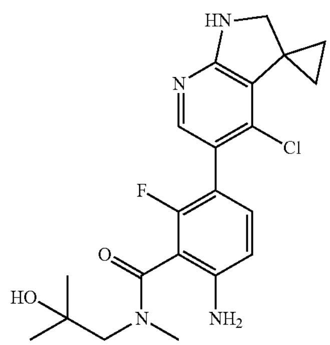 [SMILES: CN(CC(C)(C)O)C(=O)c1c(N)ccc(-c2cnc3c(c2Cl)C2(CC2)CN3)c1F] | 6-amino-3-(4'-chloro-1',2'-dihydrospiro[cyclopropane-1,3'-pyrrolo[2,3-b]pyridin]-5'-yl)-2-fluoro-N-(2-hydroxy-2-methylpropyl)-N-methylbenzamide |
| 36 | 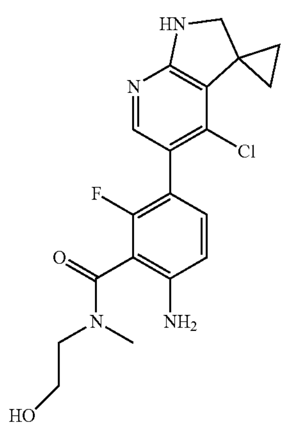 [SMILES: CN(CCO)C(=O)c1c(N)ccc(-c2cnc3c(c2Cl)C2(CC2)CN3)c1F] | 6-Amino-3-(4'-chloro-1',2'-dihydrospiro[cyclopropane-1,3'-pyrrolo[2,3-b]pyridin]-5'-yl)-2-fluoro-N-(2-hydroxyethyl)-N-methylbenzamide |
| 37 | 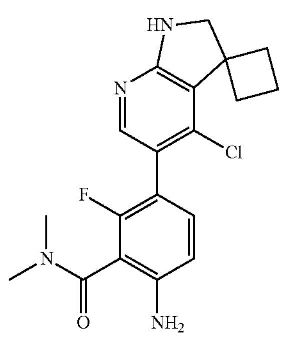 [SMILES: CN(C)C(=O)c1c(N)ccc(-c2cnc3c(c2Cl)C2(CCC2)CN3)c1F] | 6-Amino-3-(4'-chloro-1',2'-dihydrospiro[cyclobutane-1,3'-pyrrolo[2,3-b]pyridin]-5'-yl)-2-fluoro-N,N-dimethylbenzamide |

TABLE 1-continued

| No. | Structure | Name |
|---|---|---|
| 38 | 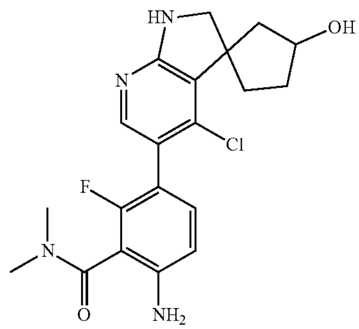 [SMILES: CN(C)C(=O)c1c(N)ccc(-c2cnc3c(c2Cl)C2(CCC(O)C2)CN3)c1F] | 6-Amino-3-(4'-chloro-3-hydroxy-1',2'-dihydrospiro[cyclopentane-1,3'-pyrrolo[2,3-b]pyridin]-5'-yl)-2-fluoro-N,N-dimethylbenzamide |
| 38a | | 6-Amino-3-((1R,3R)-4'-chloro-3-hydroxy-1',2'-dihydrospiro[cyclopentane-1,3'-pyrrolo[2,3-b]pyridin]-5'-yl)-2-fluoro-N,N-dimethylbenzamide 6-Amino-3-((1S, 3S)-4'-chloro-3-hydroxy-1',2'-dihydrospiro[cyclopentane-1,3'-pyrrolo[2,3-b]pyridin]-5'-yl)-2-fluoro-N,N-dimethylbenzamide |
| 38b | | 6-Amino-3-((1R,3S)-4'-chloro-3-hydroxy-1',2'-dihydrospiro[cyclopentane-1,3'-pyrrolo[2,3-b]pyridin]-5'-yl)-2-fluoro-N,N-dimethylbenzamide 6-Amino-3-((1S, 3R)-4'-chloro-3-hydroxy-1',2'-dihydrospiro[cyclopentane-1,3'-pyrrolo[2,3-b]pyridin]-5'-yl)-2-fluoro-N,N-dimethylbenzamide |
| 39 | 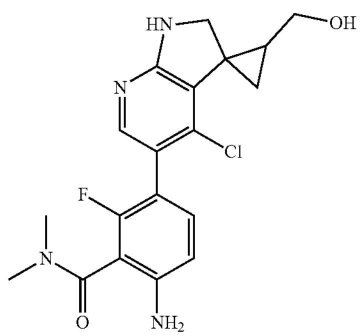 [SMILES: CN(C)C(=O)c1c(N)ccc(-c2cnc3c(c2Cl)C2(CN3)CC2CO)c1F] | 6-Amino-3-(4'-chloro-2-(hydroxymethyl)-1',2'-dihydrospiro[cyclopropane-1,3'-pyrrolo[2,3-b]pyridin]-5'-yl)-2-fluoro-N,N-dimethylbenzamide |
| 39a | | 6-Amino-3-((1R,2R)-4'-chloro-2-(hydroxymethyl)-1',2'-dihydrospiro[cyclopropane-1,3'-pyrrolo[2,3-b]pyridin]-5'-yl)-2-fluoro-N,N-dimethylbenzamide |
| 39b | | 6-Amino-3-((1S,2S)-4'-chloro-2-(hydroxymethyl)-1',2'-dihydrospiro[cyclopropane-1,3'-pyrrolo[2,3-b]pyridin]-5'-yl)-2-fluoro-N,N-dimethylbenzamide |
| 39c | | 6-Amino-3-((1R,2S)-4'-chloro-2-(hydroxymethyl)-1',2'-dihydrospiro[cyclopropane-1,3'-pyrrolo[2,3-b]pyridin]-5'-yl)-2-fluoro-N,N-dimethylbenzamide |
| 39d | | 6-Amino-3-((1S, 2R)-4'-chloro-2-(hydroxymethyl)-1',2'-dihydrospiro[cyclopropane-1,3'-pyrrolo[2,3-b]pyridin]-5'-yl)-2-fluoro-N,N-dimethylbenzamide |
| 40 | 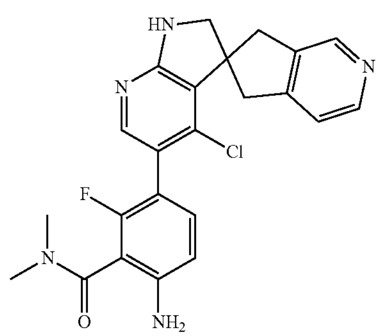 [SMILES: CN(C)C(=O)c1c(N)ccc(-c2cnc3c(c2Cl)C2(CN3)Cc3ccncc3C2)c1F] | 6-Amino-3-(4'-chloro-1',2',5,7-tetrahydrospiro[cyclopenta[c]pyridine-6,3'-pyrrolo[2,3-b]pyridin]-5'-yl)-2-fluoro-N,N-dimethylbenzamide |

TABLE 1-continued

| No. | Structure | Name |
|---|---|---|
| 40a | | (R)-6-Amino-3-(4'-chloro-1',2',5,7-tetrahydrospiro[cyclopenta[c]pyridine-6,3'-pyrrolo[2,3-b]pyridin]-5'-yl)-2-fluoro-N,N-dimethylbenzamide |
| 40b | | (S)-6-Amino-3-(4'-chloro-1',2',5,7-tetrahydrospiro[cyclopenta[c]pyridine-6,3'-pyrrolo[2,3-b]pyridin]-5'-yl)-2-fluoro-N,N-dimethylbenzamide |
| 41 | 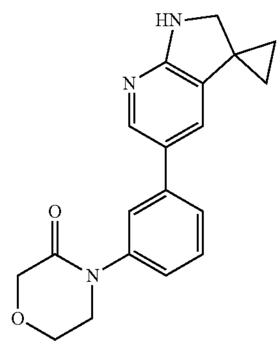 [SMILES: O=C1COCCN1c1cccc(-c2cnc3c(c2)C2(CC2)CN3)c1] | 4-(3-(1',2'-Dihydrospiro[cyclopropane-1,3'-pyrrolo[2,3-b]pyridin]-5'-yl)phenyl)morpholin-3-one |
| 42 | 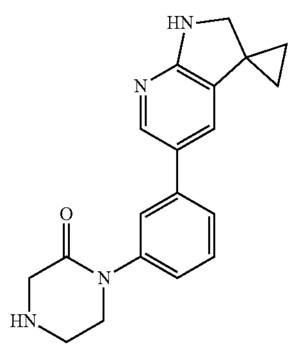 [SMILES: O=C1CNCCN1c1cccc(-c2cnc3c(c2)C2(CC2)CN3)c1] | 1-(3-(1'2'-Dihydrospiro[cyclopropane-1,3'-pyrrolo[2,3-b]pyridin]-5'-yl)phenyl)piperazin-2-one |
| 43 | 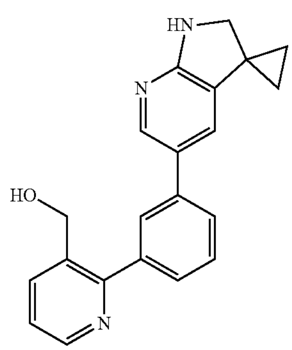 [SMILES: OCc1cccnc1-c1cccc(-c2cnc3c(c2)C2(CC2)CN3)c1] | (2-(3-(1',2'-Dihydrospiro[cyclopropane-1,3'-pyrrolo[2,3-b]pyridin]-5'-yl)phenyl)pyridin-3-yl)methanol |
| 44 | 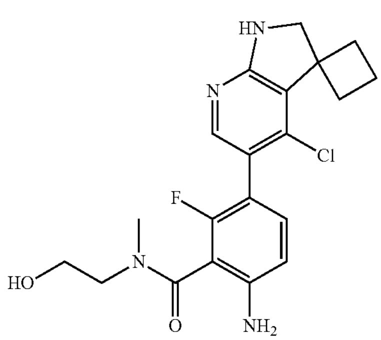 [SMILES: CN(CCO)C(=O)c1c(N)ccc(-c2cnc3c(c2Cl)C2(CCC2)CN3)c1F] | 6-Amino-3-(4'-chloro-1',2'-dihydrospiro[cyclobutane-1,3'-pyrrolo[2,3-b]pyridin]-5'-yl)-2-fluoro-N-(2-hydroxyethyl)-N-methylbenzamide |

TABLE 1-continued

| No. | Structure | Name |
|---|---|---|
| 45 | 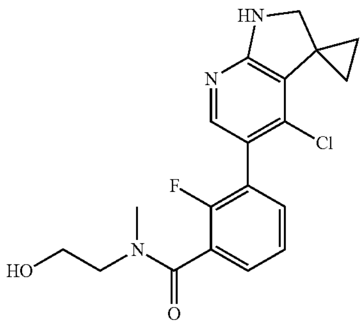 [SMILES: CN(CCO)C(=O)c1cccc(-c2cnc3c(c2Cl)C2(CC2)CN3)c1F] | 3-(4'-Chloro-1',2'-dihydrospiro[cyclopropane-1,3'-pyrrolo[2,3-b]pyridin]-5'-yl)-2-fluoro-N-(2-hydroxyethyl)-N-methylbenzamide |
| 46 | 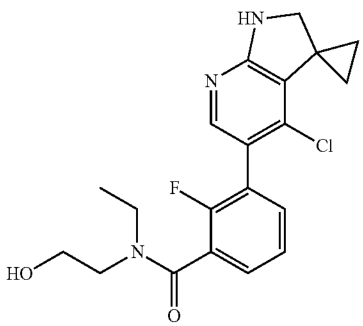 [SMILES: CCN(CCO)C(=O)c1cccc(-c2cnc3c(c2Cl)C2(CC2)CN3)c1F] | 3-(4'-Chloro-1',2'-dihydrospiro[cyclopropane-1,3'-pyrrolo[2,3-b]pyridin]-5'-yl)-N-ethyl-2-fluoro-N-(2-hydroxyethyl)benzamide |
| 47 | 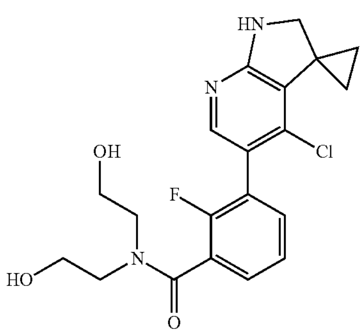 [SMILES: O=C(c1cccc(-c2cnc3c(c2Cl)C2(CC2)CN3)c1F)N(CCO)CCO] | 3-(4'-Chloro-1',2'-dihydrospiro[cyclopropane-1,3'-pyrrolo[2,3-b]pyridin]-5'-yl)-2-fluoro-N,N-bis(2-hydroxyethyl)benzamide |
| 48 | 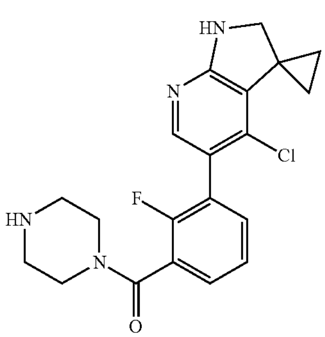 [SMILES: O=C(c1cccc(-c2cnc3c(c2Cl)C2(CC2)CN3)c1F)N1CCNCC1] | (3-(4'-Chloro-1',2'-dihydrospiro[cyclopropane-1,3'-pyrrolo[2,3-b]pyridin]-5'-yl)-2-fluorophenyl)(piperazin-1-yl)methanone |

TABLE 1-continued

| No. | Structure | Name |
| --- | --- | --- |
| 49 | 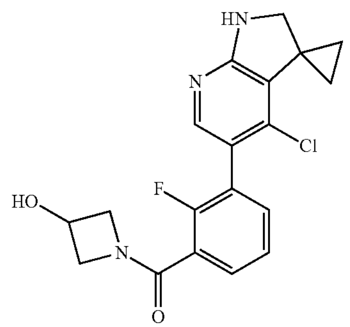 [SMILES: O=C(c1cccc(-c2cnc3c(c2Cl)C2(CC2)CN3)c1F)N1CC(O)C1] | ((3-(4'-Chloro-1',2'-dihydrospiro[cyclopropane-1,3'-pyrrolo[2,3-b]pyridin]-5'-yl)-2-fluorophenyl)(3-hydroxyazetidin-1-yl)methanone |
| 50 | 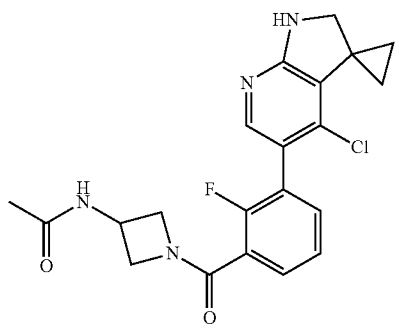 [SMILES: CC(=O)NC1CN(C(=O)c2cccc(-c3cnc4c(c3Cl)C3(CC3)CN4)c2F)C1] | N-(1-(3-(4'-Chloro-1',2'-dihydrospiro[cyclopropane-1,3'-pyrrolo[2,3-b]pyridin]-5'-yl)-2-fluorobenzoyl)azetidin-3-yl)acetamide |
| 51 | 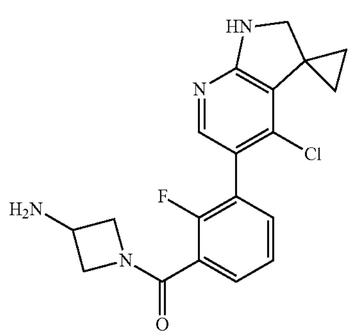 [SMILES: NC1CN(C(=O)c2cccc(-c3cnc4c(c3Cl)C3(CC3)CN4)c2F)C1] | (3-Aminoazetidin-1-yl)(3-(4'-chloro-1',2'-dihydrospiro[cyclopropane-1,3'-pyrrolo[2,3-b]pyridin]-5'-yl)-2-fluorophenyl)methanone |
| 52 | 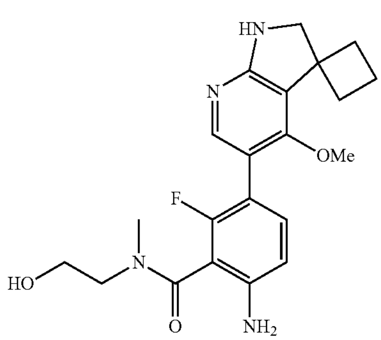 | 6-Amino-2-fluoro-N-(2-hydroxyethyl)-3-(4'-methoxy-1',2'-dihydrospiro[cyclobutane-1,3'-pyrrolo[2,3-b]pyridin]-5'-yl)-N-methylbenzamide |

TABLE 1-continued

| No. | Structure | Name |
|---|---|---|
| 53 | 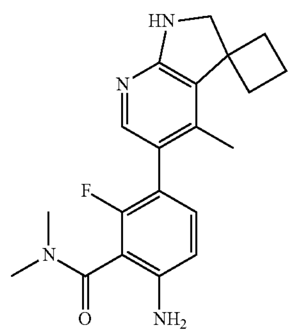 [SMILES: Cc1c(-c2ccc(N)c(C(=O)N(C)C)c2F)cnc2c1C1(CCC1)CN2] | 6-Amino-2-fluoro-N,N-dimethyl-3-(4'-methyl-1',2'-dihydrospiro[cyclobutane-1,3'-pyrrolo[2,3-b]pyridin]-5'-yl)benzamide |
| 55 | 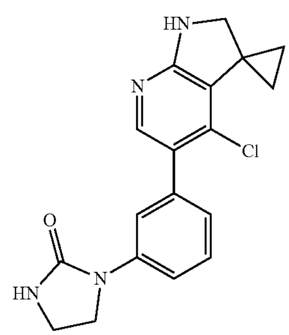 [SMILES: O=C1NCCN1c1cccc(-c2cnc3c(c2Cl)C2(CC2)CN3)c1] | 1-(3-(4'-Chloro-1',2'-dihydrospiro[cyclopropane-1,3'-pyrrolo[2,3-b]pyridin]-5'-yl)phenyl)imidazolidin-2-one |
| 57 | 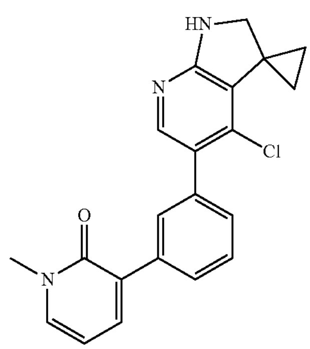 [SMILES: Cn1cccc(-c2cccc(-c3cnc4c(c3Cl)C3(CC3)CN4)c2)c1=O] | 3-(3-(4'-Chloro-1',2'-dihydrospiro[cyclopropane-1,3'-pyrrolo[2,3-b]pyridin]-5'-yl)phenyl)-1-methylpyridin-2(1H)-one |
| 58 | 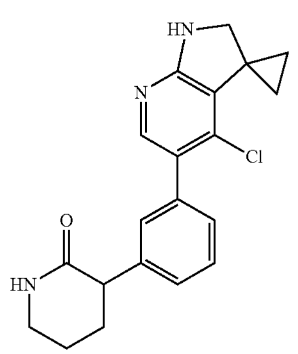 [SMILES: O=C1NCCCC1c1cccc(-c2cnc3c(c2Cl)C2(CC2)CN3)c1] | 3-(3-(4'-Chloro-1',2'-dihydrospiro[cyclopropane-1,3'-pyrrolo[2,3-b]pyridin]-5'-yl)phenyl)piperidin-2-one |

TABLE 1-continued

| No. | Structure | Name |
|---|---|---|
| 59 | 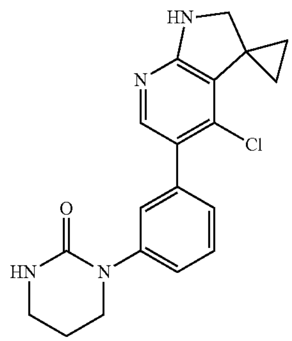 [SMILES: O=C1NCCCN1c1cccc(-c2cnc3c(c2Cl)C2(CC2)CN3)c1] | 1-(3-(4'-Chloro-1',2'-dihydrospiro[cyclopropane-1,3'-pyrrolo[2,3-b]pyridin]-5'-yl)phenyl)tetrahydropyrimidin-2(1H)-one |
| 60 | 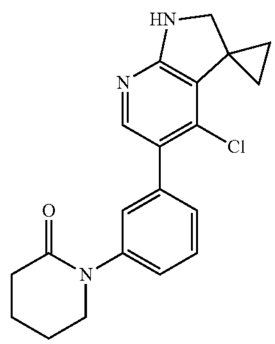 [SMILES: O=C1CCCCN1c1cccc(-c2cnc3c(c2Cl)C2(CC2)CN3)c1] | 1-(3-(4'-Chloro-1',2'-dihydrospiro[cyclopropane-1,3'-pyrrolo[2,3-b]pyridin]-5'-yl)phenyl)piperidin-2-one |
| 61 | 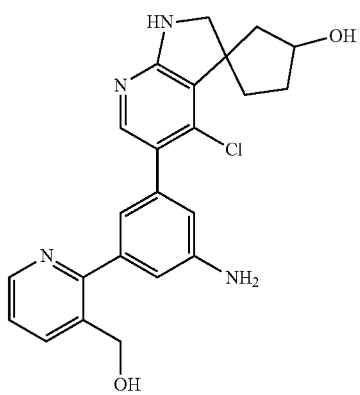 [SMILES: Nc1cc(-c2cnc3c(c2Cl)C2(CCC(O)C2)CN3)cc(-c2ncccc2CO)c1] | 5'-(3-Amino-5-(3-(hydroxymethyl)pyridin-2-yl)phenyl)-4'-chloro-1'2'-dihydrospiro[cyclopentane-1,3'-pyrrolo[2,3-b]pyridin]-3-ol |
| 61a | | (1R,3S)-5'-(3-Amino-5-(3-(hydroxymethyl)pyridin-2-yl)phenyl)-4'-chloro-1',2'-dihydrospiro[cyclopentane-1,3'-pyrrolo[2,3-b]pyridin]-3-ol |
| 61b | | (1S,3R)-5'-(3-Amino-5-(3-(hydroxymethyl)pyridin-2-yl)phenyl)-4'-chloro-1',2'-dihydrospiro[cyclopentane-1,3'-pyrrolo[2,3-b]pyridin]-3-ol |
| 62 | 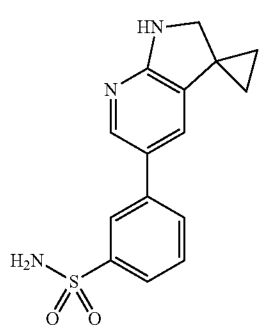 [SMILES: NS(=O)(=O)c1cccc(-c2cnc3c(c2)C2(CC2)CN3)c1] | 3-(1',2'-Dihydrospiro[cyclopropane-1,3'-pyrrolo[2,3-b]pyridin]-5'-yl)benzenesulfonamide |

TABLE 1-continued

| No. | Structure | Name |
|---|---|---|
| 63 | 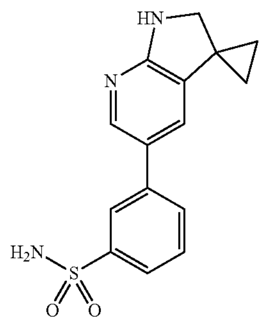 [SMILES: NS(=O)(=O)c1cccc(-c2cnc3c(c2)C2(CC2)CN3)c1] | 5'-(3-(Methylsulfonyl)phenyl)-1',2'-dihydrospiro[cyclopropane-1,3'-pyrrolo[2,3-b]pyridine] |
| 64 | 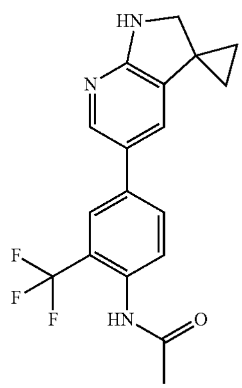 [SMILES: CC(=O)Nc1ccc(-c2cnc3c(c2)C2(CC2)CN3)cc1C(F)(F)F] | N-(4-(1',2'-Dihydrospiro[cyclopropane-1,3'-pyrrolo[2,3-b]pyridin]-5'-yl)-2-(trifluoromethyl)phenyl)acetamide |
| 65 | 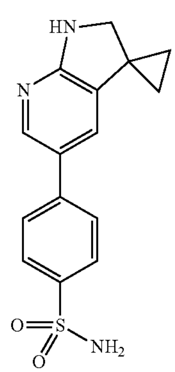 [SMILES: NS(=O)(=O)c1ccc(-c2cnc3c(c2)C2(CC2)CN3)cc1] | 4-(1',2'-Dihydrospiro[cyclopropane-1,3'-pyrrolo[2,3-b]pyridin]-5'-yl)benzenesulfonamide |
| 66 | 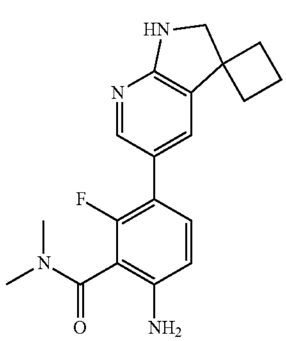 [SMILES: CN(C)C(=O)c1c(N)ccc(-c2cnc3c(c2)C2(CCC2)CN3)c1F] | 6-Amino-3-(1',2'-dihydrospiro[cyclobutane-1,3'-pyrrolo[2,3-b]pyridin]-5'-yl)-2-fluoro-N,N-dimethylbenzamide |

TABLE 1-continued

| No. | Structure | Name |
|---|---|---|
| 67 | 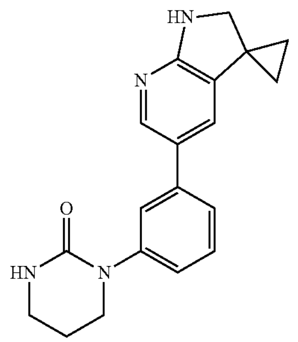 [SMILES: O=C1NCCCN1c1cccc(-c2cnc3c(c2)C2(CC2)CN3)c1] | 1-(3-(1',2'-Dihydrospiro[cyclopropane-1,3'-pyrrolo[2,3-b]pyridin]-5'-yl)phenyl)tetrahydropyrimidin-2(1H)-one |
| 68 | 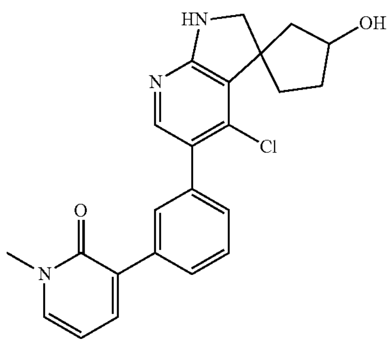 [SMILES: Cn1cccc(-c2cccc(-c3cnc4c(c3Cl)C3(CCC(O)C3)CN4)c2)c1=O] | 3-(3-(4'-chloro-3-hydroxy-1',2'-dihydrospiro[cyclopentane-1,3'-pyrrolo[2,3-b]pyridin]-5'-yl)phenyl)-1-methylpyridin-2(1H)-one |
| 68a | | 3-(3-((1R,3R)-4'-chloro-3-hydroxy-1',2'-dihydrospiro[cyclopentane-1,3'-pyrrolo[2,3-b]pyridin]-5'-yl)phenyl)-1-methylpyridin-2(1H)-one |
| 68b | | 3-(3-((1S,3S)-4'-chloro-3-hydroxy-1',2'-dihydrospiro[cyclopentane-1,3'-pyrrolo[2,3-b]pyridin]-5'-yl)phenyl)-1-methylpyridin-2(1H)-one |
| 68c | | 3-(3-((1R,3S)-4'-chloro-3-hydroxy-1',2'-dihydrospiro[cyclopentane-1,3'-pyrrolo[2,3-b]pyridin]-5'-yl)phenyl)-1-methylpyridin-2(1H)-one |
| 68d | | 3-(3-((1S,3R)-4'-chloro-3-hydroxy-1',2'-dihydrospiro[cyclopentane-1,3'-pyrrolo[2,3-b]pyridin]-5'-yl)phenyl)-1-methylpyridin-2(1H)-one |
| 69 | 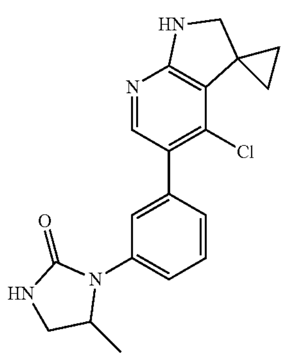 [SMILES: CC1CNC(=O)N1c1cccc(-c2cnc3c(c2Cl)C2(CC2)CN3)c1] | 1-(3-(4'-Chloro-1',2'-dihydrospiro[cyclopropane-1,3'-pyrrolo[2,3-b]pyridin]-5'-yl)phenyl)-5-methylimidazolidin-2-one |

TABLE 1-continued

| No. | Structure | Name |
|---|---|---|
| 69a | 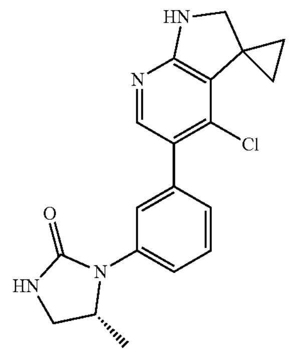 [SMILES: C[C@@H]1CNC(=O)N1c1cccc(-c2cnc3c(c2Cl)C2(CC2)CN3)c1] | (R)-1-(3-(4'-Chloro-1',2'-dihydrospiro[cyclopropane-1,3'-pyrrolo[2,3-b]pyridin]-5'-yl)phenyl)-5-methylimidazolidin-2-one |
| 69b | 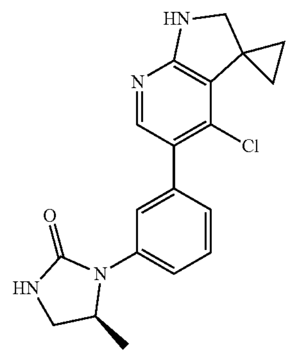 [SMILES: C[C@H]1CNC(=O)N1c1cccc(-c2cnc3c(c2Cl)C2(CC2)CN3)c1] | (S)-1-(3-(4'-Chloro-1',2'-dihydrospiro[cyclopropane-1,3'-pyrrolo[2,3-b]pyridin]-5'-yl)phenyl)-5-methylimidazolidin-2-one |
| 70 | 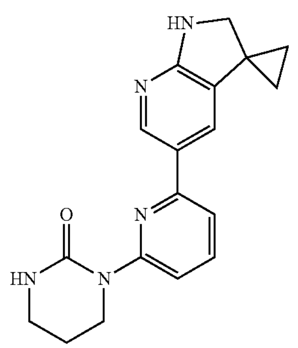 [SMILES: O=C1NCCCN1c1cccc(-c2cnc3c(c2)C2(CC2)CN3)n1] | 1-(6-(1',2'-Dihydrospiro[cyclopropane-1,3'-pyrrolo[2,3-b]pyridin]-5'-yl)pyridin-2-yl)tetrahydropyrimidin-2(1H)-one |
| 71 | 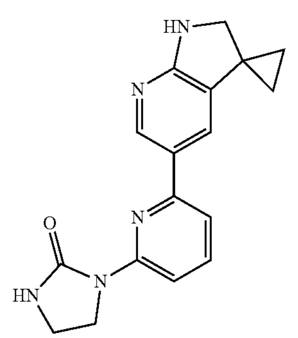 [SMILES: O=C1NCCN1c1cccc(-c2cnc3c(c2)C2(CC2)CN3)n1] | 1-(6-(1',2'-Dihydrospiro[cyclopropane-1,3'-pyrrolo[2,3-b]pyridin]-5'-yl)pyridin-2-yl)imidazolidin-2-one |

TABLE 1-continued

| No. | Structure | Name |
|---|---|---|
| 72 | 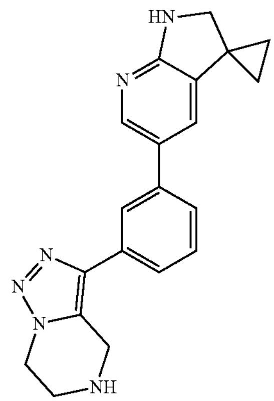 [SMILES: c1cc(-c2cnc3c(c2)C2(CC2)CN3)cc(-c2nnn3c2CNCC3)c1] | 5'-(3-(4,5,6,7-Tetrahydro-[1,2,3]triazolo[1,5-a]pyrazin-3-yl)phenyl)-1',2'-dihydrospiro[cyclopropane-1,3'-pyrrolo[2,3-b]pyridine] |
| 73 | 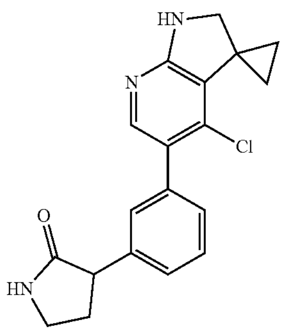 [SMILES: O=C1NCCC1c1cccc(-c2cnc3c(c2Cl)C2(CC2)CN3)c1] | 3-(3-(4'-Chloro-1',2'-dihydrospiro[cyclopropane-1,3'-pyrrolo[2,3-b]pyridin]-5'-yl)phenyl)piperidin-2-one |
| 73a | | (R)-3-(3-(4'-Chloro-1'2'-dihydrospiro[ cyclopropane-1,3'-pyrrolo[2,3-b]pyridin]-5'-yl)phenyl)piperidin-2-one |
| 73b | | (S)-3-(3-(4'-Chloro-1',2'-dihydrospiro[cyclopropane-1,3'-pyrrolo[2,3-b]pyridin]-5'-yl)phenyl)piperidin-2-one |
| 75 | 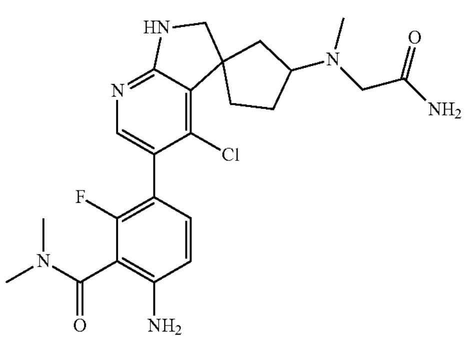 [SMILES: CN(C)C(=O)c1c(N)ccc(-c2cnc3c(c2Cl)C2(CCC(N(C)CC(N)=O)C2)CN3)c1F] | 6-Amino-3-(3-((2-amino-2-oxoethyl)(methyl)amino)-4'-chloro-1',2'-dihydrospiro[cyclopentane-1,3'-pyrrolo[2,3-b]pyridin]-5'-yl)-2-fluoro-N,N-dimethylbenzamide |
| 76 | 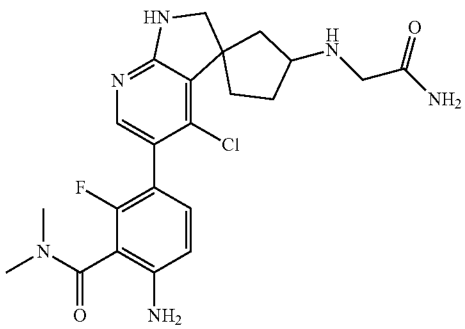 [SMILES: CN(C)C(=O)c1c(N)ccc(-c2cnc3c(c2Cl)C2(CCC(NCC(N)=O)C2)CN3)c1F] | 6-Amino-3-(3-((2-amino-2-oxoethyl)amino)-4'-chloro-1',2'-dihydrospiro[cyclopentane-1,3'-pyrrolo[2,3-b]pyridin]-5'-yl)-2-fluoro-N,N-dimethylbenzamide |

TABLE 1-continued

| No. | Structure | Name |
|---|---|---|
| 77 | 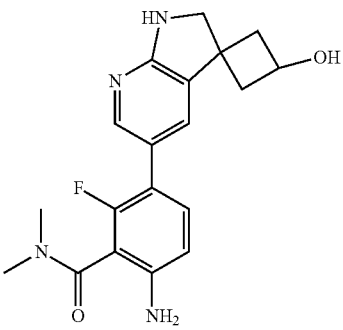 [SMILES: CN(C)C(=O)c1c(N)ccc(-c2cnc3c(c2)C2(CN3)CC(O)C2)c1F] | 6-Amino-2-fluoro-3-(3-hydroxy-1',2'-dihydrospiro[cyclobutane-1,3'-pyrrolo[2,3-b]pyridin]-5'-yl)-N,N-dimethylbenzamide |
| 77a | 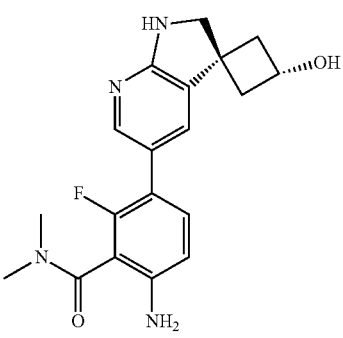 [SMILES: CN(C)C(=O)c1c(N)ccc(-c2cnc3c(c2)[C@]2(CN3)C[C@H](O)C2)c1F] | 6-Amino-2-fluoro-3-((1r,3r)-3-hydroxy-1',2'-dihydrospiro[cyclobutane-1,3'-pyrrolo[2,3-b]pyridin]-5'-yl)-N,N-dimethylbenzamide |
| 77b | 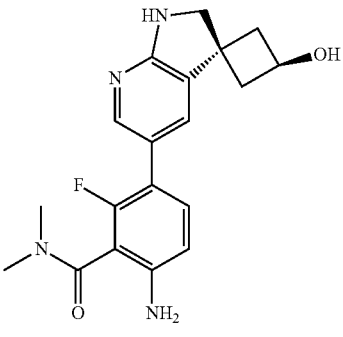 [SMILES: CN(C)C(=O)c1c(N)ccc(-c2cnc3c(c2)[C@]2(CN3)C[C@@H](O)C2)c1F] | 6-Amino-2-fluoro-3-((1s,3s)-3-hydroxy-1',2'-dihydrospiro[cyclobutane-1,3'-pyrrolo[2,3-b]pyridin]-5'-yl)-N,N-dimethylbenzamide |
| 78 | 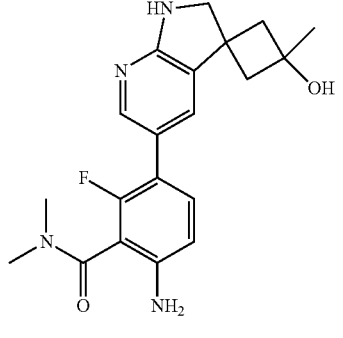 | 6-Amino-2-fluoro-3-(3-hydroxy-3-methyl-1',2'-dihydrospiro[cyclobutane-1,3'-pyrrolo[2,3-b]pyridin]-5'-yl)-N,N-dimethylbenzamide |

TABLE 1-continued

| No. | Structure | Name |
| --- | --- | --- |
| 78a | 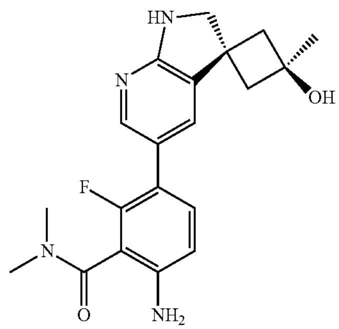 | 6-Amino-2-fluoro-3-((1r,3r)-3-hydroxy-3-methyl-1',2'-dihydrospiro[cyclobutane-1,3'-pyrrolo[2,3-b]pyridin]-5'-yl)-N,N-dimethylbenzamide |
| 78b | 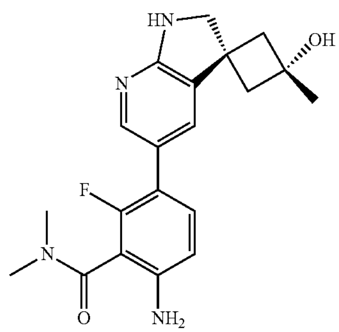 [SMILES: CN(C)C(=O)c1c(N)ccc(-c2cnc3c(c2)[C@]2(CN3)C[C@@](C)(O)C2)c1F] | 6-Amino-2-fluoro-3-((1s,3s)-3-hydroxy-3-methyl-1',2'-dihydrospiro[cyclobutane-1,3'-pyrrolo[2,3-b]pyridin]-5'-yl)-N,N-dimethylbenzamide |
| 79 | 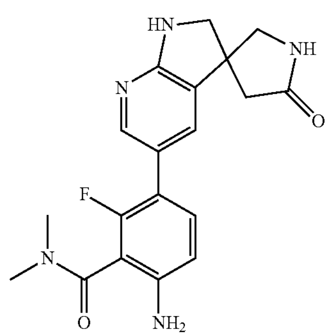 [SMILES: CN(C)C(=O)c1c(N)ccc(-c2cnc3c(c2)C2(CNC(=O)C2)CN3)c1F] | 6-Amino-2-fluoro-N,N-dimethyl-3-(5-oxo-1',2'-dihydrospiro[pyrrolidine-3,3'-pyrrolo[2,3-b]pyridin]-5'-yl)benzamide |
| 79a | | (R)-6-Amino-2-fluoro-N,N-dimethyl-3-(5-oxo-1',2'-dihydrospiro[pyrrolidine-3,3'-pyrrolo[2,3-b]pyridin]-5'-yl)benzamide |
| 79b | | (S)-6-Amino-2-fluoro-N,N-dimethyl-3-(5-oxo-1',2'-dihydrospiro[pyrrolidine-3,3'-pyrrolo[2,3-b]pyridin]-5'-yl)benzamide |
| 80 | 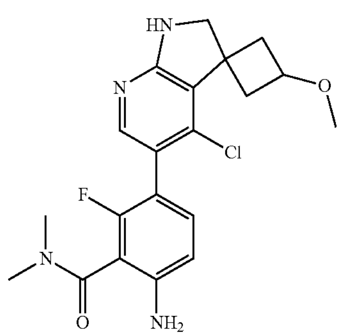 | 6-Amino-3-(4'-chloro-3-methoxy-1',2'-dihydrospiro[cyclobutane-1,3'-pyrrolo[2,3-b]pyridin]-5'-yl)-2-fluoro-N,N-dimethylbenzamide |

TABLE 1-continued

| No. | Structure | Name |
|---|---|---|
| 80a | 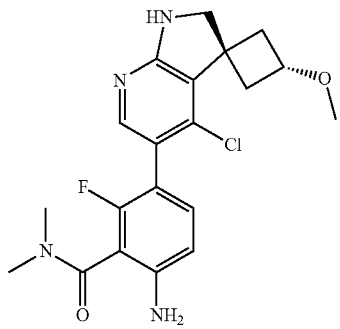 | 6-Amino-3-((1r,3r)-4'-chloro-3-methoxy-1',2'-dihydrospiro[cyclobutane-1,3'-pyrrolo[2,3-b]pyridin]-5'-yl)-2-fluoro-N,N-dimethylbenzamide |
| 80b | 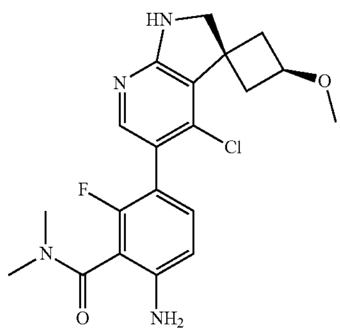 | 6-Amino-3-((1s, 3s)-4'-chloro-3-methoxy-1',2'-dihydrospiro[cyclobutane-1,3'-pyrrolo[2,3-b]pyridin]-5'-yl)-2-fluoro-N,N-dimethylbenzamide |
| 81 | 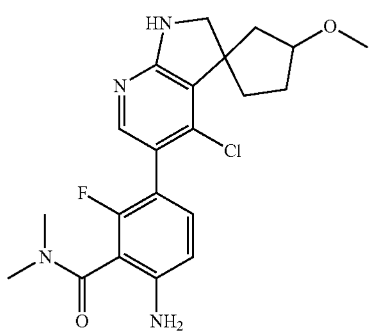 | 6-Amino-3-(4'-chloro-3-methoxy-1',2'-dihydrospiro[cyclopentane-1,3'-pyrrolo[2,3-b]pyridin]-5'-yl)-2-fluoro-N,N-dimethylbenzamide |
| 81a | | 6-Amino-3-((1R,3R)-4'-chloro-3-methoxy-1',2'-dihydrospiro[cyclopentane-1,3'-pyrrolo[2,3-b]pyridin]-5'-yl)-2-fluoro-N,N-dimethylbenzamide<br>6-Amino-3-((1S,3S)-4'-chloro-3-methoxy-1',2'-dihydrospiro[cyclopentane-1,3'-pyrrolo[2,3-b]pyridin]-5'-yl)-2-fluoro-N,N-dimethylbenzamide |
| 81b | | 6-Amino-3-((1R,3S)-4'-chloro-3-methoxy-1',2'-dihydrospiro [cyclopentane-1,3'-pyrrolo[2,3-b]pyridin]-5'-yl)-2-fluoro-N,N-dimethylbenzamide<br>6-Amino-3-((1S,3R)-4'-chloro-3-methoxy-1',2'-dihydrospiro[cyclopentane-1,3'-pyrrolo[2,3-b]pyridin]-5'-yl)-2-fluoro-N,N-dimethylbenzamide |
| 82 | 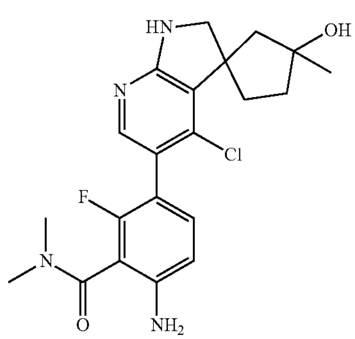 | 6-Amino-3-(4'-chloro-3-hydroxy-3-methyl-1',2'-dihydrospiro[cyclopentane-1,3'-pyrrolo[2,3-b]pyridin]-5'-yl)-2-fluoro-N,N-dimethylbenzamide |

TABLE 1-continued

| No. | Structure | Name |
|---|---|---|
| 82a | | 6-Amino-3-((1R,3S)-4'-chloro-3-hydroxy-3-methyl-1',2'-dihydrospiro[cyclopentane-1,3'-pyrrolo[2,3-b]pyridin]-5'-yl)-2-fluoro-N,N-dimethylbenzamide<br>6-Amino-3-((1S,3R)-4'-chloro-3-hydroxy-3-methyl-1',2'-dihydrospiro[cyclopentane-1,3'-pyrrolo[2,3-b]pyridin]-5'-yl)-2-fluoro-N,N-dimethylbenzamide |
| 83 | 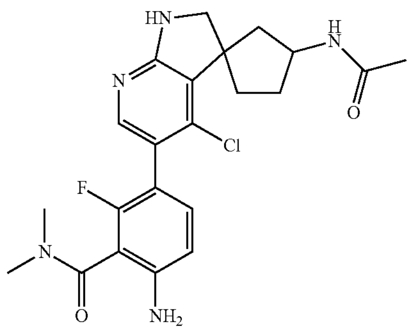 [SMILES: CC(=O)NC1CCC2(CNc3ncc(-c4ccc(N)c(C(=O)N(C)C)c4F)c(Cl)c32)C1] | 3-(3-Acetamido-4'-chloro-1',2'-dihydrospiro[cyclopentane-1,3'-pyrrolo[2,3-b]pyridin]-5'-yl)-6-amino-2-fluoro-N,N-dimethylbenzamide |
| 84 | 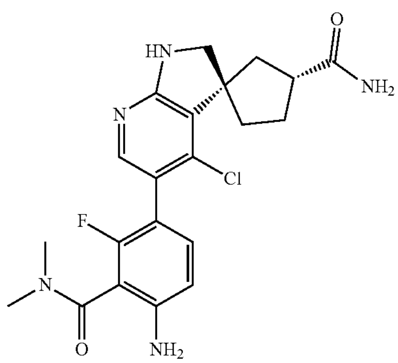 [SMILES: CN(C)C(=O)c1c(N)ccc(-c2cnc3c(c2Cl)[C@]2(CC[C@@H](C(N)=O)C2)CN3)c1F] | 5'-(4-amino-3-(dimethylcarbamoyl)-2-fluorophenyl)-4'-chloro-1',2'-dihydrospiro[cyclopentane-1,3'-pyrrolo[2,3-b]pyridine]-3-carboxamide |
| 84a | | (1R,3R)-5'-(4-amino-3-(dimethylcarbamoyl)-2-fluorophenyl)-4'-chloro-1',2'-dihydrospiro[cyclopentane-1,3'-pyrrolo[2,3-b]pyridine]-3-carboxamide<br>(1S,3S)-5'-(4-amino-3-(dimethylcarbamoyl)-2-fluorophenyl)-4'-chloro-1',2'-dihydrospiro[cyclopentane-1,3'-pyrrolo[2,3-b]pyridine]-3-carboxamide |
| 84b | | (1R,3S)-5'-(4-amino-3-(dimethylcarbamoyl)-2-fluorophenyl)-4'-chloro-1',2'-dihydrospiro[cyclopentane-1,3'-pyrrolo[2,3-b]pyridine]-3-carboxamide<br>(1S,3R)-5'-(4-amino-3-(dimethylcarbamoyl)-2-fluorophenyl)-4'-chloro-1',2'-dihydrospiro[cyclopentane-1,3'-pyrrolo[2,3-b]pyridine]-3-carboxamid |
| 85 | 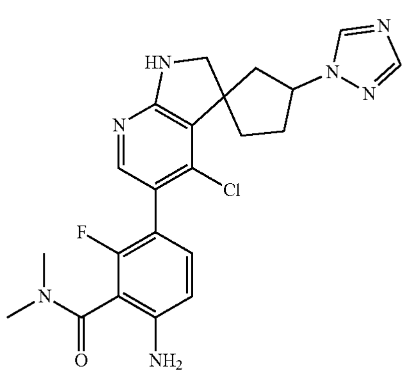 [SMILES: CN(C)C(=O)c1c(N)ccc(-c2cnc3c(c2Cl)C2(CCC(n4cncn4)C2)CN3)c1F] | 6-Amino-3-(4'-chloro-3-(1H-1,2,4-triazol-1-yl)-1',2'-dihydrospiro[cyclopentane-1,3'-pyrrolo[2,3-b]pyridin]-5'-yl)-2-fluoro-N,N-dimethylbenzamide |

TABLE 1-continued

| No. | Structure | Name |
|---|---|---|
| 85a | 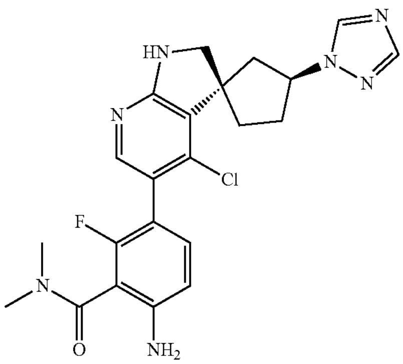 [SMILES: CN(C)C(=O)c1c(N)ccc(-c2cnc3c(c2Cl)[C@]2(CC[C@H](n4cncn4)C2)CN3)c1F] | 6-Amino-3-((1R,3S)-4'-chloro-3-(1H-1,2,4-triazol-1-yl)-1',2'-dihydrospiro[cyclopentane-1,3'-pyrrolo[2,3-b]pyridin]-5'-yl)-2-fluoro-N,N-dimethylbenzamide<br>6-Amino-3-((1S,3R)-4'-chloro-3-(1H-1,2,4-triazol-1-yl)-1',2'-dihydrospiro[cyclopentane-1,3'-pyrrolo[2,3-b]pyridin]-5'-yl)-2-fluoro-N,N-dimethylbenzamide |
| 85b | 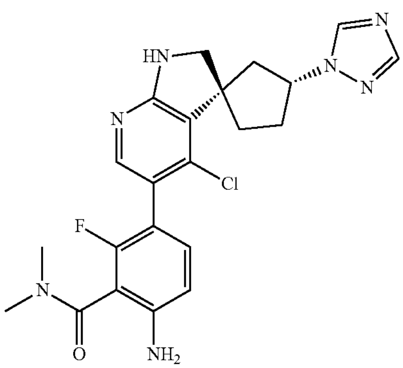 [SMILES: CN(C)C(=O)c1c(N)ccc(-c2cnc3c(c2Cl)[C@]2(CC[C@@H](n4cncn4)C2)CN3)c1F] | 6-Amino-3-((1R,3R)-4'-chloro-3-(1H-1,2,4-triazol-1-yl)-1',2'-dihydrospiro[cyclopentane-1,3'-pyrrolo[2,3-b]pyridin]-5'-yl)-2-fluoro-N,N-dimethylbenzamide<br>6-Amino-3-((1S,3S)-4'-chloro-3-(1H-1,2,4-triazol-1-yl)-1',2'-dihydrospiro[cyclopentane-1,3'-pyrrolo[2,3-b]pyridin]-5'-yl)-2-fluoro-N,N-dimethylbenzamide |
| 86 | 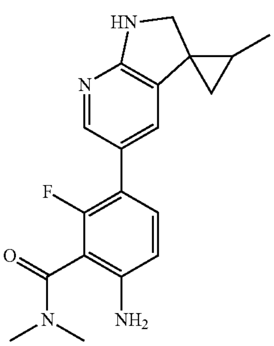 [SMILES: CC1CC12CNc1ncc(-c3ccc(N)c(C(=O)N(C)C)c3F)cc12] | 6-Amino-2-fluoro-N,N-dimethyl-3-(2-methyl-1',2'-dihydrospiro[cyclopropane-1,3'-pyrrolo[2,3-b]pyridin]-5'-yl)benzamide |
| 86a | 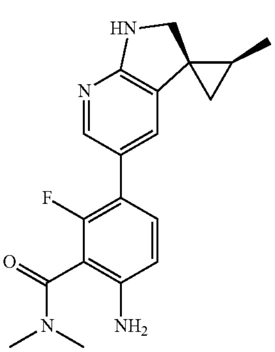 [SMILES: C[C@H]1C[C@@]12CNc1ncc(-c3ccc(N)c(C(=O)N(C)C)c3F)cc12] | 6-Amino-2-fluoro-N,N-dimethyl-3-((1R,2S)-2-methyl-1',2'-dihydrospiro[cyclopropane-1,3'-pyrrolo[2,3-b]pyridin]-5'-yl)benzamide<br>6-Amino-2-fluoro-N,N-dimethyl-3-((1S, 2R)-2-methyl-1',2'-dihydrospiro[cyclopropane-1,3'-pyrrolo[2,3-b]pyridin]-5'-yl)benzamide |

TABLE 1-continued

| No. | Structure | Name |
|---|---|---|
| 86b | 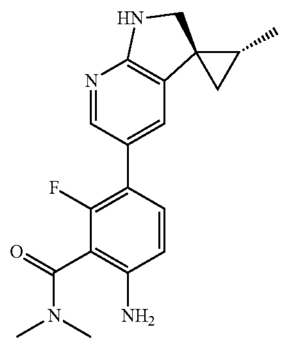 [SMILES: C[C@@H]1C[C@@]12CNc1ncc(-c3ccc(N)c(C(=O)N(C)C)c3F)cc12] | 6-Amino-2-fluoro-N,N-dimethyl-3-((1R,2R)-2-methyl-1',2'-dihydrospiro[cyclopropane-1,3'-pyrrolo[2,3-b]pyridin]-5'-yl)benzamide<br>6-Amino-2-fluoro-N,N-dimethyl-3-((1S,2S)-2-methyl-1',2'-dihydrospiro [cyclopropane-1,3'-pyrrolo[2,3-b]pyridin]-5'-yl)benzamide |
| 87 | | 6-Amino-3-(4'-chloro-3-hydroxy-3-(trifluoromethyl)-1',2'-dihydrospiro[cyclobutane-1,3'-pyrrolo[2,3-b]pyridin]-5'-yl)-2-fluoro-N,N-dimethylbenzamide |
| 87a | 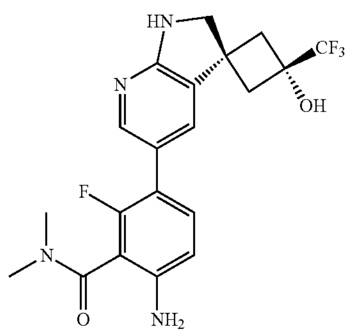 [SMILES: CN(C)C(=O)c1c(N)ccc(-c2cnc3c(c2)[C@]2(CN3)C[C@@](O)(C(F)(F)F)C2)c1F] | 6-Amino-3-((1r,3r)-4'-chloro-3-hydroxy-3-(trifluoromethyl)-1',2'-dihydrospiro[cyclobutane-1,3'-pyrrolo[2,3-b]pyridin]-5'-yl)-2-fluoro-N,N-dimethylbenzamide |
| 88 | 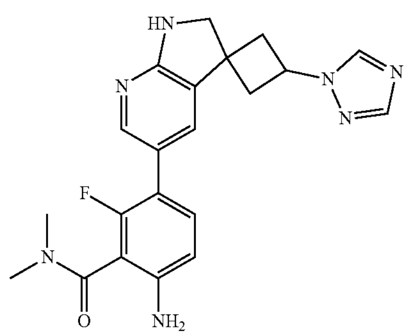 [SMILES: CN(C)C(=O)c1c(N)ccc(-c2cnc3c(c2)C2(CN3)CC(n3cncn3)C2)c1F] | 6-Amino-3-(4'-chloro-3-(1H-1,2,4-triazol-1-yl)-1',2'-dihydrospiro[cyclobutane-1,3'-pyrrolo[2,3-b]pyridin]-5'-yl)-2-fluoro-N,N-dimethylbenzamide |
| 88a | 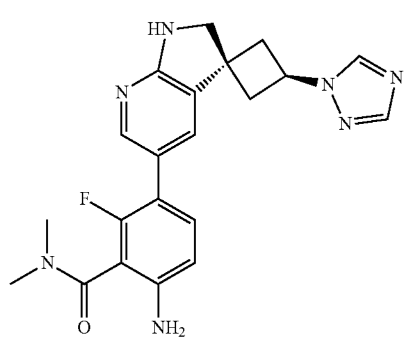 [SMILES: CN(C)C(=O)c1c(N)ccc(-c2cnc3c(c2)[C@]2(CN3)C[C@@H](n3cncn3)C2)c1F] | 6-Amino-3-((1s,3s)-4'-chloro-3-(1H-1,2,4-triazol-1-yl)-1',2'-dihydrospiro[cyclobutane-1,3'-pyrrolo[2,3-b]pyridin]-5'-yl)-2-fluoro-N,N-dimethylbenzamide |

TABLE 1-continued

| No. | Structure | Name |
|---|---|---|
| 89 | 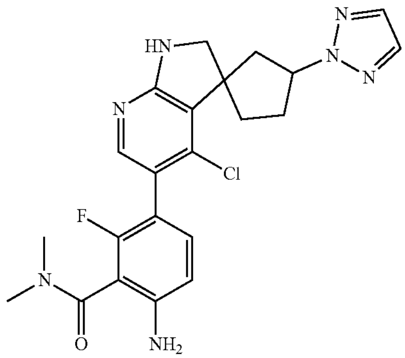 [SMILES: CN(C)C(=O)c1c(N)ccc(-c2cnc3c(c2Cl)C2(CCC(n4nccn4)C2)CN3)c1F] | 6-Amino-3-(4'-chloro-3-(2H-1,2,3-triazol-2-yl)-1',2'-dihydrospiro[cyclopentane-1,3'-pyrrolo[2,3-b]pyridin]-5'-yl)-2-fluoro-N,N-dimethylbenzamide |
| 89a | 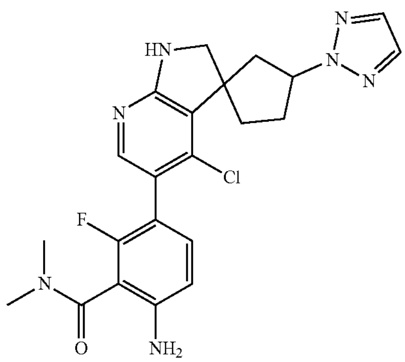 [SMILES: CN(C)C(=O)c1c(N)ccc(-c2cnc3c(c2Cl)C2(CCC(n4nccn4)C2)CN3)c1F] | 6-Amino-3-((1R,3S)-4'-chloro-3-(2H-1,2,3-triazol-2-yl)-1',2'-dihydrospiro[cyclopentane-1,3'-pyrrolo[2,3-b]pyridin]-5'-yl)-2-fluoro-N,N-dimethylbenzamide<br>6-Amino-3-((1S,3R)-4'-chloro-3-(2H-1,2,3-triazol-2-yl)-1',2'-dihydrospiro[cyclopentane-1,3'-pyrrolo[2,3-b]pyridin]-5'-yl)-2-fluoro-N,N-dimethylbenzamide |
| 89b | 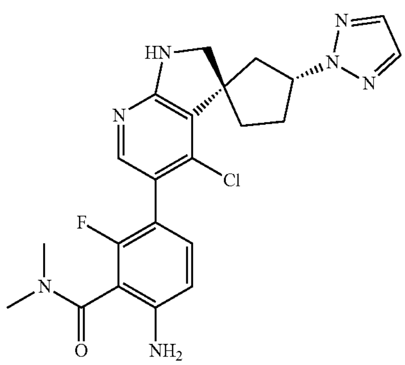 [SMILES: CN(C)C(=O)c1c(N)ccc(-c2cnc3c(c2Cl)[C@]2(CC[C@@H](n4nccn4)C2)CN3)c1F] | 6-Amino-3-((1R,3R)-4'-chloro-3-(2H-1,2,3-triazol-2-yl)-1',2'-dihydrospiro[cyclopentane-1,3'-pyrrolo[2,3-b]pyridin]-5'-yl)-2-fluoro-N,N-dimethylbenzamide<br>6-Amino-3-((1S,3S)-4'-chloro-3-(2H-1,2,3-triazol-2-yl)-1',2'-dihydrospiro[cyclopentane-1,3'-pyrrolo[2,3-b]pyridin]-5'-yl)-2-fluoro-N,N-dimethylbenzamide |
| 90 | 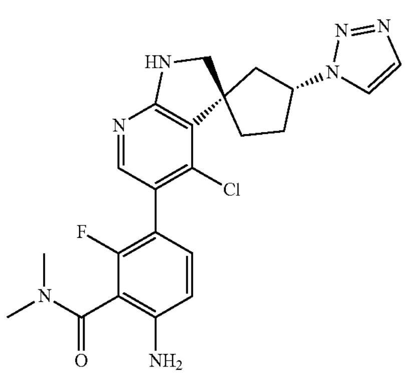 [SMILES: CN(C)C(=O)c1c(N)ccc(-c2cnc3c(c2Cl)[C@]2(CC[C@@H](n4ccnn4)C2)CN3)c1F] | 6-Amino-3-(4'-chloro-3-(1H-1,2,3-triazol-1-yl)-1',2'-dihydrospiro[cyclopentane-1,3'-pyrrolo[2,3-b]pyridin]-5'-yl)-2-fluoro-N,N-dimethylbenzamide |
| 90a | | 6-amino-3-((1R,3S)-4'-chloro-3-(1H-1,2,3-triazol-1-yl)-1',2'-dihydrospiro[cyclopentane-1,3'-pyrrolo[2,3-b]pyridin]-5'-yl)-2-fluoro-N,N-dimethylbenzamide<br>6-amino-3-((1S,3R)-4'-chloro-3-(1H-1,2,3-triazol-1-yl)-1',2'-dihydrospiro[cyclopentane-1,3'-pyrrolo[2,3-b]pyridin]-5'-yl)-2-fluoro-N,N-dimethylbenzamide |

TABLE 1-continued

| No. | Structure | Name |
|---|---|---|
| 90b | | 6-Amino-3-((1R,3R)-4'-chloro-3-(1H-1,2,3-triazol-1-yl)-1',2'-dihydrospiro[cyclopentane-1,3'-pyrrolo[2,3-b]pyridin]-5'-yl)-2-fluoro-N,N-dimethylbenzamide<br>6-Amino-3-((1S,3S)-4'-chloro-3-(1H-1,2,3-triazol-1-yl)-1',2'-dihydrospiro[cyclopentane-1,3'-pyrrolo[2,3-b]pyridin]-5'-yl)-2-fluoro-N,N-dimethylbenzamide |
| 91 | | 6-Amino-3-(4'-chloro-3-cyano-1',2'-dihydrospiro[cyclopentane-1,3'-pyrrolo[2,3-b]pyridin]-5'-yl)-2-fluoro-N,N-dimethylbenzamide |
| 91a | (structure) | 6-Amino-3-((1R,3S)-4'-chloro-3-cyano-1',2'-dihydrospiro[cyclopentane-1,3'-pyrrolo[2,3-b]pyridin]-5'-yl)-2-fluoro-N,N-dimethylbenzamide<br>6-Amino-3-((1S,3R)-4'-chloro-3-cyano-1',2'-dihydrospiro[cyclopentane-1,3'-pyrrolo[2,3-b]pyridin]-5'-yl)-2-fluoro-N,N-dimethylbenzamide |
| 91b | | 6-Amino-3-((1R,3R)-4'-chloro-3-cyano-1',2'-dihydrospiro[cyclopentane-1,3'-pyrrolo[2,3-b]pyridin]-5'-yl)-2-fluoro-N,N-dimethylbenzamide<br>6-Amino-3-((1S,3S)-4'-chloro-3-cyano-1',2'-dihydrospiro[cyclopentane-1,3'-pyrrolo[2,3-b]pyridin]-5'-yl)-2-fluoro-N,N-dimethylbenzamide |
| 92 | (structure) | 3-(3-(1'2'-dihydrospiro[cyclopropane-1,3'-pyrrolo[2,3-b]pyridin]-5'-yl)-2-fluorophenyl)pyrrolidin-2-one |
| 92a | | (R)-3-(3-(1',2'-dihydrospiro[cyclopropane-1,3'-pyrrolo[2,3-b]pyridin]-5'-yl)-2-fluorophenyl)pyrrolidin-2-one |
| 92b | | (S)-3-(3-(1',2'-dihydrospiro[cyclopropane-1,3'-pyrrolo[2,3-b]pyridin]-5'-yl)-2-fluorophenyl)pyrrolidin-2-one |
| 93 | (structure) | 3-(1-Acetyl-1',2'-dihydrospiro[azetidine-3,3'-pyrrolo[2,3-b]pyridin]-5'-yl)-6-amino-2-fluoro-N,N-dimethylbenzamide |
| 94 | | 6-Amino-3-(3-(cyanomethylene)-1',2'-dihydrospiro[cyclobutane-1,3'-pyrrolo[2,3-b]pyridin]-5'-yl)-2-fluoro-N,N-dimethylbenzamide |

TABLE 1-continued

| No. | Structure | Name |
|---|---|---|
| 94a 94b | | (s,E)-6-Amino-3-(3-(cyanomethylene)-1',2'-dihydrospiro[cyclobutane-1,3'-pyrrolo[2,3-b]pyridin]-5'-yl)-2-fluoro-N,N-dimethylbenzamide (r,Z)-6-amino-3-(3-(cyanomethylene)-1',2'-dihydrospiro[cyclobutane-1,3'-pyrrolo[2,3-b]pyridin]-5'-yl)-2-fluoro-N,N-dimethylbenzamide |
| 95 | | 6-Amino-3-(3-(cyanomethyl)-1',2'-dihydrospiro[cyclobutane-1,3'-pyrrolo[2,3-b]pyridin]-5'-yl)-2-fluoro-N,N-dimethylbenzamide |
| 95a | 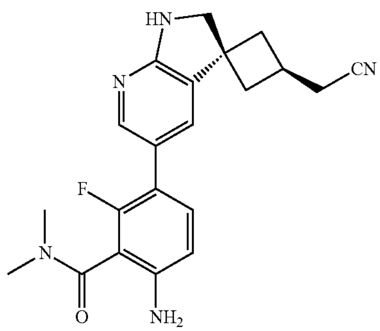 [SMILES: CN(C)C(=O)c1c(N)ccc(-c2cnc3c(c2)[C@]2(CN3)C[C@@H](CC#N)C2)c1F] | 6-Amino-3-((1R,3r)-3-(cyanomethyl)-1',2'-dihydrospiro[cyclobutane-1,3'-pyrrolo[2,3-b]pyridin]-5'-yl)-2-fluoro-N,N-dimethylbenzamide |
| 96 | | 6-Amino-3-(4'-chloro-3-cyano-1',2'-dihydrospiro[cyclobutane-1,3'-pyrrolo[2,3-b]pyridin]-5'-yl)-2-fluoro-N,N-dimethylbenzamide |
| 96a | 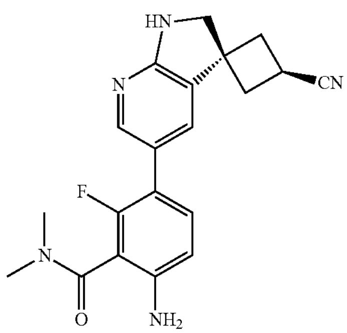 [SMILES: CN(C)C(=O)c1c(N)ccc(-c2cnc3c(c2)[C@]2(CN3)C[C@@H](C#N)C2)c1F] | 6-Amino-3-((1s,3s)-4'-chloro-3-cyano-1',2'-dihydrospiro[cyclobutane-1,3'-pyrrolo[2,3-b]pyridin]-5'-yl)-2-fluoro-N,N-dimethylbenzamide |
| 97 | | 5'-(4-Amino-3-(dimethylcarbamoyl)-2-fluorophenyl)-4'-chloro-1',2'-dihydrospiro[cyclobutane-1,3'-pyrrolo[2,3-b]pyridine]-3-carboxamide |
| 97a | 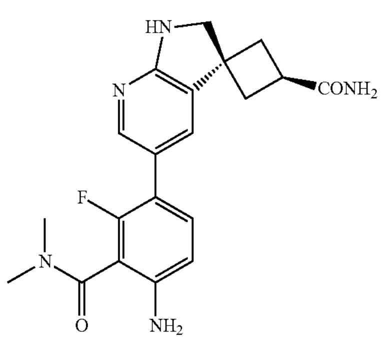 [SMILES: CN(C)C(=O)c1c(N)ccc(-c2cnc3c(c2)[C@]2(CN3)C[C@@H](C(N)=O)C2)c1F] | (1s,3s)-5'-(4-Amino-3-(dimethylcarbamoyl)-2-fluorophenyl)-4'-chloro-1',2'-dihydrospiro[cyclobutane-1,3'-pyrrolo[2,3-b]pyridine]-3-carboxamide |

TABLE 1-continued

| No. | Structure | Name |
|---|---|---|
| 98 | | 5'-(4-Amino-3-(dimethylcarbamoyl)-2-fluorophenyl)-4'-chloro-N-methyl-1',2'-dihydrospiro[cyclopentane-1,3'-pyrrolo[2,3-b]pyridine]-3-carboxamide |
| 98a | 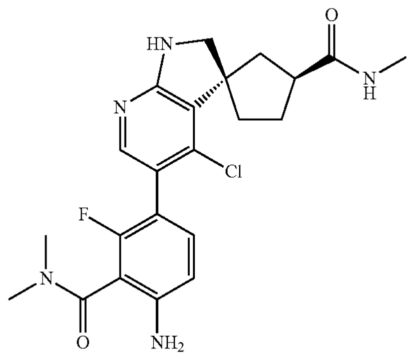 | (1R,3S)-5'-(4-Amino-3-(dimethylcarbamoyl)-2-fluorophenyl)-4'-chloro-N-methyl-1',2'-dihydrospiro[cyclopentane-1,3'-pyrrolo[2,3-b]pyridine]-3-carboxamide<br>(1S,3R)-5'-(4-Amino-3-(dimethylcarbamoyl)-2-fluorophenyl)-4'-chloro-N-methyl-1',2'-dihydrospiro[cyclopentane-1,3'-pyrrolo[2,3-b]pyridine]-3-carboxamide |
| 98b | | (1S,3S)-5'-(4-Amino-3-(dimethylcarbamoyl)-2-fluorophenyl)-4'-chloro-N-methyl-1',2'-dihydrospiro[cyclopentane-1,3'-pyrrolo[2,3-b]pyridine]-3-carboxamide<br>(1R,3R)-5'-(4-Amino-3-(dimethylcarbamoyl)-2-fluorophenyl)-4'-chloro-N-methyl-1',2'-dihydrospiro[cyclopentane-1,3'-pyrrolo[2,3-b]pyridine]-3-carboxamide |
| 99 | | 6-Amino-3-(4'-chloro-3-(1H-1,2,4-triazol-5-yl)-1',2'-dihydrospiro[cyclopentane-1,3'-pyrrolo[2,3-b]pyridin]-5'-yl)-2-fluoro-N,N-dimethylbenzamide |
| 99a | 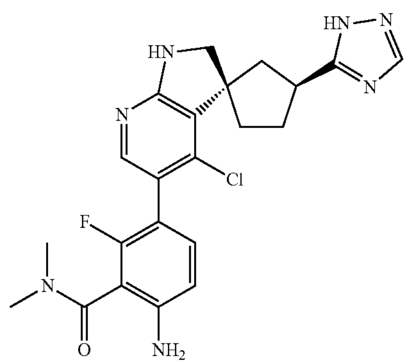 [SMILES: CN(C)C(=O)c1c(N)ccc(-c2cnc3c(c2Cl)[C@]2(CC[C@H](c4ncn[nH]4)C2)CN3)c1F] | 6-Amino-3-((1R,3S)-4'-chloro-3-(1H-1,2,4-triazol-5-yl)-1',2'-dihydrospiro[cyclopentane-1,3'-pyrrolo[2,3-b]pyridin]-5'-yl)-2-fluoro-N,N-dimethylbenzamide<br>6-Amino-3-((1S,3S)-4'-chloro-3-(1H-1,2,4-triazol-5-yl)-1',2'-dihydrospiro[cyclopentane-1,3'-pyrrolo[2,3-b]pyridin]-5'-yl)-2-fluoro-N,N-dimethylbenzamide |
| 99b | | 6-Amino-3-((1S,3S)-4'-chloro-3-(1H-1,2,4-triazol-5-yl)-1',2'-dihydrospiro[cyclopentane-1,3'-pyrrolo[2,3-b]pyridin]-5'-yl)-2-fluoro-N,N-dimethylbenzamide<br>6-Amino-3-((1R,3R)-4'-chloro-3-(1H-1,2,4-triazol-5-yl)-1'2'-dihydrospiro[cyclopentane-1,3'-pyrrolo[2,3-b]pyridin]-5'-yl)-2-fluoro-N,N-dimethylbenzamide |
| 100 | | 5'-(4-Amino-3-(dimethylcarbamoyl)-2-fluorophenyl)-4'-chloro-1',2'-dihydrospiro[cyclopentane-1,3'-pyrrolo[2,3-b]pyridine]-3-carboxamide |
| 100a<br>100b | | 1R,3S)-5'-(4-Amino-3-(dimethylcarbamoyl)-2-fluorophenyl)-4'-chloro-1',2'-dihydrospiro[cyclopentane-1,3'-pyrrolo[2,3-b]pyridine]-3-carboxamide<br>(1S,3R)-5'-(4-Amino-3-(dimethylcarbamoyl)-2-fluorophenyl)-4'-chloro-1',2'-dihydrospiro[cyclopentane-1,3'-pyrrolo[2,3-b]pyridine]-3-carboxamide |

TABLE 1-continued

| No. | Structure | Name |
|---|---|---|
| 101 | 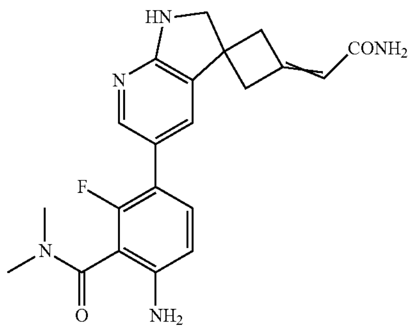 [SMILES: CN(C)C(=O)c1c(N)ccc(-c2cnc3c(c2)C2(CN3)CC(=CC(N)=O)C2)c1F] | 6-Amino-3-(3-(2-amino-2-oxoethylidene)-1',2'-dihydrospiro[cyclobutane-1,3'-pyrrolo[2,3-b]pyridin]-5'-yl)-2-fluoro-N,N-dimethylbenzamide |
| 101a | | (R)-6-Amino-3-(3-(2-amino-2-oxoethylidene)-1',2'-dihydrospiro[cyclobutane-1,3'-pyrrolo[2,3-b]pyridin]-5'-yl)-2-fluoro-N,N-dimethylbenzamide |
| 101b | | (S)-6-Amino-3-(3-(2-amino-2-oxoethylidene)-1',2'-dihydrospiro[cyclobutane-1,3'-pyrrolo[2,3-b]pyridin]-5'-yl)-2-fluoro-N,N-dimethylbenzamide |
| 102 | | 6-Amino-3-(3-(2-amino-2-oxoethyl)-1',2'-dihydrospiro[cyclobutane-1,3'-pyrrolo[2,3-b]pyridin]-5'-yl)-2-fluoro-N,N-dimethylbenzamide |
| 102a | 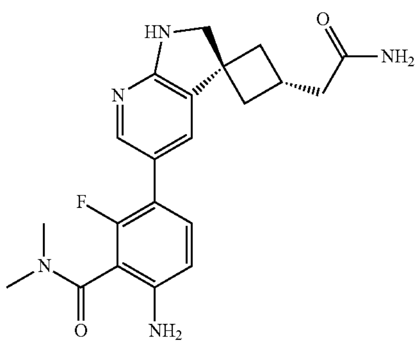 [SMILES: CN(C)C(=O)c1c(N)ccc(-c2cnc3c(c2)[C@]2(CN3)C[C@H](CC(N)=O)C2)c1F] | 6-Amino-3-((1R,3r)-3-(2-amino-2-oxoethyl)-1',2'-dihydrospiro[cyclobutane-1,3'-pyrrolo[2,3-b]pyridin]-5'-yl)-2-fluoro-N,N-dimethylbenzamide |
| 103 | 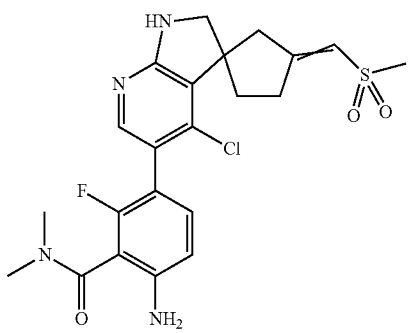 | 6-Amino-3-(4'-chloro-3-((methylsulfonyl)methylene)-1',2'-dihydrospiro[cyclopentane-1,3'-pyrrolo[2,3-b]pyridin]-5'-yl)-2-fluoro-N,N-dimethylbenzamide |
| 104 | 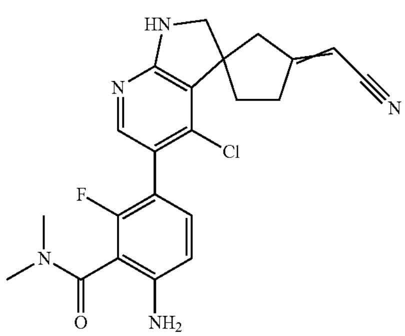 [SMILES: CN(C)C(=O)c1c(N)ccc(-c2cnc3c(c2Cl)C2(CCC(=CC#N)C2)CN3)c1F] | 6-Amino-3-(4'-chloro-3-(cyanomethylene)-1',2'-dihydrospiro[cyclopentane-1,3'-pyrrolo[2,3-b]pyridin]-5'-yl)-2-fluoro-N,N-dimethylbenzamide |

TABLE 1-continued

| No. | Structure | Name |
|---|---|---|
| 105 | 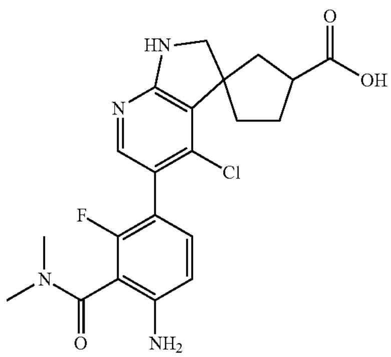 [SMILES: CN(C)C(=O)c1c(N)ccc(-c2cnc3c(c2Cl)C2(CCC(C(=O)O)C2)CN3)c1F] | 5'-(4-Amino-3-(dimethylcarbamoyl)-2-fluorophenyl)-4'-chloro-1',2'-dihydrospiro[cyclopentane-1,3'-pyrrolo[2,3-b]pyridine]-3-carboxylic acid |
| 105a 105b | | (1R,3S)-5'-(4-Amino-3-(dimethylcarbamoyl)-2-fluorophenyl)-4'-chloro-1',2'-dihydrospiro[cyclopentane-1,3'-pyrrolo[2,3-b]pyridine]-3-carboxylic acid (1S,3R)-5'-(4-Amino-3-(dimethylcarbamoyl)-2-fluorophenyl)-4'-chloro-1',2'-dihydrospiro[cyclopentane-1,3'-pyrrolo[2,3-b]pyridine]-3-carboxylic acid |
| 105c | | (1S,3S)-5'-(4-Amino-3-(dimethylcarbamoyl)-2-fluorophenyl)-4'-chloro-1',2'-dihydrospiro[cyclopentane-1,3'-pyrrolo[2,3-b]pyridine]-3-carboxylic acid |
| 105d | | (1R,3R)-5'-(4-Amino-3-(dimethylcarbamoyl)-2-fluorophenyl)-4'-chloro-1',2'-dihydrospiro[cyclopentane-1,3'-pyrrolo[2,3-b]pyridine]-3-carboxylic acid |
| 106 | | 5'-(4-Amino-3-(dimethylcarbamoyl)-2-fluorophenyl)-4'-chloro-N-(2-hydroxyethyl)-1',2'-dihydrospiro[cyclopentane-1,3'-pyrrolo[2,3-b]pyridine]-3-carboxamide |
| 106a 106b | | (1R,3S)-5'-(4-Amino-3-(dimethylcarbamoyl)-2-fluorophenyl)-4'-chloro-N-(2-hydroxyethyl)-1',2'-dihydrospiro[cyclopentane-1,3'-pyrrolo[2,3-b]pyridine]-3-carboxamide (1S,3R)-5'-(4-Amino-3-(dimethylcarbamoyl)-2-fluorophenyl)-4'-chloro-N-(2-hydroxyethyl)-1',2'-dihydrospiro[cyclopentane-1,3'-pyrrolo[2,3-b]pyridine]-3-carboxamide |
| 106c | | (1R,3R)-5'-(4-Amino-3-(dimethylcarbamoyl)-2-fluorophenyl)-4'-chloro-N-(2-hydroxyethyl)-1',2'-dihydrospiro[cyclopentane-1,3'-pyrrolo[2,3-b]pyridine]-3-carboxamide |
| 106d | | (1S,3S)-5'-(4-Amino-3-(dimethylcarbamoyl)-2-fluorophenyl)-4'-chloro-N-(2-hydroxyethyl)-1',2'-dihydrospiro[cyclopentane-1,3'-pyrrolo[2,3-b]pyridine]-3-carboxamide |
| 107 | | 5'-(4-Amino-3-(dimethylcarbamoyl)-2-fluorophenyl)-4'-chloro-N,N-dimethyl-1',2'-dihydrospiro[cyclopentane-1,3'-pyrrolo[2,3-b]pyridine]-3-carboxamide |

TABLE 1-continued

| No. | Structure | Name |
|---|---|---|
| 107a 107b | | (1R,3S)-5'-(4-Amino-3-(dimethylcarbamoyl)-2-fluorophenyl)-4'-chloro-N,N-dimethyl-1',2'-dihydrospiro[cyclopentane-1,3'-pyrrolo[2,3-b]pyridine]-3-carboxamide<br>(1S,3R)-5'-(4-Amino-3-(dimethylcarbamoyl)-2-fluorophenyl)-4'-chloro-N,N-dimethyl-1',2'-dihydrospiro[cyclopentane-1,3'-pyrrolo[2,3-b]pyridine]-3-carboxamide |
| 107c 107d | | (1R,3R)-5'-(4-Amino-3-(dimethylcarbamoyl)-2-fluorophenyl)-4'-chloro-N,N-dimethyl-1',2'-dihydrospiro[cyclopentane-1,3'-pyrrolo[2,3-b]pyridine]-3-carboxamide<br>(1S,3S)-5'-(4-Amino-3-(dimethylcarbamoyl)-2-fluorophenyl)-4'-chloro-N,N-dimethyl-1',2'-dihydrospiro[cyclopentane-1,3'-pyrrolo[2,3-b]pyridine]-3-carboxamide |
| 108 | | 6-Amino-3-(4'-chloro-3-(3-methyl-1,2,4-oxadiazol-5-yl)-1',2'-dihydrospiro[cyclopentane-1,3'-pyrrolo[2,3-b]pyridin]-5'-yl)-2-fluoro-N,N-dimethylbenzamide |
| 108a 108b | | 6-Amino-3-((1R,3S)-4'-chloro-3-(3-methyl-1,2,4-oxadiazol-5-yl)-1',2'-dihydrospiro[cyclopentane-1,3'-pyrrolo[2,3-b]pyridin]-5'-yl)-2-fluoro-N,N-dimethylbenzamide<br>6-Amino-3-((1S,3R)-4'-chloro-3-(3-methyl-1,2,4-oxadiazol-5-yl)-1',2'-dihydrospiro[cyclopentane-1,3'-pyrrolo[2,3-b]pyridin]-5'-yl)-2-fluoro-N,N-dimethylbenzamide |
| 108c 108d | | 6-Amino-3-((1R,3R)-4'-chloro-3-(3-methyl-1,2,4-oxadiazol-5-yl)-1',2'-dihydrospiro[cyclopentane-1,3'-pyrrolo[2,3-b]pyridin]-5'-yl)-2-fluoro-N,N-dimethylbenzamide<br>6-Amino-3-((1S,3S)-4'-chloro-3-(3-methyl-1,2,4-oxadiazol-5-yl)-1',2'-dihydrospiro[cyclopentane-1,3'-pyrrolo[2,3-b]pyridin]-5'-yl)-2-fluoro-N,N-dimethylbenzamide |
| 109 | | 6-Amino-3-(4'-chloro-3-(cyanomethyl)-3-hydroxy-1',2'-dihydrospiro[cyclopentane-1,3'-pyrrolo[2,3-b]pyridin]-5'-yl)-2-fluoro-N,N-dimethylbenzamide |
| 109a | | 6-Amino-3-((1R,3R)-4'-chloro-3-(cyanomethyl)-3-hydroxy-1'2'-dihydrospiro[cyclopentane-1,3'-pyrrolo[2,3-b]pyridin]-5'-yl)-2-fluoro-N,N-dimethylbenzamide<br>6-Amino-3-((1S,3S)-4'-chloro-3-(cyanomethyl)-3-hydroxy-1',2'-dihydrospiro[cyclopentane-1,3'-pyrrolo[2,3-b]pyridin]-5'-yl)-2-fluoro-N,N-dimethylbenzamide |

TABLE 1-continued

| No. | Structure | Name |
|---|---|---|
| 109b | 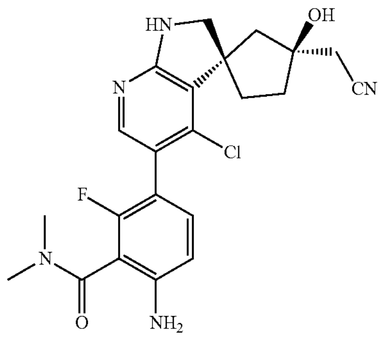 [SMILES: CN(C)C(=O)c1c(N)ccc(-c2cnc3c(c2Cl)[C@]2(CC[C@@](O)(CC#N)C2)CN3)c1F] | 6-Amino-3-((1R,3S)-4'-chloro-3-(cyanomethyl)-3-hydroxy-1',2'-dihydrospiro[cyclopentane-1,3'-pyrrolo[2,3-b]pyridin]-5'-yl)-2-fluoro-N,N-dimethylbenzamide<br>6-Amino-3-((1S,3R)-4'-chloro-3-(cyanomethyl)-3-hydroxy-1'2'-dihydrospiro[cyclopentane-1,3'-pyrrolo[2,3-b]pyridin]-5'-yl)-2-fluoro-N,N-dimethylbenzamide |
| 110 | 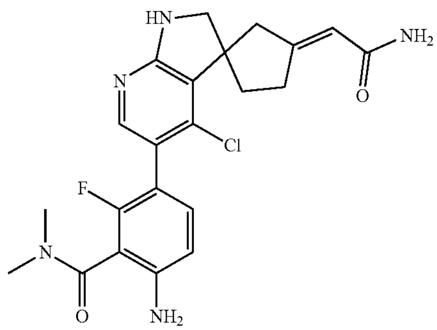 [SMILES: CN(C)C(=O)c1c(N)ccc(-c2cnc3c(c2Cl)C2(CC/C(=C\C(N)=O)C2)CN3)c1F] | 6-Amino-3-(3-(2-amino-2-oxoethylidene)-4'-chloro-1',2'-dihydrospiro[cyclopentane-1,3'-pyrrolo[2,3-b]pyridin]-5'-yl)-2-fluoro-N,N-dimethylbenzamide |
| 111 | | 6-Amino-2-fluoro-3-(4-hydroxy-1',2'-dihydrospiro[cyclohexane-1,3'-pyrrolo[2,3-b]pyridin]-5'-yl)-N,N-dimethylbenzamide |
| 111a | 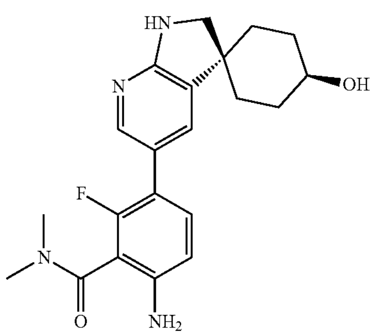 [SMILES: CN(C)C(=O)c1c(N)ccc(-c2cnc3c(c2)[C@]2(CC[C@H](O)CC2)CN3)c1F] | 6-Amino-2-fluoro-3-((1s,4s)-4-hydroxy-1',2'-dihydrospiro[cyclohexane-1,3'-pyrrolo[2,3-b]pyridin]-5'-yl)-N,N-dimethylbenzamide |
| 111b | 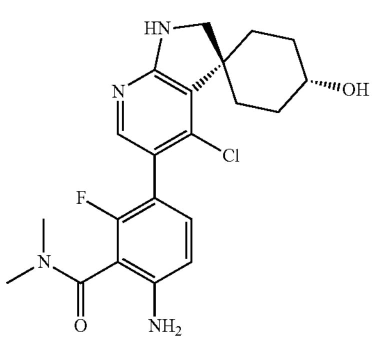 [SMILES: CN(C)C(=O)c1c(N)ccc(-c2cnc3c(c2Cl)[C@]2(CC[C@@H](O)CC2)CN3)c1F] | 6-Amino-2-fluoro-3-((1R,4R)-4-hydroxy-1',2'-dihydrospiro[cyclohexane-1,3'-pyrrolo[2,3-b]pyridin]-5'-yl)-N,N-dimethylbenzamide |

TABLE 1-continued

| No. | Structure | Name |
|---|---|---|
| 112 | 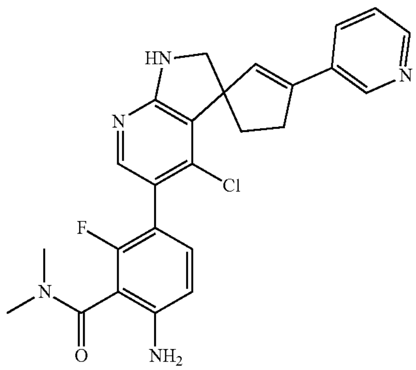 [SMILES: CN(C)C(=O)c1c(N)ccc(-c2cnc3c(c2Cl)C2(C=C(c4cccnc4)CC2)CN3)c1F] | 6-Amino-3-(4'-chloro-3-(pyridin-3-yl)-1',2'-dihydrospiro[cyclopentane-1,3'-pyrrolo[2,3-b]pyridin]-2-en-5'-yl)-2-fluoro-N,N-dimethylbenzamide |
| 113 | 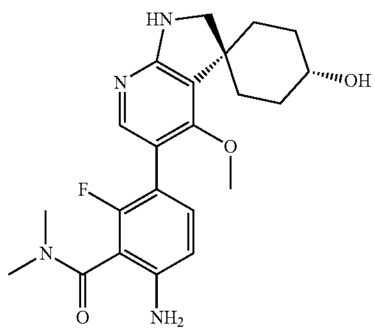 [SMILES: COc1c(-c2ccc(N)c(C(=O)N(C)C)c2F)cnc2c1[C@]1(CC[C@@H](O)CC1)CN2] | 6-Amino-2-fluoro-3-(4-hydroxy-4'-methoxy-1',2'-dihydrospiro[cyclohexane-1,3'-pyrrolo[2,3-b]pyridin]-5'-yl)-N,N-dimethylbenzamide |
| 113a | 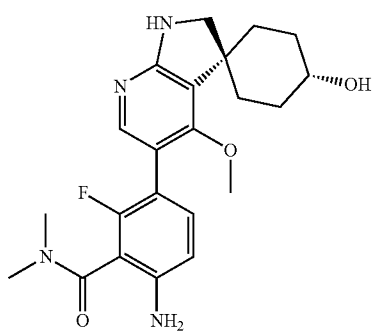 [SMILES: COc1c(-c2ccc(N)c(C(=O)N(C)C)c2F)cnc2c1[C@]1(CC[C@@H](O)CC1)CN2] | 6-Amino-2-fluoro-3-((1R,4R)-4-hydroxy-4'-methoxy-1',2'-dihydrospiro[cyclohexane-1,3'-pyrrolo[2,3-b]pyridin]-5'-yl)-N,N-dimethylbenzamide |
| 113b | 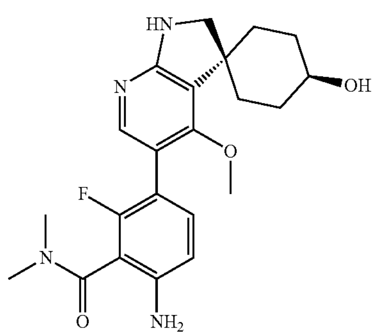 [SMILES: COc1c(-c2ccc(N)c(C(=O)N(C)C)c2F)cnc2c1[C@]1(CC[C@H](O)CC1)CN2] | 6-Amino-2-fluoro-3-((1S,4s)-4-hydroxy-4'-methoxy-1',2'-dihydrospiro[cyclohexane-1,3'-pyrrolo[2,3-b]pyridin]-5'-yl)-N,N-dimethylbenzamide |
| 114 | | 6-Amino-3-(4'-chloro-3-(4-methyl-2H-1,2,3-triazol-2-yl)-1'2'-dihydrospiro[cyclopentane-1,3'-pyrrolo[2,3-b]pyridin]-5'-yl)-2-fluoro-N,N-dimethylbenzamide |

TABLE 1-continued

| No. | Structure | Name |
|---|---|---|
| 114a 114b | (structure shown) | 6-Amino-3-((1R,3S)-4'-chloro-3-(4-methyl-2H-1,2,3-triazol-2-yl)-1'2'-dihydrospiro[cyclopentane-1,3'-pyrrolo[2,3-b]pyridin]-5'-yl)-2-fluoro-N,N-dimethylbenzamide<br>6-Amino-3-((1S,3R)-4'-chloro-3-(4-methyl-2H-1,2,3-triazol-2-yl)-1'2'-dihydrospiro[cyclopentane-1,3'-pyrrolo[2,3-b]pyridin]-5'-yl)-2-fluoro-N,N-dimethylbenzamide |
| 114c | | 6-Amino-3-((1R,3R)-4'-chloro-3-(4-methyl-2H-1,2,3-triazol-2-yl)-1',2'-dihydrospiro[cyclopentane-1,3'-pyrrolo[2,3-b]pyridin]-5'-yl)-2-fluoro-N,N-dimethylbenzamide |
| 114d | | 6-Amino-3-((1S,3S)-4'-chloro-3-(4-methyl-2H-1,2,3-triazol-2-yl)-1',2'-dihydrospiro[cyclopentane-1,3'-pyrrolo[2,3-b]pyridin]-5'-yl)-2-fluoro-N,N-dimethylbenzamide |
| 115 | | 6-Amino-3-(4'-chloro-3-(2-oxoimidazolidin-1-yl)-1',2'-dihydrospiro[cyclopentane-1,3'-pyrrolo[2,3-b]pyridin]-5'-yl)-2-fluoro-N,N-dimethylbenzamide |
| 115a 115b | (structure shown) | 6-Amino-3-((1R,3S)-4'-chloro-3-(2-oxoimidazolidin-1-yl)-1',2'-dihydrospiro[cyclopentane-1,3'-pyrrolo[2,3-b]pyridin]-5'-yl)-2-fluoro-N,N-dimethylbenzamide<br>6-Amino-3-((1S,3R)-4'-chloro-3-(2-oxoimidazolidin-1-yl)-1',2'-dihydrospiro[cyclopentane-1,3'-pyrrolo[2,3-b]pyridin]-5'-yl)-2-fluoro-N,N-dimethylbenzamide |
| 115c | | 6-Amino-3-((1R,3R)-4'-chloro-3-(2-oxoimidazolidin-1-yl)-1',2'-dihydrospiro[cyclopentane-1,3'-pyrrolo[2,3-b]pyridin]-5'-yl)-2-fluoro-N,N-dimethylbenzamide |
| 115d | | 6-Amino-3-((1S,3S)-4'-chloro-3-(2-oxoimidazolidin-1-yl)-1',2'-dihydrospiro[cyclopentane-1,3'-pyrrolo[2,3-b]pyridin]-5'-yl)-2-fluoro-N,N-dimethylbenzamide |
| 116 | | 3-(3-((1H-1,2,4-Triazol-1-yl)methyl)-4'-chloro-3-hydroxy-1',2'-dihydrospiro[cyclopentane-1,3'-pyrrolo[2,3-b]pyridin]-5'-yl)-6-amino-2-fluoro-N,N-dimethylbenzamide |

TABLE 1-continued

| No. | Structure | Name |
|---|---|---|
| 116a | 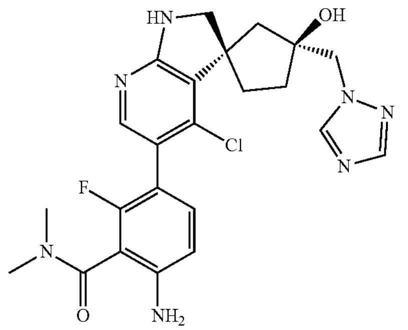 [SMILES: CN(C)C(=O)c1c(N)ccc(-c2cnc3c(c2Cl)[C@]2(CC[C@@](O)(Cn4cncn4)C2)CN3)c1F] | 3-((1R,3S)-3-((1H-1,2,4-Triazol-1-yl)methyl)-4'-chloro-3-hydroxy-1'2'-dihydrospiro[cyclopentane-1,3'-pyrrolo[2,3-b]pyridin]-5'-yl)-6-amino-2-fluoro-N,N-dimethylbenzamide<br>3-((1S,3R)-3-((1H-1,2,4-Triazol-1-yl)methyl)-4'-chloro-3-hydroxy-1'2'-dihydrospiro[cyclopentane-1,3'-pyrrolo[2,3-b]pyridin]-5'-yl)-6-amino-2-fluoro-N,N-dimethylbenzamide |
| 116b | 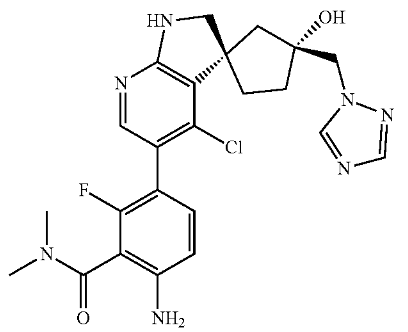 [SMILES: CN(C)C(=O)c1c(N)ccc(-c2cnc3c(c2Cl)[C@]2(CC[C@](O)(Cn4cncn4)C2)CN3)c1F] | 3-((1R,3R)-3-((1H-1,2,4-Triazol-1-yl)methyl)-4'-chloro-3-hydroxy-1',2'-dihydrospiro[cyclopentane-1,3'-pyrrolo[2,3-b]pyridin]-5'-yl)-6-amino-2-fluoro-N,N-dimethylbenzamide<br>3-((1S,3S)-3-((1H-1,2,4-Triazol-1-yl)methyl)-4'-chloro-3-hydroxy-1',2'-dihydrospiro[cyclopentane-1,3'-pyrrolo[2,3-b]pyridin]-5'-yl)-6-amino-2-fluoro-N,N-dimethylbenzamide |
| 117 | | 3-(3-((1H-Imidazol-1-yl)methyl)-4'-chloro-3-hydroxy-1',2'-dihydrospiro[cyclopentane-1,3'-pyrrolo[2,3-b]pyridin]-5'-yl)-6-amino-2-fluoro-N,N-dimethylbenzamide |
| 117a | 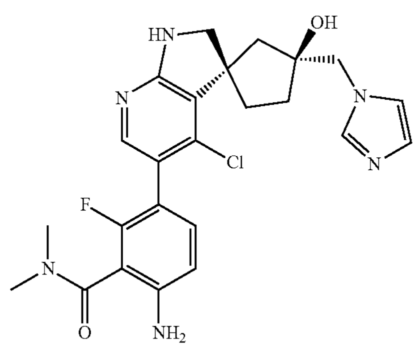 [SMILES: CN(C)C(=O)c1c(N)ccc(-c2cnc3c(c2Cl)[C@]2(CC[C@@](O)(Cn4ccnc4)C2)CN3)c1F] | 3-((1R,3S)-3-((1H-Imidazol-1-yl)methyl)-4'-chloro-3-hydroxy-1',2'-dihydrospiro[cyclopentane-1,3'-pyrrolo[2,3-b]pyridin]-5'-yl)-6-amino-2-fluoro-N,N-dimethylbenzamide<br>3-((1S,3R)-3-((1H-Imidazol-1-yl)methyl)-4'-chloro-3-hydroxy-1',2'-dihydrospiro[cyclopentane-1,3'-pyrrolo[2,3-b]pyridin]-5'-yl)-6-amino-2-fluoro-N,N-dimethylbenzamide |
| 118 | | 6-Amino-3-((1RS,3SR)-3-(5-amino-1H-1,2,4-triazol-1-yl)-4'-chloro-1',2'-dihydrospiro[cyclopentane-1,3'-pyrrolo[2,3-b]pyridin]-5'-yl)-2-fluoro-N,N-dimethylbenzamide |
| 118a | 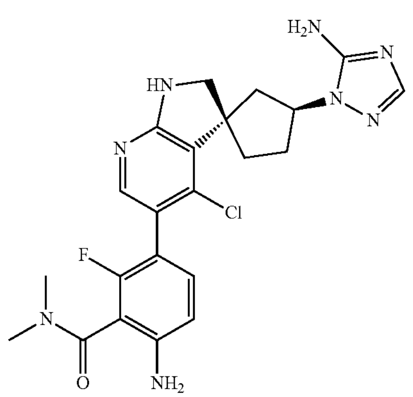 [SMILES: CN(C)C(=O)c1c(N)ccc(-c2cnc3c(c2Cl)[C@]2(CC[C@H](n4ncnc4N)C2)CN3)c1F] | 6-Amino-3-((1R,3S)-3-(5-amino-1H-1,2,4-triazol-1-yl)-4'-chloro-1',2'-dihydrospiro[cyclopentane-1,3'-pyrrolo[2,3-b]pyridin]-5'-yl)-2-fluoro-N,N-dimethylbenzamide<br>6-Amino-3-((1S,3R)-3-(5-amino-1H-1,2,4-triazol-1-yl)-4'-chloro-1',2'-dihydrospiro[cyclopentane-1,3'-pyrrolo[2,3-b]pyridin]-5'-yl)-2-fluoro-N,N-dimethylbenzamide |

TABLE 1-continued

| No. | Structure | Name |
|---|---|---|
| 119 | | 6-Amino-3-(3-(3-amino-1H-1,2,4-triazol-1-yl)-4'-chloro-1',2'-dihydrospiro[cyclopentane-1,3'-pyrrolo[2,3-b]pyridin]-5'-yl)-2-fluoro-N,N-dimethylbenzamide |
| 119a | 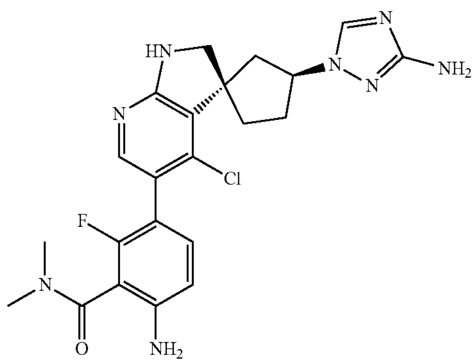 [SMILES: CN(C)C(=O)c1c(N)ccc(-c2cnc3c(c2Cl)[C@]2(CC[C@H](n4cnc(N)n4)C2)CN3)c1F] | 6-Amino-3-((1R,3S)-3-(3-amino-1H-1,2,4-triazol-1-yl)-4'-chloro-1',2'-dihydrospiro[cyclopentane-1,3'-pyrrolo[2,3-b]pyridin]-5'-yl)-2-fluoro-N,N-dimethylbenzamide<br>6-Amino-3-((1S,3R)-3-(3-amino-1H-1,2,4-triazol-1-yl)-4'-chloro-1',2'-dihydrospiro[cyclopentane-1,3'-pyrrolo[2,3-b]pyridin]-5'-yl)-2-fluoro-N,N-dimethylbenzamide |
| 120 | | 6-Amino-3-(4'-chloro-3-morpholino-1',2'-dihydrospiro[cyclopentane-1,3'-pyrrolo[2,3-b]pyridin]-5'-yl)-2-fluoro-N,N-dimethylbenzamide |
| 120a | 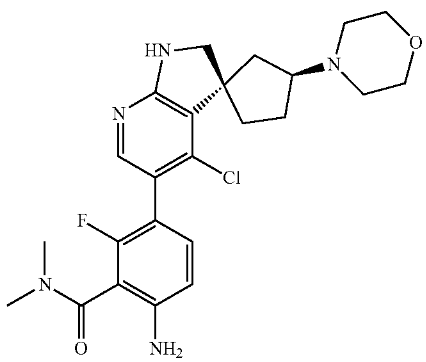 [SMILES: CN(C)C(=O)c1c(N)ccc(-c2cnc3c(c2Cl)[C@]2(CC[C@H](N4CCOCC4)C2)CN3)c1F] | 6-Amino-3-((1R,3S)-4'-chloro-3-morpholino-1',2'-dihydrospiro[cyclopentane-1,3'-pyrrolo[2,3-b]pyridin]-5'-yl)-2-fluoro-N,N-dimethylbenzamide<br>6-Amino-3-((1S,3R)-4'-chloro-3-morpholino-1',2'-dihydrospiro[cyclopentane-1,3'-pyrrolo[2,3-b]pyridin]-5'-yl)-2-fluoro-N,N-dimethylbenzamide |
| 121 | | 6-Amino-3-(4'-chloro-3-(pyrrolidin-1-yl)-1',2'-dihydrospiro[cyclopentane-1,3'-pyrrolo[2,3-b]pyridin]-5'-yl)-2-fluoro-N,N-dimethylbenzamide |
| 121a | 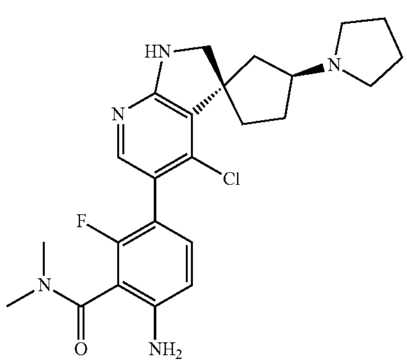 | 6-Amino-3-((1R,3S)-4'-chloro-3-(pyrrolidin-1-yl)-1',2'-dihydrospiro[cyclopentane-1,3'-pyrrolo[2,3-b]pyridin]-5'-yl)-2-fluoro-N,N-dimethylbenzamide<br>6-Amino-3-((1S,3R)-4'-chloro-3-(pyrrolidin-1-yl)-1',2'-dihydrospiro[cyclopentane-1,3'-pyrrolo[2,3-b]pyridin]-5'-yl)-2-fluoro-N,N-dimethylbenzamide |
| 122 | | 6-Amino-3-(4'-chloro-2-oxo-1',2'-dihydrospiro[piperidine-4,3'-pyrrolo[2,3-b]pyridin]-5'-yl)-2-fluoro-N,N-dimethylbenzamide |

TABLE 1-continued

| No. | Structure | Name |
|---|---|---|
| 122a 122b | | (R)-6-Amino-3-(4'-chloro-2-oxo-1',2'-dihydrospiro[piperidine-4,3'-pyrrolo[2,3-b]pyridin]-5'-yl)-2-fluoro-N,N-dimethylbenzamide (S)-6-Amino-3-(4'-chloro-2-oxo-1',2'-dihydrospiro[piperidine-4,3'-pyrrolo[2,3-b]pyridin]-5'-yl)-2-fluoro-N,N-dimethylbenzamide |
| 123 | | 6-Amino-3-(4'-chloro-6-oxo-1',2'-dihydrospiro[piperidine-3,3'-pyrrolo[2,3-b]pyridin]-5'-yl)-2-fluoro-N,N-dimethylbenzamide |
| 123a | 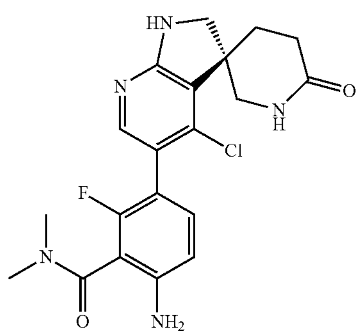 [SMILES: CN(C)C(=O)c1c(N)ccc(-c2cnc3c(c2Cl)[C@]2(CCC(=O)NC2)CN3)c1F] | (R)-6-Amino-3-(4'-chloro-6-oxo-1',2'-dihydrospiro[piperidine-3,3'-pyrrolo[2,3-b]pyridin]-5'-yl)-2-fluoro-N,N-dimethylbenzamide |
| 123b | 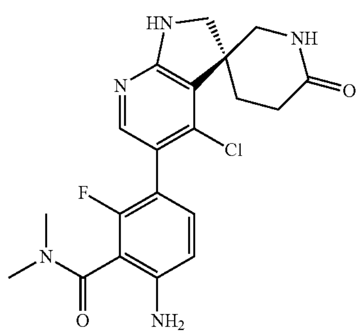 [SMILES: CN(C)C(=O)c1c(N)ccc(-c2cnc3c(c2Cl)[C@@]2(CCC(=O)NC2)CN3)c1F] | (S)-6-Amino-3-(4'-chloro-6-oxo-1',2'-dihydrospiro[piperidine-3,3'-pyrrolo[2,3-b]pyridin]-5'-yl)-2-fluoro-N,N-dimethylbenzamide |
| 124 | | 6-Amino-3-(4'-chloro-3-(2-oxooxazolidin-3-yl)-1',2'-dihydrospiro[cyclopentane-1,3'-pyrrolo[2,3-b]pyridin]-5'-yl)-2-fluoro-N,N-dimethylbenzamide |
| 124a | 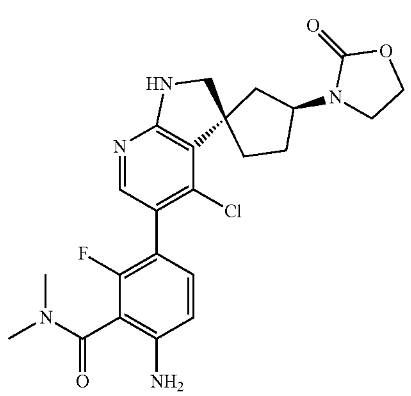 [SMILES: CN(C)C(=O)c1c(N)ccc(-c2cnc3c(c2Cl)[C@]2(CC[C@H](N4CCOC4=O)C2)CN3)c1F] | 6-Amino-3-((1R,3S)-4'-chloro-3-(2-oxooxazolidin-3-yl)-1',2'-dihydrospiro[cyclopentane-1,3'-pyrrolo[2,3-b]pyridin]-5'-yl)-2-fluoro-N,N-dimethylbenzamide 6-Amino-3-((1S,3R)-4'-chloro-3-(2-oxooxazolidin-3-yl)-1',2'-dihydrospiro[cyclopentane-1,3'-pyrrolo[2,3-b]pyridin]-5'-yl)-2-fluoro-N,N-dimethylbenzamide |

TABLE 1-continued

| No. | Structure | Name |
|---|---|---|
| 125 | | 6-Amino-3-(4'-chloro-3-(4-methyl-1H-pyrazol-1-yl)-1',2'-dihydrospiro[cyclopentane-1,3'-pyrrolo[2,3-b]pyridin]-5'-yl)-2-fluoro-N,N-dimethylbenzamide |
| 125a | 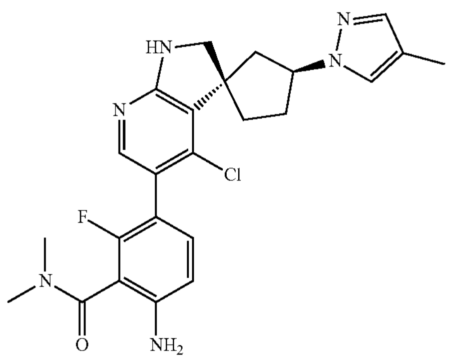 | 6-Amino-3-((1R,3S)-4'-chloro-3-(4-methyl-1H-pyrazol-1-yl)-1',2'-dihydrospiro[cyclopentane-1,3'-pyrrolo[2,3-b]pyridin]-5'-yl)-2-fluoro-N,N-dimethylbenzamide<br>6-Amino-3-((1S,3R)-4'-chloro-3-(4-methyl-1H-pyrazol-1-yl)-1',2'-dihydrospiro[cyclopentane-1,3'-pyrrolo[2,3-b]pyridin]-5'-yl)-2-fluoro-N,N-dimethylbenzamide |
| 126 | | 6-Amino-3-(4'-chloro-3-(1H-pyrazol-1-yl)-1',2'-dihydrospiro[cyclopentane-1,3'-pyrrolo[2,3-b]pyridin]-5'-yl)-2-fluoro-N,N-dimethylbenzamide |
| 126a | 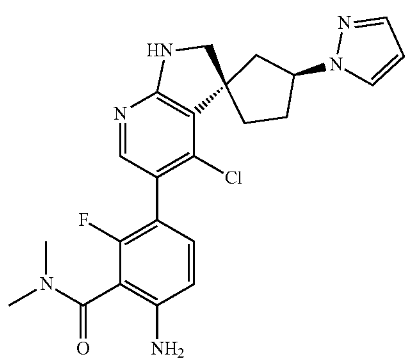 [SMILES: CN(C)C(=O)c1c(N)ccc(-c2cnc3c(c2Cl)[C@]2(CC[C@H](n4cccn4)C2)CN3)c1F] | 6-Amino-3-((1R,3S)-4'-chloro-3-(1H-pyrazol-1-yl)-1',2'-dihydrospiro[cyclopentane-1,3'-pyrrolo[2,3-b]pyridin]-5'-yl)-2-fluoro-N,N-dimethylbenzamide<br>6-Amino-3-((1S,3R)-4'-chloro-3-(1H-pyrazol-1-yl)-1',2'-dihydrospiro[cyclopentane-1,3'-pyrrolo[2,3-b]pyridin]-5'-yl)-2-fluoro-N,N-dimethylbenzamide |
| 127 | | 6-Amino-3-(3-(aminomethyl)-4'-chloro-1',2'-dihydrospiro[cyclopentane-1,3'-pyrrolo[2,3-b]pyridin]-5'-yl)-2-fluoro-N,N-dimethylbenzamide |
| 127a | 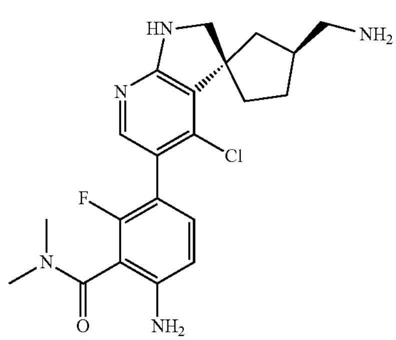 [SMILES: CN(C)C(=O)c1c(N)ccc(-c2cnc3c(c2Cl)[C@]2(CC[C@H](CN)C2)CN3)c1F] | 6-Amino-3-((1R,3S)-3-(aminomethyl)-4'-chloro-1',2'-dihydrospiro[cyclopentane-1,3'-pyrrolo[2,3-b]pyridin]-5'-yl)-2-fluoro-N,N-dimethylbenzamide<br>6-Amino-3-((1S, 3R)-3-(aminomethyl)-4'-chloro-1',2'-dihydrospiro[cyclopentane-1,3'-pyrrolo[2,3-b]pyridin]-5'-yl)-2-fluoro-N,N-dimethylbenzamide |
| 128 | | 6-Amino-2-fluoro-N,N-dimethyl-3-(2'-methyl-1',2'-dihydrospiro[cyclopropane-1,3'-pyrrolo[2,3-b]pyridin]-5'-yl)benzamide |

TABLE 1-continued

| No. | Structure | Name |
|---|---|---|
| 128a 128b | | (R)-6-Amino-2-fluoro-N,N-dimethyl-3-(2'-methyl-1',2'-dihydrospiro[cyclopropane-1,3'-pyrrolo[2,3-b]pyridin]-5'-yl)benzamide<br>(S)-6-Amino-2-fluoro-N,N-dimethyl-3-(2'-methyl-1',2'-dihydrospiro[cyclopropane-1,3'-pyrrolo[2,3-b]pyridin]-5'-yl)benzamide |
| 129 | 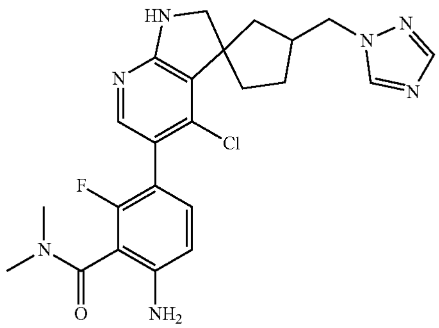 [SMILES: CN(C)C(=O)c1c(N)ccc(-c2cnc3c(c2Cl)C2(CCC(Cn4cncn4)C2)CN3)c1F] | 3-(3-((1H-1,2,4-Triazol-1-yl)methyl)-4'-chloro-1',2'-dihydrospiro[cyclopentane-1,3'-pyrrolo[2,3-b]pyridin]-5'-yl)-6-amino-2-fluoro-N,N-dimethylbenzamide |
| 130 | 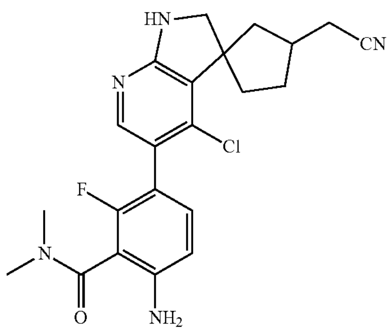 [SMILES: CN(C)C(=O)c1c(N)ccc(-c2cnc3c(c2Cl)C2(CCC(CC#N)C2)CN3)c1F] | 6-Amino-3-(4'-chloro-3-(cyanomethyl)-1',2'-dihydrospiro[cyclopentane-1,3'-pyrrolo[2,3-b]pyridin]-5'-yl)-2-fluoro-N,N-dimethylbenzamide |
| 131 | | 6-Amino-3-(4'-chloro-3-cyano-3-methyl-1',2'-dihydrospiro[cyclopentane-1,3'-pyrrolo[2,3-b]pyridin]-5'-yl)-2-fluoro-N,N-dimethylbenzamide |
| 131a | 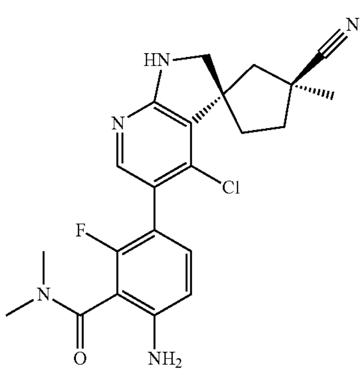 [SMILES: CN(C)C(=O)c1c(N)ccc(-c2cnc3c(c2Cl)[C@]2(CC[C@](C)(C#N)C2)CN3)c1F] | 6-Amino-3-((1R,3S)-4'-chloro-3-cyano-3-methyl-1',2'-dihydrospiro[cyclopentane-1,3'-pyrrolo[2,3-b]pyridin]-5'-yl)-2-fluoro-N,N-dimethylbenzamide<br>6-Amino-3-((1S,3R)-4'-chloro-3-cyano-3-methyl-1',2'-dihydrospiro[cyclopentane-1,3'-pyrrolo[2,3-b]pyridin]-5'-yl)-2-fluoro-N,N-dimethylbenzamide |
| 132 | | 5'-(4-Amino-3-(dimethylcarbamoyl)-2-fluorophenyl)-4'-chloro-3-methyl-1',2'-dihydrospiro[cyclopentane-1,3'-pyrrolo[2,3-b]pyridine]-3-carboxamide |

TABLE 1-continued

| No. | Structure | Name |
|---|---|---|
| 132a | 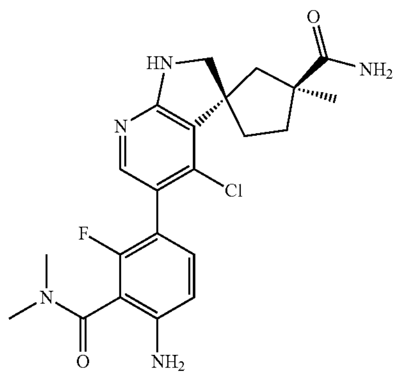 [SMILES: CN(C)C(=O)c1c(N)ccc(-c2cnc3c(c2Cl)[C@]2(CC[C@](C)(C(N)=O)C2)CN3)c1F] | (1R,3S)-5'-(4-Amino-3-(dimethylcarbamoyl)-2-fluorophenyl)-4'-chloro-3-methyl-1',2'-dihydrospiro[cyclopentane-1,3'-pyrrolo[2,3-b]pyridine]-3-carboxamide<br>(1S,3R)-5'-(4-Amino-3-(dimethylcarbamoyl)-2-fluorophenyl)-4'-chloro-3-methyl-1',2'-dihydrospiro[cyclopentane-1,3'-pyrrolo[2,3-b]pyridine]-3-carboxamide |
| 133 | | 6-Amino-3-(3-(3-amino-1H-pyrazol-1-yl)-4'-chloro-1',2'-dihydrospiro[cyclopentane-1,3'-pyrrolo[2,3-b]pyridin]-5'-yl)-2-fluoro-N,N-dimethylbenzamide |
| 133a | 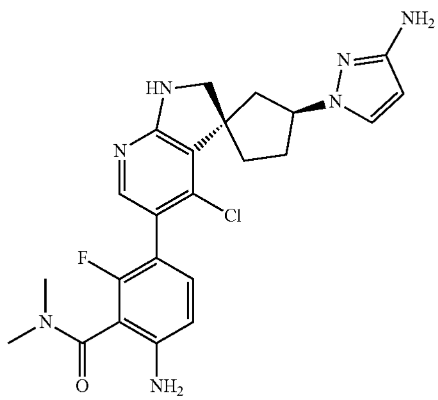 [SMILES: CN(C)C(=O)c1c(N)ccc(-c2cnc3c(c2Cl)[C@]2(CC[C@H](n4ccc(N)n4)C2)CN3)c1F] | 6-Amino-3-((1R,3S)-3-(3-amino-1H-pyrazol-1-yl)-4'-chloro-1',2'-dihydrospiro[cyclopentane-1,3'-pyrrolo[2,3-b]pyridin]-5'-yl)-2-fluoro-N,N-dimethylbenzamide<br>6-Amino-3-((1S,3R)-3-(3-amino-1H-pyrazol-1-yl)-4'-chloro-1',2'-dihydrospiro[cyclopentane-1,3'-pyrrolo[2,3-b]pyridin]-5'-yl)-2-fluoro-N,N-dimethylbenzamide |
| 134 | | 6-Amino-3-(3-(5-amino-1H-pyrazol-1-yl)-4'-chloro-1',2'-dihydrospiro[cyclopentane-1,3'-pyrrolo[2,3-b]pyridin]-5'-yl)-2-fluoro-N,N-dimethylbenzamide |
| 134a | 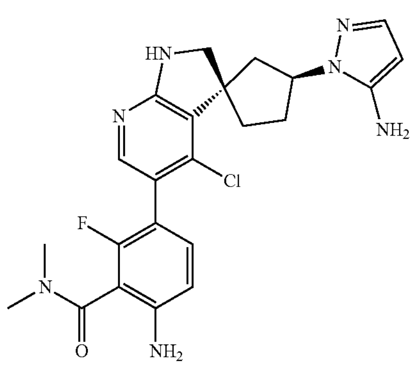 [SMILES: CN(C)C(=O)c1c(N)ccc(-c2cnc3c(c2Cl)[C@]2(CC[C@H](n4nccc4N)C2)CN3)c1F] | 6-Amino-3-((1R,3S)-3-(5-amino-1H-pyrazol-1-yl)-4'-chloro-1',2'-dihydrospiro[cyclopentane-1,3'-pyrrolo[2,3-b]pyridin]-5'-yl)-2-fluoro-N,N-dimethylbenzamide<br>6-Amino-3-((1S,3R)-3-(5-amino-1H-pyrazol-1-yl)-4'-chloro-1'2'-dihydrospiro[cyclopentane-1,3'-pyrrolo[2,3-b]pyridin]-5'-yl)-2-fluoro-N,N-dimethylbenzamide |
| 135 | | 6-Amino-3-(3-(2-amino-2-oxoethyl)-4'-chloro-1',2'-dihydrospiro[cyclopentane-1,3'-pyrrolo[2,3-b]pyridin]-5'-yl)-2-fluoro-N,N-dimethylbenzamide |

TABLE 1-continued

| No. | Structure | Name |
|---|---|---|
| 135a | 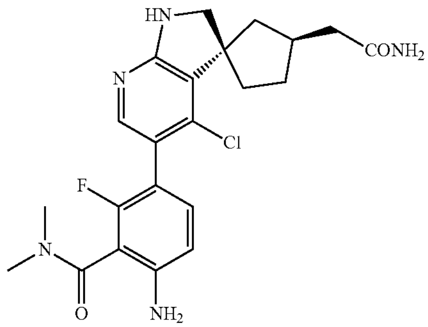 [SMILES: CN(C)C(=O)c1c(N)ccc(-c2cnc3c(c2Cl)[C@]2(CC[C@H](CC(N)=O)C2)CN3)c1F] | 6-Amino-3-((1R,3S)-3-(2-amino-2-oxoethyl)-4'-chloro-1',2'-dihydrospiro[cyclopentane-1,3'-pyrrolo[2,3-b]pyridin]-5'-yl)-2-fluoro-N,N-dimethylbenzamide<br>6-Amino-3-((1S, 3R)-3-(2-amino-2-oxoethyl)-4'-chloro-1',2'-dihydrospiro[cyclopentane-1,3'-pyrrolo[2,3-b]pyridin]-5'-yl)-2-fluoro-N,N-dimethylbenzamide |
| 135b | 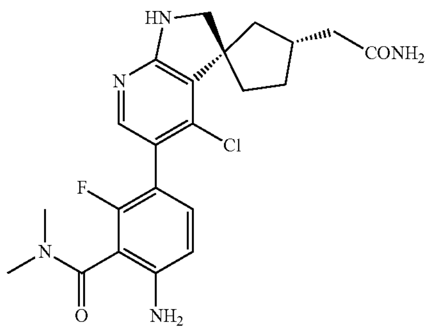 [SMILES: CN(C)C(=O)c1c(N)ccc(-c2cnc3c(c2Cl)[C@]2(CC[C@@H](CC(N)=O)C2)CN3)c1F] | 6-Amino-3-((1R,3R)-3-(2-amino-2-oxoethyl)-4'-chloro-1',2'-dihydrospiro[cyclopentane-1,3'-pyrrolo[2,3-b]pyridin]-5'-yl)-2-fluoro-N,N-dimethylbenzamide<br>6-Amino-3-((1S, 3S)-3-(2-amino-2-oxoethyl)-4'-chloro-1',2'-dihydrospiro[cyclopentane-1,3'-pyrrolo[2,3-b]pyridin]-5'-yl)-2-fluoro-N,N-dimethylbenzamide |
| 136 | 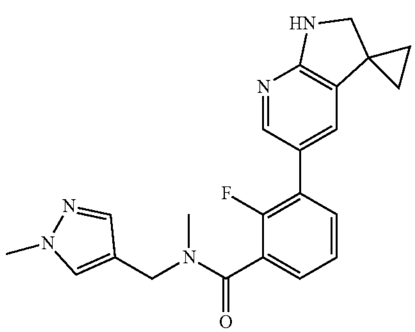 [SMILES: CN(Cc1cnn(C)c1)C(=O)c1cccc(-c2cnc3c(c2)C2(CC2)CN3)c1F] | 3-(1',2'-dihydrospiro[cyclopropane-1,3'-pyrrolo[2,3-b]pyridin]-5'-yl)-2-fluoro-N-methyl-N-((1-methyl-1H-pyrazol-4-yl)methyl)benzamide |
| 137 | 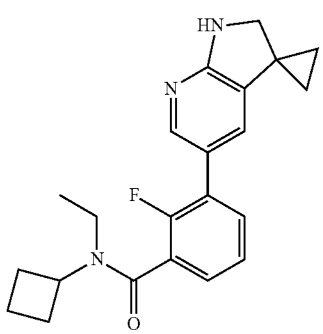 [SMILES: CCN(C(=O)c1cccc(-c2cnc3c(c2)C2(CC2)CN3)c1F)C1CCC1] | N-cyclobutyl-3-(1',2'-dihydrospiro[cyclopropane-1,3'-pyrrolo[2,3-b]pyridin]-5'-yl)-N-ethyl-2-fluorobenzamide |

TABLE 1-continued

| No. | Structure | Name |
|---|---|---|
| 138 | 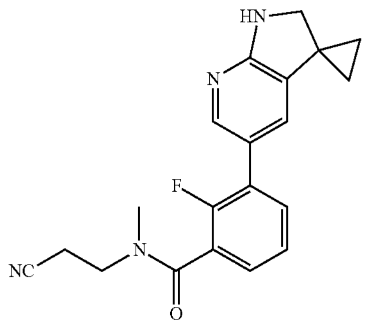 [SMILES: CN(CCC#N)C(=O)c1cccc(-c2cnc3c(c2)C2(CC2)CN3)c1F] | N-(2-cyanoethyl)-3-(1'2'-dihydrospiro[cyclopropane-1,3'-pyrrolo[2,3-b]pyridin]-5'-yl)-2-fluoro-N-methylbenzamide |
| 139 | 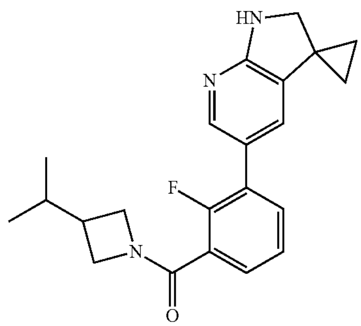 [SMILES: CC(C)C1CN(C(=O)c2cccc(-c3cnc4c(c3)C3(CC3)CN4)c2F)C1] | (3-(1',2'-dihydrospiro[cyclopropane-1,3'-pyrrolo[2,3-b]pyridin]-5'-yl)-2-fluorophenyl)(3-isopropylazetidin-1-yl)methanone |
| 140 | | 6-Amino-3-(4'-chloro-3-hydroxy-4-methoxy-1',2'-dihydrospiro[cyclopentane-1,3'-pyrrolo[2,3-b]pyridin]-5'-yl)-2-fluoro-N,N-dimethylbenzamide |
| 140a | 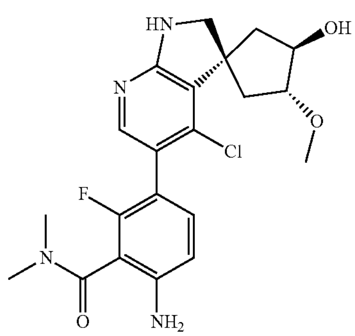 [SMILES: CO[C@@H]1C[C@@]2(CNc3ncc(-c4ccc(N)c(C(=O)N(C)C)c4F)c(Cl)c32)C[C@H]1O] | 6-Amino-3-((1R,3S, 4S)-4'-chloro-3-hydroxy-4-methoxy-1',2'-dihydrospiro[cyclopentane-1,3'-pyrrolo[2,3-b]pyridin]-5'-yl)-2-fluoro-N,N-dimethylbenzamide<br>6-Amino-3-((1S, 3R,4R)-4'-chloro-3-hydroxy-4-methoxy-1',2'-dihydrospiro[ cyclopentane-1,3'-pyrrolo[2,3-b]pyridin]-5'-yl)-2-fluoro-N,N-dimethylbenzamide |
| 140b | 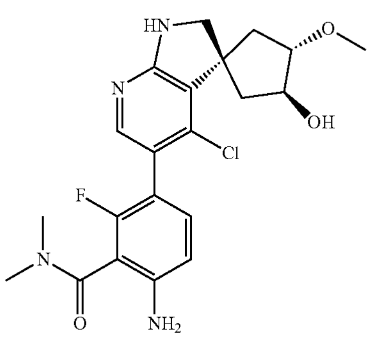 | 6-Amino-3-((1R,3S, 4S)-4'-chloro-3-hydroxy-4-methoxy-1',2'-dihydrospiro[cyclopentane-1,3'-pyrrolo[2,3-b]pyridin]-5'-yl)-2-fluoro-N,N-dimethylbenzamide<br>6-Amino-3-((1S, 3R,4R)-4'-chloro-3-hydroxy-4-methoxy-1',2'-dihydrospiro[cyclopentane-1,3'-pyrrolo[2,3-b]pyridin]-5'-yl)-2-fluoro-N,N-dimethylbenzamide |

TABLE 1-continued

| No. | Structure | Name |
|---|---|---|
| 141 | 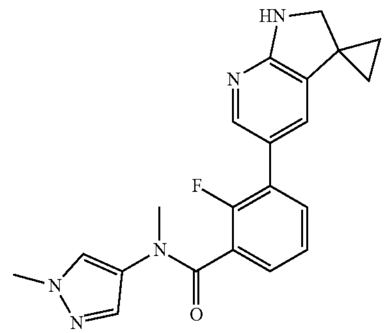 [SMILES: CN(C(=O)c1cccc(-c2cnc3c(c2)C2(CC2)CN3)c1F)c1cnn(C)c1] | 3-(1',2'-dihydrospiro[cyclopropane-1,3'-pyrrolo[2,3-b]pyridin]-5'-yl)-2-fluoro-N-methyl-N-(1-methyl-1H-pyrazol-4-yl)benzamide |
| 142 | 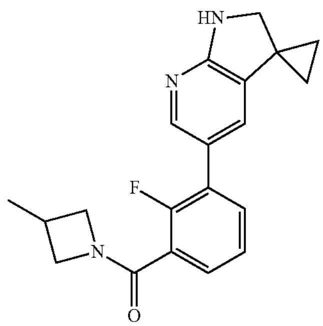 [SMILES: CC1CN(C(=O)c2cccc(-c3cnc4c(c3)C3(CC3)CN4)c2F)C1] | (3-(1',2'-dihydrospiro[cyclopropane-1,3'-pyrrolo[2,3-b]pyridin]-5'-yl)-2-fluorophenyl)(3-methylazetidin-1-yl)methanone |
| 143 | | 6-Amino-3-(4'-chloro-3-(2-oxopyrrolidin-1-yl)-1',2'-dihydrospiro[cyclopentane-1,3'-pyrrolo[2,3-b]pyridin]-5'-yl)-2-fluoro-N,N-dimethylbenzamide |
| 143a | 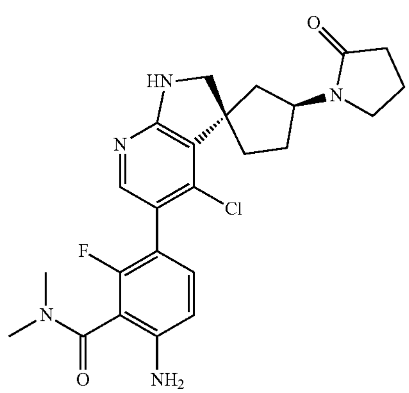 | 6-Amino-3-((1R,3S)-4'-chloro-3-(2-oxopyrrolidin-1-yl)-1',2'-dihydrospiro[cyclopentane-1,3'-pyrrolo[2,3-b]pyridin]-5'-yl)-2-fluoro-N,N-dimethylbenzamide<br>6-Amino-3-((1S,3R)-4'-chloro-3-(2-oxopyrrolidin-1-yl)-1',2'-dihydrospiro[cyclopentane-1,3'-pyrrolo[2,3-b]pyridin]-5'-yl)-2-fluoro-N,N-dimethylbenzamide |
| 144 | | 6-Amino-3-(4'-chloro-4-hydroxy-1',2'-dihydrospiro[cyclohexane-1,3'-pyrrolo[2,3-b]pyridin]-5'-yl)-2-fluoro-N,N-dimethylbenzamide |
| 144a | 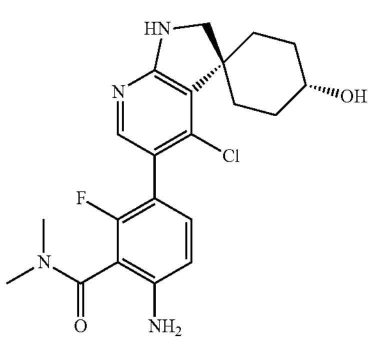 [SMILES: CN(C)C(=O)c1c(N)ccc(-c2cnc3c(c2Cl)[C@]2(CC[C@@H](O)CC2)CN3)c1F] | 6-Amino-3-((1R,4R)-4'-chloro-4-hydroxy-1',2'-dihydrospiro[cyclohexane-1,3'-pyrrolo[2,3-b]pyridin]-5'-yl)-2-fluoro-N,N-dimethylbenzamide |

TABLE 1-continued

| No. | Structure | Name |
|---|---|---|
| 144b | 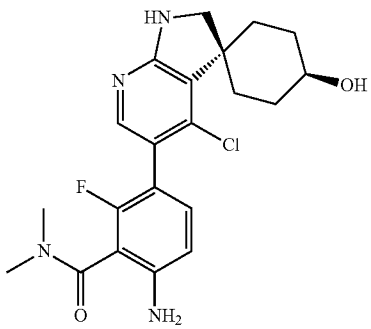 [SMILES: CN(C)C(=O)c1c(N)ccc(-c2cnc3c(c2Cl)[C@]2(CC[C@H](O)CC2)CN3)c1F] | 6-Amino-3-((1S,4s)-4'-chloro-4-hydroxy-1',2'-dihydrospiro[cyclohexane-1,3'-pyrrolo[2,3-b]pyridin]-5'-yl)-2-fluoro-N,N-dimethylbenzamide |
| 145 | 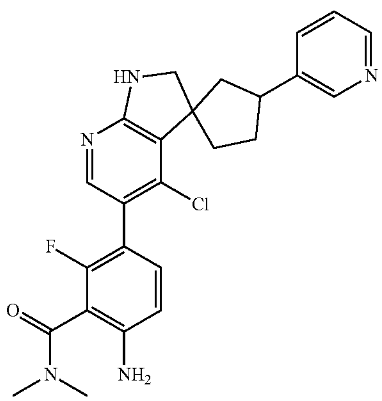 [SMILES: CN(C)C(=O)c1c(N)ccc(-c2cnc3c(c2Cl)C2(CCC(c4cccnc4)C2)CN3)c1F] | 6-Amino-3-(4'-chloro-3-(pyridin-3-yl)-1',2'-dihydrospiro[cyclopentane-1,3'-pyrrolo[2,3-b]pyridin]-5'-yl)-2-fluoro-N,N-dimethylbenzamide |
| 145a | 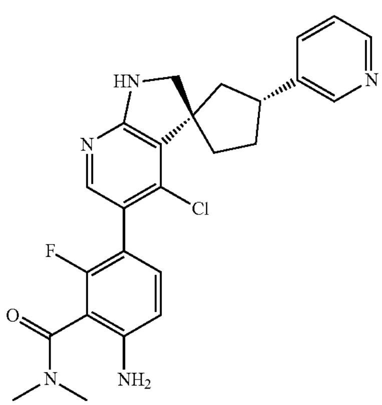 [SMILES: CN(C)C(=O)c1c(N)ccc(-c2cnc3c(c2Cl)[C@]2(CC[C@@H](c4cccnc4)C2)CN3)c1F] | 6-Amino-3-((1R,3R)-4'-chloro-3-(pyridin-3-yl)-1',2'-dihydrospiro[cyclopentane-1,3'-pyrrolo[2,3-b]pyridin]-5'-yl)-2-fluoro-N,N-dimethylbenzamide<br>6-Amino-3-((1S, 3S)-4'-chloro-3-(pyridin-3-yl)-1',2'-dihydrospiro[cyclopentane-1,3'-pyrrolo[2,3-b]pyridin]-5'-yl)-2-fluoro-N,N-dimethylbenzamide |
| 145b<br>145c | | 6-Amino-3-((1R,3S)-4'-chloro-3-(pyridin-3-yl)-1',2'-dihydrospiro[cyclopentane-1,3'-pyrrolo[2,3-b]pyridin]-5'-yl)-2-fluoro-N,N-dimethylbenzamide<br>6-Amino-3-((1S, 3R)-4'-chloro-3-(pyridin-3-yl)-1',2'-dihydrospiro[cyclopentane-1,3'-pyrrolo[2,3-b]pyridin]-5'-yl)-2-fluoro-N,N-dimethylbenzamide |

TABLE 1-continued

| No. | Structure | Name |
|---|---|---|
| 146 | | 6-Amino-3-(4'-chloro-3-hydroxy-4-(1H-1,2,3-triazol-1-yl)-1',2'-dihydrospiro[cyclopentane-1,3'-pyrrolo[2,3-b]pyridin]-5'-yl)-2-fluoro-N,N-dimethylbenzamide |
| 146a | 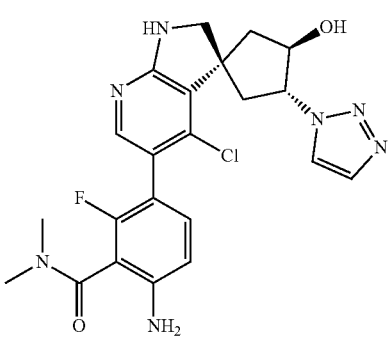 [SMILES: CN(C)C(=O)c1c(N)ccc(-c2cnc3c(c2Cl)[C@]2(CN3)C[C@@H](O)[C@H](n3ccnn3)C2)c1F] | 6-Amino-3-((1R,3S, 4S)-4'-chloro-3-hydroxy-4-(1H-1,2,3-triazol-1-yl)-1',2'-dihydrospiro[cyclopentane-1,3'-pyrrolo[2,3-b]pyridin]-5'-yl)-2-fluoro-N,N-dimethylbenzamide<br>6-Amino-3-((1S, 3R,4R)-4'-chloro-3-hydroxy-4-(1H-1,2,3-triazol-1-yl)-1'2'-dihydrospiro[ cyclopentane-1,3'-pyrrolo[2,3-b]pyridin]-5'-yl)-2-fluoro-N,N-dimethylbenzamide |
| 146b | 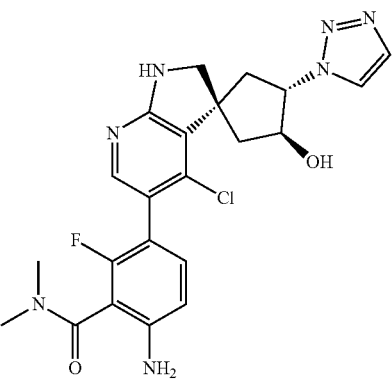 [SMILES: CN(C)C(=O)c1c(N)ccc(-c2cnc3c(c2Cl)[C@@]2(CN3)C[C@H](O)[C@@H](n3ccnn3)C2)c1F] | 6-Amino-3-((1R,3R,4R)-4'-chloro-3-hydroxy-4-(1H-1,2,3-triazol-1-yl)-1',2'-dihydrospiro[cyclopentane-1,3'-pyrrolo[2,3-b]pyridin]-5'-yl)-2-fluoro-N,N-dimethylbenzamide<br>6-Amino-3-((1S, 3S, 4S)-4'-chloro-3-hydroxy-4-(1H-1,2,3-triazol-1-yl)-1'2'-dihydrospiro[ cyclopentane-1,3'-pyrrolo[2,3-b]pyridin]-5'-yl)-2-fluoro-N,N-dimethylbenzamide |
| 147 | 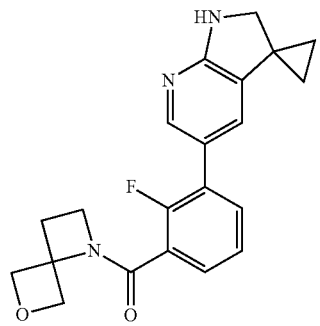 [SMILES: O=C(c1cccc(-c2cnc3c(c2)C2(CC2)CN3)c1F)N1CCC12COC2] | (3-(1',2'-dihydrospiro[cyclopropane-1,3'-pyrrolo[2,3-b]pyridin]-5'-yl)-2-fluorophenyl)(6-oxa-1-azaspiro[3.3]heptan-1-yl)methanone |
| 148 | | 6-Amino-3-(4'-chloro-4-(4-methyl-1H-pyrazol-1-yl)-1',2'-dihydrospiro[cyclohexane-1,3'-pyrrolo[2,3-b]pyridin]-5'-yl)-2-fluoro-N,N-dimethylbenzamide |
| 148a | 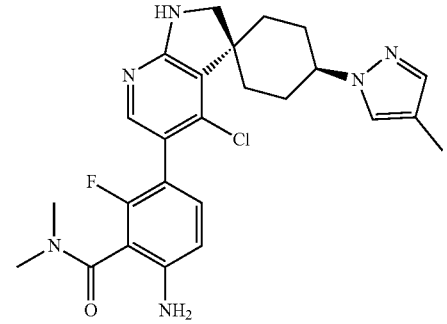 | 6-Amino-3-((1S,4s)-4'-chloro-4-(4-methyl-1H-pyrazol-1-yl)-1',2'-dihydrospiro[cyclohexane-1,3'-pyrrolo[2,3-b]pyridin]-5'-yl)-2-fluoro-N,N-dimethylbenzamide |

TABLE 1-continued

| No. | Structure | Name |
|---|---|---|
| 149 | 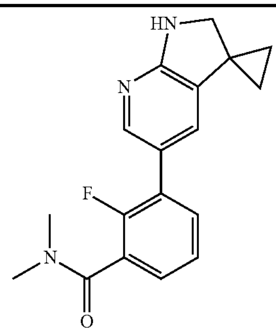 | 3-(1',2'-dihydrospiro[cyclopropane-1,3'-pyrrolo[2,3-b]pyridin]-5'-yl)-2-fluoro-N,N-dimethylbenzamide |
| 150 | | 6-Amino-3-((1RS,2SR)-4'-chloro-2-ethyl-1',2'-dihydrospiro[cyclopropane-1,3'-pyrrolo[2,3-b]pyridin]-5'-yl)-2-fluoro-N,N-dimethylbenzamide |
| 150a | 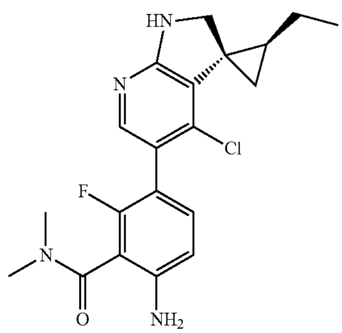 [SMILES: CC[C@H]1C[C@@]12CNc1ncc(-c3ccc(N)c(C(=O)N(C)C)c3F)c(Cl)c12] | 6-Amino-3-((1R,2S)-4'-chloro-2-ethyl-1',2'-dihydrospiro[cyclopropane-1,3'-pyrrolo[2,3-b]pyridin]-5'-yl)-2-fluoro-N,N-dimethylbenzamide 6-Amino-3-((1S,2R)-4'-chloro-2-ethyl-1',2'-dihydrospiro[cyclopropane-1,3'-pyrrolo[2,3-b]pyridin]-5'-yl)-2-fluoro-N,N-dimethylbenzamide |
| 150b | 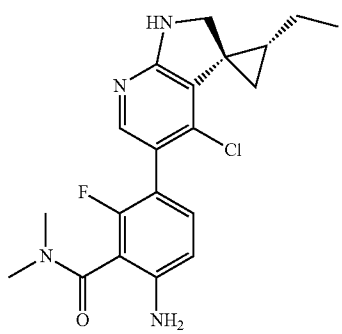 [SMILES: CC[C@@H]1C[C@@]12CNc1ncc(-c3ccc(N)c(C(=O)N(C)C)c3F)c(Cl)c12] | 6-Amino-3-((1R,2R)-4'-chloro-2-ethyl-1',2'-dihydrospiro[cyclopropane-1,3'-pyrrolo[2,3-b]pyridin]-5'-yl)-2-fluoro-N,N-dimethylbenzamide 6-Amino-3-((1S,2S)-4'-chloro-2-ethyl-1',2'-dihydrospiro[cyclopropane-1,3'-pyrrolo[2,3-b]pyridin]-5'-yl)-2-fluoro-N,N-dimethylbenzamide |
| 151 | | 6-Amino-3-(4'-chloro-3-cyano-3-methyl-1',2'-dihydrospiro[cyclopentane-1,3'-pyrrolo[2,3-b]pyridin]-5'-yl)-2-fluoro-N,N-dimethylbenzamide |
| 151a | 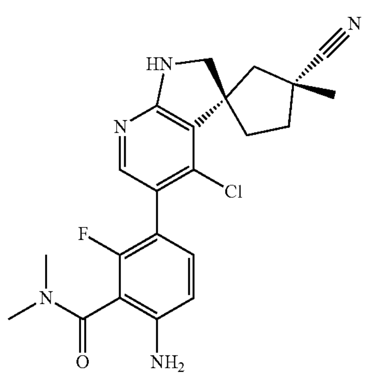 [SMILES: CN(C)C(=O)c1c(N)ccc(-c2cnc3c(c2Cl)[C@]2(CC[C@@](C)(C#N)C2)CN3)c1F] | 6-Amino-3-((1R,3R)-4'-chloro-3-cyano-3-methyl-1',2'-dihydrospiro[cyclopentane-1,3'-pyrrolo[2,3-b]pyridin]-5'-yl)-2-fluoro-N,N-dimethylbenzamide 6-Amino-3-((1S,3S)-4'-chloro-3-cyano-3-methyl-1',2'-dihydrospiro[cyclopentane-1,3'-pyrrolo[2,3-b]pyridin]-5'-yl)-2-fluoro-N,N-dimethylbenzamide |
| 152 | | 6-Amino-3-(4'-chloro-3-cyano-3-ethyl-1',2'-dihydrospiro[cyclopentane-1,3'-pyrrolo[2,3-b]pyridin]-5'-yl)-2-fluoro-N,N-dimethylbenzamide |

TABLE 1-continued

| No. | Structure | Name |
| --- | --- | --- |
| 152a | 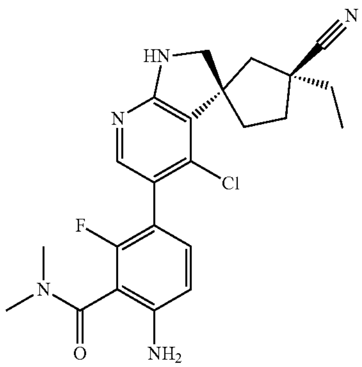 [SMILES: CC[C@]1(C#N)CC[C@@]2(CNc3ncc(-c4ccc(N)c(C(=O)N(C)C)c4F)c(Cl)c32)C1] | 6-Amino-3-((1R,3S)-4'-chloro-3-cyano-3-ethyl-1',2'-dihydrospiro[cyclopentane-1,3'-pyrrolo[2,3-b]pyridin]-5'-yl)-2-fluoro-N,N-dimethylbenzamide<br>6-Amino-3-((1S,3R)-4'-chloro-3-cyano-3-ethyl-1',2'-dihydrospiro[cyclopentane-1,3'-pyrrolo[2,3-b]pyridin]-5'-yl)-2-fluoro-N,N-dimethylbenzamide |
| 153 | | 5'-(4-Amino-3-(dimethylcarbamoyl)-2-fluorophenyl)-4'-chloro-3-ethyl-1'2'-dihydrospiro[cyclopentane-1,3'-pyrrolo[2,3-b]pyridine]-3-carboxamide |
| 153a | 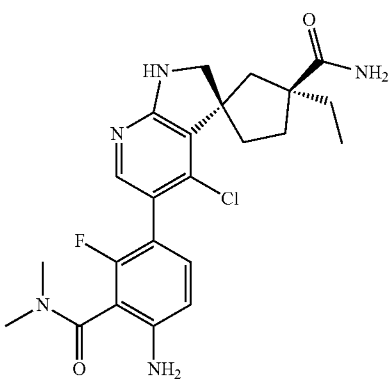 [SMILES: CC[C@]1(C(N)=O)CC[C@@]2(CNc3ncc(-c4ccc(N)c(C(=O)N(C)C)c4F)c(Cl)c32)C1] | (1R,3S)-5'-(4-Amino-3-(dimethylcarbamoyl)-2-fluorophenyl)-4'-chloro-3-ethyl-1',2'-dihydrospiro[cyclopentane-1,3'-pyrrolo[2,3-b]pyridine]-3-carboxamide<br>(1S,3R)-5'-(4-Amino-3-(dimethylcarbamoyl)-2-fluorophenyl)-4'-chloro-3-ethyl-1',2'-dihydrospiro[cyclopentane-1,3'-pyrrolo[2,3-b]pyridine]-3-carboxamide |
| 154 | | 1-(3-(1',2'-dihydrospiro[cyclopropane-1,3'-pyrrolo[2,3-b]pyridin]-5'-yl)-2-fluorobenzoyl)pyrrolidine-2-carbonitrile |
| 154a | 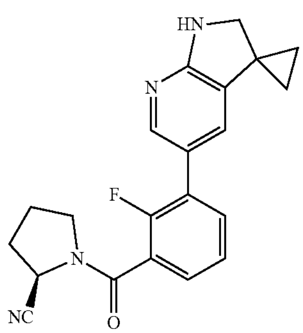 [SMILES: N#C[C@H]1CCCN1C(=O)c1cccc(-c2cnc3c(c2)C2(CC2)CN3)c1F] | (R)-1-(3-(1',2'-dihydrospiro[cyclopropane-1,3'-pyrrolo[2,3-b]pyridin]-5'-yl)-2-fluorobenzoyl)pyrrolidine-2-carbonitrile |
| 155 | | 5'-(4-Amino-3-(dimethylcarbamoyl)-2-fluorophenyl)-4'-chloro-3-methyl-1'2'-dihydrospiro[cyclopentane-1,3'-pyrrolo[2,3-b]pyridine]-3-carboxamide |

TABLE 1-continued

| No. | Structure | Name |
|---|---|---|
| 155a | 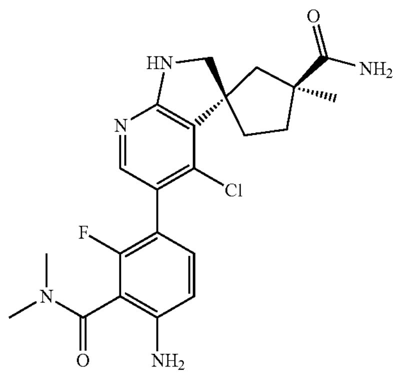 [SMILES: CN(C)C(=O)c1c(N)ccc(-c2cnc3c(c2Cl)[C@]2(CC[C@](C)(C(N)=O)C2)CN3)c1F] | (1R,3S)-5'-(4-Amino-3-(dimethylcarbamoyl)-2-fluorophenyl)-4'-chloro-3-methyl-1',2'-dihydrospiro[cyclopentane-1,3'-pyrrolo[2,3-b]pyridine]-3-carboxamide (1S,3R)-5'-(4-Amino-3-(dimethylcarbamoyl)-2-fluorophenyl)-4'-chloro-3-methyl-1',2'-dihydrospiro [cyclopentane-1,3'-pyrrolo[2,3-b]pyridine]-3-carboxamide |
| 155b | 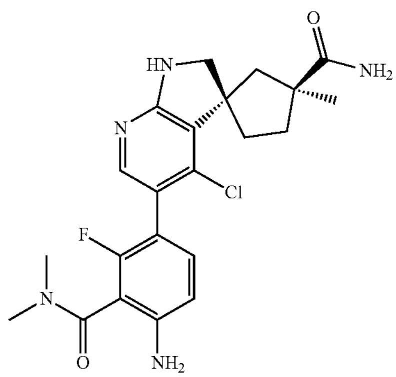 [SMILES: CN(C)C(=O)c1c(N)ccc(-c2cnc3c(c2Cl)[C@]2(CC[C@](C)(C(N)=O)C2)CN3)c1F] | (1R,3S)-5'-(4-Amino-3-(dimethylcarbamoyl)-2-fluorophenyl)-4'-chloro-3-methyl-1',2'-dihydrospiro[cyclopentane-1,3'-pyrrolo[2,3-b]pyridine]-3-carboxamide (1S,3R)-5'-(4-Amino-3-(dimethylcarbamoyl)-2-fluorophenyl)-4'-chloro-3-methyl-1',2'-dihydrospiro[cyclopentane-1,3'-pyrrolo[2,3-b]pyridine]-3-carboxamide |
| 156 | | 6-Amino-3-(4'-chloro-3-methyl-3-(3-methyl-1,2,4-oxadiazol-5-yl)-1'2'-dihydrospiro[cyclopentane-1,3'-pyrrolo[2,3-b]pyridin]-5'-yl)-2-fluoro-N,N-dimethylbenzamide |
| 156a | | 6-Amino-3-((1R,3S)-4'-chloro-3-methyl-3-(3-methyl-1,2,4-oxadiazol-5-yl)-1',2'-dihydrospiro[cyclopentane-1,3'-pyrrolo[2,3-b]pyridin]-5'-yl)-2-fluoro-N,N-dimethylbenzamide 6-Amino-3-((1S,3R)-4'-chloro-3-methyl-3-(3-methyl-1,2,4-oxadiazol-5-yl)-1',2'-dihydrospiro[cyclopentane-1,3'-pyrrolo[2,3-b]pyridin]-5'-yl)-2-fluoro-N,N-dimethylbenzamide |
| 157 | | 6-Amino-3-(3-(3-amino-5-methyl-1H-1,2,4-triazol-1-yl)-4'-chloro-1',2'-dihydrospiro[cyclopentane-1,3'-pyrrolo[2,3-b]pyridin]-5'-yl)-2-fluoro-N,N-dimethylbenzamide |

TABLE 1-continued

| No. | Structure | Name |
| --- | --- | --- |
| 157a | 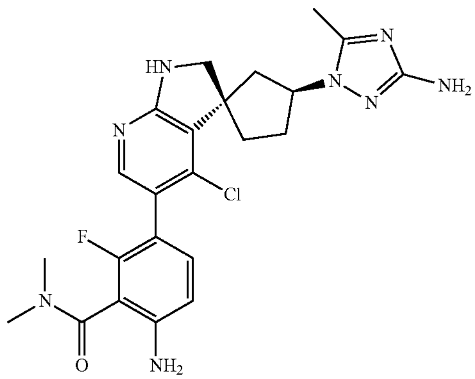 [SMILES: Cc1nc(N)nn1[C@H]1CC[C@@]2(CNc3ncc(-c4ccc(N)c(C(=O)N(C)C)c4F)c(Cl)c32)C1] | 6-Amino-3-((1R,3S)-3-(3-amino-5-methyl-1H-1,2,4-triazol-1-yl)-4'-chloro-1',2'-dihydrospiro[cyclopentane-1,3'-pyrrolo[2,3-b]pyridin]-5'-yl)-2-fluoro-N,N-dimethylbenzamide<br>6-Amino-3-((1S,3R)-3-(3-amino-5-methyl-1H-1,2,4-triazol-1-yl)-4'-chloro-1',2'-dihydrospiro[cyclopentane-1,3'-pyrrolo[2,3-b]pyridin]-5'-yl)-2-fluoro-N,N-dimethylbenzamide |
| 158 | | 6-Amino-3-(3-(5-amino-3-methyl-1H-1,2,4-triazol-1-yl)-4'-chloro-1',2'-dihydrospiro[cyclopentane-1,3'-pyrrolo[2,3-b]pyridin]-5'-yl)-2-fluoro-N,N-dimethylbenzamide |
| 158a | 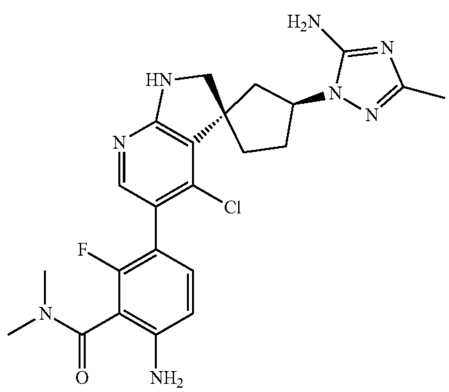 | 6-Amino-3-((1R,3S)-3-(5-amino-3-methyl-1H-1,2,4-triazol-1-yl)-4'-chloro-1',2'-dihydrospiro[cyclopentane-1,3'-pyrrolo[2,3-b]pyridin]-5'-yl)-2-fluoro-N,N-dimethylbenzamide<br>6-Amino-3-((1S,3R)-3-(5-amino-3-methyl-1H-1,2,4-triazol-1-yl)-4'-chloro-1',2'-dihydrospiro[cyclopentane-1,3'-pyrrolo[2,3-b]pyridin]-5'-yl)-2-fluoro-N,N-dimethylbenzamide |
| 159 | | 6-Amino-3-(4'-chloro-3-(3-methyl-1H-pyrazol-1-yl)-1',2'-dihydrospiro[cyclopentane-1,3'-pyrrolo[2,3-b]pyridin]-5'-yl)-2-fluoro-N,N-dimethylbenzamide |
| 159a | 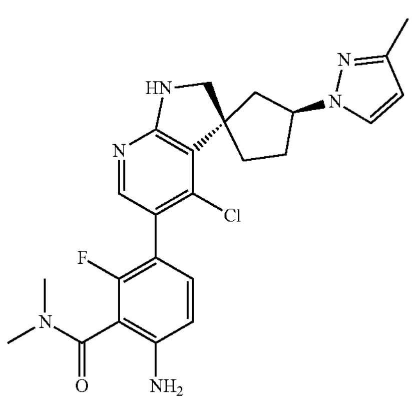 | 6-Amino-3-((1R,3S)-4'-chloro-3-(3-methyl-1H-pyrazol-1-yl)-1',2'-dihydrospiro[cyclopentane-1,3'-pyrrolo[2,3-b]pyridin]-5'-yl)-2-fluoro-N,N-dimethylbenzamide<br>6-Amino-3-((1S,3R)-4'-chloro-3-(3-methyl-1H-pyrazol-1-yl)-1',2'-dihydrospiro[cyclopentane-1,3'-pyrrolo[2,3-b]pyridin]-5'-yl)-2-fluoro-N,N-dimethylbenzamide |
| 160 | | 6-Amino-3-(4'-chloro-3-(5-methyl-1H-pyrazol-1-yl)-1',2'-dihydrospiro[cyclopentane-1,3'-pyrrolo[2,3-b]pyridin]-5'-yl)-2-fluoro-N,N-dimethylbenzamide |

TABLE 1-continued

| No. | Structure | Name |
|---|---|---|
| 160a | 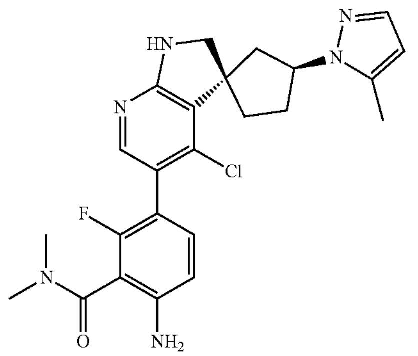 | 6-Amino-3-((1R,3S)-4'-chloro-3-(5-methyl-1H-pyrazol-1-yl)-1',2'-dihydrospiro[cyclopentane-1,3'-pyrrolo[2,3-b]pyridin]-5'-yl)-2-fluoro-N,N-dimethylbenzamid<br>6-Amino-3-((1S,3R)-4'-chloro-3-(5-methyl-1H-pyrazol-1-yl)-1',2'-dihydrospiro[cyclopentane-1,3'-pyrrolo[2,3-b]pyridin]-5'-yl)-2-fluoro-N,N-dimethylbenzamide e |
| 161 | | 6-Amino-3-(4'-chloro-3-(5-cyano-3-methyl-1H-pyrazol-1-yl)-1',2'-dihydrospiro[cyclopentane-1,3'-pyrrolo[2,3-b]pyridin]-5'-yl)-2-fluoro-N,N-dimethylbenzamide |
| 161a | 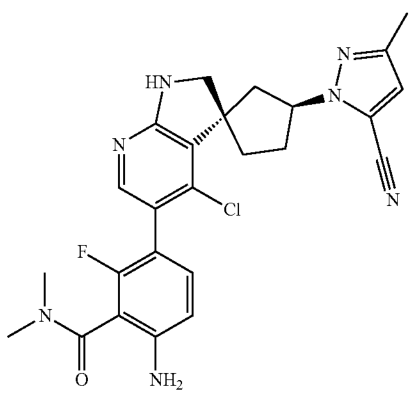 | 6-Amino-3-((1R,3S)-4'-chloro-3-(5-cyano-3-methyl-1H-pyrazol-1-yl)-1',2'-dihydrospiro[cyclopentane-1,3'-pyrrolo[2,3-b]pyridin]-5'-yl)-2-fluoro-N,N-dimethylbenzamide<br>6-Amino-3-((1S,3R)-4'-chloro-3-(5-cyano-3-methyl-1H-pyrazol-1-yl)-1',2'-dihydrospiro[cyclopentane-1,3'-pyrrolo[2,3-b]pyridin]-5'-yl)-2-fluoro-N,N-dimethylbenzamide |
| 162 | | 6-Amino-3-(4'-chloro-3-(3-cyano-5-methyl-1H-pyrazol-1-yl)-1',2'-dihydrospiro[cyclopentane-1,3'-pyrrolo[2,3-b]pyridin]-5'-yl)-2-fluoro-N,N-dimethylbenzamide |
| 162a | 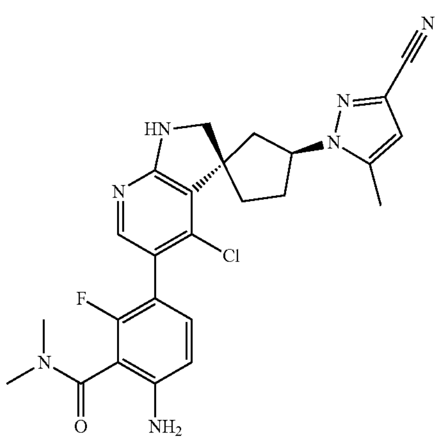 [SMILES: Cc1cc(C#N)nn1[C@H]1CC[C@@]2(CNc3ncc(-c4ccc(N)c(C(=O)N(C)C)c4F)c(Cl)c32)C1] | 6-Amino-3-((1R,3S)-4'-chloro-3-(3-cyano-5-methyl-1H-pyrazol-1-yl)-1'2'-dihydrospiro[ cyclopentane-1,3'-pyrrolo[2,3-b]pyridin]-5'-yl)-2-fluoro-N,N-dimethylbenzamide<br>6-Amino-3-((1S,3R)-4'-chloro-3-(3-cyano-5-methyl-1H-pyrazol-1-yl)-1',2'-dihydrospiro[cyclopentane-1,3'-pyrrolo[2,3-b]pyridin]-5'-yl)-2-fluoro-N,N-dimethylbenzamide |
| 163 | | 6-Amino-3-(4'-chloro-3-(3,5-dimethyl-1H-pyrazol-1-yl)-1'2'-dihydrospiro[cyclopentane-1,3'-pyrrolo[2,3-b]pyridin]-5'-yl)-2-fluoro-N,N-dimethylbenzamide |

TABLE 1-continued

| No. | Structure | Name |
|---|---|---|
| 163a | 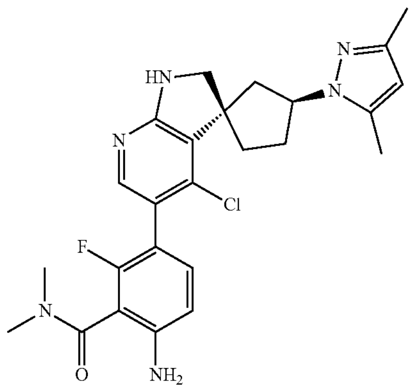 | 6-Amino-3-((1R,3S)-4'-chloro-3-(3,5-dimethyl-1H-pyrazol-1-yl)-1',2'-dihydrospiro[cyclopentane-1,3'-pyrrolo[2,3-b]pyridin]-5'-yl)-2-fluoro-N,N-dimethylbenzamide<br>6-Amino-3-((1S,3R)-4'-chloro-3-(3,5-dimethyl-1H-pyrazol-1-yl)-1',2'-dihydrospiro[cyclopentane-1,3'-pyrrolo[2,3-b]pyridin]-5'-yl)-2-fluoro-N,N-dimethylbenzamide |
| 164 | | 6-Amino-3-(4'-chloro-3-(4-(trifluoromethyl)-1H-pyrazol-1-yl)-1',2'-dihydrospiro[cyclopentane-1,3'-pyrrolo[2,3-b]pyridin]-5'-yl)-2-fluoro-N,N-dimethylbenzamide |
| 164a | 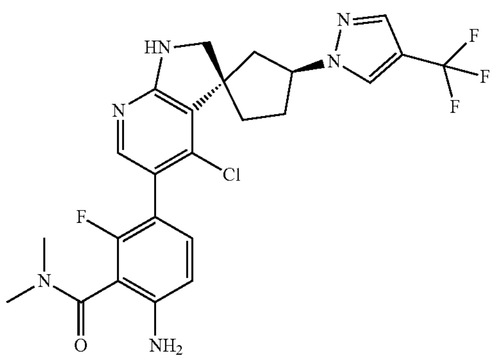 [SMILES: CN(C)C(=O)c1c(N)ccc(-c2cnc3c(c2Cl)[C@]2(CC[C@H](n4cc(C(F)(F)F)cn4)C2)CN3)c1F] | 6-Amino-3-((1R,3S)-4'-chloro-3-(4-(trifluoromethyl)-1H-pyrazol-1-yl)-1',2'-dihydrospiro[ cyclopentane-1,3'-pyrrolo[2,3-b]pyridin]-5'-yl)-2-fluoro-N,N-dimethylbenzamide<br>6-Amino-3-((1S,3R)-4'-chloro-3-(4-(trifluoromethyl)-1H-pyrazol-1-yl)-1',2'-dihydrospiro[cyclopentane-1,3'-pyrrolo[2,3-b]pyridin]-5'-yl)-2-fluoro-N,N-dimethylbenzamide |
| 165 | | 6-Amino-2-fluoro-3-(4'-methoxy-2-methyl-1',2'-dihydrospiro[cyclopropane-1,3'-pyrrolo[2,3-b]pyridin]-5'-yl)-N,N-dimethylbenzamide |
| 165a | 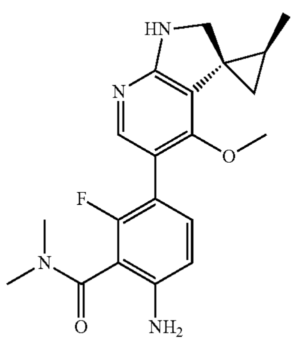 | 6-Amino-2-fluoro-3-((1R,2S)-4'-methoxy-2-methyl-1',2'-dihydrospiro[cyclopropane-1,3'-pyrrolo[2,3-b]pyridin]-5'-yl)-N,N-dimethylbenzamide<br>6-Amino-2-fluoro-3-((1S, 2R)-4'-methoxy-2-methyl-1',2'-dihydrospiro[cyclopropane-1,3'-pyrrolo[2,3-b]pyridin]-5'-yl)-N,N-dimethylbenzamide |
| 166 | 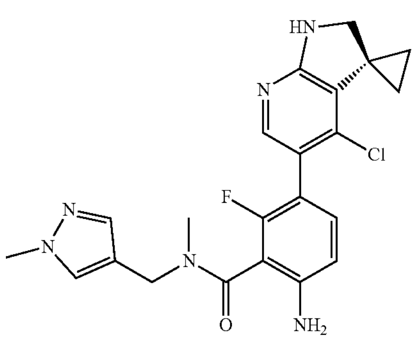 | 6-Amino-3-(4'-chloro-1',2'-dihydrospiro[cyclopropane-1,3'-pyrrolo[2,3-b]pyridin]-5'-yl)-2-fluoro-N-methyl-N-((1-methyl-1H-pyrazol-4-yl)methyl)benzamide |

TABLE 1-continued

| No. | Structure | Name |
|---|---|---|
| 167 | | 6-Amino-3-(4'-chloro-3-(2-methyl-1H-imidazol-1-yl)-1',2'-dihydrospiro[cyclopentane-1,3'-pyrrolo[2,3-b]pyridin]-5'-yl)-2-fluoro-N,N-dimethylbenzamide |
| 167a | 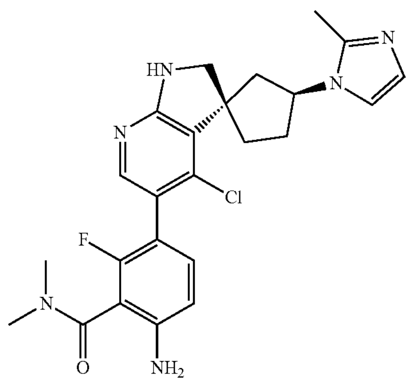 [SMILES: Cc1nccn1[C@H]1CC[C@@]2(CNc3ncc(-c4ccc(N)c(C(=O)N(C)C)c4F)c(Cl)c32)C1] | 6-Amino-3-((1R,3S)-4'-chloro-3-(2-methyl-1H-imidazol-1-yl)-1',2'-dihydrospiro[cyclopentane-1,3'-pyrrolo[2,3-b]pyridin]-5'-yl)-2-fluoro-N,N-dimethylbenzamide<br>6-Amino-3-((1S,3R)-4'-chloro-3-(2-methyl-1H-imidazol-1-yl)-1',2'-dihydrospiro[cyclopentane-1,3'-pyrrolo[2,3-b]pyridin]-5'-yl)-2-fluoro-N,N-dimethylbenzamide |
| 168 | | 6-Amino-3-(4'-chloro-3-(3-(trifluoromethyl)-1H-pyrazol-1-yl)-1',2'-dihydrospiro[cyclopentane-1,3'-pyrrolo[2,3-b]pyridin]-5'-yl)-2-fluoro-N,N-dimethylbenzamide |
| 168a | 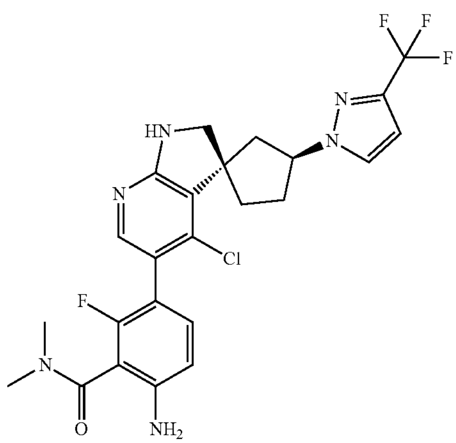 [SMILES: CN(C)C(=O)c1c(N)ccc(-c2cnc3c(c2Cl)[C@]2(CC[C@H](n4ccc(C(F)(F)F)n4)C2)CN3)c1F] | 6-Amino-3-((1R,3S)-4'-chloro-3-(3-(trifluoromethyl)-1H-pyrazol-1-yl)-1',2'-dihydrospiro[cyclopentane-1,3'-pyrrolo[2,3-b]pyridin]-5'-yl)-2-fluoro-N,N-dimethylbenzamide<br>6-Amino-3-((1S,3R)-4'-chloro-3-(3-(trifluoromethyl)-1H-pyrazol-1-yl)-1',2'-dihydrospiro[cyclopentane-1,3'-pyrrolo[2,3-b]pyridin]-5'-yl)-2-fluoro-N,N-dimethylbenzamide |
| 169 | | 6-Amino-3-(4'-chloro-3-(5-(trifluoromethyl)-1H-pyrazol-1-yl)-1',2'-dihydrospiro[cyclopentane-1,3'-pyrrolo[2,3-b]pyridin]-5'-yl)-2-fluoro-N,N-dimethylbenzamide |
| 169a | 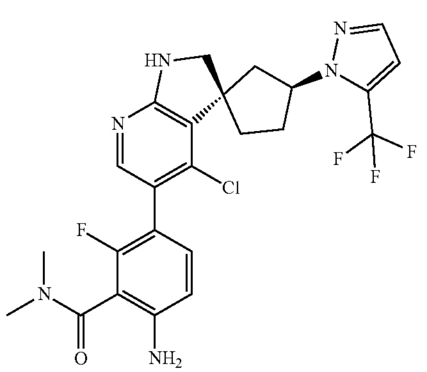 [SMILES: CN(C)C(=O)c1c(N)ccc(-c2cnc3c(c2Cl)[C@]2(CC[C@H](n4nccc4C(F)(F)F)C2)CN3)c1F] | 6-Amino-3-((1R,3S)-4'-chloro-3-(5-(trifluoromethyl)-1H-pyrazol-1-yl)-1',2'-dihydrospiro[ cyclopentane-1,3'-pyrrolo[2,3-b]pyridin]-5'-yl)-2-fluoro-N,N-dimethylbenzamide<br>6-Amino-3-((1S,3R)-4'-chloro-3-(5-(trifluoromethyl)-1H-pyrazol-1-yl)-1',2'-dihydrospiro[ cyclopentane-1,3'-pyrrolo[2,3-b]pyridin]-5'-yl)-2-fluoro-N,N-dimethylbenzamide |
| 170 | | 6-Amino-3-(4'-chloro-3-(4-ethyl-1H-pyrazol-1-yl)-1',2'-dihydrospiro[cyclopentane-1,3'-pyrrolo[2,3-b]pyridin]-5'-yl)-2-fluoro-N,N-dimethylbenzamide |

TABLE 1-continued

| No. | Structure | Name |
|---|---|---|
| 170a | 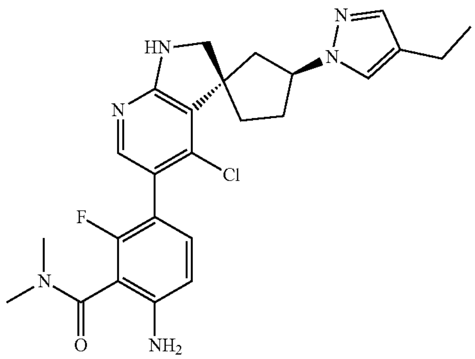 [SMILES: CCc1cnn([C@H]2CC[C@@]3(CNc4ncc(-c5ccc(N)c(C(=O)N(C)C)c5F)c(Cl)c43)C2)c1] | 6-Amino-3-((1R,3S)-4'-chloro-3-(4-ethyl-1H-pyrazol-1-yl)-1',2'-dihydrospiro[cyclopentane-1,3'-pyrrolo[2,3-b]pyridin]-5'-yl)-2-fluoro-N,N-dimethylbenzamide<br>6-Amino-3-((1S,3R)-4'-chloro-3-(4-ethyl-1H-pyrazol-1-yl)-1',2'-dihydrospiro[cyclopentane-1,3'-pyrrolo[2,3-b]pyridin]-5'-yl)-2-fluoro-N,N-dimethylbenzamide |
| 171 | | 6-Amino-3-(4'-chloro-3-(4-chloro-1H-pyrazol-1-yl)-1',2'-dihydrospiro[cyclopentane-1,3'-pyrrolo[2,3-b]pyridin]-5'-yl)-2-fluoro-N,N-dimethylbenzamide |
| 171a | 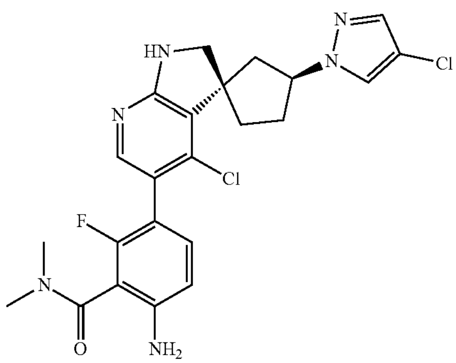 [SMILES: CN(C)C(=O)c1c(N)ccc(-c2cnc3c(c2Cl)[C@]2(CC[C@H](n4cc(Cl)cn4)C2)CN3)c1F] | 6-Amino-3-((1R,3S)-4'-chloro-3-(4-chloro-1H-pyrazol-1-yl)-1',2'-dihydrospiro[cyclopentane-1,3'-pyrrolo[2,3-b]pyridin]-5'-yl)-2-fluoro-N,N-dimethylbenzamide<br>6-Amino-3-((1S,3R)-4'-chloro-3-(4-chloro-1H-pyrazol-1-yl)-1',2'-dihydrospiro[cyclopentane-1,3'-pyrrolo[2,3-b]pyridin]-5'-yl)-2-fluoro-N,N-dimethylbenzamide |
| 172 | 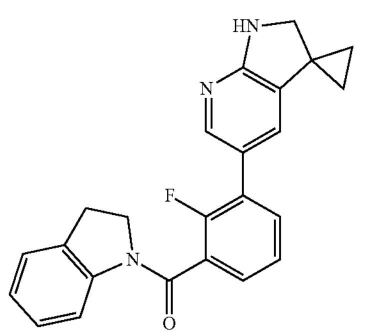 [SMILES: O=C(c1cccc(-c2cnc3c(c2)C2(CC2)CN3)c1F)N1CCc2ccccc21] | (3-(1',2'-dihydrospiro[cyclopropane-1,3'-pyrrolo[2,3-b]pyridin]-5'-yl)-2-fluorophenyl)(indolin-1-yl)methanone |
| 173 | | 6-Amino-3-(4'-chloro-3-(pyridin-2-yloxy)-1',2'-dihydrospiro[cyclopentane-1,3'-pyrrolo[2,3-b]pyridin]-5'-yl)-2-fluoro-N,N-dimethylbenzamide |
| 173a | 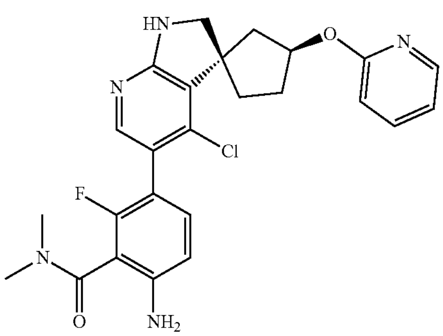 [SMILES: CN(C)C(=O)c1c(N)ccc(-c2cnc3c(c2Cl)[C@]2(CC[C@H](Oc4ccccn4)C2)CN3)c1F] | 6-Amino-3-((1R,3S)-4'-chloro-3-(pyridin-2-yloxy)-1',2'-dihydrospiro[cyclopentane-1,3'-pyrrolo[2,3-b]pyridin]-5'-yl)-2-fluoro-N,N-dimethylbenzamide<br>6-Amino-3-((1S,3R)-4'-chloro-3-(pyridin-2-yloxy)-1',2'-dihydrospiro[cyclopentane-1,3'-pyrrolo[2,3-b]pyridin]-5'-yl)-2-fluoro-N,N-dimethylbenzamide |

TABLE 1-continued

| No. | Structure | Name |
|---|---|---|
| 174 | | (3-(1',2'-dihydrospiro[cyclopropane-1,3'-pyrrolo[2,3-b]pyridin]-5'-yl)-2-fluorophenyl)(2-(1-methyl-1H-pyrazol-4-yl)pyrrolidin-1-yl)methanone |
| 174a | 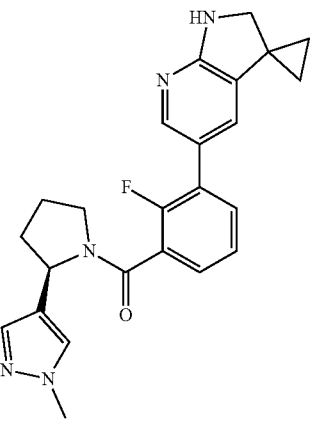 [SMILES: Cn1cc([C@H]2CCCN2C(=O)c2cccc(-c3cnc4c(c3)C3(CC3)CN4)c2F)cn1] | (R)-(3-(1',2'-dihydrospiro[cyclopropane-1,3'-pyrrolo[2,3-b]pyridin]-5'-yl)-2-fluorophenyl)(2-(1-methyl-1H-pyrazol-4-yl)pyrrolidin-1-yl)methanone (S)-(3-(1',2'-dihydrospiro[cyclopropane-1,3'-pyrrolo[2,3-b]pyridin]-5'-yl)-2-fluorophenyl)(2-(1-methyl-1H-pyrazol-4-yl)pyrrolidin-1-yl)methanone |
| 174b | 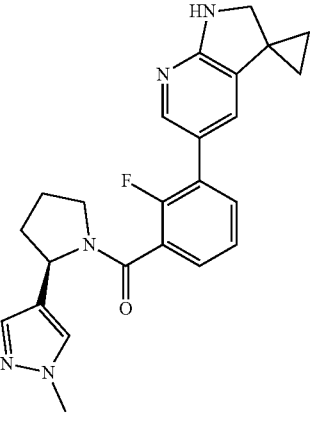 [SMILES: Cn1cc([C@H]2CCCN2C(=O)c2cccc(-c3cnc4c(c3)C3(CC3)CN4)c2F)cn1] | (R)-(3-(1',2'-dihydrospiro[cyclopropane-1,3'-pyrrolo[2,3-b]pyridin]-5'-yl)-2-fluorophenyl)(2-(1-methyl-1H-pyrazol-4-yl) pyrrolidin-1-yl)methanone (S)-(3-(1',2'-dihydrospiro[cyclopropane-1,3'-b]pyridin]-5'-yl)-2-fluorophenyl)(2-(1-methyl-1H-pyrazol-4-yl) pyrrolidin-1-yl)methanone |
| 175 | | 3-(1',2'-dihydrospiro[cyclopropane-1,3'-pyrrolo[2,3-b]pyridin]-5'-yl)-2-fluorophenyl)(2-(1-methyl-1H-pyrazol-4-yl)piperidin-1-yl)methanone |
| 175a | 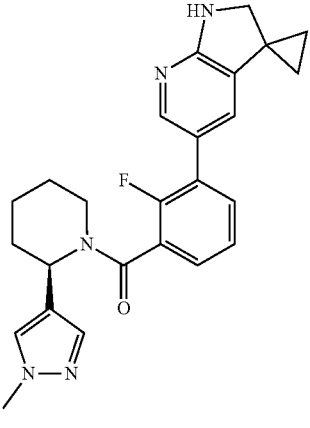 [SMILES: Cn1cc([C@H]2CCCCN2C(=O)c2cccc(-c3cnc4c(c3)C3(CC3)CN4)c2F)cn1] | (R)-(3-(1',2'-dihydrospiro[cyclopropane-1,3'-pyrrolo[2,3-b]pyridin]-5'-yl)-2-fluorophenyl)(2-(1-methyl-1H-pyrazol-4-yl)piperidin-1-yl)methanone (S)-(3-(1'2'-dihydrospiro[cyclopropane-1,3'-pyrrolo[2,3-b]pyridin]-5'-yl)-2-fluorophenyl)(2-(1-methyl-1H-pyrazol-4-yl)piperidin-1-yl)methanone |

TABLE 1-continued

| No. | Structure | Name |
|---|---|---|
| 175b | 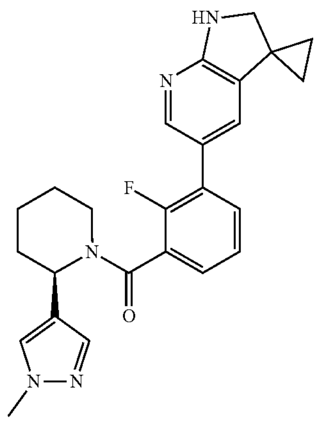 [SMILES: Cn1cc([C@H]2CCCCN2C(=O)c2cccc(-c3cnc4c(c3)C3(CC3)CN4)c2F)cn1] | (R)-(3-(1',2'-dihydrospiro[cyclopropane-1,3'-pyrrolo[2,3-b]pyridin]-5'-yl)-2-fluorophenyl)(2-(1-methyl-1H-pyrazol-4-yl)piperidin-1-yl)methanone<br>(S)-(3-(1',2'-dihydrospiro[cyclopropane-1,3'-pyrrolo[2,3-b]pyridin]-5'-yl)-2-fluorophenyl)(2-(1-methyl-1H-pyrazol-4-yl)piperidin-1-yl)methanone |
| 176 | 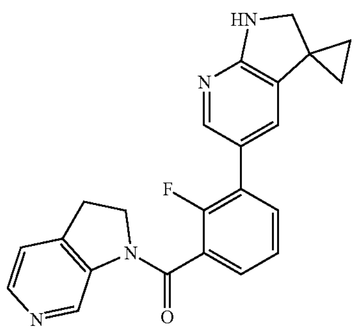 [SMILES: O=C(c1cccc(-c2cnc3c(c2)C2(CC2)CN3)c1F)N1CCc2ccncc21] | (2,3-dihydro-1H-pyrrolo[2,3-c]pyridin-1-yl)(3-(1',2'-dihydrospiro[cyclopropane-1,3'-pyrrolo[2,3-b]pyridin]-5'-yl)-2-fluorophenyl)methanone |
| 177 | | 6-Amino-3-(3-(3-amino-4-methyl-1H-pyrazol-1-yl)-4'-chloro-1',2'-dihydrospiro[cyclopentane-1,3'-pyrrolo[2,3-b]pyridin]-5'-yl)-2-fluoro-N,N-dimethylbenzamide |
| 177a | 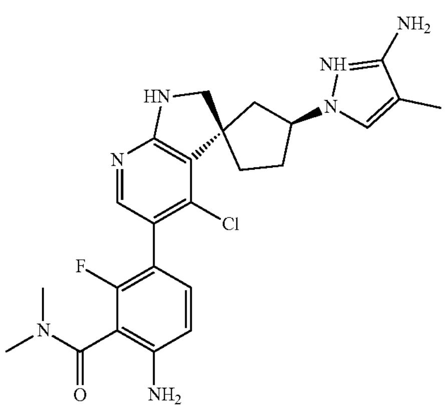 | 6-Amino-3-((1R,3S)-3-(3-amino-4-methyl-1H-pyrazol-1-yl)-4'-chloro-1',2'-dihydrospiro[cyclopentane-1,3'-pyrrolo[2,3-b]pyridin]-5'-yl)-2-fluoro-N,N-dimethylbenzamide<br>6-Amino-3-((1S,3R)-3-(3-amino-4-methyl-1H-pyrazol-1-yl)-4'-chloro-1',2'-dihydrospiro[cyclopentane-1,3'-pyrrolo[2,3-b]pyridin]-5'-yl)-2-fluoro-N,N-dimethylbenzamide |
| 178 | | 6-Amino-3-(3-(5-amino-4-methyl-1H-pyrazol-1-yl)-4'-chloro-1',2'-dihydrospiro[cyclopentane-1,3'-pyrrolo[2,3-b]pyridin]-5'-yl)-2-fluoro-N,N-dimethylbenzamide |

TABLE 1-continued

| No. | Structure | Name |
|---|---|---|
| 178a | 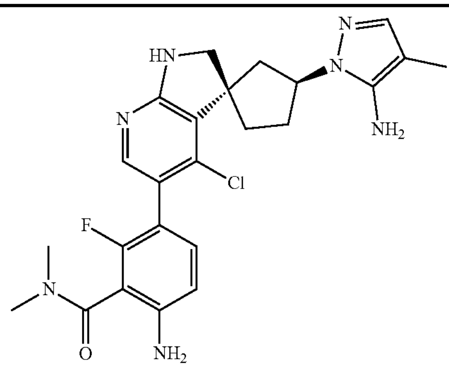 | 6-Amino-3-((1R,3S)-3-(5-amino-4-methyl-1H-pyrazol-1-yl)-4'-chloro-1',2'-dihydrospiro[cyclopentane-1,3'-pyrrolo[2,3-b]pyridin]-5'-yl)-2-fluoro-N,N-dimethylbenzamide 6-Amino-3-((1S,3R)-3-(5-amino-4-methyl-1H-pyrazol-1-yl)-4'-chloro-1',2'-dihydrospiro[cyclopentane-1,3'-pyrrolo[2,3-b]pyridin]-5'-yl)-2-fluoro-N,N-dimethylbenzamide |
| 179 | | 4'-Chloro-3-methyl-5'-(3-(1-methyl-2-oxo-1,2-dihydropyridin-3-yl)phenyl)-1',2'-dihydrospiro[cyclopentane-1,3'-pyrrolo[2,3-b]pyridine]-3-carboxamide |
| 179a 179b | 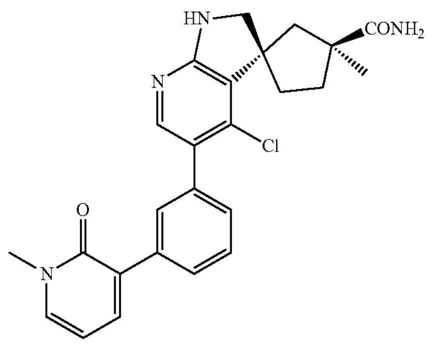 [SMILES: Cn1cccc(-c2cccc(-c3cnc4c(c3Cl)[C@]3(CC[C@](C)(C(N)=O)C3)CN4)c2)c1=O] | (1R,3S)-4'-Chloro-3-methyl-5'-(3-(1-methyl-2-oxo-1,2-dihydropyridin-3-yl)phenyl)-1',2' dihydrospiro[cyclopentane-1,3'-pyrrolo[2,3-b]pyridine]-3-carboxamide (1S,3R)-4'-Chloro-3-methyl-5'-(3-(1-methyl-2-oxo-1,2-dihydropyridin-3-yl)phenyl)-1',2'-dihydrospiro [cyclopentane-1,3'-pyrrolo[2,3-b]pyridine]-3-carboxamide |
| 180 | | 1-(5'-(4-Amino-3-(dimethylcarbamoyl)-2-fluorophenyl)-4'-chloro-1',2'-dihydrospiro[cyclopentane-1,3'-pyrrolo[2,3-b]pyridin]-3-yl)-1H-pyrazole-4-carboxamide |
| 180a | 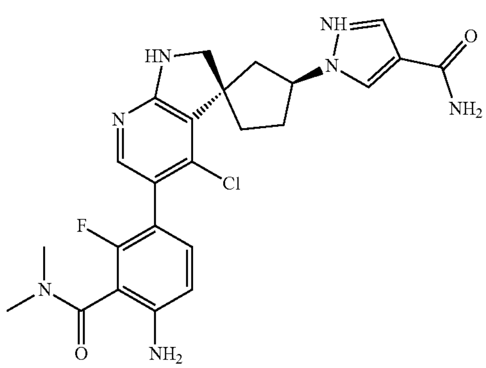 [SMILES: CN(C)C(=O)c1c(N)ccc(-c2cnc3c(c2Cl)[C@]2(CC[C@H](n4cc(C(N)=O)cn4)C2)CN3)c1F] | 1-((1R,3S)-5'-(4-Amino-3-(dimethylcarbamoyl)-2-fluorophenyl)-4'-chloro-1',2'-dihydrospiro[cyclopentane-1,3'-pyrrolo[2,3-b]pyridin]-3-yl)-1H-pyrazole-4-carboxamide 1-((1S,3R)-5'-(4-Amino-3-(dimethylcarbamoyl)-2-fluorophenyl)-4'-chloro-1',2'-dihydrospiro[cyclopentane-1,3'-pyrrolo[2,3-b]pyridin]-3-yl)-1H-pyrazole-4-carboxamide |
| 181 | 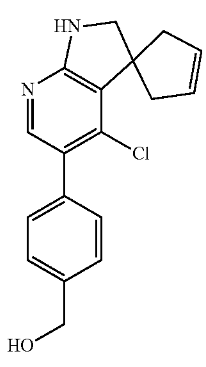 [SMILES: OCc1ccc(-c2cnc3c(c2Cl)C2(CC=CC2)CN3)cc1] | (4-(4'-Chloro-1',2'-dihydrospiro[cyclopentane-1,3'-pyrrolo[2,3-b]pyridin]-3-en-5'-yl)phenyl)methanol |

TABLE 1-continued

| No. | Structure | Name |
|---|---|---|
| 182 | 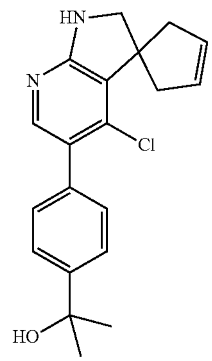 [SMILES: CC(C)(O)c1ccc(-c2cnc3c(c2Cl)C2(CC=CC2)CN3)cc1] | 2-(4-(4'-Chloro-1',2'-dihydrospiro[cyclopentane-1,3'-pyrrolo[2,3-b]pyridin]-3-en-5'-yl)phenyl)propan-2-ol |
| 183 | 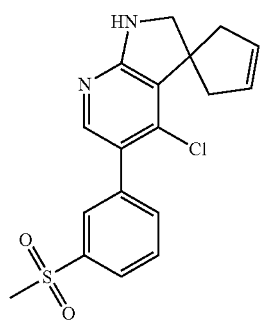 [SMILES: CS(=O)(=O)c1cccc(-c2cnc3c(c2Cl)C2(CC=CC2)CN3)c1] | 4'-Chloro-5'-(3-(methylsulfonyl)phenyl)-1',2'-dihydrospiro[cyclopentane-1,3'-pyrrolo[2,3-b]pyridin]-3-ene |
| 184 | 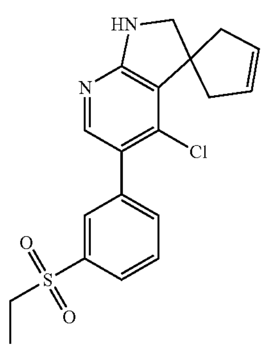 [SMILES: CCS(=O)(=O)c1cccc(-c2cnc3c(c2Cl)C2(CC=CC2)CN3)c1] | 4'-Chloro-5'-(3-(ethylsulfonyl)phenyl)-1',2'-dihydrospiro[cyclopentane-1,3'-pyrrolo[2,3-b]pyridin]-3-ene |
| 185 | 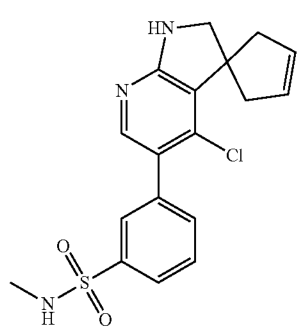 [SMILES: CNS(=O)(=O)c1cccc(-c2cnc3c(c2Cl)C2(CC=CC2)CN3)c1] | 3-(4'-Chloro-1',2'-dihydrospiro[cyclopentane-1,3'-pyrrolo[2,3-b]pyridin]-3-en-5'-yl)-N-methylbenzenesulfonamide |

TABLE 1-continued

| No. | Structure | Name |
|---|---|---|
| 186 | 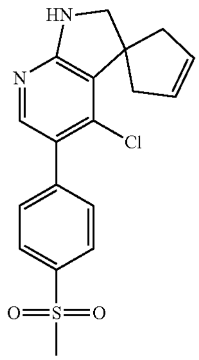 [SMILES: CS(=O)(=O)c1ccc(-c2cnc3c(c2Cl)C2(CC=CC2)CN3)cc1] | 4'-Chloro-5'-(4-(methylsulfonyl)phenyl)-1',2'-dihydrospiro[cyclopentane-1,3'-pyrrolo[2,3-b]pyridin]-3-ene |
| 187 | 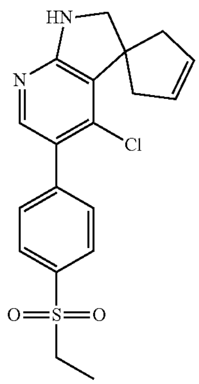 [SMILES: CCS(=O)(=O)c1ccc(-c2cnc3c(c2Cl)C2(CC=CC2)CN3)cc1] | 4'-Chloro-5'-(4-(ethylsulfonyl)phenyl)-1',2'-dihydrospiro[cyclopentane-1,3'-pyrrolo[2,3-b]pyridin]-3-ene |
| 188 | 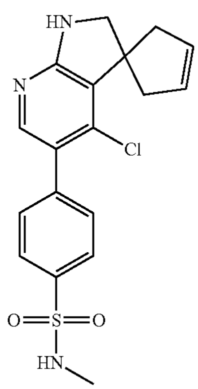 [SMILES: CNS(=O)(=O)c1ccc(-c2cnc3c(c2Cl)C2(CC=CC2)CN3)cc1] | 4-(4'-Chloro-1',2'-dihydrospiro[cyclopentane-1,3'-pyrrolo[2,3-b]pyridin]-3-en-5'-yl)-N-methylbenzenesulfonamide |
| 189 | 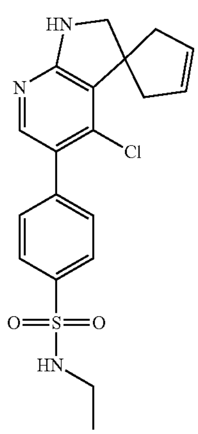 [SMILES: CCNS(=O)(=O)c1ccc(-c2cnc3c(c2Cl)C2(CC=CC2)CN3)cc1] | 4-(4'-Chloro-1',2'-dihydrospiro[cyclopentane-1,3'-pyrrolo[2,3-b]pyridin]-3-en-5'-yl)-N-ethylbenzenesulfonamide |

TABLE 1-continued

| No. | Structure | Name |
|---|---|---|
| 190 | 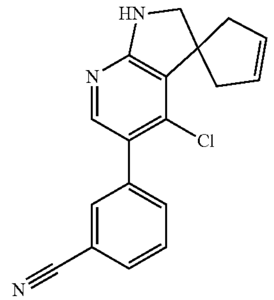 | 3-(4'-Chloro-1',2'-dihydrospiro[cyclopentane-1,3'-pyrrolo[2,3-b]pyridin]-3-en-5'-yl)benzonitrile |
| 191 | | 1-(3-(1'2'-dihydrospiro[cyclopropane-1,3'-pyrrolo[2,3-b]pyridin]-5'-yl)-2-fluorobenzoyl)-2-methylpyrrolidine-2-carbonitrile |
| 191a | 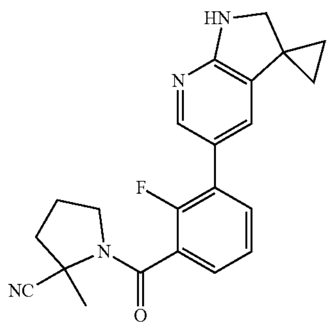 [SMILES: CC1(C#N)CCCN1C(=O)c1cccc(-c2cnc3c(c2)C2(CC2)CN3)c1F] | (R)-1-(3-(1',2'-dihydrospiro[cyclopropane-1,3'-pyrrolo[2,3-b]pyridin]-5'-yl)-2-fluorobenzoyl)-2-methylpyrrolidine-2-carbonitrile (S)-1-(3-(1',2'-dihydrospiro[cyclopropane-1,3'-pyrrolo[2,3-b]pyridin]-5'-yl)-2-fluorobenzoyl)-2-methylpyrrolidine-2-carbonitrile |
| 192 | 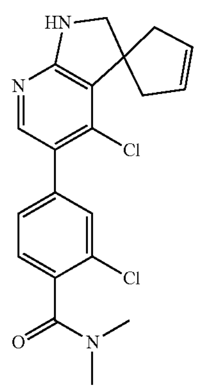 [SMILES: CN(C)C(=O)c1ccc(-c2cnc3c(c2Cl)C2(CC=CC2)CN3)cc1Cl] | 2-Chloro-4-(4'-chloro-1',2'-dihydrospiro[cyclopentane-1,3'-pyrrolo[2,3-b]pyridin]-3-en-5'-yl)-N,N-dimethylbenzamide |
| 193 | | 6-Amino-3-(4'-chloro-2-isopropyl-1',2'-dihydrospiro[cyclopropane-1,3'-pyrrolo[2,3-b]pyridin]-5'-yl)-2-fluoro-N,N-dimethylbenzamide |
| 193a | 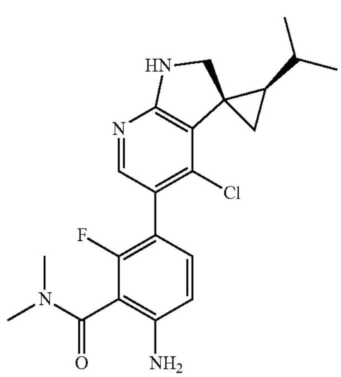 [SMILES: CC(C)[C@H]1C[C@@]12CNc1ncc(-c3ccc(N)c(C(=O)N(C)C)c3F)c(Cl)c12] | 6-Amino-3-((1R,2R)-4'-chloro-2-isopropyl-1',2'-dihydrospiro[cyclopropane-1,3'-pyrrolo[2,3-b]pyridin]-5'-yl)-2-fluoro-N,N-dimethylbenzamide 6-Amino-3-((1S, 2S)-4'-chloro-2-isopropyl-1',2'-dihydrospiro[cyclopropane-1,3'-pyrrolo[2,3-b]pyridin]-5'-yl)-2-fluoro-N,N-dimethylbenzamide |

TABLE 1-continued

| No. | Structure | Name |
|---|---|---|
| 193b | 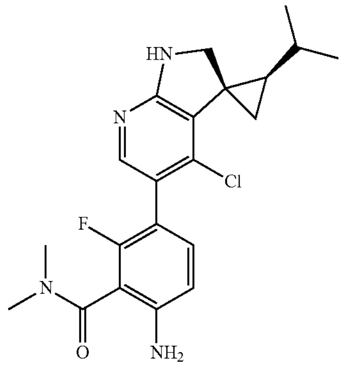 [SMILES: CC(C)[C@H]1C[C@@]12CNc1ncc(-c3ccc(N)c(C(=O)N(C)C)c3F)c(Cl)c12] | 6-Amino-3-((1R,2R)-4'-chloro-2-isopropyl-1',2'-dihydrospiro[cyclopropane-1,3'-pyrrolo[2,3-b]pyridin]-5'-yl)-2-fluoro-N,N-dimethylbenzamide<br>6-Amino-3-((1S, 2S)-4'-chloro-2-isopropyl-1',2'-dihydrospiro[cyclopropane-1,3'-pyrrolo[2,3-b]pyridin]-5'-yl)-2-fluoro-N,N-dimethylbenzamide |
| 194 | | 6-Amino-3-(4'-chloro-4-hydroxy-4-methyl-1',2'-dihydrospiro[cyclohexane-1,3'-pyrrolo[2,3-b]pyridin]-5'-yl)-2-fluoro-N,N-dimethylbenzamide |
| 194a | 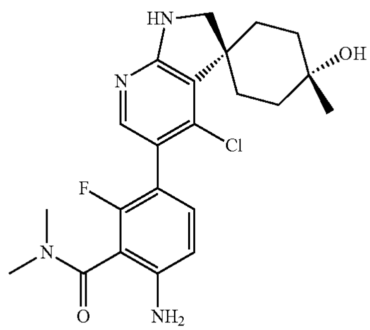 [SMILES: CN(C)C(=O)c1c(N)ccc(-c2cnc3c(c2Cl)[C@]2(CC[C@@](C)(O)CC2)CN3)c1F] | 6-Amino-3-((1R,4R)-4'-chloro-4-hydroxy-4-methyl-1',2'-dihydrospiro[cyclohexane-1,3'-pyrrolo[2,3-b]pyridin]-5'-yl)-2-fluoro-N,N-dimethylbenzamide |
| 194b | 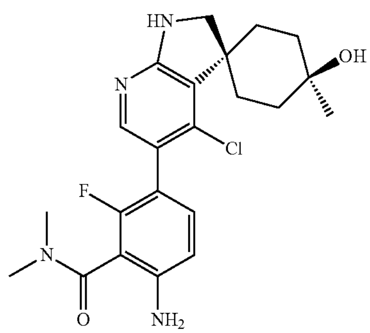 [SMILES: CN(C)C(=O)c1c(N)ccc(-c2cnc3c(c2Cl)[C@]2(CC[C@](C)(O)CC2)CN3)c1F] | 6-Amino-3-((1S,4s)-4'-chloro-4-hydroxy-4-methyl-1',2'-dihydrospiro[cyclohexane-1,3'-pyrrolo[2,3-b]pyridin]-5'-yl)-2-fluoro-N,N-dimethylbenzamide |
| 195 | | 4'-Chloro-5'-(3-(dimethylcarbamoyl)-2-fluorophenyl)-3-methyl-1',2'-dihydrospiro[cyclopentane-1,3'-pyrrolo[2,3-b]pyridine]-3-carboxamide |
| 195a<br>195b | | (1R,3S)-4'-Chloro-5'-(3-(dimethylcarbamoyl)-2-fluorophenyl)-3-methyl-1',2'-dihydrospiro[cyclopentane-1,3'-pyrrolo[2,3-b]pyridine]-3-carboxamide<br>(1S,3R)-4'-Chloro-5'-(3-(dimethylcarbamoyl)-2-fluorophenyl)-3-methyl-1',2'-dihydrospiro[cyclopentane-1,3'-pyrrolo[2,3-b]pyridine]-3-carboxamide |

TABLE 1-continued

| No. | Structure | Name |
|---|---|---|
| 196 | | 6-Amino-3-(4'-chloro-3-(2-oxopyridin-1(2H)-yl)-1',2'-dihydrospiro[cyclopentane-1,3'-pyrrolo[2,3-b]pyridin]-5'-yl)-2-fluoro-N,N-dimethylbenzamide |
| 196a | 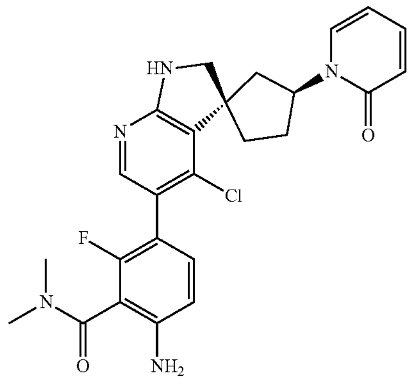 [SMILES: CN(C)C(=O)c1c(N)ccc(-c2cnc3c(c2Cl)[C@]2(CC[C@H](n4ccccc4=O)C2)CN3)c1F] | 6-Amino-3-((1R,3S)-4'-chloro-3-(2-oxopyridin-1(2H)-yl)-1',2'-dihydrospiro[cyclopentane-1,3'-pyrrolo[2,3-b]pyridin]-5'-yl)-2-fluoro-N,N-dimethylbenzamide<br>6-Amino-3-((1S,3R)-4'-chloro-3-(2-oxopyridin-1(2H)-yl)-1',2'-dihydrospiro[cyclopentane-1,3'-pyrrolo[2,3-b]pyridin]-5'-yl)-2-fluoro-N,N-dimethylbenzamide |
| 197 | | 6-Amino-3-(4'-chloro-2-propyl-1',2'-dihydrospiro[cyclopropane-1,3'-pyrrolo[2,3-b]pyridin]-5'-yl)-2-fluoro-N,N-dimethylbenzamide |
| 197a<br>197b | | 6-Amino-3-((1R,2S)-4'-chloro-2-propyl-1',2'-dihydrospiro[cyclopropane-1,3'-pyrrolo[2,3-b]pyridin]-5'-yl)-2-fluoro-N,N-dimethylbenzamide<br>6-Amino-3-((1S, 2R)-4'-chloro-2-propyl-1',2'-dihydrospiro[cyclopropane-1,3'-pyrrolo[2,3-b]pyridin]-5'-yl)-2-fluoro-N,N-dimethylbenzamide |
| 198 | | 6-Amino-3-(4'-chloro-2-(pyridin-4-yl)-1',2'-dihydrospiro[cyclopropane-1,3'-pyrrolo[2,3-b]pyridin]-5'-yl)-2-fluoro-N,N-dimethylbenzamide |
| 198a | 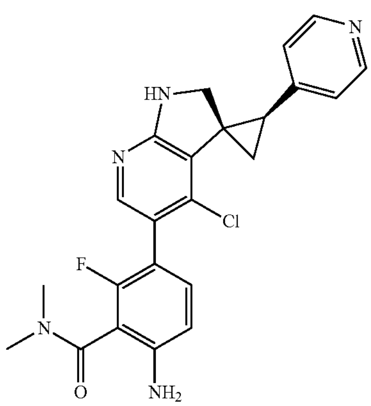 [SMILES: CN(C)C(=O)c1c(N)ccc(-c2cnc3c(c2Cl)[C@@]2(CN3)C[C@@H]2c2ccncc2)c1F] | 6-Amino-3-((1R,2R)-4'-chloro-2-(pyridin-4-yl)-1',2'-dihydrospiro[cyclopropane-1,3'-pyrrolo[2,3-b]pyridin]-5'-yl)-2-fluoro-N,N-dimethylbenzamide<br>6-Amino-3-((1S, 2S)-4'-chloro-2-(pyridin-4-yl)-1',2'-dihydrospiro[cyclopropane-1,3'-pyrrolo[2,3-b]pyridin]-5'-yl)-2-fluoro-N,N-dimethylbenzamide |
| 199 | | 5'-(3-(Dimethylcarbamoyl)-2-fluorophenyl)-3-methyl-1',2'-dihydrospiro[cyclopentane-1,3'-pyrrolo[2,3-b]pyridine]-3-carboxamide |

TABLE 1-continued

| No. | Structure | Name |
|---|---|---|
| 199a 199b | | (1R,3S)-5'-(3-(Dimethylcarbamoyl)-2-fluorophenyl)-3-methyl-1',2'-dihydrospiro[cyclopentane-1,3'-pyrrolo[2,3-b]pyridine]-3-carboxamide (1S,3R)-5'-(3-(Dimethylcarbamoyl)-2-fluorophenyl)-3-methyl-1',2'-dihydrospiro[cyclopentane-1,3'-pyrrolo[2,3-b]pyridine]-3-carboxamide |
| 200 | 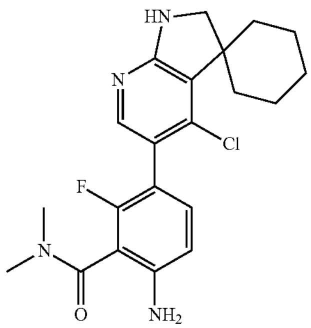 [SMILES: CN(C)C(=O)c1c(N)ccc(-c2cnc3c(c2Cl)C2(CCCCC2)CN3)c1F] | 6-Amino-3-(4'-chloro-1',2'-dihydrospiro[cyclohexane-1,3'-pyrrolo[2,3-b]pyridin]-5'-yl)-2-fluoro-N,N-dimethylbenzamide |
| 201 | | 6-Amino-3-(4'-chloro-2-phenyl-1',2'-dihydrospiro[cyclopropane-1,3'-pyrrolo[2,3-b]pyridin]-5'-yl)-2-fluoro-N,N-dimethylbenzamide |
| 201a | 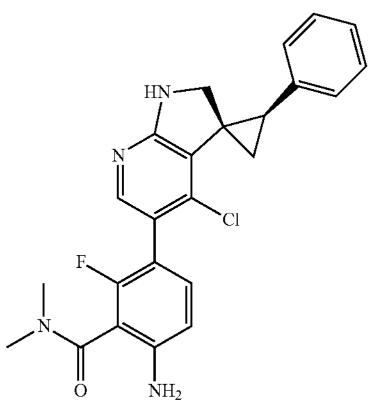 [SMILES: CN(C)C(=O)c1c(N)ccc(-c2cnc3c(c2Cl)[C@@]2(CN3)C[C@@H]2c2ccccc2)c1F] | 6-Amino-3-((1R,2R)-4'-chloro-2-phenyl-1',2'-dihydrospiro[cyclopropane-1,3'-pyrrolo[2,3-b]pyridin]-5'-yl)-2-fluoro-N,N-dimethylbenzamide 6-Amino-3-((1S, 2S)-4'-chloro-2-phenyl-1',2'-dihydrospiro[cyclopropane-1,3'-pyrrolo[2,3-b]pyridin]-5'-yl)-2-fluoro-N,N-dimethylbenzamide |
| 202 | | 4'-Chloro-5'-(2-fluoro-3-(3-oxomorpholino)phenyl)-3-methyl-1',2'-dihydrospiro[cyclopentane-1,3'-pyrrolo[2,3-b]pyridine]-3-carboxamide |
| 202a 202b | | (1R,3S)-4'-Chloro-5'-(2-fluoro-3-(3-oxomorpholino)phenyl)-3-methyl-1',2'-dihydrospiro[cyclopentane-1,3'-pyrrolo[2,3-b]pyridine]-3-carboxamide (1S,3R)-4'-Chloro-5'-(2-fluoro-3-(3-oxomorpholino)phenyl)-3-methyl-1',2'-dihydrospiro[cyclopentane-1,3'-pyrrolo[2,3-b]pyridine]-3-carboxamide |

TABLE 1-continued

| No. | Structure | Name |
|---|---|---|
| 203 | 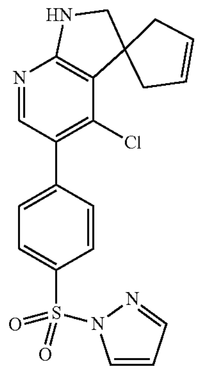 [SMILES: O=S(=O)(c1ccc(-c2cnc3c(c2Cl)C2(CC=CC2)CN3)cc1)n1cccn1] | 5'-(4-((1H-Pyrazol-1-yl)sulfonyl)phenyl)-4'-chloro-1',2'-dihydrospiro[cyclopentane-1,3'-pyrrolo[2,3-b]pyridin]-3-ene |
| 204 | 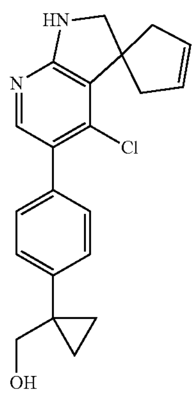 [SMILES: OCC1(c2ccc(-c3cnc4c(c3Cl)C3(CC=CC3)CN4)cc2)CC1] | (1-(4-(4'-Chloro-1',2'-dihydrospiro[cyclopentane-1,3'-pyrrolo[2,3-b]pyridin]-3-en-5'-yl)phenyl)cyclopropyl)methanol |
| 205 | 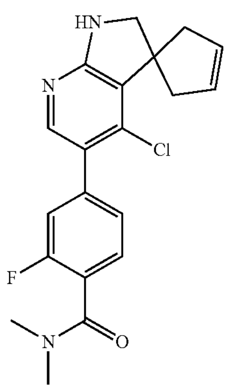 [SMILES: CN(C)C(=O)c1ccc(-c2cnc3c(c2Cl)C2(CC=CC2)CN3)cc1F] | 4-(4'-Chloro-1',2'-dihydrospiro[cyclopentane-1,3'-pyrrolo[2,3-b]pyridin]-3-en-5'-yl)-2-fluoro-N,N-dimethylbenzamide |
| 206 | 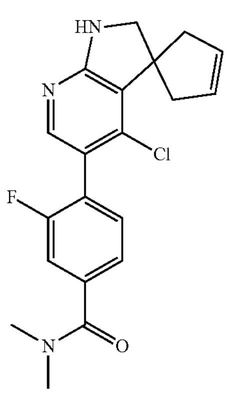 [SMILES: CN(C)C(=O)c1ccc(-c2cnc3c(c2Cl)C2(CC=CC2)CN3)c(F)c1] | 4-(4'-Chloro-1',2'-dihydrospiro[cyclopentane-1,3'-pyrrolo[2,3-b]pyridin]-3-en-5'-yl)-3-fluoro-N,N-dimethylbenzamide |

TABLE 1-continued

| No. | Structure | Name |
|---|---|---|
| 207 | 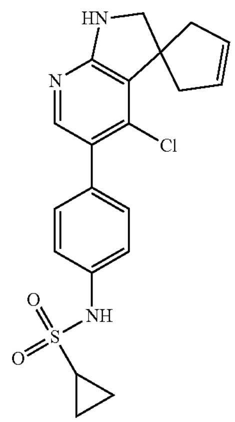 [SMILES: O=S(=O)(Nc1ccc(-c2cnc3c(c2Cl)C2(CC=CC2)CN3)cc1)C1CC1] | N-(4-(4'-Chloro-1',2'-dihydrospiro[cyclopentane-1,3'-pyrrolo[2,3-b]pyridin]-3-en-5'-yl)phenyl)cyclopropanesulfonamide |
| 208 | 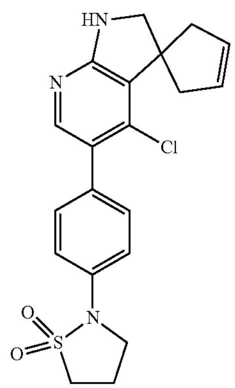 [SMILES: O=S1(=O)CCCN1c1ccc(-c2cnc3c(c2Cl)C2(CC=CC2)CN3)cc1] | 2-(4-(4'-Chloro-1',2'-dihydrospiro[cyclopentane-1,3'-pyrrolo[2,3-b]pyridin]-3-en-5'-yl)phenyl)isothiazolidine 1,1-dioxide |
| 209 | 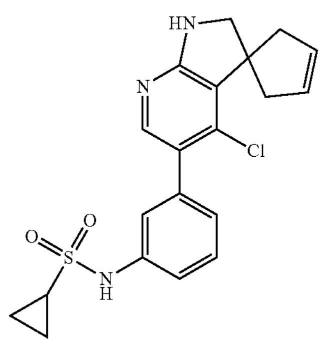 [SMILES: O=S(=O)(Nc1cccc(-c2cnc3c(c2Cl)C2(CC=CC2)CN3)c1)C1CC1] | N-(3-(4'-Chloro-1',2'-dihydrospiro[cyclopentane-1,3'-pyrrolo[2,3-b]pyridin]-3-en-5'-yl)phenyl)cyclopropanesulfonamide |
| 210 | 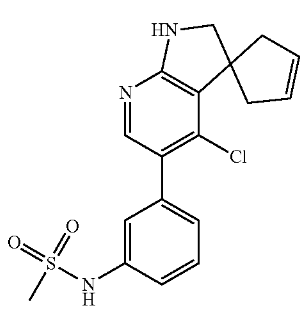 [SMILES: CS(=O)(=O)Nc1cccc(-c2cnc3c(c2Cl)C2(CC=CC2)CN3)c1] | N-(3-(4'-Chloro-1',2'-dihydrospiro[cyclopentane-1,3'-pyrrolo[2,3-b]pyridin]-3-en-5'-yl)phenyl)methanesulfonamide |

TABLE 1-continued

| No. | Structure | Name |
| --- | --- | --- |
| 211 | 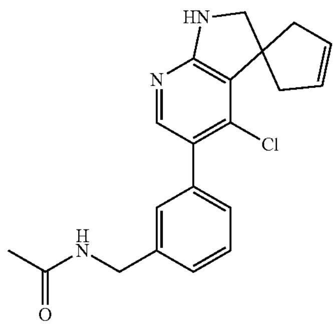 [SMILES: CC(=O)NCc1cccc(-c2cnc3c(c2Cl)C2(CC=CC2)CN3)c1] | N-(3-(4'-Chloro-1',2'-dihydrospiro[cyclopentane-1,3'-pyrrolo[2,3-b]pyridin]-3-en-5'-yl)benzyl)acetamide |
| 212 | 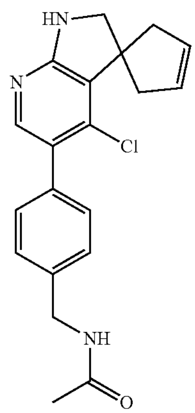 [SMILES: CC(=O)NCc1ccc(-c2cnc3c(c2Cl)C2(CC=CC2)CN3)cc1] | N-(4-(4'-Chloro-1',2'-dihydrospiro[cyclopentane-1,3'-pyrrolo[2,3-b]pyridin]-3-en-5'-yl)benzyl)acetamide |
| 213 | 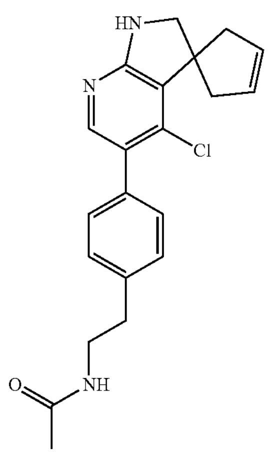 [SMILES: CC(=O)NCCc1ccc(-c2cnc3c(c2Cl)C2(CC=CC2)CN3)cc1] | N-(4-(4'-chloro-1',2'-dihydrospiro[cyclopentane-1,3'-pyrrolo[2,3-b]pyridin]-3-en-5'-yl)phenethyl)acetamide |
| 214 | 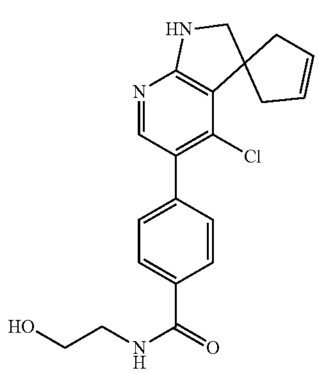 [SMILES: O=C(NCCO)c1ccc(-c2cnc3c(c2Cl)C2(CC=CC2)CN3)cc1] | 4-(4'-Chloro-1',2'-dihydrospiro[cyclopentane-1,3'-pyrrolo[2,3-b]pyridin]-3-en-5'-yl)-N-(2-hydroxyethyl)benzamide |

TABLE 1-continued

| No. | Structure | Name |
|---|---|---|
| 215 | 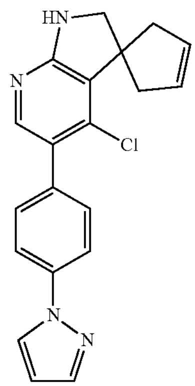 | 5'-(4-(1H-Pyrazol-1-yl)phenyl)-4'-chloro-1',2'-dihydrospiro[cyclopentane-1,3'-pyrrolo[2,3-b]pyridin]-3-ene |
| 216 | 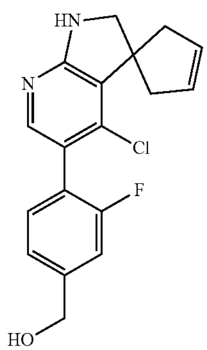 | (4-(4'-Chloro-1',2'-dihydrospiro[cyclopentane-1,3'-pyrrolo[2,3-b]pyridin]-3-en-5'-yl)-3-fluorophenyl)methanol |
| 217 | 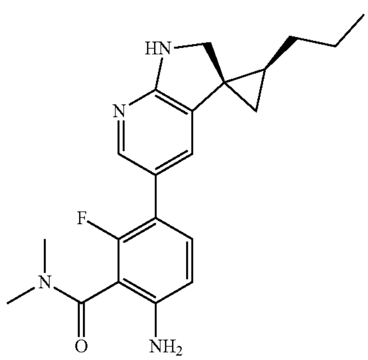 [SMILES: CCC[C@H]1C[C@@]12CNc1ncc(-c3ccc(N)c(C(=O)N(C)C)c3F)cc12] | 6-Amino-2-fluoro-N,N-dimethyl-3-(2-propyl-1',2'-dihydrospiro[cyclopropane-1,3'-pyrrolo[2,3-b]pyridin]-5'-yl)benzamide |
| 217a | | 6-Amino-2-fluoro-N,N-dimethyl-3-((1R,2S)-2-propyl-1',2'-dihydrospiro[cyclopropane-1,3'-pyrrolo[2,3-b]pyridin]-5'-yl)benzamide |
| 217b | | 6-Amino-2-fluoro-N,N-dimethyl-3-((1S,2R)-2-propyl-1',2'-dihydrospiro[cyclopropane-1,3'-pyrrolo[2,3-b]pyridin]-5'-yl)benzamide |
| 217c | | 6-Amino-2-fluoro-N,N-dimethyl-3-((1R,2R)-2-propyl-1'2'-dihydrospiro[cyclopropane-1,3'-pyrrolo[2,3-b]pyridin]-5'-yl)benzamide |
| 217d | | 6-Amino-2-fluoro-N,N-dimethyl-3-((1S, 2S)-2-propyl-1',2'-dihydrospiro[cyclopropane-1,3'-pyrrolo[2,3-b]pyridin]-5'-yl)benzamide |

TABLE 1-continued

| No. | Structure | Name |
|---|---|---|
| 218 | 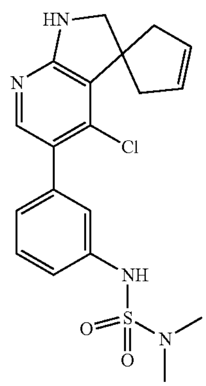 [SMILES: CN(C)S(=O)(=O)Nc1cccc(-c2cnc3c(c2Cl)C2(CC=CC2)CN3)c1] | N-(3-(4'-Chloro-1',2'-dihydrospiro[cyclopentane-1,3'-pyrrolo[2,3-b]pyridin]-3-en-5'-yl)phenyl)-N'N'-dimethylsulfamide |
| 219 | 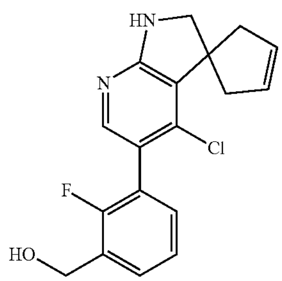 [SMILES: OCc1cccc(-c2cnc3c(c2Cl)C2(CC=CC2)CN3)c1F] | (3-(4'-Chloro-1',2'-dihydrospiro[cyclopentane-1,3'-pyrrolo[2,3-b]pyridin]-3-en-5'-yl)-2-fluorophenyl)methanol |
| 220 | 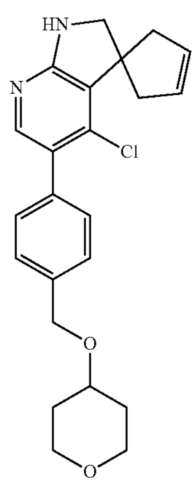 [SMILES: Clc1c(-c2ccc(COC3CCOCC3)cc2)cnc2c1C1(CC=CC1)CN2] | 4'-Chloro-5'-(4-(((tetrahydro-2H-pyran-4-yl)oxy)methyl)phenyl)-1',2'-dihydrospiro[cyclopentane-1,3'-pyrrolo[2,3-b]pyridin]-3-ene |
| 221 | 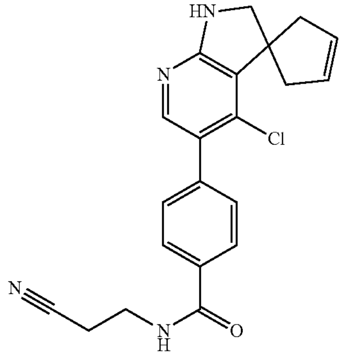 [SMILES: N#CCCNC(=O)c1ccc(-c2cnc3c(c2Cl)C2(CC=CC2)CN3)cc1] | 4-(4'-Chloro-1',2'-dihydrospiro[cyclopentane-1,3'-pyrrolo[2,3-b]pyridin]-3-en-5'-yl)-N-(2-cyanoethyl)benzamide |

TABLE 1-continued

| No. | Structure | Name |
|---|---|---|
| 222 | 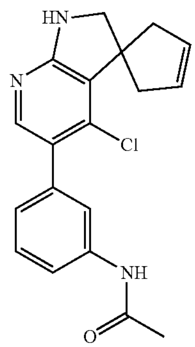 [SMILES: CC(=O)Nc1cccc(-c2cnc3c(c2Cl)C2(CC=CC2)CN3)c1] | N-(3-(4'-Chloro-1',2'-dihydrospiro[cyclopentane-1,3'-pyrrolo[2,3-b]pyridin]-3-en-5'-yl)phenyl)acetamide |
| 223 | 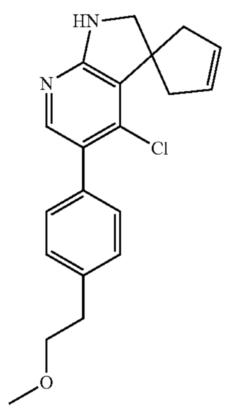 [SMILES: COCCc1ccc(-c2cnc3c(c2Cl)C2(CC=CC2)CN3)cc1] | 4'-Chloro-5'-(4-(2-methoxyethyl)phenyl)-1',2'-dihydrospiro[cyclopentane-1,3'-pyrrolo[2,3-b]pyridin]-3-ene |
| 224 | 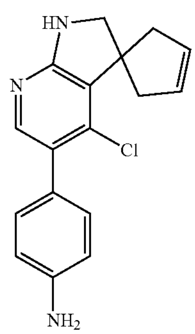 [SMILES: Nc1ccc(-c2cnc3c(c2Cl)C2(CC=CC2)CN3)cc1] | 4-(4'-Chloro-1',2'-dihydrospiro[cyclopentane-1,3'-pyrrolo[2,3-b]pyridin]-3-en-5'-yl)aniline |
| 225 | 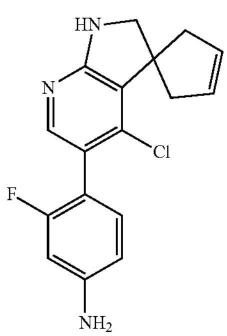 [SMILES: Nc1ccc(-c2cnc3c(c2Cl)C2(CC=CC2)CN3)c(F)c1] | 4-(4'-Chloro-1',2'-dihydrospiro[cyclopentane-1,3'-pyrrolo[2,3-b]pyridin]-3-en-5'-yl)-3-fluoroaniline |

TABLE 1-continued

| No. | Structure | Name |
|---|---|---|
| 226 | 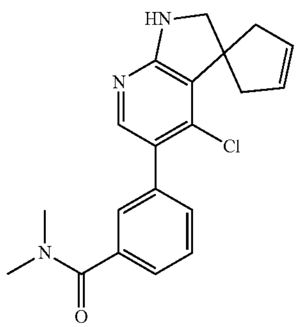 [SMILES: CN(C)C(=O)c1cccc(-c2cnc3c(c2Cl)C2(CC=CC2)CN3)c1] | 3-(4'-Chloro-1',2'-dihydrospiro[cyclopentane-1,3'-pyrrolo[2,3-b]pyridin]-3-en-5'-yl)-N,N-dimethylbenzamide |
| 227 | 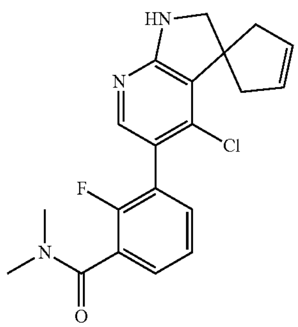 [SMILES: CN(C)C(=O)c1cccc(-c2cnc3c(c2Cl)C2(CC=CC2)CN3)c1F] | 3-(4'-Chloro-1',2'-dihydrospiro[cyclopentane-1,3'-pyrrolo[2,3-b]pyridin]-3-en-5'-yl)-2-fluoro-N,N-dimethylbenzamide |
| 228 | | 6-Amino-3-(4'-chloro-2-methyl-1',2'-dihydrospiro[cyclopropane-1,3'-pyrrolo[2,3-b]pyridin]-5'-yl)-2-fluoro-N,N-dimethylbenzamide |
| 228a 228b | | 6-Amino-3-((1R,2S)-4'-chloro-2-methyl-1',2'-dihydrospiro[cyclopropane-1,3'-pyrrolo[2,3-b]pyridin]-5'-yl)-2-fluoro-N,N-dimethylbenzamide<br>6-Amino-3-((1S, 2R)-4'-chloro-2-methyl-1',2'-dihydrospiro[cyclopropane-1,3'-pyrrolo[2,3-b]pyridin]-5'-yl)-2-fluoro-N,N-dimethylbenzamide |
| 229 | | 3-(1',2'-dihydrospiro[cyclopropane-1,3'-pyrrolo|2,3-b]pyridin]-5'-yl)-2-fluoro-N-methyl-N-(1-(1-methyl-1H-pyrazol-4-yl)ethyl)benzamide |
| 229a 229b | | (R)-3-(1',2'-dihydrospiro[cyclopropane-1,3'-pyrrolo[2,3-b]pyridin]-5'-yl)-2-fluoro-N-methyl-N-(1-(1-methyl-1H-pyrazol-4-yl)ethyl)benzamide<br>(S)-3-(1'2'-dihydrospiro[cyclopropane-1,3'-pyrrolo[2,3-b]pyridin]-5'-yl)-2-fluoro-N-methyl-N-(1-(1-methyl-1H-pyrazol-4-yl)ethyl)benzamide |

TABLE 1-continued

| No. | Structure | Name |
|---|---|---|
| 230 | 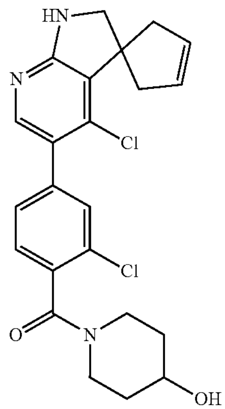 | (2-Chloro-4-(4'-chloro-1',2'-dihydrospiro[cyclopentane-1,3'-pyrrolo[2,3-b]pyridin]-3-en-5'-yl)phenyl)(4-hydroxypiperidin-1-yl)methanone |
| 231 | 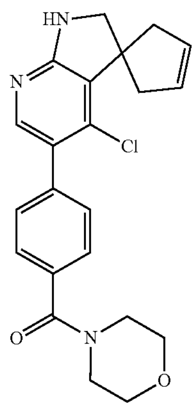 [SMILES: O=C(c1ccc(-c2cnc3c(c2Cl)C2(CC=CC2)CN3)cc1)N1CCOCC1] | (4-(4'-Chloro-1',2'-dihydrospiro[cyclopentane-1,3'-pyrrolo[2,3-b]pyridin]-3-en-5'-yl)phenyl)(morpholino)methanone |
| 232 | 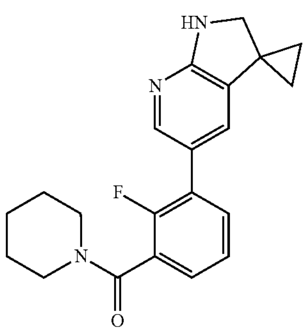 [SMILES: O=C(c1cccc(-c2cnc3c(c2)C2(CC2)CN3)c1F)N1CCCCC1] | (3-(1'2'-dihydrospiro[cyclopropane-1,3'-pyrrolo[2,3-b]pyridin]-5'-yl)-2-fluorophenyl)(piperidin-1-yl)methanone |
| 233 | 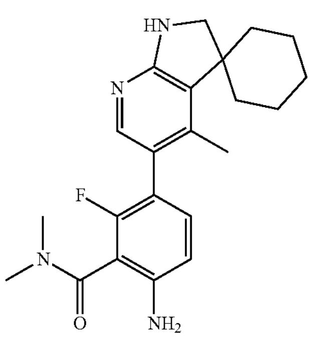 [SMILES: Cc1c(-c2ccc(N)c(C(=O)N(C)C)c2F)cnc2c1C1(CCCCC1)CN2] | 6-Amino-2-fluoro-N,N-dimethyl-3-(4'-methyl-1',2'-dihydrospiro[cyclohexane-1,3'-pyrrolo[2,3-b]pyridin]-5'-yl)benzamide |

TABLE 1-continued

| No. | Structure | Name |
|---|---|---|
| 234 | 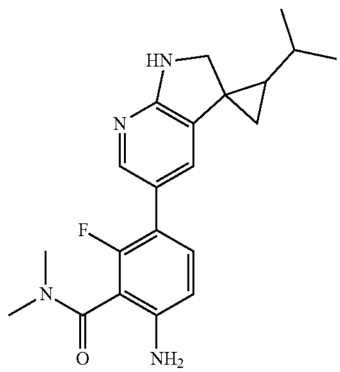 [SMILES: CC(C)C1CC12CNc1ncc(-c3ccc(N)c(C(=O)N(C)C)c3F)cc12] | 6-Amino-2-fluoro-3-(2-isopropyl-1',2'-dihydrospiro[cyclopropane-1,3'-pyrrolo[2,3-b]pyridin]-5'-yl)-N,N-dimethylbenzamide |
| 234a | | 6-Amino-2-fluoro-3-((1R,2R)-2-isopropyl-1',2'-dihydrospiro[cyclopropane-1,3'-pyrrolo[2,3-b]pyridin]-5'-yl)-N,N-dimethylbenzamide |
| 234b | | 6-Amino-2-fluoro-3-((1S, 2S)-2-isopropyl-1',2'-dihydrospiro[cyclopropane-1,3'-pyrrolo[2,3-b]pyridin]-5'-yl)-N,N-dimethylbenzamide |
| 234c | | 6-Amino-2-fluoro-3-((1R,2S)-2-isopropyl-1',2'-dihydrospiro[cyclopropane-1,3'-pyrrolo[2,3-b]pyridin]-5'-yl)-N,N-dimethylbenzamide |
| 234d | | 6-Amino-2-fluoro-3-((1S, 2R)-2-isopropyl-1',2'-dihydrospiro[cyclopropane-1,3'-pyrrolo[2,3-b]pyridin]-5'-yl)-N,N-dimethylbenzamide |
| 235 | | 5'-(4-Amino-3-(dimethylcarbamoyl)-2-fluorophenyl)-4'-chloro-1',2'-dihydrospiro[cyclohexane-1,3'-pyrrolo[2,3-b]pyridine]-4-carboxamide |
| 235a | 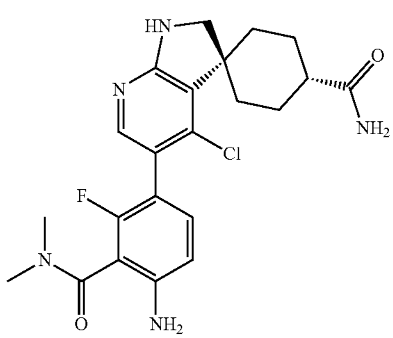 [SMILES: CN(C)C(=O)c1c(N)ccc(-c2cnc3c(c2Cl)[C@]2(CC[C@@H](C(N)=O)CC2)CN3)c1F] | (1R,4R)-5'-(4-Amino-3-(dimethylcarbamoyl)-2-fluorophenyl)-4'-chloro-1',2'-dihydrospiro[cyclohexane-1,3'-pyrrolo[2,3-b]pyridine]-4-carboxamide |
| 235b | 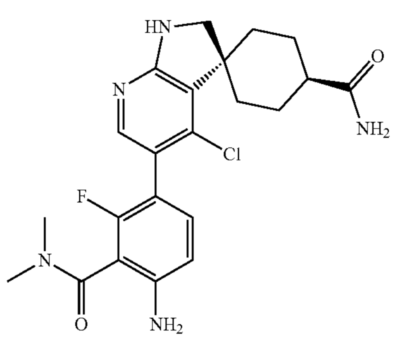 [SMILES: CN(C)C(=O)c1c(N)ccc(-c2cnc3c(c2Cl)[C@]2(CC[C@H](C(N)=O)CC2)CN3)c1F] | (1s,4s)-5'-(4-Amino-3-(dimethylcarbamoyl)-2-fluorophenyl)-4'-chloro-1',2'-dihydrospiro[cyclohexane-1,3'-pyrrolo[2,3-b]pyridine]-4-carboxamide |

TABLE 1-continued

| No. | Structure | Name |
| --- | --- | --- |
| 236 | 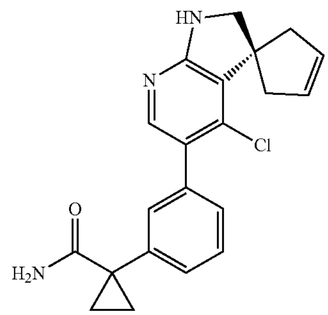 | 1-(3-(4'-Chloro-1',2'-dihydrospiro[cyclopentane-1,3'-pyrrolo[2,3-b]pyridin]-3-en-5'-yl)phenyl)cyclopropane-1-carboxamide |
| 237 | 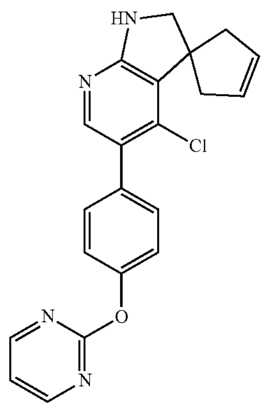 [SMILES: Clc1c(-c2ccc(Oc3ncccn3)cc2)cnc2c1C1(CC=CC1)CN2] | 4'-Chloro-5'-(4-(pyrimidin-2-yloxy)phenyl)-1',2'-dihydrospiro[cyclopentane-1,3'-pyrrolo[2,3-b]pyridin]-3-ene |
| 238 | 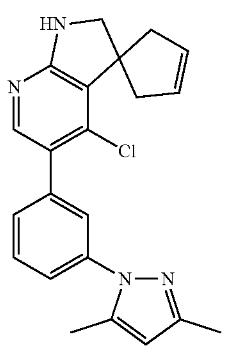 [SMILES: Cc1cc(C)n(-c2cccc(-c3cnc4c(c3Cl)C3(CC=CC3)CN4)c2)n1] | 4'-Chloro-5'-(3-(3,5-dimethyl-1H-pyrazol-1-yl)phenyl)-1'2'-dihydrospiro[cyclopentane-1,3'-pyrrolo[2,3-b]pyridin]-3-ene |
| 239 | | (6-Amino-3-(4'-chloro-1',2'-dihydrospiro[cyclopentane-1,3'-pyrrolo[2,3-b]pyridin]-3-en-5'-yl)-2-fluorophenyl)(2-(1-methyl-1H-pyrazol-4-yl)piperidin-1-yl)methanone |
| 239a 239b | | (R)-(6-Amino-3-(4'-chloro-1',2'-dihydrospiro[cyclopentane-1,3'-pyrrolo[2,3-b]pyridin]-3-en-5'-yl)-2-fluorophenyl)(2-(1-methyl-1H-pyrazol-4-yl)piperidin-1-yl)methanone (S)-(6-Amino-3-(4'-chloro-1',2'-dihydrospiro[cyclopentane-1,3'-pyrrolo[2,3-b]pyridin]-3-en-5'-yl)-2-fluorophenyl)(2-(1-methyl-1H-pyrazol-4-yl)piperidin-1-yl)methanone |

TABLE 1-continued

| No. | Structure | Name |
|---|---|---|
| 240 | | (3-(4'-Chloro-1',2'-dihydrospiro[cyclopentane-1,3'-pyrrolo[2,3-b]pyridin]-3-en-5'-yl)-2-fluorophenyl)(2-(1-methyl-1H-pyrazol-4-yl)piperidin-1-yl)methanone |
| 240a 240b | (structure shown) | (R)-(3-(4'-Chloro-1',2'-dihydrospiro[cyclopentane-1,3'-pyrrolo[2,3-b]pyridin]-3-en-5'-yl)-2-fluorophenyl)(2-(1-methyl-1H-pyrazol-4-yl)piperidin-1-yl)methanone<br>(S)-(3-(4'-Chloro-1',2'-dihydrospiro[cyclopentane-1,3'-pyrrolo[2,3-b]pyridin]-3-en-5'-yl)-2-fluorophenyl)(2-(1-methyl-1H-pyrazol-4-yl)piperidin-1-yl)methanone |
| 241 | | 6-Amino-3-(4'-chloro-4-cyano-1',2'-dihydrospiro[cyclohexane-1,3'-pyrrolo[2,3-b]pyridin]-5'-yl)-2-fluoro-N,N-dimethylbenzamide |
| 241a | (structure shown) | 6-Amino-3-((1R,4R)-4'-chloro-4-cyano-1',2'-dihydrospiro[cyclohexane-1,3'-pyrrolo[2,3-b]pyridin]-5'-yl)-2-fluoro-N,N-dimethylbenzamide |
| 241b | (structure shown) | 6-Amino-3-((1S,4s)-4'-chloro-4-cyano-1',2'-dihydrospiro[cyclohexane-1,3'-pyrrolo[2,3-b]pyridin]-5'-yl)-2-fluoro-N,N-dimethylbenzamide |
| 242 | (structure shown) | 2-(2-(3-(1',2'-Dihydrospiro[cyclopropane-1,3'-pyrrolo[2,3-b]pyridin]-5'-yl)phenyl)-3-methylpyridin-4-yl)acetonitrile |

TABLE 1-continued

| No. | Structure | Name |
|---|---|---|
| 243 | | 6-Amino-3-(2-ethyl-1',2'-dihydrospiro[cyclopropane-1,3'-pyrrolo[2,3-b]pyridin]-5'-yl)-2-fluoro-N,N-dimethylbenzamide |
| 243a 243b | | 6-Amino-3-((1R,2S)-2-ethyl-1',2'-dihydrospiro[cyclopropane-1,3'-pyrrolo[2,3-b]pyridin]-5'-yl)-2-fluoro-N,N-dimethylbenzamide 6-Amino-3-((1S,2R)-2-ethyl-1',2'-dihydrospiro[cyclopropane-1,3'-pyrrolo[2,3-b]pyridin]-5'-yl)-2-fluoro-N,N-dimethylbenzamide |
| 243c 243d | | 6-Amino-3-((1R,2R)-2-ethyl-1',2'-dihydrospiro[cyclopropane-1,3'-pyrrolo[2,3-b]pyridin]-5'-yl)-2-fluoro-N,N-dimethylbenzamide 6-Amino-3-((1S,2S)-2-ethyl-1',2'-dihydrospiro[cyclopropane-1,3'-pyrrolo[2,3-b]pyridin]-5'-yl)-2-fluoro-N,N-dimethylbenzamide |
| 244 | 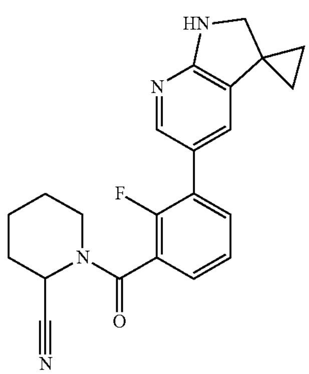 [SMILES: N#CC1CCCCN1C(=O)c1cccc(-c2cnc3c(c2)C2(CC2)CN3)c1F] | 1-(3-(1',2'-Dihydrospiro[cyclopropane-1,3'-pyrrolo[2,3-b]pyridin]-5'-yl)-2-fluorobenzoyl)piperidine-2-carbonitrile |
| 244a | | (R)-1-(3-(1',2'-Dihydrospiro[cyclopropane-1,3'-pyrrolo[2,3-b]pyridin]-5'-yl)-2-fluorobenzoyl)piperidine-2-carbonitrile |
| 244b | | (S)-1-(3-(1',2'-Dihydrospiro[cyclopropane-1,3'-pyrrolo[2,3-b]pyridin]-5'-yl)-2-fluorobenzoyl)piperidine-2-carbonitrile |
| 245 | | (2-Fluoro-3-(4-hydroxy-1',2'-dihydrospiro[cyclohexane-1,3'-pyrrolo[2,3-b]pyridin]-5'-yl)phenyl)(2-(1-methyl-1H-pyrazol-4-yl)piperidin-1-yl)methanone |

TABLE 1-continued

| No. | Structure | Name |
|---|---|---|
| 245a 245b | | (2-Fluoro-3-((1S,4s)-4-hydroxy-1',2'-dihydrospiro[cyclohexane-1,3'-pyrrolo[2,3-b]pyridin]-5'-yl)phenyl)((R)-2-(1-methyl-1H-pyrazol-4-yl)piperidin-1-yl)methanone (2-Fluoro-3-((1s,4s)-4-hydroxy-1',2'-dihydrospiro[cyclohexane-1,3'-pyrrolo[2,3-b]pyridin]-5'-yl)phenyl)((S)-2-(1-methyl-1H-pyrazol-4-yl)piperidin-1-yl)methanone |
| 246 | | (3-((1s,4s)-4'-Chloro-4-hydroxy-1',2'-dihydrospiro[cyclohexane-1,3'-pyrrolo[2,3-b]pyridin]-5'-yl)-2-fluorophenyl)(2-(1-methyl-1H-pyrazol-4-yl)piperidin-1-yl)methanone |
| 246a 246b | | (3-((1s,4s)-4'-Chloro-4-hydroxy-1',2'-dihydrospiro[cyclohexane-1,3'-pyrrolo[2,3-b]pyridin]-5'-yl)-2-fluorophenyl)((R)-2-(1-methyl-1H-pyrazol-4-yl)piperidin-1-yl)methanone (3-((1s,4s)-4'-Chloro-4-hydroxy-1',2'-dihydrospiro[cyclohexane-1,3'-pyrrolo[2,3-b]pyridin]-5'-yl)-2-fluorophenyl)((S)-2-(1-methyl-1H-pyrazol-4-yl)piperidin-1-yl)methanone |
| 247 | 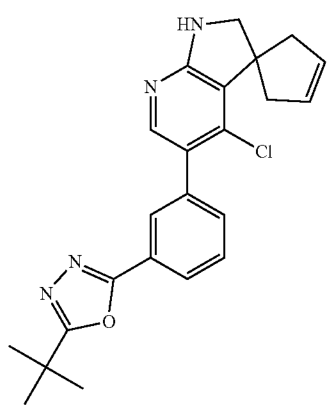 [SMILES: CC(C)(C)c1nnc(-c2cccc(-c3cnc4c(c3Cl)C3(CC=CC3)CN4)c2)o1] | 2-(tert-Butyl)-5-(3-(4'-chloro-1',2'-dihydrospiro[cyclopentane-1,3'-pyrrolo[2,3-b]pyridin]-3-en-5'-yl)phenyl)-1,3,4-oxadiazole |
| 248 | | 6-Amino-3-(4'-chloro-4-(hydroxymethyl)-1',2'-dihydrospiro[cyclohexane-1,3'-pyrrolo[2,3-b]pyridin]-5'-yl)-2-fluoro-N,N-dimethylbenzamide |

TABLE 1-continued

| No. | Structure | Name |
|---|---|---|
| 248a | 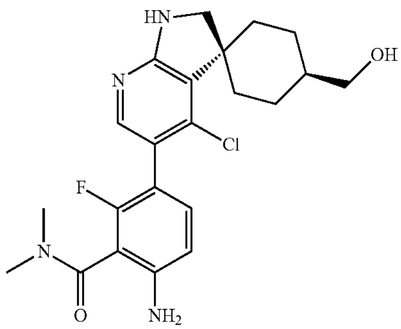 [SMILES: CN(C)C(=O)c1c(N)ccc(-c2cnc3c(c2Cl)[C@]2(CC[C@H](CO)CC2)CN3)c1F] | 6-Amino-3-((1s,4s)-4'-chloro-4-(hydroxymethyl)-1',2'-dihydrospiro[cyclohexane-1,3'-pyrrolo[2,3-b]pyridin]-5'-yl)-2-fluoro-N,N-dimethylbenzamide |
| 248b | 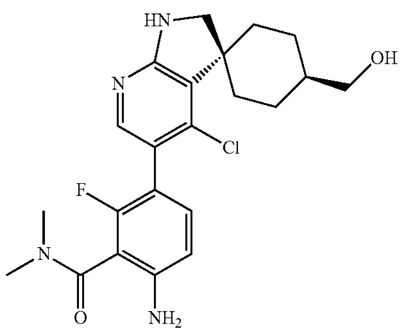 [SMILES: CN(C)C(=O)c1c(N)ccc(-c2cnc3c(c2Cl)[C@]2(CC[C@H](CO)CC2)CN3)c1F] | 6-Amino-3-((1R,4R)-4'-chloro-4-(hydroxymethyl)-1',2'-dihydrospiro[cyclohexane-1,3'-pyrrolo[2,3-b]pyridin]-5'-yl)-2-fluoro-N,N-dimethylbenzamide |
| 249 | 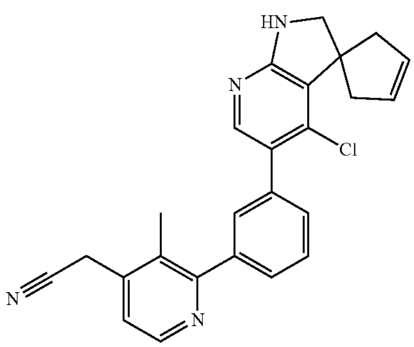 [SMILES: Cc1c(CC#N)ccnc1-c1cccc(-c2cnc3c(c2Cl)C2(CC=CC2)CN3)c1] | 2-(2-(3-(4'-Chloro-1',2'-dihydrospiro[cyclopentane-1,3'-pyrrolo[2,3-b]pyridin]-3-en-5'-yl)phenyl)-3-methylpyridin-4-yl)acetonitrile |
| 250 | | 6-Amino-3-(4'-chloro-4-cyano-4-methyl-1',2'-dihydrospiro[cyclohexane-1,3'-pyrrolo[2,3-b]pyridin]-5'-yl)-2-fluoro-N,N-dimethylbenzamide |
| 250a | 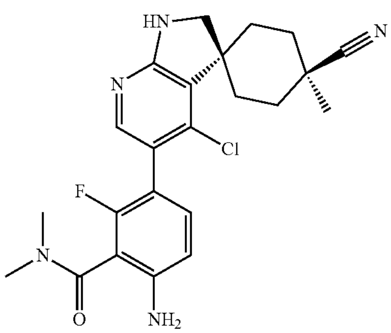 [SMILES: CN(C)C(=O)c1c(N)ccc(-c2cnc3c(c2Cl)[C@]2(CC[C@](C)(C#N)CC2)CN3)c1F] | 6-Amino-3-((1s,4s)-4'-chloro-4-cyano-4-methyl-1',2'-dihydrospiro[cyclohexane-1,3'-pyrrolo[2,3-b]pyridin]-5'-yl)-2-fluoro-N,N-dimethylbenzamide |

TABLE 1-continued

| No. | Structure | Name |
|---|---|---|
| 250b | 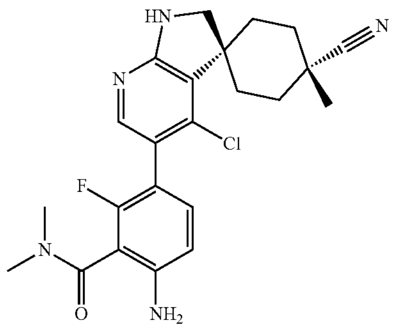 | 6-Amino-3-((1R,4R)-4'-chloro-4-cyano-4-methyl-1',2'-dihydrospiro[cyclohexane-1,3'-pyrrolo[2,3-b]pyridin]-5'-yl)-2-fluoro-N,N-dimethylbenzamide |
| 251 | 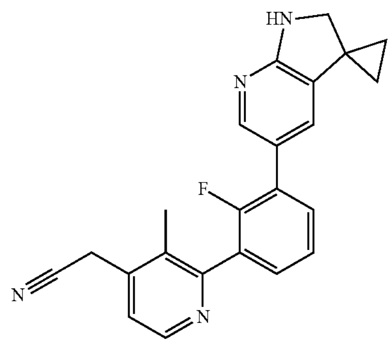 [SMILES: Cc1c(CC#N)ccnc1-c1cccc(-c2cnc3c(c2)C2(CC2)CN3)c1F] | 2-(2-(3-(1',2'-Dihydrospiro[cyclopropane-1,3'-pyrrolo[2,3-b]pyridin]-5'-yl)-2-fluorophenyl)-3-methylpyridin-4-yl)acetonitrile |
| 252 | 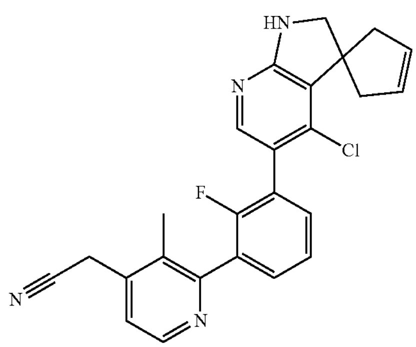 [SMILES: Cc1c(CC#N)ccnc1-c1cccc(-c2cnc3c(c2Cl)C2(CC=CC2)CN3)c1F] | 2-(2-(3-(4'-Chloro-1',2'-dihydrospiro[cyclopentane-1,3'-pyrrolo[2,3-b]pyridin]-3-en-5'-yl)-2-fluorophenyl)-3-methylpyridin-4-yl)acetonitrile |
| 253 | | (6-Amino-2-fluoro-3-(4-hydroxy-1',2'-dihydrospiro[cyclohexane-1,3'-pyrrolo[2,3-b]pyridin]-5'-yl)phenyl)(2-(1-methyl-1H-pyrazol-4-yl)piperidin-1-yl)methanone |
| 253a 253b | | (6-Amino-2-fluoro-3-((1s,4s)-4-hydroxy-1',2'-dihydrospiro[cyclohexane-1,3'-pyrrolo[2,3-b]pyridin]-5'-yl)phenyl)((R)-2-(1-methyl-1H-pyrazol-4-yl)piperidin-1-yl)methanone (6-Amino-2-fluoro-3-((1S,4s)-4-hydroxy-1',2'-dihydrospiro[cyclohexane-1,3'-pyrrolo[2,3-b]pyridin]-5'-yl)phenyl)((S)-2-(1-methyl-1H-pyrazol-4-yl)piperidin-1-yl)methanone |

| No. | Structure | Name |
|---|---|---|
| 254 | | (6-Amino-3-(4'-chloro-4-hydroxy-1',2'-dihydrospiro[cyclohexane-1,3'-pyrrolo[2,3-b]pyridin]-5'-yl)-2-fluorophenyl)(2-(1-methyl-1H-pyrazol-4-yl)piperidin-1-yl)methanone |
| 254a 254b | | (6-Amino-3-((1S,4s)-4'-chloro-4-hydroxy-1',2'-dihydrospiro[cyclohexane-1,3'-pyrrolo[2,3-b]pyridin]-5'-yl)-2-fluorophenyl)((R)-2-(1-methyl-1H-pyrazol-4-yl)piperidin-1-yl)methanone (6-Amino-3-((1S,4s)-4'-chloro-4-hydroxy-1',2'-dihydrospiro[cyclohexane-1,3'-pyrrolo[2,3-b]pyridin]-5'-yl)-2-fluorophenyl)((S)-2-(1-methyl-1H-pyrazol-4-yl)piperidin-1-yl)methanone |
| 255 | | 6-Amino-3-(4'-chloro-4-(2-hydroxypropan-2-yl)-1',2'-dihydrospiro[cyclohexane-1,3'-pyrrolo[2,3-b]pyridin]-5'-yl)-2-fluoro-N,N-dimethylbenzamide |
| 255a | 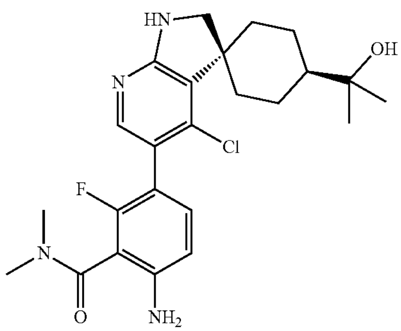 [SMILES: CN(C)C(=O)c1c(N)ccc(-c2cnc3c(c2Cl)[C@]2(CC[C@H](C(C)(C)O)CC2)CN3)c1F] | 6-Amino-3-((1s,4s)-4'-chloro-4-(2-hydroxypropan-2-yl)-1',2'-dihydrospiro[cyclohexane-1,3'-pyrrolo[2,3-b]pyridin]-5'-yl)-2-fluoro-N,N-dimethylbenzamide |
| 255b | 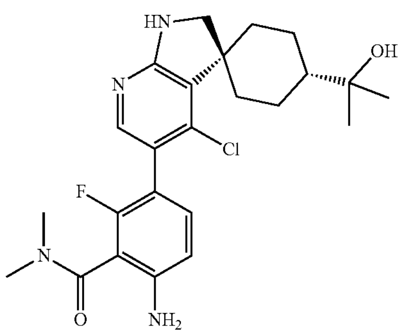 [SMILES: CN(C)C(=O)c1c(N)ccc(-c2cnc3c(c2Cl)[C@]2(CC[C@@H](C(C)(C)O)CC2)CN3)c1F] | 6-Amino-3-((1R,4R)-4'-chloro-4-(2-hydroxypropan-2-yl)-1',2'-dihydrospiro[cyclohexane-1,3'-pyrrolo[2,3-b]pyridin]-5'-yl)-2-fluoro-N,N-dimethylbenzamide |
| 256 | | 6-Amino-3-(4'-chloro-4-(hydroxymethyl)-4-methyl-1',2'-dihydrospiro[cyclohexane-1,3'-pyrrolo[2,3-b]pyridin]-5'-yl)-2-fluoro-N,N-dimethylbenzamide |

TABLE 1-continued

| No. | Structure | Name |
|---|---|---|
| 256a | 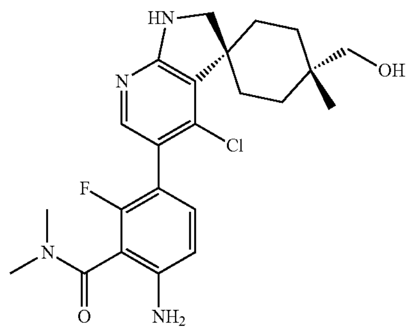 [SMILES: CN(C)C(=O)c1c(N)ccc(-c2cnc3c(c2Cl)[C@]2(CC[C@@](C)(CO)CC2)CN3)c1F] | 6-Amino-3-((1R,4R)-4'-chloro-4-(hydroxymethyl)-4-methyl-1',2'-dihydrospiro[cyclohexane-1,3'-pyrrolo[2,3-b]pyridin]-5'-yl)-2-fluoro-N,N-dimethylbenzamide |
| 257 | 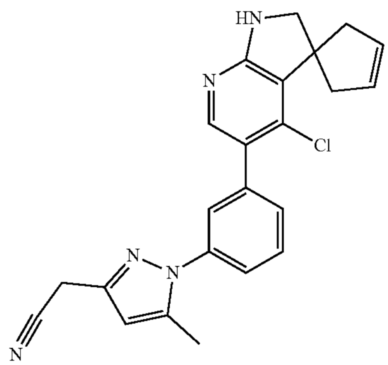 [SMILES: Cc1cc(CC#N)nn1-c1cccc(-c2cnc3c(c2Cl)C2(CC=CC2)CN3)c1] | 2-(1-(3-(4'-Chloro-1',2'-dihydrospiro[cyclopentane-1,3'-pyrrolo[2,3-b]pyridin]-3-en-5'-yl)phenyl)-5-methyl-1H-pyrazol-3-yl)acetonitrile |
| 258 | | 6-Amino-3-(4-(aminomethyl)-4'-chloro-1',2'-dihydrospiro[cyclohexane-1,3'-pyrrolo[2,3-b]pyridin]-5'-yl)-2-fluoro-N,N-dimethylbenzamide |
| 258a | 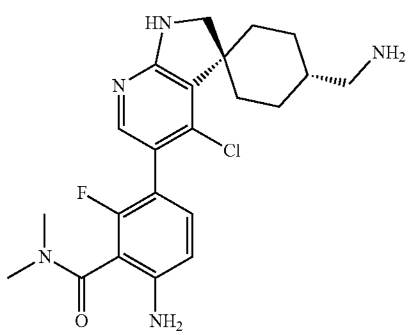 [SMILES: CN(C)C(=O)c1c(N)ccc(-c2cnc3c(c2Cl)[C@]2(CC[C@@H](CN)CC2)CN3)c1F] | 6-Amino-3-((1R,4R)-4-(aminomethyl)-4'-chloro-1',2'-dihydrospiro[cyclohexane-1,3'-pyrrolo[2,3-b]pyridin]-5'-yl)-2-fluoro-N,N-dimethylbenzamide |
| 258b | 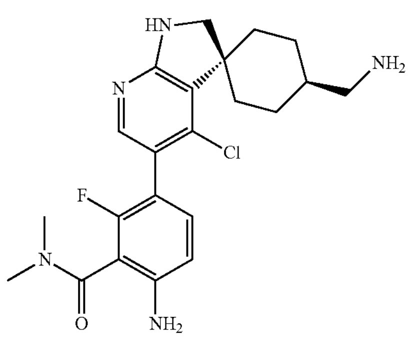 [SMILES: CN(C)C(=O)c1c(N)ccc(-c2cnc3c(c2Cl)[C@]2(CC[C@H](CN)CC2)CN3)c1F] | 6-Amino-3-((1s,4s)-4-(aminomethyl)-4'-chloro-1',2'-dihydrospiro[cyclohexane-1,3'-pyrrolo[2,3-b]pyridin]-5'-yl)-2-fluoro-N,N-dimethylbenzamide |
| 259 | | 6-Amino-3-(4'-chloro-3-(hydroxymethyl)-1',2'-dihydrospiro[cyclopentane-1,3'-pyrrolo[2,3-b]pyridin]-5'-yl)-2-fluoro-N,N-dimethylbenzamide |

TABLE 1-continued

| No. | Structure | Name |
|---|---|---|
| 259a | 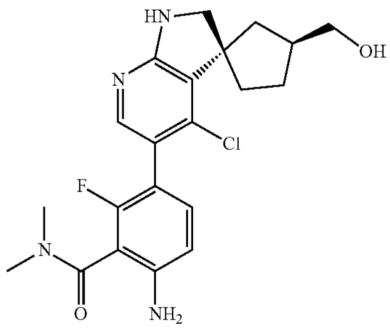 [SMILES: CN(C)C(=O)c1c(N)ccc(-c2cnc3c(c2Cl)[C@]2(CC[C@H](CO)C2)CN3)c1F] | 6-Amino-3-((1R,3S)-4'-chloro-3-(hydroxymethyl)-1',2'-dihydrospiro[cyclopentane-1,3'-pyrrolo[2,3-b]pyridin]-5'-yl)-2-fluoro-N,N-dimethylbenzamide 6-Amino-3-((1S,3R)-4'-chloro-3-(hydroxymethyl)-1',2'-dihydrospiro[cyclopentane-1,3'-pyrrolo[2,3-b]pyridin]-5'-yl)-2-fluoro-N,N-dimethylbenzamide |
| 259b | 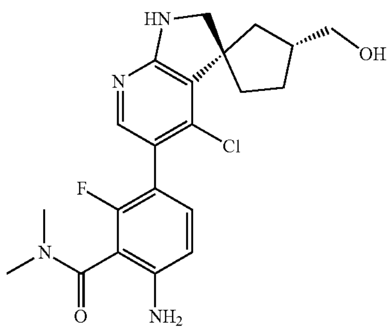 [SMILES: CN(C)C(=O)c1c(N)ccc(-c2cnc3c(c2Cl)[C@]2(CC[C@@H](CO)C2)CN3)c1F] | 6-Amino-3-((1R,3R)-4'-chloro-3-(hydroxymethyl)-1',2'-dihydrospiro[cyclopentane-1,3'-pyrrolo[2,3-b]pyridin]-5'-yl)-2-fluoro-N,N-dimethylbenzamide 6-Amino-3-((1S,3S)-4'-chloro-3-(hydroxymethyl)-1',2'-dihydrospiro[cyclopentane-1,3'-pyrrolo[2,3-b]pyridin]-5'-yl)-2-fluoro-N,N-dimethylbenzamide |
| 260 | 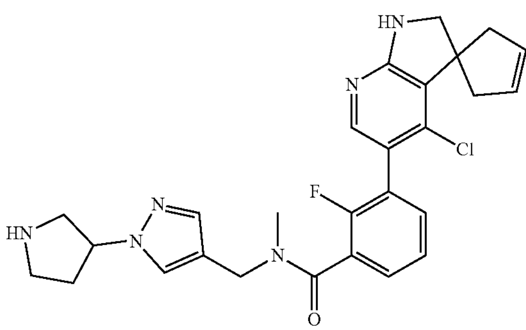 [SMILES: CN(Cc1cnn(C2CCNC2)c1)C(=O)c1cccc(-c2cnc3c(c2Cl)C2(CC=CC2)CN3)c1F] | 3-(4'-Chloro-1',2'-dihydrospiro[cyclopentane-1,3'-pyrrolo[2,3-b]pyridin]-3-en-5'-yl)-2-fluoro-N-methyl-N-((1-(pyrrolidin-3-yl)-1H-pyrazol-4-yl)methyl)benzamide |
| 261 | | 6-Amino-3-(4'-chloro-3-cyano-3-methyl-1',2'-dihydrospiro[cyclopentane-1,3'-pyrrolo[2,3-b]pyridin]-5'-yl)-2-fluoro-N,N-dimethylbenzamide |
| 261a 261b | 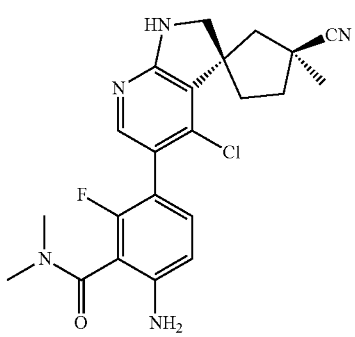 [SMILES: CN(C)C(=O)c1c(N)ccc(-c2cnc3c(c2Cl)[C@]2(CC[C@](C)(C#N)C2)CN3)c1F] | 6-Amino-3-((1R,3S)-4'-chloro-3-cyano-3-methyl-1',2'-dihydrospiro[cyclopentane-1,3'-pyrrolo[2,3-b]pyridin]-5'-yl)-2-fluoro-N,N-dimethylbenzamide 6-Amino-3-((1S,3R)-4'-chloro-3-cyano-3-methyl-1',2'-dihydrospiro[cyclopentane-1,3'-pyrrolo[2,3-b]pyridin]-5'-yl)-2-fluoro-N,N-dimethylbenzamide |

TABLE 1-continued

| No. | Structure | Name |
|---|---|---|
| 262 | 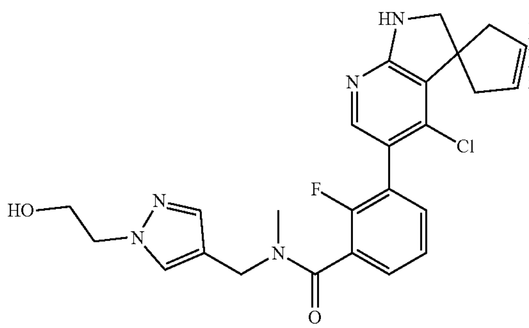 [SMILES: CN(Cc1cnn(CCO)c1)C(=O)c1cccc(-c2cnc3c(c2Cl)C2(CC=CC2)CN3)c1F] | 3-(4'-Chloro-1',2'-dihydrospiro[cyclopentane-1,3'-pyrrolo[2,3-b]pyridin]-3-en-5'-yl)-2-fluoro-N-((1-(2-hydroxyethyl)-1H-pyrazol-4-yl)methyl)-N-methylbenzamide |
| 263 | 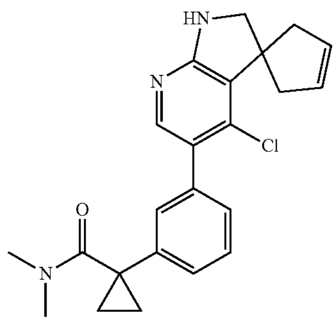 [SMILES: CN(C)C(=O)C1(c2cccc(-c3cnc4c(c3Cl)C3(CC=CC3)CN4)c2)CC1] | 1-(3-(4'-Chloro-1',2'-dihydrospiro[cyclopentane-1,3'-pyrrolo[2,3-b]pyridin]-3-en-5'-yl)phenyl)-N,N-dimethylcyclopropane-1-carboxamide |
| 264 | 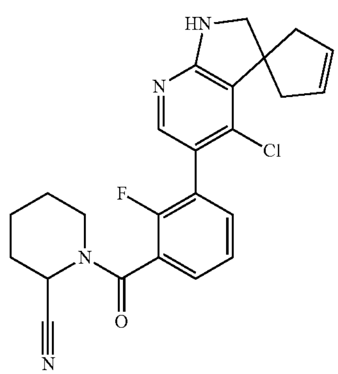 [SMILES: N#CC1CCCCN1C(=O)c1cccc(-c2cnc3c(c2Cl)C2(CC=CC2)CN3)c1F] | 1-(3-(4'-chloro-1'2'-dihydrospiro[cyclopentane-1,3'-pyrrolo[2,3-b]pyridin]-3-en-5'-yl)-2-fluorobenzoyl)piperidine-2-carbonitrile |
| 265 | 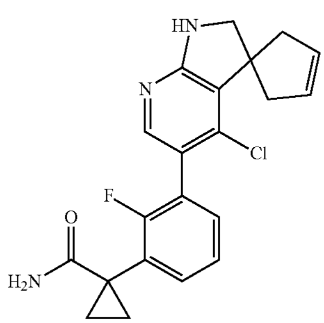 [SMILES: NC(=O)C1(c2cccc(-c3cnc4c(c3Cl)C3(CC=CC3)CN4)c2F)CC1] | 1-(3-(4'-Chloro-1',2'-dihydrospiro[cyclopentane-1,3'-pyrrolo[2,3-b]pyridin]-3-en-5'-yl)-2-fluorophenyl)cyclopropane-1-carboxamide |
| 266 | | 4'-Chloro-5'-(3-(4-(cyanomethyl)-3-methylpyridin-2-yl)-2-fluorophenyl)-3-methyl-1',2'-dihydrospiro[cyclopentane-1,3'-pyrrolo[2,3-b]pyridine]-3-carbonitrile |

TABLE 1-continued

| No. | Structure | Name |
|---|---|---|
| 266a 266b | | (1R,3S)-4'-Chloro-5'-(3-(4-(cyanomethyl)-3-methylpyridin-2-yl)-2-fluorophenyl)-3-methyl-1',2'-dihydrospiro [cyclopentane-1,3'-pyrrolo[2,3-b]pyridine]-3-carbonitrile |
| 267 | | (1S, 3R)-4'-Chloro-5'-(3-(4-(cyanomethyl)-3-methylpyridin-2-yl)-2-fluorophenyl)-3-methyl-1',2'-dihydrospiro[cyclopentane-1,3'-pyrrolo[2,3-b]pyridine]-3-carbonitrile<br>4'-Chloro-5'-(3-(4-(cyanomethyl)-3-methylpyridin-2-yl)-2-fluorophenyl)-3-methyl-1',2'-dihydrospiro[cyclopentane-1,3'-pyrrolo[2,3-b]pyridine]-3-carboxamide |
| 267a 267b | | (1R,3S)-4'-Chloro-5'-(3-(4-(cyanomethyl)-3-methylpyridin-2-yl)-2-fluorophenyl)-3-methyl-1',2'-dihydrospiro[cyclopentane-1,3'-pyrrolo[2,3-b]pyridine]-3-carboxamide<br>(1S, 3R)-4'-Chloro-5'-(3-(4-(cyanomethyl)-3-methylpyridin-2-yl)-2-fluorophenyl)-3-methyl-1',2'-dihydrospiro[cyclopentane-1,3'-pyrrolo[2,3-b]pyridine]-3-carboxamide |
| 268 | | (1-(3-(4'-Chloro-1',2'-dihydrospiro[cyclopentane-1,3'-pyrrolo[2,3-b]pyridin]-3-en-5'-yl)phenyl)cyclopropyl)(morpholino)methanone |
| 269 | | 2-(3-(4'-Chloro-1',2'-dihydrospiro[cyclopentane-1,3'-pyrrolo[2,3-b]pyridin]-3-en-5'-yl)-2-fluorophenyl)-N-(cyanomethyl)isonicotinamide |

TABLE 1-continued

| No. | Structure | Name |
|---|---|---|
| 270 | 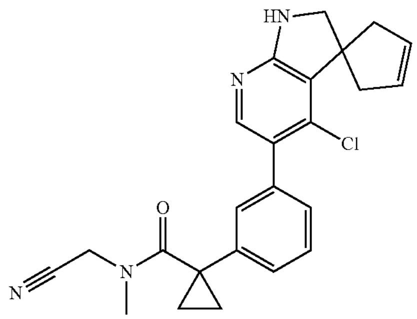 [SMILES: CN(CC#N)C(=O)C1(c2cccc(-c3cnc4c(c3Cl)C3(CC=CC3)CN4)c2)CC1] | 1-(3-(4'-Chloro-1',2'-dihydrospiro[cyclopentane-1,3'-pyrrolo[2,3-b]pyridin]-3-en-5'-yl)phenyl)-N-(cyanomethyl)-N-methylcyclopropane-1-carboxamide |
| 271 | | 6-Amino-3-(4'-chloro-3-cyano-3-methyl-1',2'-dihydrospiro[cyclopentane-1,3'-pyrrolo[2,3-b]pyridin]-5'-yl)-N-(2-(dimethylamino)ethyl)-2-fluoro-N-methylbenzamide |
| 271a | 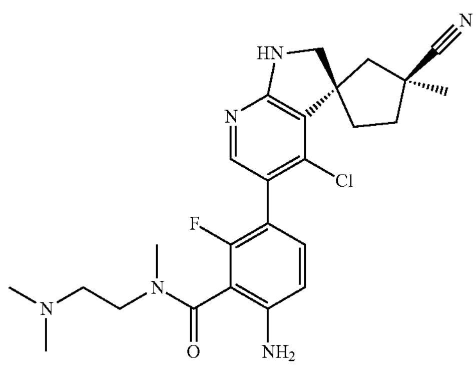 [SMILES: CN(C)CCN(C)C(=O)c1c(N)ccc(-c2cnc3c(c2Cl)[C@]2(CC[C@](C)(C#N)C2)CN3)c1F] | 6-Amino-3-((1R,3R)-4'-chloro-3-cyano-3-methyl-1',2'-dihydrospiro[cyclopentane-1,3'-pyrrolo[2,3-b]pyridin]-5'-yl)-N-(2-(dimethylamino)ethyl)-2-fluoro-N-methylbenzamide<br>6-Amino-3-((1S,3R)-4'-chloro-3-cyano-3-methyl-1',2'-dihydrospiro[cyclopentane-1,3'-pyrrolo[2,3-b]pyridin]-5'-yl)-N-(2-(dimethylamino)ethyl)-2-fluoro-N-methylbenzamide |
| 272 | | 6-Amino-3-(4'-chloro-3-cyano-3-methyl-1',2'-dihydrospiro[cyclopentane-1,3'-pyrrolo[2,3-b]pyridin]-5'-yl)-2-fluoro-N-methyl-N-(2-morpholinoethyl)benzamide |
| 272a | 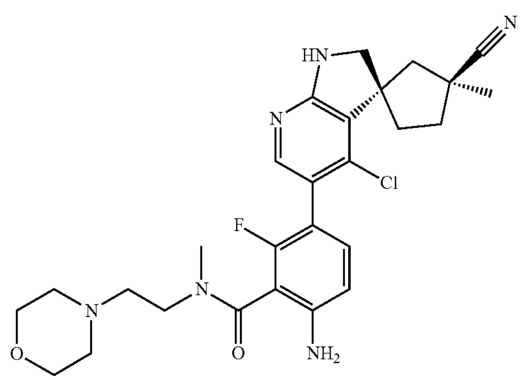 [SMILES: CN(CCN1CCOCC1)C(=O)c1c(N)ccc(-c2cnc3c(c2Cl)[C@]2(CC[C@](C)(C#N)C2)CN3)c1F] | 6-Amino-3-((1R,3S)-4'-chloro-3-cyano-3-methyl-1',2'-dihydrospiro[cyclopentane-1,3'-pyrrolo[2,3-b]pyridin]-5'-yl)-2-fluoro-N-methyl-N-(2-morpholinoethyl)benzamide<br>6-Amino-3-((1S,3R)-4'-chloro-3-cyano-3-methyl-1',2'-dihydrospiro[cyclopentane-1,3'-pyrrolo[2,3-b]pyridin]-5'-yl)-2-fluoro-N-methyl-N-(2-morpholinoethyl)benzamide |
| 273 | | 6-Amino-3-(4'-chloro-4-(methylsulfonyl)-1',2'-dihydrospiro[cyclohexane-1,3'-pyrrolo[2,3-b]pyridin]-5'-yl)-2-fluoro-N,N-dimethylbenzamide |

TABLE 1-continued

| No. | Structure | Name |
|---|---|---|
| 273a | 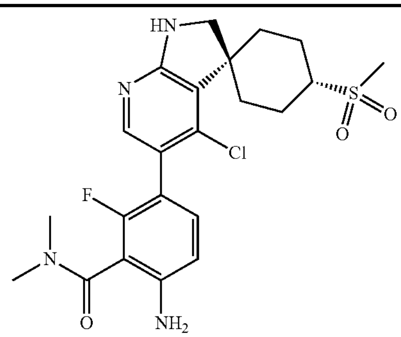 | 6-Amino-3-((1R,4R)-4'-chloro-4-(methylsulfonyl)-1',2'-dihydrospiro[cyclohexane-1,3'-pyrrolo[2,3-b]pyridin]-5'-yl)-2-fluoro-N,N-dimethylbenzamide |
| 274 | | 5'-(3-Amino-5-(4-(cyanomethyl)-3-methylpyridin-2-yl)phenyl)-4'-chloro-3-methyl-1',2'-dihydrospiro[cyclopentane-1,3'-pyrrolo[2,3-b]pyridine]-3-carbonitrile |
| 274a 274b | | (1R,3S)-5'-(3-Amino-5-(4-(cyanomethyl)-3-methylpyridin-2-yl)phenyl)-4'-chloro-3-methyl-1',2'-dihydrospiro[cyclopentane-1,3'-pyrrolo[2,3-b]pyridine]-3-carbonitrile<br>(1S, 3R)-5'-(3-Amino-5-(4-(cyanomethyl)-3-methylpyridin-2-yl)phenyl)-4'-chloro-3-methyl-1',2'-dihydrospiro[cyclopentane-1,3'-pyrrolo[2,3-b]pyridine]-3-carbonitrile |
| 275 | | 6-Amino-3-(4'-chloro-3-cyano-3-methyl-1',2'-dihydrospiro[cyclopentane-1,3'-pyrrolo[2,3-b]pyridin]-5'-yl)-N-(3-(dimethylamino)propyl)-2-fluoro-N-methylbenzamide |
| 275a | 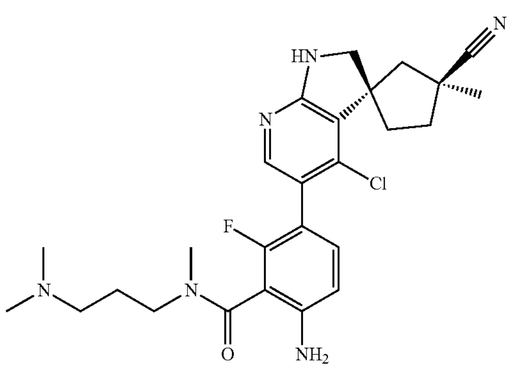 [SMILES: CN(C)CCCN(C)C(=O)c1c(N)ccc(-c2cnc3c(c2Cl)[C@]2(CC[C@](C)(C#N)C2)CN3)c1F] | 6-Amino-3-((1R,3S)-4'-chloro-3-cyano-3-methyl-1',2'-dihydrospiro[cyclopentane-1,3'-pyrrolo[2,3-b]pyridin]-5'-yl)-N-(3-(dimethylamino)propyl)-2-fluoro-N-methylbenzamide<br>6-Amino-3-((1S,3R)-4'-chloro-3-cyano-3-methyl-1',2'-dihydrospiro[cyclopentane-1,3'-pyrrolo[2,3-b]pyridin]-5'-yl)-N-(3-(dimethylamino)propyl)-2-fluoro-N-methylbenzamide |
| 276 | 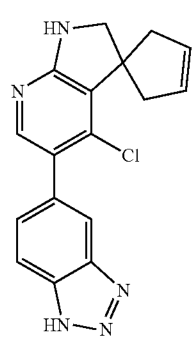 [SMILES: Clc1c(-c2ccc3[nH]nnc3c2)cnc2c1C1(CC=CC1)CN2] | 5'-(1H-Benzo[d][1,2,3]triazol-5-yl)-4'-chloro-1',2'-dihydrospiro[cyclopentane-1,3'-pyrrolo[2,3-b]pyridin]-3-ene |

TABLE 1-continued

| No. | Structure | Name |
| --- | --- | --- |
| 277 | 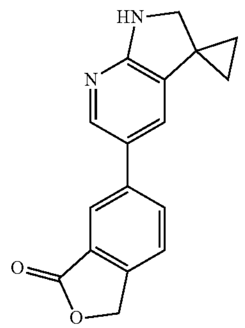 [SMILES: O=C1OCc2ccc(-c3cnc4c(c3)C3(CC3)CN4)cc21] | 6-(1',2'-dihydrospiro[cyclopropane-1,3'-pyrrolo[2,3-b]pyridin]-5'-yl)isobenzofuran-1(3H)-one |
| 278 | 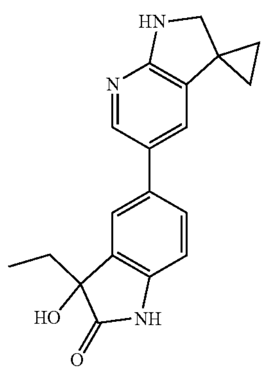 [SMILES: CCC1(O)C(=O)Nc2ccc(-c3cnc4c(c3)C3(CC3)CN4)cc21] | (RS)-5-(1',2'-dihydrospiro[cyclopropane-1,3'-pyrrolo[2,3-b]pyridin]-5'-yl)-3-ethyl-3-hydroxyindolin-2-one |
| 279 | 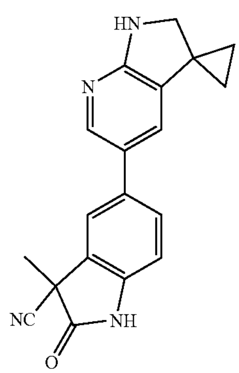 [SMILES: CC1(C#N)C(=O)Nc2ccc(-c3cnc4c(c3)C3(CC3)CN4)cc21] | (RS)-5-(1',2'-dihydrospiro[cyclopropane-1,3'-pyrrolo[2,3-b]pyridin]-5'-yl)-3-methyl-2-oxoindoline-3-carbonitrile |
| 280 | 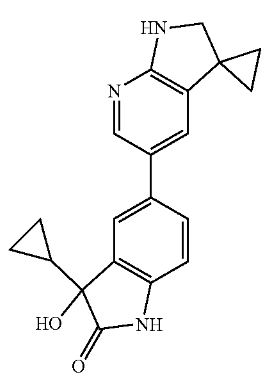 [SMILES: O=C1Nc2ccc(-c3cnc4c(c3)C3(CC3)CN4)cc2C1(O)C1CC1] | (RS)-5-(4'-chloro-1',2'-dihydrospiro[cyclopropane-1,3'-pyrrolo[2,3-b]pyridin]-5'-yl)-3-cyclopropyl-3-hydroxyindolin-2-one |

TABLE 1-continued

| No. | Structure | Name |
|---|---|---|
| 281 | 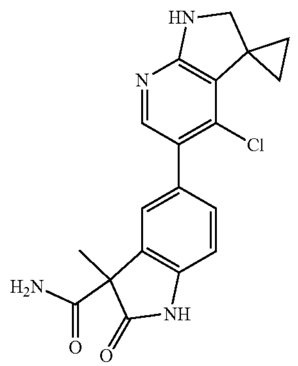 [SMILES: CC1(C(N)=O)C(=O)Nc2ccc(-c3cnc4c(c3Cl)C3(CC3)CN4)cc21] | (RS)-5-(4'-chloro-1',2'-dihydrospiro[ cyclopropane-1,3'-pyrrolo[2,3-b]pyridin]-5'-yl)-3-methyl-2-oxoindoline-3-carboxamide |
| 282 | 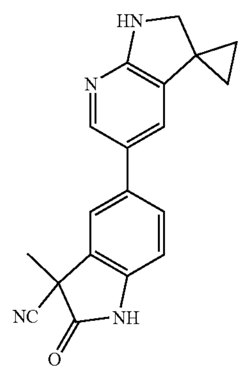 [SMILES: CC1(C#N)C(=O)Nc2ccc(-c3cnc4c(c3)C3(CC3)CN4)cc21] | (RS)-5-(4'-chloro-1',2'-dihydrospiro[ cyclopropane-1,3'-pyrrolo[2,3-b]pyridin]-5'-yl)-3-methyl-2-oxoindoline-3-carbonitrile |
| 283 | 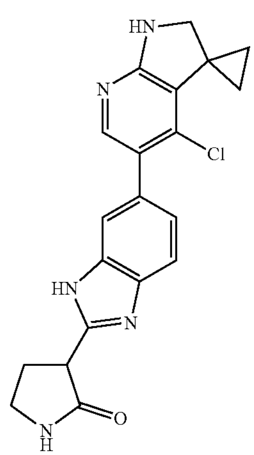 [SMILES: O=C1NCCC1c1nc2ccc(-c3cnc4c(c3Cl)C3(CC3)CN4)cc2[nH]1] | (+)-3-(6-(4'-Chloro-1',2'-dihydrospiro[cyclopropane-1,3'-pyrrolo[2,3-b]pyridin]-5'-yl)-1H-benzo[d]imidazol-2-yl)pyrrolidin-2-one |
| 284 | 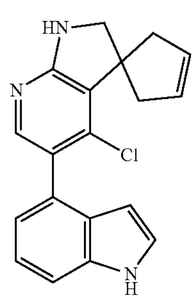 [SMILES: Clc1c(-c2cccc3[nH]ccc23)cnc2c1C1(CC=CC1)CN2] | 4'-Chloro-5'-(1H-indol-4-yl)-1',2'-dihydrospiro[cyclopentane-1,3'-pyrrolo[2,3-b]pyridin]-3-ene |

TABLE 1-continued

| No. | Structure | Name |
| --- | --- | --- |
| 285 | 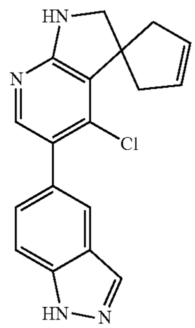 [SMILES: Clc1c(-c2ccc3[nH]ncc3c2)cnc2c1C1(CC=CC1)CN2] | 4'-Chloro-5'-(1H-indazol-5-yl)-1',2'-dihydrospiro[cyclopentane-1,3'-pyrrolo[2,3-b]pyridin]-3-ene |
| 286 | 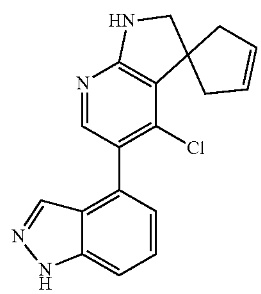 [SMILES: Clc1c(-c2cccc3[nH]ncc23)cnc2c1C1(CC=CC1)CN2] | 4'-Chloro-5'-(1H-indazol-4-yl)-1',2'-dihydrospiro[cyclopentane-1,3'-pyrrolo[2,3-b]pyridin]-3-ene |
| 287 | 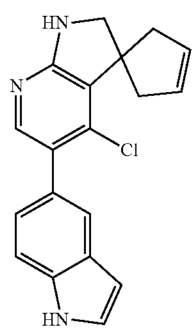 [SMILES: Clc1c(-c2ccc3[nH]ccc3c2)cnc2c1C1(CC=CC1)CN2] | 4'-Chloro-5'-(1H-indol-5-yl)-1',2'-dihydrospiro[cyclopentane-1,3'-pyrrolo[2,3-b]pyridin]-3-ene |
| 288 | | 3-Amino-6-(4'-chloro-3-cyano-3-methyl-1',2'-dihydrospiro[cyclopentane-1,3'-pyrrolo[2,3-b]pyridin]-5'-yl)-N,N-dimethylpicolinamide |
| 288a | 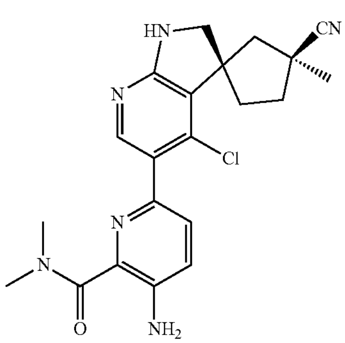 | 3-Amino-6-(((1R,3S)-4'-chloro-3-cyano-3-methyl-1',2'-dihydrospiro[cyclopentane-1,3'-pyrrolo[2,3-b]pyridin]-5'-yl)-N,N-dimethylpicolinamide |

TABLE 1-continued

| No. | Structure | Name |
|---|---|---|
| 289 | 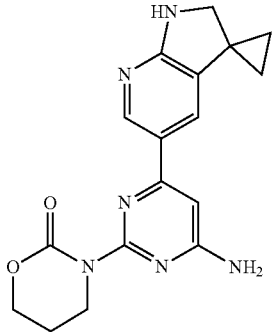 [SMILES: Nc1cc(-c2cnc3c(c2)C2(CC2)CN3)nc(N2CCCOC2=O)n1] | 3-(4-amino-6-(1',2'-dihydrospiro[cyclopropane-1,3'-pyrrolo[2,3-b]pyridin]-5'-yl)pyrimidin-2-yl)-1,3-oxazinan-2-one |
| 290a | 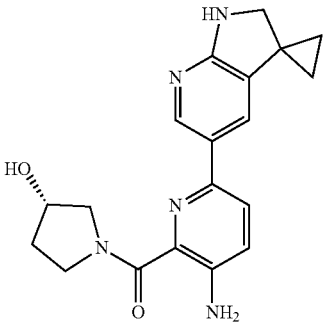 [SMILES: Nc1ccc(-c2cnc3c(c2)C2(CC2)CN3)nc1C(=O)N1CC[C@H](O)C1] | (S)-(3-amino-6-(1',2'-dihydrospiro[cyclopropane-1,3'-pyrrolo[2,3-b]pyridin]-5'-yl)pyridin-2-yl)(3-hydroxypyrrolidin-1-yl)methanone |
| 290b | 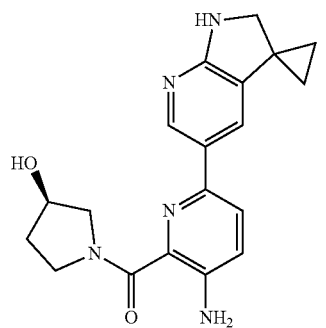 [SMILES: Nc1ccc(-c2cnc3c(c2)C2(CC2)CN3)nc1C(=O)N1CC[C@@H](O)C1] | (R)-(3-amino-6-(1',2'-dihydrospiro[cyclopropane-1,3'-pyrrolo[2,3-b]pyridin]-5'-yl)pyridin-2-yl)(3-hydroxypyrrolidin-1-yl)methanone |
| 291 | 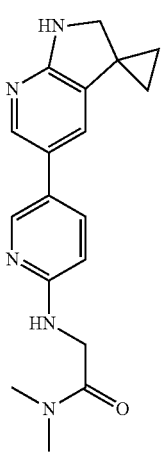 | 2-((5-(1',2'-dihydrospiro[cyclopropane-1,3'-pyrrolo[2,3-b]pyridin]-5'-yl)pyridin-2-yl)amino)-N,N-dimethylacetamide |

TABLE 1-continued

| No. | Structure | Name |
| --- | --- | --- |
| 292 | 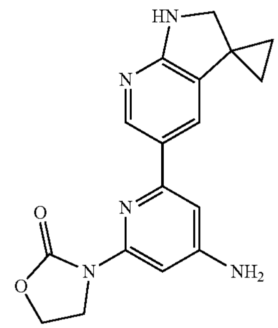 [SMILES: Nc1cc(-c2cnc3c(c2)C2(CC2)CN3)nc(N2CCOC2=O)c1] | 3-(4-amino-6-(1',2'-dihydrospiro[cyclopropane-1,3'-pyrrolo[2,3-b]pyridin]-5'-yl)pyridin-2-yl)oxazolidin-2-one |
| 293 | 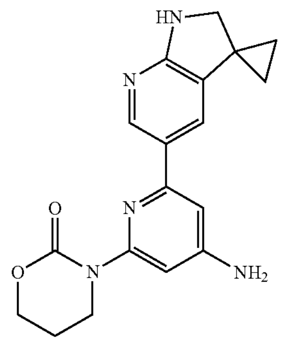 [SMILES: Nc1cc(-c2cnc3c(c2)C2(CC2)CN3)nc(N2CCCOC2=O)c1] | 3-(4-amino-6-(1',2'-dihydrospiro[cyclopropane-1,3'-pyrrolo[2,3-b]pyridin]-5'-yl)pyridin-2-yl)-1,3-oxazinan-2-one |
| 294 | 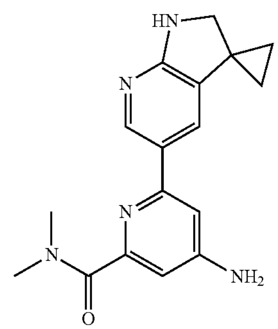 [SMILES: CN(C)C(=O)c1cc(N)cc(-c2cnc3c(c2)C2(CC2)CN3)n1] | 4-amino-6-(1',2'-dihydrospiro[cyclopropane-1,3'-pyrrolo[2,3-b]pyridin]-5'-yl)-N,N-dimethylpicolinamide |
| 295 | 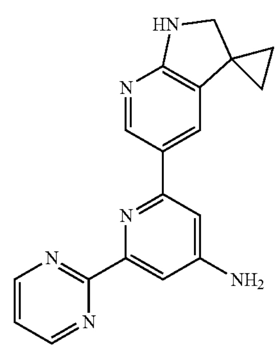 [SMILES: Nc1cc(-c2cnc3c(c2)C2(CC2)CN3)nc(-c2ncccn2)c1] | 2-(1',2'-dihydrospiro[cyclopropane-1,3'-pyrrolo[2,3-b]pyridin]-5'-yl)-6-(pyrimidin-2-yl)pyridin-4-amine |

TABLE 1-continued

| No. | Structure | Name |
| --- | --- | --- |
| 296 | 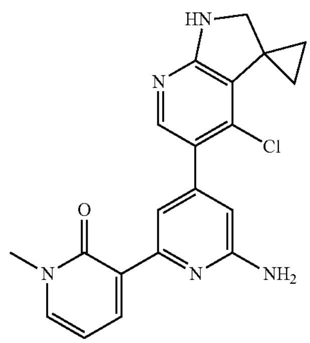 [SMILES: Cn1cccc(-c2cc(-c3cnc4c(c3Cl)C3(CC3)CN4)cc(N)n2)c1=O] | 6-amino-4-(4'-chloro-1',2'-dihydrospiro[cyclopropane-1,3'-pyrrolo[2,3-b]pyridin]-5'-yl)-1'-methyl-[2,3'-bipyridin]-2'(1'H)-one |
| 297 | 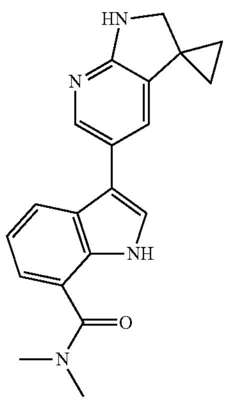 [SMILES: CN(C)C(=O)c1cccc2c(-c3cnc4c(c3)C3(CC3)CN4)c[nH]c12] | 3-(1',2'-Dihydrospiro[cyclopropane-1,3'-pyrrolo[2,3-b]pyridin]-5'-yl)-N,N-dimethyl-1H-indole-7-carboxamide |
| 298 | 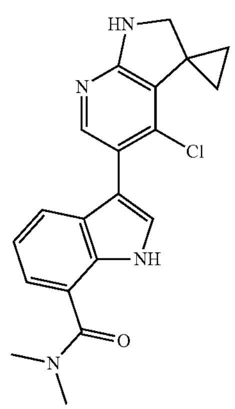 [SMILES: CN(C)C(=O)c1cccc2c(-c3cnc4c(c3Cl)C3(CC3)CN4)c[nH]c12] | 3-(4'-Chloro-1',2'-dihydrospiro[cyclopropane-1,3'-pyrrolo[2,3-b]pyridin]-5'-yl)-N,N-dimethyl-1H-indole-7-carboxamide |
| 299 | 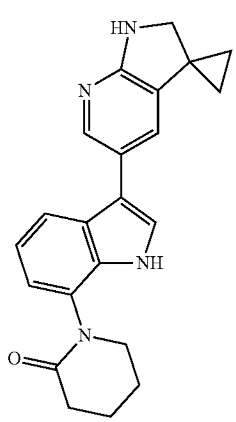 [SMILES: O=C1CCCCN1c1cccc2c(-c3cnc4c(c3)C3(CC3)CN4)c[nH]c12] | 1-(3-(1',2'-Dihydrospiro[cyclopropane-1,3'-pyrrolo[2,3-b]pyridin]-5'-yl)-1H-indol-7-yl)piperidin-2-one |

TABLE 1-continued

| No. | Structure | Name |
|---|---|---|
| 300 | | 1-(3-(4'-Chloro-3-hydroxy-1',2'-dihydrospiro[cyclopentane-1,3'-pyrrolo[2,3-b]pyridin]-5'-yl)-1H-indol-7-yl)piperidin-2-one |
| 300a | 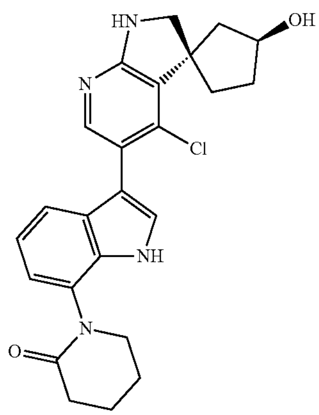 [SMILES: O=C1CCCCN1c1cccc2c(-c3cnc4c(c3Cl)[C@]3(CC[C@H](O)C3)CN4)c[nH]c12] | 1-(3-((1R,3S)-4'-Chloro-3-hydroxy-1',2'-dihydrospiro[cyclopentane-1,3'-pyrrolo[2,3-b]pyridin]-5'-yl)-1H-indol-7-yl)piperidin-2-one 1-(3-((1S,3R)-4'-Chloro-3-hydroxy-1',2'-dihydrospiro[cyclopentane-1,3'-pyrrolo[2,3-b]pyridin]-5'-yl)-1H-indol-7-yl)piperidin-2-one |
| 300b 300c | 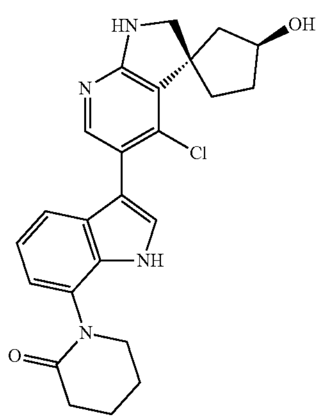 [SMILES: O=C1CCCCN1c1cccc2c(-c3cnc4c(c3Cl)[C@]3(CC[C@H](O)C3)CN4)c[nH]c12] | 1-(3-((1R,3S)-4'-Chloro-3-hydroxy-1',2'-dihydrospiro[cyclopentane-1,3'-pyrrolo[2,3-b]pyridin]-5'-yl)-1H-indol-7-yl)piperidin-2-one 1-(3-((1S,3R)-4'-Chloro-3-hydroxy-1',2'-dihydrospiro[cyclopentane-1,3'-pyrrolo[2,3-b]pyridin]-5'-yl)-1H-indol-7-yl)piperidin-2-one |
| 301 | 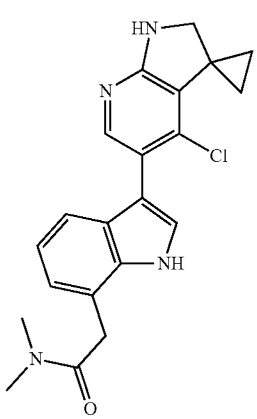 [SMILES: CN(C)C(=O)Cc1cccc2c(-c3cnc4c(c3Cl)C3(CC3)CN4)c[nH]c12] | 2-(3-(4'-Chloro-1',2'-dihydrospiro[cyclopropane-1,3'-pyrrolo[2,3-b]pyridin]-5'-yl)-1H-indol-7-yl)-N,N-dimethylacetamide |

TABLE 1-continued

| No. | Structure | Name |
|---|---|---|
| 302 | 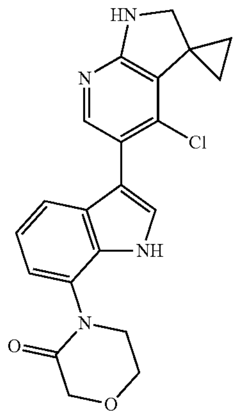 [SMILES: O=C1COCCN1c1cccc2c(-c3cnc4c(c3Cl)C3(CC3)CN4)c[nH]c12] | 4-(3-(4'-Chloro-1',2'-dihydrospiro[cyclopropane-1,3'-pyrrolo[2,3-b]pyridin]-5'-yl)-1H-indol-7-yl)morpholin-3-one |
| 303 | 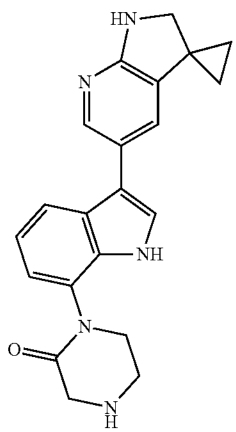 [SMILES: O=C1CNCCN1c1cccc2c(-c3cnc4c(c3)C3(CC3)CN4)c[nH]c12] | 1-(3-(1'2'-Dihydrospiro[cyclopropane-1,3'-pyrrolo[2,3-b]pyridin]-5'-yl)-1H-indol-7-yl)piperazin-2-one |
| 304 | | 4'-Chloro-5'-(7-(4-methyl-2-oxopiperazin-1-yl)-1H-indol-3-yl)-1',2'-dihydrospiro[cyclopentane-1,3'-pyrrolo[2,3-b]pyridine]-3-carboxamide |
| 304a | 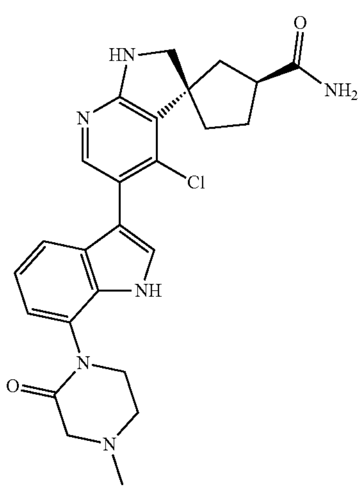 [SMILES: CN1CCN(c2cccc3c(-c4cnc5c(c4Cl)[C@]4(CC[C@H](C(N)=O)C4)CN5)c[nH]c23)C(=O)C1] | (1R,3S)-4'-Chloro-5'-(7-(4-methyl-2-oxopiperazin-1-yl)-1H-indol-3-yl)-1',2'-dihydrospiro[cyclopentane-1,3'-pyrrolo[2,3-b]pyridine]-3-carboxamide (1S, 3R)-4'-Chloro-5'-(7-(4-methyl-2-oxopiperazin-1-yl)-1H-indol-3-yl)-1',2'-dihydrospiro[cyclopentane-1,3'-pyrrolo[2,3-b]pyridine]-3-carboxamide |
| 305 | | 4'-Chloro-5'-(7-(2-oxopiperazin-1-yl)-1H-indol-3-yl)-1',2'-dihydrospiro[cyclopentane-1,3'-pyrrolo[2,3-b]pyridine]-3-carboxamide |

TABLE 1-continued

| No. | Structure | Name |
|---|---|---|
| 305a | 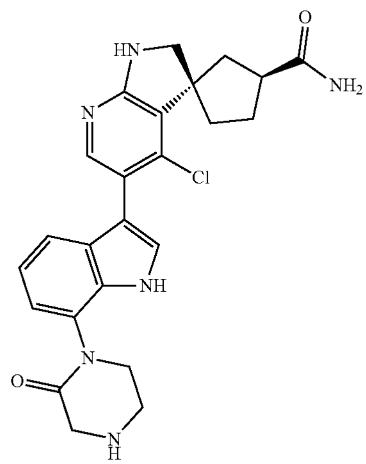 [SMILES: NC(=O)[C@H]1CC[C@@]2(CNc3ncc(-c4c[nH]c5c(N6CCNCC6=O)cccc45)c(Cl)c32)C1] | (1R,3S)-4'-Chloro-5'-(7-(2-oxopiperazin-1-yl)-1H-indol-3-yl)-1',2'-dihydrospiro[cyclopentane-1,3'-pyrrolo[2,3-b]pyridine]-3-carboxamide<br>(1S, 3R)-4'-Chloro-5'-(7-(2-oxopiperazin-1-yl)-1H-indol-3-yl)-1'2'-dihydrospiro[cyclopentane-1,3'-pyrrolo[2,3-b]pyridine]-3-carboxamide |
| 306 | | 1-(3-(2-methyl-1',2'-dihydrospiro[cyclopropane-1,3'-pyrrolo[2,3-b]pyridin]-5'-yl)-1H-indol-7-yl)piperazin-2-one |
| 306a | 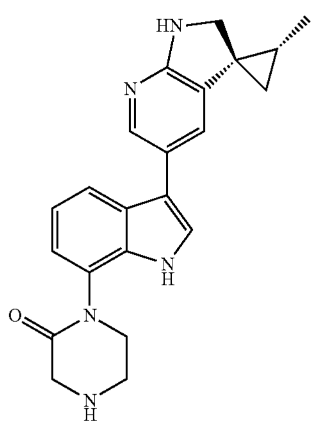 [SMILES: C[C@@H]1C[C@@]12CNc1ncc(-c3c[nH]c4c(N5CCNCC5=O)cccc34)cc12] | 1-(3-((1R,2R)-2-methyl-1',2'-dihydrospiro[cyclopropane-1,3'-pyrrolo[2,3-b]pyridin]-5'-yl)-1H-indol-7-yl)piperazin-2-one<br>1-(3-((1S, 2S)-2-methyl-1',2'-dihydrospiro[cyclopropane-1,3'-pyrrolo[2,3-b]pyridin]-5'-yl)-1H-indol-7-yl)piperazin-2-one |
| 307 | 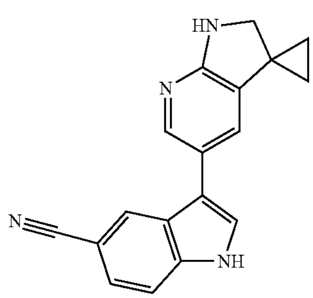 [SMILES: N#Cc1ccc2[nH]cc(-c3cnc4c(c3)C3(CC3)CN4)c2c1] | 3-(1',2'-Dihydrospiro[cyclopropane-1,3'-pyrrolo[2,3-b]pyridin]-5'-yl)-1H-indole-5-carbonitrile |
| 308 | 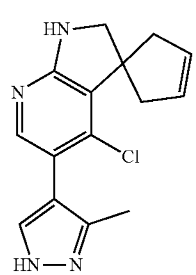 [SMILES: Cc1n[nH]cc1-c1cnc2c(c1Cl)C1(CC=CC1)CN2] | 4'-Chloro-5'-(3-methyl-1H-pyrazol-4-yl)-1',2'-dihydrospiro[cyclopentane-1,3'-pyrrolo[2,3-b]pyridin]-3-ene |

TABLE 1-continued

| No. | Structure | Name |
|---|---|---|
| 309 | 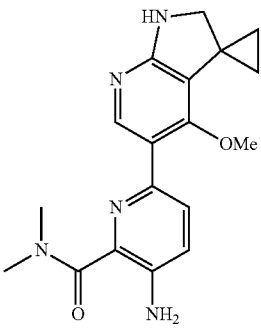 [SMILES: COc1c(-c2ccc(N)c(C(=O)N(C)C)n2)cnc2c1C1(CC1)CN2] | 3-Amino-6-(4'-methoxy-1',2'-dihydrospiro[cyclopropane-1,3'-pyrrolo[2,3-b]pyridin]-5'-yl)-N,N-dimethylpicolinamide |
| 310 | 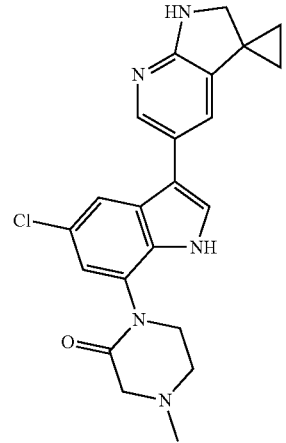 [SMILES: CN1CCN(c2cc(Cl)cc3c(-c4cnc5c(c4)C4(CC4)CN5)c[nH]c23)C(=O)C1] | 1-(5-Chloro-3-(1',2'-dihydrospiro[cyclopropane-1,3'-pyrrolo[2,3-b]pyridin]-5'-yl)-1H-indol-7-yl)-4-methylpiperazin-2-one |
| 311 | 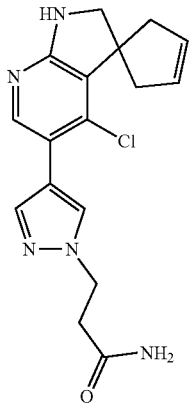 | 3-(4-(4'-Chloro-1',2'-dihydrospiro[cyclopentane-1,3'-pyrrolo[2,3-b]pyridin]-3-en-5'-yl)-1H-pyrazol-1-yl)propanamide |
| 312 | 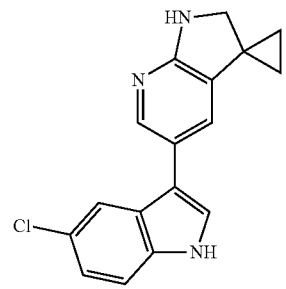 [SMILES: Clc1ccc2[nH]cc(-c3cnc4c(c3)C3(CC3)CN4)c2c1] | 5'-(5-Chloro-1H-indol-3-yl)-1',2'-dihydrospiro[cyclopropane-1,3'-pyrrolo[2,3-b]pyridine] |

TABLE 1-continued

| No. | Structure | Name |
|---|---|---|
| 313 | 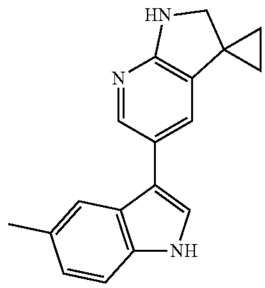 [SMILES: Cc1ccc2[nH]cc(-c3cnc4c(c3)C3(CC3)CN4)c2c1] | 5'-(5-Methyl-1H-indol-3-yl)-1',2'-dihydrospiro[cyclopropane-1,3'-pyrrolo[2,3-b]pyridine] |
| 314 | 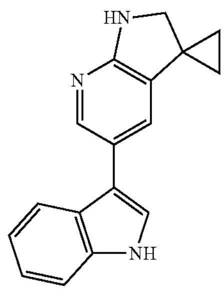 [SMILES: c1ccc2c(-c3cnc4c(c3)C3(CC3)CN4)c[nH]c2c1] | 5'-(1H-Indol-3-yl)-1',2'-dihydrospiro[cyclopropane-1,3'-pyrrolo[2,3-b]pyridine] |
| 315 | 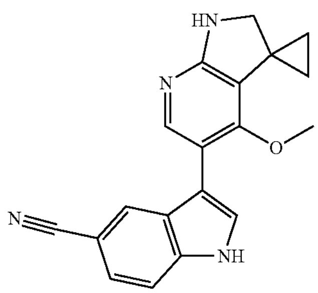 [SMILES: COc1c(-c2c[nH]c3ccc(C#N)cc23)cnc2c1C1(CC1)CN2] | 3-(4'-Methoxy-1',2'-dihydrospiro[cyclopropane-1,3'-pyrrolo[2,3-b]pyridin]-5'-yl)-1H-indole-5-carbonitrile |
| 316 | 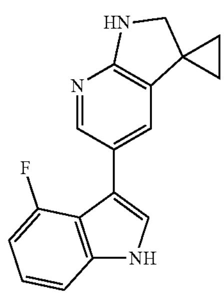 [SMILES: Fc1cccc2[nH]cc(-c3cnc4c(c3)C3(CC3)CN4)c12] | 5'-(4-Fluoro-1H-indol-3-yl)-1',2'-dihydrospiro[cyclopropane-1,3'-pyrrolo[2,3-b]pyridine] |
| 317 | 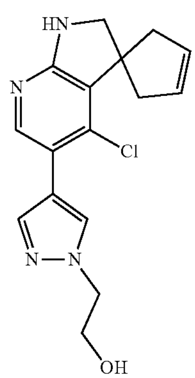 [SMILES: OCCn1cc(-c2cnc3c(c2Cl)C2(CC=CC2)CN3)cn1] | 2-(4-(4'-Chloro-1',2'-dihydrospiro[cyclopentane-1,3'-pyrrolo[2,3-b]pyridin]-3-en-5'-yl)-1H-pyrazol-1-yl)ethan-1-ol |

TABLE 1-continued

| No. | Structure | Name |
| --- | --- | --- |
| 318 | 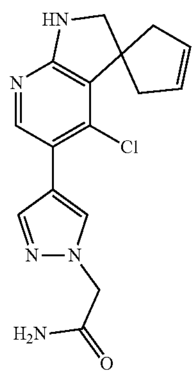 [SMILES: NC(=O)Cn1cc(-c2cnc3c(c2Cl)C2(CC=CC2)CN3)cn1] | 2-(4-(4'-Chloro-1',2'-dihydrospiro[cyclopentane-1,3'-pyrrolo[2,3-b]pyridin]-3-en-5'-yl)-1H-pyrazol-1-yl)acetamide |
| 319 | 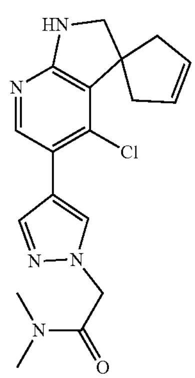 [SMILES: CN(C)C(=O)Cn1cc(-c2cnc3c(c2Cl)C2(CC=CC2)CN3)cn1] | 2-(4-(4'-Chloro-1'2'-dihydrospiro[cyclopentane-1,3'-pyrrolo[2,3-b]pyridin]-3-en-5'-yl)-1H-pyrazol-1-yl)-N,N-dimethylacetamide |
| 320 | 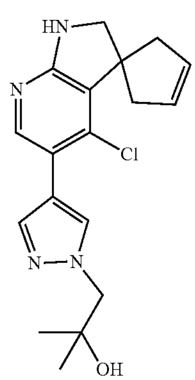 [SMILES: CC(C)(O)Cn1cc(-c2cnc3c(c2Cl)C2(CC=CC2)CN3)cn1] | 1-(4-(4'-Chloro-1',2'-dihydrospiro[cyclopentane-1,3'-pyrrolo[2,3-b]pyridin]-3-en-5'-yl)-1H-pyrazol-1-yl)-2-methylpropan-2-ol |
| 321 | 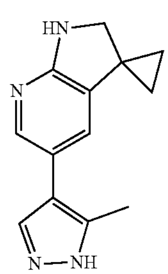 [SMILES: Cc1[nH]ncc1-c1cnc2c(c1)C1(CC1)CN2] | 5'-(5-Methyl-1H-pyrazol-4-yl)-1',2'-dihydrospiro[cyclopropane-1,3'-pyrrolo[2,3-b]pyridine] |

TABLE 1-continued

| No. | Structure | Name |
|---|---|---|
| 322 | 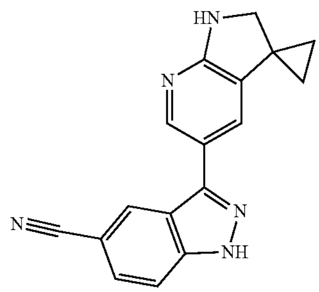 [SMILES: N#Cc1ccc2[nH]nc(-c3cnc4c(c3)C3(CC3)CN4)c2c1] | 3-(1',2'-Dihydrospiro[cyclopropane-1,3'-pyrrolo[2,3-b]pyridin]-5'-yl)-1H-indazole-5-carbonitrile |
| 323 | 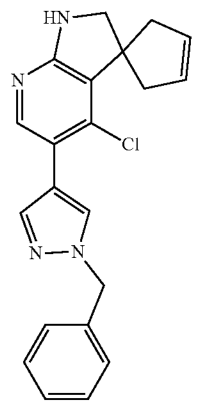 [SMILES: Clc1c(-c2cnn(Cc3ccccc3)c2)cnc2c1C1(CC=CC1)CN2] | 5'-(1-Benzyl-1H-pyrazol-4-yl)-4'-chloro-1',2'-dihydrospiro[cyclopentane-1,3'-pyrrolo[2,3-b]pyridin]-3-ene |
| 324 | 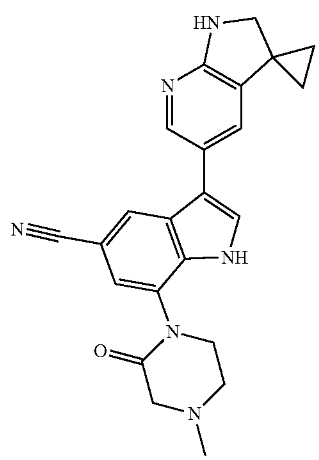 [SMILES: CN1CCN(c2cc(C#N)cc3c(-c4cnc5c(c4)C4(CC4)CN5)c[nH]c23)C(=O)C1] | 3-(1',2'-Dihydrospiro[cyclopropane-1,3'-pyrrolo[2,3-b]pyridin]-5'-yl)-7-(4-methyl-2-oxopiperazin-1-yl)-1H-indole-5-carbonitrile |
| 325 | | 3-(4'-Chloro-4-hydroxy-1',2'-dihydrospiro[cyclohexane-1,3'-pyrrolo[2,3-b]pyridin]-5'-yl)-1H-indole-5-carbonitrile |
| 325a | 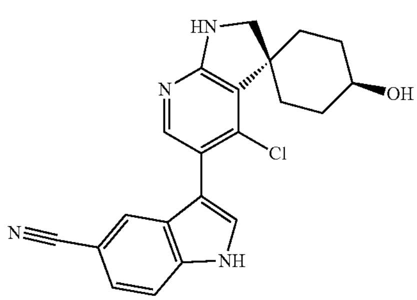 [SMILES: N#Cc1ccc2[nH]cc(-c3cnc4c(c3Cl)[C@]3(CC[C@H](O)CC3)CN4)c2c1] | 3-((1s,4s)-4'-Chloro-4-hydroxy-1',2'-dihydrospiro[cyclohexane-1,3'-pyrrolo[2,3-b]pyridin]-5'-yl)-1H-indole-5-carbonitrile |

TABLE 1-continued

| No. | Structure | Name |
|---|---|---|
| 326 | 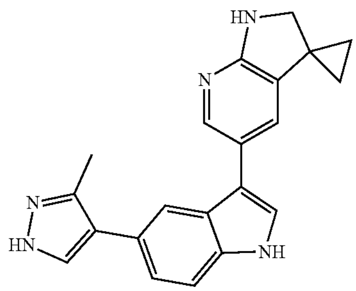 [SMILES: Cc1n[nH]cc1-c1ccc2[nH]cc(-c3cnc4c(c3)C3(CC3)CN4)c2c1] | 5'-(5-(3-Methyl-1H-pyrazol-4-yl)-1H-indol-3-yl)-1',2'-dihydrospiro[cyclopropane-1,3'-pyrrolo[2,3-b]pyridine] |
| 327 | 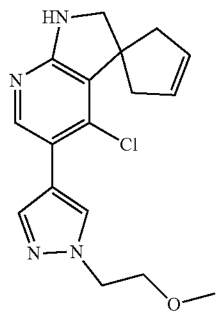 [SMILES: COCCn1cc(-c2cnc3c(c2Cl)C2(CC=CC2)CN3)cn1] | 4'-Chloro-5'-(1-(2-methoxyethyl)-1H-pyrazol-4-yl)-1',2'-dihydrospiro[cyclopentane-1,3'-pyrrolo[2,3-b]pyridin]-3-ene |
| 328 | 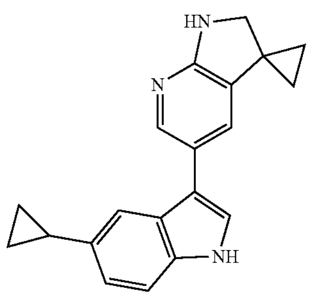 [SMILES: c1nc2c(cc1-c1c[nH]c3ccc(C4CC4)cc13)C1(CC1)CN2] | 5'-(5-Cyclopropyl-1H-indol-3-yl)-1',2'-dihydrospiro[cyclopropane-1,3'-pyrrolo[2,3-b]pyridine] |
| 329 | 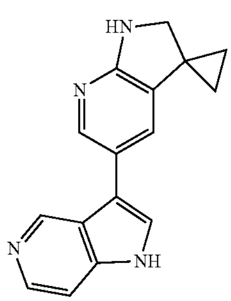 [SMILES: c1cc2[nH]cc(-c3cnc4c(c3)C3(CC3)CN4)c2cn1] | 5-(1H-Pyrrolo[3,2-c]pyridin-3-yl)spiro[1,2-dihydropyrrolo[2,3-b]pyridine-3,1'-cyclopropane] |
| 330 | | 4'-Chloro-5'-(5-cyano-1H-indol-3-yl)-3-methyl-1',2'-dihydrospiro[cyclopentane-1,3'-pyrrolo[2,3-b]pyridine]-3-carbonitrile |
| 330a | 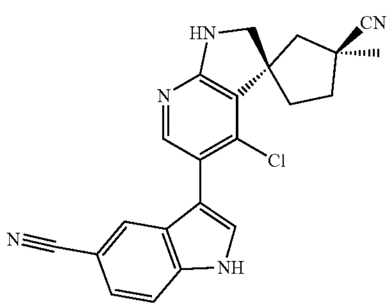 [SMILES: C[C@]1(C#N)CC[C@@]2(CNc3ncc(-c4c[nH]c5ccc(C#N)cc45)c(Cl)c32)C1] | (1R,3S)-4'-Chloro-5'-(5-cyano-1H-indol-3-yl)-3-methyl-1',2'-dihydrospiro[cyclopentane-1,3'-pyrrolo[2,3-b]pyridine]-3-carbonitrile<br>(1S, 3R)-4'-Chloro-5'-(5-cyano-1H-indol-3-yl)-3-methyl-1',2'-dihydrospiro[cyclopentane-1,3'-pyrrolo[2,3-b]pyridine]-3-carbonitrile |

TABLE 1-continued

| No. | Structure | Name |
|-----|-----------|------|
| 331 | 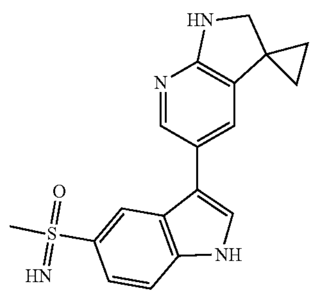 [SMILES: CS(=N)(=O)c1ccc2[nH]cc(-c3cnc4c(c3)C3(CC3)CN4)c2c1] | (3-(1',2'-Dihydrospiro[cyclopropane-1,3'-pyrrolo[2,3-b]pyridin]-5'-yl)-1H-indol-5-yl)(imino)(methyl)-γ6-sulfanone |
| 332 | 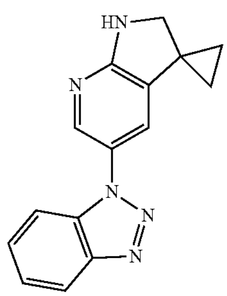 [SMILES: c1ccc2c(c1)nnn2-c1cnc2c(c1)C1(CC1)CN2] | 5-(Benzotriazol-1-yl)spiro[1,2-dihydropyrrolo[2,3-b]pyridine-3,1'-cyclopropane |
| 333 | 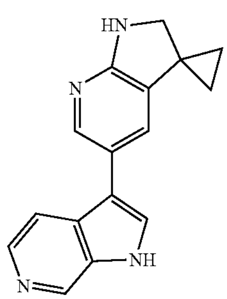 [SMILES: c1cc2c(-c3cnc4c(c3)C3(CC3)CN4)c[nH]c2cn1] | 5-(1H-Pyrrolo[2,3-c]pyridin-3-yl)spiro[1,2-dihydropyrrolo[2,3-b]pyridine-3,1'-cyclopropane] |
| 334 | 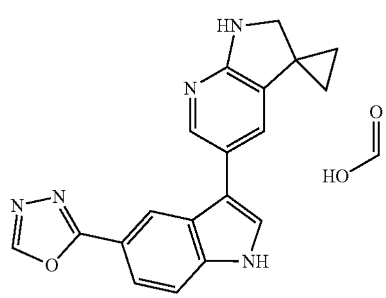 | 2-(3-(1',2'-Dihydrospiro[cyclopropane-1,3'-pyrrolo[2,3-b]pyridin]-5'-yl)-1H-indol-5-yl)-1,3,4-oxadiazole formate salt |
| 335 | 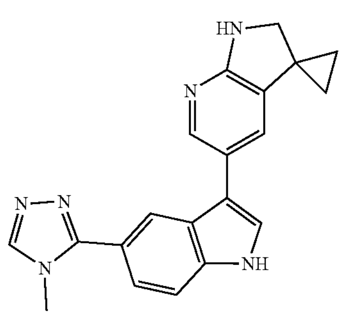 [SMILES: Cn1cnnc1-c1ccc2[nH]cc(-c3cnc4c(c3)C3(CC3)CN4)c2c1] | 5'-(5-(4-Methyl-4H-1,2,4-triazol-3-yl)-1H-indol-3-yl)-1',2'-dihydrospiro[cyclopropane-1,3'-pyrrolo[2,3-b]pyridine] |

TABLE 1-continued

| No. | Structure | Name |
|---|---|---|
| 336 | 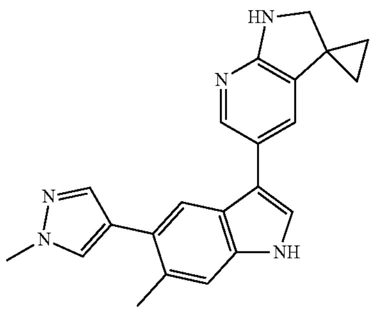 [SMILES: Cc1cc2[nH]cc(-c3cnc4c(c3)C3(CC3)CN4)c2cc1-c1cnn(C)c1] | 5'-(6-Methyl-5-(1-methyl-1H-pyrazol-4-yl)-1H-indol-3-yl)-1',2'-dihydrospiro[cyclopropane-1,3'-pyrrolo[2,3-b]pyridine] |
| 337 | | 4'-Chloro-5'-(5-cyano-1H-indol-3-yl)-3-methyl-1',2'-dihydrospiro[cyclopentane-1,3'-pyrrolo[2,3-b]pyridine]-3-carboxamide |
| 337a | 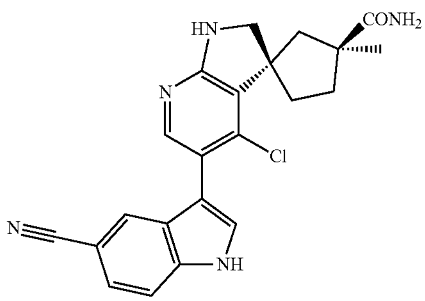 [SMILES: C[C@]1(C(N)=O)CC[C@@]2(CNc3ncc(-c4c[nH]c5ccc(C#N)cc45)c(Cl)c32)C1] | (1R,3S)-4'-Chloro-5'-(5-cyano-1H-indol-3-yl)-3-methyl-1',2'-dihydrospiro[cyclopentane-1,3'-pyrrolo[2,3-b]pyridine]-3-carboxamide (1S,3R)-4'-Chloro-5'-(5-cyano-1H-indol-3-yl)-3-methyl-1',2'-dihydrospiro[cyclopentane-1,3'-pyrrolo[2,3-b]pyridine]-3-carboxamide |
| 338 | 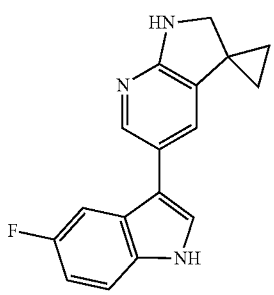 [SMILES: Fc1ccc2[nH]cc(-c3cnc4c(c3)C3(CC3)CN4)c2c1] | 5'-(5-Fluoro-1H-indol-3-yl)-1',2'-dihydrospiro[cyclopropane-1,3'-pyrrolo[2,3-b]pyridine] |
| 339 | 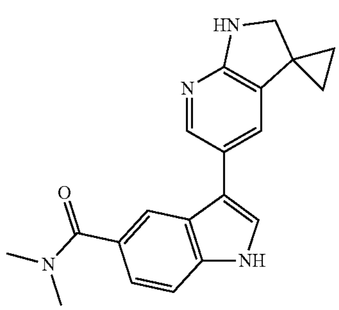 [SMILES: CN(C)C(=O)c1ccc2[nH]cc(-c3cnc4c(c3)C3(CC3)CN4)c2c1] | 3-(1'2'-Dihydrospiro[cyclopropane-1,3'-pyrrolo[2,3-b]pyridin]-5'-yl)-N,N-dimethyl-1H-indole-5-carboxamide |

TABLE 1-continued

| No. | Structure | Name |
| --- | --- | --- |
| 340 | 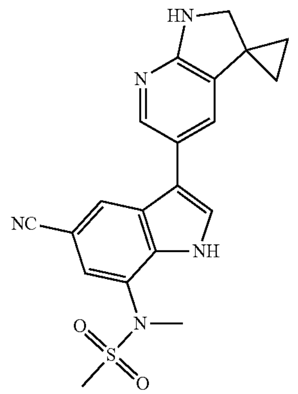 [SMILES: CN(c1cc(C#N)cc2c(-c3cnc4c(c3)C3(CC3)CN4)c[nH]c12)S(C)(=O)=O] | N-(5-Cyano-3-(1',2'-dihydrospiro[cyclopropane-1,3'-pyrrolo[2,3-b]pyridin]-5'-yl)-1H-indol-7-yl)-N-methylmethanesulfonamide |
| 341 | 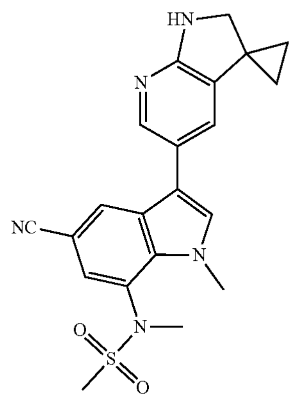 [SMILES: CN(c1cc(C#N)cc2c(-c3cnc4c(c3)C3(CC3)CN4)cn(C)c12)S(C)(=O)=O] | N-(5-Cyano-3-(1',2'-dihydrospiro[cyclopropane-1,3'-pyrrolo[2,3-b]pyridin]-5'-yl)-1-methyl-1H-indol-7-yl)-N-methylmethanesulfonamide |
| 342 | 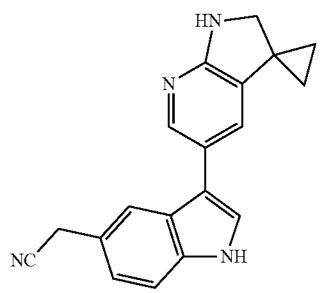 [SMILES: N#CCc1ccc2[nH]cc(-c3cnc4c(c3)C3(CC3)CN4)c2c1] | 2-(3-(1'2'-Dihydrospiro[cyclopropane-1,3'-pyrrolo[2,3-b]pyridin]-5'-yl)-1H-indol-5-yl)acetonitrile |
| 343 | 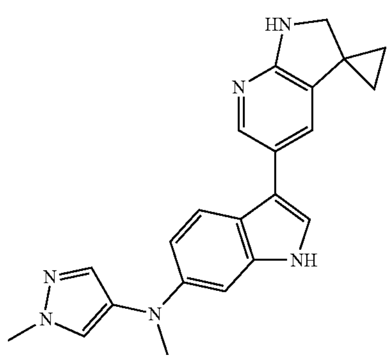 [SMILES: CN(c1ccc2c(-c3cnc4c(c3)C3(CC3)CN4)c[nH]c2c1)c1cnn(C)c1] | 3-(1',2'-Dihydrospiro[cyclopropane-1,3'-pyrrolo[2,3-b]pyridin]-5'-yl)-N-methyl-N-(1-methyl-1H-pyrazol-4-yl)-1H-indol-6-amine |

TABLE 1-continued

| No. | Structure | Name |
| --- | --- | --- |
| 344 | 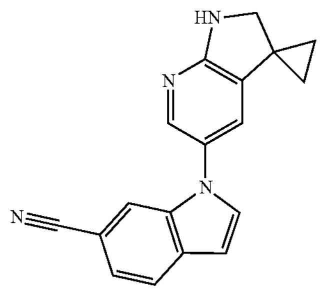 [SMILES: N#Cc1ccc2ccn(-c3cnc4c(c3)C3(CC3)CN4)c2c1] | 1-(1',2'-Dihydrospiro[cyclopropane-1,3'-pyrrolo[2,3-b]pyridin]-5'-yl)-1H-indole-6-carbonitrile |
| 345 | 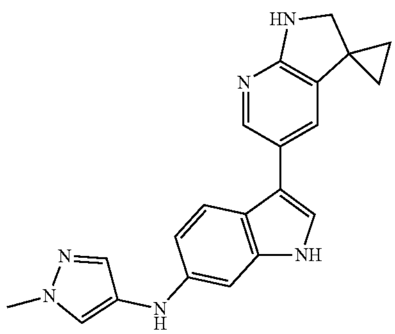 [SMILES: Cn1cc(Nc2ccc3c(-c4cnc5c(c4)C4(CC4)CN5)c[nH]c3c2)cn1] | 3-(1',2'-Dihydrospiro[cyclopropane-1,3'-pyrrolo[2,3-b]pyridin]-5'-yl)-N-(1-methyl-1H-pyrazol-4-yl)-1H-indol-6-amine |
| 346 | 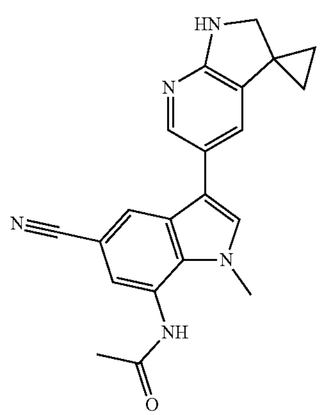 [SMILES: CC(=O)Nc1cc(C#N)cc2c(-c3cnc4c(c3)C3(CC3)CN4)cn(C)c12] | N-(5-Cyano-3-(1',2'-dihydrospiro[cyclopropane-1,3'-pyrrolo[2,3-b]pyridin]-5'-yl)-1-methyl-1H-indol-7-yl)acetamide |
| 347 | 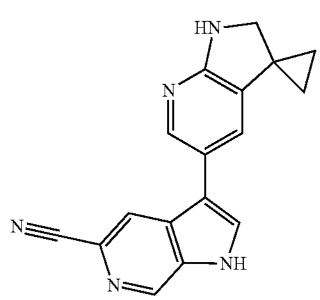 [SMILES: N#Cc1cc2c(-c3cnc4c(c3)C3(CC3)CN4)c[nH]c2cn1] | 3-(1',2'-Dihydrospiro[cyclopropane-1,3'-pyrrolo[2,3-b]pyridin]-5'-yl)-1H-pyrrolo[2,3-c]pyridine-5-carbonitrile |

TABLE 1-continued

| No. | Structure | Name |
|---|---|---|
| 348 | 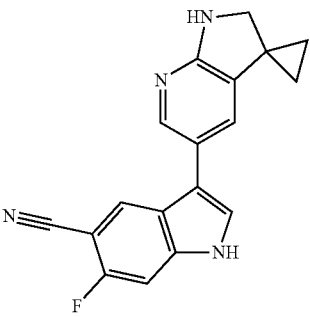 [SMILES: N#Cc1cc2c(-c3cnc4c(c3)C3(CC3)CN4)c[nH]c2cc1F] | 3-(1',2'-Dihydrospiro[cyclopropane-1,3'-pyrrolo[2,3-b]pyridin]-5'-yl)-6-fluoro-1H-indole-5-carbonitrile]. |

28. A pharmaceutical composition comprising the compound of claim 1, or a pharmaceutically acceptable salt thereof, and a pharmaceutically acceptable excipient.

29. The pharmaceutical composition of claim 28, wherein said composition further comprises a chemotherapeutic agent.

* * * * *